US008772007B2

(12) United States Patent
Amin et al.

(10) Patent No.: US 8,772,007 B2
(45) Date of Patent: Jul. 8, 2014

(54) PERHYDROLASE

(75) Inventors: Neelam S. Amin, Palo Alto, CA (US); Matthew G. Boston, Dixon, CA (US); Richard R. Bott, Burlingame, CA (US); Marguerite A. Cervin, Redwood City, CA (US); Edward M. Concar, San Francisco, CA (US); Marc E. Gustwiller, Cincinnati, OH (US); Brian E. Jones, Leidchendam (NL); Klaus Liebeton, Zwingenberg (DE); Gregory S. Miracle, Hamilton, OH (US); Hiroshi Oh, Cincinnati, OH (US); Ayrookaran J. Poulose, Belmont, CA (US); Sandra W. Ramer, Sunnyvale, CA (US); Jeffrey J. Scheibel, Loveland, OH (US); Walter Weyler, San Francisco, CA (US); Gregory M. Whited, Belmont, CA (US)

(73) Assignee: Danisco US Inc., Palo Alto, CA (US)

( * ) Notice: Subject to any disclaimer, the term of this patent is extended or adjusted under 35 U.S.C. 154(b) by 1832 days.

(21) Appl. No.: 10/581,014

(22) PCT Filed: Dec. 3, 2004

(86) PCT No.: PCT/US2004/040438
§ 371 (c)(1),
(2), (4) Date: Sep. 11, 2007

(87) PCT Pub. No.: WO2005/056782
PCT Pub. Date: Jun. 23, 2005

(65) Prior Publication Data
US 2008/0145353 A1    Jun. 19, 2008

Related U.S. Application Data

(60) Provisional application No. 60/526,764, filed on Dec. 3, 2003.

(51) Int. Cl.
*C12N 9/14* (2006.01)
*C12N 9/18* (2006.01)
*C12P 21/06* (2006.01)
*C12N 1/20* (2006.01)
*C12N 15/00* (2006.01)
*C11D 3/386* (2006.01)
*C11D 3/00* (2006.01)
*C07H 21/04* (2006.01)

(52) U.S. Cl.
USPC ....... 435/195; 435/197; 435/69.1; 435/252.3; 435/320.1; 510/305; 510/320; 510/393; 536/23.2

(58) Field of Classification Search
None
See application file for complete search history.

(56) References Cited

U.S. PATENT DOCUMENTS

| | | |
|---|---|---|
| 3,823,070 A | 7/1974 | Minato et al. |
| 3,974,082 A | 8/1976 | Weyn |
| 4,008,125 A | 2/1977 | Kurozumi et al. |
| 4,261,868 A | 4/1981 | Hora et al. |
| 4,400,237 A | 8/1983 | Kruger et al. |
| 4,404,128 A | 9/1983 | Anderson |
| 4,415,657 A | 11/1983 | Umezawa et al. |
| 4,430,243 A | 2/1984 | Bragg |
| 4,594,324 A | 6/1986 | Dalton et al. |
| 4,683,195 A | 7/1987 | Mullis et al. |
| 4,683,202 A | 7/1987 | Mullis |
| 4,965,188 A | 10/1990 | Mullis et al. |
| 4,977,252 A | 12/1990 | Chiu |
| 5,030,240 A | 7/1991 | Wiersema et al. |
| 5,108,457 A | 4/1992 | Poulose et al. |
| 5,204,015 A | 4/1993 | Caldwell et al. |
| 5,240,835 A | 8/1993 | Pettrone et al. |
| 5,254,283 A | 10/1993 | Arnold et al. |
| 5,296,161 A | 3/1994 | Wiersema et al. |
| 5,296,616 A | 3/1994 | Namekawa et al. |
| 5,338,474 A | 8/1994 | Kaiserman et al. |
| 5,352,594 A | 10/1994 | Poulouse |
| 5,354,559 A | 10/1994 | Morehouse |
| 5,370,770 A | 12/1994 | Johnson et al. |
| 5,486,303 A | 1/1996 | Capeci et al. |
| 5,489,392 A | 2/1996 | Capeci et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |

(Continued)

FOREIGN PATENT DOCUMENTS

| | | |
|---|---|---|
| EP | 0 248 660 | 6/1987 |
| EP | 0 275 509 | 12/1987 |

(Continued)

OTHER PUBLICATIONS

Whisstock et al. Quaterly Reviews of Biophysics, 2003, "Prediction of protein function from protein sequence and structure", 36(3): 307-340.*

(Continued)

*Primary Examiner* — Iqbal H Chowdhury
(74) *Attorney, Agent, or Firm* — Danisco US Inc.

(57) ABSTRACT

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

99 Claims, 18 Drawing Sheets

(56) References Cited

U.S. PATENT DOCUMENTS

| | | | |
|---|---|---|---|
| 5,597,936 | A | 1/1997 | Perkins et al. |
| 5,601,750 | A | 2/1997 | Domke et al. |
| 5,691,297 | A | 11/1997 | Nassano et al. |
| 5,785,812 | A | 7/1998 | Linsten et al. |
| 5,879,584 | A | 3/1999 | Bianchetti et al. |
| 5,935,826 | A | 8/1999 | Blue et al. |
| 5,989,526 | A | 11/1999 | Aaslyng et al. |
| 6,165,318 | A | 12/2000 | Paren et al. |
| 6,225,464 | B1 | 5/2001 | Hiler, II et al. |
| 6,306,812 | B1 | 10/2001 | Perkins et al. |
| 6,326,348 | B1 | 12/2001 | Vinson et al. |
| 6,379,653 | B1 | 4/2002 | Aaslyng et al. |
| 6,569,286 | B1 | 5/2003 | Withenshaw et al. |
| 7,510,859 | B2 | 3/2009 | Wieland et al. |
| 7,754,460 | B2 * | 7/2010 | Amin et al. .................. 435/195 |
| 2002/0007516 | A1 | 1/2002 | Wang |
| 2003/0191033 | A1 | 10/2003 | Ryu et al. |
| 2007/0105740 | A1 | 5/2007 | Dicosimo et al. |

FOREIGN PATENT DOCUMENTS

| | | |
|---|---|---|
| EP | 0 280 232 | 2/1988 |
| EP | 0268456 | 5/1988 |
| EP | 0359087 | 3/1990 |
| EP | 0375102 | 6/1990 |
| EP | 1 255 888 | 2/2001 |
| GB | 2 094 826 A | 3/1982 |
| WO | WO 91/17235 | 5/1991 |
| WO | WO 97/11151 | 9/1996 |
| WO | WO01/16172 | 3/2001 |
| WO | WO 03/002810 A1 | 1/2003 |
| WO | WO 03/083125 | 3/2003 |

OTHER PUBLICATIONS

Chica et al. Semi-rational approaches to engineering enzyme activity: combining the benefits of directed evolution and rational design, Curr Opin Biotechnol. Aug. 2005;16(4):378-84. Review.*

Witkowski et al. Conversion of a beta-ketoacyl synthase to a malonyl decarboxylase by replacement of the active-site cysteine with glutamine, Biochemistry. Sep. 7, 1999;38(36):11643-50.*

Hydrolase, UniProt Accession No. Q92XZ6, created Dec. 1, 2001.*

Novo Nordisk A/S, "Use of Lipolytic Enzyme from Aeromonas in Detergents (Novo Nordisk NS)", Research Disclosure No. 390030, Research Disclosure Journal, Oct. 1996.

Altschul et al., "Basic Local Alignment Search Tool," *J. Mol. Biol.*, V. 215, 1990, pp. 403-410.

Altschul et al., "Basic Local Alignment Statistics," *Methods in Enzymology*, V. 266, pp. 460-480 (1996).

Baldry, "The bactericidal, fungicidal and sporicidal properties of hydrogen peroxide and peracetic acid," *J. of Applied Bact.*, 1983, 54, 417-423.

Chamberlin et al., "New RNA polymerase from *Escherichia coli* infected with Bacteriophase T7," *Nature*, V. 228, pp. 227-231, Oct. 17, 1970.

Chang, Shing et al., "High Frequency Transformation of *Bacillus subtilis* Protoplasts by Plasmid DNA," *Mol. Gen. Genet.*, 168:111-115, 1979.

Devereux et al., "A Comprehensive set of sequence analysis programs for the VAX," *Nucl. Acids Res.*, vol. 12, p. 387-395, 1984.

Feng et al., "Progressive Sequence Alignment as a Prerequisite to Correct Phylogenetic Tress" *J. Mol Evol.* vol. 25, pp. 351-360, 1987.

Ferrari, E. et al., "Genetics" *Bacillus*, Harwood (ed.), Plenum Publishing Corporation, pp. 5772, 1989.

Goffin and Ghysen, "Biochemistry and comparative genomics of SxxK superfamily acyltransferases offer a club to the mycobacterial paradox: presence of penicillin-susceptible target proteins versus lack of efficiency of penicillin as therapeutic agent", *Microbiology and Molecular Biology Reviews*, Dec. 2002, V. 66, N. 4, pp. 702-728.

Henikoff, Steven et al., "Amino acid substitution matrices from protein blocks," *Proc. Natl. Acad. Sci. USA*, 89:10915-10919, Nov. 1992.

Higgins et al., "Clustal: a package for performing multiple sequence alighment on a microcomputer," *Gene*, 73 (1988) 237-244.

Higgins et al., "Fast and sensitive multiple sequence alignments on microcomputer," *CABIOS*, vol. 5, 1989, p. 151-153.

Hofmann et al., "Bleaching Activators and the Mechanism of Bleaching Activation," *J. prakt. Chem.*, 334 (1992) 293-297.

Hosie et al., "p-Nitrophenyl and Cholesteryl-N-Alkyl Carbamates as Inhibitors of Cholesterol Esterase", *J. of Biological Chemistry*, V. 262, N. 1, pp. 260-264, Jan. 5, 1987.

Kacian et al., "A replicating RNA molecule suitable for a detailed analysis of extracellular evolution and replication", *Proc. Nat. Acad. Sci. USA*, V. 69, N. 10, pp. 3038-3042, Oct. 1972.

Karlin et al., "Applications and statistics for multiple high-scoring segments in molecular sequences," *Proc. Natl. Acad. Sci. USA*, vol. 90, pp. 5873-5877, Jun. 1993.

Molgaard et al., "Rhamnogalacturonan acetylesterase elucidates the structure and function of a new family of hydrolases," *Structure* 2000, V. 8, N. 4., pp. 373-383.

Needleman et al., "A General Method App licable to the Search for Similarities in the Amino Acid Sequence of Two Proteins," *J. Mol. Biol.*, vol. 48, pp. 443-453, 1970.

Pearson et al., "Improved tools for biological sequence comparison," *Proc. Natl. Acad. Sci. USA*, vol. 85, pp. 2444-2448, Apr. 1988.

Pinkernell et al., "Selective Phtometric Deermination of Peroxycarboxylic Acids in the Presence of Hydrogen Peroxide," *Analyst*, Jun. 1997, KV. 122 567-571.

Sakai et al., "A novel arylesterase active toward 7-Aminocephalosporanic Acid from *Agrobacterium radiobacter* IFO 12607: Nucleotide sequence, gene expression in *Escherichia coli*, and site-directed mutagenesis", *J. of Fermentation and Bioengineering*, (1998) 85:138-143.

Salazar et al., "Transciption analysis of the dnaA gene and oriC region of the chromosome of *Mycobacterium smegmatis* and *Mycobacterium bovis* BCG, and its regulation by the DnaA protein," *Microbiology*, V. 149, pp. 773-784.

Smith et al., "Comparison of Biosequences," *Adv. In App. Math*, vol. 2, pp. 482-489, 1981.

Smith, Michael et al., "Protoplast Transformation in Coryneform Bacteria and Introduction of an a-Amylase Gene from *Bacillus amyloliquefaciens* into *Brevibacterium lactofermentum*," *Applied and Environmental Microbiology*, vol. 51, No. 3, pp. 634-639, Mar. 1986.

Upton et al., "A New Family of Llpolytic enzymes". *TIBS*, V. 20—pp. 178-179 May 1995.

Vagner, et al., "A vector for systematic gene inactivation in *Bacillus subtilis*," *Microbiology*, (1998) V.144, pp. 3097-3104.

Wu et al., "The ligation amplification reaction (LAR)—amplication of specific DNA sequences using sequential rounds of template-dependant ligation", *Genomics*, V. 4, pp. 560-569 (1989).

Akoh, C.C., et al., "GDSL family of serine esterases/lipases." Progress in Lipid Research 43(6): 534-552, 2011.

Bennett, M.J., et al., "Nucleotide sequence and predicted functions of the entire *Sinorhizobium meliloti* pSymA megaplasmid." *Proc. Nat. Acad. Sci.* 98(17): 9883-9888, 2011.

Bernhardt, P., et al., "Molecular Basis of Perhydrolase Activity in Serine Hydrolases." *Angewandte Chemi.* 44(18): 2742-2746, 2005.

Mathews, I., et al., "Structure of a novel enzyme that catalyzes acyl transfer to alcohols in aqueous conditions." *Biochemistry* 46(31): 8969-8979, 2007.

GenBank Accession No. AAO7232, Arylesterase precursor [*Vibrio vulnificus* CMCP6], Kim, Y.R., et al., Jan. 25, 2011.

GenBank Accession No. AAC38796, outer membrane esterase [*Salmonella enteric* subsp. *enterica* Serovar *Typhimurium*], Carinato, M.E., et al., Jul. 20, 1998.

GenBank Accession No. AAD02335, arylesterase [*Agrobactgerium tumefaciens*], Sakai, Y., et al., Jan. 5, 1999.

GenBank Accession No. AAK53448, lipase/phospholipase B [*Moraxella bovis*], Farn, J.L., et al., Oct. 30, 2001.

GenBank Accession No. AAK65750, hydrolase [*Sinorhizobium meliloti* 1021], Barnett, M.J., et al., Nov. 16, 2010.

AAK65755, hydrolase [*Sinorhizobium meliloti* 1021], Barnett, M.J., et al, Nov. 16, 2010.

(56) References Cited

OTHER PUBLICATIONS

AAK87224, arylesterase [*Agrobacterium fabrum* str. C58], Wood, D.W., et al, Dec. 3, 2012.
AAK89941, arylesterase [*Agrobacterium fabrum* str. C58], Wood,D. W., et al, Jun. 5, 2013.
ATCC Accession No. 10143, *M. smegmatis, Mycobacterium smegmatis* (Trevisan) Lehmann and Neumann, 1953.
ATCC 19686 *Mycobacterium parafortuitum* Tsukamura et al., 1966.
BAB47978 arylesterase [*Mesorhizobium loti* MAFF303099], Kaneko,T., et al., May 16, 2009.
CAC46027, Esterase [*Sinorhizobium meliloti* 1021], Capela, D., et al., May 6, 2008.
NCBI Accession No. NP_066654, hypothetical protein [*Agrobacterium rhizogenes*], Moriguchu, K., et al., Jun. 10, 2013.
NCBI Reference Sequence: NP_865748, hypothetical protein RB3832 [*Rhodopirellula baltica* SH 1], Wecker,P., et al., Jul. 22, 2013.
UniProt Accession No. Q7NRP5, Acyl-CoA thioesterase, Vasconcelos, A.T.R.,et al., Oct. 31, 2006.
UniProt Accession No. Q88KH2, *Pseudomonas putida* (strain KT2440), Nelson, K.E., et al., Jun. 1, 2003.
UniProtKB/Swiss-Prot: Accession No. Q8UAC0, Arylesterase (AGR_L_2749p), Wood, D.W., et al., Oct. 31, 2006.
UniProtKB/Swiss-Prot Accession No. Q8UFG4, Arylesterase (AGR_C_2642p), Wood, D.W., et al., Oct. 31, 2006.
UniProtKB/Swiss-Prot: Q8XQI0, Putative arylesterase protein, Salanoubat,M., et al., Oct. 31, 2006.
UniProt. Accession No. Q92XZ1, *Rhizobium meliloti* (strain 1021) (*Ensifer meliloti*) (*Sinorhizobium meliloti*), Barnett, M.J., et al., Dec. 1, 2001.
UniProt Accession No. Q98MY5, *Rhizobium loti* (strain MAFF303099) (*Mesorhizobium loti*), Kaneko, T., et al., Oct. 1, 2001.
UniProt Accession No. Q9EV56, *Rhizobium meliloti* (*Ensifer meliloti*) (*Sinorhizobium meliloti*), Soto, M.J., et al., Mar. 1, 2001.
UniProt Accession No. Q9KWA6, *Agrobacterium rhizogenes*, Moriguchi, K., et al., Oct. 1, 2000.
UniProt Accession No. Q9KWB1, *Agrobacterium rhizogenes*, Moriguchi, K., et al., Oct. 1, 2000.
UniProt Accession No. Q46ZX5, *Cupriavidus pinatubonensis* (strain JMP 134 / LMG 1197) (*Ralstonia eutropha* (strain JMP 134)), Hammon, N., et al., Sep. 13, 2005.
International Search Report and the Written Opinion of the International Searching Authority for International Application No. PCT/US2004/040438 dated Nov. 29, 2005.
International Preliminary Report on Patentability for International Application No. PCT/US2004/040438 dated Jun. 7, 2006.
Partial European Search Report for European Application No. EP10 01 1491 dated Feb. 4, 2011.
Extended European Search Report for European Patent Application No. 10 01 1491 dated May 20, 2011.
Partial European Search Report for European Application No. EP10011487.5 dated Feb. 10, 2011.
Extended European Search Report for European Patent Application No. 1001487.5 dated Jun. 8, 2011.
Extended European Search Report for European Patent Application No. 13176407 dated Oct. 21, 2013.

\* cited by examiner

FIGURE 6

| | Volume (ml) | Protein (mg/ml) | Total Protein (mg) | pNB Activity d410/min/ml | SpAc d410/min/mg | Total activity d410 | Recovery (%) | Purification (fold) |
|---|---|---|---|---|---|---|---|---|
| Crude extract 55C | 128 | 7.5 | 960 | 3840 | 512 | 491520 | 100 | 1.0 |
| 10min Phenyl | 118 | 5.4 | 637 | 3760 | 696 | 443680 | 90 | 1.4 |
| seph HQ | 241 | 0.37 | 89 | 1700 | 4595 | 409700 | 83 | 9.0 |
| Anion | 0.74 | 22.7 | 17 | 250000 | 11013 | 185000 | 38 | 21.5 |

SEQUENCE LISTING

<160> NUMBER OF SEQ ID NOS: 711

<210> SEQ ID NO 1
<211> LENGTH: 651
<212> TYPE: DNA
<213> ORGANISM: Mycobacterium smegmatis

<400> SEQUENCE: 1

```
atggccaagc gaattctgtg tttcggtgat tccctgacct ggggctgggt ccccgtcgaa      60
gacggggcac ccaccgagcg gttcgccccc gacgtgcgct ggaccggtgt gctggccag      120 cagctcggag cggacttcga ggtgatcgag gagggactga gcgcgcgcac caccaacatc      180
```

```
gacgacccca ccgatccgcg gctcaacggc gcgagctacc tgccgtcgtg cctcgcgacg      240
cacctgccgc tcgacctggt gatcatcatg ctgggcacca acgacaccaa ggcctacttc      300
cggcgcaccc cgctcgacat cgcgctgggc atgtcggtgc tcgtcacgca ggtgctcacc      360
agcgcgggcg gcgtcggcac cacgtacccg gcacccaagg tgctggtggt ctcgccgcca      420
ccgctggcgc ccatgccgca ccctggttc cagttgatct cgagggcgg cgagcagaag       480 accactgagc tcgcccgcgt gtacagcgcg ctcgcgtcgt tcatgaaggt gccgttcttc      540
gacgcgggtt cggtgatcag caccgacggc gtcgacggaa tccacttcac cgaggccaac      600
aatcgcgatc tcggggtggc cctcgcggaa caggtgcgga gcctgctgta a              651
```

```
<210> SEQ ID NO 2
<211> LENGTH: 216
<212> TYPE: PRT
<213> ORGANISM: Mycobacterium smegmatis

<400> SEQUENCE: 2

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr
    50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
        115                 120                 125

Tyr Pro Ala Pro Lys Val Leu Val Val Ser Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215

<210> SEQ ID NO 3
<211> LENGTH: 19
<212> TYPE: PRT
<213> ORGANISM: Mycobacterium parafortuitum

<400> SEQUENCE: 3

Lys Val Pro Phe Phe Asp Ala Gly Ser Val Ile Ser Thr Asp Gly Val
1               5                   10                  15

Asp Gly Ile
```

<210> SEQ ID NO 4
<211> LENGTH: 19
<212> TYPE: PRT
<213> ORGANISM: Mycobacterium parafortuitum

<400> SEQUENCE: 4

Gly Thr Arg Arg Ile Leu Ser Phe Gly Asp Ser Leu Thr Trp Gly Trp
1               5                   10                  15

Ile Pro Val

<210> SEQ ID NO 5
<211> LENGTH: 59
<212> TYPE: DNA
<213> ORGANISM: Artificial Sequence
<220> FEATURE:
<223> OTHER INFORMATION: primer

<400> SEQUENCE: 5
ctaacaggag gaattaacca tggccaagcg aattctgtgt ttcggtgatt ccctgacct        59

<210> SEQ ID NO 6
<211> LENGTH: 59
<212> TYPE: DNA
<213> ORGANISM: Artificial Sequence
<220> FEATURE:
<223> OTHER INFORMATION: primer

<400> SEQUENCE: 6
gcgcgcggat ccgcgcgctt acagcaggct ccgcacctgt tccgcgaggg ccaccccga        59

<210> SEQ ID NO 7
<211> LENGTH: 10
<212> TYPE: DNA
<213> ORGANISM: Mycobacterium smegmatis

<400> SEQUENCE: 7
ggctgggggc                                                             10

<210> SEQ ID NO 8
<211> LENGTH: 1779
<212> TYPE: DNA
<213> ORGANISM: Mycobacterium smegmatis

<400> SEQUENCE: 8
atgcacttac gtcccgctct gacgtggctc ctggttgtcg gtctgttcat atcggtcgtc        60
ggatgttcgt cgtccccgga tccggccgac cggttctcgg cgttcgccga ggcgctgggc      120
cgcaaggatg cggccgcggc ggccgcccag accagcgatc cggcggccgc ggaggcggcc      180
atcaccgcga tgctggccgg gatgggcgac gccgcgaacg tctcggtggc cgccgaaccc      240
gaggaaggcg acgacgcggg cgcgacgctg aagtacacgt ggacctgggg tgagggccgc      300
gacttcggct acgacaccac cgcgacggcg gccaaatccg gtgacgactg gctgatcacc      360
tggtccccca ccgtgttgca ccgcgacctc accccggatc tgcgcttcca gtacagcgag      420
gacagcgaat tgcagacccc ggtgctcgac cgcaccggcc agccgttgat gacatggcag      480
accgtcggtg tcatcactgt cgaacgcgca catccggagt cggccgcacc gctcgccgcc      540
ctgctggcgc ccttcgatcc gaccaccacc accgaatcgg tcaccgcaca actcaattcg      600
acgaccgatg accgcgtgac ggtgatgaag ctgcgcgagg acgatctggg tcaggtgcgc      660
gatcagctcg cgcagatccc cggcgtgacc gtgcgtgagc agggtgagct gctcaccgcc      720

```
gaccggcagc tgtcctcgcc cgccatcagc ggcctggacg agctgtggca cgaccggatc    780
accgccaacg cgggctggtc ggtgtacctg gtcgacgccg acggtgcacc cgcacaacag    840
ctcacgtcca cgccgcccaa ggacaccggg cccgtgcgca ccacgctgga cctgcgcatg    900
caactgctcg cgcagcaggc cgtggccaag gagacccgcc cggccgtggt ggtcgcgatc    960
tccggatcga ccgggggcat cctggccgcc gcacagaacc cggccgccga tccgcaaggt   1020
gcgatcgcgt tttcgggcct gtacccgccg gggtcgacgt tcaagaccat caccacggcg   1080
gcagccctcg acgcgggcct ggccaccccg gacacaccgg tggcctgccc gggtgagctc   1140
accatcgaga accgcacgat ccccaacgac gacaacttcg acctgggcac cgtgccgttg   1200
tcgtcggcgt tctcgcactc ctgcaacacc agcatggccg ccctgtccga cgagctgccg   1260
cccaacgcac tgaccgacat ggcaaaggac ttcgggatcg cgtcgacttc atggtgccc    1320
ggcctgacca ccgtgaccgg ccgtgtcccc aacgccgaca cgccgccca gcgtgtcgag   1380
aacggcatcg ccagggcac cgtgaccgtc agcccgttcg cctcgccgt cgccgaggcc   1440
agcctggcgc acggttcgac gatcctgccg acgctggtcg acggcgagaa gaccacggcc   1500
gacaccccgt cggtgccgtt gccgcccaac atcaccgacg cgctgcgcgc gatgatgcgc   1560
ggaacggtca ccgagggcac ggccaccgcg ttgagcgaca tccccgacct gggcggcaag   1620
accggcacgg cggaattcgg cgacaacacg cactcgcacg gctggttcgc gggcatcgcg   1680
ggcgacatcg cgttcgcgac gctggtggtc ggcggcgact cgtcggcacc ggccgtcgcg   1740
atctcaggag acttcctgcg ccccgcgctc gccggctag                          1779
```

<210> SEQ ID NO 9
<211> LENGTH: 592
<212> TYPE: PRT
<213> ORGANISM: Mycobacterium smegmatis

<400> SEQUENCE: 9

```
Met His Leu Arg Pro Ala Leu Thr Trp Leu Leu Val Val Gly Leu Phe
1               5                   10                  15

Ile Ser Val Val Gly Cys Ser Ser Ser Pro Asp Pro Ala Asp Arg Phe
            20                  25                  30

Ser Ala Phe Ala Glu Ala Leu Gly Arg Lys Asp Ala Ala Ala Ala
        35                  40                  45

Ala Gln Thr Ser Asp Pro Ala Ala Glu Ala Ala Ile Thr Ala Met
    50                  55                  60

Leu Ala Gly Met Gly Asp Ala Ala Asn Val Ser Val Ala Ala Glu Pro
65                  70                  75                  80

Glu Glu Gly Asp Asp Ala Gly Ala Thr Leu Lys Tyr Thr Trp Thr Trp
                85                  90                  95

Gly Glu Gly Arg Asp Phe Gly Tyr Asp Thr Thr Ala Thr Ala Ala Lys
            100                 105                 110

Ser Gly Asp Asp Trp Leu Ile Thr Trp Ser Pro Thr Val Leu His Arg
        115                 120                 125

Asp Leu Thr Pro Asp Leu Arg Phe Gln Tyr Ser Glu Asp Ser Glu Leu
    130                 135                 140

Gln Thr Pro Val Leu Asp Arg Thr Gly Gln Pro Leu Met Thr Trp Gln
145                 150                 155                 160

Thr Val Gly Val Ile Thr Val Glu Arg Ala His Pro Glu Ser Ala Ala
                165                 170                 175

Pro Leu Ala Ala Leu Leu Ala Pro Phe Asp Pro Thr Thr Thr Thr Glu
```

```
            180                 185                 190
Ser Val Thr Ala Gln Leu Asn Ser Thr Thr Asp Asp Arg Val Thr Val
            195                 200                 205
Met Lys Leu Arg Glu Asp Asp Leu Gly Gln Val Arg Asp Gln Leu Ala
            210                 215                 220
Gln Ile Pro Gly Val Thr Val Arg Glu Gln Gly Glu Leu Leu Thr Ala
225                 230                 235                 240
Asp Arg Gln Leu Ser Ser Pro Ala Ile Ser Gly Leu Asp Glu Leu Trp
                245                 250                 255
His Asp Arg Ile Thr Ala Asn Ala Gly Trp Ser Val Tyr Leu Val Asp
                260                 265                 270
Ala Asp Gly Ala Pro Ala Gln Gln Leu Thr Ser Thr Pro Lys Asp
            275                 280                 285
Thr Gly Pro Val Arg Thr Leu Asp Leu Arg Met Gln Leu Leu Ala
            290                 295                 300
Gln Gln Ala Val Ala Lys Glu Thr Arg Pro Ala Val Val Ala Ile
305                 310                 315                 320
Ser Gly Ser Thr Gly Gly Ile Leu Ala Ala Gln Asn Pro Ala Ala
                325                 330                 335
Asp Pro Gln Gly Ala Ile Ala Phe Ser Gly Leu Tyr Pro Pro Gly Ser
                340                 345                 350
Thr Phe Lys Thr Ile Thr Thr Ala Ala Ala Leu Asp Ala Gly Leu Ala
                355                 360                 365
Thr Pro Asp Thr Pro Val Ala Cys Pro Gly Glu Leu Thr Ile Glu Asn
            370                 375                 380
Arg Thr Ile Pro Asn Asp Asp Asn Phe Asp Leu Gly Thr Val Pro Leu
385                 390                 395                 400
Ser Ser Ala Phe Ser His Ser Cys Asn Thr Ser Met Ala Ala Leu Ser
                405                 410                 415
Asp Glu Leu Pro Pro Asn Ala Leu Thr Asp Met Ala Lys Asp Phe Gly
                420                 425                 430
Ile Gly Val Asp Phe Met Val Pro Gly Leu Thr Thr Val Thr Gly Arg
                435                 440                 445
Val Pro Asn Ala Asp Asn Ala Ala Gln Arg Val Glu Asn Gly Ile Gly
            450                 455                 460
Gln Gly Thr Val Thr Val Ser Pro Phe Gly Leu Ala Val Ala Glu Ala
465                 470                 475                 480
Ser Leu Ala His Gly Ser Thr Ile Leu Pro Thr Leu Val Asp Gly Glu
                485                 490                 495
Lys Thr Thr Ala Asp Thr Pro Ser Val Pro Leu Pro Asn Ile Thr
            500                 505                 510
Asp Ala Leu Arg Ala Met Met Arg Gly Thr Val Thr Glu Gly Thr Ala
            515                 520                 525
Thr Ala Leu Ser Asp Ile Pro Asp Leu Gly Gly Lys Thr Gly Thr Ala
            530                 535                 540
Glu Phe Gly Asp Asn Thr His Ser His Gly Trp Phe Ala Gly Ile Ala
545                 550                 555                 560
Gly Asp Ile Ala Phe Ala Thr Leu Val Val Gly Gly Asp Ser Ser Ala
                565                 570                 575
Pro Ala Val Ala Ile Ser Gly Asp Phe Leu Arg Pro Ala Leu Ala Gly
            580                 585                 590

<210> SEQ ID NO 10
```

```
<211> LENGTH: 592
<212> TYPE: PRT
<213> ORGANISM: Artificial Sequence
<220> FEATURE:
<223> OTHER INFORMATION: penicillin binding protein

<400> SEQUENCE: 10

Met His Leu Arg Pro Ala Leu Thr Trp Leu Leu Val Val Gly Leu Phe
1               5                   10                  15

Ile Ser Val Val Gly Cys Ser Ser Ser Pro Asp Pro Ala Asp Arg Phe
            20                  25                  30

Ser Ala Phe Ala Glu Ala Leu Gly Arg Lys Asp Ala Ala Ala Ala Ala
        35                  40                  45

Ala Gln Thr Ser Asp Pro Ala Ala Glu Ala Ala Ile Thr Ala Met
    50                  55                  60

Leu Ala Gly Met Gly Asp Ala Ala Asn Val Ser Val Ala Ala Glu Pro
65                  70                  75                  80

Glu Glu Gly Asp Asp Ala Gly Ala Thr Leu Lys Tyr Thr Trp Thr Trp
                85                  90                  95

Gly Glu Gly Arg Asp Phe Gly Tyr Asp Thr Thr Ala Thr Ala Ala Lys
            100                 105                 110

Ser Gly Asp Asp Trp Leu Ile Thr Trp Ser Pro Thr Val Leu His Arg
        115                 120                 125

Asp Leu Thr Pro Asp Leu Arg Phe Gln Tyr Ser Glu Asp Ser Glu Leu
130                 135                 140

Gln Thr Pro Val Leu Asp Arg Thr Gly Gln Pro Leu Met Thr Trp Gln
145                 150                 155                 160

Thr Val Gly Val Ile Thr Val Glu Arg Ala His Pro Glu Ser Ala Ala
                165                 170                 175

Pro Leu Ala Ala Leu Leu Ala Pro Phe Asp Pro Thr Thr Thr Thr Glu
            180                 185                 190

Ser Val Thr Ala Gln Leu Asn Ser Thr Thr Asp Asp Arg Val Thr Val
        195                 200                 205

Met Lys Leu Arg Glu Asp Asp Leu Gly Gln Val Arg Asp Gln Leu Ala
210                 215                 220

Gln Ile Pro Gly Val Thr Val Arg Glu Gln Gly Glu Leu Leu Thr Ala
225                 230                 235                 240

Asp Arg Gln Leu Ser Ser Pro Ala Ile Ser Gly Leu Asp Glu Leu Trp
                245                 250                 255

His Asp Arg Ile Thr Ala Asn Ala Gly Trp Ser Val Tyr Leu Val Asp
            260                 265                 270

Ala Asp Gly Ala Pro Ala Gln Gln Leu Thr Ser Thr Pro Pro Lys Asp
        275                 280                 285

Thr Gly Pro Val Arg Thr Thr Leu Asp Leu Arg Met Gln Leu Leu Ala
290                 295                 300

Gln Gln Ala Val Ala Lys Glu Thr Arg Pro Ala Val Val Val Ala Ile
305                 310                 315                 320

Ser Gly Ser Thr Gly Gly Ile Leu Ala Ala Ala Gln Asn Pro Ala Ala
                325                 330                 335

Asp Pro Gln Gly Ala Ile Ala Phe Ser Gly Leu Tyr Pro Pro Gly Ser
            340                 345                 350

Thr Phe Lys Thr Ile Thr Thr Ala Ala Ala Leu Asp Ala Gly Leu Ala
        355                 360                 365

Thr Pro Asp Thr Pro Val Ala Cys Pro Gly Glu Leu Thr Ile Glu Asn
370                 375                 380
```

```
Arg Thr Ile Pro Asn Asp Asp Asn Phe Asp Leu Gly Thr Val Pro Leu
385                 390                 395                 400

Ser Ser Ala Phe Ser His Ser Cys Asn Thr Ser Met Ala Ala Leu Ser
            405                 410                 415

Asp Glu Leu Pro Pro Asn Ala Leu Thr Asp Met Ala Lys Asp Phe Gly
        420                 425                 430

Ile Gly Val Asp Phe Met Val Pro Gly Leu Thr Thr Val Thr Gly Arg
            435                 440                 445

Val Pro Asn Ala Asp Asn Ala Ala Gln Arg Val Glu Asn Gly Ile Gly
        450                 455                 460

Gln Gly Thr Val Thr Val Ser Pro Phe Gly Leu Ala Val Ala Glu Ala
465                 470                 475                 480

Ser Leu Ala His Gly Ser Thr Ile Leu Pro Thr Leu Val Asp Gly Glu
                485                 490                 495

Lys Thr Thr Ala Asp Thr Pro Ser Val Pro Leu Pro Pro Asn Ile Thr
            500                 505                 510

Asp Ala Leu Arg Ala Met Met Arg Gly Thr Val Thr Glu Gly Thr Ala
        515                 520                 525

Thr Ala Leu Ser Asp Ile Pro Asp Leu Gly Gly Lys Thr Gly Thr Ala
    530                 535                 540

Glu Phe Gly Asp Asn Thr His Ser His Gly Trp Phe Ala Gly Ile Ala
545                 550                 555                 560

Gly Asp Ile Ala Phe Ala Thr Leu Val Val Gly Asp Ser Ser Ala
                565                 570                 575

Pro Ala Val Ala Ile Ser Gly Asp Phe Leu Arg Pro Ala Leu Ala Gly
            580                 585                 590

<210> SEQ ID NO 11
<211> LENGTH: 43
<212> TYPE: DNA
<213> ORGANISM: Artificial Sequence
<220> FEATURE:
<223> OTHER INFORMATION: primer

<400> SEQUENCE: 11
atgggtaccc gacgaattct gtccttcggt gattccctga cct                43

<210> SEQ ID NO 12
<211> LENGTH: 51
<212> TYPE: DNA
<213> ORGANISM: Artificial Sequence
<220> FEATURE:
<223> OTHER INFORMATION: primer

<400> SEQUENCE: 12
gattccgtcg acgccgtcgg tgctgatcac cgaacccgcg tcgaagaacg g          51

<210> SEQ ID NO 13
<211> LENGTH: 4189
<212> TYPE: DNA
<213> ORGANISM: Artificial Sequence
<220> FEATURE:
<223> OTHER INFORMATION: pMSATNcoI plasmid

<400> SEQUENCE: 13
agcgcccaat acgcaaaccg cctctccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
```

-continued

```
ttgtgagcgg ataacaattt cacacaggaa acagctatga ccatgattac gccaagctat    240
ttaggtgaca ctatagaata ctcaagctat gcatcaagct tggtaccgag ctcggatcca    300
ctagtaacgg ccgccagtgt gctggaattc gcccttctaa caggaggaat taaccatggc    360
caagcgaatt ctgtgtttcg gtgattccct gacctgggc tgggtccccg tcgaagacgg     420
ggcacccacc gagcggttcg cccccgacgt gcgctggacc ggtgtgctgg cccagcagct    480
cggagcggac ttcgaggtga tcgaggaggg actgagcgcg cgcaccacca acatcgacga    540
ccccaccgat ccgcggctca acggcgcgag ctacctgccg tcgtgcctcg cgacgcacct    600
gccgctcgac ctggtgatca tcatgctggg caccaacgac accaaggcct acttccggcg    660
caccccgctc gacatcgcgc tgggcatgtc ggtgctcgtc acgcaggtgc tcaccagcgc    720
gggcggcgtc ggcaccacgt acccggcacc caaggtgctg gtggtctcgc cgccaccgct    780
ggcgcccatg ccgcacccct ggttccagtt gatcttcgag ggcggcgagc agaagaccac    840
tgagctcgcc cgcgtgtaca gcgcgctcgc gtcgttcatg aaggtgccgt tcttcgacgc    900
gggttcggtg atcagcaccg acggcgtcga cggaatccac ttcaccgagg ccaacaatcg    960
cgatctcggg gtgccctcg cggaacaggt gcagagcctg ctgtaaaagg gcgaattctg    1020
cagatatcca tcacactggc ggccgctcga gcatgcatct agagggccca attcgcccta   1080
tagtgagtcg tattacaatt cactggccgt cgttttacaa cgtcgtgact gggaaaaccc   1140
tggcgttacc caacttaatc gccttgcagc acatccccct ttcgccagct ggcgtaatag   1200
cgaagaggcc cgcaccgatc gcccttccca acagttgcgc agcctatacg tacggcagtt   1260
taaggtttac acctataaaa gagagagccg ttatcgtctg tttgtggatg tacagagtga   1320
tattattgac acgccgggc gacggatggt gatcccctg gccagtgcac gtctgctgtc     1380
agataaagtc tcccgtgaac tttacccggt ggtgcatatc ggggatgaaa gctggcgcat   1440
gatgaccacc gatatggcca gtgtgccggt ctccgttatc ggggaagaag tggctgatct   1500
cagccaccgc gaaaatgaca tcaaaaacgc cattaacctg atgttctggg aatataaat    1560
gtcaggcatg agattatcaa aaaggatctt cacctagatc cttttcacgt agaaagccag   1620
tccgcagaaa cggtgctgac cccggatgaa tgtcagctac tgggctatct ggacaaggga   1680
aaacgcaagc gcaaagagaa agcaggtagc ttgcagtggg cttacatggc gatagctaga   1740
ctgggcggtt ttatgacag caagcgaacc ggaattgcca gctggggcgc cctctggtaa     1800
ggttgggaag ccctgcaaag taaactggat ggctttctcg ccgccaagga tctgatggcg   1860
caggggatca agctctgatc aagagacagg atgaggatcg tttcgcatga ttgaacaaga   1920
tggattgcac gcaggttctc cggccgcttg ggtggagagg ctattcggct atgactgggc   1980
acaacagaca atcggctgct ctgatgccgc cgtgttccgg ctgtcagcgc aggggcgccc   2040
ggttcttttt gtcaagaccg acctgtccgg tgccctgaat gaactgcaag acgaggcagc   2100
gcggctatcg tggctggcca cgacgggcgt tccttgcgca gctgtgctcg acgttgtcac   2160
tgaagcggga agggactggc tgctattggg cgaagtgccg gggcaggatc tcctgtcatc   2220
tcaccttgct cctgccgaga aagtatccat catggctgat gcaatgcggc ggctgcatac   2280
gcttgatccg gctacctgcc cattcgacca ccaagcgaaa catcgcatcg agcgagcacg   2340
tactcggatg gaagccggtc ttgtcgatca ggatgatctg gacgaagagc atcaggggct   2400
cgcgccagcc gaactgttcg ccaggctcaa ggcgagcatg cccgacggcg aggatctcgt   2460
cgtgacccat ggcgatgcct gcttgccgaa tatcatggtg gaaaatggcc gcttttctgg   2520
```

```
attcatcgac tgtggccggc tgggtgtggc ggaccgctat caggacatag cgttggctac    2580
ccgtgatatt gctgaagagc ttggcggcga atgggctgac cgcttcctcg tgctttacgg    2640
tatcgccgct cccgattcgc agcgcatcgc cttctatcgc cttcttgacg agttcttctg    2700
aattattaac gcttacaatt tcctgatgcg gtattttctc cttacgcatc tgtgcggtat    2760
ttcacaccgc atacaggtgg cacttttcgg ggaaatgtgc gcggaacccc tatttgttta    2820
tttttctaaa tacattcaaa tatgtatccg ctcatgagac aataaccctg ataaatgctt    2880
caataatagc acgtgaggag ggccaccatg gccaagttga ccagtgccgt tccggtgctc    2940
accgcgcgcg acgtcgccgg agcggtcgag ttctggaccg accggctcgg gttctcccgg    3000
gacttcgtgg aggacgactt cgccggtgtg gtccgggacg acgtgaccct gttcatcagc    3060
gcggtccagg accaggtggt gccggacaac accctggcct gggtgtgggt gcgcggcctg    3120
gacgagctgt acgccgagtg gtcggaggtc gtgtccacga acttccggga cgcctccggg    3180
ccggccatga ccgagatcgg cgagcagccg tggggcgggg agttcgccct gcgcgacccg    3240
gccggcaact gcgtgcactt cgtggccgag gagcaggact gacacgtgct aaaacttcat    3300
ttttaattta aaaggatcta ggtgaagatc ctttttgata atctcatgac caaaatccct    3360
taacgtgagt tttcgttcca ctgagcgtca gaccccgtag aaaagatcaa aggatcttct    3420
tgagatcctt ttttctgcg cgtaatctgc tgcttgcaaa caaaaaaacc accgctacca    3480
gcggtggttt gtttgccgga tcaagagcta ccaactcttt ttccgaaggt aactggcttc    3540
agcagagcgc agataccaaa tactgtcctt ctagtgtagc cgtagttagg ccaccacttc    3600
aagaactctg tagcaccgcc tacatacctc gctctgctaa tcctgttacc agtggctgct    3660
gccagtggcg ataagtcgtg tcttaccggg ttggactcaa gacgatagtt accggataag    3720
gcgcagcggt cgggctgaac ggggggttcg tgcacacagc ccagcttgga gcgaacgacc    3780
tacaccgaac tgagatacct acagcgtgag ctatgagaaa gcgccacgct tcccgaaggg    3840
agaaaggcgg acaggtatcc ggtaagcggc agggtcggaa caggagagcg cacgagggag    3900
cttccagggg gaaacgcctg gtatctttat agtcctgtcg ggtttcgcca cctctgactt    3960
gagcgtcgat ttttgtgatg ctcgtcaggg gggcggagcc tatggaaaaa cgccagcaac    4020
gcggcctttt tacggttcct ggcttttgc tggccttttg ctcacatgtt ctttcctgcg    4080
ttatcccctg attctgtgga taaccgtatt accgcctttg agtgagctga taccgctcgc    4140
cgcagccgaa cgaccgagcg cagcgagtca gtgagcgagg aagcggaag               4189
```

<210> SEQ ID NO 14
<211> LENGTH: 226
<212> TYPE: PRT
<213> ORGANISM: Agrobacterium rhizogenes

<400> SEQUENCE: 14

```
Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80
```

```
Ala Ser His Leu Pro Leu Asp Leu Val Ile Ile Leu Leu Gly Thr Asn
            85                  90                  95
Asp Thr Lys Ser Tyr Phe Arg Arg Thr Pro Tyr Glu Ile Ala Asn Gly
            100                 105                 110
Met Gly Lys Leu Ala Gly Gln Val Leu Thr Ser Ala Gly Gly Ile Gly
            115                 120                 125
Thr Pro Tyr Pro Ala Pro Lys Leu Leu Ile Val Ser Pro Pro Leu
            130                 135                 140
Ala Pro Met Pro Asp Pro Trp Phe Glu Gly Met Phe Gly Gly Gly Tyr
145                 150                 155                 160
Glu Lys Ser Leu Glu Leu Ala Lys Gln Tyr Lys Ala Leu Ala Asn Phe
            165                 170                 175
Leu Lys Val Asp Phe Leu Asp Ala Gly Glu Phe Val Lys Thr Asp Gly
            180                 185                 190
Cys Asp Gly Ile His Phe Ser Ala Glu Thr Asn Ile Thr Leu Gly His
            195                 200                 205
Ala Ile Ala Ala Lys Val Glu Ala Ile Phe Ser Gln Glu Ala Lys Asn
            210                 215                 220
Ala Ala
225

<210> SEQ ID NO 15
<211> LENGTH: 226
<212> TYPE: PRT
<213> ORGANISM: Rhizobium rhizogenes

<400> SEQUENCE: 15

Met Ala Glu Ser Arg Ser Ile Leu Cys Phe Gly Asp Ser Leu Thr Trp
1               5                   10                  15
Gly Trp Ile Pro Val Pro Glu Ser Ser Pro Thr Leu Arg Tyr Pro Phe
            20                  25                  30
Glu Gln Arg Trp Thr Gly Ala Met Ala Ala Leu Gly Asp Gly Tyr
            35                  40                  45
Ser Ile Ile Glu Glu Gly Leu Ser Ala Arg Thr Thr Ser Val Glu Asp
        50                  55                  60
Pro Asn Asp Pro Arg Leu Asn Gly Ser Ala Tyr Leu Pro Met Ala Leu
65                  70                  75                  80
Ala Ser His Leu Pro Leu Asp Leu Val Ile Ile Leu Leu Gly Thr Asn
            85                  90                  95
Asp Thr Lys Ser Tyr Phe Arg Arg Thr Pro Tyr Glu Ile Ala Asn Gly
            100                 105                 110
Met Gly Lys Leu Ala Gly Gln Val Leu Thr Ser Ala Gly Gly Ile Gly
            115                 120                 125
Thr Pro Tyr Pro Ala Pro Lys Leu Leu Ile Val Ser Pro Pro Leu
            130                 135                 140
Ala Pro Met Pro Asp Pro Trp Phe Glu Gly Met Phe Gly Gly Gly Tyr
145                 150                 155                 160
Glu Lys Ser Leu Glu Leu Ala Lys Gln Tyr Lys Ala Leu Ala Asn Phe
            165                 170                 175
Leu Lys Val Asp Phe Leu Asp Ala Gly Glu Phe Val Lys Thr Asp Gly
            180                 185                 190
Cys Asp Gly Ile His Phe Ser Ala Glu Thr Asn Ile Thr Leu Gly His
            195                 200                 205
Ala Ile Ala Ala Lys Val Glu Ala Ile Phe Ser Gln Glu Ala Lys Asn
            210                 215                 220
```

Ala Ala
225

<210> SEQ ID NO 16
<211> LENGTH: 229
<212> TYPE: PRT
<213> ORGANISM: Sinorhizobium meliloti

<400> SEQUENCE: 16

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Ala Pro Pro Leu Ala Pro Met Pro Asp
145                 150                 155                 160

Pro Trp Phe Glu Gly Met Phe Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225

<210> SEQ ID NO 17
<211> LENGTH: 218
<212> TYPE: PRT
<213> ORGANISM: Sinorhizobium meliloti

<400> SEQUENCE: 17

Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

```
Ala Ser His Leu Pro Leu Asp Leu Val Ile Ile Met Leu Gly Thr Asn
            85                  90                  95

Asp Thr Lys Ser Tyr Phe His Arg Thr Pro Tyr Glu Ile Ala Asn Gly
            100                 105                 110

Met Gly Lys Leu Val Gly Gln Val Leu Thr Cys Ala Gly Gly Val Gly
            115                 120                 125

Thr Pro Tyr Pro Ala Pro Lys Val Leu Val Ala Pro Pro Leu
    130                 135                 140

Ala Pro Met Pro Asp Pro Trp Phe Glu Gly Met Phe Gly Gly Tyr
145                 150                 155                 160

Glu Lys Ser Lys Glu Leu Ser Gly Leu Tyr Lys Ala Leu Ala Asp Phe
            165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
            195                 200                 205

Ala Ile Ala Asp Lys Val Ala Ala Leu Phe
    210                 215

<210> SEQ ID NO 18
<211> LENGTH: 216
<212> TYPE: PRT
<213> ORGANISM: Mycobacterium smegmatis

<400> SEQUENCE: 18

Met Ala Lys Arg Ile Leu Cys Phe Gly Asp Ser Leu Thr Trp Gly Trp
1               5                   10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
            35                  40                  45

Ile Glu Glu Gly Leu Ser Ala Arg Thr Thr Asn Ile Asp Asp Pro Thr
        50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Ile Met Leu Gly Thr Asn Asp Thr
            85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
            115                 120                 125

Tyr Pro Ala Pro Lys Val Leu Val Val Ser Pro Pro Leu Ala Pro
    130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
            165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
            195                 200                 205

Ala Glu Gln Val Arg Ser Leu Leu
    210                 215
```

```
<210> SEQ ID NO 19
<211> LENGTH: 194
<212> TYPE: PRT
<213> ORGANISM: Mycobacterium parafortuitum

<400> SEQUENCE: 19

Gly Thr Arg Arg Ile Leu Ser Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Ala Glu Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Thr Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
        115                 120                 125

Tyr Pro Ala Pro Gln Val Leu Ile Val Ala Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile

<210> SEQ ID NO 20
<211> LENGTH: 216
<212> TYPE: PRT
<213> ORGANISM: Prosthecobacter dejongeii

<400> SEQUENCE: 20

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140
```

```
Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
            165                 170                 175

Glu Tyr Phe Asn Ser Gln Glu Ile Val Glu Thr Ser Pro Val Asp Gly
        180                 185                 190

Ile His Leu Glu Ala Ser Glu His Leu Lys Leu Gly Glu Ala Leu Ala
    195                 200                 205

Glu Lys Val Lys Val Leu Leu Gly
    210                 215

<210> SEQ ID NO 21
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 21
acggtcctgt gctttggnga ytcnyt                                      26

<210> SEQ ID NO 22
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t

<400> SEQUENCE: 22
acggtcctgt gctttggnga yagyyt                                      26

<210> SEQ ID NO 23
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 23
gcggtcctgt tctwnggnga ytcnyt                                      26

<210> SEQ ID NO 24
<211> LENGTH: 26
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 24
gcggtcctgt tctwnggnga yagyyt                                        26

<210> SEQ ID NO 25
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 25
gctcgaaccg tcctctgttt tggngaytcn yt                                 32

<210> SEQ ID NO 26
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t

<400> SEQUENCE: 26
gctcgaaccg tcctctgttt tggngayagy yt                                 32

<210> SEQ ID NO 27
<211> LENGTH: 29
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 27
gctcgaaccg tcctctgttt nggngaytc                                     29

<210> SEQ ID NO 28
<211> LENGTH: 33
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 28
gctcgaaccg tcctctgttt tggngaytcn ytn                33

<210> SEQ ID NO 29
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 29
gctcgaaccg tcctctgttt tggngaytcn ytg                33

<210> SEQ ID NO 30
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 30
gccaagcgaa ttctgtgttt cggngaytcn yt                 32

<210> SEQ ID NO 31
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t

<400> SEQUENCE: 31
gccaagcgaa ttctgtgttt cggngayagy yt                 32

<210> SEQ ID NO 32
<211> LENGTH: 26
<212> TYPE: DNA
<213> ORGANISM: Artificial Sequence
```

```
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 32
attccgcgct tcagrtcrtt nvtncc                                              26

<210> SEQ ID NO 33
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 33
attccgcgct tcagrtcrtt nwgncc                                              26

<210> SEQ ID NO 34
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 34
attccgcgct tcagrtcrtt nscncc                                              26

<210> SEQ ID NO 35
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 35
attccgcgct tcagrtcrtt nrancc                                              26

<210> SEQ ID NO 36
<211> LENGTH: 26
<212> TYPE: DNA
```

```
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 36
attccgcgct tcagrtcrtt nrtncc                                        26

<210> SEQ ID NO 37
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 37
attccgcgct tcagrtcrtt nytncc                                        26

<210> SEQ ID NO 38
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 38
attccgcgct tcagrtcrtt nsgncc                                        26

<210> SEQ ID NO 39
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 39
attccgcgct tcagrtcrtt nwcncc                                        26

<210> SEQ ID NO 40
<211> LENGTH: 26
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 40
attccgcgct tcagrtcrtt nyancc                                          26

<210> SEQ ID NO 41
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 41
attccgcgct tgrsrtcrtt nrtncc                                          26

<210> SEQ ID NO 42
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 42
attccgcgct tgrsrtcrtt nytncc                                          26

<210> SEQ ID NO 43
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 43
attccgcgct tgrsrtcrtt nsgncc                                          26

<210> SEQ ID NO 44
```

```
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(26)
<223> OTHER INFORMATION: n is a, c, g, or t

<400> SEQUENCE: 44
attccgcgct tgrsrtcrtt nwcnnn                                    26

<210> SEQ ID NO 45
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 45
attccgcgct tgrsrtcrtt nyancc                                    26

<210> SEQ ID NO 46
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 46
gcgccggaag taggccttgg trtcrttnvt ncc                            33

<210> SEQ ID NO 47
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 47
gcgccggaag taggccttgg trtcrttnwg ncc                            33
```

```
<210> SEQ ID NO 48
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 48
gcgccggaag taggccttgg trtcrttnsc ncc                                    33

<210> SEQ ID NO 49
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 49
gcgccggaag taggccttgg trtcrttnra ncc                                    33

<210> SEQ ID NO 50
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 50
cggaattatc atgctgggna bnaayga                                           27

<210> SEQ ID NO 51
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 51
cggaattatc atgctgggnc wnaayga                                           27
```

```
<210> SEQ ID NO 52
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 52
cggaattatc atgctgggng snaayga                                              27

<210> SEQ ID NO 53
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 53
cggaattatc atgctgggnt ynaayga                                              27

<210> SEQ ID NO 54
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 54
ccggaattat catgctnggn abnaayga                                             28

<210> SEQ ID NO 55
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
```

```
<220> FEATURE:
<221> NAME/KEY: misc_feature
<222> LOCATION: (23)..(23)
<223> OTHER INFORMATION: n is a, c, g, or t

<400> SEQUENCE: 55
ccggaattat catgctnggn cwnaayga                                              28

<210> SEQ ID NO 56
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 56
ccggaattat catgctnggn gsnaayga                                              28

<210> SEQ ID NO 57
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 57
ccggaattat catgctnggn tynaayga                                              28

<210> SEQ ID NO 58
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 58
acccttagcg tttggrtgnr tnccrtc                                               27

<210> SEQ ID NO 59
```

```
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 59
atccttagcg tttggrtgna vnccrtc                                           27

<210> SEQ ID NO 60
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 60
aatcttagcc gtgrrrtgnr tnccrtc                                           27

<210> SEQ ID NO 61
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 61
aatcttagcc gtgrrrtgnr cnccrtc                                           27

<210> SEQ ID NO 62
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 62
aatcttagcc gtgrrrtgnt rnccrtc                                           27
```

```
<210> SEQ ID NO 63
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 63
ccgctggtcc tcatctggrt gnrtnccrtc                                    30

<210> SEQ ID NO 64
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 64
ccgctggtcc tcatctggrt gnrcnccrtc                                    30

<210> SEQ ID NO 65
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 65
ccgctggtcc tcatctggrt gntrnccrtc                                    30

<210> SEQ ID NO 66
<211> LENGTH: 27
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 66
ccgctggtcc tcatcraart gnrtncc                                       27
```

<210> SEQ ID NO 67
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 67
cgattgttcg cctcgtgtga artgnrtncc rtc                              33

<210> SEQ ID NO 68
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 68
cgattgttcg cctcgtgtga artgnrcncc rtc                              33

<210> SEQ ID NO 69
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 69
cgattgttcg cctcgtgtga artgntrncc rtc                              33

<210> SEQ ID NO 70
<211> LENGTH: 603
<212> TYPE: DNA
<213> ORGANISM: Artificial Sequence
<220> FEATURE:
<223> OTHER INFORMATION: S248_M2bB11 clone

<400> SEQUENCE: 70
atgttcgcgc tttgcacggc cgcgtcagcg gcccccgatc gcaccgtcgt ctttttlggg    60 gacagcctga ccgcggggta cggcctcgat gacccgcaga cccagtccta cccggccagg   120
atccaggaga aggtcgacgc cgcgggcctg cgctggaagg tcgtgaatgc cggcctctcg   180
ggcgagacga gcgccggcgg cctgcggcgg gtcgactggg tgctcggcca gcacatcgac   240
gcctttgtcc tggcgcttgg cgccaacgat ggcctgcggg ggatcgaccc ccaggtcacg   300

```
agggccaatc tccaggagat catcaaccgg gtccgctccc ggtggcccccg cgcggcgatc    360 gtcatcgccg ggatgaaaat gccccagagc atgggacagg actacgccgc gaattttgac    420
cggatcttcc ccggtctcgc cgcgaggaat tcggccacgc tcatcccctt tctattagaa    480
ggggtcgccg cccatcctag cctcaaccaa ggcgacggca tccacccgac ggccgccggg    540
gacgcactcg ttgcagggac cgtgtggacg tacctgcttc cgatcctgcg gtcagcacac    600
taa                                                                  603
```

```
<210> SEQ ID NO 71
<211> LENGTH: 200
<212> TYPE: PRT
<213> ORGANISM: Artificial Sequence
<220> FEATURE:
<223> OTHER INFORMATION: S248_M2bB11 clone

<400> SEQUENCE: 71
```

Met Phe Ala Leu Cys Thr Ala Ala Ser Ala Ala Pro Asp Arg Thr Val
1               5                   10                  15

Val Phe Phe Gly Asp Ser Leu Thr Ala Gly Tyr Gly Leu Asp Asp Pro
            20                  25                  30

Gln Thr Gln Ser Tyr Pro Ala Arg Ile Gln Glu Lys Val Asp Ala Ala
        35                  40                  45

Gly Leu Arg Trp Lys Val Val Asn Ala Gly Leu Ser Gly Glu Thr Ser
    50                  55                  60

Ala Gly Gly Leu Arg Arg Val Asp Trp Val Leu Gly Gln His Ile Asp
65                  70                  75                  80

Ala Phe Val Leu Ala Leu Gly Ala Asn Asp Gly Leu Arg Gly Ile Asp
                85                  90                  95

Pro Gln Val Thr Arg Ala Asn Leu Gln Glu Ile Ile Asn Arg Val Arg
            100                 105                 110

Ser Arg Trp Pro Arg Ala Ala Ile Val Ile Ala Gly Met Lys Met Pro
        115                 120                 125

Gln Ser Met Gly Gln Asp Tyr Ala Ala Asn Phe Asp Arg Ile Phe Pro
    130                 135                 140

Gly Leu Ala Ala Arg Asn Ser Ala Thr Leu Ile Pro Phe Leu Leu Glu
145                 150                 155                 160

Gly Val Ala Ala His Pro Ser Leu Asn Gln Gly Asp Gly Ile His Pro
                165                 170                 175

Thr Ala Ala Gly Asp Ala Leu Val Ala Gly Thr Val Trp Thr Tyr Leu
            180                 185                 190

Leu Pro Ile Leu Arg Ser Ala His
        195                 200

```
<210> SEQ ID NO 72
<211> LENGTH: 626
<212> TYPE: PRT
<213> ORGANISM: Artificial Sequence
<220> FEATURE:
<223> OTHER INFORMATION: S248_M40cD4 clone

<400> SEQUENCE: 72
```

Ala Thr Gly Cys Gly Cys Thr Thr Gly Cys Thr Ala Ala Gly Cys
1               5                   10                  15

Thr Cys Ala Cys Thr Gly Cys Cys Gly Thr Cys Ala Thr Cys Thr Thr
            20                  25                  30

Thr Gly Cys Cys Cys Thr Gly Ala Thr Ala Gly Thr Cys Thr Thr Gly 35 40 45

Cys Ala Cys Ala Gly Cys Cys Cys Cys Cys Thr Thr Gly Cys Cys Gly
50 55 60

Cys Cys Gly Cys Cys Gly Cys Gly Cys Cys Gly Cys Cys Cys Ala Cys
65 70 75 80

Cys Gly Thr Gly Ala Thr Gly Gly Thr Gly Thr Thr Thr Gly Gly Cys
85 90 95

Gly Ala Cys Ala Gly Thr Cys Thr Gly Ala Cys Cys Gly Cys Cys Gly
100 105 110

Gly Gly Thr Thr Gly Gly Gly Ala Thr Thr Gly Cys Cys Gly Gly Cys
115 120 125

Cys Gly Ala Thr Gly Cys Thr Gly Cys Ala Thr Thr Thr Cys Cys Gly
130 135 140

Gly Cys Gly Cys Ala Gly Cys Thr Cys Cys Ala Gly Gly Cys Ala Ala
145 150 155 160

Ala Gly Cys Thr Gly Cys Ala Cys Gly Ala Thr Ala Thr Gly Gly Gly
165 170 175

Thr Ala Thr Cys Cys Thr Gly Cys Ala Gly Ala Ala Ala Thr Cys Gly
180 185 190

Cys Cys Gly Cys Gly Cys Gly Cys Gly Cys Cys Ala Cys Cys Thr Cys
195 200 205

Gly Gly Gly Gly Cys Ala Ala Ala Cys Gly Ala Cys Gly Gly Cys Cys
210 215 220

Gly Gly Cys Gly Gly Gly Thr Thr Gly Gly Cys Gly Ala Gly Cys Cys
225 230 235 240

Thr Thr Gly Cys Gly Gly Ala Thr Gly Cys Gly Cys Thr Gly Gly Cys
245 250 255

Cys Gly Cys Ala Ala Ala Gly Cys Cys Gly Gly Ala Thr Thr Thr Gly
260 265 270

Gly Thr Gly Ala Thr Cys Cys Thr Cys Gly Ala Ala Cys Thr Cys Gly
275 280 285

Gly Cys Gly Cys Cys Ala Ala Thr Gly Ala Cys Ala Thr Gly Cys Thr
290 295 300

Gly Cys Gly Cys Gly Cys Gly Gly Thr Cys Gly Ala Thr Cys Cys Gly
305 310 315 320

Gly Cys Cys Ala Gly Cys Gly Thr Gly Cys Gly Cys Gly Cys Cys Ala
325 330 335

Ala Thr Cys Thr Cys Gly Ala Thr Gly Cys Ala Ala Thr Gly Ala Thr
340 345 350

Gly Ala Cys Gly Ala Ala Ala Ala Thr Cys Cys Ala Gly Gly Cys Gly
355 360 365

Ala Gly Cys Gly Gly Cys Gly Cys Thr Ala Ala Ala Cys Thr Gly Cys
370 375 380

Thr Gly Cys Thr Gly Ala Cys Cys Gly Gly Ala Ala Thr Gly Cys Ala
385 390 395 400

Gly Gly Cys Gly Gly Cys Gly Cys Cys Cys Ala Ala Thr Thr Gly Gly
405 410 415

Gly Gly Cys Gly Ala Gly Gly Ala Cys Thr Ala Thr Ala Ala Gly Cys
420 425 430

Ala Cys Gly Ala Thr Thr Thr Cys Gly Ala Cys Cys Gly Cys Cys Thr
435 440 445

Thr Thr Ala Thr Cys Cys Cys Gly Ala Gly Cys Thr Thr Gly Cys Gly
450 455 460

```
Ala Ala Gly Gly Cys Gly Cys Ala Cys Gly Gly Gly Thr Gly Ala
465                 470                 475                 480

Cys Gly Cys Thr Thr Thr Ala Thr Cys Cys Ala Thr Thr Cys Thr
                485                 490                 495

Thr Cys Thr Thr Gly Ala Thr Gly Gly Gly Thr Gly Gly Cys Gly
            500                 505                 510

Cys Thr Gly Gly Ala Cys Cys Gly Cys Gly Cys Thr Gly Ala
        515                 520                 525

Ala Cys Cys Ala Gly Gly Cys Gly Gly Ala Thr Gly Ala Ala Thr
530                 535                 540

Gly Cys Ala Cys Cys Gly Ala Ala Cys Gly Cys Ala Ala Gly
545                 550                 555                 560

Gly Gly Gly Gly Thr Cys Gly Cys Gly Thr Gly Ala Thr Cys Gly
                565                 570                 575

Thr Cys Gly Ala Cys Cys Gly Thr Ala Thr Cys Gly Cys Cys
            580                 585                 590

Cys Gly Thr Cys Gly Thr Cys Gly Cys Ala Ala Gly Ala Thr Gly
        595                 600                 605

Cys Thr Gly Ala Gly Ala Gly Gly Cys Cys Ala Gly Thr Cys Ala
            610                 615                 620

Ala Ala
625

<210> SEQ ID NO 73
<211> LENGTH: 208
<212> TYPE: PRT
<213> ORGANISM: Artificial Sequence
<220> FEATURE:
<223> OTHER INFORMATION: S248_M40cD4 clone

<400> SEQUENCE: 73

Met Arg Phe Ala Lys Leu Thr Ala Val Ile Phe Ala Leu Ile Val Leu
1               5                   10                  15

His Ser Pro Leu Ala Ala Ala Pro Pro Thr Val Met Val Phe Gly
                20                  25                  30

Asp Ser Leu Thr Ala Gly Leu Gly Leu Pro Ala Asp Ala Ala Phe Pro
            35                  40                  45

Ala Gln Leu Gln Ala Lys Leu His Asp Met Gly Ile Pro Ala Glu Ile
        50                  55                  60

Ala Ala Arg Ala Thr Ser Gly Gln Thr Thr Ala Gly Gly Leu Ala Ser
65                  70                  75                  80

Leu Ala Asp Ala Leu Ala Ala Lys Pro Asp Leu Val Ile Leu Glu Leu
                85                  90                  95

Gly Ala Asn Asp Met Leu Arg Ala Val Asp Pro Ala Ser Val Arg Ala
            100                 105                 110

Asn Leu Asp Ala Met Met Thr Lys Ile Gln Ala Ser Gly Ala Lys Leu
        115                 120                 125

Leu Leu Thr Gly Met Gln Ala Ala Pro Asn Trp Gly Glu Asp Tyr Lys
130                 135                 140

His Asp Phe Asp Arg Leu Tyr Pro Glu Leu Ala Lys Ala His Gly Val
145                 150                 155                 160

Thr Leu Tyr Pro Phe Phe Leu Asp Gly Val Ala Leu Asp Pro Ala Leu
                165                 170                 175

Asn Gln Ala Asp Gly Met His Pro Asn Ala Lys Gly Val Ala Val Ile
            180                 185                 190
```

Val Asp Arg Ile Ala Pro Val Val Ala Lys Met Leu Arg Gly Gln Ser
         195                 200                 205

<210> SEQ ID NO 74
<211> LENGTH: 705
<212> TYPE: DNA
<213> ORGANISM: Artificial Sequence
<220> FEATURE:
<223> OTHER INFORMATION: S248_M44aA5 clone

<400> SEQUENCE: 74

```
atgatcgcat ggcttaccgg atgcggcagc gcaaagacgc aaccgcagcc cgcaagttcc    60
atcccgccat ccagtattcc agcaaccgca aaacctgcga caacggatat cagaccgatc   120
atcgttgctt tcggcgacag cctgactgca ggatacggcg tcagtagtga acaaagctat   180
ccggccaatc ttcaacgcga tctggatgcg cgtggatatc atgccacgt catcaacgaa    240
ggcatcagcg gcaacacatc gaaagacggc gttctcaggg cccaggcgat tgcggcactc   300
catccggctg tcgtcatcgt tgccttcggc ggcaacgacg tctgcgtgg cctcccatc    360
ggagacacgg aaatgaatct ggcaacgatc atctcaacca tgcagcatgc ccatgccaag   420
gtaattttag gcggaattac tttgcctccc aactatggca gaatacat cgccaaattc     480
aatgcgatct ataaaaagca ggcagccgcg tatcatgtgc ccctgctgcc cttcatgctg   540
aagggggtgt atggcgtgcc cggttccatg cagagcgacg gcatccatcc gaccgccaag   600
ggctgccagc aagtggccag aaacttcctg cccttgttat tgccgctcct gcacaaatca   660
gggaagaaat ccatggagtc gaaagcattg tctcgacgtc attaa                   705
```

<210> SEQ ID NO 75
<211> LENGTH: 234
<212> TYPE: PRT
<213> ORGANISM: Artificial Sequence
<220> FEATURE:
<223> OTHER INFORMATION: S248_M44aA5 clone

<400> SEQUENCE: 75

Met Ile Ala Trp Leu Thr Gly Cys Gly Ser Ala Lys Thr Gln Pro Gln
1               5                   10                  15

Pro Ala Ser Ser Ile Pro Pro Ser Ser Ile Pro Ala Thr Ala Lys Pro
            20                  25                  30

Ala Thr Thr Asp Ile Arg Pro Ile Ile Val Ala Phe Gly Asp Ser Leu
        35                  40                  45

Thr Ala Gly Tyr Gly Val Ser Ser Glu Gln Ser Tyr Pro Ala Asn Leu
    50                  55                  60

Gln Arg Asp Leu Asp Ala Arg Gly Tyr His Ala His Val Ile Asn Glu
65                  70                  75                  80

Gly Ile Ser Gly Asn Thr Ser Lys Asp Gly Val Leu Arg Ala Gln Ala
                85                  90                  95

Ile Ala Ala Leu His Pro Ala Val Val Ile Val Ala Phe Gly Gly Asn
            100                 105                 110

Asp Gly Leu Arg Gly Leu Pro Ile Gly Asp Thr Glu Met Asn Leu Ala
        115                 120                 125

Thr Ile Ile Ser Thr Met Gln His Ala His Ala Lys Val Ile Leu Gly
    130                 135                 140

Gly Ile Thr Leu Pro Pro Asn Tyr Gly Ser Glu Tyr Ile Ala Lys Phe
145                 150                 155                 160

Asn Ala Ile Tyr Lys Lys Gln Ala Ala Ala Tyr His Val Pro Leu Leu

```
                165                 170                 175
Pro Phe Met Leu Lys Gly Val Tyr Gly Val Pro Gly Ser Met Gln Ser
            180                 185                 190

Asp Gly Ile His Pro Thr Ala Lys Gly Cys Gln Gln Val Ala Arg Asn
            195                 200                 205

Phe Leu Pro Leu Leu Pro Leu Leu His Lys Ser Gly Lys Lys Ser
            210                 215                 220

Met Glu Ser Lys Ala Leu Ser Arg Arg His
225                 230

<210> SEQ ID NO 76
<211> LENGTH: 639
<212> TYPE: DNA
<213> ORGANISM: Artificial Sequence
<220> FEATURE:
<223> OTHER INFORMATION: S261_M2aA12 clone

<400> SEQUENCE: 76
atgaaaaaca tccttgcatt tggcgacagt ctgacctggg gttttgtggc cggacaggat      60
gcgcgccatc cgtttgaaac ccgctggcca aacgcattgg cggccggcct tgggggcaaa     120
gcccgcgtaa ttgaagaggg tcagaacggc cgcactacgg tgttcgacga tgccgccacc     180
ttcgaatctc gaaatggctc ggtggcattg ccgctgctac tgatcagcca ccagccgttg     240
gacctggtaa tcatcatgct cggcaccaat gacatcaagt ttgccgcccg ctgccgcgcc     300
tttgatgctt caatgggcat ggaacggctg atccagatcg tcagaagtgc caactacatg     360
aagggctaca gataccctga atcctcatc atatcgccgc ccagcctcgt gccgacgcag      420
gatgaatggt tcaacgacct ctggggccat gccatcgccg agtcaaaact cttcgccaag     480
cactacaagc gcgtggccga gaactgaaa gtgcatttct ttgatgcagg cacggtggcc      540
gtcgccgaca gaccgacgg cggacatctc gatgctgtga atactaaagc cattggcgtc      600
gcattggtgc cggtggtgaa atcaatactc gctctctaa                            639

<210> SEQ ID NO 77
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 77

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
            35                  40                  45

Asn Gly Arg Thr Thr Val Phe Asp Asp Ala Ala Thr Phe Glu Ser Arg
            50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
            85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
            115                 120                 125
```

Leu Ile Ile Ser Pro Pro Ser Leu Val Pro Thr Gln Asp Glu Trp Phe
        130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
                180                 185                 190

Val Asn Thr Lys Ala Ile Gly Val Ala Leu Val Pro Val Val Lys Ser
                195                 200                 205

Ile Leu Ala Leu
        210

<210> SEQ ID NO 78
<211> LENGTH: 546
<212> TYPE: DNA
<213> ORGANISM: Artificial Sequence
<220> FEATURE:
<223> OTHER INFORMATION: S279_M70aE8 clone

<400> SEQUENCE: 78
atgccgaaaa tagccaaact cgcgccgtcg gatgtgatcg tagctttcgg cgacagtctg      60
acgttcggca ccggcgcaac ggaagcggag agttatccca tcgtgctcgc acaattgatc     120
ggtcgcaccg tggtgcgcgc gggtgtgccg ggtgaggtaa ccgaaggcgg gcttgcgcgc     180
ctgaccgacg ttatcgaaga acacaagccg aagctgatta ttgtttgcct gggcggcaac     240
gacatgctgc gcaaggtcca ggaagaccag acccgcgcca atttgcgcgc cattattaaa     300
accatcaagg cgcaaggcat cgccgtggta ctggtcggtg tgccgaagcc cgcgctggtg     360
accagtgcgc gccgttctac gaggagatc gccaaagagt tcggtatccc ttacgaaggc     420
aagattgtta ccgacgtgtt gtaccaacgc gatcagaaat ccgattccat acatcccaat     480
gccaaaggct atcggcgcat ggccgaagcg atagccacgc tgctgaaaaa atccggagcc     540
atttaa                                                                546

<210> SEQ ID NO 79
<211> LENGTH: 181
<212> TYPE: PRT
<213> ORGANISM: Artificial Sequence
<220> FEATURE:
<223> OTHER INFORMATION: S279_M70aE8 clone

<400> SEQUENCE: 79

Met Pro Lys Ile Ala Lys Leu Ala Pro Ser Asp Val Ile Val Ala Phe
1               5                   10                  15

Gly Asp Ser Leu Thr Phe Gly Thr Gly Ala Thr Glu Ala Glu Ser Tyr
                20                  25                  30

Pro Ile Val Leu Ala Gln Leu Ile Gly Arg Thr Val Val Arg Ala Gly
            35                  40                  45

Val Pro Gly Glu Val Thr Glu Gly Gly Leu Ala Arg Leu Thr Asp Val
        50                  55                  60

Ile Glu Glu His Lys Pro Lys Leu Ile Ile Val Cys Leu Gly Gly Asn
65                  70                  75                  80

Asp Met Leu Arg Lys Val Gln Glu Asp Gln Thr Arg Ala Asn Leu Arg
                85                  90                  95

Ala Ile Ile Lys Thr Ile Lys Ala Gln Gly Ile Ala Val Val Leu Val
                100                 105                 110

```
Gly Val Pro Lys Pro Ala Leu Val Thr Ser Ala Pro Pro Phe Tyr Glu
        115                 120                 125

Glu Ile Ala Lys Glu Phe Gly Ile Pro Tyr Glu Gly Lys Ile Val Thr
    130                 135                 140

Asp Val Leu Tyr Gln Arg Asp Gln Lys Ser Asp Ser Ile His Pro Asn
145                 150                 155                 160

Ala Lys Gly Tyr Arg Arg Met Ala Glu Ala Ile Ala Thr Leu Leu Lys
                165                 170                 175

Lys Ser Gly Ala Ile
            180

<210> SEQ ID NO 80
<211> LENGTH: 1209
<212> TYPE: DNA
<213> ORGANISM: Artificial Sequence
<220> FEATURE:
<223> OTHER INFORMATION: S279_M75bA2 clone

<400> SEQUENCE: 80
atggaacgga ccggccgcgc tggcgatcgg tgtcggcgtg gggctggcga gcctgagccc      60
ggtcgcgctg gcgacgccgc cgcggggcac cgtgccggtg ttcacccgat cggggacagc     120
ctgacggacg agtattttga gccgttcttc cagtgggggt tctgcgggaa gtcgtgggcc     180
gagattttgg tggagacggg gcgggcgagc atgggcccga cggcgcagca ggcggggatc     240
agcgagccgg agggatggtc ggatccgcgg aacacggggt atcagcacaa ctgggcgcgg     300
tactcgtgga gctcctcaga cgcgctgacc gaggagtcgc cggggcgac gctgagcgtg      360
ctgcttgggg cggagtacgc ggtggtgttc attgggacca acgacttcaa tccgtcgtgg     420
ccggcgtatc agagcgtgta tctgagccag tggagcgacg agcagatcga cacgtacgtg     480
aacggggtgg tgcagaacat cgcgcagatg gtggactcgc tgaagtcggt cggggcgaag     540
gtggtgcttg cgccgccggt ggattttcag ttcgcggggt cctgcggaa ctcatgcccg      600
gatccgatgc tgcgcgagca ggcgggtatt ctgacacgga agtgccacga ccgggtgcgg     660
tcgatggcgc ggcagaagca cgtggtgttc gtggacatgt ggcggctgaa ccgcgatttg     720
ttcggcaacg ggttcgcgat cagctacggc cttcggaaca cggtgcgcgt ggggactcg      780
gagatcgggc tgcaactggc cgggctgacg ggatcggcgg ggctggttcc ggacgggatc     840
catccgcagc gggtggtgca ggggatctgg gcgaatgcgt tcatcgtggg tctgaacgcg     900
catggggcga acatcgcgcc catcggcgag gcggagatgt gcgcgatggg ggggtcgtg     960
tacgggggaa cggacacgct ggcgaacttc ctgccgccgg tcgcgggcta cgtggaggac    1020
ttccgcaacg cggggacttt cgtgtgcacg gcggacttca accatgacct tggcgtgacg    1080
ccgacggaca tcttcgcgtt catcaacgcg tggttcatga atgatccctc ggcgcggatg    1140
agcaacccgg agcacacgca gatcgaggac atcttcgtgt ttctgaatct gtggctggtg    1200
gggtgctaa                                                           1209

<210> SEQ ID NO 81
<211> LENGTH: 402
<212> TYPE: PRT
<213> ORGANISM: Artificial Sequence
<220> FEATURE:
<223> OTHER INFORMATION: S279_M75bA2 clone

<400> SEQUENCE: 81

Met Glu Arg Thr Gly Arg Ala Gly Asp Arg Cys Arg Arg Gly Ala Gly
```

```
              1               5              10              15
            Glu Pro Glu Pro Gly Arg Ala Gly Asp Ala Ala Gly His Arg Ala
                           20              25              30
            Gly Val His Pro Ile Gly Asp Ser Leu Thr Asp Glu Tyr Phe Glu Pro
                           35              40              45
            Phe Phe Gln Trp Gly Phe Cys Gly Lys Ser Trp Ala Glu Ile Leu Val
             50              55              60
            Glu Thr Gly Arg Ala Ser Met Gly Pro Thr Ala Gln Gln Ala Gly Ile
             65              70              75              80
            Ser Glu Pro Glu Gly Trp Ser Asp Pro Arg Asn Thr Gly Tyr Gln His
                           85              90              95
            Asn Trp Ala Arg Tyr Ser Trp Ser Ser Asp Ala Leu Thr Glu Glu
                          100             105             110
            Ser Pro Gly Ala Thr Leu Ser Val Leu Leu Gly Ala Glu Tyr Ala Val
                          115             120             125
            Val Phe Ile Gly Thr Asn Asp Phe Asn Pro Ser Trp Pro Ala Tyr Gln
                          130             135             140
            Ser Val Tyr Leu Ser Gln Trp Ser Asp Glu Gln Ile Asp Thr Tyr Val
            145             150             155             160
            Asn Gly Val Val Gln Asn Ile Ala Gln Met Val Asp Ser Leu Lys Ser
                          165             170             175
            Val Gly Ala Lys Val Val Leu Ala Pro Pro Val Asp Phe Gln Phe Ala
                          180             185             190
            Gly Phe Leu Arg Asn Ser Cys Pro Asp Pro Met Leu Arg Glu Gln Ala
                          195             200             205
            Gly Ile Leu Thr Arg Lys Cys His Asp Arg Val Arg Ser Met Ala Arg
                          210             215             220
            Gln Lys His Val Val Phe Val Asp Met Trp Arg Leu Asn Arg Asp Leu
            225             230             235             240
            Phe Gly Asn Gly Phe Ala Ile Ser Tyr Gly Leu Arg Asn Thr Val Arg
                          245             250             255
            Val Gly Asp Ser Glu Ile Gly Leu Gln Leu Ala Gly Leu Thr Gly Ser
                          260             265             270
            Ala Gly Leu Val Pro Asp Gly Ile His Pro Gln Arg Val Val Gln Gly
                          275             280             285
            Ile Trp Ala Asn Ala Phe Ile Val Gly Leu Asn Ala His Gly Ala Asn
                          290             295             300
            Ile Ala Pro Ile Gly Glu Ala Glu Met Cys Ala Met Gly Gly Val Val
            305             310             315             320
            Tyr Gly Gly Thr Asp Thr Leu Ala Asn Phe Leu Pro Pro Val Ala Gly
                          325             330             335
            Tyr Val Glu Asp Phe Arg Asn Ala Gly Asp Phe Val Cys Thr Ala Asp
                          340             345             350
            Phe Asn His Asp Leu Gly Val Thr Pro Thr Asp Ile Phe Ala Phe Ile
                          355             360             365
            Asn Ala Trp Phe Met Asn Asp Pro Ser Ala Arg Met Ser Asn Pro Glu
                          370             375             380
            His Thr Gln Ile Glu Asp Ile Phe Val Phe Leu Asn Leu Trp Leu Val
            385             390             395             400
            Gly Cys

<210> SEQ ID NO 82
<211> LENGTH: 648
```

```
<212> TYPE: DNA
<213> ORGANISM: Artificial Sequence
<220> FEATURE:
<223> OTHER INFORMATION: M091_M4aE11 clone

<400> SEQUENCE: 82
atgaagacca ttctcgccta tggcgacagc ctgacctatg ggccaaccc gatcccgggc      60
gggccgcggc atgcctatga ggatcgctgg cccacggcgc tggagcaggg gctgggcggc    120
aaggcgcggg tgattgccga ggggctgggt ggtcgcacca cggtgcatga cgactggttt    180
gcgaatgcgg acaggaacgg tgcgcgggtg ctgccgacgc tgctcgagag ccattcgccg    240
ctcgacctga tcgtcatcat gctcggcacc aacgacatca gcccgcatca cgggcggacg    300
gccggcgagg ccgggcgggg catggcgcgg ctggtgcaga tcatccgcgg cactatgcc    360
ggccgcatgc aggacgagcc gcagatcatc ctcgtgtcgc cgccgccgat catcctcggc    420
gactgggcgg acatgatgga ccatttcggc ccgcacgaag cgatcgccac ctcggtggat    480
ttcgctcgcg agtacaagaa gcgggccgac gagcagaagg tgcatttctt cgacgccggc    540
acggtggcga cgaccagcaa ggccgatggc atccacctcg acccggccaa tacgcgcgcc    600
atcggggcag gctggtgcc gctggtgaag caggtgctcg gcctgtaa                  648

<210> SEQ ID NO 83
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 83

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
        195                 200                 205

Val Lys Gln Val Leu Gly Leu
    210                 215
```

<210> SEQ ID NO 84
<211> LENGTH: 1830
<212> TYPE: DNA
<213> ORGANISM: Artificial Sequence
<220> FEATURE:
<223> OTHER INFORMATION: Est105 clone

<400> SEQUENCE: 84

| | | | | | | |
|---|---|---|---|---|---|---|
| atgcgcacgc | ttcaccgaag | cctgctcgca | agcgcggccg | cgcttttcct | agcggcatcc | 60 |
| ggcaacgcaa | cggcgcagtt | ctcgaacgtc | tatttcttcg | gcgacagcct | gaccgacgcg | 120 |
| ggttccttca | agcctgtgct | gcctcctggt | acaggattat | tcacgacgaa | tcccggcccg | 180 |
| gtatggccgc | aggtattcgg | ggcgaactac | ggcgtcgcgg | tgacgcccgc | aaaccagggt | 240 |
| gggaccgatt | atgcgcaggg | tggcgcgcgc | gtgacgagcc | tgcctggcgt | tccgacgtcg | 300 |
| cagccgaccg | gcagcgcggt | accgatcgct | acgcagattt | cgcagttcct | cggctcgggt | 360 |
| ccggcggatc | cgaacgcatt | ctattcggtg | tggggcggcg | cgaacgacat | cttttttccag | 420 |
| ctggggttgg | cgcaggcggg | catggcgacg | ccggcgcagg | tccagtcggc | cgtcggcttg | 480 |
| gccgcggtcc | agctggcgca | ggcaactgcg | gcgctcaacg | ccagcggcgc | gcgattcatc | 540 |
| acggttatca | acgtgccgga | catcggtaaa | acgccgttcg | gcgtcggctc | cggtcaagga | 600 |
| gcgcagatca | ccgctctgtc | gtctttcttc | aacagcacgc | tgttcggcgc | gctcgacgcc | 660 |
| acgggcatcc | agacgatgcg | cgtgaacggg | ttcgcggtgc | tgaacgaggt | ggtcgcggac | 720 |
| ccggcggctt | atggcttcgc | gaatgcatca | acgccagcgt | gcggggccac | gccatcgctc | 780 |
| gtctgcacgt | cggcgaactt | cgtcacgccc | ttggccgcgc | agaccttcct | cttcgcagac | 840 |
| ggcgttcacc | ccaccacggc | cgggcacgcc | ctcatcgccc | aagcggtcca | ggcgatgatc | 900 |
| accggtcccc | aacagatggc | ggcgttgggc | gacgccccgc | tcgccgtcga | gcaggccaac | 960 |
| ttccgcgcgc | tcgacaaccg | catgtggtcg | agcctcaatg | cgccgcgcag | cccgggcaag | 1020 |
| ctccagggtt | gggcggccta | cgactacagc | cacacggacc | tgcaggcggg | accgaccaat | 1080 |
| ggcagcggac | acatgaacac | cgttgcggtc | ggggtcgaca | tgaaagtctc | cgatcatatg | 1140 |
| ctcgccggcg | cgatgttcgg | ctataccaac | accaagggcg | acttcggcgg | ccccggcggc | 1200 |
| ggatacacac | tgaagcagcc | tgtgggcact | gcctatgcgg | gttacggcgt | gggcccttgg | 1260 |
| tatgtcggcg | cgacgctcgg | cacaggtggc | ctcgactact | cggacgtcac | gcgcgccatc | 1320 |
| ccgcttggct | tggcggttcg | caccgagagc | gccgaggccc | gaggctacga | gttcacgggc | 1380 |
| cggatcctcg | gcggctactg | gttcacgatg | cgcgacctga | tgcacgggcc | gtacgcgcgt | 1440 |
| ctcgcgtgga | cgaaggccgt | cgtcaagcgg | ttttccgagg | agagcaccga | cagcacggcg | 1500 |
| ttgaactacg | acaggcagga | gcgcaagcaa | ctgctgtgga | gcctcggatg | gcaactcgcc | 1560 |
| ggcaacgtcg | gcagcatccg | tccctacgcg | cgggcgacct | gggagatcga | ctccaaggat | 1620 |
| caggaccgca | gcgttggcgc | atcgtcggtc | acgctgggcg | gcttttacag | tgttccggtc | 1680 |
| gcgaagccgg | acaatagcta | tgcgctcttc | agcctcggcg | cgagtaccga | gctcgggagc | 1740 |
| gtcaccgggt | ttgtcgcggg | ctcggccacc | gcaggccggg | cggatgccaa | ctattgggcg | 1800 |
| gtcacggtcg | gcctgcggat | gccgttgtag | | | | 1830 |

<210> SEQ ID NO 85
<211> LENGTH: 609
<212> TYPE: PRT
<213> ORGANISM: Artificial Sequence

```
<220> FEATURE:
<223> OTHER INFORMATION: Est105 clone

<400> SEQUENCE: 85

Met Arg Thr Leu His Arg Ser Leu Leu Ala Ser Ala Ala Leu Phe
1               5                   10                  15

Leu Ala Ala Ser Gly Asn Ala Thr Ala Gln Phe Ser Asn Val Tyr Phe
            20                  25                  30

Phe Gly Asp Ser Leu Thr Asp Ala Gly Ser Phe Lys Pro Val Leu Pro
        35                  40                  45

Pro Gly Thr Gly Leu Phe Thr Thr Asn Pro Gly Pro Val Trp Pro Gln
    50                  55                  60

Val Phe Gly Ala Asn Tyr Gly Val Ala Val Thr Pro Ala Asn Gln Gly
65                  70                  75                  80

Gly Thr Asp Tyr Ala Gln Gly Gly Ala Arg Val Thr Ser Leu Pro Gly
                85                  90                  95

Val Pro Thr Ser Gln Pro Thr Gly Ser Ala Val Pro Ile Ala Thr Gln
            100                 105                 110

Ile Ser Gln Phe Leu Gly Ser Gly Pro Ala Asp Pro Asn Ala Phe Tyr
        115                 120                 125

Ser Val Trp Gly Gly Ala Asn Asp Ile Phe Phe Gln Leu Gly Leu Ala
    130                 135                 140

Gln Ala Gly Met Ala Thr Pro Ala Gln Val Gln Ser Ala Val Gly Leu
145                 150                 155                 160

Ala Ala Val Gln Leu Ala Gln Ala Thr Ala Ala Leu Asn Ala Ser Gly
                165                 170                 175

Ala Arg Phe Ile Thr Val Ile Asn Val Pro Asp Ile Gly Lys Thr Pro
            180                 185                 190

Phe Gly Val Gly Ser Gly Gln Gly Ala Gln Ile Thr Ala Leu Ser Ser
        195                 200                 205

Phe Phe Asn Ser Thr Leu Phe Gly Ala Leu Asp Ala Thr Gly Ile Gln
    210                 215                 220

Thr Met Arg Val Asn Gly Phe Ala Val Leu Asn Glu Val Val Ala Asp
225                 230                 235                 240

Pro Ala Ala Tyr Gly Phe Ala Asn Ala Ser Thr Pro Ala Cys Gly Ala
                245                 250                 255

Thr Pro Ser Leu Val Cys Thr Ser Ala Asn Phe Val Thr Pro Leu Ala
            260                 265                 270

Ala Gln Thr Phe Leu Phe Ala Asp Gly Val His Pro Thr Thr Ala Gly
        275                 280                 285

His Ala Leu Ile Ala Gln Ala Val Gln Ala Met Ile Thr Gly Pro Gln
    290                 295                 300

Gln Met Ala Ala Leu Gly Asp Ala Pro Leu Ala Val Glu Gln Ala Asn
305                 310                 315                 320

Phe Arg Ala Leu Asp Asn Arg Met Trp Ser Ser Leu Asn Ala Pro Arg
                325                 330                 335

Ser Pro Gly Lys Leu Gln Gly Trp Ala Ala Tyr Asp Tyr Ser His Thr
            340                 345                 350

Asp Leu Gln Ala Gly Pro Thr Asn Gly Ser Gly His Met Asn Thr Val
        355                 360                 365

Ala Val Gly Val Asp Met Lys Val Ser Asp His Met Leu Ala Gly Ala
    370                 375                 380

Met Phe Gly Tyr Thr Asn Thr Lys Gly Asp Phe Gly Gly Pro Gly Gly
385                 390                 395                 400
```

Gly Tyr Thr Leu Lys Gln Pro Val Gly Thr Ala Tyr Ala Gly Tyr Gly
            405                 410                 415

Val Gly Pro Trp Tyr Val Gly Ala Thr Leu Gly Thr Gly Gly Leu Asp
        420                 425                 430

Tyr Ser Asp Val Thr Arg Ala Ile Pro Leu Gly Leu Ala Val Arg Thr
    435                 440                 445

Glu Ser Ala Glu Ala Arg Gly Tyr Glu Phe Thr Gly Arg Ile Leu Gly
450                 455                 460

Gly Tyr Trp Phe Thr Met Arg Asp Leu Met His Gly Pro Tyr Ala Arg
465                 470                 475                 480

Leu Ala Trp Thr Lys Ala Val Val Lys Arg Phe Ser Glu Glu Ser Thr
            485                 490                 495

Asp Ser Thr Ala Leu Asn Tyr Asp Arg Gln Glu Arg Lys Gln Leu Leu
        500                 505                 510

Trp Ser Leu Gly Trp Gln Leu Ala Gly Asn Val Gly Ser Ile Arg Pro
    515                 520                 525

Tyr Ala Arg Ala Thr Trp Glu Ile Asp Ser Lys Asp Gln Asp Arg Ser
530                 535                 540

Val Gly Ala Ser Ser Val Thr Leu Gly Gly Phe Tyr Ser Val Pro Val
545                 550                 555                 560

Ala Lys Pro Asp Asn Ser Tyr Ala Leu Phe Ser Leu Gly Ala Ser Thr
            565                 570                 575

Glu Leu Gly Ser Val Thr Gly Phe Val Ala Gly Ser Ala Thr Ala Gly
        580                 585                 590

Arg Ala Asp Ala Asn Tyr Trp Ala Val Thr Val Gly Leu Arg Met Pro
    595                 600                 605

Leu

<210> SEQ ID NO 86
<211> LENGTH: 921
<212> TYPE: DNA
<213> ORGANISM: Artificial Sequence
<220> FEATURE:
<223> OTHER INFORMATION: Est114 clone

<400> SEQUENCE: 86
atggggcgat cgagagttct gaaggctgtt ttcctggtgg cgtgccttgt gggtcggctc        60
gcggcgcatg ccgaggcgtc gcccatcgtg gtctacggcg atagcctctc tgacaacggc       120
aatctgtttg cgctcaccgg cggtgtcgcg ccgccctcgc cgccgtactt caacggacgg       180
ttttctaatg gcccggtggc cgtggagtat ctcgcggccg cgctgggatc tccgctgatc       240
gatttcgcgg tcggcggggc gacgaccggc ctcggcgtca acggcgatcc cggtggttcg       300
ccgacgagtc tcggcgcggc gggattgccg gggcttcaga cgacattcgc cgccacgcaa       360
ggcacgctgg gtccgtacgt tggtggtctc ttcgtggtgt gggcgggtcc gaacgacttc       420
ttgtcgccct cgccgcttga cacgaacgct tttcagattg cgaaccgggc cgtgtccaac       480
atcctcggcg tggtggcatc acttcaggca ctcggcgtcg agcgcatcct cgtccccggc       540
atgcccgatc tcgtctgac gcccgctctt cagcccatcg caggcgcagc caccgcgttc       600
accgatttgt tcaactcgat gctgcgcgcg ggcttgccga cgacgtgct gtacctggac       660 acggcgacaa tcttccgatc gatcgtggca gaccctgggg cctacggctt gaccaacgtg       720
accacgccgt gcctgattgg tgcgaccgtc tgcgcgaatc cggatcagta cctgttctgg       780
gatggtattc atcctacgac ggcggggcac gcgatcttgg gcaatgccct cgtcgcccag       840

```
gcagtccccg agcccgcgac catggtgctc gtgctgacgg gtctgtccat gcacgtgatt    900
gcgcgccggc ggcgggcgta a                                              921
```

<210> SEQ ID NO 87
<211> LENGTH: 306
<212> TYPE: PRT
<213> ORGANISM: Artificial Sequence
<220> FEATURE:
<223> OTHER INFORMATION: Est114 clone

<400> SEQUENCE: 87

```
Met Gly Arg Ser Arg Val Leu Lys Ala Val Phe Leu Val Ala Cys Leu
1               5                   10                  15

Val Gly Arg Leu Ala Ala His Ala Glu Ala Ser Pro Ile Val Val Tyr
            20                  25                  30

Gly Asp Ser Leu Ser Asp Asn Gly Asn Leu Phe Ala Leu Thr Gly Gly
        35                  40                  45

Val Ala Pro Pro Ser Pro Pro Tyr Phe Asn Gly Arg Phe Ser Asn Gly
    50                  55                  60

Pro Val Ala Val Glu Tyr Leu Ala Ala Ala Leu Gly Ser Pro Leu Ile
65                  70                  75                  80

Asp Phe Ala Val Gly Gly Ala Thr Thr Gly Leu Gly Val Asn Gly Asp
                85                  90                  95

Pro Gly Gly Ser Pro Thr Ser Leu Gly Ala Ala Gly Leu Pro Gly Leu
            100                 105                 110

Gln Thr Thr Phe Ala Ala Thr Gln Gly Thr Leu Gly Pro Tyr Val Gly
        115                 120                 125

Gly Leu Phe Val Val Trp Ala Gly Pro Asn Asp Phe Leu Ser Pro Ser
    130                 135                 140

Pro Leu Asp Thr Asn Ala Phe Gln Ile Ala Asn Arg Ala Val Ser Asn
145                 150                 155                 160

Ile Leu Gly Val Val Ala Ser Leu Gln Ala Leu Gly Val Glu Arg Ile
                165                 170                 175

Leu Val Pro Gly Met Pro Asp Leu Gly Leu Thr Pro Ala Leu Gln Pro
            180                 185                 190

Ile Ala Gly Ala Ala Thr Ala Phe Thr Asp Leu Phe Asn Ser Met Leu
        195                 200                 205

Arg Ala Gly Leu Pro Asn Asp Val Leu Tyr Leu Asp Thr Ala Thr Ile
    210                 215                 220

Phe Arg Ser Ile Val Ala Asp Pro Gly Ala Tyr Gly Leu Thr Asn Val
225                 230                 235                 240

Thr Thr Pro Cys Leu Ile Gly Ala Thr Val Cys Ala Asn Pro Asp Gln
                245                 250                 255

Tyr Leu Phe Trp Asp Gly Ile His Pro Thr Thr Ala Gly His Ala Ile
            260                 265                 270

Leu Gly Asn Ala Leu Val Ala Gln Ala Val Pro Glu Pro Ala Thr Met
        275                 280                 285

Val Leu Val Leu Thr Gly Leu Ser Met His Val Ile Ala Arg Arg Arg
    290                 295                 300

Arg Ala
305
```

<210> SEQ ID NO 88
<211> LENGTH: 687
<212> TYPE: DNA

<213> ORGANISM: Sinorhizobium meliloti

<400> SEQUENCE: 88

```
atgacaatca acagccattc atggaggacg ttaatggtgg aaaagcgctc agtactgtgc      60
tttggggatt cgctgacatg gggctggatt ccggtgaagg gatcctcacc gaccttgcgc     120
tatccctatg aacaacggtg gaccggcgca atggccgcga ggcttggcga cggttaccac     180
atcatcgaag aggggctgag cgcccgcacc accagcctcg acgacccaa cgacgcgcgg      240
ctcaacggca gcacctacct gcccatggca ctcgccagcc acctcccact cgacctcgtc     300
atcatcatgc tgggcacgaa cgacacgaaa tcctatttcc accgcacgcc ttacgagatc     360
gccaacggca tgggcaagct agtcggccag gtgctgacct gcgccggtgg cgtcggcacg     420
ccatatcccg cgccgaaggt gcttgtcgtc gctccgccgc cgctcgcgcc gatgcccgac     480
ccgtggttcg aaggcatgtt cggcggcggc tacgagaagt cgaaggaact ctccggcctc     540
tacaaggcgc ttgccgattt catgaaggtc gagtttttcg ccgccggtga ttgcatttcc     600
accgatggga tcgacggcat tcacctctcg gcgaaaacca acatcagact cgggcacgcg     660
atcgcggaca aagttgcggc gttgttc                                          687
```

<210> SEQ ID NO 89
<211> LENGTH: 229
<212> TYPE: PRT
<213> ORGANISM: Sinorhizobium meliloti

<400> SEQUENCE: 89

```
Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Gly Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
```

<210> SEQ ID NO 90
<211> LENGTH: 663
<212> TYPE: DNA
<213> ORGANISM: Sinorhizobium meliloti

<400> SEQUENCE: 90

```
atggaggaga cagtggcacg gaccgttcta tgcttcggag attccaacac tcacggccag    60
gtacctggcc gcggaccgct tgatcgctac cgacgcgaac agcgctgggg cggtgttctg   120
caaggcctgc tcggcccgaa ctggcaggtt atcgaagaag gcctgagcgg acgcacgacc   180
gtgcatgacg atccgatcga aggttcgctc aagaacggcc ggacctatct cgcccctgt   240
ctgcagagcc atgcaccact cgaccttatc atcattatgc tcggcaccaa tgacctgaag   300
cggcgcttca acatgccacc gtccgaggtc gcaatgggca tcggctgtct cgtgcacgat   360
atccgagaac tctcgcccgg ccggaccggc aacgatcccg aaatcatgat cgtcgccccg   420
ccgccgatgc tggaagatct caaggaatgg gagtcgattt tctcaggcgc acaggaaaaa   480
tctcgcaagc tggcgctgga gttcgagata atggcggatt ctctggaggc gcatttcttc   540
gacgccggta cggtctgcca gtgttcgccg gccgatggct ccacatcga cgaggatgcc   600
accgcctgc tcggcgaggc tctcgcccag gaagtgctgg cgatcgggtg cccgatgcg   660
taa                                                                 663
```

<210> SEQ ID NO 91
<211> LENGTH: 220
<212> TYPE: PRT
<213> ORGANISM: Sinorhizobium meliloti

<400> SEQUENCE: 91

```
Met Glu Glu Thr Val Ala Arg Thr Val Leu Cys Phe Gly Asp Ser Asn
 1               5                  10                  15

Thr His Gly Gln Val Pro Gly Arg Gly Pro Leu Asp Arg Tyr Arg Arg
            20                  25                  30

Glu Gln Arg Trp Gly Gly Val Leu Gln Gly Leu Leu Gly Pro Asn Trp
        35                  40                  45

Gln Val Ile Glu Glu Gly Leu Ser Gly Arg Thr Thr Val His Asp Asp
    50                  55                  60

Pro Ile Glu Gly Ser Leu Lys Asn Gly Arg Thr Tyr Leu Arg Pro Cys
65                  70                  75                  80

Leu Gln Ser His Ala Pro Leu Asp Leu Ile Ile Ile Met Leu Gly Thr
                85                  90                  95

Asn Asp Leu Lys Arg Arg Phe Asn Met Pro Pro Ser Glu Val Ala Met
            100                 105                 110

Gly Ile Gly Cys Leu Val His Asp Ile Arg Glu Leu Ser Pro Gly Arg
        115                 120                 125

Thr Gly Asn Asp Pro Glu Ile Met Ile Val Ala Pro Pro Pro Met Leu
    130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
```

```
                195                 200                 205
Ala Gln Glu Val Leu Ala Ile Gly Trp Pro Asp Ala
    210                 215                 220

<210> SEQ ID NO 92
<211> LENGTH: 642
<212> TYPE: DNA
<213> ORGANISM: Sinorhizobium meliloti

<400> SEQUENCE: 92
atgaagacag tcctttgcta cggtgacagt ctgacctggg gatacgatgc aaccggttcc      60
ggccggcatg cgctggagga ccgttggccg agcgtgctgc agaaggcgct cggttcggac     120
gcgcatgtca tcgccgaagg gctgaacggg cggacgaccg cctatgacga ccatctcgcc     180
gattgcgacc ggaacggcgc gcgtgtcctc ccgacggtcc tgcacaccca cgcgccactc     240
gatctcatcg tgttcatgct cggctcgaac gacatgaagc cgatcattca cggcaccgct     300
ttcggcgcgg tgaagggcat cgagcgcctc gtcaatctgg tgcgcaggca cgactggccg     360
acggaaacgg aggaggggcc cgagattctc atcgtctcgc cgccgccgct ctgcgagacg     420
gccaacagcg cctttgccgc catgttcgcg ggcggggtcg agcaatccgc aatgctggcg     480
ccgctttatc gcgatctcgc cgacgagctc gactgcggct tcttcgacgg cggatcggtg     540
gccaggacga cgccgatcga cggtgtccac ctcgacgcgg agaacacccg ggcggtcggc     600
agagggttgg agcctgtcgt gcggatgatg ctcgggcttt aa                        642

<210> SEQ ID NO 93
<211> LENGTH: 213
<212> TYPE: PRT
<213> ORGANISM: Sinorhizobium meliloti

<400> SEQUENCE: 93

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
    50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Pro Leu Cys Glu Thr Ala Asn Ser Ala
    130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190
```

```
Ala Glu Asn Thr Arg Ala Val Gly Arg Gly Leu Glu Pro Val Val Arg
        195                 200                 205

Met Met Leu Gly Leu
    210
```

<210> SEQ ID NO 94
<211> LENGTH: 645
<212> TYPE: DNA
<213> ORGANISM: Agrobacterium tumefaciens

<400> SEQUENCE: 94

```
atggtgaagt cggtcctctg ctttggcgat tccctcacct ggggatcaaa tgcggaaacg      60
ggtggccggc acagccatga cgatctttgg ccgagcgtct tgcagaaggc gctcggtcct     120
gacgtgcatg tgattcacga aggtctgggt ggtcgcacca ccgcctatga cgacaacacc     180
gccgattgcg accgcaacgg cgcgcgggtt cttccgacgt tgttgcacag ccatgcgccg     240
ctggatctgg tgattgtcat gctcgggacc aacgacctga agccgtcaat ccatggatcg     300
gcgatcgttg ccatgaaggg tgtcgaaagg ctggtgaagc tcacgcgcaa ccacatctgg     360
caggtgccgg actgggaggc gcctgacgtg ctgatcgtcg caccgccgca gctgtgtgaa     420
acggccaatc cgttcatggg cgcgatcttt cgtgatgcga tcgatgaatc ggcgatgctg     480
gcgtccgttt accgggacct tgccgacgag cttgattgcg gcttttttcga tgcgggttcc     540 gtcgcccgaa cgacgccggt ggatggcgtt catctcgatg ctgaaaatac gcgggccatc     600 ggcgggggc tggagcccgt cgttcgcatg atgctcggac tttaa                      645
```

<210> SEQ ID NO 95
<211> LENGTH: 214
<212> TYPE: PRT
<213> ORGANISM: Agrobacterium tumefaciens

<400> SEQUENCE: 95

```
Met Val Lys Ser Val Leu Cys Phe Gly Asp Ser Leu Thr Trp Gly Ser
1               5                   10                  15

Asn Ala Glu Thr Gly Gly Arg His Ser His Asp Asp Leu Trp Pro Ser
            20                  25                  30

Val Leu Gln Lys Ala Leu Gly Pro Asp Val His Val Ile His Glu Gly
        35                  40                  45

Leu Gly Gly Arg Thr Thr Ala Tyr Asp Asp Asn Thr Ala Asp Cys Asp
    50                  55                  60

Arg Asn Gly Ala Arg Val Leu Pro Thr Leu Leu His Ser His Ala Pro
65                  70                  75                  80

Leu Asp Leu Val Ile Val Met Leu Gly Thr Asn Asp Leu Lys Pro Ser
                85                  90                  95

Ile His Gly Ser Ala Ile Val Ala Met Lys Gly Val Glu Arg Leu Val
            100                 105                 110

Lys Leu Thr Arg Asn His Ile Trp Gln Val Pro Asp Trp Glu Ala Pro
        115                 120                 125

Asp Val Leu Ile Val Ala Pro Pro Gln Leu Cys Glu Thr Ala Asn Pro
    130                 135                 140

Phe Met Gly Ala Ile Phe Arg Asp Ala Ile Asp Glu Ser Ala Met Leu
145                 150                 155                 160

Ala Ser Val Tyr Arg Asp Leu Ala Asp Glu Leu Asp Cys Gly Phe Phe
                165                 170                 175

Asp Ala Gly Ser Val Ala Arg Thr Thr Pro Val Asp Gly Val His Leu
            180                 185                 190
```

Asp Ala Glu Asn Thr Arg Ala Ile Gly Arg Gly Leu Glu Pro Val Val
            195                 200                 205

Arg Met Met Leu Gly Leu
    210

<210> SEQ ID NO 96
<211> LENGTH: 636
<212> TYPE: DNA
<213> ORGANISM: Mesorhizobium loti

<400> SEQUENCE: 96

```
atgaagacgg tgctttgcta cggcgactcg ctgacctggg gctacaatgc cgaaggcggc      60
cgccatgcgc tggaagaccg ctggccgagc gtgctgcaag cagcgttagg cgccggcgtg     120
caagtgattg ccgatggcct caacggccgc accacggcct cgacgatca tctgccggt      180
gctgatcgca acggcgccag ctgctgccg acggtcctga cgacgcacgc gccgatcgac     240
ctgatcatct tcatgctcgg cgccaacgac atgaagcctt ggatccacgg caatccggtc     300
gcagccaagc aaggcatcca gcggttgatc gacatcgtgc gtggtcacga ctacccgttc     360
gactggccgg cgccgcagat cctgatcgtc gcgccgcctg tagtcagccg caccgaaaat     420
gccgacttca aggaaatgtt cgccggtggc gatgacgcct cgaagttttt ggcaccgcaa     480
tatgccgcgc tcgccgacga agccggctgt ggcttcttcg acgccggcag cgtggcccaa     540
accacaccgc tcgatggcgt tcacctcgat gccgaaaaca cgcgagaaat cggcaaggcg     600
ctgacgccga tcgtgcgcgt catgctggaa ttgtaa                               636
```

<210> SEQ ID NO 97
<211> LENGTH: 211
<212> TYPE: PRT
<213> ORGANISM: Mesorhizobium loti

<400> SEQUENCE: 97

Met Lys Thr Val Leu Cys Tyr Gly Asp Ser Leu Thr Trp Gly Tyr Asn
1               5                   10                  15

Ala Glu Gly Gly Arg His Ala Leu Glu Asp Arg Trp Pro Ser Val Leu
            20                  25                  30

Gln Ala Ala Leu Gly Ala Gly Val Gln Val Ile Ala Asp Gly Leu Asn
        35                  40                  45

Gly Arg Thr Thr Ala Phe Asp Asp His Leu Ala Gly Ala Asp Arg Asn
    50                  55                  60

Gly Ala Arg Leu Leu Pro Thr Val Leu Thr Thr His Ala Pro Ile Asp
65                  70                  75                  80

Leu Ile Ile Phe Met Leu Gly Ala Asn Asp Met Lys Pro Trp Ile His
                85                  90                  95

Gly Asn Pro Val Ala Ala Lys Gln Gly Ile Gln Arg Leu Ile Asp Ile
            100                 105                 110

Val Arg Gly His Asp Tyr Pro Phe Asp Trp Pro Ala Pro Gln Ile Leu
        115                 120                 125

Ile Val Ala Pro Pro Val Val Ser Arg Thr Glu Asn Ala Asp Phe Lys
    130                 135                 140

Glu Met Phe Ala Gly Gly Asp Asp Ala Ser Lys Phe Leu Ala Pro Gln
145                 150                 155                 160

Tyr Ala Ala Leu Ala Asp Glu Ala Gly Cys Gly Phe Phe Asp Ala Gly
                165                 170                 175

Ser Val Ala Gln Thr Thr Pro Leu Asp Gly Val His Leu Asp Ala Glu 180                 185                 190
Asn Thr Arg Glu Ile Gly Lys Ala Leu Thr Pro Ile Val Arg Val Met
    195                 200                 205

Leu Glu Leu
    210

<210> SEQ ID NO 98
<211> LENGTH: 1851
<212> TYPE: DNA
<213> ORGANISM: Moraxella bovis

<400> SEQUENCE: 98

```
atgaaaaaat ccgcctttgc caaatactca gcacttgccc taatggttgg gatgtgcctg      60
cacaccgctt acgccaagga gtttagccaa gtcatcattt tggggacag cttgtccgat     120
acaggtcgcc taaagatat ggtcgcccga aagatggca cccttggcaa caccttacag     180
ccatctttta ccaccaaccc cgaccctgta tggtcaagct tatttgccca agttatggc     240
aaaaccgcca gtcccaacac gcctgacaat cccactggca ctaactatgc cgtgggcgga     300
gctcgctctg gctcggaggt caattggaat ggttttgtga atgtaccctc caccaaaacg     360
caaatcaccg accatttgac cgccacaggt ggcaaagccg accctaatac cctgtatgcc     420
atttggattg gctctaatga cttaatttca gcttctcaag ccaccacaac agccgaagcc     480
caaaacgcca ttaaaggtgc ggtaactcgc accgtgatag acatcgaaac actcaatcaa     540
gcagggcga caaccatttt ggtgccaaat gtgcctgatt tgagcctcac gccccgagcc     600
atctatggca aaagcctcat ggcaggcgtg caagacaaag ccaaactcgc ctcaagtctg     660
tataatagcg gtctgtttga agcattaaat caatccaccg ccaacatcat ccctgccaac     720
acctttgccc tactccaaga agcgaccaca aataaagaag cctttggttt taaaaacacg     780
caaggcgtgg cgtgtcaaat gcccgctcgt accacagggg cggatgatgt ggcttctact     840
tccttggcat gtaccaaagc caatcttata gaaaacgggg caaatgacac ctacgccttt     900
gccgatgaca ttcacccatc gggacgcacg caccgcattt tggcacagta ttaccgttct     960
atcatggacg cccctactca catgggtaaa ctctcaggcg agcttgtcaa aacaggttca    1020
gcccacgacc gtcatgttta ccgtcagctt gacaggctta gtggctcaca gcacagcatt    1080
tgggcaaacg tctatgccag cgaccgtacc gaccccacca cccaaatcgg cttgacgtg     1140
gcaggttcat caagccatac aggggcgtat ctgagccacc aaaaccaaga ttatgtgctg    1200
gatgacaccc tatcatcaga tgtcaaaacc attggcatgg ggctgtatca tcgccatgac    1260
atcggcaatg tccgtctaaa aggcgtggca ggtatcgacc gacttagcgt ggatacgcac    1320
cgccatatcg actgggaggg acaagccgt tcgcacaccg cagataccac cgccagacgt    1380
tttcatgcag ggctacaagc cagctatggc atagacatgg caaagccac cgtgcgtccg    1440
cttatcggcg tacatgccca aaagtcaaa gtaaatgaca tgaccgagag cgaatcaact    1500
ttatccaccg ccatgcgttt tggcgagcaa gaacaaaagt ccctacaagg cgagattggc    1560
gtcgatgtgg cttatccgat tagccctgct ttgactctga cgggcggtat cgctcacgct    1620
catgagttta cgatgatga acgcaccatt aatgccactt aacctccat tcgtgaatac    1680
acgaagggct ttaatacaag cgttagcacc gacaaatctc acgccaccac cgctcatctg    1740
ggcgtacaag gcaacttggg caaggcaaat attcatgcag gcgttcacgc cacccaccaa    1800
gacagcgata cagacgtggg tggttcgctt ggggttcgct tgatgttta a              1851
```

<210> SEQ ID NO 99
<211> LENGTH: 616
<212> TYPE: PRT
<213> ORGANISM: Moraxella bovis

<400> SEQUENCE: 99

```
Met Lys Lys Ser Ala Phe Ala Lys Tyr Ser Ala Leu Ala Leu Met Val
1               5                   10                  15

Gly Met Cys Leu His Thr Ala Tyr Ala Lys Glu Phe Ser Gln Val Ile
            20                  25                  30

Ile Phe Gly Asp Ser Leu Ser Asp Thr Gly Arg Leu Lys Asp Met Val
        35                  40                  45

Ala Arg Lys Asp Gly Thr Leu Gly Asn Thr Leu Gln Pro Ser Phe Thr
    50                  55                  60

Thr Asn Pro Asp Pro Val Trp Ser Ser Leu Phe Ala Gln Ser Tyr Gly
65                  70                  75                  80

Lys Thr Ala Ser Pro Asn Thr Pro Asp Asn Pro Thr Gly Thr Asn Tyr
                85                  90                  95

Ala Val Gly Gly Ala Arg Ser Gly Ser Glu Val Asn Trp Asn Gly Phe
            100                 105                 110

Val Asn Val Pro Ser Thr Lys Thr Gln Ile Thr Asp His Leu Thr Ala
        115                 120                 125

Thr Gly Gly Lys Ala Asp Pro Asn Thr Leu Tyr Ala Ile Trp Ile Gly
    130                 135                 140

Ser Asn Asp Leu Ile Ser Ala Ser Gln Ala Thr Thr Ala Glu Ala
145                 150                 155                 160

Gln Asn Ala Ile Lys Gly Ala Val Thr Arg Thr Val Ile Asp Ile Glu
                165                 170                 175

Thr Leu Asn Gln Ala Gly Ala Thr Thr Ile Leu Val Pro Asn Val Pro
            180                 185                 190

Asp Leu Ser Leu Thr Pro Arg Ala Ile Tyr Gly Glu Ser Leu Met Ala
        195                 200                 205

Gly Val Gln Asp Lys Ala Lys Leu Ala Ser Ser Leu Tyr Asn Ser Gly
    210                 215                 220

Leu Phe Glu Ala Leu Asn Gln Ser Thr Ala Asn Ile Ile Pro Ala Asn
225                 230                 235                 240

Thr Phe Ala Leu Leu Gln Glu Ala Thr Thr Asn Lys Glu Ala Phe Gly
                245                 250                 255

Phe Lys Asn Thr Gln Gly Val Ala Cys Gln Met Pro Ala Arg Thr Thr
            260                 265                 270

Gly Ala Asp Asp Val Ala Ser Thr Ser Leu Ala Cys Thr Lys Ala Asn
        275                 280                 285

Leu Ile Glu Asn Gly Ala Asn Asp Thr Tyr Ala Phe Ala Asp Asp Ile
    290                 295                 300

His Pro Ser Gly Arg Thr His Arg Ile Leu Ala Gln Tyr Tyr Arg Ser
305                 310                 315                 320

Ile Met Asp Ala Pro Thr His Met Gly Lys Leu Ser Gly Glu Leu Val
                325                 330                 335

Lys Thr Gly Ser Ala His Asp Arg His Val Tyr Arg Gln Leu Asp Arg
            340                 345                 350

Leu Ser Gly Ser Gln His Ser Ile Trp Ala Asn Val Tyr Ala Ser Asp
        355                 360                 365

Arg Thr Asp Pro Thr Thr Gln Ile Gly Leu Asp Val Ala Gly Ser Ser
    370                 375                 380
```

Ser His Thr Gly Ala Tyr Leu Ser His Gln Asn Gln Asp Tyr Val Leu
385                 390                 395                 400

Asp Asp Thr Leu Ser Ser Asp Val Lys Thr Ile Gly Met Gly Leu Tyr
            405                 410                 415

His Arg His Asp Ile Gly Asn Val Arg Leu Lys Gly Val Ala Gly Ile
        420                 425                 430

Asp Arg Leu Ser Val Asp Thr His Arg His Ile Asp Trp Glu Gly Thr
    435                 440                 445

Ser Arg Ser His Thr Ala Asp Thr Thr Ala Arg Arg Phe His Ala Gly
450                 455                 460

Leu Gln Ala Ser Tyr Gly Ile Asp Met Gly Lys Ala Thr Val Arg Pro
465                 470                 475                 480

Leu Ile Gly Val His Ala Gln Lys Val Lys Val Asn Asp Met Thr Glu
                485                 490                 495

Ser Glu Ser Thr Leu Ser Thr Ala Met Arg Phe Gly Glu Gln Glu Gln
            500                 505                 510

Lys Ser Leu Gln Gly Glu Ile Gly Val Asp Val Ala Tyr Pro Ile Ser
        515                 520                 525

Pro Ala Leu Thr Leu Thr Gly Gly Ile Ala His Ala His Glu Phe Asn
530                 535                 540

Asp Asp Glu Arg Thr Ile Asn Ala Thr Leu Thr Ser Ile Arg Glu Tyr
545                 550                 555                 560

Thr Lys Gly Phe Asn Thr Ser Val Ser Thr Asp Lys Ser His Ala Thr
                565                 570                 575

Thr Ala His Leu Gly Val Gln Gly Gln Leu Gly Lys Ala Asn Ile His
            580                 585                 590

Ala Gly Val His Ala Thr His Gln Asp Ser Asp Thr Asp Val Gly Gly
        595                 600                 605

Ser Leu Gly Val Arg Leu Met Phe
    610                 615

<210> SEQ ID NO 100
<211> LENGTH: 597
<212> TYPE: DNA
<213> ORGANISM: Chromobacterium violaceum

<400> SEQUENCE: 100
atgcgctcta tcgtctgcaa aatgctgttc cctttgttgc tgctgtggca gctgcccgcc      60
ctggccgcca ccgtgctggt gttcggcgac agcctgtccg ccggctacgg cctggccccg     120
ggccagggat gggcggcgct gctggcgcgc gacctctcgc cccggcacaa ggtggtcaac     180
gccagcgtgt ccggcgaaac cagcgccggc ggcctgtcca ggctgcccga cgcgctcgcc     240
cgccaccagc ccgacgtgct ggtgctggaa ctcggcgcca acgatggcct gcgcggcctg     300
ccgatggctg acatgaggcg caacctgcag cggatgatag acctggccca ggcgcgcaag     360
gccaaggtgc tgctggtggg catggcgctg ccacccaact atggccccg ctacggcgcc      420 gagttccgcg ccgtttatga cgatttggcc cgccgcaacc gcctggccta cgtgccgctg     480
ctggtcgagg gcttcgccgg cgacctcggc gccttccagc ccgacggcct gcatccccgc     540
gcggagaagc aggccaccat gatgcgcacg gtcaaggcaa aactgccagt gaaataa        597

<210> SEQ ID NO 101
<211> LENGTH: 198
<212> TYPE: PRT
<213> ORGANISM: Chromobacterium violaceum

<400> SEQUENCE: 101

Met Arg Ser Ile Val Cys Lys Met Leu Phe Pro Leu Leu Leu Leu Trp
1               5                   10                  15

Gln Leu Pro Ala Leu Ala Ala Thr Val Leu Val Phe Gly Asp Ser Leu
            20                  25                  30

Ser Ala Gly Tyr Gly Leu Ala Pro Gly Gln Gly Trp Ala Ala Leu Leu
        35                  40                  45

Ala Arg Asp Leu Ser Pro Arg His Lys Val Val Asn Ala Ser Val Ser
    50                  55                  60

Gly Glu Thr Ser Ala Gly Gly Leu Ser Arg Leu Pro Asp Ala Leu Ala
65                  70                  75                  80

Arg His Gln Pro Asp Val Leu Val Leu Glu Leu Gly Ala Asn Asp Gly
                85                  90                  95

Leu Arg Gly Leu Pro Met Ala Asp Met Arg Arg Asn Leu Gln Arg Met
            100                 105                 110

Ile Asp Leu Ala Gln Ala Arg Lys Ala Lys Val Leu Leu Val Gly Met
        115                 120                 125

Ala Leu Pro Pro Asn Tyr Gly Pro Arg Tyr Gly Ala Glu Phe Arg Ala
    130                 135                 140

Val Tyr Asp Asp Leu Ala Arg Arg Asn Arg Leu Ala Tyr Val Pro Leu
145                 150                 155                 160

Leu Val Glu Gly Phe Ala Gly Asp Leu Gly Ala Phe Gln Pro Asp Gly
                165                 170                 175

Leu His Pro Arg Ala Glu Lys Gln Ala Thr Met Met Arg Thr Val Lys
            180                 185                 190

Ala Lys Leu Pro Val Lys
        195

<210> SEQ ID NO 102
<211> LENGTH: 576
<212> TYPE: DNA
<213> ORGANISM: Vibrio vulnificus

<400> SEQUENCE: 102 atgttttttcc tttctagcgt cgcacacgca accgagaaag tgttaattct tggcgacagc    60
ctaagtgcag gatacaacat gtctgcagag caggcttggc ctaatttgtt accagaagca   120
ttgaatacat acggaaaaaa cgtagaagtg atcaacgcca gtatctctgg agacacaacc   180
ggcaatggac tatctcgtct gcctgagttg ttaaaaacgc actcaccaga ctgggtgctt   240
attgagttgg gtgccaatga tggcttgcga ggtttcccgc ataaagtgat ctcttcaaac   300
ctttcgcgaa tgattcaact cagtaaagcc tcagacgcta agtcgcatt gatgcaaatt   360 cgtgtaccgc ctaactatgg caagcgctac accgatgcat tgtcgaact ctaccctacg   420 cttgctgaac atcaccaagt cccgttgctc ccctttttct tagaggaagt gatcgtgaaa   480
ccggaatgga tgatgcctga tggcttacac ccaatgcccg aagctcagcc ttggatcgct   540
caatttgttg caaaaacgtt ttacaaacat ctctaa                             576

<210> SEQ ID NO 103
<211> LENGTH: 191
<212> TYPE: PRT
<213> ORGANISM: Vibrio vulnificus

<400> SEQUENCE: 103

Met Phe Phe Leu Ser Ser Val Ala His Ala Thr Glu Lys Val Leu Ile
1               5                   10                  15

Leu Gly Asp Ser Leu Ser Ala Gly Tyr Asn Met Ser Ala Glu Gln Ala
            20                  25                  30

Trp Pro Asn Leu Leu Pro Glu Ala Leu Asn Thr Tyr Gly Lys Asn Val
        35                  40                  45

Glu Val Ile Asn Ala Ser Ile Ser Gly Asp Thr Thr Gly Asn Gly Leu
 50                  55                  60

Ser Arg Leu Pro Glu Leu Leu Lys Thr His Ser Pro Asp Trp Val Leu
 65                  70                  75                  80

Ile Glu Leu Gly Ala Asn Asp Gly Leu Arg Gly Phe Pro His Lys Val
                85                  90                  95

Ile Ser Ser Asn Leu Ser Arg Met Ile Gln Leu Ser Lys Ala Ser Asp
            100                 105                 110

Ala Lys Val Ala Leu Met Gln Ile Arg Val Pro Pro Asn Tyr Gly Lys
        115                 120                 125

Arg Tyr Thr Asp Ala Phe Val Glu Leu Tyr Pro Thr Leu Ala Glu His
130                 135                 140

His Gln Val Pro Leu Leu Pro Phe Phe Leu Glu Glu Val Ile Val Lys
145                 150                 155                 160

Pro Glu Trp Met Met Pro Asp Gly Leu His Pro Met Pro Glu Ala Gln
                165                 170                 175

Pro Trp Ile Ala Gln Phe Val Ala Lys Thr Phe Tyr Lys His Leu
            180                 185                 190

<210> SEQ ID NO 104
<211> LENGTH: 693
<212> TYPE: DNA
<213> ORGANISM: Ralstonia eutropha

<400> SEQUENCE: 104

| | | |
|---|---|---|
| atgccattga ccgcgccgtc tgaagtcgat ccgctgcaaa tcctggtcta tgccgattcg | 60 |
| ctttcgtggg gcatcgtgcc cggcacccgc cggcggcttc ccttcccggt cgctggccca | 120 |
| ggccggctcg aactcggcct gaacgccgac ggcggcgccc cggtccgcat catcgaggac | 180 |
| tgcctgaacg gccggcgcac cgtctgggac gacccattca aaccgggccg caacggcttg | 240 |
| caagggctgg cgcagcgcat cgagatccat tccccggtgg cgctcgtggt tttgatgctg | 300 |
| ggcaacaacg atttccagtc catgcatccg cacaacgcct ggcatgcggc acagggcgtc | 360 |
| ggcgcgctgg tccacgccat ccggacggcg ccgatcgaac cgggaatgcc ggtgccgccg | 420 |
| atcctggtgg tggtgccgcc gccgatccgc acgccctgcg ggccgctcgc gcccaagttc | 480 |
| gccggcggcg aacacaagtg gcaggcctg cccgaggcgc tgcgcgaact gtgcgccact | 540 |
| gtcgactgct cgctgttcga tgcgggtacc gtgatccaga gcagtgccgt cgacggcgta | 600 |
| caccttgacg ccgatgccca tgtcgccctg ggcgatgccc tgcaaccggt cgttcgtgcg | 660 |
| ctgctcgccg aatcctcggg acatccctcc taa | 693 |

<210> SEQ ID NO 105
<211> LENGTH: 230
<212> TYPE: PRT
<213> ORGANISM: Ralstonia eutropha

<400> SEQUENCE: 105

Met Pro Leu Thr Ala Pro Ser Glu Val Asp Pro Leu Gln Ile Leu Val
1               5                   10                  15

Tyr Ala Asp Ser Leu Ser Trp Gly Ile Val Pro Gly Thr Arg Arg Arg
            20                  25                  30

Leu Pro Phe Pro Val Arg Trp Pro Gly Arg Leu Glu Leu Gly Leu Asn
            35                  40                  45

Ala Asp Gly Gly Ala Pro Val Arg Ile Ile Glu Asp Cys Leu Asn Gly
        50                  55                  60

Arg Arg Thr Val Trp Asp Asp Pro Phe Lys Pro Gly Arg Asn Gly Leu
65                  70                  75                  80

Gln Gly Leu Ala Gln Arg Ile Glu Ile His Ser Pro Val Ala Leu Val
                85                  90                  95

Val Leu Met Leu Gly Asn Asn Asp Phe Gln Ser Met His Pro His Asn
            100                 105                 110

Ala Trp His Ala Ala Gln Gly Val Gly Ala Leu Val His Ala Ile Arg
        115                 120                 125

Thr Ala Pro Ile Glu Pro Gly Met Pro Val Pro Ile Leu Val Val
130                 135                 140

Val Pro Pro Pro Ile Arg Thr Pro Cys Gly Pro Leu Ala Pro Lys Phe
145                 150                 155                 160

Ala Gly Gly Glu His Lys Trp Ala Gly Leu Pro Glu Ala Leu Arg Glu
                165                 170                 175

Leu Cys Ala Thr Val Asp Cys Ser Leu Phe Asp Ala Gly Thr Val Ile
            180                 185                 190

Gln Ser Ser Ala Val Asp Gly Val His Leu Asp Ala Asp Ala His Val
        195                 200                 205

Ala Leu Gly Asp Ala Leu Gln Pro Val Val Arg Ala Leu Leu Ala Glu
    210                 215                 220

Ser Ser Gly His Pro Ser
225                 230

<210> SEQ ID NO 106
<211> LENGTH: 1971
<212> TYPE: DNA
<213> ORGANISM: Salmonella typhimurium

<400> SEQUENCE: 106
atgacccaaa agcgtaccct gctaaaatac ggcatactct cgctggcgct ggccgcgcca      60
ttatctgcct gtgcgtttga ctctcttacg gtgattggcg atagccttag cgataccggt     120
aataacggtc gctggacctg ggatagtggt caaaataagc tctacgacga acagttggcc     180
gaacgatatg gcctggaatt aagcccttcc agcaatggcg gctctaatta tgccgccggc     240
ggcgcgacgg cgaccccgga attaaacccg caggataata ccgcggatca ggtacggcag     300
tggcttgcca aaacgggggg aaaagccgac cacaacggtt tgtatattca ctgggtcggc     360
ggaaacgatc tggcggcggc catcgcgcaa ccaaccatgg cacagcaaat agccggtaat     420
agcgccacta gcgcggcggc gcaggtaggg ctgttactgg atgccggcgc cgggctggtc     480
gtggtgccaa acgtaccgga tattagtgcg acgccaatgc ttctggaggc ggtaatcacc     540
gctgggctgg gcgcagcggc gccccggcg ctaaaagcgg cgttagatgc gctggcggag     600
ggcgctacgc ccgatttcgc cagtcggcaa caggcgatcc gcaaggcgct gctggcggcg     660
gctgcaacgg taagcagcaa tccatttatt cagcaactgc tcgttgaaca actgctggcg     720
ggctatgaag cggcggcagg gcaggcgtca gctctgaccg attattataa tcagatggaa     780
gagaaggggc tggagcaaca cggcggcaat atagcccgtg ccgatatcaa cggcctcttt     840
aaggaaattc ttgccaaccc gcaggcgttt ggtctgacaa ataccgtagg tatggcctgc     900
ccgcctggcg tatccgcttc ggcgtgctcc tcggcaatgc ctggatttaa tgcgtcgcag     960

-continued

```
gactatgtgt tgccgatca tttacatccc ggtccgcagg tccataccat tattgcgcaa    1020
tatattcagt cgatcattgc cgcgccggta caggcgacat acctgaacca aagcgttcag    1080
tcgatggcgc aaggcagtcg taccacgctt gacagccgtt atcagcagct cgccagggg    1140 gaaaatcctg ttggttcgct gggcatgttc ggcggataca gcggggata tcaacgttat    1200 gataataatg aggccgacgg gaacggtaat cataataatc tgacggttgg cgtcgattat    1260
cagcttaacg agcaggttct gctgggaggg ctgatagccg ttctctgga taagcaacat    1320 cctgacgata attatcgtta tgatgcccgc ggttttcagg ccgccgtatt cagccattta    1380
cgcgccggtc aggcgtggct ggatagcgat ttacactttc tgtccgctaa attcagtaac    1440
attcagcgca gtataacgct cggtgcgcta agacgggtgg aagagggcga aaccaacggt    1500
cggctgtcgg gcgcgagctt aaccagcggt tatgattttg tcatggtgcc gtggttaacg    1560
accggaccga tgctgcaata tgcatgggat tacagccacg ttaatggtta tagcgagaag    1620
ctcaatacca gtacatcaat gcgttttggt gaccaaaacg cccattcgca ggtgggtagc    1680
gcgggttggc gtctggatct tcgccacagc atcattcact cctgggcgca gattaattat    1740
cgccgtcagt ttggcgatga tacgtatgtg gcgaacggcg gccttaaatc gaccgcgctg    1800
acgtttagcc gcgacggaaa aacgcaggat aaaaactggg ttgatatcgc gattggcgca    1860
gattttccgc tgtcggcaac ggtgtccgct ttcgccgggc tgtcgcaaac ggcagggtta    1920
agcgatggca atcaaacccg ttataacgtt gggtttagcg cccgattta a             1971
```

<210> SEQ ID NO 107
<211> LENGTH: 656
<212> TYPE: PRT
<213> ORGANISM: Salmonella typhimurium

<400> SEQUENCE: 107

```
Met Thr Gln Lys Arg Thr Leu Leu Lys Tyr Gly Ile Leu Ser Leu Ala
1               5                   10                  15

Leu Ala Ala Pro Leu Ser Ala Cys Ala Phe Asp Ser Leu Thr Val Ile
            20                  25                  30

Gly Asp Ser Leu Ser Asp Thr Gly Asn Asn Gly Arg Trp Thr Trp Asp
        35                  40                  45

Ser Gly Gln Asn Lys Leu Tyr Asp Glu Gln Leu Ala Glu Arg Tyr Gly
    50                  55                  60

Leu Glu Leu Ser Pro Ser Ser Asn Gly Gly Ser Asn Tyr Ala Ala Gly
65                  70                  75                  80

Gly Ala Thr Ala Thr Pro Glu Leu Asn Pro Gln Asp Asn Thr Ala Asp
                85                  90                  95

Gln Val Arg Gln Trp Leu Ala Lys Thr Gly Lys Ala Asp His Asn
            100                 105                 110

Gly Leu Tyr Ile His Trp Val Gly Asn Asp Leu Ala Ala Ile
        115                 120                 125

Ala Gln Pro Thr Met Ala Gln Gln Ile Ala Gly Asn Ser Ala Thr Ser
    130                 135                 140

Ala Ala Ala Gln Val Gly Leu Leu Asp Ala Gly Ala Gly Leu Val
145                 150                 155                 160

Val Val Pro Asn Val Pro Asp Ile Ser Ala Thr Pro Met Leu Leu Glu
                165                 170                 175

Ala Val Ile Thr Ala Gly Leu Gly Ala Ala Ala Pro Pro Ala Leu Lys
            180                 185                 190
```

-continued

Ala Ala Leu Asp Ala Leu Ala Glu Gly Ala Thr Pro Asp Phe Ala Ser
        195                 200                 205

Arg Gln Gln Ala Ile Arg Lys Ala Leu Leu Ala Ala Ala Thr Val
210                 215                 220

Ser Ser Asn Pro Phe Ile Gln Gln Leu Leu Val Glu Gln Leu Leu Ala
225                 230                 235                 240

Gly Tyr Glu Ala Ala Ala Gly Gln Ala Ser Ala Leu Thr Asp Tyr Tyr
                245                 250                 255

Asn Gln Met Glu Glu Lys Gly Leu Gln His Gly Gly Asn Ile Ala
                260                 265                 270

Arg Ala Asp Ile Asn Gly Leu Phe Lys Glu Ile Leu Ala Asn Pro Gln
                275                 280                 285

Ala Phe Gly Leu Thr Asn Thr Val Gly Met Ala Cys Pro Pro Gly Val
290                 295                 300

Ser Ala Ser Ala Cys Ser Ser Ala Met Pro Gly Phe Asn Ala Ser Gln
305                 310                 315                 320

Asp Tyr Val Phe Ala Asp His Leu His Pro Gly Pro Gln Val His Thr
                325                 330                 335

Ile Ile Ala Gln Tyr Ile Gln Ser Ile Ile Ala Ala Pro Val Gln Ala
                340                 345                 350

Thr Tyr Leu Asn Gln Ser Val Gln Ser Met Ala Gln Gly Ser Arg Thr
            355                 360                 365

Thr Leu Asp Ser Arg Tyr Gln Gln Leu Arg Gln Gly Glu Asn Pro Val
            370                 375                 380

Gly Ser Leu Gly Met Phe Gly Gly Tyr Ser Gly Gly Tyr Gln Arg Tyr
385                 390                 395                 400

Asp Asn Asn Glu Ala Asp Gly Asn Gly Asn His Asn Asn Leu Thr Val
                405                 410                 415

Gly Val Asp Tyr Gln Leu Asn Glu Gln Val Leu Leu Gly Gly Leu Ile
                420                 425                 430

Ala Gly Ser Leu Asp Lys Gln His Pro Asp Asp Asn Tyr Arg Tyr Asp
            435                 440                 445

Ala Arg Gly Phe Gln Ala Ala Val Phe Ser His Leu Arg Ala Gly Gln
450                 455                 460

Ala Trp Leu Asp Ser Asp Leu His Phe Leu Ser Ala Lys Phe Ser Asn
465                 470                 475                 480

Ile Gln Arg Ser Ile Thr Leu Gly Ala Leu Arg Arg Val Glu Glu Gly
                485                 490                 495

Glu Thr Asn Gly Arg Leu Ser Gly Ala Ser Leu Thr Ser Gly Tyr Asp
                500                 505                 510

Phe Val Met Val Pro Trp Leu Thr Thr Gly Pro Met Leu Gln Tyr Ala
                515                 520                 525

Trp Asp Tyr Ser His Val Asn Gly Tyr Ser Glu Lys Leu Asn Thr Ser
            530                 535                 540

Thr Ser Met Arg Phe Gly Asp Gln Asn Ala His Ser Gln Val Gly Ser
545                 550                 555                 560

Ala Gly Trp Arg Leu Asp Leu Arg His Ser Ile Ile His Ser Trp Ala
                565                 570                 575

Gln Ile Asn Tyr Arg Arg Gln Phe Gly Asp Thr Tyr Val Ala Asn
            580                 585                 590

Gly Gly Leu Lys Ser Thr Ala Leu Thr Phe Ser Arg Asp Gly Lys Thr
595                 600                 605

Gln Asp Lys Asn Trp Val Asp Ile Ala Ile Gly Ala Asp Phe Pro Leu

Ser Ala Thr Val Ser Ala Phe Ala Gly Leu Ser Gln Thr Ala Gly Leu
625                 630                 635                 640

Ser Asp Gly Asn Gln Thr Arg Tyr Asn Val Gly Phe Ser Ala Arg Phe
                645                 650                 655

<210> SEQ ID NO 108
<211> LENGTH: 222
<212> TYPE: PRT
<213> ORGANISM: Agrobacterium rhizogenes

<400> SEQUENCE: 108

Met Ile Cys His Lys Gly Gly Glu Glu Met Arg Ser Val Leu Cys Tyr
1               5                   10                  15

Gly Asp Ser Asn Thr His Gly Gln Ile Pro Gly Gly Ser Pro Leu Asp
            20                  25                  30

Arg Tyr Gly Pro Asn Glu Arg Trp Pro Gly Val Leu Arg Arg Glu Leu
        35                  40                  45

Gly Ser Gln Trp Tyr Val Ile Glu Glu Gly Leu Ser Gly Arg Thr Thr
    50                  55                  60

Val Arg Asp Asp Pro Ile Glu Gly Thr Met Lys Asn Gly Arg Thr Tyr
65                  70                  75                  80

Leu Arg Pro Cys Leu Met Ser His Ala Ile Leu Asp Leu Val Ile Ile
                85                  90                  95

Met Leu Gly Thr Asn Asp Leu Lys Ala Arg Phe Gly Gln Pro Pro Ser
            100                 105                 110

Glu Val Ala Met Gly Ile Gly Cys Leu Val Tyr Asp Ile Arg Glu Leu
        115                 120                 125

Ala Pro Gly Pro Gly Lys Pro Pro Glu Ile Met Val Val Ala Pro
    130                 135                 140

Pro Pro Met Leu Asp Asp Ile Lys Glu Trp Glu Pro Ile Phe Ser Gly
145                 150                 155                 160

Ala Gln Glu Lys Ser Arg Arg Leu Ala Leu Glu Phe Glu Ile Ile Ala
                165                 170                 175

Asp Ser Leu Glu Val His Phe Phe Asp Ala Ala Thr Val Ala Ser Cys
            180                 185                 190

Asp Pro Cys Asp Gly Phe His Ile Asn Arg Glu Ala His Glu Ala Leu
        195                 200                 205

Gly Thr Ala Leu Ala Arg Glu Val Glu Ala Ile Gly Trp Arg
    210                 215                 220

<210> SEQ ID NO 109
<211> LENGTH: 672
<212> TYPE: DNA
<213> ORGANISM: Agrobacterium rhizogenes

<400> SEQUENCE: 109
atgatttgcc ataaaggtgg ggaggaaatg cggtcagtct tatgctacgg cgactcgaat     60
acgcacggcc agattccggg gggctcaccg ctcgaccgat acgggccgaa cgagcgctgg    120
cctggcgttt tgagacggga gcttggaagc cagtggtatg tgatcgagga gggcctgagt    180
ggccgcacga cggttcgcga cgatccgatc gagggcacga tgaaaaacgg ccggacctac    240
ctgcgtccgt gcctcatgag ccacgcgatc ctcgatctcg tgattatcat gctcgggacg    300
aacgacctga aagcgcgctt cggtcaaccg ccatcggaag tggcgatggg gatcggctgc    360
ctcgtctacg atatcaggga gctggcgccc ggaccgggcg gcaagccccc cgaaatcatg    420

```
gtggttgctc cgccgccgat gctggacgat atcaaggaat gggaacccat attttccggc    480
gcccaggaga aatcccggcg tctcgcgctt gagtttgaaa ttattgctga ttcgcttgaa    540
gtacacttct ttgacgccgc gaccgtcgca tcgtgtgatc cttgcgatgg ttttcacatc    600
aaccgggaag cgcatgaagc cttgggaaca gcgcttgcca gggaagtgga ggcgatcggt    660
tggagatgat ga                                                        672
```

<210> SEQ ID NO 110
<211> LENGTH: 227
<212> TYPE: PRT
<213> ORGANISM: Agrobacterium rhizogenes

<400> SEQUENCE: 110

```
Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

Ala Ser His Leu Pro Leu Asp Leu Val Ile Ile Leu Leu Gly Thr Asn
                85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
        115                 120                 125

Thr Pro Tyr Pro Ala Pro Lys Leu Leu Ile Val Ser Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Leu Glu Leu Ala Lys Gln Tyr Lys Ala Leu Ala Asn Phe
                165                 170                 175

Leu Lys Val Asp Phe Leu Asp Ala Gly Glu Phe Val Lys Thr Asp Gly
            180                 185                 190

Cys Asp Gly Ile His Phe Ser Ala Glu Thr Asn Ile Thr Leu Gly His
        195                 200                 205

Ala Ile Ala Ala Lys Val Glu Ala Ile Phe Ser Gln Glu Ala Lys Asn
    210                 215                 220

Ala Ala Ala
225
```

<210> SEQ ID NO 111
<211> LENGTH: 684
<212> TYPE: DNA
<213> ORGANISM: Agrobacterium rhizogenes

<400> SEQUENCE: 111

```
atggcagaga gccgctcaat attatgtttt ggggattcac tcacatgggg ttggattccg    60
gtaccggagt cgtcgccgac gctcagatat ccctttgagc agcgctggac cggtgcaatg    120
gctgcggcac tcggtgacgg ctattcaatc atcgaggaag cctttccgc cgcacgacc    180 agcgtcgagg atccgaacga tcccaggctg aacggcagcg cctacctgcc gatggcgctc    240
```

```
gccagccatc tgccgctcga tctcgtcatc atccttctcg gcaccaacga caccaagtcc    300
tatttccgcc gcacgcccta tgagatcgcc aacggcatgg gcaagcttgc cggacaggtt    360
ctgacctcgg ccggcgggat cggcacgccc taccctgccc cgaagcttct gatcgtttcg    420
ccgccgccgc tcgctcccat gcctgacccg tggttcgaag gcatgttcgg tggcggttac    480
gaaaagtcgc tcgaactcgc aaagcagtac aaggcgctcg ccaacttcct gaaggtcgac    540
ttcctcgacg ccggcgagtt tgtaaagacc gacggctgcg atggaatcca tttctccgcc    600
gagacgaaca tcacgctcgg ccatgcgatc gcggcgaagg tcgaagcgat tttctcacaa    660
gaggcgaaga acgctgcggc ttag                                           684
```

<210> SEQ ID NO 112
<211> LENGTH: 212
<212> TYPE: PRT
<213> ORGANISM: Mesorhizobium loti

<400> SEQUENCE: 112

```
Met Lys Thr Ile Leu Cys Tyr Gly Asp Ser Leu Thr Trp Gly Tyr Asp
1               5                   10                  15

Ala Val Gly Pro Ser Arg His Ala Tyr Glu Asp Arg Trp Pro Ser Val
            20                  25                  30

Leu Gln Gly Arg Leu Gly Ser Ser Ala Arg Val Ile Ala Glu Gly Leu
        35                  40                  45

Cys Gly Arg Thr Thr Ala Phe Asp Asp Trp Val Ala Gly Ala Asp Arg
    50                  55                  60

Asn Gly Ala Arg Ile Leu Pro Thr Leu Leu Ala Thr His Ser Pro Leu
65                  70                  75                  80

Asp Leu Val Ile Val Met Leu Gly Thr Asn Asp Met Lys Ser Phe Val
                85                  90                  95

Cys Gly Arg Ala Ile Gly Ala Lys Gln Gly Met Glu Arg Ile Val Gln
            100                 105                 110

Ile Ile Arg Gly Gln Pro Tyr Ser Phe Asn Tyr Lys Val Pro Ser Ile
        115                 120                 125

Leu Leu Val Ala Pro Pro Leu Cys Ala Thr Glu Asn Ser Asp Phe
    130                 135                 140

Ala Glu Ile Phe Glu Gly Gly Met Ala Glu Ser Gln Lys Leu Ala Pro
145                 150                 155                 160

Leu Tyr Ala Ala Leu Ala Gln Gln Thr Gly Cys Ala Phe Phe Asp Ala
                165                 170                 175

Gly Thr Val Ala Arg Thr Thr Pro Leu Asp Gly Ile His Leu Asp Ala
            180                 185                 190

Glu Asn Thr Arg Ala Ile Gly Ala Gly Leu Glu Pro Val Val Arg Gln
        195                 200                 205

Ala Leu Gly Leu
    210
```

<210> SEQ ID NO 113
<211> LENGTH: 699
<212> TYPE: DNA
<213> ORGANISM: Mesorhizobium loti

<400> SEQUENCE: 113

```
atgaagacca tcctttgtta cggtgactcc ctcacttggg gctatgatgc cgtcggaccc     60
atgaagacca tcctttgtta cggtgactcc ctcacttggg gctatgatgc cgtcggaccc    120
```

-continued

```
tcacggcatg cttatgagga tcgatggccc tccgtactgc aaggccgcct cggtagcagt    180
gcgcgggtga tcgccgaggg gctttgcggc cgcacaactg cgtttgacga ctgggtcgct    240
ggtgcggacc ggaacggtgc gcgcatcctg ccgacgcttc ttgcgaccca ttcaccgctt    300
gacctcgtta tcgtcatgct cgggacgaac gacatgaaat cgttcgtttg cgggcgcgct    360
atcggcgcca agcaggggat ggagcggatc gtccagatca tccgcgggca gccttattcc    420
ttcaattata aggtaccgtc gattcttctc gtggcgccgc cgccgctgtg cgctaccgaa    480
aacagcgatt tcgcggaaat ttttgaaggt ggcatggctg aatcgcaaaa gctcgcgccg    540
ctttatgccg cgctggccca gcaaaccgga tgcgccttct tcgatgcagg cactgtggcc    600
cgcacgacac cgctcgacgg tattcacctc gatgctgaaa acacgcgcgc cattggtgcc    660
ggcctggagc cggtggtccg ccaagcgctt ggattgtga                           699
```

<210> SEQ ID NO 114
<211> LENGTH: 213
<212> TYPE: PRT
<213> ORGANISM: Ralstonia solanacearum

<400> SEQUENCE: 114

```
Met Gln Gln Ile Leu Leu Tyr Ser Asp Ser Leu Ser Trp Gly Ile Ile
1               5                   10                  15

Pro Gly Thr Arg Arg Arg Leu Pro Phe Ala Ala Arg Trp Ala Gly Val
            20                  25                  30

Met Glu His Ala Leu Gln Ala Gln Gly His Ala Val Arg Ile Val Glu
        35                  40                  45

Asp Cys Leu Asn Gly Arg Thr Thr Val Leu Asp Asp Pro Ala Arg Pro
    50                  55                  60

Gly Arg Asn Gly Leu Gln Gly Leu Ala Gln Arg Ile Glu Ala His Ala
65                  70                  75                  80

Pro Leu Ala Leu Val Ile Leu Met Leu Gly Thr Asn Asp Phe Gln Ala
                85                  90                  95

Ile Phe Arg His Thr Ala Gln Asp Ala Ala Gln Gly Val Ala Gln Leu
            100                 105                 110

Val Arg Ala Ile Arg Gln Ala Pro Ile Glu Pro Gly Met Pro Val Pro
        115                 120                 125

Pro Val Leu Ile Val Val Pro Pro Ala Ile Thr Ala Pro Ala Gly Ala
    130                 135                 140

Met Ala Asp Lys Phe Ala Asp Ala Gln Pro Lys Cys Ala Gly Leu Ala
145                 150                 155                 160

Gln Ala Tyr Arg Ala Thr Ala Gln Thr Leu Gly Cys His Val Phe Asp
                165                 170                 175

Ala Asn Ser Val Thr Pro Ala Ser Arg Val Asp Gly Ile His Leu Asp
            180                 185                 190

Ala Asp Gln His Ala Gln Leu Gly Arg Ala Met Ala Gln Val Val Gly
        195                 200                 205

Thr Leu Leu Ala Gln
    210
```

<210> SEQ ID NO 115
<211> LENGTH: 642
<212> TYPE: DNA
<213> ORGANISM: Ralstonia solanacearum

<400> SEQUENCE: 115

```
atgcaacaga tcctgctcta ttccgactcg ctctcctggg gcatcatccc cggcacccgc     60
```

-continued

```
cggcgcctgc cgttcgccgc ccgctgggcc ggggtcatgg aacacgcgct gcaggcgcaa    120
gggcacgccg tgcgcatcgt cgaagactgc ctcaatggac gcaccacggt gctcgacgat    180
cccgcgcggc cggggcgcaa cggactgcag ggctcgcgc agcggatcga agcgcacgcc     240
ccgcttgccc tggtcatcct gatgctcggc accaacgact tccaggcgat cttccggcac    300
accgcccagg acgcggcgca aggcgtggcg cagctggtgc gggccatccg ccaggcgccg    360
atcgaacccg gcatgccggt gccgcccgtg ctgatcgtgg tgccgccggc catcaccgcg    420
ccggccgggg cgatggccga caagtttgcc gacgcgcagc ccaagtgcgc cggccttgcg    480
caggcctatc gggcaacggc gcaaacgcta ggctgccacg tcttcgatgc gaacagcgtc    540
acgccggcca gccgcgtgga cggcatccac ctcgatgccg accagcatgc gcagctgggc    600
cgggcgatgg cgcaggtcgt cgggacgctg cttgcgcaat aa                       642
```

<210> SEQ ID NO 116
<211> LENGTH: 651
<212> TYPE: DNA
<213> ORGANISM: Burkholderia cepacia

<400> SEQUENCE: 116

```
atgacgatga cgcagaaaac cgtgctctgc tacggcgatt cgaacacgca tggcacacgc     60
ccgatgacgc atgctggcgg actggggcgg tttgcacgcg aagaacgctg gaccggcgtg    120
ctggcgcaaa cgctcggtgc gagctggcgg gtcattgaag aagggttgcc cgcgcgtacg    180
accgtgcatg acgatccgat cgaaggccgg cacaagaatg gtttgtcgta tctgcgcgcg    240
tgcgtcgaaa gccacttgcc cgtcgatgtc gtcgtgctga tgctcgggac caacgatctg    300
aagacacgct tctcggtcac gcccgccgac atcgcgacat cggtcggcgt attgcttgcc    360
aagatcgctg cgtgcggcgc cggtccgtcc ggtgcgtcac cgaagctcgt gctgatggcg    420
cctgcgccga tcgtcgaggt cggattcctc ggcgagatct ttgcgggcgg cgcagcgaag    480
tcgcggcagc tcgcgaagcg gtacgaacag gtggcaagcg atgccggtgc gcactttctc    540
gatgccggcg cgatcgtcga ggtgagcccg gtggatggcg ttcacttcgc ggccgatcag    600
catcgtgtgc tcgggcagcg ggtcgctgcc cttctgcagc agattgcgta a             651
```

<210> SEQ ID NO 117
<211> LENGTH: 216
<212> TYPE: PRT
<213> ORGANISM: Burkholderia cepacia

<400> SEQUENCE: 117

```
Met Thr Met Thr Gln Lys Thr Val Leu Cys Tyr Gly Asp Ser Asn Thr
1               5                   10                  15

His Gly Thr Arg Pro Met Thr His Ala Gly Gly Leu Gly Arg Phe Ala
            20                  25                  30

Arg Glu Glu Arg Trp Thr Gly Val Leu Ala Gln Thr Leu Gly Ala Ser
        35                  40                  45

Trp Arg Val Ile Glu Glu Gly Leu Pro Ala Arg Thr Thr Val His Asp
    50                  55                  60

Asp Pro Ile Glu Gly Arg His Lys Asn Gly Leu Ser Tyr Leu Arg Ala
65                  70                  75                  80

Cys Val Glu Ser His Leu Pro Val Asp Val Val Val Leu Met Leu Gly
                85                  90                  95

Thr Asn Asp Leu Lys Thr Arg Phe Ser Val Thr Pro Ala Asp Ile Ala
            100                 105                 110
```

```
Thr Ser Val Gly Val Leu Leu Ala Lys Ile Ala Ala Cys Gly Ala Gly
    115                 120                 125

Pro Ser Gly Ala Ser Pro Lys Leu Val Leu Met Ala Pro Ala Pro Ile
    130                 135                 140

Val Glu Val Gly Phe Leu Gly Glu Ile Phe Ala Gly Ala Ala Lys
145                 150                 155                 160

Ser Arg Gln Leu Ala Lys Arg Tyr Glu Gln Val Ala Ser Asp Ala Gly
                165                 170                 175

Ala His Phe Leu Asp Ala Gly Ala Ile Val Glu Val Ser Pro Val Asp
                180                 185                 190

Gly Val His Phe Ala Ala Asp Gln His Arg Val Leu Gly Gln Arg Val
                195                 200                 205

Ala Ala Leu Leu Gln Gln Ile Ala
    210                 215

<210> SEQ ID NO 118
<211> LENGTH: 214
<212> TYPE: PRT
<213> ORGANISM: Pirellula spp.

<400> SEQUENCE: 118

Met His Ser Ile Leu Ile Tyr Gly Asp Ser Leu Ser Trp Gly Ile Ile
1               5                   10                  15

Pro Gly Thr Arg Arg Phe Ala Phe His Gln Arg Trp Pro Gly Val
                20                  25                  30

Met Glu Ile Glu Leu Arg Gln Thr Gly Ile Asp Ala Arg Val Ile Glu
                35                  40                  45

Asp Cys Leu Asn Gly Arg Arg Thr Val Leu Glu Asp Pro Ile Lys Pro
    50                  55                  60

Gly Arg Asn Gly Leu Asp Gly Leu Gln Gln Arg Ile Glu Ile Asn Ser
65              70                  75                  80

Pro Leu Ser Leu Val Val Leu Phe Leu Gly Thr Asn Asp Phe Gln Ser
                85                  90                  95

Val His Glu Phe His Ala Glu Gln Ser Ala Gln Gly Leu Ala Leu Leu
                100                 105                 110

Val Asp Ala Ile Arg Arg Ser Pro Phe Glu Pro Gly Met Pro Thr Pro
                115                 120                 125

Lys Ile Leu Leu Val Ala Pro Pro Thr Val His His Pro Lys Leu Asp
    130                 135                 140

Met Ala Ala Lys Phe Gln Asn Ala Glu Thr Lys Ser Thr Gly Leu Ala
145                 150                 155                 160

Asp Ala Ile Arg Lys Val Ser Thr Glu His Ser Cys Glu Phe Phe Asp
                165                 170                 175

Ala Ala Thr Val Thr Thr Thr Ser Val Val Asp Gly Val His Leu Asp
                180                 185                 190

Gln Glu Gln His Gln Ala Leu Gly Thr Ala Leu Ala Ser Thr Ile Ala
                195                 200                 205

Glu Ile Leu Ala Asp Cys
    210

<210> SEQ ID NO 119
<211> LENGTH: 645
<212> TYPE: DNA
<213> ORGANISM: Pirellula spp.

<400> SEQUENCE: 119
```

```
atgcattcaa tcctcatcta tggcgattct ctcagttggg gaatcattcc cggcacgcgt    60
cgtcgcttcg cgttccatca gcgttggccg ggcgtcatgg agattgaact gcgacaaact   120
ggaatcgatg cccgcgtcat cgaagactgc ctcaatggcc gacgaaccgt cttggaagat   180
ccaatcaaac ccggacgcaa tggcctggat ggtttgcagc aacggatcga atcaattca    240 cctctgtcac tggtcgtgct ctttctgggg accaacgatt ccagtccgt ccacgaattc    300 catgccgagc aatcggcaca aggactcgca ctgcttgtcg acgccattcg tcgctcccct   360
ttcgaaccag gaatgccgac accgaaaatc ctgcttgtcg caccaccgac ggttcaccac   420
ccgaaacttg atatggcggc gaagttccaa aacgcggaaa cgaaatcgac gggactcgca   480
gatgcgattc gcaaggtctc aacagaacac tcctgcgaat tcttcgatgc ggccacggtc   540
accacaacaa gtgtcgtcga cggagtccat ctcgatcaag aacaacatca agcactcggt   600
accgcactgg catcgacaat cgctgaaata ctagcagact gttga                   645
```

<210> SEQ ID NO 120
<211> LENGTH: 708
<212> TYPE: DNA
<213> ORGANISM: Artificial Sequence
<220> FEATURE:
<223> OTHER INFORMATION: S248_M31bA11 clone
<220> FEATURE:
<221> NAME/KEY: misc_feature
<222> LOCATION: (695)..(695)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (700)..(700)
<223> OTHER INFORMATION: n is a, c, g, or t

<400> SEQUENCE: 120

```
cggaattatc atgctgggtt ttaatgacca gcgcgagagg atcaacgaca acctcgatta    60
ctgggacgcc taccactccg tcctgggcga gagacagtt tattccggca attccaagat   120
gttcgtcccc atcaccaaga tcgcggtgaa ggcgcgcaag acccggttca ccaatcagat   180
ttttcctcag tccggccgca acgtcgatgt caccaccacg gacggcacac tcccccacgc   240
caccatgtcc ctggtcgagc actacatccg ggcctgccgc ctgcgcaccc agatcgttcc   300
ggccctgatc gttaacggcg attgcgaagg catgtacagc atctatgtcg gctggtcgaa   360
aaccaccaag catgttgttt cacgtgaaac aaagccggtc gaaagcgacg gcatggaatt   420
tcccgaactg ggcgaagccg acgacatcac cgaagaaacg cttgagtgtg gccttcccga   480
catcgaattg atctcggacg ccgatcttct cgtccttcca ccagcgccga caacattcca   540
aggcgcttga gatgggcggg ttcggtcacg atcttgcgcc gtggacaagg gcaaggtccg   600
cagatgatcg acgaggcgcg atcaccgaga tgccgcgacg atctgtcgac gctatgtcac   660
cagcgcatgt ccgacggtgg aatgcaagac aggtnggntn gatcgggg               708
```

<210> SEQ ID NO 121
<211> LENGTH: 229
<212> TYPE: PRT
<213> ORGANISM: Artificial Sequence
<220> FEATURE:
<223> OTHER INFORMATION: S248_M31bA11 clone

<400> SEQUENCE: 121

-continued

```
Arg Asn Tyr His Ala Gly Phe Pro Ala Arg Glu Asp Gln Arg Gln Pro
1               5                   10                  15

Arg Leu Leu Gly Arg Leu Pro Leu Arg Pro Gly Arg Glu Thr Val Leu
            20                  25                  30

Phe Arg Gln Phe Gln Asp Val Arg Pro His His Gln Asp Arg Gly Glu
        35                  40                  45

Gly Ala Gln Asp Pro Val His Gln Ser Asp Phe Ser Ser Val Arg Pro
    50                  55                  60

Gln Arg Arg Cys His His His Gly Arg His Thr Pro Pro Arg His His
65                  70                  75                  80

Val Pro Gly Arg Ala Leu His Pro Gly Leu Pro Pro Ala His Pro Asp
                85                  90                  95

Arg Ser Gly Pro Asp Arg Arg Leu Arg Arg His Val Gln His Leu
            100                 105                 110

Cys Arg Leu Val Glu Asn His Gln Ala Cys Cys Phe Thr Asn Lys Ala
        115                 120                 125

Gly Arg Lys Arg Arg His Gly Ile Ser Arg Thr Gly Arg Ser Arg Arg
    130                 135                 140

His His Arg Arg Asn Ala Val Trp Pro Ser Arg His Arg Ile Asp Leu
145                 150                 155                 160

Gly Arg Arg Ser Ser Arg Pro Ser Thr Ser Ala Asp Asn Ile Pro Arg
                165                 170                 175

Arg Leu Arg Trp Ala Gly Ser Val Thr Ile Leu Arg Arg Gly Gln Gly
            180                 185                 190

Gln Gly Pro Gln Met Ile Asp Glu Ala Arg Ser Pro Cys Arg Asp
        195                 200                 205

Asp Leu Ser Thr Leu Cys His Gln Arg Met Ser Asp Gly Gly Met Gln
    210                 215                 220

Asp Arg Ser Gly Ala
225

<210> SEQ ID NO 122
<211> LENGTH: 231
<212> TYPE: PRT
<213> ORGANISM: Artificial Sequence
<220> FEATURE:
<223> OTHER INFORMATION: S248_M31bA11 clone

<400> SEQUENCE: 122

Gly Ile Ile Met Leu Gly Phe Asn Asp Gln Arg Glu Arg Ile Asn Asp
1               5                   10                  15

Asn Leu Asp Tyr Trp Asp Ala Tyr His Ser Val Leu Gly Glu Arg Gln
            20                  25                  30

Phe Tyr Ser Gly Asn Ser Lys Met Phe Val Pro Ile Thr Lys Ile Ala
        35                  40                  45

Val Lys Ala Arg Lys Thr Arg Phe Thr Asn Gln Ile Phe Pro Gln Ser
    50                  55                  60

Gly Arg Asn Val Asp Val Thr Thr Thr Asp Gly Thr Leu Pro His Ala
65                  70                  75                  80

Thr Met Ser Leu Val Glu His Tyr Ile Arg Ala Cys Arg Leu Arg Thr
                85                  90                  95

Gln Ile Val Pro Ala Leu Ile Val Asn Gly Asp Cys Glu Gly Met Tyr
            100                 105                 110

Ser Ile Tyr Val Gly Trp Ser Lys Thr Lys His Val Val Ser Arg
        115                 120                 125
```

```
Glu Thr Lys Pro Val Glu Ser Asp Gly Met Glu Phe Pro Glu Leu Gly
130                 135                 140

Glu Ala Asp Asp Ile Thr Glu Thr Leu Glu Cys Gly Leu Pro Asp
145                 150                 155                 160

Ile Glu Leu Ile Ser Asp Ala Asp Leu Leu Val Leu Pro Pro Ala Pro
                165                 170                 175

Thr Thr Phe Gln Gly Ala Asp Gly Arg Val Arg Ser Arg Ser Cys Ala
                180                 185                 190

Val Asp Lys Gly Lys Val Arg Arg Ser Thr Arg Arg Asp His Arg Asp
                195                 200                 205

Ala Ala Thr Ile Cys Arg Arg Tyr Val Thr Ser Ala Cys Pro Thr Val
210                 215                 220

Glu Cys Lys Thr Gly Asp Arg
225                 230

<210> SEQ ID NO 123
<211> LENGTH: 229
<212> TYPE: PRT
<213> ORGANISM: Artificial Sequence
<220> FEATURE:
<223> OTHER INFORMATION: S248_M31bA11 clone

<400> SEQUENCE: 123

Glu Leu Ser Cys Trp Val Leu Met Thr Ser Ala Arg Gly Ser Thr Thr
1               5                   10                  15

Thr Ser Ile Thr Gly Thr Pro Thr Thr Pro Ser Trp Ala Arg Asp Ser
                20                  25                  30

Phe Ile Pro Ala Ile Pro Arg Cys Ser Ser Pro Ser Pro Arg Ser Arg
                35                  40                  45

Arg Arg Ala Arg Pro Gly Ser Pro Ile Arg Phe Phe Leu Ser Pro Ala
50                  55                  60

Ala Thr Ser Met Ser Pro Pro Arg Thr Ala His Ser Pro Thr Pro Pro
65                  70                  75                  80

Cys Pro Trp Ser Ser Thr Ser Gly Pro Ala Ala Cys Ala Pro Arg
                85                  90                  95

Ser Phe Arg Pro Ser Leu Thr Ala Ile Ala Lys Ala Cys Thr Ala Ser
                100                 105                 110

Met Ser Ala Gly Arg Lys Pro Pro Ser Met Leu Phe His Val Lys Gln
                115                 120                 125

Ser Arg Ser Lys Ala Thr Ala Trp Asn Phe Pro Asn Trp Ala Lys Pro
130                 135                 140

Thr Thr Ser Pro Lys Lys Arg Leu Ser Val Ala Phe Pro Thr Ser Asn
145                 150                 155                 160

Ser Arg Thr Pro Ile Phe Ser Ser Phe His Gln Arg Gln His Ser
                165                 170                 175

Lys Ala Leu Glu Met Gly Gly Phe Gly His Asp Leu Ala Pro Trp Thr
                180                 185                 190

Arg Ala Arg Ser Ala Asp Asp Arg Gly Ala Ile Thr Glu Met Pro
                195                 200                 205

Arg Arg Ser Val Asp Ala Met Ser Pro Ala His Val Arg Arg Trp Asn
210                 215                 220

Ala Arg Gln Ile Gly
225

<210> SEQ ID NO 124
<211> LENGTH: 5
```

<212> TYPE: PRT
<213> ORGANISM: Artificial Sequence
<220> FEATURE:
<223> OTHER INFORMATION: synthetic putative block V

<400> SEQUENCE: 124

Asp Gly Thr His Pro
1               5

<210> SEQ ID NO 125
<211> LENGTH: 1216
<212> TYPE: DNA
<213> ORGANISM: Artificial Sequence
<220> FEATURE:
<223> OTHER INFORMATION: M091_M24dG12 clone

<400> SEQUENCE: 125

| | | | | | |
|---|---|---|---|---|---|
| gcctgatggc | ttcgagttcg | tcgaattcac | ctcgccccag | cccggcgtgc | tggaggcggt | 60 |
| gtttgaaaag | ctgggtttca | ccctggtcgc | caagcaccgg | tccaaggatg | tggtgctgta | 120 |
| ccgccagaac | ggcatcaact | tcatcctgaa | ccgcagccc | cacagccagg | ccgcctactt | 180 |
| tggtgccgag | catggcccct | ccgcctgtgg | cctggccttc | cgtgtgaagg | atgcgcataa | 240 |
| ggcttataac | cgcgcgctgg | aactgggcgc | ccagcccatc | gagatcccca | ccggccccat | 300 |
| ggaactgcgc | ctgcccgcca | tcaagggcat | tggcggcgcc | gcctctgtat | tgatcgacc | 360 |
| gctttgaaga | cggcaagtcc | atctacgaca | tcgacttcga | gttcatcgaa | ggcgtggacc | 420 |
| gccgccccgc | ggggcatggc | ctgaacgaga | tcgatcacct | cacgcacaac | gtgtaccggg | 480 |
| gccgcatggg | cttctgggcc | aacttctacg | aaaagctgtt | caacttccgc | gaaatccgct | 540 |
| acttcgacat | ccagggcgaa | tacacgggcc | tgacctccaa | ggccatgacc | gcgcccgacg | 600 |
| gcaagattcg | catcccgctg | aacgaagagt | ccaagcaggg | cggcggccag | atcgaagaat | 660 |
| ttttgatgca | attcaacggc | gagggcattc | agcacatcgc | gctgatctgc | gacaacctgc | 720 |
| tggacgtggt | ggacaagctg | ggcatggccg | gcgtgcagct | ggccaccgcg | cccaacgagg | 780 |
| tctattacga | aatgctggac | acccgcctgc | ccggccacgg | ccagccggtg | cccgagctgc | 840 |
| agtcgcgcgg | catcttgctg | gacggcacca | cggccgacgg | cacgcacccg | cctgctagct | 900 |
| tcagatcttc | tccacgccca | tgctgggccc | ggtgttcttc | gaattcatcc | agcgcgaggg | 960 |
| cgactaccgc | gacggctttg | gcgaaggcaa | cttcaaggcg | ctgttcgagt | cgctggaacg | 1020 |
| cgaccagatc | cgccgtggtg | tgctgaacac | ataagacatc | agacatccag | ggttaaccct | 1080 |
| gcacaggtgc | ctatactgcg | cgctccccgg | aactcaaaag | gatccgatg | tcgctccgta | 1140 |
| gcaccctgtt | cagcacccctt | ttggccggcg | cagccactgt | cgcgctggcg | cagaacccgt | 1200 |
| ctgcccgctc | acatcg | | | | | 1216 |

<210> SEQ ID NO 126
<211> LENGTH: 394
<212> TYPE: PRT
<213> ORGANISM: Artificial Sequence
<220> FEATURE:
<223> OTHER INFORMATION: M091_M24dG12 clone

<400> SEQUENCE: 126

Ala Trp Leu Arg Val Arg Arg Ile His Leu Ala Pro Ala Arg Arg Ala
1               5                   10                  15

Gly Gly Gly Val Lys Ala Gly Phe His Pro Gly Arg Gln Ala Pro Val
            20                  25                  30

Gln Gly Cys Gly Ala Val Pro Pro Glu Arg His Gln Leu His Pro Glu

```
            35                  40                  45
Pro Arg Ala Pro Gln Pro Gly Arg Leu Leu Trp Cys Arg Ala Trp Pro
         50                  55                  60
Leu Arg Leu Trp Pro Gly Leu Pro Cys Glu Gly Cys Ala Gly Leu Pro
 65                  70                  75                  80
Arg Ala Gly Thr Gly Arg Pro Ala His Arg Asp Pro His Arg Pro His
                 85                  90                  95
Gly Thr Ala Pro Ala Arg His Gln Gly His Trp Arg Arg Leu Cys
            100                 105                 110
Ile Ser Thr Ala Leu Lys Thr Ala Ser Pro Ser Thr Thr Ser Thr Ser
            115                 120                 125
Ser Ser Ser Lys Ala Trp Thr Ala Ala Pro Arg Gly Met Ala Thr Arg
130                 135                 140
Ser Ile Thr Ser Arg Thr Thr Cys Thr Gly Ala Ala Trp Ala Ser Gly
145                 150                 155                 160
Pro Thr Ser Thr Lys Ser Cys Ser Thr Ser Ala Lys Ser Ala Thr Ser
                165                 170                 175
Thr Ser Arg Ala Asn Thr Arg Ala Pro Pro Arg Pro Arg Pro Thr
            180                 185                 190
Ala Arg Phe Ala Ser Arg Thr Lys Ser Pro Ser Arg Ala Ala Ala Arg
            195                 200                 205
Ser Lys Asn Phe Cys Asn Ser Thr Ala Arg Ala Phe Ser Thr Ser Arg
210                 215                 220
Ser Ala Thr Thr Cys Trp Thr Trp Thr Ser Trp Ala Trp Pro Ala
225                 230                 235                 240
Cys Ser Trp Pro Pro Arg Pro Thr Arg Ser Ile Thr Lys Cys Trp Thr
                245                 250                 255
Pro Ala Cys Pro Ala Thr Ala Ser Arg Cys Pro Ser Cys Ser Arg Ala
            260                 265                 270
Ala Ser Cys Trp Thr Ala Pro Arg Pro Thr Ala Arg Thr Arg Leu Leu
            275                 280                 285
Ala Ser Asp Leu Leu His Ala His Ala Gly Pro Gly Val Leu Arg Ile
            290                 295                 300
His Pro Ala Arg Gly Arg Leu Pro Arg Arg Leu Trp Arg Arg Gln Leu
305                 310                 315                 320
Gln Gly Ala Val Arg Val Ala Gly Thr Arg Pro Asp Pro Pro Trp Cys
                325                 330                 335
Ala Glu His Ile Arg His Gln Thr Ser Arg Val Asn Pro Ala Gln Val
            340                 345                 350
Pro Ile Leu Arg Ala Pro Arg Asn Ser Lys Gly Ser Arg Cys Arg Ser
            355                 360                 365
Val Ala Pro Cys Ser Ala Pro Phe Trp Pro Ala Gln Pro Leu Ser Arg
            370                 375                 380
Trp Arg Arg Thr Arg Leu Pro Ala His Ile
385                 390
```

<210> SEQ ID NO 127
<211> LENGTH: 401
<212> TYPE: PRT
<213> ORGANISM: Artificial Sequence
<220> FEATURE:
<223> OTHER INFORMATION: M091_M24dG12 clone

<400> SEQUENCE: 127

Pro Asp Gly Phe Glu Phe Val Glu Phe Thr Ser Pro Gln Pro Gly Val

-continued

```
 1               5                   10                  15
Leu Glu Ala Val Phe Glu Lys Leu Gly Phe Thr Leu Val Ala Lys His
                 20                  25                  30

Arg Ser Lys Asp Val Val Leu Tyr Arg Gln Asn Gly Ile Asn Phe Ile
             35                  40                  45

Leu Asn Arg Glu Pro His Ser Gln Ala Ala Tyr Phe Gly Ala Glu His
         50                  55                  60

Gly Pro Ser Ala Cys Gly Leu Ala Phe Arg Val Lys Asp Ala His Lys
 65                  70                  75                  80

Ala Tyr Asn Arg Ala Leu Glu Leu Gly Ala Gln Pro Ile Glu Ile Pro
                 85                  90                  95

Thr Gly Pro Met Glu Leu Arg Leu Pro Ala Ile Lys Gly Ile Gly Gly
                100                 105                 110

Ala Ala Ser Val Phe Asp Arg Pro Leu Arg Arg Gln Val His Leu Arg
                115                 120                 125

His Arg Leu Arg Val His Arg Arg Gly Pro Pro Arg Gly Ala
             130                 135                 140

Trp Pro Glu Arg Asp Arg Ser Pro His Ala Gln Arg Val Pro Gly Pro
145                 150                 155                 160

His Gly Leu Leu Gly Gln Leu Leu Arg Lys Ala Val Gln Leu Pro Arg
                165                 170                 175

Asn Pro Leu Leu Arg His Pro Gly Arg Ile His Gly Pro Asp Leu Gln
            180                 185                 190

Gly His Asp Arg Ala Arg Arg Gln Asp Ser His Pro Ala Glu Arg Arg
        195                 200                 205

Val Gln Ala Gly Arg Arg Pro Asp Arg Arg Ile Phe Asp Ala Ile Gln
    210                 215                 220

Arg Arg Gly His Ser Ala His Arg Ala Asp Leu Arg Gln Pro Ala Gly
225                 230                 235                 240

Arg Gly Gly Gln Ala Gly His Gly Arg Ala Ala Gly His Arg Ala
                245                 250                 255

Gln Arg Gly Leu Leu Arg Asn Ala Gly His Pro Pro Ala Arg Pro Arg
            260                 265                 270

Pro Ala Gly Ala Arg Ala Ala Val Ala Arg His Leu Ala Gly Arg His
        275                 280                 285

His Gly Arg Arg His Ala Pro Ala Cys Leu Gln Ile Phe Ser Thr Pro
    290                 295                 300

Met Leu Gly Pro Val Phe Phe Glu Phe Ile Gln Arg Glu Gly Asp Tyr
305                 310                 315                 320

Arg Asp Gly Phe Gly Glu Gly Asn Phe Lys Ala Leu Phe Glu Ser Leu
                325                 330                 335

Glu Arg Asp Gln Ile Arg Arg Gly Val Leu Asn Thr Asp Ile Arg His
            340                 345                 350

Pro Gly Leu Thr Leu His Arg Cys Leu Tyr Cys Ala Leu Pro Gly Thr
        355                 360                 365

Gln Lys Asp Pro Asp Val Ala Pro His Pro Val Gln His Pro Phe Gly
    370                 375                 380

Arg Arg Ser His Cys Arg Ala Gly Ala Glu Pro Val Cys Pro Leu Thr
385                 390                 395                 400

Ser
```

<210> SEQ ID NO 128
<211> LENGTH: 400

<212> TYPE: PRT
<213> ORGANISM: Artificial Sequence
<220> FEATURE:
<223> OTHER INFORMATION: M091_M24dG12 clone

<400> SEQUENCE: 128

```
Leu Met Ala Ser Ser Ser Asn Ser Pro Arg Pro Ser Pro Ala Cys
1               5                   10                  15

Trp Arg Arg Cys Leu Lys Ser Trp Val Ser Pro Trp Ser Pro Ser Thr
            20                  25                  30

Gly Pro Arg Met Trp Cys Cys Thr Ala Arg Thr Ala Ser Thr Ser Ser
                35                  40                  45

Thr Ala Ser Pro Thr Ala Arg Pro Pro Thr Leu Val Pro Ser Met Ala
        50                  55                  60

Pro Pro Pro Val Ala Trp Pro Ser Val Arg Met Arg Ile Arg Leu Ile
65                  70                  75                  80

Thr Ala Arg Trp Asn Trp Ala Pro Ser Pro Ser Arg Ser Pro Pro Ala
                85                  90                  95

Pro Trp Asn Cys Ala Cys Pro Pro Ser Arg Ala Leu Ala Ala Pro Pro
            100                 105                 110

Leu Tyr Leu Ile Asp Arg Phe Glu Asp Gly Lys Ser Ile Tyr Asp Ile
        115                 120                 125

Asp Phe Glu Phe Ile Glu Gly Val Asp Arg Arg Pro Ala Gly His Gly
130                 135                 140

Leu Asn Glu Ile Asp His Leu Thr His Asn Val Tyr Arg Gly Arg Met
145                 150                 155                 160

Gly Phe Trp Ala Asn Phe Tyr Glu Lys Leu Phe Asn Phe Arg Glu Ile
                165                 170                 175

Arg Tyr Phe Asp Ile Gln Gly Tyr Thr Gly Leu Thr Ser Lys Ala
            180                 185                 190

Met Thr Ala Pro Asp Gly Lys Ile Arg Ile Pro Leu Asn Glu Glu Ser
                195                 200                 205

Lys Gln Gly Gly Gly Gln Ile Glu Glu Phe Leu Met Gln Phe Asn Gly
210                 215                 220

Glu Gly Ile Gln His Ile Ala Leu Ile Cys Asp Asn Leu Leu Asp Val
225                 230                 235                 240

Val Asp Lys Leu Gly Met Ala Gly Val Gln Leu Ala Thr Ala Pro Asn
                245                 250                 255

Glu Val Tyr Tyr Glu Met Leu Asp Thr Arg Leu Pro Gly His Gly Gln
                260                 265                 270

Pro Val Pro Glu Leu Gln Ser Arg Gly Ile Leu Leu Asp Gly Thr Thr
            275                 280                 285

Ala Asp Gly Thr His Pro Pro Ala Ser Phe Arg Ser Ser Pro Arg Pro
        290                 295                 300

Cys Trp Ala Arg Cys Ser Ser Asn Ser Ser Ala Arg Ala Thr Thr
305                 310                 315                 320

Ala Thr Ala Leu Ala Lys Ala Thr Ser Arg Arg Cys Ser Ser Arg Trp
                325                 330                 335

Asn Ala Thr Arg Ser Ala Val Val Cys Thr His Lys Thr Ser Asp Ile
            340                 345                 350

Gln Gly Pro Cys Thr Gly Ala Tyr Thr Ala Arg Ser Pro Glu Leu Lys
        355                 360                 365

Arg Ile Pro Met Ser Leu Arg Ser Thr Leu Phe Ser Thr Leu Leu Ala
    370                 375                 380
```

Gly Ala Ala Thr Val Ala Leu Ala Gln Asn Pro Ser Ala Arg Ser His
385                 390                 395                 400

<210> SEQ ID NO 129
<211> LENGTH: 648
<212> TYPE: DNA
<213> ORGANISM: Artificial Sequence
<220> FEATURE:
<223> OTHER INFORMATION: M4aE11 clone

<400> SEQUENCE: 129

```
atgaagacca ttctcgccta tggcgacagc ctgacctatg ggccaaccc gatcccgggc      60
gggccgcggc atgcctatga ggatcgctgg cccacggcgc tggagcaggg gctgggcggc    120
aaggcgcggg tgattgccga ggggctgggt ggtcgcacca cggtgcatga cgactggttt    180
gcgaatgcgg acaggaacgg tgcgcgggtg ctgccgacgc tgctcgagag ccattcgccg    240
ctcgacctga tcgtcatcat gctcggcacc aacgacatca agccgcatca cgggcggacg    300
gccggcgagg ccgggcgggg catggcgcgg ctggtgcaga tcatccgcgg gcactatgcc    360
ggccgcatgc aggacgagcc gcagatcatc ctcgtgtcgc cgccgccgat catcctcggc    420
gactgggcgg acatgatgga ccatttcggc ccgcacgaag cgatcgccac ctcggtggat    480
ttcgctcgcg agtacaagaa gcgggccgac gagcagaagg tgcatttctt cgacgccggc    540
acggtggcga cgaccagcaa ggccgatggc atccacctcg acccggccaa tacgcgcgcc    600
atcggggcag ggctggtgcc gctggtgaag caggtgctcg gcctgtaa                648
```

<210> SEQ ID NO 130
<211> LENGTH: 215
<212> TYPE: PRT
<213> ORGANISM: Artificial Sequence
<220> FEATURE:
<223> OTHER INFORMATION: M4aE11 clone

<400> SEQUENCE: 130

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His

```
                    180                 185                 190
Leu Asp Pro Ala Asn Thr Arg Ala Ile Gly Ala Gly Leu Val Pro Leu
        195                 200                 205

Val Lys Gln Val Leu Gly Leu
        210                 215

<210> SEQ ID NO 131
<211> LENGTH: 6297
<212> TYPE: DNA
<213> ORGANISM: Artificial Sequence
<220> FEATURE:
<223> OTHER INFORMATION: pMSATNcoI-1 plasmid

<400> SEQUENCE: 131
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atccgcgcgc ttacagcagg ctccgcacct gttccgcgag     360
ggccaccccg agatcgcgat tgttggcctc ggtgaagtgg attccgtcga cgccgtcggt     420
gctgatcacc gaacccgcgt cgaagaacgg caccttcatg aacgacgcga gcgcgctgta     480
cacgcgggcg agctcagtgg tcttctgctc gccgccctcg aagatcaact ggaaccaggg     540
gtgcggcatg ggcgccagcg gtggcggcga gaccaccagc accttgggtg ccgggtacgt     600
ggtgccgacg ccgcccgcgc tggtgagcac ctgcgtgacg agcaccgaca tgcccagcgc     660
gatgtcgagc ggggtgcgcc ggaagtaggc cttggtgtcg ttggtgccca gcatgatgat     720
caccaggtcg agcggcaggt gcgtcgcgag gcacgacggc aggtagctcg cgccgttgag     780
ccgcggatcg gtgggtcgt cgatgttggt ggtgcgcgcg ctcagtccct cctcgatcac     840
ctcgaagtcc gctccgagct gctgggccag cacaccggtc cagcgcacgt cggggggcgaa     900 ccgctcggtg ggtgccccgt cttcgacggg gacccagccc caggtcaggg aatcaccgaa     960
acacagaatt cgcttggcca tggtatatct ccttcttaaa gttaaacaaa attatttcta    1020 gagggggaatt gttatccgct cacaattccc ctatagtgag tcgtattaat ttcgcgggat    1080
cgagatctcg atcctctacg ccggacgcat cgtggccggc atcaccggcg ccacaggtgc    1140
ggttgctggc gcctatatcg ccgacatcac cgatggggaa gatcgggctc gccacttcgg    1200
gctcatgagc gcttgtttcg gcgtgggtat ggtggcaggc cccgtggccg ggggactgtt    1260
gggcgccatc tccttgcatg caccattcct gcggcggcg gtgctcaacg gcctcaacct    1320
actactgggc tgcttcctaa tgcaggagtc gcataaggga gagcgtcgag atcccggaca    1380
ccatcgaatg gcgcaaaacc tttcgcggta tggcatgata gcgcccggaa gagagtcaat    1440
tcagggtggt gaatgtgaaa ccagtaacgt tatacgatgt cgcagagtat gccggtgtct    1500
cttatcagac cgtttcccgc gtggtgaacc aggccagcca cgtttctgcg aaaacgcggg    1560
aaaaagtgga agcggcgatg gcggagctga attacattcc caaccgcgtg gcacaacaac    1620
tggcgggcaa acagtcgttg ctgattggcg ttgccacctc cagtctggcc ctgcacgcgc    1680
cgtcgcaaat tgtcgcggcg attaaatctc gcgccgatca actgggtgcc agcgtggtgg    1740
tgtcgatggt agaacgaagc ggcgtcgaag cctgtaaagc ggcggtgcac aatcttctcg    1800
cgcaacgcgt cagtgggctg atcattaact atccgctgga tgaccaggat gccattgctg    1860
```

-continued

```
tggaagctgc ctgcactaat gttccggcgt tatttcttga tgtctctgac cagacaccca   1920
tcaacagtat tattttctcc catgaagacg gtacgcgact gggcgtggag catctggtcg   1980
cattgggtca ccagcaaatc gcgctgttag cgggcccatt aagttctgtc tcggcgcgtc   2040
tgcgtctggc tggctggcat aaatatctca ctcgcaatca aattcagccg atagcggaac   2100
gggaaggcga ctggagtgcc atgtccggtt ttcaacaaac catgcaaatg ctgaatgagg   2160
gcatcgttcc cactgcgatg ctggttgcca acgatcagat ggcgctgggc gcaatgcgcg   2220
ccattaccga gtccgggctg cgcgttggtg cggatatctc ggtagtggga tacgacgata   2280
ccgaagacag ctcatgttat atcccgccgt taaccaccat caaacaggat tttcgcctgc   2340
tggggcaaac cagcgtggac cgcttgctgc aactctctca gggccaggcg gtgaagggca   2400
atcagctgtt gcccgtctca ctggtgaaaa gaaaaaccac cctggcgccc aatacgcaaa   2460
ccgcctctcc ccgcgcgttg gccgattcat taatgcagct ggcacgacag gtttcccgac   2520
tggaaagcgg gcagtgagcg caacgcaatt aatgtaagtt agctcactca ttaggcaccg   2580
ggatctcgac cgatgccctt gagagccttc aacccagtca gctccttccg gtgggcgcgg   2640
ggcatgacta tcgtcgccgc acttatgact gtcttcttta tcatgcaact cgtaggacag   2700
gtgccggcag cgctctgggt catttttcggc gaggaccgct ttcgctggag cgcgacgatg   2760
atcggcctgt cgcttgcggt attcggaatc ttgcacgccc tcgctcaagc cttcgtcact   2820
ggtcccgcca ccaaacgttt cggcgagaag caggccatta tcgccggcat ggcggccgac   2880
gcgctgggct acgtcttgct ggcgttcgcg acgcgaggct ggatggcctt ccccattatg   2940
attcttctcg cttccggcgg catcgggatg cccgcgttgc aggccatgct gtccaggcag   3000
gtagatgacg accatcaggg acagcttcaa ggatcgctcg cggctcttac cagcctaact   3060
tcgatcactg gaccgctgat cgtcacggcg atttatgccg cctcggcgag cacatggaac   3120
gggttggcat ggattgtagg cgccgcccta taccttgtct gcctccccgc gttgcgtcgc   3180
ggtgcatgga gccgggccac ctcgacctga atggaagccg gcggcacctc gctaacggat   3240
tcaccactcc aagaattgga gccaatcaat tcttgcggag aactgtgaat gcgcaaacca   3300
acccttggca gaacatatcc atcgcgtccg ccatctccag cagccgcacg cggcgcatct   3360
cgggcagcgt tgggtcctgg ccacgggtgc gcatgatcgt gctcctgtcg ttgaggaccc   3420
ggctaggctg gcggggttgc cttactggtt agcagaatga atcaccgata cgcgagcgaa   3480
cgtgaagcga ctgctgctgc aaaacgtctg cgacctgagc aacaacatga atggtcttcg   3540
gtttccgtgt ttcgtaaagt ctggaaacgc ggaagtcagc gccctgcacc attatgttcc   3600
ggatctgcat cgcaggatgc tgctggctac cctgtggaac acctacatct gtattaacga   3660
agcgctggca ttgaccctga gtgattttc tctggtcccg ccgcatccat accgccagtt   3720
gtttaccctc acaacgttcc agtaaccggg catgttcatc atcagtaacc cgtatcgtga   3780
gcatcctctc tcgtttcatc ggtatcatta ccccccatgaa cagaaatccc ccttacacgg   3840
aggcatcagt gaccaaacag gaaaaaaccg cccttaacat ggcccgcttt atcagaagcc   3900
agacattaac gcttctggag aaactcaacg agctggacgc ggatgaacag gcagacatct   3960
gtgaatcgct tcacgaccac gctgatgagc tttaccgcag ctgcctcgcg cgtttcggtg   4020
atgacggtga aaacctctga cacatgcagc tcccggagac ggtcacagct tgtctgtaag   4080
cggatgccgg gagcagacaa gcccgtcagg gcgcgtcagc gggtgttggc gggtgtcggg   4140
gcgcagccat gacccagtca cgtagcgata gcggagtgta tactggctta actatgcggc   4200
```

```
atcagagcag attgtactga gagtgcacca tatatgcggt gtgaaatacc gcacagatgc    4260
gtaaggagaa ataccgcat caggcgctct ccgcttcct cgctcactga ctcgctgcgc      4320
tcggtcgttc ggctgcggcg agcggtatca gctcactcaa aggcggtaat acggttatcc    4380
acagaatcag gggataacgc aggaaagaac atgtgagcaa aaggccagca aaaggccagg    4440
aaccgtaaaa aggccgcgtt gctggcgttt ttccataggc tccgccccc tgacgagcat     4500
cacaaaaatc gacgctcaag tcagaggtgg cgaaacccga caggactata aagataccag    4560
gcgtttcccc ctggaagctc cctcgtgcgc tctcctgttc cgaccctgcc gcttaccgga    4620
tacctgtccg cctttctccc ttcgggaagc gtggcgcttt ctcatagctc acgctgtagg    4680
tatctcagtt cggtgtaggt cgttcgctcc aagctgggct gtgtgcacga accccccgtt    4740
cagcccgacc gctgcgcctt atccggtaac tatcgtcttg agtccaaccc ggtaagacac    4800
gacttatcgc cactggcagc agccactggt aacaggatta gcagagcgag gtatgtaggc    4860
ggtgctacag agttcttgaa gtggtggcct aactacggct acactagaag gacagtattt    4920
ggtatctgcg ctctgctgaa gccagttacc ttcggaaaaa gagttggtag ctcttgatcc    4980
ggcaaacaaa ccaccgctgg tagcggtggt ttttttgttt gcaagcagca gattacgcgc    5040
agaaaaaaag gatctcaaga agatccttg atcttttcta cggggtctga cgctcagtgg    5100
aacgaaaact cacgttaagg gattttggtc atgagattat caaaaaggat cttcacctag    5160
atccttttaa attaaaaatg aagttttaaa tcaatctaaa gtatatatga gtaaacttgg    5220
tctgacagtt accaatgctt aatcagtgag gcacctatct cagcgatctg tctatttcgt    5280
tcatccatag ttgcctgact ccccgtcgtg tagataacta cgatacggga gggcttacca    5340
tctggcccca gtgctgcaat gataccgcga gacccacgct caccggctcc agatttatca    5400
gcaataaacc agccagccgg aagggccgag cgcagaagtg gtcctgcaac tttatccgcc    5460
tccatccagt ctattaattg ttgccgggaa gctagagtaa gtagttcgcc agttaatagt    5520
ttgcgcaacg ttgttgccat tgctgcaggc atcgtggtgt cacgctcgtc gtttggtatg    5580
gcttcattca gctccggttc ccaacgatca aggcgagtta catgatcccc catgttgtgc    5640
aaaaaagcgg ttagctcctt cggtcctccg atcgttgtca gaagtaagtt ggccgcagtg    5700
ttatcactca tggttatggc agcactgcat aattctctta ctgtcatgcc atccgtaaga    5760
tgcttttctg tgactggtga gtactcaacc aagtcattct gagaatagtg tatgcggcga    5820
ccgagttgct cttgcccggc gtcaacacgg gataataccg cgccacatag cagaacttta    5880
aaagtgctca tcattggaaa acgttcttcg ggcgaaaac tctcaaggat cttaccgctg     5940
ttgagatcca gttcgatgta acccactcgt gcacccaact gatcttcagc atcttttact    6000
ttcaccagcg tttctgggtg agcaaaaaca ggaaggcaaa atgccgcaaa aagggaata    6060
agggcgacac ggaaatgttg aatactcata ctcttccttt ttcaatatta ttgaagcatt    6120
tatcagggtt attgtctcat gagcggatac atatttgaat gtatttagaa aaataaacaa    6180
ataggggttc cgcgcacatt tccccgaaaa gtgccacctg acgtctaaga aaccattatt    6240
atcatgacat aacctataa aaataggcgt atcacgaggc cctttcgtct tcaagaa       6297
```

<210> SEQ ID NO 132
<211> LENGTH: 14
<212> TYPE: PRT
<213> ORGANISM: Bacillus subtilis pnbA

<400> SEQUENCE: 132

Ala Thr Ala Ala Gly Gly Ala Gly Gly Thr Gly Ala Thr Cys

<210> SEQ ID NO 133
<211> LENGTH: 4100
<212> TYPE: DNA
<213> ORGANISM: Artificial Sequence
<220> FEATURE:
<223> OTHER INFORMATION: pAH502R plasmid

<400> SEQUENCE: 133

```
ctaaattgta agcgttaata ttttgttaaa attcgcgtta aattttttgtt aaatcagctc      60
atttttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tgggtaccgg    660
gccccccctc gaggtcgacg gtatcgataa gcttgatatc gaattcctgc agcccggggg    720
atccgcccaa gcttaaggag gtgatctaga attccatggc caagcgaatt ctgtgtttcg    780
gtgattccct gacctggggc tgggtccccg tcgaagacgg ggcacccacc gagcggttcg    840
cccccgacgt gcgctggacc ggtgtgctgg cccagcagct cggagcggac ttcgaggtga    900
tcgaggaggg actgagcgcg cgcaccacca acatcgacga ccccaccgat ccgcggctca    960
acggcgcgag ctacctgccg tcgtgcctcg cgacgcacct gccgctcgac ctggtgatca   1020
tcatgctggg caccaacgac accaaggcct acttccggcg caccccgctc gacatcgcgc   1080
tgggcatgtc ggtgctcgtc acgcaggtgc tcaccagcgc gggcggcgtc ggcaccacgt   1140
acccggcacc caaggtgctg gtggtctcgc cgccaccgct ggcgcccatg ccgcacccct   1200
ggttccagtt gatcttcgag ggcggcgagc agaagaccac tgagctcgcc cgcgtgtaca   1260
gcgcgctcgc gtcgttcatg aaggtgccgt tcttcgacgc gggttcggtg atcagcaccg   1320
acggcgtcga cggaatccac ttcaccgagg ccaacaatcg cgatctcggg gtggccctcg   1380
cggaacaggt gcggagcctg ctgtaaaagg atccccggga agcttgcatg gctagagcg   1440
gccgccaccg cggtggagct ccagcttttg ttccctttag tgagggttaa ttgcgcgctt   1500
ggcgtaatca tggtcatagc tgtttcctgt gtgaaattgt tatccgctca caattccaca   1560
caacatacga gccggaagca taaagtgtaa agcctgggt gcctaatgag tgagctaact   1620
cacattaatt gcgttgcgct cactgcccgc tttccagtcg ggaaacctgt cgtgccagct   1680
gcattaatga atcggccaac gcgcgggag aggcggtttg cgtattgggc gctcttccgc    1740
ttcctcgctc actgactcgc tgcgctcggt cgttcggctg cggcgagcgg tatcagctca   1800
ctcaaaggcg gtaatacggt tatccacaga atcagggat aacgcaggaa agaacatgtg   1860
agcaaaaggc cagcaaaagg ccaggaaccg taaaaaggcc gcgttgctgg cgtttttcca   1920
taggctccgc cccctgacg agcatcacaa aaatcgacg ctcaagtcaga ggtggcgaaa    1980
cccgacagga ctataaagat accaggcgtt tcccctgga agctccctcg tgcgctctcc   2040
```

```
tgttccgacc ctgccgctta ccggatacct gtccgccttt ctcccttcgg gaagcgtggc    2100
gctttctcat agctcacgct gtaggtatct cagttcggtg taggtcgttc gctccaagct    2160
gggctgtgtg cacgaacccc ccgttcagcc cgaccgctgc gccttatccg gtaactatcg    2220
tcttgagtcc aacccggtaa gacacgactt atcgccactg gcagcagcca ctggtaacag    2280
gattagcaga gcgaggtatg taggcggtgc tacagagttc ttgaagtggt ggcctaacta    2340
cggctacact agaaggacag tatttggtat ctgcgctctg ctgaagccag ttaccttcgg    2400
aaaaagagtt ggtagctctt gatccggcaa acaaaccacc gctggtagcg gtggtttttt    2460
tgtttgcaag cagcagatta cgcgcagaaa aaaggatct caagaagatc ctttgatctt    2520
ttctacgggg tctgacgctc agtggaacga aaactcacgt taagggattt tggtcatgag    2580
attatcaaaa aggatcttca cctagatcct tttcgaccga ataaatacct gtgacggaag    2640
atcacttcgc agaataaata atcctggtg tccctgttga taccgggaag ccctgggcca    2700
acttttggcg aaaatgagac gttgatcggc acgtaagagg ttccaacttt caccataatg    2760
aaataagatc actaccgggc gtattttttg agttgtcgag attttcagga gctaaggaag    2820
ctaaaatgga gaaaaaaatc actggatata ccaccgttga tatatcccaa tggcatcgta    2880
aagaacattt tgaggcattt cagtcagttg ctcaatgtac ctataaccag accgttcagc    2940
tggatattac ggcctttta agaccgtaa agaaaaataa gcacaagttt atccggcct    3000 ttattcacat tcttgcccgc ctgatgaatg ctcatccgga attacgtatg gcaatgaaag    3060
acggtgagct ggtgatatgg gatagtgttc acccttgtta caccgttttc catgagcaaa    3120
ctgaaacgtt ttcatcgctc tggagtgaat accacgacga tttccggcag tttctacaca    3180
tatattcgca agatgtggcg tgttacggtg aaaacctggc ctatttccct aaagggttta    3240
ttgagaatat gttttcgtc tcagccaatc cctgggtgag tttcaccagt tttgatttaa    3300
acgtggccaa tatggacaac ttcttcgccc cgttttcacc atgggcaaat attatacgca    3360
aggcgacaag gtgctgatgc cgctggcgat tcaggttcat catgccgttt gtgatggctt    3420
ccatgtcggc agaatgctta atgaattaca acagtactgc gatgagtggc agggcggggc    3480
gtaatttttt taaggcagtt attggtgccc ttaaacgcct ggttgctacg cctgaataag    3540
tgataataag cggatgaatg gcagaaattc gaaagcaaat cgacccggt cgtcggttca    3600 gggcagggtc gttaaatagc cgcttatgtc tattgctggt ttaccggttt attgactacc    3660
ggaagcagtg tgaccgtgtg cttctcaaat gcctgaggcc agtttgctca ggctctcccc    3720
gtggaggtaa taattgacga tatgatcctt tttttctgat caaaagtgct catcattgga    3780
aaacgttctt cggggcgaaa actctcaagg atcttaccgc tgttgagatc cagttcgatg    3840
taacccactc gtgcacccaa ctgatcttca gcatctttta ctttcaccag cgtttctggg    3900
tgagcaaaaa caggaaggca aaatgccgca aaaagggaa taagggcgac acggaaatgt    3960
tgaatactca tactcttcct ttttcaatat tattgaagca tttatcaagg ttattgtct    4020 catgagcgga tacatatttg aatgtattta gaaaaataaa caataggggg ttccgcgcac    4080
atttccccga aaagtgccac                                                 4100
```

<210> SEQ ID NO 134
<211> LENGTH: 54
<212> TYPE: DNA
<213> ORGANISM: Artificial Sequence
<220> FEATURE:
<223> OTHER INFORMATION: primer

<400> SEQUENCE: 134

```
ccaagcttaa ggaggtgatc tagaattcca tggccaagcg aattctgtgt ttcg        54
```

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135

```
ggggatccott ttacagcagg ctccgcacct                                   30
```

<210> SEQ ID NO 136
<211> LENGTH: 9262
<212> TYPE: DNA
<213> ORGANISM: Artificial Sequence
<220> FEATURE:
<223> OTHER INFORMATION: pAH503 construct

<400> SEQUENCE: 136

```
ataattctac acagcccagt ccagactatt cggcactgaa attatgggtg aagtggtcaa    60
gacctcacta ggcaccttaa aaatagcgca ccctgaagaa gatttatttg aggtagccct   120
tgcctaccta gcttccaaga aagatatcct aacagcacaa gagcggaaag atgttttgtt   180
ctacatccag aacaacctct gctaaaattc ctgaaaaatt ttgcaaaaag ttgttgactt   240
tatctacaag gtgtggcata atgtgtggaa ttgtgagcgc tcacaattaa gcttaaggag   300
gtgatctaga attccatggc caagcgaatt ctgtgtttcg gtgattccct gacctggggc   360
tgggtccccg tcgaagacgg ggcacccacc gagcggttcg cccccgacgt gcgctggacc   420
ggtgtgctgg cccagcagct cggagcggac ttcgaggtga tcgaggaggg actgagcgcg   480
cgcaccacca acatcgacga ccccaccgat ccgcggctca acggcgcgag ctacctgccg   540
tcgtgcctcg cgacgcacct gccgctcgac ctggtgatca tcatgctggg caccaacgac   600
accaaggcct acttccggcg cacccccgctc gacatcgcgc tgggcatgtc ggtgctcgtc   660
acgcaggtgc tcaccagcgc gggcggcgtc ggcaccacgt acccggctcc caaggtgctg   720
gtggtctcgc cgccaccgct ggcgcccatg ccgcacccct ggttccagtt gatcttcgag   780
ggcggcgagc agaagaccac tgagctgccc cgcgtgtaca gcgcgctcgc gtcgttcatg   840
aaggtgccgt tcttcgacgc gggttcggtg atcagcaccg acggcgtcga cggaatccac   900
ttcaccgagg ccaacaatcg cgatctcggg gtggccctcg cggaacaggt gcggagcctg   960
ctgtaaaagg atccccagct tgttgataca ctaatgcttt tatatatggga aaaggtggtg  1020
aactactgtg gaagttactg acgtaagatt acgggtcgac cgggaaaacc ctggcgttac  1080
ccaacttaat cgccttgcag cacatccccc tttcgccagc tggcgtaata gcgaagaggc  1140
ccgcaccgat cgcccttccc aacagttgcg cagcctgaat ggcgaatggc gctttgcctg  1200
gtttccggca ccagaagcgg tgccggaaag ctggctggag tgcgatcttc ctgaggccga  1260
tactgtcgtc gtcccctcaa actggcagat gcacggttac gatgcgccca tctacaccaa  1320
cgtaacctat cccattacgg tcaatccgcc gtttgttccc acgagaatc cgacgggttg  1380
ttactcgctc acatttaatg ttgatgaaag ctggctacag gaaggccaga cgcgaattat  1440
ttttgatggc gttaactcgg cgtttcatct gtggtgcaac gggcgctggg tcggttacgg  1500
ccaggacagt cgtttgccgt ctgaatttga cctgagcgca ttttttacgcg ccggagaaaa  1560
ccgcctcgcg gtgatggtgc tgcgttggag tgacggcagt tatctggaag atcaggatat  1620
```

```
gtggcggatg agcggcattt tccgtgacgt ctcgttgctg cataaaccga ctacacaaat    1680
cagcgatttc catgttgcca ctcgctttaa tgatgatttc agccgcgctg tactggaggc    1740
tgaagttcag atgtgcggcg agttgcgtga ctacctacgg gtaacagttt ctttatggca    1800
gggtgaaacg caggtcgcca gcggcaccgc gcctttcggc ggtgaaatta tcgatgagcg    1860
tggtggttat gccgatcgcg tcacactacg tctgaacgtc gaaaacccga actgtggag    1920 cgccgaaatc ccgaatctct atcgtgcggt ggttgaactg cacaccgccg acggcacgct    1980
gattgaagca gaagcctgcg atgtcggttt ccgcgaggtg cggattgaaa atggtctgct    2040
gctgctgaac ggcaagccgt tgctgattcg aggcgttaac cgtcacgagc atcatcctct    2100
gcatggtcag gtcatggatg agcagacgat ggtgcaggat atcctgctga tgaagcagaa    2160
caactttaac gccgtgcgct gttcgcatta tccgaaccat ccgctgtggt acacgctgtg    2220
cgaccgctac ggcctgtatg tggtggatga agccaatatt gaaacccacg gcatggtgcc    2280
aatgaatcgt ctgaccgatg atccgcgctg gctaccggcg atgagcgaac gcgtaacgcg    2340
aatggtgcag cgcgatcgta atcacccgag tgtgatcatc tggtcgctgg ggaatgaatc    2400
aggccacggc gctaatacg acgcgctgta tcgctggatc aaatctgtcg atccttcccg    2460
cccggtgcag tatgaaggcg gcggagccga caccacggcc accgatatta tttgcccgat    2520
gtacgcgcgc gtgatgaag accagcccctt cccggctgtg ccgaaatggt ccatcaaaaa    2580
atggctttcg ctacctggag agacgcgccc gctgatcctt tgcgaatacg cccacgcgat    2640
gggtaacagt cttggcggtt tcgctaaata ctggcaggcg tttcgtcagt atccccgttt    2700
acagggcggc ttcgtctggg actgggtgga tcagtcgctg attaaatatg atgaaaacgg    2760
caacccgtgg tcggcttacg gcggtgattt tggcgatacg ccgaacgatc gccagttctg    2820
tatgaacggt ctggtctttg ccgaccgcac gccgcatcca gcgctgacgg aagcaaaaca    2880
ccagcagcag ttttccagt tccgtttatc gggcaaacc atcgaagtga ccagcgaata    2940
cctgttccgt catagcgata acgagctcct gcactggatg gtggcgctgg atggtaagcc    3000
gctggcaagc ggtgaagtgc ctctggatgt cgctccacaa ggtaaacagt tgattgaact    3060
gcctgaacta ccgcagccgg agagcgccgg gcaactctgg ctcacagtac gcgtagtgca    3120
accgaacgcg accgcatggt cagaagccgg gcacatcagc gcctggcagc agtggcgtct    3180
ggcggaaaac ctcagtgtga cgctccccgc cgcgtcccac gccatcccgc atctgaccac    3240
cagcgaaatg gattttgca tcgagctggg taataagcgt tggcaattta accgccagtc    3300
aggctttctt tcacagatgt ggattggcga taaaaacaa ctgctgacgc cgctgcgcga    3360
tcagttcacc cgtgcaccgc tggataacga cattggcgta agtgaagcga cccgcattga    3420
ccctaacgcc tgggtcgaac gctggaaggc ggcgggccat taccaggccg aagcagcgtt    3480
gttgcagtgc acggcagata cacttgctga tgcggtgctg attacgaccg ctcacgcgtg    3540
gcagcatcag gggaaaacct tatttatcag ccggaaaacc taccgattg atggtagtgg    3600 tcaaatggcg attaccgttg atgttgaagt ggcgagcgat acaccgcatc cggcgcggat    3660
tggcctgaac tgccagctgg cgcaggtagc agagcgggta aactggctcg gattagggcc    3720
gcaagaaaac tatcccgacc gccttactgc cgcctgtttt gaccgctggg atctgccatt    3780
gtcagacatg tataccccgt acgtcttccc gagcgaaaac ggtctgcgct gcgggacgcg    3840
cgaattgaat tatggcccac accagtggcg cggcgacttc cagttcaaca tcagccgcta    3900
cagtcaacag caactgatgg aaaccagcca tcgccatctg ctgcacgcgg aagaaggcac    3960
```

```
atggctgaat atcgacggtt tccatatggg gattggtggc gacgactcct ggagcccgtc   4020
agtatcggcg gaattacagc tgagcgccgg tcgctaccat taccagttgg tctggtgtca   4080
aaaataataa taaccgggca ggccatgtct gcccgtattt cgcgtaagga aatccattat   4140
gtactatttc aagctaattc cggtggaaac gaggtcatca tttccttccg aaaaaacggt   4200
tgcatttaaa tcttacatat gtaatacttt caaagactac atttgtaaga tttgatgttt   4260
gagtcggctg aaagatcgta cgtaccaatt attgtttcgt gattgttcaa gccataacac   4320
tgtagggata gtggaaagag tgcttcatct ggttacgatc aatcaaatat tcaaacggag   4380
ggagacgatt ttgatgaaac cagtaacgtt atacgatgtc gcagagtatg ccggtgtctc   4440
ttatcagacc gtttcccgcg tggtgaacca ggccagccac gtttctgcga aacgcggga   4500
aaaagtggaa gcggcgatgg cggagctgaa ttacattccc aaccgcgtgg cacaacaact   4560
ggcgggcaaa cagtcgttgc tgattggcgt tgccacctcc agtctggccc tgcacgcgcc   4620
gtcgcaaatt gtcgcggcga ttaaatctcg cgccgatcaa ctgggtgcca gcgtggtggt   4680
gtcgatggta gaacgaagcg gcgtcgaagc ctgtaaagcg gcggtgcaca atcttctcgc   4740
gcaacgcgtc agtgggctga tcattaacta tccgctggat gaccaggatg ccattgctgt   4800
ggaagctgcc tgcactaatg ttccggcgtt atttcttgat gtctctgacc agacacccat   4860
caacagtatt attttctccc atgaagacgg tacgcgactg ggcgtggagc atctggtcgc   4920
attgggtcac cagcaaatcg cgctgttagc gggcccatta agttctgtct cggcgcgtct   4980
gcgtctggct ggctggcata aatatctcac tcgcaatcaa attcagccga tagcggaacg   5040
ggaaggcgac tggagtgcca tgtccggttt tcaacaaacc atgcaaatgc tgaatgaggg   5100
catcgttccc actgcgatgc tggttgccaa cgatcagatg gcgctgggcg caatgcgcgc   5160
cattaccgag tccgggctgc gcgttggtgc ggatatctcg gtagtgggat acgacgatac   5220
cgaagacagc tcatgttata tcccgccgtc aaccaccatc aaacaggatt ttcgcctgct   5280
ggggcaaacc agcgtggacc gcttgctgca actctctcag gccaggcggt gaagggcaa   5340
tcagctgttg cccgtctcac tggtgaaaag aaaaaccacc ctggcgccca atacgcaaac   5400
cgcctctccc cgcgcgttgg ccgattcatt aatgcagctg gcacgacagg tttcccgact   5460
ggaaagcggg cagtgagcgc aacgcaatta atgtgagtta ggcatcgcat cctgtctcgc   5520
gtcgtcggtg atgacggtga aaacctctga cacatgcagc tcccggagac ggtcacagct   5580
tgtctgtaag cggatgccgg gagcagacaa gcccgtcagg gcgcgtcagc gggtgttggc   5640
gggtgtcggg gcgcagccat gacccagtca cgtagcgata gcggagtgta tactggctta   5700
actatgcggc atcagagcag attgtactga gagtgcacca tatgcggtgt gaaataccgc   5760
acagatgcgt aaggagaaaa taccgcatca ggcgctcttc cgcttcctcg ctcactgact   5820
cgctgcgctc ggtcgttcgg ctgcggcgag cggtatcagc tcactcaaag gcggtaatac   5880
ggttatccac agaatcaggg gataacgcag gaaagaacat gtgagcaaaa ggccagcaaa   5940
aggccaggaa ccgtaaaaag gccgcgttgc tggcgttttt ccataggctc cgcccccctg   6000
acgagcatca caaaaatcga cgctcaagtc agaggtggcg aaacccgaca ggactataaa   6060
gataccaggc gtttccccct ggaagctccc tcgtgcgctc tcctgttccg accctgccgc   6120
ttaccggata cctgtccgcc tttctccctt cgggaagcgt ggcgctttct caatgctcac   6180
gctgtaggta tctcagttcg gtgtaggtcg ttcgctccaa gctgggctgt gtgcacgaac   6240
cccccgttca gcccgaccgc tgcgccttat ccggtaacta tcgtcttgag tccaacccgg   6300
taagacacga cttatcgcca ctggcagcag ccactggtaa caggattagc agagcgaggt   6360
```

```
atgtaggcgg tgctacagag ttcttgaagt ggtggcctaa ctacggctac actagaagga   6420
cagtatttgg tatctgcgct ctgctgaagc cagttacctt cggaaaaaga gttggtagct   6480
cttgatccgg caaacaaacc accgctggta gcggtggttt ttttgtttgc aagcagcaga   6540
ttacgcgcag aaaaaaagga tctcaagaag atcctttgat cttttctacg ggtctgacg    6600 ctcagtggaa cgaaaactca cgttaaggga ttttggtcat gagattatca aaaaggatct   6660
tcacctagat ccttttaaat taaaaatgaa gttttaaatc aatctaaagt atatatgagt   6720
aaacttggtc tgacagttac caatgcttaa tcagtgaggc acctatctca gcgatctgtc   6780
tatttcgttc atccatagtt gcctgactcc ccgtcgtgta gataactacg atacgggagg   6840
gcttaccatc tggccccagt gctgcaatga taccgcgaga cccacgctca ccggctccag   6900
atttatcagc aataaaccag ccagccggaa gggccgagcg cagaagtggt cctgcaactt   6960
tatccgcctc catccagtct attaattgtt gccgggaagc tagagtaagt agttcgccag   7020
ttaatagttt gcgcaacgtt gttgccattg ctgcaggcat cgtggtgtca cgctcgtcgt   7080
ttggtatggc ttcattcagc tccggttccc aacgatcaag gcgagttaca tgatccccca   7140
tgttgtgcaa aaaagcggtt agctccttcg gtcctccgat cgttgtcaga gtaagttgg    7200 ccgcagtgtt atcactcatg gttatggcag cactgcataa ttctcttact gtcatgccat   7260
ccgtaagatg cttttctgtg actggtgagt actcaaccaa gtcattctga atagtgta    7320 tgcggcgacc gagttgctct tgcccggcgt caacacggga taataccgcg ccacatagca   7380
gaactttaaa agtgctcatc attggaaaac gttcttcggg gcgaaaactc tcaaggatct   7440
taccgctgtt gagatccagt tcgatgtaac ccactcgtgc acccaactga tcttcagcat   7500
cttttacttt caccagcgtt tctgggtgag caaaaacagg aaggcaaaat gccgcaaaaa   7560
agggaataag ggcgacacgg aaatgttgaa tactcatact cttccttttt caatattatt   7620
gaagcattta tcagggttat tgtctcatga gcggatacat atttgaatgt atttagaaaa   7680
ataaacaaat aggggttccg cgcacatttc cccgaaaagt gccacctgac gtctaagaaa   7740
ccattattat catgacatta acctataaaa ataggcgtat cacgaggccc tttcgtcttc   7800
aagaattgat cctctagcac aaaagaaaaa cgaaatgata caccaatcag tgcaaaaaaa   7860
gatataatgg gagataagac ggttcgtgtt cgtgctgact tgcaccatat cataaaaatc   7920
gaaacagcaa agaatggcgg aaacgtaaaa gaagttatgg aaataagact tagaagcaaa   7980
cttaagagtg tgttgatagt gcagtatctt aaaattttgt ataataggaa ttgaagttaa   8040
attagatgct aaaaatttgt aattaagaag gagtgattac atgaacaaaa atataaaata   8100
ttctcaaaac ttttttaacga gtgaaaaagt actcaaccaa ataataaaac aattgaattt   8160
aaaagaaacc gataccgttt acgaaattgg aacaggtaaa gggcatttaa cgacgaaact   8220
ggctaaaata agtaaacagg taacgtctat tgaattagac agtcatctat tcaacttatc   8280
gtcagaaaaa ttaaaactga atactcgtgt cactttaatt caccaagata ttctacagtt   8340
tcaattccct aacaaacaga ggtataaaat tgttgggagt attccttacc atttaagcac   8400
acaaattatt aaaaagtgg ttttttgaaag ccatgcgtct gacatctatc tgattgttga   8460
agaaggattc tacaagcgta ccttggatat tcaccgaaca ctagggttgc tcttgcacac   8520
tcaagtctcg attcagcaat tgcttaagct gccagcggaa tgctttcatc ctaaaccaaa   8580
agtaaacagt gtcttaataa aacttacccg ccataccaca gatgttccag ataaatattg   8640
gaagctatat acgtactttg tttcaaaatg ggtcaatcga gaatatcgtc aactgtttac   8700
```

-continued

| | |
|---|---|
| taaaaatcag tttcatcaag caatgaaaca cgccaaagta aacaatttaa gtaccgttac | 8760 |
| ttatgagcaa gtattgtcta tttttaatag ttatctatta tttaacggga ggaaataatt | 8820 |
| ctatgagtcg cttttgtaaa tttggaaagt tacacgttac taaagggaat gtagataaat | 8880 |
| tattaggtat actactgaca gcttccaagg agctaaagag gtccctagac tctagacccg | 8940 |
| gggatctctg cagtcggatc tggtaatgac tctctagctt gaggcatcaa ataaaacgaa | 9000 |
| aggctcagtc gaaagactgg gcctttcgtt ttatctgttg tttgtcggtg aacgctctcc | 9060 |
| tgagtaggac aaatccgccg ctctagctaa gcagaaggcc atcctgacgg atggcctttt | 9120 |
| tgcgttctta caaactcttg ttaactctag agctgcctgc gcgtttcgg tgatgaagat | 9180 |
| cttcccgatg attaattaat tcagaacgct cggttgccgc cgggcgtttt ttatgcagca | 9240 |
| atggcaagaa cgttgctcta ga | 9262 |

<210> SEQ ID NO 137
<211> LENGTH: 4335
<212> TYPE: DNA
<213> ORGANISM: Artificial Sequence
<220> FEATURE:
<223> OTHER INFORMATION: pAH505 plasmi

<400> SEQUENCE: 137

| | |
|---|---|
| gatcttccaa gatatcctaa cagcacaaga gcggaaagat gttttgttct acatccagaa | 60 |
| caacctctgc taaaattcct gaaaattttt gcaaaaagtt gttgacttta tctacaaggt | 120 |
| gtggcataat gtgtggaatt gtgagcgctc acaattaagc ttaaggaggt gatctagaat | 180 |
| tccatggcca gcgaattct gtgtttcggt gattccctga cctggggctg gtccccgtc | 240 |
| gaagacgggg cacccaccga gcggttcgcc cccgacgtgc gctggaccgg tgtgctggcc | 300 |
| cagcagctcg gagcggactt cgaggtgatc gaggagggac tgagcgcgcg caccaccaac | 360 |
| atcgacgacc ccaccgatcc gcggctcaac ggcgcgagct acctgccgtc gtgcctcgcg | 420 |
| acgcacctgc cgctcgacct ggtgatcatc atgctgggca ccaacgacac caaggcctac | 480 |
| ttccggcgca ccccgctcga catcgcgctg gcatgtcgg tgctcgtcac gcaggtgctc | 540 |
| accagcgcgg gcgcgtcgg caccacgtac ccggctccca aggtgctggt ggtctcgccg | 600 |
| ccaccgctgg cgcccatgcc gcaccctgg ttccagttga tcttcgaggg cggcgagcag | 660 |
| aagaccactg agctcgcccg cgtgtacagc gcgctcgcgt cgttcatgaa ggtgccgttc | 720 |
| ttcgacgcgg gttcggtgat cagcaccgac ggcgtcgacg gaatccactt caccgaggcc | 780 |
| aacaatcgcg atctcggggt ggccctcgcg gaacaggtgc ggagcctgct gtaaaaggat | 840 |
| cccatcgcat gcggtacctc tagaagaagc ttggagacaa ggtaaaggat aaaacagcac | 900 |
| aattccaaga aaacacgat ttagaaccta aaagaacga atttgaacta actcataacc | 960 |
| gagaggtaaa aaagaacga agtcgagatc agggaatgag tttataaaat aaaaaaagca | 1020 |
| cctgaaaagg tgtctttttt tgatggtttt gaacttgttc tttcttatct tgatacatat | 1080 |
| agaaataacg tcatttttat tttagttgct gaaaggtgcg ttgaagtgtt ggtatgtatg | 1140 |
| tgttttaaag tattgaaaac ccttaaaatt ggttgcacag aaaaacccca tctgttaaag | 1200 |
| ttataagtga ctaaacaaat aactaaatag atggggtt cttttaatat tatgtgtcct | 1260 |
| aatagtagca tttattcaga tgaaaaatca agggttttag tggacaagac aaaaagtgga | 1320 |
| aaagtgagac catggagaga aaagaaaatc gctaatgttg attactttga acttctgcat | 1380 |
| attcttgaat ttaaaaaggc tgaaagagta aaagattgtg ctgaaatatt agagtataaa | 1440 |
| caaaatcgtg aaacaggcga agaaagttg tatcgagtgt ggttttgtaa atccaggctt | 1500 |

```
tgtccaatgt gcaactggag gagagcaatg aaacatggca ttcagtcaca aaaggttgtt    1560
gctgaagtta ttaaacaaaa gccaacagtt cgttggttgt ttctcacatt aacagttaaa    1620
aatgtttatg atggcgaaga attaaataag agtttgtcag atatggctca aggatttcgc    1680
cgaatgatgc aatataaaaa aattaataaa aatcttgttg gttttatgcg tgcaacggaa    1740
gtgacaataa ataataaaga taattcttat aatcagcaca tgcatgtatt ggtatgtgtg    1800
gaaccaactt attttaagaa tacagaaaac tacgtgaatc aaaaacaatg gattcaattt    1860
tggaaaaagg caatgaaatt agactatgat ccaaatgtaa aagttcaaat gattcgaccg    1920
aaaaataaat ataaatcgga tatacaatcg gcaattgacg aaactgcaaa atatcctgta    1980
aaggatacgg attttatgac cgatgatgaa gaaaagaatt tgaaacgttt gtctgatttg    2040
gaggaaggtt tacaccgtaa aaggttaatc tcctatggtg gtttgttaaa agaaatacat    2100
aaaaaattaa accttgatga cacagaagaa ggcgatttga ttcatacaga tgatgacgaa    2160
aaagccgatg aagatggatt ttctattatt gcaatgtgga attgggaacg gaaaaattat    2220
tttattaaag agtagttcaa caaacgggcc agtttgttga agattagatg ctataattgt    2280
tattaaaagg attgaaggat gcttaggaag acgagttatt aatagctgaa taagaacggt    2340
gctctccaaa tattcttatt tagaaaagca aatctaaaat tatctgaaaa gggaatgaga    2400
atagtgaatg gaccaataat aatgactaga gaagaaagaa tgaagattgt tcatgaaatt    2460
aaggaacgaa tattggataa atatggggat gatgttaagg ctattggtgt ttatggctct    2520
cttggtcgtc agactgatgg gcccttcg gatattgaga tgatgtgtgt catgtcaaca    2580
gaggaagcag agttcagcca tgaatggaca accggtgagt ggaaggtgga agtgaatttt    2640
gatagcgaag agattctact agattatgca tctcaggtgg aatcagattg gccgcttaca    2700
catggtcaat tttctctat tttgccgatt tatgattcag gtggatactt agagaaagtg    2760
tatcaaactg ctaaatcggt agaagcccaa acgttccacg atgcgatttg tgcccttatc    2820
gtagaagagc tgtttgaata tgcaggcaaa tggcgtaata ttcgtgtgca aggaccgaca    2880
acatttctac catccttgac tgtacaggta gcaatggcag gtgccatgtt gattggtctg    2940
catcatcgca tctgttatac gacgagcgct tcggtcttaa ctgaagcagt taagcaatca    3000
gatcttcctt caggttatga ccatctgtgc cagttcgtaa tgtctggtca actttccgac    3060
tctgagaaac ttctggaatc gctagagaat ttctggaatg ggattcagga gtggacagaa    3120
cgacacggat atatagtgga tgtgtcaaaa cgcataccat tttgaacgat gacctctaat    3180
aattgttaat catgttggtt acgtatttat taacttctcc tagtattagt aattatcatg    3240
gctgtcatgg cgcattaacg gaataaaggg tgtgcttaaa tcgggccatt ttgcgtaata    3300
agaaaaagga ttaattatga gcgaattgaa ttaataataa ggtaatagat ttacattaga    3360
aaatgaaagg ggatttatg cgtgagaatg ttacagtcta tcccggcatt gccagtcggg    3420
gatattaaaa agagtatagg ttttattgc gataaactag gtttcacttt ggttcaccat    3480
gaagatggat tcgcagttct aatgtgtaat gaggttcgga ttcatctatg ggaggcaagt    3540
gatgaaggct ggcgctctcg tagtaatgat tcaccggttt gtacaggtgc ggagtcgttt    3600
attgctggta ctgctagttg ccgcattgaa gtagagggaa ttgatgaatt atatcaacat    3660
attaagcctt tgggcatttt gcaccccaat acatcattaa aagatcagtg gtgggatgaa    3720
cgagactttg cagtaattga tcccgacaac aatttgatta gctttttcca acaaataaaa    3780
agctaaaatc tattattaat ctgttcagca atcgggcgcg attgctgaat aaaagatacg    3840
```

```
agagacctct cttgtatctt ttttattttg agtggttttg tccgttacac tagaaaaccg    3900
aaagacaata aaatttttat tcttgctgag tctggctttc ggtaagctag acaaaacgga    3960
caaaataaaa attggcaagg gtttaaaggt ggagattttt tgagtgatct tctcaaaaaa    4020
tactacctgt cccttgctga ttttaaacg agcacgagag caaaaccccc ctttgctgag    4080
gtggcagagg gcaggttttt ttgtttcttt tttctcgtaa aaaaagaaa ggtcttaaag    4140 gttttatggt tttggtcggc actgccgaca gcctcgcagg acacacactt tatgaatata    4200
aagtatagtg tgttatactt tacttggaag tggttgccgg aaagagcgaa aatgcctcac    4260
atttgtgcca cctaaaaagg agcgatttac atatgagtta tgcagtttgt agaatgcaaa    4320
aagtgaaatc agggg                                                    4335
```

<210> SEQ ID NO 138
<211> LENGTH: 23
<212> TYPE: DNA
<213> ORGANISM: Artificial Sequence
<220> FEATURE:
<223> OTHER INFORMATION: primer

<400> SEQUENCE: 138

```
caggctgcgc aactgttggg aag                                            23
```

<210> SEQ ID NO 139
<211> LENGTH: 81
<212> TYPE: DNA
<213> ORGANISM: Artificial Sequence
<220> FEATURE:
<223> OTHER INFORMATION: primer

<400> SEQUENCE: 139

```
agtagttcac cacctttcc ctatataaaa gcattagtgt atcaatttca gatccacaat    60
tttttgcttc tcactcttta c                                              81
```

<210> SEQ ID NO 140
<211> LENGTH: 75
<212> TYPE: DNA
<213> ORGANISM: Artificial Sequence
<220> FEATURE:
<223> OTHER INFORMATION: primer

<400> SEQUENCE: 140

```
aattgataca ctaatgcttt tatataggga aaaggtggtg aactactatg gccaagcgaa    60
ttctgtgttt cggtg                                                    75
```

<210> SEQ ID NO 141
<211> LENGTH: 36
<212> TYPE: DNA
<213> ORGANISM: Artificial Sequence
<220> FEATURE:
<223> OTHER INFORMATION: primer

<400> SEQUENCE: 141

```
gtgagaggca ttcggatcct tttacagcag gctccg                              36
```

<210> SEQ ID NO 142
<211> LENGTH: 7239
<212> TYPE: DNA
<213> ORGANISM: Artificial Sequence
<220> FEATURE:
<223> OTHER INFORMATION: pBSFNASally plasmid

<400> SEQUENCE: 142

-continued

```
ctaaattgta agcgttaata ttttgttaaa attcgcgtta aattttttgtt aaatcagctc    60 atttttttaac caataggccg aaatcggcaa atcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc ctaaagggag    300 cccccgattt agagcttgac ggggaaagcc ggcgaacgtg gcgagaaagg aagggaagaa   360
agcgaaagga gcggcgcta gggcgctggc aagtgtagcg gtcacgctgc gcgtaaccac    420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat ggagctcca    660 ccgcggtggc ggccgctcta gaactagtgg atccccgggg ctgcaggaat tctccatttt   720
cttctgctat caaaataaca gactcgtgat tttccaaacg agctttcaaa aaagcctctg   780 cccccttgcaa atcggatgcc tgtctataaa attcccgata ttggttaaac agcggcgcaa   840
tggcggccgc atctgatgtc tttgcttggc gaatgttcat cttatttctt cctccctctc   900 aataatttttt tcattctatc cctttttctgt aaagtttatt tttcagaata cttttatcat   960
catgctttga aaaaatatca cgataatatc cattgttctc acggaagcac acgcaggtca  1020
tttgaacgaa ttttttcgac aggaatttgc cgggactcag gagcatttaa cctaaaaaag  1080
catgacattt cagcataatg aacatttact catgtctatt ttcgttcttt tctgtatgaa  1140
aatagttatt tcgagtctct acggaaatag cgagagatga tatacctaaa tagagataaa  1200
atcatctcaa aaaaatgggt ctactaaaat attattccat ctattacaat aaattcacag  1260
aatagtcttt taagtaagtc tactctgaat tttttaaaa ggagagggta aagagtgaga   1320
agcaaaaaat tgtggatcag tttgctgttt gctttagcgt taatctttac gatggcgttc  1380
ggcagcacat cctctgccca ggcggcaggg aaatcaaacg gggaaaagaa atatattgtc  1440
gggtttaaac agacaatgag cacgatgagc gccgctaaga agaaagatgt catttctgaa  1500
aaaggcggga aagtgcaaaa gcaattcaaa tatgtagacg cagcttcagc tacattaaac  1560
gaaaaagctg taaagaatt gaaaaagac ccgagcgtcg cttacgttga agaagatcac   1620
gtagcacatg cgtacgcgca gtccgtgcct tacggcgtat cacaaattaa agcccctgct  1680
ctgcactctc aaggctacac tggatcaaat gttaaagtag cggttatcga cagcggtatc  1740
gattcttctc atcctgattt aaaggtagca ggcggagcca gcatggttcc ttctgaaaca  1800
aatcctttcc aagacaacaa ctctcacgga actcacgttg ccggcacagt gcggctctt   1860 aataactcaa tcggtgtatt aggcgttgcg ccaagcgcat cactttacgc tgtaaaagtt  1920
ctcggtgctg acggttccgg ccaatacagc tggatcatta acggaatcga gtgggcgatc  1980
gcaaacaata tggacgttat taacatgagc ctcggcggac cttctggttc tgctgcttta  2040
aaagcggcag ttgataaagc cgttgcatcc ggcgtcgtag tcgttgcggc agccggtaac  2100
gaaggcactt ccggcagctc aagcacagtg ggctaccctg gtaaataccc ttctgtcatt  2160
gcagtaggcg ctgttgacag cagcaaccaa agagcatctt tctcaagcgt aggacctgag  2220
cttgatgtca tggcacctgg cgtatctatc caaagcacgc ttcctggaaa caaatacggc  2280
gcgttgaacg gtacatcaat ggcatctccg cacgttgccg gagcggctgc tttgattctt  2340
```

```
tctaagcacc cgaactggac aaacactcaa gtccgcagca gtttagaaaa caccactaca    2400
aaacttggtg attcttttcta ctatggaaaa gggctgatca acgtacaggc ggcagctcag    2460
taaaacataa aaaaccggcc ttggccccgc cggtttttta ttattttttct tcctccgcat    2520 gttcaatccg ctccataatc gacggatggc tccctctgaa aatttaacg agaaacggcg    2580 ggttgacccg gctcagtccc gtaacggcca agtcctgaaa cgtctcaatc gccgcttccc    2640
ggtttccggt cagctcaatg ccgtaacggt cggcggcgtt ttcctgatac cgggagacgg    2700
cattcgtaat cggatcctct agagtcgatt tttacaagaa ttagctttat ataatttctg    2760
tttttctaaa gttttatcag ctacaaaaga cagaaatgta ttgcaatctt caactaaatc    2820
catttgattc tctccaatat gacgtttaat aaatttctga atacttgat ttctttgttt    2880 tttctcagta tacttttcca tgttataaca cataaaaaca acttagtttt cacaaactat    2940
gacaataaaa aaagttgctt tttcccctttt ctatgtatgt tttttactag tcatttaaaa    3000
cgatacatta ataggtacga aaaagcaact ttttttgcgc ttaaaaccag tcataccaat    3060
aacttaaggg taactagcct cgccggcaat agttacccctt attatcaaga taagaaagaa    3120
aaggattttt cgctacgctc aaatccttta aaaaaacaca aaagaccaca ttttttaatg    3180
tggtctttat tcttcaacta aagcacccat tagttcaaca aacgaaaatt ggataaagtg    3240
ggatattttt aaaatatata tttatgttac agtaatattg acttttaaaa aaggattgat    3300
tctaatgaag aaagcagaca agtaagcctc ctaaattcac tttagataaa aatttaggag    3360
gcatatcaaa tgaactttaa taaaattgat ttagacaatt ggaagagaaa agagatattt    3420
aatcattatt tgaaccaaca aacgactttt agtataacca cagaaattga tattagtgtt    3480
ttataccgaa acataaaaca agaaggatat aaatttttacc ctgcatttat tttcttagtg    3540
acaagggtga taaactcaaa tacagctttt agaactggtt acaatagcga cggagagtta    3600
ggttattggg ataagttaga gccacttttat acaatttttg atggtgtatc taaaacattc    3660
tctggtattt ggactcctgt aaagaatgac ttcaaagagt tttatgattt ataccttttct    3720 gatgtagaga aatataatgg ttcggggaaa ttgtttccca aaacaccttat acctgaaaat    3780 gctttttctc tttctattat tccatggact tcatttactg ggtttaactt aaatatcaat    3840
aataatagta attaccttct acccattatt acagcaggaa aattcattaa taaaggtaat    3900
tcaatatatt taccgctatc tttacaggta catcattctg tttgtgatgg ttatcatgca    3960
ggattgttta tgaactctat tcaggaattg tcagataggc ctaatgactg gcttttataa    4020
tatgagataa tgccgactgt acttttaca gtcggttttc taatgtcact aacctgcccc    4080
gttagttgaa gaaggttttt atattacagc tccagatcca tatccttctt tttctgaacc    4140
gacttctcct ttttcgcttc tttattccaa ttgctttatt gacgttgagc tcggaaccc    4200 ttaacaatcc caaaacttgt cgaatggtcg gcttaatagc tcacgctatg ccgacattcg    4260
tctgcaagtt tagttaaggg ttcttctcaa cgcacaataa atttttctcgg cataaatgcg    4320 tggtctaatt tttatttttta ataaccttga tagcaaaaaa tgccattcca atacaaaacc    4380 acataccctat aatcgaccgg aattaattct ccatttttctt ctgctatcaa ataacagac    4440 tcgtgatttt ccaaacgagc tttcaaaaaa gcctctgccc cttgcaaatc ggatgcctgt    4500
ctataaaatt cccgatattg gttaaacagc ggcgcaatgg cggccgcatc tgatgtctttt    4560 gcttggcgaa tgttcatctt atttcttcct ccctctcaat aatttttttca ttctatccct    4620 tttctgtaaa gtttatttttt cagaatactt ttatcatcat gctttgaaaa aatatcacga    4680
taatatccat tgttctcacg gaagcacacg caggtcattt gaacgaattt tttcgacagg    4740
```

```
aatttgccgg gactcaggag catttaacct aaaaaagcat gacatttcag cataatgaac    4800
atttactcat gtctattttc gttcttttct gtatgaaaat agttatttcg agtctctacg    4860
gaaatagcga gagatgatat acctaaatag agataaaatc atctcaaaaa aatgggtcta    4920
ctaaaatatt attccatcta ttacaataaa ttcacagaat agtcttttaa gtaagtctac    4980
tctgaatttt tttatcaagc ttatcgatac cgtcgacctc gagggggggc ccggtaccca    5040
gcttttgttc cctttagtga gggttaattg cgcgcttggc gtaatcatgg tcatagctgt    5100
ttcctgtgtg aaattgttat ccgctcacaa ttccacacaa catacgagcc ggaagcataa    5160
agtgtaaagc ctggggtgcc taatgagtga gctaactcac attaattgcg ttgcgctcac    5220
tgcccgcttt ccagtcggga aacctgtcgt gccagctgca ttaatgaatc ggccaacgcg    5280
cggggagagg cggtttgcgt attgggcgct cttccgcttc ctcgctcact gactcgctgc    5340
gctcggtcgt tcggctgcgg cgagcggtat cagctcactc aaaggcggta atacggttat    5400
ccacagaatc aggggataac gcaggaaaga acatgtgagc aaaaggccag caaaaggcca    5460
ggaaccgtaa aaaggccgcg ttgctggcgt ttttccatag gctccgcccc cctgacgagc    5520
atcacaaaaa tcgacgctca agtcagaggt ggcgaaaccc gacaggacta taaagatacc    5580
aggcgtttcc ccctggaagc tccctcgtgc gctctcctgt tccgaccctg ccgcttaccg    5640
gatacctgtc cgcctttctc ccttcgggaa gcgtggcgct ttctcatagc tcacgctgta    5700
ggtatctcag ttcggtgtag tcgttcgctc caagctggg ctgtgtgcac gaaccccccg     5760
ttcagcccga ccgctgcgcc ttatccggta actatcgtct gagtccaacc cggtaagac     5820
acgacttatc gccactggca gcagccactg gtaacaggat tagcagagcg aggtatgtag    5880
gcggtgctac agagttcttg aagtggtggc ctaactacgg ctacactaga aggacagtat    5940
ttggtatctg cgctctgctg aagccagtta ccttcggaaa aagagttggt agctcttgat    6000
ccggcaaaca aaccaccgct ggtagcggtg gtttttttgt ttgcaagcag cagattacgc    6060
gcagaaaaaa aggatctcaa gaagatcctt tgatcttttc tacggggtct gacgctcagt    6120
ggaacgaaaa ctcacgttaa gggattttgg tcatgagatt atcaaaaagg atcttcacct    6180
agatcctttt aaattaaaaa tgaagtttta atcaatcta aagtatatat gagtaaactt      6240
ggtctgacag ttaccaatgc ttaatcagtg aggcacctat ctcagcgatc tgtctatttc    6300
gttcatccat agttgcctga ctccccgtcg tgtagataac tacgatacgg gagggcttac    6360
catctggccc cagtgctgca atgataccgc gagacccacg ctcaccggct ccagatttat    6420
cagcaataaa ccagccagcc ggaagggccg agcgcagaag tggtcctgca actttatccg    6480
cctccatcca gtctattaat tgttgccggg aagctagagt aagtagttcg ccagttaata    6540
gtttgcgcaa cgttgttgcc attgctacag gcatcgtggt gtcacgctcg tcgtttggta    6600
tggcttcatt cagctccggt tcccaacgat caaggcgagt tacatgatcc cccatgttgt    6660
gcaaaaaagc ggttagctcc ttcggtcctc cgatcgttgt cagaagtaag ttggccgcag    6720
tgttatcact catggttatg gcagcactgc ataattctct tactgtcatg ccatccgtaa    6780
gatgcttttc tgtgactggt gagtactcaa ccaagtcatt ctgagaatag tgtatgcggc    6840
gaccgagttg ctcttgcccg gcgtcaatac gggataatac cgcgccacat agcagaactt    6900
taaaagtgct catcattgga aaacgttctt cggggcgaaa actctcaagg atcttaccgc    6960
tgttgagatc cagttcgatg taacccactc gtgcacccaa ctgatcttca gcatctttta    7020
ctttcaccag cgtttctggg tgagcaaaaa caggaaggca aaatgccgca aaaaagggaa    7080
```

```
taagggcgac acggaaatgt tgaatactca tactcttcct ttttcaatat tattgaagca    7140
tttatcaggg ttattgtctc atgagcggat acatatttga atgtatttag aaaaataaac    7200 aaatagggt  tccgcgcaca tttccccgaa aagtgccac                           7239

<210> SEQ ID NO 143
<211> LENGTH: 5520
<212> TYPE: DNA
<213> ORGANISM: Artificial Sequence
<220> FEATURE:
<223> OTHER INFORMATION: pCP609 clone

<400> SEQUENCE: 143
caggctgcgc aactgttggg aagggcgatc ggtgcgggcc tcttcgctat tacgccagct      60
ggcgaaaggg ggatgtgctg caaggcgatt aagttgggta acgccagggt tttcccagtc     120
acgacgttgt aaaacgacgg ccagtgagcg cgcgtaatac gactcactat agggcgaatt     180
ggagctccac cgcggtggcg gccgctctag aactagtgga tccccccggc tgcaggaatt     240
ctccattttc ttctgctatc aaaataacag actcgtgatt ttccaaacga ctttcaaaa     300 aagcctctgc cccttgcaaa tcggatgcct gtctataaaa ttcccgatat tggttaaaca     360
gcggcgcaat ggcggccgca tctgatgtct ttgcttggcg aatgttcatc ttatttcttc     420
ctccctctca ataattttt  cattctatcc cttttctgta agtttatttt ttcagaatac     480
ttttatcatc atgctttgaa aaaatatcac gataatatcc attgttctca cggaagcaca     540
cgcaggtcat ttgaacgaat ttttcgaca ggaatttgcc gggactcagg agcatttaac     600
ctaaaaaagc atgacatttc agcataatga acatttactc atgtctattt tcgttctttt     660
ctgtatgaaa atagttattt cgagtctcta cggaaatagc gagagatgat atacctaaat     720
agagataaaa tcatctcaaa aaaatgggtc tactaaaata ttattccatc tattacaata     780
aattcacaga atagtctttt aagtaagtct actctgaatt tttttaaaag gagagggtaa     840
agagtgagaa gcaaaaaatt gtggatctga aattgataca ctaatgcttt tatataggga     900
aaaggtggtg aactactatg ccaagcgaa  ttctgtgttt cggtgattcc ctgacctggg     960
gctgggtccc cgtcgaagac ggggcaccca ccgagcggtt cgcccccgac gtgcgctgga    1020
ccggtgtgct ggcccagcag ctcggagcgg acttcgaggt gatcgaggag ggactgagcg    1080
cgcgcaccac caacatcgac gaccccaccg atccgcggct caacggcgcg agctacctgc    1140
cgtcgtgcct cgcgacgcac ctgccgctcg acctggtgat catcatgctg gcaccaacg    1200 acaccaaggc ctacttccgg cgcacccccgc tcgacatcgc gctgggcatg tcggtgctcg    1260
tcacgcaggt gctcaccagc gcgggcggcg tcggcaccac gtacccggct cccaaggtgc    1320
tggtggtctc gccgccaccg ctggcgccca tgccgcaccc ctggttccag ttgatcttcg    1380
agggcggcga gcagaagacc actgagctcg cccgcgtgta cagcgcgctc gcgtcgttca    1440
tgaaggtgcc gttcttcgac gcgggttcgg tgatcagcac cgacggcgtc gacgaatcc    1500 acttcaccga ggccaacaat cgcgatctcg ggtggccct cgcggaacag gtgcggagcc    1560
tgctgtaaaa ggatccgaat gcctctcaca agggcgaatt ctgcagatat ccatcacact    1620
ggcggccgct cgagcatgca tctagagggc ccaattcgcc ctatagtgag tcgtattaca    1680
attcactggc cgtcgtttta caacgtcgtg actgggaaaa ccctggcgtt acccaactta    1740
atcgccttgc agcacatccc ctttcgcca gctggcgtaa tagcgaagag gcccgcaccg    1800 atcgccttc ccaacagttg cgcagcctga atggcgaatg gacgcgccct gtagcggcgc    1860
attaagcgcg gcgggtgtgg tggttacgcg cagcgtgacc gctacacttg ccagcgccct    1920
```

```
agcgcccgct cctttcgctt tcttcccttc ctttctcgcc acgttcgccg gctttccccg   1980
tcaagctcta aatcgggggc tccctttagg gttccgattt agtgctttac ggcacctcga   2040
ccccaaaaaa cttgattagg gtgatggttc acgtagtggg ccatcgccct gatagacggt   2100
ttttcgccct ttgacgttgg agtccacgtt ctttaatagt ggactcttgt tccaaactgg   2160
aacaacactc aaccctatct cggtctattc ttttgattta taagggattt tgccgatttc   2220
ggcctattgg ttaaaaaatg agctgattta acaaaaattt aacgcgaatt ttaacaaaat   2280
tcagggcgca agggctgcta aggaagcgg aacacgtaga aagccagtcc gcagaaacgg    2340
tgctgacccc ggatgaatgt cagctactgg gctatctgga caagggaaaa cgcaagcgca   2400
aagagaaagc aggtagcttg cagtgggctt acatggcgat agctagactg gcggttttta   2460
tggacagcaa gcgaaccgga attgccagct ggggcgccct ctggtaaggt tgggaagccc   2520
tgcaaagtaa actggatggc tttcttgccg ccaaggatct gatggcgcag gggatcaaga   2580
tctgatcaag agacaggatg aggatcgttt cgcatgattg aacaagatgg attgcacgca   2640
ggttctccgg ccgcttgggt ggagaggcta ttcggctatg actgggcaca acagacaatc   2700
ggctgctctg atgccgccgt gttccggctg tcagcgcagg ggcgcccggt tcttttttgtc  2760 aagaccgacc tgtccggtgc cctgaatgaa ctgcaggacg aggcagcgcg gctatcgtgg   2820
ctggccacga cgggcgttcc ttgcgcagct gtgctcgacg ttgtcactga agcgggaagg   2880
gactggctgc tattgggcga agtgccgggg caggatctcc tgtcatccca ccttgctcct   2940
gccgagaaag tatccatcat ggctgatgca atgcggcggc tgcatacgct tgatccggct   3000
acctgcccat tcgaccacca agcgaaacat cgcatcgagc gagcacgtac tcggatggaa   3060
gccggtcttg tcgatcagga tgatctggac gaagagcatc aggggctcgc gccagccgaa   3120
ctgttcgcca ggctcaaggc gcgcatgccc gacggcgagg atctcgtcgt gacccatggc   3180
gatgcctgct tgccgaatat catggtggaa aatggccgct tttctggatt catcgactgt   3240
ggccggctgg gtgtggcgga ccgctatcag gacatagcgt tggctacccg tgatattgct   3300
gaagagcttg gcggcgaatg ggctgaccgc ttcctcgtgc tttacggtat cgccgctccc   3360
gattcgcagc gcatcgcctt ctatcgcctt cttgacgagt tcttctgaat tgaaaaagga   3420
agagtatgag tattcaacat ttccgtgtcg cccttattcc ctttttttgcg gcattttgcc   3480 ttcctgttttt tgctcaccca gaaacgctgg tgaaagtaaa agatgctgaa gatcagttgg   3540
gtgcacgagt gggttacatc gaactggatc tcaacagcgg taagatcctt gagagttttc   3600
gccccgaaga acgttttcca atgatgagca cttttaaagt tctgctatgt ggcgcggtat   3660
tatcccgtat tgacgccggg caagagcaac tcggtcgccg catacactat tctcagaatg   3720
acttggttga gtactcacca gtcacagaaa agcatcttac ggatggcatg acagtaagag   3780
aattatgcag tgctgccata accatgagtg ataacactgc ggccaactta cttctgacaa   3840
cgatcggagg accgaaggag ctaaccgctt ttttgcacaa catgggggat catgtaactc   3900
gccttgatcg ttgggaaccg gagctgaatg aagccatacc aaacgacgag cgtgacacca   3960
cgatgcctgt agcaatggca acaacgttgc gcaaactatt aactggcgaa ctacttactc   4020
tagcttcccg gcaacaatta atagactgga tggaggcgga taaagttgca ggaccacttc   4080
tgcgctcggc ccttccggct ggctggttta ttgctgataa atctggagcc ggtgagcgtg   4140
ggtctcgcgg tatcattgca gcactggggc cagatggtaa gccctcccgt atcgtagtta   4200
tctacacgac ggggagtcag gcaactatgg atgaacgaaa tagacagatc gctgagatag   4260
```

```
gtgcctcact gattaagcat tggtaactgt cagaccaagt ttactcatat atactttaga    4320
ttgatttaaa acttcatttt taatttaaaa ggatctaggt gaagatcctt tttgataatc    4380
tcatgaccaa atcccttaa cgtgagtttt cgttccactg agcgtcagac cccgtagaaa     4440
agatcaaagg atcttcttga tccttttt ttctgcgcgt aatctgctgc ttgcaaacaa      4500
aaaaaccacc gctaccagcg gtggtttgtt tgccggatca agagctacca actcttttc    4560 cgaaggtaac tggcttcagc agagcgcaga taccaaatac tgttcttcta gtgtagccgt    4620
agttaggcca ccacttcaag aactctgtag caccgcctac atacctcgct ctgctaatcc    4680
tgttaccagt ggctgctgcc agtggcgata agtcgtgtct taccgggttg gactcaagac    4740
gatagttacc ggataaggcg cagcggtcgg gctgaacggg gggttcgtgc acacagccca    4800
gcttggagcg aacgacctac accgaactga gatacctaca gcgtgagcta tgagaaagcg    4860
ccacgcttcc cgaagggaga aaggcggaca ggtatccggt aagcggcagg gtcggaacag    4920
gagagcgcac gagggagctt ccaggggaa acgcctggta tctttatagt cctgtcgggt     4980
ttcgccacct ctgacttgag cgtcgatttt tgtgatgctc gtcagggggg cggagcctat    5040
ggaaaaacgc cagcaacgcg gcctttttac ggttcctggc cttttgctgg ccttttgctc    5100
acatgttctt cctgcgtta tcccctgatt ctgtggataa ccgtattacc gcctttgagt    5160
gagctgatac cgctcgccgc agccgaacga ccgagcgcag cgagtcagtg agcgaggaag    5220
cggaagagcg cccaatacgc aaaccgcctc tccccgcgcg ttggccgatt cattaatgca    5280
gctggcacga caggtttccc gactggaaag cgggcagtga gcgcaacgca attaatgtga    5340
gttagctcac tcattaggca ccccaggctt tacactttat gcttccggct cgtatgttgt    5400
gtggaattgt gagcggataa caatttcaca caggaaacag ctatgaccat gattacgcca    5460
agcttggtac cgagctcgga tccactagta acggccgcca gtgtgctgga attcgccctt    5520
```

<210> SEQ ID NO 144
<211> LENGTH: 6640
<212> TYPE: DNA
<213> ORGANISM: Artificial Sequence
<220> FEATURE:
<223> OTHER INFORMATION: pCP649 clone

<400> SEQUENCE: 144

```
tagaactagt ggatccccg ggctgcagga attctccatt tcttctgct atcaaaataa       60 cagactcgtg attttccaaa cgagctttca aaaaagcctc tgccccttgc aaatcggatg     120
cctgtctata aaattcccga tattggttaa acagcggcgc aatggcggcc gcatctgatg    180
tctttgcttg gcgaatgttc atcttatttc ttcctccctc tcaataattt ttcattcta     240 tcccttttct gtaaagttta ttttcagaa tactttatc atcatgcttt gaaaaaatat      300
cacgataata tccattgttc tcacggaagc acacgcaggt catttgaacg aattttttcg    360
acaggaattt gccgggactc aggagcattt aacctaaaaa agcatgacat ttcagcataa    420
tgaacattta ctcatgtcta ttttcgttct tttctgtatg aaaatagtta tttcgagtct    480
ctacggaaat agcgagagat gatataccta atagagata aatcatctc aaaaaaatgg     540 gtctactaaa atattattcc atctattaca ataaattcac agaatagtct tttaagtaag    600
tctactctga atttttttaa aaggagaggg taaagagtga gaagcaaaaa attgtggatc    660
tgaaattgat acactaatgc ttttatatag ggaaaaggtg gtgaactact atggccaagc    720
gaattctgtg tttcggtgat tccctgacct ggggctgggt cccccgtcgaa gacggggcac    780 ccaccgagcg gttcgccccc gacgtgcgct ggaccggtgt gctggcccag cagctcggag    840
```

```
cggacttcga ggtgatcgag gagggactga gcgcgcgcac caccaacatc gacgacccca      900
ccgatccgcg gctcaacggc gcgagctacc tgccgtcgtg cctcgcgacg cacctgccgc      960
tcgacctggt gatcatcatg ctgggcacca acgacaccaa ggcctacttc ggcgcaccc      1020
cgctcgacat cgcgctgggc atgtcggtgc tcgtcacgca ggtgctcacc agcgcgggcg     1080
gcgtcggcac cacgtacccg gctcccaagg tgctggtggt ctcgccgcca ccgctggcgc     1140
ccatgccgca cccctggttc cagttgatct tcgagggcgg cgagcagaag accactgagc     1200
tcgcccgcgt gtacagcgcg ctcgcgtcgt tcatgaaggt gccgttcttc gacgcgggtt     1260
cggtgatcag caccgacggc gtcgacgaa tccacttcac cgaggccaac aatcgcgatc      1320
tcggggtggc cctcgcggaa caggtgcgga gcctgctgta acggaatgcc tctcacaagg     1380
atccaagccg aattctgcag atatccatca cactggcggc cgctcgagca tgcatctaga     1440
gtcgattttt acaagaatta gctttatata atttctgttt ttctaaagtt ttatcagcta     1500
caaaagacaa aaatgtattg caatcttcaa ctaaatccat tgattctct ccaatatgac      1560
gtttaataaa tttctgaaat acttgatttc tttgtttttt ctcagtatac ttttccatgt     1620
tataacacat aaaaacaact tagttttcac aaactatgac aataaaaaaa gttgcttttt     1680
ccccttttcta tgtatgtttt ttactagtca tttaaaacga tacattaata ggtacgaaaa     1740
agcaactttt tttgcgctta aaaccagtca taccaataac ttaagggtaa ctagcctcgc     1800
cggcaatagt taccccttatt atcaagataa gaaagaaaag gattttttcgc tacgctcaaa    1860
tcctttaaaa aaacacaaaa gaccacattt tttaatgtgg tctttattct tcaactaaag     1920
cacccattag ttcaacaaac gaaaattgga taaagtggga tattttaaa atatatattt      1980
atgttacagt aatattgact tttaaaaaag gattgattct aatgaagaaa gcagacaagt     2040
aagcctccta aattcacttt agataaaaat ttaggaggca tatcaaatga actttaataa     2100
aattgattta gacaattgga agagaaaaga gatatttaat cattatttga accaacaaac     2160
gactttagt ataaccacag aaattgatat tagtgtttta taccgaaaca taaaacaaga      2220
aggatataaa ttttaccctg catttatttt cttagtgaca agggtgataa actcaaatac     2280
agcttttaga actggttaca atagcgacgg agagttaggt tattgggata agttagagcc     2340
acttttataca atttttgatg gtgtatctaa aacattctct ggtatttgga ctcctgtaaa    2400
gaatgacttc aaagagtttt atgatttata cctttctgat gtagagaaat ataatggttc     2460
ggggaaattg tttcccaaaa cacctatacc tgaaaatgct ttttctcttt ctattattcc     2520
atggacttca tttactgggt ttaacttaaa tatcaataat aatagtaatt accttctacc     2580
cattattaca gcaggaaaat tcattaataa aggtaattca atatatttac cgctatcttt     2640
acaggtacat cattctgttt gtgatggtta tcatgcagga ttgtttatga actctattca     2700
ggaattgtca gataggccta atgactggct tttataatat gagataatgc cgactgtact     2760
ttttacagtc ggttttctaa tgtcactaac ctgccccgtt agttgaagaa ggttttttata     2820
ttacagctcc agatccatat ccttcttttt ctgaaccgac ttctcctttt tcgcttcttt     2880
attccaattg ctttattgac gttgagcctc ggaacccttta acaatcccaa aacttgtcga     2940
atggtcggct taatagctca cgctatgccg acattcgtct gcaagtttag ttaagggttc     3000
ttctcaacgc acaataaatt ttctcggcat aaatgcgtgg tctaattttt attttttaata    3060
accttgatag caaaaaatgc cattccaata caaaaccaca tacctataat cgacctgcag     3120
gaattaattc ctccattttc ttctgctatc aaaataacag actcgtgatt ttccaaacga     3180
```

-continued

```
gctttcaaaa aagcctctgc cccttgcaaa tcggatgcct gtctataaaa ttcccgatat    3240
tggcttaaac agcggcgcaa tggcggccgc atctgatgtc tttgcttggc gaatgttcat    3300
cttatttctt cctccctctc aataattttt tcattctatc ccttttctgt aaagtttatt    3360
tttcagaata cttttatcat catgctttga aaaaatatca cgataatatc cattgttctc    3420
acggaagcac acgcaggtca tttgaacgaa tttttcgac aggaatttgc cgggactcag    3480
gagcatttaa cctaaaaaag catgacattt cagcataatg aacatttact catgtctatt    3540
ttcgttcttt tctgtatgaa aatagttatt tcgagtctct acggaaatag cgagagatga    3600
tatacctaaa tagagataaa atcatctcaa aaaaatgggt ctactaaaat attattccat    3660
ctattacaat aaattcacag aatagtcttt taagtaagtc tactctgaat ttttttatca    3720
agcttatcga taccgtcgac ctcgaggggg ggcccggtac ccagcttttg ttccctttag    3780
tgagggttaa ttgcgcgctt ggcgtaatca tggtcatagc tgtttcctgt gtgaaattgt    3840
tatccgctca caattccaca acatacga gccggaagca taagtgtaa agcctggggt    3900 gcctaatgag tgagctaact cacattaatt gcgttgcgct cactgcccgc tttccagtcg    3960
ggaaacctgt cgtgccagct gcattaatga atcggccaac gcgcggggag aggcggtttg    4020
cgtattgggc gctcttccgc ttcctcgctc actgactcgc tgcgctcggt cgttcggctg    4080
cggcgagcgg tatcagctca ctcaaaggcg gtaatacggt tatccacaga atcaggggat    4140
aacgcaggaa agaacatgtg agcaaaaggc cagcaaaagg ccaggaaccg taaaaaggcc    4200
gcgttgctgg cgttttccca taggctccgc cccctgacg agcatcacaa aaatcgacgc    4260
tcaagtcaga ggtggcgaaa cccgacagga ctataaagat accaggcgtt ccccctgga    4320 agctccctcg tgcgctctcc tgttccgacc ctgccgctta ccggatacct gtccgccttt    4380
ctcccttcgg gaagcgtggc gctttctcat agctcacgct gtaggtatct cagttcggtg    4440
taggtcgttc gctccaagct gggctgtgtg cacgaacccc ccgttcagcc cgaccgctgc    4500
gccttatccg gtaactatcg tcttgagtcc aacccggtaa gacacgactt atcgccactg    4560
gcagcagcca ctggtaacag gattagcaga gcgaggtatg taggcggtgc tacagagttc    4620
ttgaagtggt ggcctaacta cggctacact agaaggacag tatttggtat ctgcgctctg    4680
ctgaagccag ttaccttcgg aaaaagagtt ggtagctctt gatccggcaa acaaaccacc    4740
gctggtagcg gtggtttttt tgtttgcaag cagcagatta cgcgcagaaa aaaggatct    4800 caagaagatc ctttgatctt ttctacgggg tctgacgctc agtggaacga aaactcacgt    4860
taagggattt tggtcatgag attatcaaaa aggatcttca cctagatcct tttaaattaa    4920
aaatgaagtt ttaaatcaat ctaaagtata tatgagtaaa cttggtctga cagttaccaa    4980
tgcttaatca gtgaggcacc tatctcagcg atctgtctat ttcgttcatc catagttgcc    5040
tgactccccg tcgtgtagat aactacgata cgggagggct taccatctgg ccccagtgct    5100
gcaatgatac cgcgagaccc acgctcaccg gctccagatt tatcagcaat aaaccagcca    5160
gccggaaggg ccgagcgcag aagtggtcct gcaactttat ccgcctccat ccagtctatt    5220
aattgttgcc gggaagctag agtaagtagt tcgccagtta atagtttgcg caacgttgtt    5280
gccattgcta caggcatcgt ggtgtcacgc tcgtcgtttg gtatggcttc attcagctcc    5340
ggttcccaac gatcaaggcg agttacatga tcccccatgt tgtgcaaaaa agcggttagc    5400
tccttcggtc ctccgatcgt tgtcagaagt aagttggccg cagtgttatc actcatggtt    5460
atggcagcac tgcataattc tcttactgtc atgccatccg taagatgctt ttctgtgact    5520
ggtgagtact caaccaagtc attctgagaa tagtgtatgc ggcgaccgag ttgctcttgc    5580
```

```
ccggcgtcaa tacgggataa taccgcgcca catagcagaa ctttaaaagt gctcatcatt    5640
ggaaaacgtt cttcggggcg aaaactctca aggatcttac cgctgttgag atccagttcg    5700
atgtaaccca ctcgtgcacc caactgatct tcagcatctt ttactttcac cagcgtttct    5760
gggtgagcaa aaacaggaag gcaaaatgcc gcaaaaaagg gaataagggc gacacggaaa    5820
tgttgaatac tcatactctt ccttttcaa tattattgaa gcatttatca gggttattgt    5880
ctcatgagcg gatacatatt tgaatgtatt tagaaaaata acaaatagg ggttccgcgc     5940 acatttcccc gaaaagtgcc acctaaattg taagcgttaa tattttgtta aaattcgcgt    6000 taaattttg ttaaatcagc tcattttta accaataggc cgaaatcggc aaaatccctt      6060
ataaatcaaa agaatagacc gagatagggt tgagtgttgt tccagtttgg aacaagagtc    6120
cactattaaa gaacgtggac tccaacgtca agggcgaaa aaccgtctat cagggcgatg    6180
gcccactacg tgaaccatca ccctaatcaa gttttttggg gtcgaggtgc cgtaaagcac    6240
taaatcggaa ccctaaaggg agccccccgat ttagagcttg acggggaaag ccggcgaacg    6300
tggcgagaaa ggaagggaag aaagcgaaag gagcgggcgc tagggcgctg gcaagtgtag    6360
cggtcacgct gcgcgtaacc accacacccg ccgcgcttaa tgcgccgcta cagggcgcgt    6420
cccattcgcc attcaggctg cgcaactgtt gggaagggcg atcggtgcgg gcctcttcgc    6480
tattacgcca gctggcgaaa gggggatgtg ctgcaaggcg attaagttgg gtaacgccag    6540
ggttttccca gtcacgacgt tgtaaaacga cggccagtga gcgcgcgtaa tacgactcac    6600
tatagggcga attggagctc caccgcggtg gcggccgctc                          6640

<210> SEQ ID NO 145
<211> LENGTH: 8819
<212> TYPE: DNA
<213> ORGANISM: Artificial Sequence
<220> FEATURE:
<223> OTHER INFORMATION: pSECGT-MSAT plasmid

<400> SEQUENCE: 145
ctagagtcga ccacgcaggc cgccaggtag tcgacgttga tctcgcagcc gagcccggcc      60
ggaccggcgg cgctgagcgc gaggccgacg gcgggacggc cggcaccggt acgcggtggc     120
gggtcgagtt cggtgagcag cccaccggcg atcaggtcgt cgacgagcgc ggagacggtg     180
gcccgggtga gccggtgac ggcggcaact cccgcgcggg agagccgatc tgtgctgttt     240
gccacggtat gcagcaccag cgcgagatta tgggctcgca cgctcgactg tcggacgggg     300
gcactggaac gagaagtcag gcgagccgtc acgcccttga caatgccaca tcctgagcaa     360
ataattcaac cactaaacaa atcaaccgcg tttcccggag gtaaccatgg ccaagcgaat     420
tctgtgtttc ggtgattccc tgacctgggg ctgggtcccc gtcgaagacg gggcacccac     480
cgagcggttc gccccccgacg tgcgctggac cggtgtgctg gcccagcagc tcggagcgga     540
cttcgaggtg atcgaggagg gactgagcgc gcgcaccacc aacatcgacg accccaccga    600
tccgcggctc aacggcgcga gctacctgcc gtcgtgcctc gcgacgcacc tgccgctcga    660
cctggtgatc atcatgctgg gcaccaacga caccaaggcc tacttccggc gcaccccgct    720
cgacatcgcg ctgggcatgt cggtgctcgt cacgcaggtc ctcaccagcg cgggcggcgt    780
cggcaccacg tacccggcac ccaaggtgct ggtggtctcg ccgccaccgc tggcgcccat    840
gccgcacccc tggttccagt tgatcttcga gggcggcgag cagaagacca ctgagctcgc    900
ccgcgtgtac agcgcgctcg cgtcgttcat gaaggtgccg ttcttcgacg cgggttcggt    960
```

-continued

```
gatcagcacc gacggcgtcg acggaatcca cttcaccgag gccaacaatc gcgatctcgg      1020
ggtggccctc gcggaacagg tgcggagcct gctgtaacgg gatccgcgag cggatcggct      1080
gaccggagcg gggaggagga cgggcggccg gcggaaaagt ccgccggtcc gctgaatcgc      1140
tccccgggca cggacgtggc agtatcagcg ccatgtccgg catatcccag ccctccgcat      1200
gccccgaatt cggcgtaatc atggtcatag ctgtttcctg tgtgaaattg ttatccgctc      1260
acaattccac acaacatacg agccggaagc ataaagtgta aagcctgggg tgcctaatga      1320
gtgagctaac tcacattaat tgcgttgcgc tcactgcccg ctttccagtc gggaaacctg      1380
tcgtgccagc tgcattaatg aatcggccaa cgcgcgggga gaggcggttt gcgtattggg      1440
cgctcttccg cttcctcgct cactgactcg ctgcgctcgg tcgttcggct gcggcgagcg      1500
gtatcagctc actcaaaggc ggtaatacgg ttatccacag aatcagggga taacgcagga      1560
aagaacatgt gagcaaaagg ccagcaaaag gccaggaacc gtaaaaaggc cgcgttgctg      1620 gcgttttttcc ataggctccg ccccctgac gagcatcaca aaaatcgacg ctcaagtcag      1680
aggtggcgaa acccgacagg actataaaga taccaggcgt ttccccctgg aagctccctc      1740
gtgcgctctc ctgttccgac cctgccgctt accggatacc tgtccgcctt tctcccttcg      1800
ggaagcgtgg cgctttctca tagctcacgc tgtaggtatc tcagttcggt gtaggtcgtt      1860
cgctccaagc tgggctgtgt gcacgaaccc cccgttcagc ccgaccgctg cgccttatcc      1920
ggtaactatc gtcttgagtc aacccggta agacacgact tatcgccact ggcagcagcc      1980
actggtaaca ggattagcag agcgaggtat gtaggcggtg ctacagagtt cttgaagtgg      2040
tggcctaact acggctacac tagaaggaca gtatttggta tctgcgctct gctgaagcca      2100
gttaccttcg gaaaaagagt tggtagctct tgatccggca acaaaccac cgctggtagc      2160 ggtggttttt ttgtttgcaa gcagcagatt acgcgcagaa aaaaaggatc tcaagaagat      2220
cctttgatct tttctacggg gtctgacgct cagtggaacg aaaactcacg ttaagggatt      2280
ttggtcatga gattatcaaa aaggatcttc acctagatcc ttttaaatta aaaatgaagt      2340
tttaaatcaa tctaaagtat atatgagtaa acttggtctg acagttacca atgcttaatc      2400
agtgaggcac ctatctcagc gatctgtcta tttcgttcat ccatagttgc ctgactcccc      2460
gtcgtgtaga taactacgat acgggagggc ttaccatctg gccccagtgc tgcaatgata      2520
ccgcgagacc cacgctcacc ggctccagat ttatcagcaa taaaccagcc agccggaagg      2580
gccgagcgca gaagtggtcc tgcaacttta tccgcctcca tccagtctat taattgttgc      2640
cgggaagcta gagtaagtag ttcgccagtt aatagtttgc gcaacgttgt tgccattgct      2700
acaggcatcg tggtgtcacg ctcgtcgttt ggtatggctt cattcagctc cggttcccaa      2760
cgatcaaggc gagttacatg atcccccatg ttgtgcaaaa aagcggttag ctccttcggt      2820
cctccgatcg ttgtcagaag taagttggcc gcagtgttat cactcatggt tatggcagca      2880
ctgcataatt ctcttactgt catgccatcc gtaagatgct tttctgtgac tggtgagtac      2940
tcaaccaagt cattctgaga atagtgtatg cggcgaccga gttgctcttg cccggcgtca      3000
atacgggata taccgcgcc acatagcaga actttaaaag tgctcatcat tggaaaacgt      3060
tcttcggggc gaaaactctc aaggatctta ccgctgttga tccagttc gatgtaaccc      3120 actcgtgcac ccaactgatc ttcagcatct tttactttca ccagcgtttc tgggtgagca      3180
aaaacaggaa ggcaaaatgc cgcaaaaaag gaataagggc gacacggaa atgttgaata      3240 ctcatactct tcctttttca atattattga agcatttatc agggttattg tctcatgagc      3300
ggatacatat ttgaatgtat ttagaaaaat aaacaaatag gggttccgcg cacatttccc      3360
```

```
cgaaaagtgc cacctgacgt ctaagaaacc attattatca tgacattaac ctataaaaat    3420
aggcgtatca cgaggcccett tcgtctcgcg cgtttcggtg atgacggtga aaacctcttg   3480
acacatgcag ctcccggaga cggtcacagc ttgtctgtaa gcggatgccg ggagcagaca   3540
agcccgtcag ggcgcgtcag cgggtgttgg cgggtgtcgg ggctggctta actatgcggc   3600
atcagagcag attgtactga gagtgcacca tatgcggtgt gaaataccgc acagatgcgt   3660
aaggagaaaa taccgcatca ggcgccattc gccattcagg ctgcgcaact gttgggaagg   3720
gcgatcggtg cgggcctctt cgctattacg ccagctggcg aaaggggggat gtgctgcaag   3780
gcgattaagt tgggtaacgc cagggttttc ccagtcacga cgttgtaaaa cgacggccag   3840
taagcttgca tgcctgcagg agtggggagg cacgatggcc gctttggtcg acctcaacga   3900
gacgatgaag ccgtggaacg acaccacccc ggcggccctg ctggaccaca cccggcacta   3960
caccttcgac gtctgatcat cactgacgaa tcgaggtcga ggaaccgagc gtccgaggaa   4020
cacaggcgct tatcggttgg ccgcgagatt cctgtcgatc ctctcgtgca gcgcgattcc   4080
gagggaaacg gaaacgttga gagactcggt ctggctcatc atggggatgg aaaccgaggc   4140
ggaagacgcc tcctcgaaca ggtcggaagg cccacccttt tcgctgccga acagcaaggc   4200
cagccgatcc ggattgtccc cgagttcctt cacggaaatg tcgccatccg ccttgagcgt   4260
catcagctgc ataccgctgt cccgaatgaa ggcgatggcc tcctcgcgac cggagagaac   4320
gacgggaagg gagaagacgt aacctcggct ggcccctttgg agacgccggt ccgcgatgct   4380
ggtgatgtca ctgtcgacca ggatgatccc cgacgctccg agcgcgagcg acgtgcgtac   4440
tatcgcgccg atgttcccga cgatcttcac cccgtcgaga cgacgacgt ccccacgccg   4500
gctcgcgata tcgccgaacc tggccggggcg agggacgcgg gcgatgccga atgtcttggc   4560
cttccgctcc cccttgaaca actggttgac gatcgaggag tcgatgaggc ggaccggtat   4620
gttctgccgc ccgcacagat ccagcaactc agatggaaaa ggactgctgt cgctgccgta   4680
gacctcgatg aactccaccc cggccgcgat gctgtgcatg aggggctcga cgtcctcgat   4740
caacgttgtc tttatgttgg atcgcgacgg cttggtgaca tcgatgatcc gctgcaccgc   4800
gggatcggac ggatttgcga tggtgtccaa ctcagtcatg gtcgtcctac cggctgctgt   4860
gttcagtgac gcgattcctg gggtgtgaca ccctacgcga cgatggcgga tggctgccct   4920
gaccggcaat caccaacgca aggggaagtc gtcgctctct ggcaaagctc cccgctcttc   4980
cccgtccggg acccgcgcgg tcgatccccg catatgaagt attcgccttg atcagtcccg   5040
gtggacgcgc cagcggcccg ccggagcgac ggactccccg acctcgatcg tgtcgccctg   5100
agcgtccacg tagacgttgc gtgagagcag gactgggccg ccgccgaccg caccgccctc   5160
accaccgacc gcgaccgcgc catggccgcc gccgacggcc tggtcgccgc cgccgccgc   5220
cggttcggcg cctgacccga ccaaccccccg cggggcgccg gcacttcgtg ctggcgcccc   5280
gcccccaccc accaggagac cgaccatgac cgacttcgac ggacgcctga ccgagggggac   5340
cgtgaacctg gtccaggacc ccaacggcgg tggctggtcc gcccactgcg ctgagcccgg   5400
ttgcgactgg gccgacttcg ccggaccgct cggcttccag ggcctcgtgg ccatcgctcg   5460
ccgacacacg cactgaccgc acgtcaaagc cccgccggat accggcgggg ctctcttcg   5520
gccctccaag tcacaccagc ccaagggggc gtcgggagtg cggaggggaa cctctggccc   5580
gattggtgcc aggattccca ccagaccaaa gagcaacggg ccggacttcg cacctccgac   5640
ccgtccgctc ccagactcgc gcccccttagc cgggcgagac aggaacgttg ctcgtgccca   5700
```

```
gagtacggag cgatgccgag gcattgccag atcggcccgc cgggccccgc tgccactgcg    5760
ggaccgcaat tgcccacaca ccgggcaaac ggccgcgtat ctactgctca gaccgctgcc    5820
ggatggcagc gaagcgggcg atcgcgcgtg tgacgcgaga tgccgcccga ggcaaaagcg    5880
aacaccttgg gaaagaaaca acagagtttc ccgcacccct ccgacctgcg gtttctccgg    5940
acggggtgga tggggagagc ccgagaggcg acagcctctg ggaagtagga agcacgtcgc    6000
ggaccgagcc tgcccgactg cggaaagccg cccggtacag ccgccgccgg acgtgtggc    6060 ggatcagcgg ggacgccgcg tgcaagggct gcggccgcgc cctgatggac cctgcctccg    6120
gcgtgatcgt cgcccagacg gcggccggaa cgtccgtggt cctgggcctg atgcggtgcg    6180
ggcggatctg gctctgcccg gtctgcgccg ccacgatccg gcacaagcgg gccgaggaga    6240
tcaccgccgc cgtggtcgag tggatcaagc gcgggggac cgcctacctg gtcaccttca    6300
cggcccgcca tgggcacacg gaccggctcg cggacctcat ggacgccctc cagggcaccc    6360
ggaagacgcc ggacagcccc cggcggccgg gcgcctacca gcgactgatc acgggcggca    6420
cgtgggccgg acgccgggcc aaggacgggc accgggccgc cgaccgcgag ggcatccgag    6480
accggatcgg gtacgtcggc atgatccgcg cgaccgaagt caccgtgggg cagatcaacg    6540
gctggcaccc gcacatccac gcgatcgtcc tggtcggcgg ccggaccgag ggggagcggt    6600
ccgcgaagca gatcgtcgcc accttcgagc cgaccggcgc cgcgctcgac gagtggcagg    6660
ggcactggcg gtccgtgtgg accgccgccc tgcgcaaggt caaccccgcc ttcacgcccg    6720
acgaccggca cggcgtcgac ttcaagcggc tggagaccga gcgcgacgcc aacgacctcg    6780
ccgagtacat cgccaagacc caggacggga aggcgcccgc cctcgaactc gcccgcgccg    6840
acctcaagac ggcgaccggc gggaacgtcg ccccgttcga actcctcgga cggatcgggg    6900
acctgaccgg cggcatgacc gaggacgacg ccgccgggct cggctcgctg gagtggaacc    6960
tctcgcgctg gcacgagtac gagcgggcaa cccggggacg ccgggccatc gaatggaccc    7020
gctacctgcg gcagatgctc gggctcgacg gcggcgacac cgaggccgac gacctcgatc    7080
tgctcctggc ggccgacgcc gacggcgggg agctgcgggc cggggtcgcc gtgaccgagg    7140
acggatggca cgcggtcacc cgccgcgccc tcgacctcga ggcgacccgg ccgccgaag    7200 gcaaggacgg caacgaggat tcggcggccg tgggcgaacg ggtgcgggag gtcctggcgc    7260
tggccgacgc ggccgacaca gtggtggtgc tcacggcggg ggaggtggcc gaggcgtacg    7320
ccgacatgct cgccgccctc gcccagcgcc gcgaggaagc aactgcacgc cgacggcgag    7380
agcaggacga cgaccaggac gacgacgccg acgaccgcca ggagcgggcc gcccggcaca    7440
tcgcccggct cgcaagtggg cccacttcgc actaactcgc tccccccgc cgtacgtcat    7500 cccggtgacg tacggcgggg gtcggtgacg tacgcggcga cggcggccgg ggtcgaagcc    7560
gcgggagtaa tcctgggatt actcgcccgg ggtcggcccc gccggcactt cgtgcaggcg    7620
gtacctcgcg cccgactcgc ctcgctacga gacgtgccgc gtacggtcgt cggccatgag    7680
caccaccacc cccagggacg ccgacggcgc gaagctctgc gcctggtgcg gctcggagat    7740
caagcaatcc ggcgtcggcc ggagccggga ctactgccgc cgctcctgcc gccagcgggc    7800
gtacgaggcc cggcgccagc gcgaggcgat cgtgtccgcc gtggcgtcgg cagtcgctcg    7860
ccgagatacg tcacgtgacg aaatgcagca gccttccatt ccgtcacgtg acgaaactcg    7920
ggccgcaggt cagagcacgg ttccgcccgc tccggcccctg ccggacccc ggctgcagct    7980 cgcccggccg ccggtccccc tgccgtccgg cccgtcccag aggcagcgtc ggcggctcct    8040 gcctccccg cccggcgccg accgggaccc gcaaacccct tgatccgctg tcggggtga    8100
```

```
tcactacggt gggtgccgaa gtgatcacgg ggaggactga tgcaccacca ggaccgggac    8160
caggaccagg cgttagcggc agtgctggcc gcactgctcc tggtcggcgg gacgctgatc    8220
gtgcgggagc tcctgggcct gtggcccgcc gtggcggtcg gcatggcgcc cgccctcgcc    8280
ctctacggag gcccgcccgc ggcccgccgg atagccgtcg cggtcgaggt ccgcggttc     8340 cgccggcatc ttgcccacca cgatcgggca gccggatgac cggccacgac ggagccgcac    8400
ggctgaccag ctcgacggcc gccacctcat cgcggcagca ggtgctcccc agcaacccac    8460
gacggggctc agggtcgcct cacgcggctc agcaccgcga cggcggggt acggcgctcc     8520 gggaggctga caggcgctca gacggccgcg tagggccgcg agtcccccac ccctccccgc    8580
tgccctgtcg gcgagcacaa cggcgatgcc cgcagtcggc ggagcaggcg ccacgtaaac    8640
cgcccaccga tgccgccccc gtcgtgtgcg cgggccggtc ggcggccggg ccggagcggg    8700
gcgaagacag gagcgtcggc cgggccgtgg gccgggccgc gcggcccgct cgcgggccgc    8760
cttgatgacg tagggaaagt tgtaccgcaa aaaacgcagc ctgaactagt tgcgatcct     8819

<210> SEQ ID NO 146
<211> LENGTH: 8742
<212> TYPE: DNA
<213> ORGANISM: Artificial Sequence
<220> FEATURE:
<223> OTHER INFORMATION: pSEGT-phdA4 plasmid
<220> FEATURE:
<221> NAME/KEY: misc_feature
<222> LOCATION: (193)..(193)
<223> OTHER INFORMATION: n is a, c, g, or t

<400> SEQUENCE: 146
ctagagatcg aacttcatgt tcgagttctt gttcacgtag aagccggaga tgtgagaggt      60
gatctggaac tgctcaccct cgttggtggt gacctggagg taaagcaagt gacccttctg     120
gcggaggtgg taaggaacgg ggttccacgg ggagagagag atggccttga cggtcttggg     180 aagggggagct tcngcgcggg ggaggatggt cttgagagag ggggagctag taatgtcgta    240
cttggacagg gagtgctcct tctccgacgc atcagccacc tcagcggaga tggcatcgtg    300
cagagacaga cccccggagg taaccatggc caagcgaatt ctgtgtttcg gtgattccct    360
gacctggggc tgggtccccg tcgaagacgg ggcaccacc gagcggttcg ccccgacgt      420 gcgctggacc ggtgtgctgg cccagcagct cggagcggac ttcgaggtga tcgaggaggg    480
actgagcgcg cgcaccacca acatcgacga ccccaccgat ccgcggctca acggcgcgag    540
ctacctgccg tcgtgcctcg cgacgcacct gccgctcgac ctggtgatca tcatgctggg    600
caccaacgac accaaggcct acttccggcg caccccgctc gacatcgcgc tgggcatgtc    660
ggtgctcgtc acgcaggtgc tcaccagcgc gggcggcgtc ggcaccacgt acccggcacc    720
caaggtgctg gtggtctcgc cgccaccgct ggcgcccatg ccgcacccct ggttccagtt    780
gatcttcgag ggcggcgagc agaagaccac tgagctcgcc cgcgtgtaca gcgcgctcgc    840
gtcgttcatg aaggtgccgt tcttcgacgc gggttcggtg atcagcaccg acggcgtcga    900
cggaatccac ttcaccgagg ccaacaatcg cgatctcggg gtggccctcg cggaacaggt    960
gcggagcctg ctgtaacaat ggggatccgc gagcggatcg gctgaccgga gcggagga     1020 ggacgggcgg ccggcggaaa agtccgccgg tccgctgaat cgctccccgg gcacggacgt    1080
ggcagtatca gcgccatgtc cggcatatcc cagccctccg catgcccgga attcggcgta    1140
atcatggtca tagctgtttc ctgtgtgaaa ttgttatccg ctcacaattc cacacaacat    1200
```

-continued

```
acgagccgga agcataaagt gtaaagcctg gggtgcctaa tgagtgagct aactcacatt    1260
aattgcgttg cgctcactgc ccgctttcca gtcgggaaac ctgtcgtgcc agctgcatta    1320
atgaatcggc caacgcgcgg ggagaggcgg tttgcgtatt gggcgctctt ccgcttcctc    1380
gctcactgac tcgctgcgct cggtcgttcg gctgcggcga gcggtatcag ctcactcaaa    1440
ggcggtaata cggttatcca cagaatcagg ggataacgca ggaaagaaca tgtgagcaaa    1500
aggccagcaa aaggccagga accgtaaaaa ggccgcgttg ctggcgtttt tccataggct    1560
ccgcccccct gacgagcatc acaaaaatcg acgctcaagt cagaggtggc gaaacccgac    1620
aggactataa agataccagg cgtttccccc tggaagctcc ctcgtgcgct ctcctgttcc    1680
gaccctgccg cttaccggat acctgtccgc ctttctccct tcgggaagcg tggcgctttc    1740
tcatagctca cgctgtaggt atctcagttc ggtgtaggtc gttcgctcca agctgggctg    1800
tgtgcacgaa ccccccgttc agcccgaccg ctgcgcctta tccggtaact atcgtcttga    1860
gtccaacccg gtaagacacg acttatcgcc actggcagca gccactggta acaggattag    1920
cagagcgagg tatgtaggcg gtgctacaga gttcttgaag tggtggccta actacggcta    1980
cactagaagg acagtatttg gtatctgcgc tctgctgaag ccagttacct tcggaaaaag    2040
agttggtagc tcttgatccg gcaaacaaac caccgctggt agcggtggtt tttttgtttg    2100
caagcagcag attacgcgca gaaaaaaagg atctcaagaa gatcctttga tcttttctac    2160
ggggtctgac gctcagtgga acgaaaactc acgttaaggg attttggtca tgagattatc    2220
aaaaaggatc ttcacctaga tccttttaaa ttaaaaatga agttttaaat caatctaaag    2280
tatatatgag taaacttggt ctgacagtta ccaatgctta atcagtgagg cacctatctc    2340
agcgatctgt ctatttcgtt catccatagt tgcctgactc cccgtcgtgt agataactac    2400
gatacgggag ggcttaccat ctggccccag tgctgcaatg ataccgcgag acccacgctc    2460
accggctcca gatttatcag caataaacca gccagccgga agggccgagc gcagaagtgg    2520
tcctgcaact ttatccgcct ccatccagtc tattaattgt tgccgggaag ctagagtaag    2580
tagttcgcca gttaatagtt tgcgcaacgt tgttgccatt gctacaggca tcgtggtgtc    2640
acgctcgtcg tttggtatgg cttcattcag ctccggttcc caacgatcaa ggcgagttac    2700
atgatccccc atgttgtgca aaaaagcggt tagctccttc ggtcctccga tcgttgtcag    2760
aagtaagttg gccgcagtgt tatcactcat ggttatggca gcactgcata attctcttac    2820
tgtcatgcca tccgtaagat gcttttctgt gactggtgag tactcaacca agtcattctg    2880
agaatagtgt atgcggcgac cgagttgctc ttgcccggcg tcaatacggg ataataccgc    2940
gccacatagc agaactttaa aagtgctcat cattggaaaa cgttcttcgg ggcgaaaact    3000
ctcaaggatc ttaccgctgt tgagatccag ttcgatgtaa cccactcgtg cacccaactg    3060
atcttcagca tcttttactt tcaccagcgt ttctgggtga gcaaaaacag gaaggcaaaa    3120
tgccgcaaaa aagggaataa gggcgacacg gaaatgttga atactcatac tcttcctttt    3180
tcaatattat tgaagcattt atcagggtta ttgtctcatg agcggataca tatttgaatg    3240
tatttagaaa aataaacaaa taggggttcc gcgcacattt ccccgaaaag tgccacctga    3300
cgtctaagaa accattatta tcatgacatt aacctataaa aataggcgta tcacgaggcc    3360
ctttcgtctc gcgcgtttcg gtgatgacgg tgaaaacctc ttgacacatg cagctcccgg    3420
agacggtcac agcttgtctg taagcggatg ccgggagcag acaagcccgt cagggcgcgt    3480
cagcgggtgt tggcgggtgt cggggctggc ttaactatgc ggcatcagag cagattgtac    3540
tgagagtgca ccatatgcgg tgtgaaatac cgcacagatg cgtaaggaga aaataccgca    3600
```

```
tcaggcgcca ttcgccattc aggctgcgca actgttggga agggcgatcg gtgcgggcct    3660
cttcgctatt acgccagctg gcgaaagggg gatgtgctgc aaggcgatta agttgggtaa    3720
cgccagggtt ttcccagtca cgacgttgta aaacgacggc cagtaagctt gcatgcctgc    3780
aggagtgggg aggcacgatg gccgctttgg tcgacctcaa cgagacgatg aagccgtgga    3840
acgacaccac cccggcggcc ctgctggacc acacccggca ctacaccttc gacgtctgat    3900
catcactgac gaatcgaggt cgaggaaccg agcgtccgag gaacacaggc gcttatcggt    3960
tggccgcgag attcctgtcg atcctctcgt gcagcgcgat tccgagggaa acggaaacgt    4020
tgagagactc ggtctggctc atcatgggga tggaaaccga ggcggaagac gcctcctcga    4080
acaggtcgga aggcccaccc ttttcgctgc cgaacagcaa ggccagccga tccggattgt    4140
ccccgagttc cttcacggaa atgtcgccat ccgccttgag cgtcatcagc tgcataccgc    4200
tgtcccgaat gaaggcgatg gcctcctcgc gaccggagag aacgacggga agggagaaga    4260
cgtaacctcg gctggccctt tggagacgcc ggtccgcgat gctggtgatg tcactgtcga    4320
ccaggatgat ccccgacgct ccgagcgcga gcgacgtgcg tactatcgcg ccgatgttcc    4380
cgacgatctt caccccgtcg agaacgacga cgtcccacg ccggctcgcg atatcgccga    4440
acctggccgg gcgagggacg cgggcgatgc cgaatgtctt ggccttccgc tcccccttga    4500
acaactggtt gacgatcgag gagtcgatga ggcggaccgg tatgttctgc cgcccgcaca    4560
gatccagcaa ctcagatgga aaaggactgc tgtcgctgcc gtagacctcg atgaactcca    4620
ccccggccgc gatgctgtgc atgagggggct cgacgtcctc gatcaacgtt gtctttatgt    4680
tggatcgcga cggcttggtg acatcgatga tccgctgcac cgcgggatcg gacggatttg    4740
cgatggtgtc caactcagtc atggtcgtcc taccggctgc tgtgttcagt gacgcgattc    4800
ctggggtgtg acaccctacg cgacgatggc ggatggctgc cctgaccggc aatcaccaac    4860
gcaaggggaa gtcgtcgctc tctggcaaag ctccccgctc ttccccgtcc gggaccgcg    4920 cggtcgatcc ccgcatatga agtattcgcc ttgatcagtc ccggtggacg cgccagcggc    4980
ccgccggagc gacggactcc ccgacctcga tcgtgtcgcc ctgagcgtcc acgtagacgt    5040
tgcgtgagag caggactggg ccgccgccga ccgcaccgcc ctcaccaccg accgcgaccg    5100
cgccatggcc gccgccgacg gcctggtcgc cgccgccgcc cgccggttcg gcgcctgacc    5160
cgaccaaccc ccgcggggcg ccggcacttc gtgctggcgc ccgccccca cccaccagga    5220 gaccgaccat gaccgacttc gacggacgcc tgaccgaggg gaccgtgaac ctggtccagg    5280
accccaacgc cggtggctgg tccgcccact gcgctgagcc cggttgcgac tgggccgact    5340
tcgccggacc gctcggcttc cagggcctcg tggccatcgc tcgccgacac acgcactgac    5400
cgcacgtcaa agcccgccg gatacccggc ggggctctct tcggccctcc aagtcacacc    5460
agccccaagg ggcgtcggga gtggcggagg gaacctctgg cccgattggt gccaggattc    5520
ccaccagacc aaagagcaac gggccggact tcgcacctcc gacccgtccg ctcccagact    5580 cgcgccccctt agccgggcga gacaggaacg ttgctcgtgc ccagagtacg gagcgatgcc    5640
gaggcattgc cagatcggcc cgccgggccc cgctgccact gcggaccgc aattgcccac    5700 acaccgggca aacggccgcg tatctactgc tcagaccgct gccggatggc agcgaagcgg    5760
gcgatcgcgc gtgtgacgcg agatgccgcc cgaggcaaaa gcgaacacct tgggaaagaa    5820
acaacgagag ttccccgcacc cctccgacct gcggtttctc cggacggggt ggatggggag    5880
agcccgagag gcgacagcct ctgggaagta ggaagcacgt cgcggaccga ggctgcccga    5940
```

-continued

```
ctgcggaaag ccgcccggta cagccgccgc cggacgctgt ggcggatcag cggggacgcc    6000
gcgtgcaagg gctgcggccg cgccctgatg gaccctgcct ccggcgtgat cgtcgcccag    6060
acggcggccg gaacgtccgt ggtcctgggc ctgatgcggt gcggcggat ctggctctgc     6120 ccggtctgcg ccgccacgat ccggcacaag cgggccgagg agatcaccgc cgccgtggtc    6180
gagtggatca agcgcggggg gaccgcctac ctggtcacct tcacggcccg ccatgggcac    6240
acggaccggc tcgcggacct catggacgcc ctccagggca cccggaagac gccggacagc    6300
ccccggcggc cgggcgccta ccagcgactg atcacgggcg gcacgtgggc cggacgccgg    6360
gccaaggacg ggcaccgggc cgccgaccgc gagggcatcc gagaccggat cgggtacgtc    6420
ggcatgatcc gcgcgaccga agtcaccgtg ggcagatca acggctggca cccgcacatc     6480
cacgcgatcg tcctggtcgg cggcggacc gaggggagc ggtccgcgaa gcagatcgtc      6540
gccaccttcg agccgaccgg cgccgcgctc gacgagtggc aggggcactg gcggtccgtg    6600
tggaccgccg ccctgcgcaa ggtcaacccc gccttcacgc ccgacgaccg gcacggcgtc    6660
gacttcaagc ggctggagac cgagcgcgac gccaacgacc tcgccgagta catcgccaag    6720
acccaggacg ggaaggcgcc cgccctcgaa ctcgcccgcg ccgacctcaa gacggcgacc    6780
ggcgggaacg tcgccccgtt cgaactcctc ggacggatcg gggacctgac cggcggcatg    6840
accgaggacg acgccgccgg ggtcggctcg ctggagtgga acctctcgcg ctggcacgag    6900
tacgagcggg caacccgggg acgcggggcc atcgaatgga cccgctacct gcggcagatg    6960
ctcgggctcg acggcggcga caccgaggcc gacgacctcg atctgctcct ggcggccgac    7020
gccgacggcg gggagctgcg ggccggggtc gccgtgaccg aggacggatg gcacgcggtc    7080
acccgccgcg ccctcgacct cgaggcgacc cgggccgccg aaggcaagga cggcaacgag    7140
gattcggcgg ccgtgggcga acgggtgcgg gaggtcctgg cgctggccga cgcggccgac    7200
acagtggtgg tgctcacggc ggggaggtg gccgaggcgt acgccgacat gctcgccgcc     7260
ctcgcccagc gccgcgagga agcaactgca cgccgacggc gagagcagga cgacgaccag    7320
gacgacgacg ccgacgaccg ccaggagcgg gccgcccggc acatcgcccg gctcgcaagt    7380
gggcccactt cgcactaact cgctcccccc cgccgtacgt catcccggtg acgtacggcg    7440
ggggtcggtg acgtacgcgg cgacggcggc cggggtcgaa gccgcgggag taatcctggg    7500
attactcgcc cggggtcggc cccgccggca cttcgtgcag gcggtacctc cgcccgact    7560 cgcctcgcta cgagacgtgc cgcgtacggt cgtcggccat gagcaccacc accccaggg    7620 acgccgacgg cgcgaagctc tgcgcctggt gcggctcgga gatcaagcaa tccggcgtcg    7680
gccggagccg ggactactgc cgccgctcct gccgccagcg ggcgtacgag gcccggcgcc    7740
agcgcgaggc gatcgtgtcc gccgtggcgt cggcagtcgc tcgccgagat acgtcacgtg    7800
acgaaatgca gcagccttcc attccgtcac gtgacgaaac tcgggccgca ggtcagagca    7860
cggttccgcc cgctccggcc ctgccggacc cccggctgca gctcgcccgg ccgccggtcc    7920
ccctgccgtc cggcccgtcc cagaggcagc gtcgcgggct cctgcctccc ccgcccggcg    7980
ccgaccggga cccgcaaacc ccttgatccg ctgtcggggg tgatcactac ggtgggtgcc    8040
gaagtgatca cggggaggac tgatgcacca ccaggaccgg gaccaggacc aggcgttagc    8100
ggcagtgctg gccgcactgc tcctggtcgg cgggacgctg atcgtgcggg agctcctggg    8160
cctgtggccc gccgtggcgg tcggcatggc gccgccctc gccctctacg gaggcccgcc    8220
cgcggcccgc cggatagccg tcgcggtcga ggtccgccgg ttccgccggc atcttgccca    8280
ccacgatcgg gcagccggat gaccggccac gacggagccg cacggctgac cagctcgacg    8340
```
gccgccacct catcgcggca gcaggtgctc cccagcaacc cacgacgggg ctcagggtcg    8400
cctcacgcgg ctcagcaccg cgacggcggg ggtacggcgc tccggaggc tgacaggcgc    8460 tcagacggcc gcgtagggcc gcgagtcccc caccctccc cgctgccctg tcggcgagca    8520
caacggcgat gcccgcagtc ggcggagcag gcgccacgta aaccgcccac cgatgccgcc    8580
cccgtcgtgt gcgcgggccg gtcggcggcc ggggccggagc ggggcgaaga caggagcgtc    8640
ggccgggccg tgggccgggc cgcgcggccc gctcgcgggc cgccttgatg acgtagggaa    8700
agttgtaccg caaaaaacgc agcctgaact agttgcgatc ct    8742

<210> SEQ ID NO 147
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 147
taacaggagg aattaaccnn sgccaagcga attctgtgt                              39

<210> SEQ ID NO 148
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 148
caggaggaat taaccatgnn saagcgaatt ctgtgtttc                              39

<210> SEQ ID NO 149
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 149
gaggaattaa ccatggccnn scgaattctg tgtttcggt                              39

<210> SEQ ID NO 150
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 150
gaattaacca tggccaagnn sattctgtgt ttcggtgat                              39

<210> SEQ ID NO 151
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 151
ttaaccatgg ccaagcgann sctgtgtttc ggtgattcc                              39

<210> SEQ ID NO 152
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 152
accatggcca agcgaattnn stgtttcggt gattccctg                              39

<210> SEQ ID NO 153
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 153
atggccaagc gaattctgnn sttcggtgat tccctgacc                              39

<210> SEQ ID NO 154
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 154
gccaagcgaa ttctgtgtnn sggtgattcc ctgacctgg                              39

<210> SEQ ID NO 155
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 155
aagcgaattc tgtgtttcnn sgattccctg acctggggc                              39

<210> SEQ ID NO 156
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 156
cgaattctgt gtttcggtnn stccctgacc tggggctgg                                  39

<210> SEQ ID NO 157
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 157
attctgtgtt tcggtgatnn sctgacctgg ggctgggtc                                  39

<210> SEQ ID NO 158
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 158
ctgtgtttcg gtgattccnn sacctggggc tgggtcccc                                  39

<210> SEQ ID NO 159
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 159
tgtttcggtg attccctgnn stggggctgg gtccccgtc                                  39

<210> SEQ ID NO 160
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 160
ttcggtgatt ccctgaccnn sggctgggtc cccgtcgaa                                      39

<210> SEQ ID NO 161
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 161
ggtgattccc tgacctggnn stgggtcccc gtcgaagac                                      39

<210> SEQ ID NO 162
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 162
gattccctga cctggggcnn sgtccccgtc gaagacggg                                      39

<210> SEQ ID NO 163
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 163
tccctgacct ggggctggnn scccgtcgaa gacggggca                                      39

<210> SEQ ID NO 164
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 164
ctgacctggg gctgggtcnn sgtcgaagac ggggcaccc                                      39

<210> SEQ ID NO 165
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 165
acctggggct gggtccccnn sgaagacggg gcacccacc    39

<210> SEQ ID NO 166
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 166
tggggctggg tccccgtcnn sgacggggca cccaccgag    39

<210> SEQ ID NO 167
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 167
ggctgggtcc ccgtcgaann sggggcaccc accgagcgg    39

<210> SEQ ID NO 168
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 168
tgggtccccg tcgaagacnn sgcacccacc gagcggttc    39

<210> SEQ ID NO 169
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 169
gtccccgtcg aagacgggnn scccaccgag cggttcgcc    39

<210> SEQ ID NO 170
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

```
<400> SEQUENCE: 170
cccgtcgaag acggggcann saccgagcgg ttcgccccc                    39

<210> SEQ ID NO 171
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 171
gtcgaagacg gggcacccnn sgagcggttc gccccgac                     39

<210> SEQ ID NO 172
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 172
gaagacgggg cacccaccnn scggttcgcc ccgacgtg                     39

<210> SEQ ID NO 173
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 173
gacggggcac ccaccgagnn sttcgccccc gacgtgcgc                    39

<210> SEQ ID NO 174
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 174
ggggcaccca ccgagcggnn sgcccccgac gtgcgctgg                    39

<210> SEQ ID NO 175
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t
```

<400> SEQUENCE: 175
gcacccaccg agcggttcnn scccgacgtg cgctggacc            39

<210> SEQ ID NO 176
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 176
cccaccgagc ggttcgccnn sgacgtgcgc tggaccggt            39

<210> SEQ ID NO 177
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 177
accgagcggt tcgccccnn sgtgcgctgg accggtgtg            39

<210> SEQ ID NO 178
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 178
gagcggttcg ccccgacnn scgctggacc ggtgtgctg            39

<210> SEQ ID NO 179
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 179
cggttcgccc ccgacgtgnn stggaccggt gtgctggcc            39

<210> SEQ ID NO 180
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 180 ttcgccccg acgtgcgcnn saccggtgtg ctggcccag                               39

<210> SEQ ID NO 181
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 181
gcccccgacg tgcgctggnn sggtgtgctg gcccagcag                              39

<210> SEQ ID NO 182
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 182
cccgacgtgc gctggaccnn sgtgctggcc cagcagctc                              39

<210> SEQ ID NO 183
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 183
gacgtgcgct ggaccggtnn sctggcccag cagctcgga                              39

<210> SEQ ID NO 184
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 184
gtgcgctgga ccggtgtgnn sgcccagcag ctcggagcg                              39

<210> SEQ ID NO 185
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (19)..(20)
<223> OTHER INFORMATION: n is a, c, g, or t

<400> SEQUENCE: 185
cgctggaccg gtgtgctgnn scagcagctc ggagcggac                    39

<210> SEQ ID NO 186
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 186
tggaccggtg tgctggccnn scagctcgga gcggacttc                    39

<210> SEQ ID NO 187
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 187
accggtgtgc tggcccagnn sctcggagcg gacttcgag                    39

<210> SEQ ID NO 188
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 188
ggtgtgctgg cccagcagnn sggagcggac ttcgaggtg                    39

<210> SEQ ID NO 189
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 189
gtgctggccc agcagctcnn sgcggacttc gaggtgatc                    39

<210> SEQ ID NO 190
<211> LENGTH: 39
<212> TYPE: DNA
<213> ORGANISM: Artificial Sequence
<220> FEATURE:
<223> OTHER INFORMATION: primer
<220> FEATURE:
```

<221> NAME/KEY: misc_feature
<222> LOCATION: (19)..(20)
<223> OTHER INFORMATION: n is a, c, g, or t

<400> SEQUENCE: 190
ctggcccagc agctcggann sgacttcgag gtgatcgag                    39

<210> SEQ ID NO 191
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 191
gcccagcagc tcggagcgnn sttcgaggtg atcgaggag                    39

<210> SEQ ID NO 192
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 192
cagcagctcg gagcggacnn sgaggtgatc gaggaggga                    39

<210> SEQ ID NO 193
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 193
cagctcggag cggacttcnn sgtgatcgag gagggactg                    39

<210> SEQ ID NO 194
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 194
ctcggagcgg acttcgagnn satcgaggag ggactgagc                    39

<210> SEQ ID NO 195
<211> LENGTH: 39
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (19)..(20)
<223> OTHER INFORMATION: n is a, c, g, or t

<400> SEQUENCE: 195
ggagcggact tcgaggtgnn sgaggaggga ctgagcgcg                               39

<210> SEQ ID NO 196
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 196
gcggacttcg aggtgatcnn sgagggactg agcgcgcgc                               39

<210> SEQ ID NO 197
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 197
gacttcgagg tgatcgagnn sggactgagc gcgcgcacc                               39

<210> SEQ ID NO 198
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 198
ttcgaggtga tcgaggagnn sctgagcgcg cgcaccacc                               39

<210> SEQ ID NO 199
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 199
gaggtgatcg aggagggann sagcgcgcgc accaccaac                               39

<210> SEQ ID NO 200
<211> LENGTH: 39
<212> TYPE: DNA
<213> ORGANISM: Artificial Sequence
<220> FEATURE:
```

```
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 200
gtgatcgagg agggactgnn sgcgcgcacc accaacatc                              39

<210> SEQ ID NO 201
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 201
atcgaggagg gactgagcnn scgcaccacc aacatcgac                              39

<210> SEQ ID NO 202
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 202
gaggagggac tgagcgcgnn saccaccaac atcgacgac                              39

<210> SEQ ID NO 203
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 203
gagggactga gcgcgcgcnn saccaacatc gacgacccc                              39

<210> SEQ ID NO 204
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 204
ggactgagcg cgcgcaccnn saacatcgac gacccacc                               39

<210> SEQ ID NO 205
<211> LENGTH: 39
<212> TYPE: DNA
<213> ORGANISM: Artificial Sequence
```

```
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 205
ctgagcgcgc gcaccaccnn satcgacgac cccaccgat                              39

<210> SEQ ID NO 206
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 206
agcgcgcgca ccaccaacnn sgacgacccc accgatccg                              39

<210> SEQ ID NO 207
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 207
gcgcgcacca ccaacatcnn sgaccccacc gatccgcgg                              39

<210> SEQ ID NO 208
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 208
cgcaccacca acatcgacnn scccaccgat ccgcggctc                              39

<210> SEQ ID NO 209
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 209
accaccaaca tcgacgacnn saccgatccg cggctcaac                              39

<210> SEQ ID NO 210
<211> LENGTH: 39
<212> TYPE: DNA
```

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 210
accaacatcg acgaccccnn sgatccgcgg ctcaacggc    39

<210> SEQ ID NO 211
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 211
aacatcgacg accccaccnn sccgcggctc aacggcgcg    39

<210> SEQ ID NO 212
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 212
atcgacgacc ccaccgatnn scggctcaac ggcgcgagc    39

<210> SEQ ID NO 213
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 213
gacgacccca ccgatccgnn sctcaacggc gcgagctac    39

<210> SEQ ID NO 214
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 214
gaccccaccg atccgcggnn saacggcgcg agctacctg    39

<210> SEQ ID NO 215
<211> LENGTH: 39

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 215
cccaccgatc cgcggctcnn sggcgcgagc tacctgccg                                39

<210> SEQ ID NO 216
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 216
accgatccgc ggctcaacnn sgcgagctac ctgccgtcg                                39

<210> SEQ ID NO 217
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 217
gatccgcggc tcaacggcnn sagctacctg ccgtcgtgc                                39

<210> SEQ ID NO 218
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 218
ccgcggctca acggcgcgnn stacctgccg tcgtgcctc                                39

<210> SEQ ID NO 219
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 219
cggctcaacg gcgcgagcnn sctgccgtcg tgcctcgcg                                39

<210> SEQ ID NO 220
```

```
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 220
ctcaacggcg cgagctacnn sccgtcgtgc ctcgcgacg                    39

<210> SEQ ID NO 221
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 221
aacggcgcga gctacctgnn stcgtgcctc gcgacgcac                    39

<210> SEQ ID NO 222
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 222
ggcgcgagct acctgccgnn stgcctcgcg acgcacctg                    39

<210> SEQ ID NO 223
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 223
gcgagctacc tgccgtcgnn sctcgcgacg cacctgccg                    39

<210> SEQ ID NO 224
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 224
agctacctgc cgtcgtgcnn sgcgacgcac ctgccgctc                    39
```

```
<210> SEQ ID NO 225
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 225
tacctgccgt cgtgcctcnn sacgcacctg ccgctcgac                    39

<210> SEQ ID NO 226
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 226
ctgccgtcgt gcctcgcgnn scacctgccg ctcgacctg                    39

<210> SEQ ID NO 227
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 227
ccgtcgtgcc tcgcgacgnn sctgccgctc gacctggtg                    39

<210> SEQ ID NO 228
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 228
tcgtgcctcg cgacgcacnn sccgctcgac ctggtgatc                    39

<210> SEQ ID NO 229
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 229
tgcctcgcga cgcacctgnn sctcgacctg gtgatcatc                    39
```

```
<210> SEQ ID NO 230
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 230
ctcgcgacgc acctgccgnn sgacctggtg atcatcatg                          39

<210> SEQ ID NO 231
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 231
gcgacgcacc tgccgctcnn sctggtgatc atcatgctg                          39

<210> SEQ ID NO 232
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 232
acgcacctgc cgctcgacnn sgtgatcatc atgctgggc                          39

<210> SEQ ID NO 233
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 233
cacctgccgc tcgacctgnn satcatcatg ctgggcacc                          39

<210> SEQ ID NO 234
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 234
ctgccgctcg acctggtgnn satcatgctg ggcaccaac                          39
```

<210> SEQ ID NO 235
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 235
ccgctcgacc tggtgatcnn satgctgggc accaacgac                          39

<210> SEQ ID NO 236
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 236
ctcgacctgg tgatcatcnn sctgggcacc aacgacacc                          39

<210> SEQ ID NO 237
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 237
gacctggtga tcatcatgnn sggcaccaac gacaccaag                          39

<210> SEQ ID NO 238
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 238
ctggtgatca tcatgctgnn saccaacgac accaaggcc                          39

<210> SEQ ID NO 239
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 239
gtgatcatca tgctgggcnn saacgacacc aaggcctac                                          39

<210> SEQ ID NO 240
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 240
atcatcatgc tgggcaccnn sgacaccaag gcctacttc                                          39

<210> SEQ ID NO 241
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 241
atcatgctgg gcaccaacnn saccaaggcc tacttccgg                                          39

<210> SEQ ID NO 242
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 242
atgctgggca ccaacgacnn saaggcctac ttccggcgc                                          39

<210> SEQ ID NO 243
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 243
ctgggcacca acgacaccnn sgcctacttc cggcgcacc                                          39

<210> SEQ ID NO 244
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 244
ggcaccaacg acaccaagnn stacttccgg cgcaccccg 39

<210> SEQ ID NO 245
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 245
accaacgaca ccaaggccnn sttccggcgc accccgctc 39

<210> SEQ ID NO 246
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 246
aacgacacca aggcctacnn ncggcgcacc ccgctcgac 39

<210> SEQ ID NO 247
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 247
gacaccaagg cctacttcnn ncgcaccccg ctcgacatc 39

<210> SEQ ID NO 248
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 248
accaaggcct acttccggnn saccccgctc gacatcgcg 39

<210> SEQ ID NO 249
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 249
aaggcctact tccggcgcnn sccgctcgac atcgcgctg        39

<210> SEQ ID NO 250
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 250
gcctacttcc ggcgcaccnn sctcgacatc gcgctgggc        39

<210> SEQ ID NO 251
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 251
tacttccggc gcaccccgnn sgacatcgcg ctgggcatg        39

<210> SEQ ID NO 252
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 252
ttccggcgca ccccgctcnn satcgcgctg ggcatgtcg        39

<210> SEQ ID NO 253
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 253
cggcgcaccc cgctcgacnn sgcgctgggc atgtcggtg        39

<210> SEQ ID NO 254
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 254
cgcaccccgc tcgacatcnn sctgggcatg tcggtgctc                                      39

<210> SEQ ID NO 255
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 255
accccgctcg acatcgcgnn sggcatgtcg gtgctcgtc                                      39

<210> SEQ ID NO 256
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 256
ccgctcgaca tcgcgctgnn satgtcggtg ctcgtcacg                                      39

<210> SEQ ID NO 257
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 257
ctcgacatcg cgctgggcnn stcggtgctc gtcacgcag                                      39

<210> SEQ ID NO 258
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 258
gacatcgcgc tgggcatgnn sgtgctcgtc acgcaggtg                                      39

<210> SEQ ID NO 259
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 259
atcgcgctgg gcatgtcgnn sctcgtcacg caggtgctc						39

<210> SEQ ID NO 260
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 260
gcgctgggca tgtcggtgnn sgtcacgcag gtgctcacc						39

<210> SEQ ID NO 261
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 261
ctgggcatgt cggtgctcnn sacgcaggtg ctcaccagc						39

<210> SEQ ID NO 262
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 262
ggcatgtcgg tgctcgtcnn scaggtgctc accagcgcg						39

<210> SEQ ID NO 263
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 263
atgtcggtgc tcgtcacgnn sgtgctcacc agcgcgggc						39

<210> SEQ ID NO 264
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 264
tcggtgctcg tcacgcagnn sctcaccagc gcgggcggc                                  39

<210> SEQ ID NO 265
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 265
gtgctcgtca cgcaggtgnn saccagcgcg ggcggcgtc                                  39

<210> SEQ ID NO 266
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 266
ctcgtcacgc aggtgctcnn sagcgcgggc ggcgtcggc                                  39

<210> SEQ ID NO 267
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 267
gtcacgcagg tgctcaccnn sgcgggcggc gtcggcacc                                  39

<210> SEQ ID NO 268
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 268
acgcaggtgc tcaccagcnn sggcggcgtc ggcaccacg                                  39

<210> SEQ ID NO 269
<211> LENGTH: 39
<212> TYPE: DNA
<213> ORGANISM: Artificial Sequence
<220> FEATURE:
<223> OTHER INFORMATION: primer
<220> FEATURE:

```
<221> NAME/KEY: misc_feature
<222> LOCATION: (19)..(20)
<223> OTHER INFORMATION: n is a, c, g, or t

<400> SEQUENCE: 269
caggtgctca ccagcgcgnn sggcgtcggc accacgtac                    39

<210> SEQ ID NO 270
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 270
gtgctcacca gcgcgggcnn sgtcggcacc acgtacccg                    39

<210> SEQ ID NO 271
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 271
ctcaccagcg cgggcggcnn sggcaccacg tacccggca                    39

<210> SEQ ID NO 272
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 272
accagcgcgg gcggcgtcnn saccacgtac ccggcaccc                    39

<210> SEQ ID NO 273
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 273
agcgcgggcg gcgtcggcnn sacgtacccg gcacccaag                    39

<210> SEQ ID NO 274
<211> LENGTH: 39
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (19)..(20)
<223> OTHER INFORMATION: n is a, c, g, or t

<400> SEQUENCE: 274
gcgggcggcg tcggcaccnn stacccggca cccaaggtg                    39

<210> SEQ ID NO 275
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 275
ggcggcgtcg gcaccacgnn sccggcaccc aaggtgctg                    39

<210> SEQ ID NO 276
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 276
ggcgtcggca ccacgtacnn sgcacccaag gtgctggtg                    39

<210> SEQ ID NO 277
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 277
gtcggcacca cgtacccgnn scccaaggtg ctggtggtc                    39

<210> SEQ ID NO 278
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 278
ggcaccacgt acccggcann saaggtgctg gtggtctcg                    39

<210> SEQ ID NO 279
<211> LENGTH: 39
<212> TYPE: DNA
<213> ORGANISM: Artificial Sequence
<220> FEATURE:
```

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 279
accacgtacc cggcacccnn sgtgctggtg gtctcgccg                     39

<210> SEQ ID NO 280
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 280
acgtacccgg cacccaagnn sctggtggtc tcgccgcca                     39

<210> SEQ ID NO 281
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 281
tacccggcac caaggtgnn sgtggtctcg ccgccaccg                      39

<210> SEQ ID NO 282
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 282
ccggcaccca aggtgctgnn sgtctcgccg ccaccgctg                     39

<210> SEQ ID NO 283
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 283
gcacccaagg tgctggtgnn stcgccgcca ccgctggcg                     39

<210> SEQ ID NO 284
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 284
cccaaggtgc tggtggtcnn sccgccaccg ctggcgccc                            39

<210> SEQ ID NO 285
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 285
aaggtgctgg tggtctcgnn sccaccgctg gcgcccatg                            39

<210> SEQ ID NO 286
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 286
gtgctggtgg tctcgccgnn sccgctggcg cccatgccg                            39

<210> SEQ ID NO 287
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 287
ctggtggtct cgccgccann sctggcgccc atgccgcac                            39

<210> SEQ ID NO 288
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 288
gtggtctcgc cgccaccgnn sgcgcccatg ccgcacccc                            39

<210> SEQ ID NO 289
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 289
gtctcgccgc caccgctgnn scccatgccg caccccctgg    39

<210> SEQ ID NO 290
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 290
tcgccgccac cgctggcgnn satgccgcac ccctggttc    39

<210> SEQ ID NO 291
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 291
ccgccaccgc tggcgcccnn sccgcacccc tggttccag    39

<210> SEQ ID NO 292
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 292
ccaccgctgg cgcccatgnn scaccctgg ttccagttg    39

<210> SEQ ID NO 293
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 293
ccgctggcgc ccatgccgnn sccctggttc cagttgatc    39

<210> SEQ ID NO 294
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 294
ctggcgccca tgccgcacnn stggttccag ttgatcttc        39

<210> SEQ ID NO 295
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 295
gcgcccatgc cgcaccccnn sttccagttg atcttcgag        39

<210> SEQ ID NO 296
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 296
cccatgccgc acccctggnn scagttgatc ttcgagggc        39

<210> SEQ ID NO 297
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 297
atgccgcacc cctggttcnn sttgatcttc gagggcggc        39

<210> SEQ ID NO 298
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 298
ccgcacccct ggttccagnn satcttcgag ggcggcgag        39

<210> SEQ ID NO 299

```
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 299
cacccctggt tccagttgnn sttcgagggc ggcgagcag                              39

<210> SEQ ID NO 300
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 300
ccctggttcc agttgatcnn sgagggcggc gagcagaag                              39

<210> SEQ ID NO 301
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 301
tggttccagt tgatcttcnn sggcggcgag cagaagacc                              39

<210> SEQ ID NO 302
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 302
ttccagttga tcttcgagnn sggcgagcag aagaccact                              39

<210> SEQ ID NO 303
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 303
cagttgatct tcgagggcnn sgagcagaag accactgag                              39
```

```
<210> SEQ ID NO 304
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 304
ttgatcttcg agggcggcnn scagaagacc actgagctc                              39

<210> SEQ ID NO 305
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 305
atcttcgagg gcggcgagnn saagaccact gagctcgcc                              39

<210> SEQ ID NO 306
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 306
ttcgagggcg gcgagcagnn saccactgag ctcgcccgc                              39

<210> SEQ ID NO 307
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 307
gagggcggcg agcagaagnn sactgagctc gcccgcgtg                              39

<210> SEQ ID NO 308
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 308
ggcggcgagc agaagaccnn sgagctcgcc cgcgtgtac                              39
```

```
<210> SEQ ID NO 309
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 309
ggcgagcaga agaccactnn sctcgcccgc gtgtacagc                               39

<210> SEQ ID NO 310
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 310
gagcagaaga ccactgagnn sgcccgcgtg tacagcgcg                               39

<210> SEQ ID NO 311
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 311
cagaagacca ctgagctcnn scgcgtgtac agcgcgctc                               39

<210> SEQ ID NO 312
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 312
aagaccactg agctcgccnn sgtgtacagc gcgctcgcg                               39

<210> SEQ ID NO 313
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 313
accactgagc tcgcccgcnn stacagcgcg ctcgcgtcg                               39
```

<210> SEQ ID NO 314
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 314
actgagctcg cccgcgtgnn sagcgcgctc gcgtcgttc                              39

<210> SEQ ID NO 315
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 315
gagctcgccc gcgtgtacnn sgcgctcgcg tcgttcatg                              39

<210> SEQ ID NO 316
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 316
ctcgcccgcg tgtacagcnn sctcgcgtcg ttcatgaag                              39

<210> SEQ ID NO 317
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 317
gcccgcgtgt acagcgcgnn sgcgtcgttc atgaaggtg                              39

<210> SEQ ID NO 318
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 318
cgcgtgtaca gcgcgctcnn stcgttcatg aaggtgccg            39

<210> SEQ ID NO 319
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 319
gtgtacagcg cgctcgcgnn sttcatgaag gtgccgttc            39

<210> SEQ ID NO 320
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 320
tacagcgcgc tcgcgtcgnn satgaaggtg ccgttcttc            39

<210> SEQ ID NO 321
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 321
agcgcgctcg cgtcgttcnn saaggtgccg ttcttcgac            39

<210> SEQ ID NO 322
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 322
gcgctcgcgt cgttcatgnn sgtgccgttc ttcgacgcg            39

<210> SEQ ID NO 323
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 323
ctcgcgtcgt tcatgaagnn sccgttcttc gacgcgggt                      39

<210> SEQ ID NO 324
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 324
gcgtcgttca tgaaggtgnn sttcttcgac gcgggttcg                      39

<210> SEQ ID NO 325
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 325
tcgttcatga aggtgccgnn sttcgacgcg ggttcggtg                      39

<210> SEQ ID NO 326
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 326
ttcatgaagg tgccgttcnn sgacgcgggt tcggtgatc                      39

<210> SEQ ID NO 327
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 327
atgaaggtgc cgttcttcnn sgcgggttcg gtgatcagc                      39

<210> SEQ ID NO 328
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 328
aaggtgccgt tcttcgacnn sggttcggtg atcagcacc                          39

<210> SEQ ID NO 329
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 329
gtgccgttct tcgacgcgnn stcggtgatc agcaccgac                          39

<210> SEQ ID NO 330
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 330
ccgttcttcg acgcgggtnn sgtgatcagc accgacggc                          39

<210> SEQ ID NO 331
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 331
ttcttcgacg cgggttcgnn satcagcacc gacggcgtc                          39

<210> SEQ ID NO 332
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 332
ttcgacgcgg gttcggtgnn sagcaccgac ggcgtcgac                          39

<210> SEQ ID NO 333
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 333
gacgcgggtt cggtgatcnn saccgacggc gtcgacgga                                    39

<210> SEQ ID NO 334
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 334
gcgggttcgg tgatcagcnn sgacggcgtc gacggaatc                                    39

<210> SEQ ID NO 335
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 335
ggttcggtga tcagcaccnn sggcgtcgac ggaatccac                                    39

<210> SEQ ID NO 336
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 336
tcggtgatca gcaccgacnn sgtcgacgga atccacttc                                    39

<210> SEQ ID NO 337
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 337
gtgatcagca ccgacggcnn sgacggaatc cacttcacc                                    39

<210> SEQ ID NO 338
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t

<400> SEQUENCE: 338
atcagcaccg acggcgtcnn sggaatccac ttcaccgag      39

<210> SEQ ID NO 339
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 339
agcaccgacg gcgtcgacnn satccacttc accgaggcc      39

<210> SEQ ID NO 340
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 340
accgacggcg tcgacggann scacttcacc gaggccaac      39

<210> SEQ ID NO 341
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 341
gacggcgtcg acggaatcnn sttcaccgag gccaacaat      39

<210> SEQ ID NO 342
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 342
ggcgtcgacg gaatccacnn saccgaggcc aacaatcgc      39

<210> SEQ ID NO 343
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (19)..(20)
<223> OTHER INFORMATION: n is a, c, g, or t

<400> SEQUENCE: 343
gtcgacggaa tccacttcnn sgaggccaac aatcgcgat                              39

<210> SEQ ID NO 344
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 344
gacggaatcc acttcaccnn sgccaacaat cgcgatctc                              39

<210> SEQ ID NO 345
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 345
ggaatccact tcaccgagnn saacaatcgc gatctcggg                              39

<210> SEQ ID NO 346
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 346
atccacttca ccgaggccnn saatcgcgat ctcggggtg                              39

<210> SEQ ID NO 347
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 347
cacttcaccg aggccaacnn scgcgatctc ggggtggcc                              39

<210> SEQ ID NO 348
<211> LENGTH: 39
<212> TYPE: DNA
<213> ORGANISM: Artificial Sequence
<220> FEATURE:
<223> OTHER INFORMATION: primer
<220> FEATURE:
```

<221> NAME/KEY: misc_feature
<222> LOCATION: (19)..(20)
<223> OTHER INFORMATION: n is a, c, g, or t

<400> SEQUENCE: 348
ttcaccgagg ccaacaatnn sgatctcggg gtggccctc       39

<210> SEQ ID NO 349
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 349
accgaggcca acaatcgcnn sctcggggtg gccctcgcg       39

<210> SEQ ID NO 350
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 350
gaggccaaca atcgcgatnn sggggtggcc ctcgcggaa       39

<210> SEQ ID NO 351
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 351
gccaacaatc gcgatctcnn sgtggccctc gcggaacag       39

<210> SEQ ID NO 352
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 352
aacaatcgcg atctcgggnn sgccctcgcg gaacaggtg       39

<210> SEQ ID NO 353
<211> LENGTH: 39
<212> TYPE: DNA
<213> ORGANISM: Artificial Sequence
<220> FEATURE:
<223> OTHER INFORMATION: primer

```
<220> FEATURE:
<221> NAME/KEY: misc_feature
<222> LOCATION: (19)..(20)
<223> OTHER INFORMATION: n is a, c, g, or t

<400> SEQUENCE: 353
aatcgcgatc tcggggtgnn sctcgcggaa caggtgcag                        39

<210> SEQ ID NO 354
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 354
cgcgatctcg gggtggccnn sgcggaacag gtgcagagc                        39

<210> SEQ ID NO 355
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 355
gatctcgggg tggccctcnn sgaacaggtg cagagcctg                        39

<210> SEQ ID NO 356
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 356
ctcggggtgg ccctcgcgnn scaggtgcag agcctgctg                        39

<210> SEQ ID NO 357
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 357
ggggtggccc tcgcggaann sgtgcagagc ctgctgtaa                        39

<210> SEQ ID NO 358
<211> LENGTH: 39
<212> TYPE: DNA
<213> ORGANISM: Artificial Sequence
<220> FEATURE:
```

<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 358
gtggccctcg cggaacagnn scagagcctg ctgtaaaag                                39

<210> SEQ ID NO 359
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 359
gccctcgcgg aacaggtgnn sagcctgctg taaaagggc                                39

<210> SEQ ID NO 360
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 360
ctcgcggaac aggtgcagnn sctgctgtaa aagggcgaa                                39

<210> SEQ ID NO 361
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 361
gcggaacagg tgcagagcnn sctgtaaaag ggcgaattc                                39

<210> SEQ ID NO 362
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 362
gaacaggtgc agagcctgnn staaaagggc gaattctgc                                39

<210> SEQ ID NO 363
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 363
acacagaatt cgcttggcsn nggttaattc ctcctgtta                    39

<210> SEQ ID NO 364
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 364
gaaacacaga attcgcttsn ncatggttaa ttcctcctg                    39

<210> SEQ ID NO 365
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 365
accgaaacac agaattcgsn nggccatggt taattcctc                    39

<210> SEQ ID NO 366
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 366
atcaccgaaa cacagaatsn ncttggccat ggttaattc                    39

<210> SEQ ID NO 367
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 367
ggaatcaccg aaacacagsn ntcgcttggc catggttaa                    39

<210> SEQ ID NO 368
<211> LENGTH: 39
<212> TYPE: DNA

<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 368
cagggaatca ccgaaacasn naattcgctt ggccatggt          39

<210> SEQ ID NO 369
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 369
ggtcagggaa tcaccgaasn ncagaattcg cttggccat          39

<210> SEQ ID NO 370
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 370
ccaggtcagg gaatcaccsn nacacagaat tcgcttggc          39

<210> SEQ ID NO 371
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 371
gccccaggtc agggaatcsn ngaaacacag aattcgctt          39

<210> SEQ ID NO 372
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 372
ccagccccag gtcagggasn naccgaaaca cagaattcg          39

<210> SEQ ID NO 373
<211> LENGTH: 39

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 373
gacccagccc caggtcagsn natcaccgaa acacagaat                    39

<210> SEQ ID NO 374
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 374
ggggacccag ccccaggtsn nggaatcacc gaaacacag                    39

<210> SEQ ID NO 375
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 375
gacggggacc cagccccasn ncagggaatc accgaaaca                    39

<210> SEQ ID NO 376
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 376
ttcgacgggg acccagccsn nggtcaggga atcaccgaa                    39

<210> SEQ ID NO 377
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 377
gtcttcgacg gggacccasn nccaggtcag ggaatcacc                    39

<210> SEQ ID NO 378
```

```
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 378
cccgtcttcg acggggacsn ngccccaggt cagggaatc                              39

<210> SEQ ID NO 379
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 379
tgccccgtct tcgacgggsn nccagcccca ggtcaggga                              39

<210> SEQ ID NO 380
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 380
gggtgccccg tcttcgacsn ngacccagcc ccaggtcag                              39

<210> SEQ ID NO 381
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 381
ggtgggtgcc ccgtcttcsn ngggaccca gccccaggt                               39

<210> SEQ ID NO 382
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 382
ctcggtgggt gccccgtcsn ngacggggac ccagcccca                              39
```

```
<210> SEQ ID NO 383
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 383
ccgctcggtg ggtgccccsn nttcgacggg gacccagcc                         39

<210> SEQ ID NO 384
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 384
gaaccgctcg gtgggtgcsn ngtcttcgac ggggaccca                         39

<210> SEQ ID NO 385
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 385
ggcgaaccgc tcggtgggsn ncccgtcttc gacggggac                         39

<210> SEQ ID NO 386
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 386
gggggcgaac cgctcggtsn ntgccccgtc ttcgacggg                         39

<210> SEQ ID NO 387
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 387
gtcgggggcg aaccgctcsn ngggtgcccc gtcttcgac                         39
```

```
<210> SEQ ID NO 388
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 388
cacgtcgggg gcgaaccgsn nggtgggtgc cccgtcttc                    39

<210> SEQ ID NO 389
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 389
gcgcacgtcg ggggcgaasn nctcggtggg tgccccgtc                    39

<210> SEQ ID NO 390
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 390
ccagcgcacg tcgggggcsn nccgctcggt gggtgcccc                    39

<210> SEQ ID NO 391
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 391
ggtccagcgc acgtcgggsn ngaaccgctc ggtgggtgc                    39

<210> SEQ ID NO 392
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 392
accggtccag cgcacgtcsn nggcgaaccg ctcggtggg                    39
```

<210> SEQ ID NO 393
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 393
cacaccggtc cagcgcacsn nggggggcgaa ccgctcggt                                    39

<210> SEQ ID NO 394
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 394
cagcacaccg gtccagcgsn ngtcggggggc gaaccgctc                                    39

<210> SEQ ID NO 395
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 395
ggccagcaca ccggtccasn ncacgtcggg ggcgaaccg                                     39

<210> SEQ ID NO 396
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 396
ctgggccagc acaccggtsn ngcgcacgtc gggggcgaa                                     39

<210> SEQ ID NO 397
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 397
ctgctgggcc agcacaccsn nccagcgcac gtcggggc    39

<210> SEQ ID NO 398
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 398
gagctgctgg gccagcacsn nggtccagcg cacgtcggg    39

<210> SEQ ID NO 399
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 399
tccgagctgc tgggccagsn naccggtcca gcgcacgtc    39

<210> SEQ ID NO 400
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 400
cgctccgagc tgctgggcsn ncacaccggt ccagcgcac    39

<210> SEQ ID NO 401
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 401
gtccgctccg agctgctgsn ncagcacacc ggtccagcg    39

<210> SEQ ID NO 402
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 402
gaagtccgct ccgagctgsn nggccagcac accggtcca         39

<210> SEQ ID NO 403
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 403
ctcgaagtcc gctccgagsn nctgggccag cacaccggt         39

<210> SEQ ID NO 404
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 404
cacctcgaag tccgctccsn nctgctgggc cagcacacc         39

<210> SEQ ID NO 405
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 405
gatcacctcg aagtccgcsn ngagctgctg ggccagcac         39

<210> SEQ ID NO 406
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 406
ctcgatcacc tcgaagtcsn ntccgagctg ctgggccag         39

<210> SEQ ID NO 407
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 407
ctcctcgatc acctcgaasn ncgctccgag ctgctgggc					39

<210> SEQ ID NO 408
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 408
tccctcctcg atcacctcsn ngtccgctcc gagctgctg					39

<210> SEQ ID NO 409
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 409
cagtccctcc tcgatcacsn ngaagtccgc tccgagctg					39

<210> SEQ ID NO 410
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 410
gctcagtccc tcctcgatsn nctcgaagtc cgctccgag					39

<210> SEQ ID NO 411
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 411
cgcgctcagt ccctcctcsn ncacctcgaa gtccgctcc					39

<210> SEQ ID NO 412
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 412
gcgcgcgctc agtccctcsn ngatcacctc gaagtccgc                                39

<210> SEQ ID NO 413
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 413
ggtgcgcgcg ctcagtccsn nctcgatcac ctcgaagtc                                39

<210> SEQ ID NO 414
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 414
ggtggtgcgc gcgctcagsn nctcctcgat cacctcgaa                                39

<210> SEQ ID NO 415
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 415
gttggtggtg cgcgcgctsn ntccctcctc gatcacctc                                39

<210> SEQ ID NO 416
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 416
gatgttggtg gtgcgcgcsn ncagtccctc ctcgatcac                                39

<210> SEQ ID NO 417
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 417
gtcgatgttg gtggtgcgsn ngctcagtcc ctcctcgat                          39

<210> SEQ ID NO 418
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 418
gtcgtcgatg ttggtggtsn ncgcgctcag tccctcctc                          39

<210> SEQ ID NO 419
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 419
ggggtcgtcg atgttggtsn ngcgcgcgct cagtccctc                          39

<210> SEQ ID NO 420
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 420
ggtggggtcg tcgatgttsn nggtgcgcgc gctcagtcc                          39

<210> SEQ ID NO 421
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 421
atcggtgggg tcgtcgatsn nggtggtgcg cgcgctcag                          39

<210> SEQ ID NO 422
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 422
cggatcggtg gggtcgtcsn ngttggtggt gcgcgcgct                                39

<210> SEQ ID NO 423
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 423
ccgcggatcg gtggggtcsn ngatgttggt ggtgcgcgc                                39

<210> SEQ ID NO 424
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 424
gagccgcgga tcggtgggsn ngtcgatgtt ggtggtgcg                                39

<210> SEQ ID NO 425
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 425
gttgagccgc ggatcggtsn ngtcgtcgat gttggtggt                                39

<210> SEQ ID NO 426
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 426
gccgttgagc cgcggatcsn ngggtcgtc gatgttggt                                 39

<210> SEQ ID NO 427
<211> LENGTH: 39
<212> TYPE: DNA
<213> ORGANISM: Artificial Sequence
<220> FEATURE:
<223> OTHER INFORMATION: primer
<220> FEATURE:

<221> NAME/KEY: misc_feature
<222> LOCATION: (20)..(21)
<223> OTHER INFORMATION: n is a, c, g, or t

<400> SEQUENCE: 427
cgcgccgttg agccgcggsn nggtggggtc gtcgatgtt          39

<210> SEQ ID NO 428
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 428
gctcgcgccg ttgagccgsn natcggtggg gtcgtcgat          39

<210> SEQ ID NO 429
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 429
gtagctcgcg ccgttgagsn ncggatcggt ggggtcgtc          39

<210> SEQ ID NO 430
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 430
caggtagctc gcgccgttsn nccgcggatc ggtggggtc          39

<210> SEQ ID NO 431
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 431
cggcaggtag ctcgcgccsn ngagccgcgg atcggtggg          39

<210> SEQ ID NO 432
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 432
cgacggcagg tagctcgcsn ngttgagccg cggatcggt                        39

<210> SEQ ID NO 433
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 433
gcacgacggc aggtagctsn ngccgttgag ccgcggatc                        39

<210> SEQ ID NO 434
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 434
gaggcacgac ggcaggtasn ncgcgccgtt gagccgcgg                        39

<210> SEQ ID NO 435
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 435
cgcgaggcac gacggcagsn ngctcgcgcc gttgagccg                        39

<210> SEQ ID NO 436
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 436
cgtcgcgagg cacgacggsn ngtagctcgc gccgttgag                        39

<210> SEQ ID NO 437
<211> LENGTH: 39
<212> TYPE: DNA
<213> ORGANISM: Artificial Sequence
<220> FEATURE:

```
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 437
gtgcgtcgcg aggcacgasn ncaggtagct cgcgccgtt                              39

<210> SEQ ID NO 438
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 438
caggtgcgtc gcgaggcasn ncggcaggta gctcgcgcc                              39

<210> SEQ ID NO 439
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 439
cggcaggtgc gtcgcgagsn ncgacggcag gtagctcgc                              39

<210> SEQ ID NO 440
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 440
gagcggcagg tgcgtcgcsn ngcacgacgg caggtagct                              39

<210> SEQ ID NO 441
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 441
gtcgagcggc aggtgcgtsn ngaggcacga cggcaggta                              39

<210> SEQ ID NO 442
<211> LENGTH: 39
<212> TYPE: DNA
<213> ORGANISM: Artificial Sequence
```

<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 442
caggtcgagc ggcaggtgsn ncgcgaggca cgacggcag                          39

<210> SEQ ID NO 443
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 443
caccaggtcg agcggcagsn ncgtcgcgag gcacgacgg                          39

<210> SEQ ID NO 444
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 444
gatcaccagg tcgagcggsn ngtgcgtcgc gaggcacga                          39

<210> SEQ ID NO 445
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 445
gatgatcacc aggtcgagsn ncaggtgcgt cgcgaggca                          39

<210> SEQ ID NO 446
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 446
catgatgatc accaggtcsn ncggcaggtg cgtcgcgag                          39

<210> SEQ ID NO 447
<211> LENGTH: 39
<212> TYPE: DNA

```
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 447
cagcatgatg atcaccagsn ngagcggcag gtgcgtcgc                              39

<210> SEQ ID NO 448
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 448
gcccagcatg atgatcacsn ngtcgagcgg caggtgcgt                              39

<210> SEQ ID NO 449
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 449
ggtgcccagc atgatgatsn ncaggtcgag cggcaggtg                              39

<210> SEQ ID NO 450
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 450
gttggtgccc agcatgatsn ncaccaggtc gagcggcag                              39

<210> SEQ ID NO 451
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 451
gtcgttggtg cccagcatsn ngatcaccag gtcgagcgg                              39

<210> SEQ ID NO 452
<211> LENGTH: 39
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 452
ggtgtcgttg gtgcccagsn ngatgatcac caggtcgag          39

<210> SEQ ID NO 453
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 453
cttggtgtcg ttggtgccsn ncatgatgat caccaggtc          39

<210> SEQ ID NO 454
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 454
ggccttggtg tcgttggtsn ncagcatgat gatcaccag          39

<210> SEQ ID NO 455
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 455
gtaggccttg gtgtcgttsn ngcccagcat gatgatcac          39

<210> SEQ ID NO 456
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 456
gaagtaggcc ttggtgtcsn nggtgcccag catgatgat          39

<210> SEQ ID NO 457
```

```
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 457
ccggaagtag gccttggtsn ngttggtgcc cagcatgat                              39

<210> SEQ ID NO 458
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 458
gcgccggaag taggccttsn ngtcgttggt gcccagcat                              39

<210> SEQ ID NO 459
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 459
ggtgcgccgg aagtaggcsn nggtgtcgtt ggtgcccag                              39

<210> SEQ ID NO 460
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 460
cggggtgcgc cggaagtasn ncttggtgtc gttggtgcc                              39

<210> SEQ ID NO 461
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 461
gagcggggtg cgccggaasn nggccttggt gtcgttggt                              39
```

```
<210> SEQ ID NO 462
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 462
gtcgagcggg gtgcgccgsn ngtaggcctt ggtgtcgtt                              39

<210> SEQ ID NO 463
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 463
gatgtcgagc ggggtgcgsn ngaagtaggc cttggtgtc                              39

<210> SEQ ID NO 464
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 464
cgcgatgtcg agcggggtsn nccggaagta ggccttggt                              39

<210> SEQ ID NO 465
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 465
cagcgcgatg tcgagcggsn ngcgccggaa gtaggcctt                              39

<210> SEQ ID NO 466
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 466
gcccagcgcg atgtcgagsn nggtgcgccg gaagtaggc                              39
```

```
<210> SEQ ID NO 467
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 467
catgcccagc gcgatgtcsn ncggggtgcg ccggaagta                              39

<210> SEQ ID NO 468
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 468
cgacatgccc agcgcgatsn ngagcggggt gcgccggaa                              39

<210> SEQ ID NO 469
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 469
caccgacatg cccagcgcsn ngtcgagcgg ggtgcgccg                              39

<210> SEQ ID NO 470
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 470
gagcaccgac atgcccagsn ngatgtcgag cggggtgcg                              39

<210> SEQ ID NO 471
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 471
gacgagcacc gacatgccsn ncgcgatgtc gagcgggt                               39
```

<210> SEQ ID NO 472
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 472
cgtgacgagc accgacatsn ncagcgcgat gtcgagcgg                        39

<210> SEQ ID NO 473
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 473
ctgcgtgacg agcaccgasn ngcccagcgc gatgtcgag                        39

<210> SEQ ID NO 474
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 474
cacctgcgtg acgagcacsn ncatgcccag cgcgatgtc                        39

<210> SEQ ID NO 475
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 475
gagcacctgc gtgacgagsn ncgacatgcc cagcgcgat                        39

<210> SEQ ID NO 476
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 476
ggtgagcacc tgcgtgacsn ncaccgacat gcccagcgc    39

<210> SEQ ID NO 477
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 477
gctggtgagc acctgcgtsn ngagcaccga catgcccag    39

<210> SEQ ID NO 478
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 478
cgcgctggtg agcacctgsn ngacgagcac cgacatgcc    39

<210> SEQ ID NO 479
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 479
gcccgcgctg gtgagcacsn ncgtgacgag caccgacat    39

<210> SEQ ID NO 480
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 480
gccgcccgcg ctggtgagsn nctgcgtgac gagcaccga    39

<210> SEQ ID NO 481
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 481

```
gacgccgccc gcgctggtsn ncacctgcgt gacgagcac                              39
```

<210> SEQ ID NO 482
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 482

```
gccgacgccg cccgcgctsn ngagcacctg cgtgacgag                              39
```

<210> SEQ ID NO 483
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 483

```
ggtgccgacg ccgcccgcsn nggtgagcac ctgcgtgac                              39
```

<210> SEQ ID NO 484
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 484

```
cgtggtgccg acgccgccsn ngctggtgag cacctgcgt                              39
```

<210> SEQ ID NO 485
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 485

```
gtacgtggtg ccgacgccsn ncgcgctggt gagcacctg                              39
```

<210> SEQ ID NO 486
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 486
cgggtacgtg gtgccgacsn ngcccgcgct ggtgagcac     39

<210> SEQ ID NO 487
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 487
tgccgggtac gtggtgccsn ngccgcccgc gctggtgag     39

<210> SEQ ID NO 488
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 488
gggtgccggg tacgtggtsn ngacgccgcc cgcgctggt     39

<210> SEQ ID NO 489
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 489
cttgggtgcc gggtacgtsn ngccgacgcc gcccgcgct     39

<210> SEQ ID NO 490
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 490
caccttgggt gccgggtasn nggtgccgac gccgcccgc     39

<210> SEQ ID NO 491
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 491
cagcaccttg ggtgccggsn ncgtggtgcc gacgccgcc                                    39

<210> SEQ ID NO 492
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 492
caccagcacc ttgggtgcsn ngtacgtggt gccgacgcc                                    39

<210> SEQ ID NO 493
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 493
gaccaccagc accttgggsn ncgggtacgt ggtgccgac                                    39

<210> SEQ ID NO 494
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 494
cgagaccacc agcaccttsn ntgccgggta cgtggtgcc                                    39

<210> SEQ ID NO 495
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 495
cggcgagacc accagcacsn ngggtgccgg gtacgtggt                                    39

<210> SEQ ID NO 496
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

<223> OTHER INFORMATION: n is a, c, g, or t

<400> SEQUENCE: 496
tggcggcgag accaccagsn ncttgggtgc cgggtacgt                                    39

<210> SEQ ID NO 497
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 497
cggtggcggc gagaccacsn ncaccttggg tgccgggta                                    39

<210> SEQ ID NO 498
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 498
cagcggtggc ggcgagacsn ncagcacctt gggtgccgg                                    39

<210> SEQ ID NO 499
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 499
cgccagcggt ggcggcgasn ncaccagcac cttgggtgc                                    39

<210> SEQ ID NO 500
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 500
gggcgccagc ggtggcggsn ngaccaccag caccttggg                                    39

<210> SEQ ID NO 501
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (20)..(21)
<223> OTHER INFORMATION: n is a, c, g, or t

<400> SEQUENCE: 501
catgggcgcc agcggtggsn ncgagaccac cagcacctt                              39

<210> SEQ ID NO 502
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 502
cggcatgggc gccagcggsn ncggcgagac caccagcac                              39

<210> SEQ ID NO 503
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 503
gtgcggcatg ggcgccagsn ntggcggcga gaccaccag                              39

<210> SEQ ID NO 504
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 504
ggggtgcggc atgggcgcsn ncggtggcgg cgagaccac                              39

<210> SEQ ID NO 505
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 505
ccaggggtgc ggcatgggsn ncagcggtgg cggcgagac                              39

<210> SEQ ID NO 506
<211> LENGTH: 39
<212> TYPE: DNA
<213> ORGANISM: Artificial Sequence
<220> FEATURE:
<223> OTHER INFORMATION: primer
<220> FEATURE:
```

<221> NAME/KEY: misc_feature
<222> LOCATION: (20)..(21)
<223> OTHER INFORMATION: n is a, c, g, or t

<400> SEQUENCE: 506
gaaccagggg tgcggcatsn ncgccagcgg tggcggcga                          39

<210> SEQ ID NO 507
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 507
ctggaaccag gggtgcggsn ngggcgccag cggtggcgg                          39

<210> SEQ ID NO 508
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 508
caactggaac caggggtgsn ncatgggcgc cagcggtgg                          39

<210> SEQ ID NO 509
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 509
gatcaactgg aaccagggsn ncggcatggg cgccagcgg                          39

<210> SEQ ID NO 510
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 510
gaagatcaac tggaaccasn ngtgcggcat gggcgccag                          39

<210> SEQ ID NO 511
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 511
ctcgaagatc aactggaasn ngggtgcgg catgggcgc         39

<210> SEQ ID NO 512
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 512
gccctcgaag atcaactgsn nccaggggtg cggcatggg         39

<210> SEQ ID NO 513
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 513
gccgccctcg aagatcaasn ngaaccaggg gtgcggcat         39

<210> SEQ ID NO 514
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 514
ctcgccgccc tcgaagatsn nctggaacca ggggtgcgg         39

<210> SEQ ID NO 515
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 515
ctgctcgccg ccctcgaasn ncaactggaa ccaggggtg         39

<210> SEQ ID NO 516
<211> LENGTH: 39
<212> TYPE: DNA
<213> ORGANISM: Artificial Sequence
<220> FEATURE:

```
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 516
cttctgctcg ccgccctcsn ngatcaactg gaaccaggg                    39

<210> SEQ ID NO 517
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 517
ggtcttctgc tcgccgccsn ngaagatcaa ctggaacca                    39

<210> SEQ ID NO 518
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 518
agtggtcttc tgctcgccsn nctcgaagat caactggaa                    39

<210> SEQ ID NO 519
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 519
ctcagtggtc ttctgctcsn ngccctcgaa gatcaactg                    39

<210> SEQ ID NO 520
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 520
gagctcagtg gtcttctgsn ngccgccctc gaagatcaa                    39

<210> SEQ ID NO 521
<211> LENGTH: 39
<212> TYPE: DNA
<213> ORGANISM: Artificial Sequence
```

```
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 521
ggcgagctca gtggtcttsn nctcgccgcc ctcgaagat                    39

<210> SEQ ID NO 522
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 522
gcgggcgagc tcagtggtsn nctgctcgcc gccctcgaa                    39

<210> SEQ ID NO 523
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 523
cacgcgggcg agctcagtsn ncttctgctc gccgccctc                    39

<210> SEQ ID NO 524
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 524
gtacacgcgg gcgagctcsn nggtcttctg ctcgccgcc                    39

<210> SEQ ID NO 525
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 525
gctgtacacg cgggcgagsn nagtggtctt ctgctcgcc                    39

<210> SEQ ID NO 526
<211> LENGTH: 39
<212> TYPE: DNA
```

<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 526
cgcgctgtac acgcgggcsn nctcagtggt cttctgctc                    39

<210> SEQ ID NO 527
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 527
gagcgcgctg tacacgcgsn ngagctcagt ggtcttctg                    39

<210> SEQ ID NO 528
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 528
cgcgagcgcg ctgtacacsn nggcgagctc agtggtctt                    39

<210> SEQ ID NO 529
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 529
cgacgcgagc gcgctgtasn ngcgggcgag ctcagtggt                    39

<210> SEQ ID NO 530
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 530
gaacgacgcg agcgcgctsn ncacgcgggc gagctcagt                    39

<210> SEQ ID NO 531
<211> LENGTH: 39

<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 531
catgaacgac gcgagcgcsn ngtacacgcg ggcgagctc         39

<210> SEQ ID NO 532
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 532
cttcatgaac gacgcgagsn ngctgtacac gcgggcgag         39

<210> SEQ ID NO 533
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 533
caccttcatg aacgacgcsn ncgcgctgta cacgcgggc         39

<210> SEQ ID NO 534
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 534
cggcaccttc atgaacgasn ngagcgcgct gtacacgcg         39

<210> SEQ ID NO 535
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 535
gaacggcacc ttcatgaasn ncgcgagcgc gctgtacac         39

<210> SEQ ID NO 536

```
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 536
gaagaacggc accttcatsn ncgacgcgag cgcgctgta                       39

<210> SEQ ID NO 537
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 537
gtcgaagaac ggcaccttsn ngaacgacgc gagcgcgct                       39

<210> SEQ ID NO 538
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 538
cgcgtcgaag aacggcacsn ncatgaacga cgcgagcgc                       39

<210> SEQ ID NO 539
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 539
acccgcgtcg aagaacggsn ncttcatgaa cgacgcgag                       39

<210> SEQ ID NO 540
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 540
cgaacccgcg tcgaagaasn ncaccttcat gaacgacgc                       39
```

```
<210> SEQ ID NO 541
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 541
caccgaaccc gcgtcgaasn ncggcacctt catgaacga                    39

<210> SEQ ID NO 542
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 542
gatcaccgaa cccgcgtcsn ngaacggcac cttcatgaa                    39

<210> SEQ ID NO 543
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 543
gctgatcacc gaacccgcsn ngaagaacgg caccttcat                    39

<210> SEQ ID NO 544
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 544
ggtgctgatc accgaaccsn ngtcgaagaa cggcacctt                    39

<210> SEQ ID NO 545
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 545
gtcggtgctg atcaccgasn ncgcgtcgaa gaacggcac                    39
```

<210> SEQ ID NO 546
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 546
gccgtcggtg ctgatcacsn nacccgcgtc gaagaacgg          39

<210> SEQ ID NO 547
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 547
gacgccgtcg gtgctgatsn ncgaacccgc gtcgaagaa          39

<210> SEQ ID NO 548
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 548
gtcgacgccg tcggtgctsn ncaccgaacc cgcgtcgaa          39

<210> SEQ ID NO 549
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 549
tccgtcgacg ccgtcggtsn ngatcaccga acccgcgtc          39

<210> SEQ ID NO 550
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 550
gattccgtcg acgccgtcsn ngctgatcac cgaacccgc          39

<210> SEQ ID NO 551
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 551
gtggattccg tcgacgccsn nggtgctgat caccgaacc                                   39

<210> SEQ ID NO 552
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 552
gaagtggatt ccgtcgacsn ngtcggtgct gatcaccga                                   39

<210> SEQ ID NO 553
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 553
ggtgaagtgg attccgtcsn ngccgtcggt gctgatcac                                   39

<210> SEQ ID NO 554
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 554
ctcggtgaag tggattccsn ngacgccgtc ggtgctgat                                   39

<210> SEQ ID NO 555
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 555
ggcctcggtg aagtggatsn ngtcgacgcc gtcggtgct          39

<210> SEQ ID NO 556
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 556
gttggcctcg gtgaagtgsn ntccgtcgac gccgtcggt          39

<210> SEQ ID NO 557
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 557
attgttggcc tcggtgaasn ngattccgtc gacgccgtc          39

<210> SEQ ID NO 558
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 558
gcgattgttg gcctcggtsn ngtggattcc gtcgacgcc          39

<210> SEQ ID NO 559
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 559
atcgcgattg ttggcctcsn ngaagtggat tccgtcgac          39

<210> SEQ ID NO 560
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 560
gagatcgcga ttgttggcsn nggtgaagtg gattccgtc                          39

<210> SEQ ID NO 561
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 561
cccgagatcg cgattgttsn nctcggtgaa gtggattcc                          39

<210> SEQ ID NO 562
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 562
caccccgaga tcgcgattsn nggcctcggt gaagtggat                          39

<210> SEQ ID NO 563
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 563
ggccaccccg agatcgcgsn ngttggcctc ggtgaagtg                          39

<210> SEQ ID NO 564
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 564
gagggccacc ccgagatcsn nattgttggc ctcggtgaa                          39

<210> SEQ ID NO 565
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 565
cgcgagggcc accccgagsn ngcgattgtt ggcctcggt          39

<210> SEQ ID NO 566
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 566
ttccgcgagg gccaccccsn natcgcgatt gttggcctc          39

<210> SEQ ID NO 567
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 567
ctgttccgcg agggccacsn ngagatcgcg attgttggc          39

<210> SEQ ID NO 568
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 568
cacctgttcc gcgagggcsn ncccgagatc gcgattgtt          39

<210> SEQ ID NO 569
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 569
ctgcacctgt tccgcgagsn ncaccccgag atcgcgatt          39

<210> SEQ ID NO 570
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 570
gctctgcacc tgttccgcsn nggccacccc gagatcgcg                                    39

<210> SEQ ID NO 571
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 571
caggctctgc acctgttcsn ngagggccac cccgagatc                                    39

<210> SEQ ID NO 572
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 572
cagcaggctc tgcacctgsn ncgcgagggc caccccgag                                    39

<210> SEQ ID NO 573
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 573
ttacagcagg ctctgcacsn nttccgcgag ggccacccc                                    39

<210> SEQ ID NO 574
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 574
cttttacagc aggctctgsn nctgttccgc gagggccac                                    39

<210> SEQ ID NO 575
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)

-continued

<223> OTHER INFORMATION: n is a, c, g, or t

<400> SEQUENCE: 575
gcccttttac agcaggctsn ncacctgttc cgcgagggc                                          39

<210> SEQ ID NO 576
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 576
ttcgcccttt tacagcagsn nctgcacctg ttccgcgag                                          39

<210> SEQ ID NO 577
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 577
gaattcgccc ttttacagsn ngctctgcac ctgttccgc                                          39

<210> SEQ ID NO 578
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (20)..(21)
<223> OTHER INFORMATION: n is a, c, g, or t

<400> SEQUENCE: 578
gcagaattcg ccctttttasn ncaggctctg cacctgttc                                         39

<210> SEQ ID NO 579
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 579
gtgatcgagg agggactgnn sgcgcgcacc accaacatc                                          39

<210> SEQ ID NO 580
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(19)
<223> OTHER INFORMATION: n is a, c, g, or t

<400> SEQUENCE: 580
acgaccccac cgatccgnns ctcaacggcg cgagctac        38

<210> SEQ ID NO 581
<211> LENGTH: 39
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 581
ctcaccagcg cgggcggcnn sggcaccacg tacccggca        39

<210> SEQ ID NO 582
<211> LENGTH: 39
<212> TYPE: DNA
<213> ORGANISM: Artificial Sequence
<220> FEATURE:
<223> OTHER INFORMATION: primer

<400> SEQUENCE: 582
ctgtgtttcg gtgattcctg cacctggggc tgggtcccc        39

<210> SEQ ID NO 583
<211> LENGTH: 39
<212> TYPE: DNA
<213> ORGANISM: Artificial Sequence
<220> FEATURE:
<223> OTHER INFORMATION: primer

<400> SEQUENCE: 583
ctgtgtttcg gtgattccca gacctggggc tgggtcccc        39

<210> SEQ ID NO 584
<211> LENGTH: 39
<212> TYPE: DNA
<213> ORGANISM: Artificial Sequence
<220> FEATURE:
<223> OTHER INFORMATION: primer

<400> SEQUENCE: 584
ctgtgtttcg gtgattccat cacctggggc tgggtcccc        39

<210> SEQ ID NO 585
<211> LENGTH: 39
<212> TYPE: DNA
<213> ORGANISM: Artificial Sequence
<220> FEATURE:
<223> OTHER INFORMATION: primer

<400> SEQUENCE: 585
ctgtgtttcg gtgattccat gacctggggc tgggtcccc        39

<210> SEQ ID NO 586
<211> LENGTH: 39
<212> TYPE: DNA
<213> ORGANISM: Artificial Sequence
<220> FEATURE:
<223> OTHER INFORMATION: primer

```
<400> SEQUENCE: 586
ctgtgtttcg gtgattccac gacctggggc tgggtcccc                              39

<210> SEQ ID NO 587
<211> LENGTH: 39
<212> TYPE: DNA
<213> ORGANISM: Artificial Sequence
<220> FEATURE:
<223> OTHER INFORMATION: primer

<400> SEQUENCE: 587
gtcgaagacg gggcacccag cgagcggttc gcccccgac                              39

<210> SEQ ID NO 588
<211> LENGTH: 39
<212> TYPE: DNA
<213> ORGANISM: Artificial Sequence
<220> FEATURE:
<223> OTHER INFORMATION: primer

<400> SEQUENCE: 588
gtcgaagacg gggcacccgg cgagcggttc gcccccgac                              39

<210> SEQ ID NO 589
<211> LENGTH: 39
<212> TYPE: DNA
<213> ORGANISM: Artificial Sequence
<220> FEATURE:
<223> OTHER INFORMATION: primer

<400> SEQUENCE: 589
gtcgaagacg gggcaccccc ggagcggttc gcccccgac                              39

<210> SEQ ID NO 590
<211> LENGTH: 39
<212> TYPE: DNA
<213> ORGANISM: Artificial Sequence
<220> FEATURE:
<223> OTHER INFORMATION: primer

<400> SEQUENCE: 590
gaggtgatcg aggagggaca cagcgcgcgc accaccaac                              39

<210> SEQ ID NO 591
<211> LENGTH: 39
<212> TYPE: DNA
<213> ORGANISM: Artificial Sequence
<220> FEATURE:
<223> OTHER INFORMATION: primer

<400> SEQUENCE: 591
gaggtgatcg aggagggaca gagcgcgcgc accaccaac                              39

<210> SEQ ID NO 592
<211> LENGTH: 39
<212> TYPE: DNA
<213> ORGANISM: Artificial Sequence
<220> FEATURE:
<223> OTHER INFORMATION: primer

<400> SEQUENCE: 592
gaggtgatcg aggagggagg cagcgcgcgc accaccaac                              39

<210> SEQ ID NO 593
<211> LENGTH: 39
```

```
<212> TYPE: DNA
<213> ORGANISM: Artificial Sequence
<220> FEATURE:
<223> OTHER INFORMATION: primer

<400> SEQUENCE: 593
gaggtgatcg aggagggaag cagcgcgcgc accaccaac                    39

<210> SEQ ID NO 594
<211> LENGTH: 39
<212> TYPE: DNA
<213> ORGANISM: Artificial Sequence
<220> FEATURE:
<223> OTHER INFORMATION: primer

<400> SEQUENCE: 594
gaggtgatcg aggagggaca cgtggcgcgc accaccaac                    39

<210> SEQ ID NO 595
<211> LENGTH: 39
<212> TYPE: DNA
<213> ORGANISM: Artificial Sequence
<220> FEATURE:
<223> OTHER INFORMATION: primer

<400> SEQUENCE: 595
gaggtgatcg aggagggaca ggtggcgcgc accaccaac                    39

<210> SEQ ID NO 596
<211> LENGTH: 39
<212> TYPE: DNA
<213> ORGANISM: Artificial Sequence
<220> FEATURE:
<223> OTHER INFORMATION: primer

<400> SEQUENCE: 596
gaggtgatcg aggagggagg cgtggcgcgc accaccaac                    39

<210> SEQ ID NO 597
<211> LENGTH: 39
<212> TYPE: DNA
<213> ORGANISM: Artificial Sequence
<220> FEATURE:
<223> OTHER INFORMATION: primer

<400> SEQUENCE: 597
gaggtgatcg aggagggaag cgtggcgcgc accaccaac                    39

<210> SEQ ID NO 598
<211> LENGTH: 39
<212> TYPE: DNA
<213> ORGANISM: Artificial Sequence
<220> FEATURE:
<223> OTHER INFORMATION: primer

<400> SEQUENCE: 598
gtgatcgagg agggactggt ggcgcgcacc accaacatc                    39

<210> SEQ ID NO 599
<211> LENGTH: 39
<212> TYPE: DNA
<213> ORGANISM: Artificial Sequence
<220> FEATURE:
<223> OTHER INFORMATION: primer

<400> SEQUENCE: 599
```
gtgatcgagg agggactgct ggcgcgcacc accaacatc                                    39

<210> SEQ ID NO 600
<211> LENGTH: 39
<212> TYPE: DNA
<213> ORGANISM: Artificial Sequence
<220> FEATURE:
<223> OTHER INFORMATION: primer

<400> SEQUENCE: 600
atcgaggagg gactgagcgg ccgcaccacc aacatcgac                                    39

<210> SEQ ID NO 601
<211> LENGTH: 39
<212> TYPE: DNA
<213> ORGANISM: Artificial Sequence
<220> FEATURE:
<223> OTHER INFORMATION: primer

<400> SEQUENCE: 601
atcgaggagg gactgagcac gcgcaccacc aacatcgac                                    39

<210> SEQ ID NO 602
<211> LENGTH: 39
<212> TYPE: DNA
<213> ORGANISM: Artificial Sequence
<220> FEATURE:
<223> OTHER INFORMATION: primer

<400> SEQUENCE: 602
atcgaggagg gactggtggg ccgcaccacc aacatcgac                                    39

<210> SEQ ID NO 603
<211> LENGTH: 39
<212> TYPE: DNA
<213> ORGANISM: Artificial Sequence
<220> FEATURE:
<223> OTHER INFORMATION: primer

<400> SEQUENCE: 603
atcgaggagg gactggtgac gcgcaccacc aacatcgac                                    39

<210> SEQ ID NO 604
<211> LENGTH: 39
<212> TYPE: DNA
<213> ORGANISM: Artificial Sequence
<220> FEATURE:
<223> OTHER INFORMATION: primer

<400> SEQUENCE: 604
gacgacccca ccgatccgac gctcaacggc gcgagctac                                    39

<210> SEQ ID NO 605
<211> LENGTH: 39
<212> TYPE: DNA
<213> ORGANISM: Artificial Sequence
<220> FEATURE:
<223> OTHER INFORMATION: primer

<400> SEQUENCE: 605
gacgacccca ccgatccgca gctcaacggc gcgagctac                                    39

<210> SEQ ID NO 606
<211> LENGTH: 39
<212> TYPE: DNA
<213> ORGANISM: Artificial Sequence -continued
<220> FEATURE:
<223> OTHER INFORMATION: primer

<400> SEQUENCE: 606 gacgaccccca ccgatccgaa cctcaacggc gcgagctac                         39

<210> SEQ ID NO 607
<211> LENGTH: 39
<212> TYPE: DNA
<213> ORGANISM: Artificial Sequence
<220> FEATURE:
<223> OTHER INFORMATION: primer

<400> SEQUENCE: 607
ctgggcacca acgacacccg cgcctacttc cggcgcacc                          39

<210> SEQ ID NO 608
<211> LENGTH: 39
<212> TYPE: DNA
<213> ORGANISM: Artificial Sequence
<220> FEATURE:
<223> OTHER INFORMATION: primer

<400> SEQUENCE: 608
ctcaccagcg cgggcggcag cggcaccacg tacccggca                          39

<210> SEQ ID NO 609
<211> LENGTH: 39
<212> TYPE: DNA
<213> ORGANISM: Artificial Sequence
<220> FEATURE:
<223> OTHER INFORMATION: primer

<400> SEQUENCE: 609
ctcaccagcg cgggcggcgg cggcaccacg tacccggca                          39

<210> SEQ ID NO 610
<211> LENGTH: 39
<212> TYPE: DNA
<213> ORGANISM: Artificial Sequence
<220> FEATURE:
<223> OTHER INFORMATION: primer

<400> SEQUENCE: 610
ctcaccagcg cgggcggccg cggcaccacg tacccggca                          39

<210> SEQ ID NO 611
<211> LENGTH: 39
<212> TYPE: DNA
<213> ORGANISM: Artificial Sequence
<220> FEATURE:
<223> OTHER INFORMATION: primer

<400> SEQUENCE: 611
ctcaccagcg cgggcggcgc gggcaccacg tacccggca                          39

<210> SEQ ID NO 612
<211> LENGTH: 39
<212> TYPE: DNA
<213> ORGANISM: Artificial Sequence
<220> FEATURE:
<223> OTHER INFORMATION: primer

<400> SEQUENCE: 612
ctcaccagcg cgggcggccc gggcaccacg tacccggca                          39

<210> SEQ ID NO 613
<211> LENGTH: 39
<212> TYPE: DNA
<213> ORGANISM: Artificial Sequence
<220> FEATURE:
<223> OTHER INFORMATION: primer

<400> SEQUENCE: 613
ccctggttcc agttgatcta cgagggcggc gagcagaag                    39

<210> SEQ ID NO 614
<211> LENGTH: 39
<212> TYPE: DNA
<213> ORGANISM: Artificial Sequence
<220> FEATURE:
<223> OTHER INFORMATION: primer

<400> SEQUENCE: 614
ggcgtcgacg gaatccacgg caccgaggcc aacaatcgc                    39

<210> SEQ ID NO 615
<211> LENGTH: 39
<212> TYPE: DNA
<213> ORGANISM: Artificial Sequence
<220> FEATURE:
<223> OTHER INFORMATION: primer

<400> SEQUENCE: 615
gacgacccca ccgatccggg cctcaacggc gcgagctac                    39

<210> SEQ ID NO 616
<211> LENGTH: 39
<212> TYPE: DNA
<213> ORGANISM: Artificial Sequence
<220> FEATURE:
<223> OTHER INFORMATION: primer

<400> SEQUENCE: 616
gacgacccca ccgatccgga gctcaacggc gcgagctac                    39

<210> SEQ ID NO 617
<211> LENGTH: 39
<212> TYPE: DNA
<213> ORGANISM: Artificial Sequence
<220> FEATURE:
<223> OTHER INFORMATION: primer

<400> SEQUENCE: 617
gacgacccca ccgatccgtt cctcaacggc gcgagctac                    39

<210> SEQ ID NO 618
<211> LENGTH: 39
<212> TYPE: DNA
<213> ORGANISM: Artificial Sequence
<220> FEATURE:
<223> OTHER INFORMATION: primer

<400> SEQUENCE: 618
gacgacccca ccgatccgct gctcaacggc gcgagctac                    39

<210> SEQ ID NO 619
<211> LENGTH: 39
<212> TYPE: DNA
<213> ORGANISM: Artificial Sequence
<220> FEATURE:
<223> OTHER INFORMATION: primer

```
<400> SEQUENCE: 619
gtgatcgagg agggactgcc ggcgcgcacc accaacatc                    39

<210> SEQ ID NO 620
<211> LENGTH: 39
<212> TYPE: DNA
<213> ORGANISM: Artificial Sequence
<220> FEATURE:
<223> OTHER INFORMATION: primer

<400> SEQUENCE: 620
gtgatcgagg agggactgcg cgcgcgcacc accaacatc                    39

<210> SEQ ID NO 621
<211> LENGTH: 39
<212> TYPE: DNA
<213> ORGANISM: Artificial Sequence
<220> FEATURE:
<223> OTHER INFORMATION: primer

<400> SEQUENCE: 621
gtgatcgagg agggactggg cgcgcgcacc accaacatc                    39

<210> SEQ ID NO 622
<211> LENGTH: 39
<212> TYPE: DNA
<213> ORGANISM: Artificial Sequence
<220> FEATURE:
<223> OTHER INFORMATION: primer

<400> SEQUENCE: 622
gtgatcgagg agggactgac ggcgcgcacc accaacatc                    39

<210> SEQ ID NO 623
<211> LENGTH: 39
<212> TYPE: DNA
<213> ORGANISM: Artificial Sequence
<220> FEATURE:
<223> OTHER INFORMATION: primer

<400> SEQUENCE: 623
gtgatcgagg agggactgat cgcgcgcacc accaacatc                    39

<210> SEQ ID NO 624
<211> LENGTH: 39
<212> TYPE: DNA
<213> ORGANISM: Artificial Sequence
<220> FEATURE:
<223> OTHER INFORMATION: primer

<400> SEQUENCE: 624
gtgatcgagg agggactgaa ggcgcgcacc accaacatc                    39

<210> SEQ ID NO 625
<211> LENGTH: 657
<212> TYPE: DNA
<213> ORGANISM: Artificial Sequence
<220> FEATURE:
<223> OTHER INFORMATION: RSM02162 gene

<400> SEQUENCE: 625
atggtggaaa aacgttccgt tctgtgcttt ggtgattctc tgacttgggg ctggattccg    60
gtgaaagaga gctccccaac tctgcgttac ccatacgaac agcgttggac cggtgctatg   120
```

-continued

```
gctgcacgtc tgggtgatgg ttaccacatc attgaagaag gcctgtccgc tcgtactact    180
agcctggacg acccaaacga cgctcgtctg aacggctcta cctacctgcc gatggctctg    240
gcttctcacc tgccactgga tctggtaatc attatgctgg gtaccaacga caccaaaagc    300
tactttcatc gtaccccata cgagattgcc aacggcatgg gtaaactggt aggtcaggtc    360
ctgacctgtg caggtggtgt tggtacgcct tatccagcac cgaaagtcct ggtggttgca    420
cctccaccac tggcaccaat gccagatccg tggttcgaag gtatgttcgg cggtggttac    480
gagaaatcta aggaactgtc cggtctgtac aaagcactgg ctgatttcat gaaagtggag    540
ttcttcgcag cgggtgattg tatctccacc gacggtatcg acggtatcca cctgagcgct    600
gaaaccaaca tccgcctggg tcatgctatt gctgacaaag tagcggctct gttctaa      657
```

<210> SEQ ID NO 626
<211> LENGTH: 50
<212> TYPE: DNA
<213> ORGANISM: Artificial Sequence
<220> FEATURE:
<223> OTHER INFORMATION: primer

<400> SEQUENCE: 626

```
ggccctaaca ggaggaatta accatggtgg aaaaacgttc cgttctgtgc                50
```

<210> SEQ ID NO 627
<211> LENGTH: 33
<212> TYPE: DNA
<213> ORGANISM: Artificial Sequence
<220> FEATURE:
<223> OTHER INFORMATION: primer

<400> SEQUENCE: 627

```
gcgcgcttag aacagagccg ctactttgtc agc                                  33
```

<210> SEQ ID NO 628
<211> LENGTH: 218
<212> TYPE: PRT
<213> ORGANISM: Artificial Sequence
<220> FEATURE:
<223> OTHER INFORMATION: G00355 protein

<400> SEQUENCE: 628

```
Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

Ala Ser His Leu Pro Leu Asp Leu Val Ile Ile Met Leu Gly Thr Asn
                85                  90                  95

Asp Thr Lys Ser Tyr Phe His Arg Thr Pro Tyr Glu Ile Ala Asn Gly
            100                 105                 110

Met Gly Lys Leu Val Gly Gln Val Leu Thr Cys Ala Gly Gly Val Gly
        115                 120                 125

Thr Pro Tyr Pro Ala Pro Lys Val Leu Val Val Ala Pro Pro Leu
    130                 135                 140
```

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
            165                 170                 175

Met Lys Val Glu Phe Phe Ala Ala Gly Asp Cys Ile Ser Thr Asp Gly
        180                 185                 190

Ile Asp Gly Ile His Leu Ser Ala Glu Thr Asn Ile Arg Leu Gly His
    195                 200                 205

Ala Ile Ala Asp Lys Val Ala Ala Leu Phe
    210                 215

<210> SEQ ID NO 629
<211> LENGTH: 4510
<212> TYPE: DNA
<213> ORGANISM: Artificial Sequence
<220> FEATURE:
<223> OTHER INFORMATION: pDRIVEG00355 plasmid

<400> SEQUENCE: 629

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg ccaagctcta | 240 |
| atacgactca ctatagggaa agctcggtac cacgcatgct gcagacgcgt tacgtatcgg | 300 |
| atccagaatt cgtgatttta gaacagagcc gctactttgt cagcaatagc atgacccagg | 360 |
| cggatgttgg tttcagcgct caggtggata ccgtcgatac cgtcggtgga gatacaatca | 420 |
| cccgctgcga agaactccac tttcatgaaa tcagccagtg cttttgtacag accgacagt | 480 |
| tccttagatt tctcgtaacc accgccgaac ataccttcga accacggatc tggcattggt | 540 |
| gccagtggtg gaggtgcaac caccaggact ttcggtgctg ataaggcgt accaacacca | 600 |
| cctgcacagg tcaggacctg acctaccagt ttacccatgc cgttggcaat ctcgtatggg | 660 |
| gtacgatgaa agtagctttt ggtgtcgttg gtacccagca taatgattac cagatccagt | 720 |
| ggcaggtgag aagccagagc catcggcagg taggtagagc cgttcagacg agcgtcgttt | 780 |
| gggtcgtcca ggctagtagt acgagcggac aggccttctt caatgatgtg gtaaccatca | 840 |
| cccagacgtg cagccatagc accggtccaa cgctgttcgt atgggtaacg cagagttggg | 900 |
| gagctctctt tcaccggaat ccagccccaa gtcagagaat caccaaagca cagaacggaa | 960 |
| cgttttccca ccataatctg aattcgtcga caagcttctc gagcctaggc tagctctaga | 1020 |
| ccacacgtgt gggggcccga gctcgcggcc gctgtattct atagtgtcac ctaaatggcc | 1080 |
| gcacaattca ctggccgtcg ttttacaacg tcgtgactgg gaaaaccctg gcgttaccca | 1140 |
| acttaatcgc cttgcagcac atcccccttt cgccagctgg cgtaatagcg aagaggcccg | 1200 |
| caccgatcgc ccttcccaac agttgcgcag cctgaatggc gaatgaaat tgtaagcgtt | 1260 |
| aatattttgt taaaattcgc gttaaatttt tgttaaatca gctcattttt taaccaatag | 1320 |
| gccgaaatcg gcaaaatccc ttataaatca aagaataga ccgagatagg gttgagtgtt | 1380 |
| gttccagttt ggaacaagag tccactatta agaacgtgg actccaacgt caagggcga | 1440 |
| aaaccgtct atcagggcga tggcccacta cgtgaaccat caccctaatc aagttttttg | 1500 |
| gggtcgaggt gccgtaaagc actaaatcgg aaccctaaag ggagccccg atttagagct | 1560 |
| tgacggggaa agccggcgaa cgtggcgaga aggaaggga agaaagcgaa aggagcgggc | 1620 |

```
gctagggcgc tggcaagtgt agcggtcacg ctgcgcgtaa ccaccacacc cgccgcgctt   1680
aatgcgccgc tacagggcgc gtcagtggc acttttcggg gaaatgtgcg cggaaccccct   1740 atttgtttat ttttctaaat acattcaaat atgtatccgc tcatgagaca ataaccctga   1800
taaatgcttc aataatattg aaaaggaag agtatgagta ttcaacattt ccgtgtcgcc   1860
cttattccct tttttgcggc attttgcctt cctgttttg ctcacccaga aacgctggtg   1920
aaagtaaaag atgctgaaga tcagttgggt gcacgagtgg gttacatcga actggatctc   1980
aacagcggta agatccttga gagttttcgc cccgaagaac gttttccaat gatgagcact   2040
tttaaagttc tgctatgtgg cgcggtatta cccgtattg acgccgggca agagcaactc   2100
ggtcgccgca tacactattc tcagaatgac ttggttgagt actcaccagt cacagaaaag   2160
catcttacgg atggcatgac agtaagagaa ttatgcagtg ctgccataac catgagtgat   2220
aacactgcgg ccaacttact tctgacaacg atcggaggac cgaaggagct aaccgctttt   2280
ttgcacaaca tgggggatca tgtaactcgc cttgatcgtt gggaaccgga gctgaatgaa   2340
gccataccaa acgacgagcg tgacaccacg atgcctgtag caatggcaac aacgttgcgc   2400
aaactattaa ctggcgaact acttactcta gcttcccggc aacaattaat agactggatg   2460
gaggcggata aagttgcagg accacttctg cgctcggccc ttccggctgg ctggtttatt   2520
gctgataaat ctggagccgg tgagcgtggg tctcgcggta tcattgcagc actggggcca   2580
gatggtaagc cctcccgtat cgtagttatc tacacgacgg ggagtcaggc aactatggat   2640
gaacgaaata gacagatcgc tgagataggt gcctcactga ttaagcattg gtaactgtca   2700
gaccaagttt actcatatat actttagatt gatttaaaac ttcatttta atttaaaagg   2760 atctaggtga agatcctttt tgataatctc atgaacaata aaactgtctg cttacataaa   2820
cagtaataca aggggtgtta tgagccatat tcaacgggaa acgtcttgct ctaggccgcg   2880
attaaattcc aacatggatg ctgatttata tgggtataaa tgggctcgcg ataatgtcgg   2940
gcaatcaggt gcgacaatct atcgattgta tgggaagccc gatgcgccag agttgtttct   3000
gaaacatggc aaaggtagcg ttgccaatga tgttacagat gagatggtca gactaaactg   3060
gctgacggaa tttatgcctc ttccgaccat caagcatttt atccgtactc ctgatgatgc   3120
atggttactc accactgcga tccccgggaa aacagcattc caggtattag aagaatatcc   3180
tgattcaggt gaaaatattg ttgatgcgct ggcagtgttc ctgcgccggt tgcattcgat   3240
tcctgtttgt aattgtcctt ttaacagcga tcgcgtattt cgtctcgctc aggcgcaatc   3300
acgaatgaat aacggtttgg ttgatgcgag tgattttgat gacgagcgta atggctggcc   3360
tgttgaacaa gtctggaaag aaatgcataa acttttgcca ttctcaccgg attcagtcgt   3420
cactcatggt gatttctcac ttgataacct tattttgac gagggggaat taataggttg   3480
tattgatgtt ggacgagtcg gaatcgcaga ccgataccag gatcttgcca tcctatggaa   3540
ctgcctcggt gagttttctc cttcattaca gaaacggctt tttcaaaaat atggtattga   3600
taatcctgat atgaataaat tgcagtttca tttgatgctc gatgagtttt tctaagaatt   3660
aattcatgac caaaatccct taacgtgagt tttcgttcca ctgagcgtca ccccgtag     3720 aaaagatcaa aggatcttct tgagatcctt ttttctgcg cgtaatctgc tgcttgcaaa   3780
caaaaaaacc accgctacca gcggtggttt gtttgccgga tcaagagcta ccaactcttt   3840
ttccgaaggt aactggcttc agcagagcgc agataccaaa tactgtcctt ctagtgtagc   3900
cgtagttagg ccaccacttc aagaactctg tagcaccgcc tacatacctc gctctgctaa   3960
tcctgttacc agtggctgct gccagtggcg ataagtcgtg tcttaccggg ttggactcaa   4020
```

| gacgatagtt | accggataag | gcgcagcggt | cgggctgaac | gggggggttcg | tgcacacagc | 4080 |
| ccagcttgga | gcgaacgacc | tacaccgaac | tgagatacct | acagcgtgag | ctatgagaaa | 4140 |
| gcgccacgct | tcccgaaggg | agaaaggcgg | acaggtatcc | ggtaagcggc | agggtcggaa | 4200 |
| caggagagcg | cacgagggag | cttccagggg | gaaacgcctg | gtatctttat | agtcctgtcg | 4260 |
| ggtttcgcca | cctctgactt | gagcgtcgat | ttttgtgatg | ctcgtcaggg | gggcggagcc | 4320 |
| tatgaaaaa | cgccagcaac | gcggcctttt | tacggttcct | ggccttttgc | tggccttttg | 4380 |
| ctcacatgtt | ctttcctgcg | ttatcccctg | attctgtgga | taaccgtatt | accgcctttg | 4440 |
| agtgagctga | taccgctcgc | cgcagccgaa | cgaccgagcg | cagcgagtca | gtgagcgagg | 4500 |
| aagcggaaga | | | | | | 4510 |

```
<210> SEQ ID NO 630
<211> LENGTH: 4617
<212> TYPE: DNA
<213> ORGANISM: Artificial Sequence
<220> FEATURE:
<223> OTHER INFORMATION: pMC355rbs plasmid

<400> SEQUENCE: 630
```

| agcgcccaat | acgcaaaccg | cctctccccg | cgcgttggcc | gattcattaa | tgcagctggc | 60 |
| acgacaggtt | tcccgactgg | aaagcgggca | gtgagcgcaa | cgcaattaat | gtgagttagc | 120 |
| tcactcatta | ggcaccccag | gctttacact | ttatgcttcc | ggctcgtatg | ttgtgtggaa | 180 |
| ttgtgagcgg | ataacaattt | cacacaggaa | acagctatga | ccatgattac | gccaagcttg | 240 |
| gtaccgagct | cggatccact | agtaacggcc | gccagtgtgc | tggaattcgc | ccttggccct | 300 |
| aacaggagga | attaaccatg | gtggaaaaac | gttccgttct | gtgctttggt | gattctctga | 360 |
| cttgggggctg | gattccggtg | aaagagagct | ccccaactct | gcgttaccca | tacgaacagc | 420 |
| gttggaccgg | tgctatggct | gcacgtctgg | gtgatggtta | ccacatcatt | gaagaaggcc | 480 |
| tgtccgctcg | tactactagc | ctggacgacc | caaacgacgc | tcgtctgaac | ggctctacct | 540 |
| acctgccgat | ggctctggct | tctcacctgc | cactggatct | ggtaatcatt | atgctgggta | 600 |
| ccaacgacac | caaaagctac | tttcatcgta | ccccatacga | gattgccaac | ggcatgggta | 660 |
| aactggtagg | tcaggtcctg | acctgtgcag | gtggtgttgg | tacgccttat | ccagcaccga | 720 |
| aagtcctggt | ggttgcacct | ccaccactgg | caccaatgcc | agatccgtgg | ttcgaaggta | 780 |
| tgttcggcgg | tggttacgag | aaatctaagg | aactgtccgg | tctgtacaaa | gcactggctg | 840 |
| atttcatgaa | agtggagttc | ttcgcagcgg | gtgattgtat | ctccaccgac | ggtatcgacg | 900 |
| gtatccacct | gagcgctgaa | accaacatcc | gcctgggtca | tgctattgct | gacaaagtag | 960 |
| cggctctgtt | ctaagcgcgc | aagggcgaat | tctgcagata | tccatcacac | tggcggccgc | 1020 |
| tcgagcatgc | atctagaggg | cccaattcgc | cctatagtga | gtcgtattac | aattcactgg | 1080 |
| ccgtcgtttt | acaacgtcgt | gactgggaaa | accctggcgt | tacccaactt | aatcgccttg | 1140 |
| cagcacatcc | ccctttcgcc | agctggcgta | atagcgaaga | ggcccgcacc | gatcgccctt | 1200 |
| cccaacagtt | gcgcagcctg | aatggcgaat | ggacgcgccc | tgtagcggcg | cattaagcgc | 1260 |
| ggcgggtgtg | gtggttacgc | gcagcgtgac | cgctacactt | gccagcgccc | tagcgcccgc | 1320 |
| tcctttcgct | ttcttccctt | cctttctcgc | cacgttcgcc | ggctttcccc | gtcaagctct | 1380 |
| aaatcggggg | ctccctttag | ggttccgatt | tagtgcttta | cggcacctcg | accccaaaaa | 1440 |
| acttgattag | ggtgatggtt | cacgtagtgg | gccatcgccc | tgatagacgg | tttttcgccc | 1500 |

```
tttgacgttg gagtccacgt tctttaatag tggactcttg ttccaaactg gaacaacact    1560
caaccctatc tcggtctatt cttttgattt ataagggatt ttgccgattt cggcctattg    1620
gttaaaaaat gagctgattt aacaaaaatt taacgcgaat tttaacaaaa ttcagggcgc    1680
aagggctgct aaaggaagcg gaacacgtag aaagccagtc cgcagaaacg gtgctgaccc    1740
cggatgaatg tcagctactg ggctatctgg acaagggaaa acgcaagcgc aaagagaaag    1800
caggtagctt gcagtgggct tacatggcga tagctagact gggcggtttt atggacagca    1860
agcgaaccgg aattgccagc tggggcgccc tctggtaagg ttgggaagcc ctgcaaagta    1920
aactggatgg ctttcttgcc gccaaggatc tgatggcgca ggggatcaag atctgatcaa    1980
gagacaggat gaggatcgtt tcgcatgatt gaacaagatg gattgcacgc aggttctccg    2040
gccgcttggg tggagaggct attcggctat gactgggcac aacagacaat cggctgctct    2100
gatgccgccg tgttccggct gtcagcgcag gggcgcccgg ttcttttgt caagaccgac    2160 ctgtccggtg ccctgaatga actgcaggac gaggcagcgc ggctatcgtg gctggccacg    2220
acgggcgttc cttgcgcagc tgtgctcgac gttgtcactg aagcgggaag ggactggctg    2280
ctattgggcg aagtgccggg gcaggatctc ctgtcatccc accttgctcc tgccgagaaa    2340
gtatccatca tggctgatgc aatgcggcgg ctgcatacgc ttgatccggc tacctgccca    2400
ttcgaccacc aagcgaaaca tcgcatcgag cgagcacgta ctcggatgga agccggtctt    2460
gtcgatcagg atgatctgga cgaagagcat caggggctcg cgccagccga actgttcgcc    2520
aggctcaagg cgcgcatgcc cgacggcgag gatctcgtcg tgacccatgg cgatgcctgc    2580
ttgccgaata tcatggtgga aaatggccgc ttttctggat tcatcgactg tggccggctg    2640
ggtgtggcgg accgctatca ggacatagcg ttggctaccc gtgatattgc tgaagagctt    2700
ggcggcgaat gggctgaccg cttcctcgtg ctttacggta tcgccgctcc cgattcgcag    2760
cgcatcgcct tctatcgcct tcttgacgag ttcttctgaa ttgaaaaagg aagagtatga    2820
gtattcaaca tttccgtgtc gcccttattc ccttttttgc ggcattttgc cttcctgttt    2880
ttgctcaccc agaaacgctg gtgaaagtaa aagatgctga agatcagttg ggtgcacgag    2940
tgggttacat cgaactggat ctcaacagcg gtaagatcct tgagagtttt cgccccgaag    3000
aacgttttcc aatgatgagc acttttaaag ttctgctatg tggcgcggta ttatcccgta    3060
ttgacgccgg gcaagagcaa ctcggtcgcc gcatacacta ttctcagaat gacttggttg    3120
agtactcacc agtcacagaa aagcatctta cggatggcat gacagtaaga gaattatgca    3180
gtgctgccat aaccatgagt gataacactg cggccaactt acttctgaca acgatcggag    3240
gaccgaagga gctaaccgct tttttgcaca acatggggga tcatgtaact cgccttgatc    3300
gttgggaacc ggagctgaat gaagccatac caaacgacga gcgtgacacc acgatgcctg    3360
tagcaatggc aacaacgttg cgcaaactat taactggcga actacttact ctagcttccc    3420
ggcaacaatt aatagactgg atggaggcgg ataaagttgc aggaccactt ctgcgctcgg    3480
cccttccggc tggctggttt attgctgata atctggagc cggtgagcgt gggtctcgcg    3540
gtatcattgc agcactgggg ccagatggta agccctcccg tatcgtagtt atctacacga    3600
cggggagtca ggcaactatg gatgaacgaa atagacagat cgctgagata ggtgcctcac    3660
tgattaagca ttggtaactg tcagaccaag tttactcata tactttag attgatttaa    3720 aacttcattt ttaatttaaa aggatctagg tgaagatcct ttttgataat ctcatgacca    3780
aaatccctta acgtgagttt tcgttccact gagcgtcaga ccccgtagaa aagatcaaag    3840
gatcttcttg agatcctttt tttctgcgcg taatctgctg cttgcaaaca aaaaaaccac    3900
```

```
cgctaccagc ggtggtttgt ttgccggatc aagagctacc aactcttttt ccgaaggtaa    3960
ctggcttcag cagagcgcag ataccaaata ctgttcttct agtgtagccg tagttaggcc    4020
accacttcaa gaactctgta gcaccgccta catacctcgc tctgctaatc ctgttaccag    4080
tggctgctgc cagtggcgat aagtcgtgtc ttaccgggtt ggactcaaga cgatagttac    4140
cggataaggc gcagcggtcg ggctgaacgg ggggttcgtg cacacagccc agcttggagc    4200
gaacgaccta caccgaactg agatacctac agcgtgagct atgagaaagc gccacgcttc    4260
ccgaagggag aaaggcggac aggtatccgg taagcggcag ggtcggaaca ggagagcgca    4320
cgagggagct tccaggggga aacgcctggt atctttatag tcctgtcggg tttcgccacc    4380
tctgacttga gcgtcgattt tgtgatgct cgtcaggggg gcggagccta tggaaaaacg    4440
ccagcaacgc ggccttttta cggttcctgg ccttttgctg gccttttgct cacatgttct    4500
ttcctgcgtt atcccctgat tctgtggata accgtattac cgcctttgag tgagctgata    4560
ccgctcgccg cagccgaacg accgagcgca gcgagtcagt gagcgaggaa gcggaag      4617

<210> SEQ ID NO 631
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 631
gccaagcgaa ttctgtgttt cggngaytcn yt                                    32

<210> SEQ ID NO 632
<211> LENGTH: 33
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 632
cgattgttcg cctcgtgtga artgnrtncc rtc                                   33

<210> SEQ ID NO 633
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
```

```
<223> OTHER INFORMATION: n is a, c, g, or t

<400> SEQUENCE: 633
acggtcctgt gctttggnga ytcnyt                                              26

<210> SEQ ID NO 634
<211> LENGTH: 30
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 634
ccgctggtcc tcatctggrt gntcnccrtc                                          30

<210> SEQ ID NO 635
<211> LENGTH: 596
<212> TYPE: DNA
<213> ORGANISM: Artificial Sequence
<220> FEATURE:
<223> OTHER INFORMATION: 2D Perhydrolase Homologue gene

<400> SEQUENCE: 635
attctgtgtt tcggggattc cttgacgtgg ggatggatcc ctgtcgaaga aggtgtgccc         60
accgagcggt tcccgcgtga cgtccggtgg accggcgtgc tggccgacct gctgggcgac        120
cgctacgagg tgatcgagga aggcctgtcg gcgcgcacca ccaccgccga cgacccggcc        180 gaccccggc tcaacggttc gcagtatctg ccgtcgtgtc tggccagcca tctgccgctg        240
gacctggtga tcctgatgct cggcatcaac gacaccaagg cgaattttgg ccgcacccg         300 ttcgacatcg ccaccggtat gggagtgctt gccacgcagg tgctcaccag cgccggtggc        360
gtggggacca gctatcccgc gccgcaggtg ctgatcgtgg cgccgccgcc gctgggcgag        420
ctgccccacc cctggttcga cctggtgttc tccggcggcc gtgagaagac cgccgagttg        480
gcccgcgtgt acagcgcgct ggcgtcgttc atgaaggtgc cgttcttcga cgccggctcg        540
gtgatcagca ccgacggcgt ggacggcacc cacttcacac gaggcgaaac aatcga           596

<210> SEQ ID NO 636
<211> LENGTH: 198
<212> TYPE: PRT
<213> ORGANISM: Artificial Sequence
<220> FEATURE:
<223> OTHER INFORMATION: 2D Perhydrolase Homologue protein

<400> SEQUENCE: 636

Ile Leu Cys Phe Gly Asp Ser Leu Thr Trp Gly Trp Ile Pro Val Glu
1               5                   10                  15

Glu Gly Val Pro Thr Glu Arg Phe Pro Arg Asp Val Arg Trp Thr Gly
            20                  25                  30

Val Leu Ala Asp Leu Leu Gly Asp Arg Tyr Glu Val Ile Glu Glu Gly
        35                  40                  45

Leu Ser Ala Arg Thr Thr Thr Ala Asp Asp Pro Ala Asp Pro Arg Leu
    50                  55                  60

Asn Gly Ser Gln Tyr Leu Pro Ser Cys Leu Ala Ser His Leu Pro Leu
```

```
                65                  70                  75                  80
Asp Leu Val Ile Leu Met Leu Gly Ile Asn Asp Thr Lys Ala Asn Phe
                    85                  90                  95
Gly Arg Thr Pro Phe Asp Ile Ala Thr Gly Met Gly Val Leu Ala Thr
                100                 105                 110
Gln Val Leu Thr Ser Ala Gly Val Gly Thr Ser Tyr Pro Ala Pro
            115                 120                 125
Gln Val Leu Ile Val Ala Pro Pro Leu Gly Glu Leu Pro His Pro
        130                 135                 140
Trp Phe Asp Leu Val Phe Ser Gly Gly Arg Glu Lys Thr Ala Glu Leu
145                 150                 155                 160
Ala Arg Val Tyr Ser Ala Leu Ala Ser Phe Met Lys Val Pro Phe Phe
                165                 170                 175
Asp Ala Gly Ser Val Ile Ser Thr Asp Gly Val Asp Thr His Phe
            180                 185                 190
Thr Arg Gly Glu Thr Ile
        195
```

<210> SEQ ID NO 637
<211> LENGTH: 648
<212> TYPE: DNA
<213> ORGANISM: Mycobacterium gilvum

<400> SEQUENCE: 637

```
taccgtcgat gtgtggcctc gtgtgaagtg ggtgccgttg ccaagcgaat tctgtgtttc      60
ggggattcgt tgacgtgggg ctggatcccg gtcgaggaag gtgtaccgac ccaacgtttt     120
ccgaagcggg tgcgctggac cggggtgctg gccgacgaac tgggtgctgg ctatgaggtt     180
gtcgaggagg ggttgagcgc gcgcaccacc accgctgacg accctaccga tccccggctg     240
aacggctcgg actacctccc cgcatgcctg gccagccacc tgccgctgga cctggtgatc     300
ctgatgctcg ggaccaacga caccaaggcg aatctgaatc gcacacccgt cgacatcgcc     360
agcggaatgg gcgtcctggc cacccaggtg ctcaccagcg cgggcggggt cggcaccagc     420
tacccggccc cgcaggtgtt gatcgtggca ccgccgccgc tggccgagat gccgcacccg     480
tggttcgagc tggtcttcga cggcggccgg gagaagaccg cccaactggc ccgggtgtac     540
agcgcgctgg cgtcgttcat gaaggtgccg ttcttcgacg ccggatcggt gatcagcacc     600
gacggtgtcg acggcaccca cttcacacga ggcgaaacaa tcgaccgg                  648
```

<210> SEQ ID NO 638
<211> LENGTH: 216
<212> TYPE: PRT
<213> ORGANISM: Mycobacterium gilvum

<400> SEQUENCE: 638

```
Gly Gly Arg Cys Val Ala Ser Cys Glu Val Gly Ala Val Ala Lys Arg
1               5                   10                  15
Ile Leu Cys Phe Gly Asp Ser Leu Thr Trp Gly Trp Ile Pro Val Glu
                20                  25                  30
Glu Gly Val Pro Thr Gln Arg Phe Pro Lys Arg Val Arg Trp Thr Gly
            35                  40                  45
Val Leu Ala Asp Glu Leu Gly Ala Gly Tyr Glu Val Val Glu Glu Gly
        50                  55                  60
Leu Ser Ala Arg Thr Thr Thr Ala Asp Asp Pro Thr Asp Pro Arg Leu
65                  70                  75                  80
```

Asn Gly Ser Asp Tyr Leu Pro Ala Cys Leu Ala Ser His Leu Pro Leu
             85                  90                  95

Asp Leu Val Ile Leu Met Leu Gly Thr Asn Asp Thr Lys Ala Asn Leu
        100                 105                 110

Asn Arg Thr Pro Val Asp Ile Ala Ser Gly Met Gly Val Leu Ala Thr
        115                 120                 125

Gln Val Leu Thr Ser Ala Gly Val Gly Thr Ser Tyr Pro Ala Pro
        130                 135                 140

Gln Val Leu Ile Val Ala Pro Pro Leu Ala Glu Met Pro His Pro
145                 150                 155                 160

Trp Phe Glu Leu Val Phe Asp Gly Gly Arg Glu Lys Thr Ala Gln Leu
                165                 170                 175

Ala Arg Val Tyr Ser Ala Leu Ala Ser Phe Met Lys Val Pro Phe Phe
                180                 185                 190

Asp Ala Gly Ser Val Ile Ser Thr Asp Gly Val Asp Gly Thr His Phe
            195                 200                 205

Thr Arg Gly Glu Thr Ile Asp Arg
    210                 215

<210> SEQ ID NO 639
<211> LENGTH: 584
<212> TYPE: DNA
<213> ORGANISM: Mycobacterium gilvum

<400> SEQUENCE: 639
attctgtgtt tcggagattc gttgacgtgg ggctggatcc cggtcgagga aggtgtaccc    60
acccaacgtt ttccgaagcg ggtgcgctgg accggggtgc tggccgacga actgggtgct   120
ggctatgagg ttgtcgagga ggggttgagc gcgcgcacca ccaccgctga cgaccctacc   180
gatccccggc tgaacggctc ggactacctc cccgcatgcc tggccagcca cctgccgctg   240
gacctggtga tcctgatgct cgggaccaac gacaccaagg cgaatctgaa tcgcacaccc   300
gtcgacatcg ccagcggaat gggcgtcctg gccacccagg tgctcaccag cgcgggcggg   360
gtcggcacca gctacccggc cccgcaggtg ttgatcgtgg caccgccgcc gctggccgag   420
atgccgcacc cgtggttcga gctggtcttc gacgcgggcc gggagaagac cgcccaactg   480
gcccgggtgt acagcgcgct ggcgtcgttc atgaaggtgc cgttcttcga cgccggatcg   540
gtgatcagca ccgacggtgt cgacggcacc cacttcacac gagg                    584

<210> SEQ ID NO 640
<211> LENGTH: 194
<212> TYPE: PRT
<213> ORGANISM: Mycobacterium gilvum

<400> SEQUENCE: 640

Ile Leu Cys Phe Gly Asp Ser Leu Thr Trp Gly Trp Ile Pro Val Glu
1               5                   10                  15

Glu Gly Val Pro Thr Gln Arg Phe Pro Lys Arg Val Arg Trp Thr Gly
            20                  25                  30

Val Leu Ala Asp Glu Leu Gly Ala Gly Tyr Glu Val Val Glu Glu Gly
        35                  40                  45

Leu Ser Ala Arg Thr Thr Thr Ala Asp Asp Pro Thr Asp Pro Arg Leu
    50                  55                  60

Asn Gly Ser Asp Tyr Leu Pro Ala Cys Leu Ala Ser His Leu Pro Leu
65                  70                  75                  80

Asp Leu Val Ile Leu Met Leu Gly Thr Asn Asp Thr Lys Ala Asn Leu 85                  90                  95
Asn Arg Thr Pro Val Asp Ile Ala Ser Gly Met Gly Val Leu Ala Thr
            100                 105                 110

Gln Val Leu Thr Ser Ala Gly Val Gly Thr Ser Tyr Pro Ala Pro
        115                 120                 125

Gln Val Leu Ile Val Ala Pro Pro Leu Ala Glu Met Pro His Pro
    130                 135                 140

Trp Phe Glu Leu Val Phe Asp Gly Gly Arg Glu Lys Thr Ala Gln Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg

<210> SEQ ID NO 641
<211> LENGTH: 608
<212> TYPE: DNA
<213> ORGANISM: Mycobacterium parafortuitum

<400> SEQUENCE: 641
ttgccaagcg gaattctgtg tttcggggat tctttgacgt ggggatggat ccctgtcgaa    60
gaaggtgtgc ccaccgagcg gttcccgcgt gacgtccggt ggaccggcgt gctggccgac   120
ctgctgggcg accgctacga ggtgatcgag gaaggcctgt cggcgcgcac caccaccgcc   180
gacgaccccg ccgaccccg gctcaacggt tcgcagtatc tgccgtcgtg tctggccagc   240
catctgccgc tggacctggt gatcctgatg ctcggcatca acgacaccaa ggcgaatttt   300
ggccgcaccc cgttcgacat cgccaccggt atgggagtgc ttgccacgca ggtgctcacc   360
agcgccggtg gcgtggggac cagctatccc gcgccgcagg tgctgatcgt ggcgccgccg   420
ccgctgggcg agctgcccca ccctggttc gacctggtgt tctccggcgg ccgtgagaag   480
accgccgagt tggcccgcgt gtacagcgcg ctggcgtcgt tcatgaaggt gccgttcttc   540
gacgccggct cggtgatcag caccgacggc gtggacggca cccacttcac acgaggcgaa   600
acaatcga                                                            608

<210> SEQ ID NO 642
<211> LENGTH: 202
<212> TYPE: PRT
<213> ORGANISM: Mycobacterium parafortuitum

<400> SEQUENCE: 642

Leu Pro Ser Gly Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Thr Ala Asp Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Ile Asn Asp Thr
                85                  90                  95

Lys Ala Asn Phe Gly Arg Thr Pro Phe Asp Ile Ala Thr Gly Met Gly

```
                    100                 105                 110
Val Leu Ala Thr Gln Val Leu Thr Ser Ala Gly Gly Val Gly Thr Ser
            115                 120                 125

Tyr Pro Ala Pro Gln Val Leu Ile Val Ala Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
                180                 185                 190

Gly Thr His Phe Thr Arg Gly Glu Thr Ile
                195                 200

<210> SEQ ID NO 643
<211> LENGTH: 216
<212> TYPE: PRT
<213> ORGANISM: Mycobacterium smegmatis
<220> FEATURE:
<221> NAME/KEY: MISC_FEATURE
<222> LOCATION: (1)..(216)
<223> OTHER INFORMATION: Xaa is selenocysteine

<400> SEQUENCE: 643

Met Ala Lys Arg Ile Leu Cys Phe Gly Asp Ser Leu Xaa Trp Gly Trp
1               5                   10                  15

Val Pro Val Glu Asp Gly Ala Pro Xaa Glu Arg Phe Ala Pro Asp Val
                20                  25                  30

Arg Trp Xaa Gly Val Leu Ala Gln Gln Leu Gly Ala Asp Phe Glu Val
                35                  40                  45

Ile Glu Glu Gly Leu Ser Ala Arg Xaa Xaa Asn Ile Asp Asp Pro Xaa
        50                  55                  60

Asp Pro Arg Leu Asn Gly Ala Ser Tyr Leu Pro Ser Cys Leu Ala Xaa
65              70                  75                  80

His Leu Pro Leu Asp Leu Val Ile Ile Met Leu Gly Xaa Asn Asp Xaa
                85                  90                  95

Lys Ala Tyr Phe Arg Arg Xaa Pro Leu Asp Ile Ala Leu Gly Met Ser
                100                 105                 110

Val Leu Val Xaa Gln Val Leu Xaa Ser Ala Gly Gly Val Gly Xaa Xaa
            115                 120                 125

Tyr Pro Ala Pro Lys Val Leu Val Ser Pro Pro Leu Ala Pro
    130                 135                 140

Met Pro His Pro Trp Phe Gln Leu Ile Phe Glu Gly Glu Gln Lys
145                 150                 155                 160

Xaa Xaa Glu Leu Ala Arg Val Tyr Ser Ala Leu Ala Ser Phe Met Lys
                165                 170                 175

Val Pro Phe Phe Asp Ala Gly Ser Val Ile Ser Xaa Asp Gly Val Asp
                180                 185                 190

Gly Ile His Phe Xaa Glu Ala Asn Asn Arg Asp Leu Gly Val Ala Leu
                195                 200                 205

Ala Glu Gln Val Arg Ser Leu Leu
    210                 215

<210> SEQ ID NO 644
<211> LENGTH: 194
<212> TYPE: PRT
<213> ORGANISM: Mycobacterium gilvum
```

<400> SEQUENCE: 644

Ile Leu Cys Phe Gly Asp Ser Leu Thr Trp Gly Trp Ile Pro Val Glu
1               5                   10                  15

Glu Gly Val Pro Thr Gln Arg Phe Pro Lys Arg Val Arg Trp Thr Gly
            20                  25                  30

Val Leu Ala Asp Glu Leu Gly Ala Gly Tyr Glu Val Glu Glu Gly
        35                  40                  45

Leu Ser Ala Arg Thr Thr Ala Asp Pro Thr Asp Pro Arg Leu
50                  55                  60

Asn Gly Ser Asp Tyr Leu Pro Ala Cys Leu Ala Ser His Leu Pro Leu
65                  70                  75                  80

Asp Leu Val Ile Leu Met Leu Gly Thr Asn Asp Thr Lys Ala Asn Leu
                85                  90                  95

Asn Arg Thr Pro Val Asp Ile Ala Ser Gly Met Gly Val Leu Ala Thr
            100                 105                 110

Gln Val Leu Thr Ser Ala Gly Gly Val Gly Thr Ser Tyr Pro Ala Pro
        115                 120                 125

Gln Val Leu Ile Val Ala Pro Pro Leu Ala Glu Met Pro His Pro
130                 135                 140

Trp Phe Glu Leu Val Phe Asp Gly Gly Arg Glu Lys Thr Ala Gln Leu
145                 150                 155                 160

Ala Arg Val Tyr Ser Ala Leu Ala Ser Phe Met Lys Val Pro Phe Phe
                165                 170                 175

Asp Ala Gly Ser Val Ile Ser Thr Asp Gly Val Asp Gly Thr His Phe
            180                 185                 190

Thr Arg

<210> SEQ ID NO 645
<211> LENGTH: 202
<212> TYPE: PRT
<213> ORGANISM: Mycobacterium parafortuitum

<400> SEQUENCE: 645

Leu Pro Ser Gly Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Ala Asp Asp Pro Ala
50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Ile Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
        115                 120                 125

Tyr Pro Ala Pro Gln Val Leu Ile Val Ala Pro Pro Leu Gly Glu
130                 135                 140

Leu Pro His Pro Trp Phe Asp Leu Val Phe Ser Gly Gly Arg Glu Lys
145                 150                 155                 160

```
Thr Ala Glu Leu Ala Arg Val Tyr Ser Ala Leu Ala Ser Phe Met Lys
            165                 170                 175
Val Pro Phe Phe Asp Ala Gly Ser Val Ile Ser Thr Asp Gly Val Asp
        180                 185                 190
Gly Thr His Phe Thr Arg Gly Glu Thr Ile
        195                 200

<210> SEQ ID NO 646
<211> LENGTH: 198
<212> TYPE: PRT
<213> ORGANISM: Mycobacterium parafortuitum

<400> SEQUENCE: 646

Ile Leu Cys Phe Gly Asp Ser Leu Thr Trp Gly Trp Ile Pro Val Glu
1               5                   10                  15
Glu Gly Val Pro Thr Glu Arg Phe Pro Arg Asp Val Arg Trp Thr Gly
            20                  25                  30
Val Leu Ala Asp Leu Leu Gly Asp Arg Tyr Glu Val Ile Glu Glu Gly
        35                  40                  45
Leu Ser Ala Arg Thr Thr Thr Ala Asp Asp Pro Ala Asp Pro Arg Leu
50                  55                  60
Asn Gly Ser Gln Tyr Leu Pro Ser Cys Leu Ala Ser His Leu Pro Leu
65                  70                  75                  80
Asp Leu Val Ile Leu Met Leu Gly Ile Asn Asp Thr Lys Ala Asn Phe
                85                  90                  95
Gly Arg Thr Pro Phe Asp Ile Ala Thr Gly Met Gly Val Leu Ala Thr
            100                 105                 110
Gln Val Leu Thr Ser Ala Gly Gly Val Gly Thr Ser Tyr Pro Ala Pro
        115                 120                 125
Gln Val Leu Ile Val Ala Pro Pro Leu Gly Glu Leu Pro His Pro
    130                 135                 140
Trp Phe Asp Leu Val Phe Ser Gly Gly Arg Glu Lys Thr Ala Glu Leu
145                 150                 155                 160
Ala Arg Val Tyr Ser Ala Leu Ala Ser Phe Met Lys Val Pro Phe Phe
                165                 170                 175
Asp Ala Gly Ser Val Ile Ser Thr Asp Gly Val Asp Gly Thr His Phe
            180                 185                 190
Thr Arg Gly Glu Thr Ile
        195

<210> SEQ ID NO 647
<211> LENGTH: 216
<212> TYPE: PRT
<213> ORGANISM: Mycobacterium gilvum

<400> SEQUENCE: 647

Gly Gly Arg Cys Val Ala Ser Cys Glu Val Gly Ala Val Ala Lys Arg
1               5                   10                  15
Ile Leu Cys Phe Gly Asp Ser Leu Thr Trp Gly Trp Ile Pro Val Glu
            20                  25                  30
Glu Gly Val Pro Thr Gln Arg Phe Pro Lys Arg Val Arg Trp Thr Gly
        35                  40                  45
Val Leu Ala Asp Glu Leu Gly Ala Gly Tyr Glu Val Val Glu Glu Gly
    50                  55                  60
Leu Ser Ala Arg Thr Thr Thr Ala Asp Asp Pro Thr Asp Pro Arg Leu
65                  70                  75                  80
```

```
Asn Gly Ser Asp Tyr Leu Pro Ala Cys Leu Ala Ser His Leu Pro Leu
                85                  90                  95

Asp Leu Val Ile Leu Met Leu Gly Thr Asn Asp Thr Lys Ala Asn Leu
            100                 105                 110

Asn Arg Thr Pro Val Asp Ile Ala Ser Gly Met Gly Val Leu Ala Thr
            115                 120                 125

Gln Val Leu Thr Ser Ala Gly Val Gly Thr Ser Tyr Pro Ala Pro
    130                 135                 140

Gln Val Leu Ile Val Ala Pro Pro Leu Ala Glu Met Pro His Pro
145                 150                 155                 160

Trp Phe Glu Leu Val Phe Asp Gly Gly Arg Glu Lys Thr Ala Gln Leu
            165                 170                 175

Ala Arg Val Tyr Ser Ala Leu Ala Ser Phe Met Lys Val Pro Phe Phe
            180                 185                 190

Asp Ala Gly Ser Val Ile Ser Thr Asp Gly Val Asp Gly Thr His Phe
            195                 200                 205

Thr Arg Gly Glu Thr Ile Asp Arg
    210                 215

<210> SEQ ID NO 648
<211> LENGTH: 203
<212> TYPE: PRT
<213> ORGANISM: Mycobacterium parafortuitum CO1

<400> SEQUENCE: 648

Met Ala Lys Arg Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
            35                  40                  45

Ile Glu Glu Gly Leu Ser Ala Arg Thr Thr Ala Glu Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Thr Asn Asp Thr
                85                  90                  95

Lys Ala Asn Phe Gly Arg Thr Pro Phe Asp Ile Ala Thr Gly Met Gly
            100                 105                 110

Val Leu Ala Thr Gln Val Leu Thr Ser Ala Gly Gly Val Gly Thr Ser
            115                 120                 125

Tyr Pro Ala Pro Gln Val Leu Ile Val Ala Pro Pro Leu Gly Glu
    130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
            165                 170                 175

Val Pro Phe Phe Asp Ala Gly Ser Val Ile Ser Thr Asp Gly Val Asp
            180                 185                 190

Gly Ile His Phe Thr Arg Gly Glu Gln Ser Thr
    195                 200

<210> SEQ ID NO 649
<211> LENGTH: 213
<212> TYPE: PRT
<213> ORGANISM: Sinorhizobium meliloti
```

<400> SEQUENCE: 649

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp His Leu Ala Asp Cys Asp Arg
50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Leu Cys Glu Thr Ala Asn Ser Ala
130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
        210

<210> SEQ ID NO 650
<211> LENGTH: 209
<212> TYPE: PRT
<213> ORGANISM: Agrobacterium tumefaciens

<400> SEQUENCE: 650

Met Lys Thr Val Leu Ala Phe Gly Asp Ser Leu Thr Trp Gly Ala Asp
1               5                   10                  15

Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45

Gly Gly Arg Thr Thr Cys Tyr Asp Asp His Ala Gly Pro Ala Cys Arg
50                  55                  60

Asn Gly Ala Arg Ala Leu Glu Val Ala Leu Ser Cys His Met Pro Leu
65                  70                  75                  80

Asp Leu Val Ile Ile Met Leu Gly Thr Asn Asp Ile Lys Pro Val His
                85                  90                  95

Gly Gly Arg Ala Glu Ala Ala Val Ser Gly Met Arg Arg Leu Ala Gln
            100                 105                 110

Ile Val Glu Thr Phe Ile Tyr Lys Pro Arg Glu Ala Val Pro Lys Leu
        115                 120                 125

Leu Ile Val Ala Pro Pro Pro Cys Val Ala Gly Pro Gly Gly Glu Pro
130                 135                 140

Ala Gly Gly Arg Asp Ile Glu Gln Ser Met Arg Leu Ala Pro Leu Tyr
145                 150                 155                 160

Arg Lys Leu Ala Ala Glu Leu Gly His His Phe Phe Asp Ala Gly Ser
                165                 170                 175

Val Ala Ser Ala Ser Pro Val Asp Gly Val His Leu Ala Ser Ala
            180                 185                 190

Thr Ala Ala Ile Gly Arg Ala Leu Ala Ala Pro Val Arg Asp Ile Leu
        195                 200                 205

Gly

<210> SEQ ID NO 651
<211> LENGTH: 220
<212> TYPE: PRT
<213> ORGANISM: Agrobacterium tumefaciens

<400> SEQUENCE: 651

Met Val Lys Ser Val Leu Cys Phe Gly Asp Ser Leu Thr Trp Gly Ser
1               5                   10                  15

Asn Ala Glu Thr Gly Gly Arg His Ser His Asp Asp Leu Trp Pro Ser
            20                  25                  30

Val Leu Gln Lys Ala Leu Gly Ser Asp Val His Val Ile Phe Thr His
        35                  40                  45

Glu Gly Leu Gly Gly Arg Thr Thr Ala Tyr Asp Asp His Thr Gly Asp
    50                  55                  60

Cys Asp Arg Asn Gly Ala Arg Leu Leu Pro Thr Leu His Ser His
65                  70                  75                  80

Ala Pro Leu Asp Met Val Ile Ile Met Leu Gly Thr Asn Asp Met Lys
                85                  90                  95

Pro Ala Ile His Gly Ser Ala Ile Val Ala Phe Thr Met Lys Gly Val
            100                 105                 110

Glu Arg Leu Val Lys Leu Thr Arg Asn His Val Trp Gln Val Ser Asp
        115                 120                 125

Trp Glu Ala Pro Asp Val Leu Ile Val Ala Pro Pro Gln Leu Cys Glu
    130                 135                 140

Thr Ala Asn Pro Phe Met Gly Ala Ile Phe Arg Asp Ala Ile Asp Glu
145                 150                 155                 160

Ser Ala Met Leu Ala Ser Val Phe Thr Tyr Arg Asp Leu Ala Asp Glu
                165                 170                 175

Leu Asp Cys Gly Phe Phe Asp Ala Gly Ser Val Ala Arg Thr Thr Pro
            180                 185                 190

Val Asp Gly Val His Leu Asp Ala Glu Asn Thr Arg Ala Ile Gly Arg
        195                 200                 205

Gly Leu Glu Pro Val Val Arg Met Met Leu Gly Leu
    210                 215                 220

<210> SEQ ID NO 652
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 652

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr

```
                        20                  25                  30
Ala Leu Glu Gln Gly Leu Gly Gly Lys Ala Arg Val Ile Ala Glu Gly
                35                  40                  45

Leu Gly Gly Arg Thr Thr Val His Asp Asp Trp Phe Ala Asn Ala Asp
         50                  55                  60

Arg Asn Gly Ala Arg Val Leu Pro Thr Leu Leu Glu Ser His Ser Pro
 65                  70                  75                  80

Leu Asp Leu Ile Val Ile Met Leu Gly Thr Asn Asp Ile Lys Pro His
                 85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
                180                 185                 190

Leu Asp Pro Ala Asn Thr Arg Ala Ile Gly Ala Gly Leu Val Pro Leu
            195                 200                 205

Val Lys Gln Val Leu Gly Leu
        210                 215

<210> SEQ ID NO 653
<211> LENGTH: 223
<212> TYPE: PRT
<213> ORGANISM: Mesorhizobium loti

<400> SEQUENCE: 653

Met Ala Gly Gly Thr Arg Leu Asp Glu Cys Thr Gly Glu Arg Met Lys
1               5                   10                  15

Thr Val Leu Cys Tyr Gly Asp Ser Leu Thr Trp Gly Tyr Asn Ala Glu
                20                  25                  30

Gly Gly Arg His Ala Leu Glu Asp Arg Trp Pro Ser Val Leu Gln Ala
            35                  40                  45

Ser Leu Gly Gly Gly Val Gln Val Ile Ala Asp Gly Leu Asn Gly Arg
        50                  55                  60

Thr Thr Ala Phe Asp His Leu Ala Gly Ala Asp Arg Asn Gly Ala
 65                  70                  75                  80

Arg Leu Leu Pro Thr Ala Leu Thr Thr His Ala Pro Ile Asp Leu Ile
                85                  90                  95

Val Ile Met Leu Gly Ala Asn Asp Met Lys Pro Trp Ile His Gly Asn
            100                 105                 110

Pro Val Ala Ala Lys Gln Gly Ile Gln Arg Leu Ile Asp Ile Val Arg
        115                 120                 125

Gly His Asp Tyr Pro Phe Asp Trp Pro Ala Pro Gln Ile Leu Ile Val
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175
```

```
Ala Leu Ala Asp Glu Val Gly Cys Gly Phe Phe Asp Ala Gly Thr Val
            180                 185                 190

Ala Gln Thr Thr Pro Leu Asp Gly Val His Leu Asp Ala Glu Asn Thr
        195                 200                 205

Arg Asn Ile Gly Lys Ala Leu Thr Ser Val Val Arg Val Met Leu
    210                 215                 220

<210> SEQ ID NO 654
<211> LENGTH: 216
<212> TYPE: PRT
<213> ORGANISM: Prosthecobacter dejongeii

<400> SEQUENCE: 654

Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
    50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
    210                 215

<210> SEQ ID NO 655
<211> LENGTH: 220
<212> TYPE: PRT
<213> ORGANISM: Sinorhizobium meliloti

<400> SEQUENCE: 655

Met Glu Glu Thr Val Ala Arg Thr Val Leu Cys Phe Gly Asp Ser Asn
1               5                   10                  15

Thr His Gly Gln Val Pro Gly Arg Gly Pro Leu Asp Arg Tyr Arg Arg
            20                  25                  30

Glu Gln Arg Trp Gly Gly Val Leu Gln Gly Leu Leu Gly Pro Asn Trp
        35                  40                  45

Gln Val Ile Glu Glu Gly Leu Ser Gly Arg Thr Thr Val His Asp Asp
    50                  55                  60
```

```
Pro Ile Glu Gly Ser Leu Lys Asn Gly Arg Ile Tyr Leu Arg Pro Cys
 65                  70                  75                  80

Leu Gln Ser His Ala Pro Leu Asp Leu Ile Ile Met Leu Gly Thr
                 85                  90                  95

Asn Asp Leu Lys Arg Arg Phe Asn Met Pro Ser Glu Val Ala Met
                100                 105                 110

Gly Ile Gly Cys Leu Val His Asp Ile Arg Glu Leu Ser Pro Gly Arg
                115                 120                 125

Thr Gly Asn Asp Pro Glu Ile Met Ile Val Ala Pro Pro Met Leu
130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
                180                 185                 190

Gly Phe His Ile Asp Glu Asp Ala His Arg Leu Leu Gly Glu Ala Leu
                195                 200                 205

Ala Gln Glu Val Leu Ala Ile Gly Trp Pro Asp Ala
210                 215                 220

<210> SEQ ID NO 656
<211> LENGTH: 211
<212> TYPE: PRT
<213> ORGANISM: Mesorhizobium loti

<400> SEQUENCE: 656

Met Lys Thr Val Leu Cys Tyr Gly Asp Ser Leu Thr Trp Gly Tyr Asn
 1               5                  10                  15

Ala Glu Gly Gly Arg His Ala Leu Glu Asp Arg Trp Pro Ser Val Leu
                20                  25                  30

Gln Ala Ser Leu Gly Gly Val Gln Val Ile Ala Asp Gly Leu Asn
                35                  40                  45

Gly Arg Thr Thr Ala Phe Asp Asp His Leu Ala Gly Ala Asp Arg Asn
 50                  55                  60

Gly Ala Arg Leu Leu Pro Thr Ala Leu Thr Thr His Ala Pro Ile Asp
 65                  70                  75                  80

Leu Ile Val Ile Met Leu Gly Ala Asn Asp Met Lys Pro Trp Ile His
                 85                  90                  95

Gly Asn Pro Val Ala Ala Lys Gln Gly Ile Gln Arg Leu Ile Asp Ile
                100                 105                 110

Val Arg Gly His Asp Tyr Pro Phe Asp Trp Pro Ala Pro Gln Ile Leu
                115                 120                 125

Ile Val Ser Pro Pro Val Val Ser Arg Thr Glu Asn Ala Asp Phe Arg
130                 135                 140

Glu Met Phe Ala Gly Gly Asp Glu Ala Ser Lys Gln Leu Ala Pro Gln
145                 150                 155                 160

Tyr Ala Ala Leu Ala Asp Glu Val Gly Cys Gly Phe Phe Asp Ala Gly
                165                 170                 175

Thr Val Ala Gln Thr Thr Pro Leu Asp Gly Val His Leu Asp Ala Glu
                180                 185                 190

Asn Thr Arg Asn Ile Gly Lys Ala Leu Thr Ser Val Val Arg Val Met
                195                 200                 205

Leu Glu Leu
210
```

<210> SEQ ID NO 657
<211> LENGTH: 218
<212> TYPE: PRT
<213> ORGANISM: Sinorhizobium meliloti

<400> SEQUENCE: 657

```
Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

Ala Ser His Leu Pro Leu Asp Leu Val Ile Ile Met Leu Gly Thr Asn
                85                  90                  95

Asp Thr Lys Ser Tyr Phe His Arg Thr Pro Tyr Glu Ile Ala Asn Gly
            100                 105                 110

Met Gly Lys Leu Val Gly Gln Val Leu Thr Cys Ala Gly Gly Val Gly
        115                 120                 125

Thr Pro Tyr Pro Ala Pro Lys Val Leu Val Val Ala Pro Pro Pro Leu
    130                 135                 140

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
                165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
        195                 200                 205

Ala Ile Ala Asp Lys Val Ala Ala Leu Phe
    210                 215
```

<210> SEQ ID NO 658
<211> LENGTH: 212
<212> TYPE: PRT
<213> ORGANISM: Artificial Sequence
<220> FEATURE:
<223> OTHER INFORMATION: primer

<400> SEQUENCE: 658

```
Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
        35                  40                  45

Asn Gly Arg Thr Thr Val Phe Asp Asp Ala Ala Thr Phe Glu Ser Arg
    50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
                85                  90                  95
```

```
Arg Cys Arg Ala Phe Asp Ala Ser Met Gly Met Glu Arg Leu Ile Gln
                100                 105                 110

Ile Val Arg Ser Ala Asn Tyr Met Lys Gly Tyr Lys Ile Pro Glu Ile
            115                 120                 125

Leu Ile Ile Ser Pro Pro Ser Leu Val Pro Thr Gln Asp Glu Trp Phe
        130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210

<210> SEQ ID NO 659
<211> LENGTH: 229
<212> TYPE: PRT
<213> ORGANISM: Sinorhizobium meliloti

<400> SEQUENCE: 659

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Leu Ala Pro Met Pro Asp
145                 150                 155                 160

Pro Trp Phe Glu Gly Met Phe Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225

<210> SEQ ID NO 660
```

```
<211> LENGTH: 222
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (101)..(103)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid
<220> FEATURE:
<221> NAME/KEY: misc_feature
```

```
<222> LOCATION: (111)..(113)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (131)..(134)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (150)..(152)
<223> OTHER INFORMATION: Xaa can be any naturally occurring amino acid
<220> FEATURE:
<221> NAME/KEY: misc_feature
<222> LOCATION: (154)..(154)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(161)
<223> OTHER INFORMATION: Xaa can be any naturally occurring amino acid
<220> FEATURE:
<221> NAME/KEY: misc_feature
<222> LOCATION: (164)..(164)
<223> OTHER INFORMATION: Xaa can be any naturally occurring amino acid
<220> FEATURE:
<221> NAME/KEY: misc_feature
<222> LOCATION: (168)..(169)
<223> OTHER INFORMATION: Xaa can be any naturally occurring amino acid
<220> FEATURE:
<221> NAME/KEY: misc_feature
<222> LOCATION: (175)..(175)
<223> OTHER INFORMATION: Xaa can be any naturally occurring amino acid
<220> FEATURE:
<221> NAME/KEY: misc_feature
<222> LOCATION: (180)..(180)
<223> OTHER INFORMATION: Xaa can be any naturally occurring amino acid
<220> FEATURE:
<221> NAME/KEY: misc_feature
<222> LOCATION: (184)..(184)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (215)..(217)
<223> OTHER INFORMATION: Xaa can be any naturally occurring amino acid
<220> FEATURE:
<221> NAME/KEY: misc_feature
<222> LOCATION: (220)..(220)
<223> OTHER INFORMATION: Xaa can be any naturally occurring amino acid
```

<400> SEQUENCE: 660

Lys Thr Ile Leu Cys Phe Gly Asp Ser Leu Thr Trp Gly Trp Ile Pro
1               5                   10                  15

Val Xaa Glu Gly Xaa Pro Xaa Xaa Xaa Arg His Pro Xaa Glu Xaa Arg
            20                  25                  30

Trp Xaa Gly Val Leu Ala Xaa Xaa Leu Gly Gly Xaa Tyr Xaa Val Ile
        35                  40                  45

Glu Xaa Xaa Glu Gly Leu Ser Gly Arg Thr Thr Xaa Xaa Asp Asp Pro
    50                  55                  60

Xaa Asp Xaa Xaa Leu Xaa Asn Gly Ser Xaa Tyr Leu Pro Thr Xaa Leu
65                  70                  75                  80

Ala Ser His Leu Pro Leu Asp Leu Val Ile Ile Met Leu Gly Thr Asn
                85                  90                  95

Asp Met Lys Ala Xaa Xaa Xaa Arg Thr Pro Xaa Asp Ile Ala Xaa Xaa
                100                 105                 110

Xaa Gly Met Gly Arg Leu Val Xaa Xaa Val Leu Thr Xaa Ala Gly Gly
            115                 120                 125

Val Gly Xaa Xaa Xaa Xaa Ala Pro Gln Val Leu Ile Val Ala Pro Pro
    130                 135                 140

Pro Leu Xaa Glu Met Xaa Xaa Xaa Pro Xaa Phe Glu Xaa Val Phe Xaa
145                 150                 155                 160

Xaa Gly Gly Xaa Glu Lys Ser Xaa Xaa Leu Ala Arg Val Tyr Xaa Ala
                165                 170                 175

Leu Ala Asp Xaa Met Lys Val Xaa Phe Phe Asp Ala Gly Ser Val Ile
                180                 185                 190

Ser Thr Asp Xaa Val Asp Gly Ile His Leu Asp Ala Xaa Xaa Thr Xaa
            195                 200                 205

Xaa Ile Gly Xaa Ala Leu Xaa Xaa Xaa Val Arg Xaa Leu Leu
    210                 215                 220

<210> SEQ ID NO 661
<211> LENGTH: 213
<212> TYPE: PRT
<213> ORGANISM: Artificial Sequence
<220> FEATURE:
<223> OTHER INFORMATION: consensus

<400> SEQUENCE: 661

Thr Ile Leu Cys Phe Gly Asp Ser Leu Thr Trp Gly Trp Ile Pro Val
1               5                   10                  15

Glu Glu Gly Ala Pro Thr Glu Arg His Pro Pro Glu Val Arg Trp Thr
            20                  25                  30

Gly Val Leu Ala Gln Gln Leu Gly Gly Asp Tyr Glu Val Ile Glu Glu
        35                  40                  45

Gly Leu Ser Gly Arg Thr Thr Asn Ile Asp Asp Pro Thr Asp Pro Arg
    50                  55                  60

Leu Asn Gly Ser Ser Tyr Leu Pro Thr Cys Leu Ala Ser His Leu Pro
65                  70                  75                  80

Leu Asp Leu Val Ile Ile Met Leu Gly Thr Asn Asp Met Lys Ala Tyr
                85                  90                  95

Phe Arg Arg Thr Pro Leu Asp Ile Ala Leu Gly Met Gly Arg Leu Val
                100                 105                 110

Thr Gln Val Leu Thr Ser Ala Gly Gly Val Gly Thr Thr Tyr Pro Ala
            115                 120                 125

Pro Gln Val Leu Ile Val Ala Pro Pro Leu Ala Glu Met Pro His

```
                130             135             140
Pro Trp Phe Glu Leu Val Phe Glu Gly Gly Glu Lys Ser Thr Glu
145                 150                 155                 160

Leu Ala Arg Val Tyr Ser Ala Leu Ala Asp Phe Met Lys Val Pro Phe
                165                 170                 175

Phe Asp Ala Gly Ser Val Ile Ser Thr Asp Gly Val Asp Gly Ile His
                180                 185                 190

Leu Asp Ala Ala Asn Thr Arg Asp Ile Gly Val Ala Leu Ala Glu Gln
                195                 200                 205

Val Arg Ser Leu Leu
    210

<210> SEQ ID NO 662
<211> LENGTH: 216
<212> TYPE: PRT
<213> ORGANISM: Artificial Sequence
<220> FEATURE:
<223> OTHER INFORMATION: ACT MSMEG clone
<220> FEATURE:
<221> NAME/KEY: MISC_FEATURE
<222> LOCATION: (1)..(216)
<223> OTHER INFORMATION: Xaa is selenocysteine

<400> SEQUENCE: 662

Met Ala Lys Arg Ile Leu Cys Phe Gly Asp Ser Leu Xaa Trp Gly Trp
1               5                   10                  15

Val Pro Val Glu Asp Gly Ala Pro Xaa Glu Arg Phe Ala Pro Asp Val
                20                  25                  30

Arg Trp Xaa Gly Val Leu Ala Gln Gln Leu Gly Ala Asp Phe Glu Val
                35                  40                  45

Ile Glu Glu Gly Leu Ser Ala Arg Xaa Xaa Asn Ile Asp Asp Pro Xaa
50                  55                  60

Asp Pro Arg Leu Asn Gly Ala Ser Tyr Leu Pro Ser Cys Leu Ala Xaa
65                  70                  75                  80

His Leu Pro Leu Asp Leu Val Ile Ile Met Leu Gly Xaa Asn Asp Xaa
                85                  90                  95

Lys Ala Tyr Phe Arg Arg Xaa Pro Leu Asp Ile Ala Leu Gly Met Ser
                100                 105                 110

Val Leu Val Xaa Gln Val Leu Xaa Ser Ala Gly Gly Val Gly Xaa Xaa
                115                 120                 125

Tyr Pro Ala Pro Lys Val Leu Val Ser Pro Pro Leu Ala Pro
                130                 135                 140

Met Pro His Pro Trp Phe Gln Leu Ile Phe Glu Gly Gly Glu Gln Lys
145                 150                 155                 160

Xaa Xaa Glu Leu Ala Arg Val Tyr Ser Ala Leu Ala Ser Phe Met Lys
                165                 170                 175

Val Pro Phe Phe Asp Ala Gly Ser Val Ile Ser Xaa Asp Gly Val Asp
                180                 185                 190

Gly Ile His Phe Xaa Glu Ala Asn Asn Arg Asp Leu Gly Val Ala Leu
                195                 200                 205

Ala Glu Gln Val Arg Ser Leu Leu
    210                 215

<210> SEQ ID NO 663
<211> LENGTH: 211
<212> TYPE: PRT
<213> ORGANISM: Mesorhizobium loti
```

<400> SEQUENCE: 663

Met Lys Thr Val Leu Cys Tyr Gly Asp Ser Leu Thr Trp Gly Tyr Asn
1               5                   10                  15

Ala Glu Gly Gly Arg His Ala Leu Glu Asp Arg Trp Pro Ser Val Leu
            20                  25                  30

Gln Ala Ser Leu Gly Gly Val Gln Val Ile Ala Asp Gly Leu Asn
        35                  40                  45

Gly Arg Thr Thr Ala Phe Asp Asp His Leu Ala Gly Ala Asp Arg Asn
50                  55                  60

Gly Ala Arg Leu Leu Pro Thr Ala Leu Thr Thr His Ala Pro Ile Asp
65                  70                  75                  80

Leu Ile Val Ile Met Leu Gly Ala Asn Asp Met Lys Pro Trp Ile His
                85                  90                  95

Gly Asn Pro Val Ala Ala Lys Gln Gly Ile Gln Arg Leu Ile Asp Ile
            100                 105                 110

Val Arg Gly His Asp Tyr Pro Phe Asp Trp Pro Ala Pro Gln Ile Leu
        115                 120                 125

Ile Val Ser Pro Pro Val Val Ser Arg Thr Glu Asn Ala Asp Phe Arg
130                 135                 140

Glu Met Phe Ala Gly Gly Asp Glu Ala Ser Lys Gln Leu Ala Pro Gln
145                 150                 155                 160

Tyr Ala Leu Ala Asp Glu Val Gly Cys Gly Phe Phe Asp Ala Gly
                165                 170                 175

Thr Val Ala Gln Thr Thr Pro Leu Asp Gly Val His Leu Asp Ala Glu
            180                 185                 190

Asn Thr Arg Asn Ile Gly Lys Ala Leu Thr Ser Val Val Arg Val Met
        195                 200                 205

Leu Glu Leu
    210

<210> SEQ ID NO 664
<211> LENGTH: 229
<212> TYPE: PRT
<213> ORGANISM: Sinorhizobium meliloti

<400> SEQUENCE: 664

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
130                 135                 140

```
Pro Lys Val Leu Val Val Ala Pro Pro Leu Ala Pro Met Pro Asp
145                 150                 155                 160

Pro Trp Phe Glu Gly Met Phe Gly Gly Tyr Glu Lys Ser Lys Glu
            165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
            195                 200                 205

Leu Ser Ala Glu Thr Asn Ile Arg Leu Gly His Ala Ile Ala Asp Lys
            210                 215                 220

Val Ala Ala Leu Phe
225
```

<210> SEQ ID NO 665
<211> LENGTH: 220
<212> TYPE: PRT
<213> ORGANISM: Sinorhizobium meliloti

<400> SEQUENCE: 665

```
Met Glu Glu Thr Val Ala Arg Thr Val Leu Cys Phe Gly Asp Ser Asn
1               5                   10                  15

Thr His Gly Gln Val Pro Gly Arg Gly Pro Leu Asp Arg Tyr Arg Arg
            20                  25                  30

Glu Gln Arg Trp Gly Gly Val Leu Gln Gly Leu Leu Gly Pro Asn Trp
        35                  40                  45

Gln Val Ile Glu Glu Gly Leu Ser Gly Arg Thr Thr Val His Asp Asp
    50                  55                  60

Pro Ile Glu Gly Ser Leu Lys Asn Gly Arg Ile Tyr Leu Arg Pro Cys
65                  70                  75                  80

Leu Gln Ser His Ala Pro Leu Asp Leu Ile Ile Met Leu Gly Thr
                85                  90                  95

Asn Asp Leu Lys Arg Arg Phe Asn Met Pro Pro Ser Glu Val Ala Met
            100                 105                 110

Gly Ile Gly Cys Leu Val His Asp Ile Arg Glu Leu Ser Pro Gly Arg
        115                 120                 125

Thr Gly Asn Asp Pro Glu Ile Met Ile Val Ala Pro Pro Met Leu
    130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
                165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
        195                 200                 205

Ala Gln Glu Val Leu Ala Ile Gly Trp Pro Asp Ala
    210                 215                 220
```

<210> SEQ ID NO 666
<211> LENGTH: 216
<212> TYPE: PRT
<213> ORGANISM: Prosthecobacter dejongeii

<400> SEQUENCE: 666

```
Met Lys Thr Ile Leu Cys Phe Gly Asp Ser Asn Thr Trp Gly Tyr Asp
1               5                   10                  15
```

```
Pro Ala Ser Met Thr Ala Pro Phe Pro Arg Arg His Gly Pro Glu Val
            20                  25                  30

Arg Trp Thr Gly Val Leu Ala Lys Ala Leu Gly Ala Gly Phe Arg Val
        35                  40                  45

Ile Glu Glu Gly Gln Asn Gly Arg Thr Thr Val His Glu Asp Pro Leu
 50                  55                  60

Asn Ile Cys Arg Lys Gly Lys Asp Tyr Leu Pro Ala Cys Leu Glu Ser
65                  70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
            100                 105                 110

Val Leu Gly Arg Met Ile Leu Ala Gly Asp Ala Gly Pro Glu Asn Arg
        115                 120                 125

Pro Pro Gln Leu Leu Leu Met Cys Pro Pro Lys Val Arg Asp Leu Ser
130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
            180                 185                 190

Ile His Leu Glu Ala Ser Glu His Leu Lys Leu Gly Glu Ala Leu Ala
        195                 200                 205

Glu Lys Val Lys Val Leu Leu Gly
210                 215

<210> SEQ ID NO 667
<211> LENGTH: 213
<212> TYPE: PRT
<213> ORGANISM: Sinorhizobium meliloti

<400> SEQUENCE: 667

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
 50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Glu Gly Pro Glu
        115                 120                 125

Ile Leu Ile Val Ser Pro Pro Leu Cys Glu Thr Ala Asn Ser Ala
130                 135                 140

Phe Ala Ala Met Phe Ala Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175
```

```
Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
    210

<210> SEQ ID NO 668
<211> LENGTH: 218
<212> TYPE: PRT
<213> ORGANISM: Sinorhizobium meliloti

<400> SEQUENCE: 668

Met Val Glu Lys Arg Ser Val Leu Cys Phe Gly Asp Ser Leu Thr Trp
1               5                   10                  15

Gly Trp Ile Pro Val Lys Glu Ser Ser Pro Thr Leu Arg Tyr Pro Tyr
            20                  25                  30

Glu Gln Arg Trp Thr Gly Ala Met Ala Ala Arg Leu Gly Asp Gly Tyr
        35                  40                  45

His Ile Ile Glu Glu Gly Leu Ser Ala Arg Thr Thr Ser Leu Asp Asp
    50                  55                  60

Pro Asn Asp Ala Arg Leu Asn Gly Ser Thr Tyr Leu Pro Met Ala Leu
65                  70                  75                  80

Ala Ser His Leu Pro Leu Asp Leu Val Ile Met Leu Gly Thr Asn
                85                  90                  95

Asp Thr Lys Ser Tyr Phe His Arg Thr Pro Tyr Glu Ile Ala Asn Gly
                100                 105                 110

Met Gly Lys Leu Val Gly Gln Val Leu Thr Cys Ala Gly Gly Val Gly
            115                 120                 125

Thr Pro Tyr Pro Ala Pro Lys Val Leu Val Val Ala Pro Pro Leu
        130                 135                 140

Ala Pro Met Pro Asp Pro Trp Phe Glu Gly Met Phe Gly Gly Gly Tyr
145                 150                 155                 160

Glu Lys Ser Lys Glu Leu Ser Gly Leu Tyr Lys Ala Leu Ala Asp Phe
                165                 170                 175

Met Lys Val Glu Phe Phe Ala Ala Gly Asp Cys Ile Ser Thr Asp Gly
            180                 185                 190

Ile Asp Gly Ile His Leu Ser Ala Glu Thr Asn Ile Arg Leu Gly His
        195                 200                 205

Ala Ile Ala Asp Lys Val Ala Ala Leu Phe
    210                 215

<210> SEQ ID NO 669
<211> LENGTH: 209
<212> TYPE: PRT
<213> ORGANISM: Agrobacterium tumefaciens

<400> SEQUENCE: 669

Met Lys Thr Val Leu Ala Phe Gly Asp Ser Leu Thr Trp Gly Ala Asp
1               5                   10                  15

Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45

Gly Gly Arg Thr Thr Cys Tyr Asp Asp His Ala Gly Pro Ala Cys Arg
    50                  55                  60
```

-continued

```
Asn Gly Ala Arg Ala Leu Glu Val Ala Leu Ser Cys His Met Pro Leu
 65                  70                  75                  80

Asp Leu Val Ile Ile Met Leu Gly Thr Asn Asp Ile Lys Pro Val His
                 85                  90                  95

Gly Gly Arg Ala Glu Ala Ala Val Ser Gly Met Arg Arg Leu Ala Gln
            100                 105                 110

Ile Val Glu Thr Phe Ile Tyr Lys Pro Arg Glu Ala Val Pro Lys Leu
        115                 120                 125

Leu Ile Val Ala Pro Pro Cys Val Ala Gly Pro Gly Glu Pro
130                 135                 140

Ala Gly Gly Arg Asp Ile Glu Gln Ser Met Arg Leu Ala Pro Leu Tyr
145                 150                 155                 160

Arg Lys Leu Ala Ala Glu Leu Gly His His Phe Phe Asp Ala Gly Ser
                165                 170                 175

Val Ala Ser Ala Ser Pro Val Asp Gly Val His Leu Asp Ala Ser Ala
            180                 185                 190

Thr Ala Ala Ile Gly Arg Ala Leu Ala Ala Pro Val Arg Asp Ile Leu
        195                 200                 205

Gly

<210> SEQ ID NO 670
<211> LENGTH: 220
<212> TYPE: PRT
<213> ORGANISM: Agrobacterium tumefaciens

<400> SEQUENCE: 670

Met Val Lys Ser Val Leu Cys Phe Gly Asp Ser Leu Thr Trp Gly Ser
  1               5                  10                  15

Asn Ala Glu Thr Gly Gly Arg His Ser His Asp Asp Leu Trp Pro Ser
             20                  25                  30

Val Leu Gln Lys Ala Leu Gly Ser Asp Val His Val Ile Phe Thr His
         35                  40                  45

Glu Gly Leu Gly Gly Arg Thr Thr Ala Tyr Asp Asp His Thr Gly Asp
     50                  55                  60

Cys Asp Arg Asn Gly Ala Arg Leu Leu Pro Thr Leu Leu His Ser His
 65                  70                  75                  80

Ala Pro Leu Asp Met Val Ile Ile Met Leu Gly Thr Asn Asp Met Lys
                 85                  90                  95

Pro Ala Ile His Gly Ser Ala Ile Val Ala Phe Thr Met Lys Gly Val
            100                 105                 110

Glu Arg Leu Val Lys Leu Thr Arg Asn His Val Trp Gln Val Ser Asp
        115                 120                 125

Trp Glu Ala Pro Asp Val Leu Ile Val Ala Pro Pro Gln Leu Cys Glu
130                 135                 140

Thr Ala Asn Pro Phe Met Gly Ala Ile Phe Arg Asp Ala Ile Asp Glu
145                 150                 155                 160

Ser Ala Met Leu Ala Ser Val Phe Thr Tyr Arg Asp Leu Ala Asp Glu
                165                 170                 175

Leu Asp Cys Gly Phe Phe Asp Ala Gly Ser Val Ala Arg Thr Thr Pro
            180                 185                 190

Val Asp Gly Val His Leu Asp Ala Glu Asn Thr Arg Ala Ile Gly Arg
        195                 200                 205

Gly Leu Glu Pro Val Val Arg Met Met Leu Gly Leu
210                 215                 220
```

<210> SEQ ID NO 671
<211> LENGTH: 223
<212> TYPE: PRT
<213> ORGANISM: Mesorhizobium loti

<400> SEQUENCE: 671

Met Ala Gly Gly Thr Arg Leu Asp Glu Cys Thr Gly Glu Arg Met Lys
1               5                   10                  15

Thr Val Leu Cys Tyr Gly Asp Ser Leu Thr Trp Gly Tyr Asn Ala Glu
            20                  25                  30

Gly Gly Arg His Ala Leu Glu Asp Arg Trp Pro Ser Val Leu Gln Ala
        35                  40                  45

Ser Leu Gly Gly Val Gln Val Ile Ala Asp Gly Leu Asn Gly Arg
    50                  55                  60

Thr Thr Ala Phe Asp Asp His Leu Ala Gly Ala Asp Arg Asn Gly Ala
65                  70                  75                  80

Arg Leu Leu Pro Thr Ala Leu Thr Thr His Ala Pro Ile Asp Leu Ile
                85                  90                  95

Val Ile Met Leu Gly Ala Asn Asp Met Lys Pro Trp Ile His Gly Asn
            100                 105                 110

Pro Val Ala Ala Lys Gln Gly Ile Gln Arg Leu Ile Asp Ile Val Arg
        115                 120                 125

Gly His Asp Tyr Pro Phe Asp Trp Pro Ala Pro Gln Ile Leu Ile Val
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175

Ala Leu Ala Asp Glu Val Gly Cys Gly Phe Phe Asp Ala Gly Thr Val
            180                 185                 190

Ala Gln Thr Thr Pro Leu Asp Gly Val His Leu Asp Ala Glu Asn Thr
        195                 200                 205

Arg Asn Ile Gly Lys Ala Leu Thr Ser Val Val Arg Val Met Leu
    210                 215                 220

<210> SEQ ID NO 672
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 672

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
        35                  40                  45

Asn Gly Arg Thr Thr Val Phe Asp Asp Ala Ala Thr Phe Glu Ser Arg
    50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
                85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
            115                 120                 125

Leu Ile Ile Ser Pro Pro Ser Leu Val Pro Thr Gln Asp Glu Trp Phe
        130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Lys Ser
            195                 200                 205

Ile Leu Ala Leu
    210

<210> SEQ ID NO 673
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 673

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
        195                 200                 205

Val Lys Gln Val Leu Gly Leu
    210                 215

<210> SEQ ID NO 674
<211> LENGTH: 224

```
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (21)..(26)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (68)..(70)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (102)..(103)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (108)..(108)
```

```
<223> OTHER INFORMATION: Xaa can be any naturally occurring amino acid
<220> FEATURE:
<221> NAME/KEY: misc_feature
<222> LOCATION: (112)..(114)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (121)..(121)
<223> OTHER INFORMATION: Xaa can be any naturally occurring amino acid
<220> FEATURE:
<221> NAME/KEY: misc_feature
<222> LOCATION: (125)..(127)
<223> OTHER INFORMATION: Xaa can be any naturally occurring amino acid
<220> FEATURE:
<221> NAME/KEY: misc_feature
<222> LOCATION: (130)..(134)
<223> OTHER INFORMATION: Xaa can be any naturally occurring amino acid
<220> FEATURE:
<221> NAME/KEY: misc_feature
<222> LOCATION: (136)..(138)
<223> OTHER INFORMATION: Xaa can be any naturally occurring amino acid
<220> FEATURE:
<221> NAME/KEY: misc_feature
<222> LOCATION: (148)..(149)
<223> OTHER INFORMATION: Xaa can be any naturally occurring amino acid
<220> FEATURE:
<221> NAME/KEY: misc_feature
<222> LOCATION: (151)..(153)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (161)..(163)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (167)..(167)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (173)..(174)
<223> OTHER INFORMATION: Xaa can be any naturally occurring amino acid
<220> FEATURE:
<221> NAME/KEY: misc_feature
<222> LOCATION: (184)..(185)
<223> OTHER INFORMATION: Xaa can be any naturally occurring amino acid
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (213)..(213)
<223> OTHER INFORMATION: Xaa can be any naturally occurring amino acid
<220> FEATURE:
<221> NAME/KEY: misc_feature
<222> LOCATION: (217)..(217)
<223> OTHER INFORMATION: Xaa can be any naturally occurring amino acid
<220> FEATURE:
<221> NAME/KEY: misc_feature
```

<222> LOCATION: (221)..(221)
<223> OTHER INFORMATION: Xaa can be any naturally occurring amino acid

<400> SEQUENCE: 674

Met Lys Thr Val Leu Cys Phe Gly Asp Ser Leu Thr Trp Gly Tyr Xaa
1               5                   10                  15

Pro Xaa Xaa Gly Xaa Xaa Xaa Xaa Xaa Arg His Ala Xaa Glu Xaa
            20                  25                  30

Arg Trp Pro Xaa Val Leu Xaa Ala Xaa Leu Gly Gly Xaa Xaa Xaa Val
        35                  40                  45

Ile Glu Xaa Xaa Glu Gly Leu Xaa Gly Arg Thr Thr Ala His Asp Asp
    50                  55                  60

Xaa Xaa Ala Xaa Xaa Xaa Arg Asn Gly Ala Arg Xaa Leu Pro Thr Xaa
65                  70                  75                  80

Leu Xaa Ser His Ala Pro Leu Asp Leu Val Ile Met Leu Gly Thr
            85                  90                  95

Asn Asp Met Lys Pro Xaa Xaa His Xaa Xaa Pro Xaa Glu Ala Ala Xaa
                100                 105                 110

Xaa Xaa Gly Met Xaa Arg Leu Val Xaa Ile Val Arg Xaa Xaa Xaa Tyr
        115                 120                 125

Gly Xaa Xaa Xaa Xaa Pro Xaa Xaa Xaa Ile Leu Ile Val Ser Pro
    130                 135                 140

Pro Pro Leu Xaa Xaa Thr Xaa Xaa Xaa Asp Phe Xaa Ala Met Phe Gly
145                 150                 155                 160

Xaa Xaa Xaa Gly Xaa Glu Xaa Ser Lys Xaa Leu Ala Xaa Xaa Tyr Lys
                165                 170                 175

Ala Leu Ala Asp Glu Leu Lys Xaa Xaa Phe Phe Asp Ala Gly Thr Val
            180                 185                 190

Ala Xaa Thr Ser Pro Val Asp Gly Ile His Leu Asp Ala Glu Asn Thr
        195                 200                 205

Arg Xaa Ile Gly Xaa Ala Leu Ala Xaa Val Val Arg Xaa Leu Leu Gly
    210                 215                 220

<210> SEQ ID NO 675
<211> LENGTH: 202
<212> TYPE: PRT
<213> ORGANISM: Mycobacterium parafortuitum

<400> SEQUENCE: 675

Leu Pro Ser Gly Ile Leu Cys Phe Gly Asp Ser Leu Thr Trp Gly Trp
1               5                   10                  15

Ile Pro Val Glu Gly Val Pro Thr Glu Arg Phe Pro Arg Asp Val
            20                  25                  30

Arg Trp Thr Gly Val Leu Ala Asp Leu Leu Gly Asp Arg Tyr Glu Val
        35                  40                  45

Ile Glu Glu Gly Leu Ser Ala Arg Thr Thr Ala Asp Asp Pro Ala
    50                  55                  60

Asp Pro Arg Leu Asn Gly Ser Gln Tyr Leu Pro Ser Cys Leu Ala Ser
65                  70                  75                  80

His Leu Pro Leu Asp Leu Val Ile Leu Met Leu Gly Ile Asn Asp Thr
            85                  90                  95

Lys Ala Asn Phe Gly Arg Thr Pro Phe Asp Ile Ala Thr Gly Met Gly
                100                 105                 110

Val Leu Ala Thr Gln Val Leu Thr Ser Ala Gly Gly Val Gly Thr Ser
        115                 120                 125

```
Tyr Pro Ala Pro Gln Val Leu Ile Val Ala Pro Pro Leu Gly Glu
        130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Thr His Phe Thr Arg Gly Glu Thr Ile
            195                 200

<210> SEQ ID NO 676
<211> LENGTH: 216
<212> TYPE: PRT
<213> ORGANISM: Mycobacterium gilvum

<400> SEQUENCE: 676

Gly Gly Arg Cys Val Ala Ser Cys Glu Val Gly Ala Val Ala Lys Arg
1               5                   10                  15

Ile Leu Cys Phe Gly Asp Ser Leu Thr Trp Gly Trp Ile Pro Val Glu
            20                  25                  30

Glu Gly Val Pro Thr Gln Arg Phe Pro Lys Arg Val Arg Trp Thr Gly
        35                  40                  45

Val Leu Ala Asp Glu Leu Gly Ala Gly Tyr Glu Val Val Glu Glu Gly
    50                  55                  60

Leu Ser Ala Arg Thr Thr Thr Ala Asp Asp Pro Thr Asp Pro Arg Leu
65                  70                  75                  80

Asn Gly Ser Asp Tyr Leu Pro Ala Cys Leu Ala Ser His Leu Pro Leu
                85                  90                  95

Asp Leu Val Ile Leu Met Leu Gly Thr Asn Asp Thr Lys Ala Asn Leu
            100                 105                 110

Asn Arg Thr Pro Val Asp Ile Ala Ser Gly Met Gly Val Leu Ala Thr
        115                 120                 125

Gln Val Leu Thr Ser Ala Gly Val Gly Thr Ser Tyr Pro Ala Pro
    130                 135                 140

Gln Val Leu Ile Val Ala Pro Pro Leu Ala Glu Met Pro His Pro
145                 150                 155                 160

Trp Phe Glu Leu Val Phe Asp Gly Gly Arg Glu Lys Thr Ala Gln Leu
                165                 170                 175

Ala Arg Val Tyr Ser Ala Leu Ala Ser Phe Met Lys Val Pro Phe Phe
            180                 185                 190

Asp Ala Gly Ser Val Ile Ser Thr Asp Gly Val Asp Gly Thr His Phe
        195                 200                 205

Thr Arg Gly Glu Thr Ile Asp Arg
    210                 215

<210> SEQ ID NO 677
<211> LENGTH: 203
<212> TYPE: PRT
<213> ORGANISM: Mesorhizobium parafortuitum

<400> SEQUENCE: 677

Met Ala Lys Arg Ile Leu Cys Phe Gly Asp Ser Leu Thr Trp Gly Trp
1               5                   10                  15

Ile Pro Val Glu Glu Gly Val Pro Thr Glu Arg Phe Pro Arg Asp Val
            20                  25                  30
```

```
Arg Trp Thr Gly Val Leu Ala Asp Leu Leu Gly Asp Arg Tyr Glu Val
            35                  40                  45

Ile Glu Glu Gly Leu Ser Ala Arg Thr Thr Thr Ala Glu Asp Pro Ala
 50                      55                  60

Asp Pro Arg Leu Asn Gly Ser Gln Tyr Leu Pro Ser Cys Leu Ala Ser
 65                  70                  75                  80

His Leu Pro Leu Asp Leu Val Ile Leu Met Leu Gly Thr Asn Asp Thr
                85                  90                  95

Lys Ala Asn Phe Gly Arg Thr Pro Phe Asp Ile Ala Thr Gly Met Gly
                100                 105                 110

Val Leu Ala Thr Gln Val Leu Thr Ser Ala Gly Gly Val Gly Thr Ser
            115                 120                 125

Tyr Pro Ala Pro Gln Val Leu Ile Val Ala Pro Pro Leu Gly Glu
        130                 135                 140

Leu Pro His Pro Trp Phe Asp Leu Val Phe Ser Gly Gly Arg Glu Lys
145                 150                 155                 160

Thr Ala Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
                180                 185                 190

Gly Ile His Phe Thr Arg Gly Glu Gln Ser Thr
                195                 200

<210> SEQ ID NO 678
<211> LENGTH: 216
<212> TYPE: PRT
<213> ORGANISM: Mycobacterium smegmatis

<400> SEQUENCE: 678

Met Ala Lys Arg Ile Leu Cys Phe Gly Asp Ser Leu Thr Trp Gly Trp
 1               5                  10                  15

Val Pro Val Glu Asp Gly Ala Pro Thr Glu Arg Phe Ala Pro Asp Val
            20                  25                  30

Arg Trp Thr Gly Val Leu Ala Gln Gln Leu Gly Ala Asp Phe Glu Val
            35                  40                  45

Ile Glu Glu Gly Leu Ser Ala Arg Thr Thr Asn Ile Asp Asp Pro Thr
 50                      55                  60

Asp Pro Arg Leu Asn Gly Ala Ser Tyr Leu Pro Ser Cys Leu Ala Thr
 65                  70                  75                  80

His Leu Pro Leu Asp Leu Val Ile Ile Met Leu Gly Thr Asn Asp Thr
                85                  90                  95

Lys Ala Tyr Phe Arg Arg Thr Pro Leu Asp Ile Ala Leu Gly Met Ser
                100                 105                 110

Val Leu Val Thr Gln Val Leu Thr Ser Ala Gly Gly Val Gly Thr Thr
            115                 120                 125

Tyr Pro Ala Pro Lys Val Leu Val Val Ser Pro Pro Pro Leu Ala Pro
        130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
                180                 185                 190

Gly Ile His Phe Thr Glu Ala Asn Asn Arg Asp Leu Gly Val Ala Leu
                195                 200                 205
```

Ala Glu Gln Val Arg Ser Leu Leu
    210                 215

<210> SEQ ID NO 679
<211> LENGTH: 213
<212> TYPE: PRT
<213> ORGANISM: Sinorhizobium meliloti

<400> SEQUENCE: 679

Met Lys Thr Val Leu Cys Tyr Gly Asp Ser Leu Thr Trp Gly Tyr Asp
1               5                   10                  15

Ala Thr Gly Ser Gly Arg His Ala Leu Glu Asp Arg Trp Pro Ser Val
            20                  25                  30

Leu Gln Lys Ala Leu Gly Ser Asp Ala His Val Ile Ala Glu Gly Leu
        35                  40                  45

Asn Gly Arg Thr Thr Ala Tyr Asp Asp His Leu Ala Asp Cys Asp Arg
50                  55                  60

Asn Gly Ala Arg Val Leu Pro Thr Val Leu His Thr His Ala Pro Leu
65                  70                  75                  80

Asp Leu Ile Val Phe Met Leu Gly Ser Asn Asp Met Lys Pro Ile Ile
                85                  90                  95

His Gly Thr Ala Phe Gly Ala Val Lys Gly Ile Glu Arg Leu Val Asn
            100                 105                 110

Leu Val Arg Arg His Asp Trp Pro Thr Glu Thr Glu Gly Pro Glu
        115                 120                 125

Ile Leu Ile Val Ser Pro Pro Leu Cys Glu Thr Ala Asn Ser Ala
130                 135                 140

Phe Ala Ala Met Phe Ala Gly Gly Val Glu Gln Ser Ala Met Leu Ala
145                 150                 155                 160

Pro Leu Tyr Arg Asp Leu Ala Asp Glu Leu Asp Cys Gly Phe Phe Asp
                165                 170                 175

Gly Gly Ser Val Ala Arg Thr Thr Pro Ile Asp Gly Val His Leu Asp
            180                 185                 190

Ala Glu Asn Thr Arg Ala Val Gly Arg Gly Leu Glu Pro Val Val Arg
        195                 200                 205

Met Met Leu Gly Leu
    210

<210> SEQ ID NO 680
<211> LENGTH: 209
<212> TYPE: PRT
<213> ORGANISM: Agrobacterium tumefaciens

<400> SEQUENCE: 680

Met Lys Thr Val Leu Ala Phe Gly Asp Ser Leu Thr Trp Gly Ala Asp
1               5                   10                  15

Pro Ala Thr Gly Leu Arg His Pro Val Glu His Arg Trp Pro Asp Val
            20                  25                  30

Leu Glu Ala Glu Leu Ala Gly Lys Ala Lys Val His Pro Glu Gly Leu
        35                  40                  45

Gly Gly Arg Thr Thr Cys Tyr Asp Asp His Ala Gly Pro Ala Cys Arg
50                  55                  60

Asn Gly Ala Arg Ala Leu Glu Val Ala Leu Ser Cys His Met Pro Leu
65                  70                  75                  80

Asp Leu Val Ile Ile Met Leu Gly Thr Asn Asp Ile Lys Pro Val His
                85                  90                  95

```
Gly Gly Arg Ala Glu Ala Ala Val Ser Gly Met Arg Leu Ala Gln
            100                 105                 110

Ile Val Glu Thr Phe Ile Tyr Lys Pro Arg Glu Ala Val Pro Lys Leu
            115                 120                 125

Leu Ile Val Ala Pro Pro Cys Val Ala Gly Pro Gly Glu Pro
130                 135                 140

Ala Gly Gly Arg Asp Ile Glu Gln Ser Met Arg Leu Ala Pro Leu Tyr
145                 150                 155                 160

Arg Lys Leu Ala Ala Glu Leu Gly His His Phe Phe Asp Ala Gly Ser
                165                 170                 175

Val Ala Ser Ala Ser Pro Val Asp Gly Val His Leu Ala Ser Ala
            180                 185                 190

Thr Ala Ala Ile Gly Arg Ala Leu Ala Ala Pro Val Arg Asp Ile Leu
            195                 200                 205

Gly
```

<210> SEQ ID NO 681
<211> LENGTH: 220
<212> TYPE: PRT
<213> ORGANISM: Agrobacterium tumefaciens

<400> SEQUENCE: 681

```
Met Val Lys Ser Val Leu Cys Phe Gly Asp Ser Leu Thr Trp Gly Ser
1               5                   10                  15

Asn Ala Glu Thr Gly Gly Arg His Ser His Asp Asp Leu Trp Pro Ser
            20                  25                  30

Val Leu Gln Lys Ala Leu Gly Ser Asp Val His Val Ile Phe Thr His
        35                  40                  45

Glu Gly Leu Gly Gly Arg Thr Thr Ala Tyr Asp Asp His Thr Gly Asp
    50                  55                  60

Cys Asp Arg Asn Gly Ala Arg Leu Leu Pro Thr Leu Leu His Ser His
65                  70                  75                  80

Ala Pro Leu Asp Met Val Ile Ile Met Leu Gly Thr Asn Asp Met Lys
                85                  90                  95

Pro Ala Ile His Gly Ser Ala Ile Val Ala Phe Thr Met Lys Gly Val
            100                 105                 110

Glu Arg Leu Val Lys Leu Thr Arg Asn His Val Trp Gln Val Ser Asp
        115                 120                 125

Trp Glu Ala Pro Asp Val Leu Ile Val Ala Pro Pro Gln Leu Cys Glu
    130                 135                 140

Thr Ala Asn Pro Phe Met Gly Ala Ile Phe Arg Asp Ala Ile Asp Glu
145                 150                 155                 160

Ser Ala Met Leu Ala Ser Val Phe Thr Tyr Arg Asp Leu Ala Asp Glu
                165                 170                 175

Leu Asp Cys Gly Phe Phe Asp Ala Gly Ser Val Ala Arg Thr Thr Pro
            180                 185                 190

Val Asp Gly Val His Leu Asp Ala Glu Asn Thr Arg Ala Ile Gly Arg
        195                 200                 205

Gly Leu Glu Pro Val Val Arg Met Met Leu Gly Leu
    210                 215                 220
```

<210> SEQ ID NO 682
<211> LENGTH: 215
<212> TYPE: PRT
<213> ORGANISM: Artificial Sequence
<220> FEATURE:
<223> OTHER INFORMATION: M091_M4aE11 clone

<400> SEQUENCE: 682

Met Lys Thr Ile Leu Ala Tyr Gly Asp Ser Leu Thr Tyr Gly Ala Asn
1               5                   10                  15

Pro Ile Pro Gly Gly Pro Arg His Ala Tyr Glu Asp Arg Trp Pro Thr
            20                  25                  30

Ala Leu Glu Gln Gly Leu Gly Gly Lys Ala Arg Val Ile Ala Glu Gly
        35                  40                  45

Leu Gly Gly Arg Thr Thr Val His Asp Asp Trp Phe Ala Asn Ala Asp
    50                  55                  60

Arg Asn Gly Ala Arg Val Leu Pro Thr Leu Leu Glu Ser His Ser Pro
65                  70                  75                  80

Leu Asp Leu Ile Val Ile Met Leu Gly Thr Asn Asp Ile Lys Pro His
                85                  90                  95

His Gly Arg Thr Ala Gly Glu Ala Gly Arg Gly Met Ala Arg Leu Val
            100                 105                 110

Gln Ile Ile Arg Gly His Tyr Ala Gly Arg Met Gln Asp Glu Pro Gln
        115                 120                 125

Ile Ile Leu Val Ser Pro Pro Ile Ile Leu Gly Asp Trp Ala Asp
    130                 135                 140

Met Met Asp His Phe Gly Pro His Glu Ala Ile Ala Thr Ser Val Asp
145                 150                 155                 160

Phe Ala Arg Glu Tyr Lys Lys Arg Ala Asp Glu Gln Lys Val His Phe
                165                 170                 175

Phe Asp Ala Gly Thr Val Ala Thr Thr Ser Lys Ala Asp Gly Ile His
            180                 185                 190

Leu Asp Pro Ala Asn Thr Arg Ala Ile Gly Ala Gly Leu Val Pro Leu
        195                 200                 205

Val Lys Gln Val Leu Gly Leu
    210                 215

<210> SEQ ID NO 683
<211> LENGTH: 223
<212> TYPE: PRT
<213> ORGANISM: Mesorhizobium loti

<400> SEQUENCE: 683

Met Ala Gly Gly Thr Arg Leu Asp Glu Cys Thr Gly Glu Arg Met Lys
1               5                   10                  15

Thr Val Leu Cys Tyr Gly Asp Ser Leu Thr Trp Gly Tyr Asn Ala Glu
            20                  25                  30

Gly Gly Arg His Ala Leu Glu Asp Arg Trp Pro Ser Val Leu Gln Ala
        35                  40                  45

Ser Leu Gly Gly Val Gln Val Ile Ala Asp Gly Leu Asn Gly Arg
    50                  55                  60

Thr Thr Ala Phe Asp Asp His Leu Ala Gly Ala Asp Arg Asn Gly Ala
65                  70                  75                  80

Arg Leu Leu Pro Thr Ala Leu Thr Thr His Ala Pro Ile Asp Leu Ile
                85                  90                  95

Val Ile Met Leu Gly Ala Asn Asp Met Lys Pro Trp Ile His Gly Asn
            100                 105                 110

Pro Val Ala Ala Lys Gln Gly Ile Gln Arg Leu Ile Asp Ile Val Arg
        115                 120                 125

```
Gly His Asp Tyr Pro Phe Asp Trp Pro Ala Pro Gln Ile Leu Ile Val
    130                 135                 140

Ser Pro Pro Val Val Ser Arg Thr Glu Asn Ala Asp Phe Arg Glu Met
145                 150                 155                 160

Phe Ala Gly Gly Asp Glu Ala Ser Lys Gln Leu Ala Pro Gln Tyr Ala
                165                 170                 175

Ala Leu Ala Asp Glu Val Gly Cys Gly Phe Phe Asp Ala Gly Thr Val
                180                 185                 190

Ala Gln Thr Thr Pro Leu Asp Gly Val His Leu Asp Ala Glu Asn Thr
                195                 200                 205

Arg Asn Ile Gly Lys Ala Leu Thr Ser Val Val Arg Val Met Leu
    210                 215                 220
```

<210> SEQ ID NO 684
<211> LENGTH: 216
<212> TYPE: PRT
<213> ORGANISM: Prosthecobacter dejongeii

<400> SEQUENCE: 684

```
Met Lys Thr Ile Leu Cys Phe Gly Asp Ser Asn Thr Trp Gly Tyr Asp
1               5                   10                  15

Pro Ala Ser Met Thr Ala Pro Phe Pro Arg Arg His Gly Pro Glu Val
                20                  25                  30

Arg Trp Thr Gly Val Leu Ala Lys Ala Leu Gly Ala Gly Phe Arg Val
            35                  40                  45

Ile Glu Glu Gly Gln Asn Gly Arg Thr Thr Val His Glu Asp Pro Leu
        50                  55                  60

Asn Ile Cys Arg Lys Gly Lys Asp Tyr Leu Pro Ala Cys Leu Glu Ser
65              70                  75                  80

His Lys Pro Leu Asp Leu Val Ile Leu Met Leu Gly Thr Asn Asp Leu
                85                  90                  95

Lys Ser Thr Phe Asn Val Pro Pro Gly Glu Ile Ala Ala Gly Ala Gly
                100                 105                 110

Val Leu Gly Arg Met Ile Leu Ala Gly Asp Ala Gly Pro Glu Asn Arg
            115                 120                 125

Pro Pro Gln Leu Leu Leu Met Cys Pro Pro Lys Val Arg Asp Leu Ser
    130                 135                 140

Ala Met Pro Asp Leu Asp Ala Lys Ile Pro His Gly Ala Ala Arg Ser
145                 150                 155                 160

Ala Glu Phe Pro Arg His Tyr Lys Ala Gln Ala Val Ala Leu Lys Cys
                165                 170                 175

Glu Tyr Phe Asn Ser Gln Glu Ile Val Glu Thr Ser Pro Val Asp Gly
                180                 185                 190

Ile His Leu Glu Ala Ser Glu His Leu Lys Leu Gly Glu Ala Leu Ala
            195                 200                 205

Glu Lys Val Lys Val Leu Leu Gly
    210                 215
```

<210> SEQ ID NO 685
<211> LENGTH: 220
<212> TYPE: PRT
<213> ORGANISM: Sinorhizobium meliloti

<400> SEQUENCE: 685

```
Met Glu Glu Thr Val Ala Arg Thr Val Leu Cys Phe Gly Asp Ser Asn
1               5                   10                  15
```

Thr His Gly Gln Val Pro Gly Arg Gly Pro Leu Asp Arg Tyr Arg Arg
            20                  25                  30

Glu Gln Arg Trp Gly Gly Val Leu Gln Gly Leu Leu Gly Pro Asn Trp
            35                  40                  45

Gln Val Ile Glu Glu Gly Leu Ser Gly Arg Thr Thr Val His Asp Asp
50                  55                  60

Pro Ile Glu Gly Ser Leu Lys Asn Gly Arg Ile Tyr Leu Arg Pro Cys
65                  70                  75                  80

Leu Gln Ser His Ala Pro Leu Asp Leu Ile Ile Met Leu Gly Thr
                85                  90                  95

Asn Asp Leu Lys Arg Arg Phe Asn Met Pro Pro Ser Glu Val Ala Met
            100                 105                 110

Gly Ile Gly Cys Leu Val His Asp Ile Arg Glu Leu Ser Pro Gly Arg
            115                 120                 125

Thr Gly Asn Asp Pro Glu Ile Met Ile Val Ala Pro Pro Met Leu
130                 135                 140

Glu Asp Leu Lys Glu Trp Glu Ser Ile Phe Ser Gly Ala Gln Glu Lys
145                 150                 155                 160

Ser Arg Lys Leu Ala Leu Glu Phe Glu Ile Met Ala Asp Ser Leu Glu
            165                 170                 175

Ala His Phe Phe Asp Ala Gly Thr Val Cys Gln Cys Ser Pro Ala Asp
            180                 185                 190

Gly Phe His Ile Asp Glu Asp Ala His Arg Leu Leu Gly Glu Ala Leu
            195                 200                 205

Ala Gln Glu Val Leu Ala Ile Gly Trp Pro Asp Ala
210                 215                 220

<210> SEQ ID NO 686
<211> LENGTH: 212
<212> TYPE: PRT
<213> ORGANISM: Artificial Sequence
<220> FEATURE:
<223> OTHER INFORMATION: S261_M2aA12 clone

<400> SEQUENCE: 686

Met Lys Asn Ile Leu Ala Phe Gly Asp Ser Leu Thr Trp Gly Phe Val
1               5                   10                  15

Ala Gly Gln Asp Ala Arg His Pro Phe Glu Thr Arg Trp Pro Asn Ala
            20                  25                  30

Leu Ala Ala Gly Leu Gly Gly Lys Ala Arg Val Ile Glu Glu Gly Gln
            35                  40                  45

Asn Gly Arg Thr Thr Val Phe Asp Asp Ala Ala Thr Phe Glu Ser Arg
50                  55                  60

Asn Gly Ser Val Ala Leu Pro Leu Leu Leu Ile Ser His Gln Pro Leu
65                  70                  75                  80

Asp Leu Val Ile Ile Met Leu Gly Thr Asn Asp Ile Lys Phe Ala Ala
            85                  90                  95

Arg Cys Arg Ala Phe Asp Ala Ser Met Gly Met Glu Arg Leu Ile Gln
            100                 105                 110

Ile Val Arg Ser Ala Asn Tyr Met Lys Gly Tyr Lys Ile Pro Glu Ile
            115                 120                 125

Leu Ile Ile Ser Pro Pro Ser Leu Val Pro Thr Gln Asp Glu Trp Phe
130                 135                 140

Asn Asp Leu Trp Gly His Ala Ile Ala Glu Ser Lys Leu Phe Ala Lys
145                 150                 155                 160

His Tyr Lys Arg Val Ala Glu Glu Leu Lys Val His Phe Phe Asp Ala
                165                 170                 175

Gly Thr Val Ala Val Ala Asp Lys Thr Asp Gly Gly His Leu Asp Ala
            180                 185                 190

Val Asn Thr Lys Ala Ile Gly Val Ala Leu Val Pro Val Val Lys Ser
        195                 200                 205

Ile Leu Ala Leu
    210

<210> SEQ ID NO 687
<211> LENGTH: 229
<212> TYPE: PRT
<213> ORGANISM: Sinorhizobium meliloti

<400> SEQUENCE: 687

Met Thr Ile Asn Ser His Ser Trp Arg Thr Leu Met Val Glu Lys Arg
1               5                   10                  15

Ser Val Leu Cys Phe Gly Asp Ser Leu Thr Trp Gly Trp Ile Pro Val
            20                  25                  30

Lys Glu Ser Ser Pro Thr Leu Arg Tyr Pro Tyr Glu Gln Arg Trp Thr
        35                  40                  45

Gly Ala Met Ala Ala Arg Leu Gly Asp Gly Tyr His Ile Ile Glu Glu
    50                  55                  60

Gly Leu Ser Ala Arg Thr Thr Ser Leu Asp Asp Pro Asn Asp Ala Arg
65                  70                  75                  80

Leu Asn Gly Ser Thr Tyr Leu Pro Met Ala Leu Ala Ser His Leu Pro
                85                  90                  95

Leu Asp Leu Val Ile Ile Met Leu Gly Thr Asn Asp Thr Lys Ser Tyr
            100                 105                 110

Phe His Arg Thr Pro Tyr Glu Ile Ala Asn Gly Met Gly Lys Leu Val
        115                 120                 125

Gly Gln Val Leu Thr Cys Ala Gly Gly Val Gly Thr Pro Tyr Pro Ala
    130                 135                 140

Pro Lys Val Leu Val Val Ala Pro Pro Leu Ala Pro Met Pro Asp
145                 150                 155                 160

Pro Trp Phe Glu Gly Met Phe Gly Gly Gly Tyr Glu Lys Ser Lys Glu
                165                 170                 175

Leu Ser Gly Leu Tyr Lys Ala Leu Ala Asp Phe Met Lys Val Glu Phe
            180                 185                 190

Phe Ala Ala Gly Asp Cys Ile Ser Thr Asp Gly Ile Asp Gly Ile His
        195                 200                 205

Leu Ser Ala Glu Thr Asn Ile Arg Leu Gly His Ala Ile Ala Asp Lys
    210                 215                 220

Val Ala Ala Leu Phe
225

<210> SEQ ID NO 688
<211> LENGTH: 212
<212> TYPE: PRT
<213> ORGANISM: Mesorhizobium loti

<400> SEQUENCE: 688

Met Lys Thr Ile Leu Cys Tyr Gly Asp Ser Leu Thr Trp Gly Tyr Asp
1               5                   10                  15

Ala Val Gly Pro Ser Arg His Ala Tyr Glu Asp Arg Trp Pro Ser Val
            20                  25                  30

```
Leu Gln Gly Arg Leu Gly Ser Ser Ala Arg Val Ile Ala Glu Gly Leu
        35                  40                  45

Cys Gly Arg Thr Thr Ala Phe Asp Asp Trp Val Ala Gly Ala Asp Arg
 50                  55                  60

Asn Gly Ala Arg Ile Leu Pro Thr Leu Leu Ala Thr His Ser Pro Leu
 65                  70                  75                  80

Asp Leu Val Ile Val Met Leu Gly Thr Asn Asp Met Lys Ser Phe Val
                 85                  90                  95

Cys Gly Arg Ala Ile Gly Ala Lys Gln Gly Met Glu Arg Ile Val Gln
            100                 105                 110

Ile Ile Arg Gly Gln Pro Tyr Ser Phe Asn Tyr Lys Val Pro Ser Ile
        115                 120                 125

Leu Leu Val Ala Pro Pro Leu Cys Ala Thr Glu Asn Ser Asp Phe
130                 135                 140

Ala Glu Ile Phe Glu Gly Gly Met Ala Glu Ser Gln Lys Leu Ala Pro
145                 150                 155                 160

Leu Tyr Ala Ala Leu Ala Gln Gln Thr Gly Cys Ala Phe Phe Asp Ala
                165                 170                 175

Gly Thr Val Ala Arg Thr Thr Pro Leu Asp Gly Ile His Leu Asp Ala
            180                 185                 190

Glu Asn Thr Arg Ala Ile Gly Ala Gly Leu Glu Pro Val Val Arg Gln
        195                 200                 205

Ala Leu Gly Leu
    210
```

<210> SEQ ID NO 689
<211> LENGTH: 216
<212> TYPE: PRT
<213> ORGANISM: Burkholderia cepacia

<400> SEQUENCE: 689

```
Met Thr Met Thr Gln Lys Thr Val Leu Cys Tyr Gly Asp Ser Asn Thr
 1               5                  10                  15

His Gly Thr Arg Pro Met Thr His Ala Gly Gly Leu Gly Arg Phe Ala
                20                  25                  30

Arg Glu Glu Arg Trp Thr Gly Val Leu Ala Gln Thr Leu Gly Ala Ser
        35                  40                  45

Trp Arg Val Ile Glu Glu Gly Leu Pro Ala Arg Thr Thr Val His Asp
 50                  55                  60

Asp Pro Ile Glu Gly Arg His Lys Asn Gly Leu Ser Tyr Leu Arg Ala
 65                  70                  75                  80

Cys Val Glu Ser His Leu Pro Val Asp Val Val Leu Met Leu Gly
                 85                  90                  95

Thr Asn Asp Leu Lys Thr Arg Phe Ser Val Thr Pro Ala Asp Ile Ala
            100                 105                 110

Thr Ser Val Gly Val Leu Leu Ala Lys Ile Ala Ala Cys Gly Ala Gly
        115                 120                 125

Pro Ser Gly Ala Ser Pro Lys Leu Val Leu Met Ala Pro Ala Pro Ile
130                 135                 140

Val Glu Val Gly Phe Leu Gly Glu Ile Phe Ala Gly Ala Ala Lys
145                 150                 155                 160

Ser Arg Gln Leu Ala Lys Arg Tyr Glu Gln Val Ala Ser Asp Ala Gly
                165                 170                 175

Ala His Phe Leu Asp Ala Gly Ala Ile Val Glu Val Ser Pro Val Asp
            180                 185                 190
```

Gly Val His Phe Ala Ala Asp Gln His Arg Val Leu Gly Gln Arg Val
            195                 200                 205

Ala Ala Leu Leu Gln Gln Ile Ala
    210                 215

<210> SEQ ID NO 690
<211> LENGTH: 222
<212> TYPE: PRT
<213> ORGANISM: Agrobacterium tumefaciens

<400> SEQUENCE: 690

Met Ile Cys His Lys Gly Gly Glu Met Arg Ser Val Leu Cys Tyr
1               5                   10                  15

Gly Asp Ser Asn Thr His Gly Gln Ile Pro Gly Gly Ser Pro Leu Asp
            20                  25                  30

Arg Tyr Gly Pro Asn Glu Arg Trp Pro Gly Val Leu Arg Arg Glu Leu
        35                  40                  45

Gly Ser Gln Trp Tyr Val Ile Glu Glu Gly Leu Ser Gly Arg Thr Thr
    50                  55                  60

Val Arg Asp Asp Pro Ile Glu Gly Thr Met Lys Asn Gly Arg Thr Tyr
65                  70                  75                  80

Leu Arg Pro Cys Leu Met Ser His Ala Ile Leu Asp Leu Val Ile Ile
                85                  90                  95

Met Leu Gly Thr Asn Asp Leu Lys Ala Arg Phe Gly Gln Pro Pro Ser
            100                 105                 110

Glu Val Ala Met Gly Ile Gly Cys Leu Val Tyr Asp Ile Arg Glu Leu
        115                 120                 125

Ala Pro Gly Pro Gly Gly Lys Pro Pro Glu Ile Met Val Val Ala Pro
    130                 135                 140

Pro Pro Met Leu Asp Asp Ile Lys Glu Trp Glu Pro Ile Phe Ser Gly
145                 150                 155                 160

Ala Gln Glu Lys Ser Arg Arg Leu Ala Leu Glu Phe Glu Ile Ile Ala
                165                 170                 175

Asp Ser Leu Glu Val His Phe Phe Asp Ala Ala Thr Val Ala Ser Cys
            180                 185                 190

Asp Pro Cys Asp Gly Phe His Ile Asn Arg Glu Ala His Glu Ala Leu
        195                 200                 205

Gly Thr Ala Leu Ala Arg Glu Val Glu Ala Ile Gly Trp Arg
    210                 215                 220

<210> SEQ ID NO 691
<211> LENGTH: 227
<212> TYPE: PRT
<213> ORGANISM: Agrobacterium tumefaciens

<400> SEQUENCE: 691

Met Ala Glu Ser Arg Ser Ile Leu Cys Phe Gly Asp Ser Leu Thr Trp
1               5                   10                  15

Gly Trp Ile Pro Val Pro Glu Ser Ser Pro Thr Leu Arg Tyr Pro Phe
            20                  25                  30

Glu Gln Arg Trp Thr Gly Ala Met Ala Ala Ala Leu Gly Asp Gly Tyr
        35                  40                  45

Ser Ile Ile Glu Glu Gly Leu Ser Ala Arg Thr Thr Ser Val Glu Asp
    50                  55                  60

Pro Asn Asp Pro Arg Leu Asn Gly Ser Ala Tyr Leu Pro Met Ala Leu
65                  70                  75                  80

```
Ala Ser His Leu Pro Leu Asp Leu Val Ile Ile Leu Gly Thr Asn
            85                  90                  95

Asp Thr Lys Ser Tyr Phe Arg Arg Thr Pro Tyr Glu Ile Ala Asn Gly
            100                 105                 110

Met Gly Lys Leu Ala Gly Gln Val Leu Thr Ser Ala Gly Gly Ile Gly
            115                 120                 125

Thr Pro Tyr Pro Ala Pro Lys Leu Leu Ile Val Ser Pro Pro Leu
130                 135                 140

Ala Pro Met Pro Asp Pro Trp Phe Glu Gly Met Phe Gly Gly Tyr
145                 150                 155                 160

Glu Lys Ser Leu Glu Leu Ala Lys Gln Tyr Lys Ala Leu Ala Asn Phe
            165                 170                 175

Leu Lys Val Asp Phe Leu Asp Ala Gly Glu Phe Val Lys Thr Asp Gly
            180                 185                 190

Cys Asp Gly Ile His Phe Ser Ala Gly Thr Asn Ile Thr Leu Gly His
            195                 200                 205

Ala Ile Ala Ala Lys Val Glu Ala Ile Phe Ser Gln Glu Ala Lys Asn
    210                 215                 220

Ala Ala Ala
225

<210> SEQ ID NO 692
<211> LENGTH: 213
<212> TYPE: PRT
<213> ORGANISM: Ralstonia solanacearum

<400> SEQUENCE: 692

Met Gln Gln Ile Leu Leu Tyr Ser Asp Ser Leu Ser Trp Gly Ile Ile
1               5                   10                  15

Pro Gly Thr Arg Arg Leu Pro Phe Ala Ala Arg Trp Ala Gly Val
            20                  25                  30

Met Glu His Ala Leu Gln Ala Gln Gly His Ala Val Arg Ile Val Glu
            35                  40                  45

Asp Cys Leu Asn Gly Arg Thr Thr Val Leu Asp Asp Pro Ala Arg Pro
50                  55                  60

Gly Arg Asn Gly Leu Gln Gly Leu Ala Gln Arg Ile Glu Ala His Ala
65                  70                  75                  80

Pro Leu Ala Leu Val Ile Leu Met Leu Gly Thr Asn Asp Phe Gln Ala
            85                  90                  95

Ile Phe Arg His Thr Ala Gln Asp Ala Ala Gln Gly Val Ala Gln Leu
            100                 105                 110

Val Arg Ala Ile Arg Gln Ala Pro Ile Glu Pro Gly Met Pro Val Pro
            115                 120                 125

Pro Val Leu Ile Val Val Pro Pro Ala Ile Thr Ala Pro Gly Ala
130                 135                 140

Met Ala Asp Lys Phe Ala Asp Ala Gln Pro Lys Cys Ala Gly Leu Ala
145                 150                 155                 160

Gln Ala Tyr Arg Ala Thr Ala Gln Thr Leu Gly Cys His Val Phe Asp
            165                 170                 175

Ala Asn Ser Val Thr Pro Ala Ser Arg Val Asp Gly Ile His Leu Asp
            180                 185                 190

Ala Asp Gln His Ala Gln Leu Gly Arg Ala Met Ala Gln Val Val Gly
            195                 200                 205

Thr Leu Leu Ala Gln
```

```
<210> SEQ ID NO 693
<211> LENGTH: 225
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (51)..(53)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(71)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
```

-continued

```
<222> LOCATION: (103)..(103)
<223> OTHER INFORMATION: Xaa can be any naturally occurring amino acid
<220> FEATURE:
<221> NAME/KEY: misc_feature
<222> LOCATION: (105)..(106)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (111)..(112)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
<221> NAME/KEY: misc_feature
<222> LOCATION: (122)..(123)
<223> OTHER INFORMATION: Xaa can be any naturally occurring amino acid
<220> FEATURE:
<221> NAME/KEY: misc_feature
<222> LOCATION: (126)..(128)
<223> OTHER INFORMATION: Xaa can be any naturally occurring amino acid
<220> FEATURE:
<221> NAME/KEY: misc_feature
<222> LOCATION: (130)..(132)
<223> OTHER INFORMATION: Xaa can be any naturally occurring amino acid
<220> FEATURE:
<221> NAME/KEY: misc_feature
<222> LOCATION: (134)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (152)..(155)
<223> OTHER INFORMATION: Xaa can be any naturally occurring amino acid
<220> FEATURE:
<221> NAME/KEY: misc_feature
<222> LOCATION: (158)..(161)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (175)..(176)
<223> OTHER INFORMATION: Xaa can be any naturally occurring amino acid
<220> FEATURE:
<221> NAME/KEY: misc_feature
<222> LOCATION: (182)..(183)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
```

<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (219)..(220)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid

<400> SEQUENCE: 693

```
Met Lys Thr Ile Leu Cys Phe Gly Asp Ser Leu Thr Trp Gly Trp Ile
1               5                   10                  15

Pro Val Xaa Xaa Xaa Xaa Pro Xaa Xaa Arg Arg Xaa Xaa Xaa Glu Xaa
            20                  25                  30

Arg Trp Xaa Gly Val Leu Ala Xaa Xaa Leu Gly Ala Xaa Tyr Xaa Val
        35                  40                  45

Ile Glu Xaa Xaa Xaa Glu Gly Leu Xaa Gly Arg Thr Thr Xaa Xaa Asp
    50                  55                  60

Asp Pro Xaa Asp Xaa Xaa Xaa Arg Asn Gly Ala Xaa Tyr Leu Pro Xaa
65                  70                  75                  80

Xaa Leu Xaa Ser His Xaa Pro Leu Asp Leu Val Ile Ile Met Leu Gly
                85                  90                  95

Thr Asn Asp Leu Lys Ala Xaa Phe Xaa Xaa Thr Pro Xaa Asp Xaa Xaa
            100                 105                 110

Ile Ala Xaa Gly Met Gly Arg Leu Val Xaa Xaa Val Arg Xaa Xaa Xaa
        115                 120                 125

Gly Xaa Xaa Xaa Gly Xaa Xaa Tyr Xaa Ala Pro Xaa Ile Leu Ile Val
    130                 135                 140

Ala Pro Pro Pro Leu Xaa Glu Xaa Xaa Xaa Xaa Trp Phe Xaa Xaa Xaa
145                 150                 155                 160

Xaa Ile Phe Gly Gly Ala Xaa Xaa Lys Ser Xaa Xaa Leu Ala Xaa Xaa
                165                 170                 175

Tyr Lys Ala Leu Ala Xaa Xaa Leu Lys Val Xaa Phe Phe Asp Ala Gly
            180                 185                 190

Ser Val Xaa Xaa Thr Ser Pro Val Asp Gly Ile His Leu Asp Ala Glu
        195                 200                 205

Asn Thr Arg Xaa Leu Gly Xaa Ala Leu Ala Xaa Xaa Val Arg Xaa Ile
    210                 215                 220

Leu
225
```

<210> SEQ ID NO 694
<211> LENGTH: 215
<212> TYPE: PRT
<213> ORGANISM: Artificial Sequence
<220> FEATURE:
<223> OTHER INFORMATION: consensus

<400> SEQUENCE: 694

```
Lys Thr Ile Leu Cys Phe Gly Asp Ser Leu Thr Trp Gly Trp Ile Pro
1               5                   10                  15

Val Glu Asp Gly Ala Pro Thr Glu Arg Arg Ala Pro Glu Val Arg Trp
            20                  25                  30
```

Thr Gly Val Leu Ala Gln Gln Leu Gly Ala Asp Tyr Glu Val Ile Glu
    35                  40                  45

Glu Gly Leu Ser Gly Arg Thr Thr Asn Ile Asp Asp Pro Thr Asp Pro
 50                  55                  60

Arg Leu Arg Asn Gly Ala Ser Tyr Leu Pro Ser Cys Leu Ala Ser His
 65                  70                  75                  80

Leu Pro Leu Asp Leu Val Ile Ile Met Leu Gly Thr Asn Asp Leu Lys
                 85                  90                  95

Ala Tyr Phe Arg Arg Thr Pro Leu Asp Ile Ala Leu Gly Met Gly Arg
            100                 105                 110

Leu Val Thr Gln Val Arg Thr Ser Ala Gly Val Gly Thr Thr Tyr
            115                 120                 125

Pro Ala Pro Lys Ile Leu Ile Val Ala Pro Pro Leu Ala Glu Met
        130                 135                 140

Pro His Pro Trp Phe Gln Leu Ile Phe Gly Gly Ala Glu Gln Lys Ser
145                 150                 155                 160

Thr Glu Leu Ala Arg Val Tyr Lys Ala Leu Ala Ser Phe Leu Lys Val
                165                 170                 175

Pro Phe Phe Asp Ala Gly Ser Val Ile Ser Thr Ser Pro Val Asp Gly
            180                 185                 190

Ile His Leu Asp Ala Glu Asn Thr Arg Asp Leu Gly Val Ala Leu Ala
        195                 200                 205

Glu Gln Val Arg Ser Ile Leu
    210                 215

<210> SEQ ID NO 695
<211> LENGTH: 216
<212> TYPE: PRT
<213> ORGANISM: Mycobacterium smegmatis

<400> SEQUENCE: 695

Met Ala Lys Arg Ile Leu Cys Phe Gly Asp Ser Leu Thr Trp Gly Trp
 1               5                  10                  15

Val Pro Val Glu Asp Gly Ala Pro Thr Glu Arg Phe Ala Pro Asp Val
             20                  25                  30

Arg Trp Thr Gly Val Leu Ala Gln Gln Leu Gly Ala Asp Phe Glu Val
         35                  40                  45

Ile Glu Glu Gly Leu Ser Ala Arg Thr Thr Asn Ile Asp Asp Pro Thr
     50                  55                  60

Asp Pro Arg Leu Asn Gly Ala Ser Tyr Leu Pro Ser Cys Leu Ala Thr
 65                  70                  75                  80

His Leu Pro Leu Asp Leu Val Ile Ile Met Leu Gly Thr Asn Asp Thr
                 85                  90                  95

Lys Ala Tyr Phe Arg Arg Thr Pro Leu Asp Ile Ala Leu Gly Met Ser
            100                 105                 110

Val Leu Val Thr Gln Val Leu Thr Ser Ala Gly Gly Val Gly Thr Thr
            115                 120                 125

Tyr Pro Ala Pro Lys Val Leu Val Ser Pro Pro Leu Ala Pro
        130                 135                 140

Met Pro His Pro Trp Phe Gln Leu Ile Phe Glu Gly Gly Glu Gln Lys
145                 150                 155                 160

Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
            180                 185                 190

Gly Ile His Phe Thr Glu Ala Asn Asn Arg Asp Leu Gly Val Ala Leu
        195                 200                 205

Ala Glu Gln Val Arg Ser Leu Leu
    210                 215

<210> SEQ ID NO 696
<211> LENGTH: 217
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (113)..(114)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (190)..(191)
<223> OTHER INFORMATION: Xaa can be any naturally occurring amino acid
<220> FEATURE:
<221> NAME/KEY: misc_feature
<222> LOCATION: (197)..(200)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid

<400> SEQUENCE: 696

Xaa Xaa Lys Xaa Ile Leu Cys Phe Gly Asp Ser Leu Thr Trp Gly Trp
1               5                   10                  15

Ile Pro Val Glu Asp Gly Ala Pro Thr Glu Arg Xaa Ala Pro Asp Val
            20                  25                  30

Arg Trp Thr Gly Val Leu Ala Gln Gln Leu Gly Ala Asp Phe Glu Val
        35                  40                  45

Ile Glu Glu Gly Leu Ser Ala Arg Thr Thr Asn Ile Asp Asp Pro Thr

```
                50                  55                  60
Asp Pro Arg Leu Xaa Xaa Gly Ala Ser Tyr Leu Pro Ser Cys Leu Ala
 65                  70                  75                  80

Ser His Leu Pro Leu Asp Leu Val Ile Ile Met Leu Gly Thr Asn Asp
                 85                  90                  95

Xaa Lys Ala Tyr Phe Arg Arg Thr Pro Leu Asp Ile Ala Leu Gly Met
                100                 105                 110

Xaa Xaa Leu Val Thr Gln Val Xaa Thr Ser Ala Gly Gly Val Gly Thr
            115                 120                 125

Thr Tyr Pro Ala Pro Lys Ile Leu Ile Val Ala Pro Pro Pro Leu Ala
            130                 135                 140

Xaa Met Pro His Pro Trp Phe Gln Leu Ile Phe Xaa Gly Ala Glu Gln
145                 150                 155                 160

Lys Ser Thr Glu Leu Ala Arg Val Tyr Xaa Ala Leu Ala Ser Phe Leu
                165                 170                 175

Lys Val Pro Phe Phe Asp Ala Gly Ser Val Ile Ser Thr Xaa Xaa Val
                180                 185                 190

Asp Gly Ile His Xaa Xaa Xaa Xaa Asn Xaa Arg Asp Leu Gly Val Ala
            195                 200                 205

Leu Ala Glu Gln Val Arg Ser Ile Leu
            210                 215

<210> SEQ ID NO 697
<211> LENGTH: 214
<212> TYPE: PRT
<213> ORGANISM: Rhodopirellula baltica

<400> SEQUENCE: 697

Met His Ser Ile Leu Ile Tyr Gly Asp Ser Leu Ser Trp Gly Ile Ile
 1               5                  10                  15

Pro Gly Thr Arg Arg Phe Ala Phe His Gln Arg Trp Pro Gly Val
                20                  25                  30

Met Glu Ile Glu Leu Arg Gln Thr Gly Ile Asp Ala Arg Val Ile Glu
                35                  40                  45

Asp Cys Leu Asn Gly Arg Arg Thr Val Leu Glu Asp Pro Ile Lys Pro
 50                  55                  60

Gly Arg Asn Gly Leu Asp Gly Leu Gln Gln Arg Ile Glu Ile Asn Ser
 65                  70                  75                  80

Pro Leu Ser Leu Val Val Leu Phe Leu Gly Thr Asn Asp Phe Gln Ser
                 85                  90                  95

Val His Glu Phe His Ala Glu Gln Ser Ala Gln Gly Leu Ala Leu Leu
                100                 105                 110

Val Asp Ala Ile Arg Arg Ser Pro Phe Glu Pro Gly Met Pro Thr Pro
            115                 120                 125

Lys Ile Leu Leu Val Ala Pro Pro Thr Val His Pro Lys Leu Asp
            130                 135                 140

Met Ala Ala Lys Phe Gln Asn Ala Glu Thr Lys Ser Thr Gly Leu Ala
145                 150                 155                 160

Asp Ala Ile Arg Lys Val Ser Thr Glu His Ser Cys Glu Phe Phe Asp
                165                 170                 175

Ala Ala Thr Val Thr Thr Thr Ser Val Val Asp Gly Val His Leu Asp
            180                 185                 190

Gln Glu Gln His Gln Ala Leu Gly Thr Ala Leu Ala Ser Thr Ile Ala
            195                 200                 205
```

Glu Ile Leu Ala Asp Cys
    210

<210> SEQ ID NO 698
<211> LENGTH: 222
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(26)
<223> OTHER INFORMATION: Xaa can be any naturally occurring amino acid
<220> FEATURE:
<221> NAME/KEY: misc_feature
<222> LOCATION: (30)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (67)..(68)
<223> OTHER INFORMATION: Xaa can be any naturally occurring amino acid
<220> FEATURE:
<221> NAME/KEY: misc_feature
<222> LOCATION: (70)..(71)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:

```
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (82)..(85)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (102)..(110)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (119)..(132)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (146)..(148)
<223> OTHER INFORMATION: Xaa can be any naturally occurring amino acid
<220> FEATURE:
<221> NAME/KEY: misc_feature
<222> LOCATION: (150)..(156)
<223> OTHER INFORMATION: Xaa can be any naturally occurring amino acid
<220> FEATURE:
<221> NAME/KEY: misc_feature
<222> LOCATION: (158)..(159)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (169)..(173)
<223> OTHER INFORMATION: Xaa can be any naturally occurring amino acid
<220> FEATURE:
<221> NAME/KEY: misc_feature
<222> LOCATION: (177)..(181)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid
<220> FEATURE:
<221> NAME/KEY: misc_feature
<222> LOCATION: (192)..(193)
<223> OTHER INFORMATION: Xaa can be any naturally occurring amino acid
<220> FEATURE:
<221> NAME/KEY: misc_feature
<222> LOCATION: (199)..(202)
<223> OTHER INFORMATION: Xaa can be any naturally occurring amino acid
```

```
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (209)..(209)
<223> OTHER INFORMATION: Xaa can be any naturally occurring amino acid
<220> FEATURE:
<221> NAME/KEY: misc_feature
<222> LOCATION: (213)..(214)
<223> OTHER INFORMATION: Xaa can be any naturally occurring amino acid
<220> FEATURE:
<221> NAME/KEY: misc_feature
<222> LOCATION: (216)..(217)
<223> OTHER INFORMATION: Xaa can be any naturally occurring amino acid
<220> FEATURE:
<221> NAME/KEY: misc_feature
<222> LOCATION: (220)..(222)
<223> OTHER INFORMATION: Xaa can be any naturally occurring amino acid

<400> SEQUENCE: 698

Xaa Xaa Xaa Xaa Ile Leu Xaa Phe Gly Asp Ser Leu Ser Trp Gly Xaa
 1               5                  10                  15

Ile Pro Xaa Xaa Xaa Xaa Xaa Xaa Xaa Arg Phe Ala Xaa Xaa Xaa
             20                  25                  30

Arg Trp Xaa Gly Val Leu Xaa Xaa Xaa Xaa Gln Xaa Gly Xaa Asp
         35                  40                  45

Xaa Xaa Val Ile Glu Asp Xaa Leu Xaa Ala Arg Xaa Thr Xaa Ile Asp
     50                  55                  60

Asp Pro Xaa Xaa Pro Xaa Xaa Asn Gly Xaa Xaa Xaa Leu Xaa Xaa Xaa
65                  70                  75                  80

Ile Xaa Xaa Xaa Xaa Pro Leu Xaa Leu Val Ile Ile Xaa Leu Gly Thr
                 85                  90                  95

Asn Asp Xaa Xaa Ala Xaa Xaa Xaa Xaa Xaa Xaa Xaa Xaa Ala Xaa
             100                 105                 110

Gly Leu Ala Leu Leu Val Xaa Xaa Xaa Xaa Xaa Xaa Xaa Xaa Xaa
         115                 120                 125

Xaa Xaa Xaa Xaa Pro Xaa Pro Lys Ile Leu Leu Val Ala Pro Pro Xaa
130                 135                 140

Leu Xaa Xaa Xaa Pro Xaa Xaa Xaa Xaa Xaa Xaa Phe Xaa Xaa Ala
145                 150                 155                 160

Glu Xaa Lys Ser Thr Xaa Leu Ala Xaa Xaa Xaa Xaa Leu Ala Ser
             165                 170                 175

Xaa Xaa Xaa Xaa Xaa Phe Phe Asp Ala Ala Ser Val Xaa Ser Thr Xaa
             180                 185                 190

Xaa Val Asp Gly Ile His Xaa Xaa Xaa Xaa Asn Xaa Xaa Xaa Leu Gly
         195                 200                 205

Xaa Ala Leu Ala Xaa Xaa Ile Xaa Xaa Ile Leu Xaa Xaa Xaa
     210                 215                 220

<210> SEQ ID NO 699
<211> LENGTH: 230
<212> TYPE: PRT
<213> ORGANISM: Ralstonia eutropha

<400> SEQUENCE: 699

Met Pro Leu Thr Ala Pro Ser Glu Val Asp Pro Leu Gln Ile Leu Val
 1               5                  10                  15

Tyr Ala Asp Ser Leu Ser Trp Gly Ile Val Pro Gly Thr Arg Arg Arg
             20                  25                  30
```

```
Leu Pro Phe Pro Val Arg Trp Pro Gly Arg Leu Glu Leu Gly Leu Asn
         35                  40                  45

Ala Asp Gly Gly Ala Pro Val Arg Ile Ile Glu Asp Cys Leu Asn Gly
 50                  55                  60

Arg Arg Thr Val Trp Asp Asp Pro Phe Lys Pro Gly Arg Asn Gly Leu
 65                  70                  75                  80

Gln Gly Leu Ala Gln Arg Ile Glu Ile His Ser Pro Val Ala Leu Val
                 85                  90                  95

Val Leu Met Leu Gly Asn Asn Asp Phe Gln Ser Met His Pro His Asn
            100                 105                 110

Ala Trp His Ala Ala Gln Gly Val Gly Ala Leu Val His Ala Ile Arg
        115                 120                 125

Thr Ala Pro Ile Glu Pro Gly Met Pro Val Pro Pro Ile Leu Val Val
130                 135                 140

Val Pro Pro Pro Ile Arg Thr Pro Cys Gly Pro Leu Ala Pro Lys Phe
145                 150                 155                 160

Ala Gly Gly Glu His Lys Trp Ala Gly Leu Pro Glu Ala Leu Arg Glu
                165                 170                 175

Leu Cys Ala Thr Val Asp Cys Ser Leu Phe Asp Ala Gly Thr Val Ile
            180                 185                 190

Gln Ser Ser Ala Val Asp Gly Val His Leu Asp Ala Asp Ala His Val
        195                 200                 205

Ala Leu Gly Asp Ala Leu Gln Pro Val Val Arg Ala Leu Leu Ala Glu
    210                 215                 220

Ser Ser Gly His Pro Ser
225                 230

<210> SEQ ID NO 700
<211> LENGTH: 237
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: 3, 12, 13, 15-28, 31-37, 39-43, 46, 50, 55-56, 59-65,
      67-69, 71-76, 78, 83, 84, 88, 91-125, 127-132, 135-165, 167-185,
      188
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid
<220> FEATURE:
<221> NAME/KEY: misc_feature
<222> LOCATION: (37)..(40)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(55)
```

```
<223> OTHER INFORMATION: Xaa can be any naturally occurring amino acid
<220> FEATURE:
<221> NAME/KEY: misc_feature
<222> LOCATION: (58)..(60)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(73)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(81)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(90)
<223> OTHER INFORMATION: Xaa can be any naturally occurring amino acid
<220> FEATURE:
<221> NAME/KEY: misc_feature
<222> LOCATION: (92)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
<221> NAME/KEY: misc_feature
<222> LOCATION: (112)..(120)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
```

```
<222> LOCATION: (139)..(142)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (151)..(151)
<223> OTHER INFORMATION: Xaa can be any naturally occurring amino acid
<220> FEATURE:
<221> NAME/KEY: misc_feature
<222> LOCATION: (156)..(158)
<223> OTHER INFORMATION: Xaa can be any naturally occurring amino acid
<220> FEATURE:
<221> NAME/KEY: misc_feature
<222> LOCATION: (160)..(166)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(176)
<223> OTHER INFORMATION: Xaa can be any naturally occurring amino acid
<220> FEATURE:
<221> NAME/KEY: misc_feature
<222> LOCATION: (178)..(183)
<223> OTHER INFORMATION: Xaa can be any naturally occurring amino acid
<220> FEATURE:
<221> NAME/KEY: misc_feature
<222> LOCATION: (185)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (189)..(192)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (209)..(216)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (222)..(224)
<223> OTHER INFORMATION: Xaa can be any naturally occurring amino acid
<220> FEATURE:
<221> NAME/KEY: misc_feature
<222> LOCATION: (230)..(237)
<223> OTHER INFORMATION: Xaa can be any naturally occurring amino acid

<400> SEQUENCE: 700

Xaa Xaa Xaa Xaa Xaa Xaa Xaa Xaa Xaa Xaa Xaa Xaa Xaa Ile Leu Xaa
1               5                   10                  15
```

```
Phe Ala Asp Ser Leu Ser Trp Gly Xaa Val Pro Xaa Xaa Xaa Xaa Xaa
            20                  25                  30

Xaa Xaa Xaa Arg Xaa Xaa Xaa Val Arg Trp Xaa Gly Xaa Leu Xaa
        35                  40                  45

Xaa Xaa Xaa Xaa Xaa Xaa Xaa Gly Ala Xaa Xaa Xaa Ile Ile Glu Asp
    50                  55                  60

Xaa Leu Xaa Ala Arg Xaa Thr Xaa Xaa Asp Asp Pro Xaa Xaa Pro Xaa
65                  70                  75                  80

Xaa Asn Gly Xaa Xaa Xaa Leu Xaa Xaa Xaa Ile Xaa Xaa His Xaa Pro
                85                  90                  95

Leu Xaa Leu Val Ile Ile Met Leu Gly Xaa Asn Asp Xaa Xaa Ala Xaa
        100                 105                 110

Xaa Xaa Xaa Xaa Xaa Xaa Xaa Ala Xaa Gly Met Xaa Xaa Leu Val
        115                 120                 125

Xaa Xaa Xaa Xaa Xaa Xaa Xaa Ala Xaa Ile Xaa Xaa Xaa Xaa Pro Xaa
    130                 135                 140

Pro Xaa Ile Leu Val Val Xaa Pro Pro Ile Xaa Xaa Xaa Pro Xaa
145                 150                 155                 160

Xaa Xaa Xaa Xaa Xaa Xaa Phe Xaa Gly Gly Glu Xaa Lys Xaa Xaa Xaa
                165                 170                 175

Leu Xaa Xaa Xaa Xaa Xaa Leu Xaa Ala Xaa Met Xaa Xaa Xaa Xaa
        180                 185                 190

Phe Asp Ala Gly Ser Val Ile Xaa Ser Xaa Ala Val Asp Gly Ile His
        195                 200                 205

Xaa Xaa Xaa Xaa Xaa Xaa Xaa Leu Gly Xaa Ala Leu Xaa Xaa Xaa
    210                 215                 220

Val Arg Ala Leu Leu Xaa Xaa Xaa Xaa Xaa Xaa Xaa Xaa
225                 230                 235

<210> SEQ ID NO 701
<211> LENGTH: 189
<212> TYPE: PRT
<213> ORGANISM: Artificial Sequence
<220> FEATURE:
<223> OTHER INFORMATION: consensus
<220> FEATURE:
<221> NAME/KEY: misc_feature
<222> LOCATION: 1, 44, 82
<223> OTHER INFORMATION: Xaa can be Ile or Val
<220> FEATURE:
<221> NAME/KEY: misc_feature
<222> LOCATION: 3, 12, 13, 15-28, 31-37, 39-43, 46, 50, 55-56, 59-65,
       67-69, 71-76, 78, 83, 84, 88, 91-125, 127-132, 135-165, 167-185,
       188
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Phe or Tyr
<220> FEATURE:
<221> NAME/KEY: misc_feature
<222> LOCATION: (5)..(5)
<223> OTHER INFORMATION: Xaa can be Gly or Ser
<220> FEATURE:
<221> NAME/KEY: misc_feature
<222> LOCATION: (8)..(8)
<223> OTHER INFORMATION: Xaa can be Asn or Leu
<220> FEATURE:
<221> NAME/KEY: misc_feature
<222> LOCATION: (9)..(9)
<223> OTHER INFORMATION: Xaa can be Thr or Ser
<220> FEATURE:
<221> NAME/KEY: misc_feature
<222> LOCATION: (10)..(10)
```

<223> OTHER INFORMATION: Xaa can be Trp, Tyr, or His
<220> FEATURE:
<221> NAME/KEY: misc_feature
<222> LOCATION: 14, 134
<223> OTHER INFORMATION: Xaa can be Ala or Pro
<220> FEATURE:
<221> NAME/KEY: misc_feature
<222> LOCATION: (29)..(29)
<223> OTHER INFORMATION: Xaa can be Arg or Leu
<220> FEATURE:
<221> NAME/KEY: misc_feature
<222> LOCATION: (45)..(45)
<223> OTHER INFORMATION: Xaa can be Ile, His, or Val
<220> FEATURE:
<221> NAME/KEY: misc_feature
<222> LOCATION: (47)..(47)
<223> OTHER INFORMATION: Xaa can be Asp or Glu
<220> FEATURE:
<221> NAME/KEY: misc_feature
<222> LOCATION: (48)..(48)
<223> OTHER INFORMATION: Xaa can be Cys or Gly
<220> FEATURE:
<221> NAME/KEY: misc_feature
<222> LOCATION: (49)..(49)
<223> OTHER INFORMATION: Xaa can be Leu or Gln
<220> FEATURE:
<221> NAME/KEY: misc_feature
<222> LOCATION: (51)..(51)
<223> OTHER INFORMATION: Xaa can be Gly or Ala
<220> FEATURE:
<221> NAME/KEY: misc_feature
<222> LOCATION: (57)..(57)
<223> OTHER INFORMATION: Xaa can be Asp or Glu
<220> FEATURE:
<221> NAME/KEY: misc_feature
<222> LOCATION: (79)..(79)
<223> OTHER INFORMATION: Xaa can be Ile or Pro
<220> FEATURE:
<221> NAME/KEY: misc_feature
<222> LOCATION: (80)..(80)
<223> OTHER INFORMATION: Xaa can be Ile, Leu, or Val
<220> FEATURE:
<221> NAME/KEY: misc_feature
<222> LOCATION: (81)..(81)
<223> OTHER INFORMATION: Xaa can be Ala or Asp
<220> FEATURE:
<221> NAME/KEY: misc_feature
<222> LOCATION: (85)..(85)
<223> OTHER INFORMATION: Xaa can be Leu or Met

<400> SEQUENCE: 701

Xaa Leu Xaa Xaa Xaa Asp Ser Xaa Xaa Xaa Gly Xaa Xaa Xaa Xaa
1               5                   10                  15

Xaa Xaa Xaa Xaa Xaa Xaa Xaa Xaa Xaa Xaa Xaa Xaa Trp Xaa Xaa
                20                  25                  30

Xaa Xaa Xaa Xaa Xaa Leu Xaa Xaa Xaa Xaa Xaa Xaa Xaa Xaa Xaa
            35                  40                  45

Xaa Xaa Xaa Arg Thr Thr Xaa Xaa Xaa Asp Xaa Xaa Xaa Xaa Xaa
        50                  55                  60

Xaa Gly Xaa Xaa Xaa Leu Xaa Xaa Xaa Xaa Xaa His Xaa Xaa Xaa
65                  70                  75                  80

Xaa Xaa Xaa Xaa Leu Gly Xaa Asn Asp Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Pro Xaa Xaa Xaa
        115                 120                 125

Xaa Xaa Xaa Pro Xaa Xaa Xaa Xaa Xaa Xaa Xaa Xaa Xaa Xaa
    130                 135                 140

```
Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Ala Xaa Xaa Xaa Xaa Xaa Xaa Xaa Xaa Xaa
            165                 170                 175

Xaa Xaa Xaa Xaa Xaa Xaa Xaa Xaa Xaa Asp Gly Xaa His
            180                 185

<210> SEQ ID NO 702
<211> LENGTH: 1380
<212> TYPE: DNA
<213> ORGANISM: Artificial Sequence
<220> FEATURE:
<223> OTHER INFORMATION: S279_M75bA2 clone

<400> SEQUENCE: 702
tgggcggttt cgcggagtcg agcagggaga gatgctcctg ggtcgtacga gttggtacgg    60
aggcatcgtt gaagatctca cgcctgcttg aatgcgcgcg gatatggaac ggaccggccg   120
cgctggcgat cggtgtcggc gtggggctgg cgagcctgag cccggtcgcg ctggcgacgc   180
cgccgcgggg caccgtgccg gtgttcaccc gatcgggac agcctgacgg acgagtattt   240
tgagccgttc ttccagtggg ggttctgcgg gaagtcgtgg gccgagattt tggtggagac   300
ggggcgggcg agcatgggcc cgacggcgca gcaggcgggg atcagcgagc cggagggatg   360
gtcggatccg cggaacacgg ggtatcagca caactgggcg cggtactcgt ggagctcctc   420
agacgcgctg accgaggagt cgccgggggc gacgctgagc gtgctgcttg ggcggagta    480 cgcggtggtg ttcattggga ccaacgactt caatccgtcg tggccggcgt atcagagcgt   540
gtatctgagc cagtggagcg acgagcagat cgacacgtac gtgaacgggg tggtgcagaa   600
catcgcgcag atggtggact cgctgaagtc ggtcggggcg aaggtggtgc ttgcgccgcc   660
ggtggatttt cagttcgcgg ggttcctgcg gaactcatgc ccggatccga tgctgcgcga   720
gcaggcgggt attctgacac ggaagtgcca cgaccgggtg cggtcgatgg cgcggcagaa   780
gcacgtggtg ttcgtggaca tgtggcggct gaaccgcgat ttgttcggca acgggttcgc   840
gatcagctac ggccttcgga cacggtgcg cgtgggggac tcggagatcg gctgcaact    900 ggccgggctg acgggatcgg cggggctggt tccggacggg atccatccgc agcgggtggt   960 gcagggggatc tgggcgaatg cgttcatcgt gggtctgaac gcgcatgggg cgaacatcgc  1020
gcccatcggc gaggcggaga tgtgcgcgat ggggggggtc gtgtacgggg aacggacac   1080 gctggcgaac ttcctgccgc cggtcgcggg ctacgtggag gacttccgca acgcggggga  1140
cttcgtgtgc acgcgggact tcaaccatga ccttggcgtg acgccgacgg acatcttcgc  1200
gttcatcaac gcgtggttca tgaatgatcc ctcggcgcgg atgagcaacc cggagcacac  1260
gcagatcgag gacatcttcg tgtttctgaa tctgtggctg gtgggggtgct gaggcagagt  1320 gggaaggggg tcagcccact tcgcgcgtct ggaagaggat gacggcgacg gagaggaaga  1380

<210> SEQ ID NO 703
<211> LENGTH: 457
<212> TYPE: PRT
<213> ORGANISM: Artificial Sequence
<220> FEATURE:
<223> OTHER INFORMATION: S248_M31bA11 clone

<400> SEQUENCE: 703

Gly Arg Phe Arg Gly Val Glu Gln Gly Glu Met Leu Leu Gly Arg Thr
1               5                   10                  15

Ser Trp Tyr Gly Gly Ile Val Glu Asp Leu Thr Pro Ala Met Arg Ala
```

```
                     20                  25                  30
Asp Met Glu Arg Thr Gly Arg Ala Gly Asp Arg Cys Arg Arg Gly Ala
                35                  40                  45
Gly Glu Pro Glu Pro Gly Arg Ala Gly Asp Ala Ala Gly His Arg
             50                  55                  60
Ala Gly Val His Pro Ile Gly Asp Ser Leu Thr Asp Glu Tyr Phe Glu
 65                  70                  75                  80
Pro Phe Phe Gln Trp Gly Phe Cys Gly Lys Ser Trp Ala Glu Ile Leu
                 85                  90                  95
Val Glu Thr Gly Arg Ala Ser Met Gly Pro Thr Ala Gln Gln Ala Gly
                100                 105                 110
Ile Ser Glu Pro Glu Gly Trp Ser Asp Pro Arg Asn Thr Gly Tyr Gln
                115                 120                 125
His Asn Trp Ala Arg Tyr Ser Trp Ser Ser Asp Ala Leu Thr Glu
            130                 135                 140
Glu Ser Pro Gly Ala Thr Leu Ser Val Leu Leu Gly Ala Glu Tyr Ala
145                 150                 155                 160
Val Val Phe Ile Gly Thr Asn Asp Phe Asn Pro Ser Trp Pro Ala Tyr
                165                 170                 175
Gln Ser Val Tyr Leu Ser Gln Trp Ser Asp Glu Gln Ile Asp Thr Tyr
                180                 185                 190
Val Asn Gly Val Val Gln Asn Ile Ala Gln Met Val Asp Ser Leu Lys
                195                 200                 205
Ser Val Gly Ala Lys Val Val Leu Ala Pro Pro Val Asp Phe Gln Phe
    210                 215                 220
Ala Gly Phe Leu Arg Asn Ser Cys Pro Asp Pro Met Leu Arg Glu Gln
225                 230                 235                 240
Ala Gly Ile Leu Thr Arg Lys Cys His Asp Arg Val Arg Ser Met Ala
                245                 250                 255
Arg Gln Lys His Val Val Phe Val Asp Met Trp Arg Leu Asn Arg Asp
                260                 265                 270
Leu Phe Gly Asn Gly Phe Ala Ile Ser Tyr Gly Leu Arg Asn Thr Val
            275                 280                 285
Arg Val Gly Asp Ser Glu Ile Gly Leu Gln Leu Ala Gly Leu Thr Gly
    290                 295                 300
Ser Ala Gly Leu Val Pro Asp Gly Ile His Pro Gln Arg Val Val Gln
305                 310                 315                 320
Gly Ile Trp Ala Asn Ala Phe Ile Val Gly Leu Asn Ala His Gly Ala
                325                 330                 335
Asn Ile Ala Pro Ile Gly Glu Ala Glu Met Cys Ala Met Gly Gly Val
            340                 345                 350
Val Tyr Gly Gly Thr Asp Thr Leu Ala Asn Phe Leu Pro Pro Val Ala
            355                 360                 365
Gly Tyr Val Glu Asp Phe Arg Asn Ala Gly Asp Phe Val Cys Thr Ala
    370                 375                 380
Asp Phe Asn His Asp Leu Gly Val Thr Pro Thr Asp Ile Phe Ala Phe
385                 390                 395                 400
Ile Asn Ala Trp Phe Met Asn Asp Pro Ser Ala Arg Met Ser Asn Pro
                405                 410                 415
Glu His Thr Gln Ile Glu Asp Ile Phe Val Phe Leu Asn Leu Trp Leu
            420                 425                 430
Val Gly Cys Gly Arg Val Gly Arg Gly Ser Ala His Phe Ala Arg Leu
            435                 440                 445
```

Glu Glu Asp Asp Gly Asp Gly Glu Glu
    450                 455

<210> SEQ ID NO 704
<211> LENGTH: 4
<212> TYPE: PRT
<213> ORGANISM: Sinorhizobium meliloti

<400> SEQUENCE: 704

Gly Asp Ser Leu
1

<210> SEQ ID NO 705
<211> LENGTH: 4
<212> TYPE: PRT
<213> ORGANISM: Sinorhizobium meliloti

<400> SEQUENCE: 705

Ala Arg Thr Thr
1

<210> SEQ ID NO 706
<211> LENGTH: 4
<212> TYPE: PRT
<213> ORGANISM: Sinorhizobium meliloti

<400> SEQUENCE: 706

Gly Thr Asn Asp
1

<210> SEQ ID NO 707
<211> LENGTH: 4
<212> TYPE: PRT
<213> ORGANISM: Sinorhizobium meliloti

<400> SEQUENCE: 707

Gly Asp Ser Asn
1

<210> SEQ ID NO 708
<211> LENGTH: 4
<212> TYPE: PRT
<213> ORGANISM: Sinorhizobium meliloti

<400> SEQUENCE: 708

Gly Arg Thr Thr
1

<210> SEQ ID NO 709
<211> LENGTH: 4
<212> TYPE: PRT
<213> ORGANISM: Mesorhizobium loti

<400> SEQUENCE: 709

Gly Ala Asn Asp
1

<210> SEQ ID NO 710
<211> LENGTH: 4
<212> TYPE: PRT
<213> ORGANISM: Moraxella bovis

<400> SEQUENCE: 710

Gly Ser Asn Asp

```
<210> SEQ ID NO 711
<211> LENGTH: 4
<212> TYPE: PRT
<213> ORGANISM: Sinorhizobium meliloti

<400> SEQUENCE: 711

Ala Arg Thr Thr
1
```

PERHYDROLASE

The present application claims priority under 35 U.S.C. §119, to U.S. Provisional Patent Application Ser. No. 60/526,764, filed Dec. 3, 2003.

FIELD OF THE INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

BACKGROUND OF THE INVENTION

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes. Despite the complexity of current detergents, there are many stains that are difficult to completely remove. Furthermore, there is often residue build-up, which results in discoloration (e.g., yellowing) and diminished aesthetics due to incomplete cleaning. These problems are compounded by the increased use of low (e.g., cold water) wash temperatures and shorter washing cycles. Moreover, many stains are composed of complex mixtures of fibrous material, mainly incorporating carbohydrates and carbohydrate derivatives, fiber, and cell wall components (e.g., plant material, wood, mud/clay based soil, and fruit). These stains present difficult challenges to the formulation and use of cleaning compositions.

In addition, colored garments tend to wear and show appearance losses. A portion of this color loss is due to abrasion in the laundering process, particularly in automated washing and drying machines. Moreover, tensile strength loss of fabric appears to be an unavoidable result of mechanical and chemical action due to use, wearing, and/or washing and drying. Thus, a means to efficiently and effectively wash colored garments so that these appearance losses are minimized is needed.

Cleaning compositions that comprise esterases, lipases and cutinases are well-known in the art. However, these enzymes have a very low ratio of perhydrolysis to hydrolysis. This results in the conversion of most of the ester substrate into acid, instead of the more desirable peracid. This is a serious drawback, since formula space and cost considerations render it feasible to include only a limited amount of substrate.

In sum, despite improvements in the capabilities of cleaning compositions, there remains a need in the art for detergents that remove stains, maintain fabric color and appearance, and prevent dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintain the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching.

In addition to the fabric and garment cleaning area, bleaching is commonly used in the pulp and paper industry. Prior to production of paper, pulp is typically treated to remove undesirable colored contaminants. This provides pulp that is suitable for production of paper of higher quality than pulp that is not treated to remove colored contaminants and other undesirable components present in pulp. For example, in the paper recycling industry, removal of ink is necessary. Although standard methods are suitable for deinking paper with oil or water-based inks, the increased use of electrostatic inks has made deinking problematic, as these inks are much more difficult to remove. There are various methods available for deinking paper, including the use of enzymes (See e.g., U.S. Pat. No. 5,370,770). However, there remains a need in the art for efficient, cost-effective methods for treatment of pulp for paper (recycled and new) product production.

Bleaching is also commonly used in the personal care market (e.g., dental whiteners, hair bleachers, etc.). Although personal care bleaching products have improved over the years, there remains a need for mild, easy to use, cost-effective bleaching methods for this setting.

SUMMARY OF THE INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

In some embodiments, the present invention provides compositions comprising at least one perhydrolase, wherein the perhydrolase exhibits a perhydrolysis to hydrolysis ratio that is greater than 1.

The present invention also provides isolated perhydrolases, wherein the perhydrolases exhibit a perhydrolysis to hydrolysis ratio that is greater than 1. In some preferred embodiments, the perhydrolase is *M. smegmatis* perhydrolase. In alternative preferred embodiments, the perhydrolase is at least approximately about 35% homologous to *M. smegmatis* perhydrolase. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2. In some preferred embodiments, the perhydrolases have immunological cross-reactivity with *M. smegmatis* perhydrolase. In still further embodiments, the perhydrolase is at least a portion of *M. smegmatis* perhydrolase, wherein the perhydrolase has a perhydrolysis to hydrolysis ration that is greater than 1. In alternative embodiments, the perhydrolase is a structural homologue of *M. smegmatis* perhydrolase, in which the active site is homologous to at least one amino acid selected from the group consisting of S11, D192, and H195 of the *M. smegmatis* perhydrolase.

The present invention also provides isolated perhydrolase variants having amino acid sequences comprising at least one modification of an amino acid made at a position equivalent to a position in *M. smegmatis* perhydrolase comprising the amino acid sequence set forth in SEQ ID NO:2. In some embodiments, at least one modification is made at an amino acid position equivalent to a position in *M. smegmatis* perhydrolase comprising the amino acid sequence set forth in SEQ ID NO:2, wherein the modified amino acid is selected from the group consisting of Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. In further embodiments, the modification comprises at least one substitution at an amino acid position equivalent to a position in *M. smegmatis* perhydrolase comprising the amino acid sequence set forth in SEQ ID NO:2, wherein at least one substitution is selected from the group consisting of M1, K3, R4, I5, L6, C7, D10, S11, L12, T13, W14, W16, G15, V17, P18, V19, D21, G22, A23, P24, T25, E26, R27, F28, A29, P30, D31, V32, R33, W34, T35, G36, L38, Q40, Q41, D45, L42, G43, A44, F46, E47, V48, I49, E50, E51, G52, L53, S54, A55, R56, T57, T58, N59, I60, D61, D62, P63, T64, D65, P66, R67, L68, N69, G70, A71, S72, Y73, S76, C77, L78, A79, T80, L82, P83, L84, D85, L86, V87, N94, D95, T96, K97, Y99F100, R101, R102, P104, L105, D106, I107, A108, L109, G110, M111, S112, V113, L114, V115, T116, Q117, V118, L119, T120, S121, A122, G124, V125, G126, T127, T128, Y129, P146, P148, W149, F150, I153, F154, I194, and F196.

In some preferred embodiments, the variant perhydrolase exhibits a change in peracid hydrolysis compared to the wild-type perhydrolase. In some embodiments, the change in peracid hydrolysis is a decrease, while in other embodiments, the change in peracid hydrolysis is an increase.

In some alternative preferred embodiments, the variant perhydrolase exhibits a ratio of peracid hydrolysis of about 0.1 or less, in comparison with wild-type perhydrolase. In alternative preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, L12, G15, P18, R27, W34L38, A44, E51, G52, L53, S54, T58, R67, L68, S72, A79, T80, D85, L86, V87, N94, K97, R101, V118, L119, G124, G126, and I194.

In further alternative embodiments, the variant perhydrolase exhibits a ratio of peracid hydrolysis of about 0.2 or less, in comparison with wild-type perhydrolase. In yet additional embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, D10, L12, W14, G15, P18, V19, T25, R27, W34, L38, A44, I49, E50, E51, G52, L53, S54, A55, R56, T58, N59, D62, T64, D65, R67, L68, N69, S72, S76, C77, A79, T80, L82, P83, D85, L86, V87, N94, T96, K97, R101, L82, P83, L86, V87, N94, T96, K97, F100, R101, L109, M111, L114, V118, L119, A122, G124, G126, T127, Y129, W149, and I194.

In additional embodiments, the variant perhydrolase exhibits a ratio of peracid hydrolysis of about 0.3 or less, in comparison with wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, D10, L12, W14, G15, P18, V19, G22, A23, T25, E26, R27, W34, G36, L38, Q41, L42, G43, A44, I49, E50, E51, G52, L53, S54, A55, R56, T57, N59, T58, D62, T64, D65, R67, L68, N69, G70, S72, Y73, S76, C77, A79, T80, L82, P83, D85, L86, V87, N94, T96, K97, Y99, F100, R101, R102, P104, L109, G110, M111, L114, V118, L119, A122, G124, V125, G126, T127, Y129, W149, F154, and I194.

In yet further embodiments, the variant perhydrolase exhibits a ratio of peracid hydrolysis of about 0.4 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of R4, I5, L6, D10, S11, L12, W14, G15, W16, P18, V19, G22, A23, T25, E26, R27, F28, W34, T35, G36, L38, Q41, L42, G43, A44, D45, E47, I49, E50, E51, G52, L53, S54, A55, R56, T57, T58, N59, T58, I60, D62, T64, D65, R67, L68, N69, G70, S72, Y73, S76, C77, A79, T80, L82, P83, D85, L86, V87, N94, P66, T96, K97, Y99, F100, R101, R102, P104, I107, L109, G110, M111, S112, L114, V118, L119, S121, A122, G124, V125, G126, T127, Y129, W149, F150, F154, I194, and F196.

In some embodiments, the variant perhydrolase exhibits a ratio of peracid hydrolysis of about 0.5 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, Y99, G190, V191, G193, T197, N201, D203, L208, A209, V212, L215, and L216.

In additional embodiments, the variant perhydrolase exhibits a ratio of peracid hydrolysis of about 0.6 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, V125, V19, W16, Y129, Y73, Y99, G190, V191, G193, T197, N201, D203, L208, A209, V212, L215, and L216.

In yet additional embodiments, the variant perhydrolase exhibits a ratio of peracid hydrolysis of about 0.7 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R10, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, and L216.

In still further embodiments, the variant perhydrolase exhibits a ratio of peracid hydrolysis of about 0.8 or less, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y1d29, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, Y73, G190, V191, G193, T197, N201, D203, L208, A209, V212, L215, and L216.

In additional embodiments, the variant perhydrolase exhibits a ratio of peracid hydrolysis of about 1.5 or greater, in comparison with wild-type perhydrolase. In some preferred embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R10, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R10, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, I42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, and Y73, Y99, A108, A44, C7, D10, D106, D31, D61, D85, E26, E51, F100, F28, F46, G110, G22, G36, G43, G52, G70, I107, I153, I49, I5, I89, K3, L105, L53, L6, L78, L86, M1, N69, P104, P146, P18, P24, P30, P83, Q117, Q40, Q41, R102, R27, R33, R4, S121, S72, S76, T120, T128, T13, T35, T80, T96, V115, V118, V32V48, V87, W34, G190, V191, G193, T197, E198, A199, R202, D203, G205, V206, A209, E210, Q211, S214, and L215.

In additional embodiments, the variant perhydrolase exhibits a ratio of peracid hydrolysis between about 1.2 and about 1.5, in comparison with wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, C7, D106, D31, D61, D85, E26, E50, E51, F100, F150, F28, F46, G110, G126, G22, G70, I107, K3, L105, L42, L6, L78, M111, N59, N69, P104, P146, P148, P18, P30, P63, Q117, Q40, Q41, R102, R27, R33, R4, S54, S76, T116, T120, T128, T64, T80, T96, V113, V115, V118, W34, and Y73.

In yet further embodiments, the present invention provides variant perhydrolases in which the variant perhydrolases exhibit a change in perhydrolysis, such that the ratio of variant perhydrolase perhydrolysis to wild-type perhydrolase perhydrolysis is at least about 1.2. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, and F196.

In further embodiments, the variant perhydrolase exhibits a change in perhydrolysis, such that the ratio of variant perhydrolase perhydrolysis to wild-type perhydrolase perhydrolysis is about 0.8 or less. In some embodiments, the variant perhydrolase comprising at least one modification comprises at least one substitution at an amino acid position equivalent to a position in *M. smegmatis* perhydrolase comprising the amino acid sequence set forth in SEQ ID NO:2, wherein at least one substitution is selected from the group consisting of A108, A122, A23, A29, A44, A55, A71, A79, C7, C77, D10, D106, D21, D45, D61, D62, D65, D85, E26, E47, E50, E51, F100, F150, F154, F196, F28, F46, G110, G124, G126, G15, G22, G36, G52, G70, I107, I153, I194, I49, I5, I60, I89, K3, K97, L105, L109, L114, L119, L12, L38, L42, L53, L6, L68, L78, L82, L84, K86, M1, M111, N59N94, P146, P18, P24, P30, P66, P83, Q40, Q41, R10, R102, R27, R33, R4, R56, R67, S11, S112, S54, S72, S76, T103, T116, T120, T127, T128, T13, T25, T57, T64, T80, T96, V113, V115, V118, V125, V17, V19, V32, V48, V87, W13, W149, W16, W34, Y129, Y73, and Y99.

In alternative embodiments, the present invention provides variant perhydrolases comprising at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A108, A122, A23, A29, A44, A55, A71, A79, C7, C77, D10, D106, D21, D31, D45, D61, D62, D65, D85, E26, E47, E50, E51, F100, F150, F154F196, F28, F46, G110, G124, G126, G15, G22, G36, G43, G52, G70, I107, I153, I194, I49, I5, I60, I89, K3, K97, L105, L109, L114, L119, L12, L38, L42, L53, L6, L68, L78, L82, L84, L86, M1, M111, N59, N69, N94, P104, P146, P148, P18, P24, P30, P63, P66, P83, Q117, Q40, Q41, R10, R102, R27, R33, R4, R56, R67, S11, S112, S121, S54, S72, S76, T103, T116, T120, T127, T128, T13, T25, T35, T57, T58, T64, T80, T96, V113, V115, V118, V125, V17, V19, V32, V48, V87, W14, W149, W16, W34, Y129, Y73, and Y99.

In yet additional embodiments, the variant perhydrolase exhibits a change in perhydrolysis, such that the ratio of variant perhydrolase perhydrolysis to wild-type perhydrolase perhydrolysis is between about 1.2 and about 2. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, F196, G190, E198, A199, R202, D203, V206, A209, E210, Q211, and V212.

In still further embodiments, the variant perhydrolase exhibits a change in perhydrolysis, such that the ratio of variant perhydrolase perhydrolysis to wild-type perhydrolase perhydrolysis is between about 2 and about 2.5. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A44, C7, D10, D85, D95, E26, E47, I107, L12, L42, P104, P148, S54, Q40, Q117, D203, V206, E210. In still further embodiments, the variant perhydrolase exhibits a change in perhydrolysis, such that the ratio of variant perhydrolase perhydrolysis to wild-type perhydrolase perhydrolysis is between about 2.5 and about 3. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A44, C7, I107, K97, L12, L78, P104, Q40, and V125.

In further embodiments, the variant perhydrolase exhibits a change in perhydrolysis, such that the ratio of variant perhydrolase perhydrolysis to wild-type perhydrolase perhydrolysis is between about 3.0 and about 5. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of D10, D85, L53, L78, and S54.

In still further embodiments, the variant perhydrolase exhibits a change in perhydrolysis, such that the ratio of variant perhydrolase perhydrolysis to wild-type perhydrolase perhydrolysis is about 0.1 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, and W34.

In further embodiments, the variant perhydrolase exhibits a change in perhydrolysis, such that the ratio of variant perhydrolase perhydrolysis to wild-type perhydrolase perhydrolysis is about 0.2 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, and Y73.

In additional embodiments, the variant perhydrolase exhibits a change in perhydrolysis, such that the ratio of variant perhydrolase perhydrolysis to wild-type perhydrolase perhydrolysis is about 0.3 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, and Y129.

In yet additional embodiments, the variant perhydrolase exhibits a change in perhydrolysis, such that the ratio of variant perhydrolase perhydrolysis to wild-type perhydrolase perhydrolysis is about 0.4 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, and V87.

In additional embodiments, the variant perhydrolase exhibits a change in perhydrolysis, such that the ratio of variant perhydrolase perhydrolysis to wild-type perhydrolase perhydrolysis is about 0.5 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, and Y129.

In further embodiments, the variant perhydrolase exhibits a change in perhydrolysis, such that the ratio of variant perhydrolase perhydrolysis to wild-type perhydrolase perhydrolysis is about 0.6 or less. In some embodiments, the variant perhydrolase comprises at least one modification comprising t least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, and Y73.

In yet further embodiments, the variant perhydrolase exhibits a change in perhydrolysis, such that the ratio of variant perhydrolase perhydrolysis to wild-type perhydrolase perhydrolysis is about 0.7 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, and Y99.

In additional embodiments, the variant perhydrolase exhibits a change in perhydrolysis, such that the ratio of variant perhydrolase perhydrolysis to wild-type perhydrolase perhydrolysis is about 0.8 or less. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R10, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, Y99, A108, A122, A29, A55, C77, D10, D106, D45, D61, D62, D65, D85, E47, E50, F100, F150, F28, F46, G110, G124, G126, G15, G36, I153, I194, I5, I60, I89, K3, K97, L105, L109, L114, L119, L38, L42, L68, L84, L86, M1, N59, P24, P30, P83, R101, R27, R4, R56, S112, S54, S76, T103, T116, T120, T127, T128, T13, T35, T64, V113, V17, V19, V32, V48, V87, Y129, Y73, and Y99.

The present invention also provides perhydrolase variants, wherein the perhydrolase variants exhibit greater perhydrolysis activity and decreased peracid hydrolysis activity as compared to wild-type perhydrolase. In some embodiments, the variant perhydrolases exhibit perhydrolysis activity ratio of at least about 1.2, and peracid hydrolysis activity ratio of about 0.8 or less, as compared to wild-type perhydrolase. In alternative embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A29, A44, A55, A71, A79, C7, D10, D106, D31, D85, E26, E47, F150, F154, F196, F28, G124, G126, G36, G43, I153, L109, I42, L53, L109, L42, L53, L109, I42, L53, L68, L82, L86, M111, N69, P104, P148, P18, P63, P66, P83, Q117, Q40, R101, R67, S54, S121, S72, S76, T25, T64, V115, and V19.

In additional embodiments, the perhydrolase exhibits perhydrolysis activity ratio of at least about 1.2, a peracid hydrolysis activity ratio of about 0.8 or less, and a protein concentration ratio of at least 0.5, as compared to wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A29, A44, A71, A79, C7, D85, E26, E47, E51, F150, F154, F196, F28, G124, G126, G36, I153, L109, L12, L53, L68, L82, M111, N69, P104, P148, P18, P63, P66, P83, Q117, Q40, R101, R67, S121, S54, S72, S76, T25, T64, V125, and V19.

The present invention provides variant perhydrolases that exhibit an increase in expression of the perhydrolase variants, as compared to the expression of wild-type perhydrolase. In some embodiments, the variant perhydrolase comprises at least one modification comprising at least one substitution at an amino acid position equivalent to a position in *M. smegmatis* perhydrolase comprising the amino acid sequence set forth in SEQ ID NO:2, wherein at least one substitution is selected from the group consisting of A2, I5, C7, F8, S11, L12, T13, W14, W16, V17, P18, V19, E20, G22, A23, P24, T25, A29, P30, V32, T35, G36, V37, A39, F46, E47, S54, A55, R56, T58, I60, D61, D62, P63, T64, P66, R67, L68, N69, G70, S72, Y73, L74, P75, S76, C77, L78, A79, T80, L82, P83, L84, L86, I89, T93, T96, K97, A98, Y99, F100, R101, R102, T103, P104, L105, D106, I107, A108, L109, G110, S112, V113, L114, V115, T116, Q117, V118, L119, T120, S121, A122, G124, V125, G126, T127, T128, Y129, P130, P132, K133, L135, V136, S138, P141, L142, A143, M145, H147, W149, F150, Q151, I153, G157, Q159, T161, T162, L164, A165, R166, V167, Y168, A170, L171, A172, M175, K176, P178, A182, G183, S184, V185, I186, T188, I194, F196, V191, N201, L208, A209, Q211, Q213, S214, L215, and L216.

The present invention also provides isolated proteins comprising homologs of *M. smegmatis* perhydrolase, wherein the homologs are proteins within the SGNH-hydrolase family of proteins. In alternative preferred embodiments, the isolated proteins have at least about 35% identity with the amino acid sequence of *M. smegmatis* perhydrolase, in which the protein comprises at least three residues selected from the group consisting of L6, W14, W34, L38, R56, D62, L74, L78, H81, P83, M90, K97, G110, L114, L135, F180, G205, S11, D192, and H195. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2.

The present invention also provides isolated proteins having at least about 38% identity with the amino acid sequence of *M. smegmatis* perhydrolase, wherein the protein exhibits perhydrolysis activity. In further embodiments, the perhydrolase is at least approximately about 40%, 45%, 50%, 55%, 60%, 65%, 70%, 75%, 80%, 85%, 90%, 95%, or 99% homologous to *M. smegmatis* perhydrolase. In additional preferred embodiments, the perhydrolase comprises the amino acid sequence set forth in SEQ ID NO:2.

The present invention also provides homologs of *M. smegmatis* perhydrolase, wherein the homologs are perhydrolases comprising at least one motif selected from the group consisting of GDSL-GRTT, GDSL-ARTT, GDSN-GRTT, GDSN-ARTT, and SDSL-GRTT. In preferred embodiments, the homologs exhibit perhydrolysis. In some particularly preferred embodiments, the homologs exhibit a perhydrolysis to hydrolysis ratio that is great than about 1. In still further embodiments, the homologs are immunologically cross-reactive with antibodies raised against *M. smegmatis* perhydrolase. In yet additional embodiments, antibodies raised against the homolog cross-react with *M. smegmatis* perhydrolase.

The present invention also provides isolated proteins having at least about 35% identity with the amino acid sequence of at least one *M. smegmatis* perhydrolase homolog, wherein the proteins exhibit perhydrolysis activity.

In some particularly preferred embodiments, the present invention provides proteins having perhydrolase activity, wherein the proteins are in the form of a multimer in solution. In some more preferred embodiments, the protein is a perhydrolase that comprises a dimer. In alternative particularly preferred embodiments, the protein is a perhydrolase that comprises an octamer. In still further embodiments, the protein is in the form of a multimer in solution and the protein is selected from the group consisting of *M. smegmatis* perhydrolase, *M. smegmatis* perhydrolase homologs, and *M. smegmatis* perhydrolase variants. In yet further embodiments, the protein is selected from the group consisting of modified serine hydrolases and modified cysteine hydrolases, wherein the modified serine hydrolases or modified cysteine hydrolases comprise increased perhydrolase activity as compared to unmodified serine hydrolases or unmodified cysteine hydrolases The present invention also provides proteins having perhydrolase activity, wherein the protein comprises at least one motif selected from the group consisting of GDSL-GRTT, GDSL-ARTT, GDSN-GRTT, GDSN-ARTT, and SDSL-GRTT. In some embodiments, the protein is obtained from a member of the *Rhizobiales*. In some preferred embodiments, the protein is obtained from a member of the genus *Mycobacterium*.

The present invention also provides isolated genes identified using at least one primer selected from the group consisting of SEQ ID NOS:21-69.

The present invention also provides methods for identifying a perhydrolase, comprising the steps of: identifying source of the perhydrolase; analyzing the source to identify sequences comprising at least one motif selected from the group consisting of GDSL-GRTT, GDS-ARTT, GDSN-GRTT, GDSN-ARTT, and SDSL-GRTT; expressing the sequences identified in step b) to produce the perhydrolase; and testing the perhydrolase for perhydrolysis activity. In some embodiments, the analyzing step is an amplification step wherein the primer sequences set forth in SEQ ID NOS: 21-69 are used to amplifying the sequences comprising at least one motif selected from the group consisting of GDSL-GRTT, GDSL-ARTT, GDSN-GRTT, GDSN-ARTT, and SDSL-GRTT. In still further embodiments, the source is selected from the group consisting of environmental sources and metagenomic sources. The present invention also provides proteins identified using the methods set forth herein. The present invention further provides isolated nucleic acid sequences encoding the proteins identified using the methods set forth herein. In some particularly preferred embodiments, the proteins exhibit a perhydrolysis to hydrolysis ratio that is greater than about 1. In still further embodiments, the proteins exhibit a perhydrolysis activity that is at least about 0.2, compared to the perhydrolysis activity exhibited by *M. smegmatis* perhydrolase. In yet additional embodiments, the proteins comprise at least three residues selected from the group consisting of L6, W14, W34, L38, R56, D62, L74, L78, H81, P83, M90, K97, G110, L114, L135, F180, G205, S11, D192, and H195.

In further embodiments, the analyzing step comprises searching at least one amino acid database. In yet further embodiments, the analyzing step comprises searching at least one nucleic acid database to identify nucleic acid sequences encoding the amino acid sequences of the perhydrolase. In still further embodiments, the source is selected from the group consisting of environmental sources and metagenomic sources. The present invention further provides isolated nucleic acid sequences encoding the proteins identified using the methods set forth herein. In some particularly preferred embodiments, the proteins exhibit a perhydrolysis to hydrolysis ratio that is greater than about 1. In still further embodiments, the proteins exhibit a perhydrolysis activity that is at least about 0.2, compared to the perhydrolysis activity exhibited by *M. smegmatis* perhydrolase. In yet additional embodiments, the proteins comprise at least three residues selected from the group consisting of L6, W14, W34, L38, R56, D62, L74, L78, H81, P83, M90, K97, G110, L114, L135, F180, G205, S11, D192, and H195, as set forth in SEQ ID NO:2.

The present invention also provides variant perhydrolases having altered substrate specificities as compared to wild-type *M. smegmatis* perhydrolase. In some embodiments, the variant perhydrolases have altered para nitrophenyl caproate (PNC) activity, as compared to wild-type *M. smegmatis* perhydrolase.

The present invention also provides variant perhydrolases having altered pI values as compared to wild-type *M. smegmatis* perhydrolase. In some embodiments, the variant perhydrolases comprise at least one positively charged mutation, while in alternative embodiments, the variant perhydrolases comprise at least one negatively charged mutation.

The present invention also provides variant perhydrolases that have increased stability, as compared to wild-type *M. smegmatis* perhydrolase. In some preferred embodiments, the stability of the variant perhydrolase is selected from the group consisting of thermostability, enzymatic stability, and chemical stability.

The present invention also provides variant perhydrolases, wherein the variant perhydrolase exhibits at least one altered surface property. In some preferred embodiments, the variants comprise at least one mutation comprising at least one substitution at sites selected from the group consisting of the residues set forth in Table 15-1.

The present invention also provides perhydrolase variants having at least one improved property as compared to wild-type perhydrolase.

The present invention also provides expression vectors comprising a polynucleotide sequence encoding at least one perhydrolase variant. The present invention further provides host cells comprising at least one such expression vector. In some preferred embodiments, a host cell is selected from the group consisting of *Bacillus* sp., *Streptomyces* sp., *Escherichia*, and *Pantoea* sp. The present invention also provides perhydrolases produced by the host cells.

The present invention also provides compositions comprising at least a portion of at least one perhydrolase. In some preferred embodiments, the perhydrolase comprises the amino acid sequence set forth in SEQ ID NO:2. In further embodiments, the perhydrolase is encoded by a polynucleotide sequence comprises SEQ ID NO:1. In additional embodiments, the sequence comprises at least a portion of SEQ ID NO:1. In further embodiments, the present invention provides expression vectors comprising the polynucleotide sequence encoding at least a portion of at least one perhydrolase. The present invention also provides host comprising at least one expression vectors. In some embodiments, the host cells are selected from the group consisting of *Bacillus* sp., *Streptomyces* sp., *Escherichia*, and *Pantoea* sp. The present invention also provides perhydrolases produced by these host cells.

The present invention also provides variant perhydrolases, wherein the perhydrolases comprise at least one substitution corresponding to the amino acid positions in SEQ ID NO:2, and wherein the variant perhydrolase has better performance in at least one property, compared to wild-type *M. smegmatis* perhydrolase.

The present invention further provides isolated polynucleotides comprising a nucleotide sequence (i) having at least about 70% identity to SEQ ID NO:1, or (ii) being capable of hybridizing to a probe derived from the nucleotide sequence set forth in SEQ ID NO:1, under conditions of intermediate to high stringency, or (iii) being complementary to the nucleotide sequence set forth in SEQ ID NO:1. In some embodiments, the present invention also provides vectors comprising these polynucleotide sequences. In additional embodiments, the present invention also provides host comprising at least one expression vectors. In some embodiments, the host cells are selected from the group consisting of *Bacillus* sp., *Streptomyces* sp., *Escherichia*, and *Pantoea* sp. The present invention also provides perhydrolases produced by these host cells.

The present invention also provides polynucleotides comprising a sequence complementary to at least a portion of the sequence set forth in SEQ ID NO:1.

The present invention also provides methods of producing enzymes having perhydrolase activity, comprising: transforming a host cell with an expression vector comprising a polynucleotide having at least 70% sequence identity to SEQ ID NO:1; cultivating the transformed host cell under conditions suitable for the host cell to produce the perhydrolase; and recovering the perhydrolase. In some preferred embodiments, the host cell is selected from the group consisting of *Streptomyces, Pantoea, Escherichia*, and *Bacillus* species.

The present invention also provides probes comprising a 4 to 150 polynucleotide sequence substantially identical to a corresponding fragment of SEQ ID NO:1, wherein the probe is used to detect a nucleic acid sequence coding for an enzyme having perhydrolase activity.

The present invention also provides cleaning compositions comprising: a) at least 0.0001 weight percent of a perhydrolase that exhibits a perhydrolysis to hydrolysis ratio that is greater than 1; b) a molecule comprising an ester moiety, and c) optionally, an adjunct ingredient.

The present invention further provides cleaning compositions comprising: a) at least 0.0001 weight percent of a perhydrolase that exhibits a perhydrolysis to hydrolysis ratio that is greater than 1; b) a material selected from the group consisting of a peroxygen source, hydrogen peroxide and mixtures thereof, the peroxygen source being selected from the group consisting of: a per-salt; an organic peroxyacid; urea hydrogen peroxide; a carbohydrate and carbohydrate oxidase mixture, and mixtures thereof; c) from about 0.01 to about 50 weight percent of a molecule comprising an ester moiety, and d) optionally, an adjunct ingredient.

The present invention also provides cleaning compositions comprising: a) from about 0.0001 to about 1 weight percent of a variant perhydrolase having an amino acid sequence comprising at least one modification of an amino acid made at a position equivalent to a position in *M. smegmatis* perhydrolase comprising the amino acid sequence set forth in SEQ ID NO:2; b) a material selected from the group consisting of a peroxygen source, hydrogen peroxide and mixtures thereof, the peroxygen source being selected from the group consisting of: a per-salt; an organic peroxyacid; urea hydrogen peroxide; a carbohydrate and carbohydrate oxidase mixture; and mixtures thereof; c) from about 0.01 to about 50 weight percent of a molecule comprising an ester moiety; and d) optionally, an adjunct ingredient. In some preferred embodiments, the cleaning compositions further comprise at least one adjunct ingredient. In some particularly preferred embodiments, the adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, pigments and mixtures thereof.

In additional embodiments, the present invention provides cleaning compositions wherein: the perhydrolase exhibits a perhydrolysis to hydrolysis molar ratio that is greater than about 0.1; the per-salt is selected from the group consisting of alkalimetal perborate, alkalimetal percarbonate, alkalimetal perphosphates, alkalimetal persulphates and mixtures thereof; the carbohydrate is selected from the group consisting of mono-carbohydrates, di-carbohydrates, tri-carbohydrates, oligo-carbohydrates and mixtures thereof; the carbohydrate oxidase is selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) hexose oxidase (IUPAC classification EC1.1.3.5). glucose oxidase (IUPAC classification EC1.1.3.4) and mixtures thereof; and the molecule comprising an ester moiety has the formula:

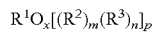

(i) wherein $R^1$ is a moiety selected from the group consisting of H, substituted or unsubstituted alkyl, heteroalkyl, alkenyl, alkynyl, aryl, alkylaryl, alkylheteroaryl, and heteroaryl;
  (ii) each $R^2$ is an alkoxylate moiety;
  (iii) $R^3$ is an ester-forming moiety having the formula: $R^4CO$— wherein $R^4$ is H, alkyl, alkenyl, alkynyl, aryl, alkylaryl, alkylheteroaryl, and heteroaryl;
  (iv) x is 1 when $R^1$ is H; when $R^1$ is not H, x is an integer that is equal to or less than the number of carbons in $R^1$;
  (v) p is an integer that is equal to or less than x;
  (vi) m is an integer from 0 to 50; and
  (vii) n is at least 1

In alternative embodiments, the present invention provides cleaning compositions wherein: a) $R^1$ is an $C_2$-$C_{32}$ substituted or unsubstituted alkyl or heteroalkyl moiety, b) each $R^1$ is independently an ethoxylate or propoxylate moiety; and c) m is an integer from 1 to 12. In some embodiments, $R^3$ is an ester-forming moiety having the formula: $R^4CO$— wherein $R^4$ is: a) a substituted or unsubstituted alkyl, alkenyl or alkynyl moiety comprising from 1 to 22 carbon atoms; or b) a substituted or unsubstituted aryl, alkylaryl, alkylheteroaryl or heteroaryl moiety comprising from 4 to 22 carbon atoms.

In still further embodiments of the cleaning compositions, the molecule comprising the ester moiety has the formula:

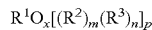

wherein: a) $R^1$ is H or a moiety that comprises a primary, secondary, tertiary or quaternary amine moiety, the $R^1$ moiety that comprises an amine moiety being selected from the group consisting of substituted or unsubstituted alkyl, heteroalkyl, alkenyl, alkynyl, aryl, alkylaryl, alkylheteroaryl, and heteroaryl; b) each $R^2$ is an alkoxylate moiety; c) $R^3$ is an ester-forming moiety having the formula: $R^4Co$— wherein $R^4$ may be H, substituted or unsubstituted alkyl, alkenyl, alkynyl, aryl, alkylaryl, alkylheteroaryl, and heteroaryl; d) x is 1 when $R^1$ is H; when $R^1$ is not H, x is an integer that is equal to or less than the number of carbons in $R^1$; e) p is an integer that is equal to or less than x; f) m is an integer from 0 to 12; and g) n is at least 1.

In still further embodiments of the present cleaning compositions, the molecule comprising an ester moiety has a weight average molecular weight of less than 600,000 Daltons. In yet additional embodiments, an adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/antiredeposition agents, brighteners, suds suppressors, dyes, perfumes, structure elasticizing agents, fabric softeners, carriers, hydrotropes, processing aids, pigments and mixtures thereof.

The present invention further provides methods of cleaning comprising the steps of: a) contacting a surface and/or an article comprising a fabric with any of the cleaning compositions provided above and/or a composition comprising any of the cleaning compositions provided above; and b) optionally washing and/or rinsing the surface or material.

In alternative embodiments, the present invention provides methods of cleaning, the method comprising the steps of: a) contacting a surface and/or an article comprising a fabric with any suitable cleaning composition provided above and/or a composition comprising any suitable cleaning provided above; and b) optionally washing and/or rinsing the surface or material.

The present invention also provides bleaching compositions comprising at least one perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant having an amino acid sequence comprising at least one modification of an amino acid made at a position equivalent to a position in *M. smegmatis* perhydrolase comprising the amino acid sequence set forth in SEQ ID NO:2. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant having at least one improved property as compared to wild-type perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase variant comprising at least one substitution corresponding to the amino acid positions in SEQ ID NO:2, and wherein the variant perhydrolase has better performance in at least one property compared to wild-type *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides bleaching compositions comprising at least one perhydrolase that is at least approximately about 35% homologous to *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant having an amino acid sequence comprising at least one modification of an amino acid made at a position equivalent to a position in *M. smegmatis* perhydrolase comprising the amino acid sequence set forth in SEQ ID NO:2. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant having at least one improved property as compared to wild-type perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase variant comprising at least one substitution corresponding to the amino acid positions in SEQ ID NO:2, and wherein the variant perhydrolase has better performance in at least one property compared to wild-type *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

The present invention also provides disinfecting compositions comprising at least one perhydrolase that is at least approximately about 35% homologous to *M. smegmatis* perhydrolase. In some particularly preferred embodiments, the perhydrolase exhibits a perhydrolysis to hydrolysis ratio that is greater than 1. In some embodiments, the bleaching compositions further comprise at least one additional enzymes or enzyme derivatives selected from the group consisting of proteases, amylases, lipases, mannanases, pectinases, cutinases, oxidoreductases, hemicellulases, and cellulases.

In some preferred embodiments, the perhydrolase is at least approximately 70% homologous to *M. smegmatis* perhydrolase comprising the amino acid sequence set forth in SEQ ID NO:2. In some embodiments, the present invention provides perhydrolases that cross react with antibody generated against *M. smegmatis* perhydrolase, particularly that comprising the amino acid sequence set forth in SEQ ID NO:2. In further embodiments, the present invention provides perhydrolases that are structural homologs of the *M. smegmatis* perhydrolase, in which active site comprises sites homologous to S11, D192, and H195 of the *M. smegmatis* perhydrolase. In yet additional embodiments, the present invention provides perhydrolases comprising one or more modifications at the following residues: Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. However, it is not intended that the present invention be limited to perhydrolases with these modifications only at these residues, as perhydrolases with other modifications also find use with the present invention.

In some embodiments, at least one perhydrolase of the present invention is used in a cleaning process wherein an article to be cleaned is exposed to a sufficient amount of the at least one perhydrolase under conditions such that the perhydrolase cleans and/or bleaches, and/or decolorizes any/all stains present on the article (e.g., laundry and dish detergents). In some embodiments, the cleaning further comprises disinfecting. In some embodiments, the article cleaned, bleached and/or disinfected using at least one perhydrolase of the present invention comprises textiles and/or hard surfaces, while in other embodiments, the article is paper or pulp, and in still further embodiments, at least one perhydrolase is used as a personal care product to whiten or bleach hair, teeth, skin, etc. Thus, in some embodiments, the present invention provides compositions for use in various cleaning, bleaching, and/or disinfecting applications. Indeed, it is not intended that the present invention be limited to any particular application.

In some preferred embodiments, the perhydrolase comprises SEQ ID NO:2. In some preferred alternative embodiments, the perhydrolase is encoded by the nucleic acid sequence set forth in SEQ ID NO:1.

In some embodiments, the present invention provides enzymes with activities that result in high peracid/acid ratios. In alternative embodiments, the present invention provides the perhydrolase of *Mycobacterium smegmatis*, as well as sequence and/or structural homologs of this protein. In additional embodiments, the present invention provides enzymes that have been modified so as to express perhydrolase activity with a high perhydrolysis to hydrolase ratio either in addition to or instead of the enzyme's original activity. In additional embodiments, the present invention provides modified enzymes with altered substrate specificity, Km, kcat, perhydrolase activity, and/or peracid degradation activity.

In additional embodiments, the present invention provides means to identify, produce, and characterize enzymes that comprise the perhydrolysis activity of the present invention. The present invention further provides methods and compositions comprising at least one perhydrolase for cleaning, disinfecting, bleaching, and other applications, including but not limited to paper and pulp bleaching, fabric and garment cleaning, hard surface cleaning, and personal care applications (e.g., oral care, hair care, and skin care). In some preferred embodiments, the present invention provides methods and compositions for bleaching cotton and other fabrics. Indeed, the present invention finds use in the bleaching and cleaning of various textiles. It is not intended that the present invention be limited to any particular setting, application or use, as it is contemplated that it will find use in numerous areas where an enzymatic generation of peracids is desired over the use of preformed peracids or hydrogen peroxide or other bleaching chemicals, under conditions including but not limited to a wide range of pHs and temperatures. The present invention also finds use in applications where peracid hydrolysis is useful, such as in the clean up of peracids.

Furthermore, the present invention provides means to produce perhydrolase enzymes suitable for cleaning, disinfecting, bleaching, and other applications, including personal care.

DESCRIPTION OF THE FIGURES

FIG. 6 provides a purification table showing the enzyme activity of the enzyme of the present invention through various steps in the purification process.

DESCRIPTION OF THE INVENTION

Figure 1:
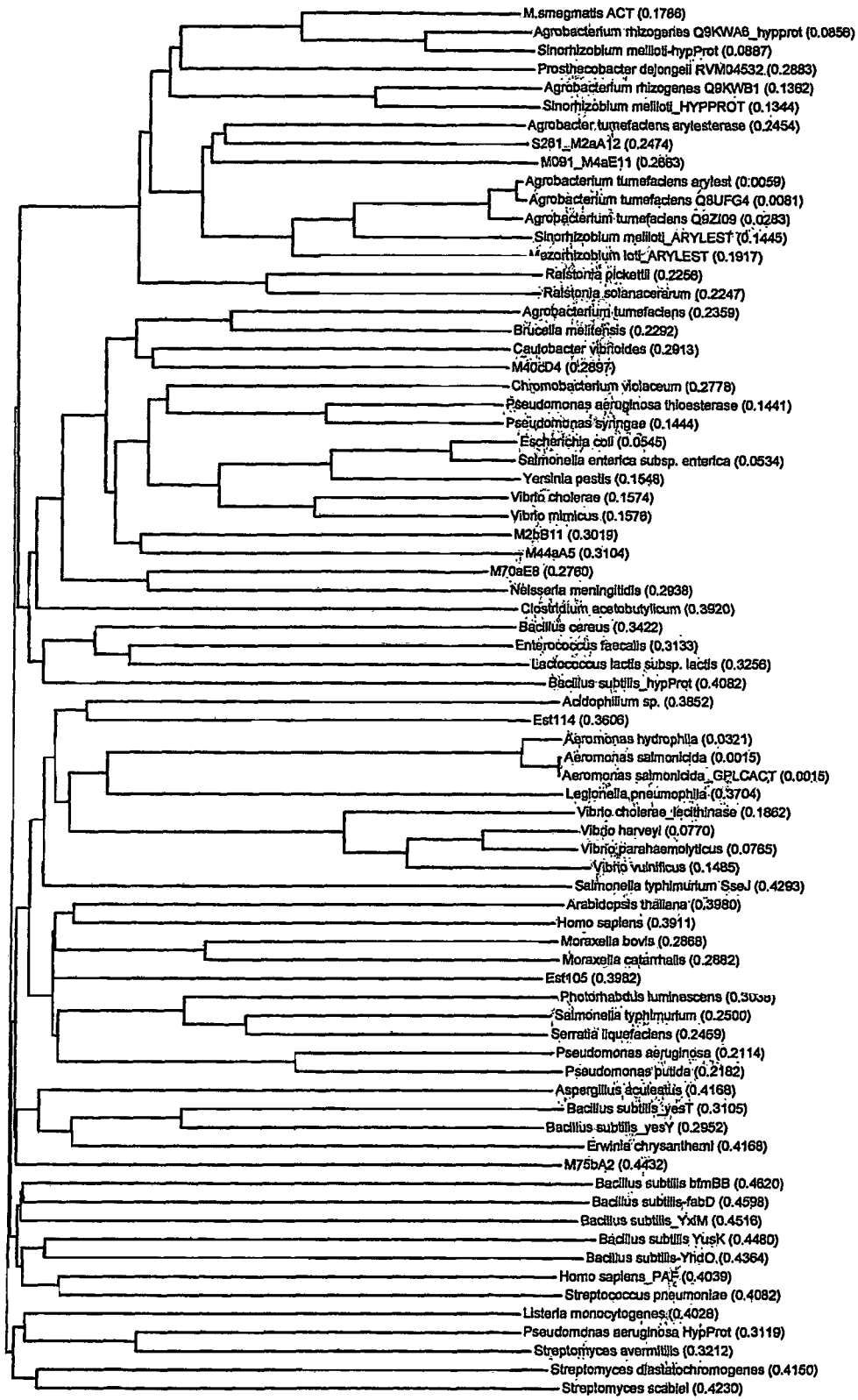
FIG. 1 provides a phylogenetic tree of *M. smegmatis* perhydrolase and other related sequences.

The present invention provides methods and compositions comprising at least one perhydrolase enzyme for cleaning and other applications. In some particularly preferred embodiments, the present invention provides methods and compositions for generation of peracids. In particular, the present invention provides improved methods and compositions comprising perhydrolysis enzymes with high peracid/acid ratios for cleaning, bleaching, disinfecting and other applications. In some preferred embodiments, the present invention provides improved methods and compositions for generation of peracids. The present invention finds particular use in applications involving cleaning, bleaching and disinfecting.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "perhydrolase" refers to an enzyme that is capable of catalyzing a reaction that results in the formation of sufficiently high amounts of peracid suitable for applications such as cleaning, bleaching, and disinfecting. In particularly preferred embodiments, the perhydrolase enzymes of the present invention produce very high perhydrolysis to hydrolysis ratios. The high perhydrolysis to hydrolysis ratios of these distinct enzymes makes these enzymes suitable for use in a very wide variety of applications. In additional preferred embodiments, the perhydrolases of the present invention are characterized by having distinct tertiary structure and primary sequence. In particularly preferred embodiments, the perhydrolases of the present invention comprises distinct primary and tertiary structures. In some particularly preferred embodiments, the perhydrolases of the present invention comprise distinct quaternary structure. In some preferred embodiments, the perhydrolase of the present invention is the *M. smegmatis* perhydrolase, while in alternative embodiments, the perhydrolase is a variant of this perhydrolase, while in still further embodiments, the perhydrolase is a homolog of this perhydrolase. In further preferred embodiments, a monomeric hydrolase is engineered to produce a multimeric enzyme that has better perhydrolase activity than the monomer. However, it is not intended that the present invention be limited to this specific *M. smegmatis* perhydrolase, specific variants of this perhydrolase, nor specific homologs of this perhydrolase.

As used herein, the term "multimer" refers to two or more proteins or peptides that are covalently or non-covalently associated and exist as a complex in solution. A "dimer" is a multimer that contains two proteins or peptides; a "trime" contains three proteins or peptides, etc. As used herein, "octamer" refers to a multimer of eight proteins or peptides.

As used herein, the phrase "perhydrolysis to hydrolysis ratio" is the ratio of the amount of enzymatically produced-peracid to that of enzymatically produced acid by the perhydrolase, under defined conditions and within a defined time. In some preferred embodiments, the assays provided herein are used to determine the amounts of peracid and acid produced by the enzyme.

As used herein, "personal care products" means products used in the cleaning, bleaching and/or disinfecting of hair, skin, scalp, and teeth, including, but not limited to shampoos, body lotions, shower gels, topical moisturizers, toothpaste, and/or other topical cleansers. In some particularly preferred embodiments, these products are utilized on humans, while in other embodiments, these products find use with non-human animals (e.g., in veterinary applications).

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pretreat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g. "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "enhanced performance" in a detergent is defined as increasing cleaning of bleach-sensitive stains (e.g., grass, tea, wine, blood, dingy, etc.), as determined by usual evaluation after a standard wash cycle. In particular embodiments, the perhydrolase of the present invention provides enhanced performance in the oxidation and removal of colored stains and soils. In further embodiments, the perhydrolase of the present invention provides enhanced performance in the removal and/or decolorization of stains. In yet additional embodiments, the perhydrolase of the present invention provides enhanced performance in the removal of lipid-based stains and soils. In still further embodiments, the perhydrolase of the present invention provides enhanced performance in removing soils and stains from dishes and other items.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular and liquid forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the perhydrolase to such an extent that the perhydrolase is not effective as desired during normal use situations. Specific cleaning composition materials are exemplified in detail hereinafter.

As used herein, "effective amount of perhydrolase enzyme" refers to the quantity of perhydrolase enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like.

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Oral care compositions that find use in conjunction with the perhydrolases of the present invention are well known in the art (See e.g., U.S. Pat. Nos. 5,601,750, 6,379,653, and 5,989,526, all of which are incorporated herein by reference).

As used herein, "pulp treatment compositions" refers to the use of the present perhydrolase enzymes in compositions suitable for use in papermaking. It is intended that the term encompass compositions suitable for the treatment of any pulp material, including wood, as well as non-wood materials, such as "agricultural residues" and "fiber crops," including but not limited to wheat straw, rice straw, corn stalks, bagasse (sugar cane), rye grass straw, seed flax straw, flax straw, kenaf, industrial hemp, sisal, textile flat straw, hesperaloe, etc. Thus, the present invention also encompasses the use of the perhydrolases of the present invention in pulp treatment methods.

As used herein, "oxidizing chemical" refers to a chemical that has the capability of bleaching pulp or any other material. The oxidizing chemical is present at an amount, pH and temperature suitable for bleaching. The term includes, but is not limited to hydrogen peroxide and peracids.

As used herein, "acyl" is the general name for organic acid groups, which are the residues of carboxylic acids after removal of the —OH group (e.g., ethanoyl chloride, $CH_3CO$—Cl, is the acyl chloride formed from ethanoic acid, $CH_3COO$—H). The names of the individual acyl groups are formed by replacing the "-ic" of the acid by "-yl."

As used herein, the term "acylation" refers to the chemical transformation which substitutes the acyl (RCO—) group into a molecule, generally for an active hydrogen of an —OH group.

As used herein, the term "transferase" refers to an enzyme that catalyzes the transfer of functional compounds to a range of substrates.

As used herein, "leaving group" refers to the nucleophile which is cleaved from the acyl donor upon substitution by another nucleophile.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase "detergent stability" refers to the stability of a detergent composition. In some embodiments, the stability is assessed during the use of the detergent, while in other embodiments, the term refers to the stability of a detergent composition during storage.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$ and/or peracid. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to a different temperature (i.e., higher or lower) than optimum temperature for enzymatic activity. However, it is not intended that the present invention be limited to any temperature stability level nor temperature range.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the phrase "perhydrolase activity improvement" refers to the relative improvement of perhydrolase activity, in comparison with a standard enzyme. In some embodiments, the term refers to an improved rate of perhydrolysis product, while in other embodiments, the term encompasses perhydrolase compositions that produce less hydrolysis product. In additional embodiments, the term refers to perhydrolase compositions with altered substrate specificity.

As used herein, the phrase "alteration in substrate specificity" refers to changes in the substrate specificity of an enzyme. In some embodiments, a change in substrate specificity is defined as a difference between the $K_{cat}/K_m$ ratio observed with an enzyme compared to enzyme variants or other enzyme compositions. Enzyme substrate specificities vary, depending upon the substrate tested. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios for particular substrates of interest. For example, the perhydrolase enzymes of the present invention are more efficient in producing peracid from an ester substrate than enzymes currently being used in cleaning, bleaching and disinfecting applications. Another example of the present invention is a perhydrolase with a lower activity on peracid degradation compared to the wild type. Another example of the present invention is a perhydrolase with higher activity on more hydrophobic acyl groups than acetic acid. However, it is not intended that the present invention be limited to any particular substrate composition nor any specific substrate specificity.

As used herein, "surface property" is used in reference to an electrostatic charge, as well as properties such as the hydrophobicity and/or hydrophilicity exhibited by the surface of a protein.

As used herein, the phrase "is independently selected from the group consisting of . . ." means that moieties or elements that are selected from the referenced Markush group can be the same, can be different or any mixture of elements as indicated in the following example:

A molecule having 3 R groups wherein each R group is independently selected from the group consisting of A, B and C. Here the three R groups may be: AAA, BBB, CCC, AAB, AAC, BBA, BBC, CCA, CCB, or ABC.

In reference to chemical compositions, the term "substituted" as used herein, means that the organic composition or radical to which the term is applied is:
 (a) made unsaturated by the elimination of at least one element or radical; or
 (b) at least one hydrogen in the compound or radical is replaced with a moiety containing one or more (i) carbon, (ii) oxygen, (iii) sulfur, (iv) nitrogen or (v) halogen atoms; or
 (c) both (a) and (b).

Moieties which may replace hydrogen as described in (b) immediately above, that contain only carbon and hydrogen atoms, are hydrocarbon moieties including, but not limited to, alkyl, alkenyl, alkynyl, alkyldienyl, cycloalkyl, phenyl, alkyl phenyl, naphthyl, anthryl, phenanthryl, fluoryl, steroid groups, and combinations of these groups with each other and with polyvalent hydrocarbon groups such as alkylene, alkylidene and alkylidyne groups. Moieties containing oxygen atoms that may replace hydrogen as described in (b) immediately above include, but are not limited to, hydroxy, acyl or keto, ether, epoxy, carboxy, and ester containing groups. Moieties containing sulfur atoms that may replace hydrogen as described in (b) immediately above include, but are not limited to, the sulfur-containing acids and acid ester groups, thioether groups, mercapto groups and thioketo groups. Moieties containing nitrogen atoms that may replace hydrogen as described in (b) immediately above include, but are not limited to, amino groups, the nitro group, azo groups, ammonium groups, amide groups, azido groups, isocyanate groups, cyano groups and nitrile groups. Moieties containing halogen atoms that may replace hydrogen as described in (b) immediately above include chloro, bromo, fluoro, iodo groups and any of the moieties previously described where a hydrogen or a pendant alkyl group is substituted by a halo group to form a stable substituted moiety.

It is understood that any of the above moieties (b)(i) through (b)(v) can be substituted into each other in either a monovalent substitution or by loss of hydrogen in a polyvalent substitution to form another monovalent moiety that can replace hydrogen in the organic compound or radical.

As used herein, the terms "purified" and "isolated" refer to the removal of contaminants from a sample. For example, perhydrolases are purified by removal of contaminating proteins and other compounds within a solution or preparation that are not perhydrolases. In some embodiments, recombinant perhydrolases are expressed in bacterial or fungal host cells and these recombinant perhydrolases are purified by the removal of other host cell constituents; the percent of recombinant perhydrolase polypeptides is thereby increased in the sample.

As used herein, "protein of interest," refers to a protein (e.g., an enzyme or "enzyme of interest") which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide" and polypeptide are used interchangeably herein. Wherein a peptide is a portion of a protein, those skilled in the art understand the use of the term in context.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the perhydrolase of the present invention). In further embodiments, the term encompasses proteins that are immunologically cross-reactive. In most particularly preferred embodiments, the related proteins of the present invention very high ratios of perhydrolysis to hydrolysis.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the perhydrolase enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

In particularly preferred embodiments, homologous proteins are engineered to produce enzymes with the desired activity(ies). In some particularly preferred embodiments, the engineered proteins are included within the SGNH-hydrolase family of proteins. In some most preferred embodiments, the engineered proteins comprise at least one or a combination of the following conserved residues: L6, W14, W34, L38, R56, D62, L74, L78, H81, P83, M90, K97, G110, L114, L135, F180, G205. In alternative embodiments, these engineered proteins comprise the GDSL-GRTT and/or ARTT motifs. In further embodiments, the enzymes are multimers, including but not limited to dimers, octamers, and tetramers. In yet additional preferred embodiments, the engineered proteins exhibit a perhydrolysis to hydrolysis ratio that is greater than 1.

An amino acid residue of a perhydrolase is equivalent to a residue of M. smegmatis perhydrolase if it is either homologous (i.e., having a corresponding position in either the primary and/or tertiary structure) or analogous to a specific residue or portion of that residue in M. smegmatis perhydrolase (i.e., having the same or similar functional capacity to combine, react, and/or chemically interact).

In some embodiments, in order to establish homology to primary structure, the amino acid sequence of a perhydrolase is directly compared to the M. smegmatis perhydrolase primary sequence and particularly to a set of residues known to be invariant in all perhydrolases for which sequence is known. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of M. smegmatis perhydrolase are defined. In preferred embodiments, alignment of conserved residues conserves 100% of such residues. However, alignment of greater than 75% or as little as 50% of conserved residues are also adequate to define equivalent residues. In preferred embodiments, conservation of the catalytic serine and histidine residues are maintained. Conserved residues are used to define the corresponding equivalent amino acid residues of M. smegmatis perhydrolase in other perhydrolases (e.g., perhydrolases from other Mycobacterium species, as well as any other organisms).

In some embodiments of the present invention, the DNA sequence encoding M. smegmatis perhydrolase is modified. In some embodiments, the following residues are modified: Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. However, it is not intended that the present invention be limited to sequence that are modified at these positions. Indeed, it is intended that the present invention encompass various modifications and combinations of modifications.

In additional embodiments, equivalent residues are defined by determining homology at the level of tertiary structure for a perhydrolase whose tertiary structure has been determined by x-ray crystallography. In this context, "equivalent residues" are defined as those for which the atomic coordinates of two or more of the main chain atoms of a particular amino acid residue of the carbonyl hydrolase and M. smegmatis perhydrolase (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the perhydrolase in question to the M. smegmatis perhydrolase. As known in the art, the best model is the crystallographic model giving the lowest R factor for experimental diffraction data at the highest resolution available. Equivalent residues which are functionally and/or structurally analogous to a specific residue of M. smegmatis perhydrolase are defined as those amino acids of the perhydrolases that preferentially adopt a conformation such that they either alter, modify or modulate the protein structure, to effect changes in substrate binding and/or catalysis in a manner defined and attributed to a specific residue of the M. smegmatis perhydrolase. Further, they are those residues of the perhydrolase (in cases where a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *M. smegmatis* perhydrolase. The coordinates of the three dimensional structure of *M. smegmatis* perhydrolase were determined and are set forth herein (See e.g. Example 14) and find use as outlined above to determine equivalent residues on the level of tertiary structure.

In some embodiments, some of the residues identified for substitution, insertion or deletion are conserved residues whereas others are not. The perhydrolase mutants of the present invention include various mutants, including those encoded by nucleic acid that comprises a signal sequence. In some embodiments of perhydrolase mutants that are encoded by such a sequence are secreted by an expression host. In some further embodiments, the nucleic acid sequence comprises a homolog having a secretion signal.

Characterization of wild-type and mutant proteins is accomplished via any means suitable and is preferably based on the assessment of properties of interest. For example, pH and/or temperature, as well as detergent and/or oxidative stability is/are determined in some embodiments of the present invention. Indeed, it is contemplated that enzymes having various degrees of stability in one or more of these characteristics (pH, temperature, proteolytic stability, detergent stability, and/or oxidative stability) will find use. In still other embodiments, perhydrolases with low peracid degradation activity are selected.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

In some preferred embodiments, the perhydrolase gene is ligated into an appropriate expression plasmid. The cloned perhydrolase gene is then used to transform or transfect a host cell in order to express the perhydrolase gene. This plasmid may replicate in hosts in the sense that it contains the well-known elements necessary for plasmid replication or the plasmid may be designed to integrate into the host chromosome. The necessary elements are provided for efficient gene expression (e.g. a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the perhydrolase gene. In some embodiments, a selection gene such as an antibiotic resistance gene that enables continuous cultural maintenance of plasmid-infected host cells by growth in antimicrobial-containing media is also included.

The following cassette mutagenesis method may be used to facilitate the construction of the perhydrolase variants of the present invention, although other methods may be used.

First, as described herein, a naturally-occurring gene encoding the perhydrolase is obtained and sequenced in whole or in part. Then, the sequence is scanned for a point at which it is desired to make a mutation (deletion, insertion or substitution) of one or more amino acids in the encoded perhydrolase. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the perhydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "analogous sequence" refers to a sequence within a protein that provides similar function, tertiary structure, and/or conserved residues as the protein of interest (i.e., typically the original protein of interest). For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some preferred embodiments, the tertiary structure and/or conserved residues of the amino acids in the protein of interest are located at or near the segment or fragment of interest. Thus, where the segment or fragment of interest contains, for example, an alpha-helix or a beta-sheet structure, the replacement amino acids preferably maintain that specific structure.

As used herein, "homologous protein" refers to a protein (e.g., perhydrolase) that has similar action and/or structure, as a protein of interest (e.g., an perhydrolase from another source). It is not intended that homologs be necessarily related evolutionarily. Thus, it is intended that the term encompass the same or similar enzyme(s) (i.e., in terms of structure and function) obtained from different species. In some preferred embodiments, it is desirable to identify a homolog that has a quaternary, tertiary and/or primary structure similar to the protein of interest, as replacement for the segment or fragment in the protein of interest with an analogous segment from the homolog will reduce the disruptiveness of the change. In some embodiments, homologous proteins have induce similar immunological response(s) as a protein of interest.

As used herein, "homologous genes" refers to at least a pair of genes from different species, which genes correspond to each other and which are identical or very similar to each other. The term encompasses genes that are separated by speciation (i.e., the development of new species) (e.g., orthologous genes), as well as genes that have been separated by genetic duplication (e.g. paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that are identical with the nucleotide residues of the sequence.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25o below the Tm. Alternatively, or in addition, hybridization conditions can be based upon the salt or ionic strength conditions of hybridization and/or one or more stringency washes. For example, 6×SSC=very low stringency, 3×SSC=low to medium stringency, 1×SSC=medium stringency, and 0.5× SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, it is typically desirable to use relatively stringent conditions to form the hybrids (e.g., relatively low salt and/or high temperature conditions are used).

The phrases "substantially similar and "substantially identical" in the context of at least two nucleic acids or polypeptides typically means that a polynucleotide or polypeptide comprises a sequence that has at least about 40% identity, more preferable at least about 50% identity, yet more preferably at least about 60% identity, preferably at least about 75% identity, more preferably at least about 80% identity, yet more preferably at least about 90%, still more preferably about 95%, most preferably about 97% identity, sometimes as much as about 98% and about 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et. al., Proc. Natl. Acad. Sci. USA 89:10915 [1989]; Karin et al., Proc. Natl. Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "equivalent residues" refers to proteins that share particular amino acid residues. For example, equivalent resides may be identified by determining homology at the level of tertiary structure for a protein (e.g., perhydrolase) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

As used herein, the terms "hybrid perhydrolases" and "fusion perhydrolases" refer to proteins that are engineered from at least two different or "parental" proteins. In preferred embodiments, these parental proteins are homologs of one another. For example, in some embodiments, a preferred hybrid perhydrolase or fusion protein contains the N-terminus of a protein and the C-terminus of a homolog of the protein. In some preferred embodiment, the two terminal ends are combined to correspond to the full-length active protein.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA and the like as known in the art. (See, Chang and Cohen, Mol. Gen. Genet., 168:111-115 [1979]; Smith et al., Appl. Env. Microbiol., 51:634 [1986]; and the review article by Ferrari et al., in Harwood, *Bacillus*, Plenum Publishing Corporation, pp. 57-72 [1989]).

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhabitable enzyme) results in the amplification of either the endogenous gene encoding the gene product required for growth in the presence of the drug or by amplification of exogenous (i.e., input) sequences encoding this gene product, or both. Selection of cells by growth in the presence of a drug (e.g., an inhibitor of an inhabitable enzyme) may result in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a marker, gene or a vector encoding a gene which permits the amplification of that gene under appropriate growth conditions.

As used herein, the term "amplifiable nucleic acid" refers to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al, Proc. Natl. Acad. Sci. USA 69:3038 [1972]). Other nucleic acids are not replicated by this amplification enzyme. Similarly, in the case of T7 RNA polymerase, this amplification enzyme has a stringent specificity for its own promoters (See, Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to amplification methods (e.g., the polymerase chain reaction), refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195, 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

The Present Invention

In some most particularly preferred embodiments, the present invention finds use in the enzymatic generation of peracids from ester substrates and hydrogen peroxide. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Importantly, the present invention provides means for effective cleaning, bleaching, and disinfecting over broad pH and temperature ranges. In some embodiments, the pH range utilized in this generation is 4-12. In alternative embodiments, the temperature range utilized is between 5° and 90° C. The present invention provides advantages over the presently used systems (See e.g., EP Appln. 87-304933.9) in that bleaching is possible at the optimum pH of peracid oxidation, as well as providing bleaching at neutral pH, acidic pHs, and at low temperatures. While the present invention is described herein most fully in regard to laundry and fabric care, it is not intended that the present invention be limited to these applications. Indeed, the present invention finds use in various settings, particularly those in which bleaching by peracids and/or hydrogen peroxide are desired, including but not limited to laundry, fabric treatment, pulp and paper processing, personal care applications, disinfection and cleaning of hard surfaces. For example, it is contemplated that the compositions of the present invention will find use in bleaching of pulp, including use in methods such as those set forth in U.S. Pat. Nos. 6,569,286, 5,785,812, 6,165,318, and 4,400,237, all of which are herein incorporated by reference.

Historically, sodium perborate, and more recently, sodium percarbonate, have been used as bleaching compounds, particularly in European laundry detergents. This compound decomposes rapidly in aqueous solution to yield hydrogen peroxide ($H_2O_2$), which is the active bleaching species. As sodium perborate is more active at temperatures above 80° C., and less active in the temperature range of 40-60° C. (i.e., wash temperatures that have become most commonly preferred as of the 1950s), bleaching activators have been incorporated into laundry detergents that contain sodium perborate. Indeed, most laundry detergents contain bleaching activators. These activators are compounds with O- or N-bounded acetyl groups that are able to react with the strongly nucleophilic hydroperoxy anion to yield peroxyacetic acid. Since the reacting species is hydroperoxy anion, alkaline pHs are essential for the efficient conversion of these activators to peracids. The peroxyacetic acid is decomposed in weakly basic media to form singlet oxygen (See, Hofmann et al., J. Prakt. Chem., 334:293-297 [1992]).

Hydrogen peroxide is a particularly effective bleach at high temperatures (e.g., >40° C.) and pH (>10), conditions that are typically used in washing fabrics in some settings. However, as indicated above, cold water washing is becoming more commonly used and results in less effective bleaching by $H_2O_2$ than use of hot water. To overcome this low temperature disadvantage, detergent formulations typically include bleach boosters, such as TAED (N,N,N'N'-tetraacetylethylenediamine), NOBS (nonanoyloxybenzene sulfonate), etc. These boosters combine with $H_2O_2$ to form peracetic acid, a peracid species that is more effective than $H_2O_2$ alone. Although it helps the bleaching capability of detergent, the TAED reaction is only approximately 50% efficient, as only two out of the four acetyl groups in TAED are converted to peracids. Additionally, conversion of TAED into peracetic acid by hydrogen peroxide is efficient only at alkaline pHs and high temperatures. Thus, the TAED reaction is not optimized for use in all bleaching applications (e.g., those involving neutral or acidic pHs, and cold water). The present invention provides means to overcome the disadvantages of TAED use. For example, the present invention finds use in cold water applications, as well as those involving neutral or acidic pH levels. Furthermore, the present invention provides means for peracid generation from hydrogen peroxide, with a high perhydrolysis to hydrolysis ratio. The present invention further provides advantages over compositions that contain enzymes such as esterases and lipases) which have very low perhydrolysis to hydrolysis ratios.

In addition to its applications in detergents, the present invention provides methods and compositions for the use of peracids in textile bleaching and in various other applications. In some embodiments, the present invention provides one-step methods for textile processing applications, including but not limited to one-step desizing, scouring and bleaching processes (See e.g., EP WO 03002810, EP 1255888, WO 0164993, and US 20020007516, all of which are hereby incorporated by reference). As described in greater detail herein, in some embodiments, bleaching involves processing textile material before it is dyed and/or after it is incorporated into textile goods. However, it is not intended that the present invention be limited to any particular regimen of use nor any particular textile material.

Furthermore, the peracetic technology of the present invention finds use as an effective bactericide (See, Baldry, J. Appl. Bacteriol., 54:417-423 [1983]). Thus, the present invention provides compositions and methods for the sterilization/disinfection of various objects, including but not limited to medical devices, medical equipment, industrial equipment, and fermentors, as well as any additional object that needs to be sterilized or disinfected. As discussed in greater detail below, during the development of the present invention, the enzyme of the present invention was used in a standard cell kill experiment to demonstrate this suitability. In additional embodiments, the present invention provides compositions and methods suitable for use in biofilm control, such as in cooling towers.

Also as described in more detail in the Examples below, the present invention provides many advantages for cleaning and/or sterilization of a wide-range of objects, including but not limited to clothing, fabrics, medical devices, etc. In addition, the present invention provides compositions that are effective in cleaning, bleaching, and disinfecting, over a range of wash temperatures and pHs. In additional embodiments, the present invention finds use in degradation of peracids through the perhydrolase peracid degradation activity. In some preferred embodiments, this activity is used in peracid waste clean up applications.

Furthermore, the perhydrolase enzymes of the present invention are active on various acyl donor substrates, as well as being active at low substrate concentrations, and provide means for efficient perhydrolysis due to the high peracid:acid ratio. Indeed, it has been recognized that higher perhydrolysis to hydrolysis ratios are preferred for bleaching applications (See e.g., U.S. Pat. Nos. 5,352,594, 5,108,457, 5,030,240, 3974,082, and 5,296,616, all of which are herein incorporated by reference). In preferred embodiments, the perhydrolase enzymes of the present invention provide perhydrolysis to hydrolysis ratios that are greater than 1. In particularly preferred embodiments, the perhydrolase enzymes provide a perhydrolysis to hydrolysis ratio greater than 1 and are find use in bleaching.

In addition, it has been shown to be active in commonly used detergent formulations (e.g., Ariel Futur, WOB, etc.). Thus, the present invention provides many advantages in various cleaning settings.

As indicated above, key components to peracid production by enzymatic perhydrolysis are enzyme, ester substrate, and hydrogen peroxide. Hydrogen peroxide can be either added directly in batch, or generated continuously "in situ." Current washing powders use batch additions of $H_2O_2$, in the form of percarbonate or perborate salts that spontaneously decompose to $H_2O_2$. The perhydrolase enzymes of the present invention find use in the same washing powder batch method as the $H_2O_2$ source. However, these enzymes also find use with any other suitable source of $H_2O_2$, including that generated by chemical, electro-chemical, and/or enzymatic means. Examples of chemical sources are the percarbonates and perborates mentioned above, while an example of an electrochemical source is a fuel cell fed oxygen and hydrogen gas, and an enzymatic example includes production of $H_2O_2$ from the reaction of glucose with glucose oxidase. The following equation provides an example of a coupled system that finds use with the present invention.

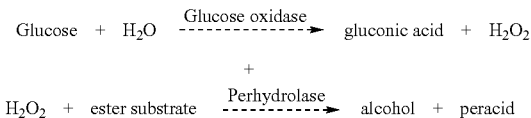

It is not intended that the present invention be limited to any specific enzyme, as any enzyme that generates $H_2O_2$ with a suitable substrate finds use in the methods of the present invention. For example, lactate oxidases from *Lactobacillus* species which are known to create $H_2O_2$ from lactic acid and oxygen find use with the present invention. Indeed, one advantage of the methods of the present invention is that the generation of acid (e.g., gluconic acid in the above example) reduces the pH of a basic solution to the pH range in which the peracid is most effective in bleaching (i.e., at or below the pKa). Other enzymes (e.g., alcohol oxidase, ethylene glycol oxidase, glycerol oxidase, amino acid oxidase, etc.) that can generate hydrogen peroxide also find use with ester substrates in combination with the perhydrolase enzymes of the present invention to generate peracids. In some preferred embodiments, the ester substrates are selected from one or more of the following acids: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Thus, as described herein, the present invention provides definite advantages over the currently used methods and compositions for detergent formulation and use, as well as various other applications.

DETAILED DESCRIPTION OF THE PRESENT INVENTION

The present invention provides methods and compositions comprising at least one perhydrolase enzyme for cleaning and other applications. In some particularly preferred embodiments, the present invention provides methods and compositions for generation of peracids. The present invention finds particular use in applications involving cleaning, bleaching and disinfecting.

Cloning and Characterization of *M. smegmatis* Perhydrolase

The cloning of the *M. smegmatis* perhydrolase (i.e., referred to herein as the "phd" gene, which encodes the "Phd" protein; this perhydrolase gene is sometimes herein referred to as the "act" gene and the protein is sometimes referred to as the "Act" protein) of the present invention was based on peptide sequence data from the acyltransferase purified from *Mycobacterium parafortuitum* (previously known as *Corynebacterium oxydans*) and published information regarding the 7-aminocephalosporanic acid (7-ACA) arylesterase gene of *Agrobacterium radiobacter* (Sakai et al., J. Ferment. Bioengineer., 85: 138-143 [1998]). Two peptide sequences from purified *M. parafortuitum* acyltransferase were found to be similar to internal N- and C-terminal regions of the *A. radiobacter* 7-ACA-arylesterase (47% and 42% identity respectively).

A set of PCR primers was designed based on the amino acid sequence of these internal peptides (designated "AtintF" and "AtintR"). Another set of primers was developed based on the 5' and 3' ends ("ATNcoI" and "ATBamH1") of the *A. radiobacter* 7-ACA DNA sequence. A single product of the expected size was amplified from *M. parafortuitum* chromosomal DNA using both sets of primers. The full length product, amplified by the ATNcoI/ATBamH1 primer pair, was cloned into pET16b and transformed into BL21 cells (Novagen, Madison, Wis.). This clone had a sequence identical to that of the *A. radiobacter* 7-ACA gene. As it was determined that purified *M. parafortuitum* perhydrolase was not the 7-ACA acyl esterase, it was concluded that this was not the gene encoding the perhydrolase of the present invention.

Thus, efforts were further focused on *M. smegmatis* for cloning and expression of the perhydrolase of the present invention. To identify the *M. parafortuitum* gene based on enzyme activity screening, a plasmid library of *M. parafortuitum* DNA in *M. smegmatis* was constructed using a plasmid with a promoter to drive expression of cloned genes. Surprisingly, *M. smegmatis* itself was found to be positive for perhydrolase and acyltransferase activity. Thus, in some instances herein, the perhydrolase is referred to as "ACT" (or "Act"). A protein BLAST search of the *M. smegmatis* unfinished genome using the sequence of the *A. radiobacter* 7-ACA identified a 2 kb contig containing an ORF (open reading frame) that encoded a hypothetical protein that was similar but not identical to the 7-ACA protein. Based on this sequence, primers were designed and used to amplify the gene from *M. smegmatis* (ATCC 10143). By adding an *E. coli* ribosome binding site upstream of the start codon, a clone that expressed active enzyme was obtained. The vector used was either pCR2.1TOPO or pBluntIITOPO Invitrogen, Carlsbad, Calif.), in *E. coli* Top10 cells. The gene was expressed constitutively from the plasmid-encoded lac promoter. This enzyme carried out the same reactions as the originally described *M. parafortuitum* acyltransferase.

During the characterization of the perhydrolase of the present invention, standard protein BLAST searches identified a few proteins (<20) with sequence similarity of 30-80%. This group included the 7-ACA arylesterases from *A. radiobacter* and other organisms, which have 43% identity with *M. smegmatis* perhydrolase. All of the identified homologs with at least 40% similarity have a GDS motif very near the N-terminal end. All of the proteins also contain most of the conserved residues which could place them within the suggested GDSL family of lipolytic enzymes (See e.g., Upton and Buckley, Trends Biochem. Sci., 20:178 [1995]). However, enzymes mentioned in this paper do not appear on homology searches with the perhydrolase protein. Indeed these proteins have less than 20% similarity with the perhydrolase and its homologs, suggesting that the acyltransferase-related (and perhydrolase of the present invention) enzymes form a subfamily.

The natural function of the enzyme of the present invention and the closely related proteins, apart from the 7-ACA arylesterase, have not been biochemically determined. *M. smegmatis* appears to be the only organism with the acyltransferase/perhydrolase in an operon with a putative penicillin binding protein (PBP). While it is not intended that the present invention be limited to any particular mechanism, this suggests that the enzyme may be involved in cell wall synthesis/structure or modification of molecules taken up from the environment. There are no homologues of the perhydrolase of the present invention that have been identified in *M. tuberculosis* or *M. leprae* to date. However, some organisms were determined to have multiple homologues (e.g., *S. meliloti*).

During the development of the present invention, various mutations were made in the *M. smegmatis* perhydrolase in order to assess its activity. This enzyme contains two cysteine residues, which were hypothesized as potentially forming disulfide bonds, both of which were changed to alanine, in order to determine whether or not the C residues had any effect on the activity of the enzyme. Activity assay results obtained using the transesterification (in aqueous solution) assay described herein indicated that C7A, as well as C77A, and a double mutant (C7A and C77A) were of the same size and specific activity.

Many enzymes have the amino acid serine as part of their active site and are therefore referred to, among other designations, as "serine hydrolases." The active site may consist of a catalytic triad of S (serine), D (aspartic acid) and H (histidine). Examples of such enzymes include, but are not limited to subtilisin (D32-H64-S215), chymotrypsin (H57-D102-S195) and lipases in the alpha/beta hydrolase family (e.g., S126-D176-H206). A typical motif for lipases is the GDSL motif (Upton and Buckley, supra [1995]) in which the S is the active site serine. Since the perhydrolase of the present invention was determined to have a GDSL (amino acids 9-12) motif, the S11 was mutated to an A, in order to confirm the involvement of this S in the active site. As indicated in the Examples, the activity assay results indicated that S11A had only 1% of the activity of the wild-type enzyme. Deletion of the C-terminal 25 amino acids also resulted in abrogation of the activity, suggesting that these amino acids either contained a residue involved directly in the active site, and/or that the structure of the protein was affected such that the active site was no longer able to catalyze the reactions. In addition, the predicted active site residues, D192 and H195 were mutated to A. Neither mutant had activity, confirming that the active site residues of the perhydrolase of the present invention consist of S11, D192 and H195. However, it is not intended that the present invention be limited to any particular mechanism, nor is the present invention limited to mutation(s) at any particular active site residues.

Cloning of *M. Parafortuitum* Perhydrolase

There were some differences between the N-terminal peptide sequence obtained from the *M. parafortuitum* enzyme and the N-terminal sequence of *M. smegmatis* perhydrolase. However, there was a sequence in the C-terminal region of the *M. smegmatis* perhydrolase identical to the C-terminal peptide sequence of the *M. parafortuitum* enzyme. Two primers were designed to amplify a partial sequence of the *M. parafortuitum* perhydrolase gene; the sequence of the reverse primer was identical to the sequence of the corresponding region in *M. smegmatis* perhydrolase gene, and the sequence of the forward primer was based on *M. smegmatis* codon usage. The forward primer, MP5: 5'-ATGGGTACCCGAC-GAATTCTGTCCTTCGGTGATTCCCTGACCT-3' (SEQ ID NO:11) and the reverse primer MPC-intR 5'-GATTC-CGTCGACGCCGTCGGTGCTGATCAC-CGAACCCGCGTCGAAGAACGG-3' (SEQ ID NO:12). The partial gene was amplified from the chromosome of *M. parafortuitum* and cloned into pCR2.1TOPO (Invitrogen, Carlsbad, Calif.). Sequence analysis showed that the enzyme is very similar, but not identical to the *M. smegmatis* perhydrolase (77% identity). Based on the molecular weights of the monomers of the perhydrolases determined by SDS-PAGE (MP AT: 26 kDa, MSAT: 24 kDa, MP cloned AT: ~18 kDa), the clone from primers made to the internal fragment was determined to be missing approximately 70 amino acids (~8 kDa). The remaining sequence at the 5'-end of the *M. parafortuitum* gene can be obtained by any of several methods suitable and familiar to those skilled in the art of molecular biology, including, but not limited to, inverse PCR, probing of plasmid/cosmid libraries of *M. parafortuitum* chromosomal DNA, sequencing of the gene directly from chromosomal DNA (e.g., as performed by Fidelity Systems, Bethesda Md.).

Expression of the *M. smegmatis* Perhydrolase

The perhydrolase is an intracellular protein in its native host. Production of the perhydrolase in non-native hosts may also be done intracellularly. However, in some embodiments, a signal sequence is added to the perhydrolase, which facilitates expression of the perhydrolase by secretion into the periplasm (i.e., in Gram-negative organisms, such as *E. coli*), or into the extracellular space (i.e., in Gram-positive organisms, such as *Bacillus* and *Actinomycetes*), or eukaryotic hosts (e.g., *Trichoderma, Aspergillus, Saccharomyces*, and *Pichia*). Of course, these are just a few examples of possible prokaryotic and eukaryotic hosts. It is not intended that the present invention be limited to these specific hosts, as various other organisms find use as expression hosts in the present invention.

A variety of commercially available expression systems, including but not limited to pBAD, plac, T7, find use in the expression of the perhydrolase in Gram-negative hosts (e.g.,

*E. coli*). In some embodiments, the same types of promoters find use in another Gram-negative host, *Pantoea citrea*.

To test expression in *E. coli* two strategies were used: 1) adding an RBS (ribosome binding site) to the 5' end of the phd gene and cloning the gene into pCRBLUNTIITOPO (Invitrogen), thus allowing expression directly from the pLac promoter available in that vector; and 2) cloning the phd gene under control of the T7 promoter in the plasmid pET16b (Novagen). In the latter system, expression of the gene is inducible by addition of IPTG to the growing culture and use of a specific host cell (e.g., BL21(λDE3)pLysS (Novagen)) that contains the λDE3 lysogen encoding the T7 RNA polymerase. The first strategy produces a plasmid capable of allowing expression of the perhydrolase protein in other Gram-negative hosts (e.g., *P. citrea*);

To express protein in *E. coli* or *P. citrea* using the first strategy, cultures were grown from single, purified colonies at 37° C. overnight in L broth plus the appropriate antibiotic (example, kanamycin 50 μg/ml). Expression of the protein was determined by the pNB assay (See, Example 1) after lysis of the cells.

Expression of the perhydrolase using the T7 expression system requires induction of the culture with the addition of IPTG (e.g., 100 mmole IPTG added at an $OD_{550}$ of 0.4). Overnight cultures, inoculated from a single colony, are used to inoculate the expression culture of the desired volume (25 mls to several liters) at an $OD_{550}$ of 0.1. The expression culture was then grown at the desired temperature (e.g. 25° C., 30° C., 37° C.) until an $OD_{550}$ of 0.4 was reached, after which IPTG was added. Expression was allowed to continue for 3 hours to overnight. Protein expression was monitored by pNB activity assay as described in Example 1. Usually, expression from the T7 system gives a high titer of protein, sufficient for further analysis such as crystallography.

*Bacillus* species are well-known as suitable hosts for expression of extracellular proteins (e.g., proteases). Intracellular expression of proteins is less well known. Expression of the perhydrolase protein intracellularly in *Bacillus subtilis* can be done using a variety of promoters, including, but not limited to pveg, pSPAC, pAprE, or pAmyE in the absence of a signal sequence on the 5' end of the gene. In some embodiments, expression is achieved from a replicating plasmid (high or low copy number), while in alternative embodiments, expression is achieved by integrating the desired construct into the chromosome. Integration can be done at any locus, including but not limited to the aprE, amyE, or pps locus. In some embodiments, the perhydrolase is expressed from one or more copies of the integrated construct. In alternative embodiments, multiple integrated copies are obtained by the integration of a construct capable of amplification (e.g., linked to an antibiotic cassette and flanked by direct repeat sequences), or by ligation of multiple copies and subsequent integration into the chromosome. In some embodiments, expression of the perhydrolase with either the replicating plasmid or the integrated construct is monitored using the pNB activity assay (described herein) in an appropriate culture.

As with *Bacillus*, in some embodiments, expression of the perhydrolase in the Gram-positive host *Streptomyces* is done using a replicating plasmid, while in other embodiments, expression of the perhydrolase is accomplished via integration of the vector into the *Streptomyces* chromosome. Any promoter capable of being recognized in *Streptomyces* finds use in driving transcription of the perhydrolase gene (e.g., glucose isomerase promoter, A4 promoter). Replicating plasmids, either shuttle vectors or *Streptomyces* only, also find use in the present invention for expression (e.g, pSECGT).

Structure of *M. smegmatis* Perhydrolase

Figure 3:
FIG. 3 provides a schematic of four structural families of serine hydrolases, including perhydrolase (SGNH-hydrolase family), chymotrypsin, subtilisin, and α/β hydrolase.
Figure 4:
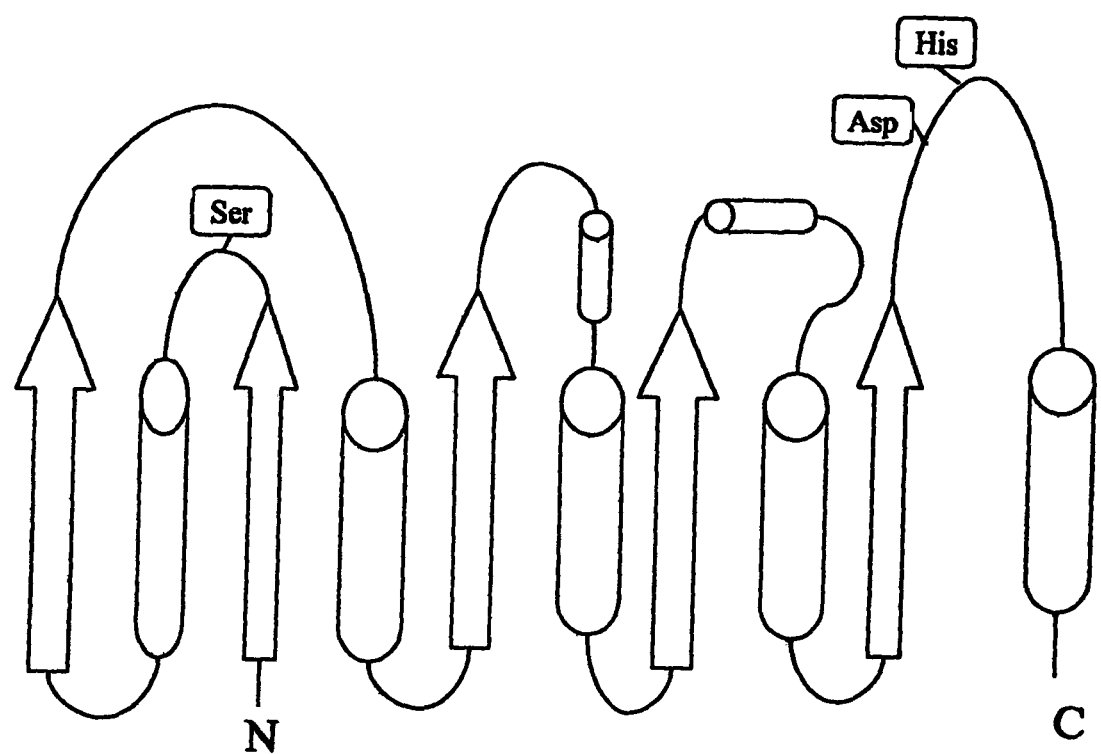
FIG. 4 provides a diagram of the structure of the perhydrolase fold.

The crystal structure of the *M. smegmatis* perhydrolase was determined to 2.2 Angstroms. The structure confirmed findings with gel filtration sizing columns, that indicated this enzyme is an octamer. The structure of the monomer places the enzyme in the class known as SGNH-hydrolases (See e.g., Molgaard et al., Structure 8: 373-383 [2000]). The active site residues were identified as S11-D192-H195, based on homology, confirming the identification of the catalytic triad based on loss of activity in the S11A, D192A, and H195A mutations described above. FIG. 3 provides schematics showing the structure of the *M. smegmatis* perhydrolase, as well as other serine hydrolases. As indicated, this enzyme has a different structure than the enzymes shown here (chymotrypsin, subtilisin, and α/β hydrolase). Indeed, the structural analysis of the perhydrolases of the present invention indicates that this group of enzymes has a different form and active site than do these other enzymes. A schematic diagram of the structure of the monomer is illustrated in FIG. 4. The structures of four other enzymes in the SGNH-hydrolase family have been solved, namely *Aspergillus aculeatus* rhamnogalucturonan acetylesterase (RGAE), *Bos taurus* platelet activating factor (PAF-AH(1b)a), *Streptomyces scabies* esterase (SsEst) and the thioesterase/Protease I/Phospholipase $L_1$ (TAP or Tes) from *E. coli*. Very little sequence or functional homology is present in these enzymes. Basically, the sequence identity is reserved for the residues involved in the active site and those defining the family. While the overall folding of the enzymes is similar (See e.g., Molgaard et al., supra [2000], for overlaying of structures), there are structural differences. For example, there is a loop covering the active site in SsEst, compared to RGAE and TAP which have active sites that are surface-exposed. The *M. smegmatis* perhydrolase has an active site that is somewhat buried. The binding residues of the *M. smegmatis* perhydrolase were identified as Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196. These sites were derived from direct observation and by modeling studies to model substrate binding to the enzyme, using methods known in the art.

As indicated above, the *M. smegmatis* perhydrolase was found to be an octamer in the crystalline state. However, it is contemplated to be either a hexamer or octamer in solution. The octamer is seen to be a tetramer of dimers, two molecules are much more closely and extensively interacting and these are termed the "act transferase" dimers. Several of the conserved sites are found along this dimer interface. For example, residues Trp 14, Arg 27, Arg 56, His 81 and Pro 83, were found to be conserved in natural isolates that have perhydrolase activity and are contemplated to be critical in forming the interface. In addition one other residue, Glu 51, which is conserved in all but one of the natural isolates (and in that case it is a homologous enzyme) was identified.

One additional feature of interest in that in the natural isolates showing perhydrolase activity, all share an insertion of residues 69-81. This region forms a loop that is at the dimer interface. Without this loop, it is believed that much of the dimer interface would be lost and it is likely that dimers and subsequent aggregation would not occur. Thus, there is a correlation of the insertion with the structural aggregation particularly dimer formations and the appearance of perhydrolase activity. However, it is not intended that the present invention be limited to any particular mechanisms.

Key residues were found to be associated with desired activity in selected homologs. Indeed, there are several conserved residues that are contemplated to have importance for acyltransferase activity. These include Leu 6, Trp 14, Arg 27, Trp 34, Asp 62, Leu74, Leu 78 His 81, Pro83, Met 90, Lys 97, and Leu 114.

In additional analyses, the association of the perhydrolase with carbamate was investigated. The native octamer was determined in space group P4 with unit cell dimensions: a=98.184 b=98.184 and c=230.119 α=90.00 β=90.00 γ=90.00, this crystal diffracted to about 2.0 Å. The carbamate-inhibited crystal grew in the space group P1 with unit cell dimensions a=67.754, b=80.096, and c=85.974 α=104.10 °, β=112.10°, and γ=97.40° and these crystals diffract to a resolution exceeding 1.0 Å.

The carbamate was bound in a manner to exploit the interactions between the keto oxygen of the carbamate and residues forming the oxyanion hole, the amide N atoms of Ser 11 and Ala 55 and Asn 94 ND2. The hydrophobic side chain extends along the hydrophobic surface of the binding site out into the surface opening between pairs of dimers in the octamer structure. The carbamate moiety direction highlights the pivotal role of the S54V mutation. The hydrophobic moiety passes adjacent to the side chain of ser 54. Mutating the serine side to valine increased the hydrophobicity, and also served as a gatekeeper to prevent hydrophilic nucleophiles (e.g., water) for competing with desired deacylating nucleophiles. The residues surrounding the carbamate moiety on the same and neighboring molecules forming the extended entry are expected to influence the selection of the optimal deacylating nucleophile. The structure showed that each monomer was inhibited with carbamate covalently attached. Thus, all octamer active sites were found to be active and functional. The side chain of carbamate resembles the leaving groups of the substrates tested. Thus, the carbamate moiety indicates the access direction for substrate.

*M. smegmatis* Perhydrolase is an SGNH-Hydrolase

The perhydrolase of the present invention has certain components that indicate it is in the SGNH-hydrolase family of enzymes. This family is defined by having the four conserved amino acids SGN and H in four blocks, similar to the blocks that describe the lipolytic family of enzymes (See, Upton and Buckley, supra). In the case of the *M. smegmatis* perhydrolase, these correspond to S11, G52, N94 and H195 which correspond to Blocks I II, III and V according to Upton and Buckley (Upton and Buckley, supra) and Molgaard et al. (Molgaard et al., supra). These amino acids are also conserved within the closest sequence homologs of the perhydrolase.

As indicated herein, the sequences were aligned using the Alignment program in Vector NTi (Informax, Invitrogen) In the following alignment providing a comparison of homolog sequences, the double underline indicates the residues involved in the active site. AR: *Agrobacterium rhizogenes* Q9 KWA6; RR: *Rhizobium rhizogenes* NF006; SM: *Sinorhizobium meliloti* RSM02162; MS: *Mycobacterium smegmatis* Act; MP: *Mycobacterium parafortuitum* Phd partial sequence; PD: *Prosthecobacter dejongeii* RVM04532. The amino acids within the blocks defining the SGNH-hydrolase family are indicated in bold letters.

```
                  Block I                                      Block II
                    GDB                                           G
AR(1)     ----------MAESRSILCFGDSLTWGWIPVPESSP   TLRYPFEQRWTGAMAAALGDGYSIIEEGLSARTTSVED--PN
RR(1)     ----------MAESRSILCFGDSLTWGWIPVPESSP   TLRYPFEQRWTGAMAAALGDGYSIIEEGLSARTTSVED-PN
RM(1)     MTINSHSWRTLMVEKRSVLCFGDSLTWGWIPVEESSP   TLRYPYEQRWTGAMAARLGDGYHIIEEGLSARTTSLDD-PN
SM(1)     ----------MVEKRSVLCFGDSLTWGWIPVKESSP   TLRYPYEQRWTGAMAARLGDGYHIIEEGLSARTTSLDD-PN
MS(1)     --------------MAKRILCFGDSLTWGWVPVEDGAP   TERFAPDVRWTGVLAQQLGADFEVIEEGLSARTTNIDD-PT
MP        --------------GTRRILSFGDSLTWGWIPVEEGVP   TERFPRDVRWTGVLADLLGDRYEVIEEGLSARTTTAED-PA
PD(1)     --------------MKTILCFGDSNTWGYDPASMTAPF   PRRHGPEVRWTGVLAKALGAGFRVIEEGQNGRTTVHED--PL Block III
                                   GxND
AR(67)   DPRLNGSAYLPMALASHLPLDLVIILLGTNDTKSYFRRTPYEIANGMGKLAGQVLTSAGGIGTPYPAPKLLIVSPPPLAP
RR(67)   DPRLNGSAYLPMALASHLPLDLVIILLGTNDTKSYFRRTPYEIANGMGKLAGQVLTSAGGIGTPYPAPKLLIVSPPPLAP
RM(78)   DARLNGSTYLPMALASHLPLDLVIIMLGTNDTKSYFHRTPYEIANGMGKLVGQVLTCAGGVGTPYPAPKVLVVAPPPLAP
SM(67)   DARLNGSTYLPMALASHLPLDLVIIMLGTNDTKSYFHRTPYEIANGMGKLVGQVLTCAGGVGTPYPAPKVLVVAPPPLAP
MS(65)   DPRLNGASYLPSCLATHLPLDLVIIMLGTNDTKAYFRRTPLDIALGMSVLVTQVLTSAGGVGTTYPAPKVLVVSPPPLAP
MP(65)   DPRLNGSQYLPSCLASHLPLDLVILMLGTNDTKANFGRTPFDIATGMGVLATQVLTSAGGVGTSYPAPQVLIVAPPPLGE
PD(65)   NICRKGKDYLPACLESHKPLDLVILMLGTNDLKSTFNVPPGEIAAGAGVLGRMILAGDAGP-ENRPPQLLLMCPPKVRDL Block V
                                  DGIHF
AR(147)  MPDPWFEGMFGGGYEKSLELAKQYKALANFLKVDFLDAGEFVKTDGCDGIHFSAETNITLGHAIAAKVEAIFSQEAKNAA    (SEQ ID NO: 14)
RR(147)  MPDPWFEGMFGGGYEKSLELAKQYKALANFLKVDFLDAGEFVKTDGCDGIHFSAETNITLGHAIAAKVEAIFSQEAKNAA    (SEQ ID NO: 15)
RM(158)  MPDPWFEGMFGGGYEKSKELSGLYKALADFMKVEFFAAGDCISTDGIDGIHLSAETNIRLGHAIADKVAALF--------    (SEQ ID NO: 16)
SM(147)  MPDPWFEGMFGGGYEKSKELSGLYKALADFMKVEFFAAGDCISTDGIDGIHLSAETNIRLGHAIADKVAALF--------    (SEQ ID NO: 17)
MS(145)  MPHPWFQLIFEGGEQKTTELARVYSALASFMKVPFFDAGSVISTDGVDGIHFTEANNRDLGVALAEQVRSLL--------    (SEQ ID NO: 18)
MP 145)  LPHPWFDLVFSGGREKTAELARVYSALASFMKVPFFDAGSVISTDGVDGI------------------------    (SEQ ID NO: 19)
PD(144)  SAMPDLDAKIPHGAARSAEFPRHYKAQAVALKCEYFNSQEIVETSPVDGIHLEASEHLKLGEALAEKVKVLLG-------    (SEQ ID NO: 20)
```

The primers used to identify homologs for each of the Blocks indicated above are provided below:

```
Block I (forward 5'-3)
1e: acggtcctgtgctttggngaytcnyt           (SEQ ID NO: 21)

1f: acggtcctgtgctttggngayagyyt           (SEQ ID NO: 22)

1g: gcggtcctgttctwnggngaytcnyt           (SEQ ID NO: 23)

1h: gcggtcctgttctwnggngayagyyt           (SEQ ID NO: 24)

1i: gctcgaaccgtcctctgttttggngaytcnyt     (SEQ ID NO: 25)

1j: gctcgaaccgtcctctgttttggngayagyyt     (SEQ ID NO: 26)

1k: gctcgaaccgtcctctgtttnggngaytc        (SEQ ID NO: 27)

1l: gctcgaaccgtcctctgttttggngaytcnytn    (SEQ ID NO: 28)

1m: gctcgaaccgtcctctgttttggngaytcnytg    (SEQ ID NO: 29)

1A: gccaagcgaattctgtgtttcggngaytcnyt     (SEQ ID NO: 30)

1B: gccaagcgaattctgtgtttcggngayagyyt     (SEQ ID NO: 31)

Block III (reverse 5'-3)
3c: attccgcgcttcagrtcrttnvtncc           (SEQ ID NO: 32)

3d: attccgcgcttcagrtcrttnwgncc           (SEQ ID NO: 33)

3e: attccgcgcttcagrtcrttnscncc           (SEQ ID NO: 34)

3f: attccgcgcttcagrtcrttnrancc           (SEQ ID NO: 35)

3k: attccgcgcttcagrtcrttnrtncc           (SEQ ID NO: 36)

3l: attccgcgcttcagrtcrttnytncc           (SEQ ID NO: 37)

3m: attccgcgcttcagrtcrttnsgncc           (SEQ ID NO: 38)

3n: attccgcgcttcagrtcrttnwcncc           (SEQ ID NO: 39)

3o: attccgcgcttcagrtcrttnyancc           (SEQ ID NO: 40)

3p: attccgcgcttgrsrtcrttnrtncc           (SEQ ID NO: 41)

3q: attccgcgcttgrsrtcrttnytncc           (SEQ ID NO: 42)

3r: attccgcgcttgrsrtcrttnsgncc           (SEQ ID NO: 43)

3s: attccgcgcttgrsrtcrttnwcnnn           (SEQ ID NO: 44)

3t: attccgcgcttgrsrtcrttnyancc           (SEQ ID NO: 45)

3A: gcgccggaagtaggccttggtrtcrttnvtncc    (SEQ ID NO: 46)

3B: gcgccggaagtaggccttggtrtcrttnwgncc    (SEQ ID NO: 47)

3C: gcgccggaagtaggccttggtrtcrttnscncc    (SEQ ID NO: 48)

3D: gcgccggaagtaggccttggtrtcrttnrancc    (SEQ ID NO: 49)

Block III (forward 5'-3)
3g: cggaattatcatgctgggnabnaayga          (SEQ ID NO: 50)

3h: cggaattatcatgctgggncwnaayga          (SEQ ID NO: 51)

3i: cggaattatcatgctgggngsnaayga          (SEQ ID NO: 52)

3j: cggaattatcatgctgggntynaayga          (SEQ ID NO: 53)

3u: ccggaattatcatgctnggnabnaayga         (SEQ ID NO: 54)

3v: ccggaattatcatgctnggncwnaayga         (SEQ ID NO: 55)

3w: ccggaattatcatgctnggngsnaayga         (SEQ ID NO: 56)

3x: ccggaattatcatgctnggntynaayga         (SEQ ID NO: 57)

Block V (reverse 5'-3)
```

-continued

| | | |
|---|---|---|
| 5c: | acccttagcgtttggrtgnrtnccrtc | (SEQ ID NO: 58) |
| 5d: | atccttagcgtttggrtgnavnccrtc | (SEQ ID NO: 59) |
| 5e: | aatcttagccgtgrrrtgnrtnccrtc | (SEQ ID NO: 60) |
| 5f: | aatcttagccgtgrrrtgnrcnccrtc | (SEQ ID NO: 61) |
| 5g: | aatcttagccgtgrrrtgntrnccrtc | (SEQ ID NO: 62) |
| 5h: | ccgctggtcctcatctggrtgnrtnccrtc | (SEQ ID NO: 63) |
| 5i: | ccgctggtcctcatctggrtgnrcnccrtc | (SEQ ID NO: 64) |
| 5j: | ccgctggtcctcatctggrtgntrnccrtc | (SEQ ID NO: 65) |
| 5k: | ccgctggtcctcatcraartgnrtncc | (SEQ ID NO: 66) |
| 5A: | cgattgttcgcctcgtgtgaartgnrtnccrtc | (SEQ ID NO: 67) |
| 5B: | cgattgttcgcctcgtgtgaartgnrcnccrtc | (SEQ ID NO: 68) |
| 5C: | cgattgttcgcctcgtgtgaartgntrnccrtc | (SEQ ID NO: 69) |

As described in greater detail herein, the sequence and structure results are supported by the activity data that indicate the perhydrolase enzymes of the present invention differ from lipolytic enzymes known in the art.

Identification of Homologs

As well known in the art, proteins with a desired activity may be identified in several ways, including but not limited to: 1) searching available databases for proteins with sequence homology (30-100%); 2) screening environmental isolates for the desired activity; and 3) examining type strains from ATCC of the genus identified to have activities (e.g., *Mycobacterium* and *Corynebacterium*, as described herein in particular embodiments).

By doing a standard protein-protein BLAST search, several homologs were identified from fully or partially sequenced genomes. From the known gene sequence, several homologs were amplified by PCR from the chromosome of the parent organism and cloned into a pET expression vector, essentially as described for the cloning of phd from *M. smegmatis* into pET16b. Homologues identified by this BLAST search included: *Agrobacterium rhizogenes* Q9 KWA6, *A. rhizogenes* Q9 KWB1 *A. tumefaciens* Q8UFG4, *A. tumefaciens* Q8UACO (now AgrL, identical to 7-ACA arylesterase), *A. tumefaciens* Q9ZI09, *A. tumefaciens* (radiobacter) ACA, *Prosthecobacter. dejongeii* RVM04532, *Rhizobium. loti* Q98MY5, *R. meliloti* Q92XZ1, *R. meliloti* Q9EV56, *R. rhizogenes* NF006, *R. rhizogenes* NF00602875, *R. solanacerarum* Q8XQIO, *Sinorhizobium meliloti* RSM02162, *S. meliloti* RSM05666, *Mesorhizobium loti* RMLO00301, *A. rhizogenes* Q9 KWA6, and *A. rhizogenes* Q9 KWB1.

Figure 2:
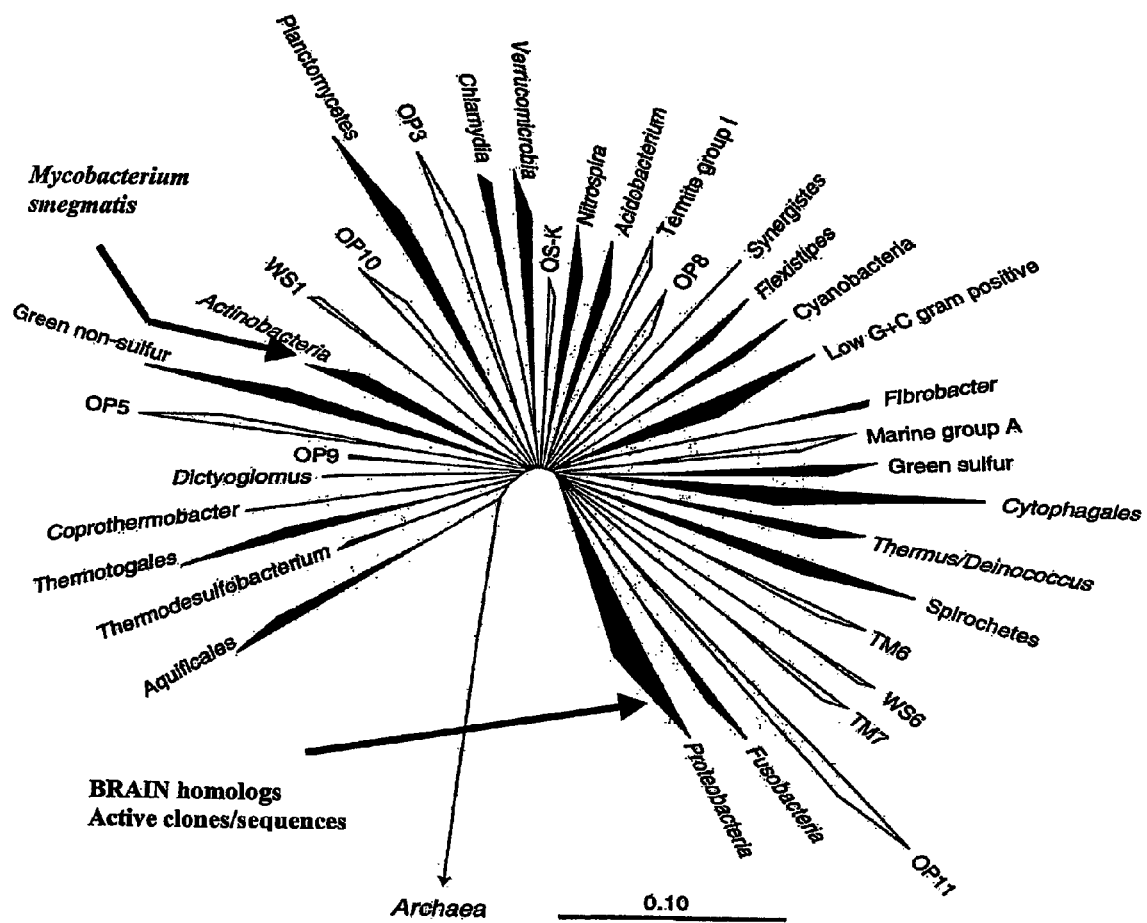
FIG. 2 provides an overview phylogenetic tree, showing the major branches of the bacteria and the origin of the active clones/sequences compared to *M. smegmatis*.

Based on these results, a homology tree of proteins with sequence homology (20-80%) to *M. smegmatis* perhydrolase was generated. As shown in FIG. 2, an enzyme in the family of lipolytic enzymes described by Upton and Buckley (supra) is that of *V. mimicus*. This phylogenetic tree was generated using the alignment program in Vector NTi (Informax, Invitrogen). The green arrow indicates *M. smegmatis* perhydrolase, the red arrow indicates *A. radiobacter* 7-ACA arylesterase, the blue arrow indicates *E. coli* TAP, and the black arrow indicates *A. aculeatus* RGAE.

As further indicated in FIG. 2, the perhydrolase is not closely related to this enzyme. The perhydrolase and its closest relatives, *Prosthecobacter dejongeii* RVM04532, *R. rhizogenes* NF006, *A. rhizogenes* Q9 KWA6, *R. meliloti* Q92XZ1, *S. meliloti* RSM02162, *A. rhizogenes* Q9 KWB1 and *R. rhizogenes* NF00602875 come off their own branch (i.e., a branch that is different from the 7-ACA arylesterase-like proteins and the RGAE/TAP-like proteins). However, it is contemplated that some additional, more distantly related homologs will find use in the present invention due to perhydrolase activity or will serve as a suitable backbone for modification to the desired perhydrolase activity.

In addition to the sequence and homology analysis, environmental isolates were grown on a rich medium (N-MISO: g/l: glucose 10 g, yeast extract 10 g, $KNO_3$ 1.5, $KH_2PO_4$ 3.4 g, $NaH_2PO_4 \cdot H_2O$ 3.4 g, Salt Solution C 10 ml [Salt Solution C: g/l: $MgSO_4 7H_2O$ 25, $FeSO_4 7H_2O$ 2.8, $MnSO_4 H_2O$ 1.7, NaCl 0.6, $NaMoSO_4 \cdot 2H_2O$, $ZnSO_4 \cdot 7H_2O$ 0.06, in 0.1 N HCl]), assayed and those positive for the transesterification reaction were purified as described in the Examples. This is one of the screening methods that can be used to identify perhydrolase These data show that the present invention finds use in identification of additional enzymes with the desired perhydrolase activity.

Additional Investigations of Homologues

In addition to the above analyses, an enzyme library of novel "GDSL-type" esterases which are homologous to the prototype *M. smegmatis* perhydrolase was created. In order to identify new "GDSL"-type esterases, a sequence homology based screening procedure was established and used to screen libraries set up from complex metagenomic DNA (at BRAIN).

An enzyme library comprising 19 "GDSL"-type esterases (See, below) was developed. The sequences in this library were:

S248_M2bB11 (DNA)
(SEQ ID NO: 70)
ATGTTCGCGCTTTGCACGGCCGCGTCAGCGGCCCCCGATCGCACCGTCGT

CTTTTTTGGGGACAGCCTGACCGCGGGGTACGGCCTCGATGACCCGCAGA

CCCAGTCCTACCCGGCCAGGATCCAGGAGAAGGTCGACGCCGCGGGCCTG

CGCTGGAAGGTCGTGAATGCGGGCCTCTCGGGCGAGACGAGCGCCGGCGG

CCTGCGGCGGGTCGACTGGGTGCTCGGCCAGCACATCGACGCCTTTGTCC

TGGCGCTTGGCGCCAACGATGGCCTGCGGGGGATCGACCCCCAGGTCACG

AGGGCCAATCTCCAGGAGATCATCAACCGGGTCCGCTCCCGGTGGGCCCG

CGCGGCGATCGTCATCGCCGGGATGAAAATGCCCCAGAGCATGGGACAGG

ACTACGCCGCGAATTTTGACCGGATCTTCCCCGGTCTCGCCGCGAGGAAT

TCGGCCACGCTCATCCCCTTTCTATTAGAAGGGGTCGCCGCCCATCCTAG

CCTCAACCAAGGCGACGGCATCCACCCGACGGCCGCCGGGGACGCACTCG

TTGCAGGGAGCGTGTGGACGTACCTGCTTCCGATCCTGCGGTCAGCACAC

TAA

S248_M2bB11 (Amino Acid)
(SEQ ID NO: 71)
MFALCTAASAAPDRTVVFFGDSLTAGYGLDDPQTQSYPARIQEKVDAAGL

RWKVVNAGLSGETSAGGLRRVDWVLGQHIDAFVLALGANDGLRGIDPQVT

RANLQEIINRVRSRWPRAAIVIAGMKMPQSMGQDYAANFDRIFPGLAARN

SATLIPFLLEGVAAHPSLNQGDGIHPTAAGDALVAGTVWTYLLPILRSAH

S248_M40cD4 (DNA)
(SEQ ID NO: 72)
ATGCGCTTTGCTAAGCTCACTGCCGTCATCTTTGCCCTGATAGGGGTGAC

GCTTTATCCATTCTTTCTTGATGGGGTGGCGCTGGACCCGGCGCTGAACC

AGGCGGATGAATGCACCCGAACGCCAAGGGGGTCGCCGTGATCGTCGAC

CGTATCGCGCCCGTCGTCGCCAAGATGCTGAGAGGCCAGTCATAA

S248_M40cD4 (Amino Acid)
(SEQ ID NO: 73)
MRFAKLTAVIFALIVLHSPLAAAAPPTVMVFGDSLTAGLGLPADAAFPAQ

LQAKLHDMGIPAEIAARATSGQTTAGGLASLADALAAKPDLVILELGAND

MLRAVDPASVRANLDAMMTKIQASGAKLLLTGMQAAPNWGEDYKHDFDRL

YPELAKAHGVTLYPFFLDGVALDPALNQADGMHPNAKGVAVIVDRIAPVV

AKMLRGQS

S248_M44aA5 (DNA)
(SEQ ID NO: 74)
ATGATCGCATGGCTTACCGGATGCGGCAGCGCAAAGACGCAACCGCAGCC

CGCAAGTTCCATCCCGCCATCCAGTATTCGAGCAACCGCAAAACCTGCGA

CAACGGATATCAGACCGATCATCGTTGCTTTCGGCGACAGCCTGACTGCA

GGATACGGCGTCAGTAGTGAACAAAGCTATCCGGCCAATCTTCAACGCGA

TCTGGATGCGCGTGGATATCATGCCCACGTCATCAACGAAGGCATCAGCG

GCAACACATCGAAAGACGGCGTTCTCAGGGCCCAGGCGATTGCGGCACTC

CATCCGGCTGTCGTCATCGTTGCCTTCGGCGGCAACGACGGTCTGCGTGG

CCTCCCCATCGGAGACACGGAAATGAATCTGGCAACGATCATCTCAACCA

TGCAGCATGCCCATGCCAAGGTAATTTTAGGCGGAATTACTTTGCCTCCC

AACTATGGCAGCGAATACATCGCCAAATTCAATGCGATCTATAAAAAGCA

GGCAGCCGCGTATCATGTGCCCCTGCTGCCCTTCATGCTGAAGGGGGTGT

ATGGCGTGCCCGGTTCCATGCAGAGCGACGGCATCCATCCGACCGCCAAG

GGCTGCCAGCAAGTGGCCAGAAACTTCCTGCCCTTGTTATTGCCGCTCCT

GCACAAATCAGGGAAGAAATCCATGGAGTCGAAAGCATTGTCTCGACGTC

ATTAA

S248_M44aA5 (Amino Acid)
(SEQ ID NO: 75)
MIAWLTGCGSAKTQPQPASSIPPSSIPATAKPATTDIRPIIVAFGDSLTA

GYGVSSEQSYPANLQRDLDARGYHAHVINEGISGNTSKDGVLRAQAIAAL

HPAVVIVAFGGNDGLRGLPIGDTEMNLATIISTMQHAHAKVILGGITLPP

NYGSEYIAKFNAIYKKQAAAYHVPLLPFMLKGVYGVPGSMQSDGIHPTAK

GCQQVARNFLPLLLPLLHKSGKKSMESKALSRRH

S261_M2aA12 (DNA)
(SEQ ID NO: 76)
ATGAAAAACATCCTTGCATTTGGCGACAGTCTGACCTGGGGTTTTGTGGC

CGGACAGGATGCGCGCCATCCGTTTGAAACCCGCTGGCCAAACGCATTGG

CGGCCGGCCTTGGGGGCAAAGCCCGCGTAATTGAAGAGGGTCAGAACGGC

CGCACTACGGTGTTCGACGATGCCGCCACCTTCGAATCTCGAAATGGCTC

GGTGGCATTGCCGCTGCTACTGATCAGCCACCAGCCGTTGGACCTGGTAA

TCATCATGCTCGGCACCAATGACATCAAGTTTGCCGCCCGCTGCCGCGCC

TTTGATGCTTCAATGGGCATGGAACGGCTGATCCAGATCGTCAGAAGTGC

CAACTACATGAAGGGCTACAAGATACCTGAAATCCTCATCATATCGCCGC

CCAGCCTCGTGCCGACGCAGGATGAATGGTTCAACGACCTCTGGGGCCAT

GCCATCGCCGAGTCAAAACTCTTCGCCAAGCACTACAAGCGCGTGGCCGA

AGAACTGAAAGTGCATTTCTTTGATGCAGGCACGGTGGCCGTCGCCGACA

AGACCGACGGCGGACATCTCGATGCTGTGAATACTAAAGCCATTGGCGTC

GCATTGGTGCCGGTGGTGAAATCAATACTCGCTCTCTAA

S261_M2aA12 (Amino Acid)
(SEQ ID NO: 77)
MKNILAFGDSLTWGFVAGQDARHPFETRWPNALAAGLGGKARVIEEGQNG

RTTVFDDAATFESRNGSVALPLLLISHQPLDLVIIMLGTNDIKFAARCRA

FDASMGMERLIQIVRSANYMKGYKIPEILIISPPSLVPTQDEWFNDLWGH

AIAESKLFAKHYKRVAEELKVHFFDAGTVAVADKTDGGHLDAVNTKAIGV

ALVPVVKSILAL

S279_M70aE8 (DNA)
(SEQ ID NO: 78)
ATGCCGAAAATAGCCAAACTCGCGCCGTCGGATGTGATCGTAGCTTTCGG

CGACAGTCTGACGTTCGGCACCGGCGCAACGGAAGCGGAGAGTTATCCCA

TCGTGCTCGCACAATTGATCGGTCGCACCGTGGTGCGCGCGGGTGTGCCG

GGTGAGGTAACCGAAGGCGGGCTTGCGCGCCTGACCGACGTTATCGAAGA

ACACAAGCCGAAGCTGATTATTGTTTGCCTGGGCGGCAACGACATGCTGC

GCAAGGTCCAGGAAGACCAGACCCGCGCCAATTTGCGCGCCATTATTAAA

ACCATCAAGGCGCAAGGCATCGCCGTGGTACTGGTCGGTGTGCCGAAGCC

CGCGCTGGTGACCAGTGCGCCGCCGTTCTACGAGGAGATCGCCAAAGAGT

TCGGTATCCCTTACGAAGGCAAGATTGTTACCGACGTGTTGTACCAACGC

GATCAGAAATCCGATTCCATACATCCCAATGCCAAGGCTATCGGCGCAT

GGCCGAAGCGATAGCCACGCTGCTGAAAAAATCCGGAGCCATTTAA

S279:M70aE8 (Amino Acid)
(SEQ ID NO: 79)
MPKIAKLAPSDVIVAFGDSLTFGTGATEAESYPIVLAQLIGRTVVRAGVP

GEVTEGGLARLTDVIEEHKPKLIIVCLGGNDMLRKVQEDQTRANLRAIIK

TIKAQGIAVVLVGVPKPALVTSAPPFYEEIAKEFGIPYEGKIVTDVLYQR

DQKSDSIHPNAKGYRRMAEAIATLLKKSGAI

S279_M75bA2 (DNA)
(SEQ ID NO: 80)
ATGGAACGGACCGGCCGCGCTGGCGATCGGTGTCGGCGTGGGGCTGGCGA
GCCTGAGCCCGGTCGCGCTGGCGACGCCGCCGCGGGGCACCGTGCCGGTG
TTCACCCGATCGGGGACAGCCTGACGGACGAGTATTTTGAGCCGTTCTTC
CAGTGGGGGTTCTGCGGGAAGTCGTGGGCCGAGATTTTGGTGGAGACGGG
GCGGGCGAGCATGGGCCCGACGGCGCAGCAGGCGGGGATCAGCGAGCCGG
AGGGATGGTCGGATCCGCGGAACACGGGGTATCAGCACAACTGGGCGCGG
TACTCGTGGAGCTCCTCAGACGCGCTGACCGAGGAGTCGCCGGGGGCGAC
GCTGAGCGTGCTGCTTGGGGCGGAGTACGCGGTGGTGTTCATTGGGACCA
ACGACTTCAATCCGTCGTGGCCGGCGTATCAGAGCGTGTATCTGAGCCAG
TGGAGCGACGAGCAGATCGACACGTACGTGAACGGGGTGGTGCAGAACAT
CGCGCAGATGGTGGACTCGCTGAAGTCGGTCGGGGCGAAGGTGGTGCTTG
CGCCGCCGGTGGATTTTCAGTTCGCGGGGTTCCTGCGGAACTCATGCCCG
GATCCGATGCTGCGCGAGCAGGCGGGTATTCTGACACGGAAGTGCCACGA
CCGGGTGCGGTCGATGGCGCGGCAGAAGCACGTGGTGTTCGTGGACATGT
GGCGGCTGAACCGCGATTTGTTCGGCAACGGGTTCGCGATCAGCTACGGC
CTTCGGAACACGGTGCGCGTGGGGGACTCGGAGATCGGGCTGCAACTGGC
CGGGCTGACGGGATCGGCGGGGCTGGTTCCGGACGGGATCCATCCGCAGC
GGGTGGTGCAGGGGATCTGGGCGAATGCGTTCATCGTGGGTCTGAACGCG
CATGGGGCGAACATCGCGCCCATCGGCGAGGCGGAGATGTGCGCGATGGG
GGGGGTCGTGTACGGGGAACGGACACGCTGGCGAACTTCCTGCCGCCGG
TCGCGGGCTACGTGGAGGACTTCCGCAACGCGGGGGACTTCGTGTGCACG
GCGGACTTCAACCATGACCTTGGCGTGACGCCGACGGACATCTCGCGTTC
ATCAACGCGTGGTTCATGAATGATCCCTCGGCGCGGATGAGCAACCCGGA
GCACACGCAGATCGAGGACATCTTCGTGTTTCTGAATCTGTGGCTGGTGG
GGTGCTAA

S279_M75bA2 (Amino Acid)
(SEQ ID NO: 81)
MERTGRAGDRCRRGAGEPEPGRAGDAAAGHRAGVHPIGDSLTDEYFEPFF
QWGFCGKSWAEILVETGRASMGPTAQQAGISEPEGWSDPRNTGYQHNWAR
YSWSSSDALTEESPGATLSVLLGAEYAVVFIGTNDFNPSWPAYQSVYLSQ
WSDEQIDTYVNGVVQNIAQMVDSLKSVGAKVVLAPPVDFQFAGFLRNSCP
DPMLREQAGILTRKCHDRVRSMARQKHVVFVDMWRLNRDLFGNGFAISYG
LRNTVRVGDSEIGLQLAGLTGSAGLVPDGIHPQRVVQGIWANAFIVGLNA
HGANIAPIGEAEMCAMGGVVYGGTDTLANFLPPVAGYVEDFRNAGDFVCT
ADFNHDLGVTPTDIFAFINAWFMNDPSARMSNPEHTQIEDIFVFLNLWLV
GC M091_M4aE11 (DNA)
(SEQ ID NO: 82)
ATGAAGACCATTCTCGCCTATGGCGACAGCCTGACCTATGGGGCCAACCC
GATCCCGGGCGGGCCGCGGCATGCCTATGAGGATCGCTGGCCCACGGCGC
TGGAGCAGGGGCTGGGCGGCAAGGCGCGGGTGATTGCCGAGGGGCTGGGT
GGTCGCACCACGGTGCATGACGACTGGTTTGCGAATGCGGACAGGAACGG
TGCGCGGGTGCTGCCGACGCTGCTCGAGAGCCATTCGCCGCTCGACCTGA
TCGTCATCATGCTCGGCACCAACGACATCAAGCCGCATCACGGGCGGACG
GCCGGCGAGGCCGGGCGGGGCATGGCGCGGCTGGTGCAGATCATCCGCGG
GCACTATGCCGGCCGCATGCAGGACGAGCCGCAGATCATCCTCGTGTCGC
CGCCGCCGATCATCCTCGGCGACTGGGCGGACATGATGGACCATTTCGGC
CCGCACGAAGCGATCGCCACCTCGGTGGATTTCGCTCGCGAGTACAAGAA
GCGGGCCGACGAGCAGAAGGTGCATTTCTTCGACGCCGGCACGGTGGCGA
CGACCAGCAAGGCCGATGGCATCCACCTCGACCCGGCCAATACGCGCGCC
ATCGGGGCAGGGCTGGTGCCGCTGGTGAAGCAGGTGCTGGGCCTGTAA M091_M4aE11 (Amino Acid)
(SEQ ID NO: 83)
MKTILAYGDSLTYGANPIPGGPRHAYEDRWPTALEQGLGGKARVIAEGLG
GRTTVHDDWFANADRNGARVLPTLLESHSPLDLIVIMLGTNDIKPHHGRT
AGEAGRGMARLVQIIRGHYAGRMQDEPQIILVSPPPIILGDWADMMDHFG
PHEAIATSVDFAREYKKRADEQKVHFFDAGTVATTSKADGIHLDPANTRA
IGAGLVPLVKQVLGL Est105 (DNA)
(SEQ ID NO: 84)
ATGCGCACGCTTCACCGAAGCCTGCTCGCAAGCGCGGCCGCGCTTTTTCT
AGCGGCATCCGGCAACGCAACGGCGCAGTTCTCGAACGTCTATTTCTTCG
GCGACAGCCTGACCGACGCGGGTTCCTTCAAGCCTGTGCTGCCTCCTGGT
ACAGGATTATTCACGACGAATCCCGGCCCGGTATGGCCGCAGGTATTCGG
GGCGAACTACGGCGTCGCGGTGACGCCCGCAAACCAGGGTGGGACCGATT
ATGCGCAGGGTGGCGCGCGCGTGACGAGCCTGCCTGGCGTTCCGACGTCG
CAGCCGACCGGCAGCGCGGTACCGATCGCTACGCAGATTTCGCAGTTCCT
CGGCTCGGGTCCGGCGGATCCGAACGCATTCTATTCGGTGTGGGGCGGCG
CGAACGACATCTTTTTCCAGCTGGGGTTGGCGCAGGCGGGCATGGCGACG
CCGGCGCAGGTCCAGTCGGCCGTCGGCTTGGCCGCGGTCCAGCTGGCGCA
GGCAACTGCGGCGCTCAACGCCAGCGGCGCGCGATTCATCACGGTTATCA
ACGTGCCGGACATCGGTAAAACGCCGTTCGGCGTCGGCTCCGGTCAAGGA
GCGCAGATCACCGCTCTGTCGTCTTTCTTCAACAGCACGCTGTTCGGCGC
GCTCGACGCCACGGGCATCCAGACGATGCGCGTGAACGGGTTCGCGGTGC
TGAACGAGGTGGTCGCGGACCCGGCGGCTTATGGCTTCGCGAATGCATCA
ACGCCAGCGTGCGGGCCACGCCATCGCTCGTCTGCACGTCGGCGAACTT
CGTCACGCCCTTGGCCGCGCAGACCTTCCTCTTCGCAGACGGCGTTCACC
CCACCACGGCCGGGCACGCCCTCATCGCCCAAGCGGTCCAGGCGATGATC
ACCGGTCCCCAACAGATGCGGCGTTGGGCGACGCCCCGCTCGCCGTCGA
GCAGGCCAACTTCCGCGCGCTCGACAACGCATGTGGTCGAGCCTCAATG
CGCCGCGCAGCCCGGGCAAGCTCCAGGGTTGGGCGGCCTACGACTACAGC
CACACGGACCTGCAGGCGGGACCGACCAATGGCAGCGGACATGAACAC
CGTTGCGGTCGGGGTCGACATGAAAGTCTCCGATCATATGCTCGCCGGCG
CGATGTTCGGCTATACCAACACCAAGGGCGACTTCGGCGGCCCCGGCGGC -continued GGATACACACTGAAGCAGCCTGTGGGCACTGCCTATGCGGGTTACGGCGT
GGGCCCTTGGTATGTCGGCGC-
GACGCTCG CGCGAGTACCGAGCTCGGGAGCGTCACCGGG
TTTGTCGCGGGCTCGGCCACCGCAGGCCGGGCGGATGCCAACTATTGGGC
GGTCACGGTCGGCCTGCGGATGCCGTTGTAG Est105 (Amino Acid)
(SEQ ID NO: 85)
MRTLHRSLLASAAALFLAASGNATAQFSNVYFFGDSLTDAGSFKPVLPPG
TGLFTTNPGPVWPQVFGANYGVAVTPANQGGTDYAQGGARVTSLPGVPTS
QPTGSAVPIATQISQFLGSGPADPNAFYSVWGGANDIFFQLGLAQAGMAT
PAQVQSAVGLAAVQLAQATAALNASGARFITVINVPDIGKTPFGVGSGQG
AQITALSSFFNSTLFGALDATGIQTMRVNGFAVLNEVVADPAAYGFANAS
TPACGATPSLVCTSANFVTPLAAQTFLFADGVHPTTAGHALIAQAVQAMI
TGPQQMAALGDAPLAVEQANFRALDNRMWSSLNAPRSPGKLQGWAAYDYS
HTDLQAGPTNGSGHMNTVAVGVDMKVSDHMLAGAMFGYTNTKGDFGGPGG
GYTLKQPVGTAYAGYGVGPWYVGATLGTGGLDYSDVTRAIPLGLAVRTES
AEARGYEFTGRILGGYWFTMRDLMHGPYARLAWTKAVVKRFSEESTDSTA
LNYDRQERKQLLWSLGWQLAGNVGSIRPYARATWEIDSKDQDRSVGASSV
TLGGFYSVPVAKPDNSYALFSLGASTELGSVTGFVAGSATAGRADANYWA
VTVGLRMPL Est114 (DNA)
(SEQ ID NO: 86)
ATGGGGCGATCGAGAGTTCTGAAGGCTGTTTTCCTGGTGGCGTGCCTTGT
GGGTCGGCTCGCGGCGCATGCCGAGGCGTCGCCCATCGTGGTCTACGGCG
ATAGCCTCTCTGACAACGGCAATCTGTTTGCGCTCACCGGCGGTGTCGCG
CCGCCCTCGCCGCCGTACTTCAACGGACGGTTTTCTAATGGCCCGGTGGC
CGTGGAGTATCTCGCGGCCGCGCTGGGATCTCCGCTGATCGATTTCGCGG
TCGGCGGGGCGACGACCGGCCTCGGCGTCAACGGCGATCCCGGTGGTTCG
CCGACGAGTCTCGGCGCGGCGGGATTGCCGGGGCTTCAGACGACATTCGC
CGCCACGCAAGGCACGCTGGGTCCGTACGTTGGTGGTCTCTTCGTGGTGT
GGGCGGGTCCGAACGACTTCTTGTCGCCCTCGCCGCTTGACACGAACGCT
TTTCAGATTGCGAACCGGGCCGTGTCCAACATCCTCGGCGTGGTGGCATC
ACTTCAGGCACTCGGCGTCGAGCGCATCCTCGTCCCCGGCATGCCCGATC
TCGGTCTGACGCCCGCTCTTCAGCCCATCGCAGGCGCAGCCACCGCGTTC
ACCGATTTGTTCAACTCGATGCTGCGCGCGGGCTTGCCGAACGACGTGCT
GTACCTGGACACGGCGACAATCTTCCGATCGATCGTGGCAGACCCTGGGG
CCTACGGCTTGACCAACGTGACCACGCCGTGCCTGATTGGTGCGACCGTC
TGCGCGAATCCGGATCAGTACCTGTTCTGGGATGGTATTCATCCTACGAC
GGCGGGGCACGCGATCTTGGGCAATGCCCTCGTCGCCCAGGCAGTCCCCG
AGCCCGCGACCATGGTGCTCGTGCTGACGGGTCTGTCCATGCACGTGATT
GCGCGCCGGCGGCGGGCGTAA Est114 (Amino Acid)
(SEQ ID NO: 87)
MGRSRVLKAVFLVACLVGRLAAHAEASPIVVYGDSLSDNGNLFALTGGVA
PPSPPYFNGRFSNGPVAVEYLAAALGSPLIDFAVGGATTGLGVNGDPGGS
PTSLGAAGLPGLQTTFAATQGTLGPYVGGLFVVWAGPNDFLSPSPLDTNA
FQIANRAVSNILGVVASLQALGVERILVPGMPDLGLTPALQPIAGAATAF
TDLFNSMLRAGLPNDVLYLDTATIFRSIVADPGAYGLTNVTTPCLIGATV
CANPDQYLFWDGIHPTTAGHAILGNALVAQAVPEPATMVLVLTGLSMHVI
ARRRRA Sinorhizobium meliloti SmeI (SMa1993) (DNA)
(SEQ ID NO: 88)
ATGACAATCAACAGCCATTCATGGAGGACGTTAATGGTGGAAAAGCGCTC
AGTACTGTGCTTTGGGGATTCGCTGACATGGGGCTGGATTCCGGTGAAGG
GATCCTCACCGACCTTGCGCTATCCCTATGAACAACGGTGGACCGGCGCA
ATGGCCGCGAGGGCTTGGCGACGGTTACCACATCATCGAAGAGGGGCTGA
GCGCCCCGCACCACCAGCCTCGACGACCCCAACGACGCGCGGCTCAACGG
CAGCACCTACCTGCCCATGGCACTCGCCAGCCACCTCCCACTCGACCTCG
TCATCATCATGCTGGGCACGAACGACACGAAATCCTATTTCCACCGCACG
CCTTACGAGATCGCCAACGGCATGGGCAAGCTAGTCGGCCAGGTGCTGAC
CTGCGCCGGTGGCGTCGGCACGCCATATCCCGCGCCGAAGGTGCTTGTCG
TCGCTCCGCCGCCGCTCGCGCCGATGCCCGACCCGTGGTTCGAAGGCATG
TTCGGCGGCGGCTACGAGAAGTCGAAGGAACTCTCCGGCCTCTACAAGGC
GCTTGCCGATTTCATGAAGGTCGAGTTTTTCGCCGCCGGTGATTGCATTT
CCACCGATGGGATCGACGGCATTCACCTCTCGGCGGAAACCAACATCAGA
CTCGGGCACGCGATCGCGGACAAAGTTGCGGCGTTGTTC Sinorhizobium meliloti SmeI (SMa1993) (Amino Acid)
(SEQ ID NO: 89)
MTINSHSWRTLMVEKRSVLCFGDSLTWGWIPVKGSSPTLRYPYEQRWTGA
MAARLGDGYHIIEEGLSARTTSLDDPNDARLNGSTYLPMALASHLPLDLV
IIMLGTNDTKSYFHRTPYEIANGMGKLVGQVLTCAGGVGTPYPAPKVLVV
APPPLAPMPDPWFEGMFGGGYEKSKELSGLYKALADFMKVEFFAAGDCIS
TDGIDGIHLSAETNIRLGHAIADKVAALF Sinorhizobium meliloti SmeII (Q92XZ1) (DNA)
(SEQ ID NO: 90)
ATGGAGGAGACAGTGGCACGGACCGTTCTATGCTTCGGAGATTCCAACAC
TCACGGCCAGGTACCTGGCCGCGGACCGCTTGATCGCTACCGACGCGAAC
AGCGCTGGGGCGGTGTTCTGCAAGGCCTGCTCGGCCCGAACTGGCAGGTT
ATCGAAGAAGGCCTGAGCGGACGCACGACCGTGCATGACGATCCGATCGA
AGGTTCGCTCAAGAACGGCCGGACCTATCTGCGCCCCTGTCTGCAGAGCC
ATGCACCACTCGACCTTATCATCATTATGCTCGGCACCAATGACCTGAAG
CGGCGCTTCAACATGCCACCGTCCGAGGTCGGAATGGGCATCGGCTGTCT
CGTGCACGATATCCGAGAACTCTCGCCCGGCCGGACCGGCAACGATCCCG
AAATCATGATCGTCGCCCCGCCGCCGATGCTGGAAGATCTCAAGGAATGG
GAGTCGATTTTCTCAGGCGCACAGGAAAAATCTCGCAAGCTGGCGCTGGA -continued
```
GTTCGAGATAATGGCGGATTCTCTGGAGGCGCATTTCTTCGACGCCGGTA
CGGTCTGCCAGTGTTCGCCGGCCGATGGCTTCCACATCGACGAGGATGCC
CACCGCCTGCTCGGCGAGGCTCTCGCCCAGGAAGTGCTGGCGATCGGGTG
GCCCGATGCGTAA
```

Sinorhizobium meliloti SmeII (Q92XZ1) (Amino Acid)
(SEQ ID NO: 91)
```
MEETVARTVLCFGDSNTHGQVPGRGPLDRYRREQRWGGVLQGLLGPNWQV
IEEGLSGRTTVHDDPIEGSLKNGRTYLRPCLQSHAPLDLIIMLGTNDLK
RRFNMPPSEVAMGIGCLVHDIRELSPGRTGNDPEIMIVAPPPMLEDLKEW
ESIFSGAQEKSRKLALEFEIMADSLEAHFFDAGTVCQCSPADGFHIDEDA
HRLLGEALAQEVLAIGWPDA
```

Sinorhizobium meliloti SmeII (Q9EV56) (DNA)
(SEQ ID NO: 92)
```
ATGAAGACAGTCCTTTGCTACGGTGACAGTCTGACCTGGGGATACGATGC
AACCGGTTCCGGCCGGCATGCGCTGGAGGACCGTTGGCCGAGCGTGCTGC
AGAAGGCGCTCGGTTCGGACGCGCATGTCATCGCCGAAGGGCTGAACGGG
CGGACGACCGCCTATGACGACCATCTCGCCGATTGCGACCGGAACGGCGC
GCGTGTCCTCCCGACGGTCCTGCACACCCACGCGCCACTCGATCTCATCG
TGTTCATGCTCGGCTCGAACGACATGAAGCCGATCATTCACGGCACCGCT
TTCGGCGCGGTGAAGGGCATCGAGCGCCTCGTCAATCTGGTGCGCAGGCA
CGACTGGCCGACGGAAACGGAGGAGGGGCCCGAGATTCTCATCGTCTCGC
CGCCGCCGCTCTGCGAGACGGCCAACAGCGCCTTTGCCGCCATGTTCGCG
GGCGGGGTCGAGCAATCCGCAATGCTGGCGCCGCTTTATCGCGATCTCGC
CGACGAGCTCGACTGCGGCTTCTTCGACGGCGGATGGGTGGCCAGGACGA
CGCCGATCGACGGTGTCCACCTCGACGCGGAGAACACCCGGGCGGTCGGC
AGAGGGTTGGAGCCTGTCGTGCGGATGATGCTCGGGCTTTAA
```

Sinorhizobium meliloti SmeII (Q9EV56) (Amino Acid)
(SEQ ID NO: 93)
```
MKTVLCYGDSLTWGYDATGSGRHALEDRWPSVLQKALGSDAHVIAEGLNG
RTTAYDDHLADCDRNGARVLPTVLHTHAPLDLIVFMLGSNDMKPIIHGTA
FGAVKGIERLVNLVRRHDWPTETEEGPEILIVSPPPLCETANSAFAAMFA
GGVEQSAMLAPLYRDLADELDCGFFDGGSVARTTPIDGVHLDAENTRAVG
RGLEPVVRMMLGL
```

Agrobacterium tumefaciens Atu III (AAD02335) (DNA)
(SEQ ID NO: 94)
```
ATGGTGAAGTCGGTCCTCTGCTTTGGCGATTCCCTCACCTGGGGATCAAA
TGCGGAAACGGGTGGCCGGCACAGCCATGACGATCTTTGGCCGAGCGTCT
TGCAGAAGGCGCTCGGTCCTGACGTGCATGTGATTCACGAAGGTCTGGGT
GGTCGCACCACCGCCTATGACGACAACACCGCCGATTGCGACCGCAACGG
CGCGCGGGTTCTTCCGACGTTGTTGCACAGCCATGCGCCGCTGGATCTGG
TGATTGTCATGCTCGGGACCAACGACCTGAAGCCGTCAATCCATGGATCG
GCGATCGTTGCCATGAAGGGTGTCGAAAGGCTGGTGAAGCTCACGCGCAA
CCACATCTGGCAGGTGCCGGACTGGGAGGGGCCTGACGTGCTGATCGTCG
CACCGCCGCAGCTGTGTGAAACGGCCAATCCGTTCATGGGCGCGATCTTT
CGTGATGCGATCGATGAATCGGCGATGCTGGCGTCCGTTTACCGGGACCT
TGCCGACGAGCTTGATTGCGGCTTTTTCGATGCGGGTTCCGTCGCCCGAA
CGACGCCGGTGGATGGCGTTCATCTCGATGCTGAAAATACGCGGGCCATC
GGGCGGGGGCTGGAGCCCGTCGTTCGCATGATGCTCGGACTTTAA
```

Agrobacterium tumefaciens Atu III (AAD02335) (Amino Acid)
(SEQ ID NO: 95)
```
MYKSVLCFGDSLTWGSNAETGGRHSHDDLWPSVLQKALGPDVHVIHEGLG
GRTTAYDDNTADCDRNGARVLPTLLHSHAPLDLVIVMLGTNDLKPSIHGS
AIVAMKGVERLVKLTRNHIWQVPDWEAPDVLIVAPPQLCETANPFMGAIF
RDAIDESAMLASVYRDLADELDCGFFDAGSVARTTPVDGVHLDAENTRAI
GRGLEPVVRMMLGL
```

Mesorhizobium loti Mlo I (Q98MY5) (DNA)
(SEQ ID NO: 96)
```
ATGAAGACGGTGCTTTGCTACGGCGACTCGCTGACCTGGGGCTACAATGC
CGAAGGCGGCCGCCATGCGCTGGAAGACCGCTGGCCGAGCGTGCTGCAAG
CAGCGTTAGGCGCCGGCGTGCAAGTGATTGGCGATGGCCTGAACGGCCGC
ACCACGGCCTTCGACGATCATCTGGCCGGTGCTGATCGCAACGGCGCCAG
GCTGCTGCCGACGGTCCTGACGACGCACGCGCCGATCGACCTGATCATCT
TCATGCTCGGCGCCAACGACATGAAGCCTTGGATCCACGGCAATCCGGTC
GCAGCCAAGCAAGGCATCCAGCGGTTGATCGACATCGTGCGTGGTCACGA
CTACCGGTTCGACTGGCCGGCGCCGCAGATCCTGATCGTCGCGCCGCCTG
TAGTCAGCCGCACCGAAAATGCCGACTTCAAGGAAATGTTCGCCGGTGGC
GATGACGCCTCGAAGTTTTTGGCACCGCAATATGCCGGGCTCGCCGACGA
AGCCGGCTGTGGCTTCTTCGACGCCGGCAGGGTGGCCCAAACCACACCGC
TCGATGGCGTTCACCTCGATGCCGAAAACACGCGAGAAATCGGCAAGGCG
CTGACGCCGATCGTGCGCGTCATGCTGGAATTGTAA
```

Mesorhizobium loti Mlo I (Q98MY5) (Amino Acid)
(SEQ ID NO: 97)
```
MKTVLCYGDSLTWGYNAEGGRHALEDRWPSVLQAALGAGVQVIADGLNGR
TTAFDDHLAGADRNGARLLPTVLTTHAPIDLIIFMLGANDMKPWIHGNPV
AAKQGIQRLIDIVRGHDYPFDWPAPQILIVAPPVVSRTENADFKEMFAGG
DDASKFLAPQYAALADEAGCGFFDAGSVAQTTPLDGVHLDAENTREIGKA
LTPIVRVMLEL
```

Moraxella bovis Mbo (AAK53448) (DNA)
(SEQ ID NO: 98)
```
ATGAAAAAATCCGCCTTTGCCAAATACTCAGCACTTGCCCTAATGGTTGG
GATGTGCCTGCACACCGCTTACGCCAAGGAGTTTAGCCAAGTCATCATTT
TTGGGGACAGCTTGTCCGATACAGGTCGCCTAAAAGATATGGTCGCCCGA
AAAGATGGCACCCTTGGCAACACCTTACAGCCATCTTTTACCACCAACCC
CGACCCTGTATGGTCAAGCTTATTTGCCCAAAGTTATGGCAAAACCGCCA
GTCCCAACACGCCTGACAATCCCACTGGCACTAACTATGCCGTGGGCGGA
GCTCGCTCTGGCTCGGAGGTCAATTGGAATGGTTTTGTGAATGTACCCTC
CACCAAAACGCAAATCACCGACCATTTGACCGCCACAGGTGGCAAAGCCG
ACCCTAATACCCTGTATGCCATTTGGATTGGCTCTAATGACTTAATTTCA
GCTTCTCAAGCCACCACAACAGCCGAAGCCCAAAACGCCATTAAAGGTGC
```

-continued

GGTAACTCGCACCGTGATAGACATCGAAACACTCAATCAAGCAGGGGCGA

CAACCATTTTGGTGCCAAATGTGCCTGATTTGAGCCTCACGCCCCGAGCC

ATCTATGGCGAAAGCCTCATGGCAGGCGTGCAAGACAAAGCCAAACTCGC

CTCAAGTCTGTATAATAGCGGTCTGTTTGAAGCATTAAATCAATCCACCG

CCAACATCATCCCTGCCAACACCTTTGCCCTACTCCAAGAAGCGACCACA

AATAAAGAAGCCTTTGGTTTTAAAAACACGCAAGGCGTGGCGTGTCAAAT

GCCCGCTCGTACCACAGGGGCGGATGATGTGGCTTCTACTTCCTTGGCAT

GTACCAAAGCCAATCTTATAGAAAACGGGGCAAATGACACCTACGCCTTT

GGCGATGACATTCACCCATCGGGACGCACGCACCGCATTTTGGCACAGTA

TTACCGTTCTATCATGGACGCCCCTACTCACATGGGTAAACTCTCAGGCG

AGCTTGTCAAAAGAGGTTCAGCCCACGACCGTCATGTTTACCGTCAGCTT

GACAGGCTTAGTGGCTCACAGCACAGCATTTGGGCAAACGTCTATGCCAG

CGACCGTACCGACCCCACCACCCAAATCGGCTTGGACGTGGCAGGTTCAT

CAAGCCATACAGGGGCGTATCTGAGCCACCAAAACCAAGATTATGTGCTG

GATGACACCCTATCATCAGATGTCAAAACCATTGGCATGGGGCTGTATCA

TCGCCATGACATCGGCAATGTCCGTCTAAAAGGCGTGGCAGGTATCGACC

GACTTAGCGTGGATACGCACCGCCATATCGACTGGGAGGGGACAAGCCGT

TCGCACACCGCAGATACCACCGCCAGACGTTTTCATGCAGGGCTACAAGC

GAGCTATGGCATAGACATGGGCAAAGCCACCGTGCGTCCGCTTATCGGCG

TACATGCCCAAAAAGTCAAAGTAAATGACATGACCGAGAGCGAATCAACT

TTATCCACCGCCATGCGTTTTGGCGAGCAAGAACAAAAGTCCCTACAAGG

CGAGATTGGCGTCGATGTGGCTTATCCGATTAGCCCTGCTTTGACTCTGA

CGGGCGGTATCGCTCACGCTCATGAGTTTAACGATGATGAACGCACCATT

AATGCCACTTTAACCTCCATTCGTGAATACACGAAGGGCTTTAATACAAG

CGTTAGCACCGACAAATCTCACGCCACCACCGCTCATCTGGGCGTACAAG

GGCAACTTGGCAAGGCAAATATTCATGCAGGCGTTCACGCCACCCACCAA

GACAGCGATACAGACGTGGGTGGTTCGCTTGGGGTTCGCTTGATGTTTTA

A

Moraxella bovis Mbo (AAK53448) (Amino Acid)
(SEQ ID NO: 99)
MKKSAFAKYSALALMVGMCLHTAYAKEFSQVIIFGDSLSDTGRLKDMVAR

KDGTLGNTLQPSFTTNPDPVWSSLFAQSYGKTASPNTPDNPTGTNYAVGG

ARSGSEVNWNGFVNVPSTKTQITDHLTATGGKADPNTLYAIWIGSNDLIS

ASQATTTAEAQNAIDGAVTRTVIDIETLNQAGATTILVPNVPDLSLTPRA

IYGESLMAGVQDKAKLASSLYNSGLFEALNQSTANIIPANTFALLQEATT

NKEAFGFKNTQGVACQMPARTTGADDVASTSLACTKANLIENGANDTYAF

ADDIHPSGRTHRILAQYYRSIMDAPTHMGKLSGELVKTGSAHDRHVYRQL

DRLSGSQHSIWANVYASDRTDPTTQIGLDVAGSSSHTGAYLSHQNQDYVL

DDTLSSDVKTIGMGLYHRHDIGNVRLKGVAGIDRLSVDTHRHIDWEGTSR

SHTADTTARRFHAGLQASYGIDMGKATVRPLIGVHAQKVKVNDMTESEST

LSTAMRFGEQEQKSLQGEIGVDVAYPISPALTLTGGIAHAHEFNDDERTI

NATLTSIREYTKGFNTSVSTDKSHATTAHLGVQGQLGKANIHAGVHATHQ

DSDTDVGGSLGVRLMF

Chromobacterium violaceum Cvi (Q7NRP5) (DNA)
(SEQ ID NO: 100)
ATGCGCTCTATCGTCTGCAAAATGCTGTTCCCTTTGTTGCTGCTGTGGCA

GCTGCCCGCCCTGGCCGCCACCGTGCTGGTGTTCGGCGACAGCCTGTCCG

CCGGCTACGGCCTGGCCCCGGGCCAGGGATGGGCGGCGCTGCTGGCGCGC

GACCTCTCGCCCCGGCACAAGGTGGTCAACGCCAGCGTGTCCGGCGAAAC

CAGCGCCGGCGGCCTGTCCAGGCTGCCCGACGCGCTCGCCCGCCACCAGC

CCGACGTGCTGGTGCTGGAACTCGGCGCCAACGATGGCCTGCGCGGCCTG

CCGATGGCTGACATGAGGCGCAACCTGCAGCGGATGATAGACCTGGCCCA

GGCGCGCAAGGCCAAGGTGCTGCTGGTGGGCATGGCGCTGCCACCCAACT

ATGGCCCCCGCTACGGCGCCGAGTTCCGCGCCGTTTATGACGATTTGGCC

CGCCGCAACCGCCTGGCCTACGTGCCGCTGCTGGTCGAGGGCTTCGCCGG

CGAGCTCGGCGCCTTCCAGCCCGACGGCCTGCATCCCCGCGCGGAGAAGC

AGGCCACCATGATGCGCACGGTCAAGGCAAAACTGCCAGTGAAATAA

Chromobacterium violaceum Cvi (Q7NRP5) (Amino Acid)
(SEQ ID NO: 101)
MRSIVCKMLFPLLLLWQLPALAATVLVFGDSLSAGYGLAPGQGWAALLAR

DLSPRHKVVNASVSGETSAGGLSRLPDALARHQPDVLVLELGANDGLRGL

PMADMRRNLQRMIDLAQARKAKVLLVGMALPPNYGPRYGAEFRAVYDDLA

RRNRLAYVPLLVEGFAGDLGAFQPDGLHPRAEKQATMMRTVKAKLPVK

Vibrio vulnificus Vvu (AA007232) (DNA)
(SEQ ID NO: 102)
ATGTTTTTCCTTTCTAGCGTCGCACACGCAACCGAGAAAGTGTTAATTCT

TGGCGACAGCCTAAGTGCAGGATACAACATGTCTGCAGAGCAGGCTTGGC

CTAATTTGTTACCAGAAGCATTGAATACATACGGAAAAAACGTAGAAGTG

ATCAACGCCAGTATCTCTGGAGACACAACCGGCAATGGACTATCTCGTCT

GCCTGAGTTGTTAAAAACGCACTCACCAGACTGGGTGCTTATTGAGTTGG

GTGCCAATGATGGCTTGCGAGGTTTCCCGCATAAAGTGATCTCTTCAAAC

CTTTCGCGAATGATTCAACTCAGTAAAGCCTCAGACGCTAAAGTCGCATT

GATGCAAATTCGTGTACCGCCTAACTATGGCAAGCGCTACACCGATGCAT

TTGTCGAACTCTACCCTACGCTTGCTGAACATCACCAAGTCCCGTTGCTC

CCCTTTTTCTTAGAGGAAGTGATCGTGAAACCGGAATGGATGATGCCTGA

TGGCTTACACCCAATGCCCGAAGCTCAGCCTTGGATCGCTCAATTTGTTG

CAAAAACGTTTTACAAACATCTCTAA

Vibrio vulnificus Vvu (AA007232) (Amino Acid)
(SEQ ID NO: 103)
MFFLSSVAHATEKVLILGDSLSAGYNMSAEQAWPNLLPEALNTYGKNVEV

INASISGDTTGNGLSRLPELLKTHSPDWVLIELGANDGLRGFPHKVISSN

LSRMIQLSKASDAKVALMQIRVPPNYGKRYTDAFVELYPTLAEHHQVPLL

PFFLEEVIVKPEWMMPDGLHPMPEAQPWIAQFVAKTFYKHL

Ralstonia eutropha Reu (ZP00166901) (DNA)
(SEQ ID NO: 104)
ATGCCATTGACCGCGCCGTCTGAAGTCGATCCGCTGCAAATCCTGGTCTA

TGCCGATTCGCTTTCGTGGGGCATCGTGCCCGGCACCCGCCGGCGGCTTC

CCTTCCCGGTTCGCTGGCCAGGCCGGCTCGAACTCGGCCTGAACGCCGAC

GGCGGCGCCCCGGTCCGCATCATCGAGGACTGCCTGAACGGCCGGCGCAC

CGTCTGGGACGACCCATTCAAACCGGGCCGCAACGGCTTGCAAGGGCTGG

CGCAGCGCATCGAGATCCATTCCCCGGTGGCGCTCGTGGTTTTGATGCTG

GGCAACAACGATTTCCAGTCCATGCATCCGCACAACGCCTGGCATGCGGC

ACAGGGCGTCGGCGCGCTGGTCCACGCCATCCGGACGGCGCCGATCGAAC

CGGGAATGCCGGTGCCGCCGATCCTGGTGGTGGTGCCGCCGCCGATCCGC

ACGCCCTGCGGGCCGCTCGCGCCCAAGTTCGCCGGCGGCGAACACAAGTG

GGCAGGCCTGCCCGAGGCGCTGCGCGAACTGTGCGCCACTGTCGACTGCT

CGCTGTTCGATGCGGGTACCGTGATCCAGAGCAGTGCCGTCGACGGCGTA

CACCTTGACGCCGATGCCCATGTCGCCCTGGGCGATGCCCTGCAACCGGT

CGTTCGTGCGCTGCTCGCCGAATCCTCGGGACATCCCTCCTAA

Ralstonia eutropha Reu (ZP00166901) (Amino Acid)
(SEQ ID NO: 105)
MPLTAPSEVDPLQILVYADSLSWGIVPGTRRRLPFPVRWPGRLELGLNAD

GGAPVRIIEDCLNGRRTVWDDPFKPGRNGLQGLAQRIEIHSPVALVVLML

GNNDFQSMHPHNAWHAAQGVGALVHAIRTAPIEPGMPVPPILVVVPPPIR

TPCGPLAPKFAGGEHKWAGLPEALRELCATVDCSLFDAGTVIQSSAVDGV

HLDADAHVALGDALQPVVRALLAESSGHPS

Salmonella typhimurium Stm (AAC38796) (DNA)
(SEQ ID NO: 106)
ATGACCCAAAAGCGTACCCTGCTAAAATACGGCATACTCTCGCTGGCGCT

GGCCGCGCCATTATCTGCCTGTGCGTTTGACTCTCTTACGGTGATTGGCG

ATAGCCTTAGCGATACCGGTAATAACGGTCGCTGGACCTGGGATAGTGGT

CAAAATAAGCTCTACGACGAACAGTTGGCCGAACGATATGGGCTGGAATT

AAGCCCTTCCAGCAATGGCGGCTCTAATTATGCCGCCGGCGGCGCGACGG

CGACCCCGGAATTAAACCCGCAGGATAATACCGCGGATCAGGTACGGCAG

TGGCTTGCCAAAACGGGGGGAAAAGCCGACCACAACGGTTTGTATATTCA

CTGGGTCGGCGGAAACGATCTGGCGGCGGCCATCGCGCAACCAACCATGG

CACAGCAAATAGCCGGTAATAGCGCCACTAGGGCGGCGGCGCAGGTAGGG

CTGTTACTGGATGCCGGCGCCGGGCTGGTCGTGGTGCCAAACGTACCGGA

TATTAGTGCGACGCCAATGCTTCTGGAGGCGGTAATCACCGCTGGGCTGG

GCGCAGCGGCGCCCCCGGCGCTAAAAGCGGCGTTAGATGCGCTGGCGGAG

GGCGCTACGCCCGATTTCGCCAGTCGGCAACAGGCGATCCGCAAGGCGCT

GCTGGCGGCGGCTGCAACGGTAAGCAGCAATCCATTTATTCAGCAACTGC

TCGTTGAACAACTGCTGGCGGGCTATGAAGCGGCGGCAGGGCAGGCGTCA

GCTCTGACCGATTATTATAATCAGATGGAAGAGAAGGGGCTGGAGCAACA

CGGCGGCAATATAGCCCGTGCCGATATCAACGGCCTCTTTAAGGAAATTC

TTGCCAACCCGCAGGCGTTTGGTCTGACAAATACCGTAGGTATGGCCTGC

CCGCCTGGCGTATCCGCTTCGGCGTGCTCCTCGGCAATGCCTGGATTTAA

TGCGTCGCAGGACTATGTGTTTGCCGATCATTTACATCCCGGTCCGCAGG

TCCATACCATTATTGCGCAATATATTCAGTCGATCATTGCCGCGCCGGTA

CAGGCGACATACCTGAACCAAAGCGTTCAGTCGATGGCGCAAGGCAGTCG

TACCACGCTTGACAGCCGTTATCAGCAGCTTCGCCAGGGGGAAAATCCTG

TTGGTTCGCTGGGCATGTTCGGCGGATACAGCGGGGGATATCAACGTTAT

GATAATAATGAGGCCGACGGGAACGGTAATCATAATAATCTGACGGTTGG

CGTCGATTATCAGCTTAACGAGCAGGTTCTGCTGGGAGGGCTGATAGCCG

GTTCTCTGGATAAGCAACATCCTGACGATAATTATCGTTATGATGCCCGC

GGTTTTCAGGCCGCCGTATTCAGCCATTTACGCGCCGGTCAGGCGTGGCT

GGATAGCGATTTACACTTTCTGTCCGCTAAATTCAGTAACATTCAGCGCA

GTATAACGCTCGGTGCGCTAAGACGGGTGGAAGAGGGCGAAACCAACGGT

CGGCTGTCGGGCGCGAGCTTAACCAGCGGTTATGATTTTGTCATGGTGCC

GTGGTTAACGACCGGACCGATGCTGCAATATGCATGGGATTACAGCCACG

TTAATGGTTATAGCGAGAAGCTCAATACCAGTACATCAATGCGTTTTGGT

GACCAAAACGCCCATTCGCAGGTGGGTAGCGCGGGTTGGCGTCTGGATCT

TCGCCACAGCATCATTCACTCCTGGGCGCAGATTAATTATCGCCGTCAGT

TTGGCGATGATACGTATGTGGCGAACGGCGGCCTTAAATCGACCGCGCTG

ACGTTTAGCCGCGACGGAAAAACGCAGGATAAAAACTGGGTTGATATCGC

GATTGGCGCAGATTTTCCGCTGTCGGCAACGGTGTCCGCTTTCGCCGGGC

TGTCGCAAACGGCAGGGTTAAGCGATGGCAATCAAACCCGTTATAACGTT

GGGTTTAGCGCCCGATTTTAA

Salmonella typhimurium Stm (AAC38796) (Amino Acid)
(SEQ ID NO: 107)
MTQKRTLLKYGILSLALAAPLSACAFDSLTVIGDSLSDTGNNGRWTWDSG

QNKLYDEQLAERYGLELSPSSNGGSNYAAGGATATPELNPQDNTADQVRQ

WLAKTGGKADHNGLYIHWVGGNDLAAAIAQPTMAQQIAGNSATSAAAQVG

LLLDAGAGLVVVPNVPDISATPMLLEAVITAGLGAAAPPALKAALDALAE

GATPDFASRQQAIRKALLAAAATVSSNPFIQQLLVEQLLAGYEAAAGQAS

ALTDYYNQMEEKGLEQHGGNIARADINGLFKEILANPQAFGLTNTVGMAC

PPGVSASACSSAMPGFNASQDYVFADHLHPGPQVHTIIAQYIQSIIAAPV

QATYLNQSVQSMAQGSRTTLDSRYQQLRQGENPVGSLGMFGGYSGGYQRY

DNNEADGNGNHNNLTVGVDYQLNEQVLLGGLIAGSLDKQHPDDNYRYDAR

GFQAAVFSHLRAGQAWLDSDLHFLSAKFSNIQRSITLGALRRVEEGETNG

RLSGASLTSGYDFVMVPWLTTGPMLQYAWDYSHVNGYSEKLNTSTSMRFG

DQNAHSQVGSAGWRLDLRHSIIHSWAQINYRRQFGDDTYVANGGLKSTAL

TFSRDGKTQDKNWVDIAIGADFPLSATVSAFAGLSQTAGLSDGNQTRYNY

GFSARF

In total, nine of the new "GDSL"-type esterases were identified in 6 metagenomic libraries and BRAIN's esterase/lipase library. Eight of these genes were heterologously expressed in E. coli and the resulting enzymes analyzed for activity in the assays described herein. The characterization of these enzymes for perhydrolase activity revealed that one displayed the desired activity. A second one was predicted to show this activity due to the presence of amino acids conserved among this group of enzymes.

Comparison of the sequences of enzymes for which the presence or absence of the desired perhydrolase activity was determined led to the identification of 19 amino acid positions which were conserved among the enzymes which displayed the desired perhydrolase activity. Thus, it is contemplated that these conserved amino acids are essential for the perhydrolase reaction and/or is a structural feature of perhydrolase enzymes.

One of the identified structural motifs ("G/ARTT") conserved among esterases with the desired perhydrolase activity was used to design degenerate primers which provided the means to focus the screening on true perhydrolases among "GDSL"-type esterases. Indeed, the use of these "G/ARTT" primers led to the identification of enzymes with the desired perhydrolase activity from the metagenome. However, it is not intended that the use of the metagenome be limited to any particular assay method. Indeed, it is contemplated that the metagenome be searched by assaying for a particular enzyme activity or activities desired (e.g., perhydrolysis and/or acyltransferase (cofactor dependent or independent) activity). In addition, screening using poly and/or monoclonal anti-sera directed against a protein of interest finds use in the present invention. In additional embodiments, the metagenome is searched using degenerate primer sets based on the sequence of the protein of interest.

In addition, the knowledge of the structure/function relationship of perhydrolases allowed searching for these enzymes in genome sequences of cultivable microorganisms. Of 16 "GDSL"-type esterases identified in different bacterial isolates, the corresponding genes of 10 enzymes were amplified and heterologously expressed in E. coli. The resulting enzyme samples of seven clones were analyzed using the assays described herein. Of five samples characterized to date, 4 enzymes indeed showed the desired activity and all results confirmed the proposed relationship between primary structural determinants and the function of perhydrolases. Thus, an enzyme library of 19 "GDSL"-type esterases comprising at least 6 perhydrolases with the desired perhydrolase activity was set up. The identified correlation between the structure and function of perhydrolases provides a definition of the sequence space used by enzymes with the desired perhydrolase activity.

Comparisons were made of protein sequences of enzymes for which the absence or presence of the desired perhydrolase activity. This revealed a correlation between the presence of certain amino acids and the capability to perform perhydrolase reactions. This knowledge was used to identify enzymes containing these conserved amino acids in sequenced genomes from cultivable microorganisms. The following enzymes were identified and experiments to amplify the genes from the genomic DNA of the corresponding strains using specific primers were performed.

TABLE 1

"GDSL"-type Esterases with a "GRTT"-Motif From Bacterial Isolates

| Isolate | Protein Identifier | Acronym | Amplicon | Expression Vector |
|---|---|---|---|---|
| Sinorhizobium meliloti | Sma1993 | Sme I | yes | pLO_SmeI |
| Sinorhizobium meliloti | Q92XZ1 | Sme II | yes | pET26_SmeII |
| Sinorhizobium meliloti | Q9EV56 | Sme III | yes | pET26_SmeIII |
| Agrobacterium rhizogenes | Q9KWB1 | Arh I | no | — |
| Agrobacterium rhizogenes | Q9KWA6 | Arh II | no | — |
| Agrobacterium tumefaciens | AAD02335 | Atu III | yes | pET26_AtuIII |
| Mesorhizobium loti | Q98MY5 | Mlo I | yes | pET26_Mlo |
| Mesorhizobium loti | ZP_00197751 | Mlo II | no | — |
| Ralstonia solanacearum | Q8XQI0 | Rso | no | — |
| Ralstonia eutropha | ZP_00166901 | Reu | yes | n.d. |
| Moraxella bovis | AAK53448 | Mbo | yes | pET26_Mbo |
| Burkholderia cepacia | ZP_00216984 | Bce | no | — |
| Chromobacterium violaceum | Q7NRP5 | Cvi | yes | pET26_Cvi |
| Pirellula sp. | NP_865746 | Psp | n.d. | n.d. |
| Vibrio vulnificus | AAO07232 | Vvu | yes | pET26_Vvu |
| Salmonella typhimurium | AAC38796 | Sty | yes | pET26_Sty |

In the cases of A. rhizogenes, M. loti (enzyme II), R. solanacearum and B. cepacia no amplicon could be generated. It was thought that this was probably due to genetic differences between the strains used in this investigation and those used for the sequencing of the genes deposited in the public domain databases. One reason might be that the corresponding genes are located on plasmids which are not present in the strains used in this investigation. However, it is not intended that the present invention be limited to any particular mechanism or theory.

The amplicons from all other strains were sequenced. In many cases there were differences between the sequence from the databases and the sequence determined during the development of the present invention. By sequencing two clones from independent amplifications, mutations introduced by the polymerase could be nearly excluded. The sequences of the genes and the deduced amino acid sequences of "GDSL"-type esterases with a "GRTT"-motif or variations from bacterial isolates are provided below:

```
                                  (SEQ ID NOS: 88 and 89)
SMa1993_Sinorhizobium meliloti (Sme I)

(SEQ ID NOS: 90 and 91)
Q92XZ1_Sinorhizobium meliloti (Sme II)

(SEQ ID NOS: 92 and 93)
Q9EV56_Sinorhizobium meliloti (Sme III)

(SEQ ID NOS: 94 and 95)
AAD02335_Agrobacterium tumefaciens (Atu III)

(SEQ ID NOS: 96 and 97)
Q98MY5_Mesorhizobium loti (Mlo I)

(SEQ ID NOS: 104 and 105)
ZP_00166901_Ralstonia eutropha (Reu)
```

(SEQ ID NOS: 98 and 99)
AAK53448_Moraxella bovis (Mbo)

(SEQ ID NOS: 100 and 101)
Q7NRP5_Chromobacterium violaceum (Cvi)

(SEQ ID NOS: 102 and 103)
AA007232_Vibrio vulnificus (Vvu)

(SEQ ID NOS: 106 and 107)
AAC38796_Salmonella typhimurium (Stm)

Q9KWB1_Agrobacterium rhizogenes (Arh I)
(SEQ ID NO: 108)
MICHKGGEEMRSVLCYGDSNTHGQIPGGSPLDRYGPNERWPGVLRRELGS
QWYVIEEGLSGRTTVRDDPIEGTMKNGRTYLRPCLMSHAILDLVIIMLGT
NDLKARFGQPPSEVAMGIGCLVYDIRELAPGPGGKPPEIMVVAPPPMLDD
IKEWEPIFSGAQEKSRRLALEFEIIADSLEVHFFDAATVASCDPCDGFHI
NREAHEALGTALAREVEAIGWR (SEQ ID NO: 109)
ATGATTTGCCATAAAGGTGGGGAGGAAATGCGGTCAGTCTTATGCTACGG
CGACTCGAATACGCACGGCCAGATTCCGGGGGCTCACCGCTCGACCGAT
ACGGGCCGAACGAGCGCTGGCCTGGCGTTTTGAGACGGGAGCTTGGAAGC
CAGTGGTATGTGATCGAGGAGGGCCTGAGTGGCCGCACGACGGTTCGCGA
CGATCCGATCGAGGGCACGATGAAAAACGGCCGGACCTACCTGCGTCCGT
GCCTCATGAGCCACGCGATCCTCGATCTCGTGATTATCATGCTCGGGACG
AACGACCTGAAAGCGCGCTTCGGTCAACCGGCATCGGAAGTGGCGATGGG
GATCGGCTGCCTCGTCTACGATATCAGGGAGCTGGCGCCCCGGACCGGGCG
GCAAGCCCCCCGAAATCATGGTGGTTGCTCCGCCGCCGATGCTGGACGAT
ATCAAGGAATGGGAACCCATATTTTCCGGCGCCCAGGAGAAATCCCGGCG
TCTCGCGCTTGAGTTTGAAATTATTGCTGATTCGCTTGAAGTACACTTCT
TTGACGCCGCGACCGTCGCATCGTGTGATCCTTGCGATGGTTTTCACATC
AACCGGGAAGCGCATGAAGCCTTGGGAACAGCGCTTGCCAGGGAAGTGGA
GGCGATCGGTTGGAGATGATGA Q9KWA6_Agrobacterium rhizogenes (Arh II)
(SEQ ID NO: 110)
MAESRSILCFGDSLTWGWIPVPESSPTLRYPFEQRWTGAMAAALGDGYSI
IEEGLSARTTSVEDPNDPRLNGSAYLPMALASHLPLDLVIILLGTNDTKS
YFRRTPYEIANGMGKLAGQVLTSAGGIGTPYPAPKLLIVSPPPLAPMPDP
WFEGMFGGGYEKSLELAKQYKALANFLKVDFLDAGEFVKTDGCDGIHFSA
ETNITLGHAIAAKVEAIFSQEAKNAAA (SEQ ID NO: 111)
ATGGCAGAGAGCCGCTCAATATTATGTTTTGGGGATTCACTCACATGGGG
TTGGATTCCGGTACCGGAGTCGTCGCCGACGCTCAGATATCCCTTTGAGC
AGCGCTGGACCGGTGCAATGGCTGCGGCACTCGGTGACGGCTATTCAATC
ATCGAGGAAGGCCTTTCCGCCCGCACGACCAGCGTCGAGGATCCGAACGA
TCCCAGGCTGAACGGCAGCGCCTACCTGCCGATGGCGCTCGCCAGCCATC
TGCCGCTCGATCTCGTCATCATCCTTCTCGGCACCAACGACACCAAGTCC
TATTTCCGCCGCACGCCCTATGAGATCGCCAACGGCATGGGCAAGCTTGC CGGACAGGTTCTGACCTCGGCCGGCGGGATCGGCACGCCCTACCCTGCCC
CGAAGCTTCTGATCGTTTCGCCGCCGCCGCTCGCTCCCATGCCTGACCCG
TGGTTCGAAGGCATGTTCGGTGGCGGTTACGAAAAGTCGCTCGAACTCGC
AAAGCAGTACAAGGCGCTCGCCAACTTCCTGAAGGTCGACTTCCTCGACG
CCGGCGAGTTTGTAAAGACCGACGGCTGCGATGGAATCCATTTCTCCGCC
GAGACGAACATCACGCTCGGCCATGCGATCGCGGCGAAGGTCGAAGCGAT
TTTCTCACAAGAGGCGAAGAACGCTGCGGCTTAG ZP_00197751_Mesorhizobium loti (Mlo II)
(SEQ ID NO: 112)
MKTILCYGDSLTWGYDAVGPSRHAYEDRWPSVLQGRLGSSARVIAEGLCG
RTTAFDDWVAGADRNGARILPTLLATHSPLDLVIVMLGTNDMKSFVCGRA
IGAKQGMERIVQIIRGQPYSFNYKVPSILLVAPPPLCATENSDFAEIFEG
GMAESQKLAPLYAALAQQTGCAFFDAGTVARTTPLDGIHLDAENTRAIGA
GLEPVVRQALGL (SEQ ID NO: 113)
ATGAAGACCATCCTTTGTTACGGTGACTCCCTCACTTGGGGCTATGATGC
CGTCGGACCCATGAAGACCATCCTTTGTTACGGTGACTCCCTCACTTGGG
GCTATGATGCCGTCGGACCCTCACGGCATGCTTATGAGGATCGATGGCCC
TCCGTACTGCAAGGCCGCCTCGGTAGCAGTGCGCGGGTGATCGCCGAGGG
GCTTTGCGGCCGCACAACTGCGTTTGACGACTGGGTCGCTGGTGCGGACC
GGAACGGTGCGCGCATCCTGCCGACGCTTCTTGCGACCCATTCACCGCTT
GACCTCGTTATCGTCATGCTCGGGACGAACGACATGAAATCGTTCGTTTG
CGGGCGCGCTATCGGCGCCAAGCAGGGGATGGAGCGGATCGTCCAGATCA
TCCGCGGGCAGCCTTATTCCTTCAATTATAAGGTACCGTCGATTCTTCTC
GTGGCGCCGCCGCCGCTGTGCGCTACCGAAAACAGCGATTTCGCGGAAAT
TTTTGAAGGTGGCATGGCTGAATCGCAAAAGCTCGCGCCGCTTTATGCCG
CGCTGGCCCAGCAAACCGGATGCGCCTTCTTCGATGCAGGCACTGTGGCC
CGCACGACACCGCTCGACGGTATTCACCTCGATGCTGAAAACACGCGCGC
CATTGGTGCCGGCCTGGAGCCGGTGGTCCGCCAAGCGCTTGGATTGTGA Q8XQI0_Ralstonia solanacearum (Rso)
(SEQ ID NO: 114)
MQQILLYSDSLSWGIIPGTRRRLPFAARWAGVMEHALQAQGHAVRIVEDC
LNGRTTVLDDPARPGRNGLQGLAQRIEAHAPLALVILMLGTNDFQAIFRH
TAQDAAQGVAQLVRAIRQAPIEPGMPVPPVLIVVPPAITAPAGAMADKFA
DAQPKCAGLAQAYRATAQTLGCHVFDANSVTPASRVDGIHLDADQHAQLG
RAMAQVVGTLLAQ (SEQ ID NO: 115)
ATGCAACAGATCCTGCTCTATTCCGACTCGCTCTCCTGGGGCATCATCCC
CGGCACCCGCCGGCGCCTGCCGTTCGCCGCCCGCTGGGCCGGGGTCATGG
AACACGCGCTGCAGGCGCAAGGGCACGCCGTGCGCATCGTCGAAGACTGC
CTCAATGGACGCACCACGGTGCTCGACGATCCCGCGCGGCCGGGGCGCAA
CGGACTGCAGGGGCTCGCGCAGCGGATCGAAGCGCACGCCCCGCTTGCCC
TGGTCATCCTGATGCTCGGCACCAACGACTTCCAGGCGATCTTCCGGCAC
ACCGCCCAGGACGCGGCGCAAGGCGTGGCGCAGCTGGTGCGGGCCATCCG -continued

CCAGGCGCCGATCGAACCCGGCATGCCGGTGCCGCCCGTGCTGATCGTGG

TGCCGCCGGCCATCACCGCGCCGGCCGGGGCGATGGCCGACAAGTTTGCC

GACGCGCAGCCCAAGTGCGCCGGCCTTGCGCAGGCCTATCGGGCAACGGC

GCAAACGCTAGGCTGCCACGTCTTCGATGCGAACAGCGTCACGCCGGCCA

GCCGCGTGGACGGCATCCACCTCGATGCCGACCAGCATGCGCAGCTGGGC

CGGGCGATGGCGCAGGTCGTCGGGACGCTGCTTGCGCAATAA

ZP_00216984 Burkholderia cepacia (Bce)
(SEQ ID NO: 116)
ATGACGATGACGCAGAAAACCGTGCTCTGCTACGGCGATTCGAACACGCA

TGGCACACGCCCGATGACGCATGCTGGCGGACTGGGGCGGTTTGCACGCG

AAGAACGCTGGACCGGCGTGCTGGCGCAAACGCTCGGTGCGAGCTGGCGG

GTCATTGAAGAAGGGTTGCCCGCGCGTACGACCGTGCATGACGATCCGAT

CGAAGGCCGGCACAAGAATGGTTTGTCGTATCTGCGCGCGTGCGTCGAAA

GCCACTTGCCCGTCGATGTCGTCGTGCTGATGCTCGGGACCAACGATCTG

AAGACACGCTTCTCGGTCACGCCCGCCGACATCGCGACATCGGTCGGCGT

ATTGCTTGCCAAGATCGCTGCGTGCGGCGCCGGTCCGTCCGGTGCGTCAC

CGAAGCTCGTGCTGATGGCGCCTGCGCCGATCGTCGAGGTCGGATTCCTC

GGCGAGATCTTTGCGGGCGGCGCAGCGAAGTCGCGGCAGCTCGCGAAGCG

GTACGAACAGGTGGCAAGCGATGCCGGTGCGCACTTTCTCGATGCCGGCG

CGATCGTCGAGGTGAGCCCGGTGGATGGCGTTCACTTCGCGGCCGATCAG

CATCGTGTGCTCGGGCAGCGGGTCGCTGCCCTTCTGCAGCAGATTGCGTA

A (SEQ ID NO: 117)
MTMTQKTVLCYGDSNTHGTRPMTHAGGLGRFAREERWTGVLAQTLGASWR

VIEEGLPARTTVHDDPIEGRHKNGLSYLRACVESHLPVDVVVLMLGTNDL

KTRFSVTPADIATSVGVLLAKIAACGAGPSGASPKLVLMAPAPIVEVGFL

GEIFAGGAAKSRQLAKRYEQVASDAGAHFLDAGAIVEVSPVDGVHFAADQ

HRVLGQRVAALLQQIA

NP_865746 Pirellula sp (Psp)
(SEQ ID NO: 118)
MHSILIYGDSLSWGIIPGTRRRFAFHQRWPGVMEIELRQTGIDARVIEDC

LNGRRTVLEDPIKPGRNGLDGLQQRIEINSPLSLVVLFLGTNDFQSVHEF

HAEQSAQGLALLVDAIRRSPFEPGMPTPKILLVAPPTVHHPKLDMAAKFQ

NAETKSTGLADAIRKVSTEHSCEFFDAATVTTTSVVDGVHLDQEQHQALG

TALASTIAEILADC (SEQ ID NO: 119)
ATGCATTCAATCCTCATCTATGGCGATTCTCTCAGTTGGGGAATCATTCC

CGGCACGCGTCGTCGCTTCGCGTTCCATCAGCGTTGGCCGGGCGTCATGG

AGATTGAACTGCGACAAACTGGAATCGATGCCCGCGTCATCGAAGACTGC

CTCAATGGCCGACGAACCGTCTTGGAAGATCCAATCAAACCCGGACGCAA

TGGCCTGGATGGTTTGCAGCAACGGATCGAAATCAATTCACCTCTGTCAC

TGGTCGTGCTCTTTCTGGGGACCAACGATTTCCAGTCCGTCCACGAATTC

CATGCCGAGCAATCGGCACAAGGACTCGCACTGCTTGTCGACGCCATTCG

TCGCTCCCCTTTCGAACCAGGAATGCCGACACCGAAAATCCTGCTTGTCG

CACCACCGACGGTTCACCACCCGAAACTTGATATGGCGGCGAAGTTCCAA

AACGCGGAAACGAAATCGACGGGACTCGCAGATGCGATTCGCAAGGTCTC

AACAGAACACTCCTGCGAATTCTTCGATGCGGCCACGGTCACCACAACAA

GTGTCGTCGACGGAGTCCATCTCGATCAAGAACAACATCAAGCACTCGGT

ACCGCACTGGCATCGACAATCGCTGAAATACTAGCAGACTGTTGA

As indicated above, the above sequences are the protein sequences and the coding sequences of "GDSL-type" esterases with a "GRTT"-motif or similar motifs from different bacterial isolates. The DNA sequences represent the target-DNA from which specific primers were deduced. All amplicons were ligated as NdeI/XhoI-fragments to pET26 thereby eliminating the pelB-leader sequence of this vector. All of the "GDSL-type" esterases from these isolates were expressed in E. coli Rosetta (DE3) at 28° C. The expression was induced by addition of 100 μM IPTG at an O.D.$_{580}$=1 and the cells were harvested 20 h after induction. Only the cells expressing the enzymes from M. bovis and S. typhimurium were collected 4 h after induction, since previous experiments had shown that the highest activity could be obtained at this point of time. Table 2 summarizes the expression experiments.

TABLE 2

Expression and Characterization of "GDSL"-type Esterases From Bacterial Isolates for Perhydrolase Activity

| Strain | Enzyme | Expression Level[2] | Solubility[3] | Activity[4] | Perhydrolase Activity | GRTT-Motif |
|---|---|---|---|---|---|---|
| S. meliloti | Sme I | +++ | ++ | 5770.0 | yes | ARTT |
| S. meliloti | Sme II | +++ | +++ | 85.0 | yes | GRTT |
| S. meliloti | Sme III | +++ | ++ | 746.5 | n.d. | GRTT |
| A. tumefaciens | Atu III | n.d.[5]. | n.d. | n.d. | n.d. | GRTT |
| M. loti | Mlo I | +++ | ++ | 1187.3 | yes | GRTT |
| M. bovis[1] | Mbo | + | n.d. | 25.2 | yes | ARTT |
| C. violaceum | Cvi | + | + | 2422.7 | n.d. | GETS |
| V vulnificus | Vvu | n.d. | n.d. | n.d. | n.d. | GDTT |

TABLE 2-continued

Expression and Characterization of "GDSL"-type Esterases From Bacterial Isolates for Perhydrolase Activity

| Strain | Enzyme | Expression Level[2] | Solubility[3] | Activity[4] | Perhydrolase Activity | GRTT-Motif |
|---|---|---|---|---|---|---|
| R. eutropha | Reu | n.d. | n.d. | n.d. | n.d. | GRRT |
| S. typhimurium[1] | Sty | + | n.d. | 17.2 | no | SRTT |

[1] outer membrane localized autotransporter protein
[2] expression level: + moderate overexpression; ++ strong overexpression; +++ very strong overexpression as judged from SDS-PAGE-analysis
[3] as judged by SDS-PAGE-analysis
[4] towards p-nitrophenyl butyrate
[6] not determined With the exception of the enzyme from *S. typhimurium*, all other enzymes tested showed the desired perhydrolase activity, confirming the correlation between the presence of certain conserved amino acids an the capability to perform perhydrolase reactions. Although the enzyme from *S. typhimurium* contains the GRTT-motif, it is different from the other enzymes by the location of this motif downstream from block V. In all other enzymes, this motif is located between block I and III, indicating that it might have a different function in the enzyme from *S. typhimurium*. Thus, the absence of perhydrolase activity in the enzyme from *S. typhimurium* also supports the identified structure/function-relationship of the perhydrolases provided by the present invention.

Screening of New "GDSL-type" Esterases in Metagenome Libraries i) Library S279

The full-length sequence of the gene from clone M75bA2 was completed, as provided below.

```
  1 tgggcggttt cgcggagtcg agcagggaga gatgctcctg ggtcgtacga gttggtacgg
      g  r  f    r  g  v    e  q  g    e  m  l  l    g  r  t    s  w  y 61 aggcatcgtt gaatatctca cgcctgcttg aatgcgcgcg gatatggaac ggaccggccg
      g  g  i    v  e  d  l    t  p  a  -  m  r  a    d  m  e    r  t  g 121 cgctggcgat cggtgtcggc gtggggctgg cgagcctgag cccggtcgcg ctggcgacgc
      r  a  g  d    r  c  r    r  g  a    g  e  p    p  g  r    a  g  d 181 cgccgcgggg caccgtgccg gtgttcaccc gatcggggac agcctgacgg acgagtattt
      a  a  a  g    h  r  a    g  v  h    p  i  g  d  s  l    t  d  e  y 241 tgagccgttc ttccagtggg ggttctgcgg gaagtcgtgg gccgagattt tggtggagac
      f  e  p  f    f  q  w    g  f  c    g  k  s  w    a  e  i    l  v  e 301 ggggcgggcg agcatgggcc cgacggcgca gcaggcgggg atcagcgagc cggagggatg
      t  g  r  a    s  m  g    p  t  a    q  q  a  g    i  s  e    p  e  g 361 gtcggatccg cggaacacgg ggtatcagca caactgggcg cggtactcgt ggagctcctc
      w  s  d  p    r  n  t    g  y  q    h  n  w  a    r  y  s    w  s  s 421 agacgcgctg accgaggagt cgccggggc gacgctgagc gtgctgcttg gggcggagta
      s  d  a  l    t  e  e    s  p  g    a  t  l  s    v  l  l    g  a  e 481 cgcggtggtg ttcattggga ccaacgactt caatccgtcg tggccggcgt atcagagcgt
      y  a  v  v    f  i  g  t  n  d    f  n  p  s    w  p  a    y  q  s 541 gtatctgagc cagtggagcg acgagcagat cgacacgtac gtgaacgggg tggtgcagaa
      v  y  l  s    q  w  s    d  e  q    i  d  t  y    v  n  g    v  v  q 601 catcgcgcag atggtggact cgctgaagtc ggtcggggcg aaggtggtgc ttgcgccgcc
      n  i  a  q    m  v  d    s  l  k    s  v  g  a    k  v  v    l  a  p 661 ggtggatttt cagttcgcgg ggttcctgcg gaactcatgc ccggatccga tgctgcgcga
      p  v  d  f    q  f  a    g  f  l    r  n  s  c    p  d  p    m  l  r 721 gcaggcgggt attctgacac ggaagtgcca cgaccgggtg cggtcgatgg cgcggcagaa
      e  q  a  g    i  l  t    r  k  c    h  d  r  v    r  s  m    a  r  q 781 gcacgtggtg ttcgtggaca tgtggcggct gaaccgcgat ttgttcggca acgggttcgc
      k  h  v  v    f  v  d    m  w  r    l  n  r  d    l  f  g    n  g  f 841 gatcagctac ggccttcgga acacggtgcg cgtgggggac tcggagatcg ggctgcaact
      a  i  s  y    g  l  r    n  t  v    r  v  g  d    s  e  i    g  l  q 901 ggccggcctg acgggatcgg cggggctggt tccggacggg atccatccgc agcgggtggt
      l  a  g  l    t  g  s    a  g  l    v  p  d  g  i  h  p    q  r  v 961 gcagggatc tgggcgaatg cgttcatcgt gggtctgaac gcgcatgggg cgaacatcgc
      v  q  g  i    w  a  n    a  f  i    v  g  l  n    a  h  g    a  n  i
```

```
1021 gcccatcggc gaggcggaga tgtgcgcgat ggggggggtc gtgtacgggg gaacggacac
      a  p  i  g   e  a  e    m  c  a  m   g  g  v  v    y  g   g  t  d 1081 gctggcgaac ttcctgccgc cggtcgcggg ctacgtggag gacttccgca acgcggggga
      t  l  a  n   f  l  p    p  v  a   g  y  v  e   d  f  r    n  a  g 1141 cttcgtgtgc acggcggact tcaaccatga ccttggcgtg acgccgacgg acatcttcgc
      d  f  v  c   t  a  d    f  n  h   d  l  g  v    t  p  t    d  i  f 1201 gttcatcaac gcgtggttca tgaatgatcc ctcggcgcgg atgagcaacc cggagcacac
      a  f  i  n   a  w  f    m  n  d   p  s  a  r    m  s  n    p  e  h 1261 gcagatcgag gacatcttcg tgtttctgaa tctgtggctg gtggggtgct gaggcagagt
      t  q  i  e   d  i  f    v  f  l   n  l  w  l    v  g  c   -   g  r 1321 gggaaggggg tcagcccact tcgcgcgtct ggaagaggat gacggcgacg gagaggaaga
      v  g  r  g   s  a  h    f  a  r   l  e  e  d    g  d   g  e  e
```

In the sequence of S279_M75bA2 provided above (DNA, SEQ ID NO:80; and amino acid sequence, SEQ ID NO:81), the coding sequence running from position 104 through 1312 is shown on a grey background. Conserved structural motifs are shown underlined and in bold.

The derived amino acid sequence showed the highest homology to a hypothetical protein (Y17D7A.2) from *Caenorhabditis elegans* (BlastP2; swisspir), although with a very high E-value of 2.5 (i.e., indicating a non-reliable hit). The fact that no esterase is among the homologous proteins identified by the BlastP2-analysis indicates that this enzyme is a rather unusual "GDSL-type" esterase. Furthermore, the enzyme is characterized by unusually long peptides between the N-terminus and the "GDSL"-motif and the "DXXH"-motif of block V (containing the active site aspartic acid and histidine) and the C-terminus. The very C-terminal sequence shows similarity to a membrane lipoprotein lipid attachment site. A corresponding signal sequence of lipoproteins was not identified. The gene encoding M75bA5 was amplified but no further efforts were taken for this enzyme since it did not have the conserved amino acids typical of the perhydrolase of the present invention.

ii) Library S248

The clone carrying the sequence-tag SP7_3j5h which could have been part of a gene encoding a "GDSL"-type esterase was identified (M31bA11), and the sequence was elongated. This facilitated the determination that this sequence did not encode a "GDSL type" esterase, because block V could not be identified. The generation of this amplicon can be explained by an "unspecific" hybridization of primer 5h with the first mismatches at nucleotides 10, 14 and 15 from the 3'-terminus of the primer. The sequence showed the highest homology to a hypothetical protein (K03E5.5) from *Caenorhabditis elegans* with an E-value of 1.6, indicating a non-reliable hit. The sequence-tag from clone S248_M31 bA11 is provided below.

```
  1 cggaattatc atgctgggtt ttaatgacca gcgcgagagg atcaacgaca acctcgatta (SEQ ID NO: 125)
            r  n  y  h   a  g  f  -  -                                (SEQ ID NO: 126)
      p  a  r  e  d  q   r  q  p  r  l
                                                                      NO: 126)
         g  i  i  m  l   g  f  n  d  q  r  e  r   i  n  d   n  l  d (SEQ ID NO: 127)
            e  l  s  c   w  v  l  m  t   s  a  r   g  s  t   t  s  i (SEQ ID NO: 127)

61 ctgggacgcc taccactccg tcctgggcga gagacagttt tattccggca attccaagat
      l  g  r   l  p  l   r  p  g  r   e  t  v   l  f  r   q  f  q  d
      y  w  d  a   y  h  s   v  l  g   e  r  q  f   y  s  g   n  s  k
       t  g  t   p  t  t  p   s  w  a  r  d  s    f  i  p  a    i  p  r 121 gttcgtcccc atcaccaaga tcgcggtgaa ggcgcgcaag acccggttca ccaatcagat
      v  r  p   h  h  q   d  r  g  e   g  a  q   d  p  v   h  q  s  d
       m  f  v  p   i  t  k    i  a  v   k  a  r  k   t  r  f   t  n  q
         c  s  s   p  s  p  r   s  r  -    r  r  a   r  p  g  s    p  i  r 181 ttttcctcag tccggccgca acgtcgatgt caccaccacg gacggcacac tcccccacgc
       f  s  s   v  r  p   q  r  r  c   h  h  h   g  r  h   t  p  p  r
         i  f  p  q   s  g  r    n  v  d   v  t  t  t   d  g  t   l  p  h
          f  f  l   s  p  a  a   t  s  m   s  p  p   r  t  a  h   s  p  t ooo_oo_ooo
241 caccatgtcc ctggtcgagc actacatccg ggcctgccgc ctgcgcaccc agatcgttcc
        h  h  v   p  g  r   a  l  h  p   g  l  p   p  a  h   p  d  r  s
         a  t  m  s   l  v  e   h  y  i   r  a  c   r  l  r  t   q  i  v
          p  p  c   p  w  s  s   t  t  s   g  p  a  a   c  a  p   r  s  f
```

```
301 ggccctgatc gttaacggcg attgcgaagg catgtacagc atctatgtcg gctggtcgaa
     g  p  d    r  -  r    r  l  r  r    h  v  q    h  l  c    r  l  v  e
      p  a  l  i    v  n  g    d  c  e    g  m  y  s    i  y  v    g  w  s
       r  p  -    s  l  t  a    i  a  k    a  c  t    a  s  m  s    a  g  r 361 aaccaccaag catgttgttt cacgtgaaac aaagccggtc gaaagcgacg gcatggaatt
     n  h  q    a  c  c    f  t  -  n    k  a  g    r  k  r    r  h  g  i
      k  t  t  k    h  v  v    s  r  e    t  k  p  v    e  s  d    g  m  e
       k  p  p    s  m  l  f    h  v  k    q  s  r    s  k  a  t    a  w  n 421 tcccgaactg ggcgaagccg acgacatcac cgaagaaacg cttgagtgtg gccttcccga
     s  r  t    g  r  s    r  r  h  h    r  r  n    a  -  v    w  p  s  r
      f  p  e  l    g  e  a    d  d  i    t  e  e  t    l  e  c    g  l  p
       f  p  n    w  a  k  p    t  t  s    p  k  k    r  l  s  v    a  f  p 481 catcgaattg atctcggacg ccgatcttct cgtccttcca ccagcgccga caacattcca
     h  r  i    d  l  g    r  r  s  s    r  p  s    t  s  a    d  n  i  p
      d  i  e  l    i  s  d    a  d  l    l  v  l  p    p  a  p    t  t  f
       t  s  n    -  s  r  t    p  i  f    s  s  f    h  q  r  r    q  h  s 541 aggcgcttga gatgggcggg ttcggtcacg atcttgcgcc gtggacaagg gcaaggtccg
     r  r  l    r  w  a    g  s  v  t    i  l  r    r  g  q    g  q  g  p
      q  g  a  -    d  g  r    v  r  s    r  s  c  a    v  d  k    g  k  v
       k  a  l    e  m  g  g    f  g  h    d  l  a    p  w  t  r    a  r  s 601 cagatgatcg acgaggcgcg atcaccgaga tgccgcgacg atctgtcgac gctatgtcac
     q  m  i    d  e  a    r  s  p  r    c  r  d    d  l  s    t  l  c  h
      r  r  -  s    t  r  r    d  h  r    d  a  a  t    i  c  r    r  y  v
       a  d  d    r  r  g  a    i  t  e    m  p  r    r  s  v  d    a  m  s 661 cagcgcatgt ccgacggtgg aatgcaagac aggtnggntn gatcgggg
     q  r  m    s  d  g    g  m  q  d    r  ?  ?    ?  s  g
      t  s  a  c    p  t  v    e  c  k    t  g  ?  ?    d  r
       p  a  h    v  r  r  w    n  a  r    q  ?  ?    ?  i  g
```

In the above sequence-tag of the clone S248_M31bA11, the primers 3j and 5h are indicated. Hybridization between primer and template is indicated by arrows, mismatches by open circles. Putative conserved structural motifs are indicated in bold and underlined.

Several further sequence-tags were generated using different primer pairs of the primers 2 and 5 but none turned out to encode a "GDSL"-type esterases. The screening of this library was completed.

iii) Library M091

The elongation of the amplicon SP3_1j5h, which was identified in the insert-DNA of clone M24dG12 proved that the corresponding sequence does not encode a "GDSL"-type esterase. Whereas the sequence encoding a putative block V (DGTHP; SEQ ID NO:124) was found, the corresponding sequence encoding block I was missing. The amplicon was generated due to an "unspecific" hybridization of primer 1j with the first mismatches at positions 5, 10, 11 and 12 from the 3'-terminus of the primer. The sequence-tag of clone M091_M24dG12 s shown below:

```
  1 gcctgatggc ttcgagttcg tcgaattcac ctcgcccag cccggcgtgc tggaggcggt    (SEQ ID NO: 120)
     a  -  w    l  r  v    r  r  i  h    l  a  p    a  r  r    a  g  g  g    (SEQ ID NO: 121)
      p  d  g    f  e  f    v  e  f    t  s  p  q    p  g  v    l  e  a    (SEQ ID NO: 122)
       l  m    a  s  s  s    s  n  s    p  r  p    s  p  a  c    w  r  r    (SEQ ID NO: 123)

61 gtttgaaaag ctgggtttca ccctggtcgc caagcaccgg tccaaggatg tggtgctgta
     v  -  k    a  g  f    h  p  g  r    q  a  p    v  q  g    c  g  a  v
      v  f  e  k    l  g  f    t  l  v    a  k  h  r    s  k  d    v  v  l
       c  l  k    s  w  v  s    p  w  s    p  s  t    g  p  r  m    w  c  c 121 ccgccagaac ggcatcaact tcatcctgaa ccgcgagccc cacagccagg ccgcctactt
     p  p  e    r  h  q    l  h  p  e    p  r  a    p  q  p    g  r  l  l
      y  r  q  n    g  i  n    f  i  l    n  r  e  p    h  s  q    a  a  y
       t  a  r    t  a  s  t    s  s  -    t  a  s    p  t  a  r    p  p  t 181 tggtgccgag catggcccct ccgcctgtgg cctggccttc cgtgtgaagg atgcgcataa
     w  c  r    a  w  p    l  r  l  w    p  g  l    p  c  e    g  c  a  -
      f  g  a  e    h  g  p    s  a  c    g  l  a  f    r  v  k    d  a  h
       l  v  p    s  m  a  p    p  p  v    a  w  p    s  v  -  r    m  r  i
```

```
241 ggcttataac cgcgcgctgg aactgggcgc ccagcccatc gagatcccca ccggccccat
      g  l  -   p  r  a  g   t  g  r   p  a  h   r  d  p   h  r  p  h
     k  a  y  n   r  a  l  e   l  g   a  q  p  i   e  i  p  t   g  p
    r   l  i   t  a  r  w   n  w  a   p  s  p   s  r  s  p   p  a  p
              ooooooーooooーoーoーーーooo一o 301 ggaactgcgc ctgcccgcca tcaagggcat tggcggcgcc gcctctgtat ttgatcgacc
      g  t  a   p  a  r   h  q  g  h   w  r  r   r  l  c   i  -   s  t
     m  e  l  r   l  p  a   i  k  g   i  g  g  a   a  s  v   f  d  r
    w   n  c   a  c  p  p   s  r  a   l  a  a   p  p  l  y   l  i  d
          →
361 gctttgaaga cggcaagtcc atctacgaca tcgacttcga gttcatcgaa ggcgtggacc
      a  l  k   t  a  s   p  s  t  t   s  t  s   s  s  s   k  a  w  t
     p  l  -   r  r  q  v   h  l  r   h  r  l  r   v  h  r   r  r  g
          ⎯
    r   f  e   d  g  k  s   i  y  d   i  d  f   e  f  i  e   g  v  d 421 gccgccccgc ggggcatggc ctgaacgaga tcgatcacct cacgcacaac gtgtaccggg
      a  a  p   r  g  m   a  -  t  r   s  i  t   s  r  t   t  c  t  g
     p  p  p  r   g  a  w   p  e  r   -  d  r  s   p  h  a   q  r  v  p
    r   r  p   a  g  h   g  l  n  e   i  d  h   l  t  h  n   v  y  r
                         ⎯⎯⎯⎯⎯⎯⎯

481 gccgcatggg cttctgggcc aacttctacg aaaagctgtt caacttccgc gaaatccgct
      a  a  w   a  s  g   p  t  s  t   k  s  c   t  s  a   k  s  a
     g  p  h  g   l  l  g   q  l  l   r  k  a  v   q  l  p   r  n  p
    g   r  m   g  f  w   a  n  f  y   e  k  l   f  n  f  r   e  i  f 541 acttcgacat ccagggcgaa tacacgggcc tgacctccaa ggccatgacc gcgcccgacg
      t  s  t   s  r  a   n  t  r  a   -  p  p   r  p  -   p  r  p  t
     l  l  r  h   p  g  r   i  h  g   p  d  l  q   g  h  d   r  a  r
    y   f  d   i  q  g  e   y  t  g   l  t  s   k  a  m  t   a  p  d 601 gcaagattcg catcccgctg aacgaagagt ccaagcaggg cggcggccag atcgaagaat
      a  r  f   a  s  r   -  t  k  s   p  s  r   a  a  a   r  s  k  n
     r  q  d  s   h  p  a   e  r  r   v  q  a  g   r  r  p   d  r  r
    g   k  i   r  i  p  l   n  e  e   s  k  q   g  g  g  q   i  e  e 661 ttttgatgca attcaacggc gagggcattc agcacatcgc gctgatctgc gacaacctgc
      f  -  c   n  s  t   a  r  a  f   s  t  s   r  -  s   a  t  t  c
     i  f  d  a   i  q  r   r  g  h   s  a  h  r   a  d  l   r  q  p
    f   l  m   q  f  n  g   e  g  i   q  h  i   a  l  i  c   d  n  l 721 tggacgtggt ggacaagctg ggcatggccg gcgtgcagct ggccaccgcg cccaacgagg
      w  t  w   w  t  s   w  a  w  p   a  c  s   w  p  p   r  p  t  r
     a  g  r  g   g  q  a   g  h  g   r  r  a  a   g  h  r   a  q  r
    l   d  v   v  d  k  l   g  m  a   g  v  q   l  a  t  a   p  n  e 781 tctattacga aatgctggac acccgcctgc ccggccacgg ccagccggtg cccgagctgc
      s  i  t   k  c  w   t  p  a  c   p  a  t   a  s  r   c  p  s  c
     g  l  l  r   n  a  g   h  p  p   a  r  p  r   p  a  g   a  r  a
    v   y  y   e  m  l  d   t  r  l   p  g  h   g  q  p  y   p  e  l
                                            ←⎯⎯ o一oo一oooo一o 841 agtcgcgcgg catcttgctg gacggcacca cggccgacgg cacgcacccg cctgctagct
      s  r  a   a  s  c   w  t  a  p   r  p  t   a  r  t   r  l  l  a
     a  v  a  r   h  l  a   g  r  h   h  g  r  r   h  a  p   a  c  -
    q   s  r   g  i  l  l   d  g  t   t  a  d   q  t  h  p   p  a  s
                                         ⎯⎯⎯⎯⎯⎯⎯⎯⎯
                  ooo-o
901 tcagatcttc tccacgccca tgctgggccc ggtgttcttc gaattcatcc agcgcgaggg
      s  d  l   l  h  a   h  a  g  p   g  v  l   r  i  h   p  a  r  g
     l  q  i  f   s  t  p   m  l  g   p  v  f  f   e  f  i   q  r  e
    f   r  s   s  p  r  p   c  w  a   r  c  s   s  n  s  s   s  a  r 961 cgactaccgc gacggctttg gcgaaggcaa cttcaaggcg ctgttcgagt cgctggaacg
      r  l  p   r  r  l   w  r  r  q   l  q  g   a  v  r   v  a  g  t
     g  d  y  r   d  g  f   g  e  g   n  f  k  a   l  f  e   s  l  e
    a   t  t   a  t  a  l   a  k  a   t  s  r   r  c  s  s   r  w  n 1021 cgaccagatc cgccgtggtg tgctgaacac ataagacatc agacatccag ggttaaccct
       r  p  d   p  p  w   c  a  e  h   i  r  h   q  t  s   r  v  n  p
      r  d  q  i   r  r  g   v  l  n   t  -  d  i   r  h  p   g  l  t
     a   t  r   s  a  v  v   c  -  t   h  k  t   s  d  i  q   g  -  p 1081 gcacaggtgc ctatactgcg cgctcccgg aactcaaaag gatccgatg tcgctccgta
       a  q  v   p  i  l   r  a  p  r   n  s  k   g  s  r   c  r  s  v
      l  h  r  c   l  y  c   a  l  p   g  t  q  k   d  p  d   v  a  p
     c   t  g   a  y  t  a   r  s  p   e  l  k   r  i  p  m   s  l  r
```

```
1141 gcaccctgtt cagcacccctt ttggccggcg cagccactgt cgcgctggcg cagaacccgt
        a  p  s   s  a  p    f  w  p  a   q  p  l   s  r  w    r  r  t  r
      -  h  p  v   q  h  p    f  g  r  r   s  h  c   r  a  g    a  e  p
        s  t  l   f  s  t  l   l  a  g    a  a  t   v  a  l  a   q  n  p 1201 ctgcccgctc acatcg
        l  p  a   h  i
        v  c  p   l  t  s
        s  a  r   s  h
```

Sequence-tag of the clone M091_M24dG12. The primers 1j and 5h are indicated in the above sequence-tag of the clone M091_M24dG12. Hybridization between primer and template is indicated by arrows, mismatches by open circles. Putative conserved structural motifs are depicted in bold and underlined.

A further sequence-tag (SP1__2b5h) was generated using the primer pair 2b/5h. A BlastX-analysis of the sequence from this tag yielded the highest homology to an arylesterase from *Agrobacterium tumefaciens*, with 70% identity. The single clone carrying the corresponding gene was identified (4aE11) and the full length sequence determined to be as shown below:

1% glucose. At an $OD_{580}$ of 1, expression was induced by addition of 100 μM IPTG. Samples were taken at 2, 4, and 20 hours after induction. Cells were separated from the culture supernatant by centrifugation and after resuspending in sample buffer, they wee incubated for 10 minutes at 90° C. An amount of cells representing an $OD_{580}$ of 0.1 was applied to a 4-12% acryl amide gradient gel, which was stained with Coomassie Brilliant Blue R250.

Strong overexpression of the gene was detected already 2 h after induction with 100 μM IPTG, as determined by SDS-PAGE analysis of crude cell extracts from *E. coli* Rosetta

```
  1 atgaagacca ttctcgccta tggcgacagc ctgacctatg gggccaaccc gatccgggc
       m  k  t   i  l  a    y  g  d  s   l  t  y    g  a  n    p  i  p  g 61 gggccgcggc atgcctatga ggatcgctgg cccacggcgc tggagcaggg gctgggcggc
       g  p  r    h  a  y    e  d  r  w    p  t  a    l  e  q    g  l  g  g 121 aaggcgcggg tgattgccga ggggctgggt ggtcgcacca cggtgcatga cgactggttt
       k  a  r    v  i  a    e  g  l    g  r  t  t    v  h  d    d  w  f 181 gcgaatgcgg acaggaacgg tgccgcggtg ctgccgacgc tgctcgagag ccattcgccg
       a  n  a    d  r  n    g  a  r  v    l  p  t    l  l  e    s  h  s  p 241 ctcgacctga tcgtcatcat gctcggcacc aacgacatca agccgcatca cgggcggacg
       l  d  l    i  v  i    m  l  g  t  n  d   i  k  p  h    h  g  r  t 301 gccggcgagg ccgggcgggg catggcgcgg ctggtgcaga tcatccgcgg gcactatgcc
       a  g  e    a  g  r    g  m  a  r    l  v  q    i  i  r    g  h  y  a 361 ggccgcatgc aggacgagcc gcagatcatc ctcgtgtcgc cgccgccgat catcctcggc
       g  r  m    q  d  e    p  q  i  i    l  v  s    p  p  p    i  i  l  g 421 gactgggcgg acatgatgga ccatttcggc ccgcacgaag cgatcgccac ctcggtggat
       d  w  a    d  m  m    d  h  f  g    p  h  e    a  i  a    t  s  v  d 481 ttcgctcgcg agtacaagaa gcgggccgac gagcagaagg tgcatttctt cgacgccggc
       f  a  r    e  y  k    k  r  a  d    e  q  k    v  h  f    f  d  a  g 541 acggtggcga cgaccagcaa ggccgatggc atccacctcg acccggccaa tacgcgcgcc
       t  v  a    t  t  s    k  a  d  g  i  h  l    d  p  a    n  t  r  a 601 atcgggggcag ggctggtgcc gctggtgaag caggtgctcg gcctgtaa            (SEQ ID NO: 129)
       i  g  a    g  l  v    p  l  v  k    q  v  l    g  l  -         (SEQ ID NO: 130)
```

Figure 5:
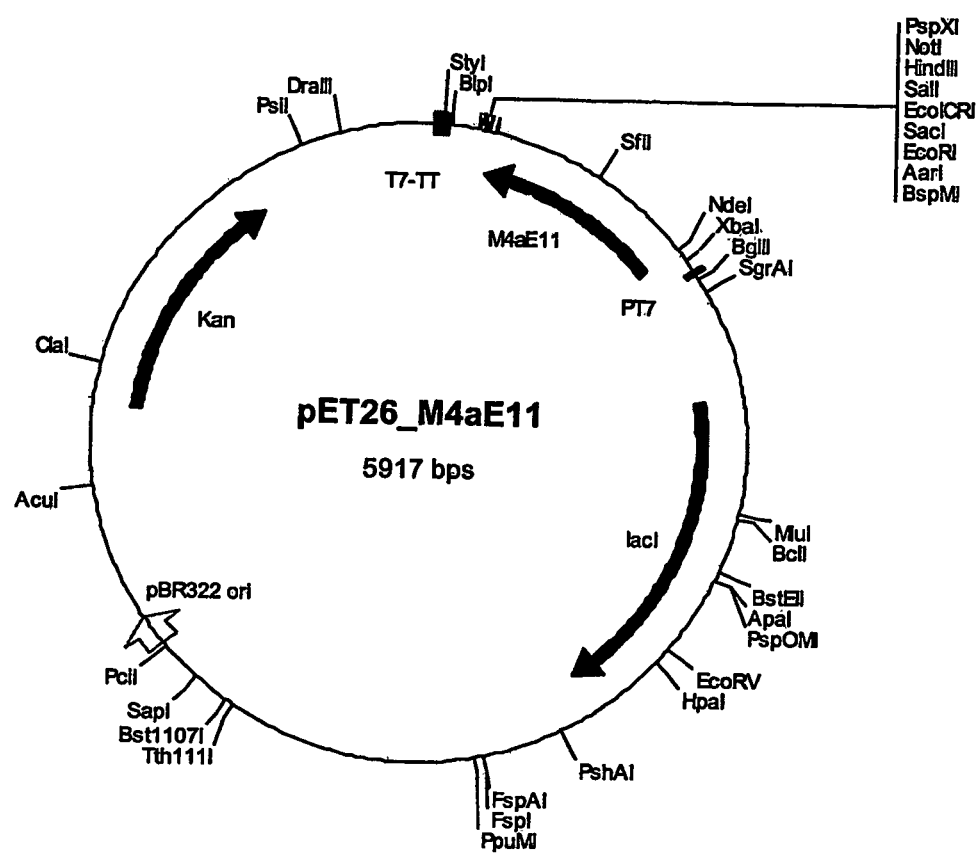
FIG. 5 provides a map of plasmid pET26-M4E11.

In the above sequence, the conserved structural motifs are shown in bold and underlined. The BlastP-analysis with the deduced full length amino acid sequence identified the same hit with a identity of 48%. The primary structure of this enzyme showed the "GRTT"-motif proving the usefulness of the primers directed towards block 2 for the identification of "GRTT"-esterases. The gene was amplified to introduce unique restriction enzyme recognition sites and the absence of second site mutations was confined by sequencing. The gene was ligated to pET26 and was expressed in *E. coli* Rosetta (DE3). The vector map is provided in FIG. 5. Expression and control strains were cultivated in LB in the presence of kanamycin (25 μg/ml), chloramphenicol (12.5 μg/ml), and (DE3) pET26_M4aE11. The amount of protein representing M4aE11 (calculated size 23.2 kDa) increased further over time.

Esterase activity of crude cell extracts from strains expressing the "GDSL"-type esterase M4aE11 was determined. An amount of cells corresponding to an $O.D._{580}=2$ were resuspended in 200 μl of 5 mM Tris/HCl pH 8.0, and lysed by ultrasonication. Then, 20 μl of each sample were used to determine the esterase activity towards p-nitrophenyl butyrate in a total volume of 200 μl. The activity was corrected for the background activity of the control strain. The activity towards p-nitrophenylbutyrate reached about 125 nmol/ml×min 20 h after induction.

In addition, SDS-PAGE analysis of the soluble and insoluble fraction of crude cell extracts from *E. coli* Rosetta (DE3) pET26_M4aE11 was conducted. Cells from a culture induced with 100 μM IPTG and harvested 4 h and 20 h after induction were lysed by ultrasonication and separated into soluble and insoluble fraction by centrifugation. Sample buffer was added and directly comparable amounts of soluble and insoluble fractions were applied to a 4-12% acryl amide gradient gel, which was stained with Coomassie Brilliant Blue R250. The results of this analysis of the solubility revealed that M4aE11 is partially (estimated 80%) soluble. The screening of the library M091 was completed.

Thus, in total nine different "GDSL"-type esterases were identified in 6 different large insert metagenomic libraries and the esterases/lipases BRAIN's library comprising more than 4.3 Gbp. Eight of these genes were heterologously expressed in *E. coli*. The resulting enzyme samples of seven clones were characterized for the desired perhydrolase activity. Two of the enzymes displayed this activity. Table 3 summarizes the screening, expression and characterization of the metagenomic "GDSL"-type esterases.

TABLE 3

Expression and Characterization of Metagenomic "GDSL"-Type Esterases

| GDSL-type Esterase | Homology[1] | Expression[2] Level | Solubility[3] | Activity[4] | Perhydrolase Activity |
|---|---|---|---|---|---|
| S248_M2bB11 | 12.9% | ++ | + | 136 | − |
| S248_M40cD4 | 14.8% | +++ | ++ | 50 | −/+[6] |
| S248_M44aA5 | 12.4% | +++ | ++ | 75 | −/+ |
| S261_M2aA12 | 36.9% | ++ | ++ | 72 | +[7] |
| S279_M70aE8 | 11.9% | +++ | + | 167 | − |
| S279_M75bA2 | 5.7% | n.d.[5] | n.d. | n.d. | n.d.[5] |
| M091_M4aE11 | 33.9% | +++ | ++ | 125 | n.d. |
| Est105 | 4.3% | +++ | − | − | n.d. |
| Est114 | 7.8% | n.d. | n.d. | 13 | − |

[1]identity to the prototype enzyme from *M. smegmatis* calculated with the dialign algorithm (Morgenstern et al., 1996)
[2]expression level: + moderate overexpression; ++ strong overexpression; +++ very strong overexpression as judged from SDS-PAGE-analysis
[3]as judged by SDS-PAGE-analysis
[4]towards p-nitrophenyl butyrate; given as nmol/(ml × min)
[5]not determined
[6]perhydrolysis activity 2x background
[7]perhydrolase activity more than 2x background Engineering of the Perhydrolase Based on the structure of the perhydrolase, residues which may alter substrate specificity (e.g., Km, kcat, Vmax, chain length, etc.) and or the multimeric nature of the protein were identified. However, it is not intended that the present invention be limited to any particular residues. Nonetheless, site saturation libraries of residues D10, L12, T13, W14, W16, S54, A55, N94, K97, Y99, P146, W149, F150, I194, F196, are constructed, as well as combinatorial libraries of residues: E51A, Y73A, H81D, T127Q and single mutations of the active site residues D192A, H195A and a site saturation library of the conserved D95. Methods for production of such libraries are known to those skilled in the art and include commercially available kits as the Stratagene Quikchange™ Site-directed mutagenesis kit and/or Quikchange™ Multi-Site-directed mutagenesis kit.

Perhydrolase Activity

The use of enzymes obtained from microorganisms is long-standing. Indeed there are numerous biocatalysts known in the art. For example, U.S. Pat. No. 5,240,835 (herein incorporated by reference) provides a description of the transacylase activity of obtained from *C. oxydans* and its production. In addition, U.S. Pat. No. 3,823,070 (herein incorporated by reference) provides a description of a *Corynebacterium* that produces certain fatty acids from an n-paraffin. U.S. Pat. No. 4,594,324 (herein incorporated by reference) provides a description of a *Methylcoccus capsulatus* that oxidizes alkenes. Additional biocatalysts are known in the art (See e.g. U.S. Pat. Nos. 4,008,125 and 4,415,657; both of which are herein incorporated by reference). EP 0 280 232 describes the use of a *C. oxydans* enzyme in a reaction between a diol and an ester of acetic acid to produce monoacetate. Additional references describe the use of a *C. oxydans* enzyme to make chiral hydroxycarboxylic acid from a prochiral diol. Additional details regarding the activity of the *C. oxydans* transacylase as well as the culture of *C. oxydans*, preparation and purification of the enzyme are provided by U.S. Pat. No. 5,240,835 (incorporated by reference, as indicated above). Thus, the transesterification capabilities of this enzyme, using mostly acetic acid esters were known. However, the determination that this enzyme could carry out perhydrolysis reaction was quite unexpected. It was even more surprising that these enzymes exhibit very high efficiencies in perhydrolysis reactions. For example, in the presence of tributyrin and water, the enzyme acts to produce butyric acid, while in the presence of tributyrin, water and hydrogen peroxide, the enzyme acts to produce mostly peracetic acid and very little butyric acid. This high perhydrolysis to hydrolysis ratio is a unique property exhibited by the perhydrolase class of enzymes of the present invention and is a unique characteristic that is not exhibited by previously described lipases, cutinases, nor esterases.

The perhydrolase of the present invention is active over a wide pH and temperature range and accepts a wide range of substrates for acyl transfer. Acceptors include water (hydrolysis), hydrogen peroxide (perhydrolysis) and alcohols (classical acyl transfer). For perhydrolysis measurements, enzyme is incubated in a buffer of choice at a specified temperature with a substrate ester in the presence of hydrogen peroxide. Typical substrates used to measure perhydrolysis include esters such as ethyl acetate, triacetin, tributyrin, ethoxylated neodol acetate esters, and others. In addition, the wild type enzyme hydrolyzes nitrophenylesters of short chain acids. The latter are convenient substrates to measure enzyme concentration. Peracid and acetic acid can be measured by the assays described herein. Nitrophenylester hydrolysis is also described.

Although the primary example used during the development of the present invention is the *M. smegmatis* perhydrolase, any perhydrolase obtained from any source which converts the ester into mostly peracids in the presence of hydrogen peroxide finds use in the present invention.

Substrates

In some preferred embodiments of the present invention, esters comprising aliphatic and/or aromatic carboxylic acids and alcohols are utilized with the perhydrolase enzymes of the present invention. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. In additional embodiments, triacetin, tributyrin, neodol esters, and/or ethoxylated neodol esters serve as acyl donors for peracid formation.

Cleaning and Detergent Formulations

The detergent compositions of the present invention are provided in any suitable form, including for example, as a liquid diluent, in granules, in emulsions, in gels, and pastes. When a solid detergent composition is employed, the detergent is preferably formulated as granules. Preferably, the granules are formulated to additionally contain a protecting agent (See e.g., U.S. application Ser. No. 07/642,669 filed Jan. 17, 1991, incorporated herein by reference). Likewise, in some embodiments, the granules are formulated so as to contain materials to reduce the rate of dissolution of the granule into the wash medium (See e.g., U.S. Pat. No. 5,254, 283, incorporated herein by reference in its entirety). In addition, the perhydrolase enzymes of the present invention find use in formulations in which substrate and enzyme are present in the same granule. Thus, in some embodiments, the efficacy of the enzyme is increased by the provision of high local concentrations of enzyme and substrate (See e.g., U.S. Patent Application Publication US2003/0191033, herein incorporated by reference).

Many of the protein variants of the present invention are useful in formulating various detergent compositions. A number of known compounds are suitable surfactants useful in compositions comprising the protein mutants of the invention. These include nonionic, anionic, cationic, anionic or zwitterionic detergents (See e.g., U.S. Pat. Nos. 4,404,128 and 4,261,868). A suitable detergent formulation is that described in U.S. Pat. No. 5,204,015 (previously incorporated by reference). Those in the art are familiar with the different formulations which find use as cleaning compositions. As indicated above, in some preferred embodiments, the detergent compositions of the present invention employ a surface active agent (i.e., surfactant) including anionic, nonionic and ampholytic surfactants well known for their use in detergent compositions. Some surfactants suitable for use in the present invention are described in British Patent Application No. 2 094 826 A, incorporated herein by reference. In some embodiments, mixtures surfactants are used in the present invention.

Suitable anionic surfactants for use in the detergent composition of the present invention include linear or branched alkylbenzene sulfonates; alkyl or alkenyl ether sulfates having linear or branched alkyl groups or alkenyl groups; alkyl or alkenyl sulfates; olefin sulfonates; alkane sulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants that find use in the present invention include quaternary ammonium salt sulfonates, betaine-type ampholytic surfactants, and the like. Such ampholytic surfactants have both the positive and negative charged groups in the same molecule.

Nonionic surfactants that find use in the present invention generally comprise polyoxyalkylene ethers, as well as higher fatty acid alkanolamides or alkylene oxide adduct thereof, fatty acid glycerine monoesters, and the like.

In some preferred embodiments, the surfactant or surfactant mixture included in the detergent compositions of the present invention is provided in an amount from about 1 weight percent to about 95 weight percent of the total detergent composition and preferably from about 5 weight percent to about 45 weight percent of the total detergent composition. In various embodiments, numerous other components are included in the compositions of the present invention. Many of these are described below. It is not intended that the present invention be limited to these specific examples. Indeed, it is contemplated that additional compounds will find use in the present invention. The descriptions below merely illustrate some optional components.

Proteins, particularly the perhydrolase of the present invention can be formulated into known powdered and liquid detergents having pH between 3 and 12.0, at levels of about 0.001 to about 5% (preferably 0.1% to 0.5%) by weight. In some embodiments, these detergent cleaning compositions further include other enzymes such as proteases, amylases, mannanases, peroxidases, oxido reductases, cellulases, lipases, cutinases, pectinases, pectin lyases, xylanases, and/or endoglycosidases, as well as builders and stabilizers.

In addition to typical cleaning compositions, it is readily understood that perhydrolase variants of the present invention find use in any purpose that the native or wild-type enzyme is used. Thus, such variants can be used, for example, in bar and liquid soap applications, dishcare formulations, surface cleaning applications, contact lens cleaning solutions or products, waste treatment, textile applications, pulp-bleaching, disinfectants, skin care, oral care, hair care, etc. Indeed, it is not intended that any variants of the perhydrolase of the present invention be limited to any particular use. For example, the variant perhydrolases of the present invention may comprise, in addition to decreased allergenicity, enhanced performance in a detergent composition (as compared to the wild-type or unmodified perhydrolase).

The addition of proteins to conventional cleaning compositions does not create any special use limitations. In other words, any temperature and pH suitable for the detergent are also suitable for the present compositions, as long as the pH is within the range in which the enzyme(s) is/are active, and the temperature is below the described protein's denaturing temperature. In addition, proteins of the invention find use in cleaning, bleaching, and disinfecting compositions without detergents, again either alone or in combination with a source of hydrogen peroxide, an ester substrate (e.g. either added or inherent in the system utilized, such as with stains that contain esters, pulp that contains esters etc), other enzymes, surfactants, builders, stabilizers, etc. Indeed it is not intended that the present invention be limited to any particular formulation or application.

Substrates

In some preferred embodiments of the present invention, esters comprising aliphatic and/or aromatic carboxylic acids and alcohols are utilized with the perhydrolase enzymes in the detergent formulations of the present invention. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Thus, in some preferred embodiments, detergents comprising at least one perhydrolase, at least one hydrogen peroxide source, and at least one ester acid are provided.

Hydrolases

In addition to the perhydrolase described herein, various hydrolases find use in the present invention, including but not limited to carboxylate ester hydrolase, thioester hydrolase, phosphate monoester hydrolase, and phosphate diester hydrolase which act on ester bonds; a thioether hydrolase which acts on ether bonds; and α-amino-acyl-peptide hydrolase, peptidyl-amino acid hydrolase, acyl-amino acid hydrolase, dipeptide hydrolase, and peptidyl-peptide hydrolase which act on peptide bonds, all these enzymes having high perhydrolysis to hydrolysis ratios (e.g., >1). Preferable among them are carboxylate ester hydrolase, and peptidyl-peptide hydrolase. Suitable hydrolases include: (1) proteases belonging to the peptidyl-peptide hydrolase class (e.g., pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D, bromelin, keratinase, chymotrypsin C, pepsin C, aspergillopeptidase B, urokinase, carboxypeptidase A and B, and aminopeptidase); (2) carboxylate ester hydrolase including carboxyl esterase, lipase, pectin esterase, and chlorophyllase; and (3) enzymes having high perhydrolysis to hydrolysis ratios. Especially effective among them are lipases, as well as esterases that exhibit high perhydrolysis to hydrolysis ratios, as well as protein engineered esterases, cutinases, and lipases, using the primary, secondary, tertiary, and/or quaternary structural features of the perhydrolases of the present invention.

The hydrolase is incorporated into the detergent composition as much as required according to the purpose. It should preferably be incorporated in an amount of 0.0001 to 5 weight percent, and more preferably 0.02 to 3 weight percent. This enzyme should be used in the form of granules made of crude enzyme alone or in combination with other enzymes and/or components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. In some embodiments, the granules are formulated so as to contain an enzyme protecting agent and a dissolution retardant material (i.e., material that regulates the dissolution of granules during use).

Cationic Surfactants and Long-Chain Fatty Acid Salts

Such cationic surfactants and long-chain fatty acid salts include saturated or fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts include those disclosed in British Patent Application No. 2 094 826 A, the disclosure of which is incorporated herein by reference. The composition may contain from about 1 to about 20 weight percent of such cationic surfactants and long-chain fatty acid salts.

Builders

In some embodiments of the present invention, the composition contains from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Examples of suitable divalent sequestering agents are disclosed in British Patent Application No. 2 094 826 A, the disclosure of which is incorporated herein by reference.

In additional embodiments, compositions of the present invention contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine Anti-Redeposition Agents In yet additional embodiments of the present invention, the compositions contain from about 0.1 to about 5 weight percent of one or more of the following compounds as antiredeposition agents: polyethylene glycol, polyvinyl alcohol, polyvinylpyrrolidone and carboxymethylcellulose. In some preferred embodiments, a combination of carboxymethylcellulose and/or polyethylene glycol are utilized with the composition of the present invention as useful dirt removing compositions.

Bleaching Agents

The use of the perhydrolases of the present invention in combination with additional bleaching agent(s) such as sodium percarbonate, sodium perborate, sodium sulfate/hydrogen peroxide adduct and sodium chloride/hydrogen peroxide adduct and/or a photo-sensitive bleaching dye such as zinc or aluminum salt of sulfonated phthalocyanine further improves the detergent effects. In additional embodiments, the perhydrolases of the present invention are used in combination with bleach boosters (e.g., TAED and/or NOBS).

Bluing Agents and Fluorescent Dyes

In some embodiments of the present invention, bluing agents and fluorescent dyes are incorporated in the composition. Examples of suitable bluing agents and fluorescent dyes are disclosed in British Patent Application No. 2 094 826 A, the disclosure of which is incorporated herein by reference.

Caking Inhibitors

In some embodiments of the present invention in which the composition is powdered or solid, caking inhibitors are incorporated in the composition. Examples of suitable caking inhibitors include p-toluenesulfonic acid salts, xylenesulfonic acid salts, acetic acid salts, sulfosuccinic acid salts, talc, finely pulverized silica, clay, calcium silicate (e.g., Micro-Cell by Johns Manville Co.), calcium carbonate and magnesium oxide.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4-hydroxy-phenyl)cyclohexane.

Solubilizers

In some embodiments, the compositions of the present invention also include solubilizers, including but not limited to lower alcohols (e.g., ethanol, benzenesulfonate salts, and lower alkylbenzenesulfonate salts such as p-toluenesulfonate salts), glycols such as propylene glycol, acetylbenzene-sulfonate salts, acetamides, pyridinedicarboxylic acid amides, benzoate salts and urea.

In some embodiments, the detergent composition of the present invention are used in a broad pH range of from acidic to alkaline pH. In a preferred embodiment, the detergent composition of the present invention is used in mildly acidic, neutral or alkaline detergent wash media having a pH of from above 4 to no more than about 12.

In addition to the ingredients described above, perfumes, buffers, preservatives, dyes and the like also find use with the present invention. These components are provided in concentrations and forms known to those in the art.

In some embodiments, the powdered detergent bases of the present invention are prepared by any known preparation methods including a spray-drying method and a granulation method. The detergent base obtained particularly by the spray-drying method and/or spray-drying granulation method are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-dryinggranulation method, various ingredients may also be added after the preparation of the base.

When the detergent base is a liquid, it may be either a homogeneous solution or an inhomogeneous dispersion.

The detergent compositions of this invention may be incubated with fabric, for example soiled fabrics, in industrial and household uses at temperatures, reaction times and liquor ratios conventionally employed in these environments. The incubation conditions (i.e., the conditions effective for treating materials with detergent compositions according to the present invention), are readily ascertainable by those of skill in the art. Accordingly, the appropriate conditions effective for treatment with the present detergents correspond to those using similar detergent compositions which include wild-type perhydrolase.

As indicated above, detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the perhydrolase enzyme is generally employed from about 0.00001% to about 5% weight percent based on the total weight of the pre-soak or pre-treatment composition. In such compositions, a surfactant may optionally be employed and when employed, is generally present at a concentration of from about 0.0005 to about 1 weight percent based on the total weight of the pre-soak. The remainder of the composition comprises conventional components used in the pre-soak (e.g., diluent, buffers, other enzymes (proteases), etc.) at their conventional concentrations.

Cleaning Compositions Comprising Perhydrolase

The cleaning compositions of the present invention may be advantageously employed for example, in laundry applications, hard surface cleaning, automatic dishwashing applications, as well as cosmetic applications such as dentures, teeth, hair and skin. However, due to the unique advantages of increased effectiveness in lower temperature solutions and the superior color-safety profile, the enzymes of the present invention are ideally suited for laundry applications such as the bleaching of fabrics. Furthermore, the enzymes of the present invention find use in both granular and liquid compositions.

The enzymes of the present invention also find use in cleaning additive products. Cleaning additive products including the enzymes of the present invention are ideally suited for inclusion in wash processes where additional bleaching effectiveness is desired. Such instances include, but are not limited to low temperature solution cleaning applications. The additive product may be, in its simplest form, one or more of the enzymes of the present invention. Such additive may be packaged in dosage form for addition to a cleaning process where a source of peroxygen is employed and increased bleaching effectiveness is desired. Such single dosage form may comprise a pill, tablet, gelcap or other single dosage unit such as pre-measured powders or liquids. A filler or carrier material may be included to increase the volume of such composition. Suitable filler or carrier materials include, but are not limited to, various salts of sulfate, carbonate and silicate as well as talc, clay and the like. Filler or carrier materials for liquid compositions may be water or low molecular weight primary and secondary alcohols including polyols and diols. Examples of such alcohols include, but are not limited to; methanol, ethanol, propanol and isopropanol. The compositions may contain from about 5% to about 90% of such materials. Acidic fillers can be used to reduce pH. Alternatively, the cleaning additive may include activated peroxygen source defined below or the adjunct ingredients as defined below.

The cleaning compositions and cleaning additives of the present invention require an effective amount of the enzymes provided by the present invention. The required level of enzyme may be achieved by the addition of one or more species of the *M. smegmatis* perhydrolase, variants, homologues, and/or other enzymes or enzyme fragments having the activity of the enzymes of the present invention. Typically, the cleaning compositions of the present invention comprise at least 0.0001 weight percent, from about 0.0001 to about 1, from about 0.001 to about 0.5, or even from about 0.01 to about 0.1 weight percent of at least one enzyme of the present invention.

In some embodiments, the cleaning compositions of the present invention comprise a material selected from the group consisting of a peroxygen source, hydrogen peroxide and mixtures thereof, said peroxygen source being selected from the group consisting of:

(i) from about 0.01 to about 50, from about 0.1 to about 20, or even from about 1 to 10 weight percent of a per-salt, an organic peroxyacid, urea hydrogen peroxide and mixtures thereof;

(ii) from about 0.01 to about 50, from about 0.1 to about 20, or even from about 1 to 10 weight percent of a carbohydrate and from about 0.0001 to about 1, from about 0.001 to about 0.5, from about 0.01 to about 0.1 weight-percent carbohydrate oxidase; and (iii) mixtures thereof.

Suitable per-salts include those selected from the group consisting of alkalimetal perborate, alkalimetal percarbonate, alkalimetal perphosphates, alkalimetal persulphates and mixtures thereof.

The carbohydrate may be selected from the group consisting of mono-carbohydrates, di-carbohydrates, tri-carbohydrates, oligo-carbohydrates and mixtures thereof. Suitable carbohydrates include carbohydrates selected from the group consisting of D-arabinose, L-arabinose, D-Cellobiose, 2-Deoxy-D-galactose, 2-Deoxy-D-ribose, D-Fructose, L-Fucose, D-Galactose, D-glucose, D-glycero-D-gulo-heptose, D-lactose, D-Lyxose, L-Lyxose, D-Maltose, D-Mannose, Melezitose, L-Melibiose, Palatinose, D-Raffinose, L-Rhamnose, D-Ribose, L-Sorbose, Stachyose, Sucrose, D-Trehalose, D-Xylose, L-Xylose and mixtures thereof.

Suitable carbohydrate oxidases include carbohydrate oxidases selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) and/or hexose oxidase (IUPAC classification EC1.1.3.5), Glucose oxidase (IUPAC classification EC1.1.3.4) and mixtures thereof.

In some preferred embodiments, the cleaning compositions of the present invention also include from about 0.01 to about 99.9, from about 0.01 to about 50, from about 0.1 to 20, or even from about 1 to about 15 weight percent a molecule comprising an ester moiety. Suitable molecules comprising an ester moiety may have the formula:

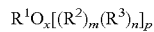

$$R^1O_x[(R^2)_m(R^3)_n]_p$$

wherein $R^1$ is a moiety selected from the group consisting of H or a substituted or unsubstituted alkyl, heteroalkyl, alkenyl, alkynyl, aryl, alkylaryl, alkylheteroaryl, and heteroaryl; in one aspect of the present invention, $R^1$ may comprise from 1 to 50,000 carbon atoms, from 1 to 10,000 carbon atoms, or even from 2 to 100 carbon atoms;

each $R^2$ is an alkoxylate moiety, in one aspect of the present invention, each $R^2$ is independently an ethoxylate, propoxylate or butoxylate moiety, $R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be substituted or unsubstituted alkyl, alkenyl, alkynyl, moiety comprising from 1 to 22 carbon atoms, an aryl, alkylaryl, alkylheteroaryl, or heteroaryl moiety comprising from 4 to 22 carbon atoms or $R^4$ may be a substituted or unsubstituted $C_1$-$C_{22}$ alkyl moiety or $R^4$ may be a substituted or unsubstituted $C_1$-$C_{12}$ alkyl moiety;

x is 1 when $R^1$ is H; when $R^1$ is not H, x is an integer that is equal to or less than the number of carbons in $R^1$ p is an integer that is equal to or less than x m is an integer from 0 to 50, an integer from 0 to 18, or an integer from 0 to 12, and n is at least 1.

In one aspect of the present invention, the molecule comprising an ester moiety is an alkyl ethoxylate or propoxylate having the formula $R^1O_x[(R^2)_m(R^3)_n]_p$ wherein:

$R^1$ is an $C_2$-$C_{32}$ substituted or unsubstituted alkyl or heteroalkyl moiety, each $R^2$ is independently an ethoxylate or propoxylate moiety;

$R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be a substituted or unsubstituted alkyl, alkenyl, or alkynyl moiety comprising from 1 to 22 carbon atoms, a substituted or unsubstituted aryl, alkylaryl, alkylheteroaryl, or heteroaryl moiety comprising from 4 to 22 carbon atoms or $R^4$ may be a substituted or unsubstituted $C_1$-$C_{12}$ alkyl moiety or $R^4$ may be a substituted or unsubstituted $C_1$-$C_{12}$ alkyl moiety, x is an integer that is equal to or less than the number of carbons in $R^1$ p is an integer that is equal to or less than x m is an integer from 1 to 12, and n is at least 1.

In one aspect of the present invention, the molecule comprising the ester moiety has the formula:

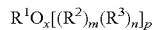

wherein $R^1$ is H or a moiety that comprises a primary, secondary, tertiary or quaternary amine moiety, said $R^1$ moiety that comprises an amine moiety being selected from the group consisting of a substituted or unsubstituted alkyl, heteroalkyl, alkenyl, alkynyl, aryl, alkylaryl, alkylheteroaryl, and heteroaryl; in one aspect of Applicants' invention $R^1$ may comprise from 1 to 50,000 carbon atoms, from 1 to 10,000 carbon atoms, or even from 2 to 100 carbon atoms;

each $R^2$ is an alkoxylate moiety, in one aspect of the present invention each $R^2$ is independently an ethoxylate, propoxylate or butoxylate moiety, $R^3$ is an ester-forming moiety having the formula:

$R^4CO$— wherein $R^4$ may be H, substituted or unsubstituted alkyl, alkenyl, alkynyl, aryl, alkylaryl, alkylheteroaryl, and heteroaryl, in one aspect of the present invention, $R^4$ may be a substituted or unsubstituted alkyl, alkenyl, or alkynyl moiety comprising from 1 to 22 carbon atoms, a substituted or unsubstituted aryl, alkylaryl, alkylheteroaryl, or heteroaryl moiety comprising from 4 to 22 carbon atoms or $R^4$ may be a substituted or unsubstituted $C_1$-$C_{22}$ alkyl moiety or $R^4$ may be a substituted or unsubstituted $C_1$-$C_{12}$ alkyl moiety;

x is 1 when $R^1$ is H; when $R^1$ is not H, x is an integer that is equal to or less than the number of carbons in $R^1$ p is an integer that is equal to or less than x m is an integer from 0 to 12 or even 1 to 12, and n is at least 1.

In any of the aforementioned aspects of the present invention, the molecule comprising an ester moiety may have a weight average molecular weight of less than 600,000 Daltons, less than 300,000 Daltons, less than 100,000 Daltons or even less than 60,000 Daltons.

Suitable molecules that comprise an ester moiety include polycarbohydrates that comprise an ester moiety.

The cleaning compositions provided herein will typically be formulated such that, during use in aqueous cleaning operations, the wash water will have a pH of from about 5.0 to about 11.5, or even from about 7.5 to about 10.5. Liquid product formulations are typically formulated to have a pH from about 3.0 and about 9.0. Granular laundry products are typically formulated to have a pH from about 9 to about 11. Techniques for controlling pH at recommended usage levels include the use of buffers, alkalis, acids, etc., and are well known to those skilled in the art.

When the enzyme(s) of the present invention is/are employed in a granular composition or liquid, it may be desirable for the enzyme(s) to be in the form of an encapsulated particle to protect such enzyme from other components of the granular composition during storage. In addition, encapsulation is also a means of controlling the availability of the enzyme(s) during the cleaning process and may enhance performance of the enzyme(s). In this regard, the enzyme(s) may be encapsulated with any encapsulating material known in the art.

The encapsulating material typically encapsulates at least part of the enzyme(s). Typically, the encapsulating material is water-soluble and/or water-dispersible. The encapsulating material may have a glass transition temperature (Tg) of 0° C. or higher. Glass transition temperature is described in more detail in WO 97/11151, especially from page 6, line 25 to page 7, line 2.

The encapsulating material may be selected from the group consisting of carbohydrates, natural or synthetic gums, chitin and chitosan, cellulose and cellulose derivatives, silicates, phosphates, borates, polyvinyl alcohol, polyethylene glycol, paraffin waxes and combinations thereof. When the encapsulating material is a carbohydrate, it may be typically selected from the group consisting of monosaccharides, oligosaccharides, polysaccharides, and combinations thereof. Typically, the encapsulating material is a starch. Suitable starches are described in EP 0 922 499; U.S. Pat. No. 4,977,252; U.S. Pat. No. 5,354,559 and U.S. Pat. No. 5,935,826.

The encapsulating material may be a microsphere made from plastic such as thermoplastics, acrylonitrile, methacrylonitrile, polyacrylonitrile, polymethacrylonitrile and mixtures thereof; commercially available microspheres that can be used are those supplied by Expancel of Stockviksverken, Sweden under the trademark EXPANCEL®, and those supplied by PQ Corp. of Valley Forge, Pa. U.S.A. under the tradename PM 6545, PM 6550, PM 7220, PM 7228, EXTENDOSPHERES®, LUXSIL®, Q-CEL® and SPHERICEL®.

Processes of Making and Using the Cleaning Compositions of the Present Invention The cleaning compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422 Del Greco et al.; U.S. Pat. No. 5,516,448; U.S. Pat. No. 5,489,392; and U.S. Pat. No. 5,486,303; all of which are incorporated herein by reference.

Adjunct Materials in Addition to the Enzymes of the Present Invention, Hydrogen Peroxide, and/or Hydrogen Peroxide Source and Material Comprising an Ester Moiety While not essential for the purposes of the present invention, the non-limiting list of adjuncts illustrated hereinafter are suitable for use in the instant cleaning compositions and may be desirably incorporated in certain embodiments of the invention, for example to assist or enhance cleaning performance, for treatment of the substrate to be cleaned, or to modify the aesthetics of the cleaning composition as is the case with perfumes, colorants, dyes or the like. It is understood that such adjuncts are in addition to the enzymes of the present invention, hydrogen peroxide and/or hydrogen peroxide source and material comprising an ester moiety. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, herein incorporated by reference. The aforementioned adjunct ingredients may constitute the balance of the cleaning compositions of the present invention.

Surfactants—

The cleaning compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof.

The surfactant is typically present at a level of from about 0.1% to about 60%, from about 1% to about 50% or even from about 5% to about 40% by weight of the subject cleaning composition.

Builders—

The cleaning compositions of the present invention may comprise one or more detergent builders or builder systems. When a builder is used, the subject cleaning composition will typically comprise at least about 1%, from about 3% to about 60% or even from about 5% to about 40% builder by weight of the subject cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—

The cleaning compositions herein may contain a chelating agent, Suitable chelating agents include copper, iron and/or manganese chelating agents and mixtures thereof.

When a chelating agent is used, the cleaning composition may comprise from about 0.1% to about 15% or even from about 3.0% to about 10% chelating agent by weight of the subject cleaning composition.

Deposition Aid—

The cleaning compositions herein may contain a deposition aid. Suitable deposition aids include, polyethylene glycol, polypropylene glycol, polycarboxylate, soil release polymers such as polytelephthalic acid, clays such as Kaolinite, montmorillonite, atapulgite, illite, bentonite, halloysite, and mixtures thereof.

Dye Transfer Inhibiting Agents—

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

When present in a subject cleaning composition, the dye transfer inhibiting agents may be present at levels from about 0.0001% to about 10%, from about 0.01% to about 5% or even from about 0.1% to about 3% by weight of the cleaning composition.

Dispersants—

The cleaning compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzymes—

The cleaning compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is cocktail of conventional applicable enzymes like protease, lipase, cutinase and/or cellulase in conjunction with amylase.

Enzyme Stabilizers—

Enzymes for use in detergents can be stabilized by various techniques. The enzymes employed herein can be stabilized by the presence of water-soluble sources of calcium and/or magnesium ions in the finished compositions that provide such ions to the enzymes.

Catalytic Metal Complexes—

The cleaning compositions of the present invention may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; and U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the active MRL species in the aqueous washing medium, and will preferably provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexadecane.

Suitable transition metal MRLs are readily prepared by known procedures, such as taught for example in WO 00/332601, and U.S. Pat. No. 6,225,464.

Method of Use

The cleaning compositions disclosed herein of can be used to clean a situs inter alia a surface or fabric. Typically at least a portion of the situs is contacted with an embodiment of Applicants' cleaning composition, in neat form or diluted in a wash liquor, and then the situs is optionally washed and/or rinsed. For purposes of the present invention, washing includes but is not limited to, scrubbing, and mechanical agitation. The fabric may comprise most any fabric capable of being laundered in normal consumer use conditions. The disclosed cleaning compositions are typically employed at concentrations of from about 500 ppm to about 15,000 ppm in solution. When the wash solvent is water, the water temperature typically ranges from about 5 C to about 90° C. and, when the situs comprises a fabric, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); bp (base pair); kb (kilobase pair); kD (kilodaltons); gm (grams); μg and ug (micrograms); mg (milligrams); ng (nanograms); μl and μl (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgC_2$ (magnesium chloride); NaCl (sodium chloride); $OD_{280}$ (optical density at 280 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris(tris(hydroxymethyl)aminomethane); TAED (N,N,N'N'-tetraacetylethylenediamine); w/v (weight to volume); v/v (volume to volume); Per (perhydrolase); per (perhydrolase gene); Ms (*M. smegmatis*); MS (mass spectroscopy); BRAIN (BRAIN Biotechnology Research and Information Network, AG, Zwingenberg, Germany); TIGR (The Institute for Genomic Research, Rockville, Md.); AATCC (American Association of Textile and Coloring Chemists); WFK (wfk Testgewebe GmbH, Bruggen-Bracht, Germany); Amersham (Amersham Life Science, Inc. Arlington Heights, Ill.); ICN (ICN Pharmaceuticals, Inc., Costa Mesa, Calif.); Pierce (Pierce Biotechnology, Rockford, Ill.); Amicon (Amicon, Inc., Beverly, Mass.); ATCC (American Type Culture Collection, Manassas, Va.); Amersham (Amersham Biosciences, Inc., Piscataway, N.J.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Novagen (Novagen, Inc., Madison, Wis.); Qiagen (Qiagen, Inc., Valencia, Calif.); Invitrogen (Invitrogen Corp., Carlsbad, Calif.); Genaissance (Genaissance Pharmaceuticals, Inc., New Haven, Conn.); DNA 2.0 (DNA 2.0, Menlo Park, Calif.); MIDI (MIDI Labs, Newark, Del.) InvivoGen (InvivoGen, San Diego, Calif.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Roche (Hoffmann La Roche, Inc., Nutley, N.J.); Agilent (Agilent Technologies, Palo Alto, Calif.); Minolta (Konica Minolta, Ramsey, N.J.); and Zeiss (Carl Zeiss, Inc., Thornwood, N.Y.).

In the following Examples, various media were used. "TS" medium (per liter) was prepared using Tryptone (16 g) (Difco), Soytone (4 g) (Difco), Casein hydrolysate (20 g) (Sigma), $K_2HPO_4$ (10 g), and d $H_2O$ (to 1 L). The medium was sterilized by autoclaving. Then, sterile glucose was added to 1.5% final concentration. *Streptomyces* Production Medium (per liter) was prepared using citric acid ($H_2O$) (2.4 g), Biospringer yeast extract (6 g), $(NH_4)_2SO_4$ (2.4 g), $MgSO_4.7H_2O$ (2.4 g), Mazu DF204 (5 ml), trace elements (5 ml). The pH was adjusted to 6.9 with NaOH. The medium was then autoclaved to sterilize. After sterilization, $CaCl_2.2H_2O$ (2 mls of 100 mg/ml solution), $KH_2PO_4$ (200 ml of a 13% (w/v) solution at pH6.9), and 20 mls of a 50% glucose solution were added to the medium.

In these experiments, a spectrophotometer was used to measure the absorbance of the products formed after the completion of the reactions. A reflectometer was used to measure the reflectance of the swatches. Unless otherwise indicated, protein concentrations were estimated by Coomassie Plus (Pierce), using BSA as the standard.

Example 1

Enzyme Analysis

In this Example, methods to assess enzyme purity and activity used in the subsequent Examples and throughout the present Specification are described.

Enzyme Activity Assay (pNB Assay)

This activity was measured by hydrolysis of p-nitrophenylbutyrate. The reaction mixture was prepared by adding 10 ul of 100 mM p-nitrophenylbutyrate in dimethylsulfoxide to 990 ml of 100 mM Tris-HCl buffer, pH 8.0 containing 0.1% triton X-100. The background rate of hydrolysis was measured before the addition of enzyme at 410 nm. The reaction was initiated by the addition of 10 ul of enzyme to 990 ml of the reaction and the change of absorbance at 410 nm was measured at room temperate (~23° C.). The background corrected results are reported as $\delta A_{410}$/min/ml or $\delta A_{410}$/min/mg protein.

Transesterification

Transesterification was measured by GC separation of products in buffered aqueous reactions. Reactions to measure ethyl acetate transesterification with propanol contained in 1 ml of 50 mM $KPO_4$, pH 7.0; 200 mM ethyl acetate, 200 mM 1-propanol, and enzyme. Reactions to measure ethyl acetate transesterification with neopentyl glycol (NPG) contained in 1 ml of 50 mM $KPO_4$, pH 7.0; 303 mM ethyl acetate, 100 mM NPG, and enzyme. The reactions were incubated at the indicated temperatures and for the indicated times. Separations were preformed using a 30M FFAP column (Phenomenex). The inlet split ratio was approximately 1:25, the injector was 250° C., head pressure of 10 psi He, and detection was by FD at 250° C. The chromatography program was 40° C. initial for 4 min, followed by a gradient of 15° C./min to 180° C. Components eluted in the following order and were not quantified; ethyl acetate, ethyl alcohol, propyl acetate, propyl alcohol, acetic acid, NPG diacetate, NPG mono acetate, and NPG.

Perhydrolase Used in Crystallography Studies

This perhydrolase preparation was used for crystallography studies. In addition, unlabelled protein was grown and purified in similar manner. A 500 ml preculture of *E. coli* BL21(DE3)/pLysS/pMSAINco1-1 was grown in a baffled 2.8 L Fembach flask on LB containing 100 ug/ml carbenicillin. After overnight culture at 37° C. and 200 rpm on a rotary shaker, the cells were harvested by centrifugation and resuspended in M9 medium containing: glucose, 2 g/L; $Na_2HPO_4$, 6 g/L; $KH_2PO_4$, 3 g/L; $NH_4Cl$, 1 g/L; NaCl, 0.5 g/L; thiamine, 5 mg/L; $MgSO_4$, 2 mM; $CaCl_2$, 100 uM; Citric acid.$H_2O$, 40 mg/L; $MnSO_4.H_2O$, 30 mg/L; NaCl, 10 mg/L; $FeSO_4.7H_2O$, 1 mg/L; $CoCl_2.6H_2O$, 1 mg/L; $ZnSO_4.7H_2O$, 1 mg/L; $CuSO_4.5H_2O$, 100 ug/L; $H_3BO_3.5H_2O$, 100 ug/L; and $NaMoO_4.2H_2O$, 100 ug/L; and supplemented with carbenicillin, 100 mg/L. The resuspended cells were used to inoculate six Fernbach flasks containing 500 ml each of M9 medium supplemented with carbenicillin (100 mg/L). The cultures were incubated at 20° C. and 200 rpm on a rotary shaker until the $OD_{600}$ reached about 0.7 at which time 100 mg/L of lysine, threonine, and phenylalanine and 50 mg/L of leucine, isoleucine, valine, and selenomethionine were added. After further incubation for 30 min, IPTG was added to a final concentration of 50 uM. The cultures were then incubated overnight (~15 hr) and harvested by centrifugation. The cell pellet was washed 2 times with 50 mM $KPO_4$ buffer, pH 6.8. The yield was 28.5 gm wet weight of cells to which was added 114 ml of 100 mM $KPO_4$ buffer, pH 8.2 and 5 mg of DNase. This mixture was frozen at −80° C. and thawed 2 times.

The thawed cell suspension was lysed by disruption in a French pressure cell at 20K psi. The unbroken cells and cell membrane material were sedimented by centrifugation at 100K times g for 1 hour. The supernatant crude extract, 128 ml (CE) was then placed in a 600 ml beaker and stirred for 10 minutes in a 55° C. water bath to precipitate unstable proteins. After 10 min the beaker was stirred in ice water for 1 min followed by centrifugation at 15K times g for 15 min. The supernatant from this procedure, HT, contained 118 ml. The HT extract was then made 20% saturating in $(NH_4)_2SO_4$ by the slow addition of 12.7 g of $(NH_4)_2SO_4$. This was loaded on to a 10 cm 11.6 cm Fast Flow Phenyl Sepharose (Pharmacia) column equilibrated in 100 mM $KPO_4$ buffer, pH 6.8, containing 20% saturation (109 g/L) $(NH_4)_2SO_4$. After loading the extract the column was washed with 1700 ml of starting buffer and eluted with a two step gradient. The first step was a linear 1900 ml gradient from start buffer to the same buffer without $(NH_4)_2SO_4$, the second was a 500 ml elution with 100 mM $KPO_4$, pH 6.8 containing 5% EtOH. Active fractions, 241 ml, were pooled, diluted 100% with water and loaded onto a 1.6 mm×16 mm Poros HQ strong anion exchange column equilibrated in 100 mM Tris-HCl, pH 7.6. After loading the extract, the column was washed with 5 column volumes of starting buffer. The protein was eluted with a 15 column volume gradient from start buffer to start buffer containing 175 mM KCl. The active fractions were pooled and concentrated using a Centriprep 30 (Miliopore) to 740 µl. FIG. 6 provides a purification table showing the enzyme activity of the enzyme of the present invention through various steps in the purification process.

The present application must be used to determine the respective values of the parameters of the present invention.

Unless otherwise noted, all component or composition levels are in reference to the active level of that component or composition, and are exclusive of impurities, for example, residual solvents or by-products, which may be present in commercially available sources.

Enzyme components weights provided herein are based on total active protein. All percentages and ratios were calculated by weight unless otherwise indicated. All percentages and ratios were calculated based on the total composition unless otherwise indicated.

Example 2

Determination of Ratio Between Peracid and Acid Formation

In this Example, methods for determining the ratio of perhydrolysis to hydrolysis are described. In particular, this Example provides methods for determining the ratio between peracid formation (i.e., perhydrolysis) and acid formation (i.e., hydrolysis) resulting from enzyme activity on an ester substrate in the presence of peroxide in an aqueous system.

A. Determination of Perhydrolysis to Hydrolysis Ratio

Preparation of Substrate

The substrates were prepared as described herein. Ethyl acetate (EtOAc) and other water soluble esters were diluted in a desired buffer to a concentration of 10 mM of ester. Tributyrin and other water insoluble substrates were prepared by making substrate swatches. Polyester swatches were cut from non-dyed polyester fabric (Polycotton, PCW 22) using a ⅝ inch punch and placed in a 24-well microtiter plate (Costar, Cell Culture Plate). The insoluble ester was diluted to 1.03 M in hexane. Then, 10 µL of the insoluble ester solution were then adsorbed onto the polyester swatch.

Determination of Hydrolysis (GC Assay)

The hydrolytic assay described below was used to determine the amount of substrate hydrolysis. In this assay, the assay solution was comprised of 50 mM potassium phosphate pH 7.5, 10 mM ester substrate, 29 mM hydrogen peroxide, and 20 mM potassium chloride in a total volume of 0.99 ml and an amount of enzyme that would generate 20 nmoles of acetic acid per minute at 25° C.

For measuring water insoluble ester hydrolysis, the reaction mixture was added to the insoluble ester fabric swatch. The swatch was prepared as described above ("Preparation of Substrate"). All the other conditions for the assay were the same except for exclusion of other ester substrates.

Hydrolytic activity was measured by monitoring the increase of acids generated by the enzyme from acyl donor substrates using gas chromatography coupled with flame ionization detection. The assay was conducted by first pipetting 50 µL of assay solution containing all the components except the enzyme into 200 mL of methanol (HPLC grade) to determine the amount of acid in the assay solution at time 0. Then, 10 µL of enzyme were added to the assay solution to a desired final concentration which produced approximately 20 nanomoles of acid per minute. A timer was started and 50 µL aliquots were taken from the assay solution and added to 200 µL of methanol at various times, typically 2, 5, 10, 15, 25, 40, and 60 minutes, after addition of the enzyme.

These methanol-quenched samples were then injected into a gas chromatograph coupled with a flame ionization detector (Agilent 6890N) and analyzed for hydrolytic components, acetic, and butyric acids. Gas chromatography was conducted using a nitroterephthalic acid modified polyethylene glycol column (Zebron FFAP; with dimensions: 30 m long, 250 um diameter, 250 nm film thickness). A 3 µL aliquot of sample was applied to the column by a splitless injection under constant a helium flow of 1.0 mL/minute. The inlet was maintained at a temperature of 250° C. and was purged of any remaining sample components after 2 minutes. When analyzing acetic acid, the temperature of the column was maintained at 75° C. for 1 minute after injection, increased 25° C./minute to 100° C., then increased 15° C./minute to 200° C.

When analyzing butyric acid, the temperature of the column was controlled as described above, except the temperature was additionally increased 25° C./minute to 225° C. and held at 225° C. for 1 minute. The flame ionization detector was maintained throughout the chromatography at 250° C. and under constant hydrogen flow of 25 mL/minute, air flow of 200 mL/minute, and a combined column and makeup helium flow of 30 mL/minute. The amount of hydrolyzed acid in the sample was then determined by integrating the acid peak in the chromatogram for total ion counts and calculating the acid from the ion count using a standard curve generated under the above conditions for acetic and butyric acids at varying concentrations in the assay solution (without enzyme).

Determination of Perhydrolysis (OPD Assay)

The perhydrolytic activity assay described below was used to determine the amount of peracid formed in the reaction. In these assays, the solution comprised 50 mM potassium phosphate pH 7.5, 10 mM ester substrate, 29 mM hydrogen peroxide, 20 mM potassium chloride, and 10 mM O-phenylenediamine.

When using water insoluble ester as the acyl donor, an ester adsorbed fabric swatch was used as the substrate, prepared as described above ("Preparation of Substrate").

Perhydrolytic activity was measured by monitoring the absorbance increase at 458 nm of oxidized O-phenylenediamine (OPD) by peracid generated with the enzyme. The perhydrolytic activity assay solution was prepared in the same manner as the hydrolytic activity assay solution, except that OPD was added to the assay solution to a final concentration of 10 mM. The OPD solution was prepared immediately before conducting the assay by dissolving 72 mg OPD (Sigma-Aldrich, dihydrochloride) in 19.94 mL of the same buffer and the pH was adjusted by slowly adding 60 µL of 13.5 M potassium hydroxide. The pH was measured and if needed, small quantities of potassium hydroxide were added to return the pH to the original pH of the buffer. Then, 495 µL of this OPD solution were added with the other assay components to a final assay volume of 0.990 mL. An assay quenching solution was also prepared by dissolving 36 mg OPD in 20 mL 100 mM citric acid and 70% ethanol.

The assay was typically conducted at 25° C. The assay was started by pipetting 100 µL of assay solution before the addition of the enzyme into 200 µL of quenching solution to determine the amount of perhydrolytic components and background absorbance in the assay solution at time 0. Then, 10 µL of enzyme were added to the assay solution to a desired final concentration which produced approximately 10 nanomoles of peracid per minute. A timer was started and 100 µL aliquots were taken from the assay solution and added to 200 µL of quenching solution at various times, typically 2, 5, 10, 15, 25, 40, and 60 minutes, after adding the enzyme. The quenched assay solutions were incubated for 30 minutes to allow any remaining peracid to oxidize the OPD. Then, 100 µL of each quenched assay solution was transferred to a 96-well microtiter plate (Costar) and the absorbance of the solution was measured at 458 nm by a spectrophotometric plate reader (Molecular Devices, SpectraMAX 250). The amount of peracid in each quenched sample was calculated using a standard curve generated under the above conditions with peracetic acid at varying concentrations in the assay solution (without enzyme).

Perhydrolysis/Hydrolysis Ratio:

Perhydrolysis/Hydrolysis ratio=Perhydrolysis measured in the Perhydrolysis assay/(Total acid detected in the hydrolysis assay-Perhydrolysis measured in the perhydrolysis assay)

Figure 7:
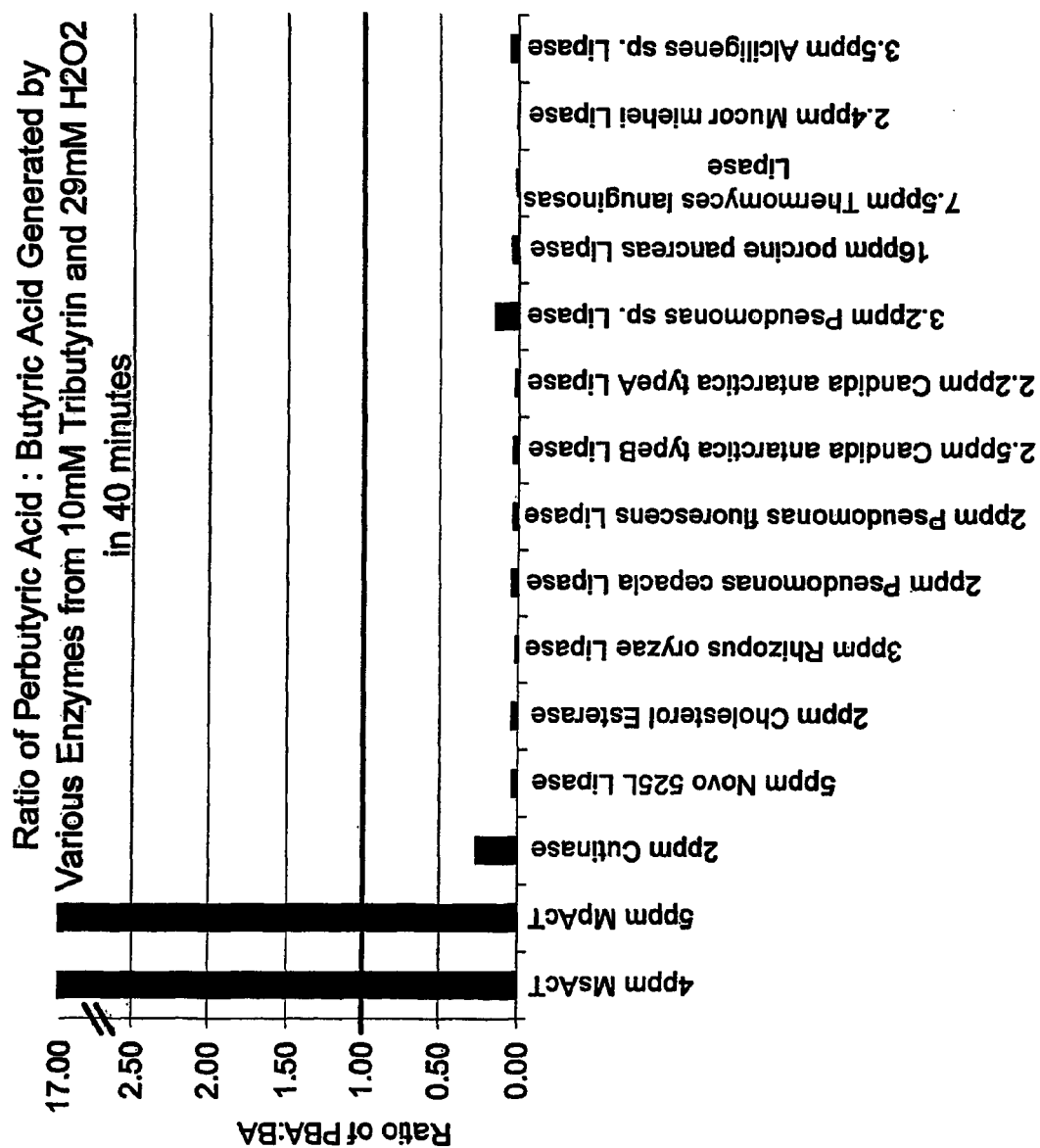
FIG. 7 provides a graph which shows the ratio of perbutyric acid to butyric acid generated by various enzymes from 10 mM tributyrin and 29 mM hydrogen peroxide in 40 minutes.
Figure 10:
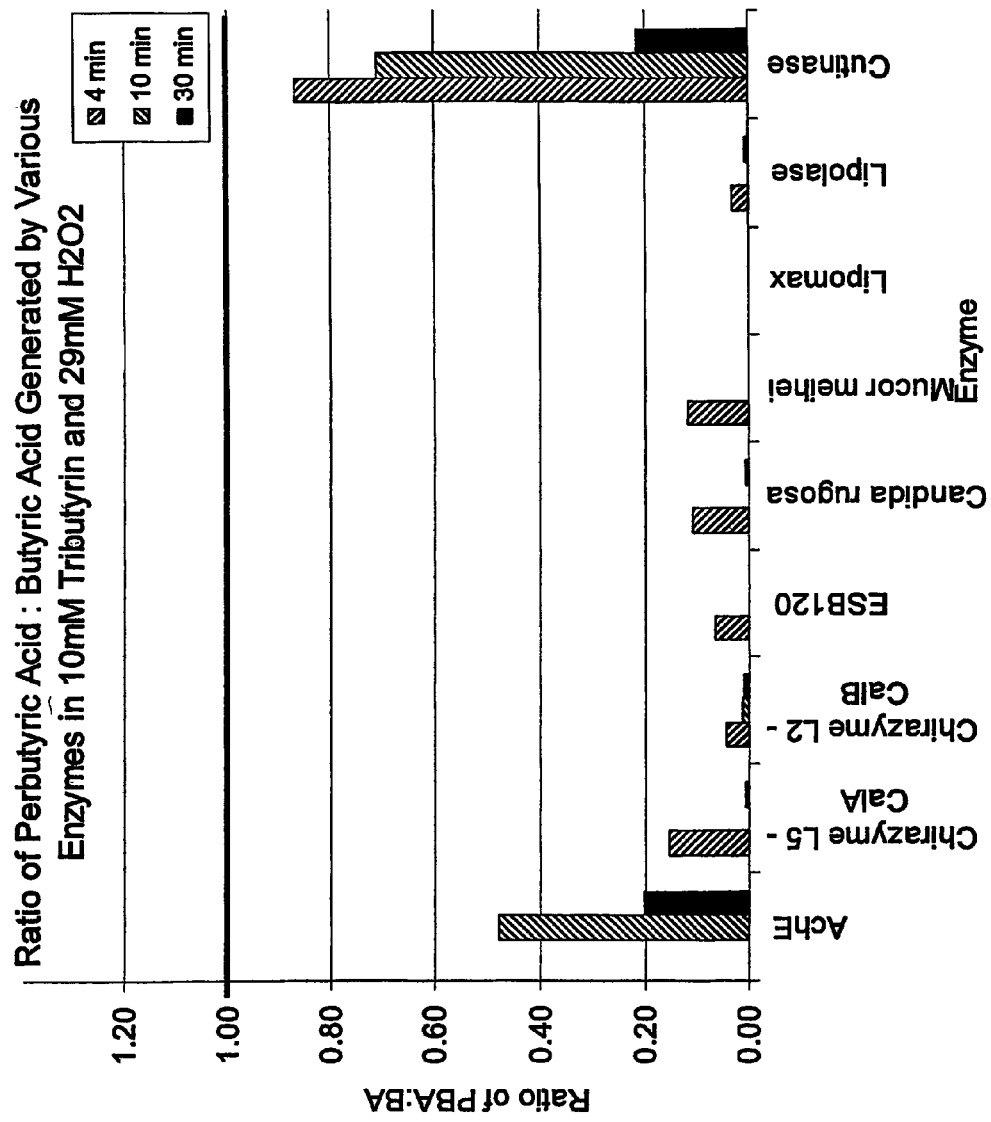
FIG. 10 provides a graph showing the ratio of perbutyric acid to butyric acid generated by various enzymes from 10 mM tributyrin and 29 mM hydrogen peroxide in 4, 10, and 30 minutes.
Figure 11:
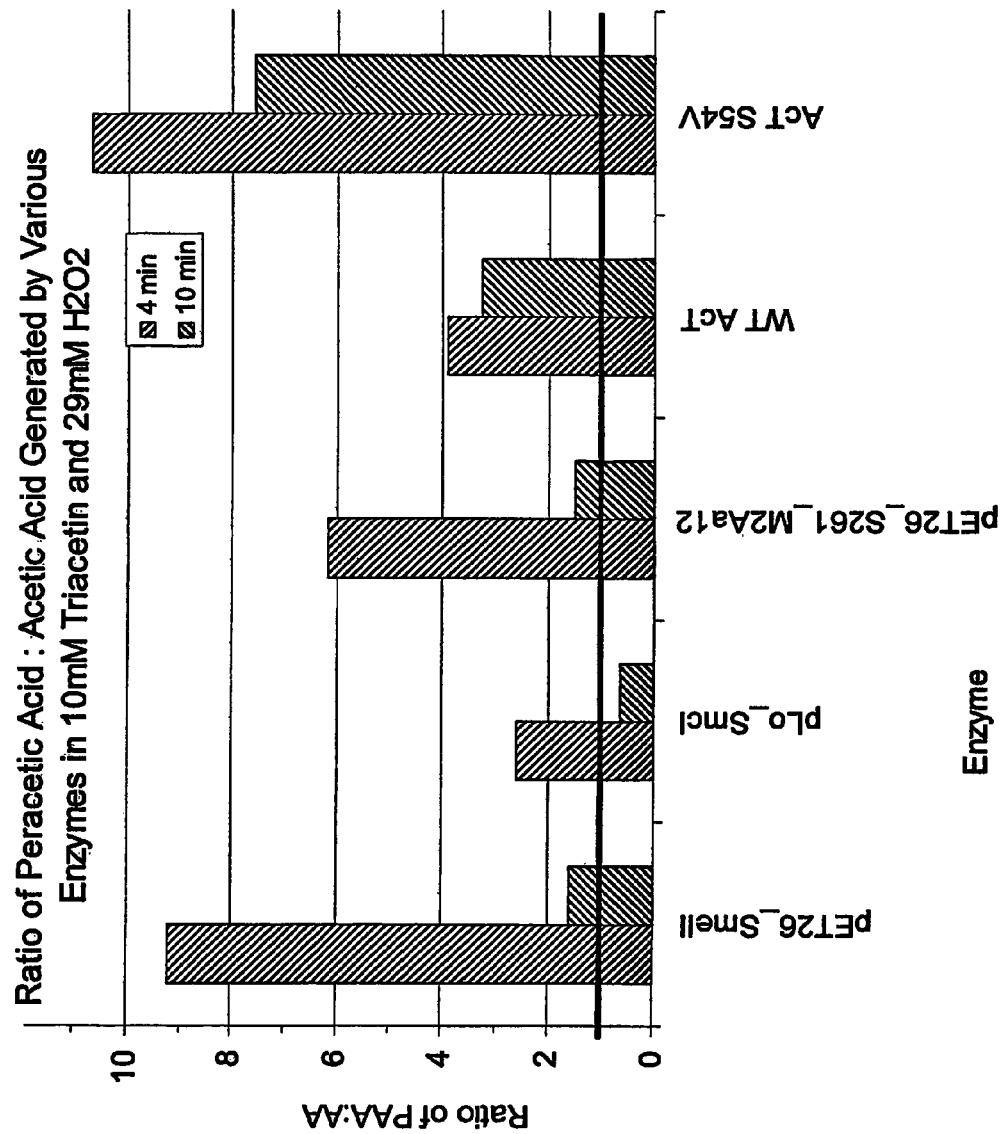
FIG. 11 provides a graph showing the ratio of peracetic acid to acetic acid generated by various enzymes from 10 mM triacetin and 29 mM hydrogen peroxide in 4 and 10 minutes.

The results of these experiments are provided in FIGS. 7, 10 and FIG. 11. FIG. 7 provides a graph which shows the ratio of perbutyric acid to butyric acid generated by various enzymes from 10 mM tributyrin and 29 mM hydrogen peroxide in 40 minutes. FIG. 10 shows the ratio of perbutyric acid to butyric acid generated by various enzymes from 10 mM tributyrin and 29 mM hydrogen peroxide in 4, 10, and 30 minutes. FIG. 11 shows the ratio of peracetic acid to acetic acid generated by various enzymes from 10 mM triacetin and 29 mM hydrogen peroxide in 4 and 10 minutes. The results obtained in these experiments indicated that *M. smegmatis* perhydrolase homologues exhibited a ratio above 1 in the OPD/GC assays described above, while other classes of enzymes exhibited ratios significantly below 1.

Figure 8:
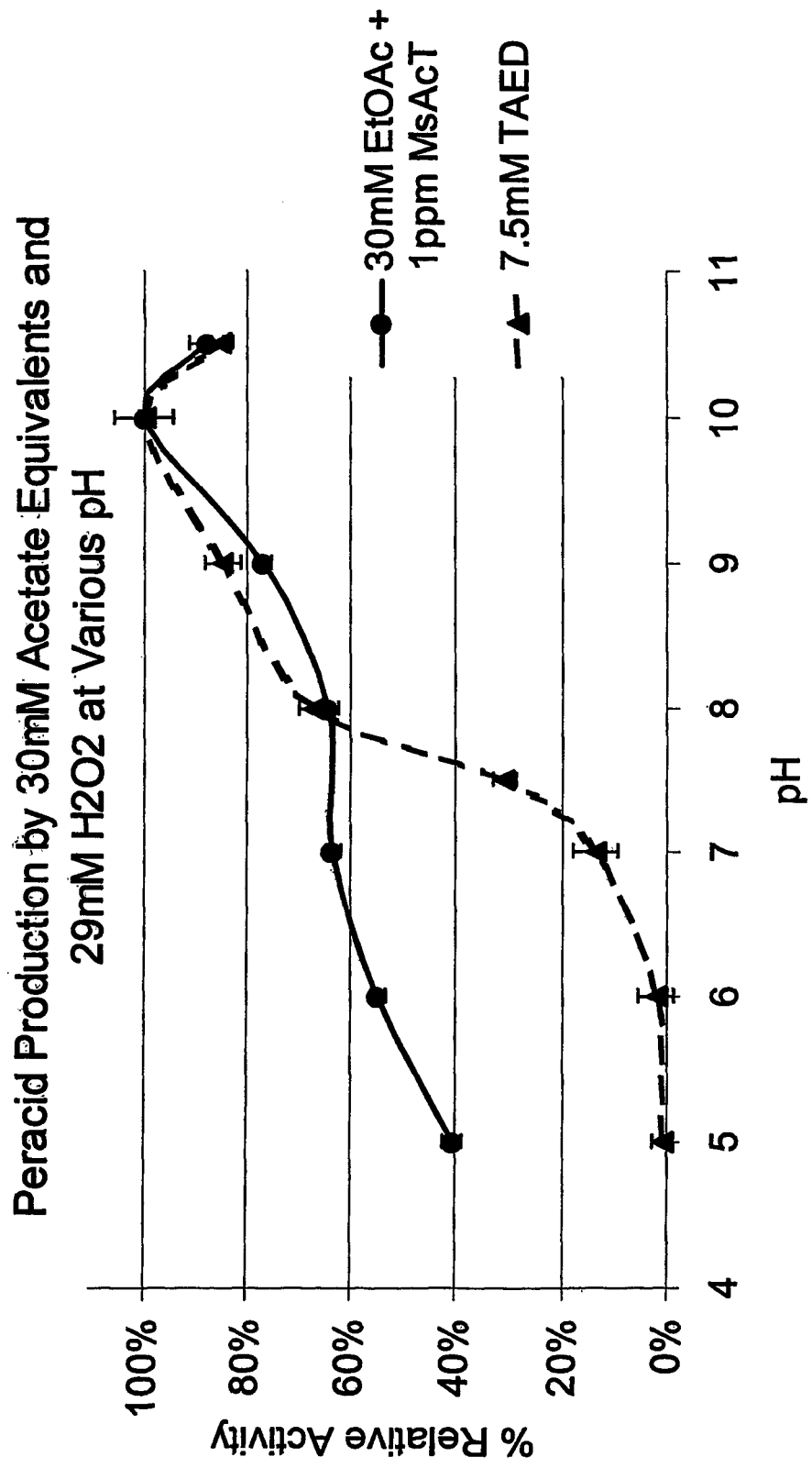
FIG. 8 provides a graph showing the peracid production by 30 mM acetate equivalents and 29 mM hydrogen peroxide, tested at various pHs. These results show that using the perhydrolase composition of the present invention, there is peracid generation over a wide pH range. In contrast, with TAED and hydrogen peroxide, peracid generation is limited to alkaline conditions.
Figure 9:
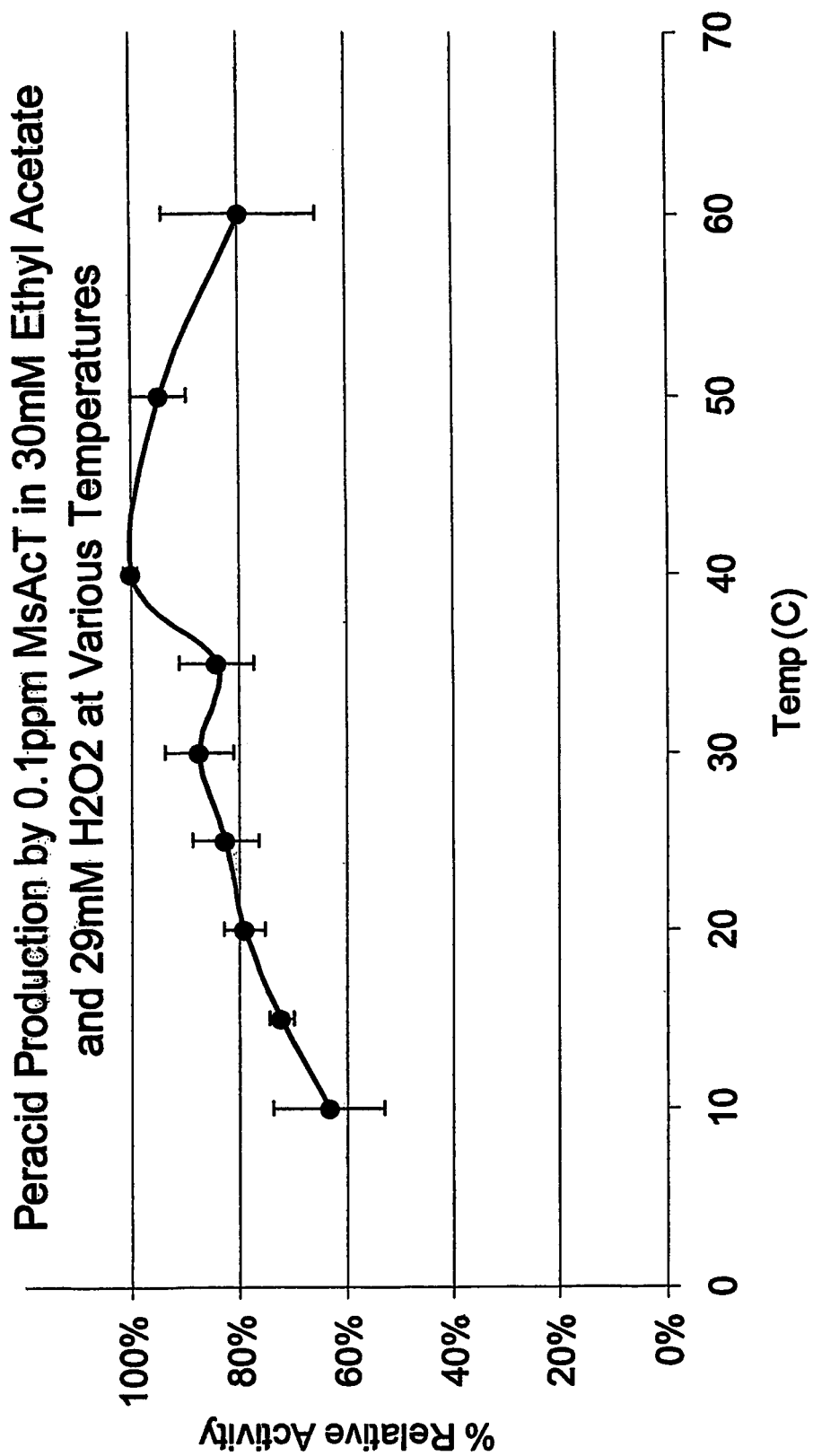
FIG. 9 provides a graph showing the peracid production by 0.1 ppm perhydrolase enzyme in 30 mM ethyl acetate and 20 mM hydrogen peroxide at various temperatures. These results show that the perhydrolase of the present invention works at a wide range of temperatures, including low temperatures.

Table 2-1 provides data showing the perhydrolysis activity of various homologues described herein on triacetin, as compared to the wild-type *M. smegmatis* perhydrolase. The results provided in Table 2-2 indicate that the perhydrolase has activity over a broad range of substrates. In addition to the results provided in these Tables, FIGS. 8 and 9 provide data showing that the perhydrolase of the present invention has broad pH and temperature range activities.

TABLE 2-1

Perhydrolysis Activity of Perhydrolase Homologues on Triacetin as Compared to *M. smegmatis* perhydrolase

| Experiment | Protein | Perhydrolysis Ratio (homolog to perhydrolase) |
|---|---|---|
| A. | pET26_Mlo | 0.6 |
|  | pET26b_Mbo | 0.87 |
|  | pET26_SmeII | 2.1 |
|  | pET26b_Stm | 0.17 |
|  | pLO_SmeI | 0.7 |
|  | Perhydrolase | 1.0000 |
|  | Blank | 0.0660 |

TABLE 2-1-continued

Perhydrolysis Activity of Perhydrolase
Homologues on Triacetin as Compared to *M. smegmatis*
perhydrolase

| Experiment | Protein | Perhydrolysis Ratio (homolog to perhydrolase) |
|---|---|---|
| B. | pET26_S261_M2aA12 | 1.5 |
| | Perhydrolase | 1 |
| | Blank | 0.3 |
| C. | pet26 M40cD4 | 0.14 |
| | pet26 M44aA5 | 0.16 |
| | Perhydrolase | 1 |
| | Blank | 0.01 |

TABLE 2-2

Peracid Production by 1 ppm Wild-Type
Perhydrolase with 29 mM H2O2 and Various Esters

| | nmol Peracetic Acid/min | | |
|---|---|---|---|
| Ester | 10 mM of Ester with 0.5% Neodol | 10 mM of Ester | 10 mM of Ester on Polycotton Swatch |
| Ethyl Acetate | | 5.00 | |
| Butyl Acetate | 8.06 | 8.72 | |
| Hexyl Acetate | 7.96 | 5.86 | |
| Octyl Acetate | 8.03 | 0.48 | |
| Ethyl Propionate | 0.90 | 1.43 | |
| Butyl Propionate | 2.47 | 3.39 | |
| Hexyl Propionate | 4.00 | 2.66 | |
| Isoamyl Acetate | 7.83 | | 17.69 |
| Citronellyl Acetate | 7.25 | | 4.27 |
| Citronellyl Propionate | 2.85 | | 3.21 |
| Dodecyl Acetate | 3.95 | | 0.19 |
| Neodol 23-3 Acetate | 2.25 | | 8.77 |
| Neodol 23-6.5 Acetate | 2.73 | | 10.12 |
| Neodol 23-9 Acetate | 2.97 | | 10.20 |
| Ethylene Glycol Diacetate | 13.30 | | |
| Propylene Glycol Diacetate | 13.17 | | |
| Triacetin | 11.91 | | |
| Tributyrin | 0.66 | | 2.70 |
| Ethyl Methoxyacetate | 0.49 | | |
| Linalyl Acetate | 0.30 | | |
| Ethyl Butyrate | 0.31 | | |
| Ethyl Isobutyrate | 0.10 | | |
| Ethyl 2-methylbutyrate | 0.11 | | |
| Ethyl Isovalerate | 0.37 | | |
| Diethyl Maleate | 0.75 | | |
| Ethyl Glycolate | 1.91 | | |

B. Typical Perhydrolase Peracid Generation Assay:

Perhydrolase is active over a wide pH and temperature range and accepts a wide range of substrates for acyl transfer. Acceptors include water (hydrolysis), hydrogen peroxide (perhydrolysis) and alcohols (classical acyl transfer). For perhydrolysis measurements enzyme was incubated in the buffer of choice at a specified temperature with a substrate ester in the presence of hydrogen peroxide. Typical substrates used to measure perhydrolysis include ethylacetate, triacetin, tributyrin, ethoxylated neodol acetate esters, and others. In addition, the wild type enzyme was found able to hydrolyze nitrophenylesters of short chain acids. The latter are convenient substrates to measure enzyme concentration. In some embodiments, peracid acid and acetic acid were measured by the ABTS or HPLC assays as described below. Nitrophenylester hydrolysis is also described below.

C. ABTS Assay (One Milliliter):

This assay provides a determination of peracetic acid produced by perhydrolase. This protocol was adapted from Karst et al., Analyst, 122:567-571 [1997]). Briefly, a 100 µL aliquot of solution to be analyzed was added to 1 mL 125 mM K$^+$ citrate pH 5, 1 mM ABTS, 50 µM KI. Absorbance was measured at 420 nm for highest sensitivity. However, multiple additional wavelengths were sometimes used over the broad absorption spectrum of ABTS. Calibration curves were constructed based on known peracid concentration series.

D. HPLC (Model-Agilent 1100) Determination of Perhydrolase Reaction Products:

For determination of the ratio of perhydrolysis to hydrolysis of the perhydrolase reaction, perhydrolase reaction samples were quenched by acidification to a final concentration of 0.24% methanesulfonic acid, and the products were separated by reverse phase HPLC on a Dionex OA column (cat #062903; Dionex Corporation, Sunnyvale, Calif.). The mobile phase was 100 mM NaPO$_4$, pH 3.9 (buffer was prepared by titrating 100 mM Na$_2$PO$_4$ with methanesulfonic acid to pH 3.9) run under isocratic conditions at 30° C. Detection was at 210 nm. Concentrations of products were calculated by comparison of the integrated peak areas against calibration standards.

E. Nitrophenylester Hydrolysis Kinetic Assay

Enzyme and substrate were incubated in 100 mM Tris/HCl pH 8.0 (or 50 mM B(OH)$_3$ pH 9.5 or another buffer). Absorbance at 402 nm was monitored. In some experiments, the assay was carried out in standard 1 mL cuvettes, while in other experiments, microtiter plate wells were used. The latter method was used for the screening of mutant libraries. Enzyme concentration was determined by comparison to standard curves obtained under the same reaction conditions.

E. Para-Nitrophenylcaproate Hydrolysis Assay

The pNC6 substrate solution was prepared by mixing 1 mM pNC6 (100 mM stock solution), 1 ml DMSO, 19 mls 100 mM Phosphate (pH8), and glycerol to a final concentration of 10%. To assay samples, 10 µl of the cell lysate were added to 190 µl of the substrate solution, and assayed at 405 nm for 15 minutes in a spectrophotometer. The results are presented as the average of two experiments.

G. Para-Nitrophenyl Acetate (pNA) Hydrolysis Assay

Aliquots of the lysed cell supernatant were diluted 1-100 in 100 mM phosphate buffer (pH 8). To assay the samples, 5111 of the 1-100 diluted cell supernatant were placed into each well of a microtiter plate. Then, 195 µl of reaction buffer/substrate mix (1 mM pNA, 100 mM phosphate, pH 8, 10% glycerol) were added, and the absorbance rate at 405 nm was measured over 3 minutes (kinetics program, microtiter plate reader). The results are presented as the average of two experiments.

Example 3

Assays Including Detergent Compositions

In this Example, assay systems used to screen for superior perhydrolase activity in detergents with particular substrates are provided. These assays include those that measure peracid degradation of perhydrolase, as well as the peracid synthesis activity of the enzyme.

Materials and Methods for Peracetic Acid Formation (PAF) and Peracetic Acid Degradation (PAD) Assays This section provides the materials and methods used to screen for a superior perhydrolases in Ariel with C9E2OAC ester substrate Materials Ariel Futur without bleach, perfume, or enzymes (P&G, Ariel "C")
C9E2OAc (P&G)
30% Hydrogen Peroxide (Sigma)
32% Peroxyacetic acid ("peracid", PAA)(Sigma cat#) MW=76.05; 4.208M
Citric Acid, anhydrous MW=192.12
Potassium Hydroxide MW=56.11
ABTS (Sigma cat# A1888) MW=548.68
Potassium Iodide MW=166.0
Potassium Phosphate, mono and di-basic Stock Solutions:

Ariel detergent stock: Ariel Futur without bleach, perfume, or enzymes ("Ariel C") was dissolved in water to 6.72 g/L. It was stirred at room temp for 30 minutes, then allowed to settle. Then, it was divided into convenient aliquots and stored at 4° C., until used. When made and used fresh, the solution was filtered, instead of settled 100 mM C9E2OAc in Ariel detergent stock: First, 30 µl C9E2OAc was added to 970 µl Ariel detergent stock, using a positive displacement pipet. It was sonicated in a bath sonicator until a milky dispersion was formed (15-60 seconds). The dispersion was stable for about two hours. When used, 10 µl of dispersion per ml of reaction mix were used.

42 mM Peroxyacetic acid stock: Right before use, the Sigma 32% PAA solution was diluted 1:100 in water. Then 5.7 µl of the 42 mM stock per ml of reaction mix was added.

2 M hydrogen peroxide: One ml of 30% Sigma hydrogen peroxide was added to 3.41 ml water. This solution was prepared fresh, right before use. It was used at 10 µl per ml of reaction mix.

125 mM Citrate buffer pH 5.0: This was prepared to 24.0 grams per liter. It was made up in 800 ml, and titrated to pH 5.0 with 50% KOH. The volume was adjusted to 1 liter and stored at room temperature.

100 mM ABTS stock: This was prepared using 549 mg of ABTS in 10 ml of water. It was frozen at −80° C., in convenient aliquots in opaque Eppendorf tubes. The stock was stable indefinitely when kept frozen in the dark. ABTS will precipitate when thawed from −80° C. but goes back into solution upon mixing. In use, 10 µl of ABTS stock was used per ml of ABTS reagent.

250 mM KI: This was prepared as 415 mg in 10 ml water. It was kept at 4° C. It was diluted to 25 mM working stock, and 2 ul of working stock was used per ml of ABTS reagent.

25 mM Potassium Phosphate buffer, pH 8.0:

Method:

The night prior to performance of the assays, the plates containing lysed cells that contain perhydrolase were checked to be sure that they were frozen twice. On the day of the assay, 30 to 45 minutes were allowed for the plates to thaw. The ABTS reagent was prepared and the Multidrop (Multidrop 384 instrument, ThermoElectron) to fill the detection plates with 200 µl per well. Store the filled plates covered at room temperature in the dark until needed. Dilutions of the standards were prepared so that when 20 µl of the diluted standard were added to the 180 µl of the reaction mix, the concentration in the well was 1 ppm. Four 4 two-fold serial dilutions were prepared to a set of six standards: 1, 0.5, 0.25, 0.125, and 0.0625 ppm final concentration in the wells.

To test, 20 µl of the standards were added to the thawed 1:10 dilution plate. The reaction mixtures were prepared and the Multidrop used to fill one reaction plate for each plate to be assayed (180 µl/well). Note that the reaction mixtures are different for the PAF and PAD assays.

Peracid Hydrolysis (Peracid Degradation, PAD) Assay:

This assay measures the amount of peracetic acid remaining after a 100 minute incubation with enzyme in an Ariel detergent background. The amount of peracid remaining is detected by reacting an aliquot of the reaction mixture with the ABTS detection reagent.

In this assay, 20 µl enzyme samples from the thawed 1:10 dilution plate were transferred, one column at a time with an 8 channel pipetter, into the corresponding column of the pre-filled PAD reaction plate. A timer was started as soon as transfer occurred from the first column; subsequent columns were transferred at 15 second intervals (i.e., the last column was finished 2 min. 45 sec. after starting the first one). The plate was mixed for 30 seconds on the thermomixer (750 rpm, to avoid splashing). The plate was then transferred to a humidified chamber at 25° C. The plate was incubated for a total of 100 minutes from the time the first column of enzyme was added. At 100 minutes incubation, the reaction plate was removed from the incubator. Then, 20 ul aliquots of the reaction mixture were transferred to an ABTS reagent plate, in the same order and with the same 15 second time interval that the enzyme samples were originally added to the reaction plate. The ABTS plate was allowed to sit at room temperature for three minutes after the last column of reaction mixture was added. The plate was then read on the spectrophotometric plate reader at 420 and 740 nm.

Perhydrolysis (Peracid Formation, PAF) Assay

Multidrop Optimized Protocol: Screening for a Superior Perhydrolysis in Ariel with C9E2OAC Ester Substrate The same materials and stock solutions described above for PAD were used in these experiments, as indicated below.

Method:

The methods were designed to assay 20 µl aliquots from a 1:100 dilution plate. The 20 µl 1:100 dilution assay plates were produced during the process of obtaining the protein concentrations and were stored at −80° C. The plates were thawed for about 30 to 45 minutes before use. Dilutions of the S54V standards were prepared, so that when 2 µl of the diluted standard are added to the 20 µl of the 1:100 diluted cell lysate, the concentration in the well was 0.1 ppm. Four two-fold serial dilutions were prepared to produced a set of six standards: 0.1, 0.05, 0.025, 0.0125, and 0.00625 ppm final concentration in the wells. Then, 2 ul of the standards were added to the thawed 20 ul 1:100 dilution assay plates in the wells indicated.

Perhydrolysis (Peracid formation, PAF) Assay:

This assay measures the amount of peroxyacetic acid that is produced in 10 minutes from the C9E20Ac substrate in an Ariel detergent background. The amount of peracid formed is detected after 10 minutes by reacting an aliquot of the reaction mixture with the ABTS detection reagent.

The Multidrop was used to deliver 180 µl/well of the PAF reaction mix to the prepared 1:100 dilution plate. The timer was started and the reaction plate was placed on the thermomixer, with the temperature set at 25° C. The plate was covered and the solutions mixed for 30 seconds at 750 rpm. The plate was then allowed to rest on the thermomixer without mixing, for a total of 10 minutes from the time the reaction mix was added. At 10 minutes, the Multidrop was used to add 20 µl/well of the 10×ABTS reagent. The 10× reagent was a milky suspension. The thermomixer was used to briefly shake the plate. The ABTS reagent quickly went into solution. The plate was allowed to sit at room temperature for three minutes after the ABTS reagent was added. The plate was then read on the spectrophotometric plate reader at 420 nm.

Example 4

Cloning of *Mycobacterium Smegmatis* Perhydrolase

In this Example, the cloning of *M. smegmatis* perhydrolase is described. An enzyme with acyltransferase activity was purified from *Corynebacterium oxydans* (now *Mycobacterium parafortuitum* ATCC19686). Two peptide sequences were obtained from the purified protein. One peptide was determined by Edman degradation from cyanogen bromide cleavage of the purified enzyme using methods known in the art. The sequence of this peptide was determined to be KVPFFDAGSVISTDGVDGI (SEQ ID NO:3). The second peptide was analyzed using N-terminal sequencing and was found to have the GTRRILSFGDSLTWGWIPV (SEQ ID NO:4). A BLAST search against the TIGR unfinished genome database identified a sequence of potential interest in *Mycobacterium smegmatis*, which is shown below:

(SEQ ID NO: 2)
MAKRILCFGDSLTWGWVPVEDGAPTERFAPDVRWTGVLAQQLGADFEVIE

EGLSARTTNIDDPTDPRLNGASYLPSCLATHLPLDLVIIMLGTNDTKAYF

RRTPLDIALGMSVLVTQVLTSAGGVGTTYPAPKVL

TTCCGGCGCACCCCGCTCGACATCGCGCTGGGCATGTCGGTGCTCGTCAC

GCAGGTGCTCACCAGCGCGGGCGGCGTCGGCACCACGTACCCGGCACCCA

AGGTGCTGGTGGTCTCGCCGCCACCGCTGGCGCCCATGCCGCACCCCTGG

TTCCAGTTGATCTTCGAGGGCGGCGAGCAGAAGACCACTGAGCTCGCCCG

CGTGTACAGCGCGCTCGCGTCGTTCATGAAGGTGCCGTTCTTCGACGCGG

GTTCGGTGATCAGCACCGACGGCGTCGACGGAATCCACTTCACCGAGGCC

AACAATCGCGATCTCGGGGTGGCCCTCGCGGAACAGGTGCGGAGCCTGCT

GTAA-3'

The corresponding DNA sequence of the gene is:

(SEQ ID NO: 1)
5'-ATGGCCAAGCGAATTCTGTGTTTCGGTGATTCCCTGACCTGGGGCTG

GGTCCCCGTCGAAGACGGGGCACCCACCGAGCGGTTCGCCCCCGACGTGC

GCTGGACCGGTGTGCTGGCCCAGCAGCTCGGAGCGGACTTCGAGGTGATC

GAGGAGGGACTGAGCGCGCGCACCACCAACATCGACGACCCCACCGATCC

GCGGCTCAACGGCGCGAGCTACCTGCCGTCGTGCCTCGCGACGCACCTGC

CGCTCGACCTGGTGATCATCATGCTGGGCACCAACGACACCAAGGCCTAC

TTCCGGCGCACCCCGCTCGACATCGCGCTGGGCATGTCGGTGCTCGTCAC

GCAGGTGCTCACCAGCGCGGGCGGCGTCGGCACCACGTACCCGGCACCCA

AGGTGCTGGTGGTCTCGCCGCCACCGCTGGCGCCCATGCCGCACCCCTGG

TTCCAGTTGATCTTCGAGGGCGGCGAGCAGAAGACCACTGAGCTCGCCCG

CGTGTACAGCGCGCTCGCGTCGTTCATGAAGGTGCCGTTCTTCGACGCGG

GTTCGGTGATCAGCACCGACGGCGTCGACGGAATCCACTTCACCGAGGCC

AACAATCGCGATCTCGGGGTGGCCCTCGCGGAACAGGTGCGGAGCCTGCT

GTAA-3'

Primers were designed based on the gene sequence to amplify and clone the gene. The primers used for amplification were:

MsRBSF:

(SEQ ID NO: 5)
5'-CTAACAGGAGGAATTAACCATGGCCAAGCGAATTCTGTGTTTCGGTG

ATTCCCTGACCT-3'

MspetBamR:

(SEQ ID NO: 6)
5'-GCGCGCGGATCCGCGCGCTTACAGCAGGCTCCGCACCTGTTCCGCGA

GGGCCACCCCGA-3'

The amplification of the gene was done by PCR using Taq DNA polymerase (Roche) per the manufacturer's instructions, with approximately 500 ng of chromosomal DNA from *Mycobacterium smegmatis* as the template DNA and the addition of 1% DMSO to the PCR reaction mix. Thirty picomoles of each of the primers MsRBSF and MspetBamR were added to the mix. The amplification cycle was: 30 cycles of (95° C. for 1 min, 55° C. for 1 min, 72° C. for 1 min).

Figure 12:
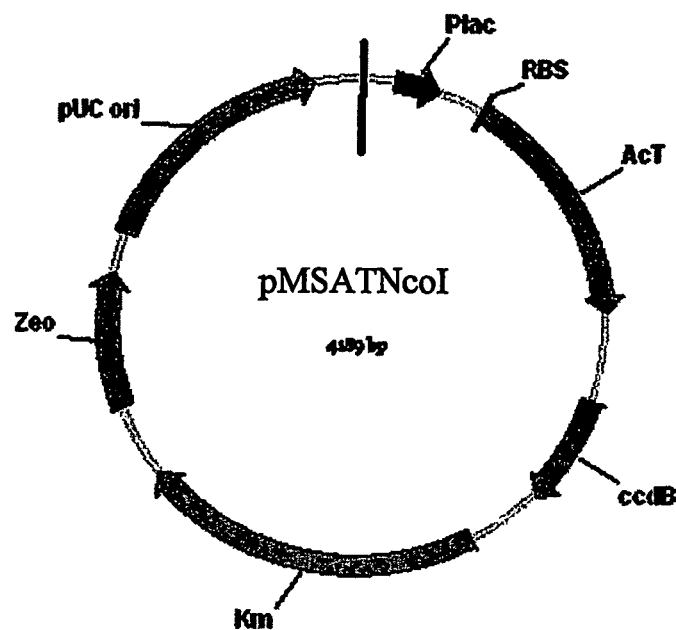
FIG. 12 provides a map of plasmid pMSATNcoI.

The fragments obtained from the PCR reaction were separated on a 1.2% agarose gel and a single band of the expected size of 651 bp (coding sequence and stop codon) was identified. This band was cloned directly into the pCR2.1 TOPO cloning vector (Invitrogen) and transformed into *E. coli* Top 10 cells Invitrogen) with selection on L agar (10 g/l tryptone, 5 g/l yeast extract, 5 g/l NaCl, 20 g/l agar) containing 100 micrograms/ml carbenicillin and X-gal (20 micrograms/ml, Sigma-Aldrich) for blue/white selection and incubated overnight at 37° C. Five white colonies were analyzed for the presence of the PCR fragment. Each colony was used to inoculate 5 mls of L broth (L agar without the addition of agar) containing 100 micrograms/ml carbenicillin and the cultures were grown overnight at 37° C. with shaking at 200 rpm. Plasmid DNA was purified from the cultures using the Quikspin kit (Qiagen). The presence of the correct fragment was determined by restriction enzyme digest with EcoR1 to release the fragment, and sequencing using primers supplied by the pCR2.1 manufacturer (Invitrogen). The correct plasmid was designated pMSATNcoI (See, FIG. 12, for the map of this plasmid)). The sequence of this plasmid is provided below (SEQ ID NO: 13)
agcgcccaatacgcaaaccgcctctccccgcgcgttggccgattcattaa tgcagctggcacgacaggtttcccgactggaaagcgggcagtgagcgcaa cgcaattaatgtgagttagctcactcattaggcaccccaggctttacact ttatgcttccggctcgtatgttgtgtggaattgtgagcggataacaattt cacacaggaaacagctatgaccatgattacgccaagctatttaggtgaca ctatagaatactcaagctatgcatcaagcttggtaccgagctcggatcca ctagtaacggccgccagtgtgctggaattcgcccttctaacaggaggaat taaccatggccaagcgaattctgtgtttcggtgattccctgacctggggc tgggtccccgtcgaagacggggcacccaccgagcggttcgcccccgacgt gcgctggaccggtgtgctggcccagcagctcggagcggacttcgaggtga tcgaggagggactgagcgcgcgcaccaccaacatcgacgacccaccgat ccgcggctcaacggcgcgagctacctgccgtcgtgcctcgcgacgcacct gccgctcgacctggtgatcatcatgctgggcaccaacgacaccaaggcct acttccggcgcaccccgctcgacatcgcgctgggcatgtcggtgctcgtc

```
acgcaggtgctcaccagcgcgggcggcgtcggcaccacgtacccggcacc
caaggtgctggtggtctcgccgccaccgctggcgcccatgccgcacccct
ggttccagttgatcttcgagggcggcgagcagaagaccactgagctcgcc
cgcgtgtacagcgcgctcgcgtcgttcatgaaggtgccgttcttcgacgc
gggttcggtgatcagcaccgacggcgtcacggaatccacttcaccgaggc
caacaatcgcgatctcggggtggccctcgcggaacaggtgcagagcctgc
tgtaaaagggcgaattctgcagatatccatcacactggcggccgctcgag
catgcatctagagggcccaattcgccctatagtgagtcgtattacaattc
actggccgtcgttttacaacgtcgtgactgggaaaaccctggcgttaccc
aacttaatcgccttgcagcacatcccccttttcgccagctggcgtaatagc
gaagaggcccgcaccgatcgcccttcccaacagttgcgcagcctatacgt
acggcagtttaaggtttacacctataaaagagagagccgttatcgtctgt
ttgtggatgtacagagtgatattattgacacgccggggcgacggatggtg
atcccctggccagtgcacgtctgctgtcagataaagtctcccgtgaact
ttaccggtggtgcatatcggggatgaaagctggcgcatgatgaccaccg
atatggccagtgtgccggtctccgttatcggggaagaagtggctgatctc
agccaccgcgaaaatgacatcaaaaacgccattaacctgatgttctgggg
aatataaatgtcaggcatgagattatcaaaaaggatcttcacctagatcc
ttttcacgtagaaagccagtccgcagaaacggtgctgaccccggatgaat
gtcagctactgggctatctggacaagggaaaacgcaagcgcaaagagaaa
gcaggtagcttgcagtgggcttacatggcgatagctagactgggcggttt
tatggacagcaagcgaaccggaattgccagctggggcgccctctggtaag
gttgggaagccctgcaaagtaaactggatggctttctcgccgccaaggat
ctgatggcgcaggggatcaagctctgatcaagagacaggatgaggatcgt
ttcgcatgattgaacaagatggattgcacgcaggttctccggccgcttgg
gtggagaggctattcggctatgactgggcacaacagacaatcggctgctc
tgatgccgccgtgttccggctgtcagcgcaggggcgcccggttcttttttg
tcaagaccgacctgtccggtgccctgaatgaactgcaagacgaggcagcg
cggctatcgtggctggccacgacgggcgttccttgcgcagctgtgctcga
cgttgtcactgaagcgggaagggactggctgctattgggcgaagtgccgg
ggcaggatctcctgtcatctcaccttgctcctgccgagaaagtatccatc
atggctgatgcaatgcggcggctgcatacgcttgatccggctacctgccc
attcgaccaccaagcgaaacatcgcatcgagcgagcacgtactcggatgg
aagccggtcttgtcgatcaggatgatctggacgaagagcatcaggggctc
gcgccagccgaactgttcgccaggctcaaggcgagcatgcccgacggcga
ggatctcgtcgtgacccatggcgatgcctgcttgccgaatatcatggtgg
aaaatggccgcttttctggattcatcgactgtggccggctgggtgtggcg
gaccgctatcaggacatagcgttggctacccgtgatattgctgaagagct
tggcggcgaatgggctgaccgcttcctcgtgctttacggtatcgccgctc
ccgattcgcagcgcatcgccttctatcgccttcttgacgagttcttctga
attattaacgcttacaatttcctgatgcggtattttctccttacgcatct
```
```
gtgcggtatttcacaccgcatacaggtggcacttttcggggaaatgtgcg
cggaacccctatttgtttattttttctaaatacattcaaatatgtatccgc
tcatgagacaataaccctgataaatgcttcaataatagcacgtgaggagg
gccaccatggccaagttgaccagtgccgttccggtgctcaccgcgcgcga
cgtcgccggagcggtcgagttctggaccgaccggctcgggttctcccggg
acttcgtggaggacgacttcgccggtgtggtccgggacgacgtgaccctg
ttcatcagcgcggtccaggaccaggtggtgccggacaacaccctggcctg
ggtgtgggtgcgcggcctggacgagctgtacgccgagtggtcggaggtcg
tgtccacgaacttccgggacgcctccgggccggccatgaccgagatcggc
gagcagccgtggggcggagttcgccctgcgcgacccggccggcaactg
cgtgcacttcgtggccgaggagcaggactgacacgtgctaaaacttcatt
tttaatttaaaaggatctaggtgaagatcctttttgataatctcatgacc
aaaatcccttaacgtgagttttcgttccactgagcgtcagacccccgtaga
aaagatcaaaggatcttcttgagatcctttttttctgcgcgtaatctgct
gcttgcaaacaaaaaaaccaccgctaccagcggtggtttgtttgccggat
caagagctaccaactctttttccgaaggtaactggcttcagcagagcgca
gataccaaatactgtccttctagtgtagccgtagttaggccaccacttca
agaactctgtagcaccgcctacatacctcgctctgctaatcctgttacca
gtggctgctgccagtggcgataagtcgtgtcttaccgggttggactcaag
acgatagttaccggataaggcgcagcggtcgggctgaacggggggttcgt
gcacacagcccagcttggagcgaacgacctacaccgaactgagataccta
cagcgtgagctatgagaaagcgccacgcttcccgaagggagaaaggcgga
caggtatccggtaagcggcagggtcggaacaggagagcgcacgagggagc
ttccaggggaaacgcctggtatctttatagtcctgtcgggtttcgccac
ctctgacttgagcgtcgatttttgtgatgctcgtcaggggggcggagcct
atggaaaaacgccagcaacgcggcctttttacggttcctggccttttgct
ggccttttgctcacatgttctttcctgcgttatcccctgattctgtggat
aaccgtattaccgcctttgagtgagctgataccgctcgccgcagccgaac
gaccgagcgcagcgagtcagtgagcgaggaagcggaag
```

Construction of Perhydrolase T7 Expression Plasmid

Figure 13:
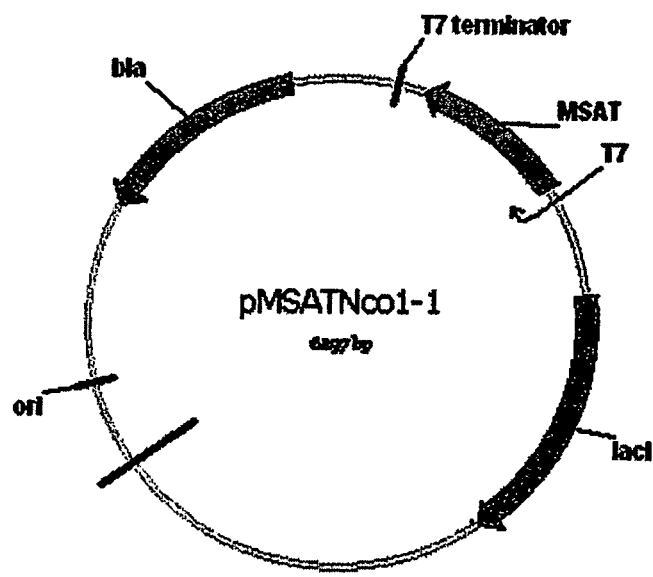
FIG. 13 provides a map of plasmid pMSATNco1-1.

The primer pair used to create pMSATNco1 was also used to create an NcoI site (CCATGG) in which the ATG is the start codon of the acyltransferase gene and a BamH1 (GGATCC) just after the TAA stop codon. The plasmid pMSATNco1 was digested with NcoI/BamH1 as recommended by the manufacturer (Roche) and the 658 bp fragment containing the perhydrolase gene was purified using standard procedures known in the art (e.g., Sambrook et al.). The fragment was ligated using standard procedures known in the art (e.g., Sambrook et al.) into the T7 promoter expression plasmid, pET16b (Novagen), also digested with NcoI/BamH1. The ligation reaction was transformed by standard procedures into *E. coli* Top 10 cells (Invitrogen) and selected on L agar containing 100 micrograms/ml carbenicillin overnight at 37° C. Ten colonies were picked from the several transformants and used to inoculate 5 ml of LB containing 100 micrograms/ml carbenicillin. Cultures were grown overnight at 37° C.

with shaking at 200 rpm. Plasmid DNA was purified from the cultures using the Qiagen Quikspin kit (Qiagen). The presence of the correct fragment was determined by restriction enzyme digest with NcoI/BamH1 as directed by the manufacturer. The correct plasmid was designated pMSATNcoI-1 (See, FIG. 13, for the map of this plasmid). In this Figure, the following elements are indicated—LacI: gene encoding the LacI repressor protein, located at bp1455-2534, ori: plasmid origin of replication at bp 4471, bla: The β-lactamase gene located at bp 6089-5232; T7 promoter: located at bp1068-1052; T7 terminator: located at bp 259-213, per: the *M. smegmatis* perhydrolase gene located at 981-334. The sequence of this plasmid is provided below:

(SEQ ID NO: 131)
ttctcatgtttgacagcttatcatcgataagctttaatgcggtagtttat cacagttaaattgctaacgcagtcaggcaccgtgtatgaaatctaacaat gcgctcatcgtcatcctcggcaccgtcaccctggatgctgtaggcatagg cttggttatgccggtactgccgggcctcttgcgggatatccggatatagt tcctcctttcagcaaaaaaccccctcaagaccccgtttagaggccccaaggg gttatgctagttattgctcagcggtggcagcagccaactcagcttcctttt cgggctttgttagcagccggatccgcgcgcttacagcaggctccgcacct gttccgcgagggccaccccgagatcgcgattgttggcctcggtgaagtgg attccgtcgacgccgtcggtgctgatcaccgaacccgcgtcgaagaacgg caccttcatgaacgacgcgagcgcgctgtacacgcgggcgagctcagtgg tcttctgctcgccgccctcgaagatcaactggaaccaggggtgcggcatg ggcgccagcggtggcggcgagaccaccagcaccttgggtgccgggtacgt ggtgccgacgccgcccgcgctggtgagcacctgcgtgacgagcaccgaca tgcccagcgcgatgtcgagcggggtgcgccggaagtaggccttggtgtcg ttggtgcccagcatgatgatcaccaggtcgagcggcaggtgcgtcgcgag gcacgacggcaggtagctcgcgccgttgagccgcggatcggtggggtcgt cgatgttggtggtgcgcgcgctcagtccctcctcgatcacctcgaagtcc gctccgagctgctgggccagcacaccggtccagcgcacgtcgggggcgaa ccgctcggtgggtgccccgtcttcgacggggacccagcccaggtcaggg aatcaccgaaacacagaattcgcttggccatggtatatctccttcttaaa gttaaacaaaattatttctagaggggaattgttatccgctcacaattccc ctatagtgagtcgtattaatttcgcgggatcgagatctcgatcctctacg ccggacgcatcgtggccggcatcaccggcgccacaggtgcggttgctggc gcctatatcgccgacatcaccgatggggaagatcgggctcgccacttcgg gctcatgagcgcttgtttcggcgtgggtatggtggcagccccgtggccg ggggactgttgggcgccatctccttgcatgcaccattccttgcggcggcg gtgctcaacggcctcaacctactactgggctgcttcctaatgcaggagtc gcataagggagagcgtcgagatcccggacaccatcgaatggcgcaaaacc tttcgcggtatggcatgatagcccggaagagagtcaattcagggtggt gaatgtgaaaccagtaacgttatacgatgtcgcagagtatgccggtgtct cttatcagaccgtttcccgcgtggtgaaccaggccagccacgtttctgcg aaaacgcgggaaaaagtggaagcggcgatggcggagctgaattacattcc caaccgcgtggcacaacaactggcgggcaaacagtcgttgctgattggcg ttgccacctccagtctggccctgcacgcgccgtcgcaaattgtcgcggcg attaaatctcgcgccgatcaactgggtgccagcgtggtggtgtcgatggt agaacgaagcggcgtcgaagcctgtaaagcggcggtgcacaatcttctcg cgcaacgcgtcagtgggctgatcattaactatccgctggatgaccaggat gccattgctgtggaagctgcctgcactaatgttccggcgttatttcttga tgtctctgaccagacacccatcaacagtattattttctcccatgaagacg gtacgcgactgggcgtggagcatctggtcgcattgggtcaccagcaaatc gcgctgttagcgggcccattaagttctgtctcggcgcgtctgcgtctggc tggctggcataaatatctcactcgcaatcaaattcagccgatagcggaac gggaaggcgactggagtgccatgtccggttttcaacaaaccatgcaaatg ctgaatgagggcatcgttcccactgcgatgctggttgccaacgatcagat ggcgctgggcgcaatgcgcgccattaccgagtccgggctgcgcgttggtg cggatatctcggtagtgggatacgacgataccgaagacagctcatgttat atcccgccgttaaccaccatcaaacaggattttcgcctgctggggcaaac cagcgtggaccgcttgctgcaactctctcagggccaggcggtgaagggca atcagctgttgcccgtctcactggtgaaaagaaaaaccaccctggcgccc aatacgcaaaccgcctctccccgcgcgttggccgattcattaatgcagct ggcacgacaggtttcccgactggaaagcgggcagtgagcgcaacgcaatt gtagatgacgaccatcagggacagcttcaaggatcgctcgcggctcttac cagcctaacttcgatcactggaccgctgatcgtcacggcgatttatgccg cctcggcgagcacatggaacgggttggcatggattgtaggcgccgcccta taccttgtctgcctccccgcgttgcgtcgcggtgcatggagccgggccac ctcgacctgaatggaagccggcggcacctcgctaacggattcaccactcc aagaattggagccaatcaattcttgcggagaactgtgaatgcgcaaacca acccttggcagaacatatccatcgcgtccgccatctccagcagccgcacg cggcgcatctcgggcagcgttgggtcctggccacgggtgcgcatgatcgt gctcctgtcgttgaggacccggctaggctggcgggggttgccttactggtt agcagaatgaatcaccgatacgcgagcgaacgtgaagcgactgctgctgc aaaacgtctgcgacctgagcaacaacatgaatggtcttcggtttccggtt tcgaatctggaaacgcggaagtcagcgccctgcaccatatgttccggatc tgcatcgcaggatgctgctggctaccctgggaacacctacatctgtatta acgaagcgctggcattgaccctgagtgatttttctctggtcccgccgcat ccataccgccagttaccctcacaacgttccagtaaccgggcatgttcatc atcagtaacccgtatcgtgagcatcctctctcgtttcatcggatcattac ccccatgaacagaaatcccccttacacggaggcatcagtgaccaaacagg aaaaaaccgcccttaacatggcccgctttatcagaagccagacattaacg cttctggagaaactcaacgagctggacgcggatgaacaggcagacatctg tgaatcgcttcacgaccacgctgatgagctttaccgcagctgcctcgcgc gtttcggtgatgacggtgaaaacctctgacacatgcagctcccggagacg -continued

```
gtcacagcttgtctgtaagcggatgccgggagcagacaagcccgtcaggg cgcgtcagcgggtgttggcgggtgtcggggcgcagccatgacccagtcac gtagcgatagcggagtgtatactggcttaactatgcggcatcagagcaga ttgtactgagagtgcaccatatatgcggtgtgaaataccgcacagatgcg taaggagaaaataccgcatcaggcgctcttccgcttcctcgctcactgac tcgctgcgctcggtcgttcggctgcggcgagcggtatcagctcactcaaa ggcggtaatacggttatccacagaatcaggggataacgcaggaaagaaca tgtgagcaaaaggccagcaaaaggccaggaaccgtaaaaaggccgcgttg ctggcgttttccataggctccgcccccctgacgagcatcacaaaaatcg acgctcaagtcagaggtggcgaaacccgacaggactataaagataccagg cgtttccccctggaagctccctcgtgcgctctcctgttccgaccctgccg cttaccggatacctgtccgcctttctcccttcgggaagcgtggcgctttc tcatagctcacgctgtaggtatctcagttcggtgtaggtcgttcgctcca agctgggctgtgtgcacgaaccccccgttcagcccgaccgctgcgcctta tccggtaactatcgtcttgagtccaacccggtaagacacgacttatcgcc actggcagcagccactggtaacaggattagcagagcgaggtatgtaggcg gtgctacagagttcttgaagtggtggcctaactacggctacactagaagg acagtatttggtatctgcgctctgctgaagccagttaccttcggaaaaag agttggtagctcttgatccggcaaacaaaccaccgctggtagcggtggtt tttttgtttgcaagcagcagattacgcgcagaaaaaaaggatctcaagaa gatcctttgatcttttctacggggtctgacgctcagtggaacgaaaactc acgttaaggattttggtcatgagattatcaaaaaggatcttcacctaga tccttttaaattaaaaatgaagttttaaatcaatctaaagtatatatgag taaacttggtctgacagttaccaatgcttaatcagtgaggcacctatctc agcgatctgtctatttcgttcatccatagttgcctgactccccgtcgtgt agataactacgatacgggagggcttaccatctggccccagtgctgcaatg ataccgcgagacccacgctcaccggctccagatttatcagcaataaacca gccagccggaagggccgagcgcagaagtggtcctgcaactttatccgcct ccatccagtctattaattgttgccgggaagctagagtaagtagttcgcca gttaatagtttgcgcaacgttgttgccattgctgcaggcatcgtggtgtc acgctcgtcgtttggtatggcttcattcagctccggttcccaacgatcaa ggcgagttacatgatcccccatgttgtgcaaaaaagcggttagctccttc ggtcctccgatcgttgtcagaagtaagttggccgcagtgttatcactcat ggttatggcagcactgcataattctcttactgtcatgccatccgtaagat gcttttctgtgactggtgagtactcaaccaagtcattctgagaatagtgt atgcggcgaccgagttgctcttgcccggcgtcaacacgggataataccgc gccacatagcagaactttaaaagtgctcatcattggaaaacgttcttcgg ggcgaaaactctcaaggatcttaccgctgttgagatccagttcgatgtaa cccactcgtgcacccaactgatcttcagcatcttttactttcaccagcgt ttctgggtgagcaaaaacaggaaggcaaaatgccgcaaaaaagggaataa
```

```
gggcgacacggaaatgttgaatactcatactcttccttttcaatattat tgaagcatttatcagggttattgtctcatgagcggatacatatttgaatg tatttagaaaaataaacaaatagggggttccgcgcacatttccccgaaaag tgccacctgacgtctagaaaccattattatcatgacattaacctataaaa ataggcgtatcacgaggccctttcgtcttcaagaa
```

This plasmid was transformed into the E. coli strain BL21 (λDE3)pLysS (Novagen), which contains the gene encoding the T7 RNA polymerase, with selection on LA containing 100 micrograms/ml carbenicillin. Cells were grown overnight at 37° C. One transformant was selected and the strain was designated MSATNco1.

Production of Perhydrolase in MSATNco1-1

Production of perhydrolase was done in cell culture. For example, 5 ml of LB with carbenicillin at a concentration of 100 micrograms/ml was inoculated with a single colony of MSATNco1 and grown overnight at 37° C. with shaking at 200 rpm. This culture was used to inoculate 100 ml of LB with carbenicillin at a concentration of 100 micrograms/ml (in a 250 ml baffled flask) to an $OD_{600}$ of 0.1. The cultures were grown at 30° C. with shaking at 200 rpm until they reached an $OD_{600}$ of 0.4. The expression of the perhydrolase gene was then induced by the addition of 100 micromolar IPTG and the incubation continued overnight. Cultures were harvested by centrifugation (10 min at 7000 rpm, Sorvall SS34 rotor), the supernatant was removed and the pellets washed in 50 mM $KPO_4$, pH 6.8. The cells were centrifuged again, the supernatants removed and the wet weight of the cells was determined. The cells were resuspended in 100 mM $KPO_4$ in a volume that was 4× the wet weight. The resuspended cells were frozen at −70° C. The cells were thawed and lysed in a French Pressure cell using standard procedures known in the art. The purification steps and assessment methods are provided in Example 1. FIG. 6 provides a purification table showing the enzyme activity of the perhydrolase of the present invention through various steps in the purification process.

M. smegmatis Perhydrolase is in an Operon

In additional experiments, it was determined that the M. smegmatis perhydrolase is part of an operon. The gene (phd) is the first gene in an operon that contains at least 2 genes, including phd, that are separated by 10 bp (GGCTGGGGGC [SEQ ID NO:7]) not including the TAA stop codon of phd. It is also possible that there are three genes in the operon, with the third being either 48 bp or 61 bp to the next ORF (open reading frame). The latter two candidate genes have no significant homology to proteins in the database.

A putative promoter was identified for M. smegmatis phd operon, TTGGGC (−35) SP (18) CCAGAT by sequence analysis and comparison with known M. smegmatis promoters (See e.g., Salazar et al., Microbiol., 149:773-784 [2003]). It is not intended that the present invention be limited to any particular promoter and/or construct design, as it is contemplated that other promoters and construct designs will find use in the present invention.

The second gene in the phd operon encodes a protein (putative PBP-3) with the sequence:

(SEQ ID NO: 9)
mhlrpaltwllvvglfisvvgcssspdpadrfsafaealgrkdaaaaaaq tsdpaaaeaaitamlagmgdaanvsvaaepeegddagatlkytwtwgegr -continued dfgydttataaksgddwlitwsptvlhrdltpdlrfqysedselqtpvld rtgqplmtwqtvgvitverahpesaaplaallapfdpttttesvtaqlns ttddrvtvmklreddlgqvrdqlaqipgvtvreqgelltadrqlsspais gldelwhdritanagwsvylvdadgapaqqltstppkdtgpvrttdlrmq llaqqavaketrpavvvaisgstggilaaaqnpaadpqgaiafsglyppg stfkittaaaldaglatpdtpvacpgeltienrtipnddnfdlgtvplss afshscntsmaalsdelppnaltdmakdfgigvdrmvpglttvtgrvpna dnaaqrvengigqgtvtvspfglavaeaslahgstilptlvdgekttadt psvplppnitdalrammrgtvtegtatalsdipdlggktgtaefgdnths hgwfagiagdiafatlvvggdssapavaisgdflrpalag The corresponding DNA sequence of the gene encoding the putative PBP-3:

(SEQ ID NO: 8)
atgcacttacgtcccgctctgacgtggctcctggttgtcggtctgttcat atcggtcgtcggatgttcgtcgtcccggatccggccgaccggttctcgg cgttcgccgaggcgctgggccgcaaggatgcggccgcggcggccgcccag accagcgatccggcggccgcggaggcggccatcaccgcgatgctggccgg gatgggcgacgccgcgaacgtctcggtggccgccgaacccgaggaaggcg acgacgcgggcgcgacgctgaagtacacgtggacctggggtgagggccgc gacttcggctacgacaccaccgcgacggcggccaaatccggtgacgactg gctgatcacctggtcccccaccgtgttcaccgcgacctcacccggatct gcgcttccagtacagcgaggacagcgaattgcagaccccggtgctcgacc gcaccggccagccgttgatgacatggcagaccgtcggtgtcatcactgtc gaacgcgcacatccggagtcggccgcaccgctcgccgccctgctggcgcc cttcgatccgaccaccaccaccgaatcggtcaccgcacaactcaattcga cgaccgatgaccgcgtgacggtgatgaagctgcgcgaggacgatctgggt caggtcgcgatcagctcgcgcagatcccggcgtgaccgtgcgtgagca gggtgagctgctcaccgccgaccggcagctgtcctcgcccgccatcagcg gcctggacgagctgtggcacgaccggatcaccgccaacgcgggctggtcg gtgtacctggtcgacgccgacggtgcaccgcacaacagctcacgtccac gccgcccaaggacaccgggccgtgcgcaccacgctggacctgcgcatgc aactgctcgcgcagcaggccgtggccaaggagacccgcccggccgtggtg gtcgcgatctccggatcgaccggggcatcctggccgccgcacagaaccc ggccgccgatccgcaaggtgcgatcgcgtttcgggcctgtaccgccgg ggtcgacgttcaagaccatcaccacggcggcagccctcgacgcgggcctg gccacccgggacacaccggtggcctgcccgggtgagctcaccatcgagaa ccgcacgatccccaacgacgacaacttcgacctgggcaccgtgccgttgt cgtcggcgttctcgcactcctgcaacaccagcatggccgccctgtccgac gagctgccgcccaacgcactgaccgacatggcaaaggacttcgggatcgg cgtcgacttcatggtgcccggcctgaccaccgtgaccggccgtgtcccca acgccgacaacgccgcccagcgtgtcgagaacggcatcggccagggcacc -continued gtgaccgtcagcccgttcggcctcgccgtcgccgaggccagcctggcgca cggttcgacgatcctgccgacgctggtcgacggcgagaagaccacggccg acaccccgtcggtgccgttgccgcccaacatcaccgacgcgctgcgcgcg atgatgcgcggaacggtcaccgagggcacggccaccgcgttgagcgacat ccccgacctgggcggcaagaccggcacggcggaattcggcgacaacacgc actcgcacggctggttcgcgggcatcgcgggcgacatcgcgttcgcgacg ctggtggtcggcggcgactcgtcggcaccggccgtcgcgatctcaggaga cttcctgcgccccgcgctcgccggctag.

A standard BLAST search against the protein database identified homology with several penicillin binding proteins, class 3 (PBP-3). By sequence alignment and comparison to literature (e.g., Goffin and Ghysen, Microbiol. Mol. Biol. Rev., 66:702-38 [2002]) the PBP was found to contain the required bar codes (conserved protein sequences that define a class of proteins) to place it in the SxxK superfamily of acyl transferases, with a C-terminal domain acyl transferase and an N-terminal domain of unknown function, but with homology to the Pen$^r$ (i.e., penicillin resistant) protein fusions of class B-like II and III. This penicillin binding protein acyl transferase domain does not share significant homology with the perhydrolase of the present invention, although it does share homology with Co-A dependent acyl transferases known in the art. The amino acid sequence is provided below.

(SEQ ID NO: 10)
MHLRPALTWLLVVGLFISVVGCSSSPDPADRFSAFAEALGRKDAAAAAAQ

TSDPAAAEAAITAMLAGMGDAANVSVAAEPEEGDDAGATLKYTWTWGEGR

DFGYDTTATAAKSGDDWLITWSPTVLHRDLTPDLRFQYSEDSELQTPVLD

RTGQPLMTWQTVGVITVERAHPESAAPLAALLAPFDPTTTTESVTAQLNS

TTDDRVTVMKLREDDLGQVRDQLAQIPGVTVREQGELLTADRQLSSPAIS

GLDELWHDRITANAGWSVYLVDADGAPAQQLTSTPPKDTGPVRTTLDLRM

QLLAQQAVAKETRPAVVVAISGSTGGILAAAQNPAADPQGAIAFSGLYPP

GSTFKTTTTAAALDAGLATPDTPVACPGELTIENRTIPNDDNFDLGTVPL

SSAFSHSCNTSMAALSDELPPNALTDMAKDFGIGVDFMVPGLTTVTGRVP

NADNAAQRVENGIGQGTVTVSPFGLAVAEASLAHGSTILPTLVDGEKTTA

DTPSVPLPPNITDALRAMMRGTVTEGTATALSDIPSLGGKTGTAEFGDNT

HSHGWFAGIAGDIAFATLVVGGDSSAPAVAISGDFLRPALAG

The family-identifying bar codes provided in the above review were: (19) V (20) G/A (140) PVxDRTG (142) TxDx3Q (22) TGGxLAx4PaxDP (13) SxxK (51) SCN (131) KTG (50) marked in bold letters in the above sequence. The letters represent the amino acid sequence defining the bar code; the numbers in brackets are the intervening number of amino acids between the particular bar codes; "x" represents any amino acid, (i.e., the amino acids are not conserved within the bar code but the number of amino acids (e.g., x3 corresponding to 3 intervening amino acids) is conserved). Based on these results and other data, as described herein, it is clear that the perhydrolase of the present invention represents a unique enzyme class.

Example 5

Expression of the Perhydrolase in *P. Citrea*

In this Example, methods used to express the perhydrolase in *P. citrea* are described. The plasmid pMSATNcoI was transformed into *P. citrea* by electroporation using the method essentially as known in the art (See e.g., Sambrook et al., supra) except that all cultures and recovery were done at 30° C. The transformants were plated on L agar+carbenicillin (200 µg/ml) and incubated overnight at 30° C. Three transformants were picked for analysis. Each colony was used to inoculate a 30 ml culture of LB+carbenicillin (200 µg/ml) and grown overnight at 30° C. with shaking at 200 rpm. The cells were pelleted by centrifugation, washed one time in 50 mM phosphate buffer pH 7.2, and finally resuspended in 4× the wet cell weight of 100 mM phosphate buffer pH 8.0. The cells were lysed by treatment with lysozyme (2 µl of a 10 mg/ml solution per one ml of *P. citrea* culture) at 37° C. for one hour. The cell debris was pelleted at 13,000 rpm in a microfuge for 5 min. The resulting supernatant was used for further analysis in SDS-PAGE and Western blots, as well as assays for enzyme activity.

SDS-PAGE analysis was carried out as known in the art (See e.g., Sambrook et al., supra) on the supernatants. Detection of the perhydrolase protein by Western blot was done using an anti-perhydrolase polyclonal anti-sera (prepared from purified perhydrolase protein by Covance). The blot was developed as per manufacturer's suggestions using the ECL plus kit (Amersham).

The enzymatic activity of the expressed perhydrolase was detected by the pNB (para-nitrophenylbutyrate) assay as described in Example 1, herein. The results are provided in the

TABLE 5-1

Enzymatic Activity of Perhydrolase Expressed by *P. citrea*

| Clone | OD405 | Rate | Concentration (mg/liter) |
|---|---|---|---|
| *P. citrea*/ pMSATNcoI | 3.1129 | 0.47948 | 7.1922 |
| Control (*P. citrea*) | 2.6187 | −9.8312 | 0 |

The SDS-PAGE and Western blot results, as well as the assay results indicated that the perhydrolase is expressed by *P. citrea* and is active.

Example 6

Expression of the Perhydrolase in *Bacillus subtilis*

The perhydrolase was expressed intracellularly in *B. subtilis*. A variety of promoters find use in this embodiment, including but not limited to pSPAC, pAprE, pAmyE, pVeg, pHpaII. In some embodiments, the construct is present on a replicating plasmid (e.g., pBH1), while in other embodiments, it is integrated into the chromosome in one or more copies. Examples of sites for integration include, but are not limited to the aprE, the amyE, the veg or the pps regions. Indeed, it is contemplated that other sites known to those skilled in the art will find use in the present invention.

A. Intracellular Expression of the Perhydrolase in *Bacillus Subtilis* from a Replicating Plasmid

*B. subtilis* expresses a lipase/esterase encoded by the gene pnbA that hydrolyzes the pNB substrate used to detect activity of the perhydrolase. To identify *B. subtilis* strains expressing the perhydrolase after transformation with replicating or integrating plasmids the pnbA gene (the entire coding sequence) was first deleted from the desired host using the laxP cassette deletion method described in WO 03/083125, herein incorporated by reference. It is also noted that other strains of *Bacillus* may contain one or more lipases/esterases capable of hydrolyzing the pNB or other substrate used as an indicator for perhydrolase activity. In some embodiments, for optimal expression and/or activity detection it is necessary to delete one or more of the lipases/esterases from the hosts. The *Bacillus subtilis* strain used in this Example has the genotype *Bacillus subtilis* comK pnbA (pnbAloxP-spec, aprE, nprE, degUHy32, oppA, spoIIE3501 and will be referred to as "*B. subtilis* pnbA" (See e.g., WO 03/083125, supra).

In these experiments, a consensus *Bacillus* ribosome binding site (RBS) was used. It is not intended that the consensus RBS be the only sequence used for expression, as a non-consensus RBS also finds use in the present invention. The RBS of pMSATNcoI (See, Example 4) was changed to a *Bacillus* consensus RBS from the 16S rRNA (5'-ATAAG-GAGGTGATC-3' [SEQ ID NO:132]) of *B. subtilis* and a HindIII site was added to the 5' end of the RBS by PCR using a primer (502rbsforward primer) containing the desired changes. The reaction was carried out using an MJ Research PCR machine with 30 cycles of (1 min at 95° C., 1 min at 55° C., and 1 min at 72° C.). Template DNA (pMSATrbs) was added to a 50 µl reaction (10 ng) and 10 picomoles of each primer were used.

The PCR-generated phd cassette was cloned into the PCR cloning vector, pCR-Script CM (Stratagene) and transformed into *E. coli* Top10 cells (Invitrogen) to make pAH502R. The complete sequence of this plasmid is provided below.

(SEQ ID NO: 133)

```
ctaaattgtaagcgttaatattttgttaaaattcgcgttaaattttttgtt aaatcagctcatttttaaccaataggccgaaatcggcaaaatcccttat aaatcaaaagaatagaccgagatagggttgagtgttgttccagtttggaa caagagtccactattaaagaacgtggactccaacgtcaaagggcgaaaaa ccgtctatcagggcgatggcccactacgtgaaccatcaccctaatcaagt ttttttggggtcgaggtgccgtaaagcactaaatcggaaccctaaagggag cccccgatttagagcttgacggggaaagccggcgaacgtggcgagaaagg aaggaagaaagcgaaaggagcgggcgctagggcgctggcaagtgtagcg gtcacgctgcgcgtaaccaccacacccgccgcgcttaatgcgccgctaca gggcgcgtcccattcgccattcaggctgcgcaactgttgggaagggcgat cggtgcgggcctcttcgctattacgccagctggcgaaaggggggatgtgct gcaaggcgattaagttgggtaacgccagggttttcccagtcacgacgttg taaaacgacggccagtgagcgcgcgtaatacgactcactatagggcgaat tgggtaccgggccccccctcgaggtcgacggtatcgataagcttgatatc gaattcctgcagcccgggggatccgcccaagcttaaggaggtgatctaga attccatggccaagcgaattctgtgtttcggtgattccctgacctgggc tgggtccccgtcgaagacggggcacccaccgagcggttcgcccccgacgt gcgctggaccggtgtgctggcccagcagctcggagcggacttcgaggtga tcgaggagggactgagcgcgcgcaccaccaacatcgacgaccccaccgat
```

-continued

```
ccgcggctcaacggcgcgagctacctgccgtcgtgcctcgcgacgcacct gccgctcgacctggtgatcatcatgctgggcaccaacgacaccaaggcct acttccggcgcaccccgctcgacatcgcgctgggcatgtcggtgctcgtc acgcaggtgctcaccagcgcgggcggcgtcggcaccacgtacccggcacc caaggtgctggtggtctcgccgccaccgctggcgcccatgccgcacccct ggttccagttgatcttcgagggcggcgagcagaagaccactgagctcgcc cgcgtgtacagcgcgctcgcgtcgttcatgaaggtgccgttcttcgacgc gggttcggtgatcagcaccgacggcgtcgacggaatccacttcaccgagg ccaacaatcgcgatctcggggtggccctcgcggaacaggtgcggagcctg ctgtaaaaggatccccgggaagcttgcatgggctagagcggccgccaccg cggtggagctccagcttttgttcccttagtgagggttaattgcgcgctt ggcgtaatcatggtcatagctgtttcctgtgtgaaattgttatccgctca caattccacacaacatacgagccggaagcataaagtgtaaagcctggggt gcctaatgagtgagctaactcacattaattgcgttgcgctcactgcccgc tttccagtcgggaaacctgtcgtgccagctgcattaatgaatcggccaac gcgcggggagaggcggtttgcgtattgggcgctcttccgcttcctcgctc actgactcgctgcgctcggtcgttcggctgcggcgagcggtatcagctca ctcaaaggcggtaatacggttatccacagaatcaggggataacgcaggaa agaacatgtgagcaaaaggccagcaaaaggccaggaaccgtaaaaaggcc gcgttgctggcgtttttccataggctccgcccccctgacgagcatcacaa aaatcgacgctcaagtcagaggtggcgaaacccgacaggactataaagat accaggcgtttccccctggaagctccctcgtgcgctctcctgttccgacc ctgccgcttaccggatacctgtccgcctttctcccttcgggaagcgtggc gctttctcatagctcacgctgtaggtatctcagttcggtgtaggtcgttc gctccaagctgggctgtgtgcacgaaccccccgttcagcccgaccgctgc gccttatccggtaactatcgtcttgagtccaacccggtaagacacgactt atcgccactggcagcagccactggtaacaggattagcagagcgaggtatg taggcggtgctacagagttcttgaagtggtggcctaactacggctacact agaaggacagtatttggtatctgcgctctgctgaagccagttaccttcgg aaaaagagttggtagctcttgatccggcaaacaaaccaccgctggtagcg gtggtttttttgtttgcaagcagcagattacgcgcagaaaaaaaggatct caagaagatcctttgatcttttctacggggtctgacgctcagtggaacga aaactcacgttaagggattttggtcatgagattatcaaaaaggatcttca cctagatccttttcgaccgaataaatacctgtgacggaagatcacttcgc agaataaataaatcctggtgtccctgttgataccgggaagccctgggcca acttttggcgaaaatgagacgttgatcggcacgtaagaggttccaacttt caccataatgaaataagatcactaccgggcgtatttttgagttgtcgag attttcaggagctaaggaagctaaaatggagaaaaaaatcactggatata ccaccgttgatatatcccaatggcatcgtaaagaacattttgaggcattt cagtcagttgctcaatgtacctataaccagaccgttcagctggatattac
```

```
ggcctttttaaagaccgtaaagaaaaataagcacaagttttatccggcct ttattcacattcttgcccgcctgatgaatgctcatccggaattacgtatg gcaatgaaagacggtgagctggtgatatgggatagtgttcacccttgtta caccgttttccatgagcaaactgaaacgttttcatcgctctggagtgaat accacgacgatttccggcagtttctacacatatattcgcaagatgtggcg tgttacggtgaaaacctggcctatttccctaaagggtttattgagaatat gttttcgtctcagccaatccctgggtgagtttcaccagttttgatttaa acgtggccaatatggacaacttcttcgcccgttttcaccatgggcaaat attatacgcaaggcgacaaggtgctgatgccgctggcgattcaggttcat catgccgtttgtgatggcttccatgtcggcagaatgcttaatgaattaca acagtactgcgatgagtggcagggcggggcgtaattttttttaaggcagtt attggtgcccttaaacgcctggttgctacgcctgaataagtgataataag cggatgaatggcagaaattcgaaagcaaattcgaccggtcgtcggttca gggcagggtcgttaaatagccgcttatgtctattgctggtttaccggttt attgactaccggaagcagtgtgaccgtgtgcttctcaaatgcctgaggcc agtttgctcaggctctccccgtggaggtaataattgacgatatgatcctt tttttctgatcaaaagtgctcatcattggaaaacgttcttcggggcgaaa actctcaaggatcttaccgctgttgagatccagttcgatgtaacccactc gtgcacccaactgatcttcagcatcttttactttcaccagcgtttctggg tgagcaaaaacaggaaggcaaaatgccgcaaaaaagggaataagggcgac acggaaatgttgaatactcatactcttcctttttcaatattattgaagca tttatcaagggttattgtctcatgagcggatacatatttgaatgtattta gaaaaataaacaaatagggggttccgcgcacatttccccgaaaagtgccac
```

Transformants were selected on L agar containing 100 μg/ml carbenicillin. The construct was confirmed by sequencing and biochemical assays (e.g., pNB activity assay)

Primer set for pAH502R construction:

502rbsForward primer:
(SEQ ID NO: 134)
5'-ccaagcttaaggaggtgatctagaattccatggccaagcgaattctg tgtttcg-3'

502Reverse Primer:
(SEQ ID NO: 135)
5'-ggggatccttttacagcaggctccgcacct-3'

The HindIII-RBS-phd-BamHI DNA fragment from pAH502R was cloned into the pSPAC containing vector, pMUTIN4 (See, Vagner et al., Microbiol., 144, 3097-3104 [1998]) creating the construct pAH503. The complete sequence of pAH503 is provided below:

(SEQ ID NO: 136)
ataattctacacagcccagtccagactattcggcactgaaattatgggtg aagtggtcaagacctcactaggcaccttaaaaatagcgcaccctgaagaa gatttatttgaggtagcccttgcctacctagcttccaagaaagatatcct aacagcacaagagcggaaagatgttttgttctacatccagaacaacctct -continued gctaaaattcctgaaaattttgcaaaaagttgttgactttatctacaag
gtgtggcataatgtgtggaattgtgagcgctcacaattaagcttaaggag
gtgatctagaattccatggccaagcgaattctgtgtttcggtgattccct
gacctggggctgggtccccgtcgaagacggggcacccaccgagcggttcg
ccccgacgtgcgctggaccggtgtgctgcccagcagctcggagcggac
ttcgaggtgatcgaggagggactgagcgcgcgcaccaccaacatcgacga
ccccaccgatccgcggctcaacggcgcgagctacctgccgtcgtgcctcg
cgacgcacctgccgctcgacctggtgatcatcatgctgggcaccaacgac
accaaggcctacttccggcgcaccccgctcgacatcgcgctgggcatgtc
ggtgctcgtcacgcaggtgctcaccagcgcgggcggcgtcggcaccacgt
acccggctcccaaggtgctggtggtctcgccgccaccgctggcgcccatg
ccgcaccctggttccagttgatcttcgagggcggcgagcagaagaccac
tgagctcgcccgcgtgtacagcgcgctcgcgtcgttcatgaaggtgccgt
tcttcgacgcgggttcggtgatcagcaccgacggcgtcgacggaatccac
ttcaccgaggccaacaatcgcgatctcggggtggccctcgcggaacaggt
gcggagcctgctgtaaaaggatccccagcttgttgatacactaatgctttt
tatatagggaaaagtggtgaactactgtggaagttactgacgtaagatt
acgggtcgaccgggaaaaccctggcgttacccaacttaatcgccttgcag
cacatccccctttcgccagctggcgtaatagcgaagaggcccgcaccgat
cgcccttcccaacagttgcgcagcctgaatggcgaatggcgcttttgcctg
gttccggcaccagaagcggtgccggaaagctggctggagtgcgatcttc
ctgaggccgatactgtcgtcgtcccctcaaactggcagatgcacggttac
gatgcgcccatctacaccaacgtaacctatcccattacggtcaatccgcc
gtttgttcccacggagaatccgacgggttgttactcgctcacatttaatg
ttgatgaaagctggctacaggaaggccagacgcgaattatttttgatggc
gttaactcggcgtttcatctgtggtgcaacgggcgctgggtcggttacgg
ccaggacagtcgtttgccgtctgaatttgacctgagcgcattttttacgcg
ccggagaaaaccgcctcgcggtgatggtgctgcgttggagtgacggcagt
tatctgaagatcaggatatgtggcggatgagcggcattttccgtgacgt
ctcgttgctgcataaaccgactacacaaatcagcgatttccatgttgcca
ctcgctttaatgatgatttcagccgcgctgtactggaggctgaagttcag
atgtgcggcgagttgcgtgactacctacgggtaacagtttctttatggca
gggtgaaacgcaggtcgccagcggcaccgcgcctttcggcggtgaaatta
tcgatgagcgtggtggttatgccgatcgcgtcacactacgtctgaacgtc
gaaaacccgaaactgtggagcgccgaaatcccgaatctctatcgtgcggt
ggttgaactgcacaccgccgacggcacgctgattgaagcagaagcctgcg
atgtcggtttccgcgaggtgcggattgaaaatggtctgctgctgctgaac
ggcaagccgttgctgattcgaggcgttaaccgtcacgagcatcatcctct
gcatggtcaggtcatggatgagcagacgatggtgcaggatatcctgctga
tgaagcagaacaactttaacgccgtgcgctgttcgcattatccgaaccat
ccgctgtggtacacgctgtgcgaccgctacggcctgtatgtggtggatga
agccaatattgaaacccacggcatggtgccaatgaatcgtctgaccgatg
atccgcgctggctaccggcgatgagcgaacgcgtaacgcgaatggtgcag
cgcgatcgtaatcacccgagtgtgatcatctggtcgctggggaatgaatc
aggccacggcgctaatcacgacgcgctgtatcgctggatcaaatctgtcg
atccttcccgcccggtgcagtatgaaggcggcggagccgacaccacggcc
accgatattatttgcccgatgtacgcgcgcgtggatgaagaccagccctt
cccggctgtgccgaaatggtccatcaaaaaatggctttcgctacctggag
agacgcgcccgctgatccttttgcgaatacgcccacgcgatgggtaacagt
cttggcggtttcgctaaatactggcaggcgtttcgtcagtatccccgttt
acagggcggcttcgtctgggactgggtggatcagtcgctgattaaatatg
atgaaaacggcaacccgtggtcggcttacggcggtgattttggcgatacg
ccgaacgatcgccagttctgtatgaacggtctggtcttgccgaccgcac
gccgcatccagcgctgacggaagcaaaacaccagcagcagttttccagt
tccgtttatccgggcaaaccatcgaagtgaccagcgaatacctgttccgt
catagcgataacgagctcctgcactggatggtggcgctggatggtaagcc
gctggcaagcggtgaagtgcctctggatgtcgctccacaaggtaaacagt
tgattgaactgcctgaactaccgcagccgagagcgccgggcaactctgg
ctcacagtacgcgtagtgcaaccgaacgcgaccgcatggtcagaagccgg
gcacatcagcgcctggcagcagtggcgtctggcggaaaacctcagtgtga
cgctccccgccgcgtcccacgccatcccgcatctgaccaccagcgaaatg
gattttgcatcgagctgggtaataagcgttggcaatttaaccgccagtc
aggctttctttcacagatgtggattggcgataaaaaacaactgctgacgc
cgctgcgcgatcagttcacccgtgcaccgctggataacgacattggcgta
agtgaagcgacccgcattgaccctaacgcctgggtcgaacgctggaaggc
ggcgggccattaccaggccgaagcagcgttgttgcagtgcacggcagata
cacttgctgatgcggtgctgattacgaccgctcacgcgtggcagcatcag
gggaaaaccttatttatcagccggaaaacctaccggattgatggtagtgg
tcaaatggcgattaccgttgatgttgaagtggcgagcgatacaccgcatc
cggcgcggattggcctgaactgccagctggcgcaggtagcagagcgggta
aactggctcggattagggccgcaagaaaactatcccgaccgccttactgc
cgcctgttttgaccgctgggatctgccattgtcagacatgtataccccgt
acgtcttcccgagcgaaaacggtctgcgctgcgggacgcgcgaattgaat
tatggcccacaccagtggcgcggcgacttccagttcaacatcagccgcta
cagtcaacagcaactgatggaaaccagccatcgccatctgctgcacgcgg
aagaaggcacatggctgaatatcgacggtttccatatggggattggtggc
gacgactcctggagcccgtcagtatcggcggaattacagctgagcgccgg
tcgctaccattaccagttggtctggtgtcaaaaataataataaccgggca
ggccatgtctgcccgtatttcgcgtaaggaaatccattatgtactatttc
aagctaattccggtggaaacgaggtcatcatttccttccgaaaaaacggt
tgcatttaaatcttacatatgtaatactttcaaagactacatttgtaaga -continued tttgatgtttgagtcggctgaaagatcgtacgtaccaattattgtttcgt
gattgttcaagccataacactgtagggatagtggaaagagtgcttcatct
ggttacgatcaatcaaatattcaaacggagggagacgattttgatgaaac
cagtaacgttatacgatgtcgcagagtatgccggtgtctcttatcagacc
gtttcccgcgtggtgaaccaggccagccacgtttctgcgaaaacgcggga
aaaagtggaagcggcgatggcggagctgaattacattcccaaccgcgtgg
cacaacaactggcgggcaaacagtcgttgctgattggcgttgccacctcc
agtctggccctgcacgcgccgtcgcaaattgtcgcggcgattaaatctcg
cgccgatcaactgggtgccagcgtggtggtgtcgatggtagaacgaagcg
gcgtcgaagcctgtaaagcggcggtgcacaatcttctcgcgcaacgcgtc
agtgggctgatcattaactatccgctggatgaccaggatgccattgctgt
ggaagctgcctgcactaatgttccggcgttatttcttgatgtctctgacc
agacacccatcaacagtattattttctcccatgaagacggtacgcgactg
ggcgtggagcatctggtcgcattgggtcaccagcaaatcgcgctgttagc
gggcccattaagttctgtctcggcgcgtctgcgtctggctggctggcata
aatatctcactcgcaatcaaattcagccgatagcggaacgggaaggcgac
tggagtgccatgtccggttttcaacaaaccatgcaaatgctgaatgaggg
catcgttcccactgcgatgctggttgccaacgatcagatggcgctgggcg
caatgcgcgccattaccgagtccgggctgcgcgttggtgcggatatctcg
gtagtgggatacgacgataccgaagacagctcatgttatatcccgccgtc
aaccaccatcaaacaggattttcgcctgctggggcaaaccagcgtggacc
gcttgctgcaactctctcagggccaggcggtgaagggcaatcagctgttg
cccgtctcactggtgaaaagaaaaaccaccctggcgcccaatacgcaaac
cgcctctccccgcgcgttggccgattcattaatgcagctggcacgacagg
tttcccgactggaaagcgggcagtgagcgcaacgcaattaatgtgagtta
ggcatcgcatcctgtctcgcgtcgtcggtgatgacggtgaaaacctctga
cacatgcagctcccggagacggtcacagcttgtctgtaagcggatgccgg
gagcagacaagcccgtcagggcgcgtcagcgggtgttggcgggtgtcggg
gcgcagccatgacccagtcacgtagcgatagcggagtgtatactggctta
actatgcggcatcagagcagattgtactgagagtgcaccatatgcggtgt
gaaataccgcacagatgcgtaaggagaaataccgcatcaggcgctcttc
cgcttcctcgctcactgactcgctgcgctcggtcgttcggctgcggcgag
cggtatcagctcactcaaaggcggtaatacggttatccacagaatcaggg
gataacgcaggaaagaacatgtgagcaaaaggccagcaaaaggccaggaa
ccgtaaaaaggccgcgttgctggcgtttttccataggctccgcccccctg
acgagcatcacaaaaatcgacgctcaagtcagaggtggcgaaacccgaca
ggactataaagataccaggcgtttccccctggaagctccctcgtgcgctc
tcctgttccgaccctgccgcttaccggatacctgtccgcctttctccctt
cgggaagcgtggcgctttctcaatgctcacgctgtaggtatctcagttcg
gtgtaggtcgttcgctccaagctgggctgtgtgcacgaaccccccgttca
gcccgaccgctgcgccttatccggtaactatcgtcttgagtccaacccgg -continued taagacacgacttatcgccactggcagcagccactggtaacaggattagc
agagcgaggtatgtaggcggtgctacagagttcttgaagtggtggcctaa
ctacggctacactagaaggacagtatttggtatctgcgctctgctgaagc
cagttaccttcggaaaaagagttggtagctcttgatccggcaaacaaacc
accgctggtagcggtggtttttttgtttgcaagcagcagattacgcgcag
aaaaaaaggatctcaagaagatcctttgatcttttctacggggtctgacg
ctcagtggaacgaaaactcacgttaagggattttggtcatgagattatca
aaaaggatcttcacctagatcctttaaattaaaaatgaagttttaaatc
aatctaaagtatatatgagtaaacttggtctgacagttaccaatgcttaa
tcagtgaggcacctatctcagcgatctgtctatttcgttcatccatagtt
gcctgactccccgtcgtgtagataactacgatacgggagggcttaccatc
tggccccagtgctgcaatgataccgcgagacccacgctcaccggctccag
atttatcagcaataaaccagccagccggaagggccgagcgcagaagtggt
cctgcaactttatccgcctccatccagtctattaattgttgccgggaagc
tagagtaagtagttcgccagttaatagtttgcgcaacgttgttgccattg
ctgcaggcatcgtggtgtcacgctcgtcgtttggtatggcttcattcagc
tccggttcccaacgatcaaggcgagttacatgatcccccatgttgtgcaa
aaaagcggttagctccttcggtcctccgatcgttgtcagaagtaagttgg
ccgcagtgttatcactcatggttatggcagcactgcataattctcttact
gtcatgccatccgtaagatgcttttctgtgactggtgagtactcaaccaa
gtcattctgagaatagtgtatgcggcgaccgagttgctcttgcccggcgt
caacacgggataataccgcgccacatagcagaactttaaaagtgctcatc
attggaaaacgttcttcggggcgaaaactctcaaggatcttaccgctgtt
gagatccagttcgatgtaacccactcgtgcacccaactgatcttcagcat
cttttactttcaccagcgtttctgggtgagcaaaaacaggaaggcaaaat
gccgcaaaaaagggaataagggcgacacggaaatgttgaatactcatact
cttcctttttcaatattattgaagcatttatcagggttattgtctcatga
gcggatacatatttgaatgtatttagaaaaataaacaaataggggttccg
cgcacatttccccgaaaagtgccacctgacgtctaagaaaccattattat
catgacattaacctataaaaataggcgtatcacgaggccctttcgtcttc
aagaattgatcctctagcacaaaagaaaacgaaatgatacaccaatcag
tgcaaaaaagatataatgggagataagacggttcgtgttcgtgctgact
tgcaccatatcataaaaatcgaaacagcaaagaatggcggaaacgtaaaa
gaagttatggaaataagacttagaagcaaacttaagagtgtgttgatagt
gcagtatcttaaaattttgtataataggaattgaagttaaattagatgct
aaaaatttgtaattaagaaggagtgattacatgaacaaaaatataaaata
ttctcaaaacttttaacgagtgaaaagtactcaaccaaataataaaac
aattgaatttaaaagaaaccgataccgtttacgaaattggaacaggtaaa
gggcatttaacgacgaaactggctaaaataagtaaacaggtaacgtctat
tgaattagacagtcatctattcaacttatcgtcagaaaaattaaaactga -continued
```
atactcgtgtcactttaattcaccaagatattctacagtttcaattccct
aacaaacagaggtataaaattgttgggagtattccttaccatttaagcac
acaaattattaaaaaagtggtttttgaaagccatgcgtctgacatctatc
tgattgttgaagaaggattctacaagcgtaccttggatattcaccgaaca
ctagggttgctcttgcacactcaagtctcgattcagcaattgcttaagct
gccagcggaatgctttcatcctaaaccaaaagtaaacagtgtcttaataa
aacttacccgccataccacagatgttccagataaatattggaagctatat
acgtactttgtttcaaaatgggtcaatcgagaatatcgtcaactgtttac
taaaaatcagtttcatcaagcaatgaaacacgccaaagtaaacaatttaa
gtaccgttacttatgagcaagtattgtctatttttaatagttatctatta
tttaacgggaggaaataattctatgagtcgcttttgtaaatttggaaagt
tacacgttactaaagggaatgtagataaattattaggtatactactgaca
gcttccaaggagctaaagaggtccctagactctagacccggggatctctg
cagtcggatctggtaatgactctctagcttgaggcatcaaataaaacgaa
aggctcagtcgaaagactgggcctttcgttttatctgttgtttgtcggtg
aacgctctcctgagtaggacaaatccgccgctctagctaagcagaaggcc
atcctgacggatggccttttgcgtttctacaaactcttgttaactctag
agctgcctgccgcgtttcggtgatgaagatcttcccgatgattaattaat
tcagaacgctcggttgccgccgggcgttttttatgcagcaatggcaagaa
cgttgctctaga
```

Figure 14:
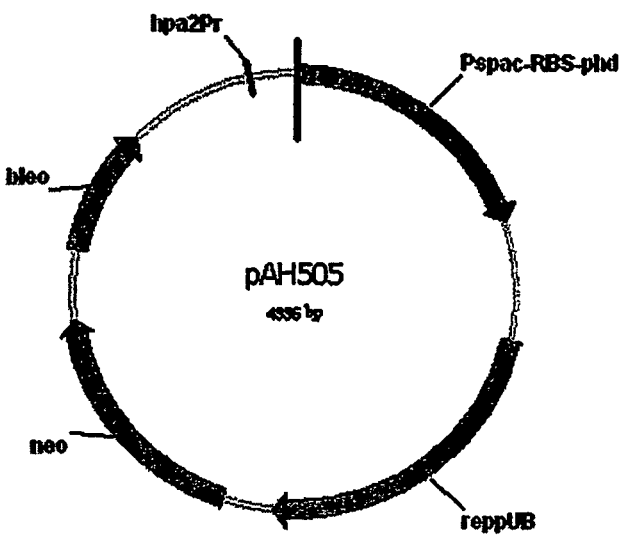
FIG. 14 provides a map of plasmid pAH505.

The construction of pAH503 was confirmed by RFLP and pNB activity assays. The pSPAC-RBS-phd DNA cassette was isolated as a BglII/SmaI digest and then subcloned into the replicating plasmid pBH1, digested with BamH1/EcoRV (See e.g., EP 0275509) to create pAH505 (See, FIG. 14). The complete sequence of the plasmid is provided below.

(SEQ ID NO: 137)
```
gatcttccaagatatcctaacagcacaagagcggaaagatgttttgttct
acatccagaacaacctctgctaaaattcctgaaaaatttgcaaaaagtt
gttgactttatctacaaggtgtggcataatgtgtggaattgtgagcgctc
acaattagcttaaggaggtgatctagaattccatggccaagcgaattctg
tgtttcggtgattccctgacctggggctgggtccccgtcgaagacggggc
acccaccgagcggttcgccccgacgtgcgctggaccggtgtgctggcc
agcagctcggagcggacttcgaggtgatcgaggagggactgagcgcgcgc
accaccaacatcgacgaccccaccgatccgcggctcaacggcgcgagcta
cctgccgtcgtgcctcgcgacgcacctgccgctcgacctggtgatcatca
tgctgggcaccaacgacaccaaggcctacttccggcgcacccgctcgac
atcgcgctgggcatgtcggtgctcgtcacgcaggtgctcaccagcgcggg
cggcgtcggcaccacgtacccggctcccaaggtgctggtggtctcgccgc
caccgctggcgcccatgccgcacccctggttccagttgatcttcgagggc
ggcgagcagaagaccactgagctcgcccgcgtgtacagccgcgctcgcgtc
gttcatgaaggtgccgttcttcgacgcgggttcggtgatcagcaccgacg
```

-continued
```
gcgtcgacggaatccacttcaccgaggccaacaatcgcgatctcggggtg
gccctcgcggaacaggtgcggagcctgctgtaaaaggatcccatcgcatg
cggtacctctagaagaagcttggagacaaggtaaaggataaaacagcaca
attccaagaaaaacacgatttagaacctaaaaagaacgaatttgaactaa
ctcataaccgagaggtaaaaaaagaacgaagtcgagatcagggaatgagt
ttataaaataaaaaaagcacctgaaaaggtgtctttttttgatggttttg
aacttgttctttcttatcttgatacatatagaaataacgtcattttttatt
ttagttgctgaaaggtgcgttgaagtgttggtatgtatgtgttttaaagt
attgaaaacccttaaaattggttgcacagaaaaacccatctgttaaagt
tataagtgactaaacaaataactaaatagatgggggtttcttttaatatt
atgtgtcctaatagtagcatttattcagatgaaaaatcaagggttttagt
ggacaagacaaaaagtggaaagtgagaccatggagagaaaagaaaatcg
ctaatgttgattactttgaacttctgcatattcttgaatttaaaaaggct
gaaagagtaaaagattgtgctgaaatattagagtataaacaaaatcgtga
acaggcgaaagaaagttgtatcgagtgtggttttgtaaatccaggcttt
gtccaatgtgcaactggaggagagcaatgaaacatggcattcagtcacaa
aaggttgttgctgaagttattaaacaaaagccaacagttcgttggttgtt
tctcacattaacagttaaaaatgtttatgatggcgaagaattaaataaga
gtttgtcagatatggctcaaggatttcgccgaatgatgcaatataaaaaa
attaataaaaatcttgttggttttatgcgtgcaacggaagtgacaataaa
taataaagataattcttataatcagcacatgcatgtattggtatgtgtgg
aaccaacttattttaagaatacagaaaactacgtgaatcaaaaacaatgg
attcaattttggaaaaaggcaatgaaattagactatgatccaaatgtaaa
agttcaaatgattcgaccgaaaaataaatataaatcggatatacaatcgg
caattgacgaaactgcaaaatatcctgtaaaggatacggattttatgacc
gatgatgaagaaaagaatttgaaacgtttgtctgatttggaggaaggttt
acaccgtaaaaggttaatctcctatggtggtttgttaaaagaaatacata
aaaaattaaaccttgatgacacagaagaaggcgatttgattcatacagat
gatgacgaaaaagccgatgaagatggattttctattattgcaatgtggaa
ttgggaacggaaaaattattttattaaagagtagttcaacaaacgggcca
gtttgttgaagattagatgctataattgttattaaaaggattgaaggatg
cttaggaagacgagttattaatagctgaataagaacggtgctctccaaat
attcttatttagaaaagcaaatctaaaattatctgaaaagggaatgagaa
tagtgaatggaccaataataatgactagagaagaaagaatgaagattgtt
catgaaattaaggaacgaatattggataaatatggggatgatgttaaggc
tattggtgtttatggctctcttggtcgtcagactgatgggccctattcgg
atattgagatgatgtgtgtcatgtcaacagaggaagcagagttcagccat
gaatggacaaccggtgagtggaaggtggaagtgaattttgatagcgaaga
gattctactagattatgcatctcaggtggaatcagattggccgcttacac
atggtcaatttttctctattttgccgatttatgattcaggtggatactta
gagaaagtgtatcaaactgctaaatcggtagaagcccaaacgttccacga
```

```
tgcgatttgtgcccttatcgtagaagagctgtttgaatatgcaggcaaat ggcgtaatattcgtgtgcaaggaccgacaacatttctaccatccttgact gtacaggtagcaatggcaggtgccatgttgattggtctgcatcatcgcat ctgttatacgacgagcgcttcggtcttaactgaagcagttaagcaatcag atcttccttcaggttatgaccatctgtgccagttcgtaatgtctggtcaa ctttccgactctgagaaacttctggaatcgctagagaatttctggaatgg gcgctctcgtagtaatgattcaccggtttgtacaggtgcggagtcgttta ttgctggtactgctagttgccgcattgaagtagagggaattgatgaatta tatcaacatattaagcctttgggcattttgcaccccaatacatcattaaa agatcagtggtgggatgaacgagactttgcagtaattgatcccgacaaca atttgattagctttttcaacaaataaaaagctaaaatctattattaatc tgttcagcaatcgggcgcgattgctgaataaaagatacgagagacctctc ttgtatctttttattttgagtggttttgtccgttacactagaaaaccga aagacaataaaaattttattcttgctgagtctggctttcggtaagctaga caaaacggacaaaataaaaattggcaagggtttaaaggtggagattttt agtgatcttctcaaaaaatactacctgtcccttgctgattttaaacgag cacgagagcaaaacccccctttgctgaggtggcagagggcaggtttttg tttcttttttctcgtaaaaaaagaaaggtcttaaaggttttatggtttt ggtcggcactgccgacagcctcgcaggacacacactttatgaatataaag tatagtgtgttatactttacttggaagtggttgccggaaagagcgaaaat gcctcacatttgtgccacctaaaaaggagcgatttacatatgagttatgc agtttgtagaatgcaaaaagtgaaatcaggg
```

The ligation mixture for pAH505 was transformed into *Bacillus subtilis* pnbA. Correct transformants were verified by RFLP and sequencing of isolated plasmid DNA. One transformant was selected for analysis (*B. subtilis* pnbA/pAH505).

Expression of the perhydrolase in *Bacillus* was assayed using the pNB Activity Assay described herein, after growth of the desired strain in shake flask. The data showed that the perhydrolase was expressed in *B. subtilis* pnbA.

B. Intracellular Expression of the Perhydrolase in *B. subtilis* pnbA by Integration into the Chromosome An additional construct useful to determine expression of the perhydrolase (act) gene integrated into the chromosome of *B. subtilis* pnbA involved use of the spoVG promoter, which was found to drive expression of the perhydrolase gene in a non-replicating (i.e., integrating plasmid). In some embodiments, one site of integration is the aprE region of *B. subtilis*, although it is intended that integration occur at any suitable site. Indeed, it is not intended that the present invention be limited to this specific site nor this specific promoter, as various other suitable sites and promoters find use in the present invention.

The configuration of the promoter/gene at the aprE locus in the chromosome of *Bacillus subtilis* was as follows:

pAprE-aprE first 7 codons-translation stop-pSpoVG-ATG-perhydrolase gene from second codon The clone was constructed as described below. The primers used were:

Up5'F
(SEQ ID NO: 138)
caggctgcgcaactgttgggaag

FuaprEAct34R
(SEQ ID NO: 139)
agtagttcaccacctttccctatataaaagcattagtgtatcaatttca gatccacaatttttgcttctcactctttac FuaprEAct4F
(SEQ ID NO: 140)
Aattgatacactaatgcttttatatagggaaaaggtggtgaactactatg gccaagcgaattctgtgtttcggtg BsmI-DnAct504R
(SEQ ID NO: 141)
gtgagaggcattcggatccttttacagcaggctccg PCR fusion is a technique well known in the art, in which two or more fragments of DNA are generated either by restriction digest or by PCR amplification. The fragments have overlapping segments, usually at least 18 bases long. In the instance that two fragments are used, the 3' end of fragment #1 has an overlapping sequence with the 5' end of fragment #2. The two fragments are used as template in a PCR reaction in which the primer set used hybridizes to the 5' end of fragment #1 (forward primer) and the 3' end of fragment #2 (reverse primer). During the amplification, the two regions of overlap hybridize forming a single template from which the two primers can amplify a full length fragment, a "fusion" of fragments #1 and #2. Multiple fragments of any length can be used in such a reaction, limited only by the ability of the chosen polymerase to amplify long DNA pieces.

Figure 15:
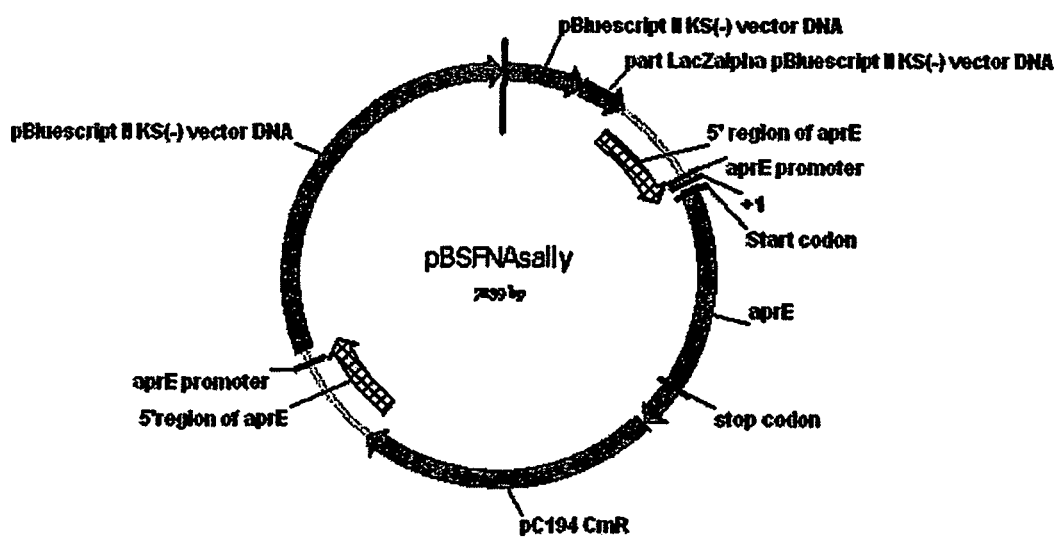
FIG. 15 provides a map of plasmid pSFNASally.

In the current example, the above construct was made by PCR fusion of two PCR products the above construct was made by PCR fusion of two PCR products. The first was a construct with the spoVG promoter added upstream of the phd gene. The second was the aprE promoter and first 7 codons of aprE, followed by a stop codon. Regions of 20 bp overlap were added on the 5' and 3' ends of the products respectively, to allow the PCR fusion reaction. The primer set FuaprEAct4F/BsmI-DnAct504R was used to amplify the perhydrolase gene from pAH505 as described above, which added the spoVG promoter sequence (contained within the primer) to the 5' end of the gene and changed the start codon from ATG to GTG. To create the second product (pAprE plus the first 7 codons of aprE) for the fusion, the primer set Up5'F/FuaprEAct34R was used to amplify a fragment from pBSFNASally. FIG. 15 provides a map of this plasmid. The complete sequence of pBSFNASally is provided below.

```
(SEQ ID NO: 142)
ctaaattgtaagcgttaatattttgttaaaattcgcgttaaattttgtt aaatcagctcattttttaaccaataggccgaaatcggcaaaatcccttat aaatcaaaagaatagaccgagatagggttgagtgttgttccagtttggaa caagagtccactattaaagaacgtggactccaacgtcaaagggcgaaaaa ccgtctatcagggcgatggcccactacgtgaaccatcaccctaatcaagt tttttgggggtcgaggtgccgtaaagcactaaatcggaaccctaaagggag ccccgatttagagcttgacggggaaagccggcgaacgtggcgagaaagg aagggaagaaagcgaaaggagcgggcgctagggcgctggcaagtgtagcg gtcacgctgcgcgtaaccaccacacccgccgcgcttaatgcgccgctaca
```

-continued gggcgcgtcccattcgccattcaggctgcgcaactgttgggaagggcgat cggtgcgggcctcttcgctattacgccagctggcgaaaggggatgtgct gcaaggcgattaagttgggtaacgccagggttttcccagtcacgacgttg taaaacgacggccagtgagcgcgcgtaatacgactcactataggcgaat tggagctccaccgcggtggcggccgctctagaactagtggatccccggg ctgcaggaattctccatttcttctgctatcaaaataacagactcgtgat tttccaaacgagctttcaaaaaagcctctgccccttgcaaatcggatgcc tgtctataaaattcccgatattggttaaacagcggcgcaatggcggccgc atctgatgtctttgcttggcgaatgttcatcttatttcttcctccctctc aataattttttcattctatccttttctgtaaagtttattttttcagaata cttttatcatcatgctttgaaaaaatatcacgataatatccattgttctc acggaagcacacgcaggtcatttgaacgaatttttttcgacaggaatttgc cgggactcaggagcatttaacctaaaaaagcatgacatttcagcataatg aacatttactcatgtctattttcgttcttttctgtatgaaaatagttatt tcgagtctctacggaaatagcgagagatgatatacctaaatagagataaa atcatctcaaaaaatgggtctactaaaatattattccatctattacaat aaattcacagaatagtcttttaagtaagtctactctgaattttttttaaaa ggagagggtaaagagtgagaagcaaaaaattgtggatcagtttgctgttt gctttagcgttaatctttacgatggcgttcggcagcacatcctctgccca ggcggcagggaaatcaaacggggaaaacggggaaaagaaatatattgtcg ggtttaaacagacaatgagcacgatgagcgccgctaagaagaaagatgtc atttctgaaaaggcgggaaagtgcaaaagcaattcaaatatgtagacgc agcttcagctacattaaacgaaaaagctgtaaaagaattgaaaaagacc cgagcgtcgcttacgttgaagaagatcacgtagcacatgcgtacgcgcag tccgtgccttacggcgtatcacaaattaaagcccctgctctgcactctca aggctacactggatcaaatgttaaagtagcggttatcgacagcggtatcg attcttctcatcctgatttaaaggtagcaggcggagccagcatggttcct tctgaaacaaatcctttccaagacaacaactctcacggaactcacgtgcc ggcacagttgcggctcttaataactcaatcggtgtattaggcgttgcgcc aagcgcatcactttacgctgtaaaagttctcggtgctgacggttccggcc aatacagctggatcattaacgaatcgagtgggcgatcgcaaacaatatg gacgttattaacatgagcctcggcggaccttctggttctgctgctttaaa agcggcagttgataaagccgttgcatccggcgtcgtagtcgttgcggcag ccggtaacgaaggcacttccggcagctcaagcacagtgggctaccctggt aaatacccttctgtcattgcagtaggcgctgttgacagcagcaaccaaag agcatctttctcaagcgtaggacctgagcttgatgtcatggcacctggcg tatctatccaaagcacgcttcctggaaacaaatacggcgcgttgaacggt acatcaatggcatctccgcacgttgccggagcggctgctttgattctttc taagcacccgaactggacaaacactcaagtccgcagcagtttagaaaaca ccactacaaaacttggtgattcttctactatggaaagggctgatcaac -continued gtacaggcggcagctcagtaaaacataaaaaaccggccttggccccgccg gtttttattattttcttcctccgcatgttcaatccgctccataatcga cggatggctccctctgaaaattttaacgagaaacggcgggttgacccggc tcagtcccgtaacggccaagtcctgaaacgtctcaatcgccgcttcccgg tttccggtcagctcaatgccgtaacggtcggcggcgttttcctgataccg ggagacggcattcgtaatcggatcctctagagtcgatttttacaagaatt agctttatataatttctgttttttctaaagttttatcagctacaaaagaca gaaatgtattgcaatcttcaactaaatccatttgattctctccaatatga cgtttaataaaatttctgaaatacttgatttcttttgttttttctcagtata cttttccatgttataacacataaaaacaacttagttttcacaaactatga caataaaaaaagttgcttttttcccctttctatgtatgttttttactagtc atttaaaacgatacattaataggtacgaaaaagcaacttttttttgcgctt aaaaccagtcataccaataacttaagggtaactagcctcgccggcaatag ttaccccttattatcaagataagaaagaaaagggattttttcgctacgctcaa atcctttaaaaaaaacacaaaagaccacatttttttaatgtggtctttattc ttcaactaaagcacccattagttcaacaaacgaaaattggataaagtggg atatttttaaaatatatatttatgttacagtaatattgacttttaaaaaa ggattgattctaatgaagaaagcagacaagtaagcctcctaaaattcactt tagataaaaatttaggaggcatatcaaatgaactttaataaaattgattt agacaattggaagagaaaagagatatttaatcattatttgaaccaacaac gacttttagtataaccacagaattgatattagtgttttataccgaaacat aaaacaagaaggatataaattttaccctgcatttattttcttagtgacaa gggtgataaactcaaatacagcttttagaactggttacaatagcgacgga gagttaggttattgggataagtagagccacttttatacaattttttgatggt gtatcaaacattctctggtatttggactcctgtaaagaatgacttcaaag agttttatgatttataccttctgatgtagagaaatataatggttcgggg aaattgtttcccaaaacacctatacctgaaaatgcttttctctttctat tattccatggacttcatttactgttaacttaaatatcaataataatagta attaccttctacccattattacagcaggaaaattcattaataaaggtaat tcaatatatttaccgctatctttacaggtacatcattctgtttgtgatgg ttatcatgcaggattgtttatgaactctattcaggaattgtcagataggc ctaatgactggcttttataatatgagataatgccgactgtacttttaca gtcggttttctaatgtcactaacctgccccgttagttgaagaaggttttt atattacagctccagatccatatccttcttttttctgaaccgacttctcct ttttcgcttctttattccaattgctttattgacgtgagcctcggaaccct taacaatcccaaaacttgtcgaatggtcggcttaatagctcacgctatgc cgacattcgtctgcaagtttagttaagggttcttctcaacgcacaataaa ttttctcggcataaatgcgtggtctaattttttattttttaataaccttgat agcaaaaaatgccattccaatacaaaaccacatacctataatcgaccga attaattctccatttcttctgctatcaaaataacagactcgtgattttc caaacgagctttcaaaaaagcctctgccccttgcaaatcggatgcctgtc

```
tataaaattcccgatattggttaaacagcggcgcaatggcggccgcatct
gatgtctttgcttggcgaatgttcatcttatttcttcctccctctcaata
atttttcattctatccttttctgtaaagtttatttttcagaatacttt
tatcatcatgctttgaaaaaatatcacgataatatccattgttctcacgg
aagcacacgcaggtcatttgaacgaattttttcgacaggaatttgccggg
actcaggagcatttaacctaaaaaagcatgacatttcagcataatgaaca
tttactcatgtctattttcgttcttttctgtatgaaaatagttatttcga
gtctctacggaaatagcgagagatgatatacctaaatagagataaaatca
tctcaaaaaaatgggtctactaaaatattattccatctattacaataaat
tcacagaatagtctttttaagtaagtctactctgaattttttttatcaagct
tatcgataccgcgacctcgagggggggcccggtacccagcttttgttccc
tttagtgagggttaattgcgcgcttggcgtaatcatggtcatagctgttt
cctgtgtgaaattgttatccgctcacaattccacacaacatacgagccgg
aagcataaagtgtaaagcctggggtgcctaatgagtgagctaactcacat
taattgcgttgcgctcactgcccgctttccagtcgggaaacctgtcgtgc
cagctgcattaatgaatcggccaacgcgcggggagaggcggtttgcgtat
tgggcgctcttccgcttcctcgctcactgactcgctgcgctcggtcgttc
ggctgcggcgagcggtatcagctcactcaaaggcggtaatacggttatcc
acagaatcaggggataacgcaggaaagaacatgtgagcaaaaggccagca
aaaggccaggaaccgtaaaaaggccgcgttgctggcgtttttccatagqc
tccgcccccctgacgagcatcacaaaaatcgacgctcaagtcagaggtgg
cgaaacccgacaggactataaagataccaggcgtttccccctggaagctc
cctcgtgcgctctcctgttccgaccctgccgcttaccggatacctgtccg
cctttctcccttcgggaagcgtggcgctttctcatagctcacgctgtagg
tatctcagttcggtgtaggtcgttcgctccaagctgggctgtgtgcacga
accccccgttcagcccgaccgctgcgccttatccggtaactatcgtcttg
agtccaacccggtaagacacgacttatcgccactggcagcagccactggt
aacaggattagcagagcgaggtatgtaggcggtgctacagagttcttgaa
gtggtggcctaactacggctacactagaaggacagtatttggtatctgcg
ctctgctgaagccagttaccttcggaaaaagagttggtagctcttgatcc
ggcaaacaaaccaccgctggtagcggtggtttttttgtttgcaagcagca
gattacgcgcagaaaaaaaggatctcaagaagatcctttgatcttttcta
cggggtctgacgctcagtggaacgaaaactcacgttaagggattttggtc
atgagattatcaaaaaggatcttcacctagatccttttaaattaaaaatg
aagttttaaatcaatctaaagtatatatgagtaaacttggtctgacagtt
accaatgcttaatcagtgaggcacctatctcagcgatctgtctatttcgt
tcatccatagttgcctgactccccgtcgtgtagataactacgatacggga
gggcttaccatctggccccagtgctgcaatgataccgcgagacccacgct
caccggctccagatttatcagcaataaaccagccagccggaagggccgag
cgcagaagtggtcctgcaactttatccgcctccatccagtctattaattg
ttgccgggaagctagagtaagtagttcgccagttaatagtttgcgcaacg
ttgttgccattgctacaggcatcgtggtgtcacgctcgtcgtttggtatg
gcttcattcagctccggttcccaacgatcaaggcgacatgttgtgcaaaa
aagcggttagctccttcggtcctccgatcgttgtcagaagtaagttggcc
gcagtgttatcactcatggttatggcagcactgcataattctcttactgt
catgccatccgtaagatgcttttctgtgactggtgagtactcaaccaagt
cattctgagaatagtgtatgcggcgaccgagttgctcttgcccggcgtca
atacggataataccgcgccacatagcagaactttaaaagtgctcatcat
tggaaaacgttcttcggggcgaaaactctcaaggatcttaccgctgttga
gatccagttcgatgtaacccactcgtgcacccaactgatcttcagcatct
tttactttcaccagcgtttctgggtagcaaaaacaggaaggcaaaatgcc
gcaaaaaagggaataagggcgacacggaaatgttgaatactcatactctt
ccttttttcaatattattgaagcatttatcaggggttattgtctcatgagcg
gatacatatttgaatgtatttagaaaaataaacaatagggggttccgcgc
acatttccccgaaaagtgccac
```

Figure 16:
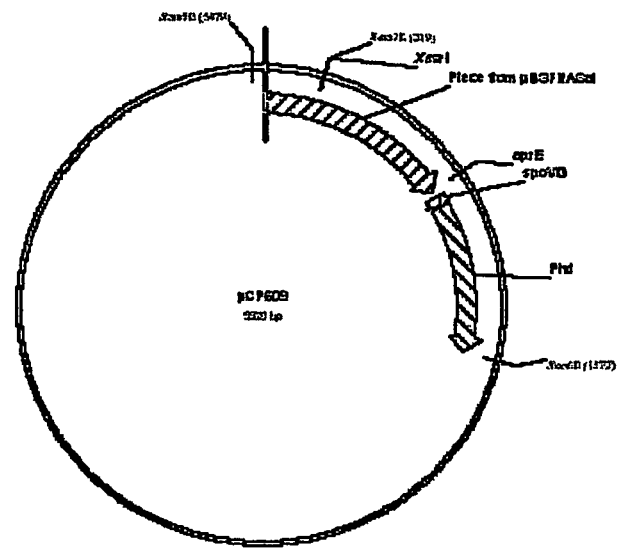
FIG. 16 provides a map of plasmid pCP606.

The two PCR products were subjected to fusion PCR as known in the art to create the 1.5 kb fusion. The resulting fusion product was then cloned into PCR2.1TOPO to produce pCP609 (See, FIG. 16) and sequence below).

```
                                        (SEQ ID NO: 143)
caggctgcgcaactgttgggaagggcgatcggtgcgggcctcttcgctat
tacgccagctggcgaaaggggggatgtgctgcaaggcgattaagttgggta
acgccagggttttcccagtcacgacgttgtaaaacgacggccagtgagcg
cgcgtaatacgactcactatagggcgaattggagctccaccgcggtggcg
gccgctctagaactagtggatccccccgggctgcaggaattctccatttc
ttctgctatcaaaataacagactcgtgattttccaaacgagcttttcaaaa
aagcctctgccccttgcaaatcggatgcctgtctataaaattcccgatat
tggttaaacagcggcgcaatggcggccgcatctgatgtctttgcttggcg
aatgttcatcttatttcttcctctctcaataattttttcattctatcc
cttttctgtaagtttatttttcagaatacttttatcatcatgctttgaaa
aaatatcacgataatatccattgttctcacggaagcacacgcaggtcatt
tgaacgaattttttcgacaggaatttgccgggactcaggagcatttaacc
taaaaaagcatgacatttcagcataatgaacatttactcatgtctatttt
cgttcttttctgtatgaaaatagttatttcgagtctctacggaaatagcg
agagatgatatacctaaatagagataaaatcatctcaaaaaatgggtct
actaaaatattattccatctattacaataaattcacagaatagtcttttta
agtaagtctactctgaatttttttaaaaggagagggtaaagagtgagaag
caaaaaattgtggatctgaaattgatacactaatgcttttatatagggaa
aaggtggtgaactactatggccaagcgaattctgtgtttcggtgattccc
tgacctggggctgggtccccgtcgaagacggggcacccaccgagcggttc
gccccgacgtgcgctggaccggtgtgctggcccagcagctcggagcgga
```

-continued

```
cttcgaggtgatcgaggagggactgagcgcgcgcaccaccaacatcgacg
accccaccgatccgcggctcaacggcgcgagctacctgccgtcgtgcctc
gcgacgcacctgccgctcgacctggtgatcatcatgctgggcaccaacga
caccaaggcctacttccggcgcaccccgctcgacatcgcgctgggcatgt
cggtgctcgtcacgcaggtgctcaccagcgcgggcggcgtcggcaccacg
tacccggctcccaaggtgctggtggtctcgccgccaccgctggcgcccat
gccgcacccctggttccagttgatcttcgagggcggcgagcagaagacca
ctgagctcgcccgcgtgtacagcgcgctcgcgtcgttcatgaaggtgccg
ttcttcgacgcgggttcggtgatcagcaccgacggcgtcgacggaatcca
cttcaccgaggccaacaatcgcgatctcggggtggccctcgcggaacagg
tgcggagcctgctgtaaaaggatccgaatgcctctcacaagggcgaattc
tgcagatatccatcacactggcggccgctcgagcatgcatctagagggcc
caattcgccctatagtgagtcgtattacaattcactggccgtcgttttac
aacgtcgtgactgggaaaaccctggcgttacccaacttaatcgccttgca
gcacatccccctttcgccagctggcgtaatagcgaagaggcccgcaccga
tcgcccttcccaacagttgcgcagcctgaatggcgaatggacgcgccctg
tagcggcgcattaagcgcggcgggtgtggtggttacgcgcagcgtgaccg
ctacacttgccagcgccctagcgcccgctcctttcgctttcttcccttcc
tttctcgccacgttcgccggctttccccgtcaagctctaaatcggggggct
ccctttagggttccgatttagtgctttacggcacctcgaccccaaaaaac
ttgattagggtgatggttcacgtagtgggccatcgccctgatagacggtt
ttcgccctttgacgttggagtccacgttctttaatagtggactcttgttc
caaactggaacaacactcaaccctatctcggtctattcttttgatttata
agggattttgccgatttcggcctattggttaaaaaatgagctgatttaac
aaaaatttaacgcgaattttaacaaaattcagggcgcaagggctgctaaa
ggaagcggaacacgtagaaagccagtccgcagaaacggtgctgaccccgg
atgaatgtcagctactgggctatctggacaagggaaaacgcaagcgcaaa
gagaaagcaggtagcttgcagtgggcttacatggcgatagctagactggg
cggttttatggacagcaagcgaaccggaattgccagctggggcgccctct
ggtaaggttgggaagccctgcaaagtaaactggatggctttcttgccgcc
aaggatctgatggcgcaggggatcaagatctgatcaagagacaggatgag
gatcgtttcgcatgattgaacaagatggattgcacgcaggttctccggcc
gcttgggtggagaggctattcggctatgactgggcacaacagacaatcgg
ctgctctgatgccgccgtgttccggctgtcagcgcaggggcgcccggttc
ttttgtcaagaccgacctgtccggtgccctgaatgaactgcaggacgag
gcagcgcggctatcgtggctggccacgacgggcgttccttgcgcagctgt
gctcgacgttgtcactgaagcgggaagggactggctgctattgggcgaag
tgccggggcaggatctcctgtcatcccaccttgctcctgccgagaaagta
tccatcatggctgatgcaatgcggcggctgcatacgcttgatccggctac
ctgcccattcgaccaccaagcgaaacatcgcatcgagcgagcacgtactc
ggatggaagccggtcttgtcgatcaggatgatctggacgaagagcatcag
```

-continued

```
gggctcgcgccagccgaactgttcgccaggctcaaggcgcgcatgcccga
cggcgaggatctcgtcgtgacccatggcgatgcctgcttgccgaatatca
tggtggaaaatggccgcttttctggattcatcgactgtggccggctgggt
gtggcggaccgctatcaggacatagcgttggctacccgtgatattgctga
agagcttggcggcgaatgggctgaccgcttcctcgtgctttacggtatcg
ccgctcccgattcgcagcgcatcgccttctatcgccttcttgacgagttc
ttctgaattgaaaaaggaagagtatgagtattcaacatttccgtgtcgcc
cttattccctttttttgcggcattttgccttcctgtttttgctcacccaga
aacgctggtgaaagtaaaagatgctgaagatcagttgggtgcacgagtgg
gttacatcgaactggatctcaacagcggtaagatccttgagagttttcgc
cccgaagaacgttttccaatgatgagcacttttaaagttctgctatgtgg
cgcggtattatcccgtattgacgccgggcaagagcaactcggtcgccgca
tacactattctcagaatgacttggttgagtactcaccagtcacagaaaag
catcttacggatggcatgacagtaagagaattatgcagtgctgccataac
catgagtgataacactgcggccaacttacttctgacaacgatcggaggac
cgaaggagctaaccgcttttttgcacaacatgggggatcatgtaactcgc
cttgatcgttgggaaccggagctgaatgaagccataccaaacgacgagcg
tgacaccacgatgcctgtagcaatggcaacaacgttgcgcaaactattaa
ctggcgaactacttactctagcttcccggcaacaattaatagactggatg
gaggcggataaagttgcaggaccacttctgcgctcggcccttccggctgg
ctggtttattgctgataaatctggagccggtgagcgtgggtctcgcggta
tcattgcagcactggggccagatggtaagccctcccgtatcgtagttatc
tacacgacggggagtcaggcaactatggatgaacgaaatagacagatcgc
tgagataggtgcctcactgattaagcattggtaactgtcagaccaagttt
actcatatatactttagattgatttaaaacttcattttttaatttaaaagg
atctaggtgaagatccttttttgataatctcatgaccaaaatcccttacgt
gagttttcgttccactgagcgtcagaccccgtagaaaagatcaaaggatc
ttcttgagatcctttttttctgcgcgtaatctgctgcttgcaaacaaaaa
aaccaccgctaccagcggtggtttgtttgccggatcaagagctaccaact
cttttttccgaaggtaactggcttcagcagagcgcagataccaaatactgt
tcttctagtgtagccgtagttaggccaccacttcaagaactctgtagcac
cgcctacatacctcgctctgctaatcctgttaccagtggctgctgccagtg
gcgataagtcgtgtcttaccgggttggactcaagacgatagttaccggat
aaggcgcagcggtcgggctgaacggggggttcgtgcacacagcccagctt
ggagcgaacgacctacaccgaactgagatacctacagcgtgagctatgag
aaagcgccacgcttcccgaagggagaaaggcggacaggtatccggtaagc
ggcagggtcggaacaggagagcgcacgagggagcttccaggggggaaacgc
ctggtatctttatagtcctgtcgggtttcgccacctctgacttgagcgtc
gatttttgtgatgctcgtcaggggggcggagcctatggaaaaacgccagc
aacgcggcctttttacggttcctggccttttgctggccttttgctcacatg
```

Figure 17:
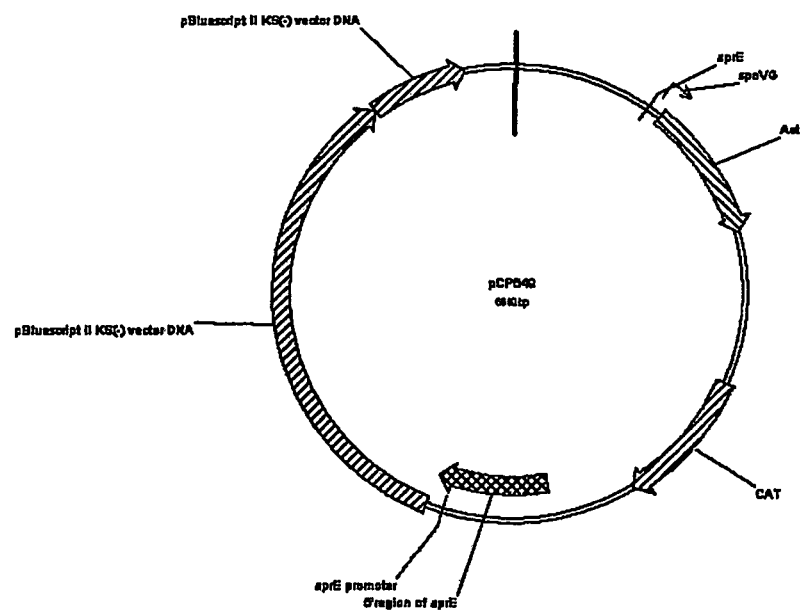
FIG. 17 provides a map of plasmid pCP649.

The plasmid PCP609 was digested with BamH1/XmaI to release the fragment containing the pAprE-aprE-stop-pSpoVG-phd construct and ligated into pBSFNASally digested with XmaI/Bc/I to give the plasmid pCP649. FIG. 17 provides a map of pCP649. The complete sequence of pCP649 is provided below.

(SEQ ID NO: 144)

```
ttctttcctgcgttatccctgattctgtggataaccgtattaccgcctt
tgagtgagctgataccgctcgccgcagccgaacgaccgagcgcagcgagt
cagtgagcgaggaagcggaagagcgcccaatacgcaaaccgcctctcccc
gcgcgttggccgattcattaatgcagctggcacgacaggtttcccgactg
gaaagcgggcagtgagcgcaacgcaattaatgtgagttagctcactcatt
aggcaccccaggctttacactttatgcttccggctcgtatgttgtgtgga
attgtgagcggataacaatttcacacaggaaacagctatgaccatgatta
cgccaagcttggtaccgagctcggatccactagtaacggccgccagtgtg
ctggaattcgccctt
tagaactagtggatccccgggctgcaggaattctccattttcttctgct
atcaaaataacagactcgtgattttccaaacgagctttcaaaaaagcctc
tgccccttgcaaatcggatgcctgtctataaaattcccgatattggttaa
acagcggcgcaatggcggccgcatctgatgtctttgcttggcgaatgttc
atcttatttcttcctccctctcaataattttttcattctatccttttct
gtaaagtttattttcagaatacttttatcatcatgctttgaaaaaatat
cacgataatatccattgttctcacggaagcacacgcaggtcatttgaacg
aattttttcgacaggaatttgccgggactcaggagcatttaacctaaaaa
agcatgacatttcagcataatgaacatttactcatgtctattttcgttct
tttctgtatgaaaatagttatttcgagtctctacggaaatagcgagagat
gatatacctaaatagagataaaatcatctcaaaaaaatgggtctactaaa
atattattccatctattacaataaattcacagaatagtcttttaagtaag
tctactctgaatttttttaaaaggagagggtaaagagtgagaagcaaaaa
attgtggatctgaaattgatacactaatgcttttatatagggaaaaggtg
gtgaactactatggccaagcgaattctgtgtttcggtgattccctgacct
ggggctgggtcccgtcgaagacggggcacccaccgagcggttcgccccc
gacgtgcgctggaccggtgtgctggcccagcagctcggagcggacttcga
ggtgatcgaggagggactgagcgcgcgcaccaccaacatcgacgacccca
ccgatccgcggctcaacggcgcgagctacctgccgtcgtgcctcgcgacg
cacctgccgctcgacctggtgatcatcatgctgggcaccaacgacaccaa
ggcctacttccggcgcaccccgctcgacatcgcgctgggcatgtcggtgc
tcgtcacgcaggtgctcaccagcgcgggcggcgtcggcaccacgtacccg
gctcccaaggtgctggtggtctcgccgccaccgctggcgcccatgccgca
ccctggttccagttgatcttcgagggcggcgagcagaagaccactgagc
tcgcccgcgtgtacagcgcgctcgcgtcgttcatgaaggtgccgttcttc
gacgcggttcggtgatcagcaccgacggcgtcgacggaatccacttcac
cgaggccaacaatcgcgatctcggggtggccctcgcggaacaggtgcgga
gcctgctgtaacggaatgcctctcacaaggatccaagccgaattctgcag
atatccatcacactggcggccgctcgagcatgcatctagagtcgatttt
acaagaattagctttatataatttctgttttttctaaagttttatcagcta
caaaagacagaaatgtattgcaatcttcaactaaatccatttgattctct
ccaatatgacgtttaataaatttctgaaatacttgatttctttgtttttt
ctcagtatacttttccatgttataacacataaaaacaacttagttttcac
aaactatgacaataaaaaaagttgctttttccccttttctatgtatgtttt
ttactagtcatttaaaacgatacattaataggtacgaaaaagcaactttt
tttgcgcttaaaaccagtcataccaataacttaagggtaactagcctcgc
cggcaatagttaccttattatcaagataagaaagaaaaggattttctcgc
tacgctcaaatcctttaaaaaaacacaaaagaccacatttttttaatgtgg
tctttattcttcaactaaagcacccattagttcaacaaacgaaaattgga
taaagtgggatatttttaaaatatatatttatgttacagtaatattgact
tttaaaaaaggattgattctaatgaagaaagcagacaagtaagcctccta
aattcactttagataaaaatttaggaggcatatcaaatgaactttaataa
aattgatttagacaattggaagagaaagagatatttaatcattatttgaa
ccaacaaacgacttttagtataaccacagaaattgatattagtgtttat
accgaaacataaaacaagaaggatataaattttaccctgcatttattttc
ttagtgacaagggtgataaactcaaatacagcttttagaactggttacaa
tagcgacggagagttaggttattgggataagttagagccacttatacaa
tttttgatggtgtatctaaaacattctctggtatttggactcctgtaaag
aatgacttcaaagagttttatgatttataccttctgatgtagagaaata
taatggttcggggaaattgtttcccaaaacacctatacctgaaaatgctt
tttctcttttctattattccatggacttcatttactgggtttaacttaaat
atcaataataatagtaattaccttctacccattattacagcaggaaaatt
cattaataaaggtaattcaatatatttaccgctatctttacaggtacatc
attctgtttgtgatggttatcatgcaggattgtttatgaactctattcag
gaattgtcagataggcctaatgactggcttttataatatgagataatgcc
gactgtacttttttacagtcggttttctaatgtcactaacctgccccgtta
gttgaagaaggttttttatattacagctccagatccatatccttcttttc
tgaaccgacttctccttttcgcttcttttattccaattgctttattgacg
ttgagcctcggaacccttaacaatcccaaaacttgtcgaatggtcggctt
aatagctcacgctatgccgacattcgtctgcaagtttagttaagggttct
tctcaacgcacaataaattttctcggcataaatgcgtggtctaattttta
ttttttaataaccttgatagcaaaaaatgccattccaatacaaaaccacat
acctataatcgacctgcaggaattaattcctccatttttcttctgctatca
aaataacagactcgtgattttccaaacgagctttcaaaaaagcctctgcc
ccttgcaaatcggatgcctgtctataaaattcccgatattggcttaaaca
gcggcgcaatggcggccgcatctgatgtctttgcttggcgaatgttcatc
ttatttcttcctccctctcaataattttttcattctatccttttctgta
```

```
aagtttattttttcagaatactttttatcatcatgctttgaaaaaatatcac
gataatatccattgttctcacggaagcacacgcaggtcatttgaacgaat
ttttcgacaggaatttgccgggactcaggagcatttaacctaaaaagc
atgacatttcagcataatgaacatttactcatgtctattttcgttcttt
ctgtatgaaaatagttatttcgagtctctacggaaatagcgagagatgat
atacctaaatagagataaaatcatctcaaaaaaatgggtctactaaaata
ttattccatctattacaataaattcacagaatagtcttttaagtaagtct
actctgaattttttttatcaagcttatcgataccgtcgacctcgaggggg
gcccggtacccagcttttgttccctttagtgagggttaattgcgcgcttg
gcgtaatcatggtcatagctgtttcctgtgtgaaattgttatccgctcac
aattccacacaacatacgagccggaagcataaagtgtaaagcctggggtg
cctaatgagtgagctaactcacattaattgcgttgcgctcactgcccgct
ttccagtcgggaaacctgtcgtgccagctgcattaatgaatcggccaacg
cgcggggagaggcggtttgcgtattgggcgctcttccgcttcctcgctca
ctgactcgctgcgctcggtcgttcggctgcggcgagcggtatcagctcac
tcaaaggcggtaatacggttatccacagaatcaggggataacgcaggaaa
gaacatgtgagcaaaaggccagcaaaaggccaggaaccgtaaaaaggccg
cgttgctggcgtttttccataggctccgcccccctgacgagcatcacaaa
aatcgacgctcaagtcagaggtggcgaaacccgacaggactataaagata
ccaggcgtttccccctggaagctccctcgtgcgctctcctgttccgaccct
gccgcttaccggatacctgtccgcctttctcccttcgggaagcgtggcgc
tttctcatagctcacgctgtaggtatctcagttcggtgtaggtcgttcgc
tccaagctgggctgtgtgcacgaaccccccgttcagcccgaccgctgcgc
cttatccggtaactatcgtcttgagtccaacccggtaagacacgacttat
cgccactggcagcagccactggtaacaggattagcagagcgaggtatgta
ggcggtgctacagagttcttgaagtggtggcctaactacggctacactag
aaggacagtatttggtatctgcgctctgctgaagccagttaccttcggaa
aaagagttggtagctcttgatccggcaaacaaaccaccgctggtagcggt
ggtttttttgtttgcaagcagcagattacgcgcagaaaaaaaggatctca
agaagatcctttgatcttttctacggggtctgacgctcagtggaacgaaa
actcacgttaagggattttggtcatgagattatcaaaaaggatcttcacc
tagatccttttaaattaaaaatgaagttttaaatcaatctaaagtatata
tgagtaaacttggtctgacagttaccaatgcttaatcagtgaggcaccta
tctcagcgatctgtctatttcgttcatccatagttgcctgactccccgtc
gtgtagataactacgatacgggagggcttaccatctggccccagtgctgc
aatgataccgcgagacccacgctcaccggctccagatttatcagcaataa
accagccagccggaagggccgagcgcagaagtggtcctgcaactttatcc
gcctccatccagtctattaattgttgccgggaagctagagtaagtagttc
gccagttaatagtttgcgcaacgttgttgccattgctacaggcatcgtgg
tgtcacgctcgtcgtttggtatggcttcattcagctccggttcccaacga
tcaaggcgagttacatgatcccccatgttgtgcaaaaaagcggttagctc
cttcggtcctccgatcgttgtcagaagtaagttggccgcagtgttatcac
tcatggttatggcagcactgcataattctcttactgtcatgccatccgta
agatgcttttctgtgactggtgagtactcaaccaagtcattctgagaata
gtgtatgcggcgaccgagttgctcttgcccggcgtcaatacgggataata
ccgcgccacatagcagaactttaaaagtgctcatcattggaaaacgttct
tcggggcgaaaactctcaaggatcttaccgctgttgagatccagttcgat
gtaacccactcgtgcacccaactgatcttcagcatcttttactttcacca
gcgtttctgggtgagcaaaaacaggaaggcaaaatgccgcaaaaaaggga
ataagggcgacacggaaatgttgaatactcatactcttcctttttcaata
ttattgaagcatttatcagggttattgtctcatgagcggatacatatttg
aatgtatttagaaaaataaacaaataggggttccgcgcacatttccccga
aaagtgccacctaaattgtaagcgttaatattttgttaaaattcgcgtta
aattttgttaaatcagctcattttttaaccaataggccgaaatcggcaa
aatcccttataaatcaaaagaatagaccgagatagggttgagtgttgttc
cagtttggaacaagagtccactattaaagaacgtggactccaacgtcaaa
gggcgaaaaaccgtctatcagggcgatggcccactacgtgaaccatcacc
ctaatcaagttttttggggtcgaggtgccgtaaagcactaaatcggaacc
ctaaagggagcccccgatttagagcttgacggggaaagccggcgaacgtg
gcgagaaaggaagggaagaaagcgaaaggagcgggcgctagggcgctggc
aagtgtagcggtcacgctgcgcgtaaccaccacaccgcgcgcttaatg
cgccgctacagggcgcgtcccattcgccattcaggctgcgcaactgttgg
gaagggcgatcggtgcgggcctcttcgctattacgccagctggcgaaagg
gggatgtgctgcaaggcgattaagttgggtaacgccagggttttcccagt
cacgacgttgtaaaacgacggccagtgagcgcgcgtaatacgactcacta
tagggcgaattggagctccaccgcggtggcggccgctc
```

All constructs were confirmed by sequence analysis. PCR reactions were done using Hercules polymerase (Roche) as per the manufacturer's directions.

pCP649 was transformed into *B. subtilis* comK pnbA and integrants selected on L agar containing chloramphenicol (5 µg/ml). The activity of the expressed perhydrolase was determined by the pNB activity assay as described herein. The results indicated that the perhydrolase was expressed and active

Example 7

Expression of the Perhydrolase in *Streptomyces*

In this Example, experiments conducted to assess the expression of the perhydrolase in *Streptomyces* are described. To test expression of the perhydrolase in *Streptomyces*, a replicating plasmid was constructed with the phd gene being expressed from either the glucose isomerase (GIT) or the A4 promoter. However, it is not intended that the present invention be limited to these specific promoters, as any suitable promoter will find use with the present invention. Also, although the strain used for perhydrolase expression in this Example was *Streptomyces lividans* TK-23, it is contemplated that any *Streptomyces* will find use in the present invention.

The *Streptomyces* strains were transformed and manipulated using methods known in the art (See e.g., Kieser et al., *Practical Streptomyces Genetics*, John Innes [2000]).

Construction of pSECGT-MSAT and pSECA4-MSAT

Figure 18:
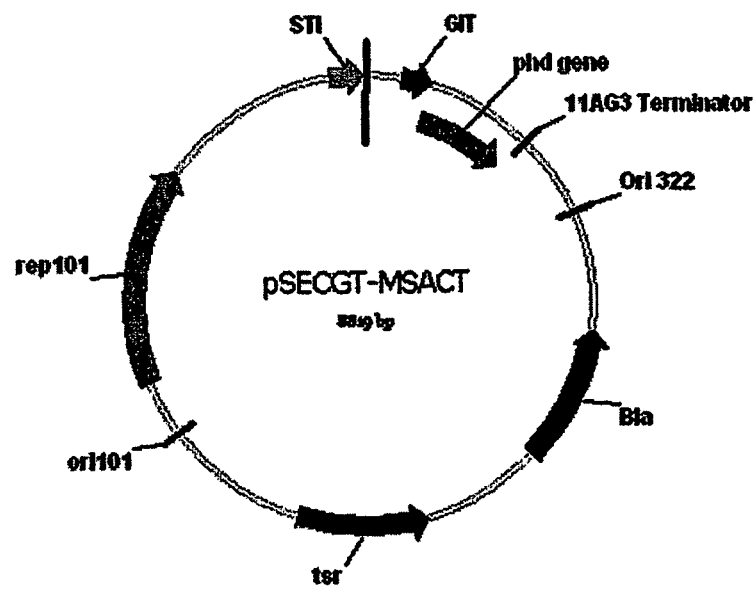
FIG. 18 provides a map of plasmid pSECGT-MSAT.

Using standard methods known in the art, the phd coding sequence (See, Example 4) was cloned into pSECGT to place the gene under control of the GI promoter. Similarly, the gene was cloned in the same plasmid with the A4 promoter using methods known in the art. Transformants were first selected in *E. coli*, verified by sequence analysis, and then transformed into *S. lividans* TK-23 using methods known in the art (See e.g., Kieser et al., [2000], supra). The correct clones expressed from the GI promoter and the A4 promoter were designated "pSECGT-MSAT" and "pSECA4-phd." The sequence of pSECGT-MSAT is provided below, while FIG. 18 provides a map of the plasmid.

```
                                        (SEQ ID NO: 145)
ctagagtcgaccacgcaggccgccaggtagtcgacgttgatctcgcagcc gagcccggccggaccggcggcgctgagcgcgaggccgacggcgggacggc cggcaccggtacgcggtggcgggtcgagttcggtgagcagcccaccggcg atcaggtcgtcgacgagcgcggagacggtggcccgggtgagcccggtgac ggcggcaactcccgcgcgggagagccgatctgtgctgtttgccacggtat gcagcaccagcgcgagattatgggctcgcacgctcgactgtcggacgggg gcactggaacgagaagtcaggcgagccgtcacgcccttgacaatgccaca tcctgagcaaataattcaaaccactaaacaaatcaaccgcgtttcccgga ggtaaccatggccaagcgaattctgtgtttcggtgattccctgacctggg gctgggtccccgtcgaagacggggcacccaccgagcggttcgccccgac gtgcgctggaccggtgtgctggcccagcagctcggagcggacttcgaggt gatcgaggagggactgagcgcgcgcaccaccaacatcgacgaccccaccg atccgcggctcaacggcgcgagctacctgccgtcgtgcctcgcgacgcac ctgccgctcgacctggtgatcatcatgctgggcaccaacgacaccaaggc ctacttccggcgcacccgctcgacatcgcgctgggcatgtcggtgctcg tcacgcaggtgctcaccagcgcgggcggcgtcggcaccacgtacccggca cccaaggtgctggtggtctcgccgccaccgctggcgcccatgccgcaccc ctggttccagttgatcttcgagggcggcgagcagaagaccactgagctcg cccgcgtgtacagcgcgctcgcgtcgttcatgaaggtgccgttcttcgac gcgggttcggtgatcagcaccgacggcgtcgacggaatccacttcaccga ggccaacaatcgcgatctcggggtggccctcgcggaacaggtgcggagcc tgctgtaacgggatccgcgagcggatcggctgaccggagcggggaggagg acgggcggccggcggaaaagtccgccggtccgctgaatcgctccccggc acggacgtggcagtatcagcgccatgtccggcatatcccagccctccgca tgccccgaattcggcgtaatcatggtcatagctgtttcctgtgtgaaatt gttatccgctcacaattccacacaacatacgagccggaagcataaagtgt aaagcctggggtgcctaatgagtgagctaactcacattaattgcgttgcg ctcactgcccgctttccagtcgggaaacctgtcgtgccagctgcattaat
```

```
-continued
gaatcggccaacgcgcggggagaggcggtttgcgtattgggcgctcttcc gcttcctcgctcactgactcgctgcgctcggtcgttcggctgcggcgagc ggtatcagctcactcaaaggcggtaatacggttatccacagaatcagggg ataacgcaggaaagaacatgtgagcaaaaggccagcaaaaggccaggaac cgtaaaaaggccgcgttgctggcgtttttccataggctccgcccccctga cgagcatcacaaaaatcgacgctcaagtcagaggtggcgaaacccgacag gactataaagataccaggcgtttccccctggaagctccctcgtgcgctct cctgttccgaccctgccgcttaccggatacctgtccgcctttctcccttc gggaagcgtggcgctttctcatagctcacgctgtaggtatctcagttcgg tgtaggtcgttcgctccaagctgggctgtgtgcacgaacccccgttcag cccgaccgctgcgccttatccggtaactatcgtcttgagtccaacccgt aagacacgacttatcgccactggcagcagccactggtaacaggattagca gagcgaggtatgtaggcggtgctacagagttcttgaagtggtggcctaac tacggctacactagaaggacagtatttggtatctgcgctctgctgaagcc agttaccttcggaaaaagagttggtagctcttgatccggcaaacaaacca ccgctggtagcggtggtttttttgtttgcaagcagcagattacgcgcaga aaaaaaggatctcaagaagatcctttgatcttttctacggggtctgacgc tcagtggaacgaaaactcacgttaagggattttggtcatgagattatcaa aaaggatcttcacctagatccttttaaattaaaaatgaagttttaaatca atctaaagtatatatgagtaaacttggtctgacagttaccaatgcttaat cagtgaggcacctatctcagcgatctgtctatttcgttcatccatagttg cctgactccccgtcgtgtagataactacgatacgggagggcttaccatct ggccccagtgctgcaatgataccgcgagacccacgctcaccggctccaga tttatcagcaataaaccagccagccggaagggccgagcgcagaagtggtc ctgcaactttatccgcctccatccagtctattaattgttgccgggaagct agagtaagtagttcgccagttaatagtttgcgcaacgttgttgccattgc tacaggcatcgtggtgtcacgctctgtcgtttggtatggcttcattcagc tccggttcccaacgatcaaggcgagttacatgatcccccatgttgtgcaa aaaagcggttagctccttcggtcctccgatcgttgtcagaagtaagttgg ccgcagtgttatcactcatggttatggcagcactgcataattctcttact gtcatgccatccgtaagatgcttttctgtgactggtgagtactcaaccaa gtcattctgagaatagtgtatgcggcgaccgagttgctcttgcccggcgt caatacgggataataccgcgccacatagcagaactttaaaagtgctcatc attggaaaacgttcttcggggcgaaaactctcaaggatcttaccgctgtt gagatccagttcgatgtaacccactcgtgcacccaactgatcttcagcat cttttactttcaccagcgtttctgggtgagcaaaaacaggaaggcaaaat gccgcaaaaaagggaataagggcgacacggaaatgttgaatactcatact cttcctttttcaatattattgaagcatttatcagggttattgtctcatga gcggatacatatttgaatgtatttagaaaaataaacaaataggggttccg cgcacatttccccgaaaagtgccacctgacgtctaagaaaccattattat
```

-continued

```
catgacattaacctataaaaataggcgtatcacgaggcccttcgtctcg
cgcgtttcggtgatgacggtgaaaacctcttgacacatgcagctcccgga
gacggtcacagcttgtctgtaagcggatgccgggagcagacaagcccgtc
agggcgcgtcagcgggtgttggcgggtgtcggggctggcttaactatgcg
gcatcagagcagattgtactgagagtgcaccatatgcggtgtgaaatacc
gcacagatgcgtaaggagaaaataccgcatcaggcgccattcgccattca
ggctgcgcaactgttgggaagggcgatcggtgcgggcctcttcgctatta
cgccagctggcgaaaggggatgtgctgcaaggcgattaagttgggtaac
gccagggttttcccagtcacgacgttgtaaaacgacggccagtaagcttg
catgcctgcaggagtggggaggcacgatggccgctttggtcgacctcaac
gagacgatgaagccgtggaacgacaccaccccggcggccctgctggacca
cacccggcactacaccttcgacgtctgatcatcactgacgaatcgaggtc
gaggaaccgagcgtccgaggaacacaggcgcttatcggttggccgcgaga
ttcctgtcgatcctctcgtgcagcgcgattccgagggaaacggaaacgtt
gagagactcggtctggctcatcatggggatggaaaccgaggcggaagacg
cctcctcgaacaggtcggaaggcccaccctttttcgctgccgaacagcaag
gccagccgatccggattgtccccgagttccttcacggaaatgtcgccatc
cgccttgagcgtcatcagctgcataccgctgtcccgaatgaaggcgatgg
cctcctcgcgaccgagagaacgacggaagggagaagacgtaacctcgg
ctggccctttggagacgccggtccgcgatgctggtgatgtcactgtcgac
caggatgatccccgacgctccgagcgcgagcgacgtgcgtactatcgcgc
cgatgttcccgacgatcttcacccccgtcgagaacgacgacgtccccacgc
cggctcgcgatatcgccgaacctggccgggcggggacgcgggcgatgcc
gaatgtcttggccttccgctcccccttgaacaactggttgacgatcgagg
agtcgatgaggcggaccggtatgttctgccgcccgcacagatccagcaac
tcagatggaaaaggactgctgtcgctgccgtagacctcgatgaactccac
cccggccgcgatgctgtgcatgaggggctcgacgtcctcgatcaacgttg
tctttatgttggatcgcgacggcttggtgacatcgatgatccgctgcacc
gcgggatcggacggatttgcgatggtgtccaactcagtcatggtcgtcct
accggctgctgtgttcagtgacgcgattcctggggtgtgacaccctacgc
gacgatggcggatggctgccctgaccggcaatcaccaacgcaaggggaag
tcgtcgctctctggcaaagctccccgctcttcccgtccgggacccgcgc
ggtcgatccccgcatatgaagtattcgccttgatcagtcccggtggacgc
gccagcggcccgccggagcgacggactccccgacctcgatcgtgtcgccc
tgagcgtccacgtagacgttgcgtgagagcaggactgggccgccgccgac
cgcaccgccctcaccaccgaccgcgaccgcgccatggccgccgccgacgg
cctggtcgccgccgccgccgccggttcggcgcctgacccgaccaacccc
cgcggggcgccggcacttcgtgctggcgccccgccccaccaccaggag
accgaccatgaccgacttcgacggacgcctgaccgaggggaccgtgaacc
tggtccaggaccccaacggcggtggctggtccgcccactgcgctgagccc
ggttgcgactgggccgacttcgccggaccgctcggcttccagggcctcgt
```

-continued

```
ggccatcgctcgccgacacacgcactgaccgcacgtcaaagccccgccgg
atacccggcggggctctcttcggccctccaagtcacaccagccccaaggg
gcgtcgggagtggcggagggaacctctggcccgattggtgccaggattcc
caccagaccaaagagcaacggccggacttcgcacctccgaccgtccgc
tcccagactcgcgcccttagccgggcgagacaggaacgttgctcgtgcc
cagagtacggagcgatgccgaggcattgccagatcggcccgccgggcccc
gctgccactgcgggaccgcaattgcccacacaccgggcaaacggccgcgt
atctactgctcagaccgctgccggatggcagcgaagcgggcgatcgcgcg
tgtgacgcgagatgccgcccgaggcaaaagcgaacaccttgggaaagaaa
caacagagtttcccgcaccctccgacctgcggtttctccggacggggtg
gatggggagagcccgagaggcgacagcctctgggaagtaggaagcacgtc
gcggaccgaggctgcccgactgcggaaagccgcccggtacagccgccgcc
ggacgctgtggcggatcagcggggacgccgcgtgcaagggctgcggccgc
gccctgatggaccctgcctccggcgtgatcgtcgcccagacggcggccgg
aacgtccgtggtcctgggcctgatgcggtgcgggcggatctggctctgcc
cggtctgcgccgccacgatccggcacaagcgggccgaggagatcaccgcc
gccgtggtcgagtggatcaagcgcggggggaccgcctacctggtcacctt
cacggcccgccatgggcacacggaccggctcgcggacctcatggacgccc
tccagggcacccggaagacgccggacagccccggcggccgggcgcctac
cagcgactgatcacgggcggcacgtgggccgacgccgggccaaggacgg
gcaccgggccgccgaccgcgagggcatccgagaccggatcgggtacgtcg
gcatgatccgcgcgaccgaagtcaccgtggggcagatcaacggctggcac
ccgcacatccacgcgatcgtcctggtcggcgccggaccgagggggagcg
gtccgcgaagcagatcgtcgccaccttcgagccgaccggcgccgcgctcg
acgagtggcaggggcactggcggtccgtgtggaccgccgccctgcgcaag
gtcaacccgccttcacgcccgacgaccggcacggcgtcgacttcaagcg
gctggagaccgagcgcgacgccaacgacctcgccgagtacatcgccaaga
cccaggacgggaaggcgcccgccctcgaactcgcccgcgccgacctcaag
acggcgaccggcgggaacgtcgccccgttcgaactcctcggacggatcgg
ggacctgaccggcggcatgaccgaggacgacgccgccggggtcggctcgc
tggagtggaacctctcgcgctggcacgagtacgagcgggcaacccgggga
cgccgggccatcgaatggacccgctacctgcggcagatgctcgggctcga
cggcggcgacaccgaggccgacgacctcgatctgctcctggcggccgacg
ccgacgcgggagctgcgggccggggtcgccgtgaccgaggacggatgg
cacgcggtcacccgccgcgccctcgacctcgaggcgacccgggccgcga
aggcaaggacggcaacgaggattcggcggccgtgggcgaacgggtgcggg
aggtcctggcgctggccgacgcggccgacacagtggtggtgctcacggcg
ggggaggtggccgaggcgtacgccgacatgctcgccgccctcgcccagcg
ccgcgaggaagcaactgcacgccgacggcgagagcaggacgacgaccagg
acgacgacgccgacgaccgccaggagcgggccgcccggcacatcgcccgg
```

```
ctcgcaagtgggcccacttcgcactaactcgctcccccccgccgtacgtc
atcccggtgacgtacggcggggtcggtgacgtacgcggcgacggcggcc
ggggtcgaagccgcgggagtaatcctgggattactcgcccggggtcggcc
ccgccggcacttcgtgcaggcggtacctcgcgcccgactcgcctcgctac
gagacgtgccgcgtacggtcgtcggccatgagcaccaccaccccaggga
cgccgacggcgcgaagctctgcgcctggtgcggctcggagatcaagcaat
ccggcgtcggccggagccgggactactgccgccgctcctgccgccagcgg
gcgtacgaggcccggcgccagcgcgaggcgatcgtgtccgccgtggcgtc
ggcagtcgctcgccgagatacgtcacgtgacgaaatgcagcagccttcca
ttccgtcacgtgacgaaactcgggccgcaggtcagagcacggttccgccc
gctccggccctgccggaccccggctgcagctcgcccggccgccggtccc
cctgccgtccggcccgtcccagaggcagcgtcggcggctcctgcctcccc
cgcccggcgccgaccgggacccgcaaaccccttgatccgctgtcgggggt
gatcactacggtgggtgccgaagtgatcacggggaggactgatgcaccac
caggaccgggaccaggaccaggcgttagcggcagtgctggccgcactgct
cctggtcggcgggacgctgatcgtgcgggagctcctgggcctgtggcccg
ccgtggcggtcggcatggcgcccgccctcgccctctacggagcccgccc
gcggcccgccggatagccgtcgcggtcgaggtccgccggttccgccggca
tcttgcccaccacgatcgggcagccggatgaccggccacgacggagccgc
acggctgaccagctcgacggccgccacctcatcgcggcagcaggtgctcc
ccagcaacccacgacggggctcaggtcgcctcacgcggctcagcaccgc
gacggcgggggtacggcgctccgggaggctgacaggcgctcagacggccg
cgtagggccgcgagtccccacccctccccgctgccctgtcggcgagcac
aacggcgatgcccgcagtcggcggagcaggcgccacgtaaaccgcccacc
gatgccgccccgtcgtgtgcgcgggccggtcggcggccggggccggagcg
gggcgaagacaggagcgtcggccgggccgtgggccgggccgcgcggcccg
ctcgcgggccgccttgatgacgtagggaaagttgtaccgcaaaaaacgca
gcctgaactagttgcgatcct
```

Figure 19:
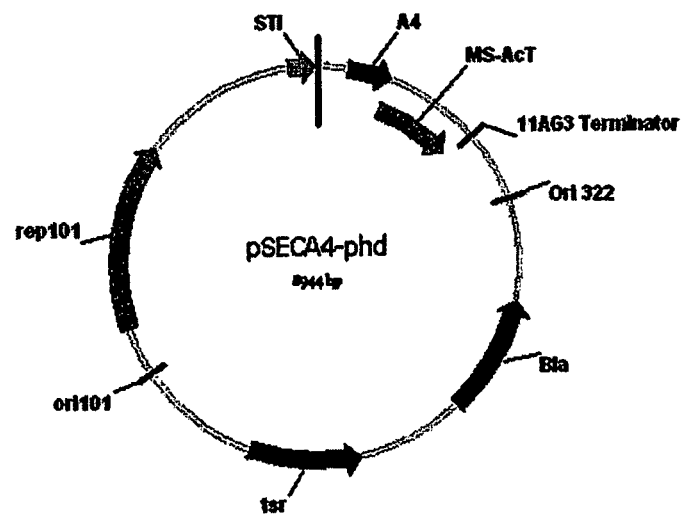
FIG. 19 provides a map of plasmid pSEGT-phdA4.

FIG. 19 provides a map of pSEGT-phdA4, while the sequence is provided below:

(SEQ ID NO: 146)
```
ctagagatcgaacttcatgttcgagttcttgttcacgtagaagccggaga
tgtgagaggtgatctggaactgctcaccctcgttggtggtgacctggagg
taaagcaagtgacccttctggcggaggtggtaaggaacggggttccacgg
ggagagagagatggccttgacggtcttgggaaggggagcttcngcgcggg
ggaggatggtcttgagagagggggagctagtaatgtcgtacttggacagg
gagtgctccttctccgacgcatcagccacctcagcggagatggcatcgtg
cagagacagaccccggaggtaaccatggccaagcgaattctgtgtttcg
gtgattccctgacctggggctgggtccccgtcgaagacggggcaccacc
gagcggttcgccccgacgtgcgctggaccggtgtgctggcccagcagct
cggagcggacttcgaggtgatcgaggaggggactgagcgcgcgcaccacca
acatcgacgaccccaccgatccgcgggctcaacggcgcgagctacctgccg
tcgtgcctcgcgacgcacctgccgctcgacctggtgatcatcatgctggg
caccaacgacaccaaggcctacttccggcgcacccccgctcgacatcgcgc
tgggcatgtcggtgctcgtcacgcaggtgctcaccagcgcgggcggcgtc
ggcaccacgtacccggcacccaaggtgctggtggtctcgccgccaccgct
ggcgcccatgccgcacccctggttccagttgatcttcgagggcggcgagc
agaagaccactgagctcgcccgcgtgtacagcgcgctcgcgtcgttcatg
aaggtgccgttcttcgacgcgggttcggtgatcagcaccgacgcgtcga
cggaatccacttcaccgaggccaacaatcgcgatctcggggtggccctcg
cggaacaggtgcggagcctgctgtaacaatggggatccgcgagcggatcg
gctgaccggagcggggaggaggacgggcggccggcggaaaagtccgcggt
ccgctgaatcgctccccgggcacggacgtggcagtatcagcgccatgtcc
ggcatatcccagccctccgcatgccccgaattcggcgtaatcatggtcat
agctgttcctgtgtgaaattgttatccgctcacaattccacacaacata
cgagccggaagcataaagtgtaaagcctggggtgcctaatgagtgagcta
actcacattaattgcgttgcgctcactgcccgctttccagtcgggaaacc
tgtcgtgccagctgcattaatgaatcggccaacgcgcggggagaggcggt
ttgcgtattgggcgctcttccgcttcctcgctcactgactcgctgcgctc
ggtcgttcggctgcggcgagcggtatcagctcactcaaaggcggtaatac
ggttatccacagaatcaggggataacgcaggaaagaacatgtgagcaaaa
ggccagcaaaaggccaggaaccgtaaaaaggccgcgttgctggcgttttt
ccataggctccgcccccctgacgagcatcacaaaaatcgacgctcaagtc
agaggtggcgaaacccgacaggactataaagataccaggcgtttccccct
ggaagctccctcgtgcgctctcctgttccgaccctgccgcttaccggata
cctgtccgcctttctcccttcgggaagcgtggcgctttctcatagctca
cgctgtaggtatctcagttcggtgtaggtcgttcgctccaagctgggctg
tgtgcacgaacccccgttcagcccgaccgctgcgccttatccggtaact
atcgtcttgagtccaacccggtaagacacgacttatcgccactggcagca
gccactggtaacaggattagcagagcgaggtatgtaggcggtgctacaga
gttcttgaagtggtggcctaactacggctacactagaaggacagtatttg
gtatctgcgctctgctgaagccagttaccttcggaaaaagagttggtagc
tcttgatccggcaaacaaaccaccgctggtagcggtggttttttgtttg
caagcagcagattacgcgcagaaaaaaggatctcaagaagatcctttga
tcttttctacggggtctgacgctcagtggaacgaaaactcacgttaaggg
attttggtcatgagattatcaaaaggatcttcacctagatccttttaaat
taaaaatgaagttttaaatcaactaaagtatatatgagtaaacttggtct
gacagttaccaatgcttaatcagtgaggcacctatctcagcgatctgtct
atttcgttcatccatagttgcctgactccccgtcgtgtagataactacga
tacgggagggcttaccatctggccccagtgctgcaatgataccgcgagac
ccacgctcaccggctccagatttatcagcaataaaccagccagccggaag
```

-continued ggccgagcgcagaagtggtcctgcaactttatccgcctccatccagtcta
ttaattgttgccgggaagctagagtaagtagttcgccagttaatagtttg
cgcaacgttgttgccattgctacaggcatcgtggtgtcacgctcgtcgtt
tggtatggcttcattcagctccggttcccaacgatcaaggcgagttacat
gatccccatgttgtgcaaaaaagcggttagctccttcggtcctccgatc
gttgtcagaagtaagttggccgcagtgttatcactcatggttatggcagc
actgcataattctcttactgtcatgccatccgtaagatgcttttctgtga
ctggtgagtactcaaccaagtcattctgagaatagtgtatgcggcgaccg
agttgctcttgcccggcgtcaatacgggataataccgcgccacatagcag
aactttaaaagtgctcatcattggaaaacgttcttcggggcgaaaactct
caaggatcttaccgctgttgagatccagttcgatgtaacccactcgtgca
cccaactgatcttcagcatcttttactttcaccagcgtttctgggtgagc
aaaaacaggaaggcaaaatgccgcaaaaaagggaataagggcgacacgga
aatgttgaatactcatactcttcctttttcaatattattgaagcatttat
cagggttattgtctcatgagcggatacatatttgaatgtatttagaaaaa
taaacaaatagggggttccgcgcacatttccccgaaaagtgccacctgacg
tctaagaaaccattattatcatgacattaacctataaaaataggcgtatc
acgaggccctttcgtctcgcgcgtttcggtgatgacggtgaaaacctctt
gacacatgcagctcccggagacggtcacagcttgtctgtaagcggatgcc
gggagcagacaagcccgtcagggcgcgtcagcgggtgttggcgggtgtcg
gggctggcttaactatgcggcatcagagcagattgtactgagagtgcacc
atatgcggtgtgaaataccgcacagatgcgtaaggagaaaataccgcatc
aggcgccattcgccattcaggctgcgcaactgttgggaagggcgatcggt
gcgggcctcttcgctattacgccagctggcgaaagggggatgtgctgcaa
ggcgattaagttgggtaacgccagggttttcccagtcacgacgttgtaaa
acgacggccagtaagcttgcatgcctgcaggagtggggaggcacgatggc
cgctttggtcgacctcaacgagacgatgaagccgtggaacgacaccaccc
cggcggccctgctggaccacacccggcactacaccttcgacgtctgatca
tcactgacgaatcgaggtcgaggaaccgagcgtccgaggaacacaggcgc
ttatcggttggccgcgagattcctgtcgatcctctcgtgcagcgcgattc
cgagggaaacgaaacgttgagagactcggtctggctcatcatgggatg
gaaaccgaggcggaagacgcctcctcgaacaggtcggaaggcccaccctt
ttcgctgccgaacagcaaggccagccgatccggattgtccccgagttcct
tcacggaaatgtcgccatccgccttgagcgtcatcagctgcataccgctg
tcccgaatgaaggcgatggcctcctcgcgaccggagagaacgacgggaag
ggagaagacgtaacctcggctggccctttggagacgccggtccgcgatgc
tggtgatgtcactgtcgaccaggatgatccccgacgctccgagcgcgagc
gacgtgcgtactatcgcgcgatgttcccgacgatcttcaccccgtcgag
aacgacgacgtccccacgccgctcgcgatatcgccgaacctggccgggc
gagggacgcgggcgatgccgaatgtcttggccttccgctcccccttgaac
aactggttgacgatcgaggagtcgatgaggcggaccggtatgttctgccg -continued cccgcacagatccagcaactcagatggaaaaggactgctgtcgctgccgt
agacctcgatgaactccacccggccgcgatgctgtgcatgaggggctcg
acgtcctcgatcaacgttgtctttatgttggatcgcgacggcttggtgac
atcgatgatccgctgcaccgcgggatcggacggatttgcgatggtgtcca
actcagtcatggtcgtcctaccggctgctgtgttcagtgacgcgattcct
ggggtgtgacaccctacgcgacgatggcggatggctgccctgaccggcaa
tcaccaacgcaaggggaagtcgtcgctctctggcaaagctcccgctctt
ccccgtccgggacccgcgcggtcgatccccgcatatgaagtattcgcctt
gatcagtcccggtggacgcgccagcggcccgccggagcgacggactcccc
gacctcgatcgtgtcgccctgagcgtccacgtagacgttgcgtgagagca
ggactgggccgccgccgaccgcaccgccctcaccaccgaccgcgaccgcg
ccatggccgccgccgacggcctggtcgccgccgccgcccgccggttcggc
gcctgacccgaccaaccccgcggggcgccggcacttcgtgctggcgccc
cgccccacccaccaggagaccgaccatgaccgacttcgacggacgcctg
accgaggggaccgtgaacctggtccaggaccccaacggcggtggctggtc
cgcccactgcgctgagcccggttgcgactgggccgacttcgccggaccgc
tcggcttccagggcctcgtggccatcgctcgccgacacacgcactgaccg
cacgtcaaagccccgccggataccggcggggctctcttcggccctccaa
gtcacaccagccccaagggcgtcgggagtggcggagggaacctctggcc
cgattggtgccaggattcccaccagaccaaagagcaacgggccggacttc
gcacctccgacccgtccgctcccagactcgcgccccttagccgggcgaga
caggaacgttgctcgtgcccagagtacggagcgatgccgaggcattgcca
gatcggcccgccgggccccgctgccactgcgggaccgcaattgcccacac
accgggcaaacggccgcgtatctactgctcagaccgctgccggatggcag
cgaagcgggcgatcgcgcgtgtgacgcgagatgccgcccgaggcaaaagc
gaacaccttgggaaagaaacaacagagtttcccgcacccctccgacctgc
ggtttctccggacggggtggatggggagagcccgagaggcgacagcctct
gggaagtaggaagcacgtcgcggaccgaggctgcccgactgcggaaagcc
gcccggtacagccgccgccggacgctgtggcggatcagcggggacgccgc
gtgcaagggctgcggccgcgccctgatggaccctgcctccggcgtgatcg
tcgcccagacggcggccggaacgtccgtggtcctgggcctgatgcggtgc
gggcggatctggctctgcccggtctgcgccgccacgatccggcacaagcg
ggccgaggagatcaccgccgccgtggtcgagtggatcaagcgcgggggga
ccgcctacctggtcaccttcacggcccgccatgggcacacggaccggctc
gcggacctcatggacgcctccagggcacccggaagacgccggacagccc
ccggcggccgggcgcctaccagcgactgatcacgggcggcacgtgggccg
gacgccgggccaaggacgggcaccgggccgcgaccgcgagggcatccga
gaccggatcgggtacgtcggcatgatccgcgcgaccgaagtcaccgtggg
gcagatcaacggctggcacccgcacatccacgcgatcgtcctggtcggcg
gccggaccgaggggagcggtccgcgaagcagatcgtcgccaccttcgag -continued
ccgaccggcgccgcgctcgacgagtggcaggggcactggcggtccgtgtg gaccgccgccctgcgcaaggtcaacccgccttcacgcccgacgaccggc acggcgtcgacttcaagcggctggagaccgagcgcgacgccaacgacctc gccgagtacatcgccaagacccaggacgggaaggcgcccgccctcgaact cgcccgcgccgacctcaagacggcgaccggcgggaacgtcgccccgttcg aactcctcggacggatcggggacctgaccggcggcatgaccgaggacgac gccgccggggtcggctcgctggagtggaacctctcgcgctggcacgagta cgagcgggcaacccggggacgccgggccatcgaatggacccgctacctgc ggcagatgctcgggctcgacggcggcgacaccgaggccgacgacctcgat ctgctcctggcggccgacgccgacggcggggagctgcgggccggggtcgc cgtgaccgaggacggatggcacgcggtcacccgccgcgccctcgacctcg aggcgacccgggccgccgaaggcaaggacggcaacgaggattcggcggcc gtgggcgaacgggtgcgggaggtcctggcgctggccgacgcggccgacac agtggtggtgctcacggcggggaggtggccgaggcgtacgccgacatgc tcgccgccctcgcccagcgccgcgaggaagcaactgcacgccgacggcga gagcaggacgacgaccaggacgacgacgccgacgaccgccaggagcgggc cgcccggcacatcgcccggctcgcaagtgggcccacttcgcactaactcg ctccccccgccgtacgtcatcccggtgacgtacggcgggggtcggtgac gtacgcggcgacggcggccggggtcgaagccgcgggagtaatcctggat tactcgcccggggtcggccccgccggcacttcgtgcaggcggtacctcgc gcccgactcgcctcgctacgagacgtgccgcgtacggtcgtcggccatga gcaccaccccccagggacgccgacggcgcgaagctctgcgcctggtgc ggctcggagatcaagcaatccggcgtcggccggagccgggactactgccg ccgctcctgccgccagcgggcgtacgaggcccggccgccagcgcgaggcga tcgtgtccgccgtggcgtcggcagtcgctcgccgagatacgtcacgtgac gaaatgcagcagccttccattccgtcacgtgacgaaactcgggccgcagg tcagagcacggttccgcccgctccggccctgccggacccccggctgcagc tcgcccggccgccggtcccctgccgtccggcccgtcccagaggcagcgt cggcggctcctgcctcccccgcccggcgccgaccgggacccgcaaacccc ttgatccgctgtcggggtgatcactacggtgggtgccgaagtgatcacg gggaggactgatgcaccaccaggacccgggaccaggaccaggcgttagcgg cagtgctggccgcactgctcctggtcggcgggacgctgatcgtgcgggag ctcctgggcctgtggcccgccgtggcggtcggcatggcgcccgccctcgc cctctacggaggcccgcccgcggccgccggatagccgtcgcggtcgagg tccgccggttccgccggcatcttgcccaccacgatcgggcagccggatga ccggccacgacggagccgcacggctgaccagctcgacggccgccacctca tcgcggcagcaggtgctccccagcaacccacgacggggctcagggtcgcc tcacgcggctcagcaccgcgacggcgggggtacggcgctccggggaggct gacaggcgctcagacggccgcgtagggccgcgcgactcccccaccccctcccc gctgccctgtcggcgagcacaacggcgatgcccgcagtcggcggagcagg cgccacgtaaaccgcccaccgatgccgcccccgtcgtgtgcgcgggccgg -continued
tcggcggccgggccggagcggggcgaagacaggagcgtcggccgggccgt gggccgggccgcgcggcccgctcgcgggccgccttgatgacgtagggaaa gttgtaccgcaaaaaacgcagcctgaactagttgcgatcct Two colonies of *S. lividans* TK-23 pSECA4-phd were inoculated in 10 ml of TS medium+50 ppm thiostrepton and incubated at 37° C. with shaking at 200 rpm for 2 days. Three mls of broth were used to inoculate 50 ml of *Streptomyces* Production medium 1 and the culture was incubated for 4 days at 37° C. with shaking at 200 rpm.

A sample was taken to assay perhydrolase activity measurement as follows: 10 µls of 20 mg/ml lysozyre were added to 200 µl of sample. After 1 hour of incubation at 37° C., samples were centrifuged and activity was measured using the pNB activity assay described herein. SDS-PAGE and Western blots were also prepared using both clones (pSECA4-phd and pSECGT-MSAT), as known in the art. Briefly, after SDS-PAGE, the proteins were transferred to PVDF membrane and Western blot analysis was conducted. The perhydrolase was detected using an anti-perhydrolase polyclonal anti-sera (1:500 dilution) prepared against purified perhydrolase protein by Covance. The blot was developed using the ECL kit from Amersham. The results indicated that *Streptomyces lividans* strains were capable of expressing active perhydrolase.

Example 8

Site-Scanning Mutagenesis of the *M. smegmatis* Perhydrolase Gene

In this Example, experiments involving site-scanning mutagenesis of the *M. smegmatis* perhydrolase gene are described. In these experiments, the QuikChange® site-directed mutagenesis (QC; Stratagene) kit or the QuikChange® Multi Site-Directed mutagenesis (QCMS; Stratagene) kit was used to create site-saturation libraries at each codon in the entire *M. smegmatis* perhydrolase gene contained in the pMSAT-NcoI plasmid. Each perhydrolase codon was mutagenized by replacement with the NNG/C (NNS; 32 combinations) degenerate codon, which encodes for all 20 amino acids and one stop codon. In the case of the QC method, complementary overlapping primers were designed for each codon of interest with 18 bases flanking the NNS codon (See, Tables 8-1 and 8-2). A comparison of cartridge purified versus unpurified primers (desalted only) revealed a better representation of amino acids in the libraries made with purified primers (15-19 amino acids versus 11-16 with unpurified primers). Thus, a majority of the libraries were created with the QC method and purified primers. A small number of the libraries were made using the QCMS method and a single 5' phosphorylated forward primer containing 18 bases flanking both sides of the NNS codon (See, Table 8-1), however this method resulted in a greater wild type background and fewer amino acid substitutions per site compared to the QC methods. Libraries "nsa301" and "nsa302" were made using the QCMS method, but a trinucleotide mix made up of a single codon for each of the 20 amino acids (i.e., rather than 32 possibilities encoded by NNS for the 20 amino acids) was incorporated within the primers at the sites of interest.

TABLE 8-1

Site-Saturation Forward Primers

| Residue | Primer | Primer Sequence |
|---|---|---|
| M1 | nsa202F | taacaggaggaattaaccnnsgccaagcgaattctgtgt (SEQ ID NO: 147) |
| A2 | nsa203F | caggaggaattaaccatgnnsaagcgaattctgtgtttc (SEQ ID NO: 148) |
| K3 | nsa204F | gaggaattaaccatggccnnscgaattctgtgtttcggt (SEQ ID NO: 149) |
| R4 | nsa205F | gaattaaccatggccaagnnsattctgtgtttcggtgat (SEQ ID NO: 150) |
| I5 | nsa206F | ttaaccatggccaagcgannsctgtgtttcggtgattcc (SEQ ID NO: 151) |
| L6 | nsa207F | accatggccaagcgaattnnstgtttcggtgattccctg (SEQ ID NO: 152) |
| C7 | nsa208F | atggccaagcgaattctgnnsttcggtgattccctgacc (SEQ ID NO: 153) |
| F8 | nsa209F | gccaagcgaattctgtgtnnsggtgattccctgacctgg (SEQ ID NO: 154) |
| G9 | nsa210F | aagcgaattctgtgtttcnnsgattccctgacctggggc (SEQ ID NO: 155) |
| D10 | nsa168F | cgaattctgtgtttcggtnnstccctgacctggggctgg (SEQ ID NO: 156) |
| S11 | nsa212F | attctgtgtttcggtgatnnsctgacctggggctgggtc (SEQ ID NO: 157) |
| L12 | nsa169F | ctgtgtttcggtgattccnnsacctggggctgggtcccc (SEQ ID NO: 158) |
| T13 | nsa170F | tgtttcggtgattccctgnnstggggctgggtccccgtc (SEQ ID NO: 159) |
| W14 | nsa171F | ttcggtgattccctgaccnnsggctgggtccccgtcgaa (SEQ ID NO: 160) |
| G15 | nsa216F | ggtgattccctgacctggnnstgggtccccgtcgaagac (SEQ ID NO: 161) |
| W16 | nsa172F | gattccctgacctggggcnnsgtccccgtcgaagacggg (SEQ ID NO: 162) |
| V17 | nsa218F | tccctgacctggggctggnnscccgtcgaagacggggca (SEQ ID NO: 163) |
| P18 | nsa219F | ctgacctggggctgggtcnnsgtcgaagacggggcaccc (SEQ ID NO: 164) |
| V19 | nsa220F | acctggggctgggtccccnnsgaagacggggcacccacc (SEQ ID NO: 165) |
| E20 | nsa221F | tggggctgggtccccgtcnnsgacggggcacccaccgag (SEQ ID NO: 166) |
| D21 | nsa222F | ggctgggtccccgtcgaannsggggcacccaccgagcgg (SEQ ID NO: 167) |
| G22 | nsa223F | tgggtccccgtcgaagacnnsgcacccaccgagcggttc (SEQ ID NO: 168) |
| A23 | nsa224F | gtccccgtcgaagacgggnnscccaccgagcggttcgcc (SEQ ID NO: 169) |
| P24 | nsa191F | cccgtcgaagacggggcannsaccgagcggttcgcccc (SEQ ID NO: 170) |
| T25 | nsa192F | gtcgaagacggggcacccnnsgagcggttcgcccccgac (SEQ ID NO: 171) |
| E26 | nsa227F | gaagacggggcacccaccnnscggttcgcccccgacgtg (SEQ ID NO: 172) |
| R27 | nsa228F | gacggggcacccaccgagnnsttcgcccccgacgtgcgc (SEQ ID NO: 173) |
| F28 | nsa229F | ggggcacccaccgagcggnnsgcccccgacgtgcgctgg (SEQ ID NO: 174) |
| A29 | nsa230F | gcacccaccgagcggttcnnsccccgacgtgcgctggacc (SEQ ID NO: 175) |
| P30 | nsa231F | cccaccgagcggttcgccnnsgacgtgcgctggaccggt (SEQ ID NO: 176) |
| D31 | nsa232F | accgagcggttcgcccccnnsgtgcgctggaccggtgtg (SEQ ID NO: 177) |
| V32 | nsa233F | gagcggttcgcccccgacnnsgctggaccggtgtgctg (SEQ ID NO: 178) |
| R33 | nsa234F | cggttcgcccccgacgtgnnstggaccggtgtgctggcc (SEQ ID NO: 179) |
| W34 | nsa235F | ttcgcccccgacgtgcgcnnsaccggtgtgctggcccag (SEQ ID NO: 180) |
| T35 | nsa236F | gcccccgacgtgcgctggnnsggtgtgctggcccagcag (SEQ ID NO: 181) |
| G36 | nsa237F | cccgacgtgcgctggaccnnsgtgctggcccagcagctc (SEQ ID NO: 182) |
| V37 | nsa238F | gacgtgcgctggaccggtnnsctggcccagcagctcgga (SEQ ID NO: 183) |
| L38 | nsa239F | gtgcgctggaccggtgtgnnsgcccagcagctcggagcg (SEQ ID NO: 184) |

TABLE 8-1-continued

Site-Saturation Forward Primers

| Residue | Primer | Primer Sequence |
|---|---|---|
| A39 | nsa240F | cgctggaccggtgtgctgnnscagcagctcggagcggac (SEQ ID NO: 185) |
| Q40 | nsa241F | tggaccggtgtgctggccnnscagctcggagcggacttc (SEQ ID NO: 186) |
| Q41 | nsa242F | accggtgtgctggcccagnnsctcggagcggacttcgag (SEQ ID NO: 187) |
| L42 | nsa243F | ggtgtgctggcccagcagnnsggagcggacttcgaggtg (SEQ ID NO: 188) |
| G43 | nsa244F | gtgctggcccagcagctcnnsgcggacttcgaggtgatc (SEQ ID NO: 189) |
| A44 | nsa245F | ctggcccagcagctcggannsgacttcgaggtgatcgag (SEQ ID NO: 190) |
| D45 | nsa246F | gcccagcagctcggagcgnnsttcgaggtgatcgaggag (SEQ ID NO: 191) |
| F46 | nsa247F | cagcagctcggagcggacnnsgaggtgatcgaggaggga (SEQ ID NO: 192) |
| E47 | nsa248F | cagctcggagcggacttcnnsgtgatcgaggagggactg (SEQ ID NO: 193) |
| V48 | nsa249F | ctcggagcggacttcgagnnsatcgaggagggactgagc (SEQ ID NO: 194) |
| I49 | nsa250F | ggagcggacttcgaggtgnnsgaggagggactgagcgcg (SEQ ID NO: 195) |
| E50 | nsa251F | gcggacttcgaggtgatcnnsgagggactgagcgcgcgc (SEQ ID NO: 196) |
| E51 | nsa252F | gacttcgaggtgatcgagnnsggactgagcgcgcgcacc (SEQ ID NO: 197) |
| G52 | nsa253F | ttcgaggtgatcgaggagnnsctgagcgcgcgcaccacc (SEQ ID NO: 198) |
| L53 | nsa193F | gaggtgatcgaggagggannsagcgcgcgcaccaccaac (SEQ ID NO: 199) |
| S54 | nsa173F | gtgatcgaggagggactgnnsgcgcgcaccaccaacatc (SEQ ID NO: 200) |
| A55 | nsa174F | atcgaggagggactgagcnnscgcaccaccaacatcgac (SEQ ID NO: 201) |
| R56 | nsa257F | gaggagggactgagcgcgnnsaccaccaacatcgacgac (SEQ ID NO: 202) |
| T57 | nsa258F | gagggactgagcgcgcgcnnsaccaacatcgacgacccc (SEQ ID NO: 203) |
| T58 | nsa259F | ggactgagcgcgcgcaccnnsaacatcgacgaccccacc (SEQ ID NO: 204) |
| N59 | nsa260F | ctgagcgcgcgcaccaccnnsatcgacgaccccaccgat (SEQ ID NO: 205) |
| I60 | nsa261F | agcgcgcgcaccaccaacnnsgacgaccccaccgatccg (SEQ ID NO: 206) |
| D61 | nsa262F | gcgcgcaccaccaacatcnnsgaccccaccgatccgcgg (SEQ ID NO: 207) |
| D62 | nsa263F | cgcaccaccaacatcgacnnscccaccgatccgcggctc (SEQ ID NO: 208) |
| P63 | nsa264F | accaccaacatcgacgacnnsaccgatccgcggctcaac (SEQ ID NO: 209) |
| T64 | nsa194F | accaacatcgacgaccccnnsgatccgcggctcaacggc (SEQ ID NO: 210) |
| D65 | nsa195F | aacatcgacgaccccaccnnsccgcggctcaacggcgcg (SEQ ID NO: 211) |
| P66 | nsa267F | atcgacgaccccaccgatnnscggctcaacggcgcgagc (SEQ ID NO: 212) |
| R67 | nsa196F | gacgaccccaccgatccgnnsctcaacggcgcgagctac (SEQ ID NO: 213) |
| L68 | nsa269F | gaccccaccgatccgcggnnsaacggcgcgagctacctg (SEQ ID NO: 214) |
| N69 | nsa270F | cccaccgatccgcggctcnnsggcgcgagctacctgccg (SEQ ID NO: 215) |
| G70 | nsa271F | accgatccgcggctcaacnnsgcgagctacctgccgtcg (SEQ ID NO: 216) |
| A71 | nsa272F | gatccgcggctcaacggcnnsagctacctgccgtcgtgc (SEQ ID NO: 217) |
| S72 | nsa273F | ccgcggctcaacggcgcgnnstacctgccgtcgtgcctc (SEQ ID NO: 218) |
| Y73 | nsa274F | cggctcaacggcgcgagcnnsctgccgtcgtgcctcgcg (SEQ ID NO: 219) |
| L74 | nsa275F | ctcaacggcgcgagctacnnsccgtcgtgcctcgcgacg (SEQ ID NO: 220) |
| P75 | nsa276F | aacggcgcgagctacctgnnstcgtgcctcgcgacgcac (SEQ ID NO: 221) |
| S76 | nsa277F | ggcgcgagctacctgccgnnstgcctcgcgacgcacctg (SEQ ID NO: 222) |

TABLE 8-1-continued

Site-Saturation Forward Primers

| Residue | Primer | Primer Sequence |
|---|---|---|
| C77 | nsa278F | gcgagctacctgccgtcgnnsctcgcgacgcacctgccg (SEQ ID NO: 223) |
| L78 | nsa279F | agctacctgccgtcgtgcnnsgcgacgcacctgccgctc (SEQ ID NO: 224) |
| A79 | nsa280F | tacctgccgtcgtgcctcnnsacgcacctgccgctcgac (SEQ ID NO: 225) |
| T80 | nsa281F | ctgccgtcgtgcctcgcgnnscacctgccgctcgacctg (SEQ ID NO: 226) |
| H81 | nsa282F | ccgtcgtgcctcgcgacgnnsctgccgctcgacctggtg (SEQ ID NO: 227) |
| L82 | nsa283F | tcgtgcctcgcgacgcacnnsccgctcgacctggtgatc (SEQ ID NO: 228) |
| P83 | nsa284F | tgcctcgcgacgcacctgnnsctcgacctggtgatcatc (SEQ ID NO: 229) |
| L84 | nsa285F | ctcgcgacgcacctgccgnnsgacctggtgatcatcatg (SEQ ID NO: 230) |
| D85 | nsa286F | gcgacgcacctgccgctcnnsctggtgatcatcatgctg (SEQ ID NO: 231) |
| L86 | nsa287F | acgcacctgccgctcgacnnsgtgatcatcatgctgggc (SEQ ID NO: 232) |
| V87 | nsa288F | cacctgccgctcgacctgnnsatcatcatgctgggcacc (SEQ ID NO: 233) |
| I88 | nsa289F | ctgccgctcgacctggtgnnsatcatgctgggcaccaac (SEQ ID NO: 234) |
| I89 | nsa290F | ccgctcgacctggtgatcnnsatgctgggcaccaacgac (SEQ ID NO: 235) |
| M90 | nsa291F | ctcgacctggtgatcatcnnsctgggcaccaacgacacc (SEQ ID NO: 236) |
| L91 | nsa292F | gacctggtgatcatcatgnnsggcaccaacgacaccaag (SEQ ID NO: 237) |
| G92 | nsa293F | ctggtgatcatcatgctgnnsaccaacgacaccaaggcc (SEQ ID NO: 238) |
| T93 | nsa294F | gtgatcatcatgctgggcnnsaacgacaccaaggcctac (SEQ ID NO: 239) |
| N94 | nsa175F | atcatcatgctgggcaccnnsgacaccaaggcctacttc (SEQ ID NO: 240) |
| D95 | nsa197F | atcatgctgggcaccaacnnsaccaaggcctacttccgg (SEQ ID NO: 241) |
| T96 | nsa297F | atgctgggcaccaacgacnnsaaggcctacttccggcgc (SEQ ID NO: 242) |
| K97 | nsa176F | ctgggcaccaacgacaccnnsgcctacttccggcgcacc (SEQ ID NO: 243) |
| A98 | nsa299F | ggcaccaacgacaccaagnnstacttccggcgcacccCg (SEQ ID NO: 244) |
| Y99 | nsa177F | accaacgacaccaaggccnnsttccggcgcaccccgctc (SEQ ID NO: 245) |
| F100 | nsa301F | aacgacaccaaggcctacXXXcggcgcaccccgctcgac (SEQ ID NO: 246) |
| R101 | nsa302F | gacaccaaggcctacttcXXXcgcaccccgctcgacatc (SEQ ID NO: 247) |
| R102 | nsa303F | accaaggcctacttccggnnsaccccgctcgacatcgcg (SEQ ID NO: 248) |
| T103 | nsa304F | aaggcctacttccggcgcnnsccgctcgacatcgcgctg (SEQ ID NO: 249) |
| P104 | nsa305F | gcctacttccggcgcaccnnsctcgacatcgcgctgggc (SEQ ID NO: 250) |
| L105 | nsa306F | tacttccggcgcaccccgnnsgacatcgcgctgggcatg (SEQ ID NO: 251) |
| D106 | nsa307F | ttccggcgcaccccgctcnnsatcgcgctgggcatgtcg (SEQ ID NO: 252) |
| I107 | nsa308F | cggcgcaccccgctcgacnnsgcgctgggcatgtcggtg (SEQ ID NO: 253) |
| A108 | nsa309F | cgcaccccgctcgacatcnnsctgggcatgtcggtgctc (SEQ ID NO: 254) |
| L109 | nsa310F | accccgctcgacatcgcgnnsggcatgtcggtgctcgtc (SEQ ID NO: 255) |
| G110 | nsa311F | ccgctcgacatcgcgctgnnsatgtcggtgctcgtcacg (SEQ ID NO: 256) |
| M111 | nsa312F | ctcgacatcgcgctgggcnnstcggtgctcgtcacgcag (SEQ ID NO: 257) |
| S112 | nsa313F | gacatcgcgctgggcatgnnsgtgctcgtcacgcaggtg (SEQ ID NO: 258) |
| V113 | nsa314F | atcgcgctgggcatgtcgnnsctcgtcacgcaggtgctc (SEQ ID NO: 259) |
| L114 | nsa315F | gcgctgggcatgtcggtgnnsgtcacgcaggtgctcacc (SEQ ID NO: 260) |

TABLE 8-1-continued

Site-Saturation Forward Primers

| Residue | Primer | Primer Sequence |
|---|---|---|
| V115 | nsa316F | ctgggcatgtcggtgctcnnsacgcaggtgctcaccagc (SEQ ID NO: 261) |
| T116 | nsa317F | ggcatgtcggtgctcgtcnnscaggtgctcaccagcgcg (SEQ ID NO: 262) |
| Q117 | nsa318F | atgtcggtgctcgtcacgnnsgtgctcaccagcgcgggc (SEQ ID NO: 263) |
| V118 | nsa319F | tcggtgctcgtcacgcagnnsctcaccagcgcgggcggc (SEQ ID NO: 264) |
| L119 | nsa320F | gtgctcgtcacgcaggtgnnsaccagcgcgggcggcgtc (SEQ ID NO: 265) |
| T120 | nsa321F | ctcgtcacgcaggtgctcnnsagcgcgggcggcgtcggc (SEQ ID NO: 266) |
| S121 | nsa322F | gtcacgcaggtgctcaccnnsgcgggcggcgtcggcacc (SEQ ID NO: 267) |
| A122 | nsa323F | acgcaggtgctcaccagcnnsggcggcgtcggcaccacg (SEQ ID NO: 268) |
| G123 | nsa324F | caggtgctcaccagcgcgnnsggcgtcggcaccacgtac (SEQ ID NO: 269) |
| G124 | nsa325F | gtgctcaccagcgcgggcnnsgtcggcaccacgtacccg (SEQ ID NO: 270) |
| V125 | nsa198F | ctcaccagcgcgggcggcnnsggcaccacgtacccggca (SEQ ID NO: 271) |
| G126 | nsa327F | accagcgcgggcggcgtcnnsaccacgtacccggcaccc (SEQ ID NO: 272) |
| T127 | nsa328F | agcgcgggcggcgtcggcnnsacgtacccggcacccaag (SEQ ID NO: 273) |
| T128 | nsa329F | gcgggcggcgtcggcaccnnstacccggcacccaaggtg (SEQ ID NO: 274) |
| Y129 | nsa330F | ggcggcgtcggcaccacgnnsccggcacccaaggtgctg (SEQ ID NO: 275) |
| P130 | nsa331F | ggcgtcggcaccacgtacnnsgcacccaaggtgctggtg (SEQ ID NO: 276) |
| A131 | nsa332F | gtcggcaccacgtacccgnnscccaaggtgctggtggtc (SEQ ID NO: 277) |
| P132 | nsa333F | ggcaccacgtacccggcannsaaggtgctggtggtctcg (SEQ ID NO: 278) |
| K133 | nsa334F | accacgtacccggcacccnnsgtgctggtggtctcgccg (SEQ ID NO: 279) |
| V134 | nsa335F | acgtacccggcacccaagnnsctggtggtctcgccgcca (SEQ ID NO: 280) |
| L135 | nsa336F | tacccggcacccaaggtgnnsgtggtctcgccgccaccg (SEQ ID NO: 281) |
| V136 | nsa337F | ccggcacccaaggtgctgnnsgtctcgccgccaccgctg (SEQ ID NO: 282) |
| V137 | nsa338F | gcacccaaggtgctggtgnnstcgccgccaccgctggcg (SEQ ID NO: 283) |
| S138 | nsa339F | cccaaggtgctggtggtcnnsccgccaccgctggcgccc (SEQ ID NO: 284) |
| P139 | nsa340F | aaggtgctggtggtctcgnnsccaccgctggcgcccatg (SEQ ID NO: 285) |
| P140 | nsa341F | gtgctggtggtctcgccgnnsccgctggcgcccatgccg (SEQ ID NO: 286) |
| P141 | nsa342F | ctggtggtctcgccgccannsctggcgcccatgccgcac (SEQ ID NO: 287) |
| L142 | nsa343F | gtggtctcgccgccaccgnnsgcgcccatgccgcacccc (SEQ ID NO: 288) |
| A143 | nsa344F | gtctcgccgccaccgctgnnscccatgccgcacccctgg (SEQ ID NO: 289) |
| P144 | nsa345F | tcgccgccaccgctggcgnnsatgccgcacccctggttc (SEQ ID NO: 290) |
| M145 | nsa346F | ccgccaccgctggcgcccnnsccgcacccctggttccag (SEQ ID NO: 291) |
| P146 | nsa178F | ccaccgctggcgcccatgnnscacccctggttccagttg (SEQ ID NO: 292) |
| H147 | nsa348F | ccgctggcgcccatgccgnnsccctggttccagttgatc (SEQ ID NO: 293) |
| P148 | nsa199F | ctggcgcccatgccgcacnnstggttccagttgatcttc (SEQ ID NO: 294) |
| W149 | nsa179F | gcgcccatgccgcacccennsttccagttgatcttcgag (SEQ ID NO: 295) |
| F150 | nsa180F | cccatgccgcacccctggnnscagttgatcttcgagggc (SEQ ID NO: 296) |
| Q151 | nsa352F | atgccgcacccctggttcnnsttgatcttcgagggcggc (SEQ ID NO: 297) |
| L152 | nsa353F | ccgcacccctggttccagnnsatcttcgagggcggcgag (SEQ ID NO: 298) |

TABLE 8-1-continued

Site-Saturation Forward Primers

| Residue | Primer | Primer Sequence |
|---|---|---|
| I153 | nsa200F | cacccctggttccagttgnnsttcgagggcggcgagcag (SEQ ID NO: 299) |
| F154 | nsa201F | ccctggttccagttgatcnnsgagggcggcgagcagaag (SEQ ID NO: 300) |
| E155 | nsa356F | tggttccagttgatcttcnnsggcggcgagcagaagacc (SEQ ID NO: 301) |
| G156 | nsa357F | ttccagttgatcttcgagnnsggcgagcagaagaccact (SEQ ID NO: 302) |
| G157 | nsa358F | cagttgatcttcgagggcnnsgagcagaagaccactgag (SEQ ID NO: 303) |
| E158 | nsa359F | ttgatcttcgagggcggcnnscagaagaccactgagctc (SEQ ID NO: 304) |
| Q159 | nsa360F | atcttcgagggcggcgagnnsaagaccactgagctcgcc (SEQ ID NO: 305) |
| K160 | nsa361F | ttcgagggcggcgagcagnnsaccactgagctcgcccgc (SEQ ID NO: 306) |
| T161 | nsa362F | gagggcggcgagcagaagnnsactgagctcgcccgcgtg (SEQ ID NO: 307) |
| T162 | nsa363F | ggcggcgagcagaagaccnnsgagctcgcccgcgtgtac (SEQ ID NO: 308) |
| E163 | nsa364F | ggcgagcagaagaccactnnsctcgcccgcgtgtacagc (SEQ ID NO: 309) |
| L164 | nsa365F | gagcagaagaccactgagnnsgcccgcgtgtacagcgcg (SEQ ID NO: 310) |
| A165 | nsa366F | cagaagaccactgagctcnnscgcgtgtacagcgcgctc (SEQ ID NO: 311) |
| R166 | nsa367F | aagaccactgagctcgccnnsgtgtacagcgcgctcgcg (SEQ ID NO: 312) |
| V167 | nsa368F | accactgagctcgcccgcnnstacagcgcgctcgcgtcg (SEQ ID NO: 313) |
| Y168 | nsa369F | actgagctcgcccgcgtgnnsagcgcgctcgcgtcgttc (SEQ ID NO: 314) |
| S169 | nsa370F | gagctcgcccgcgtgtacnnsgcgctcgcgtcgttcatg (SEQ ID NO: 315) |
| A170 | nsa371F | ctcgcccgcgtgtacagcnnsctcgcgtcgttcatgaag (SEQ ID NO: 316) |
| L171 | nsa372F | gcccgcgtgtacagcgcgnnsgcgtcgttcatgaaggtg (SEQ ID NO: 317) |
| A172 | nsa373F | cgcgtgtacagcgcgctcnnstcgttcatgaaggtgccg (SEQ ID NO: 318) |
| S173 | nsa374F | gtgtacagcgcgctcgcgnnsttcatgaaggtgccgttc (SEQ ID NO: 319) |
| F174 | nsa375F | tacagcgcgctcgcgtcgnnsatgaaggtgccgttcttc (SEQ ID NO: 320) |
| M175 | nsa376F | agcgcgctcgcgtcgttcnnsaaggtgccgttcttcgac (SEQ ID NO: 321) |
| K176 | nsa377F | gcgctcgcgtcgttcatgnnsgtgccgttcttcgacgcg (SEQ ID NO: 322) |
| V177 | nsa378F | ctcgcgtcgttcatgaagnnsccgttcttcgacgcgggt (SEQ ID NO: 323) |
| P178 | nsa379F | gcgtcgttcatgaaggtgnnsttcttcgacgcgggttcg (SEQ ID NO: 324) |
| F179 | nsa380F | tcgttcatgaaggtgccgnnsttcgacgcgggttcggtg (SEQ ID NO: 325) |
| F180 | nsa381F | ttcatgaaggtgccgttcnnsgacgcgggttcggtgatc (SEQ ID NO: 326) |
| D181 | nsa382F | atgaaggtgccgttcttcnnsgcgggttcggtgatcagc (SEQ ID NO: 327) |
| A182 | nsa383F | aaggtgccgttcttcgacnnsggttcggtgatcagcacc (SEQ ID NO: 328) |
| G183 | nsa384F | gtgccgttcttcgacgcgnnstcggtgatcagcaccgac (SEQ ID NO: 329) |
| S184 | nsa385F | ccgttcttcgacgcgggtnnsgtgatcagcaccgacggc (SEQ ID NO: 330) |
| V185 | nsa386F | ttcttcgacgcgggttcgnnsatcagcaccgacggcgtc (SEQ ID NO: 331) |
| I186 | nsa387F | ttcgacgcgggttcggtgnnsagcaccgacggcgtcgac (SEQ ID NO: 332) |
| S187 | nsa388F | gacgcgggttcggtgatcnnsaccgacggcgtcgacgga (SEQ ID NO: 333) |
| T188 | nsa389F | gcgggttcggtgatcagcnnsgacggcgtcgacggaatc (SEQ ID NO: 334) |
| D189 | nsa390F | ggttcggtgatcagcaccnnsggcgtcgacggaatccac (SEQ ID NO: 335) |
| G190 | nsa391F | tcggtgatcagcaccgacnnsgtcgacggaatccacttc (SEQ ID NO: 336) |

TABLE 8-1-continued

Site-Saturation Forward Primers

| Residue | Primer | Primer Sequence |
|---|---|---|
| V191 | nsa392F | gtgatcagcaccgacggcnnsgacggaatccacttcacc (SEQ ID NO: 337) |
| D192 | nsa393F | atcagcaccgacggcgtcnnsggaatccacttcaccgag (SEQ ID NO: 338) |
| G193 | nsa394F | agcaccgacggcgtcgacnnsatccacttcaccgaggcc (SEQ ID NO: 339) |
| I194 | nsa181F | accgacggcgtcgacggannscacttcaccgaggccaac (SEQ ID NO: 340) |
| H195 | nsa396F | gacggcgtcgacggaatcnnsttcaccgaggccaacaat (SEQ ID NO: 341) |
| F196 | nsa182F | ggcgtcgacggaatccacnnsaccgaggccaacaatcgc (SEQ ID NO: 342) |
| T197 | nsa398F | gtcgacggaatccacttcnnsgaggccaacaatcgcgat (SEQ ID NO: 343) |
| E198 | nsa399F | gacggaatccacttcaccnnsgccaacaatcgcgatctc (SEQ ID NO: 344) |
| A199 | nsa400F | ggaatccacttcaccgagnnsaacaatcgcgatctcggg (SEQ ID NO: 345) |
| N200 | nsa401F | atccacttcaccgaggccnnsaatcgcgatctcggggtg (SEQ ID NO: 346) |
| N201 | nsa402F | cacttcaccgaggccaacnnscgcgatctcggggtggcc (SEQ ID NO: 347) |
| R202 | nsa403F | ttcaccgaggccaacaatnnsgatctcggggtggccctc (SEQ ID NO: 348) |
| D203 | nsa404F | accgaggccaacaatcgcnnsctcggggtggccctcgcg (SEQ ID NO: 349) |
| L204 | nsa405F | gaggccaacaatcgcgatnnsggggtggccctcgcggaa (SEQ ID NO: 350) |
| G205 | nsa406F | gccaacaatcgcgatctcnnsgtggccctcgcggaacag (SEQ ID NO: 351) |
| V206 | nsa407F | aacaatcgcgatctcgggnnsgccctcgcggaacaggtg (SEQ ID NO: 352) |
| A207 | nsa408F | aatcgcgatctcggggtgnnsctcgcggaacaggtgcag (SEQ ID NO: 353) |
| L208 | nsa409F | cgcgatctcggggtggccnnsgcggaacaggtgcagagc (SEQ ID NO: 354) |
| A209 | nsa410F | gatctcggggtggccctcnnsgaacaggtgcagagcctg (SEQ ID NO: 355) |
| E210 | nsa411F | ctcggggtggccctcgcgnnscaggtgcagagcctgctg (SEQ ID NO: 356) |
| Q211 | nsa412F | ggggtggccctcgcggaannsgtgcagagcctgctgtaa (SEQ ID NO: 357) |
| V212 | nsa413F | gtggccctcgcggaacagnnscagagcctgctgtaaaag (SEQ ID NO: 358) |
| Q213 | nsa414F | gccctcgcggaacaggtgnnsagcctgctgtaaaagggc (SEQ ID NO: 359) |
| S214 | nsa415F | ctcgcggaacaggtgcagnnsctgctgtaaaagggcgaa (SEQ ID NO: 360) |
| L215 | nsa416F | gcggaacaggtgcagagcnnsctgtaaaagggcgaattc (SEQ ID NO: 361) |
| L216 | nsa417F | gaacaggtgcagagcctgnnstaaaagggcgaattctgc (SEQ ID NO: 362) |

TABLE 8-2

Site-Saturation Reverse Primer Sequences

| Residue | Primer | Primer Sequence |
|---|---|---|
| M1 | nsa202R | ACACAGAATTCGCTTGGCSNNGGTTAATTCCTCCTGTTA (SEQ ID NO: 363) |
| A2 | nsa203R | GAAACACAGAATTCGCTTSNNCATGGTTAATTCCTCCTG (SEQ ID NO: 364) |
| K3 | nsa204R | ACCGAAACACAGAATTCGSNNGGCCATGGTTAATTCCTC (SEQ ID NO: 365) |
| R4 | nsa205R | ATCACCGAAACACAGAATSNNCTTGGCCATGGTTAATTC (SEQ ID NO: 366) |
| I5 | nsa206R | GGAATCACCGAAACACAGSNNTCGCTTGGCCATGGTTAA (SEQ ID NO: 367) |

TABLE 8-2-continued

Site-Saturation Reverse Primer Sequences

| Residue | Primer | Primer Sequence |
|---|---|---|
| L6 | nsa207R | CAGGGAATCACCGAAACASNNAATTCGCTTGGCCATGGT (SEQ ID NO: 368) |
| C7 | nsa208R | GGTCAGGGAATCACCGAASNNCAGAATTCGCTTGGCCAT (SEQ ID NO: 369) |
| F8 | nsa209R | CCAGGTCAGGGAATCACCSNNACACAGAATTCGCTTGGC (SEQ ID NO: 370) |
| G9 | nsa210R | GCCCCAGGTCAGGGAATCSNNGAAACACAGAATTCGCTT (SEQ ID NO: 371) |
| D10 | nsa168R | CCAGCCCCAGGTCAGGGASNNACCGAAACACAGAATTCG (SEQ ID NO: 372) |
| S11 | nsa212R | GACCCAGCCCCAGGTCAGSNNATCACCGAAACACAGAAT (SEQ ID NO: 373) |
| L12 | nsa169R | GGGGACCCAGCCCCAGGTSNNGGAATCACCGAAACACAG (SEQ ID NO: 374) |
| T13 | nsa170R | GACGGGGACCCAGCCCCASNNCAGGGAATCACCGAAACA (SEQ ID NO: 375) |
| W14 | nsa171R | TTCGACGGGGACCCAGCCSNNGGTCAGGGAATCACCGAA (SEQ ID NO: 376) |
| G15 | nsa216R | GTCTTCGACGGGGACCCASNNCCAGGTCAGGGAATCACC (SEQ ID NO: 377) |
| W16 | nsa172R | CCCGTCTTCGACGGGGACSNNGCCCCAGGTCAGGGAATC (SEQ ID NO: 378) |
| V17 | nsa218R | TGCCCCGTCTTCGACGGGSNNCCAGCCCCAGGTCAGGGA (SEQ ID NO: 379) |
| P18 | nsa219R | GGGTGCCCCGTCTTCGACSNNGACCCAGCCCCAGGTCAG (SEQ ID NO: 380) |
| V19 | nsa220R | GGTGGGTGCCCCGTCTTCSNNGGGGACCCAGCCCCAGGT (SEQ ID NO: 381) |
| E20 | nsa221R | CTCGGTGGGTGCCCCGTCSNNGACGGGGACCCAGCCCCA (SEQ ID NO: 382) |
| D21 | nsa222R | CCGCTCGGTGGGTGCCCCSNNTTCGACGGGGACCCAGCC (SEQ ID NO: 383) |
| G22 | nsa223R | GAACCGCTCGGTGGGTGCSNNGTCTTCGACGGGGACCCA (SEQ ID NO: 384) |
| A23 | nsa224R | GGCGAACCGCTCGGTGGGSNNCCCGTCTTCGACGGGGAC (SEQ ID NO: 385) |
| P24 | nsa191R | GGGGGCGAACCGCTCGGTSNNTGCCCCGTCTTCGACGGG (SEQ ID NO: 386) |
| T25 | nsa192R | GTCGGGGGCGAACCGCTCSNNGGGTGCCCCGTCTTCGAC (SEQ ID NO: 387) |
| E26 | nsa227R | CACGTCGGGGGCGAACCGSNNGGTGGGTGCCCCGTCTTC (SEQ ID NO: 388) |
| R27 | nsa228R | GCGCACGTCGGGGGCGAASNNCTCGGTGGGTGCCCCGTC (SEQ ID NO: 389) |
| F28 | nsa229R | CCAGCGCACGTCGGGGGCSNNCCGCTCGGTGGGTGCCCC (SEQ ID NO: 390) |
| A29 | nsa230R | GGTCCAGCGCACGTCGGGSNNGAACCGCTCGGTGGGTGC (SEQ ID NO: 391) |
| P30 | nsa231R | ACCGGTCCAGCGCACGTCSNNGGCGAACCGCTCGGTGGG (SEQ ID NO: 392) |

TABLE 8-2-continued

Site-Saturation Reverse Primer Sequences

| Residue | Primer | Primer Sequence |
|---|---|---|
| D31 | nsa232R | CACACCGGTCCAGCGCACSNNGGGGGCGAACCGCTCGGT (SEQ ID NO: 393) |
| V32 | nsa233R | CAGCACACCGGTCCAGCGSNNGTCGGGGGCGAACCGCTC (SEQ ID NO: 394) |
| R33 | nsa234R | GGCCAGCACACCGGTCCASNNCACGTCGGGGGCGAACCG (SEQ ID NO: 395) |
| W34 | nsa235R | CTGGGCCAGCACACCGGTSNNGCGCACGTCGGGGGCGAA (SEQ ID NO: 396) |
| T35 | nsa236R | CTGCTGGGCCAGCACACCSNNCCAGCGCACGTCGGGGGC (SEQ ID NO: 397) |
| G36 | nsa237R | GAGCTGCTGGGCCAGCACSNNGGTCCAGCGCACGTCGGG (SEQ ID NO: 398) |
| V37 | nsa238R | TCCGAGCTGCTGGGCCAGSNNACCGGTCCAGCGCACGTC (SEQ ID NO: 399) |
| L38 | nsa239R | CGCTCCGAGCTGCTGGGCSNNCACACCGGTCCAGCGCAC (SEQ ID NO: 400) |
| A39 | nsa240R | GTCCGCTCCGAGCTGCTGSNNCAGCACACCGGTCCAGCG (SEQ ID NO: 401) |
| Q40 | nsa241R | GAAGTCCGCTCCGAGCTGSNNGGCCAGCACACCGGTCCA (SEQ ID NO: 402) |
| Q41 | nsa242R | CTCGAAGTCCGCTCCGAGSNNCTGGGCCAGCACACCGGT (SEQ ID NO: 403) |
| L42 | nsa243R | CACCTCGAAGTCCGCTCCSNNCTGCTGGGCCAGCACACC (SEQ ID NO: 404) |
| G43 | nsa244R | GATCACCTCGAAGTCCGCSNNGAGCTGCTGGGCCAGCAC (SEQ ID NO: 405) |
| A44 | nsa245R | CTCGATCACCTCGAAGTCSNNTCCGAGCTGCTGGGCCAG (SEQ ID NO: 406) |
| D45 | nsa246R | CTCCTCGATCACCTCGAASNNCGCTCCGAGCTGCTGGGC (SEQ ID NO: 407) |
| F46 | nsa247R | TCCCTCCTCGATCACCTCSNNGTCCGCTCCGAGCTGCTG (SEQ ID NO: 408) |
| E47 | nsa248R | CAGTCCCTCCTCGATCACSNNGAAGTCCGCTCCGAGCTG (SEQ ID NO: 409) |
| V48 | nsa249R | GCTCAGTCCCTCCTCGATSNNCTCGAAGTCCGCTCCGAG (SEQ ID NO: 410) |
| I49 | nsa250R | CGCGCTCAGTCCCTCCTCSNNCACCTCGAAGTCCGCTCC (SEQ ID NO: 411) |
| E50 | nsa251R | GCGCGCGCTCAGTCCCTCSNNGATCACCTCGAAGTCCGC (SEQ ID NO: 412) |
| E51 | nsa252R | GGTGCGCGCGCTCAGTCCSNNCTCGATCACCTCGAAGTC (SEQ ID NO: 413) |
| G52 | nsa253R | GGTGGTGCGCGCGCTCAGSNNCTCCTCGATCACCTCGAA (SEQ ID NO: 414) |
| L53 | nsa193R | GTTGGTGGTGCGCGCTSNNTCCCTCCTCGATCACCTC (SEQ ID NO: 415) |
| S54 | nsa173R | GATGTTGGTGGTGCGCGCSNNCAGTCCCTCCTCGATCAC (SEQ ID NO: 416) |
| A55 | nsa174R | GTCGATGTTGGTGGTGCGSNNGCTCAGTCCCTCCTCGAT (SEQ ID NO: 417) |

TABLE 8-2-continued

Site-Saturation Reverse Primer Sequences

| Residue | Primer | Primer Sequence |
|---|---|---|
| R56 | nsa257R | GTCGTCGATGTTGGTGGTSNNCGCGCTCAGTCCCTCCTC (SEQ ID NO: 418) |
| T57 | nsa258R | GGGGTCGTCGATGTTGGTSNNGCGCGCGCTCAGTCCCTC (SEQ ID NO: 419) |
| T58 | nsa259R | GGTGGGGTCGTCGATGTTSNNGGTGCGCGCGCTCAGTCC (SEQ ID NO: 420) |
| N59 | nsa260R | ATCGGTGGGGTCGTCGATSNNGGTGGTGCGCGCGCTCAG (SEQ ID NO: 421) |
| I60 | nsa261R | CGGATCGGTGGGGTCGTCSNNGTTGGTGGTGCGCGCGCT (SEQ ID NO: 422) |
| D61 | nsa262R | CCGCGGATCGGTGGGGTCSNNGATGTTGGTGGTGCGCGC (SEQ ID NO: 423) |
| D62 | nsa263R | GAGCCGCGGATCGGTGGGSNNGTCGATGTTGGTGGTGCG (SEQ ID NO: 424) |
| P63 | nsa264R | GTTGAGCCGCGGATCGGTSNNGTCGTCGATGTTGGTGGT (SEQ ID NO: 425) |
| T64 | nsa194R | GCCGTTGAGCCGCGGATCSNNGGGGTCGTCGATGTTGGT (SEQ ID NO: 426) |
| D65 | nsa195R | CGCGCCGTTGAGCCGCGGSNNGGTGGGGTCGTCGATGTT (SEQ ID NO: 427) |
| P66 | nsa267R | GCTCGCGCCGTTGAGCCGSNNATCGGTGGGGTCGTCGAT (SEQ ID NO: 428) |
| R67 | nsa196R | GTAGCTCGCGCCGTTGAGSNNCGGATCGGTGGGGTCGTC (SEQ ID NO: 429) |
| L68 | nsa269R | CAGGTAGCTCGCGCCGTTSNNCCGCGGATCGGTGGGGTC (SEQ ID NO: 430) |
| N69 | nsa270R | CGGCAGGTAGCTCGCGCCSNNGAGCCGCGGATCGGTGGG (SEQ ID NO: 431) |
| G70 | nsa271R | CGACGGCAGGTAGCTCGCSNNGTTGAGCCGCGGATCGGT (SEQ ID NO: 432) |
| A71 | nsa272R | GCACGACGGCAGGTAGCTSNNGCCGTTGAGCCGCGGATC (SEQ ID NO: 433) |
| S72 | nsa273R | GAGGCACGACGGCAGGTASNNCGCGCCGTTGAGCCGCGG (SEQ ID NO: 434) |
| Y73 | nsa274R | CGCGAGGCACGACGGCAGSNNGCTCGCGCCGTTGAGCCG (SEQ ID NO: 435) |
| L74 | nsa275R | CGTCGCGAGGCACGACGGSNNGTAGCTCGCGCCGTTGAG (SEQ ID NO: 436) |
| P75 | nsa276R | GTGCGTCGCGAGGCACGASNNCAGGTAGCTCGCGCCGTT (SEQ ID NO: 437) |
| S76 | nsa277R | CAGGTGCGTCGCGAGGCASNNCGGCAGGTAGCTCGCGCC (SEQ ID NO: 438) |
| C77 | nsa278R | CGGCAGGTGCGTCGCGAGSNNCGACGGCAGGTAGCTCGC (SEQ ID NO: 439) |
| L78 | nsa279R | GAGCGGCAGGTGCGTCGCSNNGCACGACGGCAGGTAGCT (SEQ ID NO: 440) |
| A79 | nsa280R | GTCGAGCGGCAGGTGCGTSNNGAGGCACGACGGCAGGTA (SEQ ID NO: 441) |
| T80 | nsa281R | CAGGTCGAGCGGCAGGTGSNNCGCGAGGCACGACGGCAG (SEQ ID NO: 442) |

TABLE 8-2-continued

Site-Saturation Reverse Primer Sequences

| Residue | Primer | Primer Sequence |
|---|---|---|
| H81 | nsa282R | CACCAGGTCGAGCGGCAGSNNCGTCGCGAGGCACGACGG (SEQ ID NO: 443) |
| L82 | nsa283R | GATCACCAGGTCGAGCGGSNNGTGCGTCGCGAGGCACGA (SEQ ID NO: 444) |
| P83 | nsa284R | GATGATCACCAGGTCGAGSNNCAGGTGCGTCGCGAGGCA (SEQ ID NO: 445) |
| L84 | nsa285R | CATGATGATCACCAGGTCSNNCGGCAGGTGCGTCGCGAG (SEQ ID NO: 446) |
| D85 | nsa286R | CAGCATGATGATCACCAGSNNGAGCGGCAGGTGCGTCGC (SEQ ID NO: 447) |
| L86 | nsa287R | GCCCAGCATGATGATCACSNNGTCGAGCGGCAGGTGCGT (SEQ ID NO: 448) |
| V87 | nsa288R | GGTGCCCAGCATGATGATSNNCAGGTCGAGCGGCAGGTG (SEQ ID NO: 449) |
| I88 | nsa289R | GTTGGTGCCCAGCATGATSNNCACCAGGTCGAGCGGCAG (SEQ ID NO: 450) |
| I89 | nsa290R | GTCGTTGGTGCCCAGCATSNNGATCACCAGGTCGAGCGG (SEQ ID NO: 451) |
| M90 | nsa291R | GGTGTCGTTGGTGCCCAGSNNGATGATCACCAGGTCGAG (SEQ ID NO: 452) |
| L91 | nsa292R | CTTGGTGTCGTTGGTGCCSNNCATGATGATCACCAGGTC (SEQ ID NO: 453) |
| G92 | nsa293R | GGCCTTGGTGTCGTTGGTSNNCAGCATGATGATCACCAG (SEQ ID NO: 454) |
| T93 | nsa294R | GTAGGCCTTGGTGTCGTTSNNGCCCAGCATGATGATCAC (SEQ ID NO: 455) |
| N94 | nsa175R | GAAGTAGGCCTTGGTGTCSNNGGTGCCCAGCATGATGAT (SEQ ID NO: 456) |
| D95 | nsa197R | CCGGAAGTAGGCCTTGGTSNNGTTGGTGCCCAGCATGAT (SEQ ID NO: 457) |
| T96 | nsa297R | GCGCCGGAAGTAGGCCTTSNNGTCGTTGGTGCCCAGCAT (SEQ ID NO: 458) |
| K97 | nsa176R | GGTGCGCCGGAAGTAGGCSNNGGTGTCGTTGGTGCCCAG (SEQ ID NO: 459) |
| A98 | nsa299R | CGGGGTGCGCCGGAAGTASNNCTTGGTGTCGTTGGTGCC (SEQ ID NO: 460) |
| Y99 | nsa177R | GAGCGGGGTGCGCCGGAASNNGGCCTTGGTGTCGTTGGT (SEQ ID NO: 461) |
| F100 | nsa301R | GTCGAGCGGGGTGCGCCGSNNGTAGGCCTTGGTGTCGTT (SEQ ID NO: 462) |
| R101 | nsa302R | GATGTCGAGCGGGGTGCGSNNGAAGTAGGCCTTGGTGTC (SEQ ID NO: 463) |
| R102 | nsa303R | CGCGATGTCGAGCGGGGTSNNCCGGAAGTAGGCCTTGGT (SEQ ID NO: 464) |
| T103 | nsa304R | CAGCGCGATGTCGAGCGGSNNGCGCCGGAAGTAGGCCTT (SEQ ID NO: 465) |
| P104 | nsa305R | GCCCAGCGCGATGTCGAGSNNGGTGCGCCGGAAGTAGGC (SEQ ID NO: 466) |
| L105 | nsa306R | CATGCCCAGCGCGATGTCSNNCGGGGTGCGCCGGAAGTA (SEQ ID NO: 467) |

TABLE 8-2-continued

Site-Saturation Reverse Primer Sequences

| Residue | Primer | Primer Sequence |
|---|---|---|
| D106 | nsa307R | CGACATGCCCAGCGCGATSNNGAGCGGGGTGCGCCGGAA (SEQ ID NO: 468) |
| I107 | nsa308R | CACCGACATGCCCAGCGCSNNGTCGAGCGGGGTGCGCCG (SEQ ID NO: 469) |
| A108 | nsa309R | GAGCACCGACATGCCCAGSNNGATGTCGAGCGGGGTGCG (SEQ ID NO: 470) |
| L109 | nsa310R | GACGAGCACCGACATGCCSNNCGCGATGTCGAGCGGGGT (SEQ ID NO: 471) |
| G110 | nsa311R | CGTGACGAGCACCGACATSNNCAGCGCGATGTCGAGCGG (SEQ ID NO: 472) |
| M111 | nsa312R | CTGCGTGACGAGCACCGASNNGCCCAGCGCGATGTCGAG (SEQ ID NO: 473) |
| S112 | nsa313R | CACCTGCGTGACGAGCACSNNCATGCCCAGCGCGATGTC (SEQ ID NO: 474) |
| V113 | nsa314R | GAGCACCTGCGTGACGAGSNNCGACATGCCCAGCGCGAT (SEQ ID NO: 475) |
| L114 | nsa315R | GGTGAGCACCTGCGTGACSNNCACCGACATGCCCAGCGC (SEQ ID NO: 476) |
| V115 | nsa316R | GCTGGTGAGCACCTGCGTSNNGAGCACCGACATGCCCAG (SEQ ID NO: 477) |
| T116 | nsa317R | CGCGCTGGTGAGCACCTGSNNGACGAGCACCGACATGCC (SEQ ID NO: 478) |
| Q117 | nsa318R | GCCCGCGCTGGTGAGCACSNNCGTGACGAGCACCGACAT (SEQ ID NO: 479) |
| V118 | nsa319R | GCCGCCCGCGCTGGTGAGSNNCTGCGTGACGAGCACCGA (SEQ ID NO: 480) |
| L119 | nsa320R | GACGCCGCCCGCGCTGGTSNNCACCTGCGTGACGAGCAC (SEQ ID NO: 481) |
| T120 | nsa321R | GCCGACGCCGCCCGCGCTSNNGAGCACCTGCGTGACGAG (SEQ ID NO: 482) |
| S121 | nsa322R | GGTGCCGACGCCGCCCGCSNNGGTGAGCACCTGCGTGAC (SEQ ID NO: 483) |
| A122 | nsa323R | CGTGGTGCCGACGCCGCCSNNGCTGGTGAGCACCTGCGT (SEQ ID NO: 484) |
| G123 | nsa324R | GTACGTGGTGCCGACGCCSNNCGCGCTGGTGAGCACCTG (SEQ ID NO: 485) |
| G124 | nsa325R | CGGGTACGTGGTGCCGACSNNGCCCGCGCTGGTGAGCAC (SEQ ID NO: 486) |
| V125 | nsa198R | TGCCGGGTACGTGGTGCCSNNGCCGCCCGCGCTGGTGAG (SEQ ID NO: 487) |
| G126 | nsa327R | GGGTGCCGGGTACGTGGTSNNGACGCCGCCCGCGCTGGT (SEQ ID NO: 488) |
| T127 | nsa328R | CTTGGGTGCCGGGTACGTSNNGCCGACGCCGCCCGCGCT (SEQ ID NO: 489) |
| T128 | nsa329R | CACCTTGGGTGCCGGGTASNNGGTGCCGACGCCGCCCGC (SEQ ID NO: 490) |
| Y129 | nsa330R | CAGCACCTTGGGTGCCGGSNNCGTGGTGCCGACGCCGCC (SEQ ID NO: 491) |
| P130 | nsa331R | CACCAGCACCTTGGGTGCSNNGTACGTGGTGCCGACGCC (SEQ ID NO: 492) |

TABLE 8-2-continued

Site-Saturation Reverse Primer Sequences

| Residue | Primer | Primer Sequence |
|---|---|---|
| A131 | nsa332R | GACCACCAGCACCTTGGGSNNCGGGTACGTGGTGCCGAC (SEQ ID NO: 493) |
| P132 | nsa333R | CGAGACCACCAGCACCTTSNNTGCCGGGTACGTGGTGCC (SEQ ID NO: 494) |
| K133 | nsa334R | CGGCGAGACCACCAGCACSNNGGGTGCCGGGTACGTGGT (SEQ ID NO: 495) |
| V134 | nsa335R | TGGCGGCGAGACCACCAGSNNCTTGGGTGCCGGGTACGT (SEQ ID NO: 496) |
| L135 | nsa336R | CGGTGGCGGCGAGACCACSNNCACCTTGGGTGCCGGGTA (SEQ ID NO: 497) |
| V136 | nsa337R | CAGCGGTGGCGGCGAGACSNNCAGCACCTTGGGTGCCGG (SEQ ID NO :498) |
| V137 | nsa338R | CGCCAGCGGTGGCGGCGASNNCACCAGCACCTTGGGTGC (SEQ ID NO: 499) |
| S138 | nsa339R | GGGCGCCAGCGGTGGCGGSNNGACCACCAGCACCTTGGG (SEQ ID NO: 500) |
| P139 | nsa340R | CATGGGCGCCAGCGGTGGSNNCGAGACCACCAGCACCTT (SEQ ID NO: 501) |
| P140 | nsa341R | CGGCATGGGCGCCAGCGGSNNCGGCGAGACCACCAGCAC (SEQ ID NO: 502) |
| P141 | nsa342R | GTGCGGCATGGGCGCCAGSNNTGGCGGCGAGACCACCAG (SEQ ID NO: 503) |
| L142 | nsa343R | GGGGTGCGGCATGGGCGCSNNCGGTGGCGGCGAGACCAC (SEQ ID NO: 504) |
| A143 | nsa344R | CCAGGGGTGCGGCATGGGSNNCAGCGGTGGCGGCGAGAC (SEQ ID NO: 505) |
| P144 | nsa345R | GAACCAGGGGTGCGGCATSNNCGCCAGCGGTGGCGGCGA (SEQ ID NO: 506) |
| M145 | nsa346R | CTGGAACCAGGGGTGCGGSNNGGGCGCCAGCGGTGGCGG (SEQ ID NO: 507) |
| P146 | nsa178R | CAACTGGAACCAGGGGTGSNNCATGGGCGCCAGCGGTGG (SEQ ID NO: 508) |
| H147 | nsa348R | GATCAACTGGAACCAGGGSNNCGGCATGGGCGCCAGCGG (SEQ ID NO: 509) |
| P148 | nsa199R | GAAGATCAACTGGAACCASNNGTGCGGCATGGGCGCCAG (SEQ ID NO: 510) |
| W149 | nsa179R | CTCGAAGATCAACTGGAASNNGGGGTGCGGCATGGGCGC (SEQ ID NO: 511) |
| F150 | nsa180R | GCCCTCGAAGATCAACTGSNNCCAGGGGTGCGGCATGGG (SEQ ID NO: 512) |
| Q151 | nsa352R | GCCGCCCTCGAAGATCAASNNGAACCAGGGGTGCGGCAT (SEQ ID NO: 513) |
| L152 | nsa353R | CTCGCCGCCCTCGAAGATSNNCTGGAACCAGGGGTGCGG (SEQ ID NO: 514) |
| I153 | nsa200R | CTGCTCGCCGCCCTCGAASNNCAACTGGAACCAGGGGTG (SEQ ID NO: 515) |
| F154 | nsa201R | CTTCTGCTCGCCGCCCTCSNNGATCAACSNNCTGCTCGC CGCCCTCGAA (SEQ ID NO: 522) |
| T161 | nsa362R | CACGCGGGCGAGCTCAGTSNNCTTCTGCTCGCCGCCCTC (SEQ ID NO: 523) |

TABLE 8-2-continued

Site-Saturation Reverse Primer Sequences

| Residue | Primer | Primer Sequence |
|---|---|---|
| T162 | nsa363R | GTACACGCGGGCGAGCTCSNNGGTCTTCTGCTCGCCGCC (SEQ ID NO: 524) |
| E163 | nsa364R | GCTGTACACGCGGGCGAGSNNAGTGGTCTTCTGCTCGCC (SEQ ID NO: 525) |
| L164 | nsa365R | CGCGCTGTACACGCGGGCSNNCTCAGTGGTCTTCTGCTC (SEQ ID NO: 526) |
| A165 | nsa366R | GAGCGCGCTGTACACGCGSNNGAGCTCAGTGGTCTTCTG (SEQ ID NO: 527) |
| R166 | nsa367R | CGCGAGCGCGCTGTACACSNNGGCGAGCTCAGTGGTCTT (SEQ ID NO: 528) |
| V167 | nsa368R | CGACGCGAGCGCGCTGTASNNGCGGGCGAGCTCAGTGGT (SEQ ID NO: 529) |
| Y168 | nsa369R | GAACGACGCGAGCGCGCTSNNCACGCGGGCGAGCTCAGT (SEQ ID NO: 530) |
| S169 | nsa370R | CATGAACGACGCGAGCGCSNNGTACACGCGGGCGAGCTC (SEQ ID NO: 531) |
| A170 | nsa371R | CTTCATGAACGACGCGAGSNNGCTGTACACGCGGGCGAG (SEQ ID NO: 532) |
| L171 | nsa372R | CACCTTCATGAACGACGCSNNCGCGCTGTACACGCGGGC (SEQ ID NO: 533) |
| A172 | nsa373R | CGGCACCTTCATGAACGASNNGAGCGCGCTGTACACGCG (SEQ ID NO: 534) |
| S173 | nsa374R | GAACGGCACCTTCATGAASNNCGCGAGCGCGCTGTACAC (SEQ ID NO: 535) |
| F174 | nsa375R | GAAGAACGGCACCTTCATSNNCGACGCGAGCGCGCTGTA (SEQ ID NO: 536) |
| M175 | nsa376R | GTCGAAGAACGGCACCTTSNNGAACGACGCGAGCGCGCT (SEQ ID NO: 537) |
| K176 | nsa377R | CGCGTCGAAGAACGGCACSNNCATGAACGACGCGAGCGC (SEQ ID NO: 538) |
| V177 | nsa378R | ACCCGCGTCGAAGAACGGSNNCTTCATGAACGACGCGAG (SEQ ID NO: 539) |
| P178 | nsa379R | CGAACCCGCGTCGAAGAASNNCACCTTCATGAACGACGC (SEQ ID NO: 540) |
| F179 | nsa380R | CACCGAACCCGCGTCGAASNNCGGCACCTTCATGAACGA (SEQ ID NO: 541) |
| F180 | nsa381R | GATCACCGAACCCGCGTCSNNGAACGGCACCTTCATGAA (SEQ ID NO: 542) |
| D181 | nsa382R | GCTGATCACCGAACCCGCSNNGAAGAACGGCACCTTCAT (SEQ ID NO: 543) |
| A182 | nsa383R | GGTGCTGATCACCGAACCSNNGTCGAAGAACGGCACCTT (SEQ ID NO: 544) |
| G183 | nsa384R | GTCGGTGCTG ATCACCGASNNCGCGTCGAAGAACGGCAC (SEQ ID NO: 545) |
| S184 | nsa385R | GCCGTCGGTGCTGATCACSNNACCCGCGTCGAAGAACGG (SEQ ID NO: 546) |
| V185 | nsa386R | GACGCCGTCGGTGCTGATSNNCGAACCCGCGTCGAAGAA (SEQ ID NO: 547) |
| I186 | nsa387R | GTCGACGCCGTCGGTGCTSNNCACCGAACCCGCGTCGAA (SEQ ID NO: 548) |

TABLE 8-2-continued

Site-Saturation Reverse Primer Sequences

| Residue | Primer | Primer Sequence |
|---|---|---|
| S187 | nsa388R | TCCGTCGACGCCGTCGGTSNNGATCACCGAACCCGCGTC (SEQ ID NO: 549) |
| T188 | nsa389R | GATTCCGTCGACGCCGTCSNNGCTGATCACCGAACCCGC (SEQ ID NO: 550) |
| D189 | nsa390R | GTGGATTCCGTCGACGCCSNNGGTGCTGATCACCGAACC (SEQ ID NO: 551) |
| G190 | nsa391R | GAAGTGGATTCCGTCGACSNNGTCGGTGCTGATCACCGA (SEQ ID NO: 552) |
| V191 | nsa392R | GGTGAAGTGGATTCCGTCSNNGCCGTCGGTGCTGATCAC (SEQ ID NO: 553) |
| D192 | nsa393R | CTCGGTGAAGTGGATTCCSNNGACGCCGTCGGTGCTGAT (SEQ ID NO: 554) |
| G193 | nsa394R | GGCCTCGGTGAAGTGGATSNNGTCGACGCCGTCGGTGCT (SEQ ID NO: 555) |
| I194 | nsa181R | GTTGGCCTCGGTGAAGTGSNNTCCGTCGACGCCGTCGGT (SEQ ID NO: 556) |
| H195 | nsa396R | ATTGTTGGCCTCGGTGAASNNGATTCCGTCGACGCCGTC (SEQ ID NO: 557) |
| F196 | nsa182R | GCGATTGTTGGCCTCGGTSNNGTGGATTCCGTCGACGCC (SEQ ID NO: 558) |
| T197 | nsa398R | ATCGCGATTGTTGGCCTCSNNGAAGTGGATTCCGTCGAC (SEQ ID NO: 559) |
| E198 | nsa399R | GAGATCGCGATTGTTGGCSNNGGTGAAGTGGATTCCGTC (SEQ ID NO: 560) |
| A199 | nsa400R | CCCGAGATCGCGATTGTTSNNCTCGGTGAAGTGGATTCC (SEQ ID NO: 561) |
| N200 | nsa401R | CACCCCGAGATCGCGATTSNNGGCCTCGGTGAAGTGGAT (SEQ ID NO: 562) |
| N201 | nsa402R | GGCCACCCCGAGATCGCGSNNGTTGGCCTCGGTGAAGTG (SEQ ID NO: 563) |
| R202 | nsa403R | GAGGGCCACCCCGAGATCSNNATTGTTGGCCTCGGTGAA (SEQ ID NO: 564) |
| D203 | nsa404R | CGCGAGGGCCACCCCGAGSNNGCGATTGTTGGCCTCGGT (SEQ ID NO: 565) |
| L204 | nsa405R | TTCCGCGAGGGCCACCCCSNNATCGCGATTGTTGGCCTC (SEQ ID NO: 566) |
| G205 | nsa406R | CTGTTCCGCGAGGGCCACSNNGAGATCGCGATTGTTGGC (SEQ ID NO: 567) |
| V206 | nsa407R | CACCTGTTCCGCGAGGGCSNNCCCGAGATCGCGATTGTT (SEQ ID NO: 568) |
| A207 | nsa408R | CTGCACCTGTTCCGCGAGSNNCACCCCGAGATCGCGATT (SEQ ID NO: 569) |
| L208 | nsa409R | GCTCTGCACCTGTTCCGCSNNGGCCACCCCGAGATCGCG (SEQ ID NO: 570) |
| A209 | nsa410R | CAGGCTCTGCACCTGTTCSNNGAGGGCCACCCCGAGATC (SEQ ID NO: 571) |
| E210 | nsa411R | CAGCAGGCTCTGCACCTGSNNCGCGAGGGCCACCCCGAG (SEQ ID NO: 572) |
| Q211 | nsa412R | TTACAGCAGGCTCTGCACSNNTTCCGCGAGGGCCACCCC (SEQ ID NO: 573) |

TABLE 8-2-continued

Site-Saturation Reverse Primer Sequences

| Residue | Primer | Primer Sequence |
|---------|--------|-----------------|
| V212 | nsa413R | CTTTTACAGCAGGCTCTGSNNCTGTTCCGCGAGGGCCAC (SEQ ID NO: 574) |
| Q213 | nsa414R | GCCCTTTTACAGCAGGCTSNNCACCTGTTCCGCGAGGGC (SEQ ID NO: 575) |
| S214 | nsa415R | TTCGCCCTTTTACAGCAGSNNCTGCACCTGTTCCGCGAG (SEQ ID NO: 576) |
| L215 | nsa416R | GAATTCGCCCTTTTACAGSNNGCTCTGCACCTGTTCCGC (SEQ ID NO: 577) |
| L216 | nsa417R | GCAGAATTCGCCCTTTTASNNCAGGCTCTGCACCTGTTC (SEQ ID NO: 578) |

QC Method to Create Site-Saturation Libraries

The QC reaction consisted of 40.25 µL of sterile distilled H$_2$O, 5 µL of PfuTurbo 10× buffer from the kit, 1 µl dNTPs from the kit, 1.25 µL of forward primer (100 ng/µL), 1.25 µL reverse primer (100 ng/µL), 0.25 µL of pMSAT-NcoI miniprep DNA as template (~50 ng), and 1 µL of PfuTurbo from the kit, for a total of 50 µL. The cycling conditions were 95° C. for 1 min, once, followed by 1920 cycles of 95° C. for 30 to 45 sec, 55° C. for 1 min, and 68° C. for 5 to 8 min. To analyze the reaction, 5 µL of the reaction was run on a 0.8% E-gel (Invitrogen) upon completion. Next, DpnI digestion was carried out twice sequentially, with 1 µL and 0.5 µL of enzyme at 37° C. for 2 to 8 hours. A negative control was carried out under similar conditions, but without any primers. Then, 1 µL of the DpnI-digested reaction product was transformed into 50 µL of one-shot TOP10 electrocompetent cells (Invitrogen) using a BioRad electroporator. Then, 300 µL of SOC provided with the TOP10 cells (Invitrogen) were added to the electroporated cells and incubated with shaking for 1 hour before plating on LA plates containing 10 ppm kanamycin. The plates were incubated at 37° C. overnight. After this incubation, 96 colonies from each of the libraries (i.e., each site) were inoculated in 200 µL of LB containing 10-50 ppm of kanamycin in 96-well microtiter plates. The plates were frozen at −80° C. after addition of glycerol to 20% final concentration; and they were used for high throughput sequencing at Genaissance with the M13F and M13R primers.

QCMS Method to Create Site-Saturation Libraries

The QCMS reaction consisted of 19.25 µL of sterile distilled H$_2$O, 2.5 µL of 10× buffer from the kit, 1 µL dNTPs from the kit, 1 µL of 5' phosphorylated forward primer (100 ng/µL), 0.25 µL of pMSAT-NcoI miniprep DNA as template (~50 ng), and 1 µL of the enzyme blend from the kit for a total of 25 µL. The cycling conditions were 95° C. for 1 min once, followed by 30 cycles of 95° C. for 1 min, 55° C. for 1 min, and 68° C. for 8 min. To analyze the reaction product, 5 µL of the reaction were run on a 0.8% E-gel (Invitrogen) upon completion. Next, DpnI digestion was carried out twice sequentially, with 0.5 µL of enzyme at 37° C. for 2 to 8 hours. The controls, transformation, and sequencing was performed as for the QC method described above.

Details of Screening Plate Preparation

Using a sterilized stamping tool with 96 pins, the frozen clones from each sequenced library plate were stamped on to a large LA plate containing 10 ppm kanamycin. The plate was then incubated overnight at 37° C. Individual mutant clones each representing each one of the 19 substitutions (or as many that were obtained) were inoculated into a Costar 96-well plate containing 195 µL of LB made with 2 fold greater yeast extract and 10 ppm kanamycin. Each mutant clone for a given site was inoculated in quadruplicate. The plate was grown at 37° C. and 225 rpm shaking for 18 hrs in a humidified chamber. In a separate 96-well plate, 26 µL of BugBuster (Novagen) with DNase were added to each well. Next, 125 µL of the library clone cultures were added to the BugBuster-containing plate in corresponding wells and the plate was frozen at −80° C. The plate was thawed, frozen and thawed again before use of the lysates in the peracid formation and peracid hydrolysis assays described herein.

Combinatorial Libraries and Mutants

From the screening of the single site-saturation libraries, the important sites and substitutions were identified and combined in different combinatorial libraries. For example, libraries described in Table 8-3 were created using the following sites and substitutions:

L12C, Q, G
T25S, G, P
L53H, Q, G, S
S54V, L, A, P, T, R
A55G, T
R67T, Q, N, G, E, L, F
K97R
V125S, G, R, A, P
F154Y
F196G

TABLE 8-3

Libraries

| Library | Description | Parent Template | Method |
|---------|-------------|-----------------|--------|
| NSAA1 | L12G S54(NNS) | L12G | QC |
| NSAA2 | S54V L12(NNS) | S54V | QC |
| NSAA3 | L12(NNS) S54(NNS) | WT | QCMS |
| NSAB1 | S54V T25(NNS) | S54V | QC |
| NSAB2 | S54V R67(NNS) | S54V | QC |
| NSAB3 | S54V V125(NNS) | S54V | QC |
| NSAB4 | L12I S54V T25(NNS) | L12I S54V | QC |
| NSAB5 | L12I S54V R67(NNS) | L12I S54V | QC |
| NSAB6 | L12I S54V V125(NNS) | L12I S54V | QC |
| NSAC1 | S54(NNS) R67(NNS) V125(NNS) | WT | QCMS |
| NSAC2 | 43 primer library; 10 sites (100 ng total primers) | S54V | QCMS |

TABLE 8-3-continued

Libraries

| Library | Description | Parent Template | Method |
|---|---|---|---|
| NSAC3 | same as nsaC2 but 300 ng total primers | S54V | QCMS |
| NSAC4 | 32 primer library, 8 sites (100 ng total primers) | S54V | QCMS |
| NSAC5 | same as nsaC4 but 300 ng total primers | S54V | QCMS |
| NSAC6 | 8 primers, 7 substitutions, 5 sites (100 ng total primers) | S54V | QCMS |
| NSAC7 | same as nsaC6 but 300 ng total primers | S54V | QCMS |

*NNS indicates site-saturation library
**All parent templates were derived from the pMSAT-NcoI plasmid and contained mutations at the indicated codons with in the *M. smegmatis* perhydrolase gene The QC or QCMS methods were used to create the combinations. The QC reaction was carried out as described above, with the exception being the template plasmid, which consisted of 0.25 μL of miniprep DNA of the L12G mutant, S54V mutant, or the L12I S54V double mutant plasmid derived from pMSAT-NcoI. The QCMS reaction was also carried out as described above, with the exception of template and primers. In this case, 0.25 μL of the pMSAT-NcoI template were used for NSAC1 and NSAA3 or S54V template for $NSAC_2$-$C_7$ libraries. The NSAA3 and the NSAC1 libraries were made using 100 ng of each of the primers shown in the Table 8-4. The NSAC2, NSAC4, and NSAC6 libraries were made with a total of 100 ng of all primers (all primers being equimolar), and NSAC3, NSAC5, NSAC7 libraries were made with a total of 300 ng of all primers (all primers being approximately equimolar)

TABLE 8-4

Libraries

| Libraries | Primer Name | Primer Sequence | |
|---|---|---|---|
| NSAC1 | S54NNS-FP | gtgatcgaggagggactgnnsgcgcgcaccaccaacatc | (SEQ ID NO: 579) |
| NSAC1 | R67NNS-FP | acgaccccaccgatccgnnsctcaacggcgcgagctac | (SEQ ID NO: 580) |
| NSAC1 | V125NNS-FP | ctcaccagcgcgggcggcnnsggcaccacgtacccggca | (SEQ ID NO: 581) |
| NSAC2-C5 | L12C | ctgtgtttcggtgattccTGCacctggggctgggtcccc | (SEQ ID NO: 582) |
| NSAC2-C7 | L12Q | ctgtgtttcggtgattccCAGacctggggctgggtcccc | (SEQ ID NO: 583) |
| NSAC2-C5 | L12I | ctgtgtttcggtgattccATCacctggggctgggtcccc | (SEQ ID NO: 584) |
| NSAC2-C3 | L12M | ctgtgtttcggtgattccATGacctggggctgggtcccc | (SEQ ID NO: 585) |
| NSAC2-C3 | L12T | ctgtgtttcggtgattccACGacctggggctgggtcccc | (SEQ ID NO: 586) |
| NSAC2-C5 | T25S | gtcgaagacggggcacccAGCgagcggttcgcccccgac | (SEQ ID NO: 587) |
| NSAC2-C5 | T25G | gtcgaagacggggcacccGGCgagcggttcgcccccgac | (SEQ ID NO: 588) |
| NSAC2-C3 | T25P | gtcgaagacggggcacccCCGgagcggttcgcccccgac | (SEQ ID NO: 589) |
| NSAC2-C7 | L53H | gaggtgatcgaggagggaCACagcgcgcgcaccaccaac | (SEQ ID NO: 590) |
| NSAC2-C3 | L53Q | gaggtgatcgaggagggaCAGagcgcgcgcaccaccaac | (SEQ ID NO: 591) |
| NSAC2-C3 | L53G | gaggtgatcgaggagggaGGCagcgcgcgcaccaccaac | (SEQ ID NO: 592) |
| NSAC2-C3 | L53S | gaggtgatcgaggagggaAGCagcgcgcgcaccaccaac | (SEQ ID NO: 593) |
| NSAC2-C7 | L53HS54V | gaggtgatcgaggagggaCACGTGgcgcgcaccaccaac | (SEQ ID NO: 594) |
| NSAC2-C3 | L53QS54V | gaggtgatcgaggagggaCAGGTGgcgcgcaccaccaac | (SEQ ID NO: 595) |
| NSAC2-C3 | L53GS54V | gaggtgatcgaggagggaGGCGTGgcgcgcaccaccaac | (SEQ ID NO: 596) |
| NSAC2-C3 | L53SS54V | gaggtgatcgaggagggaAGCGTGgcgcgcaccaccaac | (SEQ ID NO: 597) |
| NSAC2-C7 | S54V | gtgatcgaggagggactgGTGgcgcgcaccaccaacatc | (SEQ ID NO: 598) |
| NSAC2-C5 | S54L | gtgatcgaggagggactgCTGgcgcgcaccaccaacatc | (SEQ ID NO: 599) |
| NSAC2-C5 | A55G | atcgaggagggactgagcGGCcgcaccaccaacatcgac | (SEQ ID NO: 600) |
| NSAC2-C5 | A55T | atcgaggagggactgagcACGcgcaccaccaacatcgac | (SEQ ID NO: 601) |
| NSAC2-C5 | A55GS54V | atcgaggagggactgGTGGGCcgcaccaccaacatcgac | (SEQ ID NO: 602) |
| NSAC2-C5 | A55TS54V | atcgaggagggactgGTGACGcgcaccaccaacatcgac | (SEQ ID NO: 603) |
| NSAC2-C5 | R67T | gacgaccccaccgatccgACGctcaacggcgcgagctac | (SEQ ID NO: 604) |

TABLE 8-4-continued

Libraries

| Libraries | Primer Name | Primer Sequence |
|---|---|---|
| NSAC2-C5 | R67Q | gacgacccaccgatccgCAGctcaacggcgcgagctac (SEQ ID NO: 605) |
| NSAC2-C7 | R67N | gacgacccaccgatccgAACctcaacggcgcgagctac (SEQ ID NO: 606) |
| NSAC2-C5 | K97R | ctgggcaccaacgacaccCGCgcctacttccggcgcacc (SEQ ID NO: 607) |
| NSAC2-C5 | V125S | ctcaccagcgcgggcggcAGCggcaccacgtacccggca (SEQ ID NO: 608) |
| NSAC2-C7 | V125G | ctcaccagcgcgggcggcGGCggcaccacgtacccggca (SEQ ID NO: 609) |
| NSAC2-C5 | V125R | ctcaccagcgcgggcggcCGCggcaccacgtacccggca (SEQ ID NO: 610) |
| NSAC2-C5 | V125A | ctcaccagcgcgggcggcGCGggcaccacgtacccggca (SEQ ID NO: 611) |
| NSAC2-C5 | V125P | ctcaccagcgcgggcggcCCGggcaccacgtacccggca (SEQ ID NO: 612) |
| NSAC2-C3 | F154Y | ccctggttccagttgatcTACgagggcggcgagcagaag (SEQ ID NO: 613) |
| NSAC2-C3 | F196G | ggcgtcgacggaatccacGGCaccgaggccaacaatcgc (SEQ ID NO: 614) |
| NSAC2-C7 | R67G-re | gacgacccaccgatccgGGCctcaacggcgcgagctac (SEQ ID NO: 615) |
| NSAC2-C5 | R67E-re | gacgacccaccgatccgGAGctcaacggcgcgagctac (SEQ ID NO: 616) |
| NSAC2-C5 | R67F-re | gacgacccaccgatccgTTCctcaacggcgcgagctac (SEQ ID NO: 617) |
| NSAC2-C5 | R67L-re | gacgacccaccgatccgCTGctcaacggcgcgagctac (SEQ ID NO: 618) |
| NSAC2-C5 | S54P | gtgatcgaggagggactgCCGgcgcgcaccaccaacatc (SEQ ID NO: 619) |
| NSAC2-C5 | S54R | gtgatcgaggagggactgCGCgcgcgcaccaccaacatc (SEQ ID NO: 620) |
| NSAC2-C5 | S54G | gtgatcgaggagggactgGGCgcgcgcaccaccaacatc (SEQ ID NO: 621) |
| NSAC2-C5 | S54T | gtgatcgaggagggactgACGgcgcgcaccaccaacatc (SEQ ID NO: 622) |
| NSAC2-C7 | S54I | gtgatcgaggagggactgATCgcgcgcaccaccaacatc (SEQ ID NO: 623) |
| NSAC2-C5 | S54K | gtgatcgaggagggactgAAGgcgcgcaccaccaacatc (SEQ ID NO: 624) |

Screening of Combinatorial Libraries and Mutants

For each of the NSAB1-B6 libraries, a 96-well plate full of clones was first sequenced. Once the sequencing results were analyzed, the mutants obtained for each library were inoculated in quadruplicate, similar to the site-saturation libraries described above. For the NSAC$_1$-C$_7$ libraries, 96 colonies per/plate/library were initially inoculated, and each plate was screened without sequencing. Upon screening, some libraries looked better than others. Several plates for each of the NSAC1, C2, C4, C6 libraries were screened. The "winners" from these single isolate screening plates were then streaked out for singles or directly screened in quadruplicate just like the site saturation libraries (i.e., as described above). Only the "winners" identified were sequenced.

Example 9

Improved Properties of Multiply Mutated Perhydrolase Variants

In this Example, experiments conducted to assess the properties of multiply-mutated perhydrolase variants are described. In these experiments, combinatorial mutants obtained from combinatorial libraries were tested in their performance in perhydrolysis, peracid hydrolysis and perhydrolysis to hydrolysis ratio. These parameters were measured in the HPLC or ABTS assays described in Example 2, above. Combinatorial variants tested were:

L12I S54V,
L12M S54T,
L12T S54V,
L12Q T25S S54V,
L53H S54V,
S54P V125R,
S54V V125G,
S54V F196G,
S54V K97R V125G, and
A55G R67T K97R V125G, As is indicated in Table 9-1 below, all of these variants were better than wild type enzyme in at least one of the properties of interest.

TABLE 9-1

Results for Multiple Variants

| Multiple Variant | Fold-Improvement in Property | | |
|---|---|---|---|
| | Perhydrolysis | Peracid Hydrolysis | Ratio |
| L12I S54V | 2 | 2.5 | |
| L12M S54T | 1.6 | 3 | |
| L12T S54V | 1.5 | 2.5 | |
| L12Q T25S S54V | | | 4 to 5 |

TABLE 9-1-continued

Results for Multiple Variants

| Multiple Variant | Fold-Improvement in Property | | |
|---|---|---|---|
| | Perhydrolysis | Peracid Hydrolysis | Ratio |
| L53H S54V | 2 | | 4 to 5 |
| S54P V125R | | | 4 |
| S54V V125G | 2 | | 4 |
| S54V F196G | | | 2 |
| S54V K97R V125G | 2 | | |
| A55G R67T K97R V125G | 1.6 | | 4 to 5 |

Example 10

PAF and PAD Assays of Perhydrolase Variants

In this Example, assay results for PAF and PAD testing of perhydrolase variants are provided. The tests were conducted as described in Example 1, above. In addition, Tables are provided in which the protein expression of the variant was greater than wild-type under the same culture conditions (described herein). These results are indicated as the "protein performance index." Thus, a number greater than "1" in the protein performance index indicates that more protein was made for the particular variant than the wild-type. In the following Tables, "WT" indicates the wild-type amino acid residue; "Pos" indicates the position in the amino acid sequence; "Mut." and "Var" indicate the amino acid residue substituted at that particular position; "prot." indicates "protein; and "Perf. Ind" indicates the performance index.

TABLE 10-1

PAF Assay Results

| Position | WT/Pos/Mutation | Variant | PAF Perf. Ind. |
|---|---|---|---|
| 3 | K003Y | Y | 1.058244 |
| 3 | K003I | I | 1.053242 |
| 3 | K003L | L | 1.038686 |
| 3 | K003T | T | 1.009071 |
| 3 | K003H | H | 1.00528 |
| 4 | R004Q | Q | 1.025332 |
| 5 | I005T | T | 1.12089 |
| 5 | I005S | S | 1.023576 |
| 6 | L006V | V | 1.072388 |
| 6 | L006I | I | 1.066182 |
| 6 | L006T | T | 1.062078 |
| 7 | C007K | K | 2.687956 |
| 7 | C007Y | Y | 2.08507 |
| 7 | C007I | I | 1.758096 |
| 7 | C007H | H | 1.731475 |
| 7 | C007A | A | 1.423943 |
| 7 | C007G | G | 1.393781 |
| 7 | C007M | M | 1.126028 |
| 10 | D010L | L | 3.97014 |
| 10 | D010W | W | 3.179778 |
| 10 | D010K | K | 2.133852 |
| 10 | D010Y | Y | 1.508981 |
| 10 | D010T | T | 1.473387 |
| 10 | D010I | I | 1.281927 |
| 12 | L012Q | Q | 2.651732 |
| 12 | L012C | C | 2.289224 |
| 12 | L012A | A | 1.100171 |
| 15 | G015A | A | 1.543799 |
| 15 | G015S | S | 1.05273 |
| 17 | V017G | G | 1.173641 |
| 17 | V017R | R | 1.09735 |
| 17 | V017A | A | 1.012116 |
| 18 | P018Y | Y | 1.332844 |
| 18 | P018N | N | 1.331062 |
| 18 | P018C | C | 1.261104 |
| 18 | P018E | E | 1.217708 |
| 18 | P018V | V | 1.185736 |
| 18 | P018R | R | 1.16328 |
| 18 | P018Q | Q | 1.124133 |
| 18 | P018H | H | 1.120443 |
| 18 | P018G | G | 1.068272 |
| 19 | V019G | G | 1.317001 |
| 19 | V019S | S | 1.235759 |
| 19 | V019R | R | 1.025471 |
| 19 | V019L | L | 1.002833 |
| 21 | D021K | K | 1.062138 |
| 21 | D021W | W | 1.040173 |
| 22 | G022A | A | 1.554264 |
| 22 | G022T | T | 1.032118 |
| 22 | G022S | S | 1.022133 |
| 25 | T025G | G | 1.857878 |
| 25 | T025S | S | 1.59954 |
| 25 | T025A | A | 1.327579 |
| 25 | T025I | I | 1.019417 |
| 26 | E026M | M | 2.002044 |
| 26 | E026A | A | 1.927099 |
| 26 | E026R | R | 1.484814 |
| 26 | E026K | K | 1.464368 |
| 26 | E026T | T | 1.441939 |
| 26 | E026C | C | 1.403045 |
| 26 | E026V | V | 1.392881 |
| 26 | E026N | N | 1.366419 |
| 26 | E026H | H | 1.329562 |
| 26 | E026L | L | 1.295378 |
| 26 | E026G | G | 1.283477 |
| 26 | E026S | S | 1.271403 |
| 26 | E026W | W | 1.251752 |
| 27 | R027K | K | 1.215697 |
| 28 | F028M | M | 1.331874 |
| 28 | F028A | A | 1.269493 |
| 28 | F028W | W | 1.156698 |
| 28 | F028L | L | 1.08849 |
| 28 | F028S | S | 1.046063 |
| 29 | A029W | W | 1.912244 |
| 29 | A029V | V | 1.799733 |
| 29 | A029R | R | 1.757225 |
| 29 | A029Y | Y | 1.697554 |
| 29 | A029G | G | 1.595061 |
| 29 | A029S | S | 1.486877 |
| 29 | A029T | T | 1.424584 |
| 29 | A029E | E | 1.115768 |
| 29 | A029C | C | 1.07522 |
| 30 | P030K | K | 1.207673 |
| 30 | P030R | R | 1.164892 |
| 30 | P030V | V | 1.063047 |
| 30 | P030T | T | 1.05383 |
| 30 | P030A | A | 1.045476 |
| 30 | P030S | S | 1.031747 |
| 30 | P030Q | Q | 1.013468 |
| 30 | P030H | H | 1.012332 |
| 30 | P030E | E | 1.006761 |
| 31 | D031W | W | 1.834044 |
| 31 | D031L | L | 1.810564 |
| 31 | D031T | T | 1.450556 |
| 31 | D031G | G | 1.441703 |
| 31 | D031F | F | 1.438268 |
| 31 | D031N | N | 1.339422 |
| 31 | D031V | V | 1.280091 |
| 31 | D031A | A | 1.240923 |
| 31 | D031R | R | 1.222181 |
| 31 | D031S | S | 1.152736 |
| 31 | D031E | E | 1.132795 |
| 31 | D031Q | Q | 1.069797 |
| 32 | V032K | K | 1.08606 |
| 32 | V032R | R | 1.045435 |
| 33 | R033S | S | 1.000491 |

TABLE 10-1-continued

PAF Assay Results

| Position | WT/Pos/Mutation | Variant | PAF Perf. Ind. |
|---|---|---|---|
| 36 | G036I | I | 1.320156 |
| 36 | G036K | K | 1.265563 |
| 36 | G036L | L | 1.237473 |
| 38 | L038L | L | 6.528092 |
| 38 | L038V | V | 5.735873 |
| 38 | L038C | C | 4.182031 |
| 38 | L038K | K | 4.135067 |
| 38 | L038A | A | 3.844719 |
| 38 | L038S | S | 2.467764 |
| 40 | Q040K | K | 2.613726 |
| 40 | Q040I | I | 2.576806 |
| 40 | Q040W | W | 2.394926 |
| 40 | Q040L | L | 2.144687 |
| 40 | Q040T | T | 2.006487 |
| 40 | Q040R | R | 1.885154 |
| 40 | Q040Y | Y | 1.825366 |
| 40 | Q040G | G | 1.785768 |
| 40 | Q040S | S | 1.565973 |
| 40 | Q040N | N | 1.528677 |
| 40 | Q040D | D | 1.16151 |
| 40 | Q040E | E | 1.075259 |
| 41 | Q041K | K | 1.381385 |
| 41 | Q041R | R | 1.190317 |
| 41 | Q041W | W | 1.141041 |
| 41 | Q041H | H | 1.123719 |
| 41 | Q041S | S | 1.107641 |
| 41 | Q041Y | Y | 1.091652 |
| 41 | Q041V | V | 1.070265 |
| 41 | Q041A | A | 1.032945 |
| 41 | Q041L | L | 1.000416 |
| 42 | L042K | K | 2.463086 |
| 42 | L042W | W | 2.056507 |
| 42 | L042H | H | 1.917245 |
| 42 | L042R | R | 1.378137 |
| 42 | L042G | G | 1.172748 |
| 42 | L042T | T | 1.079826 |
| 42 | L042F | F | 1.072948 |
| 43 | G043A | A | 1.49082 |
| 43 | G043C | C | 1.47701 |
| 43 | G043K | K | 1.424919 |
| 43 | G043M | M | 1.371202 |
| 43 | G043Y | Y | 1.262703 |
| 43 | G043E | E | 1.250311 |
| 43 | G043L | L | 1.216516 |
| 43 | G043R | R | 1.215829 |
| 43 | G043S | S | 1.178103 |
| 43 | G043H | H | 1.169457 |
| 43 | G043P | P | 1.080176 |
| 44 | A044F | F | 2.84399 |
| 44 | A044V | V | 2.133682 |
| 44 | A044C | C | 1.796096 |
| 44 | A044L | L | 1.607918 |
| 44 | A044W | W | 1.395243 |
| 44 | A044M | M | 1.199028 |
| 45 | D045K | K | 1.342858 |
| 45 | D045T | T | 1.268367 |
| 45 | D045R | R | 1.158768 |
| 45 | D045W | W | 1.145157 |
| 45 | D045S | S | 1.133098 |
| 45 | D045G | G | 1.12761 |
| 45 | D045H | H | 1.127539 |
| 45 | D045F | F | 1.11152 |
| 45 | D045L | L | 1.054441 |
| 45 | D045V | V | 1.050576 |
| 45 | D045Q | Q | 1.04498 |
| 45 | D045A | A | 1.037993 |
| 46 | F046E | E | 1.247552 |
| 46 | F046D | D | 1.174794 |
| 46 | F046G | G | 1.016913 |
| 46 | F046K | K | 1.003326 |
| 47 | E047R | R | 2.448525 |
| 47 | E047T | T | 1.960505 |
| 47 | E047P | P | 1.361173 |
| 47 | E047S | S | 1.278809 |
| 47 | E047H | H | 1.266229 |
| 47 | E047G | G | 1.197541 |
| 47 | E047K | K | 1.19183 |
| 47 | E047F | F | 1.092281 |
| 47 | E047I | I | 1.030029 |
| 49 | I049G | G | 1.342918 |
| 49 | I049H | H | 1.265204 |
| 49 | I049S | S | 1.238211 |
| 49 | I049K | K | 1.230871 |
| 49 | I049V | V | 1.203314 |
| 49 | I049L | L | 1.136805 |
| 49 | I049Y | Y | 1.068104 |
| 49 | I049R | R | 1.052285 |
| 49 | I049E | E | 1.015762 |
| 49 | I049M | M | 1.00526 |
| 50 | E050L | L | 1.191901 |
| 50 | E050M | M | 1.178039 |
| 50 | E050A | A | 1.124087 |
| 51 | E051V | V | 1.471315 |
| 51 | E051A | A | 1.279983 |
| 51 | E051G | G | 1.217963 |
| 51 | E051T | T | 1.182792 |
| 51 | E051L | L | 1.112889 |
| 51 | E051I | I | 1.072835 |
| 53 | L053H | H | 5.05321 |
| 53 | L053Q | Q | 1.480206 |
| 53 | L053G | G | 1.317357 |
| 53 | L053S | S | 1.161011 |
| 53 | L053T | T | 1.019146 |
| 54 | S054P | P | 5.198689 |
| 54 | S054I | I | 4.775938 |
| 54 | S054V | V | 4.722033 |
| 54 | S054A | A | 3.455902 |
| 54 | S054R | R | 3.375793 |
| 54 | S054L | L | 2.015828 |
| 54 | S054T | T | 1.459971 |
| 54 | S054K | K | 1.438715 |
| 54 | S054G | G | 1.429605 |
| 54 | S054C | C | 1.259773 |
| 54 | S054Q | Q | 1.03365 |
| 55 | A055G | G | 1.694814 |
| 55 | A055T | T | 1.692885 |
| 57 | T057S | S | 1.633613 |
| 57 | T057R | R | 1.605072 |
| 57 | T057V | V | 1.281788 |
| 57 | T057I | I | 1.189062 |
| 59 | N059W | W | 1.035044 |
| 59 | N059R | R | 1.002315 |
| 60 | I060H | H | 1.02415 |
| 60 | I060R | R | 1.003947 |
| 61 | D061H | H | 1.439407 |
| 61 | D061S | S | 1.259714 |
| 61 | D061R | R | 1.105425 |
| 61 | D061I | I | 1.076937 |
| 61 | D061F | F | 1.00566 |
| 62 | D062E | E | 1.019293 |
| 63 | P063G | G | 1.709657 |
| 63 | P063T | T | 1.499483 |
| 63 | P063M | M | 1.460336 |
| 63 | P063S | S | 1.416192 |
| 63 | P063K | K | 1.404615 |
| 63 | P063A | A | 1.347541 |
| 63 | P063Y | Y | 1.346046 |
| 63 | P063W | W | 1.34587 |
| 63 | P063V | V | 1.313631 |
| 63 | P063R | R | 1.310696 |
| 63 | P063F | F | 1.246299 |
| 63 | P063L | L | 1.146416 |
| 63 | P063Q | Q | 1.093179 |
| 64 | T064G | G | 1.234467 |
| 64 | T064S | S | 1.114348 |
| 65 | D065A | A | 1.312312 |
| 65 | D065S | S | 1.166849 |
| 65 | D065H | H | 1.096335 |

TABLE 10-1-continued

PAF Assay Results

| Position | WT/Pos/Mutation | Variant | PAF Perf. Ind. |
|---|---|---|---|
| 66 | P066R | R | 1.846257 |
| 66 | P066V | V | 1.828926 |
| 66 | P066H | H | 1.589631 |
| 66 | P066I | I | 1.588219 |
| 66 | P066G | G | 1.499901 |
| 66 | P066Q | Q | 1.463705 |
| 66 | P066T | T | 1.410091 |
| 66 | P066S | S | 1.390845 |
| 66 | P066Y | Y | 1.330685 |
| 66 | P066L | L | 1.137635 |
| 66 | P066N | N | 1.122261 |
| 67 | R067N | N | 1.580401 |
| 67 | R067G | G | 1.390129 |
| 67 | R067T | T | 1.284643 |
| 67 | R067F | F | 1.25763 |
| 67 | R067L | L | 1.203316 |
| 67 | R067Q | Q | 1.164899 |
| 67 | R067W | W | 1.066028 |
| 67 | R067E | E | 1.044676 |
| 67 | R067P | P | 1.012761 |
| 68 | L068E | E | 1.435218 |
| 68 | L068W | W | 1.209193 |
| 68 | L068I | I | 1.125898 |
| 68 | L068G | G | 1.092454 |
| 68 | L068V | V | 1.088042 |
| 68 | L068H | H | 1.051612 |
| 68 | L068T | T | 1.032331 |
| 69 | N069V | V | 1.989028 |
| 69 | N069K | K | 1.71908 |
| 69 | N069R | R | 1.493163 |
| 69 | N069I | I | 1.469946 |
| 69 | N069H | H | 1.357968 |
| 69 | N069T | T | 1.351305 |
| 69 | N069L | L | 1.299547 |
| 69 | N069S | S | 1.205171 |
| 69 | N069G | G | 1.19653 |
| 69 | N069Q | Q | 1.074622 |
| 69 | N069W | W | 1.049602 |
| 69 | N069C | C | 1.048373 |
| 71 | A071S | S | 1.751794 |
| 71 | A071T | T | 1.700442 |
| 71 | A071H | H | 1.697558 |
| 71 | A071G | G | 1.58881 |
| 71 | A071I | I | 1.507841 |
| 71 | A071E | E | 1.445699 |
| 71 | A071K | K | 1.441146 |
| 71 | A071R | R | 1.401499 |
| 71 | A071N | N | 1.232241 |
| 71 | A071L | L | 1.231991 |
| 71 | A071F | F | 1.127538 |
| 71 | A071C | C | 1.00977 |
| 72 | S072L | L | 1.257945 |
| 72 | S072H | H | 1.208899 |
| 72 | S072G | G | 1.198197 |
| 72 | S072T | T | 1.10065 |
| 72 | S072V | V | 1.080089 |
| 72 | S072Y | Y | 1.066178 |
| 73 | Y073R | R | 1.2555 |
| 73 | Y073Q | Q | 1.23429 |
| 73 | Y073S | S | 1.165683 |
| 73 | Y073K | K | 1.070678 |
| 76 | S076P | P | 1.229172 |
| 77 | C077T | T | 1.120603 |
| 77 | C077V | V | 1.052586 |
| 77 | C077G | G | 1.013806 |
| 78 | L078G | G | 4.975852 |
| 78 | L078H | H | 4.824004 |
| 78 | L078E | E | 3.007159 |
| 78 | L078N | N | 2.683604 |
| 78 | L078T | T | 1.867711 |
| 78 | L078Q | Q | 1.726942 |
| 78 | L078V | V | 1.534239 |
| 78 | L078I | I | 1.434206 |
| 78 | L078Y | Y | 1.387889 |
| 79 | A079H | H | 1.927914 |
| 79 | A079L | L | 1.796126 |
| 79 | A079I | I | 1.592463 |
| 79 | A079M | M | 1.499635 |
| 79 | A079N | N | 1.475806 |
| 79 | A079Q | Q | 1.472484 |
| 79 | A079R | R | 1.465943 |
| 79 | A079W | W | 1.270538 |
| 79 | A079T | T | 1.169146 |
| 79 | A079E | E | 1.123457 |
| 80 | T080C | C | 1.310752 |
| 80 | T080V | V | 1.230659 |
| 80 | T080G | G | 1.160318 |
| 80 | T080A | A | 1.000722 |
| 82 | L082P | P | 1.456374 |
| 82 | L082G | G | 1.379439 |
| 82 | L082R | R | 1.339485 |
| 82 | L082H | H | 1.332844 |
| 82 | L082K | K | 1.1909 |
| 82 | L082T | T | 1.17992 |
| 82 | L082I | I | 1.171013 |
| 82 | L082S | S | 1.153417 |
| 82 | L082V | V | 1.019854 |
| 83 | P083K | K | 1.369406 |
| 83 | P083G | G | 1.313431 |
| 83 | P083H | H | 1.265876 |
| 83 | P083R | R | 1.194464 |
| 83 | P083S | S | 1.171208 |
| 84 | L084K | K | 1.099089 |
| 84 | L084H | H | 1.008187 |
| 85 | D085Q | Q | 3.093245 |
| 85 | D085R | R | 2.379647 |
| 85 | D085S | S | 2.284009 |
| 85 | D085H | H | 1.548556 |
| 85 | D085N | N | 1.539497 |
| 85 | D085G | G | 1.413812 |
| 85 | D085T | T | 1.329395 |
| 85 | D085E | E | 1.117228 |
| 85 | D085F | F | 1.008028 |
| 86 | L086A | A | 1.376284 |
| 86 | L086C | C | 1.156625 |
| 86 | L086G | G | 1.145834 |
| 95 | D095E | E | 2.044825 |
| 96 | T096S | S | 1.044425 |
| 97 | K097R | R | 2.798748 |
| 97 | K097Q | Q | 1.136975 |
| 100 | F100W | W | 1.082799 |
| 100 | F100E | E | 1.0116 |
| 101 | R101K | K | 1.244945 |
| 103 | T103W | W | 1.261503 |
| 103 | T103Y | Y | 1.193299 |
| 103 | T103G | G | 1.113343 |
| 103 | T103K | K | 1.093573 |
| 103 | T103I | I | 1.076338 |
| 103 | T103L | L | 1.050734 |
| 104 | P104H | H | 2.837034 |
| 104 | P104T | T | 2.696977 |
| 104 | P104G | G | 2.672719 |
| 104 | P104V | V | 2.585315 |
| 104 | P104S | S | 2.481687 |
| 104 | P104I | I | 2.431309 |
| 104 | P104W | W | 2.051785 |
| 104 | P104C | C | 1.951282 |
| 104 | P104E | E | 1.837373 |
| 104 | P104F | F | 1.785718 |
| 104 | P104N | N | 1.624722 |
| 104 | P104R | R | 1.618032 |
| 104 | P104Q | Q | 1.343174 |
| 104 | P104M | M | 1.093185 |
| 105 | L105P | P | 1.713219 |
| 105 | L105C | C | 1.557999 |
| 105 | L105F | F | 1.295759 |
| 105 | L105W | W | 1.283998 |
| 105 | L105G | G | 1.078743 |

TABLE 10-1-continued

PAF Assay Results

| Position | WT/Pos/Mutation | Variant | PAF Perf. Ind. |
|---|---|---|---|
| 106 | D106K | K | 1.278457 |
| 106 | D106L | L | 1.198148 |
| 106 | D106G | G | 1.178297 |
| 106 | D106H | H | 1.090134 |
| 106 | D106E | E | 1.084931 |
| 106 | D106T | T | 1.061622 |
| 106 | D106I | I | 1.036191 |
| 106 | D106F | F | 1.021513 |
| 106 | D106C | C | 1.005553 |
| 107 | I107E | E | 2.551108 |
| 107 | I107S | S | 2.044692 |
| 107 | I107N | N | 1.810584 |
| 107 | I107G | G | 1.764761 |
| 107 | I107V | V | 1.001703 |
| 108 | A108L | L | 1.407382 |
| 108 | A108T | T | 1.050964 |
| 109 | L109N | N | 1.523277 |
| 109 | L109W | W | 1.296964 |
| 109 | L109Q | Q | 1.182653 |
| 109 | L109Y | Y | 1.155328 |
| 109 | L109I | I | 1.053129 |
| 109 | L109D | D | 1.003394 |
| 111 | M111K | K | 1.977248 |
| 111 | M111I | I | 1.949343 |
| 111 | M111L | L | 1.546317 |
| 111 | M111T | T | 1.489808 |
| 111 | M111F | F | 1.467344 |
| 111 | M111V | V | 1.466478 |
| 111 | M111Y | Y | 1.42589 |
| 111 | M111S | S | 1.031939 |
| 112 | S112L | L | 1.027928 |
| 112 | S112H | H | 1.001485 |
| 113 | V113L | L | 1.503622 |
| 113 | V113H | H | 1.339003 |
| 113 | V113K | K | 1.192607 |
| 113 | V113R | R | 1.133751 |
| 113 | V113Y | Y | 1.113256 |
| 113 | V113F | F | 1.045057 |
| 113 | V113Q | Q | 1.032496 |
| 115 | V115W | W | 1.234 |
| 115 | V115T | T | 1.145757 |
| 115 | V115L | L | 1.117398 |
| 115 | V115G | G | 1.089596 |
| 115 | V115I | I | 1.050387 |
| 115 | V115Y | Y | 1.032052 |
| 116 | T116G | G | 1.095496 |
| 116 | T116A | A | 1.006702 |
| 117 | Q117H | H | 2.327857 |
| 117 | Q117T | T | 2.233854 |
| 117 | Q117Y | Y | 2.227983 |
| 117 | Q117W | W | 2.155359 |
| 117 | Q117V | V | 2.154646 |
| 117 | Q117G | G | 2.080223 |
| 117 | Q117A | A | 2.048752 |
| 117 | Q117S | S | 1.949232 |
| 117 | Q117F | F | 1.573776 |
| 117 | Q117R | R | 1.564466 |
| 117 | Q117M | M | 1.541944 |
| 117 | Q117E | E | 1.145341 |
| 118 | V118Y | Y | 1.25067 |
| 118 | V118K | K | 1.125917 |
| 118 | V118G | G | 1.083422 |
| 120 | T120S | S | 1.089798 |
| 121 | S121L | L | 1.348931 |
| 121 | S121W | W | 1.333741 |
| 121 | S121R | R | 1.25879 |
| 121 | S121K | K | 1.241105 |
| 121 | S121G | G | 1.204547 |
| 121 | S121C | C | 1.177769 |
| 121 | S121N | N | 1.143954 |
| 121 | S121T | T | 1.132507 |
| 121 | S121A | A | 1.120633 |
| 122 | S121V | V | 1.120454 |
| 122 | A122H | H | 1.137861 |
| 122 | A122I | I | 1.133601 |
| 122 | A122T | T | 1.083131 |
| 122 | A122K | K | 1.082552 |
| 122 | A122V | V | 1.041449 |
| 122 | A122S | S | 1.031411 |
| 124 | G124L | L | 1.91642 |
| 124 | G124I | I | 1.853337 |
| 124 | G124T | T | 1.63716 |
| 124 | G124H | H | 1.588068 |
| 124 | G124V | V | 1.441979 |
| 124 | G124F | F | 1.320782 |
| 124 | G124S | S | 1.269245 |
| 124 | G124Y | Y | 1.234423 |
| 124 | G124R | R | 1.144212 |
| 124 | G124Q | Q | 1.123498 |
| 125 | V125G | G | 2.948291 |
| 125 | V125S | S | 1.942881 |
| 125 | V125A | A | 1.689696 |
| 125 | V125P | P | 1.50166 |
| 125 | V125R | R | 1.301534 |
| 125 | V125D | D | 1.238852 |
| 125 | V125Y | Y | 1.080394 |
| 125 | V125I | I | 1.010779 |
| 126 | G126T | T | 1.577938 |
| 126 | G126P | P | 1.171092 |
| 126 | G126L | L | 1.169527 |
| 127 | T127H | H | 1.57251 |
| 127 | T127V | V | 1.073821 |
| 127 | T127I | I | 1.063668 |
| 127 | T127S | S | 1.046984 |
| 128 | T128L | L | 1.064623 |
| 128 | T128K | K | 1.062947 |
| 148 | P148V | V | 2.426937 |
| 148 | P148K | K | 1.786508 |
| 148 | P148L | L | 1.638438 |
| 148 | P148A | A | 1.637334 |
| 148 | P148R | R | 1.509086 |
| 148 | P148T | T | 1.501359 |
| 148 | P148Y | Y | 1.459512 |
| 148 | P148S | S | 1.45564 |
| 148 | P148E | E | 1.417449 |
| 148 | P148F | F | 1.367568 |
| 148 | P148Q | Q | 1.334517 |
| 148 | P148D | D | 1.030185 |
| 150 | F150L | L | 1.290835 |
| 150 | F150E | E | 1.228159 |
| 153 | I153K | K | 1.618543 |
| 153 | I153H | H | 1.464262 |
| 153 | I153T | T | 1.271928 |
| 153 | I153L | L | 1.270149 |
| 153 | I153F | F | 1.227821 |
| 153 | I153A | A | 1.194659 |
| 154 | F154Y | Y | 1.323693 |
| 196 | F196H | H | 1.774774 |
| 196 | F196L | L | 1.768072 |
| 196 | F196C | C | 1.738263 |
| 196 | F196M | M | 1.647608 |
| 196 | F196G | G | 1.590716 |
| 196 | F196S | S | 1.577837 |
| 196 | F196Y | Y | 1.414589 |
| 196 | F196V | V | 1.395387 |
| 196 | F196I | I | 1.320955 |
| 196 | F196W | W | 1.014435 |

The following Table provides variants with PAF results that were better than those observed for wild-type *M. smegmatis* perhydrolase. In this Table, the middle column indicates the amino acid residue in the wild-type perhydrolase (WT), followed by the position number and the variant amino acid in that position (Var).

TABLE 10-2

Variants with PAF Values Better Than Wild-Type

| Pos | WT/Pos./Var | Peracid formation relative to WT |
|---|---|---|
| 2 | A002W | 1.75 |
| 2 | A002D | 1.30 |
| 2 | A002F | 1.24 |
| 2 | A002I | 1.18 |
| 2 | A002G | 1.15 |
| 2 | A002S | 1.01 |
| 3 | K003Y | 1.06 |
| 3 | K003I | 1.05 |
| 3 | K003L | 1.04 |
| 3 | K003T | 1.01 |
| 3 | K003H | 1.01 |
| 4 | R004Q | 1.03 |
| 5 | I005T | 1.12 |
| 5 | I005S | 1.02 |
| 6 | L006V | 1.07 |
| 6 | L006I | 1.07 |
| 6 | L006T | 1.06 |
| 7 | C007K | 2.69 |
| 7 | C007Y | 2.09 |
| 7 | C007I | 1.76 |
| 7 | C007H | 1.73 |
| 7 | C007A | 1.42 |
| 7 | C007G | 1.39 |
| 7 | C007M | 1.13 |
| 8 | F008R | 1.43 |
| 8 | F008V | 1.18 |
| 8 | F008G | 1.09 |
| 8 | F008H | 1.02 |
| 10 | D010L | 3.97 |
| 10 | D010W | 3.18 |
| 10 | D010K | 2.13 |
| 10 | D010Y | 1.51 |
| 10 | D010T | 1.47 |
| 10 | D010I | 1.28 |
| 12 | L012Q | 2.65 |
| 12 | L012C | 2.29 |
| 12 | L012A | 1.10 |
| 15 | G015A | 1.54 |
| 15 | G015S | 1.05 |
| 17 | V017G | 1.17 |
| 17 | V017R | 1.10 |
| 17 | V017A | 1.01 |
| 18 | P018Y | 1.33 |
| 18 | P018N | 1.33 |
| 18 | P018C | 1.26 |
| 18 | P018E | 1.22 |
| 18 | P018V | 1.19 |
| 18 | P018R | 1.16 |
| 18 | P018Q | 1.12 |
| 18 | P018H | 1.12 |
| 18 | P018G | 1.07 |
| 19 | V019G | 1.32 |
| 19 | V019S | 1.24 |
| 19 | V019R | 1.03 |
| 19 | V019L | 1.00 |
| 20 | E020W | 2.94 |
| 20 | E020G | 2.36 |
| 20 | E020T | 2.22 |
| 20 | E020L | 2.20 |
| 20 | E020H | 2.17 |
| 20 | E020V | 2.11 |
| 20 | E020S | 2.01 |
| 20 | E020C | 1.57 |
| 20 | E020N | 1.40 |
| 20 | E020A | 1.29 |
| 20 | E020Q | 1.27 |
| 21 | D021K | 1.58 |
| 21 | D021W | 1.55 |
| 21 | D021L | 1.46 |
| 21 | D021A | 1.46 |
| 21 | D021G | 1.37 |
| 21 | D021Y | 1.30 |
| 21 | D021F | 1.30 |
| 21 | D021S | 1.24 |
| 22 | G022A | 1.55 |
| 22 | G022T | 1.03 |
| 22 | G022S | 1.02 |
| 25 | T025G | 1.86 |
| 25 | T025S | 1.60 |
| 25 | T025A | 1.33 |
| 25 | T025I | 1.02 |
| 26 | E026M | 2.00 |
| 26 | E026A | 1.93 |
| 26 | E026R | 1.48 |
| 26 | E026K | 1.46 |
| 26 | E026T | 1.44 |
| 26 | E026C | 1.40 |
| 26 | E026V | 1.39 |
| 26 | E026N | 1.37 |
| 26 | E026H | 1.33 |
| 26 | E026L | 1.30 |
| 26 | E026G | 1.28 |
| 26 | E026S | 1.27 |
| 26 | E026W | 1.25 |
| 27 | R027K | 1.22 |
| 28 | F028M | 1.33 |
| 28 | F028A | 1.27 |
| 28 | F028W | 1.16 |
| 28 | F028L | 1.09 |
| 28 | F028S | 1.05 |
| 29 | A029W | 1.91 |
| 29 | A029V | 1.80 |
| 29 | A029R | 1.76 |
| 29 | A029Y | 1.70 |
| 29 | A029G | 1.60 |
| 29 | A029S | 1.49 |
| 29 | A029T | 1.42 |
| 29 | A029E | 1.12 |
| 29 | A029C | 1.08 |
| 30 | P030K | 1.21 |
| 30 | P030R | 1.16 |
| 30 | P030V | 1.06 |
| 30 | P030T | 1.05 |
| 30 | P030A | 1.05 |
| 30 | P030S | 1.03 |
| 30 | P030Q | 1.01 |
| 30 | P030H | 1.01 |
| 30 | P030E | 1.01 |
| 31 | D031W | 1.83 |
| 31 | D031L | 1.81 |
| 31 | D031T | 1.45 |
| 31 | D031G | 1.44 |
| 31 | D031F | 1.44 |
| 31 | D031N | 1.34 |
| 31 | D031V | 1.28 |
| 31 | D031A | 1.24 |
| 31 | D031R | 1.22 |
| 31 | D031S | 1.15 |
| 31 | D031E | 1.13 |
| 31 | D031Q | 1.07 |
| 32 | V032K | 1.09 |
| 32 | V032R | 1.05 |
| 33 | R033S | 1.00 |
| 36 | G036I | 1.32 |
| 36 | G036K | 1.27 |
| 36 | G036L | 1.24 |
| 37 | V037S | 1.40 |
| 37 | V037I | 1.26 |
| 37 | V037A | 1.25 |
| 37 | V037H | 1.21 |
| 37 | V037L | 1.16 |
| 37 | V037C | 1.09 |
| 37 | V037T | 1.05 |
| 39 | A039L | 1.43 |

TABLE 10-2-continued

Variants with PAF Values Better Than Wild-Type

| Pos | WT/Pos./Var | Peracid formation relative to WT |
|---|---|---|
| 39 | A039K | 1.36 |
| 39 | A039Y | 1.36 |
| 39 | A039I | 1.26 |
| 39 | A039T | 1.26 |
| 39 | A039W | 1.23 |
| 39 | A039V | 1.21 |
| 39 | A039G | 1.17 |
| 39 | A039R | 1.17 |
| 39 | A039E | 1.09 |
| 40 | Q040K | 2.61 |
| 40 | Q040I | 2.58 |
| 40 | Q040W | 2.39 |
| 40 | Q040L | 2.14 |
| 40 | Q040T | 2.01 |
| 40 | Q040R | 1.89 |
| 40 | Q040Y | 1.83 |
| 40 | Q040G | 1.79 |
| 40 | Q040S | 1.57 |
| 40 | Q040N | 1.53 |
| 40 | Q040D | 1.16 |
| 40 | Q040E | 1.08 |
| 41 | Q041K | 1.38 |
| 41 | Q041R | 1.19 |
| 41 | Q041W | 1.14 |
| 41 | Q041H | 1.12 |
| 41 | Q041S | 1.11 |
| 41 | Q041Y | 1.09 |
| 41 | Q041V | 1.07 |
| 41 | Q041A | 1.03 |
| 41 | Q041L | 1.00 |
| 42 | L042K | 2.46 |
| 42 | L042W | 2.06 |
| 42 | L042H | 1.92 |
| 42 | L042R | 1.38 |
| 42 | L042G | 1.17 |
| 42 | L042T | 1.08 |
| 42 | L042F | 1.07 |
| 43 | G043A | 1.49 |
| 43 | G043C | 1.48 |
| 43 | G043K | 1.42 |
| 43 | G043M | 1.37 |
| 43 | G043Y | 1.26 |
| 43 | G043E | 1.25 |
| 43 | G043L | 1.22 |
| 43 | G043R | 1.22 |
| 43 | G043S | 1.18 |
| 43 | G043H | 1.17 |
| 43 | G043P | 1.08 |
| 44 | A044F | 2.84 |
| 44 | A044V | 2.13 |
| 44 | A044C | 1.80 |
| 44 | A044L | 1.61 |
| 44 | A044W | 1.40 |
| 44 | A044M | 1.20 |
| 45 | D045K | 1.34 |
| 45 | D045T | 1.27 |
| 45 | D045R | 1.16 |
| 45 | D045W | 1.15 |
| 45 | D045S | 1.13 |
| 45 | D045G | 1.13 |
| 45 | D045H | 1.13 |
| 45 | D045F | 1.11 |
| 45 | D045L | 1.05 |
| 45 | D045V | 1.05 |
| 45 | D045Q | 1.04 |
| 45 | D045A | 1.04 |
| 46 | F046E | 1.25 |
| 46 | F046D | 1.17 |
| 46 | F046G | 1.02 |
| 46 | F046K | 1.00 |
| 47 | E047R | 2.45 |
| 47 | E047T | 1.96 |
| 47 | E047P | 1.36 |
| 47 | E047S | 1.28 |
| 47 | E047H | 1.27 |
| 47 | E047G | 1.20 |
| 47 | E047K | 1.19 |
| 47 | E047F | 1.09 |
| 47 | E047I | 1.03 |
| 49 | I049G | 1.34 |
| 49 | I049H | 1.27 |
| 49 | I049S | 1.24 |
| 49 | I049K | 1.23 |
| 49 | I049V | 1.20 |
| 49 | I049L | 1.14 |
| 49 | I049Y | 1.07 |
| 49 | I049R | 1.05 |
| 49 | I049E | 1.02 |
| 49 | I049M | 1.01 |
| 50 | E050L | 1.19 |
| 50 | E050M | 1.18 |
| 50 | E050A | 1.12 |
| 51 | E051V | 1.47 |
| 51 | E051A | 1.28 |
| 51 | E051G | 1.22 |
| 51 | E051T | 1.18 |
| 51 | E051L | 1.11 |
| 51 | E051I | 1.07 |
| 53 | L053H | 5.05 |
| 53 | L053Q | 1.48 |
| 53 | L053G | 1.32 |
| 53 | L053S | 1.16 |
| 53 | L053T | 1.02 |
| 54 | S054P | 5.20 |
| 54 | S054I | 4.78 |
| 54 | S054V | 4.72 |
| 54 | S054A | 3.46 |
| 54 | S054R | 3.38 |
| 54 | S054L | 2.02 |
| 54 | S054T | 1.46 |
| 54 | S054K | 1.44 |
| 54 | S054G | 1.43 |
| 54 | S054C | 1.26 |
| 54 | S054Q | 1.03 |
| 55 | A055G | 1.69 |
| 55 | A055T | 1.69 |
| 57 | T057S | 1.63 |
| 57 | T057R | 1.61 |
| 57 | T057V | 1.28 |
| 57 | T057I | 1.19 |
| 59 | N059W | 1.13 |
| 59 | N059R | 1.09 |
| 59 | N059T | 1.07 |
| 59 | N059S | 1.06 |
| 59 | N059Q | 1.02 |
| 60 | I060H | 1.02 |
| 60 | I060R | 1.00 |
| 61 | D061H | 1.44 |
| 61 | D061S | 1.26 |
| 61 | D061R | 1.11 |
| 61 | D061I | 1.08 |
| 61 | D061F | 1.01 |
| 62 | D062E | 1.02 |
| 63 | P063G | 1.71 |
| 63 | P063T | 1.50 |
| 63 | P063M | 1.46 |
| 63 | P063S | 1.42 |
| 63 | P063K | 1.40 |
| 63 | P063A | 1.35 |
| 63 | P063Y | 1.35 |
| 63 | P063W | 1.35 |
| 63 | P063V | 1.31 |
| 63 | P063R | 1.31 |
| 63 | P063F | 1.25 |

TABLE 10-2-continued

Variants with PAF Values Better Than Wild-Type

| Pos | WT/Pos./Var | Peracid formation relative to WT |
|---|---|---|
| 63 | P063L | 1.15 |
| 63 | P063Q | 1.09 |
| 64 | T064G | 1.23 |
| 64 | T064S | 1.11 |
| 65 | D065A | 1.31 |
| 65 | D065S | 1.17 |
| 65 | D065H | 1.10 |
| 66 | P066R | 1.85 |
| 66 | P066V | 1.83 |
| 66 | P066H | 1.59 |
| 66 | P066I | 1.59 |
| 66 | P066G | 1.50 |
| 66 | P066Q | 1.46 |
| 66 | P066T | 1.41 |
| 66 | P066S | 1.39 |
| 66 | P066Y | 1.33 |
| 66 | P066L | 1.14 |
| 66 | P066N | 1.12 |
| 67 | R067N | 1.58 |
| 67 | R067G | 1.39 |
| 67 | R067T | 1.28 |
| 67 | R067F | 1.26 |
| 67 | R067L | 1.20 |
| 67 | R067Q | 1.16 |
| 67 | R067W | 1.07 |
| 67 | R067E | 1.04 |
| 67 | R067P | 1.01 |
| 68 | L068E | 1.44 |
| 68 | L068W | 1.21 |
| 68 | L068I | 1.13 |
| 68 | L068G | 1.09 |
| 68 | L068V | 1.09 |
| 68 | L068H | 1.05 |
| 68 | L068T | 1.03 |
| 69 | N069V | 1.99 |
| 69 | N069K | 1.72 |
| 69 | N069R | 1.49 |
| 69 | N069I | 1.47 |
| 69 | N069H | 1.36 |
| 69 | N069T | 1.35 |
| 69 | N069L | 1.30 |
| 69 | N069S | 1.21 |
| 69 | N069G | 1.20 |
| 69 | N069Q | 1.07 |
| 69 | N069W | 1.05 |
| 69 | N069C | 1.05 |
| 71 | A071S | 1.75 |
| 71 | A071T | 1.70 |
| 71 | A071H | 1.70 |
| 71 | A071G | 1.59 |
| 71 | A071I | 1.51 |
| 71 | A071E | 1.45 |
| 71 | A071K | 1.44 |
| 71 | A071R | 1.40 |
| 71 | A071N | 1.23 |
| 71 | A071L | 1.23 |
| 71 | A071F | 1.13 |
| 71 | A071C | 1.01 |
| 72 | S072L | 1.26 |
| 72 | S072H | 1.21 |
| 72 | S072G | 1.20 |
| 72 | S072T | 1.10 |
| 72 | S072V | 1.08 |
| 72 | S072Y | 1.07 |
| 73 | Y073R | 1.26 |
| 73 | Y073Q | 1.23 |
| 73 | Y073S | 1.17 |
| 73 | Y073K | 1.07 |
| 74 | L074S | 2.72 |
| 74 | L074G | 1.95 |
| 74 | L074W | 1.38 |
| 75 | P075R | 1.60 |
| 75 | P075S | 1.39 |
| 75 | P075T | 1.28 |
| 75 | P075Q | 1.21 |
| 75 | P075G | 1.16 |
| 75 | P075H | 1.05 |
| 75 | P075W | 1.04 |
| 76 | S076P | 1.23 |
| 77 | C077T | 1.12 |
| 77 | C077V | 1.05 |
| 77 | C077G | 1.01 |
| 78 | L078G | 4.98 |
| 78 | L078H | 4.82 |
| 78 | L078E | 3.01 |
| 78 | L078N | 2.68 |
| 78 | L078T | 1.87 |
| 78 | L078Q | 1.73 |
| 78 | L078V | 1.53 |
| 78 | L078I | 1.43 |
| 78 | L078Y | 1.39 |
| 79 | A079H | 1.93 |
| 79 | A079L | 1.80 |
| 79 | A079I | 1.59 |
| 79 | A079M | 1.50 |
| 79 | A079N | 1.48 |
| 79 | A079Q | 1.47 |
| 79 | A079R | 1.47 |
| 79 | A079W | 1.27 |
| 79 | A079T | 1.17 |
| 79 | A079E | 1.12 |
| 80 | T080C | 1.31 |
| 80 | T080V | 1.23 |
| 80 | T080G | 1.16 |
| 80 | T080A | 1.00 |
| 81 | H081K | 1.52 |
| 81 | H081L | 1.23 |
| 81 | H081N | 1.17 |
| 81 | H081G | 1.17 |
| 81 | H081A | 1.15 |
| 81 | H081C | 1.13 |
| 81 | H081W | 1.13 |
| 81 | H081V | 1.10 |
| 81 | H081F | 1.10 |
| 81 | H081S | 1.04 |
| 82 | L082P | 1.46 |
| 82 | L082G | 1.38 |
| 82 | L082R | 1.34 |
| 82 | L082H | 1.33 |
| 82 | L082K | 1.19 |
| 82 | L082T | 1.18 |
| 82 | L082I | 1.17 |
| 82 | L082S | 1.15 |
| 82 | L082V | 1.02 |
| 83 | P083K | 1.37 |
| 83 | P083G | 1.31 |
| 83 | P083H | 1.27 |
| 83 | P083R | 1.19 |
| 83 | P083S | 1.17 |
| 84 | L084K | 1.10 |
| 84 | L084H | 1.01 |
| 85 | D085Q | 3.09 |
| 85 | D085R | 2.38 |
| 85 | D085S | 2.28 |
| 85 | D085H | 1.55 |
| 85 | D085N | 1.54 |
| 85 | D085G | 1.41 |
| 85 | D085T | 1.33 |
| 85 | D085E | 1.12 |
| 85 | D085F | 1.01 |
| 86 | L086A | 1.38 |
| 86 | L086C | 1.16 |
| 86 | L086G | 1.15 |
| 88 | I088H | 1.20 |

TABLE 10-2-continued

Variants with PAF Values Better Than Wild-Type

| Pos | WT/Pos./Var | Peracid formation relative to WT |
|---|---|---|
| 88 | I088T | 1.03 |
| 88 | I088G | 1.01 |
| 90 | M090T | 1.27 |
| 90 | M090I | 1.13 |
| 90 | M090V | 1.08 |
| 90 | M090S | 1.06 |
| 90 | M090L | 1.02 |
| 91 | L091G | 1.21 |
| 91 | L091T | 1.06 |
| 92 | G092V | 1.49 |
| 92 | G092S | 1.26 |
| 93 | T093Y | 5.26 |
| 93 | T093F | 3.52 |
| 93 | T093A | 1.38 |
| 93 | T093C | 1.08 |
| 95 | D095E | 2.04 |
| 96 | T096S | 1.04 |
| 97 | K097R | 2.80 |
| 97 | K097Q | 1.14 |
| 98 | A098L | 2.22 |
| 98 | A098H | 2.09 |
| 98 | A098I | 2.05 |
| 98 | A098Y | 2.02 |
| 98 | A098S | 1.73 |
| 98 | A098T | 1.72 |
| 98 | A098G | 1.57 |
| 98 | A098C | 1.30 |
| 98 | A098N | 1.24 |
| 98 | A098D | 1.11 |
| 98 | A098P | 1.10 |
| 100 | F100W | 1.08 |
| 100 | F100E | 1.01 |
| 101 | R101K | 1.24 |
| 103 | T103W | 1.26 |
| 103 | T103Y | 1.19 |
| 103 | T103G | 1.11 |
| 103 | T103K | 1.09 |
| 103 | T103I | 1.08 |
| 103 | T103L | 1.05 |
| 104 | P104H | 2.84 |
| 104 | P104T | 2.70 |
| 104 | P104G | 2.67 |
| 104 | P104V | 2.59 |
| 104 | P104S | 2.48 |
| 104 | P104I | 2.43 |
| 104 | P104W | 2.05 |
| 104 | P104C | 1.95 |
| 104 | P104E | 1.84 |
| 104 | P104F | 1.79 |
| 104 | P104N | 1.62 |
| 104 | P104R | 1.62 |
| 104 | P104Q | 1.34 |
| 104 | P104M | 1.09 |
| 105 | L105P | 1.71 |
| 105 | L105C | 1.56 |
| 105 | L105F | 1.30 |
| 105 | L105W | 1.28 |
| 105 | L105G | 1.08 |
| 106 | D106K | 1.28 |
| 106 | D106L | 1.20 |
| 106 | D106G | 1.18 |
| 106 | D106H | 1.09 |
| 106 | D106E | 1.08 |
| 106 | D106T | 1.06 |
| 106 | D106I | 1.04 |
| 106 | D106F | 1.02 |
| 106 | D106C | 1.01 |
| 107 | I107E | 2.55 |
| 107 | I107S | 2.04 |
| 107 | I107N | 1.81 |
| 107 | I107G | 1.76 |
| 107 | I107V | 1.00 |
| 108 | A108L | 1.41 |
| 108 | A108T | 1.05 |
| 109 | L109N | 1.52 |
| 109 | L109W | 1.30 |
| 109 | L109Q | 1.18 |
| 109 | L109Y | 1.16 |
| 109 | L109I | 1.05 |
| 109 | L109D | 1.00 |
| 111 | M111K | 1.98 |
| 111 | M111I | 1.95 |
| 111 | M111L | 1.55 |
| 111 | M111T | 1.49 |
| 111 | M111F | 1.47 |
| 111 | M111V | 1.47 |
| 111 | M111Y | 1.43 |
| 111 | M111S | 1.03 |
| 112 | S112L | 1.03 |
| 112 | S112H | 1.00 |
| 113 | V113L | 1.50 |
| 113 | V113H | 1.34 |
| 113 | V113K | 1.19 |
| 113 | V113R | 1.13 |
| 113 | V113Y | 1.11 |
| 113 | V113F | 1.05 |
| 113 | V113Q | 1.03 |
| 115 | V115W | 1.23 |
| 115 | V115T | 1.15 |
| 115 | V115L | 1.12 |
| 115 | V115G | 1.09 |
| 115 | V115I | 1.05 |
| 115 | V115Y | 1.03 |
| 116 | T116G | 1.10 |
| 116 | T116A | 1.01 |
| 117 | Q117H | 2.33 |
| 117 | Q117T | 2.23 |
| 117 | Q117Y | 2.23 |
| 117 | Q117W | 2.16 |
| 117 | Q117V | 2.15 |
| 117 | Q117G | 2.08 |
| 117 | Q117A | 2.05 |
| 117 | Q117S | 1.95 |
| 117 | Q117F | 1.57 |
| 117 | Q117R | 1.56 |
| 117 | Q117M | 1.54 |
| 117 | Q117E | 1.15 |
| 118 | V118Y | 1.25 |
| 118 | V118K | 1.13 |
| 118 | V118G | 1.08 |
| 120 | T120S | 1.09 |
| 121 | S121L | 1.35 |
| 121 | S121W | 1.33 |
| 121 | S121R | 1.26 |
| 121 | S121K | 1.24 |
| 121 | S121G | 1.20 |
| 121 | S121C | 1.18 |
| 121 | S121N | 1.14 |
| 121 | S121T | 1.13 |
| 121 | S121A | 1.12 |
| 121 | S121V | 1.12 |
| 122 | A122H | 1.14 |
| 122 | A122I | 1.13 |
| 122 | A122T | 1.08 |
| 122 | A122K | 1.08 |
| 122 | A122V | 1.04 |
| 122 | A122S | 1.03 |
| 123 | G123D | 1.73 |
| 123 | G123V | 1.40 |
| 123 | G123P | 1.32 |
| 123 | G123E | 1.13 |
| 123 | G123T | 1.06 |
| 123 | G123H | 1.00 |
| 124 | G124L | 1.92 |

TABLE 10-2-continued

Variants with PAF Values Better Than Wild-Type

| Pos | WT/Pos./Var | Peracid formation relative to WT |
|---|---|---|
| 124 | G124I | 1.85 |
| 124 | G124T | 1.64 |
| 124 | G124H | 1.59 |
| 124 | G124V | 1.44 |
| 124 | G124F | 1.32 |
| 124 | G124S | 1.27 |
| 124 | G124Y | 1.23 |
| 124 | G124R | 1.14 |
| 124 | G124Q | 1.12 |
| 125 | V125G | 2.95 |
| 125 | V125S | 1.94 |
| 125 | V125A | 1.69 |
| 125 | V125P | 1.50 |
| 125 | V125R | 1.30 |
| 125 | V125D | 1.24 |
| 125 | V125Y | 1.08 |
| 125 | V125I | 1.01 |
| 126 | G126T | 1.58 |
| 126 | G126P | 1.17 |
| 126 | G126L | 1.17 |
| 127 | T127H | 1.57 |
| 127 | T127V | 1.07 |
| 127 | T127I | 1.06 |
| 127 | T127S | 1.05 |
| 128 | T128L | 1.06 |
| 128 | T128K | 1.06 |
| 130 | P130T | 1.19 |
| 130 | P130H | 1.17 |
| 130 | P130K | 1.16 |
| 130 | P130G | 1.16 |
| 130 | P130S | 1.16 |
| 130 | P130V | 1.15 |
| 130 | P130W | 1.15 |
| 130 | P130I | 1.12 |
| 130 | P130L | 1.12 |
| 130 | P130R | 1.11 |
| 130 | P130F | 1.08 |
| 130 | P130E | 1.00 |
| 131 | A131L | 1.83 |
| 131 | A131R | 1.76 |
| 131 | A131H | 1.72 |
| 131 | A131G | 1.66 |
| 131 | A131W | 1.61 |
| 131 | A131V | 1.59 |
| 131 | A131P | 1.52 |
| 131 | A131Y | 1.50 |
| 131 | A131S | 1.48 |
| 131 | A131E | 1.36 |
| 131 | A131D | 1.31 |
| 131 | A131Q | 1.29 |
| 132 | P132Y | 1.57 |
| 132 | P132S | 1.13 |
| 133 | K133Y | 1.12 |
| 133 | K133L | 1.05 |
| 133 | K133H | 1.02 |
| 134 | V134G | 1.71 |
| 134 | V134T | 1.25 |
| 134 | V134N | 1.18 |
| 134 | V134S | 1.16 |
| 134 | V134L | 1.13 |
| 134 | V134I | 1.12 |
| 136 | V136T | 1.13 |
| 137 | V137M | 1.22 |
| 137 | V137L | 1.09 |
| 137 | V137T | 1.08 |
| 137 | V137A | 1.07 |
| 137 | V137G | 1.02 |
| 138 | S138I | 1.15 |
| 138 | S138G | 1.05 |
| 140 | P140A | 1.90 |
| 140 | P140T | 1.74 |
| 140 | P140S | 1.31 |
| 141 | P141L | 2.32 |
| 141 | P141I | 2.29 |
| 141 | P141H | 2.07 |
| 141 | P141V | 1.96 |
| 141 | P141T | 1.84 |
| 141 | P141S | 1.70 |
| 141 | P141R | 1.65 |
| 141 | P141G | 1.64 |
| 141 | P141Q | 1.39 |
| 141 | P141N | 1.32 |
| 141 | P141A | 1.10 |
| 142 | L142W | 2.41 |
| 142 | L142K | 1.60 |
| 142 | L142F | 1.05 |
| 143 | A143K | 3.16 |
| 143 | A143H | 2.90 |
| 143 | A143L | 2.51 |
| 143 | A143V | 2.45 |
| 143 | A143W | 2.27 |
| 143 | A143T | 2.18 |
| 143 | A143R | 2.15 |
| 143 | A143S | 1.77 |
| 143 | A143Q | 1.74 |
| 143 | A143F | 1.56 |
| 143 | A143P | 1.53 |
| 143 | A143G | 1.48 |
| 143 | A143D | 1.45 |
| 143 | A143E | 1.43 |
| 143 | A143C | 1.39 |
| 143 | A143N | 1.30 |
| 144 | P144Y | 2.34 |
| 144 | P144K | 2.09 |
| 144 | P144H | 1.94 |
| 144 | P144F | 1.82 |
| 144 | P144R | 1.76 |
| 144 | P144S | 1.69 |
| 144 | P144T | 1.46 |
| 144 | P144G | 1.45 |
| 144 | P144D | 1.45 |
| 144 | P144N | 1.44 |
| 144 | P144L | 1.43 |
| 144 | P144Q | 1.37 |
| 144 | P144M | 1.24 |
| 144 | P144A | 1.09 |
| 145 | M145L | 1.72 |
| 145 | M145F | 1.49 |
| 145 | M145R | 1.15 |
| 145 | M145W | 1.15 |
| 145 | M145C | 1.02 |
| 145 | M145T | 1.01 |
| 147 | H147A | 1.28 |
| 147 | H147S | 1.26 |
| 147 | H147T | 1.20 |
| 147 | H147P | 1.12 |
| 147 | H147E | 1.11 |
| 148 | P148V | 2.43 |
| 148 | P148K | 1.79 |
| 148 | P148L | 1.64 |
| 148 | P148A | 1.64 |
| 148 | P148R | 1.51 |
| 148 | P148T | 1.50 |
| 148 | P148Y | 1.46 |
| 148 | P148S | 1.46 |
| 148 | P148E | 1.42 |
| 148 | P148F | 1.37 |
| 148 | P148Q | 1.33 |
| 148 | P148D | 1.03 |
| 150 | F150L | 1.29 |
| 150 | F150E | 1.23 |
| 151 | Q151D | 1.47 |
| 151 | Q151R | 1.36 |
| 151 | Q151P | 1.35 |

TABLE 10-2-continued

Variants with PAF Values Better Than Wild-Type

| Pos | WT/Pos./Var | Peracid formation relative to WT |
|---|---|---|
| 151 | Q151A | 1.29 |
| 151 | Q151T | 1.24 |
| 151 | Q151M | 1.24 |
| 151 | Q151E | 1.14 |
| 151 | Q151K | 1.07 |
| 151 | Q151H | 1.06 |
| 151 | Q151S | 1.05 |
| 151 | Q151C | 1.05 |
| 151 | Q151Y | 1.01 |
| 152 | L152V | 1.22 |
| 152 | L152K | 1.21 |
| 152 | L152R | 1.20 |
| 152 | L152W | 1.18 |
| 152 | L152T | 1.12 |
| 152 | L152S | 1.12 |
| 152 | L152Y | 1.09 |
| 152 | L152H | 1.09 |
| 152 | L152G | 1.08 |
| 152 | L152E | 1.08 |
| 152 | L152Q | 1.07 |
| 152 | L152D | 1.07 |
| 152 | L152I | 1.04 |
| 152 | L152C | 1.00 |
| 153 | I153K | 1.62 |
| 153 | I153H | 1.46 |
| 153 | I153T | 1.27 |
| 153 | I153L | 1.27 |
| 153 | I153F | 1.23 |
| 153 | I153A | 1.19 |
| 154 | F154Y | 1.32 |
| 155 | E155T | 1.49 |
| 155 | E155R | 1.47 |
| 155 | E155L | 1.31 |
| 155 | E155Y | 1.27 |
| 155 | E155K | 1.23 |
| 155 | E155G | 1.17 |
| 155 | E155S | 1.08 |
| 155 | E155D | 1.08 |
| 155 | E155F | 1.07 |
| 156 | G156P | 1.44 |
| 156 | G156T | 1.15 |
| 156 | G156K | 1.10 |
| 156 | G156M | 1.09 |
| 156 | G156C | 1.07 |
| 156 | G156N | 1.07 |
| 156 | G156R | 1.05 |
| 156 | G156H | 1.04 |
| 156 | G156S | 1.02 |
| 157 | G157T | 1.74 |
| 157 | G157R | 1.51 |
| 157 | G157S | 1.30 |
| 157 | G157K | 1.28 |
| 157 | G157F | 1.27 |
| 157 | G157V | 1.23 |
| 157 | G157H | 1.14 |
| 157 | G157I | 1.11 |
| 158 | E158H | 2.40 |
| 158 | E158K | 2.08 |
| 158 | E158F | 2.06 |
| 158 | E158R | 1.99 |
| 158 | E158Y | 1.77 |
| 158 | E158W | 1.77 |
| 158 | E158L | 1.59 |
| 158 | E158S | 1.57 |
| 158 | E158V | 1.52 |
| 158 | E158Q | 1.49 |
| 158 | E158C | 1.46 |
| 158 | E158A | 1.45 |
| 158 | E158T | 1.45 |
| 158 | E158P | 1.41 |
| 158 | E158N | 1.41 |
| 158 | E158M | 1.39 |
| 158 | E158I | 1.38 |
| 158 | E158D | 1.35 |
| 159 | Q159R | 1.15 |
| 159 | Q159C | 1.13 |
| 159 | Q159S | 1.10 |
| 159 | Q159D | 1.09 |
| 159 | Q159A | 1.08 |
| 159 | Q159M | 1.07 |
| 159 | Q159P | 1.06 |
| 159 | Q159L | 1.02 |
| 161 | T161R | 3.61 |
| 161 | T161Y | 2.40 |
| 161 | T161H | 1.82 |
| 161 | T161W | 1.41 |
| 161 | T161I | 1.40 |
| 161 | T161V | 1.27 |
| 161 | T161L | 1.25 |
| 161 | T161Q | 1.04 |
| 162 | T162K | 1.22 |
| 162 | T162R | 1.17 |
| 162 | T162W | 1.15 |
| 162 | T162Y | 1.03 |
| 162 | T162H | 1.02 |
| 163 | E163L | 1.50 |
| 163 | E163Y | 1.41 |
| 163 | E163H | 1.32 |
| 163 | E163G | 1.25 |
| 163 | E163W | 1.21 |
| 163 | E163V | 1.13 |
| 163 | E163R | 1.12 |
| 163 | E163S | 1.12 |
| 163 | E163A | 1.11 |
| 163 | E163C | 1.11 |
| 163 | E163F | 1.07 |
| 165 | A165R | 1.70 |
| 165 | A165K | 1.35 |
| 165 | A165F | 1.23 |
| 165 | A165Q | 1.21 |
| 165 | A165V | 1.21 |
| 165 | A165Y | 1.20 |
| 165 | A165T | 1.18 |
| 165 | A165I | 1.17 |
| 165 | A165P | 1.14 |
| 165 | A165L | 1.08 |
| 165 | A165G | 1.05 |
| 165 | A165N | 1.01 |
| 165 | A165S | 1.00 |
| 166 | R166Y | 1.29 |
| 166 | R166L | 1.27 |
| 166 | R166I | 1.26 |
| 166 | R166W | 1.25 |
| 166 | R166H | 1.20 |
| 166 | R166T | 1.19 |
| 166 | R166V | 1.17 |
| 166 | R166K | 1.17 |
| 166 | R166S | 1.16 |
| 166 | R166G | 1.15 |
| 167 | V167T | 1.13 |
| 167 | V167I | 1.08 |
| 167 | V167Y | 1.07 |
| 167 | V167H | 1.03 |
| 168 | Y168G | 1.89 |
| 168 | Y168T | 1.51 |
| 168 | Y168V | 1.19 |
| 169 | S169Y | 1.26 |
| 169 | S169R | 1.24 |
| 169 | S169K | 1.21 |
| 169 | S169I | 1.16 |
| 169 | S169T | 1.15 |
| 169 | S169L | 1.08 |
| 169 | S169C | 1.03 |
| 169 | S169Q | 1.02 |

TABLE 10-2-continued

Variants with PAF Values Better Than Wild-Type

| Pos | WT/Pos./Var | Peracid formation relative to WT |
|---|---|---|
| 170 | A170K | 1.71 |
| 170 | A170G | 1.59 |
| 170 | A170I | 1.59 |
| 170 | A170S | 1.47 |
| 170 | A170F | 1.44 |
| 170 | A170T | 1.40 |
| 170 | A170E | 1.28 |
| 170 | A170D | 1.27 |
| 170 | A170N | 1.21 |
| 170 | A170V | 1.20 |
| 170 | A170C | 1.15 |
| 170 | A170Q | 1.15 |
| 170 | A170L | 1.05 |
| 170 | A170W | 1.04 |
| 170 | A170M | 1.03 |
| 171 | L171K | 2.05 |
| 171 | L171H | 1.67 |
| 171 | L171T | 1.54 |
| 171 | L171I | 1.53 |
| 171 | L171S | 1.43 |
| 171 | L171F | 1.30 |
| 171 | L171G | 1.26 |
| 171 | L171Y | 1.20 |
| 171 | L171V | 1.02 |
| 172 | A172I | 1.70 |
| 172 | A172S | 1.59 |
| 172 | A172W | 1.43 |
| 172 | A172G | 1.41 |
| 172 | A172V | 1.40 |
| 172 | A172T | 1.25 |
| 172 | A172L | 1.20 |
| 172 | A172C | 1.20 |
| 173 | S173Y | 1.19 |
| 173 | S173K | 1.17 |
| 173 | S173W | 1.16 |
| 173 | S173L | 1.15 |
| 173 | S173R | 1.09 |
| 173 | S173H | 1.07 |
| 173 | S173T | 1.06 |
| 174 | F174G | 1.60 |
| 174 | F174P | 1.54 |
| 174 | F174Q | 1.42 |
| 174 | F174C | 1.32 |
| 174 | F174S | 1.16 |
| 174 | F174L | 1.05 |
| 175 | M175T | 2.21 |
| 175 | M175G | 2.04 |
| 175 | M175V | 1.93 |
| 175 | M175L | 1.61 |
| 175 | M175Q | 1.56 |
| 175 | M175R | 1.55 |
| 175 | M175N | 1.39 |
| 175 | M175W | 1.25 |
| 176 | K176W | 1.19 |
| 176 | K176T | 1.04 |
| 176 | K176Y | 1.04 |
| 176 | K176V | 1.04 |
| 176 | K176G | 1.01 |
| 178 | P178L | 1.82 |
| 178 | P178Y | 1.38 |
| 178 | P178K | 1.34 |
| 178 | P178W | 1.14 |
| 178 | P178G | 1.09 |
| 179 | F179L | 1.15 |
| 179 | F179Y | 1.05 |
| 180 | F180L | 1.30 |
| 180 | F180I | 1.20 |
| 180 | F180V | 1.14 |
| 180 | F180Y | 1.12 |
| 180 | F180W | 1.11 |
| 180 | F180K | 1.08 |
| 180 | F180T | 1.01 |
| 181 | D181A | 1.35 |
| 181 | D181K | 1.33 |
| 181 | D181Y | 1.29 |
| 181 | D181W | 1.26 |
| 181 | D181L | 1.25 |
| 181 | D181R | 1.23 |
| 181 | D181S | 1.21 |
| 181 | D181Q | 1.14 |
| 181 | D181E | 1.10 |
| 181 | D181G | 1.09 |
| 181 | D181C | 1.09 |
| 181 | D181P | 1.03 |
| 181 | D181T | 1.02 |
| 182 | A182T | 1.14 |
| 184 | S184Y | 1.06 |
| 184 | S184F | 1.05 |
| 184 | S184T | 1.04 |
| 184 | S184H | 1.02 |
| 185 | V185K | 1.37 |
| 185 | V185Y | 1.37 |
| 185 | V185W | 1.36 |
| 185 | V185H | 1.30 |
| 185 | V185L | 1.23 |
| 185 | V185R | 1.15 |
| 185 | V185G | 1.12 |
| 185 | V185T | 1.11 |
| 185 | V185S | 1.09 |
| 185 | V185I | 1.07 |
| 185 | V185F | 1.02 |
| 186 | I186G | 1.86 |
| 186 | I186T | 1.51 |
| 186 | I186A | 1.46 |
| 186 | I186S | 1.39 |
| 186 | I186V | 1.28 |
| 186 | I186L | 1.17 |
| 186 | I186F | 1.01 |
| 187 | S187K | 1.45 |
| 187 | S187Y | 1.43 |
| 187 | S187I | 1.38 |
| 187 | S187L | 1.37 |
| 187 | S187W | 1.30 |
| 187 | S187H | 1.29 |
| 187 | S187V | 1.23 |
| 187 | S187T | 1.12 |
| 187 | S187R | 1.04 |
| 187 | S187G | 1.03 |
| 187 | S187F | 1.02 |
| 188 | T188Y | 1.48 |
| 188 | T188V | 1.22 |
| 188 | T188S | 1.16 |
| 188 | T188I | 1.13 |
| 188 | T188H | 1.11 |
| 188 | T188R | 1.01 |
| 189 | D189L | 1.30 |
| 189 | D189H | 1.25 |
| 189 | D189W | 1.09 |
| 190 | G190W | 1.88 |
| 190 | G190K | 1.01 |
| 191 | V191Y | 1.32 |
| 191 | V191H | 1.30 |
| 191 | V191W | 1.20 |
| 191 | V191S | 1.20 |
| 191 | V191K | 1.17 |
| 191 | V191I | 1.14 |
| 191 | V191F | 1.13 |
| 191 | V191R | 1.05 |
| 191 | V191L | 1.04 |
| 196 | F196H | 1.77 |
| 196 | F196L | 1.77 |
| 196 | F196C | 1.74 |
| 196 | F196M | 1.65 |
| 196 | F196G | 1.59 |

TABLE 10-2-continued

Variants with PAF Values Better Than Wild-Type

| Pos | WT/Pos./Var | Peracid formation relative to WT |
|---|---|---|
| 196 | F196S | 1.58 |
| 196 | F196Y | 1.41 |
| 196 | F196V | 1.40 |
| 196 | F196I | 1.32 |
| 196 | F196W | 1.01 |
| 197 | T197L | 1.21 |
| 198 | E198R | 1.82 |
| 198 | E198I | 1.80 |
| 198 | E198V | 1.60 |
| 198 | E198W | 1.59 |
| 198 | E198L | 1.57 |
| 198 | E198P | 1.52 |
| 198 | E198Y | 1.48 |
| 198 | E198C | 1.38 |
| 198 | E198F | 1.37 |
| 198 | E198Q | 1.28 |
| 198 | E198T | 1.25 |
| 198 | E198N | 1.24 |
| 198 | E198M | 1.18 |
| 198 | E198S | 1.06 |
| 199 | A199C | 1.77 |
| 199 | A199K | 1.72 |
| 199 | A199E | 1.56 |
| 199 | A199L | 1.38 |
| 199 | A199T | 1.33 |
| 199 | A199R | 1.33 |
| 199 | A199V | 1.32 |
| 199 | A199D | 1.31 |
| 199 | A199H | 1.27 |
| 199 | A199Y | 1.24 |
| 199 | A199F | 1.23 |
| 199 | A199S | 1.20 |
| 199 | A199G | 1.14 |
| 199 | A199M | 1.07 |
| 201 | N201Y | 1.29 |
| 201 | N201F | 1.16 |
| 201 | N201G | 1.08 |
| 202 | R202W | 1.97 |
| 202 | R202F | 1.89 |
| 202 | R202E | 1.69 |
| 202 | R202H | 1.64 |
| 202 | R202T | 1.55 |
| 202 | R202S | 1.49 |
| 202 | R202A | 1.48 |
| 202 | R202C | 1.44 |
| 202 | R202M | 1.43 |
| 202 | R202L | 1.43 |
| 202 | R202G | 1.39 |
| 202 | R202I | 1.33 |
| 203 | D203L | 2.42 |
| 203 | D203R | 2.23 |
| 203 | D203I | 1.99 |
| 203 | D203W | 1.99 |
| 203 | D203F | 1.92 |
| 203 | D203H | 1.84 |
| 203 | D203C | 1.78 |
| 203 | D203S | 1.66 |
| 203 | D203V | 1.66 |
| 203 | D203G | 1.63 |
| 203 | D203Q | 1.60 |
| 203 | D203A | 1.53 |
| 203 | D203E | 1.34 |
| 203 | D203N | 1.05 |

The following Table, provides variants with a PAF PI greater than 1.5.

TABLE 10-3

| PAF PI > 1.5 | |
|---|---|
| Wild-Type Residue/Pos. | Variant Amino Acid(s) |
| A2 | W |
| C7 | H, I, K, Y |
| D10 | K, L, W, Y |
| L12 | C, Q |
| G15 | A |
| E20 | C, G, H, L, S, T, V, W |
| D21 | K, W |
| G22 | A |
| T25 | G, S |
| E26 | A, M |
| A29 | G, R, V, W, Y |
| D31 | L, W |
| Q40 | G, I, K, L, N, R, S, T, W, Y |
| L42 | H, K, W |
| A44 | C, F, L, V |
| E47 | R, T |
| L53 | H |
| S54 | A, I, L, P, R, V |
| A55 | G, T |
| T57 | R, S |
| P63 | G |
| P66 | H, I, R, V |
| R67 | N |
| N69 | K, V |
| A71 | G, H, I, S, T |
| L74 | G, S |
| P75 | R |
| L78 | E, G, H, N, Q, T, V |
| A79 | H, I, L |
| H81 | K |
| D85 | H, N, Q, R, S |
| T93 | F, Y |
| D95 | E |
| K97 | R |
| A98 | G, H, I, L, S, T, Y |
| P104 | C, E, F, G, H, I, N, R, S, T, V, W |
| L105 | C, P |
| I107 | E, G, N, S |
| L109 | N |
| M111 | I, K, L |
| V113 | L |
| Q117 | A, F, G, H, M, R, S, T, V, W, Y |
| G123 | D, H, I, L, T |
| G124 | I, L |
| V125 | A, G, P, S |
| G126 | T |
| T127 | H |
| A131 | G, H, L, P, R, V, W, Y |
| P132 | Y |
| V134 | G |
| P140 | A, T, |
| P141 | G, H, I, L, R, S, T, V |
| L142 | K, W |
| A143 | F, H, K, L, P, Q, R, S, T, V, W |
| P144 | F, H, K, R, S, Y |
| M145 | L |
| P148 | A, K, L, R, T, V |
| I153 | K |
| G157 | R, T |
| E158 | F, H, K, L, R, S, V, W, Y |
| T161 | H, R, Y |
| A165 | T |
| Y168 | G, T |
| A170 | G, I, K |
| L171 | H, I, K, T |
| A172 | I, S |
| F174 | G, P |
| M175 | G, L, Q, R, T, V |

TABLE 10-3-continued

PAF PI > 1.5

| Wild-Type Residue/Pos. | Variant Amino Acid(s) |
|---|---|
| P178 | L |
| F196 | C, G, H, L, M, S |
| G190 | W |
| E198 | I, L, P, R, V, W |
| A199 | C, E, K |
| R202 | E, F, H, T, W |
| D203 | A, C, F, G, H, I, L, Q, R, S, V, W |
| V206 | E, F, G, H, K, R, S |
| A209 | K |
| E210 | H, K, S, T, V, W |
| Q211 | K |
| V212 | W |

Table 10-4 provides variants with PAF PI values greater than 2.0.

TABLE 10-4

Variants with PAF PI > 2.0

| Wild-Type Residue/Pos. | Amino Acid Variant(s) |
|---|---|
| C7 | K, Y |
| D10 | K, L, W |
| L12 | C, Q |
| E20 | G, H, L, S, T, V, W |
| E26 | M |
| Q40 | I, K, L, T, W |
| L42 | K, W |
| A44 | F, V |
| E47 | R |
| L53 | H |
| S54 | A, I, L, P, R, V |
| L74 | S |
| L78 | E, G, H, N |
| D85 | Q, R, S |
| T93 | F, Y |
| D95 | E |
| K97 | R |
| A98 | H, I, L, Y |
| P104 | G, H, I, S, T, V, W |
| I107 | E, S |
| Q117 | A, G, H, T, V, W, Y |
| V125 | G |
| P141 | H, I, L |
| L142 | W |
| A143 | H, K, L, R, T, V, W |
| P144 | K, Y |
| P148 | V |
| E158 | F, H, K |
| T161 | R, Y |
| L171 | K |
| M175 | G, T |
| D203 | L, R |
| V206 | E, F, K |
| E210 | T |

The following Table provides PAD assay results for various variants.

TABLE 10-5

PAD Assay Results

| Position | WT/Pos/Mutation | Variant | PAD Perf. Ind. |
|---|---|---|---|
| 1 | M001A | A | <0.01 |
| 1 | M001E | E | <0.01 |
| 1 | M001F | F | <0.01 |
| 1 | M001G | G | <0.01 |
| 1 | M001K | K | <0.01 |
| 1 | M001N | N | <0.01 |
| 1 | M001P | P | <0.01 |
| 1 | M001R | R | <0.01 |
| 1 | M001S | S | <0.01 |
| 1 | M001T | T | <0.01 |
| 1 | M001W | W | <0.01 |
| 1 | M001V | V | 0.944944 |
| 3 | K003V | V | 0.835476 |
| 4 | R004L | L | <0.01 |
| 4 | R004V | V | 0.079216 |
| 4 | R004I | I | 0.153122 |
| 4 | R004W | W | 0.484006 |
| 4 | R004G | G | 0.78952 |
| 4 | R004S | S | 0.907174 |
| 4 | R004E | E | 0.970668 |
| 4 | R004Y | Y | 0.983327 |
| 4 | R004H | H | 0.986096 |
| 4 | R004Q | Q | 0.98766 |
| 4 | R004T | T | 0.999841 |
| 5 | I005G | G | <0.01 |
| 5 | I005N | N | <0.01 |
| 5 | I005P | P | <0.01 |
| 5 | I005R | R | <0.01 |
| 5 | I005W | W | <0.01 |
| 5 | I005F | F | 0.15045 |
| 5 | I005S | S | 0.367738 |
| 5 | I005H | H | 0.626022 |
| 5 | I005T | T | 0.7212 |
| 5 | I005V | V | 0.917243 |
| 6 | L006S | S | <0.01 |
| 6 | L006K | K | <0.01 |
| 6 | L006G | G | <0.01 |
| 6 | L006H | H | <0.01 |
| 6 | L006R | R | <0.01 |
| 6 | L006W | W | <0.01 |
| 6 | L006E | E | <0.01 |
| 6 | L006Q | Q | <0.01 |
| 6 | L006V | V | 0.352616 |
| 6 | L006T | T | 0.354148 |
| 6 | L006I | I | 0.819654 |
| 7 | C007S | S | <0.01 |
| 7 | C007R | R | <0.01 |
| 7 | C007L | L | <0.01 |
| 7 | C007P | P | <0.01 |
| 7 | C007T | T | <0.01 |
| 7 | C007W | W | <0.01 |
| 7 | C007Y | Y | 0.544454 |
| 7 | C007M | M | 0.678238 |
| 7 | C007G | G | 0.686018 |
| 10 | D010W | W | <0.01 |
| 10 | D010K | K | <0.01 |
| 10 | D010Y | Y | <0.01 |
| 10 | D010T | T | <0.01 |
| 10 | D010I | I | <0.01 |
| 10 | D010V | V | <0.01 |
| 10 | D010S | S | <0.01 |
| 10 | D010G | G | <0.01 |
| 10 | D010R | R | <0.01 |
| 10 | D010A | A | <0.01 |
| 10 | D010M | M | <0.01 |
| 10 | D010N | N | <0.01 |
| 10 | D010P | P | <0.01 |
| 10 | D010E | E | 0.147899 |
| 11 | S011T | T | <0.01 |
| 11 | S011V | V | <0.01 |
| 11 | S011D | D | <0.01 |
| 11 | S011E | E | <0.01 |
| 11 | S011F | F | <0.01 |
| 11 | S011G | G | <0.01 |
| 11 | S011L | L | <0.01 |
| 11 | S011Q | Q | <0.01 |
| 11 | S011R | R | <0.01 |

TABLE 10-5-continued

PAD Assay Results

| Position | WT/Pos/Mutation | Variant | PAD Perf. Ind. |
|---|---|---|---|
| 11 | S011H | H | 0.332012 |
| 11 | S011K | K | 0.399168 |
| 11 | S011A | A | 0.528328 |
| 11 | S011I | I | 0.562735 |
| 12 | L012V | V | <0.01 |
| 12 | L012S | S | <0.01 |
| 12 | L012G | G | <0.01 |
| 12 | L012R | R | <0.01 |
| 12 | L012D | D | <0.01 |
| 12 | L012P | P | <0.01 |
| 12 | L012W | W | <0.0162738575856614 |
| 12 | L012T | T | 0.064264 |
| 12 | L012A | A | 0.074567 |
| 12 | L012K | K | 0.134919 |
| 12 | L012H | H | 0.164894 |
| 12 | L012F | F | 0.171369 |
| 12 | L012Q | Q | 0.219754 |
| 12 | L012C | C | 0.221492 |
| 12 | L012N | N | 0.655242 |
| 13 | T013F | F | <0.01 |
| 13 | T013R | R | <0.01 |
| 13 | T013W | W | <0.01 |
| 13 | T013Q | Q | 0.508867 |
| 13 | T013V | V | 0.625148 |
| 13 | T013S | S | 0.682494 |
| 13 | T013G | G | 0.768701 |
| 14 | W014I | I | <0.01 |
| 14 | W014S | S | <0.01 |
| 14 | W014G | G | <0.01 |
| 14 | W014K | K | <0.01 |
| 14 | W014V | V | <0.01 |
| 14 | W014L | L | <0.01 |
| 14 | W014T | T | <0.01 |
| 14 | W014R | R | <0.01 |
| 14 | W014N | N | <0.01 |
| 14 | W014P | P | <0.01 |
| 14 | W014E | E | 0.150043 |
| 14 | W014F | F | 0.218073 |
| 14 | W014A | A | 0.271277 |
| 14 | W014Y | Y | 0.64896 |
| 14 | W014W | W | 0.989643 |
| 15 | G015C | C | <0.01 |
| 15 | G015N | N | <0.01 |
| 15 | G015D | D | <0.01 |
| 15 | G015E | E | <0.01 |
| 15 | G015H | H | <0.01 |
| 15 | G015K | K | <0.01 |
| 15 | G015L | L | <0.01 |
| 15 | G015P | P | <0.01 |
| 15 | G015R | R | <0.01 |
| 15 | G015Y | Y | <0.01 |
| 15 | G015A | A | 0.614319 |
| 15 | G015S | S | 0.631317 |
| 16 | W016S | S | <0.01 |
| 16 | W016G | G | <0.01 |
| 16 | W016H | H | <0.01 |
| 16 | W016N | N | <0.01 |
| 16 | W016R | R | <0.01 |
| 16 | W016T | T | <0.01 |
| 16 | W016P | P | 0.150383 |
| 16 | W016Q | Q | 0.312038 |
| 16 | W016M | M | 0.370155 |
| 16 | W016A | A | 0.553088 |
| 16 | W016D | D | 0.569713 |
| 16 | W016E | E | 0.647375 |
| 16 | W016V | V | 0.875327 |
| 17 | V017A | A | 0.675391 |
| 17 | V017E | E | 0.749717 |
| 17 | V017G | G | 0.838345 |
| 17 | V017K | K | 0.844479 |
| 17 | V017F | F | 0.847091 |
| 17 | V017T | T | 0.861827 |
| 17 | V017Y | Y | 0.876678 |
| 17 | V017R | R | 0.936013 |
| 17 | V017P | P | 0.956795 |
| 17 | V017I | I | 0.993337 |
| 17 | V017L | L | 0.996217 |
| 18 | P018A | A | <0.01 |
| 18 | P018M | M | <0.01 |
| 18 | P018S | S | 0.066689 |
| 19 | V019P | P | <0.01 |
| 19 | V019M | M | 0.117174 |
| 19 | V019R | R | 0.343385 |
| 19 | V019Q | Q | 0.395965 |
| 19 | V019A | A | 0.554598 |
| 19 | V019G | G | 0.55596 |
| 19 | V019S | S | 0.573928 |
| 19 | V019E | E | 0.620236 |
| 19 | V019Y | Y | 0.696626 |
| 19 | V019D | D | 0.785756 |
| 19 | V019L | L | 0.910961 |
| 19 | V019K | K | 0.965611 |
| 21 | D021V | V | <0.01 |
| 21 | D021P | P | 0.534939 |
| 21 | D021S | S | 0.689672 |
| 21 | D021E | E | 0.864655 |
| 21 | D021F | F | 0.876655 |
| 21 | D021W | W | 0.894205 |
| 21 | D021L | L | 0.971454 |
| 22 | G022K | K | <0.01 |
| 22 | G022W | W | 0.231005 |
| 22 | G022R | R | 0.563069 |
| 22 | G022V | V | 0.850851 |
| 22 | G022S | S | 0.981692 |
| 23 | A023R | R | 0.283095 |
| 23 | A023S | S | 0.335177 |
| 23 | A023G | G | 0.350575 |
| 23 | A023F | F | 0.438047 |
| 23 | A023V | V | 0.598414 |
| 23 | A023Q | Q | 0.732052 |
| 23 | A023P | P | 0.733451 |
| 23 | A023W | W | 0.801206 |
| 23 | A023M | M | 0.946802 |
| 23 | A023Y | Y | 0.962455 |
| 24 | P024S | S | 0.614708 |
| 24 | P024Q | Q | 0.652848 |
| 24 | P024T | T | 0.663925 |
| 24 | P024A | A | 0.681992 |
| 24 | P024G | G | 0.755229 |
| 24 | P024I | I | 0.853247 |
| 24 | P024R | R | 0.907892 |
| 24 | P024H | H | 0.969695 |
| 25 | T025P | P | <0.01 |
| 25 | T025H | H | <0.01 |
| 25 | T025L | L | <0.01 |
| 25 | T025R | R | <0.01 |
| 25 | T025M | M | <0.01 |
| 25 | T025E | E | <0.01 |
| 25 | T025D | D | <0.01 |
| 25 | T025K | K | 0.133406 |
| 25 | T025W | W | 0.144315 |
| 25 | T025I | I | 0.350917 |
| 25 | T025G | G | 0.426214 |
| 25 | T025C | C | 0.509792 |
| 25 | T025V | V | 0.514769 |
| 25 | T025S | S | 0.576256 |
| 25 | T025A | A | 0.863346 |
| 26 | E026S | S | 0.280953 |
| 26 | E026T | T | 0.39705 |
| 26 | E026W | W | 0.471182 |
| 26 | E026N | N | 0.47572 |
| 26 | E026R | R | 0.813632 |
| 26 | E026G | G | 0.869755 |
| 26 | E026C | C | 0.939981 |
| 26 | E026V | V | 0.966156 |
| 26 | E026P | P | 0.993535 |
| 27 | R027W | W | <0.01 |
| 27 | R027T | T | <0.0149789677895526 |
| 27 | R027P | P | 0.483512 |
| 27 | R027C | C | 0.58498 |

TABLE 10-5-continued

PAD Assay Results

| Position | WT/Pos/Mutation | Variant | PAD Perf. Ind. |
|---|---|---|---|
| 27 | R027S | S | 0.686775 |
| 27 | R027G | G | 0.836174 |
| 27 | R027E | E | 0.925988 |
| 27 | R027V | V | 0.943209 |
| 28 | F028G | G | <0.01 |
| 28 | F028H | H | <0.01 |
| 28 | F028I | I | <0.01 |
| 28 | F028R | R | <0.01 |
| 28 | F028P | P | 0.385272 |
| 28 | F028V | V | 0.531941 |
| 28 | F028S | S | 0.696363 |
| 29 | A029V | V | 0.43718 |
| 29 | A029T | T | 0.467508 |
| 29 | A029S | S | 0.546873 |
| 29 | A029Y | Y | 0.593264 |
| 29 | A029P | P | 0.622623 |
| 29 | A029R | R | 0.728312 |
| 29 | A029W | W | 0.738583 |
| 29 | A029M | M | 0.768108 |
| 29 | A029G | G | 0.802278 |
| 29 | A029E | E | 0.844095 |
| 29 | A029D | D | 0.996225 |
| 30 | P030M | M | 0.78893 |
| 30 | P030Q | Q | 0.905135 |
| 30 | P030A | A | 0.918048 |
| 31 | D031E | E | 0.882779 |
| 27 | R027P | P | 0.483512 |
| 27 | R027C | C | 0.58498 |
| 27 | R027S | S | 0.686775 |
| 27 | R027G | G | 0.836174 |
| 27 | R027E | E | 0.925988 |
| 27 | R027V | V | 0.943209 |
| 28 | F028G | G | <0.01 |
| 28 | F028H | H | <0.01 |
| 28 | F028I | I | <0.01 |
| 28 | F028R | R | <0.01 |
| 28 | F028P | P | 0.385272 |
| 28 | F028V | V | 0.531941 |
| 28 | F028S | S | 0.696363 |
| 29 | A029V | V | 0.43718 |
| 29 | A029T | T | 0.467508 |
| 29 | A029S | S | 0.546873 |
| 29 | A029Y | Y | 0.593264 |
| 29 | A029P | P | 0.622623 |
| 29 | A029R | R | 0.728312 |
| 29 | A029W | W | 0.738583 |
| 29 | A029M | M | 0.768108 |
| 29 | A029G | G | 0.802278 |
| 29 | A029E | E | 0.844095 |
| 29 | A029D | D | 0.996225 |
| 30 | P030M | M | 0.78893 |
| 30 | P030Q | Q | 0.905135 |
| 30 | P030A | A | 0.918048 |
| 31 | D031E | E | 0.882779 |
| 32 | V032P | P | <0.01 |
| 32 | V032R | R | 0.715259 |
| 33 | R033D | D | <0.01 |
| 33 | R033E | E | <0.01 |
| 33 | R033H | H | <0.01 |
| 33 | R033P | P | <0.01 |
| 33 | R033W | W | <0.01 |
| 33 | R033V | V | 0.935183 |
| 34 | W034R | R | <0.01 |
| 34 | W034E | E | <0.01 |
| 34 | W034K | K | <0.01 |
| 34 | W034Q | Q | 0.041311 |
| 34 | W034S | S | 0.079486 |
| 34 | W034T | T | 0.153641 |
| 34 | W034V | V | 0.72591 |
| 34 | W034G | G | 0.880049 |
| 34 | W034I | I | 0.93831 |
| 35 | T035Q | Q | <0.01 |
| 35 | T035N | N | <0.01 |
| 35 | T035R | R | <0.01 |
| 35 | T035K | K | <0.01 |
| 35 | T035L | L | <0.01 |
| 35 | T035P | P | <0.01 |
| 35 | T035W | W | <0.01 |
| 35 | T035Y | Y | <0.01 |
| 35 | T035V | V | 0.344374 |
| 36 | G036P | P | <0.01 |
| 36 | G036S | S | 0.25722 |
| 36 | G036T | T | 0.326076 |
| 36 | G036V | V | 0.375828 |
| 36 | G036M | M | 0.536338 |
| 36 | G036N | N | 0.557724 |
| 36 | G036W | W | 0.682701 |
| 36 | G036Q | Q | 0.712029 |
| 36 | G036R | R | 0.897684 |
| 38 | L038K | K | <0.01 |
| 38 | L038G | G | <0.01 |
| 38 | L038E | E | <0.01 |
| 38 | L038P | P | <0.01 |
| 38 | L038Q | Q | <0.01 |
| 38 | L038R | R | <0.01 |
| 38 | L038W | W | <0.01 |
| 40 | Q040P | P | <0.01 |
| 41 | Q041V | V | <0.01 |
| 41 | Q041S | S | 0.222419 |
| 41 | Q041P | P | 0.662368 |
| 41 | Q041Y | Y | 0.701492 |
| 41 | Q041W | W | 0.878483 |
| 42 | L042W | W | <0.01 |
| 42 | L042H | H | <0.01 |
| 42 | L042T | T | <0.01 |
| 42 | L042D | D | <0.01 |
| 42 | L042Q | Q | 0.280991 |
| 42 | L042S | S | 0.450557 |
| 42 | L042R | R | 0.64188 |
| 42 | L042I | I | 0.658658 |
| 42 | L042V | V | 0.725221 |
| 42 | L042M | M | 0.73687 |
| 42 | L042G | G | 0.759964 |
| 43 | G043S | S | 0.233902 |
| 43 | G043P | P | 0.310899 |
| 43 | G043V | V | 0.332639 |
| 43 | G043Q | Q | 0.475759 |
| 43 | G043R | R | 0.585481 |
| 43 | G043C | C | 0.725373 |
| 43 | G043I | I | 0.766408 |
| 43 | G043K | K | 0.856798 |
| 43 | G043M | M | 0.877674 |
| 43 | G043Y | Y | 0.944457 |
| 43 | G043H | H | 0.957156 |
| 44 | A044S | S | <0.01 |
| 44 | A044Y | Y | <0.01 |
| 44 | A044T | T | <0.01 |
| 44 | A044R | R | <0.01 |
| 44 | A044D | D | <0.01 |
| 44 | A044H | H | <0.01 |
| 44 | A044P | P | <0.01 |
| 44 | A044E | E | 0.028463 |
| 44 | A044V | V | 0.504951 |
| 44 | A044F | F | 0.803847 |
| 44 | A044W | W | 0.847767 |
| 44 | A044M | M | 0.975188 |
| 44 | A044L | L | 0.99381 |
| 45 | D045S | S | 0.382964 |
| 45 | D045T | T | 0.438291 |
| 45 | D045R | R | 0.492492 |
| 45 | D045V | V | 0.500129 |
| 45 | D045P | P | 0.531241 |
| 45 | D045Q | Q | 0.568687 |
| 45 | D045W | W | 0.582004 |
| 45 | D045H | H | 0.779564 |
| 45 | D045L | L | 0.781626 |
| 45 | D045M | M | 0.78286 |
| 45 | D045G | G | 0.89279 |
| 45 | D045A | A | 0.841569 |
| 45 | D045C | C | 0.844725 |

TABLE 10-5-continued

PAD Assay Results

| Position | WT/Pos/Mutation | Variant | PAD Perf. Ind. |
|---|---|---|---|
| 45 | D045K | K | 0.867296 |
| 46 | F046H | H | <0.01 |
| 46 | F046T | T | 0.429962 |
| 46 | F046W | W | 0.633171 |
| 46 | F046S | S | 0.656356 |
| 46 | F046V | V | 0.786355 |
| 46 | F046I | I | 0.882982 |
| 46 | F046G | G | 0.944614 |
| 47 | E047P | P | 0.357072 |
| 47 | E047R | R | 0.620501 |
| 47 | E047N | N | 0.627512 |
| 47 | E047S | S | 0.628088 |
| 47 | E047M | M | 0.703134 |
| 47 | E047A | A | 0.757492 |
| 47 | E047F | F | 0.763159 |
| 47 | E047C | C | 0.772744 |
| 47 | E047T | T | 0.837562 |
| 47 | E047D | D | 0.975388 |
| 47 | E047H | H | 0.99217 |
| 48 | V048R | R | <0.01 |
| 48 | V048W | W | <0.01 |
| 48 | V048S | S | 0.423613 |
| 48 | V048G | G | 0.873544 |
| 48 | V048N | N | 0.980906 |
| 48 | V048E | E | 0.987222 |
| 49 | I049P | P | 0.161279 |
| 49 | I049R | R | 0.29139 |
| 49 | I049W | W | 0.676641 |
| 49 | I049H | H | 0.740799 |
| 49 | I049S | S | 0.789362 |
| 49 | I049E | E | 0.876247 |
| 49 | I049V | V | 0.972022 |
| 50 | E050R | R | <0.01 |
| 50 | E050W | W | 0.14091 |
| 50 | E050V | V | 0.425221 |
| 50 | E050I | I | 0.575369 |
| 50 | E050S | S | 0.645021 |
| 50 | E050Q | Q | 0.906441 |
| 50 | E050L | L | 0.967983 |
| 51 | E051R | R | <0.01 |
| 51 | E051P | P | <0.01 |
| 51 | E051I | I | 0.044391 |
| 51 | E051W | W | 0.165053 |
| 51 | E051V | V | 0.367755 |
| 51 | E051Q | Q | 0.761883 |
| 51 | E051L | L | 0.927544 |
| 52 | G052H | H | <0.01 |
| 52 | G052S | S | <0.01 |
| 52 | G052V | V | <0.01 |
| 52 | G052T | T | <0.01 |
| 52 | G052M | M | <0.01 |
| 52 | G052F | F | <0.01 |
| 52 | G052I | I | 0.069022 |
| 52 | G052P | P | 0.242545 |
| 52 | G052L | L | 0.244397 |
| 52 | G052Q | Q | 0.283827 |
| 52 | G052R | R | 0.349923 |
| 52 | G052E | E | 0.549067 |
| 52 | G052A | A | 0.793929 |
| 53 | L053R | R | <0.01 |
| 53 | L053W | W | <0.01 |
| 53 | L053P | P | <0.01 |
| 53 | L053D | D | <0.01328259968325 |
| 53 | L053E | E | 0.191623 |
| 53 | L053K | K | 0.237686 |
| 53 | L053S | S | 0.260431 |
| 53 | L053G | G | 0.32712 |
| 53 | L053V | V | 0.652864 |
| 53 | L053I | I | 0.659806 |
| 53 | L053Q | Q | 0.717093 |
| 53 | L053T | T | 0.842042 |
| 54 | S054F | F | <0.01 |
| 54 | S054W | W | <0.01 |
| 54 | S054H | H | <0.01 |
| 54 | S054K | K | 0.083519 |
| 54 | S054I | I | 0.116295 |
| 54 | S054Y | Y | 0.124722 |
| 54 | S054G | G | 0.170484 |
| 54 | S054L | L | 0.258821 |
| 54 | S054V | V | 0.285755 |
| 54 | S054E | E | 0.296919 |
| 54 | S054T | T | 0.329279 |
| 54 | S054R | R | 0.354857 |
| 54 | S054M | M | 0.482666 |
| 54 | S054Q | Q | 0.531633 |
| 54 | S054D | D | 0.647787 |
| 54 | S054C | C | 0.87772 |
| 55 | A055V | V | <0.01 |
| 55 | A055I | I | <0.01 |
| 55 | A055P | P | <0.01 |
| 55 | A055W | W | <0.01 |
| 55 | A055Y | Y | 0.176777 |
| 55 | A055R | R | 0.245648 |
| 55 | A055T | T | 0.415054 |
| 55 | A055G | G | 0.731513 |
| 55 | A055L | L | 0.866592 |
| 55 | A055S | S | 0.866756 |
| 55 | A055H | H | 0.921909 |
| 56 | R056C | C | <0.01 |
| 56 | R056G | G | <0.01 |
| 56 | R056T | T | <0.01 |
| 56 | R056E | E | <0.01 |
| 56 | R056H | H | <0.01 |
| 56 | R056K | K | <0.01 |
| 56 | R056P | P | <0.01 |
| 56 | R056Q | Q | <0.01 |
| 56 | R056W | W | <0.01 |
| 56 | R056Y | Y | <0.01 |
| 56 | R056S | S | 0.123501 |
| 56 | R056L | L | 0.237933 |
| 56 | R056N | N | 0.267811 |
| 56 | R056A | A | 0.68802 |
| 57 | T057R | R | <0.01 |
| 57 | T057P | P | <0.01 |
| 57 | T057W | W | <0.01 |
| 57 | T057N | N | 0.245605 |
| 57 | T057C | C | 0.398001 |
| 57 | T057Y | Y | 0.551709 |
| 57 | T057H | H | 0.605386 |
| 57 | T057A | A | 0.651879 |
| 57 | T057L | L | 0.762087 |
| 57 | T057V | V | 0.86913 |
| 57 | T057I | I | 0.870692 |
| 58 | T058E | E | <0.01 |
| 58 | T058G | G | <0.01 |
| 58 | T058K | K | <0.01 |
| 58 | T058P | P | <0.01 |
| 58 | T058R | R | <0.01 |
| 58 | T058W | W | <0.01 |
| 58 | T058Y | Y | <0.01 |
| 58 | T058M | M | 0.026886 |
| 58 | T058A | A | 0.361258 |
| 58 | T058V | V | 0.955494 |
| 58 | T058S | S | 0.964758 |
| 59 | N059R | R | <0.01 |
| 59 | N059M | M | <0.01 |
| 59 | N059P | P | <0.01 |
| 59 | N059Q | Q | 0.165409 |
| 59 | N059T | T | 0.501362 |
| 59 | N059S | S | 0.651989 |
| 59 | N059K | K | 0.731191 |
| 59 | N059E | E | 0.879272 |
| 59 | N059V | V | 0.887341 |
| 59 | N059G | G | 0.890006 |
| 59 | N059F | F | 0.911279 |
| 59 | N059A | A | 0.929578 |
| 59 | N059Y | Y | 0.99189 |
| 59 | N059C | C | 0.99959 |
| 60 | I060P | P | 0.318965 |
| 60 | I060D | D | 0.660273 |

TABLE 10-5-continued

PAD Assay Results

| Position | WT/Pos/Mutation | Variant | PAD Perf. Ind. |
|---|---|---|---|
| 60 | I060C | C | 0.668516 |
| 60 | I060M | M | 0.682237 |
| 60 | I060A | A | 0.788799 |
| 60 | I060R | R | 0.809655 |
| 60 | I060L | L | 0.913226 |
| 60 | I060E | E | 0.923286 |
| 60 | I060K | K | 0.959958 |
| 60 | I060S | S | 0.999829 |
| 61 | D061F | F | 0.698154 |
| 61 | D061A | A | 0.708121 |
| 61 | D061C | C | 0.848446 |
| 61 | D061Y | Y | 0.948278 |
| 61 | D061V | V | 0.968066 |
| 61 | D061N | N | 0.999276 |
| 62 | D062T | T | <0.01 |
| 62 | D062I | I | <0.01 |
| 62 | D062V | V | <0.01 |
| 62 | D062H | H | <0.01 |
| 62 | D062W | W | <0.01 |
| 62 | D062S | S | <0.01 |
| 62 | D062L | L | <0.01 |
| 62 | D062G | G | <0.01 |
| 62 | D062R | R | <0.01 |
| 62 | D062M | M | <0.01 |
| 62 | D062P | P | <0.01 |
| 62 | D062Q | Q | <0.01 |
| 62 | D062A | A | 0.113753 |
| 62 | D062C | C | 0.490736 |
| 62 | D062E | E | 0.602369 |
| 63 | P063A | A | 0.598416 |
| 63 | P063R | R | 0.801911 |
| 63 | P063S | S | 0.898408 |
| 63 | P063M | M | 0.908904 |
| 63 | P063F | F | 0.925844 |
| 63 | P063Y | Y | 0.948378 |
| 64 | T064R | R | 0.106209 |
| 64 | T064D | D | 0.640095 |
| 64 | T064W | W | 0.691185 |
| 64 | T064Q | Q | 0.865168 |
| 64 | T064C | C | 0.876862 |
| 64 | T064P | P | 0.936023 |
| 64 | T064H | H | 0.960718 |
| 64 | T064N | N | 0.983933 |
| 64 | T064S | S | 0.987972 |
| 65 | D065V | V | 0.199467 |
| 65 | D065R | R | 0.215599 |
| 65 | D065H | H | 0.398178 |
| 65 | D065Y | Y | 0.42301 |
| 65 | D065P | P | 0.423122 |
| 65 | D065S | S | 0.468174 |
| 65 | D065W | W | 0.50219 |
| 65 | D065T | T | 0.5039 |
| 65 | D065G | G | 0.51655 |
| 65 | D065I | I | 0.617391 |
| 65 | D065A | A | 0.723321 |
| 66 | P066N | N | 0.381273 |
| 66 | P066Q | Q | 0.422614 |
| 66 | P066G | G | 0.444859 |
| 66 | P066R | R | 0.508806 |
| 66 | P066C | C | 0.523524 |
| 66 | P066A | A | 0.563865 |
| 66 | P066F | F | 0.672865 |
| 66 | P066Y | Y | 0.699931 |
| 66 | P066D | D | 0.718749 |
| 66 | P066I | I | 0.844376 |
| 66 | P066V | V | 0.89302 |
| 66 | P066H | H | 0.947771 |
| 66 | P066L | L | 0.987271 |
| 67 | R067F | F | <0.0149736260903786 |
| 67 | R067W | W | <0.0171329732205367 |
| 67 | R067P | P | 0.036575 |
| 67 | R067E | E | 0.113415 |
| 67 | R067V | V | 0.1203 |
| 67 | R067Q | Q | 0.126838 |
| 67 | R067L | L | 0.156654 |
| 67 | R067A | A | 0.215271 |
| 67 | R067T | T | 0.315404 |
| 67 | R067N | N | 0.333066 |
| 67 | R067G | G | 0.40823 |
| 67 | R067K | K | 0.986487 |
| 68 | L068G | G | <0.01 |
| 68 | L068A | A | <0.01 |
| 68 | L068M | M | 0.02834 |
| 68 | L068C | C | 0.05996 |
| 68 | L068S | S | 0.071622 |
| 68 | L068N | N | 0.100981 |
| 68 | L068E | E | 0.131505 |
| 68 | L068H | H | 0.222734 |
| 68 | L068Q | Q | 0.254448 |
| 68 | L068F | F | 0.254797 |
| 68 | L068T | T | 0.324904 |
| 68 | L068P | P | 0.35297 |
| 68 | L068D | D | 0.443469 |
| 68 | L068Y | Y | 0.447862 |
| 68 | L068R | R | 0.465293 |
| 68 | L068V | V | 0.507389 |
| 68 | L068W | W | 0.561612 |
| 68 | L068I | I | 0.727312 |
| 69 | N069Y | Y | 0.173925 |
| 69 | N069W | W | 0.55063 |
| 69 | N069P | P | 0.591783 |
| 69 | N069R | R | 0.828172 |
| 69 | N069G | G | 0.976332 |
| 70 | G070M | M | <0.01 |
| 70 | G070T | T | <0.01 |
| 70 | G070P | P | <0.01 |
| 70 | G070V | V | <0.01 |
| 70 | G070C | C | <0.01 |
| 70 | G070R | R | <0.01 |
| 70 | G070Y | Y | <0.01 |
| 70 | G070K | K | <0.01 |
| 70 | G070N | N | <0.01 |
| 70 | G070Q | Q | <0.01 |
| 70 | G070F | F | <0.01 |
| 70 | G070I | I | 0.270463 |
| 70 | G070E | E | 0.33356 |
| 70 | G070S | S | 0.638917 |
| 71 | A071P | P | <0.01 |
| 71 | A071N | N | 0.613838 |
| 71 | A071D | D | 0.646588 |
| 71 | A071G | G | 0.675895 |
| 71 | A071S | S | 0.693249 |
| 71 | A071R | R | 0.771492 |
| 71 | A071H | H | 0.781953 |
| 71 | A071I | I | 0.786894 |
| 71 | A071T | T | 0.79386 |
| 71 | A071E | E | 0.809505 |
| 71 | A071L | L | 0.838126 |
| 71 | A071F | F | 0.985677 |
| 71 | A071C | C | 0.993683 |
| 72 | S072Y | Y | 0.069096 |
| 72 | S072W | W | 0.339835 |
| 72 | S072P | P | 0.555612 |
| 72 | S072Q | Q | 0.655328 |
| 72 | S072L | L | 0.703483 |
| 72 | S072R | R | 0.742354 |
| 72 | S072D | D | 0.800127 |
| 72 | S072V | V | 0.82827 |
| 72 | S072E | E | 0.930527 |
| 72 | S072T | T | 0.973836 |
| 73 | Y073P | P | <0.01 |
| 73 | Y073R | R | 0.262561 |
| 73 | Y073L | L | 0.497588 |
| 73 | Y073G | G | 0.509699 |
| 73 | Y073H | H | 0.515737 |
| 73 | Y073I | I | 0.641914 |
| 73 | Y073S | S | 0.676285 |
| 73 | Y073V | V | 0.73535 |
| 73 | Y073N | N | 0.758401 |
| 73 | Y073D | D | 0.803442 |

TABLE 10-5-continued

PAD Assay Results

| Position | WT/Pos/Mutation | Variant | PAD Perf. Ind. |
|---|---|---|---|
| 73 | Y073Q | Q | 0.866092 |
| 73 | Y073K | K | 0.944166 |
| 76 | S076W | W | <0.01 |
| 76 | S076Y | Y | 0.177113 |
| 76 | S076F | F | 0.461095 |
| 76 | S076Q | Q | 0.900789 |
| 77 | C077Y | Y | <0.01 |
| 77 | C077R | R | <0.01 |
| 77 | C077W | W | <0.01 |
| 77 | C077F | F | <0.01 |
| 77 | C077N | N | <0.01 |
| 77 | C077P | P | <0.01 |
| 77 | C077G | G | 0.181068 |
| 77 | C077L | L | 0.734708 |
| 77 | C077S | S | 0.764136 |
| 77 | C077V | V | 0.802259 |
| 77 | C077A | A | 0.912937 |
| 77 | L078E | E | <0.01 |
| 77 | L078N | N | <0.01 |
| 78 | L078A | A | <0.01 |
| 78 | L078P | P | <0.01 |
| 78 | L078R | R | <0.01 |
| 78 | L078S | S | <0.01 |
| 78 | L078M | M | 0.477538 |
| 78 | L078Q | Q | 0.519566 |
| 78 | L078C | C | 0.779536 |
| 78 | L078Y | Y | 0.809511 |
| 78 | L078V | V | 0.827484 |
| 79 | A079H | H | <0.01 |
| 79 | A079F | F | <0.01 |
| 79 | A079V | V | <0.01 |
| 79 | A079C | C | 0.026887 |
| 79 | A079Q | Q | 0.268704 |
| 79 | A079E | E | 0.272158 |
| 79 | A079N | N | 0.281684 |
| 79 | A079M | M | 0.284387 |
| 79 | A079R | R | 0.321618 |
| 79 | A079W | W | 0.530746 |
| 79 | A079T | T | 0.598368 |
| 79 | A079I | I | 0.673986 |
| 79 | A079S | S | 0.779628 |
| 79 | A079G | G | 0.915372 |
| 79 | A079P | P | 0.94147 |
| 79 | A079L | L | 0.958677 |
| 80 | T080W | W | <0.01 |
| 80 | T080L | L | <0.01 |
| 80 | T080K | K | <0.01 |
| 80 | T080R | R | <0.01 |
| 80 | T080E | E | <0.01 |
| 80 | T080P | P | <0.01 |
| 80 | T080H | H | 0.049717 |
| 80 | T080Y | Y | 0.107973 |
| 80 | T080I | I | 0.146188 |
| 80 | T080N | N | 0.529867 |
| 82 | L082R | R | <0.01 |
| 82 | L082S | S | <0.01 |
| 82 | L082W | W | <0.01 |
| 82 | L082V | V | 0.187819 |
| 82 | L082G | G | 0.310823 |
| 82 | L082T | T | 0.377413 |
| 82 | L082H | H | 0.468806 |
| 82 | L082I | I | 0.508005 |
| 82 | L082K | K | 0.508537 |
| 82 | L082P | P | 0.516154 |
| 82 | L082A | A | 0.976228 |
| 83 | P083T | T | <0.01 |
| 83 | P083V | V | 0.186837 |
| 83 | P083L | L | 0.211018 |
| 83 | P083H | H | 0.611439 |
| 83 | P083W | W | 0.621496 |
| 83 | P083G | G | 0.677444 |
| 83 | P083S | S | 0.789585 |
| 83 | P083Q | Q | 0.818267 |
| 83 | P083D | D | 0.831344 |
| 83 | P083F | F | 0.99445 |
| 84 | L084W | W | <0.01 |
| 84 | L084V | V | 0.416576 |
| 84 | L084P | P | 0.43025 |
| 84 | L084T | T | 0.438956 |
| 84 | L084A | A | 0.453182 |
| 84 | L084Q | Q | 0.516002 |
| 84 | L084S | S | 0.550862 |
| 84 | L084R | R | 0.565943 |
| 84 | L084N | N | 0.665228 |
| 84 | L084K | K | 0.79008 |
| 84 | L084D | D | 0.85276 |
| 84 | L084I | I | 0.870124 |
| 84 | L084H | H | 0.993217 |
| 85 | D085I | I | 0.100248 |
| 85 | D085L | L | 0.241561 |
| 85 | D085V | V | 0.25268 |
| 85 | D085W | W | 0.341677 |
| 85 | D085P | P | 0.543807 |
| 85 | D085Y | Y | 0.554364 |
| 85 | D085S | S | 0.675803 |
| 85 | D085T | T | 0.708548 |
| 85 | D085N | N | 0.781957 |
| 85 | D085Q | Q | 0.988545 |
| 86 | L086H | H | <0.01 |
| 86 | L086S | S | <0.01 |
| 86 | L086R | R | <0.01 |
| 86 | L086E | E | <0.01 |
| 86 | L086F | F | <0.01 |
| 86 | L086Q | Q | <0.01 |
| 86 | L086W | W | 0.077717 |
| 86 | L086V | V | 0.120133 |
| 86 | L086T | T | 0.284184 |
| 86 | L086G | G | 0.696393 |
| 86 | L086Y | Y | 0.815121 |
| 86 | L086P | P | 0.987233 |
| 87 | V087S | S | <0.01 |
| 87 | V087G | G | <0.01 |
| 87 | V087Y | Y | <0.01 |
| 87 | V087R | R | <0.01 |
| 87 | V087K | K | <0.01 |
| 87 | V087D | D | <0.01 |
| 87 | V087F | F | 0.103908 |
| 87 | V087T | T | 0.147618 |
| 87 | V087A | A | 0.16806 |
| 87 | V087M | M | 0.751854 |
| 89 | I089H | H | <0.01 |
| 89 | I089S | S | <0.01 |
| 89 | I089G | G | <0.01 |
| 89 | I089W | W | <0.01 |
| 89 | I089Q | Q | <0.01 |
| 89 | I089D | D | <0.01 |
| 89 | I089E | E | <0.01 |
| 89 | I089R | R | <0.01 |
| 89 | I089F | F | 0.745747 |
| 89 | I089V | V | 0.820031 |
| 89 | I089T | T | 0.900425 |
| 94 | N094L | L | <0.01 |
| 94 | N094T | T | <0.01 |
| 94 | N094V | V | <0.01 |
| 94 | N094H | H | <0.01 |
| 94 | N094R | R | <0.01 |
| 94 | N094W | W | <0.01 |
| 94 | N094M | M | 0.031458 |
| 94 | N094C | C | 0.072751 |
| 94 | N094Y | Y | 0.123924 |
| 94 | N094G | G | 0.532837 |
| 94 | N094A | A | 0.74316 |
| 94 | N094P | P | 0.789771 |
| 94 | N094S | S | 0.877698 |
| 95 | D095A | A | <0.01 |
| 95 | D095C | C | <0.01 |
| 95 | D095G | G | <0.01 |
| 95 | D095H | H | <0.01 |
| 95 | D095K | K | <0.01 |
| 95 | D095L | L | <0.01 |

TABLE 10-5-continued

PAD Assay Results

| Position | WT/Pos/Mutation | Variant | PAD Perf. Ind. |
|---|---|---|---|
| 95 | D095N | N | <0.01 |
| 95 | D095Q | Q | <0.01 |
| 95 | D095R | R | <0.01 |
| 95 | D095S | S | <0.01 |
| 95 | D095T | T | <0.01 |
| 95 | D095V | V | <0.01 |
| 95 | D095W | W | <0.01 |
| 95 | D095Y | Y | <0.01 |
| 95 | D095E | E | 0.754335 |
| 96 | T096I | I | <0.01 |
| 96 | T096W | W | <0.01 |
| 96 | T096Y | Y | <0.01 |
| 96 | T096R | R | 0.136108 |
| 96 | T096V | V | 0.58611 |
| 96 | T096S | S | 0.786547 |
| 96 | T096P | P | 0.885134 |
| 97 | K097Q | Q | <0.01 |
| 97 | K097G | G | <0.01 |
| 97 | K097I | I | <0.01 |
| 97 | K097W | W | <0.01 |
| 97 | K097L | L | <0.01 |
| 97 | K097V | V | <0.01 |
| 97 | K097Y | Y | <0.01 |
| 97 | K097S | S | <0.01 |
| 97 | K097T | T | <0.01 |
| 97 | K097D | D | <0.01 |
| 97 | K097M | M | 0.216645 |
| 97 | K097A | A | 0.227977 |
| 97 | K097P | P | 0.26585 |
| 97 | K097R | R | 0.587184 |
| 99 | Y099R | R | 0.291941 |
| 99 | Y099V | V | 0.311502 |
| 99 | Y099S | S | 0.367181 |
| 99 | Y099W | W | 0.566038 |
| 99 | Y099H | H | 0.591623 |
| 99 | Y099I | I | 0.60574 |
| 99 | Y099G | G | 0.700083 |
| 99 | Y099P | P | 0.813989 |
| 99 | Y099A | A | 0.822549 |
| 99 | Y099L | L | 0.856204 |
| 100 | F100W | W | <0.01 |
| 100 | F100K | K | <0.01 |
| 100 | F100D | D | <0.01 |
| 100 | F100E | E | 0.152427 |
| 100 | F100S | S | 0.852784 |
| 101 | R101W | W | <0.01 |
| 101 | R101K | K | 0.068708 |
| 101 | R101Q | Q | 0.107171 |
| 101 | R101V | V | 0.442582 |
| 101 | R101D | D | 0.800722 |
| 101 | R101Y | Y | 0.803109 |
| 101 | R101P | P | 0.855496 |
| 101 | R101N | N | 0.918012 |
| 101 | R101C | C | 0.946306 |
| 101 | R101I | I | 0.955711 |
| 101 | R101F | F | 0.965422 |
| 102 | R102W | W | <0.01 |
| 102 | R102F | F | 0.226881 |
| 102 | R102G | G | 0.270733 |
| 102 | R102C | C | 0.363718 |
| 102 | R102V | V | 0.60605 |
| 102 | R102D | D | 0.684234 |
| 102 | R102P | P | 0.894709 |
| 102 | R102S | S | 0.960127 |
| 103 | T103W | W | <0.01 |
| 103 | T103Y | Y | <0.01 |
| 103 | T103G | G | <0.01 |
| 103 | T103K | K | <0.01 |
| 103 | T103I | I | <0.01 |
| 103 | T103L | L | <0.01 |
| 103 | T103H | H | <0.01 |
| 103 | T103A | A | <0.01 |
| 103 | T103V | V | <0.01 |
| 103 | T103S | S | <0.01 |
| 103 | T103C | C | <0.01 |
| 103 | T103R | R | <0.01 |
| 103 | T103N | N | <0.01 |
| 103 | T103F | F | <0.01 |
| 103 | T103P | P | <0.01 |
| 104 | P104R | R | <0.01 |
| 104 | P104A | A | <0.01 |
| 104 | P104L | L | <0.01 |
| 104 | P104W | W | 0.232802 |
| 104 | P104T | T | 0.333526 |
| 104 | P104S | S | 0.529113 |
| 104 | P104Q | Q | 0.847699 |
| 104 | P104F | F | 0.863543 |
| 104 | P104G | G | 0.984538 |
| 105 | L105V | V | <0.01 |
| 105 | L105A | A | <0.01 |
| 105 | L105M | M | <0.01 |
| 105 | L105E | E | 0.528458 |
| 105 | L105S | S | 0.609931 |
| 105 | L105Y | Y | 0.620029 |
| 105 | L105T | T | 0.638962 |
| 105 | L105P | P | 0.902642 |
| 106 | D106R | R | 0.559786 |
| 106 | D106Q | Q | 0.617485 |
| 106 | D106P | P | 0.632087 |
| 106 | D106N | N | 0.642667 |
| 106 | D106M | M | 0.855673 |
| 106 | D106I | I | 0.915931 |
| 106 | D106L | L | 0.99561 |
| 107 | I107E | E | <0.01 |
| 107 | I107G | G | <0.01 |
| 107 | I107F | F | <0.01 |
| 107 | I107Q | Q | <0.01 |
| 107 | I107R | R | <0.01 |
| 107 | I107H | H | <0.01 |
| 107 | I107W | W | <0.01 |
| 107 | I107P | P | 0.318743 |
| 107 | I107Y | Y | 0.524182 |
| 107 | I107A | A | 0.795478 |
| 107 | I107N | N | 0.929935 |
| 107 | I107V | V | 0.96863 |
| 108 | A108D | D | <0.01 |
| 108 | A108F | F | <0.01 |
| 108 | A108H | H | <0.01 |
| 108 | A108I | I | <0.01 |
| 108 | A108N | N | <0.01 |
| 108 | A108P | P | <0.01 |
| 108 | A108R | R | <0.01 |
| 108 | A108E | E | 0.60726 |
| 108 | A108Q | Q | 0.734472 |
| 108 | A108T | T | 0.865471 |
| 108 | A108V | V | 0.950481 |
| 109 | L109W | W | <0.01 |
| 109 | L109D | D | 0.106206 |
| 109 | L109I | I | 0.144257 |
| 109 | L109E | E | 0.194168 |
| 109 | L109R | R | 0.210346 |
| 109 | L109H | H | 0.220153 |
| 109 | L109Q | Q | 0.222755 |
| 109 | L109F | F | 0.317718 |
| 109 | L109A | A | 0.323528 |
| 109 | L109S | S | 0.378623 |
| 109 | L109P | P | 0.434661 |
| 109 | L109G | G | 0.51022 |
| 109 | L109V | V | 0.539733 |
| 109 | L109M | M | 0.628881 |
| 109 | L109N | N | 0.658369 |
| 109 | L109T | T | 0.79132 |
| 109 | L109Y | Y | 0.825105 |
| 110 | G110T | T | <0.01 |
| 110 | G110L | L | <0.01 |
| 110 | G110W | W | <0.01 |
| 110 | G110Y | Y | <0.01 |
| 110 | G110P | P | 0.224284 |
| 110 | G110I | I | 0.232219 |
| 110 | G110S | S | 0.30218 |

TABLE 10-5-continued

PAD Assay Results

| Position | WT/Pos/Mutation | Variant | PAD Perf. Ind. |
|---|---|---|---|
| 110 | G110Q | Q | 0.343918 |
| 110 | G110R | R | 0.476072 |
| 110 | G110H | H | 0.73456 |
| 110 | G110N | N | 0.770851 |
| 110 | G110M | M | 0.816422 |
| 111 | M111R | R | <0.01 |
| 111 | M111S | S | 0.139078 |
| 111 | M111H | H | 0.192733 |
| 111 | M111G | G | 0.315165 |
| 111 | M111P | P | 0.566892 |
| 111 | M111E | E | 0.668985 |
| 111 | M111L | L | 0.67115 |
| 111 | M111K | K | 0.706165 |
| 111 | M111T | T | 0.763332 |
| 111 | M111F | F | 0.776934 |
| 111 | M111D | D | 0.78777 |
| 111 | M111V | V | 0.92522 |
| 112 | S112Y | Y | <0.01 |
| 112 | S112R | R | <0.01 |
| 112 | S112P | P | <0.01 |
| 112 | S112H | H | 0.380254 |
| 112 | S112V | V | 0.479716 |
| 112 | S112M | M | 0.564157 |
| 112 | S112W | W | 0.582165 |
| 112 | S112K | K | 0.678369 |
| 112 | S112T | T | 0.721644 |
| 112 | S112N | N | 0.850159 |
| 112 | S112F | F | 0.878895 |
| 112 | S112A | A | 0.943049 |
| 113 | V113S | S | 0.572415 |
| 113 | V113G | G | 0.579385 |
| 113 | V113K | K | 0.716865 |
| 113 | V113H | H | 0.763416 |
| 113 | V113W | W | 0.803685 |
| 113 | V113L | L | 0.854963 |
| 113 | V113T | T | 0.861744 |
| 113 | V113D | D | 0.871104 |
| 113 | V113E | E | 0.936465 |
| 113 | V113C | C | 0.937598 |
| 113 | V113F | F | 0.959822 |
| 113 | V113Y | Y | 0.981976 |
| 114 | L114H | H | <0.01 |
| 114 | L114E | E | <0.01 |
| 114 | L114F | F | <0.01 |
| 114 | L114K | K | <0.01 |
| 114 | L114R | R | <0.01 |
| 114 | L114W | W | <0.01 |
| 114 | L114Y | Y | <0.01 |
| 114 | L114Q | Q | 0.115737 |
| 114 | L114P | P | 0.275464 |
| 114 | L114S | S | 0.545726 |
| 114 | L114V | V | 0.595416 |
| 114 | L114N | N | 0.77333 |
| 115 | V115H | H | <0.01 |
| 115 | V115K | K | <0.01 |
| 115 | V115I | I | 0.994833 |
| 116 | T116Y | Y | 0.466112 |
| 116 | T116V | V | 0.571817 |
| 116 | T116R | R | 0.619823 |
| 116 | T116L | L | 0.681201 |
| 116 | T116W | W | 0.748358 |
| 116 | T116I | I | 0.760474 |
| 116 | T116Q | Q | 0.768867 |
| 116 | T116P | P | 0.836786 |
| 116 | T116G | G | 0.901886 |
| 116 | T116E | E | 0.906124 |
| 116 | T116A | A | 0.952003 |
| 116 | T116S | S | 0.963005 |
| 117 | Q117W | W | 0.707035 |
| 117 | Q117V | V | 0.761971 |
| 117 | Q117G | G | 0.794858 |
| 117 | Q117S | S | 0.86512 |
| 118 | V118K | K | <0.01 |
| 118 | V118W | W | <0.01 |
| 118 | V118E | E | <0.01 |
| 118 | V118R | R | 0.069623 |
| 118 | V118P | P | 0.222399 |
| 118 | V118D | D | 0.40168 |
| 118 | V118I | I | 0.545694 |
| 118 | V118G | G | 0.559239 |
| 118 | V118S | S | 0.815888 |
| 118 | V118A | A | 0.852723 |
| 118 | V118T | T | 0.91759 |
| 118 | V118M | M | 0.933469 |
| 118 | V118F | F | 0.998467 |
| 119 | L119G | G | <0.01 |
| 119 | L119S | S | <0.01 |
| 119 | L119F | F | <0.01 |
| 119 | L119R | R | <0.01 |
| 119 | L119P | P | <0.01 |
| 119 | L119T | T | 0.102922 |
| 119 | L119N | N | 0.113151 |
| 119 | L119V | V | 0.150373 |
| 119 | L119W | W | 0.203313 |
| 119 | L119C | C | 0.244106 |
| 119 | L119D | D | 0.280381 |
| 119 | L119E | E | 0.322167 |
| 119 | L119I | I | 0.427476 |
| 119 | L119H | H | 0.462912 |
| 119 | L119Y | Y | 0.556343 |
| 120 | T120P | P | <0.01 |
| 120 | T120H | H | 0.498304 |
| 120 | T120R | R | 0.599376 |
| 120 | T120A | A | 0.663543 |
| 120 | T120Q | Q | 0.781096 |
| 120 | T120C | C | 0.924433 |
| 121 | S121P | P | 0.384623 |
| 121 | S121R | R | 0.701237 |
| 121 | S121W | W | 0.772781 |
| 121 | S121K | K | 0.77795 |
| 121 | S121G | G | 0.992545 |
| 122 | A122G | G | <0.01 |
| 122 | A122D | D | 0.059137 |
| 122 | A122F | F | 0.148369 |
| 122 | A122H | H | 0.169443 |
| 122 | A122R | R | 0.396041 |
| 122 | A122S | S | 0.431258 |
| 122 | A122K | K | 0.450105 |
| 122 | A122E | E | 0.467766 |
| 122 | A122T | T | 0.520454 |
| 122 | A122P | P | 0.548155 |
| 122 | A122I | I | 0.647406 |
| 122 | A122N | N | 0.704284 |
| 122 | A122Q | Q | 0.741587 |
| 122 | A122W | W | 0.862265 |
| 122 | A122V | V | 0.886387 |
| 122 | A122M | M | 0.938855 |
| 124 | G124I | I | <0.01 |
| 124 | G124H | H | <0.01 |
| 124 | G124M | M | <0.01 |
| 124 | G124W | W | <0.01 |
| 124 | G124P | P | <0.01 |
| 124 | G124A | A | 0.031196 |
| 124 | G124Q | Q | 0.208313 |
| 124 | G124T | T | 0.315233 |
| 124 | G124V | V | 0.329769 |
| 124 | G124R | R | 0.409769 |
| 124 | G124L | L | 0.536625 |
| 124 | G124S | S | 0.555215 |
| 124 | G124Y | Y | 0.559199 |
| 124 | G124N | N | 0.599171 |
| 124 | G124D | D | 0.63784 |
| 124 | G124C | C | 0.672179 |
| 124 | G124F | F | 0.950801 |
| 125 | V125W | W | 0.24527 |
| 125 | V125E | E | 0.385171 |
| 125 | V125R | R | 0.466062 |
| 125 | V125C | C | 0.541228 |
| 125 | V125D | D | 0.541318 |
| 125 | V125P | P | 0.622352 |

TABLE 10-5-continued

PAD Assay Results

| Position | WT/Pos/Mutation | Variant | PAD Perf. Ind. |
|---|---|---|---|
| 125 | V125F | F | 0.627367 |
| 125 | V125S | S | 0.790998 |
| 125 | V125Y | Y | 0.813593 |
| 125 | V125A | A | 0.925641 |
| 125 | V125I | I | 0.941326 |
| 126 | G126I | I | <0.010426347441542 |
| 126 | G126V | V | 0.175001 |
| 126 | G126Y | Y | 0.234673 |
| 126 | G126L | L | 0.540613 |
| 126 | G126A | A | 0.552538 |
| 126 | G126E | E | 0.599533 |
| 126 | G126P | P | 0.673809 |
| 126 | G126T | T | 0.737666 |
| 126 | G126R | R | 0.761417 |
| 126 | G126N | N | 0.846727 |
| 126 | G126S | S | 0.902662 |
| 126 | G126C | C | 0.980807 |
| 127 | T127L | L | <0.01 |
| 127 | T127E | E | <0.01 |
| 127 | T127Q | Q | 0.151533 |
| 127 | T127I | I | 0.203586 |
| 127 | T127H | H | 0.60105 |
| 127 | T127D | D | 0.61747 |
| 127 | T127M | M | 0.639504 |
| 127 | T127C | C | 0.653314 |
| 127 | T127V | V | 0.683337 |
| 127 | T127G | G | 0.710564 |
| 127 | T127P | P | 0.773291 |
| 127 | T127S | S | 0.828003 |
| 128 | T128D | D | 0.662836 |
| 129 | Y129W | W | <0.01 |
| 129 | Y129G | G | <0.01 |
| 129 | Y129K | K | <0.01 |
| 129 | Y129V | V | <0.01 |
| 129 | Y129T | T | 0.138769 |
| 129 | Y129A | A | 0.173554 |
| 129 | Y129R | R | 0.178362 |
| 129 | Y129M | M | 0.211662 |
| 129 | Y129D | D | 0.228506 |
| 129 | Y129L | L | 0.270643 |
| 129 | Y129N | N | 0.530034 |
| 129 | Y129P | P | 0.588917 |
| 129 | Y129C | C | 0.610384 |
| 129 | Y129S | S | 0.692051 |
| 129 | Y129F | F | 0.713199 |
| 146 | P146W | W | 0.680806 |
| 146 | P146T | T | 0.756105 |
| 146 | P146V | V | 0.768041 |
| 146 | P146S | S | 0.956673 |
| 148 | P148Q | Q | 0.975963 |
| 149 | W149R | R | <0.01 |
| 149 | W149E | E | <0.01 |
| 149 | W149P | P | <0.01 |
| 149 | W149C | C | 0.1164 |
| 149 | W149I | I | 0.235936 |
| 149 | W149A | A | 0.311848 |
| 149 | W149S | S | 0.329233 |
| 149 | W149Q | Q | 0.402387 |
| 149 | W149T | T | 0.440303 |
| 149 | W149G | G | 0.44856 |
| 149 | W149M | M | 0.494615 |
| 149 | W149F | F | 0.495779 |
| 149 | W149L | L | 0.637667 |
| 149 | W149Y | Y | 0.747652 |
| 150 | F150P | P | 0.31768 |
| 150 | F150N | N | 0.362798 |
| 150 | F150G | G | 0.458431 |
| 150 | F150V | V | 0.511676 |
| 150 | F150A | A | 0.539571 |
| 150 | F150T | T | 0.580879 |
| 150 | F150W | W | 0.622886 |
| 150 | F150M | M | 0.625886 |
| 150 | F150E | E | 0.727755 |
| 150 | F150C | C | 0.778063 |
| 150 | F150I | I | 0.78431 |
| 150 | F150K | K | 0.848249 |
| 153 | I153N | N | 0.890296 |
| 154 | F154T | T | <0.01 |
| 154 | F154D | D | <0.01 |
| 154 | F154E | E | <0.01 |
| 154 | F154G | G | <0.01 |
| 154 | F154L | L | <0.01 |
| 154 | F154P | P | <0.01 |
| 154 | F154V | V | <0.01 |
| 154 | F154S | S | 0.287767 |
| 154 | F154Q | Q | 0.973299 |
| 194 | I194S | S | <0.01 |
| 194 | I194A | A | <0.01 |
| 194 | I194C | C | <0.01 |
| 194 | I194P | P | <0.01 |
| 194 | I194F | F | <0.01 |
| 194 | I194W | W | <0.01 |
| 194 | I194R | R | <0.01 |
| 194 | I194Y | Y | <0.01 |
| 194 | I194G | G | 0.044503 |
| 194 | I194L | L | 0.577811 |
| 194 | I194V | V | 0.780569 |
| 196 | F196H | H | <0.01 |
| 196 | F196G | G | <0.01 |
| 196 | F196S | S | <0.01 |
| 196 | F196Q | Q | <0.01 |
| 196 | F196A | A | <0.01 |
| 196 | F196K | K | <0.01 |
| 196 | F196N | N | <0.01 |
| 196 | F196R | R | <0.01 |
| 196 | F196W | W | 0.38122 |
| 196 | F196P | P | 0.385754 |
| 196 | F196V | V | 0.675769 |
| 196 | F196M | M | 0.709899 |
| 196 | F196Y | Y | 0.970105 |

The following Table provides variants that are better than wild-type at degrading peracids (i.e., the performance index for the variant is better than the wild-type).

TABLE 10-6

Variants with Peracid Degradation Greater Than Wild-Type

| Pos. | WT/Pos./Var.PAD | PI |
|---|---|---|
| 1 | M001I | 1.19 |
| 1 | M001L | 2.11 |
| 2 | A002D | 1.05 |
| 2 | A002R | 1.17 |
| 2 | A002W | 1.17 |
| 2 | A002P | 1.17 |
| 2 | A002Q | 1.29 |
| 2 | A002E | 1.38 |
| 3 | K003T | 1.03 |
| 3 | K003S | 1.17 |
| 3 | K003Q | 1.19 |
| 3 | K003R | 1.29 |
| 3 | K003Y | 1.39 |
| 3 | K003M | 1.44 |
| 3 | K003P | 1.45 |
| 3 | K003C | 1.52 |
| 3 | K003L | 1.84 |
| 3 | K003H | 1.89 |
| 3 | K003A | 2.14 |
| 3 | K003I | 2.44 |
| 3 | K003E | 3.51 |
| 3 | K003G | 3.74 |
| 4 | R004D | 1.18 |
| 4 | R004C | 1.34 |
| 4 | R004P | 1.44 |

TABLE 10-6-continued

Variants with Peracid Degradation Greater Than Wild-Type

| Pos. | WT/Pos./Var.PAD | PI |
|---|---|---|
| 4 | R004A | 1.64 |
| 5 | I005M | 1.09 |
| 5 | I005E | 1.59 |
| 5 | I005L | 1.63 |
| 5 | I005A | 1.88 |
| 5 | I005C | 2.47 |
| 5 | I005D | 3.11 |
| 6 | L006C | 1.22 |
| 6 | L006M | 1.44 |
| 6 | L006A | 1.99 |
| 7 | C007A | 1.03 |
| 7 | C007H | 1.37 |
| 7 | C007I | 1.48 |
| 7 | C007E | 1.63 |
| 7 | C007K | 2.95 |
| 8 | F008M | 1.11 |
| 8 | F008L | 1.31 |
| 8 | F008A | 1.33 |
| 8 | F008C | 4.01 |
| 10 | D010L | 2.04 |
| 13 | T013I | 1.05 |
| 13 | T013E | 1.09 |
| 13 | T013L | 1.47 |
| 13 | T013M | 1.47 |
| 13 | T013C | 1.55 |
| 13 | T013A | 1.88 |
| 13 | T013N | 2.61 |
| 13 | T013P | 2.73 |
| 16 | W016K | 1.03 |
| 16 | W016I | 1.06 |
| 16 | W016Y | 1.09 |
| 16 | W016L | 1.16 |
| 17 | V017S | 1.04 |
| 18 | P018N | 1.42 |
| 18 | P018Q | 3.26 |
| 18 | P018R | 3.97 |
| 18 | P018C | 4.16 |
| 18 | P018Y | 4.17 |
| 18 | P018V | 4.85 |
| 18 | P018E | 4.87 |
| 18 | P018G | 4.96 |
| 18 | P018H | 6.05 |
| 18 | P018L | 7.40 |
| 20 | E020D | 1.14 |
| 20 | E020S | 1.18 |
| 20 | E020H | 1.20 |
| 20 | E020T | 1.25 |
| 20 | E020V | 1.27 |
| 20 | E020A | 1.28 |
| 20 | E020W | 1.30 |
| 20 | E020N | 1.34 |
| 20 | E020P | 1.43 |
| 20 | E020Q | 1.56 |
| 20 | E020C | 1.76 |
| 21 | D021S | 1.11 |
| 21 | D021E | 1.39 |
| 21 | D021F | 1.41 |
| 21 | D021W | 1.44 |
| 21 | D021L | 1.57 |
| 21 | D021A | 1.75 |
| 21 | D021G | 1.76 |
| 21 | D021K | 1.80 |
| 21 | D021Y | 2.01 |
| 22 | G022I | 1.03 |
| 22 | G022T | 1.16 |
| 22 | G022E | 1.19 |
| 22 | G022L | 1.35 |
| 22 | G022P | 1.36 |
| 22 | G022Q | 1.44 |
| 22 | G022A | 1.66 |
| 23 | A023H | 1.04 |
| 23 | A023L | 1.30 |
| 24 | P024C | 1.04 |
| 24 | P024K | 1.36 |
| 24 | P024L | 1.51 |
| 26 | E026M | 1.10 |
| 26 | E026H | 1.19 |
| 26 | E026D | 1.39 |
| 26 | E026A | 1.45 |
| 26 | E026K | 1.47 |
| 26 | E026L | 1.71 |
| 27 | R027I | 1.41 |
| 27 | R027K | 1.55 |
| 27 | R027L | 2.60 |
| 27 | R027A | 2.78 |
| 28 | F028E | 1.04 |
| 28 | F028W | 1.17 |
| 28 | F028C | 1.21 |
| 28 | F028Y | 1.36 |
| 28 | F028M | 1.37 |
| 28 | F028A | 1.48 |
| 28 | F028L | 2.02 |
| 28 | F028D | 2.07 |
| 29 | A029C | 1.15 |
| 30 | P030H | 1.08 |
| 30 | P030G | 1.09 |
| 30 | P030R | 1.14 |
| 30 | P030L | 1.17 |
| 30 | P030E | 1.24 |
| 30 | P030Y | 1.31 |
| 30 | P030I | 1.38 |
| 30 | P030K | 1.39 |
| 30 | P030S | 1.49 |
| 30 | P030T | 1.64 |
| 30 | P030V | 1.74 |
| 31 | D031V | 1.08 |
| 31 | D031T | 1.11 |
| 31 | D031Q | 1.13 |
| 31 | D031W | 1.14 |
| 31 | D031G | 1.16 |
| 31 | D031A | 1.18 |
| 31 | D031S | 1.23 |
| 31 | D031F | 1.39 |
| 31 | D031R | 1.49 |
| 31 | D031N | 1.55 |
| 31 | D031L | 1.61 |
| 32 | V032S | 1.09 |
| 32 | V032N | 1.61 |
| 32 | V032W | 1.71 |
| 32 | V032Q | 1.74 |
| 32 | V032G | 2.65 |
| 32 | V032M | 3.41 |
| 32 | V032I | 3.51 |
| 32 | V032A | 3.64 |
| 32 | V032E | 3.92 |
| 32 | V032D | 4.19 |
| 32 | V032L | 4.72 |
| 32 | V032K | 4.73 |
| 33 | R033S | 1.01 |
| 33 | R033N | 1.30 |
| 33 | R033A | 1.32 |
| 33 | R033C | 1.73 |
| 33 | R033G | 2.63 |
| 33 | R033K | 2.72 |
| 33 | R033L | 2.90 |
| 34 | W034P | 1.21 |
| 34 | W034M | 1.22 |
| 34 | W034C | 1.49 |
| 34 | W034A | 2.29 |
| 35 | T035M | 2.72 |
| 35 | T035A | 3.85 |
| 35 | T035C | 4.72 |
| 35 | T035I | 5.38 |
| 35 | T035E | 5.73 |
| 36 | G036C | 1.06 |
| 36 | G036A | 1.07 |
| 36 | G036H | 1.10 |
| 36 | G036K | 1.71 |

TABLE 10-6-continued

Variants with Peracid Degradation Greater Than Wild-Type

| Pos. | WT/Pos./Var.PAD | PI |
|---|---|---|
| 36 | G036I | 1.81 |
| 36 | G036L | 2.49 |
| 36 | G036D | 2.50 |
| 37 | V037I | 1.04 |
| 37 | V037L | 1.16 |
| 37 | V037S | 1.49 |
| 37 | V037N | 1.52 |
| 37 | V037C | 1.63 |
| 37 | V037A | 2.00 |
| 37 | V037P | 2.10 |
| 38 | L038V | 1.12 |
| 39 | A039W | 1.02 |
| 39 | A039Y | 1.13 |
| 40 | Q040N | 1.00 |
| 40 | Q040I | 1.10 |
| 40 | Q040E | 1.28 |
| 40 | Q040R | 1.48 |
| 40 | Q040L | 1.49 |
| 40 | Q040D | 1.59 |
| 40 | Q040S | 1.65 |
| 40 | Q040T | 1.81 |
| 40 | Q040Y | 2.02 |
| 40 | Q040G | 2.17 |
| 40 | Q040W | 2.59 |
| 40 | Q040K | 3.64 |
| 41 | Q041G | 1.09 |
| 41 | Q041H | 1.14 |
| 41 | Q041R | 1.27 |
| 41 | Q041K | 1.61 |
| 41 | Q041L | 1.92 |
| 41 | Q041A | 2.58 |
| 42 | L042F | 1.02 |
| 42 | L042P | 1.34 |
| 42 | L042K | 1.41 |
| 42 | L042C | 1.43 |
| 43 | G043A | 1.07 |
| 43 | G043L | 1.82 |
| 43 | G043E | 1.88 |
| 44 | A044C | 1.92 |
| 45 | D045F | 1.04 |
| 46 | F046C | 1.16 |
| 46 | F046A | 1.25 |
| 46 | F046E | 1.31 |
| 46 | F046D | 1.39 |
| 46 | F046M | 1.42 |
| 46 | F046K | 1.46 |
| 46 | F046P | 1.50 |
| 46 | F046L | 1.54 |
| 47 | E047L | 1.02 |
| 47 | E047K | 1.06 |
| 47 | E047G | 1.10 |
| 47 | E047I | 1.15 |
| 48 | V048Q | 1.39 |
| 48 | V048F | 1.42 |
| 48 | V048A | 1.63 |
| 48 | V048M | 1.79 |
| 48 | V048C | 2.25 |
| 48 | V048L | 2.29 |
| 48 | V048P | 3.08 |
| 49 | I049Y | 1.02 |
| 49 | I049M | 1.02 |
| 49 | I049L | 1.03 |
| 49 | I049G | 1.12 |
| 49 | I049K | 1.26 |
| 49 | I049A | 1.87 |
| 50 | E050P | 1.02 |
| 50 | E050M | 1.04 |
| 50 | E050G | 1.11 |
| 50 | E050D | 1.22 |
| 50 | E050A | 1.23 |
| 51 | E051T | 1.17 |
| 51 | E051M | 1.20 |
| 51 | E051D | 1.28 |
| 51 | E051G | 1.34 |
| 51 | E051K | 2.00 |
| 51 | E051A | 2.72 |
| 52 | G052W | 2.47 |
| 53 | L053H | 1.70 |
| 54 | S054N | 1.29 |
| 54 | S054P | 1.30 |
| 54 | S054A | 1.41 |
| 55 | A055N | 1.05 |
| 55 | A055K | 1.08 |
| 55 | A055C | 1.26 |
| 57 | T057S | 1.01 |
| 57 | T057G | 1.05 |
| 58 | T058L | 1.12 |
| 58 | T058H | 1.49 |
| 59 | N059Q | 1.86 |
| 59 | N059T | 5.63 |
| 59 | N059S | 7.32 |
| 59 | N059K | 8.21 |
| 59 | N059E | 9.88 |
| 59 | N059V | 9.97 |
| 59 | N059G | 10.00 |
| 59 | N059F | 10.23 |
| 59 | N059A | 10.44 |
| 59 | N059Y | 11.14 |
| 59 | N059C | 11.23 |
| 59 | N059D | 11.72 |
| 59 | N059W | 12.80 |
| 59 | N059L | 14.74 |
| 60 | I060G | 1.04 |
| 60 | I060V | 1.06 |
| 60 | I060H | 1.07 |
| 60 | I060Y | 1.19 |
| 61 | D061P | 1.13 |
| 61 | D061Q | 1.16 |
| 61 | D061L | 1.20 |
| 61 | D061G | 1.25 |
| 61 | D061S | 1.35 |
| 61 | D061R | 1.59 |
| 61 | D061I | 1.66 |
| 61 | D061H | 1.67 |
| 61 | D061K | 1.72 |
| 63 | P063K | 1.02 |
| 63 | P063V | 1.04 |
| 63 | P063Q | 1.05 |
| 63 | P063W | 1.11 |
| 63 | P063G | 1.22 |
| 63 | P063L | 1.23 |
| 63 | P063T | 1.32 |
| 64 | T064G | 1.08 |
| 64 | T064M | 1.09 |
| 64 | T064A | 1.20 |
| 64 | T064L | 1.22 |
| 66 | P066S | 1.02 |
| 66 | P066T | 1.10 |
| 69 | N069D | 1.11 |
| 69 | N069A | 1.13 |
| 69 | N069Q | 1.14 |
| 69 | N069C | 1.20 |
| 69 | N069L | 1.20 |
| 69 | N069S | 1.42 |
| 69 | N069T | 1.43 |
| 69 | N069H | 1.52 |
| 69 | N069K | 1.59 |
| 69 | N069V | 1.73 |
| 69 | N069I | 1.75 |
| 70 | G070L | 1.01 |
| 70 | G070A | 1.41 |
| 70 | G070H | 1.90 |
| 71 | A071K | 1.01 |
| 71 | A071M | 1.11 |
| 72 | S072F | 1.15 |
| 72 | S072G | 1.76 |
| 72 | S072M | 2.13 |
| 72 | S072C | 2.18 |

TABLE 10-6-continued

Variants with Peracid Degradation Greater Than Wild-Type

| Pos. | WT/Pos./Var.PAD | PI |
|---|---|---|
| 72 | S072H | 2.48 |
| 72 | S072N | 2.85 |
| 72 | S072A | 3.52 |
| 73 | Y073M | 1.13 |
| 73 | Y073C | 1.20 |
| 73 | Y073A | 1.40 |
| 74 | L074F | 1.13 |
| 74 | L074M | 1.21 |
| 74 | L074A | 2.90 |
| 75 | P075E | 1.19 |
| 75 | P075L | 1.19 |
| 75 | P075W | 1.31 |
| 75 | P075Y | 1.32 |
| 75 | P075V | 1.39 |
| 75 | P075C | 1.42 |
| 75 | P075D | 2.09 |
| 76 | S076C | 1.06 |
| 76 | S076T | 1.11 |
| 76 | S076A | 1.11 |
| 76 | S076H | 1.11 |
| 76 | S076P | 1.20 |
| 76 | S076V | 1.35 |
| 76 | S076K | 1.53 |
| 76 | S076M | 1.61 |
| 76 | S076D | 1.94 |
| 76 | S076E | 2.09 |
| 76 | S076G | 2.15 |
| 76 | S076L | 4.70 |
| 77 | C077T | 1.03 |
| 77 | C077D | 1.05 |
| 78 | L078T | 1.10 |
| 78 | L078I | 1.11 |
| 78 | L078G | 1.38 |
| 78 | L078H | 1.57 |
| 80 | T080V | 1.01 |
| 80 | T080Q | 1.07 |
| 80 | T080A | 1.11 |
| 80 | T080C | 1.15 |
| 80 | T080S | 1.40 |
| 80 | T080G | 1.50 |
| 81 | H081N | 1.00 |
| 81 | H081L | 1.03 |
| 81 | H081W | 1.09 |
| 81 | H081C | 1.09 |
| 81 | H081A | 1.45 |
| 81 | H081M | 1.54 |
| 82 | L082M | 1.06 |
| 83 | P083C | 1.01 |
| 83 | P083R | 1.09 |
| 83 | P083N | 1.10 |
| 83 | P083K | 1.16 |
| 83 | P083E | 1.26 |
| 83 | P083M | 1.88 |
| 83 | P083A | 2.36 |
| 84 | L084F | 1.01 |
| 84 | L084G | 1.01 |
| 85 | D085R | 1.03 |
| 85 | D085A | 1.09 |
| 85 | D085H | 1.24 |
| 85 | D085E | 1.25 |
| 85 | D085C | 1.50 |
| 85 | D085G | 1.60 |
| 85 | D085F | 1.98 |
| 86 | L086C | 2.44 |
| 86 | L086A | 3.32 |
| 87 | V087P | 1.64 |
| 87 | V087C | 2.22 |
| 87 | V087L | 4.30 |
| 88 | I088M | 1.09 |
| 88 | I088P | 3.51 |
| 89 | I089L | 1.22 |
| 89 | I089A | 1.83 |
| 89 | I089P | 1.91 |
| 90 | M090C | 1.09 |
| 90 | M090E | 1.15 |
| 90 | M090A | 1.41 |
| 90 | M090D | 2.88 |
| 91 | L091I | 1.05 |
| 91 | L091C | 1.27 |
| 91 | L091A | 1.45 |
| 91 | L091D | 1.47 |
| 92 | G092C | 2.05 |
| 93 | T093A | 1.05 |
| 96 | T096F | 1.24 |
| 96 | T096G | 1.28 |
| 96 | T096L | 1.93 |
| 96 | T096M | 2.53 |
| 96 | T096C | 3.76 |
| 96 | T096A | 4.20 |
| 98 | A098Y | 1.15 |
| 98 | A098P | 1.26 |
| 98 | A098N | 1.40 |
| 98 | A098C | 1.42 |
| 98 | A098L | 1.47 |
| 98 | A098D | 2.19 |
| 100 | F100C | 1.28 |
| 100 | F100T | 1.42 |
| 100 | F100N | 1.45 |
| 100 | F100A | 2.02 |
| 100 | F100M | 2.19 |
| 101 | R101L | 1.12 |
| 102 | R102Q | 1.19 |
| 102 | R102Y | 1.29 |
| 102 | R102L | 1.64 |
| 102 | R102A | 1.79 |
| 104 | P104V | 1.02 |
| 104 | P104H | 1.03 |
| 104 | P104N | 1.44 |
| 104 | P104C | 1.83 |
| 104 | P104E | 1.97 |
| 104 | P104I | 2.05 |
| 104 | P104M | 2.24 |
| 105 | L105Q | 1.04 |
| 105 | L105H | 1.23 |
| 105 | L105R | 1.25 |
| 105 | L105G | 1.40 |
| 105 | L105W | 1.71 |
| 105 | L105F | 1.73 |
| 105 | L105C | 1.92 |
| 106 | D106S | 1.02 |
| 106 | D106W | 1.07 |
| 106 | D106E | 1.09 |
| 106 | D106C | 1.10 |
| 106 | D106A | 1.13 |
| 106 | D106H | 1.18 |
| 106 | D106K | 1.24 |
| 106 | D106T | 1.38 |
| 106 | D106F | 1.45 |
| 106 | D106G | 1.45 |
| 106 | D106V | 1.68 |
| 107 | I107L | 1.04 |
| 107 | I107S | 1.33 |
| 107 | I107C | 1.41 |
| 107 | I107T | 1.53 |
| 108 | A108S | 1.00 |
| 108 | A108G | 1.13 |
| 108 | A108L | 2.56 |
| 108 | A108K | 2.97 |
| 110 | G110A | 1.01 |
| 110 | G110D | 1.40 |
| 110 | G110C | 1.43 |
| 110 | G110E | 1.76 |
| 110 | G110F | 2.29 |
| 111 | M111C | 1.01 |
| 111 | M111A | 1.02 |
| 111 | M111I | 1.03 |
| 111 | M111Y | 1.06 |
| 111 | M111W | 1.23 |

TABLE 10-6-continued

Variants with Peracid Degradation Greater Than Wild-Type

| Pos. | WT/Pos./Var.PAD | PI |
|---|---|---|
| 111 | M111N | 1.31 |
| 112 | S112L | 1.00 |
| 112 | S112E | 1.16 |
| 113 | V113M | 1.06 |
| 113 | V113Q | 1.11 |
| 113 | V113R | 1.11 |
| 113 | V113P | 1.14 |
| 113 | V113N | 1.22 |
| 113 | V113A | 1.31 |
| 114 | L114T | 1.05 |
| 114 | L114A | 1.07 |
| 114 | L114G | 1.14 |
| 114 | L114C | 1.14 |
| 114 | L114I | 1.17 |
| 114 | L114M | 1.28 |
| 115 | V115C | 1.08 |
| 115 | V115S | 1.14 |
| 115 | V115Q | 1.15 |
| 115 | V115A | 1.19 |
| 115 | V115T | 1.28 |
| 115 | V115L | 1.30 |
| 115 | V115M | 1.32 |
| 115 | V115R | 1.63 |
| 115 | V115F | 1.69 |
| 115 | V115G | 1.76 |
| 115 | V115Y | 2.07 |
| 115 | V115D | 2.21 |
| 115 | V115P | 2.21 |
| 115 | V115W | 2.48 |
| 116 | T116N | 1.05 |
| 116 | T116C | 1.05 |
| 116 | T116H | 1.08 |
| 116 | T116M | 1.39 |
| 117 | Q117F | 1.02 |
| 117 | Q117R | 1.05 |
| 117 | Q117T | 1.10 |
| 117 | Q117H | 1.12 |
| 117 | Q117Y | 1.13 |
| 117 | Q117P | 1.13 |
| 117 | Q117E | 1.21 |
| 117 | Q117A | 1.73 |
| 117 | Q117M | 1.89 |
| 118 | V118L | 1.05 |
| 118 | V118C | 1.14 |
| 118 | V118Y | 1.34 |
| 118 | V118Q | 1.50 |
| 119 | L119A | 1.02 |
| 120 | T120V | 1.07 |
| 120 | T120S | 1.07 |
| 120 | T120K | 1.09 |
| 120 | T120M | 1.22 |
| 120 | T120L | 1.26 |
| 120 | T120N | 1.42 |
| 120 | T120E | 1.53 |
| 120 | T120I | 1.56 |
| 120 | T120Y | 1.61 |
| 121 | S121E | 1.04 |
| 121 | S121N | 1.06 |
| 121 | S121Q | 1.09 |
| 121 | S121T | 1.26 |
| 121 | S121L | 1.49 |
| 121 | S121A | 1.55 |
| 121 | S121V | 1.59 |
| 121 | S121C | 1.64 |
| 122 | A122L | 1.02 |
| 123 | G123K | 1.12 |
| 123 | G123A | 1.19 |
| 123 | G123Y | 1.24 |
| 123 | G123M | 1.38 |
| 123 | G123L | 1.38 |
| 123 | G123W | 1.39 |
| 125 | V125G | 1.09 |
| 126 | G126M | 1.17 |
| 126 | G126D | 1.22 |
| 127 | T127A | 1.10 |
| 128 | T128M | 1.06 |
| 128 | T128H | 1.08 |
| 128 | T128V | 1.15 |
| 128 | T128P | 1.16 |
| 128 | T128W | 1.23 |
| 128 | T128S | 1.27 |
| 128 | T128A | 1.31 |
| 128 | T128Q | 1.34 |
| 128 | T128N | 1.36 |
| 128 | T128K | 1.57 |
| 128 | T128R | 1.70 |
| 128 | T128F | 1.71 |
| 128 | T128L | 1.72 |
| 128 | T128Y | 1.81 |
| 131 | A131R | 1.04 |
| 132 | P132N | 1.05 |
| 132 | P132L | 2.24 |
| 132 | P132E | 3.02 |
| 132 | P132Y | 4.78 |
| 132 | P132G | 4.98 |
| 132 | P132S | 5.05 |
| 132 | P132C | 5.68 |
| 132 | P132A | 6.08 |
| 132 | P132Q | 6.15 |
| 133 | K133Y | 1.44 |
| 133 | K133L | 1.92 |
| 134 | V134C | 1.37 |
| 134 | V134G | 1.42 |
| 134 | V134S | 1.44 |
| 134 | V134L | 1.45 |
| 134 | V134A | 1.64 |
| 134 | V134P | 1.71 |
| 134 | V134M | 1.89 |
| 134 | V134N | 2.80 |
| 135 | L135D | 2.90 |
| 136 | V136T | 1.13 |
| 136 | V136L | 1.13 |
| 136 | V136C | 1.23 |
| 136 | V136A | 1.60 |
| 137 | V137M | 1.13 |
| 137 | V137L | 1.27 |
| 137 | V137C | 1.42 |
| 137 | V137A | 1.46 |
| 138 | S138G | 1.11 |
| 138 | S138C | 1.18 |
| 138 | S138A | 1.28 |
| 138 | S138N | 1.31 |
| 138 | S138P | 1.39 |
| 140 | P140C | 1.07 |
| 140 | P140A | 1.83 |
| 140 | P140H | 2.25 |
| 140 | P140F | 2.89 |
| 140 | P140G | 3.11 |
| 141 | P141A | 1.08 |
| 143 | A143C | 1.07 |
| 143 | A143E | 1.13 |
| 143 | A143D | 1.22 |
| 143 | A143L | 1.28 |
| 143 | A143H | 1.36 |
| 143 | A143K | 1.37 |
| 144 | P144M | 1.01 |
| 144 | P144F | 1.08 |
| 144 | P144Q | 1.08 |
| 144 | P144K | 1.09 |
| 144 | P144R | 1.14 |
| 144 | P144L | 1.15 |
| 144 | P144D | 1.38 |
| 144 | P144N | 1.49 |
| 144 | P144H | 1.60 |
| 144 | P144Y | 1.65 |
| 146 | P146N | 1.00 |
| 146 | P146G | 1.04 |
| 146 | P146R | 1.06 |

TABLE 10-6-continued

Variants with Peracid Degradation Greater Than Wild-Type

| Pos. | WT/Pos./Var.PAD | PI |
|---|---|---|
| 146 | P146M | 1.23 |
| 146 | P146A | 1.36 |
| 146 | P146Y | 1.44 |
| 146 | P146F | 1.53 |
| 146 | P146H | 1.57 |
| 146 | P146C | 1.69 |
| 146 | P146L | 2.00 |
| 147 | H147Q | 1.03 |
| 147 | H147W | 1.05 |
| 147 | H147K | 1.06 |
| 147 | H147E | 1.10 |
| 147 | H147Y | 1.12 |
| 147 | H147C | 1.17 |
| 147 | H147D | 1.18 |
| 147 | H147P | 1.21 |
| 147 | H147N | 1.25 |
| 147 | H147L | 1.29 |
| 147 | H147M | 1.44 |
| 148 | P148V | 1.04 |
| 148 | P148A | 1.06 |
| 148 | P148T | 1.09 |
| 148 | P148E | 1.19 |
| 148 | P148G | 1.20 |
| 148 | P148S | 1.21 |
| 148 | P148R | 1.25 |
| 148 | P148K | 1.30 |
| 148 | P148D | 1.34 |
| 148 | P148Y | 1.37 |
| 148 | P148L | 1.39 |
| 148 | P148F | 1.50 |
| 149 | W149H | 1.01 |
| 150 | F150Y | 1.07 |
| 150 | F150H | 1.18 |
| 150 | F150L | 1.30 |
| 151 | Q151P | 1.91 |
| 151 | Q151E | 2.07 |
| 151 | Q151K | 2.19 |
| 151 | Q151H | 2.19 |
| 151 | Q151S | 2.25 |
| 151 | Q151R | 2.32 |
| 151 | Q151T | 2.37 |
| 151 | Q151C | 2.55 |
| 151 | Q151Y | 2.75 |
| 151 | Q151D | 2.81 |
| 151 | Q151A | 2.93 |
| 151 | Q151M | 6.36 |
| 152 | L152M | 1.10 |
| 152 | L152C | 1.14 |
| 152 | L152E | 1.23 |
| 152 | L152A | 1.29 |
| 152 | L152Y | 1.37 |
| 152 | L152W | 1.55 |
| 153 | I153V | 1.15 |
| 153 | I153A | 1.49 |
| 153 | I153L | 1.50 |
| 153 | I153T | 1.62 |
| 153 | I153S | 1.66 |
| 153 | I153F | 1.75 |
| 153 | I153P | 1.87 |
| 153 | I153H | 2.00 |
| 153 | I153K | 2.44 |
| 154 | F154Y | 4.96 |
| 155 | E155S | 1.12 |
| 155 | E155G | 1.12 |
| 155 | E155T | 1.19 |
| 155 | E155D | 1.24 |
| 155 | E155K | 1.33 |
| 155 | E155N | 1.79 |
| 155 | E155L | 2.07 |
| 155 | E155A | 2.59 |
| 155 | E155P | 2.60 |
| 155 | E155Y | 2.65 |
| 155 | E155M | 2.91 |
| 156 | G156S | 1.04 |
| 156 | G156K | 1.11 |
| 156 | G156E | 1.14 |
| 156 | G156R | 1.21 |
| 156 | G156A | 1.21 |
| 156 | G156P | 1.29 |
| 156 | G156C | 1.37 |
| 156 | G156N | 1.38 |
| 156 | G156H | 1.40 |
| 156 | G156Y | 1.40 |
| 156 | G156T | 1.53 |
| 156 | G156M | 1.62 |
| 156 | G156D | 1.62 |
| 157 | G157I | 1.33 |
| 157 | G157F | 1.42 |
| 157 | G157K | 1.47 |
| 157 | G157H | 1.57 |
| 158 | E158H | 1.01 |
| 158 | E158P | 1.19 |
| 158 | E158Q | 1.24 |
| 158 | E158S | 1.27 |
| 158 | E158A | 1.28 |
| 158 | E158R | 1.29 |
| 158 | E158W | 1.31 |
| 158 | E158C | 1.37 |
| 158 | E158N | 1.58 |
| 158 | E158M | 1.73 |
| 158 | E158F | 1.77 |
| 158 | E158K | 1.88 |
| 158 | E158L | 1.96 |
| 158 | E158Y | 2.48 |
| 159 | Q159H | 1.48 |
| 160 | K160N | 1.12 |
| 160 | K160A | 1.14 |
| 160 | K160R | 1.15 |
| 160 | K160D | 1.19 |
| 160 | K160C | 1.29 |
| 160 | K160Q | 1.41 |
| 160 | K160M | 1.47 |
| 160 | K160P | 1.66 |
| 161 | T161L | 1.16 |
| 161 | T161V | 1.24 |
| 161 | T161Q | 1.50 |
| 161 | T161M | 1.72 |
| 161 | T161Y | 2.62 |
| 162 | T162R | 1.23 |
| 162 | T162G | 1.82 |
| 162 | T162S | 2.01 |
| 162 | T162W | 2.04 |
| 162 | T162I | 2.21 |
| 162 | T162Q | 2.45 |
| 162 | T162Y | 2.89 |
| 162 | T162K | 3.13 |
| 162 | T162F | 3.23 |
| 162 | T162M | 3.49 |
| 162 | T162C | 3.57 |
| 162 | T162L | 3.59 |
| 162 | T162N | 3.84 |
| 162 | T162H | 3.91 |
| 162 | T162P | 4.37 |
| 163 | E163N | 1.00 |
| 163 | E163C | 1.08 |
| 163 | E163D | 1.08 |
| 163 | E163A | 1.79 |
| 163 | E163Y | 1.89 |
| 163 | E163L | 1.94 |
| 164 | L164Q | 1.01 |
| 164 | L164V | 1.02 |
| 164 | L164S | 1.11 |
| 164 | L164M | 1.26 |
| 164 | L164N | 1.31 |
| 164 | L164R | 1.61 |
| 164 | L164P | 2.41 |
| 165 | A165G | 1.07 |
| 165 | A165V | 1.13 |

TABLE 10-6-continued

Variants with Peracid Degradation Greater Than Wild-Type

| Pos. | WT/Pos./Var.PAD | PI |
|---|---|---|
| 165 | A165N | 1.20 |
| 165 | A165R | 1.29 |
| 165 | A165Q | 1.32 |
| 165 | A165T | 1.32 |
| 165 | A165P | 1.34 |
| 165 | A165C | 1.42 |
| 165 | A165L | 1.55 |
| 165 | A165M | 1.56 |
| 165 | A165D | 1.69 |
| 166 | R166W | 1.08 |
| 166 | R166F | 1.10 |
| 166 | R166K | 1.20 |
| 166 | R166N | 1.21 |
| 166 | R166Y | 1.22 |
| 166 | R166M | 1.29 |
| 166 | R166I | 1.39 |
| 166 | R166P | 1.50 |
| 166 | R166L | 1.50 |
| 166 | R166A | 1.51 |
| 166 | R166D | 1.55 |
| 166 | R166H | 1.56 |
| 167 | V167I | 1.00 |
| 167 | V167S | 1.86 |
| 167 | V167H | 2.11 |
| 167 | V167Y | 2.15 |
| 167 | V167R | 2.25 |
| 167 | V167Q | 2.41 |
| 167 | V167T | 2.47 |
| 167 | V167L | 2.56 |
| 167 | V167G | 2.83 |
| 167 | V167M | 3.84 |
| 167 | V167A | 4.99 |
| 167 | V167C | 5.37 |
| 167 | V167D | 5.54 |
| 167 | V167P | 6.08 |
| 168 | Y168F | 5.17 |
| 168 | Y168L | 5.39 |
| 169 | S169Y | 1.10 |
| 169 | S169A | 1.13 |
| 169 | S169R | 1.19 |
| 169 | S169K | 1.27 |
| 169 | S169Q | 1.37 |
| 169 | S169C | 1.38 |
| 169 | S169M | 1.40 |
| 169 | S169L | 1.47 |
| 169 | S169I | 1.53 |
| 170 | A170C | 1.06 |
| 170 | A170E | 1.17 |
| 170 | A170F | 1.17 |
| 170 | A170N | 1.17 |
| 170 | A170M | 1.28 |
| 170 | A170D | 1.32 |
| 170 | A170P | 1.33 |
| 171 | L171H | 1.07 |
| 171 | L171G | 1.33 |
| 171 | L171Y | 1.35 |
| 171 | L171T | 1.36 |
| 171 | L171V | 1.39 |
| 171 | L171I | 1.42 |
| 171 | L171K | 1.53 |
| 171 | L171A | 1.66 |
| 171 | L171C | 1.73 |
| 171 | L171S | 1.76 |
| 171 | L171Q | 1.93 |
| 171 | L171F | 1.97 |
| 171 | L171M | 2.22 |
| 171 | L171N | 2.79 |
| 172 | A172M | 1.06 |
| 172 | A172L | 1.22 |
| 172 | A172D | 1.42 |
| 172 | A172Y | 1.76 |
| 173 | S173T | 1.29 |
| 173 | S173H | 1.49 |
| 173 | S173I | 2.22 |
| 173 | S173F | 2.30 |
| 173 | S173R | 2.47 |
| 173 | S173V | 2.54 |
| 173 | S173E | 2.65 |
| 173 | S173P | 2.66 |
| 173 | S173A | 2.72 |
| 173 | S173M | 3.01 |
| 173 | S173K | 3.01 |
| 173 | S173C | 3.07 |
| 173 | S173Y | 3.54 |
| 173 | S173W | 3.67 |
| 173 | S173L | 3.86 |
| 174 | F174H | 1.05 |
| 174 | F174K | 1.17 |
| 174 | F174P | 1.46 |
| 174 | F174Y | 1.66 |
| 174 | F174L | 1.83 |
| 174 | F174A | 2.09 |
| 174 | F174M | 2.20 |
| 175 | M175N | 1.02 |
| 175 | M175E | 1.43 |
| 176 | K176C | 1.01 |
| 176 | K176R | 1.03 |
| 176 | K176E | 1.08 |
| 176 | K176W | 1.16 |
| 176 | K176D | 1.18 |
| 176 | K176A | 1.19 |
| 176 | K176F | 1.28 |
| 176 | K176V | 1.33 |
| 176 | K176M | 1.33 |
| 178 | P178K | 1.70 |
| 178 | P178T | 2.28 |
| 178 | P178V | 2.70 |
| 178 | P178G | 2.95 |
| 178 | P178S | 3.06 |
| 178 | P178Q | 3.64 |
| 178 | P178M | 3.87 |
| 178 | P178E | 4.15 |
| 178 | P178A | 4.39 |
| 178 | P178D | 6.44 |
| 178 | P178Y | 6.91 |
| 178 | P178L | 7.15 |
| 179 | F179G | 1.16 |
| 179 | F179V | 1.17 |
| 179 | F179Y | 1.47 |
| 179 | F179E | 1.80 |
| 179 | F179L | 1.89 |
| 180 | F180W | 1.81 |
| 180 | F180C | 1.94 |
| 180 | F180I | 2.11 |
| 180 | F180L | 2.13 |
| 180 | F180A | 2.70 |
| 180 | F180Y | 2.99 |
| 180 | F180N | 3.05 |
| 180 | F180V | 3.24 |
| 180 | F180M | 4.36 |
| 181 | D181A | 1.23 |
| 183 | G183P | 1.02 |
| 183 | G183R | 1.09 |
| 183 | G183Y | 1.45 |
| 183 | G183L | 1.50 |
| 183 | G183C | 1.99 |
| 184 | S184Y | 1.09 |
| 184 | S184Q | 1.16 |
| 184 | S184I | 1.21 |
| 184 | S184V | 1.25 |
| 184 | S184F | 1.27 |
| 184 | S184K | 1.61 |
| 184 | S184A | 1.69 |
| 184 | S184M | 1.77 |
| 184 | S184E | 1.86 |
| 184 | S184N | 1.93 |
| 184 | S184L | 2.00 |
| 184 | S184D | 2.24 |

TABLE 10-6-continued

Variants with Peracid Degradation Greater Than Wild-Type

| Pos. | WT/Pos./Var.PAD | PI |
|---|---|---|
| 184 | S184C | 2.39 |
| 185 | V185F | 1.20 |
| 185 | V185Q | 1.41 |
| 185 | V185M | 1.46 |
| 186 | I186L | 1.14 |
| 186 | I186M | 1.38 |
| 186 | I186A | 1.79 |
| 186 | I186D | 4.29 |
| 187 | S187K | 1.16 |
| 187 | S187D | 1.40 |
| 187 | S187G | 1.46 |
| 187 | S187L | 1.46 |
| 187 | S187H | 1.51 |
| 187 | S187I | 1.58 |
| 187 | S187N | 1.59 |
| 187 | S187C | 1.67 |
| 187 | S187A | 1.72 |
| 187 | S187M | 1.87 |
| 188 | T188N | 1.69 |
| 188 | T188E | 1.97 |
| 189 | D189A | 1.18 |
| 189 | D189T | 1.21 |
| 189 | D189I | 1.27 |
| 189 | D189L | 1.30 |
| 190 | G190C | 1.17 |
| 190 | G190Y | 1.39 |
| 190 | G190P | 1.86 |
| 190 | G190D | 2.02 |
| 190 | G190H | 2.92 |
| 190 | G190A | 3.42 |
| 190 | G190M | 5.54 |
| 191 | V191T | 1.03 |
| 191 | V191R | 1.91 |
| 191 | V191K | 2.17 |
| 191 | V191F | 2.75 |
| 191 | V191C | 2.81 |
| 191 | V191Y | 4.34 |
| 191 | V191L | 4.69 |
| 191 | V191A | 5.06 |
| 191 | V191E | 5.46 |
| 191 | V191Q | 5.83 |
| 191 | V191D | 6.03 |
| 191 | V191M | 7.34 |
| 193 | G193S | 1.60 |
| 193 | G193E | 3.15 |
| 193 | G193Q | 4.29 |
| 193 | G193V | 5.21 |
| 195 | H195P | 1.16 |
| 195 | H195M | 1.28 |
| 195 | H195K | 1.33 |
| 195 | H195Y | 1.49 |
| 195 | H195E | 1.70 |
| 195 | H195D | 1.93 |
| 196 | F196I | 1.12 |
| 196 | F196L | 1.17 |
| 196 | F196C | 1.18 |
| 197 | T197H | 1.24 |
| 197 | T197A | 1.42 |
| 197 | T197M | 2.38 |
| 198 | E198T | 1.16 |
| 198 | E198S | 1.18 |
| 198 | E198F | 1.21 |
| 198 | E198V | 1.44 |
| 198 | E198Q | 1.46 |
| 198 | E198A | 1.46 |
| 198 | E198I | 1.48 |
| 198 | E198L | 1.54 |
| 198 | E198N | 1.67 |
| 198 | E198P | 1.72 |
| 198 | E198Y | 1.77 |
| 198 | E198W | 1.78 |
| 198 | E198C | 1.83 |
| 198 | E198M | 1.86 |
| 198 | E198R | 1.88 |
| 199 | A199F | 1.15 |
| 199 | A199H | 1.15 |
| 199 | A199R | 1.17 |
| 199 | A199T | 1.22 |
| 199 | A199E | 1.31 |
| 199 | A199D | 1.33 |
| 199 | A199V | 1.45 |
| 199 | A199K | 1.53 |
| 199 | A199Y | 1.59 |
| 199 | A199L | 1.65 |
| 199 | A199C | 2.45 |
| 201 | N201D | 1.64 |
| 202 | R202M | 1.76 |
| 202 | R202G | 1.82 |
| 202 | R202S | 1.84 |
| 202 | R202C | 1.93 |
| 202 | R202A | 1.97 |
| 202 | R202I | 1.99 |
| 202 | R202E | 2.05 |
| 202 | R202L | 2.05 |
| 202 | R202T | 2.06 |
| 202 | R202H | 2.09 |
| 202 | R202F | 2.16 |
| 202 | R202W | 2.52 |
| 203 | D203Q | 1.03 |
| 203 | D203S | 1.13 |
| 203 | D203I | 1.19 |
| 203 | D203N | 1.28 |
| 203 | D203G | 1.33 |
| 203 | D203F | 1.34 |
| 203 | D203H | 1.54 |
| 203 | D203P | 1.71 |
| 203 | D203R | 1.77 |
| 203 | D203A | 1.96 |
| 203 | D203L | 2.08 |
| 203 | D203C | 2.09 |

The following Table provides variants that exhibited peracid degradation that was less than wild-type.

TABLE 10-7

Variants with Peracid Degradation Results Less than Wild-Type

| Pos | WT/Pos./Var.PAD | PI |
|---|---|---|
| 1 | M001V | 0.94 |
| 2 | A002Y | 0.46 |
| 2 | A002N | 0.59 |
| 2 | A002V | 0.60 |
| 2 | A002I | 0.61 |
| 2 | A002T | 0.61 |
| 2 | A002S | 0.66 |
| 2 | A002G | 0.84 |
| 2 | A002F | 0.93 |
| 3 | K003V | 0.84 |
| 4 | R004L | 0.01 |
| 4 | R004V | 0.08 |
| 4 | R004I | 0.15 |
| 4 | R004W | 0.48 |
| 4 | R004G | 0.79 |
| 4 | R004S | 0.91 |
| 4 | R004E | 0.97 |
| 4 | R004Y | 0.98 |
| 4 | R004H | 0.99 |
| 4 | R004Q | 0.99 |
| 4 | R004T | 1.00 |
| 5 | I005G | 0.01 |
| 5 | I005N | 0.01 |
| 5 | I005P | 0.01 |

TABLE 10-7-continued

Variants with Peracid Degradation Results Less than Wild-Type

| Pos | WT/Pos./Var.PAD | PI |
|---|---|---|
| 5 | I005R | 0.01 |
| 5 | I005F | 0.15 |
| 5 | I005S | 0.37 |
| 5 | I005H | 0.63 |
| 5 | I005T | 0.72 |
| 5 | I005V | 0.92 |
| 6 | L006S | 0.01 |
| 6 | L006K | 0.01 |
| 6 | L006G | 0.01 |
| 6 | L006H | 0.01 |
| 6 | L006R | 0.01 |
| 6 | L006W | 0.01 |
| 6 | L006E | 0.01 |
| 6 | L006Q | 0.01 |
| 6 | L006V | 0.35 |
| 6 | L006T | 0.35 |
| 6 | L006I | 0.82 |
| 7 | C007S | 0.01 |
| 7 | C007R | 0.01 |
| 7 | C007Y | 0.54 |
| 7 | C007M | 0.68 |
| 7 | C007G | 0.69 |
| 8 | F008S | 0.01 |
| 8 | F008R | 0.46 |
| 8 | F008H | 0.64 |
| 8 | F008G | 0.65 |
| 8 | F008T | 0.77 |
| 8 | F008K | 0.83 |
| 8 | F008P | 0.83 |
| 8 | F008V | 0.85 |
| 8 | F008Y | 0.90 |
| 8 | F008N | 0.96 |
| 9 | G009H | 0.01 |
| 9 | G009T | 0.01 |
| 10 | D010W | 0.01 |
| 10 | D010K | 0.01 |
| 10 | D010Y | 0.01 |
| 10 | D010T | 0.01 |
| 10 | D010I | 0.01 |
| 10 | D010V | 0.01 |
| 10 | D010S | 0.01 |
| 10 | D010G | 0.01 |
| 10 | D010R | 0.01 |
| 10 | D010A | 0.01 |
| 10 | D010M | 0.01 |
| 10 | D010N | 0.01 |
| 10 | D010P | 0.01 |
| 10 | D010E | 0.15 |
| 11 | S011T | 0.01 |
| 11 | S011V | 0.01 |
| 11 | S011D | 0.01 |
| 11 | S011E | 0.01 |
| 11 | S011F | 0.01 |
| 11 | S011G | 0.01 |
| 11 | S011L | 0.01 |
| 11 | S011Q | 0.01 |
| 11 | S011R | 0.01 |
| 11 | S011H | 0.33 |
| 11 | S011K | 0.40 |
| 11 | S011A | 0.53 |
| 11 | S011I | 0.56 |
| 12 | L012V | 0.01 |
| 12 | L012S | 0.01 |
| 12 | L012G | 0.01 |
| 12 | L012R | 0.01 |
| 12 | L012D | 0.01 |
| 12 | L012P | 0.01 |
| 12 | L012W | 0.02 |
| 12 | L012T | 0.06 |
| 12 | L012A | 0.07 |
| 12 | L012K | 0.13 |
| 12 | L012H | 0.16 |
| 12 | L012F | 0.17 |
| 12 | L012Q | 0.22 |
| 12 | L012C | 0.22 |
| 12 | L012N | 0.66 |
| 13 | T013Q | 0.51 |
| 13 | T013V | 0.63 |
| 13 | T013S | 0.68 |
| 13 | T013G | 0.77 |
| 14 | W014I | 0.01 |
| 14 | W014S | 0.01 |
| 14 | W014G | 0.01 |
| 14 | W014K | 0.01 |
| 14 | W014V | 0.01 |
| 14 | W014L | 0.01 |
| 14 | W014T | 0.01 |
| 14 | W014R | 0.01 |
| 14 | W014N | 0.01 |
| 14 | W014P | 0.01 |
| 14 | W014E | 0.15 |
| 14 | W014F | 0.22 |
| 14 | W014A | 0.27 |
| 14 | W014Y | 0.66 |
| 15 | G015C | 0.01 |
| 15 | G015N | 0.01 |
| 15 | G015D | 0.01 |
| 15 | G015E | 0.01 |
| 15 | G015P | 0.01 |
| 15 | G015A | 0.61 |
| 15 | G015S | 0.63 |
| 16 | W016S | 0.01 |
| 16 | W016G | 0.01 |
| 16 | W016H | 0.01 |
| 16 | W016T | 0.01 |
| 16 | W016R | 0.01 |
| 16 | W016N | 0.01 |
| 16 | W016P | 0.15 |
| 16 | W016Q | 0.31 |
| 16 | W016M | 0.37 |
| 16 | W016A | 0.55 |
| 16 | W016D | 0.57 |
| 16 | W016E | 0.65 |
| 16 | W016V | 0.88 |
| 17 | V017A | 0.68 |
| 17 | V017E | 0.75 |
| 17 | V017G | 0.84 |
| 17 | V017K | 0.84 |
| 17 | V017F | 0.85 |
| 17 | V017T | 0.86 |
| 17 | V017Y | 0.88 |
| 17 | V017R | 0.94 |
| 17 | V017P | 0.96 |
| 17 | V017I | 0.99 |
| 17 | V017L | 1.00 |
| 18 | P018S | 0.07 |
| 19 | V019P | 0.01 |
| 19 | V019M | 0.12 |
| 19 | V019R | 0.34 |
| 19 | V019Q | 0.40 |
| 19 | V019A | 0.55 |
| 19 | V019G | 0.56 |
| 19 | V019S | 0.57 |
| 19 | V019E | 0.62 |
| 19 | V019Y | 0.70 |
| 19 | V019D | 0.79 |
| 19 | V019L | 0.91 |
| 19 | V019K | 0.97 |
| 20 | E020L | 0.73 |
| 20 | E020G | 0.78 |
| 21 | D021P | 0.86 |
| 22 | G022K | 0.01 |
| 22 | G022W | 0.23 |
| 22 | G022R | 0.56 |
| 22 | G022V | 0.85 |
| 22 | G022S | 0.98 |
| 23 | A023R | 0.28 |
| 23 | A023S | 0.34 |

TABLE 10-7-continued

Variants with Peracid Degradation Results Less than Wild-Type

| Pos | WT/Pos./Var.PAD | PI |
|---|---|---|
| 23 | A023G | 0.35 |
| 23 | A023F | 0.44 |
| 23 | A023V | 0.60 |
| 23 | A023Q | 0.73 |
| 23 | A023P | 0.73 |
| 23 | A023W | 0.80 |
| 23 | A023M | 0.95 |
| 23 | A023Y | 0.96 |
| 24 | P024S | 0.61 |
| 24 | P024Q | 0.65 |
| 24 | P024T | 0.66 |
| 24 | P024A | 0.68 |
| 24 | P024G | 0.76 |
| 24 | P024I | 0.85 |
| 24 | P024R | 0.91 |
| 24 | P024H | 0.97 |
| 25 | T025P | 0.01 |
| 25 | T025H | 0.01 |
| 25 | T025L | 0.01 |
| 25 | T025R | 0.01 |
| 25 | T025M | 0.01 |
| 25 | T025E | 0.01 |
| 25 | T025D | 0.01 |
| 25 | T025K | 0.13 |
| 25 | T025W | 0.14 |
| 25 | T025I | 0.35 |
| 25 | T025G | 0.43 |
| 25 | T025C | 0.51 |
| 25 | T025V | 0.51 |
| 25 | T025S | 0.58 |
| 25 | T025A | 0.86 |
| 26 | E026S | 0.28 |
| 26 | E026T | 0.40 |
| 26 | E026W | 0.47 |
| 26 | E026N | 0.48 |
| 26 | E026R | 0.81 |
| 26 | E026G | 0.87 |
| 26 | E026C | 0.94 |
| 26 | E026V | 0.97 |
| 26 | E026P | 0.99 |
| 27 | R027W | 0.01 |
| 27 | R027T | 0.01 |
| 27 | R027P | 0.48 |
| 27 | R027C | 0.58 |
| 27 | R027S | 0.69 |
| 27 | R027G | 0.84 |
| 27 | R027E | 0.93 |
| 27 | R027V | 0.94 |
| 28 | F028G | 0.01 |
| 28 | F028P | 0.39 |
| 28 | F028V | 0.53 |
| 28 | F028S | 0.70 |
| 29 | A029V | 0.44 |
| 29 | A029T | 0.47 |
| 29 | A029S | 0.55 |
| 29 | A029Y | 0.59 |
| 29 | A029P | 0.62 |
| 29 | A029R | 0.73 |
| 29 | A029W | 0.74 |
| 29 | A029M | 0.77 |
| 29 | A029G | 0.80 |
| 29 | A029E | 0.84 |
| 29 | A029D | 1.00 |
| 30 | P030M | 0.79 |
| 30 | P030Q | 0.91 |
| 30 | P030A | 0.92 |
| 31 | D031E | 0.88 |
| 32 | V032P | 0.01 |
| 32 | V032R | 0.72 |
| 33 | R033V | 0.94 |
| 34 | W034R | 0.01 |
| 34 | W034E | 0.01 |
| 34 | W034Q | 0.04 |
| 34 | W034S | 0.08 |
| 34 | W034T | 0.15 |
| 34 | W034V | 0.73 |
| 34 | W034G | 0.88 |
| 34 | W034I | 0.94 |
| 35 | T035Q | 0.01 |
| 35 | T035N | 0.01 |
| 35 | T035R | 0.01 |
| 35 | T035V | 0.34 |
| 36 | G036S | 0.26 |
| 36 | G036T | 0.33 |
| 36 | G036V | 0.38 |
| 36 | G036M | 0.54 |
| 36 | G036N | 0.56 |
| 36 | G036W | 0.68 |
| 36 | G036Q | 0.71 |
| 36 | G036R | 0.90 |
| 37 | V037T | 0.81 |
| 37 | V037H | 0.96 |
| 37 | V037W | 0.98 |
| 38 | L038K | 0.01 |
| 38 | L038G | 0.01 |
| 38 | L038E | 0.01 |
| 38 | L038P | 0.01 |
| 38 | L038Q | 0.01 |
| 38 | L038R | 0.01 |
| 38 | L038D | 0.12 |
| 38 | L038S | 0.29 |
| 38 | L038A | 0.63 |
| 38 | L038C | 0.72 |
| 39 | A039S | 0.01 |
| 39 | A039G | 0.30 |
| 39 | A039N | 0.43 |
| 39 | A039R | 0.64 |
| 39 | A039I | 0.71 |
| 39 | A039P | 0.74 |
| 39 | A039T | 0.79 |
| 39 | A039M | 0.81 |
| 39 | A039E | 0.83 |
| 39 | A039C | 0.92 |
| 39 | A039K | 0.96 |
| 39 | A039L | 0.97 |
| 39 | A039V | 0.98 |
| 40 | Q040P | 0.01 |
| 41 | Q041V | 0.01 |
| 41 | Q041S | 0.22 |
| 41 | Q041P | 0.66 |
| 41 | Q041Y | 0.70 |
| 41 | Q041W | 0.88 |
| 42 | L042W | 0.01 |
| 42 | L042H | 0.01 |
| 42 | L042T | 0.01 |
| 42 | L042Q | 0.28 |
| 42 | L042S | 0.45 |
| 42 | L042R | 0.64 |
| 42 | L042I | 0.66 |
| 42 | L042V | 0.73 |
| 42 | L042M | 0.74 |
| 42 | L042G | 0.76 |
| 43 | G043S | 0.23 |
| 43 | G043P | 0.31 |
| 43 | G043V | 0.33 |
| 43 | G043Q | 0.48 |
| 43 | G043R | 0.59 |
| 43 | G043C | 0.73 |
| 43 | G043I | 0.77 |
| 43 | G043K | 0.86 |
| 43 | G043M | 0.88 |
| 43 | G043Y | 0.94 |
| 43 | G043H | 0.96 |
| 44 | A044S | 0.01 |
| 44 | A044Y | 0.01 |
| 44 | A044T | 0.01 |
| 44 | A044R | 0.01 |
| 44 | A044E | 0.03 |

TABLE 10-7-continued

Variants with Peracid Degradation Results Less than Wild-Type

| Pos | WT/Pos./Var.PAD | PI |
|---|---|---|
| 44 | A044V | 0.50 |
| 44 | A044F | 0.80 |
| 44 | A044W | 0.85 |
| 44 | A044M | 0.98 |
| 44 | A044L | 0.99 |
| 45 | D045S | 0.38 |
| 45 | D045T | 0.44 |
| 45 | D045R | 0.49 |
| 45 | D045V | 0.50 |
| 45 | D045P | 0.53 |
| 45 | D045Q | 0.57 |
| 45 | D045W | 0.58 |
| 45 | D045H | 0.78 |
| 45 | D045L | 0.78 |
| 45 | D045M | 0.78 |
| 45 | D045G | 0.84 |
| 45 | D045A | 0.84 |
| 45 | D045C | 0.84 |
| 45 | D045K | 0.87 |
| 46 | F046T | 0.43 |
| 46 | F046W | 0.63 |
| 46 | F046S | 0.66 |
| 46 | F046V | 0.79 |
| 46 | F046I | 0.88 |
| 46 | F046G | 0.94 |
| 47 | E047P | 0.36 |
| 47 | E047R | 0.62 |
| 47 | E047N | 0.63 |
| 47 | E047S | 0.63 |
| 47 | E047M | 0.70 |
| 47 | E047A | 0.76 |
| 47 | E047F | 0.76 |
| 47 | E047C | 0.77 |
| 47 | E047T | 0.84 |
| 47 | E047D | 0.98 |
| 47 | E047H | 0.99 |
| 48 | V048R | 0.01 |
| 48 | V048S | 0.42 |
| 48 | V048G | 0.87 |
| 48 | V048N | 0.98 |
| 48 | V048E | 0.99 |
| 49 | I049P | 0.16 |
| 49 | I049R | 0.29 |
| 49 | I049W | 0.68 |
| 49 | I049H | 0.74 |
| 49 | I049S | 0.79 |
| 49 | I049E | 0.88 |
| 49 | I049V | 0.97 |
| 50 | E050R | 0.01 |
| 50 | E050W | 0.14 |
| 50 | E050V | 0.43 |
| 50 | E050I | 0.58 |
| 50 | E050S | 0.65 |
| 50 | E050Q | 0.91 |
| 50 | E050L | 0.97 |
| 51 | E051R | 0.01 |
| 51 | E051I | 0.04 |
| 51 | E051W | 0.17 |
| 51 | E051V | 0.37 |
| 51 | E051Q | 0.76 |
| 51 | E051L | 0.93 |
| 52 | G052H | 0.01 |
| 52 | G052S | 0.01 |
| 52 | G052V | 0.01 |
| 52 | G052T | 0.01 |
| 52 | G052M | 0.01 |
| 52 | G052F | 0.01 |
| 52 | G052I | 0.07 |
| 52 | G052P | 0.24 |
| 52 | G052L | 0.24 |
| 52 | G052Q | 0.28 |
| 52 | G052R | 0.35 |
| 52 | G052E | 0.55 |
| 52 | G052A | 0.79 |
| 53 | L053R | 0.01 |
| 53 | L053W | 0.01 |
| 53 | L053P | 0.01 |
| 53 | L053D | 0.01 |
| 53 | L053E | 0.19 |
| 53 | L053K | 0.24 |
| 53 | L053S | 0.26 |
| 53 | L053G | 0.33 |
| 53 | L053V | 0.65 |
| 53 | L053I | 0.66 |
| 53 | L053Q | 0.72 |
| 53 | L053T | 0.84 |
| 54 | S054F | 0.01 |
| 54 | S054W | 0.01 |
| 54 | S054H | 0.01 |
| 54 | S054K | 0.08 |
| 54 | S054I | 0.12 |
| 54 | S054Y | 0.12 |
| 54 | S054G | 0.17 |
| 54 | S054L | 0.26 |
| 54 | S054V | 0.29 |
| 54 | S054E | 0.30 |
| 54 | S054T | 0.33 |
| 54 | S054R | 0.35 |
| 54 | S054M | 0.48 |
| 54 | S054Q | 0.53 |
| 54 | S054D | 0.65 |
| 54 | S054C | 0.88 |
| 55 | A055V | 0.01 |
| 55 | A055I | 0.01 |
| 55 | A055P | 0.01 |
| 55 | A055W | 0.01 |
| 55 | A055Y | 0.18 |
| 55 | A055R | 0.25 |
| 55 | A055T | 0.42 |
| 55 | A055G | 0.73 |
| 55 | A055L | 0.87 |
| 55 | A055S | 0.87 |
| 55 | A055H | 0.92 |
| 56 | R056C | 0.01 |
| 56 | R056G | 0.01 |
| 56 | R056T | 0.01 |
| 56 | R056E | 0.01 |
| 56 | R056Q | 0.01 |
| 56 | R056S | 0.12 |
| 56 | R056L | 0.24 |
| 56 | R056N | 0.27 |
| 56 | R056A | 0.69 |
| 57 | T057R | 0.01 |
| 57 | T057P | 0.01 |
| 57 | T057N | 0.25 |
| 57 | T057C | 0.40 |
| 57 | T057Y | 0.55 |
| 57 | T057H | 0.61 |
| 57 | T057A | 0.65 |
| 57 | T057L | 0.76 |
| 57 | T057V | 0.87 |
| 57 | T057I | 0.87 |
| 58 | T058M | 0.03 |
| 58 | T058A | 0.36 |
| 58 | T058V | 0.96 |
| 58 | T058S | 0.96 |
| 59 | N059R | 0.01 |
| 59 | N059M | 0.01 |
| 59 | N059P | 0.01 |
| 60 | I060P | 0.32 |
| 60 | I060D | 0.66 |
| 60 | I060C | 0.67 |
| 60 | I060M | 0.68 |
| 60 | I060A | 0.79 |
| 60 | I060R | 0.81 |
| 60 | I060L | 0.91 |
| 60 | I060E | 0.92 |
| 60 | I060K | 0.96 |

TABLE 10-7-continued

Variants with Peracid Degradation Results Less than Wild-Type

| Pos | WT/Pos./Var.PAD | PI |
|---|---|---|
| 60 | I060S | 1.00 |
| 61 | D061F | 0.70 |
| 61 | D061A | 0.71 |
| 61 | D061C | 0.85 |
| 61 | D061Y | 0.95 |
| 61 | D061V | 0.97 |
| 61 | D061N | 1.00 |
| 62 | D062T | 0.01 |
| 62 | D062I | 0.01 |
| 62 | D062V | 0.01 |
| 62 | D062H | 0.01 |
| 62 | D062W | 0.01 |
| 62 | D062S | 0.01 |
| 62 | D062L | 0.01 |
| 62 | D062G | 0.01 |
| 62 | D062R | 0.01 |
| 62 | D062M | 0.01 |
| 62 | D062P | 0.01 |
| 62 | D062Q | 0.01 |
| 62 | D062A | 0.11 |
| 62 | D062C | 0.49 |
| 62 | D062E | 0.60 |
| 63 | P063A | 0.60 |
| 63 | P063R | 0.80 |
| 63 | P063S | 0.90 |
| 63 | P063M | 0.91 |
| 63 | P063F | 0.93 |
| 63 | P063Y | 0.95 |
| 64 | T064R | 0.11 |
| 64 | T064D | 0.64 |
| 64 | T064W | 0.69 |
| 64 | T064Q | 0.87 |
| 64 | T064C | 0.88 |
| 64 | T064P | 0.94 |
| 64 | T064H | 0.96 |
| 64 | T064N | 0.98 |
| 64 | T064S | 0.99 |
| 65 | D065V | 0.20 |
| 65 | D065R | 0.22 |
| 65 | D065H | 0.40 |
| 65 | D065Y | 0.42 |
| 65 | D065P | 0.42 |
| 65 | D065S | 0.47 |
| 65 | D065W | 0.50 |
| 65 | D065T | 0.50 |
| 65 | D065G | 0.52 |
| 65 | D065I | 0.62 |
| 65 | D065A | 0.72 |
| 66 | P066N | 0.38 |
| 66 | P066Q | 0.42 |
| 66 | P066G | 0.44 |
| 66 | P066R | 0.51 |
| 66 | P066C | 0.52 |
| 66 | P066A | 0.56 |
| 66 | P066F | 0.67 |
| 66 | P066Y | 0.70 |
| 66 | P066D | 0.72 |
| 66 | P066I | 0.84 |
| 66 | P066V | 0.89 |
| 66 | P066H | 0.95 |
| 66 | P066L | 0.99 |
| 67 | R067F | 0.01 |
| 67 | R067W | 0.02 |
| 67 | R067P | 0.04 |
| 67 | R067E | 0.11 |
| 67 | R067V | 0.12 |
| 67 | R067Q | 0.13 |
| 67 | R067L | 0.16 |
| 67 | R067A | 0.22 |
| 67 | R067T | 0.32 |
| 67 | R067N | 0.33 |
| 67 | R067G | 0.41 |
| 67 | R067K | 0.99 |
| 68 | L068G | 0.01 |
| 68 | L068A | 0.01 |
| 68 | L068M | 0.03 |
| 68 | L068C | 0.06 |
| 68 | L068S | 0.07 |
| 68 | L068N | 0.10 |
| 68 | L068E | 0.13 |
| 68 | L068H | 0.22 |
| 68 | L068Q | 0.25 |
| 68 | L068F | 0.25 |
| 68 | L068T | 0.32 |
| 68 | L068P | 0.35 |
| 68 | L068D | 0.44 |
| 68 | L068Y | 0.45 |
| 68 | L068R | 0.47 |
| 68 | L068V | 0.51 |
| 68 | L068W | 0.56 |
| 68 | L068I | 0.73 |
| 69 | N069Y | 0.17 |
| 69 | N069W | 0.55 |
| 69 | N069P | 0.59 |
| 69 | N069R | 0.83 |
| 69 | N069G | 0.98 |
| 70 | G070M | 0.01 |
| 70 | G070T | 0.01 |
| 70 | G070P | 0.01 |
| 70 | G070V | 0.01 |
| 70 | G070C | 0.01 |
| 70 | G070R | 0.01 |
| 70 | G070Y | 0.01 |
| 70 | G070K | 0.01 |
| 70 | G070N | 0.01 |
| 70 | G070Q | 0.01 |
| 70 | G070F | 0.01 |
| 70 | G070I | 0.27 |
| 70 | G070E | 0.33 |
| 70 | G070S | 0.64 |
| 71 | A071P | 0.01 |
| 71 | A071N | 0.61 |
| 71 | A071D | 0.65 |
| 71 | A071G | 0.68 |
| 71 | A071S | 0.69 |
| 71 | A071R | 0.77 |
| 71 | A071H | 0.78 |
| 71 | A071I | 0.79 |
| 71 | A071T | 0.79 |
| 71 | A071E | 0.81 |
| 71 | A071L | 0.84 |
| 71 | A071F | 0.99 |
| 71 | A071C | 0.99 |
| 72 | S072Y | 0.07 |
| 72 | S072W | 0.34 |
| 72 | S072P | 0.56 |
| 72 | S072Q | 0.66 |
| 72 | S072L | 0.70 |
| 72 | S072R | 0.74 |
| 72 | S072D | 0.80 |
| 72 | S072V | 0.83 |
| 72 | S072E | 0.93 |
| 72 | S072T | 0.97 |
| 73 | Y073P | 0.01 |
| 73 | Y073R | 0.26 |
| 73 | Y073L | 0.50 |
| 73 | Y073G | 0.51 |
| 73 | Y073H | 0.52 |
| 73 | Y073I | 0.64 |
| 73 | Y073S | 0.68 |
| 73 | Y073V | 0.74 |
| 73 | Y073N | 0.76 |
| 73 | Y073D | 0.80 |
| 73 | Y073Q | 0.87 |
| 73 | Y073K | 0.94 |
| 74 | L074S | 0.01 |
| 74 | L074G | 0.57 |
| 74 | L074V | 0.61 |

TABLE 10-7-continued

Variants with Peracid Degradation Results Less than Wild-Type

| Pos | WT/Pos./Var.PAD | PI |
|---|---|---|
| 74 | L074I | 0.64 |
| 74 | L074W | 0.67 |
| 74 | L074Y | 0.86 |
| 75 | P075M | 0.30 |
| 75 | P075R | 0.46 |
| 75 | P075Q | 0.61 |
| 75 | P075S | 0.63 |
| 75 | P075T | 0.69 |
| 75 | P075I | 0.74 |
| 75 | P075H | 0.86 |
| 75 | P075K | 0.88 |
| 75 | P075G | 0.93 |
| 76 | S076W | 0.01 |
| 76 | S076Y | 0.18 |
| 76 | S076F | 0.46 |
| 76 | S076Q | 0.90 |
| 77 | C077Y | 0.01 |
| 77 | C077R | 0.01 |
| 77 | C077W | 0.01 |
| 77 | C077F | 0.01 |
| 77 | C077G | 0.18 |
| 77 | C077L | 0.73 |
| 77 | C077S | 0.76 |
| 77 | C077V | 0.80 |
| 77 | C077A | 0.91 |
| 78 | L078E | 0.01 |
| 78 | L078N | 0.01 |
| 78 | L078M | 0.48 |
| 78 | L078Q | 0.52 |
| 78 | L078C | 0.78 |
| 78 | L078Y | 0.81 |
| 78 | L078V | 0.83 |
| 79 | A079H | 0.01 |
| 79 | A079F | 0.01 |
| 79 | A079C | 0.03 |
| 79 | A079Q | 0.27 |
| 79 | A079E | 0.27 |
| 79 | A079N | 0.28 |
| 79 | A079M | 0.28 |
| 79 | A079R | 0.32 |
| 79 | A079W | 0.53 |
| 79 | A079T | 0.60 |
| 79 | A079I | 0.67 |
| 79 | A079S | 0.78 |
| 79 | A079G | 0.92 |
| 79 | A079P | 0.94 |
| 79 | A079L | 0.96 |
| 80 | T080W | 0.01 |
| 80 | T080L | 0.01 |
| 80 | T080K | 0.01 |
| 80 | T080R | 0.01 |
| 80 | T080E | 0.01 |
| 80 | T080P | 0.01 |
| 80 | T080H | 0.05 |
| 80 | T080Y | 0.11 |
| 80 | T080I | 0.15 |
| 80 | T080N | 0.53 |
| 81 | H081R | 0.01 |
| 81 | H081Y | 0.14 |
| 81 | H081K | 0.56 |
| 81 | H081S | 0.69 |
| 81 | H081V | 0.71 |
| 81 | H081P | 0.72 |
| 81 | H081Q | 0.75 |
| 81 | H081G | 0.80 |
| 81 | H081F | 0.90 |
| 82 | L082R | 0.01 |
| 82 | L082S | 0.01 |
| 82 | L082W | 0.01 |
| 82 | L082V | 0.19 |
| 82 | L082G | 0.31 |
| 82 | L082T | 0.38 |
| 82 | L082H | 0.47 |
| 82 | L082I | 0.51 |
| 82 | L082K | 0.51 |
| 82 | L082P | 0.52 |
| 82 | L082A | 0.98 |
| 83 | P083T | 0.01 |
| 83 | P083V | 0.19 |
| 83 | P083L | 0.21 |
| 83 | P083H | 0.61 |
| 83 | P083W | 0.62 |
| 83 | P083G | 0.68 |
| 83 | P083S | 0.79 |
| 83 | P083Q | 0.82 |
| 83 | P083D | 0.83 |
| 83 | P083F | 0.99 |
| 84 | L084W | 0.01 |
| 84 | L084V | 0.42 |
| 84 | L084P | 0.43 |
| 84 | L084T | 0.44 |
| 84 | L084A | 0.45 |
| 84 | L084Q | 0.52 |
| 84 | L084S | 0.55 |
| 84 | L084R | 0.57 |
| 84 | L084N | 0.67 |
| 84 | L084K | 0.79 |
| 84 | L084D | 0.85 |
| 84 | L084I | 0.87 |
| 84 | L084H | 0.99 |
| 85 | D085I | 0.10 |
| 85 | D085L | 0.24 |
| 85 | D085V | 0.25 |
| 85 | D085W | 0.34 |
| 85 | D085P | 0.54 |
| 85 | D085Y | 0.55 |
| 85 | D085S | 0.68 |
| 85 | D085T | 0.71 |
| 85 | D085N | 0.78 |
| 85 | D085Q | 0.99 |
| 86 | L086H | 0.01 |
| 86 | L086S | 0.01 |
| 86 | L086R | 0.01 |
| 86 | L086E | 0.01 |
| 86 | L086Q | 0.01 |
| 86 | L086W | 0.08 |
| 86 | L086V | 0.12 |
| 86 | L086T | 0.28 |
| 86 | L086G | 0.70 |
| 86 | L086Y | 0.82 |
| 86 | L086P | 0.99 |
| 87 | V087S | 0.01 |
| 87 | V087G | 0.01 |
| 87 | V087Y | 0.01 |
| 87 | V087R | 0.01 |
| 87 | V087K | 0.01 |
| 87 | V087D | 0.01 |
| 87 | V087F | 0.10 |
| 87 | V087T | 0.15 |
| 87 | V087A | 0.17 |
| 87 | V087M | 0.75 |
| 88 | I088H | 0.01 |
| 88 | I088T | 0.01 |
| 88 | I088G | 0.01 |
| 88 | I088N | 0.01 |
| 88 | I088Q | 0.01 |
| 89 | I089H | 0.01 |
| 89 | I089S | 0.01 |
| 89 | I089G | 0.01 |
| 89 | I089W | 0.01 |
| 89 | I089Q | 0.01 |
| 89 | I089E | 0.01 |
| 89 | I089F | 0.75 |
| 89 | I089V | 0.82 |
| 89 | I089T | 0.90 |
| 90 | M090S | 0.01 |
| 90 | M090W | 0.01 |
| 90 | M090G | 0.01 |

TABLE 10-7-continued

Variants with Peracid Degradation Results Less than Wild-Type

| Pos | WT/Pos./Var.PAD | PI |
|---|---|---|
| 90 | M090P | 0.01 |
| 90 | M090V | 0.08 |
| 90 | M090T | 0.15 |
| 90 | M090R | 0.36 |
| 90 | M090I | 0.66 |
| 90 | M090Q | 0.77 |
| 90 | M090L | 0.98 |
| 91 | L091G | 0.01 |
| 91 | L091T | 0.01 |
| 91 | L091Q | 0.01 |
| 91 | L091E | 0.01 |
| 91 | L091S | 0.43 |
| 91 | L091V | 0.79 |
| 91 | L091M | 0.88 |
| 92 | G092V | 0.01 |
| 92 | G092S | 0.01 |
| 92 | G092E | 0.01 |
| 92 | G092F | 0.01 |
| 93 | T093Q | 0.01 |
| 93 | T093Y | 0.03 |
| 93 | T093D | 0.23 |
| 93 | T093S | 0.49 |
| 93 | T093F | 0.54 |
| 93 | T093C | 0.95 |
| 94 | N094L | 0.01 |
| 94 | N094T | 0.01 |
| 94 | N094V | 0.01 |
| 94 | N094H | 0.01 |
| 94 | N094R | 0.01 |
| 94 | N094W | 0.01 |
| 94 | N094M | 0.03 |
| 94 | N094C | 0.07 |
| 94 | N094Y | 0.12 |
| 94 | N094G | 0.53 |
| 94 | N094A | 0.74 |
| 94 | N094P | 0.79 |
| 94 | N094S | 0.88 |
| 95 | D095E | 0.75 |
| 96 | T096I | 0.01 |
| 96 | T096W | 0.01 |
| 96 | T096Y | 0.01 |
| 96 | T096R | 0.14 |
| 96 | T096V | 0.59 |
| 96 | T096S | 0.79 |
| 96 | T096P | 0.89 |
| 97 | K097Q | 0.01 |
| 97 | K097G | 0.01 |
| 97 | K097I | 0.01 |
| 97 | K097W | 0.01 |
| 97 | K097L | 0.01 |
| 97 | K097V | 0.01 |
| 97 | K097Y | 0.01 |
| 97 | K097S | 0.01 |
| 97 | K097T | 0.01 |
| 97 | K097M | 0.22 |
| 97 | K097A | 0.23 |
| 97 | K097P | 0.27 |
| 97 | K097R | 0.59 |
| 98 | A098T | 0.27 |
| 98 | A098G | 0.56 |
| 98 | A098S | 0.65 |
| 98 | A098I | 0.65 |
| 98 | A098H | 0.92 |
| 99 | Y099R | 0.29 |
| 99 | Y099V | 0.31 |
| 99 | Y099S | 0.37 |
| 99 | Y099W | 0.57 |
| 99 | Y099H | 0.59 |
| 99 | Y099I | 0.61 |
| 99 | Y099G | 0.70 |
| 99 | Y099P | 0.81 |
| 99 | Y099A | 0.82 |
| 99 | Y099L | 0.86 |
| 100 | F100W | 0.01 |
| 100 | F100K | 0.01 |
| 100 | F100D | 0.01 |
| 100 | F100E | 0.15 |
| 100 | F100S | 0.85 |
| 101 | R101W | 0.01 |
| 101 | R101K | 0.07 |
| 101 | R101Q | 0.11 |
| 101 | R101V | 0.44 |
| 101 | R101D | 0.80 |
| 101 | R101Y | 0.80 |
| 101 | R101P | 0.86 |
| 101 | R101N | 0.92 |
| 101 | R101C | 0.95 |
| 101 | R101I | 0.96 |
| 101 | R101F | 0.97 |
| 102 | R102W | 0.01 |
| 102 | R102F | 0.23 |
| 102 | R102G | 0.27 |
| 102 | R102C | 0.36 |
| 102 | R102V | 0.61 |
| 102 | R102D | 0.68 |
| 102 | R102P | 0.89 |
| 102 | R102S | 0.96 |
| 103 | T103W | 0.01 |
| 103 | T103Y | 0.01 |
| 103 | T103G | 0.01 |
| 103 | T103K | 0.01 |
| 103 | T103I | 0.01 |
| 103 | T103L | 0.01 |
| 103 | T103H | 0.01 |
| 103 | T103A | 0.01 |
| 103 | T103V | 0.01 |
| 103 | T103S | 0.01 |
| 103 | T103C | 0.01 |
| 103 | T103R | 0.01 |
| 103 | T103N | 0.01 |
| 103 | T103F | 0.01 |
| 103 | T103P | 0.01 |
| 104 | P104R | 0.01 |
| 104 | P104W | 0.23 |
| 104 | P104T | 0.33 |
| 104 | P104S | 0.53 |
| 104 | P104Q | 0.85 |
| 104 | P104F | 0.86 |
| 104 | P104G | 0.98 |
| 105 | L105V | 0.01 |
| 105 | L105E | 0.53 |
| 105 | L105S | 0.61 |
| 105 | L105Y | 0.62 |
| 105 | L105T | 0.64 |
| 105 | L105P | 0.90 |
| 106 | D106R | 0.56 |
| 106 | D106Q | 0.62 |
| 106 | D106P | 0.63 |
| 106 | D106N | 0.64 |
| 106 | D106M | 0.86 |
| 106 | D106I | 0.92 |
| 106 | D106L | 1.00 |
| 107 | I107E | 0.01 |
| 107 | I107G | 0.01 |
| 107 | I107F | 0.01 |
| 107 | I107Q | 0.01 |
| 107 | I107R | 0.01 |
| 107 | I107P | 0.32 |
| 107 | I107Y | 0.52 |
| 107 | I107A | 0.80 |
| 107 | I107N | 0.93 |
| 107 | I107V | 0.97 |
| 108 | A108E | 0.61 |
| 108 | A108Q | 0.73 |
| 108 | A108T | 0.87 |
| 108 | A108V | 0.95 |
| 109 | L109W | 0.01 |
| 109 | L109D | 0.11 |

TABLE 10-7-continued

Variants with Peracid Degradation Results Less than Wild-Type

| Pos | WT/Pos./Var.PAD | PI |
|---|---|---|
| 109 | L109I | 0.14 |
| 109 | L109E | 0.19 |
| 109 | L109R | 0.21 |
| 109 | L109H | 0.22 |
| 109 | L109Q | 0.22 |
| 109 | L109F | 0.32 |
| 109 | L109A | 0.32 |
| 109 | L109S | 0.38 |
| 109 | L109P | 0.43 |
| 109 | L109G | 0.51 |
| 109 | L109V | 0.54 |
| 109 | L109M | 0.63 |
| 109 | L109N | 0.66 |
| 109 | L109T | 0.79 |
| 109 | L109Y | 0.83 |
| 110 | G110T | 0.01 |
| 110 | G110W | 0.01 |
| 110 | G110Y | 0.01 |
| 110 | G110P | 0.22 |
| 110 | G110I | 0.23 |
| 110 | G110S | 0.30 |
| 110 | G110Q | 0.34 |
| 110 | G110R | 0.48 |
| 110 | G110H | 0.73 |
| 110 | G110N | 0.77 |
| 110 | G110M | 0.82 |
| 111 | M111R | 0.01 |
| 111 | M111S | 0.14 |
| 111 | M111H | 0.19 |
| 111 | M111G | 0.32 |
| 111 | M111P | 0.57 |
| 111 | M111E | 0.67 |
| 111 | M111L | 0.67 |
| 111 | M111K | 0.71 |
| 111 | M111T | 0.76 |
| 111 | M111F | 0.78 |
| 111 | M111D | 0.79 |
| 111 | M111V | 0.93 |
| 112 | S112Y | 0.01 |
| 112 | S112R | 0.01 |
| 112 | S112P | 0.01 |
| 112 | S112H | 0.38 |
| 112 | S112V | 0.48 |
| 112 | S112M | 0.56 |
| 112 | S112W | 0.58 |
| 112 | S112K | 0.68 |
| 112 | S112T | 0.72 |
| 112 | S112N | 0.85 |
| 112 | S112F | 0.88 |
| 112 | S112A | 0.94 |
| 113 | V113S | 0.57 |
| 113 | V113G | 0.58 |
| 113 | V113K | 0.72 |
| 113 | V113H | 0.76 |
| 113 | V113W | 0.80 |
| 113 | V113L | 0.85 |
| 113 | V113T | 0.86 |
| 113 | V113D | 0.87 |
| 113 | V113E | 0.94 |
| 113 | V113C | 0.94 |
| 113 | V113F | 0.96 |
| 113 | V113Y | 0.98 |
| 114 | L114H | 0.01 |
| 114 | L114E | 0.01 |
| 114 | L114Q | 0.12 |
| 114 | L114P | 0.28 |
| 114 | L114S | 0.55 |
| 114 | L114V | 0.60 |
| 114 | L114N | 0.77 |
| 115 | V115I | 0.99 |
| 116 | T116Y | 0.47 |
| 116 | T116V | 0.57 |
| 116 | T116R | 0.62 |
| 116 | T116L | 0.68 |
| 116 | T116W | 0.75 |
| 116 | T116I | 0.76 |
| 116 | T116Q | 0.77 |
| 116 | T116P | 0.84 |
| 116 | T116G | 0.90 |
| 116 | T116E | 0.91 |
| 116 | T116A | 0.95 |
| 116 | T116S | 0.96 |
| 117 | Q117W | 0.71 |
| 117 | Q117V | 0.76 |
| 117 | Q117G | 0.79 |
| 117 | Q117S | 0.87 |
| 118 | V118K | 0.01 |
| 118 | V118W | 0.01 |
| 118 | V118E | 0.01 |
| 118 | V118R | 0.07 |
| 118 | V118P | 0.22 |
| 118 | V118D | 0.40 |
| 118 | V118I | 0.55 |
| 118 | V118G | 0.56 |
| 118 | V118S | 0.82 |
| 118 | V118A | 0.85 |
| 118 | V118T | 0.92 |
| 118 | V118M | 0.93 |
| 118 | V118F | 1.00 |
| 119 | L119G | 0.01 |
| 119 | L119S | 0.01 |
| 119 | L119F | 0.01 |
| 119 | L119R | 0.01 |
| 119 | L119P | 0.01 |
| 119 | L119T | 0.10 |
| 119 | L119N | 0.11 |
| 119 | L119V | 0.15 |
| 119 | L119W | 0.20 |
| 119 | L119C | 0.24 |
| 119 | L119D | 0.28 |
| 119 | L119E | 0.32 |
| 119 | L119I | 0.43 |
| 119 | L119H | 0.46 |
| 119 | L119Y | 0.56 |
| 120 | T120P | 0.01 |
| 120 | T120H | 0.50 |
| 120 | T120R | 0.60 |
| 120 | T120A | 0.66 |
| 120 | T120Q | 0.78 |
| 120 | T120C | 0.92 |
| 121 | S121P | 0.38 |
| 121 | S121R | 0.70 |
| 121 | S121W | 0.77 |
| 121 | S121K | 0.78 |
| 121 | S121G | 0.99 |
| 122 | A122G | 0.01 |
| 122 | A122D | 0.06 |
| 122 | A122F | 0.15 |
| 122 | A122H | 0.17 |
| 122 | A122R | 0.40 |
| 122 | A122S | 0.43 |
| 122 | A122K | 0.45 |
| 122 | A122E | 0.47 |
| 122 | A122T | 0.52 |
| 122 | A122P | 0.55 |
| 122 | A122I | 0.65 |
| 122 | A122N | 0.70 |
| 122 | A122Q | 0.74 |
| 122 | A122W | 0.86 |
| 122 | A122V | 0.89 |
| 122 | A122M | 0.94 |
| 123 | G123C | 0.30 |
| 123 | G123Q | 0.31 |
| 123 | G123T | 0.54 |
| 123 | G123E | 0.56 |
| 123 | G123V | 0.59 |
| 123 | G123R | 0.60 |
| 123 | G123N | 0.71 |

TABLE 10-7-continued

Variants with Peracid Degradation Results Less than Wild-Type

| Pos | WT/Pos./Var.PAD | PI |
| --- | --- | --- |
| 123 | G123H | 0.74 |
| 123 | G123F | 0.80 |
| 123 | G123P | 0.81 |
| 123 | G123D | 0.84 |
| 124 | G124I | 0.01 |
| 124 | G124H | 0.01 |
| 124 | G124M | 0.01 |
| 124 | G124W | 0.01 |
| 124 | G124P | 0.01 |
| 124 | G124A | 0.03 |
| 124 | G124Q | 0.21 |
| 124 | G124T | 0.32 |
| 124 | G124V | 0.33 |
| 124 | G124R | 0.41 |
| 124 | G124L | 0.54 |
| 124 | G124S | 0.56 |
| 124 | G124Y | 0.56 |
| 124 | G124N | 0.60 |
| 124 | G124D | 0.64 |
| 124 | G124C | 0.67 |
| 124 | G124F | 0.95 |
| 125 | V125W | 0.25 |
| 125 | V125E | 0.39 |
| 125 | V125R | 0.47 |
| 125 | V125C | 0.54 |
| 125 | V125D | 0.54 |
| 125 | V125P | 0.62 |
| 125 | V125F | 0.63 |
| 125 | V125S | 0.79 |
| 125 | V125Y | 0.81 |
| 125 | V125A | 0.93 |
| 125 | V125I | 0.94 |
| 126 | G126I | 0.01 |
| 126 | G126V | 0.18 |
| 126 | G126Y | 0.23 |
| 126 | G126L | 0.54 |
| 126 | G126A | 0.55 |
| 126 | G126E | 0.60 |
| 126 | G126P | 0.67 |
| 126 | G126T | 0.74 |
| 126 | G126R | 0.76 |
| 126 | G126N | 0.85 |
| 126 | G126S | 0.90 |
| 126 | G126C | 0.98 |
| 127 | T127L | 0.01 |
| 127 | T127E | 0.01 |
| 127 | T127Q | 0.15 |
| 127 | T127I | 0.20 |
| 127 | T127H | 0.60 |
| 127 | T127D | 0.62 |
| 127 | T127M | 0.64 |
| 127 | T127C | 0.65 |
| 127 | T127V | 0.68 |
| 127 | T127G | 0.71 |
| 127 | T127P | 0.77 |
| 127 | T127S | 0.83 |
| 128 | T128D | 0.66 |
| 129 | Y129W | 0.01 |
| 129 | Y129G | 0.01 |
| 129 | Y129K | 0.01 |
| 129 | Y129V | 0.01 |
| 129 | Y129T | 0.14 |
| 129 | Y129A | 0.17 |
| 129 | Y129R | 0.18 |
| 129 | Y129M | 0.21 |
| 129 | Y129D | 0.23 |
| 129 | Y129L | 0.27 |
| 129 | Y129N | 0.53 |
| 129 | Y129P | 0.59 |
| 129 | Y129C | 0.61 |
| 129 | Y129S | 0.69 |
| 129 | Y129F | 0.71 |
| 130 | P130T | 0.01 |
| 130 | P130H | 0.01 |
| 130 | P130G | 0.01 |
| 130 | P130S | 0.01 |
| 130 | P130L | 0.09 |
| 130 | P130E | 0.22 |
| 130 | P130W | 0.28 |
| 130 | P130V | 0.37 |
| 130 | P130I | 0.41 |
| 130 | P130A | 0.44 |
| 130 | P130F | 0.48 |
| 130 | P130R | 0.53 |
| 130 | P130K | 0.55 |
| 130 | P130C | 0.64 |
| 130 | P130M | 0.76 |
| 131 | A131W | 0.01 |
| 131 | A131D | 0.40 |
| 131 | A131Y | 0.48 |
| 131 | A131L | 0.59 |
| 131 | A131S | 0.68 |
| 131 | A131P | 0.71 |
| 131 | A131Q | 0.74 |
| 131 | A131V | 0.78 |
| 131 | A131H | 0.82 |
| 131 | A131G | 0.87 |
| 131 | A131E | 0.97 |
| 132 | P132V | 0.01 |
| 132 | P132T | 0.01 |
| 132 | P132W | 0.01 |
| 132 | P132F | 0.01 |
| 132 | P132I | 0.01 |
| 132 | P132H | 0.01 |
| 132 | P132R | 0.01 |
| 132 | P132D | 0.01 |
| 133 | K133C | 0.01 |
| 133 | K133A | 0.10 |
| 133 | K133V | 0.23 |
| 133 | K133G | 0.31 |
| 133 | K133H | 0.31 |
| 133 | K133M | 0.33 |
| 133 | K133T | 0.39 |
| 133 | K133I | 0.45 |
| 133 | K133Q | 0.52 |
| 133 | K133S | 0.58 |
| 133 | K133F | 0.59 |
| 133 | K133P | 0.71 |
| 133 | K133E | 0.76 |
| 133 | K133R | 0.83 |
| 133 | K133W | 0.99 |
| 134 | V134Q | 0.79 |
| 134 | V134T | 0.86 |
| 134 | V134I | 0.89 |
| 135 | L135T | 0.01 |
| 135 | L135W | 0.01 |
| 135 | L135K | 0.01 |
| 135 | L135S | 0.01 |
| 135 | L135F | 0.01 |
| 135 | L135G | 0.01 |
| 135 | L135R | 0.01 |
| 135 | L135P | 0.01 |
| 135 | L135Q | 0.17 |
| 135 | L135V | 0.43 |
| 135 | L135E | 0.63 |
| 135 | L135M | 0.78 |
| 136 | V136P | 0.01 |
| 136 | V136E | 0.20 |
| 136 | V136N | 0.40 |
| 137 | V137N | 0.01 |
| 137 | V137G | 0.26 |
| 137 | V137S | 0.29 |
| 137 | V137I | 0.70 |
| 137 | V137T | 0.93 |
| 138 | S138I | 0.35 |
| 138 | S138V | 0.69 |
| 139 | P139S | 0.01 |
| 139 | P139G | 0.01 |

TABLE 10-7-continued

Variants with Peracid Degradation Results Less than Wild-Type

| Pos | WT/Pos./Var.PAD | PI |
|---|---|---|
| 139 | P139R | 0.01 |
| 139 | P139C | 0.01 |
| 139 | P139D | 0.01 |
| 139 | P139E | 0.01 |
| 139 | P139F | 0.01 |
| 139 | P139H | 0.01 |
| 139 | P139I | 0.01 |
| 139 | P139K | 0.01 |
| 139 | P139N | 0.01 |
| 139 | P139Q | 0.01 |
| 139 | P139T | 0.01 |
| 139 | P139V | 0.01 |
| 140 | P140T | 0.01 |
| 140 | P140S | 0.01 |
| 140 | P140V | 0.01 |
| 140 | P140W | 0.01 |
| 140 | P140I | 0.01 |
| 140 | P140Y | 0.01 |
| 140 | P140Q | 0.01 |
| 140 | P140R | 0.01 |
| 141 | P141R | 0.01 |
| 141 | P141G | 0.01 |
| 141 | P141S | 0.02 |
| 141 | P141T | 0.12 |
| 141 | P141V | 0.16 |
| 141 | P141Q | 0.37 |
| 141 | P141I | 0.38 |
| 141 | P141L | 0.65 |
| 141 | P141H | 0.79 |
| 141 | P141N | 0.97 |
| 142 | L142W | 0.01 |
| 142 | L142I | 0.28 |
| 142 | L142S | 0.31 |
| 142 | L142Q | 0.33 |
| 142 | L142V | 0.33 |
| 142 | L142P | 0.44 |
| 142 | L142F | 0.54 |
| 142 | L142A | 0.56 |
| 142 | L142K | 0.66 |
| 142 | L142C | 0.70 |
| 143 | A143W | 0.01 |
| 143 | A143P | 0.39 |
| 143 | A143G | 0.42 |
| 143 | A143S | 0.63 |
| 143 | A143F | 0.68 |
| 143 | A143Q | 0.81 |
| 143 | A143N | 0.82 |
| 143 | A143T | 0.97 |
| 143 | A143R | 0.99 |
| 143 | A143V | 0.99 |
| 144 | P144G | 0.62 |
| 144 | P144A | 0.79 |
| 144 | P144T | 0.81 |
| 144 | P144S | 0.92 |
| 145 | M145W | 0.01 |
| 145 | M145G | 0.26 |
| 145 | M145E | 0.48 |
| 145 | M145I | 0.53 |
| 145 | M145Q | 0.57 |
| 145 | M145L | 0.61 |
| 145 | M145V | 0.63 |
| 145 | M145R | 0.69 |
| 145 | M145F | 0.77 |
| 145 | M145P | 0.78 |
| 145 | M145S | 0.78 |
| 145 | M145T | 0.79 |
| 145 | M145A | 0.79 |
| 145 | M145Y | 0.82 |
| 145 | M145C | 0.93 |
| 146 | P146W | 0.68 |
| 146 | P146T | 0.76 |
| 146 | P146V | 0.77 |
| 146 | P146S | 0.96 |
| 147 | H147S | 0.75 |
| 147 | H147T | 0.84 |
| 147 | H147I | 0.92 |
| 147 | H147V | 0.92 |
| 147 | H147R | 0.94 |
| 147 | H147A | 0.98 |
| 148 | P148Q | 0.98 |
| 149 | W149R | 0.01 |
| 149 | W149E | 0.01 |
| 149 | W149P | 0.01 |
| 149 | W149C | 0.12 |
| 149 | W149I | 0.24 |
| 149 | W149A | 0.31 |
| 149 | W149S | 0.33 |
| 149 | W149Q | 0.40 |
| 149 | W149T | 0.44 |
| 149 | W149G | 0.45 |
| 149 | W149M | 0.49 |
| 149 | W149F | 0.50 |
| 149 | W149L | 0.64 |
| 149 | W149Y | 0.75 |
| 150 | F150P | 0.32 |
| 150 | F150N | 0.36 |
| 150 | F150G | 0.46 |
| 150 | F150V | 0.51 |
| 150 | F150A | 0.54 |
| 150 | F150T | 0.58 |
| 150 | F150W | 0.62 |
| 150 | F150M | 0.63 |
| 150 | F150E | 0.73 |
| 150 | F150C | 0.78 |
| 150 | F150I | 0.78 |
| 150 | F150K | 0.85 |
| 151 | Q151L | 0.01 |
| 151 | Q151V | 0.01 |
| 151 | Q151F | 0.01 |
| 151 | Q151I | 0.01 |
| 151 | Q151W | 0.32 |
| 152 | L152I | 0.61 |
| 152 | L152P | 0.61 |
| 152 | L152T | 0.69 |
| 152 | L152Q | 0.76 |
| 152 | L152G | 0.77 |
| 152 | L152S | 0.84 |
| 152 | L152D | 0.86 |
| 152 | L152V | 0.88 |
| 152 | L152R | 0.91 |
| 152 | L152K | 0.91 |
| 152 | L152H | 0.92 |
| 153 | I153N | 0.89 |
| 154 | F154T | 0.01 |
| 154 | F154G | 0.01 |
| 154 | F154V | 0.01 |
| 154 | F154S | 0.29 |
| 154 | F154Q | 0.97 |
| 155 | E155R | 0.01 |
| 155 | E155F | 0.23 |
| 155 | E155V | 0.47 |
| 155 | E155I | 0.65 |
| 155 | E155Q | 0.69 |
| 156 | G156I | 0.01 |
| 156 | G156F | 0.73 |
| 156 | G156W | 0.90 |
| 156 | G156L | 0.94 |
| 156 | G156V | 0.97 |
| 157 | G157R | 0.01 |
| 157 | G157P | 0.01 |
| 157 | G157S | 0.19 |
| 157 | G157V | 0.40 |
| 157 | G157C | 0.61 |
| 157 | G157E | 0.84 |
| 157 | G157M | 0.85 |
| 157 | G157A | 0.87 |
| 157 | G157D | 0.94 |
| 157 | G157T | 0.99 |

TABLE 10-7-continued

Variants with Peracid Degradation Results Less than Wild-Type

| Pos | WT/Pos./Var.PAD | PI |
|---|---|---|
| 158 | E158V | 0.89 |
| 158 | E158D | 0.89 |
| 158 | E158T | 0.91 |
| 158 | E158I | 0.94 |
| 159 | Q159A | 0.28 |
| 159 | Q159C | 0.31 |
| 159 | Q159P | 0.49 |
| 159 | Q159D | 0.63 |
| 159 | Q159L | 0.70 |
| 159 | Q159G | 0.72 |
| 159 | Q159S | 0.73 |
| 159 | Q159R | 0.74 |
| 159 | Q159M | 0.84 |
| 159 | Q159E | 0.97 |
| 160 | K160W | 0.01 |
| 160 | K160G | 0.30 |
| 160 | K160H | 0.57 |
| 160 | K160S | 0.70 |
| 160 | K160L | 0.95 |
| 160 | K160I | 1.00 |
| 161 | T161R | 0.01 |
| 161 | T161H | 0.01 |
| 161 | T161W | 0.01 |
| 161 | T161N | 0.01 |
| 161 | T161G | 0.43 |
| 161 | T161C | 0.56 |
| 161 | T161S | 0.57 |
| 161 | T161I | 0.98 |
| 163 | E163F | 0.27 |
| 163 | E163R | 0.49 |
| 163 | E163V | 0.55 |
| 163 | E163P | 0.77 |
| 163 | E163G | 0.80 |
| 163 | E163H | 0.82 |
| 163 | E163S | 0.85 |
| 163 | E163W | 0.98 |
| 164 | L164Y | 0.01 |
| 164 | L164A | 0.01 |
| 164 | L164D | 0.01 |
| 164 | L164E | 0.01 |
| 164 | L164G | 0.01 |
| 164 | L164H | 0.12 |
| 164 | L164F | 0.86 |
| 164 | L164C | 0.91 |
| 164 | L164T | 0.99 |
| 165 | A165I | 0.59 |
| 165 | A165K | 0.82 |
| 165 | A165Y | 0.84 |
| 165 | A165S | 0.94 |
| 165 | A165F | 1.00 |
| 166 | R166T | 0.74 |
| 166 | R166V | 0.76 |
| 166 | R166G | 0.91 |
| 166 | R166S | 0.95 |
| 168 | Y168G | 0.01 |
| 168 | Y168T | 0.01 |
| 168 | Y168V | 0.01 |
| 168 | Y168I | 0.01 |
| 168 | Y168C | 0.01 |
| 168 | Y168Q | 0.01 |
| 169 | S169P | 0.89 |
| 169 | S169T | 0.97 |
| 170 | A170I | 0.44 |
| 170 | A170S | 0.47 |
| 170 | A170G | 0.62 |
| 170 | A170T | 0.72 |
| 170 | A170V | 0.74 |
| 170 | A170K | 0.83 |
| 170 | A170W | 0.83 |
| 170 | A170L | 0.85 |
| 170 | A170Q | 0.89 |
| 170 | A170Y | 0.89 |
| 171 | L171R | 0.01 |
| 172 | A172K | 0.01 |
| 172 | A172R | 0.01 |
| 172 | A172E | 0.01 |
| 172 | A172Q | 0.18 |
| 172 | A172V | 0.39 |
| 172 | A172W | 0.45 |
| 172 | A172P | 0.58 |
| 172 | A172I | 0.58 |
| 172 | A172T | 0.71 |
| 172 | A172N | 0.76 |
| 172 | A172G | 0.84 |
| 172 | A172S | 0.85 |
| 172 | A172C | 0.86 |
| 174 | F174W | 0.01 |
| 174 | F174Q | 0.46 |
| 174 | F174C | 0.48 |
| 174 | F174R | 0.52 |
| 174 | F174S | 0.61 |
| 174 | F174T | 0.64 |
| 174 | F174V | 0.67 |
| 174 | F174G | 0.91 |
| 175 | M175P | 0.08 |
| 175 | M175A | 0.66 |
| 175 | M175Y | 0.72 |
| 175 | M175G | 0.75 |
| 175 | M175W | 0.76 |
| 175 | M175V | 0.81 |
| 175 | M175Q | 0.83 |
| 175 | M175L | 0.86 |
| 175 | M175R | 0.86 |
| 175 | M175T | 0.90 |
| 176 | K176S | 0.72 |
| 176 | K176G | 0.73 |
| 176 | K176P | 0.78 |
| 176 | K176L | 0.92 |
| 176 | K176Y | 0.93 |
| 176 | K176N | 0.94 |
| 176 | K176T | 0.97 |
| 176 | K176Q | 0.97 |
| 178 | P178W | 0.02 |
| 179 | F179Q | 0.01 |
| 179 | F179S | 0.34 |
| 179 | F179W | 0.86 |
| 179 | F179H | 0.93 |
| 179 | F179N | 0.95 |
| 180 | F180K | 0.01 |
| 180 | F180T | 0.01 |
| 180 | F180R | 0.01 |
| 180 | F180S | 0.01 |
| 180 | F180G | 0.01 |
| 180 | F180Q | 0.01 |
| 181 | D181Y | 0.01 |
| 181 | D181W | 0.01 |
| 181 | D181L | 0.01 |
| 181 | D181T | 0.01 |
| 181 | D181V | 0.01 |
| 181 | D181R | 0.22 |
| 181 | D181K | 0.47 |
| 181 | D181G | 0.52 |
| 181 | D181S | 0.55 |
| 181 | D181Q | 0.60 |
| 181 | D181P | 0.66 |
| 181 | D181E | 0.72 |
| 181 | D181C | 0.85 |
| 182 | A182I | 0.01 |
| 182 | A182R | 0.01 |
| 182 | A182Q | 0.01 |
| 182 | A182P | 0.01 |
| 182 | A182T | 0.11 |
| 182 | A182N | 0.53 |
| 182 | A182S | 0.85 |
| 182 | A182G | 0.94 |
| 182 | A182C | 0.99 |
| 183 | G183S | 0.01 |
| 183 | G183Q | 0.01 |

TABLE 10-7-continued

Variants with Peracid Degradation Results Less than Wild-Type

| Pos | WT/Pos./Var.PAD | PI |
|---|---|---|
| 183 | G183V | 0.01 |
| 183 | G183F | 0.19 |
| 183 | G183H | 0.95 |
| 183 | G183D | 0.99 |
| 184 | S184T | 0.60 |
| 184 | S184H | 0.74 |
| 184 | S184G | 0.82 |
| 184 | S184P | 0.85 |
| 185 | V185W | 0.01 |
| 185 | V185H | 0.01 |
| 185 | V185G | 0.01 |
| 185 | V185D | 0.01 |
| 185 | V185S | 0.53 |
| 185 | V185Y | 0.58 |
| 185 | V185I | 0.63 |
| 185 | V185R | 0.79 |
| 185 | V185K | 0.79 |
| 185 | V185C | 0.83 |
| 185 | V185E | 0.88 |
| 185 | V185T | 0.91 |
| 185 | V185L | 0.93 |
| 186 | I186G | 0.01 |
| 186 | I186S | 0.01 |
| 186 | I186R | 0.01 |
| 186 | I186P | 0.01 |
| 186 | I186T | 0.23 |
| 186 | I186V | 0.48 |
| 186 | I186F | 0.76 |
| 187 | S187P | 0.01 |
| 187 | S187T | 0.23 |
| 187 | S187Q | 0.35 |
| 187 | S187W | 0.52 |
| 187 | S187R | 0.55 |
| 187 | S187V | 0.58 |
| 187 | S187F | 0.65 |
| 187 | S187Y | 0.80 |
| 188 | T188H | 0.01 |
| 188 | T188R | 0.01 |
| 188 | T188F | 0.01 |
| 188 | T188Y | 0.09 |
| 188 | T188I | 0.10 |
| 188 | T188V | 0.15 |
| 188 | T188L | 0.42 |
| 188 | T188M | 0.75 |
| 188 | T188G | 0.79 |
| 188 | T188C | 0.87 |
| 188 | T188S | 0.91 |
| 188 | T188A | 0.95 |
| 189 | D189F | 0.37 |
| 189 | D189R | 0.39 |
| 189 | D189N | 0.57 |
| 189 | D189V | 0.71 |
| 189 | D189W | 0.76 |
| 189 | D189E | 0.77 |
| 189 | D189G | 0.80 |
| 189 | D189S | 0.81 |
| 189 | D189M | 0.88 |
| 189 | D189C | 0.94 |
| 189 | D189H | 0.95 |
| 189 | D189P | 0.97 |
| 190 | G190V | 0.01 |
| 190 | G190S | 0.01 |
| 190 | G190Q | 0.29 |
| 190 | G190W | 0.41 |
| 190 | G190R | 0.51 |
| 190 | G190K | 0.57 |
| 190 | G190L | 0.82 |
| 191 | V191H | 0.01 |
| 191 | V191W | 0.01 |
| 191 | V191S | 0.01 |
| 191 | V191G | 0.01 |
| 191 | V191N | 0.01 |
| 191 | V191I | 0.02 |
| 192 | D192S | 0.01 |
| 192 | D192P | 0.01 |
| 192 | D192F | 0.01 |
| 192 | D192H | 0.01 |
| 192 | D192I | 0.01 |
| 192 | D192Q | 0.01 |
| 192 | D192R | 0.01 |
| 192 | D192T | 0.01 |
| 192 | D192V | 0.01 |
| 192 | D192W | 0.01 |
| 192 | D192N | 0.15 |
| 192 | D192C | 0.56 |
| 193 | G193H | 0.01 |
| 193 | G193C | 0.01 |
| 193 | G193T | 0.01 |
| 193 | G193N | 0.01 |
| 194 | I194S | 0.01 |
| 194 | I194A | 0.01 |
| 194 | I194C | 0.01 |
| 194 | I194P | 0.01 |
| 194 | I194F | 0.01 |
| 194 | I194W | 0.01 |
| 194 | I194R | 0.01 |
| 194 | I194Y | 0.01 |
| 194 | I194G | 0.04 |
| 194 | I194L | 0.58 |
| 194 | I194V | 0.78 |
| 195 | H195S | 0.08 |
| 195 | H195C | 0.10 |
| 195 | H195L | 0.18 |
| 195 | H195N | 0.22 |
| 195 | H195R | 0.24 |
| 195 | H195F | 0.40 |
| 195 | H195V | 0.60 |
| 195 | H195Q | 0.96 |
| 195 | H195A | 0.98 |
| 196 | F196H | 0.01 |
| 196 | F196G | 0.01 |
| 196 | F196S | 0.01 |
| 196 | F196Q | 0.01 |
| 196 | F196W | 0.38 |
| 196 | F196P | 0.39 |
| 196 | F196V | 0.68 |
| 196 | F196M | 0.71 |
| 196 | F196Y | 0.97 |
| 197 | T197R | 0.01 |
| 197 | T197L | 0.65 |
| 197 | T197S | 0.75 |
| 197 | T197G | 0.81 |
| 197 | T197I | 0.84 |
| 197 | T197C | 0.86 |
| 197 | T197V | 0.89 |
| 197 | T197N | 0.91 |
| 199 | A199M | 0.93 |
| 199 | A199S | 0.99 |
| 199 | A199G | 0.99 |
| 201 | N201Y | 0.01 |
| 201 | N201T | 0.01 |
| 201 | N201V | 0.01 |
| 201 | N201R | 0.01 |
| 201 | N201S | 0.06 |
| 201 | N201H | 0.10 |
| 201 | N201G | 0.30 |
| 201 | N201L | 0.35 |
| 201 | N201F | 0.67 |
| 201 | N201E | 0.72 |
| 203 | D203V | 0.50 |
| 203 | D203W | 0.52 |
| 203 | D203E | 0.90 |

The following Table provides variants that have protein performance indices ("Prot. PI") better than wild-type.

TABLE 10-8

Sites with Protein PI Values Better Than Wild-Type

| Pos | WT/Pos./Var.Prot. | PI |
|---|---|---|
| 2 | A002Y | 1.61 |
| 2 | A002N | 1.30 |
| 2 | A002I | 1.25 |
| 2 | A002V | 1.18 |
| 2 | A002T | 1.17 |
| 2 | A002S | 1.15 |
| 5 | I005M | 1.29 |
| 7 | C007A | 1.22 |
| 7 | C007G | 1.07 |
| 7 | C007M | 1.03 |
| 8 | F008N | 1.23 |
| 8 | F008M | 1.05 |
| 8 | F008G | 1.03 |
| 8 | F008P | 1.01 |
| 11 | S011H | 1.06 |
| 11 | S011A | 1.04 |
| 11 | S011D | 1.03 |
| 11 | S011E | 1.01 |
| 11 | S011Q | 1.01 |
| 12 | L012N | 1.06 |
| 12 | L012Q | 1.05 |
| 13 | T013V | 1.17 |
| 14 | W014Y | 1.02 |
| 16 | W016Y | 1.02 |
| 17 | V017A | 1.21 |
| 17 | V017E | 1.11 |
| 17 | V017F | 1.09 |
| 17 | V017I | 1.08 |
| 17 | V017K | 1.06 |
| 17 | V017T | 1.03 |
| 18 | P018C | 2.56 |
| 18 | P018H | 2.50 |
| 18 | P018L | 2.50 |
| 18 | P018E | 2.47 |
| 18 | P018G | 2.47 |
| 18 | P018N | 2.35 |
| 18 | P018V | 2.30 |
| 18 | P018Q | 2.13 |
| 18 | P018R | 2.01 |
| 18 | P018Y | 1.68 |
| 18 | P018S | 1.05 |
| 19 | V019G | 1.39 |
| 19 | V019A | 1.23 |
| 19 | V019E | 1.10 |
| 19 | V019Q | 1.07 |
| 19 | V019K | 1.03 |
| 19 | V019M | 1.00 |
| 20 | E020G | 1.11 |
| 20 | E020P | 1.08 |
| 20 | E020A | 1.08 |
| 20 | E020N | 1.01 |
| 20 | E020V | 1.01 |
| 22 | G022A | 1.07 |
| 22 | G022I | 1.03 |
| 23 | A023F | 1.03 |
| 24 | P024T | 1.43 |
| 24 | P024G | 1.34 |
| 24 | P024S | 1.31 |
| 24 | P024H | 1.15 |
| 24 | P024I | 1.11 |
| 24 | P024L | 1.06 |
| 25 | T025C | 1.37 |
| 25 | T025V | 1.30 |
| 25 | T025G | 1.27 |
| 25 | T025A | 1.23 |
| 25 | T025I | 1.19 |
| 25 | T025P | 1.10 |
| 25 | T025M | 1.04 |
| 29 | A029G | 1.22 |
| 29 | A029P | 1.07 |
| 29 | A029M | 1.06 |
| 29 | A029D | 1.06 |
| 29 | A029V | 1.05 |
| 29 | A029S | 1.05 |
| 29 | A029T | 1.02 |
| 29 | A029E | 1.02 |
| 30 | P030E | 1.20 |
| 30 | P030A | 1.15 |
| 30 | P030S | 1.12 |
| 30 | P030L | 1.07 |
| 30 | P030Q | 1.06 |
| 30 | P030K | 1.06 |
| 30 | P030H | 1.05 |
| 30 | P030Y | 1.04 |
| 32 | V032M | 1.11 |
| 32 | V032A | 1.10 |
| 32 | V032I | 1.08 |
| 32 | V032Q | 1.03 |
| 32 | V032L | 1.01 |
| 35 | T035C | 1.16 |
| 36 | G036C | 1.09 |
| 36 | G036N | 1.08 |
| 36 | G036Q | 1.07 |
| 36 | G036S | 1.06 |
| 36 | G036A | 1.00 |
| 37 | V037N | 1.09 |
| 39 | A039V | 1.18 |
| 39 | A039E | 1.03 |
| 46 | F046A | 1.05 |
| 46 | F046C | 1.01 |
| 47 | E047I | 1.02 |
| 54 | S054A | 1.33 |
| 54 | S054C | 1.21 |
| 54 | S054E | 1.16 |
| 54 | S054D | 1.08 |
| 54 | S054H | 1.06 |
| 54 | S054N | 1.01 |
| 54 | S054M | 1.01 |
| 55 | A055N | 1.12 |
| 55 | A055S | 1.08 |
| 56 | R056Q | 1.02 |
| 58 | T058V | 1.13 |
| 60 | I060A | 1.20 |
| 60 | I060M | 1.14 |
| 60 | I060V | 1.06 |
| 60 | I060L | 1.02 |
| 61 | D061A | 1.41 |
| 61 | D061N | 1.12 |
| 61 | D061V | 1.10 |
| 61 | D061Y | 1.03 |
| 61 | D061Q | 1.02 |
| 61 | D061L | 1.00 |
| 62 | D062A | 1.06 |
| 62 | D062M | 1.06 |
| 63 | P063S | 1.17 |
| 63 | P063Y | 1.12 |
| 63 | P063M | 1.09 |
| 63 | P063Q | 1.08 |
| 63 | P063A | 1.06 |
| 63 | P063V | 1.06 |
| 63 | P063R | 1.02 |
| 63 | P063T | 1.02 |
| 64 | T064Q | 1.13 |
| 64 | T064M | 1.07 |
| 64 | T064R | 1.05 |
| 64 | T064C | 1.05 |
| 64 | T064S | 1.03 |
| 66 | P066Q | 1.91 |
| 66 | P066G | 1.78 |
| 66 | P066N | 1.62 |
| 66 | P066C | 1.51 |
| 66 | P066I | 1.51 |
| 66 | P066R | 1.26 |
| 66 | P066H | 1.23 |
| 66 | P066V | 1.12 |
| 66 | P066Y | 1.08 |
| 66 | P066A | 1.03 |
| 66 | P066F | 1.02 |
| 67 | R067Q | 1.60 |
| 67 | R067L | 1.46 |

TABLE 10-8-continued

Sites with Protein PI Values Better Than Wild-Type

| Pos | WT/Pos./Var.Prot. | PI |
|---|---|---|
| 67 | R067A | 1.39 |
| 67 | R067V | 1.24 |
| 67 | R067P | 1.04 |
| 67 | R067F | 1.01 |
| 68 | L068A | 1.07 |
| 68 | L068V | 1.01 |
| 68 | L068G | 1.00 |
| 69 | N069C | 1.18 |
| 69 | N069G | 1.06 |
| 69 | N069D | 1.05 |
| 69 | N069S | 1.03 |
| 70 | G070A | 1.08 |
| 72 | S072L | 1.07 |
| 72 | S072A | 1.06 |
| 72 | S072Y | 1.03 |
| 73 | Y073N | 1.25 |
| 73 | Y073Q | 1.20 |
| 73 | Y073C | 1.18 |
| 73 | Y073D | 1.09 |
| 73 | Y073V | 1.08 |
| 73 | Y073M | 1.05 |
| 73 | Y073L | 1.03 |
| 74 | L074I | 1.45 |
| 74 | L074Y | 1.19 |
| 74 | L074V | 1.18 |
| 74 | L074A | 1.01 |
| 75 | P075M | 1.22 |
| 75 | P075S | 1.18 |
| 75 | P075T | 1.10 |
| 75 | P075Y | 1.08 |
| 75 | P075C | 1.06 |
| 75 | P075Q | 1.04 |
| 75 | P075L | 1.02 |
| 75 | P075E | 1.00 |
| 76 | S076W | 1.06 |
| 77 | C077L | 1.44 |
| 77 | C077V | 1.33 |
| 77 | C077A | 1.20 |
| 77 | C077S | 1.19 |
| 77 | C077T | 1.18 |
| 78 | L078I | 1.06 |
| 78 | L078V | 1.04 |
| 79 | A079C | 1.16 |
| 79 | A079E | 1.12 |
| 79 | A079S | 1.09 |
| 79 | A079Q | 1.05 |
| 79 | A079M | 1.04 |
| 79 | A079R | 1.02 |
| 80 | T080S | 1.12 |
| 80 | T080E | 1.02 |
| 80 | T080Q | 1.02 |
| 82 | L082G | 1.24 |
| 82 | L082R | 1.15 |
| 82 | L082V | 1.14 |
| 82 | L082S | 1.13 |
| 82 | L082P | 1.11 |
| 82 | L082M | 1.07 |
| 82 | L082K | 1.03 |
| 82 | L082A | 1.00 |
| 83 | P083G | 1.01 |
| 84 | L084V | 1.23 |
| 86 | L086Q | 3.66 |
| 89 | I089V | 1.09 |
| 89 | I089L | 1.07 |
| 93 | T093Q | 2.03 |
| 96 | T096A | 1.32 |
| 96 | T096V | 1.12 |
| 96 | T096S | 1.05 |
| 96 | T096G | 1.03 |
| 97 | K097A | 1.11 |
| 97 | K097R | 1.02 |
| 98 | A098S | 1.17 |
| 98 | A098T | 1.03 |
| 98 | A098N | 1.01 |
| 99 | Y099S | 1.45 |
| 99 | Y099L | 1.39 |
| 99 | Y099H | 1.30 |
| 99 | Y099A | 1.29 |
| 99 | Y099V | 1.28 |
| 99 | Y099G | 1.23 |
| 99 | Y099W | 1.20 |
| 99 | Y099I | 1.11 |
| 100 | F100M | 1.20 |
| 100 | F100N | 1.12 |
| 100 | F100W | 1.06 |
| 100 | F100S | 1.02 |
| 101 | R101L | 1.33 |
| 101 | R101N | 1.11 |
| 101 | R101Q | 1.03 |
| 101 | R101D | 1.02 |
| 102 | R102Q | 1.09 |
| 103 | T103G | 1.20 |
| 103 | T103S | 1.14 |
| 103 | T103H | 1.14 |
| 103 | T103N | 1.07 |
| 103 | T103K | 1.05 |
| 103 | T103P | 1.01 |
| 104 | P104S | 1.44 |
| 104 | P104V | 1.40 |
| 104 | P104E | 1.37 |
| 104 | P104C | 1.34 |
| 104 | P104N | 1.32 |
| 104 | P104T | 1.29 |
| 104 | P104G | 1.25 |
| 104 | P104Q | 1.24 |
| 104 | P104H | 1.11 |
| 104 | P104I | 1.07 |
| 104 | P104M | 1.01 |
| 105 | L105Y | 1.18 |
| 105 | L105H | 1.07 |
| 105 | L105G | 1.07 |
| 105 | L105C | 1.05 |
| 105 | L105Q | 1.03 |
| 105 | L105T | 1.00 |
| 105 | L105P | 1.00 |
| 106 | D106E | 1.02 |
| 107 | I107S | 1.05 |
| 107 | I107V | 1.04 |
| 107 | I107C | 1.00 |
| 108 | A108G | 1.15 |
| 108 | A108S | 1.14 |
| 108 | A108T | 1.08 |
| 109 | L109E | 1.24 |
| 109 | L109I | 1.21 |
| 109 | L109D | 1.15 |
| 109 | L109N | 1.13 |
| 109 | L109F | 1.11 |
| 109 | L109Q | 1.08 |
| 109 | L109A | 1.07 |
| 109 | L109H | 1.06 |
| 109 | L109V | 1.06 |
| 109 | L109M | 1.00 |
| 110 | G110S | 1.01 |
| 112 | S112N | 1.09 |
| 112 | S112E | 1.05 |
| 113 | V113C | 1.06 |
| 113 | V113N | 1.01 |
| 114 | L114C | 1.10 |
| 114 | L114A | 1.03 |
| 114 | L114M | 1.00 |
| 115 | V115I | 1.14 |
| 115 | V115C | 1.14 |
| 115 | V115A | 1.11 |
| 115 | V115M | 1.05 |
| 115 | V115L | 1.02 |
| 116 | T116N | 1.68 |
| 116 | T116H | 1.48 |
| 116 | T116G | 1.44 |
| 116 | T116C | 1.30 |
| 116 | T116E | 1.29 |

TABLE 10-8-continued

Sites with Protein PI Values Better Than Wild-Type

| Pos | WT/Pos./Var.Prot. | PI |
|---|---|---|
| 116 | T116Q | 1.29 |
| 116 | T116M | 1.28 |
| 116 | T116S | 1.24 |
| 116 | T116Y | 1.09 |
| 116 | T116A | 1.08 |
| 116 | T116R | 1.03 |
| 116 | T116L | 1.03 |
| 117 | Q117S | 1.13 |
| 117 | Q117H | 1.12 |
| 117 | Q117E | 1.10 |
| 117 | Q117T | 1.06 |
| 117 | Q117A | 1.03 |
| 118 | V118C | 1.28 |
| 118 | V118A | 1.20 |
| 118 | V118I | 1.01 |
| 119 | L119C | 1.18 |
| 119 | L119A | 1.18 |
| 119 | L119N | 1.14 |
| 119 | L119I | 1.06 |
| 119 | L119S | 1.05 |
| 119 | L119V | 1.04 |
| 119 | L119E | 1.04 |
| 119 | L119R | 1.00 |
| 120 | T120S | 1.35 |
| 120 | T120E | 1.19 |
| 120 | T120C | 1.14 |
| 120 | T120K | 1.12 |
| 120 | T120N | 1.10 |
| 120 | T120A | 1.09 |
| 120 | T120H | 1.07 |
| 120 | T120Q | 1.05 |
| 120 | T120Y | 1.01 |
| 120 | T120L | 1.00 |
| 121 | S121N | 1.17 |
| 121 | S121L | 1.12 |
| 121 | S121A | 1.10 |
| 121 | S121C | 1.09 |
| 121 | S121G | 1.07 |
| 121 | S121R | 1.06 |
| 121 | S121K | 1.04 |
| 121 | S121E | 1.01 |
| 121 | S121Q | 1.01 |
| 122 | A122N | 1.11 |
| 122 | A122L | 1.07 |
| 122 | A122P | 1.07 |
| 122 | A122M | 1.06 |
| 122 | A122V | 1.05 |
| 122 | A122S | 1.05 |
| 122 | A122E | 1.04 |
| 122 | A122I | 1.04 |
| 122 | A122Q | 1.02 |
| 124 | G124M | 1.36 |
| 124 | G124A | 1.20 |
| 124 | G124N | 1.18 |
| 124 | G124C | 1.07 |
| 124 | G124Q | 1.02 |
| 125 | V125I | 1.05 |
| 126 | G126N | 1.04 |
| 126 | G126E | 1.02 |
| 126 | G126A | 1.02 |
| 127 | T127A | 1.10 |
| 127 | T127S | 1.08 |
| 127 | T127V | 1.06 |
| 127 | T127C | 1.04 |
| 127 | T127G | 1.04 |
| 127 | T127D | 1.03 |
| 127 | T127E | 1.03 |
| 127 | T127M | 1.02 |
| 128 | T128N | 1.29 |
| 128 | T128M | 1.28 |
| 128 | T128Q | 1.24 |
| 128 | T128A | 1.23 |
| 128 | T128H | 1.19 |
| 128 | T128P | 1.18 |
| 128 | T128D | 1.14 |
| 128 | T128K | 1.10 |
| 128 | T128S | 1.07 |
| 128 | T128V | 1.05 |
| 128 | T128R | 1.03 |
| 128 | T128F | 1.01 |
| 129 | Y129F | 1.44 |
| 129 | Y129C | 1.42 |
| 129 | Y129A | 1.39 |
| 129 | Y129D | 1.35 |
| 129 | Y129M | 1.28 |
| 129 | Y129N | 1.24 |
| 129 | Y129L | 1.22 |
| 129 | Y129P | 1.11 |
| 129 | Y129G | 1.10 |
| 129 | Y129S | 1.08 |
| 129 | Y129W | 1.01 |
| 129 | Y129V | 1.00 |
| 130 | P130G | 1.11 |
| 130 | P130E | 1.08 |
| 130 | P130K | 1.05 |
| 130 | P130A | 1.03 |
| 130 | P130M | 1.03 |
| 133 | K133Q | 1.13 |
| 133 | K133S | 1.02 |
| 133 | K133A | 1.01 |
| 133 | K133R | 1.01 |
| 133 | K133E | 1.01 |
| 135 | L135M | 1.01 |
| 136 | V136L | 1.03 |
| 138 | S138A | 1.44 |
| 138 | S138C | 1.17 |
| 138 | S138G | 1.09 |
| 141 | P141A | 1.13 |
| 141 | P141G | 1.02 |
| 142 | L142I | 1.05 |
| 143 | A143G | 1.17 |
| 145 | M145I | 1.16 |
| 145 | M145L | 1.07 |
| 147 | H147L | 1.09 |
| 147 | H147C | 1.04 |
| 149 | W149G | 1.39 |
| 149 | W149A | 1.35 |
| 149 | W149M | 1.32 |
| 149 | W149S | 1.28 |
| 149 | W149F | 1.27 |
| 149 | W149Y | 1.15 |
| 149 | W149Q | 1.10 |
| 149 | W149L | 1.06 |
| 150 | F150A | 1.70 |
| 150 | F150M | 1.69 |
| 150 | F150N | 1.52 |
| 150 | F150C | 1.41 |
| 150 | F150P | 1.38 |
| 150 | F150K | 1.33 |
| 150 | F150E | 1.32 |
| 150 | F150T | 1.27 |
| 150 | F150V | 1.26 |
| 150 | F150W | 1.26 |
| 150 | F150Y | 1.24 |
| 150 | F150I | 1.19 |
| 150 | F150L | 1.14 |
| 150 | F150G | 1.13 |
| 150 | F150H | 1.09 |
| 151 | Q151K | 1.04 |
| 153 | I153N | 1.04 |
| 157 | G157A | 1.00 |
| 159 | Q159E | 1.14 |
| 159 | Q159A | 1.13 |
| 159 | Q159G | 1.03 |
| 161 | T161C | 1.01 |
| 162 | T162C | 1.17 |
| 162 | T162I | 1.16 |
| 162 | T162H | 1.08 |
| 162 | T162L | 1.05 |
| 162 | T162F | 1.05 |

TABLE 10-8-continued

Sites with Protein
PI Values Better Than Wild-Type

| Pos | WT/Pos./Var.Prot. | PI |
|---|---|---|
| 162 | T162Y | 1.03 |
| 164 | L164M | 1.09 |
| 164 | L164V | 1.08 |
| 165 | A165G | 1.14 |
| 165 | A165Q | 1.05 |
| 165 | A165S | 1.05 |
| 166 | R166M | 1.26 |
| 166 | R166K | 1.19 |
| 166 | R166G | 1.19 |
| 166 | R166N | 1.16 |
| 166 | R166D | 1.16 |
| 166 | R166A | 1.12 |
| 166 | R166L | 1.08 |
| 166 | R166T | 1.04 |
| 167 | V167L | 1.13 |
| 167 | V167H | 1.12 |
| 167 | V167G | 1.08 |
| 167 | V167M | 1.04 |
| 167 | V167I | 1.04 |
| 167 | V167S | 1.04 |
| 167 | V167C | 1.01 |
| 168 | Y168F | 1.28 |
| 168 | Y168L | 1.27 |
| 170 | A170C | 1.02 |
| 171 | L171I | 1.16 |
| 172 | A172C | 1.09 |
| 172 | A172G | 1.07 |
| 175 | M175Y | 1.35 |
| 175 | M175L | 1.19 |
| 175 | M175W | 1.14 |
| 175 | M175N | 1.11 |
| 175 | M175R | 1.02 |
| 176 | K176R | 1.06 |
| 176 | K176Q | 1.02 |
| 178 | P178E | 1.05 |
| 182 | A182C | 1.03 |
| 183 | G183S | 1.08 |
| 184 | S184E | 1.39 |
| 184 | S184A | 1.31 |
| 184 | S184M | 1.25 |
| 184 | S184G | 1.15 |
| 184 | S184D | 1.15 |
| 184 | S184C | 1.14 |
| 184 | S184Q | 1.09 |
| 184 | S184H | 1.07 |
| 184 | S184N | 1.03 |
| 184 | S184V | 1.03 |
| 184 | S184K | 1.02 |
| 185 | V185I | 1.03 |
| 186 | I186M | 1.11 |
| 188 | T188C | 2.04 |
| 188 | T188I | 1.85 |
| 188 | T188L | 1.76 |
| 188 | T188M | 1.60 |
| 188 | T188V | 1.53 |
| 188 | T188S | 1.52 |
| 188 | T188R | 1.41 |
| 188 | T188A | 1.40 |
| 188 | T188G | 1.32 |
| 188 | T188N | 1.24 |
| 191 | V191C | 1.04 |
| 194 | I194L | 1.32 |
| 194 | I194C | 1.17 |
| 194 | I194A | 1.15 |
| 194 | I194W | 1.12 |
| 194 | I194V | 1.03 |
| 194 | I194Y | 1.01 |
| 196 | F196L | 1.09 |
| 201 | N201H | 1.49 |

The following Table provides variants that have a PAD PI that is greater than 1.5, a PAF that is greater than or equal to 0.1, and a protein PI that is greater than or equal to 0.1

TABLE 10-9

PAD PI > 1.5
with PAF ≥ 0.1 and
protein PI ≥ 0.1

| Wild-Type Amino Acid/Pos. | Variant Amino Acid |
|---|---|
| M1 | L |
| K3 | A, C, H, I, L |
| R4 | A |
| I5 | A, C, E, L |
| L6 | A |
| C7 | K |
| T13 | A, C |
| P18 | C, E, G, H, L, Q, R, V, Y |
| E20 | C, Q |
| D21 | A, G, K, L, Y |
| G22 | A |
| P24 | L |
| E26 | L |
| R27 | A, K, L |
| F28 | D, L |
| P30 | T, V |
| D31 | L, N |
| V32 | A, D, E, G, I, K, L, M, N, Q, W |
| R33 | C, G, K, L |
| T35 | A, C, I, M |
| G36 | K |
| Q40 | D, G, K, S, T, W, Y |
| Q41 | A, K, L |
| G43 | E, L |
| A44 | C |
| F46 | L |
| V48 | A, C, L, M, P |
| I49 | A |
| E51 | A |
| L53 | H |
| N59 | A, C, D, E, F, G, K, L, Q, S, T, V, W, Y |
| D61 | I, K, R |
| N69 | H, I, K, V |
| S72 | A, C, G, H, M, N |
| P75 | D, G, K, S, T, W, Y |
| S76 | D, E, G, M |
| T80 | G |
| H81 | M |
| P83 | A, M |
| D85 | F, G |
| L86 | C |
| V87 | C, L |
| I89 | A |
| T96 | A, C, L, M |
| A98 | D |
| F100 | A, M |
| R102 | A, L |
| P104 | C, E, I, M |
| L105 | C, F, W |
| D106 | V |
| I107 | T |
| G110 | E, L |
| V115 | G |
| Q117 | A, M |
| V118 | Q |
| T120 | E, I, Y |
| S121 | A, C, V |
| T128 | F, K, L, R, Y |
| P132 | A, C, E, G, L, Q, S, Y |
| K133 | L |
| V134 | A, M |
| V136 | A |
| P140 | A |

TABLE 10-9-continued

PAD PI > 1.5 with PAF ≥ 0.1 and protein PI ≥ 0.1

| Wild-Type Amino Acid/Pos. | Variant Amino Acid |
|---|---|
| P144 | H, Y |
| P146 | C, F, H, L |
| P148 | F |
| Q151 | A, C, D, E, H, K, P, R, S, T, Y |
| L152 | W |
| I153 | F, H, K, P, S, T |
| F154 | Y |
| E155 | A, L, M, N, P, Y |
| G156 | D, M, T |
| G157 | H |
| E158 | F, K, L, M, N, Y |
| T161 | M, Q |
| T162 | C, F, G, H, I, K, L, M, N, P, Q, S, W, Y |
| E163 | A, L, Y |
| A165 | D, L, M |
| R166 | A, D, H, L |
| V167 | A, C, D, G, H, L, M, P, Q, R, S, T, Y |
| Y168 | F, L |
| S169 | I |
| L171 | A, C, F, K, M, N, Q, S |
| S173 | A, C, E, F, I, K, L, M, P, R, V, W, Y |
| F174 | A, L, M, Y |
| P178 | A, D, E, G, K, L, M, Q, S, T, V, Y |
| F179 | L |
| G190 | A, H, M |
| V191 | A, C, D, E, F, K, L, M, Q, R, Y |
| G193 | S, V |
| T197 | M |
| E198 | C, L, M, N, P, R, W, Y |
| A199 | C, K, L, Y |
| R202 | A, C, E, F, G, H, I, L, M, S, T, W |
| D203 | A, C, H, L, R |
| G205 | A |
| V206 | C, E, F, G, H, K, L, M, N, P, R |
| A209 | E, L |
| E210 | D, K |
| Q211 | M, N, P |
| S214 | A, C, D, F, G, I, K, L, R, T, V, W, |
| L215 | E, M, T, V, Y |

The following Table provides variants with a PAD PI that is less than 0.5, a PAF that is greater than or equal to 0.1, and a protein PI that is greater than or equal to 0.1.

TABLE 10-10

PAD PI < 0.5 with PAF ≥ 0.1, and Protein PI ≥ 0.1

| Wild-Type Residue/Pos. | Amino Acid Variant(s) |
|---|---|
| A2 | Y |
| R4 | I, L, V |
| I5 | S |
| L6 | S, T, V |
| F8 | R |
| D10 | G |
| L12 | A, C, F, G, K, Q, R, S, T, V |
| W14 | F, G, I, K, L, R, S, T, V |
| G15 | C, N |
| P18 | S |
| V19 | M, Q, R |
| G22 | K, W |
| A23 | G, R, S, |
| T25 | G, H, I, K, L, M, P, R, W |
| E26 | N, S, T, W |
| R27 | P, T, W |
| F28 | G |
| A29 | T, V |
| T35 | N, Q, V |
| G36 | S, T |
| L38 | G, S |
| Q41 | S, V |
| L42 | Q, S, T |
| G43 | P, Q, S, V |
| D45 | R, S, T |
| F46 | T |
| E47 | P |
| V48 | S |
| I49 | P, R |
| E50 | V |
| E51 | I, V |
| G52 | H, L, S, V |
| L53 | E, G, K, R, S |
| S54 | F, G, I, K, L, R, T, V, W, Y |
| A55 | I, R, T, V |
| R56 | C, G, S, T |
| T57 | C, N |
| T58 | A, M |
| N59 | M, R |
| I60 | P |
| D62 | C, G, H, I, L, R, S, T, V, W |
| T64 | R |
| D65 | H, R, S, V, Y |
| P66 | G, N, Q |
| R67 | E, F, G, L, N, P, Q, T, V, W |
| L68 | A, C, E, F, G, H, M, N, P, Q, R, S, T, Y |
| N69 | Y |
| G70 | C, T |
| S72 | W, Y |
| Y73 | L, R |
| P75 | M, R, R, S, W |
| S76 | F, W, Y |
| C77 | F, W, Y |
| L78 | M |
| A79 | C, E, H, M, N, Q, R |
| T80 | H, I, K, L, W, Y |
| H81 | R, Y |
| L82 | G, H, R, S, T, V, W |
| P83 | T, V |
| L84 | A, T, V, W |
| D85 | I, L, V, W |
| L86 | H, S, T, V, W |
| V87 | A, F, G, S, T, Y |
| I88 | T, V |
| I89 | S |
| M90 | S, T, V |

TABLE 10-10-continued

PAD PI < 0.5 with
PAF ≥ 0.1, and Protein PI ≥ 0.1

| Wild-Type Residue/Pos. | Amino Acid Variant(s) |
|---|---|
| L91 | T, V |
| T93 | S, Y |
| N94 | H, L, T, V |
| T96 | I, R, W, Y |
| K97 | G, I, L, P, Q, S, T, V, Y |
| A98 | T |
| Y99 | S, V |
| F100 | E, K, W |
| R101 | K, Q, V, W |
| R102 | C, G |
| T103 | A, C, F, G, H, I, K, L, N, P, R, S, V, W, Y |
| P104 | R, T |
| L105 | V |
| I107 | P, Q |
| L109 | A, D, E, F, H, I, O, |
| G110 | Q, S, T |
| M111 | G, H, R, S |
| S112 | H, R, V, Y |
| L114 | Q |
| T116 | Y |
| V118 | P, R, W |
| L119 | C, D, E, F, G, H, I, N, R, S, T, V, W |
| T120 | H |
| S121 | P |
| A122 | D, E, F, G, H, K, R, S |
| G123 | C |
| G124 | A, H, I, M, Q, R, T, V, W |
| V125 | E, R, W |
| G126 | I, V, Y |
| T127 | E, I, L, Q |
| Y129 | A, D, G, K, L, M, R, T, V, W |
| P130 | A, E, F, G, H, I, L, S, T, V, W |
| A131 | D, W, Y |
| P132 | F, H, I, T, V |
| K133 | A, C, G, H, I, M, T, V |
| L135 | F, Q, S, T, V |
| V137 | S |
| S138 | I |
| P139 | S |
| P140 | S |
| P141 | G, I, Q, R, S, T, V |
| L142 | Q, S, V |
| A143 | G, P, W |
| M145 | E, G, W |
| W149 | A, C, F, G, I, M, Q, S, T |
| F150 | G, N, P, W |
| E155 | F, R, V |
| G156 | I |
| G157 | R, S, V |
| Q159 | A, C, P |
| K160 | G |
| T161 | G, H, R, W |
| E163 | F, R |
| Y168 | C, I, V |
| A170 | I, S |
| A172 | Q, V |
| F174 | C, Q, W |
| F179 | Q, S |
| G190 | S, V, W |
| V191 | G, H, I, N, S, W |
| G193 | C, H, T |
| I194 | A, C, G, S |
| F196 | G, Q, W |
| T197 | R |
| N201 | G, H, L, R, S, T, V, Y |
| D203 | V |
| L208 | Q, S, V, Y |
| V212 | G |
| L215 | A, C, G, K, P, R |
| L216 | G, I, T |

In addition to the assay results described above, various mutations were found to result in unstable protein such that perhydrolase protein was not expressed. Thus, in contrast to the substitutions that resulted in enhanced expression as compared to wild-type, there were some substitutions that are not as favorable, at least under the conditions used herein. However, it is not intended that the present invention exclude these substitutions, as it is contemplated that these substitutions, taken alone or in combination will find use in alternative embodiments of the present invention.

TABLE 10-11

Mutations that Produced Unstable Protein

| Wild-Type/Pos. | Variant Amino Acid |
|---|---|
| M1 | A, E, F, G, K, N, P, R, S, T, W |
| I5 | W |
| C7 | L, P, T, W |
| G9 | A, C, E, K, L, P, Q, R, V |
| T13 | F, R, W |
| G15 | H, K, L, R, Y |
| P18 | A |
| D21 | V |
| F28 | H, I, R |
| R33 | D, E, H, P, W |
| W34 | K |
| T35 | K, L, P, W, Y |
| G36 | P |
| V37 | Q, R |
| L38 | W |
| A39 | F |
| L42 | D |
| A44 | D, H, P |
| F46 | H |
| V48 | W |
| E51 | P |
| R56 | H, K, P, W, Y |
| T57 | W |
| T58 | E, G, K, P, R, W, Y |
| L74 | D, H, P, Q, R, T |
| C77 | N, P |
| L78 | A, P, R, S |
| A79 | V |
| L86 | F |
| I88 | R, Y |
| I89 | D, R |
| L91 | H, K, P, R, W, Y |
| G92 | A, D, L, M, P, R, T, W, Y |
| T93 | P, R, V, W |
| D95 | A, D, G, H, K, L, N, Q, R, S, T, V, W, Y |
| K97 | D |
| P104 | A, L |
| L105 | A, M |
| I107 | H, W |
| A108 | D, F, H, I, N, P, R |
| G110 | L |
| L114 | F, K, R, W, Y |
| V115 | H, K, |
| V134 | D, K, R, W, Y |
| V136 | R, W |

TABLE 10-11-continued

Mutations that Produced Unstable Protein

| Wild-Type/Pos. | Variant Amino Acid |
|---|---|
| V137 | D, E, F, P, R, W |
| S138 | E, F, H, L, M, Q, R, W, Y |
| P139 | L, W, Y |
| P140 | D, K, L, M |
| L142 | D, G, M, N, R, T |
| H147 | G |
| F154 | E, L, P, |
| T161 | D, E, P |
| Y168 | D, E, H, K, N, P, R, S, W |
| L171 | D |
| F179 | A, P, R |
| F180 | E |
| D181 | F, H, I, M, N |
| A182 | H, K, L, M, W, Y |
| I186 | K, W, Y |
| T188 | D, K, P, Q, W |
| F196 | A, K, N, R |

The following Table provides performance indices obtained in PAF and PAD assays for various variants, as well as the protein performance index.

TABLE 10-12

Performance Indices

| Wild-Type Res./Pos. | Mut. | PAF PI | PAD PI | Prot. PI |
|---|---|---|---|---|
| M1 | A | −0.12 | −0.12 | −0.01 |
| M1 | E | −0.12 | −0.12 | −0.01 |
| M1 | F | −0.12 | −0.12 | −0.01 |
| M1 | G | −0.12 | −0.12 | −0.01 |
| M1 | I | 0.96 | 1.19 | 0.31 |
| M1 | K | −0.12 | −0.12 | −0.01 |
| M1 | L | 0.75 | 2.11 | 0.30 |
| M1 | M | 1.00 | 1.00 | 1.00 |
| M1 | N | −0.12 | −0.12 | −0.01 |
| M1 | P | −0.12 | −0.12 | −0.01 |
| M1 | R | −0.12 | −0.12 | −0.01 |
| M1 | S | −0.12 | −0.12 | −0.01 |
| M1 | T | −0.12 | −0.12 | −0.01 |
| M1 | V | 0.87 | 0.94 | 0.52 |
| M1 | W | −0.12 | −0.12 | −0.01 |
| A2 | A | 1.00 | 1.00 | 1.00 |
| A2 | D | 1.30 | 1.05 | 0.77 |
| A2 | E | 0.61 | 1.38 | 0.52 |
| A2 | F | 1.24 | 0.93 | 0.89 |
| A2 | G | 1.15 | 0.84 | 0.95 |
| A2 | I | 1.18 | 0.61 | 1.25 |
| A2 | N | 0.93 | 0.59 | 1.30 |
| A2 | P | 0.52 | 1.17 | 0.68 |
| A2 | Q | 0.81 | 1.29 | 0.65 |
| A2 | R | 0.90 | 1.17 | 0.70 |
| A2 | S | 1.01 | 0.66 | 1.15 |
| A2 | T | 0.98 | 0.61 | 1.17 |
| A2 | V | 0.89 | 0.60 | 1.18 |
| A2 | W | 1.75 | 1.17 | 0.53 |
| A2 | Y | 0.84 | 0.46 | 1.61 |
| K3 | A | 0.86 | 2.14 | 0.48 |
| K3 | C | 0.81 | 1.52 | 0.67 |
| K3 | E | 0.12 | 3.51 | 0.11 |
| K3 | G | 0.72 | 3.74 | 0.08 |
| K3 | H | 1.01 | 1.89 | 0.30 |
| K3 | I | 1.05 | 2.44 | 0.16 |
| K3 | K | 1.00 | 1.00 | 1.00 |
| K3 | L | 1.04 | 1.84 | 0.50 |
| K3 | M | 0.85 | 1.44 | 0.71 |
| K3 | P | 0.80 | 1.45 | 0.59 |
| K3 | Q | 0.87 | 1.19 | 0.69 |
| K3 | R | 0.87 | 1.29 | 0.46 |
| K3 | S | 0.94 | 1.17 | 0.44 |
| K3 | T | 1.01 | 1.03 | 0.71 |
| K3 | V | 0.81 | 0.84 | 0.33 |
| K3 | Y | 1.06 | 1.39 | 0.86 |
| R4 | A | 0.41 | 1.64 | 0.29 |
| R4 | C | 0.71 | 1.34 | 0.35 |
| R4 | D | 0.27 | 1.18 | 0.32 |
| R4 | E | 0.32 | 0.97 | 0.25 |
| R4 | G | 0.79 | 0.79 | 0.41 |
| R4 | H | 0.92 | 0.99 | 0.59 |
| R4 | I | 0.24 | 0.15 | 0.18 |
| R4 | L | 0.21 | −0.03 | 0.18 |
| R4 | P | 0.14 | 1.44 | 0.13 |
| R4 | Q | 1.03 | 0.99 | 0.70 |
| R4 | R | 1.00 | 1.00 | 1.00 |
| R4 | S | 0.65 | 0.91 | 0.64 |
| R4 | T | 0.80 | 1.00 | 0.69 |
| R4 | V | 0.29 | 0.08 | 0.22 |
| R4 | W | 0.04 | 0.48 | 0.12 |
| R4 | Y | 0.63 | 0.98 | 0.39 |
| I5 | A | 0.60 | 1.88 | 0.62 |
| I5 | C | 0.44 | 2.47 | 0.54 |
| I5 | D | −0.13 | 3.11 | 0.06 |
| I5 | E | 0.67 | 1.59 | 0.33 |
| I5 | F | −0.13 | 0.15 | 0.06 |
| I5 | G | 0.05 | −3.88 | 0.10 |
| I5 | H | 0.55 | 0.63 | 0.18 |
| I5 | I | 1.00 | 1.00 | 1.00 |
| I5 | L | 0.80 | 1.63 | 0.96 |
| I5 | M | 0.63 | 1.09 | 1.29 |
| I5 | N | −0.13 | −2.15 | 0.12 |
| I5 | P | −0.13 | −0.86 | 0.08 |
| I5 | R | −0.13 | −6.48 | 0.08 |
| I5 | S | 1.02 | 0.37 | 0.39 |
| I5 | T | 1.12 | 0.72 | 0.25 |
| I5 | V | 0.94 | 0.92 | 0.54 |
| I5 | W | −0.13 | −0.44 | −0.01 |
| L6 | A | 0.87 | 1.99 | 0.26 |
| L6 | C | 0.85 | 1.22 | 0.55 |
| L6 | E | −0.20 | −0.59 | 0.09 |
| L6 | G | 0.23 | −3.45 | 0.12 |
| L6 | H | 0.23 | −1.08 | 0.09 |
| L6 | I | 1.07 | 0.82 | 0.86 |
| L6 | K | 0.41 | −1.16 | 0.05 |
| L6 | L | 1.00 | 1.00 | 1.00 |
| L6 | M | 0.92 | 1.44 | 0.63 |
| L6 | Q | −0.20 | −1.63 | 0.12 |
| L6 | R | 0.06 | −1.59 | 0.12 |
| L6 | S | 0.58 | −1.26 | 0.23 |
| L6 | T | 1.06 | 0.35 | 0.40 |
| L6 | V | 1.07 | 0.35 | 0.44 |
| L6 | W | 0.06 | −2.97 | 0.09 |
| C7 | A | 1.42 | 1.03 | 1.22 |
| C7 | C | 1.00 | 1.00 | 1.00 |
| C7 | E | −0.26 | 1.63 | 0.20 |
| C7 | G | 1.39 | 0.69 | 1.07 |
| C7 | H | 1.73 | 1.37 | 0.41 |
| C7 | I | 1.76 | 1.48 | 0.31 |
| C7 | K | 2.69 | 2.95 | 0.21 |
| C7 | L | −0.26 | −0.16 | −0.01 |
| C7 | M | 1.13 | 0.68 | 1.03 |
| C7 | P | −0.26 | −0.16 | −0.01 |
| C7 | R | 0.22 | −1.04 | 0.15 |
| C7 | S | 0.62 | −2.83 | 0.10 |
| C7 | T | −0.26 | −0.16 | −0.01 |
| C7 | W | −0.26 | −0.16 | −0.01 |
| C7 | Y | 2.09 | 0.54 | 0.67 |
| F8 | A | 0.55 | 1.33 | 0.96 |
| F8 | C | −0.11 | 4.01 | 0.10 |
| F8 | F | 1.00 | 1.00 | 1.00 |
| F8 | G | 1.09 | 0.65 | 1.03 |
| F8 | H | 1.02 | 0.64 | 0.97 |
| F8 | K | 0.81 | 0.83 | 0.95 |
| F8 | L | 0.77 | 1.31 | 0.90 |

TABLE 10-12-continued

Performance Indices

| Wild-Type Res./Pos. | Mut. | PAF PI | PAD PI | Prot. PI |
|---|---|---|---|---|
| F8 | M | 0.56 | 1.11 | 1.05 |
| F8 | N | −0.11 | 0.96 | 1.23 |
| F8 | P | 1.00 | 0.83 | 1.01 |
| F8 | R | 1.43 | 0.46 | 0.73 |
| F8 | S | 0.71 | −2.75 | 0.13 |
| F8 | T | 0.88 | 0.77 | 0.94 |
| F8 | V | 1.18 | 0.85 | 0.88 |
| F8 | Y | 0.96 | 0.90 | 0.85 |
| G9 | A | −0.15 | −0.18 | −0.01 |
| G9 | C | −0.15 | −0.18 | −0.01 |
| G9 | E | −0.15 | −0.18 | −0.01 |
| G9 | G | 1.00 | 1.00 | 1.00 |
| G9 | H | 0.29 | −0.06 | 0.16 |
| G9 | K | −0.15 | −0.18 | −0.01 |
| G9 | L | −0.15 | −0.18 | −0.01 |
| G9 | P | −0.15 | −0.18 | −0.01 |
| G9 | Q | −0.15 | −0.18 | −0.01 |
| G9 | R | −0.15 | −0.18 | −0.01 |
| G9 | T | 0.21 | −2.56 | 0.12 |
| G9 | V | −0.15 | −0.18 | −0.01 |
| D10 | A | −0.29 | −14.24 | 0.02 |
| D10 | D | 1.00 | 1.00 | 1.00 |
| D10 | E | 0.01 | 0.15 | 0.72 |
| D10 | G | 0.41 | −0.92 | 0.17 |
| D10 | I | 1.28 | −6.86 | 0.04 |
| D10 | K | 2.13 | −5.30 | 0.02 |
| D10 | L | 3.97 | 2.04 | 0.02 |
| D10 | M | −0.29 | −5.94 | 0.04 |
| D10 | N | −0.29 | −2.23 | 0.07 |
| D10 | P | −0.29 | −4.16 | 0.05 |
| D10 | R | 0.22 | −4.36 | 0.06 |
| D10 | S | 0.79 | −0.58 | 0.06 |
| D10 | T | 1.47 | −0.45 | 0.06 |
| D10 | V | 0.98 | −4.22 | 0.06 |
| D10 | W | 3.18 | −3.70 | 0.02 |
| D10 | Y | 1.51 | −4.97 | 0.03 |
| S11 | A | 0.25 | 0.53 | 1.04 |
| S11 | D | −0.25 | −0.22 | 1.03 |
| S11 | E | −0.25 | −0.23 | 1.01 |
| S11 | F | −0.25 | −0.13 | 0.68 |
| S11 | G | −0.25 | −0.09 | 0.86 |
| S11 | H | −0.25 | 0.33 | 1.06 |
| S11 | I | −0.25 | 0.56 | 0.63 |
| S11 | K | −0.25 | 0.40 | 0.62 |
| S11 | L | −0.25 | −0.22 | 0.68 |
| S11 | Q | −0.25 | −0.26 | 1.01 |
| S11 | R | −0.25 | −0.08 | 0.69 |
| S11 | S | 1.00 | 1.00 | 1.00 |
| S11 | T | 0.04 | −0.36 | 0.87 |
| S11 | V | 0.03 | −0.15 | 0.59 |
| L12 | A | 1.10 | 0.07 | 0.71 |
| L12 | C | 2.29 | 0.22 | 0.81 |
| L12 | D | 0.04 | 0.00 | 0.39 |
| L12 | F | 0.13 | 0.17 | 0.60 |
| L12 | G | 0.44 | −0.06 | 0.60 |
| L12 | H | 0.02 | 0.16 | 0.77 |
| L12 | K | 0.18 | 0.13 | 0.40 |
| L12 | L | 1.00 | 1.00 | 1.00 |
| L12 | N | 0.53 | 0.66 | 1.06 |
| L12 | P | 0.03 | −0.16 | 0.31 |
| L12 | Q | 2.65 | 0.22 | 1.05 |
| L12 | R | 0.23 | −0.02 | 0.34 |
| L12 | S | 0.54 | −0.07 | 0.80 |
| L12 | T | 0.68 | 0.06 | 0.89 |
| L12 | V | 0.98 | −0.05 | 0.51 |
| L12 | W | 0.03 | 0.02 | 0.33 |
| T13 | A | 0.25 | 1.88 | 0.72 |
| T13 | C | 0.56 | 1.55 | 0.78 |
| T13 | E | −0.10 | 1.09 | 0.44 |
| T13 | F | −0.10 | −0.11 | −0.02 |
| T13 | G | 0.32 | 0.77 | 0.57 |
| T13 | I | 0.12 | 1.05 | 0.69 |
| T13 | L | 0.55 | 1.47 | 0.76 |
| T13 | M | 0.17 | 1.47 | 0.94 |
| T13 | N | −0.10 | 2.61 | 0.27 |
| T13 | P | −0.10 | 2.73 | 0.17 |
| T13 | Q | 0.01 | 0.51 | 0.98 |
| T13 | R | −0.10 | −0.11 | −0.02 |
| T13 | S | 0.73 | 0.68 | 0.88 |
| T13 | T | 1.00 | 1.00 | 1.00 |
| T13 | V | 0.19 | 0.63 | 1.17 |
| T13 | W | −0.10 | −0.11 | −0.02 |
| W14 | A | −0.23 | 0.27 | 0.94 |
| W14 | E | 0.06 | 0.15 | 0.80 |
| W14 | F | 0.29 | 0.22 | 0.71 |
| W14 | G | 0.30 | −0.97 | 0.70 |
| W14 | I | 0.33 | −0.42 | 0.66 |
| W14 | K | 0.29 | −0.17 | 0.71 |
| W14 | L | 0.25 | −0.36 | 0.82 |
| W14 | N | −0.23 | −0.12 | 0.81 |
| W14 | P | −0.23 | −0.29 | 0.34 |
| W14 | R | 0.23 | −0.40 | 0.66 |
| W14 | S | 0.31 | −0.99 | 0.69 |
| W14 | T | 0.24 | −0.77 | 0.64 |
| W14 | V | 0.26 | −0.49 | 0.58 |
| W14 | W | 1.00 | 1.00 | 1.00 |
| W14 | Y | 0.31 | 0.66 | 1.02 |
| G15 | A | 1.54 | 0.61 | 0.87 |
| G15 | C | 0.71 | −0.27 | 0.66 |
| G15 | D | −0.18 | 0.01 | 0.26 |
| G15 | E | −0.18 | −1.42 | 0.11 |
| G15 | G | 1.00 | 1.00 | 1.00 |
| G15 | H | −0.18 | −0.14 | −0.01 |
| G15 | K | −0.18 | −0.14 | −0.01 |
| G15 | L | −0.18 | −0.14 | −0.01 |
| G15 | N | 0.46 | −0.63 | 0.71 |
| G15 | P | −0.18 | −5.42 | 0.09 |
| G15 | R | −0.18 | −0.14 | −0.01 |
| G15 | S | 1.05 | 0.63 | 0.76 |
| G15 | Y | −0.18 | −0.14 | −0.01 |
| W16 | A | 0.12 | 0.55 | 0.50 |
| W16 | D | 0.02 | 0.57 | 0.32 |
| W16 | E | 0.06 | 0.65 | 0.46 |
| W16 | G | 0.05 | −0.07 | 0.38 |
| W16 | H | 0.03 | −0.02 | 0.55 |
| W16 | I | 0.02 | 1.06 | 0.74 |
| W16 | K | 0.01 | 1.03 | 0.73 |
| W16 | L | −0.48 | 1.16 | 0.76 |
| W16 | M | 0.04 | 0.37 | 0.56 |
| W16 | N | 0.02 | −0.03 | 0.43 |
| W16 | P | 0.03 | 0.15 | 0.37 |
| W16 | Q | 0.05 | 0.31 | 0.47 |
| W16 | R | 0.03 | −0.41 | 0.30 |
| W16 | S | 0.09 | −0.17 | 0.39 |
| W16 | T | 0.03 | −0.31 | 0.41 |
| W16 | V | 0.01 | 0.88 | 0.76 |
| W16 | W | 1.00 | 1.00 | 1.00 |
| W16 | Y | 0.22 | 1.09 | 1.02 |
| V17 | A | 1.01 | 0.68 | 1.21 |
| V17 | E | 0.82 | 0.75 | 1.11 |
| V17 | F | 0.92 | 0.85 | 1.09 |
| V17 | G | 1.17 | 0.84 | 0.93 |
| V17 | I | 0.95 | 0.99 | 1.08 |
| V17 | K | 0.94 | 0.84 | 1.06 |
| V17 | L | 0.90 | 1.00 | 0.76 |
| V17 | P | 0.77 | 0.96 | 0.97 |
| V17 | R | 1.10 | 0.94 | 0.76 |
| V17 | S | 0.96 | 1.04 | 0.89 |
| V17 | T | 0.93 | 0.86 | 1.03 |
| V17 | V | 1.00 | 1.00 | 1.00 |
| V17 | Y | 0.91 | 0.88 | 0.99 |
| P18 | A | −0.28 | −0.94 | −0.03 |
| P18 | C | 1.26 | 4.16 | 2.56 |
| P18 | E | 1.22 | 4.87 | 2.47 |
| P18 | G | 1.07 | 4.96 | 2.47 |
| P18 | H | 1.12 | 6.05 | 2.50 |
| P18 | L | 0.93 | 7.40 | 2.50 |
| P18 | N | 1.33 | 1.42 | 2.35 |

TABLE 10-12-continued

Performance Indices

| Wild-Type Res./Pos. | Mut. | PAF PI | PAD PI | Prot. PI |
|---|---|---|---|---|
| P18 | P | 1.00 | 1.00 | 1.00 |
| P18 | Q | 1.12 | 3.26 | 2.13 |
| P18 | R | 1.16 | 3.97 | 2.01 |
| P18 | S | 0.11 | 0.07 | 1.05 |
| P18 | V | 1.19 | 4.85 | 2.30 |
| P18 | Y | 1.33 | 4.17 | 1.68 |
| V19 | A | 0.61 | 0.55 | 1.23 |
| V19 | D | 0.77 | 0.79 | 0.80 |
| V19 | E | 0.74 | 0.62 | 1.10 |
| V19 | G | 1.32 | 0.56 | 1.39 |
| V19 | K | 0.96 | 0.97 | 1.03 |
| V19 | L | 1.00 | 0.91 | 0.90 |
| V19 | M | 0.33 | 0.12 | 1.00 |
| V19 | P | 0.00 | −0.41 | 0.76 |
| V19 | Q | 0.93 | 0.40 | 1.07 |
| V19 | R | 1.03 | 0.34 | 0.82 |
| V19 | S | 1.24 | 0.57 | 0.80 |
| V19 | V | 1.00 | 1.00 | 1.00 |
| V19 | Y | 0.94 | 0.70 | 0.92 |
| E20 | A | 1.29 | 1.28 | 1.08 |
| E20 | C | 1.57 | 1.76 | 0.71 |
| E20 | D | 0.87 | 1.14 | 0.97 |
| E20 | E | 1.00 | 1.00 | 1.00 |
| E20 | G | 2.36 | 0.78 | 1.11 |
| E20 | H | 2.17 | 1.20 | 0.92 |
| E20 | L | 2.20 | 0.73 | 0.92 |
| E20 | N | 1.40 | 1.34 | 1.01 |
| E20 | P | 1.00 | 1.43 | 1.08 |
| E20 | Q | 1.27 | 1.56 | 0.99 |
| E20 | S | 2.01 | 1.18 | 0.91 |
| E20 | T | 2.22 | 1.25 | 0.94 |
| E20 | V | 2.11 | 1.27 | 1.01 |
| E20 | W | 2.94 | 1.30 | 0.79 |
| D21 | A | 1.46 | 1.75 | 0.84 |
| D21 | D | 1.00 | 1.00 | 1.00 |
| D21 | E | 0.84 | 1.39 | 0.85 |
| D21 | F | 1.30 | 1.41 | 0.81 |
| D21 | G | 1.37 | 1.76 | 0.93 |
| D21 | K | 1.58 | 1.80 | 0.74 |
| D21 | L | 1.46 | 1.57 | 0.82 |
| D21 | P | 0.81 | 0.86 | 0.74 |
| D21 | S | 1.24 | 1.11 | 0.73 |
| D21 | V | −0.17 | −0.12 | −0.02 |
| D21 | W | 1.55 | 1.44 | 0.61 |
| D21 | Y | 1.30 | 2.01 | 0.42 |
| G22 | A | 1.55 | 1.66 | 1.07 |
| G22 | E | 0.15 | 1.19 | 0.56 |
| G22 | G | 1.00 | 1.00 | 1.00 |
| G22 | I | 0.37 | 1.03 | 1.03 |
| G22 | K | 0.23 | −0.22 | 0.78 |
| G22 | L | 0.38 | 1.35 | 0.84 |
| G22 | P | 0.28 | 1.36 | 0.80 |
| G22 | Q | 0.35 | 1.44 | 0.96 |
| G22 | R | 0.11 | 0.56 | 0.73 |
| G22 | S | 1.02 | 0.98 | 0.94 |
| G22 | T | 1.03 | 1.16 | 0.80 |
| G22 | V | 0.40 | 0.85 | 0.89 |
| G22 | W | 0.25 | 0.23 | 0.58 |
| A23 | A | 1.00 | 1.00 | 1.00 |
| A23 | F | 0.05 | 0.44 | 1.03 |
| A23 | G | 0.45 | 0.35 | 0.93 |
| A23 | H | 0.16 | 1.04 | 0.93 |
| A23 | L | 0.03 | 1.30 | 0.75 |
| A23 | M | 0.85 | 0.95 | 0.90 |
| A23 | P | −0.11 | 0.73 | 0.82 |
| A23 | Q | 0.23 | 0.73 | 0.91 |
| A23 | R | 0.11 | 0.28 | 0.80 |
| A23 | S | 0.69 | 0.34 | 0.87 |
| A23 | V | 0.20 | 0.60 | 0.73 |
| A23 | W | 0.29 | 0.80 | 0.71 |
| A23 | Y | 0.20 | 0.96 | 0.73 |
| P24 | A | 0.54 | 0.68 | 0.88 |
| P24 | C | 0.54 | 1.04 | 0.87 |
| P24 | G | 0.49 | 0.76 | 1.34 |
| P24 | H | 0.42 | 0.97 | 1.15 |
| P24 | I | 0.42 | 0.85 | 1.11 |
| P24 | K | 0.52 | 1.36 | 0.71 |
| P24 | L | 0.58 | 1.51 | 1.06 |
| P24 | P | 1.00 | 1.00 | 1.00 |
| P24 | Q | 0.50 | 0.65 | 0.93 |
| P24 | R | 0.58 | 0.91 | 0.85 |
| P24 | S | 0.53 | 0.61 | 1.31 |
| P24 | T | 0.44 | 0.66 | 1.43 |
| T25 | A | 1.33 | 0.86 | 1.23 |
| T25 | C | 0.67 | 0.51 | 1.37 |
| T25 | D | 0.03 | −0.07 | 0.87 |
| T25 | E | 0.08 | −0.29 | 0.98 |
| T25 | G | 1.86 | 0.43 | 1.27 |
| T25 | H | 0.42 | −0.02 | 0.94 |
| T25 | I | 1.02 | 0.35 | 1.19 |
| T25 | K | 0.36 | 0.13 | 0.87 |
| T25 | L | 0.40 | −0.04 | 0.95 |
| T25 | M | 0.29 | −0.10 | 1.04 |
| T25 | P | 0.97 | −0.05 | 1.10 |
| T25 | R | 0.32 | −0.06 | 0.94 |
| T25 | S | 1.60 | 0.58 | 0.95 |
| T25 | T | 1.00 | 1.00 | 1.00 |
| T25 | V | 0.91 | 0.51 | 1.30 |
| T25 | W | 0.33 | 0.14 | 0.86 |
| E26 | A | 1.93 | 1.45 | 0.79 |
| E26 | C | 1.40 | 0.94 | 0.82 |
| E26 | D | 0.65 | 1.39 | 0.90 |
| E26 | E | 1.00 | 1.00 | 1.00 |
| E26 | G | 1.28 | 0.87 | 0.82 |
| E26 | H | 1.33 | 1.19 | 0.71 |
| E26 | K | 1.46 | 1.47 | 0.77 |
| E26 | L | 1.30 | 1.71 | 0.77 |
| E26 | M | 2.00 | 1.10 | 0.89 |
| E26 | N | 1.37 | 0.48 | 0.88 |
| E26 | P | 0.43 | 0.99 | 0.63 |
| E26 | R | 1.48 | 0.81 | 0.77 |
| E26 | S | 1.27 | 0.28 | 0.92 |
| E26 | T | 1.44 | 0.40 | 0.82 |
| E26 | V | 1.39 | 0.97 | 0.85 |
| E26 | W | 1.25 | 0.47 | 0.68 |
| R27 | A | 0.45 | 2.78 | 0.67 |
| R27 | C | 0.35 | 0.58 | 0.50 |
| R27 | E | 0.58 | 0.93 | 0.46 |
| R27 | G | 0.42 | 0.84 | 0.24 |
| R27 | I | 0.72 | 1.41 | 0.70 |
| R27 | K | 1.22 | 1.55 | 0.69 |
| R27 | L | 0.48 | 2.60 | 0.51 |
| R27 | P | 0.93 | 0.48 | 0.46 |
| R27 | R | 1.00 | 1.00 | 1.00 |
| R27 | S | 0.53 | 0.69 | 0.56 |
| R27 | T | 0.41 | 0.01 | 0.74 |
| R27 | V | 0.71 | 0.94 | 0.85 |
| R27 | W | 0.21 | −0.59 | 0.33 |
| F28 | A | 1.27 | 1.48 | 0.92 |
| F28 | C | 0.93 | 1.21 | 0.87 |
| F28 | D | 0.67 | 2.07 | 0.40 |
| F28 | E | 0.51 | 1.04 | 0.85 |
| F28 | F | 1.00 | 1.00 | 1.00 |
| F28 | G | 0.74 | −1.53 | 0.50 |
| F28 | H | −0.20 | −0.19 | −0.01 |
| F28 | I | −0.20 | −0.19 | −0.01 |
| F28 | L | 1.09 | 2.02 | 0.51 |
| F28 | M | 1.33 | 1.37 | 0.70 |
| F28 | P | 0.02 | 0.39 | 0.42 |
| F28 | R | −0.20 | −0.19 | −0.01 |
| F28 | S | 1.05 | 0.70 | 0.82 |
| F28 | V | 0.86 | 0.53 | 0.85 |
| F28 | W | 1.16 | 1.17 | 0.89 |
| F28 | Y | 0.99 | 1.36 | 0.77 |
| A29 | A | 1.00 | 1.00 | 1.00 |
| A29 | C | 1.08 | 1.15 | 0.76 |
| A29 | D | 0.87 | 1.00 | 1.06 |
| A29 | E | 1.12 | 0.84 | 1.02 |

TABLE 10-12-continued

Performance Indices

| Wild-Type Res./Pos. | Mut. | PAF PI | PAD PI | Prot. PI |
|---|---|---|---|---|
| A29 | G | 1.60 | 0.80 | 1.22 |
| A29 | M | 0.67 | 0.77 | 1.06 |
| A29 | P | 0.78 | 0.62 | 1.07 |
| A29 | R | 1.76 | 0.73 | 0.81 |
| A29 | S | 1.49 | 0.55 | 1.05 |
| A29 | T | 1.42 | 0.47 | 1.02 |
| A29 | V | 1.80 | 0.44 | 1.05 |
| A29 | W | 1.91 | 0.74 | 0.82 |
| A29 | Y | 1.70 | 0.59 | 0.96 |
| P30 | A | 1.05 | 0.92 | 1.15 |
| P30 | E | 1.01 | 1.24 | 1.20 |
| P30 | G | 0.90 | 1.09 | 0.99 |
| P30 | H | 1.01 | 1.08 | 1.05 |
| P30 | I | 0.97 | 1.38 | 0.95 |
| P30 | K | 1.21 | 1.39 | 1.06 |
| P30 | L | 0.96 | 1.17 | 1.07 |
| P30 | M | 0.96 | 0.79 | 0.94 |
| P30 | P | 1.00 | 1.00 | 1.00 |
| P30 | Q | 1.01 | 0.91 | 1.06 |
| P30 | R | 1.16 | 1.14 | 0.94 |
| P30 | S | 1.03 | 1.49 | 1.12 |
| P30 | T | 1.05 | 1.64 | 1.00 |
| P30 | V | 1.06 | 1.74 | 0.99 |
| P30 | Y | 0.79 | 1.31 | 1.04 |
| D31 | A | 1.24 | 1.18 | 0.80 |
| D31 | D | 1.00 | 1.00 | 1.00 |
| D31 | E | 1.13 | 0.88 | 0.93 |
| D31 | F | 1.44 | 1.39 | 0.65 |
| D31 | G | 1.44 | 1.16 | 0.79 |
| D31 | L | 1.81 | 1.61 | 0.65 |
| D31 | N | 1.34 | 1.55 | 0.62 |
| D31 | Q | 1.07 | 1.13 | 0.74 |
| D31 | R | 1.22 | 1.49 | 0.50 |
| D31 | S | 1.15 | 1.23 | 0.55 |
| D31 | T | 1.45 | 1.11 | 0.76 |
| D31 | V | 1.28 | 1.08 | 0.50 |
| D31 | W | 1.83 | 1.14 | 0.60 |
| V32 | A | 0.43 | 3.64 | 1.10 |
| V32 | D | 0.45 | 4.19 | 0.95 |
| V32 | E | 0.57 | 3.92 | 1.00 |
| V32 | G | 0.58 | 2.65 | 0.98 |
| V32 | I | 0.91 | 3.51 | 1.08 |
| V32 | K | 1.09 | 4.73 | 0.75 |
| V32 | L | 0.96 | 4.72 | 1.01 |
| V32 | M | 0.64 | 3.41 | 1.11 |
| V32 | N | 0.54 | 1.61 | 0.99 |
| V32 | P | 0.01 | −1.17 | 0.31 |
| V32 | Q | 0.64 | 1.74 | 1.03 |
| V32 | R | 1.05 | 0.72 | 0.51 |
| V32 | S | 0.77 | 1.09 | 0.85 |
| V32 | V | 1.00 | 1.00 | 1.00 |
| V32 | W | 0.94 | 1.71 | 0.70 |
| R33 | A | 0.20 | 1.32 | 0.52 |
| R33 | C | 0.44 | 1.73 | 0.95 |
| R33 | D | −0.16 | −0.30 | −0.02 |
| R33 | E | −0.16 | −0.30 | −0.02 |
| R33 | G | 0.64 | 2.63 | 0.47 |
| R33 | H | −0.16 | −0.30 | −0.02 |
| R33 | K | 0.85 | 2.72 | 0.81 |
| R33 | L | 0.34 | 2.90 | 0.74 |
| R33 | N | 0.90 | 1.30 | 0.92 |
| R33 | P | −0.16 | −0.30 | −0.02 |
| R33 | R | 1.00 | 1.00 | 1.00 |
| R33 | S | 1.00 | 1.01 | 0.79 |
| R33 | V | 0.50 | 0.94 | 0.89 |
| R33 | W | −0.16 | −0.30 | −0.02 |
| W34 | A | −0.15 | 2.29 | 0.41 |
| W34 | C | −0.15 | 1.49 | 0.52 |
| W34 | E | −0.15 | −1.86 | 0.17 |
| W34 | G | 0.12 | 0.88 | 0.23 |
| W34 | I | 0.18 | 0.94 | 0.75 |
| W34 | K | −0.15 | −0.15 | −0.02 |
| W34 | M | 0.16 | 1.22 | 0.91 |
| W34 | P | −0.15 | 1.21 | 0.26 |
| W34 | Q | 0.02 | 0.04 | 0.25 |
| W34 | R | 0.22 | −0.33 | 0.16 |
| W34 | S | 0.47 | 0.08 | 0.29 |
| W34 | T | 0.36 | 0.15 | 0.29 |
| W34 | V | 0.24 | 0.73 | 0.71 |
| W34 | W | 1.00 | 1.00 | 1.00 |
| T35 | A | 0.45 | 3.85 | 0.98 |
| T35 | C | 0.55 | 4.72 | 1.16 |
| T35 | E | 0.30 | 5.73 | 0.26 |
| T35 | I | 0.63 | 5.38 | 0.45 |
| T35 | K | −0.13 | −0.54 | −0.01 |
| T35 | L | −0.13 | −0.54 | −0.01 |
| T35 | M | 0.17 | 2.72 | 0.40 |
| T35 | N | 0.20 | −2.29 | 0.43 |
| T35 | P | −0.13 | −0.54 | −0.01 |
| T35 | Q | 0.57 | −2.07 | 0.52 |
| T35 | R | 0.18 | −11.34 | 0.23 |
| T35 | T | 1.00 | 1.00 | 1.00 |
| T35 | V | 0.71 | 0.34 | 0.81 |
| T35 | W | −0.13 | −0.54 | −0.01 |
| T35 | Y | −0.13 | −0.54 | −0.01 |
| G36 | A | 0.63 | 1.07 | 1.00 |
| G36 | C | 0.53 | 1.06 | 1.09 |
| G36 | D | −0.12 | 2.50 | 0.28 |
| G36 | G | −0.12 | −0.10 | −0.02 |
| G36 | H | 0.73 | 1.10 | 0.98 |
| G36 | I | 1.32 | 1.81 | 0.31 |
| G36 | K | 1.27 | 1.71 | 0.84 |
| G36 | L | 1.24 | 2.49 | 0.39 |
| G36 | M | 0.85 | 0.54 | 0.85 |
| G36 | N | 0.49 | 0.56 | 1.08 |
| G36 | P | −0.12 | −0.10 | −0.02 |
| G36 | Q | 0.56 | 0.71 | 1.07 |
| G36 | R | 0.99 | 0.90 | 0.85 |
| G36 | S | 0.78 | 0.26 | 1.06 |
| G36 | T | 0.76 | 0.33 | 0.83 |
| G36 | V | 0.95 | 0.38 | 0.42 |
| G36 | W | 0.91 | 0.68 | 0.57 |
| V37 | A | 1.25 | 2.00 | 0.63 |
| V37 | C | 1.09 | 1.63 | 0.68 |
| V37 | H | 1.21 | 0.96 | 0.78 |
| V37 | I | 1.26 | 1.04 | 0.77 |
| V37 | L | 1.16 | 1.16 | 0.71 |
| V37 | N | 0.90 | 1.52 | 1.09 |
| V37 | P | 0.53 | 2.10 | 0.73 |
| V37 | Q | −0.11 | −0.14 | −0.02 |
| V37 | R | −0.11 | −0.14 | −0.02 |
| V37 | S | 1.40 | 1.49 | 0.81 |
| V37 | T | 1.05 | 0.81 | 0.63 |
| V37 | V | −0.11239 | −0.14412 | −0.02 |
| V37 | W | 0.92 | 0.98 | 0.62 |
| L38 | A | 0.59 | 0.63 | 0.78 |
| L38 | C | 0.64 | 0.72 | 0.89 |
| L38 | D | −0.15 | 0.12 | 0.24 |
| L38 | E | −0.15 | −0.61 | 0.26 |
| L38 | G | 0.15 | −0.72 | 0.32 |
| L38 | K | 0.63 | −0.22 | 0.16 |
| L38 | L | 1.00 | 1.00 | 1.00 |
| L38 | P | −0.15 | −0.78 | 0.28 |
| L38 | Q | −0.15 | −0.02 | 0.47 |
| L38 | R | −0.15 | −0.96 | 0.34 |
| L38 | S | 0.38 | 0.29 | 0.48 |
| L38 | V | 0.88 | 1.12 | 0.73 |
| L38 | W | −0.15 | −0.11 | −0.02 |
| A39 | A | 1.00 | 1.00 | 1.00 |
| A39 | C | 0.63 | 0.92 | 0.50 |
| A39 | E | 1.09 | 0.83 | 1.03 |
| A39 | F | −0.17 | −0.11 | −0.02 |
| A39 | G | 1.17 | 0.30 | 0.92 |
| A39 | I | 1.26 | 0.71 | 0.91 |
| A39 | K | 1.36 | 0.96 | 0.90 |
| A39 | L | 1.43 | 0.97 | 0.93 |
| A39 | M | 0.52 | 0.81 | 0.46 |
| A39 | N | 0.51 | 0.43 | 0.45 |

TABLE 10-12-continued

Performance Indices

| Wild-Type Res./Pos. | Mut. | PAF PI | PAD PI | Prot. PI |
|---|---|---|---|---|
| A39 | P | 0.69 | 0.74 | 0.45 |
| A39 | R | 1.17 | 0.64 | 0.94 |
| A39 | S | 0.49 | −4.31 | 0.16 |
| A39 | T | 1.26 | 0.79 | 0.92 |
| A39 | V | 1.21 | 0.98 | 1.18 |
| A39 | W | 1.23 | 1.02 | 0.94 |
| A39 | Y | 1.36 | 1.13 | 0.90 |
| Q40 | D | 1.16 | 1.59 | 0.69 |
| Q40 | E | 1.08 | 1.28 | 0.81 |
| Q40 | G | 1.79 | 2.17 | 0.93 |
| Q40 | I | 2.58 | 1.10 | 0.49 |
| Q40 | K | 2.61 | 3.64 | 0.52 |
| Q40 | L | 2.14 | 1.49 | 0.53 |
| Q40 | N | 1.53 | 1.00 | 0.78 |
| Q40 | P | 0.45 | −0.19 | 0.24 |
| Q40 | Q | 1.00 | 1.00 | 1.00 |
| Q40 | R | 1.89 | 1.48 | 0.61 |
| Q40 | S | 1.57 | 1.65 | 0.87 |
| Q40 | T | 2.01 | 1.81 | 0.75 |
| Q40 | W | 2.39 | 2.59 | 0.54 |
| Q40 | Y | 1.83 | 2.02 | 0.65 |
| Q41 | A | 1.03 | 2.58 | 0.73 |
| Q41 | G | 0.97 | 1.09 | 0.77 |
| Q41 | H | 1.12 | 1.14 | 0.89 |
| Q41 | K | 1.38 | 1.61 | 0.70 |
| Q41 | L | 1.00 | 1.92 | 0.79 |
| Q41 | P | 0.21 | 0.66 | 0.45 |
| Q41 | Q | 1.00 | 1.00 | 1.00 |
| Q41 | R | 1.19 | 1.27 | 0.74 |
| Q41 | S | 1.11 | 0.22 | 0.92 |
| Q41 | V | 1.07 | −0.05 | 0.90 |
| Q41 | W | 1.14 | 0.88 | 0.71 |
| Q41 | Y | 1.09 | 0.70 | 0.82 |
| L42 | C | 0.76 | 1.43 | 0.68 |
| L42 | D | −0.14 | −0.17 | −0.02 |
| L42 | F | 1.07 | 1.02 | 0.48 |
| L42 | G | 1.17 | 0.76 | 0.50 |
| L42 | H | 1.92 | −0.33 | 0.15 |
| L42 | I | 0.97 | 0.66 | 0.83 |
| L42 | K | 2.46 | 1.41 | 0.13 |
| L42 | L | 1.00 | 1.00 | 1.00 |
| L42 | M | 0.78 | 0.74 | 0.95 |
| L42 | P | 0.71 | 1.34 | 0.23 |
| L42 | Q | 0.57 | 0.28 | 0.40 |
| L42 | R | 1.38 | 0.64 | 0.15 |
| L42 | S | 0.97 | 0.45 | 0.46 |
| L42 | T | 1.08 | −0.04 | 0.41 |
| L42 | V | 0.91 | 0.73 | 0.74 |
| L42 | W | 2.06 | −0.70 | 0.14 |
| G43 | A | 1.49 | 1.07 | 0.45 |
| G43 | C | 1.48 | 0.73 | 0.36 |
| G43 | E | 1.25 | 1.88 | 0.66 |
| G43 | G | 1.00 | 1.00 | 1.00 |
| G43 | H | 1.17 | 0.96 | 0.63 |
| G43 | I | 0.94 | 0.77 | 0.42 |
| G43 | K | 1.42 | 0.86 | 0.65 |
| G43 | L | 1.22 | 1.82 | 0.42 |
| G43 | M | 1.37 | 0.88 | 0.28 |
| G43 | P | 1.08 | 0.31 | 0.65 |
| G43 | Q | 0.91 | 0.48 | 0.63 |
| G43 | R | 1.22 | 0.59 | 0.57 |
| G43 | S | 1.18 | 0.23 | 0.79 |
| G43 | V | 0.93 | 0.33 | 0.44 |
| G43 | Y | 1.26 | 0.94 | 0.36 |
| A44 | A | 1.00 | 1.00 | 1.00 |
| A44 | C | 1.80 | 1.92 | 0.46 |
| A44 | D | −0.17 | −0.11 | −0.01 |
| A44 | E | −0.17 | 0.03 | 0.10 |
| A44 | F | 2.84 | 0.80 | 0.99 |
| A44 | H | −0.17 | −0.11 | −0.01 |
| A44 | L | 1.61 | 0.99 | 0.87 |
| A44 | M | 1.20 | 0.98 | 0.71 |
| A44 | P | −0.17 | −0.11 | −0.01 |
| A44 | R | 0.29 | −2.17 | 0.08 |
| A44 | S | 0.52 | −0.92 | 0.16 |
| A44 | T | 0.30 | −1.11 | 0.14 |
| A44 | V | 2.13 | 0.50 | 0.94 |
| A44 | W | 1.40 | 0.85 | 0.61 |
| A44 | Y | 0.30 | −0.23 | 0.10 |
| D45 | A | 1.04 | 0.84 | 0.99 |
| D45 | C | 0.83 | 0.84 | 0.48 |
| D45 | D | 1.00 | 1.00 | 1.00 |
| D45 | F | 1.11 | 1.04 | 0.66 |
| D45 | G | 1.13 | 0.84 | 0.94 |
| D45 | H | 1.13 | 0.78 | 0.70 |
| D45 | K | 1.34 | 0.87 | 0.86 |
| D45 | L | 1.05 | 0.78 | 0.55 |
| D45 | M | 0.86 | 0.78 | 0.88 |
| D45 | P | 0.75 | 0.53 | 0.72 |
| D45 | Q | 1.04 | 0.57 | 0.81 |
| D45 | R | 1.16 | 0.49 | 0.72 |
| D45 | S | 1.13 | 0.38 | 0.95 |
| D45 | T | 1.27 | 0.44 | 0.86 |
| D45 | V | 1.05 | 0.50 | 0.70 |
| D45 | W | 1.15 | 0.58 | 0.54 |
| F46 | A | 0.92 | 1.25 | 1.05 |
| F46 | C | 0.84 | 1.16 | 1.01 |
| F46 | D | 1.17 | 1.39 | 0.54 |
| F46 | E | 1.25 | 1.31 | 0.38 |
| F46 | F | 1.00 | 1.00 | 1.00 |
| F46 | G | 1.02 | 0.94 | 0.61 |
| F46 | H | −0.13 | −0.13 | −0.01 |
| F46 | I | 0.90 | 0.88 | 0.91 |
| F46 | K | 1.00 | 1.46 | 0.48 |
| F46 | L | 0.78 | 1.54 | 0.74 |
| F46 | M | 0.78 | 1.42 | 0.81 |
| F46 | P | 0.64 | 1.50 | 0.26 |
| F46 | S | 0.73 | 0.66 | 0.72 |
| F46 | T | 0.86 | 0.43 | 0.79 |
| F46 | V | 0.82 | 0.79 | 0.89 |
| F46 | W | 0.94 | 0.63 | 0.91 |
| E47 | A | 0.95 | 0.76 | 0.84 |
| E47 | C | 0.83 | 0.77 | 0.99 |
| E47 | D | 0.99 | 0.98 | 0.97 |
| E47 | E | 1.00 | 1.00 | 1.00 |
| E47 | F | 1.09 | 0.76 | 0.96 |
| E47 | G | 1.20 | 1.10 | 0.76 |
| E47 | H | 1.27 | 0.99 | 0.93 |
| E47 | I | 1.03 | 1.15 | 1.02 |
| E47 | K | 1.19 | 1.06 | 0.89 |
| E47 | L | 1.00 | 1.02 | 0.96 |
| E47 | M | 0.90 | 0.70 | 0.84 |
| E47 | N | 0.91 | 0.63 | 0.99 |
| E47 | P | 1.36 | 0.36 | 0.49 |
| E47 | R | 2.45 | 0.62 | 0.75 |
| E47 | S | 1.28 | 0.63 | 0.83 |
| E47 | T | 1.96 | 0.84 | 0.98 |
| V48 | A | 0.60 | 1.63 | 0.47 |
| V48 | C | 0.83 | 2.25 | 0.91 |
| V48 | E | 0.02 | 0.99 | 0.18 |
| V48 | F | 0.67 | 1.42 | 0.57 |
| V48 | G | 0.61 | 0.87 | 0.25 |
| V48 | L | 0.92 | 2.29 | 0.91 |
| V48 | M | 0.85 | 1.79 | 0.71 |
| V48 | N | −0.15 | 0.98 | 0.23 |
| V48 | P | 0.21 | 3.08 | 0.34 |
| V48 | Q | 0.19 | 1.39 | 0.32 |
| V48 | R | 0.76 | −1.17 | 0.15 |
| V48 | S | 0.65 | 0.42 | 0.40 |
| V48 | V | 1.00 | 1.00 | 1.00 |
| V48 | W | −0.15 | −0.19 | −0.02 |
| I49 | A | 0.92 | 1.87 | 0.58 |
| I49 | E | 1.02 | 0.88 | 0.75 |
| I49 | G | 1.34 | 1.12 | 0.28 |
| I49 | H | 1.27 | 0.74 | 0.77 |
| I49 | I | 1.00 | 1.00 | 1.00 |
| I49 | K | 1.23 | 1.26 | 0.72 |
| I49 | L | 1.14 | 1.03 | 0.93 |

TABLE 10-12-continued

Performance Indices

| Wild-Type Res./Pos. | Mut. | PAF PI | PAD PI | Prot. PI |
|---|---|---|---|---|
| I49 | M | 1.01 | 1.02 | 0.69 |
| I49 | P | 0.47 | 0.16 | 0.29 |
| I49 | R | 1.05 | 0.29 | 0.56 |
| I49 | S | 1.24 | 0.79 | 0.70 |
| I49 | V | 1.20 | 0.97 | 0.94 |
| I49 | W | 0.70 | 0.68 | 0.64 |
| I49 | Y | 1.07 | 1.02 | 0.82 |
| E50 | A | 1.12 | 1.23 | 0.58 |
| E50 | D | 0.78 | 1.22 | 0.80 |
| E50 | E | 1.00 | 1.00 | 1.00 |
| E50 | G | 0.93 | 1.11 | 0.60 |
| E50 | I | 0.84 | 0.58 | 0.67 |
| E50 | L | 1.19 | 0.97 | 0.41 |
| E50 | M | 1.18 | 1.04 | 0.38 |
| E50 | P | 0.85 | 1.02 | 0.71 |
| E50 | Q | 0.98 | 0.91 | 0.70 |
| E50 | R | 0.46 | −0.77 | 0.20 |
| E50 | S | 0.87 | 0.65 | 0.76 |
| E50 | V | 1.00 | 0.43 | 0.81 |
| E50 | W | 0.75 | 0.14 | 0.19 |
| E51 | A | 1.28 | 2.72 | 0.74 |
| E51 | D | 0.66 | 1.28 | 0.91 |
| E51 | E | 1.00 | 1.00 | 1.00 |
| E51 | G | 1.22 | 1.34 | 0.84 |
| E51 | I | 1.07 | 0.04 | 0.52 |
| E51 | K | 0.38 | 2.00 | 0.36 |
| E51 | L | 1.11 | 0.93 | 0.57 |
| E51 | M | 0.40 | 1.20 | 0.84 |
| E51 | P | −0.12 | −0.39 | −0.02 |
| E51 | Q | 0.98 | 0.76 | 0.84 |
| E51 | R | 0.35 | −0.97 | 0.29 |
| E51 | T | 1.18 | 1.17 | 0.48 |
| E51 | V | 1.47 | 0.37 | 0.70 |
| E51 | W | 0.44 | 0.17 | 0.22 |
| G52 | A | 0.54 | 0.79 | 0.90 |
| G52 | E | −0.12 | 0.55 | 0.41 |
| G52 | F | −0.12 | −0.08 | 0.52 |
| G52 | G | 1.00 | 1.00 | 1.00 |
| G52 | H | 0.18 | −0.60 | 0.49 |
| G52 | I | 0.10 | 0.07 | 0.80 |
| G52 | L | 0.17 | 0.24 | 0.58 |
| G52 | M | 0.05 | −0.64 | 0.56 |
| G52 | P | −0.12 | 0.24 | 0.76 |
| G52 | Q | −0.12 | 0.28 | 0.52 |
| G52 | R | −0.12 | 0.35 | 0.18 |
| G52 | S | 0.13 | −0.18 | 0.83 |
| G52 | T | 0.10 | −0.17 | 0.76 |
| G52 | V | 0.10 | −0.16 | 0.86 |
| G52 | W | 0.92 | 2.47 | 0.13 |
| L53 | D | 0.01 | 0.01 | 0.72 |
| L53 | E | 0.88 | 0.19 | 0.77 |
| L53 | G | 1.32 | 0.33 | 0.80 |
| L53 | H | 5.05 | 1.70 | 0.27 |
| L53 | I | 0.55 | 0.66 | 0.88 |
| L53 | K | 0.89 | 0.24 | 0.70 |
| L53 | L | 1.00 | 1.00 | 1.00 |
| L53 | P | −0.11 | −0.64 | 0.07 |
| L53 | Q | 1.48 | 0.72 | 0.89 |
| L53 | R | 0.20 | −0.02 | 0.66 |
| L53 | S | 1.16 | 0.26 | 0.95 |
| L53 | T | 1.02 | 0.84 | 0.75 |
| L53 | V | 0.52 | 0.65 | 0.88 |
| L53 | W | 0.02 | −0.07 | 0.77 |
| S54 | A | 3.46 | 1.41 | 1.33 |
| S54 | C | 1.26 | 0.88 | 1.21 |
| S54 | D | −0.17 | 0.65 | 1.08 |
| S54 | E | −0.17 | 0.30 | 1.16 |
| S54 | F | 0.74 | −0.14 | 0.91 |
| S54 | G | 1.43 | 0.17 | 0.93 |
| S54 | H | −0.17 | 0.00 | 1.06 |
| S54 | I | 4.78 | 0.12 | 0.94 |
| S54 | K | 1.44 | 0.08 | 0.78 |
| S54 | L | 2.02 | 0.26 | 0.59 |
| S54 | M | 0.01 | 0.48 | 1.01 |
| S54 | N | 0.29 | 1.29 | 1.01 |
| S54 | P | 5.20 | 1.30 | 0.98 |
| S54 | Q | 1.03 | 0.53 | 0.99 |
| S54 | R | 3.38 | 0.35 | 0.84 |
| S54 | S | 1.00 | 1.00 | 1.00 |
| S54 | T | 1.46 | 0.33 | 0.88 |
| S54 | V | 4.72 | 0.29 | 0.95 |
| S54 | W | 0.11 | −0.07 | 0.83 |
| S54 | Y | 0.37 | 0.12 | 0.89 |
| A55 | A | −0.11 | −0.15 | −0.01 |
| A55 | C | 0.14 | 1.26 | 0.98 |
| A55 | G | 1.69 | 0.73 | 0.98 |
| A55 | H | 0.04 | 0.92 | 0.93 |
| A55 | I | 0.34 | −0.43 | 0.80 |
| A55 | K | 0.52 | 1.08 | 0.68 |
| A55 | L | 0.11 | 0.87 | 0.81 |
| A55 | N | 0.34 | 1.05 | 1.12 |
| A55 | P | −0.11 | −0.01 | 0.84 |
| A55 | R | 0.56 | 0.25 | 0.99 |
| A55 | S | 0.76 | 0.87 | 1.08 |
| A55 | T | 1.69 | 0.42 | 0.91 |
| A55 | V | 0.49 | −0.51 | 0.96 |
| A55 | W | 0.00 | −0.05 | 0.88 |
| A55 | Y | 0.00 | 0.18 | 0.94 |
| R56 | A | 0.22 | 0.69 | 0.85 |
| R56 | C | 0.45 | −0.02 | 0.93 |
| R56 | E | −0.12 | −0.04 | 0.16 |
| R56 | G | 0.30 | −0.59 | 0.56 |
| R56 | H | −0.12 | −0.37 | −0.02 |
| R56 | K | −0.12 | −0.37 | −0.02 |
| R56 | L | 0.05 | 0.24 | 0.87 |
| R56 | N | 0.18 | 0.27 | 0.31 |
| R56 | P | −0.12 | −0.37 | −0.02 |
| R56 | Q | 0.01 | −0.01 | 1.02 |
| R56 | R | 1.00 | 1.00 | 1.00 |
| R56 | S | 0.39 | 0.12 | 0.55 |
| R56 | T | 0.10 | −0.37 | 0.85 |
| R56 | W | −0.12 | −0.37 | −0.02 |
| R56 | Y | −0.12 | −0.37 | −0.02 |
| T57 | A | 0.60 | 0.65 | 0.59 |
| T57 | C | 0.60 | 0.40 | 0.85 |
| T57 | G | 0.92 | 1.05 | 0.53 |
| T57 | H | 0.83 | 0.61 | 0.23 |
| T57 | I | 1.19 | 0.87 | 0.65 |
| T57 | L | 0.63 | 0.76 | 0.95 |
| T57 | N | 0.89 | 0.25 | 0.69 |
| T57 | P | 0.33 | −0.87 | 0.13 |
| T57 | R | 1.61 | −0.66 | 0.14 |
| T57 | S | 1.63 | 1.01 | 0.88 |
| T57 | T | 1.00 | 1.00 | 1.00 |
| T57 | V | 1.28 | 0.87 | 0.84 |
| T57 | W | −0.08 | −0.10 | −0.01 |
| T57 | Y | 0.52 | 0.55 | 0.43 |
| T58 | A | 0.65 | 0.36 | 0.76 |
| T58 | E | −0.19 | −0.10 | −0.02 |
| T58 | G | −0.19 | −0.10 | −0.02 |
| T58 | H | 0.89 | 1.49 | 0.74 |
| T58 | K | −0.19 | −0.10 | −0.02 |
| T58 | L | 0.88 | 1.12 | 0.78 |
| T58 | M | 0.56 | 0.03 | 0.50 |
| T58 | P | −0.19 | −0.10 | −0.02 |
| T58 | R | −0.19 | −0.10 | −0.02 |
| T58 | S | 0.82 | 0.96 | 0.90 |
| T58 | T | 1.00 | 1.00 | 1.00 |
| T58 | V | 0.56 | 0.96 | 1.13 |
| T58 | W | −0.19 | −0.10 | −0.02 |
| T58 | Y | −0.19 | −0.10 | −0.02 |
| N59 | A | 0.35 | 10.44 | 0.73 |
| N59 | C | 0.40 | 11.23 | 0.78 |
| N59 | D | 0.52 | 11.72 | 0.67 |
| N59 | E | 0.66 | 9.88 | 0.38 |
| N59 | F | 0.82 | 10.23 | 0.57 |
| N59 | G | 0.88 | 10.00 | 0.66 |
| N59 | K | 0.89 | 8.21 | 0.31 |

TABLE 10-12-continued

Performance Indices

| Wild-Type Res./Pos. | Mut. | PAF PI | PAD PI | Prot. PI |
|---|---|---|---|---|
| N59 | L | 0.88 | 14.74 | 0.32 |
| N59 | M | 0.42 | −1.42 | 0.72 |
| N59 | N | 1.00 | 1.00 | 1.00 |
| N59 | P | 0.12 | −55.11 | 0.14 |
| N59 | Q | 1.02 | 1.86 | 0.73 |
| N59 | R | 1.09 | −11.28 | 0.39 |
| N59 | S | 1.06 | 7.32 | 0.74 |
| N59 | T | 1.07 | 5.63 | 0.56 |
| N59 | V | 0.81 | 9.97 | 0.96 |
| N59 | W | 1.13 | 12.80 | 0.59 |
| N59 | Y | 0.80 | 11.14 | 0.61 |
| I60 | A | 0.81 | 0.79 | 1.20 |
| I60 | C | 0.69 | 0.67 | 0.97 |
| I60 | D | 0.83 | 0.66 | 0.56 |
| I60 | E | 0.87 | 0.92 | 0.83 |
| I60 | G | 1.00 | 1.04 | 0.86 |
| I60 | H | 1.02 | 1.07 | 0.96 |
| I60 | I | 1.00 | 1.00 | 1.00 |
| I60 | K | 0.99 | 0.96 | 0.73 |
| I60 | L | 0.95 | 0.91 | 1.02 |
| I60 | M | 0.96 | 0.68 | 1.14 |
| I60 | P | 0.23 | 0.32 | 0.31 |
| I60 | R | 1.00 | 0.81 | 0.79 |
| I60 | S | 0.78 | 1.00 | 0.92 |
| I60 | V | 0.87 | 1.06 | 1.06 |
| I60 | Y | 0.78 | 1.19 | 0.89 |
| D61 | A | 0.70 | 0.71 | 1.41 |
| D61 | C | 0.79 | 0.85 | 0.92 |
| D61 | D | 1.00 | 1.00 | 1.00 |
| D61 | F | 1.01 | 0.70 | 0.61 |
| D61 | G | 0.81 | 1.25 | 0.84 |
| D61 | H | 1.44 | 1.67 | 0.97 |
| D61 | I | 1.08 | 1.66 | 0.98 |
| D61 | K | 0.92 | 1.72 | 0.97 |
| D61 | L | 0.80 | 1.20 | 1.00 |
| D61 | N | 0.79 | 1.00 | 1.12 |
| D61 | P | 0.83 | 1.13 | 0.97 |
| D61 | Q | 0.89 | 1.16 | 1.02 |
| D61 | R | 1.11 | 1.59 | 0.69 |
| D61 | S | 1.26 | 1.35 | 0.97 |
| D61 | V | 0.95 | 0.97 | 1.10 |
| D61 | Y | 0.84 | 0.95 | 1.03 |
| D62 | A | −0.24 | 0.11 | 1.06 |
| D62 | C | 0.52 | 0.49 | 0.96 |
| D62 | E | 1.02 | 0.60 | 0.93 |
| D62 | G | 0.28 | −0.21 | 0.86 |
| D62 | H | 0.61 | −0.01 | 0.89 |
| D62 | I | 0.72 | −0.25 | 0.92 |
| D62 | L | 0.51 | −0.37 | 0.95 |
| D62 | M | 0.03 | −0.24 | 1.06 |
| D62 | P | −0.24 | −0.55 | 0.69 |
| D62 | Q | −0.24 | −0.35 | 0.86 |
| D62 | R | 0.12 | −0.81 | 0.62 |
| D62 | S | 0.57 | −0.10 | 0.88 |
| D62 | T | 0.76 | −0.41 | 0.76 |
| D62 | V | 0.62 | −0.26 | 0.87 |
| D62 | W | 0.58 | −0.45 | 0.79 |
| P63 | A | 1.35 | 0.60 | 1.06 |
| P63 | F | 1.25 | 0.93 | 0.97 |
| P63 | G | 1.71 | 1.22 | 1.00 |
| P63 | K | 1.40 | 1.02 | 0.99 |
| P63 | L | 1.15 | 1.23 | 0.84 |
| P63 | M | 1.46 | 0.91 | 1.09 |
| P63 | Q | 1.09 | 1.05 | 1.08 |
| P63 | R | 1.31 | 0.80 | 1.02 |
| P63 | S | 1.42 | 0.90 | 1.17 |
| P63 | T | 1.50 | 1.32 | 1.02 |
| P63 | V | 1.31 | 1.04 | 1.06 |
| P63 | W | 1.35 | 1.11 | 0.86 |
| P63 | Y | 1.35 | 0.95 | 1.12 |
| T64 | A | 0.96 | 1.20 | 0.97 |
| T64 | C | 0.78 | 0.88 | 1.05 |
| T64 | D | 0.87 | 0.64 | 0.81 |
| T64 | G | 1.23 | 1.08 | 1.00 |
| T64 | H | 0.89 | 0.96 | 0.90 |
| T64 | L | 0.63 | 1.22 | 0.93 |
| T64 | M | 0.68 | 1.09 | 1.07 |
| T64 | N | 0.69 | 0.98 | 0.91 |
| T64 | P | 0.76 | 0.94 | 0.61 |
| T64 | Q | 0.76 | 0.87 | 1.13 |
| T64 | R | 0.15 | 0.11 | 1.05 |
| T64 | S | 1.11 | 0.99 | 1.03 |
| T64 | T | 1.00 | 1.00 | 1.00 |
| T64 | W | 0.71 | 0.69 | 0.72 |
| D65 | A | 1.31 | 0.72 | 0.72 |
| D65 | D | 1.00 | 1.00 | 1.00 |
| D65 | G | 0.80 | 0.52 | 0.88 |
| D65 | H | 1.10 | 0.40 | 0.71 |
| D65 | I | 0.53 | 0.62 | 0.46 |
| D65 | P | −0.33 | 0.42 | 0.08 |
| D65 | R | 0.41 | 0.22 | 0.84 |
| D65 | S | 1.17 | 0.47 | 0.76 |
| D65 | T | 0.90 | 0.50 | 0.68 |
| D65 | V | 0.88 | 0.20 | 0.64 |
| D65 | W | 0.77 | 0.50 | 0.65 |
| D65 | Y | 0.83 | 0.42 | 0.64 |
| P66 | A | 0.50 | 0.56 | 1.03 |
| P66 | C | 0.51 | 0.52 | 1.51 |
| P66 | D | 1.00 | 0.72 | 0.90 |
| P66 | F | 0.95 | 0.67 | 1.02 |
| P66 | G | 1.50 | 0.44 | 1.78 |
| P66 | H | 1.59 | 0.95 | 1.23 |
| P66 | I | 1.59 | 0.84 | 1.51 |
| P66 | L | 1.14 | 0.99 | 0.92 |
| P66 | N | 1.12 | 0.38 | 1.62 |
| P66 | P | −0.09 | −0.11 | −0.01 |
| P66 | Q | 1.46 | 0.42 | 1.91 |
| P66 | R | 1.85 | 0.51 | 1.26 |
| P66 | S | 1.39 | 1.02 | 0.98 |
| P66 | T | 1.41 | 1.10 | 0.72 |
| P66 | V | 1.83 | 0.89 | 1.12 |
| P66 | Y | 1.33 | 0.70 | 1.08 |
| R67 | A | −0.20 | 0.22 | 1.39 |
| R67 | E | 1.04 | 0.11 | 0.85 |
| R67 | F | 1.26 | 0.01 | 1.01 |
| R67 | G | 1.39 | 0.41 | 0.81 |
| R67 | K | 0.91 | 0.99 | 0.76 |
| R67 | L | 1.20 | 0.16 | 1.46 |
| R67 | N | 1.58 | 0.33 | 1.00 |
| R67 | P | 1.01 | 0.04 | 1.04 |
| R67 | Q | 1.16 | 0.13 | 1.60 |
| R67 | R | 1.00 | 1.00 | 1.00 |
| R67 | T | 1.28 | 0.32 | 0.76 |
| R67 | V | 0.89 | 0.12 | 1.24 |
| R67 | W | 1.07 | 0.02 | 0.95 |
| L68 | A | 0.59 | −0.11 | 1.07 |
| L68 | C | 0.76 | 0.06 | 0.85 |
| L68 | D | −0.16 | 0.44 | 0.55 |
| L68 | E | 1.44 | 0.13 | 0.87 |
| L68 | F | 0.70 | 0.25 | 1.00 |
| L68 | G | 1.09 | −0.08 | 1.00 |
| L68 | H | 1.05 | 0.22 | 0.89 |
| L68 | I | 1.13 | 0.73 | 0.86 |
| L68 | L | 1.00 | 1.00 | 1.00 |
| L68 | M | 0.59 | 0.03 | 0.99 |
| L68 | N | 0.51 | 0.10 | 0.95 |
| L68 | P | 0.29 | 0.35 | 0.82 |
| L68 | Q | 0.50 | 0.25 | 0.90 |
| L68 | R | 0.19 | 0.47 | 0.75 |
| L68 | S | 0.99 | 0.07 | 0.93 |
| L68 | T | 1.03 | 0.32 | 0.92 |
| L68 | V | 1.09 | 0.51 | 1.01 |
| L68 | W | 1.21 | 0.56 | 0.88 |
| L68 | Y | 0.71 | 0.45 | 0.97 |
| N69 | A | 0.92 | 1.13 | 0.93 |
| N69 | C | 1.05 | 1.20 | 1.18 |
| N69 | D | 0.90 | 1.11 | 1.05 |
| N69 | G | 1.20 | 0.98 | 1.06 |

TABLE 10-12-continued

Performance Indices

| Wild-Type Res./Pos. | Mut. | PAF PI | PAD PI | Prot. PI |
|---|---|---|---|---|
| N69 | H | 1.36 | 1.52 | 0.73 |
| N69 | I | 1.47 | 1.75 | 0.69 |
| N69 | K | 1.72 | 1.59 | 0.84 |
| N69 | L | 1.30 | 1.20 | 0.36 |
| N69 | N | 1.00 | 1.00 | 1.00 |
| N69 | P | 1.00 | 0.59 | 0.66 |
| N69 | Q | 1.07 | 1.14 | 0.74 |
| N69 | R | 1.49 | 0.83 | 0.84 |
| N69 | S | 1.21 | 1.42 | 1.03 |
| N69 | T | 1.35 | 1.43 | 0.87 |
| N69 | V | 1.99 | 1.73 | 0.87 |
| N69 | W | 1.05 | 0.55 | 0.36 |
| N69 | Y | 0.88 | 0.17 | 0.44 |
| G70 | A | 0.85 | 1.41 | 1.08 |
| G70 | C | 0.12 | −0.90 | 0.40 |
| G70 | E | −0.16 | 0.33 | 0.28 |
| G70 | F | 0.00 | −0.36 | 0.21 |
| G70 | G | 1.00 | 1.00 | 1.00 |
| G70 | H | 0.04 | 1.90 | 0.26 |
| G70 | I | 0.04 | 0.27 | 0.33 |
| G70 | K | 0.03 | −0.80 | 0.26 |
| G70 | L | 0.03 | 1.01 | 0.30 |
| G70 | M | 0.62 | −0.72 | 0.29 |
| G70 | N | 0.02 | −0.76 | 0.37 |
| G70 | P | 0.16 | −0.58 | 0.29 |
| G70 | Q | 0.02 | −0.83 | 0.36 |
| G70 | R | 0.08 | −1.84 | 0.25 |
| G70 | S | 0.69 | 0.64 | 0.88 |
| G70 | T | 0.27 | −0.10 | 0.45 |
| G70 | V | 0.16 | −0.52 | 0.34 |
| G70 | Y | 0.08 | −0.33 | 0.38 |
| A71 | A | 1.00 | 1.00 | 1.00 |
| A71 | C | 1.01 | 0.99 | 0.85 |
| A71 | D | 0.70 | 0.65 | 0.68 |
| A71 | E | 1.45 | 0.81 | 0.83 |
| A71 | F | 1.13 | 0.99 | 0.75 |
| A71 | G | 1.59 | 0.68 | 0.85 |
| A71 | H | 1.70 | 0.78 | 0.75 |
| A71 | I | 1.51 | 0.79 | 0.81 |
| A71 | K | 1.44 | 1.01 | 0.76 |
| A71 | L | 1.23 | 0.84 | 0.85 |
| A71 | M | 0.98 | 1.11 | 0.81 |
| A71 | N | 1.23 | 0.61 | 0.77 |
| A71 | P | −0.14 | −0.05 | 0.46 |
| A71 | R | 1.40 | 0.77 | 0.71 |
| A71 | S | 1.75 | 0.69 | 0.84 |
| A71 | T | 1.70 | 0.79 | 0.83 |
| S72 | A | 0.55 | 3.52 | 1.06 |
| S72 | C | 0.56 | 2.18 | 0.96 |
| S72 | D | 0.40 | 0.80 | 0.90 |
| S72 | E | 0.61 | 0.93 | 0.99 |
| S72 | F | 0.94 | 1.15 | 0.80 |
| S72 | G | 1.20 | 1.76 | 0.87 |
| S72 | H | 1.21 | 2.48 | 0.82 |
| S72 | L | 1.26 | 0.70 | 1.07 |
| S72 | M | 0.36 | 2.13 | 0.94 |
| S72 | N | 0.42 | 2.85 | 0.99 |
| S72 | P | −0.25 | 0.56 | 0.63 |
| S72 | Q | 0.62 | 0.66 | 0.98 |
| S72 | R | 0.86 | 0.74 | 0.87 |
| S72 | S | 1.00 | 1.00 | 1.00 |
| S72 | T | 1.10 | 0.97 | 0.88 |
| S72 | V | 1.08 | 0.83 | 0.90 |
| S72 | W | 0.98 | 0.34 | 0.92 |
| S72 | Y | 1.07 | 0.07 | 1.03 |
| Y73 | A | −0.10 | 1.40 | 0.82 |
| Y73 | C | −0.10 | 1.20 | 1.18 |
| Y73 | D | 0.13 | 0.80 | 1.09 |
| Y73 | G | 0.71 | 0.51 | 0.95 |
| Y73 | H | 0.67 | 0.52 | 0.96 |
| Y73 | I | 0.82 | 0.64 | 0.97 |
| Y73 | K | 1.07 | 0.94 | 0.95 |
| Y73 | L | 0.98 | 0.50 | 1.03 |
| Y73 | M | −0.10 | 1.13 | 1.05 |
| Y73 | N | 0.56 | 0.76 | 1.25 |
| Y73 | P | 0.64 | −0.54 | 0.42 |
| Y73 | Q | 1.23 | 0.87 | 1.20 |
| Y73 | R | 1.26 | 0.26 | 0.96 |
| Y73 | S | 1.17 | 0.68 | 0.77 |
| Y73 | V | 0.88 | 0.74 | 1.08 |
| Y73 | Y | −0.10 | −0.10 | −0.02 |
| L74 | A | 0.07 | 2.90 | 1.01 |
| L74 | D | −0.18 | −0.18 | −0.03 |
| L74 | F | 0.99 | 1.13 | 0.58 |
| L74 | G | 1.95 | 0.57 | 0.18 |
| L74 | H | −0.18 | −0.18 | −0.03 |
| L74 | I | 0.86 | 0.64 | 1.45 |
| L74 | L | 1.00 | 1.00 | 1.00 |
| L74 | M | 0.15 | 1.21 | 0.79 |
| L74 | P | −0.18 | −0.18 | −0.03 |
| L74 | Q | −0.18 | −0.18 | −0.03 |
| L74 | R | −0.18 | −0.18 | −0.03 |
| L74 | S | 2.72 | −1.52 | 0.25 |
| L74 | T | −0.18 | −0.18 | −0.03 |
| L74 | V | 0.90 | 0.61 | 1.18 |
| L74 | W | 1.38 | 0.67 | 0.50 |
| L74 | Y | 0.90 | 0.86 | 1.19 |
| P75 | C | 0.54 | 1.42 | 1.06 |
| P75 | D | 0.67 | 2.09 | 0.86 |
| P75 | E | 0.83 | 1.19 | 1.00 |
| P75 | G | 1.16 | 0.93 | 0.81 |
| P75 | H | 1.05 | 0.86 | 0.89 |
| P75 | I | 0.69 | 0.74 | 0.78 |
| P75 | K | 0.60 | 0.88 | 0.91 |
| P75 | L | 0.44 | 1.19 | 1.02 |
| P75 | M | 0.36 | 0.30 | 1.22 |
| P75 | P | 1.00 | 1.00 | 1.00 |
| P75 | Q | 1.21 | 0.61 | 1.04 |
| P75 | R | 1.60 | 0.46 | 0.89 |
| P75 | S | 1.39 | 0.63 | 1.18 |
| P75 | T | 1.28 | 0.69 | 1.10 |
| P75 | V | 0.93 | 1.39 | 0.90 |
| P75 | W | 1.04 | 1.31 | 0.84 |
| P75 | Y | 0.69 | 1.32 | 1.08 |
| S76 | A | 0.38 | 1.11 | 0.60 |
| S76 | C | 0.39 | 1.06 | 0.67 |
| S76 | D | 0.41 | 1.94 | 0.49 |
| S76 | E | 0.47 | 2.09 | 0.58 |
| S76 | F | 0.44 | 0.46 | 0.68 |
| S76 | G | 0.64 | 2.15 | 0.69 |
| S76 | H | 0.85 | 1.11 | 0.79 |
| S76 | K | 0.59 | 1.53 | 0.32 |
| S76 | L | 0.74 | 4.70 | 0.27 |
| S76 | M | 0.49 | 1.61 | 0.45 |
| S76 | P | 1.23 | 1.20 | 0.67 |
| S76 | Q | 0.84 | 0.90 | 0.88 |
| S76 | S | 1.00 | 1.00 | 1.00 |
| S76 | T | 0.75 | 1.11 | 0.80 |
| S76 | V | 0.67 | 1.35 | 0.78 |
| S76 | W | 0.57 | −0.25 | 1.06 |
| S76 | Y | 0.31 | 0.18 | 0.75 |
| C77 | A | 0.83 | 0.91 | 1.20 |
| C77 | C | 1.00 | 1.00 | 1.00 |
| C77 | D | 0.92 | 1.05 | 0.45 |
| C77 | F | 0.25 | −0.61 | 0.75 |
| C77 | G | 1.01 | 0.18 | 0.53 |
| C77 | L | 0.98 | 0.73 | 1.44 |
| C77 | N | −0.13 | −0.06 | −0.04 |
| C77 | P | −0.13 | −0.06 | −0.04 |
| C77 | R | 0.70 | −1.02 | 0.34 |
| C77 | S | 0.95 | 0.76 | 1.19 |
| C77 | T | 1.12 | 1.03 | 1.18 |
| C77 | V | 1.05 | 0.80 | 1.33 |
| C77 | W | 0.39 | −0.24 | 0.73 |
| C77 | Y | 0.95 | −0.01 | 0.66 |
| L78 | A | −0.11 | −0.14 | −0.01 |
| L78 | C | 0.92 | 0.78 | 0.91 |
| L78 | E | 3.01 | −1.14 | 0.16 |

TABLE 10-12-continued

Performance Indices

| Wild-Type Res./Pos. | Mut. | PAF PI | PAD PI | Prot. PI |
|---|---|---|---|---|
| L78 | G | 4.98 | 1.38 | 0.12 |
| L78 | H | 4.82 | 1.57 | 0.25 |
| L78 | I | 1.43 | 1.11 | 1.06 |
| L78 | L | 1.00 | 1.00 | 1.00 |
| L78 | M | 0.52 | 0.48 | 0.75 |
| L78 | N | 2.68 | −0.41 | 0.22 |
| L78 | P | −0.11 | −0.41 | −0.01 |
| L78 | Q | 1.73 | 0.52 | 0.46 |
| L78 | R | −0.11 | −0.14 | −0.01 |
| L78 | S | −0.11 | −0.14 | −0.01 |
| L78 | T | 1.87 | 1.10 | 0.47 |
| L78 | V | 1.53 | 0.83 | 1.04 |
| L78 | Y | 1.39 | 0.81 | 0.46 |
| A79 | A | −0.15 | −0.13 | −0.02 |
| A79 | C | 0.97 | 0.03 | 1.16 |
| A79 | E | 1.12 | 0.27 | 1.12 |
| A79 | F | −0.15 | −2.02 | 0.17 |
| A79 | G | 0.92 | 0.92 | 0.99 |
| A79 | H | 1.93 | −0.09 | 0.85 |
| A79 | I | 1.59 | 0.67 | 0.87 |
| A79 | L | 1.80 | 0.96 | 0.88 |
| A79 | M | 1.50 | 0.28 | 1.04 |
| A79 | N | 1.48 | 0.28 | 0.97 |
| A79 | P | 0.70 | 0.94 | 0.81 |
| A79 | Q | 1.47 | 0.27 | 1.05 |
| A79 | R | 1.47 | 0.32 | 1.02 |
| A79 | S | 0.82 | 0.78 | 1.09 |
| A79 | T | 1.17 | 0.60 | 0.90 |
| A79 | V | −0.15 | −0.13 | −0.02 |
| A79 | W | 1.27 | 0.53 | 0.46 |
| T80 | A | 1.00 | 1.11 | 0.90 |
| T80 | C | 1.31 | 1.15 | 0.91 |
| T80 | E | 0.07 | −0.16 | 1.02 |
| T80 | G | 1.16 | 1.50 | 0.81 |
| T80 | H | 0.21 | 0.05 | 0.66 |
| T80 | I | 0.50 | 0.15 | 0.78 |
| T80 | K | 0.15 | −0.32 | 0.74 |
| T80 | L | 0.15 | −0.11 | 0.68 |
| T80 | N | 0.53 | 0.53 | 0.97 |
| T80 | P | −0.11 | −0.05 | 0.55 |
| T80 | Q | 0.91 | 1.07 | 1.02 |
| T80 | R | 0.08 | −0.22 | 0.78 |
| T80 | S | 0.96 | 1.40 | 1.12 |
| T80 | T | 1.00 | 1.00 | 1.00 |
| T80 | V | 1.23 | 1.01 | 0.93 |
| T80 | W | 0.23 | −0.86 | 0.46 |
| T80 | Y | 0.15 | 0.11 | 0.69 |
| H81 | A | 1.15 | 1.45 | 0.98 |
| H81 | C | 1.13 | 1.09 | 0.92 |
| H81 | F | 1.10 | 0.90 | 0.87 |
| H81 | G | 1.17 | 0.80 | 0.94 |
| H81 | H | 1.00 | 1.00 | 1.00 |
| H81 | K | 1.52 | 0.56 | 0.31 |
| H81 | L | 1.23 | 1.03 | 0.93 |
| H81 | M | 0.94 | 1.54 | 0.82 |
| H81 | N | 1.17 | 1.00 | 0.82 |
| H81 | P | −0.10 | 0.72 | 0.42 |
| H81 | Q | 0.85 | 0.75 | 1.00 |
| H81 | R | 0.34 | −0.29 | 0.85 |
| H81 | S | 1.04 | 0.69 | 0.94 |
| H81 | V | 1.10 | 0.71 | 0.89 |
| H81 | W | 1.13 | 1.09 | 0.90 |
| H81 | Y | 0.77 | 0.14 | 0.76 |
| L82 | A | 0.62 | 0.98 | 1.00 |
| L82 | G | 1.38 | 0.31 | 1.24 |
| L82 | H | 1.33 | 0.47 | 0.95 |
| L82 | I | 1.17 | 0.51 | 0.58 |
| L82 | K | 1.19 | 0.51 | 1.03 |
| L82 | L | 1.00 | 1.00 | 1.00 |
| L82 | M | 0.65 | 1.06 | 1.07 |
| L82 | P | 1.46 | 0.52 | 1.11 |
| L82 | R | 1.34 | −0.18 | 1.15 |
| L82 | S | 1.15 | 0.00 | 1.13 |
| L82 | T | 1.18 | 0.38 | 0.97 |
| L82 | V | 1.02 | 0.19 | 1.14 |
| L82 | W | 0.27 | −0.46 | 0.93 |
| P83 | A | 0.36 | 2.36 | 0.66 |
| P83 | C | 0.53 | 1.01 | 0.81 |
| P83 | D | 0.75 | 0.83 | 0.92 |
| P83 | E | 0.84 | 1.26 | 0.92 |
| P83 | F | 0.76 | 0.99 | 0.69 |
| P83 | G | 1.31 | 0.68 | 1.01 |
| P83 | H | 1.27 | 0.61 | 0.93 |
| P83 | K | 1.37 | 1.16 | 0.88 |
| P83 | L | 0.04 | 0.21 | 0.19 |
| P83 | M | 0.58 | 1.88 | 0.71 |
| P83 | N | 0.70 | 1.10 | 0.90 |
| P83 | P | 1.00 | 1.00 | 1.00 |
| P83 | Q | 0.73 | 0.82 | 0.95 |
| P83 | R | 1.19 | 1.09 | 0.78 |
| P83 | S | 1.17 | 0.79 | 0.89 |
| P83 | T | 0.86 | −0.02 | 0.62 |
| P83 | V | 0.78 | 0.19 | 0.72 |
| P83 | W | 0.98 | 0.62 | 0.69 |
| L84 | A | 0.45 | 0.45 | 0.76 |
| L84 | D | 0.19 | 0.85 | 0.48 |
| L84 | F | 0.72 | 1.01 | 0.74 |
| L84 | G | 0.77 | 1.01 | 0.53 |
| L84 | H | 1.01 | 0.99 | 0.66 |
| L84 | I | 0.90 | 0.87 | 0.99 |
| L84 | K | 1.10 | 0.79 | 0.59 |
| L84 | L | 1.00 | 1.00 | 1.00 |
| L84 | N | 0.54 | 0.67 | 0.86 |
| L84 | P | −0.12 | 0.43 | 0.58 |
| L84 | Q | 0.41 | 0.52 | 0.93 |
| L84 | R | 0.56 | 0.57 | 0.71 |
| L84 | S | 0.75 | 0.55 | 0.93 |
| L84 | T | 0.86 | 0.44 | 0.95 |
| L84 | V | 0.79 | 0.42 | 1.23 |
| L84 | W | 0.36 | −0.28 | 0.91 |
| D85 | A | 0.79 | 1.09 | 0.63 |
| D85 | C | 0.88 | 1.50 | 0.56 |
| D85 | D | 1.00 | 1.00 | 1.00 |
| D85 | E | 1.12 | 1.25 | 0.97 |
| D85 | F | 1.01 | 1.98 | 0.52 |
| D85 | G | 1.41 | 1.60 | 0.69 |
| D85 | H | 1.55 | 1.24 | 0.76 |
| D85 | I | 0.55 | 0.10 | 0.46 |
| D85 | L | 0.53 | 0.24 | 0.52 |
| D85 | N | 1.54 | 0.78 | 0.86 |
| D85 | P | 0.97 | 0.54 | 0.63 |
| D85 | Q | 3.09 | 0.99 | 0.82 |
| D85 | R | 2.38 | 1.03 | 0.66 |
| D85 | S | 2.28 | 0.68 | 0.93 |
| D85 | T | 1.33 | 0.71 | 0.77 |
| D85 | V | 0.61 | 0.25 | 0.65 |
| D85 | W | 0.87 | 0.34 | 0.72 |
| D85 | Y | 0.98 | 0.55 | 0.78 |
| L86 | A | 1.38 | 3.32 | 0.40 |
| L86 | C | 1.16 | 2.44 | 0.85 |
| L86 | E | 0.06 | −0.92 | 0.46 |
| L86 | F | −0.15 | −0.26 | −0.02 |
| L86 | G | 1.15 | 0.70 | 0.83 |
| L86 | H | 0.88 | −0.72 | 0.57 |
| L86 | L | 1.00 | 1.00 | 1.00 |
| L86 | P | −0.15 | 0.99 | 0.22 |
| L86 | Q | −0.15 | −2.60 | 3.66 |
| L86 | R | 0.43 | −4.46 | 0.26 |
| L86 | S | 0.78 | −0.36 | 0.78 |
| L86 | T | 0.96 | 0.28 | 0.75 |
| L86 | V | 0.92 | 0.12 | 0.93 |
| L86 | W | 0.67 | 0.08 | 0.78 |
| L86 | Y | 0.85 | 0.82 | 0.92 |
| V87 | A | 0.65 | 0.17 | 0.88 |
| V87 | C | 0.67 | 2.22 | 0.93 |
| V87 | D | −0.09 | −2.53 | 0.32 |
| V87 | F | 0.60 | 0.10 | 0.56 |
| V87 | G | 0.46 | −2.95 | 0.54 |

TABLE 10-12-continued

Performance Indices

| Wild-Type Res./Pos. | Mut. | PAF PI | PAD PI | Prot. PI |
|---|---|---|---|---|
| V87 | K | 0.04 | −8.34 | 0.26 |
| V87 | L | 0.71 | 4.30 | 0.84 |
| V87 | M | 0.73 | 0.75 | 0.86 |
| V87 | P | 0.07 | 1.64 | 0.39 |
| V87 | R | 0.07 | −1.33 | 0.44 |
| V87 | S | 0.59 | −0.09 | 0.67 |
| V87 | T | 0.63 | 0.15 | 0.71 |
| V87 | V | 1.00 | 1.00 | 1.00 |
| V87 | Y | 0.33 | −1.24 | 0.42 |
| I88 | G | 1.01 | −2.63 | 0.27 |
| I88 | H | 1.20 | −6.25 | 0.21 |
| I88 | I | 1.00 | 1.00 | 1.00 |
| I88 | M | 0.24 | 1.09 | 0.86 |
| I88 | N | −0.14 | −0.55 | 0.29 |
| I88 | P | −0.14 | 3.51 | 0.18 |
| I88 | Q | 0.01 | −1.10 | 0.36 |
| I88 | R | −0.14 | −0.32 | −0.02 |
| I88 | T | 1.03 | −0.16 | 0.52 |
| I88 | Y | −0.14 | −0.32 | −0.02 |
| I89 | A | 0.55 | 1.83 | 0.63 |
| I89 | D | −0.10 | −0.14 | −0.02 |
| I89 | E | −0.10 | −2.05 | 0.24 |
| I89 | F | 0.68 | 0.75 | 0.90 |
| I89 | G | 0.64 | −3.84 | 0.29 |
| I89 | H | 1.00 | −1.01 | 0.33 |
| I89 | I | 1.00 | 1.00 | 1.00 |
| I89 | L | 0.87 | 1.22 | 1.07 |
| I89 | P | 0.38 | 1.91 | 0.30 |
| I89 | Q | 0.25 | −0.30 | 0.32 |
| I89 | R | −0.10 | −0.14 | −0.02 |
| I89 | S | 0.71 | −1.66 | 0.49 |
| I89 | T | 0.94 | 0.90 | 0.60 |
| I89 | V | 0.91 | 0.82 | 1.09 |
| I89 | W | 0.53 | −2.63 | 0.27 |
| M90 | A | 0.78 | 1.41 | 0.67 |
| M90 | C | 0.79 | 1.09 | 0.83 |
| M90 | D | −0.24 | 2.88 | 0.15 |
| M90 | E | −0.24 | 1.15 | 0.29 |
| M90 | G | 0.57 | −1.22 | 0.33 |
| M90 | I | 1.13 | 0.66 | 0.74 |
| M90 | L | 1.02 | 0.98 | 0.84 |
| M90 | M | 1.00 | 1.00 | 1.00 |
| M90 | P | −0.24 | −0.36 | 0.28 |
| M90 | Q | 0.68 | 0.77 | 0.71 |
| M90 | R | −0.24 | 0.36 | 0.23 |
| M90 | S | 1.06 | −0.17 | 0.56 |
| M90 | T | 1.27 | 0.15 | 0.59 |
| M90 | V | 1.08 | 0.08 | 0.62 |
| M90 | W | 0.79 | −4.04 | 0.21 |
| L91 | A | 0.57 | 1.45 | 0.81 |
| L91 | C | 0.67 | 1.27 | 0.87 |
| L91 | D | −0.12 | 1.47 | 0.12 |
| L91 | E | −0.12 | −0.51 | 0.13 |
| L91 | G | 1.21 | −0.58 | 0.17 |
| L91 | H | −0.12 | −0.13 | −0.01 |
| L91 | I | 0.98 | 1.05 | 0.89 |
| L91 | K | −0.12 | −0.13 | −0.01 |
| L91 | L | 1.00 | 1.00 | 1.00 |
| L91 | M | 0.28 | 0.88 | 0.80 |
| L91 | P | −0.12 | −0.13 | −0.01 |
| L91 | Q | 0.05 | −0.14 | 0.18 |
| L91 | R | −0.12 | −0.13 | −0.01 |
| L91 | S | 0.92 | 0.43 | 0.24 |
| L91 | T | 1.06 | −0.11 | 0.36 |
| L91 | V | 0.94 | 0.79 | 0.72 |
| L91 | W | −0.12 | −0.13 | −0.01 |
| L91 | Y | −0.12 | −0.13 | −0.01 |
| G92 | A | −0.10 | −0.18 | −0.02 |
| G92 | C | −0.10 | 2.05 | 0.18 |
| G92 | D | −0.10 | −0.18 | −0.02 |
| G92 | E | −0.10 | −2.31 | 0.21 |
| G92 | F | −0.10 | −3.24 | 0.17 |
| G92 | G | 1.00 | 1.00 | 1.00 |
| G92 | L | −0.10 | −0.18 | −0.02 |
| G92 | M | −0.10 | −0.18 | −0.02 |
| G92 | P | −0.10 | −0.18 | −0.02 |
| G92 | R | −0.10 | −0.18 | −0.02 |
| G92 | S | 1.26 | −2.96 | 0.21 |
| G92 | T | −0.10 | −0.18 | −0.02 |
| G92 | V | 1.49 | −3.03 | 0.20 |
| G92 | W | −0.10 | −0.18 | −0.02 |
| G92 | Y | −0.10 | −0.18 | −0.02 |
| T93 | A | 1.38 | 1.05 | 0.50 |
| T93 | C | 1.08 | 0.95 | 0.64 |
| T93 | D | −0.18 | 0.23 | 0.22 |
| T93 | F | 3.52 | 0.54 | 0.63 |
| T93 | P | −0.18 | −0.19 | −0.02 |
| T93 | Q | −0.18 | −6.75 | 2.03 |
| T93 | R | −0.18 | −0.19 | −0.02 |
| T93 | S | 0.89 | 0.49 | 0.89 |
| T93 | T | 1.00 | 1.00 | 1.00 |
| T93 | V | −0.18 | −0.19 | −0.02 |
| T93 | W | −0.18 | −0.19 | −0.02 |
| T93 | Y | 5.26 | 0.03 | 0.77 |
| N94 | A | −0.45 | 0.74 | 0.96 |
| N94 | C | 0.01 | 0.07 | 0.94 |
| N94 | G | 0.15 | 0.53 | 0.76 |
| N94 | H | 0.11 | −0.94 | 0.77 |
| N94 | L | 0.61 | −0.18 | 0.49 |
| N94 | M | −0.45 | 0.03 | 0.94 |
| N94 | N | 1.00 | 1.00 | 1.00 |
| N94 | P | −0.45 | 0.79 | 0.40 |
| N94 | R | 0.10 | −8.20 | 0.19 |
| N94 | S | 0.10 | 0.88 | 0.84 |
| N94 | T | 0.25 | −1.43 | 0.66 |
| N94 | V | 0.15 | −0.39 | 0.65 |
| N94 | W | 0.10 | −1.20 | 0.69 |
| N94 | Y | 0.08 | 0.12 | 0.76 |
| D95 | A | −0.14 | −0.14 | −0.01 |
| D95 | C | −0.14 | −0.14 | −0.01 |
| D95 | D | 1.00 | 1.00 | 1.00 |
| D95 | E | 2.04 | 0.75 | 0.66 |
| D95 | G | −0.14 | −0.14 | −0.01 |
| D95 | H | −0.14 | −0.14 | −0.01 |
| D95 | K | −0.14 | −0.14 | −0.01 |
| D95 | L | −0.14 | −0.14 | −0.01 |
| D95 | N | −0.14 | −0.14 | −0.01 |
| D95 | Q | −0.14 | −0.14 | −0.01 |
| D95 | R | −0.14 | −0.14 | −0.01 |
| D95 | S | −0.14 | −0.14 | −0.01 |
| D95 | T | −0.14 | −0.14 | −0.01 |
| D95 | V | −0.14 | −0.14 | −0.01 |
| D95 | W | −0.14 | −0.14 | −0.01 |
| D95 | Y | −0.14 | −0.14 | −0.01 |
| T96 | A | 0.36 | 4.20 | 1.32 |
| T96 | C | 0.44 | 3.76 | 0.79 |
| T96 | F | 0.53 | 1.24 | 0.69 |
| T96 | G | 0.78 | 1.28 | 1.03 |
| T96 | I | 0.95 | −0.22 | 0.88 |
| T96 | L | 0.92 | 1.93 | 0.93 |
| T96 | M | 0.39 | 2.53 | 0.80 |
| T96 | P | −0.11 | 0.89 | 0.35 |
| T96 | R | 0.17 | 0.14 | 0.50 |
| T96 | S | 1.04 | 0.79 | 1.05 |
| T96 | T | 1.00 | 1.00 | 1.00 |
| T96 | V | 0.81 | 0.59 | 1.12 |
| T96 | W | 0.38 | −4.29 | 0.51 |
| T96 | Y | 0.38 | −3.73 | 0.59 |
| K97 | A | 0.01 | 0.23 | 1.11 |
| K97 | D | −0.23 | −0.17 | −0.01 |
| K97 | G | 0.84 | −0.64 | 0.39 |
| K97 | I | 0.74 | −0.55 | 0.47 |
| K97 | K | 1.00 | 1.00 | 1.00 |
| K97 | L | 0.38 | −0.28 | 0.30 |
| K97 | M | 0.02 | 0.22 | 0.95 |
| K97 | P | 0.16 | 0.27 | 0.36 |
| K97 | Q | 1.14 | 0.00 | 0.73 |
| K97 | R | 2.80 | 0.59 | 1.02 |

TABLE 10-12-continued

Performance Indices

| Wild-Type Res./Pos. | Mut. | PAF PI | PAD PI | Prot. PI |
|---|---|---|---|---|
| K97 | S | 0.28 | −0.46 | 0.58 |
| K97 | T | 0.22 | −0.42 | 0.51 |
| K97 | V | 0.31 | −0.45 | 0.51 |
| K97 | W | 0.42 | −2.32 | 0.13 |
| K97 | Y | 0.29 | −0.65 | 0.38 |
| A98 | A | 1.00 | 1.00 | 1.00 |
| A98 | C | 1.30 | 1.42 | 1.00 |
| A98 | D | 1.11 | 2.19 | 0.81 |
| A98 | G | 1.57 | 0.56 | 0.97 |
| A98 | H | 2.09 | 0.92 | 0.82 |
| A98 | I | 2.05 | 0.65 | 0.72 |
| A98 | L | 2.22 | 1.47 | 0.71 |
| A98 | N | 1.24 | 1.40 | 1.01 |
| A98 | P | 1.10 | 1.26 | 0.90 |
| A98 | S | 1.73 | 0.65 | 1.17 |
| A98 | T | 1.72 | 0.27 | 1.03 |
| A98 | Y | 2.02 | 1.15 | 0.87 |
| Y99 | A | 0.66 | 0.82 | 1.29 |
| Y99 | G | 0.83 | 0.70 | 1.23 |
| Y99 | H | 0.77 | 0.59 | 1.30 |
| Y99 | I | 0.81 | 0.61 | 1.11 |
| Y99 | L | 0.66 | 0.86 | 1.39 |
| Y99 | P | 0.89 | 0.81 | 1.00 |
| Y99 | R | 0.61 | 0.29 | 0.97 |
| Y99 | S | 0.72 | 0.37 | 1.45 |
| Y99 | V | 0.61 | 0.31 | 1.28 |
| Y99 | W | 0.68 | 0.57 | 1.20 |
| Y99 | Y | 1.00 | 1.00 | 1.00 |
| F100 | A | 0.78 | 2.02 | 0.93 |
| F100 | C | 0.73 | 1.28 | 0.78 |
| F100 | D | 0.38 | −0.03 | 0.33 |
| F100 | E | 1.01 | 0.15 | 0.83 |
| F100 | F | 1.00 | 1.00 | 1.00 |
| F100 | K | 0.65 | −0.60 | 0.53 |
| F100 | M | 0.79 | 2.19 | 1.20 |
| F100 | N | 0.91 | 1.45 | 1.12 |
| F100 | S | 0.87 | 0.85 | 1.02 |
| F100 | T | 0.95 | 1.42 | 0.71 |
| F100 | W | 1.08 | −0.03 | 1.06 |
| R101 | C | 0.71 | 0.95 | 0.96 |
| R101 | D | 0.85 | 0.80 | 1.02 |
| R101 | F | 0.84 | 0.97 | 0.66 |
| R101 | I | 0.79 | 0.96 | 0.68 |
| R101 | K | 1.24 | 0.07 | 0.90 |
| R101 | L | 0.83 | 1.12 | 1.33 |
| R101 | N | 0.72 | 0.92 | 1.11 |
| R101 | P | 0.50 | 0.86 | 0.75 |
| R101 | Q | 0.86 | 0.11 | 1.03 |
| R101 | R | 1.00 | 1.00 | 1.00 |
| R101 | V | 0.74 | 0.44 | 0.90 |
| R101 | W | 0.95 | 0.00 | 0.89 |
| R101 | Y | 0.74 | 0.80 | 0.67 |
| R102 | A | 0.19 | 1.79 | 0.98 |
| R102 | C | 0.22 | 0.36 | 0.78 |
| R102 | D | 0.01 | 0.68 | 0.26 |
| R102 | F | 0.46 | 0.23 | 0.31 |
| R102 | G | 0.44 | 0.27 | 0.43 |
| R102 | L | 0.33 | 1.64 | 0.95 |
| R102 | P | −0.07 | 0.89 | 0.26 |
| R102 | Q | 0.67 | 1.19 | 1.09 |
| R102 | R | 1.00 | 1.00 | 1.00 |
| R102 | S | 0.46 | 0.96 | 0.98 |
| R102 | V | 0.28 | 0.61 | 0.80 |
| R102 | W | 0.29 | −1.03 | 0.34 |
| R102 | Y | 0.40 | 1.29 | 0.70 |
| T103 | A | 0.97 | −9.64 | 0.89 |
| T103 | C | 0.90 | −6.91 | 0.89 |
| T103 | F | 0.74 | −3.39 | 0.85 |
| T103 | G | 1.11 | −5.27 | 1.20 |
| T103 | H | 0.99 | −4.15 | 1.14 |
| T103 | I | 1.08 | −5.15 | 0.89 |
| T103 | K | 1.09 | −4.36 | 1.05 |
| T103 | L | 1.05 | −1.86 | 0.88 |
| T103 | N | 0.77 | −6.03 | 1.07 |
| T103 | P | 0.69 | −5.11 | 1.01 |
| T103 | R | 0.87 | −6.30 | 0.96 |
| T103 | S | 0.92 | −1.36 | 1.14 |
| T103 | T | 1.00 | 1.00 | 1.00 |
| T103 | V | 0.95 | −1.95 | 0.90 |
| T103 | W | 1.26 | −2.60 | 0.77 |
| T103 | Y | 1.19 | −4.68 | 0.88 |
| P104 | A | −0.41 | −0.19 | −0.04 |
| P104 | C | 1.95 | 1.83 | 1.34 |
| P104 | E | 1.84 | 1.97 | 1.37 |
| P104 | F | 1.79 | 0.86 | 0.67 |
| P104 | G | 2.67 | 0.98 | 1.25 |
| P104 | H | 2.84 | 1.03 | 1.11 |
| P104 | I | 2.43 | 2.05 | 1.07 |
| P104 | L | −0.41 | −0.19 | −0.04 |
| P104 | M | 1.09 | 2.24 | 1.01 |
| P104 | N | 1.62 | 1.44 | 1.32 |
| P104 | P | 1.00 | 1.00 | 1.00 |
| P104 | Q | 1.34 | 0.85 | 1.24 |
| P104 | R | 1.62 | −0.39 | 0.83 |
| P104 | S | 2.48 | 0.53 | 1.44 |
| P104 | T | 2.70 | 0.33 | 1.29 |
| P104 | V | 2.59 | 1.02 | 1.40 |
| P104 | W | 2.05 | 0.23 | 0.59 |
| L105 | A | −0.11 | −0.18 | −0.02 |
| L105 | C | 1.56 | 1.92 | 1.05 |
| L105 | E | −0.11 | 0.53 | 0.26 |
| L105 | F | 1.30 | 1.73 | 0.95 |
| L105 | G | 1.08 | 1.40 | 1.07 |
| L105 | H | 0.85 | 1.23 | 1.07 |
| L105 | L | 1.00 | 1.00 | 1.00 |
| L105 | M | −0.11 | −0.18 | −0.02 |
| L105 | P | 1.71 | 0.90 | 1.00 |
| L105 | Q | 0.94 | 1.04 | 1.03 |
| L105 | R | 0.99 | 1.25 | 0.94 |
| L105 | S | 0.93 | 0.61 | 0.95 |
| L105 | T | 0.92 | 0.64 | 1.00 |
| L105 | V | 0.15 | −0.97 | 0.37 |
| L105 | W | 1.28 | 1.71 | 0.78 |
| L105 | Y | 0.72 | 0.62 | 1.18 |
| D106 | A | 0.72 | 1.13 | 0.69 |
| D106 | C | 1.01 | 1.10 | 0.80 |
| D106 | D | 1.00 | 1.00 | 1.00 |
| D106 | E | 1.08 | 1.09 | 1.02 |
| D106 | F | 1.02 | 1.45 | 0.34 |
| D106 | G | 1.18 | 1.45 | 0.67 |
| D106 | H | 1.09 | 1.18 | 0.66 |
| D106 | I | 1.04 | 0.92 | 0.45 |
| D106 | K | 1.28 | 1.24 | 0.68 |
| D106 | L | 1.20 | 1.00 | 0.56 |
| D106 | M | 0.73 | 0.86 | 0.77 |
| D106 | N | 0.92 | 0.64 | 0.91 |
| D106 | P | −0.17 | 0.63 | 0.18 |
| D106 | Q | 0.92 | 0.62 | 0.94 |
| D106 | R | 0.98 | 0.56 | 0.91 |
| D106 | S | 0.98 | 1.02 | 0.81 |
| D106 | T | 1.06 | 1.38 | 0.64 |
| D106 | V | 0.98 | 1.68 | 0.61 |
| D106 | W | 0.78 | 1.07 | 0.34 |
| I107 | A | 0.81 | 0.80 | 0.83 |
| I107 | C | 0.95 | 1.41 | 1.00 |
| I107 | E | 2.55 | −0.28 | 0.21 |
| I107 | F | 0.99 | −0.02 | 0.19 |
| I107 | G | 1.76 | −10.12 | 0.25 |
| I107 | H | −0.07 | −0.20 | −0.02 |
| I107 | I | 1.00 | 1.00 | 1.00 |
| I107 | L | 0.96 | 1.04 | 0.52 |
| I107 | N | 1.81 | 0.93 | 0.56 |
| I107 | P | 0.65 | 0.32 | 0.40 |
| I107 | Q | 0.53 | −0.02 | 0.43 |
| I107 | R | 0.08 | −2.75 | 0.28 |
| I107 | S | 2.04 | 1.33 | 1.05 |
| I107 | T | 0.64 | 1.53 | 0.95 |
| I107 | V | 1.00 | 0.97 | 1.04 |

TABLE 10-12-continued

Performance Indices

| Wild-Type Res./Pos. | Mut. | PAF PI | PAD PI | Prot. PI |
|---|---|---|---|---|
| I107 | W | −0.07 | −0.20 | −0.02 |
| I107 | Y | 0.49 | 0.52 | 0.23 |
| A108 | A | −0.12 | −0.07 | −0.02 |
| A108 | D | −0.12 | −0.07 | −0.02 |
| A108 | E | 0.14 | 0.61 | 0.25 |
| A108 | F | −0.12 | −0.07 | −0.02 |
| A108 | G | 0.99 | 1.13 | 1.15 |
| A108 | H | −0.12 | −0.07 | −0.02 |
| A108 | I | −0.12 | −0.07 | −0.02 |
| A108 | K | 0.60 | 2.97 | 0.31 |
| A108 | L | 1.41 | 2.56 | 0.20 |
| A108 | N | −0.12 | −0.07 | −0.02 |
| A108 | P | −0.12 | −0.07 | −0.02 |
| A108 | Q | 0.58 | 0.73 | 0.98 |
| A108 | R | −0.12 | −0.07 | −0.02 |
| A108 | S | 0.94 | 1.00 | 1.14 |
| A108 | T | 1.05 | 0.87 | 1.08 |
| A108 | V | 0.76 | 0.95 | 0.99 |
| L109 | A | 0.34 | 0.32 | 1.07 |
| L109 | D | 1.00 | 0.11 | 1.15 |
| L109 | E | 0.74 | 0.19 | 1.24 |
| L109 | F | 0.83 | 0.32 | 1.11 |
| L109 | G | 0.82 | 0.51 | 0.88 |
| L109 | H | 0.85 | 0.22 | 1.06 |
| L109 | I | 1.05 | 0.14 | 1.21 |
| L109 | L | 1.00 | 1.00 | 1.00 |
| L109 | M | 0.74 | 0.63 | 1.00 |
| L109 | N | 1.52 | 0.66 | 1.13 |
| L109 | P | 0.79 | 0.43 | 0.35 |
| L109 | Q | 1.18 | 0.22 | 1.08 |
| L109 | R | 0.48 | 0.21 | 0.95 |
| L109 | S | 0.79 | 0.38 | 0.94 |
| L109 | T | 0.63 | 0.79 | 0.87 |
| L109 | V | 0.52 | 0.54 | 1.06 |
| L109 | W | 1.30 | −0.02 | 0.88 |
| L109 | Y | 1.16 | 0.83 | 0.79 |
| G110 | A | 0.91 | 1.01 | 0.88 |
| G110 | C | 0.35 | 1.43 | 0.56 |
| G110 | D | 0.76 | 1.40 | 0.87 |
| G110 | E | 0.26 | 1.76 | 0.46 |
| G110 | F | 0.04 | 2.29 | 0.30 |
| G110 | G | 1.00 | 1.00 | 1.00 |
| G110 | H | 0.63 | 0.73 | 0.46 |
| G110 | I | 0.06 | 0.23 | 0.32 |
| G110 | L | −0.20 | −0.12 | −0.02 |
| G110 | M | 0.16 | 0.82 | 0.34 |
| G110 | N | 0.70 | 0.77 | 0.89 |
| G110 | P | 0.02 | 0.22 | 0.50 |
| G110 | Q | 0.44 | 0.34 | 0.77 |
| G110 | R | 0.05 | 0.48 | 0.45 |
| G110 | S | 0.79 | 0.30 | 1.01 |
| G110 | T | 0.45 | −0.05 | 0.42 |
| G110 | W | −0.20 | −1.18 | 0.20 |
| G110 | Y | 0.01 | −0.88 | 0.40 |
| M111 | A | 0.65 | 1.02 | 0.89 |
| M111 | C | 0.92 | 1.01 | 0.95 |
| M111 | D | −0.27 | 0.79 | 0.37 |
| M111 | E | 0.25 | 0.67 | 0.56 |
| M111 | F | 1.47 | 0.78 | 0.75 |
| M111 | G | 0.85 | 0.32 | 0.44 |
| M111 | H | 0.98 | 0.19 | 0.40 |
| M111 | I | 1.95 | 1.03 | 0.91 |
| M111 | K | 1.98 | 0.71 | 0.58 |
| M111 | L | 1.55 | 0.67 | 0.93 |
| M111 | M | 1.00 | 1.00 | 1.00 |
| M111 | N | 0.49 | 1.31 | 0.79 |
| M111 | P | −0.27 | 0.57 | 0.39 |
| M111 | R | 0.27 | −0.99 | 0.34 |
| M111 | S | 1.03 | 0.14 | 0.52 |
| M111 | T | 1.49 | 0.76 | 0.77 |
| M111 | V | 1.47 | 0.93 | 0.88 |
| M111 | W | 0.96 | 1.23 | 0.30 |
| M111 | Y | 1.43 | 1.06 | 0.65 |
| S112 | A | 0.58 | 0.94 | 0.98 |
| S112 | E | 0.71 | 1.16 | 1.05 |
| S112 | F | 0.37 | 0.88 | 0.61 |
| S112 | H | 1.00 | 0.38 | 0.93 |
| S112 | K | 0.84 | 0.68 | 0.92 |
| S112 | L | 1.03 | 1.00 | 0.80 |
| S112 | M | 0.43 | 0.56 | 0.98 |
| S112 | N | 0.52 | 0.85 | 1.09 |
| S112 | P | −0.19 | −0.82 | 0.33 |
| S112 | R | 0.20 | −0.44 | 0.99 |
| S112 | S | 1.00 | 1.00 | 1.00 |
| S112 | T | 0.95 | 0.72 | 0.87 |
| S112 | V | 0.86 | 0.48 | 0.73 |
| S112 | W | 0.74 | 0.58 | 0.85 |
| S112 | Y | 0.68 | −0.10 | 0.90 |
| V113 | A | 0.71 | 1.31 | 0.70 |
| V113 | C | 0.87 | 0.94 | 1.06 |
| V113 | D | 0.78 | 0.87 | 0.97 |
| V113 | E | 0.91 | 0.94 | 0.99 |
| V113 | F | 1.05 | 0.96 | 0.80 |
| V113 | G | 0.96 | 0.58 | 0.89 |
| V113 | H | 1.34 | 0.76 | 0.84 |
| V113 | K | 1.19 | 0.72 | 0.92 |
| V113 | L | 1.50 | 0.85 | 0.85 |
| V113 | M | 0.78 | 1.06 | 0.93 |
| V113 | N | 0.88 | 1.22 | 1.01 |
| V113 | P | 0.72 | 1.14 | 0.65 |
| V113 | Q | 1.03 | 1.11 | 0.94 |
| V113 | R | 1.13 | 1.11 | 0.82 |
| V113 | S | 0.80 | 0.57 | 0.91 |
| V113 | T | 0.94 | 0.86 | 0.89 |
| V113 | V | 1.00 | 1.00 | 1.00 |
| V113 | W | 0.91 | 0.80 | 0.76 |
| V113 | Y | 1.11 | 0.98 | 0.85 |
| L114 | A | 0.78 | 1.07 | 1.03 |
| L114 | C | 0.78 | 1.14 | 1.10 |
| L114 | E | 0.32 | −0.14 | 0.42 |
| L114 | F | −0.11 | −0.21 | −0.02 |
| L114 | G | 0.96 | 1.14 | 0.78 |
| L114 | H | 0.92 | −0.55 | 0.21 |
| L114 | I | 0.97 | 1.17 | 0.86 |
| L114 | K | −0.11 | −0.21 | −0.02 |
| L114 | L | 1.00 | 1.00 | 1.00 |
| L114 | M | 0.73 | 1.28 | 1.00 |
| L114 | N | 0.65 | 0.77 | 0.95 |
| L114 | P | 0.30 | 0.28 | 0.42 |
| L114 | Q | 0.59 | 0.12 | 0.68 |
| L114 | R | −0.11 | −0.21 | −0.02 |
| L114 | S | 0.87 | 0.55 | 0.72 |
| L114 | T | 0.88 | 1.05 | 0.82 |
| L114 | V | 0.91 | 0.60 | 0.84 |
| L114 | W | −0.11 | −0.21 | −0.02 |
| L114 | Y | −0.11 | −0.21 | −0.02 |
| V115 | A | 0.60 | 1.19 | 1.11 |
| V115 | C | 0.73 | 1.08 | 1.14 |
| V115 | D | −0.15 | 2.21 | 0.19 |
| V115 | F | 0.54 | 1.69 | 0.32 |
| V115 | G | 1.09 | 1.76 | 0.43 |
| V115 | H | −0.15 | −0.13 | −0.02 |
| V115 | I | 1.05 | 0.99 | 1.14 |
| V115 | K | −0.15 | −0.13 | −0.02 |
| V115 | L | 1.12 | 1.30 | 1.02 |
| V115 | M | 0.48 | 1.32 | 1.05 |
| V115 | P | −0.15 | 2.21 | 0.26 |
| V115 | Q | −0.15 | 1.15 | 0.32 |
| V115 | R | 0.10 | 1.63 | 0.21 |
| V115 | S | 0.95 | 1.14 | 0.72 |
| V115 | T | 1.15 | 1.28 | 0.72 |
| V115 | V | 1.00 | 1.00 | 1.00 |
| V115 | W | 1.23 | 2.48 | 0.17 |
| V115 | Y | 1.03 | 2.07 | 0.28 |
| T116 | A | 1.01 | 0.95 | 1.08 |
| T116 | C | 0.89 | 1.05 | 1.30 |
| T116 | E | 0.86 | 0.91 | 1.29 |
| T116 | G | 1.10 | 0.90 | 1.44 |

TABLE 10-12-continued

Performance Indices

| Wild-Type Res./Pos. | Mut. | PAF PI | PAD PI | Prot. PI |
|---|---|---|---|---|
| T116 | H | 1.00 | 1.08 | 1.48 |
| T116 | I | 0.80 | 0.76 | 0.82 |
| T116 | L | 0.77 | 0.68 | 1.03 |
| T116 | M | 0.83 | 1.39 | 1.28 |
| T116 | N | 0.93 | 1.05 | 1.68 |
| T116 | P | 0.74 | 0.84 | 0.99 |
| T116 | Q | 0.95 | 0.77 | 1.29 |
| T116 | R | 0.64 | 0.62 | 1.03 |
| T116 | S | 0.88 | 0.96 | 1.24 |
| T116 | T | 1.00 | 1.00 | 1.00 |
| T116 | V | 0.86 | 0.57 | 0.85 |
| T116 | W | 0.89 | 0.75 | 0.96 |
| T116 | Y | 0.90 | 0.47 | 1.09 |
| Q117 | A | 2.05 | 1.73 | 1.03 |
| Q117 | E | 1.15 | 1.21 | 1.10 |
| Q117 | F | 1.57 | 1.02 | 0.61 |
| Q117 | G | 2.08 | 0.79 | 0.97 |
| Q117 | H | 2.33 | 1.12 | 1.12 |
| Q117 | M | 1.54 | 1.89 | 0.87 |
| Q117 | P | −0.25 | 1.13 | 0.61 |
| Q117 | Q | 1.00 | 1.00 | 1.00 |
| Q117 | R | 1.56 | 1.05 | 1.00 |
| Q117 | S | 1.95 | 0.87 | 1.13 |
| Q117 | T | 2.23 | 1.10 | 1.06 |
| Q117 | V | 2.15 | 0.76 | 0.67 |
| Q117 | W | 2.16 | 0.71 | 0.57 |
| Q117 | Y | 2.23 | 1.13 | 0.76 |
| V118 | A | 0.84 | 0.85 | 1.20 |
| V118 | C | 0.78 | 1.14 | 1.28 |
| V118 | D | −0.14 | 0.40 | 0.38 |
| V118 | E | −0.14 | −0.43 | 0.37 |
| V118 | F | 0.86 | 1.00 | 0.89 |
| V118 | G | 1.08 | 0.56 | 0.67 |
| V118 | I | 0.96 | 0.55 | 1.01 |
| V118 | K | 1.13 | −2.50 | 0.28 |
| V118 | L | 0.93 | 1.05 | 0.93 |
| V118 | M | 0.60 | 0.93 | 0.90 |
| V118 | P | 0.12 | 0.22 | 0.52 |
| V118 | Q | 0.38 | 1.50 | 0.57 |
| V118 | R | 0.36 | 0.07 | 0.46 |
| V118 | S | 0.95 | 0.82 | 0.96 |
| V118 | T | 0.99 | 0.92 | 0.90 |
| V118 | V | 1.00 | 1.00 | 1.00 |
| V118 | W | 0.83 | −1.28 | 0.42 |
| V118 | Y | 1.25 | 1.34 | 0.60 |
| L119 | A | 0.81 | 1.02 | 1.18 |
| L119 | C | 0.76 | 0.24 | 1.18 |
| L119 | D | 0.24 | 0.28 | 0.97 |
| L119 | E | 0.45 | 0.32 | 1.04 |
| L119 | F | 0.56 | −0.61 | 0.93 |
| L119 | G | 0.93 | −0.06 | 0.97 |
| L119 | H | 0.91 | 0.46 | 0.89 |
| L119 | I | 0.90 | 0.43 | 1.06 |
| L119 | L | 1.00 | 1.00 | 1.00 |
| L119 | N | 0.58 | 0.11 | 1.14 |
| L119 | P | −0.14 | −0.01 | 0.71 |
| L119 | R | 0.43 | −0.66 | 1.00 |
| L119 | S | 0.83 | −0.17 | 1.05 |
| L119 | T | 0.97 | 0.10 | 0.94 |
| L119 | V | 0.89 | 0.15 | 1.04 |
| L119 | W | 0.77 | 0.20 | 0.88 |
| L119 | Y | 0.77 | 0.56 | 0.89 |
| T120 | A | 0.25 | 0.66 | 1.09 |
| T120 | C | 0.75 | 0.92 | 1.14 |
| T120 | E | 0.58 | 1.53 | 1.19 |
| T120 | H | 0.88 | 0.50 | 1.07 |
| T120 | I | 0.91 | 1.56 | 1.00 |
| T120 | K | 0.87 | 1.09 | 1.12 |
| T120 | L | 0.80 | 1.26 | 1.00 |
| T120 | M | 0.05 | 1.22 | 0.98 |
| T120 | N | 0.37 | 1.42 | 1.10 |
| T120 | P | 0.07 | −0.45 | 0.82 |
| T120 | Q | 0.26 | 0.78 | 1.05 |
| T120 | R | 0.24 | 0.60 | 0.99 |
| T120 | S | 1.09 | 1.07 | 1.35 |
| T120 | T | 1.00 | 1.00 | 1.00 |
| T120 | V | 0.26 | 1.07 | 0.93 |
| T120 | Y | 0.57 | 1.61 | 1.01 |
| S121 | A | 1.12 | 1.55 | 1.10 |
| S121 | C | 1.18 | 1.64 | 1.09 |
| S121 | E | 0.89 | 1.04 | 1.01 |
| S121 | G | 1.20 | 0.99 | 1.07 |
| S121 | K | 1.24 | 0.78 | 1.04 |
| S121 | L | 1.35 | 1.49 | 1.12 |
| S121 | N | 1.14 | 1.06 | 1.17 |
| S121 | P | 0.83 | 0.38 | 0.92 |
| S121 | Q | 0.92 | 1.09 | 1.01 |
| S121 | R | 1.26 | 0.70 | 1.06 |
| S121 | S | 1.00 | 1.00 | 1.00 |
| S121 | T | 1.13 | 1.26 | 0.93 |
| S121 | V | 1.12 | 1.59 | 0.97 |
| S121 | W | 1.33 | 0.77 | 0.91 |
| A122 | A | 1.00 | 1.00 | 1.00 |
| A122 | D | 0.26 | 0.06 | 0.77 |
| A122 | E | 0.71 | 0.47 | 1.04 |
| A122 | F | 0.97 | 0.15 | 0.87 |
| A122 | G | 0.93 | −0.42 | 0.85 |
| A122 | H | 1.14 | 0.17 | 1.00 |
| A122 | I | 1.13 | 0.65 | 1.04 |
| A122 | K | 1.08 | 0.45 | 0.96 |
| A122 | L | 0.93 | 1.02 | 1.07 |
| A122 | M | 0.81 | 0.94 | 1.06 |
| A122 | N | 0.83 | 0.70 | 1.11 |
| A122 | P | 0.61 | 0.55 | 1.07 |
| A122 | Q | 0.69 | 0.74 | 1.02 |
| A122 | R | 0.71 | 0.40 | 0.94 |
| A122 | S | 1.03 | 0.43 | 1.05 |
| A122 | T | 1.08 | 0.52 | 0.97 |
| A122 | V | 1.04 | 0.89 | 1.05 |
| A122 | W | 0.99 | 0.86 | 0.88 |
| G123 | A | 0.89 | 1.19 | 0.96 |
| G123 | C | 0.95 | 0.30 | 0.92 |
| G123 | D | 1.73 | 0.84 | 0.90 |
| G123 | E | 1.13 | 0.56 | 0.96 |
| G123 | F | 0.84 | 0.80 | 0.85 |
| G123 | G | 1.00 | 1.00 | 1.00 |
| G123 | H | 1.00 | 0.74 | 0.84 |
| G123 | K | 0.97 | 1.12 | 0.93 |
| G123 | L | 0.99 | 1.38 | 0.79 |
| G123 | M | 0.84 | 1.38 | 0.85 |
| G123 | N | 0.89 | 0.71 | 0.92 |
| G123 | P | 1.32 | 0.81 | 0.89 |
| G123 | Q | 0.01 | 0.31 | 0.37 |
| G123 | R | 0.66 | 0.60 | 0.83 |
| G123 | T | 1.06 | 0.54 | 0.85 |
| G123 | V | 1.40 | 0.59 | 0.89 |
| G123 | W | 0.95 | 1.39 | 0.77 |
| G123 | Y | 0.96 | 1.24 | 0.87 |
| G124 | A | 0.84 | 0.03 | 1.20 |
| G124 | C | 0.72 | 0.67 | 1.07 |
| G124 | D | 0.76 | 0.64 | 0.99 |
| G124 | F | 1.32 | 0.95 | 0.70 |
| G124 | G | 1.00 | 1.00 | 1.00 |
| G124 | H | 1.59 | −0.10 | 0.98 |
| G124 | I | 1.85 | −0.08 | 0.92 |
| G124 | L | 1.92 | 0.54 | 0.98 |
| G124 | M | 0.97 | −0.05 | 1.36 |
| G124 | N | 0.98 | 0.60 | 1.18 |
| G124 | P | −0.11 | −0.08 | 0.37 |
| G124 | Q | 1.12 | 0.21 | 1.02 |
| G124 | R | 1.14 | 0.41 | 0.88 |
| G124 | S | 1.27 | 0.56 | 1.00 |
| G124 | T | 1.64 | 0.32 | 0.97 |
| G124 | V | 1.44 | 0.33 | 0.93 |
| G124 | W | 0.73 | −0.31 | 0.84 |
| G124 | Y | 1.23 | 0.56 | 0.66 |
| V125 | A | 1.69 | 0.93 | 0.91 |
| V125 | C | 0.96 | 0.54 | 0.67 |

TABLE 10-12-continued

Performance Indices

| Wild-Type Res./Pos. | Mut. | PAF PI | PAD PI | Prot. PI |
|---|---|---|---|---|
| V125 | D | 1.24 | 0.54 | 0.76 |
| V125 | E | 0.81 | 0.39 | 0.73 |
| V125 | F | 0.96 | 0.63 | 0.77 |
| V125 | G | 2.95 | 1.09 | 0.60 |
| V125 | I | 1.01 | 0.94 | 1.05 |
| V125 | P | 1.50 | 0.62 | 0.83 |
| V125 | R | 1.30 | 0.47 | 0.82 |
| V125 | S | 1.94 | 0.79 | 0.75 |
| V125 | V | 1.00 | 1.00 | 1.00 |
| V125 | W | 0.37 | 0.25 | 0.48 |
| V125 | Y | 1.08 | 0.81 | 0.82 |
| G126 | A | 0.96 | 0.55 | 1.02 |
| G126 | C | 0.35 | 0.98 | 0.96 |
| G126 | D | 0.33 | 1.22 | 0.93 |
| G126 | E | 0.67 | 0.60 | 1.02 |
| G126 | G | 1.00 | 1.00 | 1.00 |
| G126 | I | 0.84 | 0.01 | 0.81 |
| G126 | L | 1.17 | 0.54 | 0.90 |
| G126 | M | 0.43 | 1.17 | 0.92 |
| G126 | N | 0.38 | 0.85 | 1.04 |
| G126 | P | 1.17 | 0.67 | 0.82 |
| G126 | R | 0.43 | 0.76 | 0.89 |
| G126 | S | 0.76 | 0.90 | 0.90 |
| G126 | T | 1.58 | 0.74 | 0.90 |
| G126 | V | 0.89 | 0.18 | 0.84 |
| G126 | Y | 0.54 | 0.23 | 0.82 |
| T127 | A | 0.73 | 1.10 | 1.10 |
| T127 | C | 0.76 | 0.65 | 1.04 |
| T127 | D | 0.46 | 0.62 | 1.03 |
| T127 | E | 0.40 | -0.01 | 1.03 |
| T127 | G | 0.95 | 0.71 | 1.04 |
| T127 | H | 1.57 | 0.60 | 0.99 |
| T127 | I | 1.06 | 0.20 | 0.91 |
| T127 | L | 0.90 | -0.03 | 0.94 |
| T127 | M | 0.79 | 0.64 | 1.02 |
| T127 | P | 0.14 | 0.77 | 0.95 |
| T127 | Q | 0.55 | 0.15 | 0.86 |
| T127 | S | 1.05 | 0.83 | 1.08 |
| T127 | T | 1.00 | 1.00 | 1.00 |
| T127 | V | 1.07 | 0.68 | 1.06 |
| T128 | A | 0.76 | 1.31 | 1.23 |
| T128 | D | 0.78 | 0.66 | 1.14 |
| T128 | F | 0.79 | 1.71 | 1.01 |
| T128 | H | 0.99 | 1.08 | 1.19 |
| T128 | K | 1.06 | 1.57 | 1.10 |
| T128 | L | 1.06 | 1.72 | 0.97 |
| T128 | M | 0.72 | 1.06 | 1.28 |
| T128 | N | 0.70 | 1.36 | 1.29 |
| T128 | P | 0.87 | 1.16 | 1.18 |
| T128 | Q | 0.78 | 1.34 | 1.24 |
| T128 | R | 0.87 | 1.70 | 1.03 |
| T128 | S | 0.92 | 1.27 | 1.07 |
| T128 | T | 1.00 | 1.00 | 1.00 |
| T128 | V | 0.98 | 1.15 | 1.05 |
| T128 | W | 0.92 | 1.23 | 0.95 |
| T128 | Y | 0.95 | 1.81 | 0.96 |
| Y129 | A | 0.64 | 0.17 | 1.39 |
| Y129 | C | 0.66 | 0.61 | 1.42 |
| Y129 | D | 0.35 | 0.23 | 1.35 |
| Y129 | F | 0.71 | 0.71 | 1.44 |
| Y129 | G | 0.39 | -0.56 | 1.10 |
| Y129 | K | 0.31 | -0.29 | 1.00 |
| Y129 | L | 0.78 | 0.27 | 1.22 |
| Y129 | M | 0.68 | 0.21 | 1.28 |
| Y129 | N | 0.46 | 0.53 | 1.24 |
| Y129 | P | 0.15 | 0.59 | 1.11 |
| Y129 | R | 0.38 | 0.18 | 1.00 |
| Y129 | S | 0.67 | 0.69 | 1.08 |
| Y129 | T | 0.46 | 0.14 | 1.00 |
| Y129 | V | 0.24 | -0.29 | 1.00 |
| Y129 | W | 0.47 | -0.15 | 1.01 |
| Y129 | Y | 1.00 | 1.00 | 1.00 |
| P130 | A | 0.82 | 0.44 | 1.03 |
| P130 | C | 0.95 | 0.64 | 0.93 |
| P130 | E | 1.00 | 0.22 | 1.08 |
| P130 | F | 1.08 | 0.48 | 0.89 |
| P130 | G | 1.16 | -0.19 | 1.11 |
| P130 | H | 1.17 | 0.01 | 1.00 |
| P130 | I | 1.12 | 0.41 | 0.94 |
| P130 | K | 1.16 | 0.55 | 1.05 |
| P130 | L | 1.12 | 0.09 | 0.98 |
| P130 | M | 0.66 | 0.76 | 1.03 |
| P130 | P | 1.00 | 1.00 | 1.00 |
| P130 | R | 1.11 | 0.53 | 0.95 |
| P130 | S | 1.16 | -0.14 | 0.96 |
| P130 | T | 1.19 | -0.06 | 0.96 |
| P130 | V | 1.15 | 0.37 | 0.94 |
| P130 | W | 1.15 | 0.28 | 0.80 |
| A131 | A | 1.00 | 1.00 | 1.00 |
| A131 | D | 1.31 | 0.40 | 0.80 |
| A131 | E | 1.36 | 0.97 | 0.88 |
| A131 | G | 1.66 | 0.87 | 0.83 |
| A131 | H | 1.72 | 0.82 | 0.75 |
| A131 | L | 1.83 | 0.59 | 0.73 |
| A131 | P | 1.52 | 0.71 | 0.94 |
| A131 | Q | 1.29 | 0.74 | 0.69 |
| A131 | R | 1.76 | 1.04 | 0.61 |
| A131 | S | 1.48 | 0.68 | 0.87 |
| A131 | V | 1.59 | 0.78 | 0.89 |
| A131 | W | 1.61 | -0.42 | 0.65 |
| A131 | Y | 1.50 | 0.48 | 0.73 |
| P132 | A | 0.49 | 6.08 | 0.94 |
| P132 | C | 0.49 | 5.68 | 0.94 |
| P132 | D | -0.11 | -7.16 | 0.62 |
| P132 | E | 0.19 | 3.02 | 0.80 |
| P132 | F | 0.76 | -1.33 | 0.49 |
| P132 | G | 0.83 | 4.98 | 0.79 |
| P132 | H | 0.50 | -1.95 | 0.68 |
| P132 | I | 0.58 | -3.19 | 0.64 |
| P132 | L | 0.87 | 2.24 | 0.67 |
| P132 | N | 0.30 | 1.05 | 0.83 |
| P132 | P | 0.09 | 6.91 | 1.03 |
| P132 | Q | 0.41 | 6.15 | 0.91 |
| P132 | R | 0.02 | -2.19 | 0.65 |
| P132 | S | 1.13 | 5.05 | 0.96 |
| P132 | T | 0.85 | -2.01 | 0.75 |
| P132 | V | 0.85 | -2.29 | 0.78 |
| P132 | W | 0.77 | -2.64 | 0.37 |
| P132 | Y | 1.57 | 4.78 | 0.60 |
| K133 | A | 0.67 | 0.10 | 1.01 |
| K133 | C | 0.56 | -0.11 | 0.72 |
| K133 | E | 0.63 | 0.76 | 1.01 |
| K133 | F | 0.86 | 0.59 | 0.73 |
| K133 | G | 0.97 | 0.31 | 0.87 |
| K133 | H | 1.02 | 0.31 | 0.87 |
| K133 | I | 0.89 | 0.45 | 0.78 |
| K133 | K | 1.00 | 1.00 | 1.00 |
| K133 | L | 1.05 | 1.92 | 0.76 |
| K133 | M | 0.68 | 0.33 | 0.98 |
| K133 | P | 0.39 | 0.71 | 0.89 |
| K133 | Q | 0.69 | 0.52 | 1.13 |
| K133 | R | 0.78 | 0.83 | 1.01 |
| K133 | S | 0.84 | 0.58 | 1.02 |
| K133 | T | 0.93 | 0.39 | 0.97 |
| K133 | V | 0.90 | 0.23 | 0.87 |
| K133 | W | 0.97 | 0.99 | 0.46 |
| K133 | Y | 1.12 | 1.44 | 0.75 |
| V134 | A | 0.75 | 1.64 | 0.87 |
| V134 | C | 0.77 | 1.37 | 0.91 |
| V134 | D | -0.08 | -0.08 | -0.02 |
| V134 | G | 1.71 | 1.42 | 0.45 |
| V134 | I | 1.12 | 0.89 | 0.99 |
| V134 | K | -0.08 | -0.08 | -0.02 |
| V134 | L | 1.13 | 1.45 | 0.78 |
| V134 | M | 0.82 | 1.89 | 0.83 |
| V134 | N | 1.18 | 2.80 | 0.25 |
| V134 | P | -0.08 | 1.71 | 0.43 |
| V134 | Q | 0.04 | 0.79 | 0.44 |

TABLE 10-12-continued

Performance Indices

| Wild-Type Res./Pos. | Mut. | PAF PI | PAD PI | Prot. PI |
|---|---|---|---|---|
| V134 | R | -0.08 | -0.08 | -0.02 |
| V134 | S | 1.16 | 1.44 | 0.62 |
| V134 | T | 1.25 | 0.86 | 0.82 |
| V134 | V | 1.00 | 1.00 | 1.00 |
| V134 | W | -0.08 | -0.08 | -0.02 |
| V134 | Y | -0.08 | -0.08 | -0.02 |
| L135 | D | -0.13 | 2.90 | 0.27 |
| L135 | E | -0.13 | 0.63 | 0.39 |
| L135 | F | 0.34 | -0.03 | 0.45 |
| L135 | G | 0.33 | -1.71 | 0.28 |
| L135 | K | 0.66 | -1.23 | 0.28 |
| L135 | L | 1.00 | 1.00 | 1.00 |
| L135 | M | 0.77 | 0.78 | 1.01 |
| L135 | P | -0.13 | -1.31 | 0.22 |
| L135 | Q | 0.34 | 0.17 | 0.66 |
| L135 | R | 0.06 | -1.41 | 0.25 |
| L135 | S | 0.50 | -0.65 | 0.44 |
| L135 | T | 0.73 | -0.42 | 0.50 |
| L135 | V | 0.83 | 0.43 | 0.82 |
| L135 | W | 0.71 | -0.42 | 0.36 |
| V136 | A | 0.60 | 1.60 | 0.66 |
| V136 | C | 0.57 | 1.23 | 0.87 |
| V136 | E | -0.09 | 0.20 | 0.25 |
| V136 | L | 0.98 | 1.13 | 1.03 |
| V136 | N | -0.09 | 0.40 | 0.26 |
| V136 | P | -0.09 | -0.12 | 0.52 |
| V136 | R | -0.09 | -0.12 | -0.02 |
| V136 | T | 1.13 | 1.13 | 0.68 |
| V136 | V | 1.00 | 1.00 | 1.00 |
| V136 | W | -0.09 | -0.12 | -0.02 |
| V137 | A | 1.07 | 1.46 | 0.64 |
| V137 | C | 0.98 | 1.42 | 0.85 |
| V137 | D | -0.17 | -0.23 | -0.01 |
| V137 | E | -0.17 | -0.23 | -0.01 |
| V137 | F | -0.17 | -0.23 | -0.01 |
| V137 | G | 1.02 | 0.26 | 0.13 |
| V137 | I | 0.98 | 0.70 | 0.83 |
| V137 | L | 1.09 | 1.27 | 0.82 |
| V137 | M | 1.22 | 1.13 | 0.89 |
| V137 | N | 0.46 | -1.29 | 0.15 |
| V137 | P | -0.17 | -0.23 | -0.01 |
| V137 | R | -0.17 | -0.23 | -0.01 |
| V137 | S | 0.96 | 0.29 | 0.50 |
| V137 | T | 1.08 | 0.93 | 0.73 |
| V137 | V | 1.00 | 1.00 | 1.00 |
| V137 | W | -0.17 | -0.23 | -0.01 |
| V137 | Y | -0.17 | -0.23 | -0.01 |
| S138 | A | 0.69 | 1.28 | 1.44 |
| S138 | C | 0.64 | 1.18 | 1.17 |
| S138 | E | -0.13 | -0.19 | -0.02 |
| S138 | F | -0.13 | -0.19 | -0.02 |
| S138 | G | 1.05 | 1.11 | 1.09 |
| S138 | H | -0.13 | -0.19 | -0.02 |
| S138 | I | 1.15 | 0.35 | 0.56 |
| S138 | L | -0.13 | -0.19 | -0.02 |
| S138 | M | -0.13 | -0.19 | -0.02 |
| S138 | N | 0.62 | 1.31 | 0.77 |
| S138 | P | 0.54 | 1.39 | 0.45 |
| S138 | Q | -0.13 | -0.19 | -0.02 |
| S138 | R | -0.13 | -0.19 | -0.02 |
| S138 | S | 1.00 | 1.00 | 1.00 |
| S138 | V | 1.00 | 0.69 | 0.67 |
| S138 | W | -0.13 | -0.19 | -0.02 |
| P139 | Y | -0.13 | -0.19 | -0.02 |
| P139 | C | 0.08 | -0.12 | 1.18 |
| P139 | D | -0.13 | -1.44 | 0.15 |
| P139 | E | -0.13 | -5.11 | 0.19 |
| P139 | F | -0.13 | -4.13 | 0.16 |
| P139 | G | 0.50 | -3.08 | 0.23 |
| P139 | H | -0.13 | -6.03 | 0.19 |
| P139 | I | -0.13 | -3.71 | 0.21 |
| P139 | K | -0.13 | -4.09 | 0.12 |
| P139 | L | -0.13 | -0.17 | -0.02 |
| P139 | N | -0.13 | -2.11 | 0.16 |
| P139 | P | 1.00 | 1.00 | 1.00 |
| P139 | Q | -0.13 | -0.32 | 0.18 |
| P139 | R | 0.37 | -1.04 | 0.23 |
| P139 | S | 0.88 | -0.52 | 0.43 |
| P139 | T | 0.01 | -3.48 | 0.15 |
| P139 | V | -0.13 | -1.70 | 0.17 |
| P139 | W | -0.13 | -0.17 | -0.02 |
| P139 | Y | -0.13 | -0.17 | -0.02 |
| P140 | A | 1.90 | 1.83 | 0.61 |
| P140 | C | 0.39 | 1.07 | 0.40 |
| P140 | D | -0.45 | -0.23 | -0.02 |
| P140 | F | -0.45 | 2.89 | 0.19 |
| P140 | G | 0.96 | 3.11 | 0.20 |
| P140 | H | 0.59 | 2.25 | 0.23 |
| P140 | I | 0.45 | -1.03 | 0.24 |
| P140 | K | -0.45 | -0.23 | -0.02 |
| P140 | L | -0.45 | -0.23 | -0.02 |
| P140 | M | -0.45 | -0.23 | -0.02 |
| P140 | P | 1.00 | 1.00 | 1.00 |
| P140 | Q | -0.45 | -1.32 | 0.32 |
| P140 | R | -0.45 | -2.74 | 0.25 |
| P140 | S | 1.31 | -1.22 | 0.43 |
| P140 | T | 1.74 | -0.78 | 0.29 |
| P140 | V | 0.50 | -1.12 | 0.34 |
| P140 | W | 0.50 | -0.97 | 0.17 |
| P140 | Y | 0.32 | -1.90 | 0.24 |
| P141 | A | 1.10 | 1.08 | 1.13 |
| P141 | G | 1.64 | -0.05 | 1.02 |
| P141 | H | 2.07 | 0.79 | 0.93 |
| P141 | I | 2.29 | 0.38 | 0.90 |
| P141 | L | 2.32 | 0.65 | 0.74 |
| P141 | N | 1.32 | 0.97 | 0.96 |
| P141 | P | 1.00 | 1.00 | 1.00 |
| P141 | Q | 1.39 | 0.37 | 0.88 |
| P141 | R | 1.65 | -0.26 | 0.61 |
| P141 | S | 1.70 | 0.02 | 0.90 |
| P141 | T | 1.84 | 0.12 | 0.82 |
| P141 | V | 1.96 | 0.16 | 0.72 |
| L142 | A | 0.80 | 0.56 | 0.67 |
| L142 | C | 0.74 | 0.70 | 0.78 |
| L142 | D | -0.12 | -0.13 | -0.01 |
| L142 | F | 1.05 | 0.54 | 0.46 |
| L142 | G | -0.12 | -0.13 | -0.01 |
| L142 | I | 0.64 | 0.28 | 1.05 |
| L142 | K | 1.60 | 0.66 | 0.23 |
| L142 | L | 1.00 | 1.00 | 1.00 |
| L142 | M | -0.12 | -0.13 | -0.01 |
| L142 | N | -0.12 | -0.13 | -0.01 |
| L142 | P | 0.54 | 0.44 | 0.48 |
| L142 | Q | 0.67 | 0.33 | 0.49 |
| L142 | R | -0.12 | -0.13 | -0.01 |
| L142 | S | 0.84 | 0.31 | 0.65 |
| L142 | T | -0.12 | -0.13 | -0.01 |
| L142 | V | 0.84 | 0.33 | 0.82 |
| L142 | W | 2.41 | -1.89 | 0.16 |
| A143 | A | 1.00 | 1.00 | 1.00 |
| A143 | C | 1.39 | 1.07 | 0.81 |
| A143 | D | 1.45 | 1.22 | 0.71 |
| A143 | E | 1.43 | 1.13 | 0.71 |
| A143 | F | 1.56 | 0.68 | 0.99 |
| A143 | G | 1.48 | 0.42 | 1.17 |
| A143 | H | 2.90 | 1.36 | 0.70 |
| A143 | K | 3.16 | 1.37 | 0.62 |
| A143 | L | 2.51 | 1.28 | 0.71 |
| A143 | N | 1.30 | 0.82 | 0.79 |
| A143 | P | 1.53 | 0.39 | 0.63 |
| A143 | Q | 1.74 | 0.81 | 0.72 |
| A143 | R | 2.15 | 0.99 | 0.62 |
| A143 | S | 1.77 | 0.63 | 0.98 |
| A143 | T | 2.18 | 0.97 | 0.74 |
| A143 | V | 2.45 | 0.99 | 0.81 |
| A143 | W | 2.27 | -0.21 | 0.37 |
| P144 | A | 1.09 | 0.79 | 0.91 |
| P144 | D | 1.45 | 1.38 | 0.60 |

TABLE 10-12-continued

Performance Indices

| Wild-Type Res./Pos. | Mut. | PAF PI | PAD PI | Prot. PI |
|---|---|---|---|---|
| P144 | F | 1.82 | 1.08 | 0.66 |
| P144 | G | 1.45 | 0.62 | 0.78 |
| P144 | H | 1.94 | 1.60 | 0.66 |
| P144 | K | 2.09 | 1.09 | 0.67 |
| P144 | L | 1.43 | 1.15 | 0.86 |
| P144 | M | 1.24 | 1.01 | 0.76 |
| P144 | N | 1.44 | 1.49 | 0.74 |
| P144 | P | 1.00 | 1.00 | 1.00 |
| P144 | Q | 1.37 | 1.08 | 0.77 |
| P144 | R | 1.76 | 1.14 | 0.68 |
| P144 | S | 1.69 | 0.92 | 0.77 |
| P144 | T | 1.46 | 0.81 | 0.80 |
| P144 | Y | 2.34 | 1.65 | 0.70 |
| M145 | A | 0.44 | 0.79 | 0.94 |
| M145 | C | 1.02 | 0.93 | 0.94 |
| M145 | E | 0.28 | 0.48 | 0.74 |
| M145 | F | 1.49 | 0.77 | 0.95 |
| M145 | G | 0.48 | 0.26 | 0.92 |
| M145 | I | 0.79 | 0.53 | 1.16 |
| M145 | L | 1.72 | 0.61 | 1.07 |
| M145 | M | 1.00 | 1.00 | 1.00 |
| M145 | P | 0.64 | 0.78 | 0.78 |
| M145 | Q | 0.68 | 0.57 | 0.86 |
| M145 | R | 1.15 | 0.69 | 0.78 |
| M145 | S | 0.64 | 0.78 | 0.91 |
| M145 | T | 1.01 | 0.79 | 0.91 |
| M145 | V | 0.72 | 0.63 | 1.00 |
| M145 | W | 1.15 | −0.13 | 0.49 |
| M145 | Y | 0.94 | 0.82 | 0.68 |
| P146 | A | 0.20 | 1.36 | 0.73 |
| P146 | C | 0.31 | 1.69 | 0.62 |
| P146 | F | 0.55 | 1.53 | 0.51 |
| P146 | G | 0.24 | 1.04 | 0.51 |
| P146 | H | 0.50 | 1.57 | 0.56 |
| P146 | L | 0.56 | 2.00 | 0.53 |
| P146 | M | 0.39 | 1.23 | 0.79 |
| P146 | N | 0.37 | 1.00 | 0.78 |
| P146 | P | 1.00 | 1.00 | 1.00 |
| P146 | R | 0.36 | 1.06 | 0.66 |
| P146 | S | 0.46 | 0.96 | 0.82 |
| P146 | T | 0.38 | 0.76 | 0.80 |
| P146 | V | 0.55 | 0.77 | 0.89 |
| P146 | W | 0.56 | 0.68 | 0.64 |
| P146 | Y | 0.35 | 1.44 | 0.54 |
| H147 | A | 1.28 | 0.98 | 0.96 |
| H147 | C | 0.94 | 1.17 | 1.04 |
| H147 | D | 0.95 | 1.18 | 1.00 |
| H147 | E | 1.11 | 1.10 | 0.96 |
| H147 | G | −0.12 | −0.15 | −0.02 |
| H147 | H | 1.00 | 1.00 | 1.00 |
| H147 | I | 0.89 | 0.92 | 0.89 |
| H147 | K | 0.94 | 1.06 | 0.89 |
| H147 | L | 0.69 | 1.29 | 1.09 |
| H147 | M | 0.73 | 1.44 | 0.86 |
| H147 | N | 0.84 | 1.25 | 0.98 |
| H147 | P | 1.12 | 1.21 | 0.71 |
| H147 | Q | 0.71 | 1.03 | 0.86 |
| H147 | R | 0.89 | 0.94 | 0.69 |
| H147 | S | 1.26 | 0.75 | 0.92 |
| H147 | T | 1.20 | 0.84 | 0.85 |
| H147 | V | 0.96 | 0.92 | 0.90 |
| H147 | W | 0.88 | 1.05 | 0.79 |
| H147 | Y | 0.75 | 1.12 | 0.94 |
| P148 | A | 1.64 | 1.06 | 0.96 |
| P148 | D | 1.03 | 1.34 | 0.74 |
| P148 | E | 1.42 | 1.19 | 0.76 |
| P148 | F | 1.37 | 1.50 | 0.64 |
| P148 | G | 0.87 | 1.20 | 0.70 |
| P148 | K | 1.79 | 1.30 | 0.72 |
| P148 | L | 1.64 | 1.39 | 0.74 |
| P148 | P | 1.00 | 1.00 | 1.00 |
| P148 | Q | 1.33 | 0.98 | 0.81 |
| P148 | R | 1.51 | 1.25 | 0.79 |
| P148 | S | 1.46 | 1.21 | 0.74 |
| P148 | T | 1.50 | 1.09 | 0.79 |
| P148 | V | 2.43 | 1.04 | 0.76 |
| P148 | Y | 1.46 | 1.37 | 0.72 |
| W149 | A | 0.21 | 0.31 | 1.35 |
| W149 | C | 0.18 | 0.12 | 0.93 |
| W149 | E | 0.00 | −0.04 | 0.85 |
| W149 | F | 0.53 | 0.50 | 1.27 |
| W149 | G | 0.26 | 0.45 | 1.39 |
| W149 | H | 0.60 | 1.01 | 0.81 |
| W149 | I | 0.21 | 0.24 | 0.83 |
| W149 | L | 0.30 | 0.64 | 1.06 |
| W149 | M | 0.33 | 0.49 | 1.32 |
| W149 | P | −0.32 | −0.16 | 0.92 |
| W149 | Q | 0.11 | 0.40 | 1.10 |
| W149 | R | 0.04 | −0.32 | 0.67 |
| W149 | S | 0.16 | 0.33 | 1.28 |
| W149 | T | 0.26 | 0.44 | 0.84 |
| W149 | W | 1.00 | 1.00 | 1.00 |
| W149 | Y | 0.58 | 0.75 | 1.15 |
| F150 | A | 0.01 | 0.54 | 1.70 |
| F150 | C | 0.43 | 0.78 | 1.41 |
| F150 | E | 1.23 | 0.73 | 1.32 |
| F150 | F | 1.00 | 1.00 | 1.00 |
| F150 | G | 0.14 | 0.46 | 1.13 |
| F150 | H | 0.53 | 1.18 | 1.09 |
| F150 | I | 0.40 | 0.78 | 1.19 |
| F150 | K | 0.41 | 0.85 | 1.33 |
| F150 | L | 1.29 | 1.30 | 1.14 |
| F150 | M | 0.80 | 0.63 | 1.69 |
| F150 | N | 0.55 | 0.36 | 1.52 |
| F150 | P | 0.18 | 0.32 | 1.38 |
| F150 | T | 0.37 | 0.58 | 1.27 |
| F150 | V | 0.22 | 0.51 | 1.26 |
| F150 | W | 0.19 | 0.62 | 1.26 |
| F150 | Y | 0.72 | 1.07 | 1.24 |
| Q151 | A | 1.29 | 2.93 | 0.46 |
| Q151 | C | 1.05 | 2.55 | 0.38 |
| Q151 | D | 1.47 | 2.81 | 0.83 |
| Q151 | E | 1.14 | 2.07 | 0.99 |
| Q151 | F | 0.31 | −8.08 | 0.21 |
| Q151 | H | 1.06 | 2.19 | 0.94 |
| Q151 | I | 0.08 | −2.76 | 0.16 |
| Q151 | K | 1.07 | 2.19 | 1.04 |
| Q151 | L | 0.40 | −1.53 | 0.17 |
| Q151 | M | 1.24 | 6.36 | 0.24 |
| Q151 | P | 1.35 | 1.91 | 0.50 |
| Q151 | Q | 1.00 | 1.00 | 1.00 |
| Q151 | R | 1.36 | 2.32 | 0.68 |
| Q151 | S | 1.05 | 2.25 | 0.86 |
| Q151 | T | 1.24 | 2.37 | 0.64 |
| Q151 | V | 0.36 | −1.65 | 0.25 |
| Q151 | W | 0.77 | 0.32 | 0.33 |
| Q151 | Y | 1.01 | 2.75 | 0.41 |
| L152 | A | 0.88 | 1.29 | 0.85 |
| L152 | C | 1.00 | 1.14 | 0.87 |
| L152 | D | 1.07 | 0.86 | 0.81 |
| L152 | E | 1.08 | 1.23 | 0.93 |
| L152 | G | 1.08 | 0.77 | 0.85 |
| L152 | H | 1.09 | 0.92 | 0.93 |
| L152 | I | 1.04 | 0.61 | 0.77 |
| L152 | K | 1.21 | 0.91 | 0.93 |
| L152 | L | 1.00 | 1.00 | 1.00 |
| L152 | M | 0.99 | 1.10 | 0.82 |
| L152 | P | 0.81 | 0.61 | 0.54 |
| L152 | Q | 1.07 | 0.76 | 0.84 |
| L152 | R | 1.20 | 0.91 | 0.89 |
| L152 | S | 1.12 | 0.84 | 0.84 |
| L152 | T | 1.12 | 0.69 | 0.82 |
| L152 | V | 1.22 | 0.88 | 0.83 |
| L152 | W | 1.18 | 1.55 | 0.74 |
| I153 | Y | 1.09 | 1.37 | 0.89 |
| I153 | A | 1.19 | 1.49 | 0.76 |
| I153 | F | 1.23 | 1.75 | 0.47 |
| I153 | H | 1.46 | 2.00 | 0.56 |

TABLE 10-12-continued

Performance Indices

| Wild-Type Res./Pos. | Mut. | PAF PI | PAD PI | Prot. PI |
|---|---|---|---|---|
| I153 | I | 1.00 | 1.00 | 1.00 |
| I153 | K | 1.62 | 2.44 | 0.43 |
| I153 | L | 1.27 | 1.50 | 0.82 |
| I153 | N | 0.72 | 0.89 | 1.04 |
| I153 | P | 0.25 | 1.87 | 0.31 |
| I153 | S | 0.87 | 1.66 | 0.61 |
| I153 | T | 1.27 | 1.62 | 0.64 |
| I153 | V | 0.96 | 1.15 | 0.78 |
| F154 | D | −0.19 | −1.06 | −0.02 |
| F154 | E | −0.19 | −1.06 | −0.02 |
| F154 | F | 1.00 | 1.00 | 1.00 |
| F154 | G | −0.19 | −0.64 | 0.17 |
| F154 | L | −0.19 | −1.06 | −0.02 |
| F154 | P | −0.19 | −1.06 | −0.02 |
| F154 | Q | 0.39 | 0.97 | 0.45 |
| F154 | S | 0.13 | 0.29 | 0.35 |
| F154 | T | 0.12 | −1.76 | 0.19 |
| F154 | V | −0.19 | −14.19 | 0.18 |
| F154 | Y | 1.32 | 4.96 | 0.92 |
| E155 | A | 0.99 | 2.59 | 0.83 |
| E155 | D | 1.08 | 1.24 | 0.89 |
| E155 | E | 1.00 | 1.00 | 1.00 |
| E155 | F | 1.07 | 0.23 | 0.60 |
| E155 | G | 1.17 | 1.12 | 0.82 |
| E155 | I | 0.95 | 0.65 | 0.61 |
| E155 | K | 1.23 | 1.33 | 0.83 |
| E155 | L | 1.31 | 2.07 | 0.60 |
| E155 | M | 0.73 | 2.91 | 0.74 |
| E155 | N | 0.79 | 1.79 | 0.86 |
| E155 | P | 0.79 | 2.60 | 0.65 |
| E155 | Q | 0.90 | 0.69 | 0.87 |
| E155 | R | 1.47 | −0.07 | 0.71 |
| E155 | S | 1.08 | 1.12 | 0.82 |
| E155 | T | 1.49 | 1.19 | 0.76 |
| E155 | V | 0.79 | 0.47 | 0.63 |
| E155 | Y | 1.27 | 2.65 | 0.55 |
| G156 | A | 0.99 | 1.21 | 0.88 |
| G156 | C | 1.07 | 1.37 | 0.84 |
| G156 | D | 0.96 | 1.62 | 0.93 |
| G156 | E | 0.94 | 1.14 | 0.91 |
| G156 | F | 0.90 | 0.73 | 0.78 |
| G156 | G | 1.00 | 1.00 | 1.00 |
| G156 | H | 1.04 | 1.40 | 0.84 |
| G156 | I | 0.70 | −0.08 | 0.44 |
| G156 | K | 1.10 | 1.11 | 0.88 |
| G156 | L | 0.90 | 0.94 | 0.74 |
| G156 | M | 1.09 | 1.62 | 0.80 |
| G156 | N | 1.07 | 1.38 | 0.97 |
| G156 | P | 1.44 | 1.29 | 0.59 |
| G156 | R | 1.05 | 1.21 | 0.80 |
| G156 | S | 1.02 | 1.04 | 0.88 |
| G156 | T | 1.15 | 1.53 | 0.79 |
| G156 | V | 0.88 | 0.97 | 0.58 |
| G156 | W | 0.89 | 0.90 | 0.56 |
| G156 | Y | 0.96 | 1.40 | 0.80 |
| G157 | A | 0.77 | 0.87 | 1.00 |
| G157 | C | 0.96 | 0.61 | 0.92 |
| G157 | D | 0.93 | 0.94 | 0.41 |
| G157 | E | 0.98 | 0.84 | 0.61 |
| G157 | F | 1.27 | 1.42 | 0.61 |
| G157 | G | 1.00 | 1.00 | 1.00 |
| G157 | H | 1.14 | 1.57 | 0.70 |
| G157 | I | 1.11 | 1.33 | 0.36 |
| G157 | K | 1.28 | 1.47 | 0.46 |
| G157 | M | 0.96 | 0.85 | 0.70 |
| G157 | P | 0.86 | 0.01 | 0.31 |
| G157 | R | 1.51 | −0.10 | 0.42 |
| G157 | S | 1.30 | 0.19 | 0.93 |
| G157 | T | 1.74 | 0.99 | 0.68 |
| G157 | V | 1.23 | 0.40 | 0.59 |
| E158 | A | 1.45 | 1.28 | 0.91 |
| E158 | C | 1.46 | 1.37 | 0.67 |
| E158 | D | 1.35 | 0.89 | 0.82 |
| E158 | E | 1.00 | 1.00 | 1.00 |
| E158 | F | 2.06 | 1.77 | 0.46 |
| E158 | H | 2.40 | 1.01 | 0.59 |
| E158 | I | 1.38 | 0.94 | 0.76 |
| E158 | K | 2.08 | 1.88 | 0.62 |
| E158 | L | 1.59 | 1.96 | 0.70 |
| E158 | M | 1.39 | 1.73 | 0.71 |
| E158 | N | 1.41 | 1.58 | 0.82 |
| E158 | P | 1.41 | 1.19 | 0.85 |
| E158 | Q | 1.49 | 1.24 | 0.85 |
| E158 | R | 1.99 | 1.29 | 0.62 |
| E158 | S | 1.57 | 1.27 | 0.82 |
| E158 | T | 1.45 | 0.91 | 0.77 |
| E158 | V | 1.52 | 0.89 | 0.81 |
| E158 | W | 1.77 | 1.31 | 0.67 |
| E158 | Y | 1.77 | 2.48 | 0.57 |
| Q159 | A | 1.08 | 0.28 | 1.13 |
| Q159 | C | 1.13 | 0.31 | 0.79 |
| Q159 | D | 1.09 | 0.63 | 0.90 |
| Q159 | E | 0.99 | 0.97 | 1.14 |
| Q159 | G | 0.96 | 0.72 | 1.03 |
| Q159 | H | 0.96 | 1.48 | 0.90 |
| Q159 | L | 1.02 | 0.70 | 0.83 |
| Q159 | M | 1.07 | 0.84 | 0.83 |
| Q159 | P | 1.06 | 0.49 | 0.81 |
| Q159 | Q | 1.00 | 1.00 | 1.00 |
| Q159 | R | 1.15 | 0.74 | 0.76 |
| Q159 | S | 1.10 | 0.73 | 0.81 |
| K160 | A | 0.39 | 1.14 | 0.86 |
| K160 | C | 0.48 | 1.29 | 0.77 |
| K160 | D | −0.15 | 1.19 | 0.40 |
| K160 | G | 0.91 | 0.30 | 0.56 |
| K160 | H | 0.98 | 0.57 | 0.65 |
| K160 | I | 0.97 | 1.00 | 0.78 |
| K160 | K | 1.00 | 1.00 | 1.00 |
| K160 | L | 0.97 | 0.95 | 0.77 |
| K160 | M | 0.31 | 1.47 | 0.78 |
| K160 | N | 0.37 | 1.12 | 0.65 |
| K160 | P | −0.15 | 1.66 | 0.31 |
| K160 | Q | 0.45 | 1.41 | 0.75 |
| K160 | R | 0.83 | 1.15 | 0.76 |
| K160 | S | 0.85 | 0.70 | 0.74 |
| K160 | W | 0.89 | −0.34 | 0.21 |
| T161 | C | 0.84 | 0.56 | 1.01 |
| T161 | D | −0.14 | −0.21 | −0.02 |
| T161 | E | −0.14 | −0.21 | −0.02 |
| T161 | G | 0.92 | 0.43 | 0.94 |
| T161 | H | 1.82 | −0.15 | 0.42 |
| T161 | I | 1.40 | 0.98 | 0.91 |
| T161 | L | 1.25 | 1.16 | 0.81 |
| T161 | M | 0.57 | 1.72 | 0.83 |
| T161 | N | 0.80 | −0.86 | 0.32 |
| T161 | P | −0.14 | −0.21 | −0.02 |
| T161 | Q | 1.04 | 1.50 | 0.90 |
| T161 | R | 3.61 | −1.68 | 0.42 |
| T161 | S | 0.92 | 0.57 | 0.98 |
| T161 | T | 1.00 | 1.00 | 1.00 |
| T161 | V | 1.27 | 1.24 | 1.00 |
| T161 | W | 1.41 | 0.00 | 0.52 |
| T161 | Y | 2.40 | 2.62 | 0.23 |
| T162 | C | 0.95 | 3.57 | 1.17 |
| T162 | F | 0.99 | 3.23 | 1.05 |
| T162 | G | 1.00 | 1.82 | 0.88 |
| T162 | H | 1.02 | 3.91 | 1.08 |
| T162 | I | 0.99 | 2.21 | 1.16 |
| T162 | K | 1.22 | 3.13 | 0.98 |
| T162 | L | 1.00 | 3.59 | 1.05 |
| T162 | M | 0.77 | 3.49 | 0.89 |
| T162 | N | 0.83 | 3.84 | 0.98 |
| T162 | P | 0.96 | 4.37 | 0.81 |
| T162 | Q | 0.93 | 2.45 | 0.89 |
| T162 | R | 1.71 | 1.23 | 0.80 |
| T162 | S | 0.98 | 2.01 | 0.97 |
| T162 | T | 1.00 | 1.00 | 1.00 |
| T162 | W | 1.15 | 2.04 | 0.85 |

TABLE 10-12-continued

Performance Indices

| Wild-Type Res./Pos. | Mut. | PAF PI | PAD PI | Prot. PI |
|---|---|---|---|---|
| T162 | Y | 1.03 | 2.89 | 1.03 |
| E163 | A | 1.11 | 1.79 | 0.73 |
| E163 | C | 1.11 | 1.08 | 0.67 |
| E163 | D | 0.90 | 1.08 | 0.82 |
| E163 | E | 1.00 | 1.00 | 1.00 |
| E163 | F | 1.07 | 0.27 | 0.49 |
| E163 | G | 1.25 | 0.80 | 0.79 |
| E163 | H | 1.32 | 0.82 | 0.69 |
| E163 | L | 1.50 | 1.94 | 0.58 |
| E163 | N | 0.91 | 1.00 | 0.77 |
| E163 | P | 0.08 | 0.77 | 0.30 |
| E163 | R | 1.12 | 0.49 | 0.72 |
| E163 | S | 1.12 | 0.85 | 0.81 |
| E163 | V | 1.13 | 0.55 | 0.69 |
| E163 | W | 1.21 | 0.98 | 0.49 |
| E163 | Y | 1.41 | 1.89 | 0.60 |
| L164 | A | −0.14 | −0.85 | 0.21 |
| L164 | C | 0.09 | 0.91 | 0.63 |
| L164 | D | −0.14 | −0.85 | 0.12 |
| L164 | E | −0.14 | −0.48 | 0.18 |
| L164 | F | 0.50 | 0.86 | 0.94 |
| L164 | G | −0.14 | −0.14 | 0.19 |
| L164 | H | 0.02 | 0.12 | 0.16 |
| L164 | L | 1.00 | 1.00 | 1.00 |
| L164 | M | 0.69 | 1.26 | 1.09 |
| L164 | N | −0.14 | 1.31 | 0.26 |
| L164 | P | −0.14 | 2.41 | 0.17 |
| L164 | Q | −0.14 | 1.01 | 0.24 |
| L164 | R | −0.14 | 1.61 | 0.17 |
| L164 | S | 0.32 | 1.11 | 0.25 |
| L164 | T | 0.82 | 0.99 | 0.52 |
| L164 | V | 0.87 | 1.02 | 1.08 |
| L164 | Y | 0.43 | −1.28 | 0.20 |
| A165 | A | 1.00 | 1.00 | 1.00 |
| A165 | C | 0.99 | 1.42 | 0.97 |
| A165 | D | 0.89 | 1.69 | 0.62 |
| A165 | F | 1.23 | 1.00 | 0.74 |
| A165 | G | 1.05 | 1.07 | 1.14 |
| A165 | I | 1.17 | 0.59 | 0.64 |
| A165 | K | 1.35 | 0.82 | 0.78 |
| A165 | L | 1.08 | 1.55 | 0.70 |
| A165 | M | 0.97 | 1.56 | 0.77 |
| A165 | N | 1.01 | 1.20 | 0.91 |
| A165 | P | 1.14 | 1.34 | 0.91 |
| A165 | Q | 1.21 | 1.32 | 1.05 |
| A165 | R | 1.70 | 1.29 | 0.87 |
| A165 | S | 1.00 | 0.94 | 1.05 |
| A165 | T | 1.18 | 1.32 | 0.83 |
| A165 | V | 1.21 | 1.13 | 0.88 |
| A165 | Y | 1.20 | 0.84 | 0.67 |
| R166 | A | 0.73 | 1.51 | 1.12 |
| R166 | D | 0.56 | 1.55 | 1.16 |
| R166 | F | 1.00 | 1.10 | 0.85 |
| R166 | G | 1.15 | 0.91 | 1.19 |
| R166 | H | 1.20 | 1.56 | 0.97 |
| R166 | I | 1.26 | 1.39 | 0.86 |
| R166 | K | 1.17 | 1.20 | 1.19 |
| R166 | L | 1.27 | 1.50 | 1.08 |
| R166 | M | 0.65 | 1.29 | 1.26 |
| R166 | N | 0.75 | 1.21 | 1.16 |
| R166 | P | 0.43 | 1.50 | 0.97 |
| R166 | R | 1.00 | 1.00 | 1.00 |
| R166 | S | 1.16 | 0.95 | 0.98 |
| R166 | T | 1.19 | 0.74 | 1.04 |
| R166 | V | 1.17 | 0.76 | 0.94 |
| R166 | W | 1.25 | 1.08 | 0.80 |
| R166 | Y | 1.29 | 1.22 | 0.85 |
| V167 | A | 0.56 | 4.99 | 0.98 |
| V167 | C | 0.79 | 5.37 | 1.01 |
| V167 | D | 0.56 | 5.54 | 0.98 |
| V167 | G | 0.99 | 2.83 | 1.08 |
| V167 | H | 1.03 | 2.11 | 1.12 |
| V167 | I | 1.08 | 1.00 | 1.04 |
| V167 | L | 0.84 | 2.56 | 1.13 |
| V167 | M | 0.53 | 3.84 | 1.04 |
| V167 | P | 0.31 | 6.08 | 0.85 |
| V167 | Q | 0.55 | 2.41 | 0.97 |
| V167 | R | 0.78 | 2.25 | 0.88 |
| V167 | S | 0.96 | 1.86 | 1.04 |
| V167 | T | 1.13 | 2.47 | 0.96 |
| V167 | V | 1.00 | 1.00 | 1.00 |
| V167 | Y | 1.07 | 2.15 | 0.94 |
| Y168 | C | 0.69 | −4.73 | 0.57 |
| Y168 | D | −0.11 | −1.98 | −0.03 |
| Y168 | E | −0.11 | −1.98 | −0.03 |
| Y168 | F | 0.68 | 5.17 | 1.28 |
| Y168 | G | 1.89 | −40.74 | 0.23 |
| Y168 | H | −0.11 | −1.98 | −0.03 |
| Y168 | I | 0.83 | −0.59 | 0.90 |
| Y168 | K | −0.11 | −1.98 | −0.03 |
| Y168 | L | 0.59 | 5.39 | 1.27 |
| Y168 | N | −0.11 | −1.98 | −0.03 |
| Y168 | P | −0.11 | −1.98 | −0.03 |
| Y168 | Q | 0.28 | −8.27 | 0.25 |
| Y168 | R | −0.11 | −1.98 | −0.03 |
| Y168 | S | −0.11 | −1.98 | −0.03 |
| Y168 | T | 1.51 | −22.96 | 0.39 |
| Y168 | V | 1.19 | −12.96 | 0.57 |
| Y168 | W | −0.11 | −1.98 | −0.03 |
| Y168 | Y | 1.00 | 1.00 | 1.00 |
| S169 | A | 0.94 | 1.13 | 0.95 |
| S169 | C | 1.03 | 1.38 | 0.78 |
| S169 | I | 1.16 | 1.53 | 0.66 |
| S169 | K | 1.21 | 1.27 | 0.94 |
| S169 | L | 1.08 | 1.47 | 0.82 |
| S169 | M | 0.86 | 1.40 | 0.86 |
| S169 | P | 0.87 | 0.89 | 0.69 |
| S169 | Q | 1.02 | 1.37 | 0.88 |
| S169 | R | 1.24 | 1.19 | 0.77 |
| S169 | S | 1.00 | 1.00 | 1.00 |
| S169 | T | 1.15 | 0.97 | 0.82 |
| S169 | Y | 1.26 | 1.10 | 0.77 |
| A170 | A | 1.00 | 1.00 | 1.00 |
| A170 | C | 1.15 | 1.06 | 1.02 |
| A170 | D | 1.27 | 1.32 | 0.88 |
| A170 | E | 1.28 | 1.17 | 0.99 |
| A170 | F | 1.44 | 1.17 | 0.83 |
| A170 | G | 1.59 | 0.62 | 0.96 |
| A170 | I | 1.59 | 0.44 | 0.95 |
| A170 | K | 1.71 | 0.83 | 0.96 |
| A170 | L | 1.05 | 0.85 | 0.87 |
| A170 | M | 1.03 | 1.28 | 0.93 |
| A170 | N | 1.21 | 1.17 | 0.96 |
| A170 | P | 0.75 | 1.33 | 0.80 |
| A170 | Q | 1.15 | 0.89 | 0.98 |
| A170 | S | 1.47 | 0.47 | 0.99 |
| A170 | T | 1.40 | 0.72 | 0.86 |
| A170 | V | 1.20 | 0.74 | 0.83 |
| A170 | W | 1.04 | 0.83 | 0.82 |
| A170 | Y | 0.80 | 0.89 | 0.89 |
| L171 | A | 0.35 | 1.66 | 0.79 |
| L171 | C | 0.56 | 1.73 | 0.97 |
| L171 | D | −0.06 | −0.13 | −0.01 |
| L171 | F | 1.30 | 1.97 | 0.87 |
| L171 | G | 1.26 | 1.33 | 0.50 |
| L171 | H | 1.67 | 1.07 | 0.61 |
| L171 | I | 1.53 | 1.42 | 1.16 |
| L171 | K | 2.05 | 1.53 | 0.31 |
| L171 | L | 1.00 | 1.00 | 1.00 |
| L171 | M | 0.53 | 2.22 | 0.90 |
| L171 | N | 0.96 | 2.79 | 0.40 |
| L171 | Q | 0.97 | 1.93 | 0.67 |
| L171 | R | 0.71 | −0.20 | 0.24 |
| L171 | S | 1.43 | 1.76 | 0.72 |
| L171 | T | 1.54 | 1.36 | 0.80 |
| L171 | V | 1.02 | 1.39 | 0.92 |
| L171 | Y | 1.20 | 1.35 | 0.88 |
| A172 | A | 1.00 | 1.00 | 1.00 |

TABLE 10-12-continued

Performance Indices

| Wild-Type Res./Pos. | Mut. | PAF PI | PAD PI | Prot. PI |
|---|---|---|---|---|
| A172 | C | 1.20 | 0.86 | 1.09 |
| A172 | D | −0.15 | 1.42 | 0.16 |
| A172 | E | −0.15 | −0.44 | 0.19 |
| A172 | G | 1.41 | 0.84 | 1.07 |
| A172 | I | 1.70 | 0.58 | 0.30 |
| A172 | K | 0.95 | −0.43 | 0.17 |
| A172 | L | 1.20 | 1.22 | 0.70 |
| A172 | M | 0.84 | 1.06 | 0.84 |
| A172 | N | 0.37 | 0.76 | 0.30 |
| A172 | P | −0.15 | 0.58 | 0.16 |
| A172 | Q | 0.27 | 0.18 | 0.34 |
| A172 | R | 0.44 | −0.18 | 0.20 |
| A172 | S | 1.59 | 0.85 | 0.96 |
| A172 | T | 1.25 | 0.71 | 0.85 |
| A172 | V | 1.40 | 0.39 | 0.53 |
| A172 | W | 1.43 | 0.45 | 0.12 |
| A172 | Y | 0.87 | 1.76 | 0.13 |
| S173 | A | 0.81 | 2.72 | 0.95 |
| S173 | C | 0.82 | 3.07 | 0.59 |
| S173 | E | 0.78 | 2.65 | 0.90 |
| S173 | F | 0.96 | 2.30 | 0.71 |
| S173 | H | 1.07 | 1.49 | 0.95 |
| S173 | I | 0.99 | 2.22 | 0.78 |
| S173 | K | 1.17 | 3.01 | 0.91 |
| S173 | L | 1.15 | 3.86 | 0.77 |
| S173 | M | 0.80 | 3.01 | 0.84 |
| S173 | P | 0.19 | 2.66 | 0.35 |
| S173 | R | 1.09 | 2.47 | 0.82 |
| S173 | S | 1.00 | 1.00 | 1.00 |
| S173 | T | 1.06 | 1.29 | 0.89 |
| S173 | V | 0.95 | 2.54 | 0.75 |
| S173 | W | 1.16 | 3.67 | 0.67 |
| S173 | Y | 1.19 | 3.54 | 0.81 |
| F174 | A | 0.59 | 2.09 | 0.61 |
| F174 | C | 1.32 | 0.48 | 0.65 |
| F174 | F | 1.00 | 1.00 | 1.00 |
| F174 | G | 1.60 | 0.91 | 0.85 |
| F174 | H | 0.93 | 1.05 | 0.86 |
| F174 | K | 0.86 | 1.17 | 0.76 |
| F174 | L | 1.05 | 1.83 | 0.82 |
| F174 | M | 0.91 | 2.20 | 0.55 |
| F174 | P | 1.54 | 1.46 | 0.13 |
| F174 | Q | 1.42 | 0.46 | 0.82 |
| F174 | R | 0.70 | 0.52 | 0.95 |
| F174 | S | 1.16 | 0.61 | 0.75 |
| F174 | T | 0.80 | 0.64 | 0.62 |
| F174 | V | 0.60 | 0.67 | 0.82 |
| F174 | W | 0.96 | −0.02 | 0.85 |
| F174 | Y | 0.84 | 1.66 | 0.77 |
| M175 | A | 0.70 | 0.66 | 0.95 |
| M175 | E | 0.95 | 1.43 | 0.89 |
| M175 | G | 2.04 | 0.75 | 0.67 |
| M175 | L | 1.61 | 0.86 | 1.19 |
| M175 | M | 1.00 | 1.00 | 1.00 |
| M175 | N | 1.39 | 1.02 | 1.11 |
| M175 | P | −0.20 | 0.08 | 0.16 |
| M175 | Q | 1.56 | 0.83 | 0.98 |
| M175 | R | 1.55 | 0.86 | 1.02 |
| M175 | T | 2.21 | 0.90 | 0.98 |
| M175 | V | 1.93 | 0.81 | 1.00 |
| M175 | W | 1.25 | 0.76 | 1.14 |
| M175 | Y | 0.77 | 0.72 | 1.35 |
| K176 | A | 0.42 | 1.19 | 0.84 |
| K176 | C | 0.58 | 1.01 | 0.87 |
| K176 | D | 0.62 | 1.18 | 0.74 |
| K176 | E | 0.67 | 1.08 | 0.88 |
| K176 | F | 0.36 | 1.28 | 0.31 |
| K176 | G | 1.01 | 0.73 | 0.80 |
| K176 | K | 1.00 | 1.00 | 1.00 |
| K176 | L | 1.00 | 0.92 | 0.58 |
| K176 | M | 0.56 | 1.33 | 0.74 |
| K176 | N | 0.60 | 0.94 | 0.85 |
| K176 | P | 0.01 | 0.78 | 0.27 |
| K176 | Q | 0.59 | 0.97 | 1.02 |
| K176 | R | 0.71 | 1.03 | 1.06 |
| K176 | S | 0.76 | 0.72 | 0.93 |
| K176 | T | 1.04 | 0.97 | 0.70 |
| K176 | V | 1.04 | 1.33 | 0.71 |
| K176 | W | 1.19 | 1.16 | 0.41 |
| K176 | Y | 1.04 | 0.93 | 0.60 |
| P178 | A | 0.31 | 4.39 | 0.96 |
| P178 | D | 0.18 | 6.44 | 0.93 |
| P178 | E | 0.40 | 4.15 | 1.05 |
| P178 | G | 1.09 | 2.95 | 0.67 |
| P178 | K | 1.34 | 1.70 | 0.73 |
| P178 | L | 1.82 | 7.15 | 0.53 |
| P178 | M | 0.53 | 3.87 | 0.78 |
| P178 | P | 0.06 | 5.02 | 0.93 |
| P178 | Q | 0.15 | 3.64 | 0.93 |
| P178 | S | 0.62 | 3.06 | 0.95 |
| P178 | T | 0.70 | 2.28 | 0.81 |
| P178 | V | 0.67 | 2.70 | 0.78 |
| P178 | W | 1.14 | 0.02 | 0.64 |
| P178 | Y | 1.38 | 6.91 | 0.74 |
| F179 | A | −0.18 | −0.22 | −0.02 |
| F179 | E | 0.02 | 1.80 | 0.20 |
| F179 | F | 1.00 | 1.00 | 1.00 |
| F179 | G | 0.03 | 1.16 | 0.36 |
| F179 | H | 0.79 | 0.93 | 0.91 |
| F179 | L | 1.15 | 1.89 | 0.43 |
| F179 | N | 0.77 | 0.95 | 0.46 |
| F179 | P | −0.18 | −0.22 | −0.02 |
| F179 | Q | 0.46 | −0.87 | 0.46 |
| F179 | R | −0.18 | −0.22 | −0.02 |
| F179 | S | 0.78 | 0.34 | 0.62 |
| F179 | V | 0.70 | 1.17 | 0.69 |
| F179 | W | 0.89 | 0.86 | 0.62 |
| F179 | Y | 1.05 | 1.47 | 0.65 |
| F180 | A | 0.03 | 2.70 | 0.27 |
| F180 | C | 0.65 | 1.94 | 0.66 |
| F180 | E | −0.14 | −0.55 | −0.02 |
| F180 | F | 1.00 | 1.00 | 1.00 |
| F180 | G | 0.37 | −5.96 | 0.20 |
| F180 | I | 1.20 | 2.11 | 0.79 |
| F180 | K | 1.08 | −6.98 | 0.24 |
| F180 | L | 1.30 | 2.13 | 0.86 |
| F180 | M | 0.71 | 4.36 | 0.96 |
| F180 | N | −0.14 | 3.05 | 0.29 |
| F180 | Q | 0.21 | −1.87 | 0.36 |
| F180 | R | 0.64 | −3.57 | 0.26 |
| F180 | S | 0.56 | −2.05 | 0.29 |
| F180 | T | 1.01 | −0.68 | 0.33 |
| F180 | V | 1.14 | 3.24 | 0.76 |
| F180 | W | 1.11 | 1.81 | 0.90 |
| F180 | Y | 1.12 | 2.99 | 0.84 |
| D181 | A | 1.35 | 1.23 | 0.65 |
| D181 | C | 1.09 | 0.85 | 0.56 |
| D181 | D | 1.00 | 1.00 | 1.00 |
| D181 | E | 1.10 | 0.72 | 0.78 |
| D181 | F | −0.15 | −0.17 | −0.01 |
| D181 | G | 1.09 | 0.52 | 0.37 |
| D181 | H | −0.15 | −0.17 | −0.01 |
| D181 | I | −0.15 | −0.17 | −0.01 |
| D181 | K | 1.33 | 0.47 | 0.41 |
| D181 | L | 1.25 | −0.16 | 0.16 |
| D181 | M | −0.15 | −0.17 | −0.01 |
| D181 | N | −0.15 | −0.17 | −0.01 |
| D181 | P | 1.03 | 0.66 | 0.60 |
| D181 | Q | 1.14 | 0.60 | 0.54 |
| D181 | R | 1.23 | 0.22 | 0.45 |
| D181 | S | 1.21 | 0.55 | 0.56 |
| D181 | T | 1.02 | −0.32 | 0.24 |
| D181 | V | 0.88 | −0.34 | 0.21 |
| D181 | W | 1.26 | −0.52 | 0.28 |
| D181 | Y | 1.29 | −0.25 | 0.25 |
| A182 | A | 1.00 | 1.00 | 1.00 |
| A182 | C | 0.97 | 0.99 | 1.03 |
| A182 | G | 0.92 | 0.94 | 0.90 |

TABLE 10-12-continued

Performance Indices

| Wild-Type Res./Pos. | Mut. | PAF PI | PAD PI | Prot. PI |
|---|---|---|---|---|
| A182 | H | −0.14 | −0.18 | −0.02 |
| A182 | I | 0.89 | −2.48 | 0.20 |
| A182 | K | −0.14 | −0.18 | −0.02 |
| A182 | L | −0.14 | −0.18 | −0.02 |
| A182 | M | −0.14 | −0.18 | −0.02 |
| A182 | N | −0.14 | 0.53 | 0.14 |
| A182 | P | −0.14 | −1.13 | 0.12 |
| A182 | Q | 0.03 | −0.84 | 0.14 |
| A182 | R | 0.25 | −2.69 | 0.12 |
| A182 | S | 0.87 | 0.85 | 0.90 |
| A182 | T | 1.14 | 0.11 | 0.48 |
| A182 | W | −0.14 | −0.18 | −0.02 |
| A182 | Y | −0.14 | −0.18 | −0.02 |
| G183 | C | 0.56 | 1.99 | 0.92 |
| G183 | D | 0.30 | 0.99 | 0.62 |
| G183 | F | 0.68 | 0.19 | 0.75 |
| G183 | G | 1.00 | 1.00 | 1.00 |
| G183 | H | 0.98 | 0.95 | 0.87 |
| G183 | L | 0.82 | 1.50 | 0.47 |
| G183 | P | −0.18 | 1.02 | 0.33 |
| G183 | Q | 0.66 | −0.20 | 0.97 |
| G183 | R | 0.92 | 1.09 | 0.90 |
| G183 | S | 0.94 | −0.08 | 1.08 |
| G183 | V | 0.56 | −2.47 | 0.57 |
| G183 | Y | 0.97 | 1.45 | 0.79 |
| S184 | A | 0.60 | 1.69 | 1.31 |
| S184 | C | 0.81 | 2.39 | 1.14 |
| S184 | D | 0.84 | 2.24 | 1.15 |
| S184 | E | 0.94 | 1.86 | 1.39 |
| S184 | F | 1.05 | 1.27 | 0.89 |
| S184 | G | 0.99 | 0.82 | 1.15 |
| S184 | H | 1.02 | 0.74 | 1.07 |
| S184 | I | 0.92 | 1.21 | 0.96 |
| S184 | K | 0.97 | 1.61 | 1.02 |
| S184 | L | 0.80 | 2.00 | 0.98 |
| S184 | M | 0.51 | 1.77 | 1.25 |
| S184 | N | 0.64 | 1.93 | 1.03 |
| S184 | P | −0.15 | 0.85 | 0.40 |
| S184 | Q | 0.89 | 1.16 | 1.09 |
| S184 | S | 1.00 | 1.00 | 1.00 |
| S184 | T | 1.04 | 0.60 | 0.94 |
| S184 | V | 0.80 | 1.25 | 1.03 |
| S184 | Y | 1.06 | 1.09 | 0.84 |
| V185 | C | 0.65 | 0.83 | 0.96 |
| V185 | D | 0.40 | −2.49 | 0.21 |
| V185 | E | 0.73 | 0.88 | 0.76 |
| V185 | F | 1.02 | 1.20 | 0.83 |
| V185 | G | 1.12 | −3.67 | 0.47 |
| V185 | H | 1.30 | −0.58 | 0.71 |
| V185 | I | 1.07 | 0.63 | 1.03 |
| V185 | K | 1.37 | 0.79 | 0.66 |
| V185 | L | 1.23 | 0.93 | 0.75 |
| V185 | M | 0.39 | 1.46 | 0.77 |
| V185 | O | 0.77 | 1.41 | 0.73 |
| V185 | R | 1.15 | 0.79 | 0.57 |
| V185 | S | 1.09 | 0.53 | 0.75 |
| V185 | T | 1.11 | 0.91 | 0.79 |
| V185 | V | 1.00 | 1.00 | 1.00 |
| V185 | W | 1.36 | −0.44 | 0.53 |
| V185 | Y | 1.37 | 0.58 | 0.65 |
| I186 | A | 1.46 | 1.79 | 0.90 |
| I186 | D | −0.13 | 4.29 | 0.19 |
| I186 | F | 1.01 | 0.76 | 0.77 |
| I186 | G | 1.86 | −5.42 | 0.35 |
| I186 | I | 1.00 | 1.00 | 1.00 |
| I186 | K | −0.13 | −0.36 | −0.01 |
| I186 | L | 1.17 | 1.14 | 0.84 |
| I186 | M | 0.86 | 1.38 | 1.11 |
| I186 | P | −0.13 | −2.95 | 0.25 |
| I186 | R | 0.62 | −6.69 | 0.25 |
| I186 | S | 1.39 | −0.21 | 0.65 |
| I186 | T | 1.51 | 0.23 | 0.79 |
| I186 | V | 1.28 | 0.48 | 0.93 |
| I186 | W | −0.13 | −0.36 | −0.01 |
| I186 | Y | −0.13 | −0.36 | −0.01 |
| S187 | A | 0.51 | 1.72 | 0.86 |
| S187 | C | 0.70 | 1.67 | 0.79 |
| S187 | D | 0.59 | 1.40 | 0.82 |
| S187 | F | 1.02 | 0.65 | 0.73 |
| S187 | G | 1.03 | 1.46 | 0.88 |
| S187 | H | 1.29 | 1.51 | 0.68 |
| S187 | I | 1.38 | 1.58 | 0.78 |
| S187 | K | 1.45 | 1.16 | 0.76 |
| S187 | L | 1.37 | 1.46 | 0.75 |
| S187 | M | 0.49 | 1.87 | 0.85 |
| S187 | N | 0.59 | 1.59 | 0.90 |
| S187 | P | 0.44 | −0.31 | 0.78 |
| S187 | Q | 0.63 | 0.35 | 0.94 |
| S187 | R | 1.04 | 0.55 | 0.82 |
| S187 | S | 1.00 | 1.00 | 1.00 |
| S187 | T | 1.12 | 0.23 | 0.74 |
| S187 | V | 1.23 | 0.58 | 0.89 |
| S187 | W | 1.30 | 0.52 | 0.73 |
| S187 | Y | 1.43 | 0.80 | 0.76 |
| T188 | A | 0.97 | 0.95 | 1.40 |
| T188 | C | 0.60 | 0.87 | 2.04 |
| T188 | D | −0.05 | −0.14 | −0.02 |
| T188 | E | 0.24 | 1.97 | 0.44 |
| T188 | F | 0.96 | −0.20 | 0.63 |
| T188 | G | 0.93 | 0.79 | 1.32 |
| T188 | H | 1.11 | −0.79 | 0.74 |
| T188 | I | 1.13 | 0.10 | 1.85 |
| T188 | K | −0.05 | −0.14 | −0.02 |
| T188 | L | 0.76 | 0.42 | 1.76 |
| T188 | M | 0.49 | 0.75 | 1.60 |
| T188 | N | 0.69 | 1.69 | 1.24 |
| T188 | P | −0.05 | −0.14 | −0.02 |
| T188 | Q | −0.05 | −0.14 | −0.02 |
| T188 | R | 1.01 | −0.47 | 1.41 |
| T188 | S | 1.16 | 0.91 | 1.52 |
| T188 | T | 1.00 | 1.00 | 1.00 |
| T188 | V | 1.22 | 0.15 | 1.53 |
| T188 | W | −0.05 | −0.14 | −0.02 |
| T188 | Y | 1.48 | 0.09 | 0.47 |
| D189 | A | 0.05 | 1.18 | 0.53 |
| D189 | C | 0.19 | 0.94 | 0.56 |
| D189 | D | 0.03 | 0.89 | 0.90 |
| D189 | E | 0.35 | 0.77 | 0.85 |
| D189 | F | 0.83 | 0.37 | 0.63 |
| D189 | G | 0.80 | 0.80 | 0.83 |
| D189 | H | 1.25 | 0.95 | 0.78 |
| D189 | I | 0.73 | 1.27 | 0.69 |
| D189 | L | 1.30 | 1.30 | 0.61 |
| D189 | M | 0.06 | 0.88 | 0.48 |
| D189 | N | 0.22 | 0.57 | 0.80 |
| D189 | P | −0.12 | 0.97 | 0.67 |
| D189 | R | 0.86 | 0.39 | 0.65 |
| D189 | S | 0.88 | 0.81 | 0.85 |
| D189 | T | 1.00 | 1.21 | 0.73 |
| D189 | V | 0.73 | 0.71 | 0.72 |
| D189 | W | 1.09 | 0.76 | 0.60 |
| I194 | A | 0.29 | 0.00 | 1.15 |
| I194 | C | 0.27 | −0.02 | 1.17 |
| I194 | F | 0.07 | −0.03 | 0.95 |
| I194 | G | 0.10 | 0.04 | 0.34 |
| I194 | I | 1.00 | 1.00 | 1.00 |
| I194 | L | 0.80 | 0.58 | 1.32 |
| I194 | P | 0.15 | −1.42 | 0.16 |
| I194 | R | 0.02 | −0.40 | 0.77 |
| I194 | S | 0.30 | −0.15 | 0.48 |
| I194 | V | 0.37 | 0.78 | 1.03 |
| I194 | W | 0.04 | −0.09 | 1.12 |
| I194 | Y | −0.32 | −0.01 | 1.01 |
| F196 | A | −0.13 | −0.13 | −0.02 |
| F196 | C | 1.74 | 1.18 | 0.70 |
| F196 | F | 1.00 | 1.00 | 1.00 |
| F196 | G | 1.59 | −0.30 | 0.60 |
| F196 | H | 1.77 | −0.24 | 0.23 |

TABLE 10-12-continued

Performance Indices

| Wild-Type Res./Pos. | Mut. | PAF PI | PAD PI | Prot. PI |
|---|---|---|---|---|
| F196 | I | 1.32 | 1.12 | 0.81 |
| F196 | K | -0.13 | -0.13 | -0.02 |
| F196 | L | 1.77 | 1.17 | 1.09 |
| F196 | M | 1.65 | 0.71 | 0.93 |
| F196 | N | -0.13 | -0.13 | -0.02 |
| F196 | P | 0.05 | 0.39 | 0.42 |
| F196 | Q | 1.00 | -0.25 | 0.40 |
| F196 | R | -0.13 | -0.13 | -0.02 |
| F196 | S | 1.58 | -1.57 | 0.29 |
| F196 | V | 1.40 | 0.68 | 0.51 |
| F196 | W | 1.01 | 0.38 | 0.88 |
| F196 | Y | 1.41 | 0.97 | 0.73 |

Example 11

Figure 20:
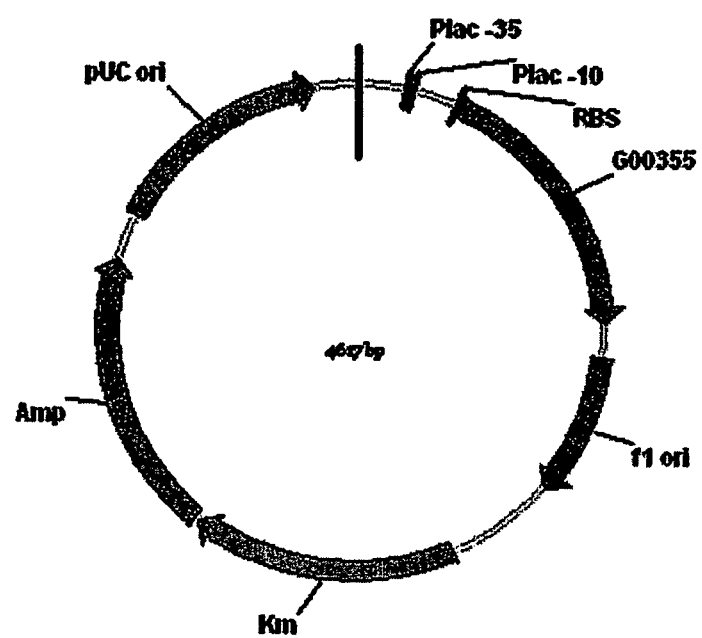
FIG. 20 provides a map of plasmid pMC355rbs.

Cloning and Expression of a *Sinorhizobium meililoti* RSM02162 *M. smegmatis* Perhydrolase Homologue In this Example, cloning and expression of a *S. meliloti* perhydrolase homologue are described. The sequences used in cloning and expression are provided below. The gene RSM02162 (SEQ ID NO:625) was synthesized by DNA2.0. The gene was given the designation "G00355" and was provided cloned into the commercially available vector, pDRIVE (InvivoGen). The gene was amplified by PCR from this clone using the primer set G00355rbsF/G00355R, Taq DNA polymerase (Roche) as per the manufacturer's directions, with G00355 as the template (10 ng/50 µl reaction) and 10 picomoles (per 50 µl reaction) of each primer. The amplification was carried out in an MJ Research PCR machine using 30 cycles of (1 minute at 95° C.; 1 minute at 55° C.; and 1 minute at 72° C.). The amplification of the correct size fragment was confirmed by agarose gel electrophoresis. The fragment was cloned directly into pCR2.1TOPO (Invitrogen) and transformed into *E. coli* Top10 cells (Invitrogen). Transformants were selected on L agar containing carbenicillin (100 µg/ml) at 37° C. The correct construct was confirmed by sequence analysis and designated "pMC355rbs." FIG. 20 provides a map of this plasmid.

```
Primer sequences:
G00355rbsF
                                    (SEQ ID NO: 626)
5'-ggccctaacaggaggaattaaccatggtggaaaaacgttccgttctg
tgc-3'

G00355R
                                    (SEQ ID NO: 627)
5'-Gcgcgcttagaacagagccgctactttgtcagc-3'

Gene sequence (including stop codon) ofRSM02162:
                                    (SEQ ID NO: 625)
5'-atggtggaaaaacgttccgttctgtgctttggtgattctctgacttg gggctggattccggtgaaagagagctccccaactctgcgttacccatacg aacagcgttggaccggtgctatggctgcacgtctgggtgatggttaccac atcattgaagaaggcctgtccgctcgtactactagcctggacgacccaaa cgacgctcgtctgaacggctctacctacctgccgatggctctggcttctc acctgccactggatctggtaatcattatgctgggtaccaacgacaccaaa agctactttcatcgtaccccatacgagattgccaacggcatgggtaaact ggtaggtcaggtcctgacctgtgcaggtggtgttggtacgccttatccag caccgaaagtcctggtggttgcacctccaccactggcaccaatgccagat ccgtggttcgaaggtatgttcggcggggttacgagaaatctaaggaactg tccggtctgtacaaagcactggctgatttcatgaaagtggagttcttcgc agcgggtgattgtatctccaccgacggtatcgacggtatccacctgagcg ctgaaaccaacatccgcctgggtcatgctattgctgacaaagtagcggct ctgttctaa-3'

G00355 Protein sequence:
                                    (SEQ ID NO: 628)
MVEKRSVLCFGDSLTWGWIPVKESSPTLRYPYEQRWTGAMAARLGDGYHI

IEEGLSARTTSLDDPNDARLNGSTYLPMALASHLPLDLVIIMLGTNDTKS

YFHRTPYEIANGMGKLVGQVLTCAGGVGTPYPAPKVLVVAPPPLAPMPDP

WFEGMFGGGYEKSKELSGLYKALADFMKVEFFAAGDCISTDGIDGIHLSA

ETNIRLGHAIADKVAALF

Complete sequence of pDRIVEG00355:
                                    (SEQ ID NO: 629)
gcgcccaatacgcaaaccgcctctccccgcgcgttggccgattcattaat gcagctggcacgacaggtttcccgactggaaagcgggcagtgagcgcaac gcaattaatgtgagttagctcactcattaggcacccaggctttacactt tatgcttccggctcgtatgttgtgtggaattgtgagcggataacaatttc acacaggaaacagctatgaccatgattacgccaagctctaatacgactca ctatagggaaagctcggtaccacgcatgctgcagacgcgttacgtatcgg atccagaattcgtgattttagaacagagccgctactttgtcagcaatagc atgaccaggcggatgttggtttcagcgctcaggtggataccgtcgatac cgtcggtggagatacaatcacccgctgcgaagaactccactttcatgaaa tcagccagtgctttgtacagaccggacagttccttagatttctcgtaacc accgccgaacataccttcgaaccacggatctggcattggtgccagtggtg gaggtgcaaccaccaggactttcggtgctggataaggcgtaccaacacca cctgcacaggtcaggacctgacctaccagtttacccatgccgttggcaat ctcgtatggggtacgatgaaagtagcttttggtgtcgttggtacccagca taatgattaccagatccagtggcaggtgagaagccagagccatcggcagg taggtagagccgttcagacgagcgtcgtttgggtcgtccaggctagtagt acgagcggacaggccttcttcaatgatgtggtaaccatcacccagacgtg cagccatagcaccggtccaacgctgtcgtatgggtaacgcagagttgggg agctctcttcaccggaatccagccccaagtcagagaatcaccaaagcac agaacggaacgtttttccaccataatctgaattcgtcgacaagcttctcg agcctaggctagctctagaccacacgtgtgggggcccgagctcgcggccg ctgtattctatagtgtcacctaaatggccgcacaattcactggccgtcgt tttacaacgtcgtgactgggaaaaccctggcgttacccaacttaatcgcc ttgcagcacatccccttttcgccagctggcgtaatagcgaagaggcccgc accgatcgcccttcccaacagttgcgcagcctgaatggcgaatggaaatt
```

```
gtaagcgttaatattttgttaaaattcgcgttaaattttttgttaaatcag
ctcattttttaaccaataggccgaaatcggcaaaatcccttatataatcaa
aagaatagaccgagataggggttgagtgttgttccagtttggaacaagagt
ccactattaaagaacgtggactccaacgtcaaagggcgaaaaaccgtcta
tcagggcgatggcccactacgtgaaccatcaccctaatcaagttttttgg
ggtcgaggtgccgtaaagcactaaatcggaacccaaagggagccccga
tttagagcttgacggggaaagccggcgaacgtggcgagaaaggaagggaa
gaaagcgaaaggagcgggcgctagggcgctggcaagtgtagcggtcacgc
tgcgcgtaaccaccacacccgccgcgcttaatgcgccgctacagggcgcg
tcaggtggcactttcgggaaatgtgcgcggaaccccctatttgtttatt
tttctaatacattcaaaatgtatccgctcatgagacaaccctgataaatg
cttcaataatattgaaaaaggaagagtatgagtattcaacatttccgtgt
cgcccttattcccttttttgcggcattttgccttcctgttttgctcacc
cagaaacgctggtgaaagtaaaagatgctgaagatcagttgggtgcacga
gtgggttacatcgaactggatctcaacagcggtaagatccttgagagttt
tcgccccgaagaacgttttccaatgatgagcactttttaaagttctgctatg
tggcgcggtattatcccgtattgacgccgggcaagagcaactcggtcgcc
gcatacactattctcagaatgacttggttgagtactcaccagtcacagaa
aagcatcttacggatggcatgacagtaagagaattatgcagtgctgccat
aaccatgagtgataacactgcggccaacttacttctgacaacgatcggag
gaccgaaggagctaaccgcttttttgcacaacatgggggatcatgtaact
cgccttgatcgttgggaaccggagctgaatgaagccataccaaacgacga
gcgtgacaccacgatgcctgtagcaatggcaacaacgttgcgcaaactat
taactggcgaactacttactctagcttcccggcaacaattaatagactgg
atggaggcggataaagttgcaggaccacttctgcgctcggcccttccggc
tggctggtttattgctgataaatctggagccggtgagcgtgggtctcgcg
gtatcattgcagcactggggccagatggtaagccctcccgtatcgtagtt
atctacacgacggggagtcaggcaactatggatgaacgaaatagacagat
cgctgagataggtgcctcactgattaagcattggtaactgtcagaccaag
tttactcatatatactttagattgatttaaaacttcattttttaatttaaa
aggatctaggtgaagatcctttttgataatctcatgaacaataaaactgt
ctgcttacataaacagtaatacaagggggtgttatgagccatattcaacgg
gaaacgtcttgctctaggccgcgtattccaacatggatgctgatttata
tgggtataaatgggctcgcgataatgtcgggcaatcaggtgcgacaatct
atcgattgtatgggaagcccgatgcgccagagttgtttctgaaacatggc
aaaggtagcgttgccaatgatgtacagatgagatggtcagactaaactgg
ctgacggaatttatgcctcttccgaccatcaagcattttatccgtactcc
tgatgatgcatgttactcaccactgcgatcccgggaaaacagcattccag
gtattagaagaatatcctgattcaggtgaaaatattgttgatgcgctggc
agtgttcctgcgccggttgcattcgattcctgtttgtaattgtccttta
acagcgatcgcgtatttcgtctcgctcaggcgcaatcacgaatgaataac
```

```
ggtttggttgatgcgagtgattttgatgacgagcgtaatggctggcctgt
tgaacaagtctggaaagaaatgcataaacttttgccattctcaccggatt
cagtcgtcactcatggtgatttctcacttgataaccttatttgacgaggg
gaaattaataggttgtattgatgttggacgagtcggaatcgcagaccgat
accaggatcttgccatcctatggaactgcctcggtgagttttctccttca
ttacagaaacggctttttcaaaaatatggtattgataatcctgatatgaa
taaattgcagtttcatttgatgctcgatgagttttctaagaattaattc
atgaccaaaatcccttaacgtgagttttcgttccactgagcgtcagaccc
cgtagaaaagatcaaaggatcttcttgagatcctttttttctgcgcgtaa
tctgctgcttgcaaacaaaaaaaccaccgctaccagcggtggtttgtttg
ccggatcaagagctaccaactctttttccgaaggtaactggcttcagcag
agcgcagataccaaatactgtccttctagtgtagccgtagttaggccacc
acttcaagaactctgtagcaccgcctacatacctcgctctgctaatcctg
ttaccagtggctgctgccagtggcgataagtcgtgtcttaccgggttgga
ctcaagacgatagttaccggataaggcgcagcggtcgggctgaacggggg
gttcgtgcacacagcccagcttggagcgaacgacctacaccgaactgaga
tacctacagcgtgagctatgagaaagcgccacgcttcccgaagggagaaa
ggcggacaggtatccggtaagcggcagggtcggaacaggagagcgcacga
gggagcttccaggggggaaacgcctggtatctttatagtcctgtcgggttt
cgccacctctgacttgagcgtcgatttttgtgatgctcgtcaggggggcg
gagcctatggaaaaacgccagcaacgcggcctttttacggttcctggcct
tttgctggccttttgctcacatgttctttcctgcgttatcccctgattct
gtggataaccgtattaccgcctttgagtgagctgataccgctcgccgcag
ccgaacgaccgagcgcagcgagtcagtgagcgaggaagcggaaga
Complete sequence pMC355rbs:
                          (SEQ ID NO: 630)
agcgcccaatacgcaaaccgcctctccccgcgcgttggccgattcattaa
tgcagctggcacgacaggtttcccgactggaaagcgggcagtgagcgcaa
cgcaattaatgtgagttagctcactcattaggcaccccaggctttacact
ttatgcttccggctcgtatgttgtgtggaattgtgagcggataacaattt
cacacaggaaacagctatgaccatgattacgccaagcttggtaccgagct
cggatccactagtaacggccgccagtgtgctggaattcgcccttggccct
aacaggaggaattaaccatggtggaaaaacgttccgttctgtgctttggt
gattctctgacttggggctggattccggtgaaagagagctcccaactct
gcgttacccatacgaacagcgttggaccggtgctatggctgcacgtctgg
gtgatggttaccacatcattgaagaaggcctgtccgctcgtactactagc
ctggacgacccaaacgacgctcgtctgaacggctctacctacctgccgat
ggctctggcttctcacctgccactggatctggtaatcattatgctgggta
ccaacgacaccaaaagctactttcatcgtaccccatacgagattgccaac
ggcatgggtaaactggtaggtcaggtcctgacctgtgcaggtggtgttgg
tacgccttatccagcaccgaaagtcctggtggttgcacctccaccactgg
```

-continued caccaatgccagatccgtggttcgaaggtatgttcggcggtggttacgag
aaatctaaggaactgtccggtctgtacaaagcactggctgatttcatgaa
agtggagttcttcgcagcgggtgattgtatctccaccgacggtatcgacg
gtatccacctgagcgctgaaaccaacatccgcctgggtcatgctattgct
gacaaagtagcggctctgttctaagcgcgcaagggcgaattctgcagata
tccatcacactggcggccgctcgagcatgcatctagagggcccaattcgc
cctatagtgagtcgtattacaattcactggccgtcgttttacaacgtcgt
gactgggaaaaccctggcgttacccaacttaatcgccttgcagcacatcc
cccttttcgccagctggcgtaatagcgaagaggcccgcaccgatcgccctt
cccaacagttgcgcagcctgaatggcgaatggacgcgccctgtagcggcg
cattaagcgcggcgggtgtggtggttacgcgcagcgtgaccgctacactt
gccagcgccctagcgcccgctcctttcgctttcttcccttcctttctcgc
cacgttcgccggctttccccgtcaagctctaaatcgggggctcccttttag
ggttccgatttagtgctttacggcacctcgaccccaaaaaacttgattag
ggtgatggttcacgtagtgggccatcgccctgatagacggtttttcgccc
tttgacgttggagtccacgttctttaatagtggactcttgttccaaactg
gaacaacactcaaccctatctcggtctattcttttgatttataagggatt
ttgccgatttcggcctattggttaaaaaatgagctgatttaacaaaaatt
taacgcgaattttaacaaaattcagggcgcaagggctgctaaaggaagcg
gaacacgtagaaagccagtccgcagaaacggtgctgaccccggatgaatg
tcagctactgggctatctggacaagggaaaacgcaagcgcaaagagaaag
caggtagcttgcagtgggcttacatggcgatagctagactgggcggtttt
atggacagcaagcgaaccgaattgccagctgggcgccctctggtaagg
ttgggaagccctgcaaagtaaactggatggctttcttgccgccaaggatc
tgatggcgcaggggatcaagatctgatcaagagacaggatgaggatcgtt
tcgcatgattgaacaagatggattgcacgcaggttctccggccgcttggg
tggagaggctattcggctatgactgggcacaacagacaatcggctgctct
gatgccgccgtgttccggctgtcagcgcaggggcgcccggttcttttgt
caagaccgacctgtccggtgccctgaatgaactgcaggacgaggcagcgc
ggctatcgtggctggccacgacgggcgttccttgcgcagctgtgctcgac
gttgtcactgaagcgggaagggactggctgctattgggcgaagtgccggg
gcaggatctcctgtcatcccaccttgctcctgccgagaaagtatccatca
tggctgatgcaatgcggcggctgcatacgcttgatccggctacctgccca
ttcgaccaccaagcgaaacatcgcatcgagcgagcacgtactcggatgga
agccggtcttgtcgatcaggatgatctggacgaagagcatcaggggctcg
cgccagccgaactgttcgccaggctcaaggcgcgcatgcccgacggcgag
gatctcgtcgtgacccatggcgatgcctgcttgccgaatatcatggtgga
aaatggccgcttttctggattcatcgactgtggccggctgggtgtggcgg
accgctatcaggacatagcgttggctacccgtgatattgctgaagagctt
ggcggcgaatgggctgaccgcttcctcgtgctttacggtatcgccgctcc
cgattcgcagcgcatcgccttctatcgccttcttgacgagttcttctgaa -continued ttgaaaaaggaagagtatgagtattcaacatttccgtgtcgcccttattc
ccttttttgcggcatttttgccttcctgttttttgctcacccagaaacgctg
gtgaaagtaaaagatgctgaagatcagttgggtgcacgagtgggttacat
cgaactggatctcaacagcggtaagatccttgagagttttcgccccgaag
aacgttttccaatgatgagcacttttaaagttctgctatgtggcgcggta
ttatcccgtattgacgccgggcaagagcaactcggtcgccgcatacacta
ttctcagaatgacttggttgagtactcaccagtcacagaaaagcatctta
cggatggcatgacagtaagagaattatgcagtgctgccataaccatgagt
gataacactgcggccaacttacttctgacaacgatcggaggaccgaagga
gctaaccgcttttttgcacaacatgggggatcatgtaactcgccttgatc
gttgggaaccggagctgaatgaagccataccaaacgacgagcgtgacacc
acgatgcctgtagcaatggcaacaacgttgcgcaaactattaactggcga
actacttactctagcttcccggcaacaattaatagactggatggaggcgg
ataaagttgcaggaccacttctgcgctcggcccttccggctggctggttt
attgctgataaatctggagccggtgagcgtgggtctcgcggtatcattgc
agcactggggccagatggtaagccctcccgtatcgtagttatctacacga
cggggagtcaggcaactatggatgaacgaaatagacagatcgctgagata
ggtgcctcactgattaagcattggtaactgtcagaccaagtttactcata
tatactttagattgatttaaaacttcatttttaatttaaaaggatctagg
tgaagatcctttttgataatctcatgaccaaaatcccttaacgtgagttt
tcgttccactgagcgtcagaccccgtagaaaagatcaaaggatcttcttg
agatcctttttttctgcgcgtaatctgctgcttgcaaacaaaaaaaccac
cgctaccagcggtggtttgtttgccggatcaagagctaccaactctttttt
ccgaaggtaactggcttcagcagagcgcagataccaaatactgttcttct
agtgtagccgtagttaggccaccacttcaagaactctgtagcaccgccta
catacctcgctctgctaatcctgttaccagtggctgctgccagtggcgat
aagtctgtcttaccggttggactcaagacgatagttaccggataaggcgc
agcggtcgggctgaacggggggttcgtgcacacagcccagcttggagcga
acgacctacaccgaactgagatacctacagcgtgagctatgagaaagcgc
cacgcttcccgaagggagaaaggcggacaggtatccggtaagcggcaggg
tcggaacaggagagcgcacgagggagcttccaggggaaacgcctggtat
ctttatagtcctgtcgggtttcgccacctctgacttgagcgtcgatttt
gtgatgctcgtcaggggggcggagcctatggaaaaacgccagcaacgcgg
ccttttacggttcctggccttttgctggccttttgctcacatgttcttt
cctgcgttatcccctgattctgtggataaccgtattaccgcctttgagtg
agctgataccgctcgccgcagccgaacgaccgagcgcagcgagtcagtga
gcgaggaagcggaag Expression of the Homologue from pMC355rbs To express the S. meliloti RSM02162 protein from the plasmid pMC355rbs (See, FIG. 20, for a map of this plasmid), a single colony was inoculated into a 5 mls of L broth containing 100 μg/ml carbenicillin and grown overnight at 37° C. with shaking at 200 rpm. Lysates were prepared by pelleting the cells from 1 ml of the overnight culture by centrifugation and lysed with BugBuster (Novagen). The supernatants were assayed using the pNA activity assay, perhydrolysis assay, and a pNC6 assay (to test its ability to hydrolyze carbon chains longer than C4), as described herein.

Assay Results

The following Table (Table I1-1) provides a comparison of the hydrolysis activity of pNA by G00355 as compared to the *M. smegmatis* perhydrolase

TABLE 11-1 pNA Hydrolysis Activity

| Strain | pNA Hydrolysis Rate* | Rate Compared to Perhydrolase |
|---|---|---|
| E. coli/pMSATNcoI | 85 | 1 |
| E. coli/pMC355rbs | 80 | 0.94 |
| E. coli/pCR2.1 | 34.6 | 0.41 |

*Rate is absorbance units/min read at 405 nm in a spectrophotometer.

The following Table (Table 11-2) provides a comparison of the perhydrolysis of triacetin by G00355 compared to the *M. smegmatis* perhydrolase.

TABLE 11-2

Triacetin Perhydrolysis Activity

| Strain | Perhydrolysis Activity | |
|---|---|---|
| | Max | Vmax |
| E. coli/pMSATNcoI | 1.04 | 11.88 |
| E. coli/pMC355rbs | 1.17 | 25.05 |
| E. coli/pCR2.1 | 0.1 | 2.9 |

The following Table (Table 11-3) provides a comparison of pNC6 hydrolysis by G00355 compared to the *M. smegmatis* perhydrolase.

TABLE 11-3 pNC6 Hydrolysis Activity

| Strain | pNC6 Hydrolysis Rate* | Rate Compared to Ms. Perhydrolase |
|---|---|---|
| E. coli/pMSATNcoI | 0.58 | 1 |
| E. coli/pMC355rbs | 6.57 | 11.3 |
| E. coli/pCR2.1 | 0.47 | 0.8 |

*Rate is absorbance units/min read at 405 nm in a spectrophotometer.

As these results indicate, the homologue RSM02162 from *S. meliloti* identified by amino acid sequence homology to the *M. smegmatis* perhydrolase demonstrated similar, albeit less perhydrolysis activity than the *M. smegmatis* perhydrolase. However, this enzyme exhibited different substrate specificity, as it was able to hydrolyze pNC6, while the wild-type *M. smegmatis* perhydrolase cannot.

The results of the pNC6 hydrolysis assay indicated that certain positions/substitutions provided an improvement in the ability of the enzyme to utilize longer chain substrates The positions and substitutions identified in preliminary screens are provided in the following Table. It is not intended that the present invention be limited to these specific positions and substitutions, as it is contemplated that additional positions and/or substitutions will also provide improved activity on longer chain substrates.

TABLE 11-4

Positions/Substitutions with Improved Activity in PNC6 Assay

| Wild-Type Residue/Position | Amino Acid Variant(s) |
|---|---|
| L12 | G, P, Q |
| S54 | L, T |
| I153 | F, P |
| F154 | Q, S, T, V |
| I194 | G |
| F196 | A, C, G, I, N, P, Q, S, V |

Example 12

Amplification of Genes Encoding *M. smegmatis* Perhydrolase Homologues from Environmental Isolates In this Example, methods used to amplify genes encoding *M. smegmatis* perhydrolase homologues from environmental isolates are described.

Organisms from soil samples that were positive for the transesterification reaction were purified to single colonies. To amplify the genes by PCR, the degenerate primer sets 1AF/5AR and 1eF/51R were used in a PCR reaction containing isolated chromosomal DNA from 8 environmental strains exhibiting the transesterification reaction. The PCR reaction was carried out using Taq DNA polymerase (Roche) as per the manufacturer's protocol, with 1 μg of chromosomal DNA added as template and 10 picomoles of each primer in a 50 μl reaction. The reaction was carried out for 30 cycles of (1 minute at 95° C.; 1 minute at 50° C., and 1 minute at 72° C.). Since the partial coding sequence of the perhydrolase gene from *Mycobacterium parafortuitum* was already isolated, the same strain was used as a positive control. The strains were designated as: 2G, 2D, 9B, 14B, 18D, 19C, 20A. As indicated below, 20A was typed as *Mycobacterium parafortuitum*, and 9B is *Mycobacterium gilvum*. Based on protein homology, it was inferred that 2D is also *M. parafortuitum* and 14B is *M. gilvum*.

Primer Sequences

```
1AF:
                                   (SEQ ID NO: 631)
5'-gccaagcgaattctgtgtttcggngaytcnyt-3'

5AR:
                                   (SEQ ID NO: 632)
5'-cgattgttcgcctcgtgtgaartgnrtnccrtc-3'

1eF:
                                   (SEQ ID NO: 633)
5'-acggtcctgtgctttggngaytcnyt-3'

51R:
                                   (SEQ ID NO: 634)
5'-ccgctggtcctcatctggrtgntcnccrtc-3'
```

Amplification with the above primer sets was expected to yield bands of approximately 500 bp. In all cases except 2G, the 1AF/5AR primer set produced a band of the expected size. In the case of 19C, both primer sets produced bands of the expected size. The ~500 bp bands were purified from agarose gels using a gel purification kit (Qiagen) and analyzed by sequencing. While the strains 2G and 19C yielded bands of the expected size with both primer sets they were not the fragments encoding the *M. smegmatis* perhydrolase homologue.

Partial Sequences of 2D Perhydrolase Homologue and Protein:

Gene:
(SEQ ID NO: 635)
```
5'-attctgtgtttcggggattccttgacgtggggatggatccctgtcga
agaaggtgtgcccaccgagcggttcccgcgtgacgtccggtggaccggcg
tgctggccgacctgctgggcgaccgctacgaggtgatcgaggaaggcctg
tcggcgcgcaccaccaccgccgacgacccggccgaccccggctcaacg
ttcgcagtatctgccgtcgtgtctggccagccatctgccgctggacctgg
tgatcctgatgctcggcatcaacgacaccaaggcgaattttggccgcacc
ccgttcgacatcgccaccggtatgggagtgcttgccacgcaggtgctcac
cagcgccggtggcgtggggaccagctatcccgcgccgcaggtgctgatcg
tggccgccgccgctgggcgagctgccccacccctggttcgacctggtg
ttctccggcggccgtgagaagaccgccgagttggcccgcgtgtacagcgc
gctggccgtcgttcatgaaggtgccgttcttcgacgccggctcggtgatca
gcaccgacggcgtggacggcacccacttcacacgaggcgaaacaatcga
```

Protein:
(SEQ ID NO: 636)
```
ILCFGDSLTWGWIPVEEGVPTERFPRDVRWTGVLADLLGDRYEVIEEGLS
ARTTTADDPADPRLNGSQYLPSCLASHLPLDLVILMLGINDTKANFGRTP
FDIATGMGVLATQVLTSAGGVGTSYPAPQVLIVAPPPLGELPHPWFDLVF
SGGREKTAELARVYSALASFMKVPFFDAGSVISTDGVDGTHFTRGETI
```

Partial Sequences of 9B Perhydrolase Homologue and Protein:

Gene:
(SEQ ID NO: 637)
```
5'-taccgtcgatgtgtggcctcgtgtgaagtgggtgccgttgccaagcg
aattctgtgtttcggggattcgttgacgtggggctggatcccggtcgagg
aaggtgtacccacccaacgttttccgaagcgggtgcgctggaccggggtg
ctggccgacgaactgggtgctggctatgaggttgtcgaggaggggttgag
cgcgcgcaccaccaccgctgacgaccctaccgatccccggctgaacggct
cggactacctccccgcatgcctggccagccacctgccgctggacctggtg
atcctgatgctcgggaccaacgacaccaaggcgaatctgaatcgcacacc
cgtcgacatcgccagcggaatgggcgtcctggccacccaggtgctcacca
gcgcgggcgggtcggcaccagctacccggccccgcaggtgttgatcgtg
gcaccgccgccgctggccgagatgccgcaccgtggttcgagctggtctt
cgacggcggcgggagaagaccgcccaactggcccgggtgtacagcgcgc
tggcgtcgttcatgaaggtgccgttcttcgacgccggatcggtgatcagc
accgacggtgtcgacggcacccacttcacacgaggcgaaacaatcgaccg
g
```

Protein:
(SEQ ID NO: 638)
```
GGRCVASCEVGAVAKRILCFGDSLTWGWIPVEEGVPTQRFPKRVRWTGVL
ADELGAGYEVVEEGLSARTTTADDPTDPRLNGSDYLPACLASHLPLDLVI
LMLGTNDTKANLNRTPVDIASGMGVLATQVLTSAGGVGTSYPAPQVLIVA
PPPLAEMPHPWFELVFDGGREKTAQLARVYSALASFMKVPFFDAGSVIST
DGVDGTHFTRGETIDR
```

Partial Sequences of 14B Perhydrolase Homologue and Protein:

Gene:
(SEQ ID NO: 639)
```
5'-attctgtgtttcggagattcgttgacgtggggctggatcccggtcga
ggaaggtgtacccacccaacgttttccgaagcgggtgcgctggaccgggg
tgctggccgacgaactgggtgctggctatgaggttgtcgaggaggggttg
agcgcgcgcaccaccaccgctgacgaccctaccgatccccggctgaacgg
ctcggactacctccccgcatgcctggccagccacctgccgctggacctgg
tgatcctgatgctcgggaccaacgacaccaaggcgaatctgaatcgcaca
cccgtcgacatcgccagcggaatgggcgtcctggccacccaggtgctcac
cagcgcgggcgggtcggcaccagctacccggccccgcaggtgttgatcg
tggcaccgccgccgctggccgagatgccgcaccgtggttcgagctggtc
ttcgacggcggcgggagaagaccgcccaactggcccgggtgtacagcgc
gctggcgtcgttcatgaaggtgccgttcttcgacgccggatcggtgatca
gcaccgacggtgtcgacggcacccacttcacacgagg
```

Protein:
(SEQ ID NO: 640)
```
ILCFGDSLTWGWIPVEEGVPTQRFPKRVRWTGVLADELGAGYEVVEEGLS
ARTTTADDPTDPRLNGSDYLPACLASHLPLDLVILMLGTNDTKANLNRTP
VDIASGMGVLATQVLTSAGGVGTSYPAPQVLIVAPPPLAEMPHPWFELVF
DGGREKTAQLARVYSALASFMKVPFFDAGSVISTDGVDGTHFTR
```

Partial Sequences of 20A Perhydrolase Homologue and Protein:

Gene:
(SEQ ID NO: 641)
```
5'-ttgccaagcggaattctgtgtttcggggattctttgacgtggggatg
gatccctgtcgaagaaggtgtgcccaccgagcggttcccgcgtgacgtcc
ggtggaccggcgtgctggccgacctgctgggcgaccgctacgaggtgatc
gaggaaggcctgtcggcgcgcaccaccaccgccgacgacccggccgaccc
ccggctcaacggttcgcagtatctgccgtcgtgtctggccagccatctgc
cgctggacctggtgatcctgatgctcggcatcaacgacaccaaggcgaat
tttggccgcacccgttcgacatcgccaccggatgggagtgcttgccacg
caggtgctcaccagcgccggtggcgtggggaccagctatcccgcgccgca
ggtgctgatcgtggccgccgccgctgggcgagctgccccacccctggt
tcgacctggtgttctccggcggccgtgagaagaccgccgagttggcccgc
gtgtacagcgcgctggcgtcgttcatgaaggtgccgttcttcgacgccgg
ctcggtgatcagcaccgacggcgtggacggcacccacttcacacgaggcg
aaacaatcga-3'
```

-continued

Protein:

(SEQ ID NO: 642)
LPSGILCFGDSLTWGWIPVEEGVPTERFPRDVRWTGVLADLLGDRYEVIE

EGLSARTTTADDPADPRLNGSQYLPSCLASHLPLDLVILMLGINDTKANF

GRTPFDIATGMGVLATQVLTSAGGVGTSYPAPQVLIVAPPPLGELPHPWF

DLVFSGGREKTAELARVYSALASFMKVPFFDAGSVISTDGVDGTHFTRGE

TI

Identification of the Natural Isolates

To type the environmental isolates used in this Example, plates of the purified strains were sent to MIDI for 16S rRNA typing. 20A is *Mycobacterium parafortuitum*, 9B is *Mycobacterium gilvum*. By protein homology we infer that 2D is also *M. parafortuitum* and 14B is *M. gilvum*.

Example 13

Sequence and Taxonomic Analyses of Perhydrolase Homologues

In this Example, sequence and taxonomic analyses of *M. smegmatis* perhydrolase homologues are provided Taxonomic Assignment The basic "List of 60" protein sequences accessed from public databases and used for construction of primer sets for screening of metagenomic libraries (BRAIN) was converted into a document illustrating the microbial taxonomic origins of the proteins, as described below. This information was used to produce the following alignment.

```
                                  1                                                50
MSAT                         (1)  --------------MAKRILCFGDSLUWGWVPVEDGAPU-ERFAPDVRWUG  (SEQ ID NO: 643)
14B natural isolate          (1)  -----------------ILCFGDSLTWGWIPVEEGVPT-QRFPKRVRWTG  (SEQ ID NO: 644)
20A                          (1)  --------------LPSGILCFGDSLTWGWIPVEEGVPT-ERFPRDVRWTG  (SEQ ID NO: 645)
2D natural isolate           (1)  -----------------ILCFGDSLTWGWIPVEEGVPT-ERFPRDVRWTG  (SEQ ID NO: 646)
9B Natural Isolate           (1)  -GGRCVASCEVGAVAKRILCFGDSLTWGWIPVEEGVPT-QRFPKRVRWTG  (SEQ ID NO: 647)
M. parafortuitum CO1         (1)  --------------MAKRILCFGDSLTWGWIPVEEGVPT-ERFPRDVRWTG  (SEQ ID NO: 648)
Sm-RSM05666                  (1)  --------------MKTVLCYGDSLTWGYDATGSG-----RHALEDRWPS  (SEQ ID NO: 649)
AtQ8UAC0                     (1)  --------------MKTVLAFGDSLTWGADPATG---L--RHPVEHRWPD  (SEQ ID NO: 650)
At-Q8UFG4                    (1)  --------------MVKSVLCFGDSLTWGSNAETGG-----RHSHDDLWPS  (SEQ ID NO: 651)
M091_M4aE11                  (1)  --------------MKTILAYGDSLTYGANPIPGGP----RHAYEDRWPT  (SEQ ID NO: 652)
M1-RMLO00301                 (1)  MAGGTRLDECTGERMKTVLCYGDSLTWGYNAEGG------RHALEDRWPS  (SEQ ID NO: 653)
P. dejongeii RVM04532        (1)  --------------MKTILCFGDSNTWGYDPASMTAPFPRRHGPEVRWTG  (SEQ ID NO: 654)
Q92XZ1 Sinorhizobium         (1)  ----------MEETVARTVLCFGDSNTHGQVPGRGPLDR---YRREQRWGG  (SEQ ID NO: 655)
meliloti
Q98MY5 Mesorhizobium         (1)  --------------MKTVLCYGDSLTWGYNAEGG------RHALEDRWPS  (SEQ ID NO: 656)
loti
RSM02162_Sm                  (1)  -----------MVEKRSVLCFGDSLTWGWIPVKESSPT-LRYPYEQRWTG  (SEQ ID NO: 657)
S261_M2aA12                  (1)  --------------MKNILAFGDSLTWGFVAGQDAR-----HPFETRWPN  (SEQ ID NO: 658)
Sma1993 Sinorhizobium        (1)  MTINSHSWRTLMVEKRSVLCFGDSLTWGWIPVKESSPT-LRYPYEQRWTG  (SEQ ID NO: 659)
meliloti
Consensus                    (1)                KTILCFGDSLTWGWIPV EG P   RHP E RW G    (SEQ ID NO: 660)

51                                               100
MSAT                        (37)  VLAQQLGADFEVIE--EGLSARUUNIDDPUDPRL-NGASYLPSCLAUHLP
14B natural isolate         (33)  VLADELGAGYEVVE--EGLSARTTTADDPTDPRL-NGSDYLPACLASHLP
20A                         (37)  VLADLLGDRYEVIE--EGLSARTTTADDPADPRL-NGSQYLPSCLASHLP
2D natural isolate          (33)  VLADLLGDRYEVIE--EGLSARTTTADDPADPRL-NGSQYLPSCLASHLP
9B Natural Isolate          (49)  VLADELGAGYEVVE--EGLSARTTTADDPTDPRL-NGSDYLPACLASHLP
M. parafortuitum CO1        (37)  VLADLLGDRYEVIE--EGLSARTTTAEDPADPRL-NGSQYLPSCLASHLP
Sm-RSM05666                 (32)  VLQKALGSDAHVIA--EGLNGRTTAYDDHLADCDRNGARVLPTVLHTHAP
AtQ8UAC0                    (32)  VLEAELAGKAKVHP--EGLGGRTTCYDDHAGPACRNGARALEVALSCHMP
At-Q8UFG4                   (33)  VLQKALGSDVHVIFTHEGLGGRTTAYDDHTGDCDRNGARLLPTLLHSHAP
M091_M4aE11                 (33)  ALEQGLGGKARVIA--EGLGGRTTVHDDWFANADRNGARVLPTLLESHSP
M1-RMLO00301                (45)  VIQASLGGGVQVIA--DGLNGRTTAFDDHLAGADRNGARLLPTALTTHAP
P. dejongeii RVM04532       (37)  VLAKALGAGFRVIE--EGQNGRTTVHEDPLNICR-KGKDYLPACLESHKP
Q92XZ1 Sinorhizobium        (39)  VLQGLLGPNWQVIE--EGLSGRTTVHDDPIEGSLKNGRIYLRPCLQSHAP
meliloti
Q98MY5 Mesorhizobium        (31)  VLQASLGGGVQVIA--DGLNGRTTAFDDHLAGADRNGARLLPTALTTHAP
loti
RSM02162_Sm                 (39)  AMAARLGDGYHIIE--EGLSARTTSLDDPNDARL-NGSTYLPMALASHLP
S261_M2aA12                 (32)  ALAAGLGGKARVIE--EGQNGRTTVFDDAATFESRNGSVALPLLLISHQP
Sma1993 Sinorhizobium       (50)  AMAARLGDGYHIIE--EGLSARTTSLDDPNDARL-NGSTYLPMALASHLP
meliloti
Consensus                   (51)  VLA  LGG Y VIE   EGLSGRTT  DDP D  L NGS YLPT LASHLP 101                                              150
MSAT                        (84)  LDLVIIMLGUNDUKAYFRRUPLDIA--LGMSVLVUQVLUSAGGVGUUYPA
14B natural isolate         (80)  LDLVILMLGTNDTKANLNRTPVDIA--SGMGVLATQVLTSAGGVGTSYPA
20A                         (84)  LDLVILMLGINDTKANFGRTPFDIA--TGMGVLATQVLTSAGGVGTSYPA
2D natural isolate          (80)  LDLVILMLGINDTKANFGRTPFDIA--TGMGVLATQVLTSAGGVGTSYPA
9B Natural Isolate          (96)  LDLVIIMLGTNDTKANLNRTPVDIA--SGMGVLATQVLTSAGGVGTSYPA
M. parafortuitum CO1        (84)  LDLVILMLGTNDTKANFGRTPFDIA--TGMGVLATQVLTSAGGVGTSYPA
Sm-RSM05666                 (80)  LDLIVFMLGSNDMKPIIHGTAFGAV--KGIERLVNLVRRHDWPTETE-EG
AtQ8UAC0                    (80)  LDLVIIMLGTNDIKPVHGGRAEAAV--SGMRRLAQIVETFIYKPREA--V
At-Q8UFG4                   (83)  LDMVIIMLGTNDMKPAIHGSAIVAFTMKGVERLVKLTRNHVWQVSDW-EA
M091_M4aE11                 (81)  LDLIVIMLGTNDIKPHHGRTAGEAG--RGMARLVQIIRGHYAGRMQD--E
M1-RMLO00301                (93)  IDLIVIMLGANDMKPWIHGNPVAAK--QGIQRLIDIVRGHDYPFDWP--A
P. dejongeii RVM04532       (84)  LDLVILMLGTNDLKSTFNVPPGEIA--AGAGVLGRMILAGDAGPENR--P
Q92XZ1 Sinorhizobium        (87)  LDLIIIMLGTNDLKRRFNMPPSEVA--MGIGCLVHDIRELSPGRTGN--D
```

```
Q98MY5 Mesorhizobium  (79)   IDLIVIMLGANDMKPWIHGNPVAAK--QGIQRLIDIVRGHDYPFDWP--A
loti
RSM02162_Sm           (86)   LDLVIIMLGTNDTKSYFHRTPYEIA--NGMGKLVGQVLTCAGGVGTPYPA
S261_M2aA12           (80)   LDLVIIMLGTNDIKFAARCRAFDAS--MGMERLIQIVRSANYMKGYK--I
Sma1993 Sinorhizobium (97)   LDLVIIMLGTNDTKSYFHRTPYEIA--NGMGKLVGQVLTCAGGVGTPYPA
meliloti
Consensus            (101)   LDLVIIMLGTNDMKA   RTP DIA   GMGRLV  VLT AGGVG    A 151                                              200
MSAT                  (132)  PKVLVVSPPPLAPM-PHPWFQLIF-EGGEQKUUELARVYSALASFMKVPF
14B natural isolate   (128)  PQVLIVAPPPLAEM-PHPWFELVF-DGGREKTAQLARVYSALASFMKVPF
20A                   (132)  PQVLIVAPPPLGEL-PHPWFDLVF-SGGREKTAELARVYSALASFMKVPF
2D natural isolate    (128)  PQVLIVAPPPLGEL-PHPWFDLVF-SGGREKTAELARVYSALASFMKVPF
9B Natural Isolate    (144)  PQTLIVAPPPLAEM-PHPWFELVF-DGGREKTAQLARVYSALASFMKVPF
M. parafortuitum CO1  (132)  PQVLIVAPPPLGEL-PHPWFDLVF-SGGREKTAELARVYSALASFMKVPF
Sm-RSM05666           (127)  PEILIVSPPPLCET--ANSAFAAMFAGGVEQSAMLAPLYRDLADELDCGF
AtQ8UAC0              (126)  PKLLIVAPPPCVAG---PGGEPAG-GRDIEQSMRLAPLYRKLAAELGHHF
At-Q8UFG4             (132)  PDVLIVAPPQLCETANPFMGAIFRDAIDESAMLASVFTYRDLADELDCGF
M091_M4aE11           (127)  PQIILVSPPPIILGDWADMMDHFGPHEAIATSVDFAREYKKRADEQKVHF
M1-RMLO00301          (139)  PQILIVSPPVVSRT--ENADFREMFAGGDEASKQLAPQYAALADEVGCGF
P. dejongeii RVM04532 (130)  PQLLLMCPPKVRDLSAMPDLDAKI-PHGAARSAEFPRHYKAQAVALKCEY
Q92XZ1 Sinorhizobium  (133)  PEIMIVAPPPMLED--LKEWESIF-SGAQEKSRKLALEFEIMADSLEAHF
meliloti
Q98MY5 Mesorhizobium  (125)  PQILIVSPPVVSRT--ENADFREMFAGGDEASKQLAPQYAALADEVGCGF
loti
RSM02162_Sm           (134)  PKVLVVAPPPLAPM-PDPWFEGMF-GGGYEKSKELSGLYKALADFMKVEF
S261_M2aA12           (126)  PEILIISPPPSLVPT--QDEWFNDLWGHAIAESKLFAKHYKRVAEELKVHF
Sma1993 Sinorhizobium (145)  PKVLVVAPPPLAPM-PDPWFEGMF-GGGYEKSKELSGLYKALADFMKVEF
meliloti
Consensus            (151)  PQVLIVAPPPL EM   P FE VF  GG EKS  LARVY ALAD MKV F 201                                     241
MSAT                  (180)  FDAGSVISUDGVDGIHFUEANNRDLGVALAEQVRSLL----
14B natural isolate   (176)  FDAGSVISTDGVDGTHFTR---------------------
20A                   (180)  FDAGSVISTDGVDGTHFTRGETI-----------------
2D natural isolate    (176)  FDAGSVISTDGVDGTHFTRGETI-----------------
9B Natural Isolate    (192)  FDAGSVISTDGVDGTHFTRGETIDR---------------
M. parafortuitum CO1  (180)  FDAGSVISTDGVDGIHFTRGEQST----------------
Sm-RSM05666           (175)  FDGGSVARTTPIDGVHLDAENTRAVGRGLEPVVRMMLGL--
AtQ8UAC0              (172)  FDAGSVASASPVDGVHLDASATAAIGRALAAPVRDILG---
At-Q8UFG4             (182)  FDAGSVARTTPVDGVHLDAENTRAIGRGLEPVVRMMLGL--
M091_M4aE11           (177)  FDAGTVATTSKADGIHLDPANTRAIGAGLVPLVKQVLGL--
M1-RMLO00301          (187)  FDAGTVAQTTPLDGVHLDAENTRNIGKALTSVVRVML----
P. dejongeii RVM04532 (179)  FNSQEIVETSPVDGIHLEASEHLKLGEALAEKVKVLLG---
Q92XZ1 Sinorhizobium  (180)  FDAGTVCQCSPADGFHIDEDAHRLLGEALAQEVLAIGWPDA
meliloti
Q98MY5 Mesorhizobium  (173)  FDAGTVAQTTPLDGVHLDAENTRNIGKALTSVVRVMLEL--
loti
RSM02162_Sm           (182)  FAAGDCISTDGIDGIHLSAETNIRLGHAIADKVAALF----
S261_M2aA12           (174)  FDAGTVAVADKTDGGHLDAVNTKAIGVALVPVVKSILAL--
Sma1993 Sinorhizobium (193)  FAAGDCISTDGIDGIHLSAETNIRLGHAIADKVAALF----
meliloti
Consensus            (201)  FDAGSVISTD VDGIHLDA    T  IG AL    VR LL
```

The alignment tree from the CLUSTALW alignment (which approximates to a phylogenetic tree) suggests 3 or 4 groupings.

From this alignment, a hypothetical protein sequence was constructed from the consensus sequence. Where no consensus existed the site was filled with the Per amino acid; gaps were ignored. This provided a Per-consensus sequence:

```
                                                    (SEQ ID NO: 661)
  1 TILCFGDSLT WGWIPVEEGA PTERHPPEVR WTGVLAQQLG GDYEVIEEGL

51 SGRTTNIDDP TDPRLNGSSY LPTCLASHLP LDLVIIMLGT NDMKAYFRRT

101 PLDIALGMQR LVTQVLTSAG GVGTTYPAPQ VLIVAPPPLA EMPHPWFELV

151 FEGGEEKSTE LARVYSALAD FMKVPFFDAG SVISTDGVDG IHLDAANTRD

201 IGVALAEQVR SLL
```

This consensus sequence was used for a BLASTP search against a non-redundant database. This search identified 55 hits. The majority of the 'hits' were GDSL or GDSI type molecules covering a wide range of microbial diversity. However, only the first 14 'hits' had e-values and bit-values in the reliable range. At first sight, this appeared to provide further molecules with a GDSL/N-G/ARTT motif, but this was found to be due to differences in coding (Swiss Prot vs GenBank)

The screening of 3 environmental libraries (at BRAIN) resulted in 10 clones with a GDSL motif A further 2 clones were derived from the BRAIN library. The following Table (Table 13-1) lists the clones and indicates their activity.

TABLE 13-1

Clones with GDSL Motifs

| Library | Clone | Perhydrolase Activity |
|---|---|---|
| S248Fa | S248__M40cD4 | No |
| S248Fa | S248__M44aA5 | No |
| S248Fa | S248__M18bH12 | Not Perhydrolase |
| S248Fa | S248__M36bC5 | Not Perhydrolase |
| S248Fa | S248__M50cD9 | Not Perhydrolase |
| S248Fa | S248__M2bB11 | ? Low |
| S261 | S261__M2aA12 | Yes |
| S279 | S279__M75bA2 | Not done |
| S279 | S279__M11aC12 | Not GDSL |
| S279 | S279__M70aE8 | ? Low |
| M091 | M091__M4aE11 | Not tested |
| BRAIN | Est114 | No |
| BRAIN | Est105 | Not done |

M40cD4

Strongest hit: arylesterase of *Brucella melitensis* (46% identical). Motifs: GDSL-GAND; GQTT instead of GRTT. Sequence alignment against the core list of organisms places it close to *Caulobacter vibrioides* and *Brucella melitensis* in the alpha-*Proteobacteria*.

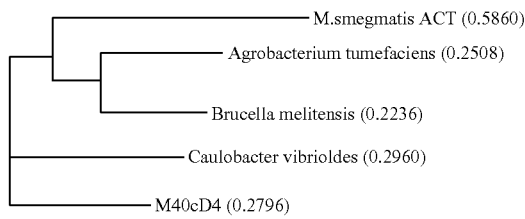

M44aA5

Strongest hit:Acyl-CoA thioesterase of *Pseudomonas aeruginosa* (43% identical). Motifs: GDSL-GGND; no GRIT or equivalent. Sequence alignment against the core list of organisms places it close to *Pseudomonas* sp in the gamma-*Proteobacteria*.

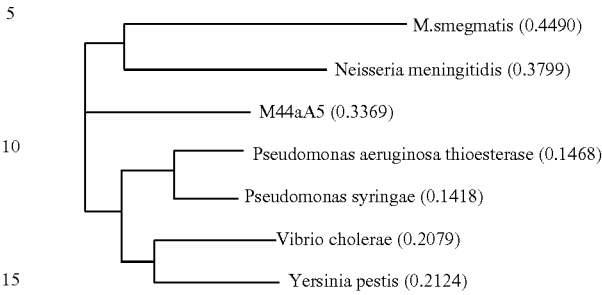

M2bB11

Strongest hit: arylesterase of *Brucella melitensis*. Motifs: GDSL-GAND; no GRIT or equivalent. Sequence alignment against the core list of organisms shows no strong association placing it between the alpha- and gamma-*Proteobacteria*.

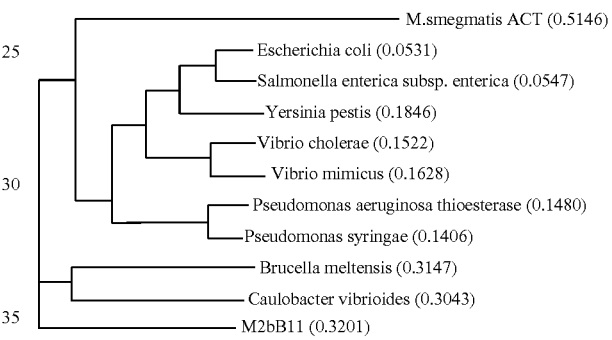

M2aA12

Strongest hit: arylesterase of *Agrobacterium tumefaciens* (42% identical) Motifs: GDSL-GRTT-GTND. Sequence alignment against the core list of organisms places it close to *Agrobacterium tumefaciens* in the alpha-*Proteobacteria*.

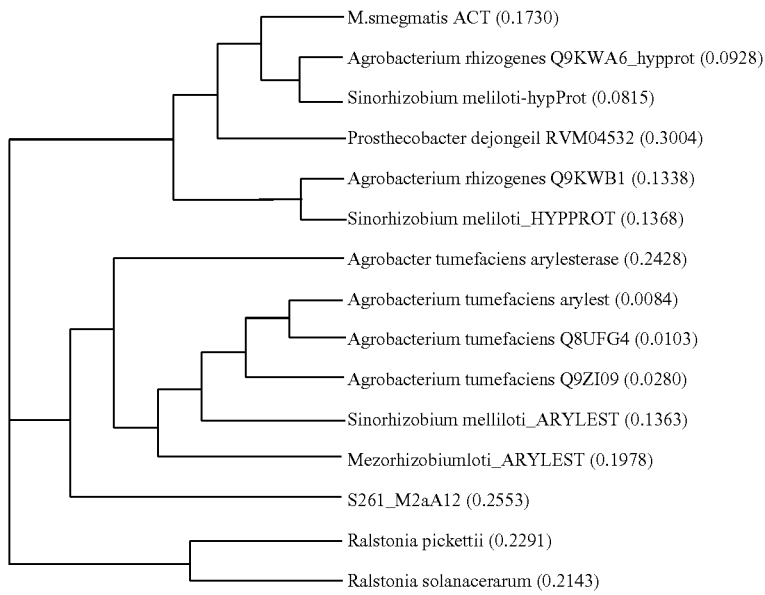

M75bA2

Strongest hit: incomplete. BLAST search revealed nothing significant. Motifs: GDSL-GTND; no GRTT or equivalent. Sequence alignment against the core list of organisms shows no convincing associations. The closest neighbors appear to be the *Vibrio-Aeromonas* groups of the gamma-*Proteobacteria*.

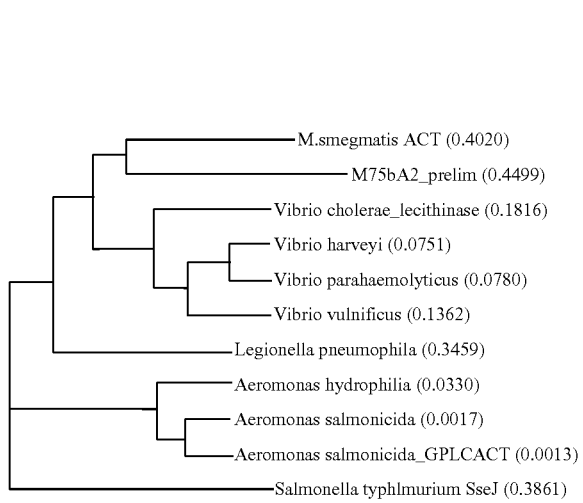

M70aE8

Strongest hit: acyl-CoA thioesterase from *E. coli* (30% identical), and aryl esterase hydrolase from *Vibrio mimicus* (27% identical). Based on incomplete sequence GDSL-type esterase (BRAIN) from *Neisseria meningitidis* (50% identical). Motifs: GDSL-GGND; no GRTT—replaced with GRTV. Sequence alignment against the core list of organisms shows the closest association to *Neisseria meningitidis*, a member of the beta-*Proteobacteria*.

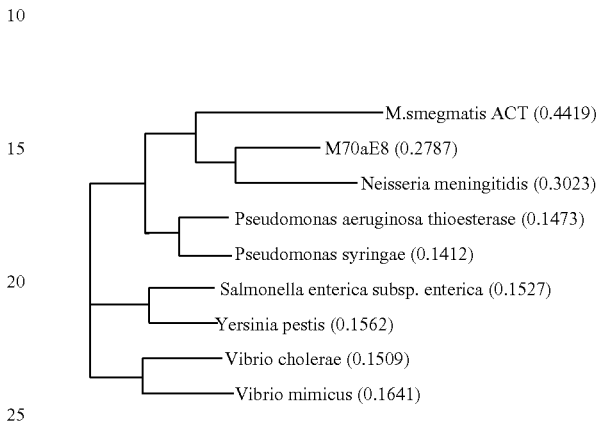

M4aE11

Strongest hit: arylesterase from *Agrobacterium tumefaciens* (59% identity) Motifs: GDSL-GRTT-GTND. Sequence alignment against the core list of organisms shows the closest association to members of the alpha-*Proteobacteria* such as *Agrobacterium*.

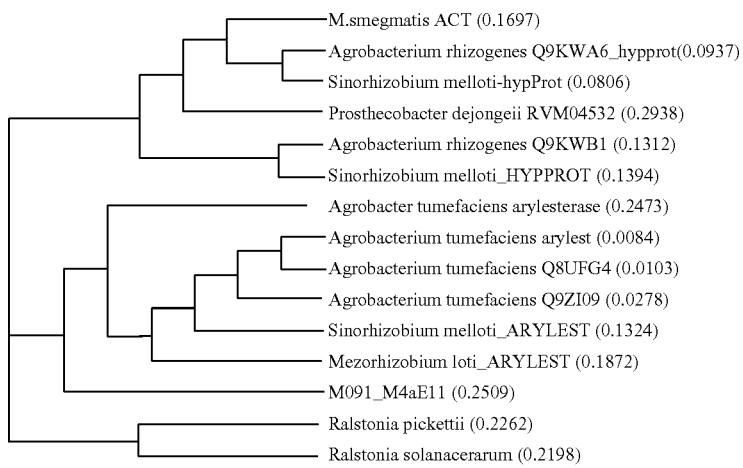

Est114

Strongest hit: phosphatidylcholine sterol acyltransferase from *Aeromonas hydrophila* (gamma-*Proteobacteria*) (30% identical). Motifs: GDSL-GPND; no GRTT but GATT may be an equivalent. Sequence alignment against the core list of organisms shows the closest association to *Acidophilium* sp. and *Aeromonas/Vibrio* within the gamma-*Proteobacteria*.

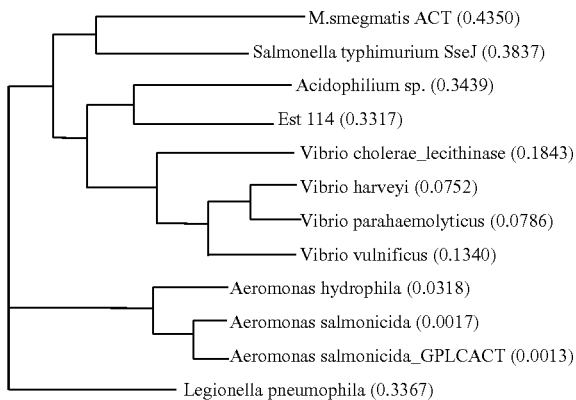

Est105

Strongest hit: *Pseudomonas aeruginosa* outer membrane esterase, and hypothetical protein *Pseudomonas putida* (27% identical). Motifs: GDSL-GAND, no GRTT or equivalent. Sequence alignment against the core list of organisms shows the closest association to members of the gamma-*Proteobacteria*.

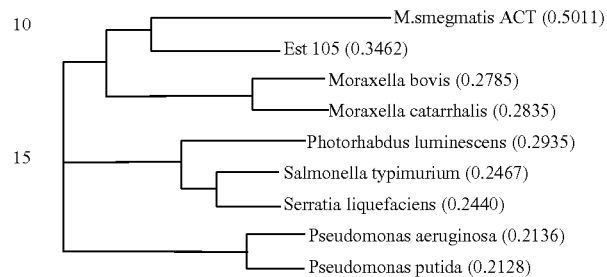

An overall alignment of these clones/sequences (here shown underlined) indicates that they are scattered throughout the alignment tree of strains indicating that the metagenomic screening has provided a variety of sequences and not a limited diversity.

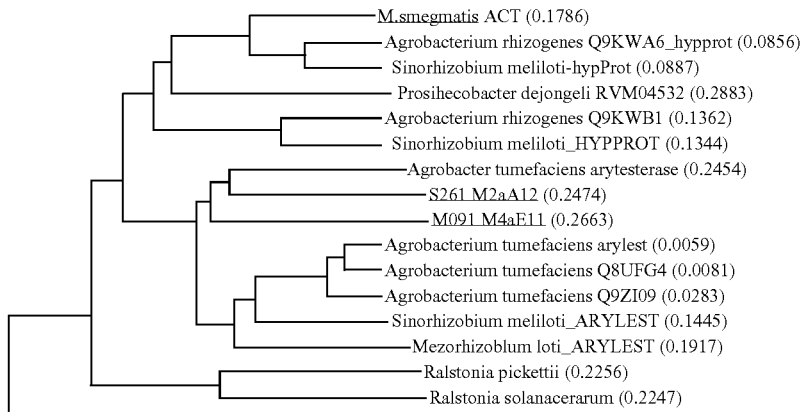

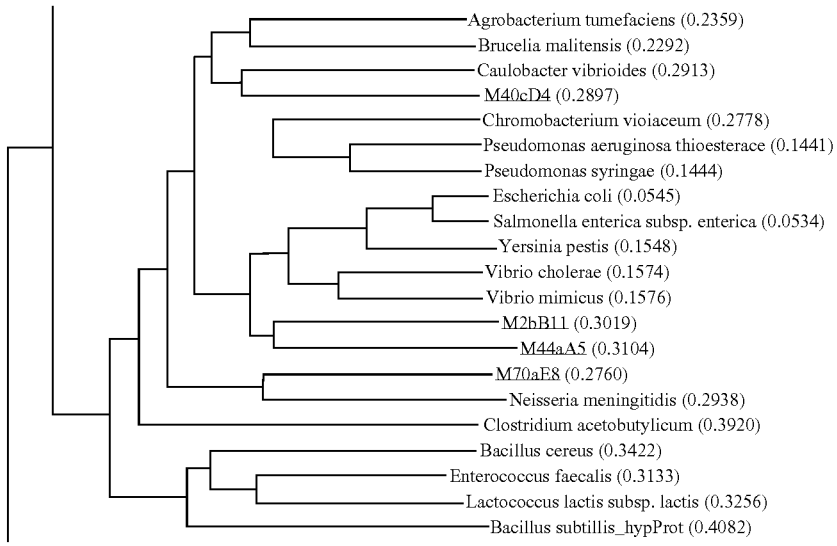

-continued

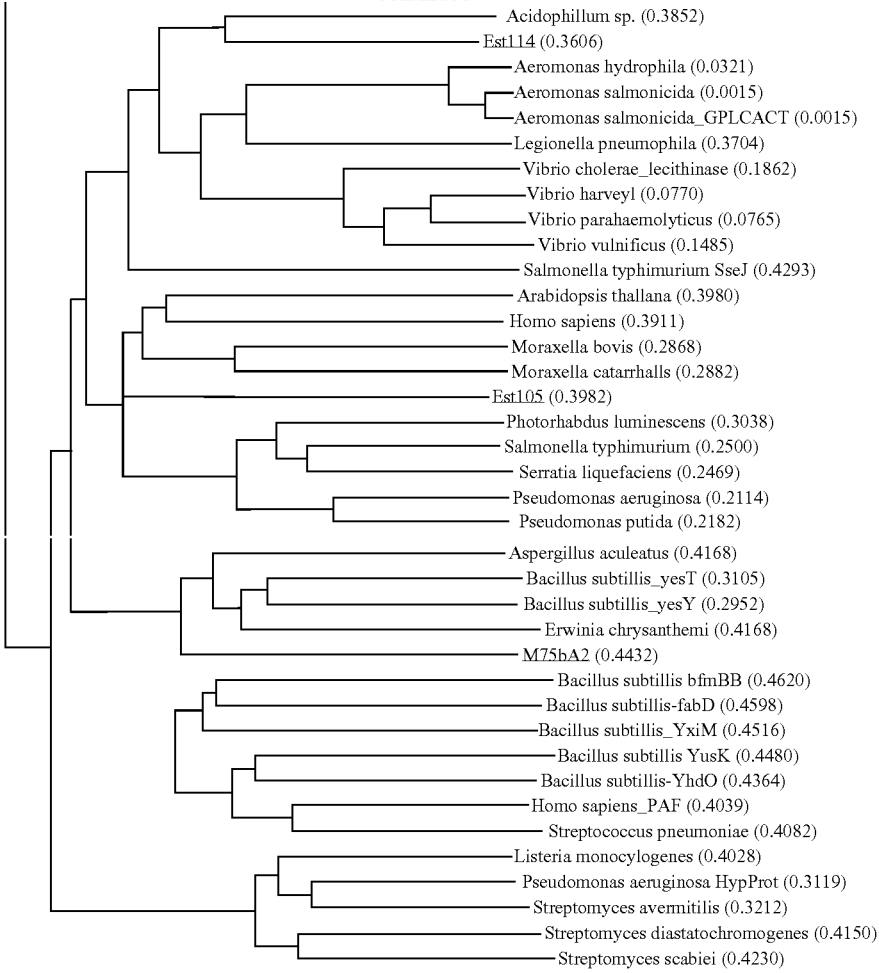

Gene Mining for GRTT-Type Esterases
(Clones with Perhydrolase Activity)
*Sinorhizobium meliloti* Sma1993-hypothetical protein_Sme
Motifs: GDSL-ARTT-GTND
*Sinorhizobium meliloti*. Q92XZ1-hypothetical protein_Sme
Motifs: GDSN-GRTT-GTND
*Mesorhizobium loti* Q98MY5-arylesterase_Mlo
Motifs:GDSL-GRTT-GAND
*Moraxella bovis* AAK53448 (lipase)
Motifs: GDSL-GSND, no GRTT or equivalent in this sequence order.
(perhydrolase activity low, questionable sequence)
*Agrobacterium tumefaciens* Q8UACO
Motifs: GDSL-GRTT-GTND
*Agrobacterium tumefaciens* Q8UFG4
Motifs: GDSL-GRIT-GTND
*Mesorhizobium loti* RMLO00301
Motifs: GDSL-GRTT-GAND
*Sinorhizobium meliloti* RSM05666
Motifs: GDSL-GRTT-GSND
(this clone was inactive for perhydrolase activity; and probably represents a false negative)
*Sinorhizobium meliloti* RSM02162
Motifs: GDSL-ARTT-GTND
*Prosthecobacter dejongeii* RVM05432
Motifs: GDSN-GRTT-GTND A GDSx$_1$-x$_2$RTT-Gx$_3$ND motif characterizes the active clones/sequences, where:
X$_1$=L or N
X$_2$=A or G
X$_3$=T or A or S The *Moraxella bovis* AAK53448 sequence does not fit this pattern and is excluded from the alignment analysis provided below:

Multiple Sequence Alignment of Active Clones/Sequences

```
                           1                                                50    (SEQ ID NO: 662)
ACT MSMEG          (1)    -------------MAKRILCFGDSLUWGWVPVEDGAPU-ERFAPDVRWUG   (SEQ ID NO: 663)
Q98MY5 Mesorhizobium (1)  --------------MKTVLCYGDSLTWGYNAEGGR------HALEDRWPS
loti
SMA1993 Sinorhizobium (1) MTINSHSWRTLMVEKRSVLCFGDSLTWGWIPVKESSPT-LRYPYEQRWTG
meliloti
Q92XZ1 Sinorhizobium (1)  ---------MEETVARTVLCFGDSNTHGQVPGRGPLDR---YRREQRWGG
meliloti
```

-continued

```
P. dejongeii RVM04532    (1)   ---------------MKTILCFGDSNTWGYDPASMTAPFPRRHGPEVRWTG  (SEQ ID NO: 667)
RSM05666_Sm              (1)   ---------------MKTVLCYGDSLTWGYDATGSG-----RHALEDRWPS  (SEQ ID NO: 668)
RSM02162_Sm              (1)   -----------MVEKRSVLCFGDSLTWGWIPVKESSPT-LRYPYEQRWTG   (SEQ ID NO: 669)
At-Q8UAC0                (1)   ---------------MKTVLAFGDSLTWGADPATGLR-----HPVEHRWPD  (SEQ ID NO: 670)
At-Q8UFG4                (1)   --------------MVKSVLCFGDSLTWGSNAETGG-----RHSHDDLWPS  (SEQ ID NO: 671)
M1-RML000301             (1)   MAGGTRLDECTGERMKTVLCYGDSLTWGYNAEGGR------HALEDRWPS   (SEQ ID NO: 672)
S261_M2aA12              (1)   ---------------MKNILAFGDSLTWGFVAGQDA-----RHPFETRWPN  (SEQ ID NO: 673)
M091_M4aE11              (1)   ---------------MKTILAYGDSLTYGANPIPGG-PR---HAYEDRWPT  (SEQ ID NO: 674)
Consensus                (1)                  MKTVLCFGDSLTWGY P G     RHA E RWP 51                                                100
ACT MSMEG                (37)  VLAQQLGADFEVIE--EGLSARUUNIDDPUDPRL-NGASYLPSCLAUHLP
Q98MY5 Mesorhizobium     (31)  VLQASLGGGVQVIA--DGLNGRTTAFDDHLAGADRNGARLLPTALTTHAP
  loti
SMA1993 Sinorhizobium    (50)  AMAARLGDGYHIIE--EGLSARTTSLDDPNDARL-NGSTYLPMALASHLP
  meliloti
Q92XZ1 Sinorhizobium     (39)  VLQGLLGPNWQVIE--EGLSGRTTVHDDPIEGSLKNGRIYLRPCLQSHAP
  meliloti
P. dejongeii RVM04532    (37)  VLAKALGAGFRVIE--EGQNGRTTVHEDPLNICR-KGKDYLPACLESHKP
RSM05666_Sm              (32)  VLQKALGSDAHVIA--EGLNGRTTAYDDHLADCDRNGARVLPTVLHTHAP
RSM02162_Sm              (39)  AMAARLGDGYHIIE--EGLSARTTSLDDPNDARL-NGSTYLPMALASHLP
At-Q8UAC0                (32)  VLEAELAGKAKVHP--EGLSGRTTCYDDHAGPACRNGARALEVALSCHMP
At-Q8UFG4                (33)  VLQKALGSDVHVIFTHEGLGGRTTAYDDHTGDCDRNGARLLPTLLHSHAP
M1-RML000301             (45)  VLQASLGGGVQVIA--DGLNGRTTAFDDHLAGADRNGARLLPTALTTHAP
S261_M2aA12              (32)  ALAAGLGGKARVIE--EGQNGRTTVFDDAATFESRNGSVALPLLLISHQP
M091_M4aE11              (33)  ALEQGLGGKARVIA--EGLGGRTTVHDDWFANADRNGARVLPTLLESHSP
Consensus                (51)  VL A LGG   VIE  EGL GRTTAHDD A  RNGAR LPT L SHAP 101                                               150
ACT MSMEG                (84)  LDLVIIMLGUNDUKAYFRRUPLDIA--LGMSVLVUQVLUSAGGVGUUYPA
Q98MY5 Mesorhizobium     (79)  IDLIVIMLGANDMKPWIHGNPVAAK--QGIQRLIDIVRGHDYPFDWPAP-
  loti
SMA1993 Sinorhizobium    (97)  LDLVIIMLGTNDTKSYFHRTPYEIA--NGMGKLVGQVLTCAGGVGTPYPA
  meliloti
Q92XZ1 Sinorhizobium     (87)  LDLIIIMLGTNDLKRRFNMPPSEVA--MGIGCLVHDIRELSPGRTGN---
  meliloti
P. dejongeii RVM04532    (84)  LDLVILMLGTNDLKSTFNVPPGEIA--AGAGVLGRMILAGDAGPENR-PP
RSM05666_Sm              (80)  LDLIVFMLGSNDMKPIIHGTAFGAV--KGIERLVNLVRRHDWPTETEEG-
RSM02162_Sm              (86)  LDLVIIMLGTNDTKSYFHRTPYEIA--NGMGKLVGQVLTCAGGVGTPYPA
At-Q8UAC0                (80)  LDLVIIMLGTNDIKPVHGGRAEAAVS--GMRRLAQIVETFIYKPREAVP-
At-Q8UFG4                (83)  LDMVIIMLGTNDMKPAIHGSAIVAFTMKGVERLVKLTRNHVWQVSDWEAP
M1-RML000301             (93)  IDLIVIMLGANDMKPWIHGNPVAAK--QGIQRLIDIVRGHDYPFDWPAP-
S261_M2aA12              (80)  LDLVIIMLGTNDIKFAARCRAFDAS--MGMERLIQIVRSANYMKGYKIP-
M091_M4aE11              (81)  LDLIVIMLGTNDIKPHHGRTAGEAG--RGMARLVQIIRGHYAGRMQDEP-
Consensus                (101) LDLVIIMLGTNDMKP  H  P EAA   GM RLV IVR   YG     P 151                                               200
ACT MSMEG                (132) PKVLVVSPPPLAPMPHPWFQLIFE--GGEQKUUELARVYSALASFMKVPF
Q98MY5 Mesorhizobium     (126) -QILIVSPPVVSRTENADFREMFAG--GDEASKQLAPQYAALADEVGCGF
  loti
SMA1993 Sinorhizobium    (145) PKVLVVAPPPLAPMPDPWFEGMFG--GGYEKSKELSGLYKALADFMKVEF
  meliloti
Q92XZ1 Sinorhizobium     (132) DPEIMIVAPPPMLEDLKEWESIFS--GAQEKSRKLALEFEIMADSLEAHF
  meliloti
P. dejongeii RVM04532    (131) QLLLMCPPKVRDLSAMPDLDAKIP--HGAARSAEFPRHYKAQAVALKCEY
RSM05666_Sm              (127) PEILIVSPPPLCETANSAFAAMFAG--GVEQSAMLAPLYRDLADELDCGF
RSM02162_Sm              (134) PKVLVVAPPPLAPMPDPWFEGMFG--GGYEKSKELSGLYKALADFMKVEF
At-Q8UAC0                (127) -KLLIVAPPPCVAGPGGEPAGGRD----IEQSMRLAPLYRKLAAELGHHF
At-Q8UFG4                (133) -DVLIVAPPQLCETANPFMGAIFRDAIDESAMLASVFTYRDLADELDCGF
M1-RML000301             (140) -QILIVSPPVVSRTENADFREMFAG--GDEASKQLAPQYAALADEVGCGF
S261_M2aA12              (127) -EILIISPPSLVPTQDEWFNDLWG--HAIAESKLFAKHYKRVAEELKVHF
M091_M4aE11              (128) -QIILVSPPPIILGDQADMMDHFGPHEAIATSVDFAREYKKRADEQKVHF
Consensus                (151)   ILIVSFPPL  T   DF AMFG   G E SK LA  YKALADELK F 201                                       241
ACT MSMEG                (180) FDAGSVISUDGVDGIHFUEANNRDLGVALAEQVRSLL----
Q98MY5 Mesorhizobium     (173) FDAGTVAQTTPLDGVHLDAENTRNIGKALTSVVRVMLEL--
  loti
SMA1993 Sinorhizobium    (193) FAAGDCISTDGIDGIHLSAETNIRLGHAIADKVAALF----
  meliloti
Q92XZ1 Sinorhizobium     (180) FDAGTVCQCSPADGFHIDEDAHRLLGEALAQEVLAIGWPDA
  meliloti
P. dejongeii RVM04532    (179) FNSQEIVETSPVDGIHLEASEHLKLGEALAEKVKVLLG---
RSM05666_Sm              (175) FDGGSVARTTPIDGVHLDAENTRAVGRGLEPVVRMMLGL--
RSM02162_Sm              (182) FAAGDCISTDGIDGIHLSAETNIRLGHAIADKVAALF----
At-Q8UAC0                (172) FDAGSVASASPVDGVHLDAENTASATAAIGRALAAPVRDILG--
At-Q8UFG4                (182) FDAGSVARTTPVDGVHLDAENTRAIGRGLEPVVRMMLGL--
M1-RML000301             (181) FDAGTVAQTTPLDGVHLDAENTRNIGKALTSVVRVML----
S261_M2aA12              (174) FDAGTVAVADKTDGGHLDAVNTKAIGVALVPVVVKSILAL--
M091_M4aE11              (177) FDAGTVATTSKADGIHLDPANTRAIGAGLVPLVKQVLGL--
Consensus                (201) FDAGTVA TSPVDGIHLDAENTR IG ALA VVR LLG
```

A guide tree (i.e., an approximation of a phylogenetic tree) of the CLUSTALW alignment of active clones/sequences is provided below.

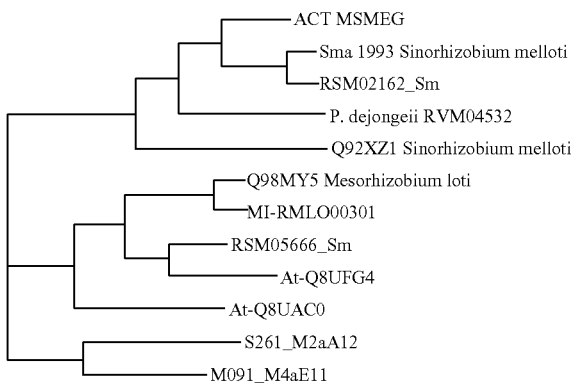

TABLE 13-2

Similarity and Identity of Clones/Sequences Compared to *M. smegmatis* Perhydrolase

| Clone/Sequence | % Identity | % Similarity |
|---|---|---|
| *Sinorhizobium meliloti* Sma1993 | 55.5 | 71.6 |
| *Sinorhizobium meliloti* Q92XZ1 | 38.7 | 54.7 |
| *Mesorhizobium loti* Q98MY5 | 38.8 | 53.4 |
| *Moraxella bovis* AAK53448 | 5.0 | 9.7 |
| *Agrobacterium tumefaciens* Q8UAC0 | 36.7 | 47.7 |
| *Agrobacterium tumefaciens* Q8UFG4 | 37.1 | 50.4 |
| *Mesorhizobium loti* RMLO00301 | 34.8 | 50.9 |

TABLE 13-2-continued

Similarity and Identity of Clones/Sequences Compared to *M. smegmatis* Perhydrolase

| Clone/Sequence | % Identity | % Similarity |
|---|---|---|
| *Sinorhizobium meliloti* RSM05666 | 37.4 | 52.5 |
| *Sinorhizobium meliloti* RSM02162 | 58.3 | 75.2 |
| *Prosthecobacter dejongeii* RVM05432 | 41.6 | 55.7 |
| S261_M2aA12 | 39.3 | 54.3 |
| M091_M4aE11 | 34.7 | 50.2 |

Based on the results, the active clones were found to have an overall identity to *M. smegmatis* perhydrolase of 38.7-58.3%. *Moraxella bovis* AAK53448 was found to be an exception and the (translated) amino acid sequence is questionable.

Redundancy

From the analyses above, it was evident that some redundancy exists in the alignment provided at the beginning of this Example that will have added undue weighting to the consensus sequence. Also, further GDSL*GRIT sequences were added. Thus, in the revised alignment below, the following changes were made:

Removed:
  Natural isolate 14B
  Natural isolate 2D
  RSM02162_Sm
  Q98MY5 *Mesorhizobium loti*
Added:
  BAB16197 (Arh II)
  BAB16192 (Arh I)
  NP 00197751 (Mlo II)
  NP 00216984 (Bce)
  NP 522806 (Rso)
Non-Redundant Alignment:

```
                                            1                                                 50
       20A(1)                    (1)    -------------LPSGILCFGDSLTWGWIPVEEGVPTERFP-RDVRWTG   (SEQ ID NO: 675)
       9B Natural Isolate        (1)    -GGRCVASCEVGAVAKRILCFGDSLTWGWIPVEEGVPTQRFP-KRVRWTG   (SEQ ID NO: 676)
       M. parafortuitum CO1      (1)    -------------MAKRILCFGDSLTWGWIPVEEGVPTERFP-RDVRWTG   (SEQ ID NO: 677)
       MSAT                      (1)    -------------MAKRILCFGDSLTWGWVPVEDGAPTERFA-PDVRWTG   (SEQ ID NO: 678)
       Sm-RSM05666               (1)    -------------MKTVLCYGDSLTWGYDATG-----SGRHALEDRWPS   (SEQ ID NO: 679)
       At-Q8UAC0                 (1)    -------------MKTVLAFGDSLTWGADPAT-----GLRHPVEHRWPD   (SEQ ID NO: 680)
       AtQ8UFG4                  (1)    -------------MVKSVLCFGDSLTWGSNAET-----GGRHSHDDLWPS   (SEQ ID NO: 681)
       M091_M4aE11               (1)    -------------MKTILAYGDSLTYGANPIP----GGPRHAYEDRWPT   (SEQ ID NO: 682)
       M1-RMLO00301              (1)    MAGGTRLDECTGERMKTVLCYGDSLTWGYNAE------GGRHALEDRWPS  (SEQ ID NO: 683)
       P. degongeii RVM04532     (1)    -------------MKTILCFGDSNTWGYDPASMTAPFPRRHGPEVRWTG   (SEQ ID NO: 684)
       Q92XZ1 Sinorhizobium      (1)    ---------MEETVARTVLCFGDSNTHGQVPG--RGPLDRYR-REQRWGG   (SEQ ID NO: 685)
        meliloti
       S261_M2aA12               (1)    -------------MKNILAFGDSLTWGFVAG-----QDARHPFETRWPN   (SEQ ID NO: 686)
       Sma1993 Sinorhizobium     (1)    MTINSHSWRTLMVEKRSVLCFGDSLTWGWIPVKESSPTLRYP-YEQRWTG  (SEQ ID NO: 687)
        meliloti
       ZP_00197751               (1)    -------------MKTILCYGDSLTWGYDAVG-----PSRHAYEDRWPS   (SEQ ID NO: 688)
       ZP_00216984               (1)    ----------MTMTQKTVLCYGDSNTHGTRPMTHAGGLGRFA-REERWTG  (SEQ ID NO: 689)
       BAB16192                  (1)    -----MICHKGGEEMRSVLCYGDSNTHGQIPG--GSFLDRYG-PNERWPG  (SEQ ID NO: 690)
       BAB16197                  (1)    -----------MAESRSILCFGDSLTWGWIPVESSPTLRYP-FEQRWTG   (SEQ ID NO: 691)
       NP_522806                 (1)    -------------MQQILLYSDSLSWGIIPG-----TRRRLPFAARWAG   (SEQ ID NO: 692)
       Consensus                 (1)                 MKTILCFGDSLTWGWIPV      P    RR     E RW G  (SEQ ID NO: 693)

51                                                100
       20A                       (37)   VLADLLGDRYEVIE---EGLSARTTTADDPADPRLN-GSQYLPSCLASHL
       9B Natural Isolate        (49)   VLADELGAGYEVVE---EGLSARTTTADDPTDPRLN-GSDYLPACLASHL
       M. parafortuitum CO1      (37)   VLADLLGDRYEVIE---EGLSARTTTAEDPADPRLN-GSQYLPSCLASHL
       MSAT                      (37)   VLAQQLGADFEVIE---EGLSARTTNIDDPTDPRLN-GASYLPSCLATHL
       Sm-RSM05666               (32)   VLQKALGSDAHVIA---EGLNGRTTAYDDHLADCDRNGARVLPTVLHTHA
       At-Q8UAC0                 (32)   VLEAELAGKAKVHP---EGLGGRTTCYDDHAGPACRNGARALEVALSCHM
       AtQ8UFG4                  (33)   VLQKALGSDVHVIFT-HEGLGGRTTAYDDHTGDSDRNGARLLPTLLHSHA
       M091_M4aE11               (33)   ALEQGLGGKARVIA---EGLGGRTTVHDDWFANADRNGARVLPTLLESHS
       M1-RMLO00301              (45)   VLQASLGGGVQVIA---DGLNGRTTAFDDHLAGADRNGARLLPTALTTHA
       P. degongeii RVM04532     (37)   VLAKALGAGFRVIE---EGQNGRTTVHEDPLNICRK-GKDYLPACLESHK
       Q92XZ1 Sinorhizobium      (39)   VLQGLLGPNWQVIE---EGLSGRTTVHDDPIEGSLKNGRIYLRPCLQSHA
        meliloti
```

-continued

```
S261_M2aA12             (32)  ALAAGLGGKARVIE---EGQNGRTTVFDDAATFESRNGSVALPLLLISHQ
Sma1993 Sinorhizobium   (50)  AMAARLGDGYHIIE---EGLSARTTSLDDPNDARLN-GSTYLPMALASHL
meliloti
ZP_00197751             (32)  VLQGRLGSSARVIA---EGLCGRTTAFDDWVAGADRNGARILPTLLATHS
ZP_00216984             (40)  VLAQTLGASWRVIE---EGLPARTTVHDDPIEGRHKNGLSYLRACVESHL
BAB16192                (43)  VLRRELGSQWYVIE---EGLSGRTTVRDDPIEGTMKNGRTYLRPCLMSHA
BAB16197                (39)  AMAAALGDGYSIIE---EGLSARTTSVEDPNDPRLN-GSAYLPMALASHL
NP_522806               (32)  VMEHALQAQGHAVRIVEDCLNGRTTVLDDPARPGRN-GLQGLAQRIEAHA
Consensus               (51)  VLA  LGA Y VIE   EGL GRTT  DDP D   RNGA YLP  L SH 101                                              150
20A                     (83)  PLDLVILMLGINDTKANFGRTPFD--IATGMGVIATQVLTSAGG-VGTSY
9B Natural Isolate      (95)  PLDLVILMLGTNDTKANLNRTPVD--IASGMGVLATQVLTSAGG-VGTSY
M. parafortuitum CO1    (83)  PLDLVILMLGTNDTKANFGRTPFD--IATQMGVLATQVLTSAGG-VGTSY
MSAT                    (83)  PLDLVIIMLGTNDTKAYFRRTPLD--IALGMSVLVTQVLTSAGG-VGTTY
Sm-RSM05666             (79)  PLDLIVFMLGSNDMKPIIHGTATG--AVKGIERLVNLVRRHDWPT--ETE
At-Q8UAC0               (79)  PLDLVIIMLGTNDIKFVHGGRAEA--AVSGMRRLAQIVETFIYK---PRE
AtQ8UFG4                (82)  PLDMVIIMLGTNDMKPAIHGSAIVAFTMKGVERLVKLTRNHVWQV--SDW
M091_M4aE11             (80)  PLDLIVIMLGTNDIKPHHGRTAGE--AGRGMARLVQIIRGHYAG---RMQ
M1-RML000301            (92)  PIDLIVIMLGANDMKPWIHGNPVA--AKQGIQRLIDIVRGHDYP---FDW
P. degongeii RVM04532   (83)  PLDLVILMLGTNDLKSTFNVPPGE--IAAGAGVLGRMILAGDA---GPEN
Q92XZ1 Sinorhizobium    (66)  PLDLIIIMLGTNDLKRRFNMPPSE--VAMGIGCLVHDIRELSP---GRTG
meliloti
S261_M2aA12             (79)  PLDLVIIMLGTNDIKFAARCRAFD--ASMGMERLIQIVRSANYM---KGY
Sma1993 Sinorhizobium   (96)  PLDLVIIMLGTNDTKSYFHRTPYE--IANGMGKLVGQVLTCAGG-VGTPY
meliloti
ZP_00197751             (79)  PLDLVIVMLGTNDMKSFVCGRAIG--AKQGMERIVQIIRGQPYS---FNY
ZP_00216984             (87)  PVDVVVLMLGTNDLKTRFSVTPAD--IATSVGVLLAKIAACGA---GPSG
BAB16192                (90)  ILDLVIIMLGTNDLKARFGQPPSE--VAMGIGCLVYDIRELAP---GPGG
BAB16197                (85)  PLDLVIILLGTNDTKSYFRRTPYE--IANGMGKLAGQVLTSAGG-IGTPY
NP_522806               (81)  PLALVILMLGTNDFQAIFRHTAQD--AAQGVAQLVRAIRQAPIEP---GM
Consensus              (101)  PLDLVIIMLGTNDLKA F  TP D  IA GMGRLV  VR  G   G Y 151                                              200
20A                    (130)  PAPQVLIVAPPPLGELPHPWFDL--VESGGREKTAELARVYSALASFMKV
9B Natural Isolate     (142)  PAPQVLIVAPPPLAEMPHPWFEL--VFDGGREKTAELARVYSALASFMKV
M. parafortuitum CO1   (130)  PAPQVLIVAPPPLGELPHPWFDL--VFSGGREKTAELARVYSALASFMKV
MSAT                   (130)  PAPKVLVVSPPPLAPMPHPWFQL--IFEGGEQKTTELARVYSALASFMKV
Sm-RSM05666            (125)  EGPEILIVSPPPLCETANSAFAAMFAGGVEQSAMLAP--LYRDLADELDC
At-Q8UAC0              (124)  AVPKLLIVAPPPCVAGP--GGEPAGGRDIEQSMRLAP--LYRKLAAELGH
AtQ8UFG4               (130)  EAPDVLIVAPPQLCETANPFMGAIFRDAIDESAMLASVFTYRDLADELDC
M091_M4aE11            (125)  DEPQIILVSPPPIILGDWADMMDHFGPHEAIATSVDFAREYKKRADEQKV
M1-RML000301           (137)  PAPQILIVSPPVVSRTENADFREMFAGGDEASKQLAP--QYAALADEVGC
P. degongeii RVM04532  (128)  RPPQLLLMCPPKVRDLSAMPDLAKIPHGAAR0SAEFRPHYKAQAVALKC
Q92XZ1 Sinorhizobium   (131)  NDPEIMIVAPPPMLEDLKEWES---IFSGAQEKSRKLALEFEIMADSLEA
meliloti
S261_M2aA12            (124)  KIPEILIISPPSLVPTQDEWFNDLWGHAIAESKLFAK--HYKRVAEELKV
Sma1993 Sinorhizobium  (143)  PAPKVLVVAPPPLAPMPDPWFEG--MFGGGYEKSKELSGLYKALADFMKV
meliloti
ZP_00197751            (124)  KVPSILLVAPPPLCATENSDFAEIFEGGMAESQKLAP--LYAALAQQTGC
ZP_00216984            (132)  ASPKLVLMAPAPIVEVGFLGEI---FAGGAAK-SRQLAKRYEQVASDAGA
BAB16192               (135)  KPPEIMVVAPPPMLDDIKEWEP---IFSGAQEKSRRLALEFEIIADSLEV
BAB16197               (132)  PAPKLLIVSPPPLAPMPDPWFEG--MFGGGYEKSLELAKQYKALANFLKV
NP_522806              (126)  PVPPVLIVVPPAITAPAGAMADK---FADAQPKCAGLAQAYRATAQTLGC
Consensus              (151)    AP ILIVAPPPL E   WF    IFGGA KS LA YKALA LKV 201                                         248
20A                    (178)  PFFDAGSVISTDGVDGTHFTRGETI---------------------
9B Natural Isolate     (190)  PFFDAGSVISTDGVDGTHFTRGETIDR-------------------
M. parafortuitum CO1   (178)  PFFDAGSVISTDGVDGIHFTRGEQST--------------------
MSAT                   (178)  PFFDAGSVISTDGVDGIHFTEANNRDLGVALAEQVRSLL--------
Sm-RSM05666            (173)  GFFDGGSVARTTPIDGVHLDAENTRAVGRGLEPVVRMMLGL-------
At-Q8UAC0              (170)  HFFDAGSVASASPVDGVHLDASATAAIGRALAAPVRDILG--------
AtQ8UFG4               (180)  GFFDAGSVARTTPVDGVHLDAENTRAIGRGLEPVVRMMLGL-------
M091_M4aE11            (175)  HFFDAGTVATTSKADGIHLDPANTRAIGAGLVPLVKQVLGL-------
M1-RML000301           (185)  GFFDAGTVAQTTPLDGVHLDAENTRNIGKALTSVVRVML---------
P. degongeii RVM04532  (177)  EYFNSQEIVETSPVDGIHLEASEHLKLGEALAEKVKVLLG--------
Q92XZ1 Sinorhizobium   (178)  HFFDAGTVCQCSPADGFHIDEDAHRLLGEALAQEVLAIGWPDA-----
meliloti
S261_M2aA12            (172)  HFFDAGTVAVADKTDGGHLDAVNTKAIGVALVPVVKSILAL-------
Sma1993 Sinorhizobium  (191)  EFFAAGDCISTDGIDGIHLSAETNIRLGHAIADKVAALF---------
meliloti
ZP_00197751            (172)  AFFDAGTVARTTPLDGIHLDAENTRAIGAGLEPVVRQALGL-------
ZP_00216984            (178)  HFLDAGAIVEVSPVDGVHFAADQHRVLGQRVAALLQQIA---------
BAB16192               (182)  HFFDAATVASCDPCDGFHINREAHEALGTALAREVEAIGWR-------
BAB16197               (180)  DFLDAGEFVKTDGCDGIHFSAETNITLGHAIAAKVEAIFSQEAKNAAA
NP_522806              (113)  HVFDANSVTPSRVDGIHLDADQHAQLGRAMAQVVGTLLAQ-------
Consensus              (201)    FFDAGSV  TSPVDGIHLDAENTR LG ALA  VR IL
```

The guide tree to the CLUSTALW alignment (which approximates to a phylogenetic tree) clearly indicates 3 groupings:
1) GDSL-ARTT group including Act
2) GDSL-GRTT group composed of members of the Rhizobiales and the metagenome; and
3) Intermediate group of mixed motifs.

It is also contemplated that the results suggest some form of gene duplication and mutation events in the Rhizobiales and lateral gene transfer to Mycobacterium.

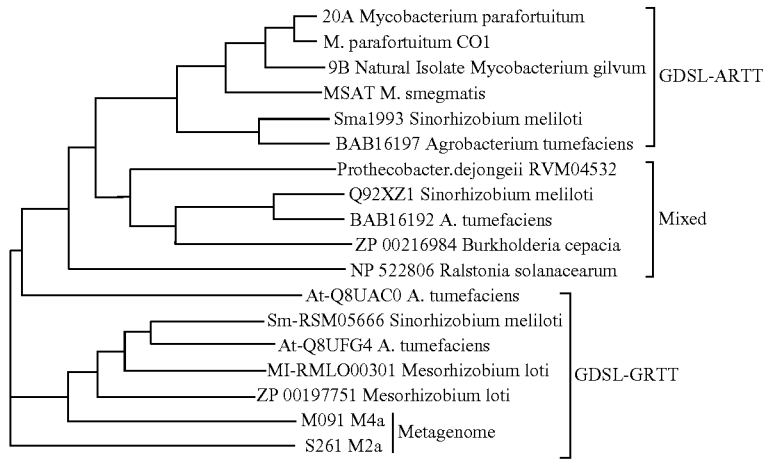

Using the non-redundant alignment a new Act consensus was constructed called "Act chimera".

```
                                                            (SEQ ID NO: 694)
  1 KTILCFGDSL TWGWIPVEDG APTERRAPEV RWTGVLAQQL GADYEVIEEG

51 LSGRTTNIDD PTDPRLRNGA SYLPSCLASH LPLDLVIIML GTNDLKAYFR

101 RTPLDIALGM GRLVTQVRTS AGGVGTTYPA PKILIVAPPP LAEMPHPWFQ

151 LIFGGAEQKS TE1ARVYKAL ASFLKVPFFD AGSVISTSPV DGIHLDAENT

201 RDLGVALAEQ VRSIL
```

An alignment of Act-chimera with Ms Act (Chimera align) indicates 91.6% similarity and 86.0% identity, as indicated below.

```
                        1                                                 50
MSAT         (1)    MAKRILCFGDSLTWGWVPVEDGAPTERFAPDVRWTGVLAQQLGADFEVIE    (SEQ ID NO: 695)
Act-Chimera  (1)    --KTILCFGDSLTWGWIPVEDGAPTERRAPEVRWTGVLAQQLGADYEVIE    (SEQ ID NO: 694)
Consensus    (1)      K ILCFGDSLTWGWIPVEDGAPTER APDVRWTGVLAQQLGADFEVIE    (SEQ ID NO: 696)

51                                                100
MSAT         (51)   EGLSARTTNIDDPTDPRLN-GASYLPSCLATHLPLDLVIIMLGTNDTKAY
Act-Chimera  (49)   EGLSGRTTNIDDPTDPRLRNGASYLPSCLASHLPLDLVIIMLGTNDLKAY
Consensus    (51)   EGLSARTTNIDDPTDPRL  GASYLPSCLASHLPLDLVIIMLGTND KAY 101                                               150
MSAT         (100)  FRRTPLDIALGMSVLVTQVLTSAGGVGTTYPAPKVLVVSPPPLAPMPHPW
Act-Chimera  (99)   FRRTPLDIALGMGRLVTQVRTSAGGVGTTYPAPKILIVAPPPLAEMPHPW
Consensus    (101)  FRRTPLDIALGM LVTQV TSAGGVGTTYPAPKILIVAPPPLA MPHPW 151                                               200
MSAT         (150)  FQLIFEGGEQKTTELARVYSALASFMKVPFFDAGSVISTDGVDGIHFTEA
Act-Chimera  (149)  FQLIFGGAEQKSTELARVYKALASFLKVPFFDAGSVISTSPVDGIHLDAE
Consensus    (151)  FQLIF GAEQKSTELARVY ALASFLKVPFFDAGSVIST  VDGIH 201         217
MSAT         (200)  NNRDLGVALAEQVRSLL
Act-Chimera  (199)  NTRDLGVALAEQVRSIL
Consensus    (201)  N RDLGVALAEQVRSIL
```

A BLASTP search with Act-chimera did not reveal any further sequences.

The Act-chimera is "forced" on the Per sequence at the positions where no consensus exists. However, a basic 'unforced' consensus sequence did not provide any more information from a blastp search or from alignment analysis. Thus, comparison with the most distant homologues in the blastp 'hit' list was considered more useful in defining the important residues/positions in Act sequence space. This was a useful exercise, as these sequences were not used in the non-redundant alignment.

For example, *Rhodopirellula baltica* (NP_865748; Psp; a *Planctomycetes* and quite different from either *Mycobacterium* or *Rhizobiales*), was compared as shown below.

alpha-*Proteobacteria*). A few members of the beta-*Proteobacteria* were found, but no *Mycobacterium* sp. This provides an indication that the perhydrolase (Per) gene/protein is not widely distributed in nature.

The *Mycobacterium* protein is characterized by the GDSL-ARTT motif, whereas most of the *Rhizobiales* are characterized by a GDSL-GRTT motif. There are also some mixed or intermediate motifs (e.g., GDSN-GRTT, GDSN-ARTT and SDSL-GRTT). This may indicate gene duplication and mutation event and lateral gene transfer. The consensus residues identified in these experiments were L6, W14, R27, W34, L38, R56, D62, L74, L78, H81, P83, M90, K97, G110, L114, L135, F180, and G205.

```
              1                                                50
MSAT      (1) MAKRILCFGDSLTWGWVPVEDGAPTERFAPDVRWTGVLA---QQLGADFE  (SEQ ID NO: 695)
NP_865746 (1) -MHSILIYGDSLSWGIIPGTR----RRFAFHQRWPGVMEIELRQTGIDAR  (SEQ ID NO: 697)
Consensus (1)    IL FGDSLSWG IP      RFA   RW GVL    Q G D      (SEQ ID NO: 698)

51                                               100
MSAT      (48)  VIEEGLSARTTNIDDPTDPRLNGASYLPSCLATHLPLDLVIIMLGTNDTK
NP_865746 (46)  VIEDCLNGRRTVLEDPIKPGRNGLDGLQQRIEINSPLSLVVLFLGTNDFQ
Consensus (51)  VIED L AR T IDDP   P NG   L    I    PL LVII LGTND 101                                              150
MSAT      (98)  AYFRRTPLDIALGMSVLVTQVLTSAGGVGTTYPAPKVLVVSPPPLAPMPH
NP_865746 (96)  SVHEFHAEQSAQGLALLV--DAIRRSPFEPGMPTPKILLVAPPTVHH-PK
Consensus (101) A         A GLALLV              P  PKILLVAPP L   P 151                                              200
MSAT      (148) PWFQLIFEGGEQKTTELARVYSALASFMKVPFFDAGSVISTDGVDGIHFT
NP_865746 (143) LDMAAKFQNAETKSTGLADAIRKVSTEHSCEFFDAATVTTTSVVDGVHLD
Consensus (151)     F   AE KST LA     LAS       FFDAASV ST  VDGIH 201        222
MSAT      (198) EANNRDLGVALAEQVRSLL---
NP_865746 (193) QEQHQALGTALASTIAEILADC
Consensus (201)  N   LG ALA  I   IL
```

The following is an alignment with *Ralstonia eutropha* (Reu):

```
                1                                              50
MSAT       (1)  ---------MAKRILCFGDSLTWGWVPVEDGAPTERFAPDVRWTGVLA--  (SEQ ID NO: 695)
ZP_00166901 (1) MPLTAPSEVDPLQILVYADSLSWGIVPGTR----RRLPFPVRWPGRLELG  (SEQ ID NO: 699)
Consensus  (1)             IL FADSLSWG VP         R    VRW G L    (SEQ ID NO: 700)

51                                             100
MSAT       (40) --QQLGADFEVIEEGLSARTTNIDDPTDPRLNGASYLPSCLATHLPLDLV
ZP_00166901 (47)LNADGGAPVRIIEDCLNGRRTVWDDPFKPGRNGLQGLAQRIEIHSPVALV
Consensus  (51)     GA    IIED L AR T DDP   P NG   L     I H PL LV 101                                            150
MSAT       (88) IIMLGTNDTKAYFRRTPLDIALGMSVLVTQVLTSAGGVGTTYPAPKVLVV
ZP_00166901 (97)VLMLGNNDFQSMHPHNAWHAAQGVGALV--HAIRTAPIEPGMPVPPILVV
Consensus  (101)IIMLG ND    A            A GM LV    A I   P P ILVV 151                                            200
MSAT       (138)SPPPLAPMPHPWFQLIFEGGEQKTTELARVYSALASFMKVPFFDAGSVIS
ZP_00166901 (145)VPPPIRT-PCGPLAPKFAGGEHKWAGLPEALRELCATVDCSLFDAGTVIQ
Consensus  (151)  PPPI  P     F GGE K       L      L A M  FDAGSVI 201                   237
MSAT       (188)TDGVDGIHFTEANNRDLGVALAEQVRSLL--------
ZP_60166901 (194)SSAVDGVHLDADAHVALGDALQPVVRALLAESSGHPS
Consensus  (201) S AVDGIH        LG AL    VRALL
```

Based on these results, the following conclusions were made. A BLASTp nr-database search with a perhydrolase consensus sequence revealed GDSL or GDSI lipases/esterases from a wide diversity of organisms. However, only 12 or 14 of these were reliable homologues of Per. Nearly all of these were derived from 1 small group of bacteria, namely the *Rhizobiales* (i.e., Gram-negative soil bacteria belonging the Using the non-redundant alignment and comparison with distant homologues the follow sequence space can be defined starting at position 5 of the *M. smegmatis* perhydrolase and ending at position 195, with perhydrolase shown in residues in bold. [I, V][L][X][F, Y][G,S][D][S][L,N][T, S][W, Y, H][G][X]$_2$[P,A][X]$_{14}$[R, L][W][X]$_7$[L][X]$_5$[V, I][I, V, H][X][E, D][G, C][L, Q][X][G,A][R][T][T] [X]$_2$[D,E][D][X]$_7$[G]

[X]₃[L][X]₆[H][X][P,I][L, I, V][D,A][V, I][X]₂[M, L][G][X][N][D][X]₃₆[P][X]₆[P][P,A][X]₃₁[A][X]₃₁[A][X]₁₉[D][G][X][H] (SEQ ID NO:701)

In sum, it is clear from the analyses above that the active clones/sequences with a GDSx₁-x₂RTT-Gx₃ND motif have all been found among the alpha-*Proteobacteria*—Gram-negative bacteria associated with the soil rhizosphere. This is in sharp contrast to the prototype perhydrolase from *M. smegmatis*—a high GC content Gram-positive bacterium assigned to the class *Actinobacteria*. This division is illustrated in FIG. 2, which provides a phylogenetic tree, showing the major branches of the bacteria and the origin of the active clones/sequences compared to *M. smegmatis*.

Example 14

Native Molecular Weight Estimation of Homologues of the Perhydrolase

In this Example, experiments conducted to estimate the native molecular weights of *M. smegmatis* perhydrolase homologues are described.

Preparation of Samples for Purification (Size Determination)

A single colony of the desired strains was inoculated in 50 ml Terrific Broth and incubated overnight at 37° C. with shaking at 200 rpm. The cells were pelleted by centrifugation for 10 minutes at 7000 rpm in a Sorvall SuperSpeed Centrifuge. The pellets were then resuspended in 10 ml 25 mM Bis-Tris (pH 6.5) and lysed by passage through a French pressure cell twice. The lysates were then centrifuged at 15000 rpm in a Sorvall SuperSpeed Centrifuge. The soluble fraction was heat treated at 55° C. for 1 hour to precipitate cellular proteins. The samples were then centrifuged at 10000 rpm in a Sorvall SuperSpeed Centrifuge and the soluble fractions used for further purification or assay.

Sizing Columns

The supernatants (prepared as described above) were run on a Sephadex 200 sizing column in 20 mM phosphate (pH 8.0), with a flow rate of 0.5 ml/min. The column was calibrated prior to running the samples with MW standards (listed below) and purified *M. smegmatis* perhydrolase protein. The crude sample elution volumes were determined by collecting 0.5 ml fractions, and assaying the fractions for pNB activity. Molecular weights and elution volumes of the standards:

Thyroglobulin MW 669 kDa: elution volume 16 ml
Aldolase MW 158 kDa: elution volume 24 ml
Ovalbumin MW 43 kDa: elution volume 26 ml
Ribonuclease MW 14 kDa: elution volume 32 ml
Perhydrolase elution volume 24 ml Results The following Table (Table 14-1) provides the elution volume of some of the *M. smegmatis* perhydrolase homologues identified herein.

TABLE 14-1

Elution Volume (Estimated Molecular Weight) of *M. smegmatis* Perhydrolase Homologues

| Homologue Sample | Elution Volume (ml) |
|---|---|
| pLO_SmeI | 24 |
| pET26_SmeII | 24 |
| pET26_MlO | 24 |
| pET26b_Stm | 24 |
| pET26b_Mbo | 24 |
| M7OaEB_pET26 | 32 |
| pET26_m2aA12 | 24 |
| pET26b_S2487am | 32 |
| *S. meliloti* RSM02162 (G00355) | 24 |
| PET_M2aA12 (5261) | 24 |
| *M. smegmatis* Perhydrolase | 24 |

The data in the above Table and the assay results obtained for these homologues indicated that these enzymes have an amino acid sequence similar to the *M. smegmatis* perhydrolase. As with the *M. smegmatis* perhydrolase, these homologues exhibit perhydrolysis activity as multimers. As described herein, the perhydrolase is an octamer, while the homologues, although they elute in a similar volume, are contemplated to be dimers, trimers, tetramers, hexamers, and/or octamers.

Example 15

Crystal Structure of Perhydrolase

In this Example, the crystallographic analysis of the perhydrolase is described. Perhydrolase crystals were obtained under two conditions: 2.0 M [NH₄]₂SO₄, 2% PEG400, 0.1 M Tris pH 7.1 (giving triclinic, P1 crystals) and 1.0 M ammonium dihydrogen phosphate, and 0.1M sodium citrate pH 5.6 (giving tetragonal, P4 crystals) Both crystal forms gave suitable diffraction beyond 2.0 Å resolution. Derivative protein for a MAD phase determination using selenium replacing sulfur containing methionine resulting in a protein molecule having four selenomethionines the N-terminal methionine is cleaved proteolytically. Of the two forms, triclinic P1 a=83.77 Å b=90.07 Åc=112.115 Å α=73.320° β=77.30° γ=88.07° and P4 a=b=98.18 Å c=230.12 Å, the P4 crystal gave data that was possible to use for structure determination. Three wavelength MAD datasets were collected at wavelengths corresponding to the Se absorption edge, near the inflection point and a third, away from the absorption edge.

Three hundred and thirty-three frames (0.3 degree oscillations per frame) for each wavelength with 1 sec exposure time were collected from a single tetragonal space group P4 crystal. The structure could be solved with either SOLVE or SHELX computer programs giving similar solutions for the 32 possible Se positions. The map was fitted using the program "O". It was possible to trace electron density for residues 3-216 in each of the eight independent molecules. The final structure of these eight molecules was refined using CNS. The current crystallographic R-factor is 21%. The coordinates are provided below.

| | | | | | | | |
|---|---|---|---|---|---|---|---|
| CRYST1 | 98.184 | 98.184 | 230.119 | 90.00 | 90.00 | 90.00 | |
| SCALE1 | 0.010185 | 0.000000 | 0.000000 | 0.000000 | | | |
| SCALE2 | 0.000000 | 0.010185 | 0.000000 | 0.000000 | | | |
| SCALE3 | 0.000000 | 0.000000 | 0.004346 | 0.000000 | | | |
| ATOM | 1 | CB | LYS | 3 | −8.167 | −61.964 | 18.588 | 1.000 | 40.95 |
| ATOM | 2 | CG | LYS | 3 | −8.685 | −63.192 | 19.323 | 1.000 | 22.95 |
| ATOM | 3 | CD | LYS | 3 | −8.635 | −64.400 | 18.399 | 1.000 | 14.97 |
| ATOM | 4 | CE | LYS | 3 | −7.963 | −65.575 | 19.090 | 1.000 | 19.83 |

| | | | | | -continued | | | |
|---|---|---|---|---|---|---|---|---|
| ATOM | 5 | NZ | LYS | 3 | −7.359 | −66.511 | 18.099 | 1.000 | 44.28 |
| ATOM | 6 | C | LYS | 3 | −9.684 | −60.377 | 17.426 | 1.000 | 13.89 |
| ATOM | 7 | O | LYS | 3 | −9.087 | −59.356 | 17.767 | 1.000 | 12.50 |
| ATOM | 8 | N | LYS | 3 | −8.000 | −61.626 | 16.153 | 1.000 | 15.57 |
| ATOM | 9 | CA | LYS | 3 | −8.919 | −61.686 | 17.284 | 1.000 | 20.71 |
| ATOM | 10 | N | ARG | 4 | −10.987 | −60.381 | 17.166 | 1.000 | 24.56 |
| ATOM | 11 | CA | ARG | 4 | −11.695 | −59.097 | 17.204 | 1.000 | 22.65 |
| ATOM | 12 | CB | ARG | 4 | −12.299 | −58.822 | 15.822 | 1.000 | 21.44 |
| ATOM | 13 | CG | ARG | 4 | −11.232 | −58.465 | 14.792 | 1.000 | 21.56 |
| ATOM | 14 | CD | ARG | 4 | −11.845 | −58.181 | 13.431 | 1.000 | 29.29 |
| ATOM | 15 | NE | ARG | 4 | −11.660 | −56.790 | 13.020 | 1.000 | 32.87 |
| ATOM | 16 | CZ | ARG | 4 | −12.643 | −56.013 | 12.585 | 1.000 | 30.24 |
| ATOM | 17 | NH1 | ARG | 4 | −13.879 | −56.487 | 12.494 | 1.000 | 17.82 |
| ATOM | 18 | NH2 | ARG | 4 | −12.399 | −54.760 | 12.229 | 1.000 | 44.53 |
| ATOM | 19 | C | ARG | 4 | −12.735 | −59.054 | 18.308 | 1.000 | 14.59 |
| ATOM | 20 | O | ARG | 4 | −13.604 | −59.909 | 18.456 | 1.000 | 18.72 |
| ATOM | 21 | N | ILE | 5 | −12.639 | −58.012 | 19.131 | 1.000 | 13.45 |
| ATOM | 22 | CA | ILE | 5 | −13.549 | −57.882 | 20.263 | 1.000 | 12.08 |
| ATOM | 23 | CB | ILE | 5 | −12.747 | −57.835 | 21.578 | 1.000 | 15.40 |
| ATOM | 24 | CG2 | ILE | 5 | −13.678 | −57.677 | 22.765 | 1.000 | 5.80 |
| ATOM | 25 | CG1 | ILE | 5 | −11.811 | −59.034 | 21.741 | 1.000 | 11.66 |
| ATOM | 26 | CD1 | ILE | 5 | −10.437 | −58.632 | 22.232 | 1.000 | 19.35 |
| ATOM | 27 | C | ILE | 5 | −14.420 | −56.640 | 20.142 | 1.000 | 8.96 |
| ATOM | 28 | O | ILE | 5 | −13.905 | −55.529 | 20.021 | 1.000 | 13.31 |
| ATOM | 29 | N | LEU | 6 | −15.736 | −56.833 | 20.169 | 1.000 | 13.04 |
| ATOM | 30 | CA | LEU | 6 | −16.675 | −55.728 | 20.059 | 1.000 | 8.54 |
| ATOM | 31 | CB | LEU | 6 | −17.879 | −56.087 | 19.178 | 1.000 | 7.42 |
| ATOM | 32 | CG | LEU | 6 | −18.959 | −54.996 | 19.120 | 1.000 | 14.12 |
| ATOM | 33 | CD1 | LEU | 6 | −18.446 | −53.783 | 18.359 | 1.000 | 12.19 |
| ATOM | 34 | CD2 | LEU | 6 | −20.245 | −55.512 | 18.494 | 1.000 | 27.94 |
| ATOM | 35 | C | LEU | 6 | −17.170 | −55.293 | 21.436 | 1.000 | 2.72 |
| ATOM | 36 | O | LEU | 6 | −17.719 | −56.101 | 22.179 | 1.000 | 13.36 |
| ATOM | 37 | N | CYS | 7 | −16.978 | −54.020 | 21.756 | 1.000 | 1.38 |
| ATOM | 38 | CA | CYS | 7 | −17.472 | −53.469 | 23.011 | 1.000 | 3.17 |
| ATOM | 39 | CB | CYS | 7 | −16.411 | −52.582 | 23.667 | 1.000 | 7.01 |
| ATOM | 40 | SG | CYS | 7 | −14.867 | −53.471 | 23.992 | 1.000 | 11.21 |
| ATOM | 41 | C | CYS | 7 | −18.755 | −52.685 | 22.776 | 1.000 | 0.65 |
| ATOM | 42 | O | CYS | 7 | −18.756 | −51.627 | 22.145 | 1.000 | 4.76 |
| ATOM | 43 | N | PHE | 8 | −19.859 | −53.228 | 23.281 | 1.000 | 0.00 |
| ATOM | 44 | CA | PHE | 8 | −21.147 | −52.568 | 23.053 | 1.000 | 1.14 |
| ATOM | 45 | CB | PHE | 8 | −22.115 | −53.578 | 22.443 | 1.000 | 5.54 |
| ATOM | 46 | CG | PHE | 8 | −23.421 | −53.000 | 21.937 | 1.000 | 3.36 |
| ATOM | 47 | CD1 | PHE | 8 | −23.456 | −52.212 | 20.800 | 1.000 | 0.89 |
| ATOM | 48 | CD2 | PHE | 8 | −24.602 | −53.262 | 22.614 | 1.000 | 1.39 |
| ATOM | 49 | CE1 | PHE | 8 | −24.644 | −51.683 | 20.333 | 1.000 | 0.00 |
| ATOM | 50 | CE2 | PHE | 8 | −25.793 | −52.733 | 22.148 | 1.000 | 4.42 |
| ATOM | 51 | CZ | PHE | 8 | −25.818 | −51.944 | 21.012 | 1.000 | 2.71 |
| ATOM | 52 | C | PHE | 8 | −21.677 | −51.978 | 24.346 | 1.000 | 4.46 |
| ATOM | 53 | O | PHE | 8 | −21.873 | −52.672 | 25.348 | 1.000 | 6.98 |
| ATOM | 54 | N | GLY | 9 | −21.923 | −50.666 | 24.384 | 1.000 | 5.61 |
| ATOM | 55 | CA | GLY | 9 | −22.396 | −50.109 | 25.646 | 1.000 | 5.44 |
| ATOM | 56 | C | GLY | 9 | −22.860 | −48.673 | 25.522 | 1.000 | 5.66 |
| ATOM | 57 | O | GLY | 9 | −23.229 | −48.222 | 24.440 | 1.000 | 14.54 |
| ATOM | 58 | N | ASP | 10 | −22.837 | −47.964 | 26.641 | 1.000 | 3.89 |
| ATOM | 59 | CA | ASP | 10 | −23.322 | −46.596 | 26.734 | 1.000 | 5.17 |
| ATOM | 60 | CB | ASP | 10 | −24.331 | −46.467 | 27.880 | 1.000 | 2.99 |
| ATOM | 61 | CG | ASP | 10 | −23.807 | −47.052 | 29.175 | 1.000 | 7.05 |
| ATOM | 62 | OD1 | ASP | 10 | −22.617 | −46.829 | 29.494 | 1.000 | 17.93 |
| ATOM | 63 | OD2 | ASP | 10 | −24.564 | −47.738 | 29.895 | 1.000 | 10.98 |
| ATOM | 64 | C | ASP | 10 | −22.154 | −45.642 | 26.939 | 1.000 | 5.15 |
| ATOM | 65 | O | ASP | 10 | −21.022 | −45.940 | 26.556 | 1.000 | 5.62 |
| ATOM | 66 | N | SER | 11 | −22.423 | −44.497 | 27.554 | 1.000 | 9.02 |
| ATOM | 67 | CA | SER | 11 | −21.394 | −43.493 | 27.802 | 1.000 | 3.43 |
| ATOM | 68 | CB | SER | 11 | −22.014 | −42.331 | 28.585 | 1.000 | 7.25 |
| ATOM | 69 | OG | SER | 11 | −22.640 | −42.813 | 29.763 | 1.000 | 18.93 |
| ATOM | 70 | C | SER | 11 | −20.199 | −44.046 | 28.561 | 1.000 | 7.58 |
| ATOM | 71 | O | SER | 11 | −19.089 | −43.508 | 28.501 | 1.000 | 16.71 |
| ATOM | 72 | N | LEU | 12 | −20.393 | −45.133 | 29.308 | 1.000 | 6.56 |
| ATOM | 73 | CA | LEU | 12 | −19.264 | −45.696 | 30.046 | 1.000 | 16.41 |
| ATOM | 74 | CB | LEU | 12 | −19.711 | −46.759 | 31.042 | 1.000 | 17.05 |
| ATOM | 75 | CG | LEU | 12 | −20.598 | −46.336 | 32.210 | 1.000 | 18.22 |
| ATOM | 76 | CD1 | LEU | 12 | −20.866 | −47.527 | 33.123 | 1.000 | 7.48 |
| ATOM | 77 | CD2 | LEU | 12 | −19.973 | −45.184 | 32.988 | 1.000 | 10.83 |
| ATOM | 78 | C | LEU | 12 | −18.269 | −46.285 | 29.048 | 1.000 | 14.99 |
| ATOM | 79 | O | LEU | 12 | −17.065 | −46.307 | 29.267 | 1.000 | 6.10 |
| ATOM | 80 | N | THR | 13 | −18.828 | −46.764 | 27.940 | 1.000 | 14.77 |
| ATOM | 81 | CA | THR | 13 | −18.014 | −47.347 | 26.876 | 1.000 | 8.83 |
| ATOM | 82 | CB | THR | 13 | −18.828 | −48.381 | 26.080 | 1.000 | 6.87 |
| ATOM | 83 | OG1 | THR | 13 | −19.109 | −49.487 | 26.949 | 1.000 | 10.08 |

-continued

| | | | | | | | | |
|---|---|---|---|---|---|---|---|---|
| ATOM | 84 | CG2 | THR | 13 | −18.033 | −48.940 | 24.914 | 1.000 | 16.85 |
| ATOM | 85 | C | THR | 13 | −17.490 | −46.245 | 25.970 | 1.000 | 4.56 |
| ATOM | 86 | O | THR | 13 | −16.315 | −46.220 | 25.616 | 1.000 | 11.71 |
| ATOM | 87 | N | TRP | 14 | −18.376 | −45.317 | 25.612 | 1.000 | 5.57 |
| ATOM | 88 | CA | TRP | 14 | −17.992 | −44.210 | 24.742 | 1.000 | 7.21 |
| ATOM | 89 | CB | TRP | 14 | −19.208 | −43.329 | 24.453 | 1.000 | 6.90 |
| ATOM | 90 | CG | TRP | 14 | −18.917 | −42.183 | 23.537 | 1.000 | 11.88 |
| ATOM | 91 | CD2 | TRP | 14 | −18.731 | −40.813 | 23.924 | 1.000 | 13.72 |
| ATOM | 92 | CE2 | TRP | 14 | −18.483 | −40.081 | 22.745 | 1.000 | 11.95 |
| ATOM | 93 | CE3 | TRP | 14 | −18.752 | −40.147 | 25.152 | 1.000 | 10.63 |
| ATOM | 94 | CD1 | TRP | 14 | −18.779 | −42.222 | 22.181 | 1.000 | 8.28 |
| ATOM | 95 | NE1 | TRP | 14 | −18.517 | −40.963 | 21.694 | 1.000 | 7.16 |
| ATOM | 96 | CZ2 | TRP | 14 | −18.255 | −38.705 | 22.763 | 1.000 | 5.39 |
| ATOM | 97 | CZ3 | TRP | 14 | −18.526 | −38.783 | 25.168 | 1.000 | 12.55 |
| ATOM | 98 | CH2 | TRP | 14 | −18.282 | −38.084 | 23.981 | 1.000 | 12.81 |
| ATOM | 99 | C | TRP | 14 | −16.880 | −43.353 | 25.327 | 1.000 | 5.41 |
| ATOM | 100 | O | TRP | 14 | −16.107 | −42.745 | 24.582 | 1.000 | 4.90 |
| ATOM | 101 | N | GLY | 15 | −16.794 | −43.283 | 26.652 | 1.000 | 8.94 |
| ATOM | 102 | CA | GLY | 15 | −15.794 | −42.475 | 27.318 | 1.000 | 4.51 |
| ATOM | 103 | C | GLY | 15 | −16.249 | −41.098 | 27.755 | 1.000 | 10.98 |
| ATOM | 104 | O | GLY | 15 | −15.480 | −40.136 | 27.646 | 1.000 | 15.11 |
| ATOM | 105 | N | TRP | 16 | −17.471 | −40.952 | 28.255 | 1.000 | 23.34 |
| ATOM | 106 | CA | TRP | 16 | −17.988 | −39.691 | 28.792 | 1.000 | 15.10 |
| ATOM | 107 | CB | TRP | 16 | −19.408 | −39.890 | 29.327 | 1.000 | 6.11 |
| ATOM | 108 | CG | TRP | 16 | −20.139 | −38.694 | 29.846 | 1.000 | 1.78 |
| ATOM | 109 | CD2 | TRP | 16 | −21.229 | −38.008 | 29.213 | 1.000 | 8.98 |
| ATOM | 110 | CE2 | TRP | 16 | −21.613 | −36.942 | 30.051 | 1.000 | 7.76 |
| ATOM | 111 | CE3 | TRP | 16 | −21.923 | −38.186 | 28.009 | 1.000 | 15.66 |
| ATOM | 112 | CD1 | TRP | 16 | −19.927 | −38.021 | 31.016 | 1.000 | 0.35 |
| ATOM | 113 | NE1 | TRP | 16 | −20.798 | −36.973 | 31.154 | 1.000 | 8.35 |
| ATOM | 114 | CZ2 | TRP | 16 | −22.649 | −36.063 | 29.734 | 1.000 | 5.16 |
| ATOM | 115 | CZ3 | TRP | 16 | −22.952 | −37.317 | 27.692 | 1.000 | 5.34 |
| ATOM | 116 | CH2 | TRP | 16 | −23.306 | −36.269 | 28.551 | 1.000 | 4.72 |
| ATOM | 117 | C | TRP | 16 | −17.059 | −39.154 | 29.881 | 1.000 | 7.85 |
| ATOM | 118 | O | TRP | 16 | −16.846 | −39.815 | 30.899 | 1.000 | 3.97 |
| ATOM | 119 | N | VAL | 17 | −16.533 | −37.952 | 29.685 | 1.000 | 5.45 |
| ATOM | 120 | CA | VAL | 17 | −15.750 | −37.256 | 30.695 | 1.000 | 12.08 |
| ATOM | 121 | CB | VAL | 17 | −14.822 | −36.191 | 30.082 | 1.000 | 17.55 |
| ATOM | 122 | CG1 | VAL | 17 | −14.084 | −35.443 | 31.185 | 1.000 | 11.59 |
| ATOM | 123 | CG2 | VAL | 17 | −13.841 | −36.807 | 29.099 | 1.000 | 7.77 |
| ATOM | 124 | C | VAL | 17 | −16.673 | −36.565 | 31.696 | 1.000 | 13.86 |
| ATOM | 125 | O | VAL | 17 | −17.390 | −35.618 | 31.351 | 1.000 | 1.02 |
| ATOM | 126 | N | PRO | 18 | −16.660 | −37.034 | 32.936 | 1.000 | 8.38 |
| ATOM | 127 | CD | PRO | 18 | −15.770 | −38.071 | 33.476 | 1.000 | 8.64 |
| ATOM | 128 | CA | PRO | 18 | −17.572 | −36.501 | 33.948 | 1.000 | 9.99 |
| ATOM | 129 | CB | PRO | 18 | −17.201 | −37.294 | 35.208 | 1.000 | 12.31 |
| ATOM | 130 | CG | PRO | 18 | −15.817 | −37.789 | 34.954 | 1.000 | 7.46 |
| ATOM | 131 | C | PRO | 18 | −17.327 | −35.017 | 34.191 | 1.000 | 13.05 |
| ATOM | 132 | O | PRO | 18 | −16.163 | −34.619 | 34.306 | 1.000 | 18.63 |
| ATOM | 133 | N | VAL | 19 | −18.381 | −34.211 | 34.266 | 1.000 | 6.92 |
| ATOM | 134 | CA | VAL | 19 | −18.214 | −32.793 | 34.585 | 1.000 | 9.29 |
| ATOM | 135 | CB | VAL | 19 | −18.482 | −31.856 | 33.388 | 1.000 | 5.33 |
| ATOM | 136 | CG1 | VAL | 19 | −17.377 | −31.995 | 32.354 | 1.000 | 6.78 |
| ATOM | 137 | CG2 | VAL | 19 | −19.850 | −32.150 | 32.796 | 1.000 | 3.72 |
| ATOM | 138 | C | VAL | 19 | −19.151 | −32.380 | 35.710 | 1.000 | 12.02 |
| ATOM | 139 | O | VAL | 19 | −20.217 | −32.962 | 35.913 | 1.000 | 14.52 |
| ATOM | 140 | N | GLU | 20 | −18.771 | −31.351 | 36.467 | 1.000 | 17.17 |
| ATOM | 141 | CA | GLU | 20 | −19.662 | −30.994 | 37.575 | 1.000 | 13.30 |
| ATOM | 142 | CB | GLU | 20 | −18.918 | −30.130 | 38.595 | 1.000 | 25.34 |
| ATOM | 143 | CG | GLU | 20 | −18.276 | −30.968 | 39.702 | 1.000 | 31.46 |
| ATOM | 144 | CD | GLU | 20 | −16.871 | −30.487 | 40.017 | 1.000 | 35.91 |
| ATOM | 145 | OE1 | GLU | 20 | −16.143 | −30.157 | 39.055 | 1.000 | 40.11 |
| ATOM | 146 | OE2 | GLU | 20 | −16.507 | −30.431 | 41.210 | 1.000 | 45.47 |
| ATOM | 147 | C | GLU | 20 | −20.913 | −30.294 | 37.080 | 1.000 | 7.56 |
| ATOM | 148 | O | GLU | 20 | −21.964 | −30.361 | 37.723 | 1.000 | 11.30 |
| ATOM | 149 | N | ASP | 21 | −20.852 | −29.610 | 35.936 | 1.000 | 19.38 |
| ATOM | 150 | CA | ASP | 21 | −22.099 | −28.983 | 35.471 | 1.000 | 23.47 |
| ATOM | 151 | CB | ASP | 21 | −21.815 | −27.740 | 34.640 | 1.000 | 17.53 |
| ATOM | 152 | CG | ASP | 21 | −21.114 | −27.991 | 33.326 | 1.000 | 14.93 |
| ATOM | 153 | OD1 | ASP | 21 | −20.984 | −29.159 | 32.908 | 1.000 | 26.78 |
| ATOM | 154 | OD2 | ASP | 21 | −20.685 | −26.996 | 32.694 | 1.000 | 8.74 |
| ATOM | 155 | C | ASP | 21 | −22.959 | −29.988 | 34.707 | 1.000 | 19.54 |
| ATOM | 156 | O | ASP | 21 | −23.988 | −29.627 | 34.131 | 1.000 | 22.49 |
| ATOM | 157 | N | GLY | 22 | −22.550 | −31.250 | 34.697 | 1.000 | 13.19 |
| ATOM | 158 | CA | GLY | 22 | −23.279 | −32.377 | 34.166 | 1.000 | 15.71 |
| ATOM | 159 | C | GLY | 22 | −23.507 | −32.377 | 32.659 | 1.000 | 20.02 |
| ATOM | 160 | O | GLY | 22 | −23.370 | −33.431 | 32.036 | 1.000 | 23.32 |
| ATOM | 161 | N | ALA | 23 | −23.846 | −31.235 | 32.138 | 1.000 | 26.40 |
| ATOM | 162 | CA | ALA | 23 | −24.265 | −30.672 | 30.873 | 1.000 | 28.79 |

-continued

| | | | | | | | | |
|---|---|---|---|---|---|---|---|---|
| ATOM | 163 | CB | ALA | 23 | −24.483 | −29.192 | 31.152 | 1.000 | 32.86 |
| ATOM | 164 | C | ALA | 23 | −23.309 | −30.988 | 29.745 | 1.000 | 22.68 |
| ATOM | 165 | O | ALA | 23 | −22.922 | −32.189 | 29.753 | 1.000 | 40.02 |
| ATOM | 166 | N | PRO | 24 | −22.847 | −30.255 | 28.748 | 1.000 | 12.97 |
| ATOM | 167 | CD | PRO | 24 | −22.892 | −28.855 | 28.309 | 1.000 | 15.92 |
| ATOM | 168 | CA | PRO | 24 | −22.051 | −31.028 | 27.767 | 1.000 | 5.31 |
| ATOM | 169 | CB | PRO | 24 | −22.024 | −30.134 | 26.520 | 1.000 | 4.03 |
| ATOM | 170 | CG | PRO | 24 | −22.002 | −28.762 | 27.105 | 1.000 | 6.80 |
| ATOM | 171 | C | PRO | 24 | −20.622 | −31.273 | 28.222 | 1.000 | 14.45 |
| ATOM | 172 | O | PRO | 24 | −20.034 | −30.591 | 29.056 | 1.000 | 19.65 |
| ATOM | 173 | N | THR | 25 | −20.062 | −32.310 | 27.600 | 1.000 | 13.21 |
| ATOM | 174 | CA | THR | 25 | −18.685 | −32.690 | 27.894 | 1.000 | 11.82 |
| ATOM | 175 | CB | THR | 25 | −18.691 | −33.772 | 28.987 | 1.000 | 12.19 |
| ATOM | 176 | OG1 | THR | 25 | −17.348 | −34.104 | 29.355 | 1.000 | 19.38 |
| ATOM | 177 | CG2 | THR | 25 | −19.372 | −35.027 | 28.454 | 1.000 | 0.00 |
| ATOM | 178 | C | THR | 25 | −18.009 | −33.160 | 26.620 | 1.000 | 14.10 |
| ATOM | 179 | O | THR | 25 | −18.555 | −33.019 | 25.518 | 1.000 | 16.46 |
| ATOM | 180 | N | GLU | 26 | −16.818 | −33.724 | 26.762 | 1.000 | 12.30 |
| ATOM | 181 | CA | GLU | 26 | −16.157 | −34.314 | 25.598 | 1.000 | 13.24 |
| ATOM | 182 | CB | GLU | 26 | −14.909 | −33.518 | 25.225 | 1.000 | 15.75 |
| ATOM | 183 | CG | GLU | 26 | −15.211 | −32.066 | 24.873 | 1.000 | 25.45 |
| ATOM | 184 | CD | GLU | 26 | −15.451 | −31.152 | 26.056 | 1.000 | 27.41 |
| ATOM | 185 | OE1 | GLU | 26 | −14.687 | −31.210 | 27.048 | 1.000 | 22.86 |
| ATOM | 186 | OE2 | GLU | 26 | −16.416 | −30.347 | 26.012 | 1.000 | 17.32 |
| ATOM | 187 | C | GLU | 26 | −15.850 | −35.775 | 25.891 | 1.000 | 8.80 |
| ATOM | 188 | O | GLU | 26 | −16.279 | −36.316 | 26.909 | 1.000 | 2.55 |
| ATOM | 189 | N | ARG | 27 | −15.121 | −36.421 | 25.001 | 1.000 | 13.28 |
| ATOM | 190 | CA | ARG | 27 | −14.783 | −37.838 | 25.124 | 1.000 | 12.71 |
| ATOM | 191 | CB | ARG | 27 | −14.857 | −38.447 | 23.726 | 1.000 | 6.07 |
| ATOM | 192 | CG | ARG | 27 | −14.491 | −39.908 | 23.585 | 1.000 | 4.38 |
| ATOM | 193 | CD | ARG | 27 | −14.879 | −40.387 | 22.186 | 1.000 | 11.29 |
| ATOM | 194 | NE | ARG | 27 | −14.974 | −41.840 | 22.110 | 1.000 | 13.10 |
| ATOM | 195 | CZ | ARG | 27 | −15.191 | −42.517 | 20.992 | 1.000 | 9.74 |
| ATOM | 196 | NH1 | ARG | 27 | −15.337 | −41.868 | 19.842 | 1.000 | 11.38 |
| ATOM | 197 | NH2 | ARG | 27 | −15.262 | −43.839 | 21.029 | 1.000 | 0.00 |
| ATOM | 198 | C | ARG | 27 | −13.413 | −38.031 | 25.746 | 1.000 | 8.79 |
| ATOM | 199 | O | ARG | 27 | −12.534 | −37.181 | 25.579 | 1.000 | 17.59 |
| ATOM | 200 | N | PHE | 28 | −13.183 | −39.133 | 26.461 | 1.000 | 12.29 |
| ATOM | 201 | CA | PHE | 28 | −11.826 | −39.379 | 26.955 | 1.000 | 9.91 |
| ATOM | 202 | CB | PHE | 28 | −11.783 | −40.575 | 27.900 | 1.000 | 10.13 |
| ATOM | 203 | CG | PHE | 28 | −12.084 | −40.263 | 29.355 | 1.000 | 11.54 |
| ATOM | 204 | CD1 | PHE | 28 | −11.250 | −39.431 | 30.084 | 1.000 | 8.88 |
| ATOM | 205 | CD2 | PHE | 28 | −13.194 | −40.802 | 29.979 | 1.000 | 11.27 |
| ATOM | 206 | CE1 | PHE | 28 | −11.535 | −39.156 | 31.408 | 1.000 | 8.90 |
| ATOM | 207 | CE2 | PHE | 28 | −13.486 | −40.533 | 31.305 | 1.000 | 5.41 |
| ATOM | 208 | CZ | PHE | 28 | −12.647 | −39.703 | 32.020 | 1.000 | 0.61 |
| ATOM | 209 | C | PHE | 28 | −10.901 | −39.635 | 25.770 | 1.000 | 11.56 |
| ATOM | 210 | O | PHE | 28 | −11.370 | −40.112 | 24.736 | 1.000 | 13.14 |
| ATOM | 211 | N | ALA | 29 | −9.612 | −39.349 | 25.896 | 1.000 | 13.02 |
| ATOM | 212 | CA | ALA | 29 | −8.674 | −39.656 | 24.818 | 1.000 | 13.91 |
| ATOM | 213 | CB | ALA | 29 | −7.275 | −39.163 | 25.151 | 1.000 | 6.49 |
| ATOM | 214 | C | ALA | 29 | −8.662 | −41.157 | 24.545 | 1.000 | 15.68 |
| ATOM | 215 | O | ALA | 29 | −8.937 | −41.954 | 25.446 | 1.000 | 31.74 |
| ATOM | 216 | N | PRO | 30 | −8.345 | −41.537 | 23.314 | 1.000 | 11.44 |
| ATOM | 217 | CD | PRO | 30 | −7.982 | −40.660 | 22.192 | 1.000 | 12.10 |
| ATOM | 218 | CA | PRO | 30 | −8.326 | −42.955 | 22.936 | 1.000 | 18.85 |
| ATOM | 219 | CB | PRO | 30 | −7.822 | −42.956 | 21.494 | 1.000 | 16.38 |
| ATOM | 220 | CG | PRO | 30 | −7.283 | −41.593 | 21.244 | 1.000 | 14.74 |
| ATOM | 221 | C | PRO | 30 | −7.386 | −43.767 | 23.826 | 1.000 | 13.40 |
| ATOM | 222 | O | PRO | 30 | −7.570 | −44.969 | 23.979 | 1.000 | 8.18 |
| ATOM | 223 | N | ASP | 31 | −6.396 | −43.115 | 24.412 | 1.000 | 22.50 |
| ATOM | 224 | CA | ASP | 31 | −5.426 | −43.715 | 25.312 | 1.000 | 26.63 |
| ATOM | 225 | CB | ASP | 31 | −4.170 | −42.841 | 25.398 | 1.000 | 30.41 |
| ATOM | 226 | CG | ASP | 31 | −3.792 | −42.143 | 24.108 | 1.000 | 39.21 |
| ATOM | 227 | OD1 | ASP | 31 | −2.577 | −42.086 | 23.802 | 1.000 | 39.00 |
| ATOM | 228 | OD2 | ASP | 31 | −4.673 | −41.634 | 23.375 | 1.000 | 37.50 |
| ATOM | 229 | C | ASP | 31 | −5.985 | −43.926 | 26.721 | 1.000 | 17.49 |
| ATOM | 230 | O | ASP | 31 | −5.482 | −44.784 | 27.450 | 1.000 | 25.27 |
| ATOM | 231 | N | VAL | 32 | −6.989 | −43.150 | 27.092 | 1.000 | 14.45 |
| ATOM | 232 | CA | VAL | 32 | −7.592 | −43.125 | 28.421 | 1.000 | 12.64 |
| ATOM | 233 | CB | VAL | 32 | −7.966 | −41.683 | 28.814 | 1.000 | 10.68 |
| ATOM | 234 | CG1 | VAL | 32 | −8.580 | −41.609 | 30.199 | 1.000 | 13.66 |
| ATOM | 235 | CG2 | VAL | 32 | −6.742 | −40.774 | 28.752 | 1.000 | 20.51 |
| ATOM | 236 | C | VAL | 32 | −8.808 | −44.042 | 28.507 | 1.000 | 9.73 |
| ATOM | 237 | O | VAL | 32 | −8.890 | −44.834 | 29.452 | 1.000 | 2.23 |
| ATOM | 238 | N | ARG | 33 | −9.722 | −43.964 | 27.553 | 1.000 | 10.63 |
| ATOM | 239 | CA | ARG | 33 | −10.888 | −44.824 | 27.410 | 1.000 | 6.85 |
| ATOM | 240 | CB | ARG | 33 | −11.369 | −44.833 | 25.961 | 1.000 | 16.41 |
| ATOM | 241 | CG | ARG | 33 | −12.281 | −43.727 | 25.488 | 1.000 | 21.19 |

-continued

| | | | | | | | | |
|---|---|---|---|---|---|---|---|---|
| ATOM | 242 | CD | ARG | 33 | −12.464 | −43.806 | 23.974 | 1.000 | 26.66 |
| ATOM | 243 | NE | ARG | 33 | −11.862 | −42.659 | 23.309 | 1.000 | 30.35 |
| ATOM | 244 | CZ | ARG | 33 | −11.493 | −42.567 | 22.044 | 1.000 | 31.60 |
| ATOM | 245 | NH1 | ARG | 33 | −11.658 | −43.585 | 21.214 | 1.000 | 34.85 |
| ATOM | 246 | NH2 | ARG | 33 | −10.952 | −41.433 | 21.610 | 1.000 | 52.70 |
| ATOM | 247 | C | ARG | 33 | −10.600 | −46.279 | 27.775 | 1.000 | 9.71 |
| ATOM | 248 | O | ARG | 33 | −9.603 | −46.830 | 27.300 | 1.000 | 16.85 |
| ATOM | 249 | N | TRP | 34 | −11.450 | −46.924 | 28.577 | 1.000 | 10.64 |
| ATOM | 250 | CA | TRP | 34 | −11.166 | −48.311 | 28.952 | 1.000 | 6.46 |
| ATOM | 251 | CB | TRP | 34 | −12.149 | −48.855 | 29.979 | 1.000 | 12.45 |
| ATOM | 252 | CG | TRP | 34 | −13.561 | −49.106 | 29.583 | 1.000 | 6.95 |
| ATOM | 253 | CD2 | TRP | 34 | −14.104 | −50.199 | 28.835 | 1.000 | 9.27 |
| ATOM | 254 | CE2 | TRP | 34 | −15.493 | −49.986 | 28.723 | 1.000 | 5.43 |
| ATOM | 255 | CE3 | TRP | 34 | −13.571 | −51.345 | 28.240 | 1.000 | 14.72 |
| ATOM | 256 | CD1 | TRP | 34 | −14.622 | −48.298 | 29.888 | 1.000 | 4.49 |
| ATOM | 257 | NE1 | TRP | 34 | −15.786 | −48.820 | 29.374 | 1.000 | 4.03 |
| ATOM | 258 | CZ2 | TRP | 34 | −16.337 | −50.864 | 28.050 | 1.000 | 8.19 |
| ATOM | 259 | CZ3 | TRP | 34 | −14.405 | −52.216 | 27.572 | 1.000 | 12.73 |
| ATOM | 260 | CH2 | TRP | 34 | −15.778 | −51.976 | 27.479 | 1.000 | 8.32 |
| ATOM | 261 | C | TRP | 34 | −11.111 | −49.214 | 27.723 | 1.000 | 7.27 |
| ATOM | 262 | O | TRP | 34 | −10.393 | −50.222 | 27.767 | 1.000 | 11.53 |
| ATOM | 263 | N | THR | 35 | −11.839 | −48.887 | 26.659 | 1.000 | 1.15 |
| ATOM | 264 | CA | THR | 35 | −11.730 | −49.673 | 25.431 | 1.000 | 5.29 |
| ATOM | 265 | CB | THR | 35 | −12.708 | −49.239 | 24.331 | 1.000 | 3.10 |
| ATOM | 266 | OG1 | THR | 35 | −12.629 | −47.820 | 24.163 | 1.000 | 15.85 |
| ATOM | 267 | CG2 | THR | 35 | −14.146 | −49.549 | 24.726 | 1.000 | 5.16 |
| ATOM | 268 | C | THR | 35 | −10.307 | −49.555 | 24.882 | 1.000 | 14.32 |
| ATOM | 269 | O | THR | 35 | −9.738 | −50.494 | 24.333 | 1.000 | 12.77 |
| ATOM | 270 | N | GLY | 36 | −9.756 | −48.361 | 25.060 | 1.000 | 15.72 |
| ATOM | 271 | CA | GLY | 36 | −8.392 | −48.056 | 24.689 | 1.000 | 15.87 |
| ATOM | 272 | C | GLY | 36 | −7.407 | −48.785 | 25.583 | 1.000 | 14.86 |
| ATOM | 273 | O | GLY | 36 | −6.374 | −49.252 | 25.101 | 1.000 | 22.97 |
| ATOM | 274 | N | VAL | 37 | −7.686 | −48.905 | 26.884 | 1.000 | 12.48 |
| ATOM | 275 | CA | VAL | 37 | −6.696 | −49.577 | 27.728 | 1.000 | 11.76 |
| ATOM | 276 | CB | VAL | 37 | −6.921 | −49.365 | 29.229 | 1.000 | 10.95 |
| ATOM | 277 | CG1 | VAL | 37 | −6.092 | −50.382 | 30.009 | 1.000 | 0.00 |
| ATOM | 278 | CG2 | VAL | 37 | −6.577 | −47.940 | 29.630 | 1.000 | 10.31 |
| ATOM | 279 | C | VAL | 37 | −6.707 | −51.081 | 27.471 | 1.000 | 16.75 |
| ATOM | 280 | O | VAL | 37 | −5.669 | −51.735 | 27.494 | 1.000 | 14.29 |
| ATOM | 281 | N | LEU | 38 | −7.911 | −51.586 | 27.238 | 1.000 | 14.60 |
| ATOM | 282 | CA | LEU | 38 | −8.094 | −52.999 | 26.917 | 1.000 | 11.25 |
| ATOM | 283 | CB | LEU | 38 | −9.573 | −53.266 | 26.660 | 1.000 | 12.92 |
| ATOM | 284 | CG | LEU | 38 | −9.975 | −54.663 | 26.198 | 1.000 | 15.77 |
| ATOM | 285 | CD1 | LEU | 38 | −9.747 | −55.691 | 27.293 | 1.000 | 0.00 |
| ATOM | 286 | CD2 | LEU | 38 | −11.425 | −54.677 | 25.733 | 1.000 | 24.28 |
| ATOM | 287 | C | LEU | 38 | −7.224 | −53.347 | 25.720 | 1.000 | 7.67 |
| ATOM | 288 | O | LEU | 38 | −6.408 | −54.262 | 25.740 | 1.000 | 13.04 |
| ATOM | 289 | N | ALA | 39 | −7.404 | −52.568 | 24.659 | 1.000 | 9.64 |
| ATOM | 290 | CA | ALA | 39 | −6.603 | −52.667 | 23.451 | 1.000 | 3.53 |
| ATOM | 291 | CB | ALA | 39 | −6.894 | −51.487 | 22.530 | 1.000 | 6.32 |
| ATOM | 292 | C | ALA | 39 | −5.112 | −52.704 | 23.761 | 1.000 | 9.32 |
| ATOM | 293 | O | ALA | 39 | −4.411 | −53.632 | 23.367 | 1.000 | 28.59 |
| ATOM | 294 | N | GLN | 40 | −4.653 | −51.665 | 24.456 | 1.000 | 21.51 |
| ATOM | 295 | CA | GLN | 40 | −3.251 | −51.553 | 24.833 | 1.000 | 18.93 |
| ATOM | 296 | CB | GLN | 40 | −2.974 | −50.365 | 25.744 | 1.000 | 28.00 |
| ATOM | 297 | CG | GLN | 40 | −3.597 | −49.034 | 25.378 | 1.000 | 37.51 |
| ATOM | 298 | CD | GLN | 40 | −3.070 | −47.877 | 26.214 | 1.000 | 40.85 |
| ATOM | 299 | OE1 | GLN | 40 | −1.998 | −47.335 | 25.933 | 1.000 | 61.34 |
| ATOM | 300 | NE2 | GLN | 40 | −3.809 | −47.475 | 27.248 | 1.000 | 9.83 |
| ATOM | 301 | C | GLN | 40 | −2.822 | −52.851 | 25.525 | 1.000 | 10.96 |
| ATOM | 302 | O | GLN | 40 | −1.856 | −53.475 | 25.106 | 1.000 | 18.66 |
| ATOM | 303 | N | GLN | 41 | −3.563 | −53.239 | 26.552 | 1.000 | 15.02 |
| ATOM | 304 | CA | GLN | 41 | −3.253 | −54.423 | 27.337 | 1.000 | 22.27 |
| ATOM | 305 | CB | GLN | 41 | −4.258 | −54.582 | 28.484 | 1.000 | 16.69 |
| ATOM | 306 | CG | GLN | 41 | −4.064 | −53.605 | 29.624 | 1.000 | 14.55 |
| ATOM | 307 | CD | GLN | 41 | −2.788 | −53.852 | 30.406 | 1.000 | 16.86 |
| ATOM | 308 | OE1 | GLN | 41 | −2.759 | −54.650 | 31.344 | 1.000 | 13.75 |
| ATOM | 309 | NE2 | GLN | 41 | −1.731 | −53.158 | 30.008 | 1.000 | 21.79 |
| ATOM | 310 | C | GLN | 41 | −3.261 | −55.694 | 26.493 | 1.000 | 28.40 |
| ATOM | 311 | O | GLN | 41 | −2.442 | −56.589 | 26.703 | 1.000 | 26.71 |
| ATOM | 312 | N | LEU | 42 | −4.190 | −55.776 | 25.546 | 1.000 | 28.62 |
| ATOM | 313 | CA | LEU | 42 | −4.373 | −57.007 | 24.780 | 1.000 | 26.50 |
| ATOM | 314 | CB | LEU | 42 | −5.707 | −56.920 | 24.012 | 1.000 | 19.31 |
| ATOM | 315 | CG | LEU | 42 | −6.934 | −57.122 | 24.914 | 1.000 | 16.32 |
| ATOM | 316 | CD1 | LEU | 42 | −8.226 | −57.077 | 24.119 | 1.000 | 10.94 |
| ATOM | 317 | CD2 | LEU | 42 | −6.810 | −58.438 | 25.673 | 1.000 | 15.03 |
| ATOM | 318 | C | LEU | 42 | −3.217 | −57.312 | 23.846 | 1.000 | 23.29 |
| ATOM | 319 | O | LEU | 42 | −2.770 | −58.457 | 23.728 | 1.000 | 20.82 |
| ATOM | 320 | N | GLY | 43 | −2.693 | −56.312 | 23.141 | 1.000 | 22.18 |

-continued

| | | | | | | | | |
|---|---|---|---|---|---|---|---|---|
| ATOM | 321 | CA | GLY | 43 | −1.605 | −56.590 | 22.215 | 1.000 | 18.95 |
| ATOM | 322 | C | GLY | 43 | −2.086 | −56.793 | 20.791 | 1.000 | 23.97 |
| ATOM | 323 | O | GLY | 43 | −3.284 | −56.838 | 20.514 | 1.000 | 27.50 |
| ATOM | 324 | N | ALA | 44 | −1.136 | −56.927 | 19.879 | 1.000 | 22.72 |
| ATOM | 325 | CA | ALA | 44 | −1.317 | −57.012 | 18.448 | 1.000 | 24.25 |
| ATOM | 326 | CB | ALA | 44 | 0.048 | −56.939 | 17.755 | 1.000 | 13.44 |
| ATOM | 327 | C | ALA | 44 | −2.034 | −58.272 | 17.990 | 1.000 | 23.83 |
| ATOM | 328 | O | ALA | 44 | −2.146 | −58.520 | 16.787 | 1.000 | 17.77 |
| ATOM | 329 | N | ASP | 45 | −2.524 | −59.086 | 18.917 | 1.000 | 21.59 |
| ATOM | 330 | CA | ASP | 45 | −3.230 | −60.298 | 18.495 | 1.000 | 17.80 |
| ATOM | 331 | CB | ASP | 45 | −2.705 | −61.491 | 19.296 | 1.000 | 18.22 |
| ATOM | 332 | CG | ASP | 45 | −1.201 | −61.625 | 19.113 | 1.000 | 24.69 |
| ATOM | 333 | OD1 | ASP | 45 | −0.710 | −61.174 | 18.053 | 1.000 | 34.10 |
| ATOM | 334 | OD2 | ASP | 45 | −0.517 | −62.159 | 20.007 | 1.000 | 33.14 |
| ATOM | 335 | C | ASP | 45 | −4.732 | −60.107 | 18.647 | 1.000 | 11.82 |
| ATOM | 336 | O | ASP | 45 | −5.535 | −60.992 | 18.364 | 1.000 | 23.89 |
| ATOM | 337 | N | PHE | 46 | −5.097 | −58.914 | 19.097 | 1.000 | 9.27 |
| ATOM | 338 | CA | PHE | 46 | −6.485 | −58.519 | 19.253 | 1.000 | 12.25 |
| ATOM | 339 | CB | PHE | 46 | −6.909 | −58.479 | 20.722 | 1.000 | 14.52 |
| ATOM | 340 | CG | PHE | 46 | −6.474 | −59.693 | 21.529 | 1.000 | 11.99 |
| ATOM | 341 | CD1 | PHE | 46 | −5.160 | −59.814 | 21.956 | 1.000 | 12.17 |
| ATOM | 342 | CD2 | PHE | 46 | −7.383 | −60.690 | 21.846 | 1.000 | 8.34 |
| ATOM | 343 | CE1 | PHE | 46 | −4.760 | −60.917 | 22.683 | 1.000 | 13.46 |
| ATOM | 344 | CE2 | PHE | 46 | −6.990 | −61.794 | 22.575 | 1.000 | 6.30 |
| ATOM | 345 | CZ | PHE | 46 | −5.680 | −61.904 | 22.998 | 1.000 | 8.44 |
| ATOM | 346 | C | PHE | 46 | −6.725 | −57.149 | 18.615 | 1.000 | 13.30 |
| ATOM | 347 | O | PHE | 46 | −5.816 | −56.366 | 18.366 | 1.000 | 27.22 |
| ATOM | 348 | N | GLU | 47 | −7.992 | −56.883 | 18.349 | 1.000 | 12.78 |
| ATOM | 349 | CA | GLU | 47 | −8.469 | −55.616 | 17.833 | 1.000 | 9.15 |
| ATOM | 350 | CB | GLU | 47 | −8.667 | −55.644 | 16.325 | 1.000 | 11.20 |
| ATOM | 351 | CG | GLU | 47 | −8.791 | −54.276 | 15.670 | 1.000 | 21.84 |
| ATOM | 352 | CD | GLU | 47 | −9.726 | −54.293 | 14.474 | 1.000 | 25.88 |
| ATOM | 353 | OE1 | GLU | 47 | −9.575 | −55.205 | 13.632 | 1.000 | 30.74 |
| ATOM | 354 | OE2 | GLU | 47 | −10.602 | −53.408 | 14.388 | 1.000 | 7.59 |
| ATOM | 355 | C | GLU | 47 | −9.781 | −55.280 | 18.550 | 1.000 | 11.37 |
| ATOM | 356 | O | GLU | 47 | −10.722 | −56.071 | 18.545 | 1.000 | 11.73 |
| ATOM | 357 | N | VAL | 48 | −9.775 | −54.103 | 19.160 | 1.000 | 10.53 |
| ATOM | 358 | CA | VAL | 48 | −10.954 | −53.604 | 19.843 | 1.000 | 8.11 |
| ATOM | 359 | CB | VAL | 48 | −10.595 | −52.826 | 21.115 | 1.000 | 9.71 |
| ATOM | 360 | CG1 | VAL | 48 | −11.842 | −52.251 | 21.773 | 1.000 | 15.31 |
| ATOM | 361 | CG2 | VAL | 48 | −9.849 | −53.732 | 22.085 | 1.000 | 7.41 |
| ATOM | 362 | C | VAL | 48 | −11.745 | −52.714 | 18.882 | 1.000 | 12.72 |
| ATOM | 363 | O | VAL | 48 | −11.147 | −51.879 | 18.203 | 1.000 | 10.16 |
| ATOM | 364 | N | ILE | 49 | −13.046 | −52.943 | 18.862 | 1.000 | 13.04 |
| ATOM | 365 | CA | ILE | 49 | −14.031 | −52.170 | 18.122 | 1.000 | 14.10 |
| ATOM | 366 | CB | ILE | 49 | −14.879 | −53.068 | 17.203 | 1.000 | 16.77 |
| ATOM | 367 | CG2 | ILE | 49 | −15.735 | −52.214 | 16.285 | 1.000 | 1.57 |
| ATOM | 368 | CG1 | ILE | 49 | −14.049 | −54.081 | 16.415 | 1.000 | 18.10 |
| ATOM | 369 | CD1 | ILE | 49 | −14.687 | −54.559 | 15.133 | 1.000 | 14.33 |
| ATOM | 370 | C | ILE | 49 | −14.930 | −51.406 | 19.091 | 1.000 | 9.02 |
| ATOM | 371 | O | ILE | 49 | −15.531 | −52.013 | 19.983 | 1.000 | 15.82 |
| ATOM | 372 | N | GLU | 50 | −15.000 | −50.085 | 18.932 | 1.000 | 5.34 |
| ATOM | 373 | CA | GLU | 50 | −15.730 | −49.277 | 19.911 | 1.000 | 12.03 |
| ATOM | 374 | CB | GLU | 50 | −14.967 | −47.984 | 20.222 | 1.000 | 10.36 |
| ATOM | 375 | CG | GLU | 50 | −13.623 | −48.203 | 20.889 | 1.000 | 7.32 |
| ATOM | 376 | CD | GLU | 50 | −12.768 | −46.966 | 21.056 | 1.000 | 7.06 |
| ATOM | 377 | OE1 | GLU | 50 | −12.744 | −46.077 | 20.177 | 1.000 | 5.78 |
| ATOM | 378 | OE2 | GLU | 50 | −12.079 | −46.870 | 22.101 | 1.000 | 25.19 |
| ATOM | 379 | C | GLU | 50 | −17.145 | −48.962 | 19.446 | 1.000 | 6.79 |
| ATOM | 380 | O | GLU | 50 | −17.358 | −48.318 | 18.423 | 1.000 | 8.80 |
| ATOM | 381 | N | GLU | 51 | −18.118 | −49.429 | 20.225 | 1.000 | 9.34 |
| ATOM | 382 | CA | GLU | 51 | −19.524 | −49.179 | 19.924 | 1.000 | 16.23 |
| ATOM | 383 | CB | GLU | 51 | −20.173 | −50.400 | 19.270 | 1.000 | 15.22 |
| ATOM | 384 | CG | GLU | 51 | −19.757 | −50.596 | 17.820 | 1.000 | 18.39 |
| ATOM | 385 | CD | GLU | 51 | −20.348 | −49.531 | 16.917 | 1.000 | 17.99 |
| ATOM | 386 | OE1 | GLU | 51 | −21.352 | −48.912 | 17.332 | 1.000 | 26.29 |
| ATOM | 387 | OE2 | GLU | 51 | −19.820 | −49.309 | 15.809 | 1.000 | 15.93 |
| ATOM | 388 | C | GLU | 51 | −20.295 | −48.788 | 21.184 | 1.000 | 10.51 |
| ATOM | 389 | O | GLU | 51 | −21.202 | −49.495 | 21.623 | 1.000 | 7.29 |
| ATOM | 390 | N | GLY | 52 | −19.906 | −47.655 | 21.751 | 1.000 | 5.90 |
| ATOM | 391 | CA | GLY | 52 | −20.533 | −47.140 | 22.961 | 1.000 | 3.93 |
| ATOM | 392 | C | GLY | 52 | −21.329 | −45.887 | 22.635 | 1.000 | 6.21 |
| ATOM | 393 | O | GLY | 52 | −20.785 | −44.950 | 22.057 | 1.000 | 16.40 |
| ATOM | 394 | N | LEU | 53 | −22.607 | −45.890 | 22.989 | 1.000 | 11.68 |
| ATOM | 395 | CA | LEU | 53 | −23.498 | −44.764 | 22.710 | 1.000 | 7.60 |
| ATOM | 396 | CB | LEU | 53 | −24.627 | −45.195 | 21.792 | 1.000 | 4.45 |
| ATOM | 397 | CG | LEU | 53 | −25.576 | −44.164 | 21.185 | 1.000 | 3.84 |
| ATOM | 398 | CD1 | LEU | 53 | −26.721 | −43.872 | 22.141 | 1.000 | 15.09 |
| ATOM | 399 | CD2 | LEU | 53 | −24.856 | −42.874 | 20.817 | 1.000 | 3.41 |

-continued

| | | | | | | | | |
|---|---|---|---|---|---|---|---|---|
| ATOM | 400 | C | LEU | 53 | −24.035 | −44.204 | 24.023 | 1.000 | 5.05 |
| ATOM | 401 | O | LEU | 53 | −24.664 | −44.920 | 24.801 | 1.000 | 5.74 |
| ATOM | 402 | N | SER | 54 | −23.771 | −42.918 | 24.251 | 1.000 | 9.85 |
| ATOM | 403 | CA | SER | 54 | −24.192 | −42.296 | 25.502 | 1.000 | 10.24 |
| ATOM | 404 | CB | SER | 54 | −23.797 | −40.819 | 25.524 | 1.000 | 7.63 |
| ATOM | 405 | OG | SER | 54 | −22.395 | −40.683 | 25.640 | 1.000 | 4.65 |
| ATOM | 406 | C | SER | 54 | −25.695 | −42.448 | 25.691 | 1.000 | 7.74 |
| ATOM | 407 | O | SER | 54 | −26.438 | −42.326 | 24.717 | 1.000 | 10.39 |
| ATOM | 408 | N | ALA | 55 | −26.127 | −42.713 | 26.920 | 1.000 | 0.00 |
| ATOM | 409 | CA | ALA | 55 | −27.554 | −42.749 | 27.218 | 1.000 | 0.00 |
| ATOM | 410 | CB | ALA | 65 | −28.209 | −41.474 | 26.713 | 1.000 | 0.00 |
| ATOM | 411 | C | ALA | 55 | −28.235 | −43.982 | 26.640 | 1.000 | 6.11 |
| ATOM | 412 | O | ALA | 55 | −29.442 | −44.179 | 26.816 | 1.000 | 2.57 |
| ATOM | 413 | N | ARG | 56 | −27.474 | −44.843 | 25.971 | 1.000 | 8.50 |
| ATOM | 414 | CA | ARG | 56 | −27.997 | −46.084 | 25.433 | 1.000 | 5.94 |
| ATOM | 415 | CB | ARG | 56 | −26.919 | −46.868 | 24.672 | 1.000 | 0.00 |
| ATOM | 416 | CG | ARG | 56 | −27.420 | −48.244 | 24.247 | 1.000 | 2.73 |
| ATOM | 417 | CD | ARG | 56 | −26.467 | −48.951 | 23.307 | 1.000 | 0.00 |
| ATOM | 418 | NE | ARG | 56 | −26.552 | −48.440 | 21.935 | 1.000 | 6.44 |
| ATOM | 419 | CZ | ARG | 56 | −25.465 | −48.325 | 21.170 | 1.000 | 11.18 |
| ATOM | 420 | NH1 | ARG | 56 | −24.283 | −48.678 | 21.666 | 1.000 | 0.00 |
| ATOM | 421 | NH2 | ARG | 56 | −25.549 | −47.861 | 19.928 | 1.000 | 1.13 |
| ATOM | 422 | C | ARG | 56 | −28.539 | −47.009 | 26.526 | 1.000 | 12.43 |
| ATOM | 423 | O | ARG | 56 | −27.886 | −47.179 | 27.556 | 1.000 | 10.16 |
| ATOM | 424 | N | THR | 57 | −29.697 | −47.592 | 26.262 | 1.000 | 9.24 |
| ATOM | 425 | CA | THR | 57 | −30.376 | −48.548 | 27.120 | 1.000 | 9.36 |
| ATOM | 426 | CB | THR | 57 | −31.855 | −48.161 | 27.315 | 1.000 | 4.78 |
| ATOM | 427 | OG1 | THR | 57 | −32.608 | −48.509 | 26.146 | 1.000 | 3.70 |
| ATOM | 428 | CG2 | THR | 57 | −31.992 | −46.656 | 27.484 | 1.000 | 0.00 |
| ATOM | 429 | C | THR | 57 | −30.284 | −49.953 | 26.532 | 1.000 | 10.18 |
| ATOM | 430 | O | THR | 57 | −29.873 | −50.099 | 25.378 | 1.000 | 12.60 |
| ATOM | 431 | N | THR | 58 | −30.648 | −50.987 | 27.286 | 1.000 | 5.87 |
| ATOM | 432 | CA | THR | 58 | −30.574 | −52.349 | 26.769 | 1.000 | 1.65 |
| ATOM | 433 | CB | THR | 58 | −30.850 | −53.410 | 27.853 | 1.000 | 5.35 |
| ATOM | 434 | OG1 | THR | 58 | −32.151 | −53.196 | 28.413 | 1.000 | 12.48 |
| ATOM | 435 | CG2 | THR | 58 | −29.859 | −53.311 | 29.002 | 1.000 | 11.47 |
| ATOM | 436 | C | THR | 58 | −31.556 | −52.569 | 25.624 | 1.000 | 1.31 |
| ATOM | 437 | O | THR | 58 | −31.162 | −52.902 | 24.506 | 1.000 | 7.78 |
| ATOM | 438 | N | ASN | 59 | −32.856 | −52.404 | 25.867 | 1.000 | 4.91 |
| ATOM | 439 | CA | ASN | 59 | −33.810 | −52.604 | 24.772 | 1.000 | 11.25 |
| ATOM | 440 | CB | ASN | 59 | −34.150 | −54.090 | 24.624 | 1.000 | 9.19 |
| ATOM | 441 | CG | ASN | 59 | −35.186 | −54.548 | 25.629 | 1.000 | 9.50 |
| ATOM | 442 | OD1 | ASN | 59 | −35.293 | −54.000 | 26.725 | 1.000 | 13.36 |
| ATOM | 443 | ND2 | ASN | 59 | −35.965 | −55.556 | 25.263 | 1.000 | 4.31 |
| ATOM | 444 | C | ASN | 59 | −35.070 | −51.775 | 24.960 | 1.000 | 8.67 |
| ATOM | 445 | O | ASN | 59 | −36.172 | −52.160 | 24.574 | 1.000 | 12.75 |
| ATOM | 446 | N | ILE | 60 | −34.938 | −50.587 | 25.548 | 1.000 | 10.46 |
| ATOM | 447 | CA | ILE | 60 | −36.128 | −49.752 | 25.722 | 1.000 | 10.70 |
| ATOM | 448 | CB | ILE | 60 | −36.572 | −49.721 | 27.198 | 1.000 | 11.36 |
| ATOM | 449 | CG2 | ILE | 60 | −35.465 | −49.223 | 28.112 | 1.000 | 0.00 |
| ATOM | 450 | CG1 | ILE | 60 | −37.872 | −48.940 | 27.417 | 1.000 | 8.05 |
| ATOM | 451 | CD1 | ILE | 60 | −38.291 | −48.800 | 28.860 | 1.000 | 27.90 |
| ATOM | 452 | C | ILE | 60 | −35.879 | −48.350 | 25.177 | 1.000 | 16.37 |
| ATOM | 453 | O | ILE | 60 | −34.813 | −47.773 | 25.374 | 1.000 | 28.53 |
| ATOM | 454 | N | ASP | 61 | −36.861 | −47.811 | 24.470 | 1.000 | 18.37 |
| ATOM | 455 | CA | ASP | 61 | −36.838 | −46.520 | 23.821 | 1.000 | 12.62 |
| ATOM | 456 | CB | ASP | 61 | −38.110 | −46.353 | 22.977 | 1.000 | 12.58 |
| ATOM | 457 | CG | ASP | 61 | −38.111 | −47.199 | 21.725 | 1.000 | 12.09 |
| ATOM | 458 | OD1 | ASP | 61 | −37.044 | −47.723 | 21.349 | 1.000 | 16.37 |
| ATOM | 459 | OD2 | ASP | 61 | −39.197 | −47.332 | 21.122 | 1.000 | 23.20 |
| ATOM | 460 | C | ASP | 61 | −36.796 | −45.350 | 24.794 | 1.000 | 11.54 |
| ATOM | 461 | O | ASP | 61 | −37.626 | −45.279 | 25.702 | 1.000 | 8.66 |
| ATOM | 462 | N | ASP | 62 | −35.860 | −44.428 | 24.603 | 1.000 | 8.03 |
| ATOM | 463 | CA | ASP | 62 | −35.844 | −43.228 | 25.431 | 1.000 | 14.39 |
| ATOM | 464 | CB | ASP | 62 | −34.430 | −42.656 | 25.565 | 1.000 | 13.94 |
| ATOM | 465 | CG | ASP | 62 | −34.384 | −41.598 | 26.656 | 1.000 | 18.06 |
| ATOM | 466 | OD1 | ASP | 62 | −33.609 | −41.768 | 27.622 | 1.000 | 13.05 |
| ATOM | 467 | OD2 | ASP | 62 | −35.129 | −40.604 | 26.536 | 1.000 | 20.19 |
| ATOM | 468 | C | ASP | 62 | −36.759 | −42.162 | 24.844 | 1.000 | 13.14 |
| ATOM | 469 | O | ASP | 62 | −36.506 | −41.698 | 23.731 | 1.000 | 14.36 |
| ATOM | 470 | N | PRO | 63 | −37.800 | −41.751 | 25.553 | 1.000 | 8.49 |
| ATOM | 471 | CD | PRO | 63 | −38.102 | −42.088 | 26.951 | 1.000 | 4.73 |
| ATOM | 472 | CA | PRO | 63 | −38.805 | −40.853 | 24.972 | 1.000 | 16.60 |
| ATOM | 473 | CB | PRO | 63 | −39.802 | −40.646 | 26.123 | 1.000 | 11.61 |
| ATOM | 474 | CG | PRO | 63 | −39.020 | −40.960 | 27.352 | 1.000 | 8.04 |
| ATOM | 475 | C | PRO | 63 | −38.251 | −39.504 | 24.531 | 1.000 | 19.70 |
| ATOM | 476 | O | PRO | 63 | −38.924 | −38.738 | 23.835 | 1.000 | 10.26 |
| ATOM | 477 | N | THR | 64 | −37.024 | −39.180 | 24.922 | 1.000 | 22.29 |
| ATOM | 478 | CA | THR | 64 | −36.429 | −37.908 | 24.534 | 1.000 | 19.30 |

-continued

| | | | | | | | | |
|---|---|---|---|---|---|---|---|---|
| ATOM | 479 | CB | THR | 64 | −35.852 | −37.191 | 25.769 | 1.000 | 20.62 |
| ATOM | 480 | OG1 | THR | 64 | −34.550 | −37.713 | 26.045 | 1.000 | 30.42 |
| ATOM | 481 | CG2 | THR | 64 | −36.718 | −37.467 | 26.992 | 1.000 | 7.89 |
| ATOM | 482 | C | THR | 64 | −35.329 | −38.087 | 23.497 | 1.000 | 19.22 |
| ATOM | 483 | O | THR | 64 | −34.609 | −37.132 | 23.183 | 1.000 | 11.15 |
| ATOM | 484 | N | ASP | 65 | −35.189 | −39.301 | 22.965 | 1.000 | 15.61 |
| ATOM | 485 | CA | ASP | 65 | −34.139 | −39.542 | 21.967 | 1.000 | 18.78 |
| ATOM | 486 | CB | ASP | 65 | −32.777 | −39.286 | 22.605 | 1.000 | 20.50 |
| ATOM | 487 | CG | ASP | 65 | −31.613 | −39.348 | 21.638 | 1.000 | 17.33 |
| ATOM | 488 | OD1 | ASP | 65 | −31.767 | −39.935 | 20.550 | 1.000 | 19.33 |
| ATOM | 489 | OD2 | ASP | 65 | −30.538 | −38.810 | 21.983 | 1.000 | 15.26 |
| ATOM | 490 | C | ASP | 65 | −34.241 | −40.945 | 21.382 | 1.000 | 14.84 |
| ATOM | 491 | O | ASP | 65 | −33.982 | −41.936 | 22.060 | 1.000 | 8.38 |
| ATOM | 492 | N | PRO | 66 | −34.638 | −41.026 | 20.115 | 1.000 | 15.75 |
| ATOM | 493 | CD | PRO | 66 | −34.896 | −39.870 | 19.235 | 1.000 | 23.61 |
| ATOM | 494 | CA | PRO | 66 | −34.882 | −42.301 | 19.441 | 1.000 | 9.14 |
| ATOM | 495 | CB | PRO | 66 | −35.693 | −41.871 | 18.206 | 1.000 | 14.38 |
| ATOM | 496 | CG | PRO | 66 | −35.210 | −40.494 | 17.902 | 1.000 | 16.45 |
| ATOM | 497 | C | PRO | 66 | −33.621 | −43.029 | 18.995 | 1.000 | 8.15 |
| ATOM | 498 | O | PRO | 66 | −33.695 | −44.041 | 18.283 | 1.000 | 12.38 |
| ATOM | 499 | N | ARG | 67 | −32.446 | −42.557 | 19.404 | 1.000 | 11.98 |
| ATOM | 500 | CA | ARG | 67 | −31.209 | −43.225 | 19.020 | 1.000 | 7.77 |
| ATOM | 501 | CB | ARG | 67 | −30.081 | −42.211 | 18.831 | 1.000 | 8.16 |
| ATOM | 502 | CG | ARG | 67 | −30.162 | −41.308 | 17.614 | 1.000 | 7.27 |
| ATOM | 503 | CD | ARG | 67 | −29.078 | −40.228 | 17.713 | 1.000 | 11.05 |
| ATOM | 504 | NE | ARG | 67 | −29.378 | −39.266 | 18.769 | 1.000 | 11.17 |
| ATOM | 505 | CZ | ARG | 67 | −28.768 | −38.115 | 19.001 | 1.000 | 13.35 |
| ATOM | 506 | NH1 | ARG | 67 | −27.756 | −37.708 | 18.245 | 1.000 | 3.80 |
| ATOM | 507 | NH2 | ARG | 67 | −29.168 | −37.347 | 20.010 | 1.000 | 9.93 |
| ATOM | 508 | C | ARG | 67 | −30.728 | −44.239 | 20.048 | 1.000 | 8.92 |
| ATOM | 509 | O | ARG | 67 | −29.714 | −44.887 | 19.774 | 1.000 | 13.65 |
| ATOM | 510 | N | LEU | 68 | −31.389 | −44.365 | 21.191 | 1.000 | 9.14 |
| ATOM | 511 | CA | LEU | 68 | −30.805 | −45.057 | 22.335 | 1.000 | 13.92 |
| ATOM | 512 | CB | LEU | 68 | −31.052 | −44.223 | 23.608 | 1.000 | 7.80 |
| ATOM | 513 | CG | LEU | 68 | −30.899 | −42.707 | 23.481 | 1.000 | 8.78 |
| ATOM | 514 | CD1 | LEU | 68 | −31.285 | −41.987 | 24.770 | 1.000 | 13.12 |
| ATOM | 515 | CD2 | LEU | 68 | −29.477 | −42.333 | 23.090 | 1.000 | 3.77 |
| ATOM | 516 | C | LEU | 68 | −31.299 | −46.478 | 22.571 | 1.000 | 16.19 |
| ATOM | 517 | O | LEU | 68 | −30.895 | −47.092 | 23.574 | 1.000 | 5.21 |
| ATOM | 518 | N | ASN | 69 | −32.139 | −47.056 | 21.716 | 1.000 | 7.75 |
| ATOM | 519 | CA | ASN | 69 | −32.520 | −48.457 | 21.927 | 1.000 | 6.53 |
| ATOM | 520 | CB | ASN | 69 | −33.807 | −48.842 | 21.198 | 1.000 | 6.25 |
| ATOM | 521 | CG | ASN | 69 | −34.377 | −50.172 | 21.658 | 1.000 | 11.70 |
| ATOM | 522 | OD1 | ASN | 69 | −33.732 | −51.219 | 21.664 | 1.000 | 2.64 |
| ATOM | 523 | ND2 | ASN | 69 | −35.646 | −50.164 | 22.057 | 1.000 | 10.84 |
| ATOM | 524 | C | ASN | 69 | −31.406 | −49.404 | 21.480 | 1.000 | 8.62 |
| ATOM | 525 | O | ASN | 69 | −31.204 | −49.617 | 20.287 | 1.000 | 14.61 |
| ATOM | 526 | N | GLY | 70 | −30.697 | −49.972 | 22.452 | 1.000 | 8.79 |
| ATOM | 527 | CA | GLY | 70 | −29.582 | −50.854 | 22.212 | 1.000 | 1.64 |
| ATOM | 528 | C | GLY | 70 | −29.911 | −52.031 | 21.316 | 1.000 | 6.17 |
| ATOM | 529 | O | GLY | 70 | −29.189 | −52.293 | 20.355 | 1.000 | 12.06 |
| ATOM | 530 | N | ALA | 71 | −30.982 | −52.744 | 21.622 | 1.000 | 1.39 |
| ATOM | 531 | CA | ALA | 71 | −31.442 | −53.885 | 20.843 | 1.000 | 5.92 |
| ATOM | 532 | CB | ALA | 71 | −32.688 | −54.457 | 21.529 | 1.000 | 3.81 |
| ATOM | 533 | C | ALA | 71 | −31.766 | −53.565 | 19.392 | 1.000 | 4.67 |
| ATOM | 534 | O | ALA | 71 | −31.565 | −54.391 | 18.490 | 1.000 | 0.00 |
| ATOM | 535 | N | SER | 72 | −32.295 | −52.371 | 19.121 | 1.000 | 3.88 |
| ATOM | 536 | CA | SER | 72 | −32.687 | −52.033 | 17.752 | 1.000 | 6.33 |
| ATOM | 537 | CB | SER | 72 | −33.678 | −50.870 | 17.759 | 1.000 | 4.05 |
| ATOM | 538 | OG | SER | 72 | −33.023 | −49.637 | 18.004 | 1.000 | 25.62 |
| ATOM | 539 | C | SER | 72 | −31.468 | −51.730 | 16.884 | 1.000 | 7.90 |
| ATOM | 540 | O | SER | 72 | −31.568 | −51.720 | 15.658 | 1.000 | 12.06 |
| ATOM | 541 | N | TYR | 73 | −30.315 | −51.505 | 17.498 | 1.000 | 8.51 |
| ATOM | 542 | CA | TYR | 73 | −29.070 | −51.210 | 16.789 | 1.000 | 8.77 |
| ATOM | 543 | CB | TYR | 73 | −28.394 | −50.029 | 17.478 | 1.000 | 10.31 |
| ATOM | 544 | CG | TYR | 73 | −27.124 | −49.453 | 16.913 | 1.000 | 11.92 |
| ATOM | 545 | CD1 | TYR | 73 | −27.113 | −48.329 | 16.090 | 1.000 | 8.49 |
| ATOM | 546 | CE1 | TYR | 73 | −25.931 | −47.812 | 15.586 | 1.000 | 1.47 |
| ATOM | 547 | CD2 | TYR | 73 | −25.888 | −50.018 | 17.201 | 1.000 | 10.36 |
| ATOM | 548 | CE2 | TYR | 73 | −24.704 | −49.512 | 16.703 | 1.000 | 9.07 |
| ATOM | 549 | CZ | TYR | 73 | −24.727 | −48.398 | 15.890 | 1.000 | 5.36 |
| ATOM | 550 | OH | TYR | 73 | −23.544 | −47.902 | 15.391 | 1.000 | 10.80 |
| ATOM | 551 | C | TYR | 73 | −28.148 | −52.419 | 16.730 | 1.000 | 13.31 |
| ATOM | 552 | O | TYR | 73 | −27.404 | −52.630 | 15.764 | 1.000 | 10.40 |
| ATOM | 553 | N | LEU | 74 | −28.172 | −53.261 | 17.759 | 1.000 | 8.99 |
| ATOM | 554 | CA | LEU | 74 | −27.204 | −54.342 | 17.901 | 1.000 | 7.76 |
| ATOM | 555 | CB | LEU | 74 | −27.554 | −55.155 | 19.155 | 1.000 | 9.47 |
| ATOM | 556 | CG | LEU | 74 | −26.402 | −55.532 | 20.080 | 1.000 | 10.36 |
| ATOM | 557 | CD1 | LEU | 74 | −26.786 | −56.729 | 20.939 | 1.000 | 25.33 |

-continued

| ATOM | 558 | CD2 | LEU | 74 | −25.137 | −55.819 | 19.288 | 1.000 | 13.92 |
| ATOM | 559 | C | LEU | 74 | −27.088 | −55.253 | 16.687 | 1.000 | 5.72 |
| ATOM | 560 | O | LEU | 74 | −25.980 | −55.383 | 16.141 | 1.000 | 7.01 |
| ATOM | 561 | N | PRO | 75 | −28.141 | −55.907 | 16.219 | 1.000 | 6.99 |
| ATOM | 562 | CD | PRO | 75 | −29.553 | −55.794 | 16.615 | 1.000 | 1.55 |
| ATOM | 563 | CA | PRO | 75 | −27.965 | −56.896 | 15.140 | 1.000 | 7.57 |
| ATOM | 564 | CB | PRO | 75 | −29.384 | −57.401 | 14.855 | 1.000 | 5.01 |
| ATOM | 565 | CG | PRO | 75 | −30.158 | −57.063 | 16.086 | 1.000 | 6.27 |
| ATOM | 566 | C | PRO | 75 | −27.364 | −56.285 | 13.882 | 1.000 | 4.16 |
| ATOM | 567 | O | PRO | 75 | −26.651 | −56.971 | 13.158 | 1.000 | 4.35 |
| ATOM | 568 | N | SER | 76 | −27.640 | −55.014 | 13.615 | 1.000 | 6.22 |
| ATOM | 569 | CA | SER | 76 | −27.050 | −54.322 | 12.473 | 1.000 | 0.00 |
| ATOM | 570 | CB | SER | 76 | −27.758 | −52.978 | 12.261 | 1.000 | 0.00 |
| ATOM | 571 | OG | SER | 76 | −29.120 | −53.249 | 11.920 | 1.000 | 0.00 |
| ATOM | 572 | C | SER | 76 | −25.554 | −54.127 | 12.674 | 1.000 | 0.69 |
| ATOM | 573 | O | SER | 76 | −24.767 | −54.280 | 11.740 | 1.000 | 4.06 |
| ATOM | 574 | N | CYS | 77 | −25.202 | −53.802 | 13.911 | 1.000 | 2.82 |
| ATOM | 575 | CA | CYS | 77 | −23.851 | −53.599 | 14.384 | 1.000 | 2.99 |
| ATOM | 576 | CB | CYS | 77 | −23.878 | −53.202 | 15.868 | 1.000 | 0.00 |
| ATOM | 577 | SG | CYS | 77 | −22.325 | −52.508 | 16.451 | 1.000 | 8.78 |
| ATOM | 578 | C | CYS | 77 | −22.962 | −54.831 | 14.225 | 1.000 | 13.77 |
| ATOM | 579 | O | CYS | 77 | −21.828 | −54.700 | 13.755 | 1.000 | 12.12 |
| ATOM | 580 | N | LEU | 78 | −23.455 | −55.996 | 14.621 | 1.000 | 15.71 |
| ATOM | 581 | CA | LEU | 78 | −22.751 | −57.268 | 14.538 | 1.000 | 10.13 |
| ATOM | 582 | CB | LEU | 78 | −23.617 | −58.387 | 15.129 | 1.000 | 2.73 |
| ATOM | 583 | CG | LEU | 78 | −23.777 | −58.354 | 16.651 | 1.000 | 7.98 |
| ATOM | 584 | CD1 | LEU | 78 | −24.866 | −59.319 | 17.085 | 1.000 | 3.36 |
| ATOM | 585 | CD2 | LEU | 78 | −22.451 | −58.676 | 17.330 | 1.000 | 8.53 |
| ATOM | 586 | C | LEU | 78 | −22.385 | −57.650 | 13.106 | 1.000 | 9.88 |
| ATOM | 587 | O | LEU | 78 | −21.222 | −57.855 | 12.761 | 1.000 | 12.55 |
| ATOM | 588 | N | ALA | 79 | −23.407 | −57.748 | 12.271 | 1.000 | 11.93 |
| ATOM | 589 | CA | ALA | 79 | −23.297 | −58.022 | 10.848 | 1.000 | 2.98 |
| ATOM | 590 | CB | ALA | 79 | −24.699 | −58.042 | 10.255 | 1.000 | 0.32 |
| ATOM | 591 | C | ALA | 79 | −22.393 | −57.026 | 10.127 | 1.000 | 7.73 |
| ATOM | 592 | O | ALA | 79 | −21.724 | −57.408 | 9.163 | 1.000 | 13.15 |
| ATOM | 593 | N | THR | 80 | −22.337 | −55.774 | 10.560 | 1.000 | 10.93 |
| ATOM | 594 | CA | THR | 80 | −21.427 | −54.757 | 10.044 | 1.000 | 6.56 |
| ATOM | 595 | CB | THR | 80 | −21.703 | −53.373 | 10.669 | 1.000 | 9.10 |
| ATOM | 596 | OG1 | THR | 80 | −23.013 | −52.897 | 10.320 | 1.000 | 4.47 |
| ATOM | 597 | CG2 | THR | 80 | −20.722 | −52.328 | 10.148 | 1.000 | 8.02 |
| ATOM | 598 | C | THR | 80 | −19.970 | −55.117 | 10.317 | 1.000 | 10.87 |
| ATOM | 599 | O | THR | 80 | −19.103 | −55.052 | 9.450 | 1.000 | 12.66 |
| ATOM | 600 | N | HIS | 81 | −19.659 | −55.512 | 11.548 | 1.000 | 13.90 |
| ATOM | 601 | CA | HIS | 81 | −18.282 | −55.720 | 11.978 | 1.000 | 13.04 |
| ATOM | 602 | CB | HIS | 81 | −18.119 | −55.195 | 13.418 | 1.000 | 15.15 |
| ATOM | 603 | CG | HIS | 81 | −18.279 | −53.704 | 13.502 | 1.000 | 10.10 |
| ATOM | 604 | CD2 | HIS | 81 | −19.202 | −52.927 | 14.111 | 1.000 | 6.25 |
| ATOM | 605 | ND1 | HIS | 81 | −17.404 | −52.833 | 12.889 | 1.000 | 7.20 |
| ATOM | 606 | CE1 | HIS | 81 | −17.775 | −51.589 | 13.117 | 1.000 | 7.73 |
| ATOM | 607 | NE2 | HIS | 81 | −18.867 | −51.616 | 13.863 | 1.000 | 6.24 |
| ATOM | 608 | C | HIS | 81 | −17.827 | −57.166 | 11.896 | 1.000 | 9.61 |
| ATOM | 609 | O | HIS | 81 | −16.674 | −57.460 | 12.216 | 1.000 | 10.35 |
| ATOM | 610 | N | LEU | 82 | −18.689 | −58.081 | 11.470 | 1.000 | 4.74 |
| ATOM | 611 | CA | LEU | 82 | −18.257 | −59.461 | 11.247 | 1.000 | 6.06 |
| ATOM | 612 | CB | LEU | 82 | −19.399 | −60.263 | 10.631 | 1.000 | 6.90 |
| ATOM | 613 | CG | LEU | 82 | −20.535 | −60.716 | 11.541 | 1.000 | 6.83 |
| ATOM | 614 | CD1 | LEU | 82 | −21.388 | −61.774 | 10.851 | 1.000 | 11.79 |
| ATOM | 615 | CD2 | LEU | 82 | −19.987 | −61.246 | 12.856 | 1.000 | 23.45 |
| ATOM | 616 | C | LEU | 82 | −17.042 | −59.500 | 10.337 | 1.000 | 6.51 |
| ATOM | 617 | O | LEU | 82 | −16.972 | −58.722 | 9.375 | 1.000 | 1.45 |
| ATOM | 618 | N | PRO | 83 | −16.056 | −60.360 | 10.556 | 1.000 | 7.15 |
| ATOM | 619 | CD | PRO | 83 | −14.823 | −60.374 | 9.731 | 1.000 | 0.00 |
| ATOM | 620 | CA | PRO | 83 | −16.043 | −61.394 | 11.583 | 1.000 | 5.44 |
| ATOM | 621 | CB | PRO | 83 | −14.941 | −62.341 | 11.067 | 1.000 | 9.33 |
| ATOM | 622 | CG | PRO | 83 | −13.968 | −61.405 | 10.415 | 1.000 | 7.09 |
| ATOM | 623 | C | PRO | 83 | −15.638 | −60.922 | 12.973 | 1.000 | 10.31 |
| ATOM | 624 | O | PRO | 83 | −14.716 | −60.125 | 13.110 | 1.000 | 16.21 |
| ATOM | 625 | N | LEU | 84 | −16.319 | −61.434 | 13.994 | 1.000 | 14.34 |
| ATOM | 626 | CA | LEU | 84 | −16.009 | −61.132 | 15.382 | 1.000 | 10.66 |
| ATOM | 627 | CB | LEU | 84 | −17.165 | −60.373 | 16.049 | 1.000 | 7.23 |
| ATOM | 628 | CG | LEU | 84 | −17.485 | −59.010 | 15.434 | 1.000 | 2.01 |
| ATOM | 629 | CD1 | LEU | 84 | −18.843 | −58.518 | 15.902 | 1.000 | 8.19 |
| ATOM | 630 | CD2 | LEU | 84 | −16.382 | −58.019 | 15.766 | 1.000 | 5.93 |
| ATOM | 631 | C | LEU | 84 | −15.734 | −62.386 | 16.203 | 1.000 | 7.34 |
| ATOM | 632 | O | LEU | 84 | −16.299 | −63.447 | 15.945 | 1.000 | 8.40 |
| ATOM | 633 | N | ASP | 85 | −14.879 | −62.247 | 17.208 | 1.000 | 8.68 |
| ATOM | 634 | CA | ASP | 85 | −14.607 | −63.332 | 18.146 | 1.000 | 10.21 |
| ATOM | 635 | CB | ASP | 85 | −13.093 | −63.433 | 18.382 | 1.000 | 15.96 |
| ATOM | 636 | CG | ASP | 85 | −12.338 | −63.789 | 17.117 | 1.000 | 11.01 |

| | | | | | -continued | | | |
|---|---|---|---|---|---|---|---|---|
| ATOM | 637 | OD1 | ASP | 85 | −12.343 | −64.975 | 16.727 | 1.000 | 9.49 |
| ATOM | 638 | OD2 | ASP | 85 | −11.739 | −62.878 | 16.518 | 1.000 | 28.18 |
| ATOM | 639 | C | ASP | 85 | −15.313 | −63.142 | 19.477 | 1.000 | 0.00 |
| ATOM | 640 | O | ASP | 85 | −15.778 | −64.067 | 20.137 | 1.000 | 5.48 |
| ATOM | 641 | N | LEU | 86 | −15.414 | −61.907 | 19.958 | 1.000 | 7.62 |
| ATOM | 642 | CA | LEU | 86 | −16.080 | −61.695 | 21.243 | 1.000 | 8.84 |
| ATOM | 643 | CB | LEU | 86 | −15.085 | −61.690 | 22.403 | 1.000 | 12.15 |
| ATOM | 644 | CG | LEU | 86 | −15.655 | −61.580 | 23.822 | 1.000 | 13.98 |
| ATOM | 645 | CD1 | LEU | 86 | −16.562 | −62.757 | 24.151 | 1.000 | 7.12 |
| ATOM | 646 | CD2 | LEU | 86 | −14.535 | −61.477 | 24.850 | 1.000 | 10.28 |
| ATOM | 647 | C | LEU | 86 | −16.841 | −60.374 | 21.221 | 1.000 | 6.69 |
| ATOM | 648 | O | LEU | 86 | −16.327 | −59.409 | 20.649 | 1.000 | 8.05 |
| ATOM | 649 | N | VAL | 87 | −18.013 | −60.361 | 21.842 | 1.000 | 4.26 |
| ATOM | 650 | CA | VAL | 87 | −18.752 | −59.127 | 22.049 | 1.000 | 2.21 |
| ATOM | 651 | CB | VAL | 87 | −20.150 | −59.126 | 21.413 | 1.000 | 8.44 |
| ATOM | 652 | CG1 | VAL | 87 | −20.848 | −57.808 | 21.722 | 1.000 | 2.51 |
| ATOM | 653 | CG2 | VAL | 87 | −20.104 | −59.352 | 19.911 | 1.000 | 0.00 |
| ATOM | 654 | C | VAL | 87 | −18.893 | −58.869 | 23.551 | 1.000 | 7.05 |
| ATOM | 655 | O | VAL | 87 | −19.472 | −59.660 | 24.289 | 1.000 | 5.76 |
| ATOM | 656 | N | ILE | 88 | −18.351 | −57.746 | 24.010 | 1.000 | 7.24 |
| ATOM | 657 | CA | ILE | 88 | −18.499 | −57.336 | 25.400 | 1.000 | 6.18 |
| ATOM | 658 | CB | ILE | 88 | −17.233 | −56.652 | 25.938 | 1.000 | 6.54 |
| ATOM | 659 | CG2 | ILE | 88 | −17.458 | −56.098 | 27.333 | 1.000 | 11.40 |
| ATOM | 660 | CG1 | ILE | 88 | −16.001 | −57.559 | 25.902 | 1.000 | 6.21 |
| ATOM | 661 | CD1 | ILE | 88 | −14.734 | −56.856 | 26.339 | 1.000 | 7.20 |
| ATOM | 662 | C | ILE | 88 | −19.693 | −56.394 | 25.506 | 1.000 | 4.68 |
| ATOM | 663 | O | ILE | 88 | −19.817 | −55.458 | 24.716 | 1.000 | 10.14 |
| ATOM | 664 | N | ILE | 89 | −20.574 | −56.672 | 26.457 | 1.000 | 7.74 |
| ATOM | 665 | CA | ILE | 89 | −21.765 | −55.857 | 26.645 | 1.000 | 12.20 |
| ATOM | 666 | CB | ILE | 89 | −23.052 | −56.635 | 26.306 | 1.000 | 12.51 |
| ATOM | 667 | CG2 | ILE | 89 | −24.253 | −55.703 | 26.339 | 1.000 | 11.52 |
| ATOM | 668 | CG1 | ILE | 89 | −22.981 | −57.390 | 24.979 | 1.000 | 6.47 |
| ATOM | 669 | CD1 | ILE | 89 | −24.250 | −58.111 | 24.597 | 1.000 | 8.71 |
| ATOM | 670 | C | ILE | 89 | −21.861 | −55.340 | 28.078 | 1.000 | 11.05 |
| ATOM | 671 | O | ILE | 89 | −22.169 | −56.106 | 28.989 | 1.000 | 3.02 |
| ATOM | 672 | N | MET | 90 | −21.590 | −54.049 | 28.236 | 1.000 | 7.01 |
| ATOM | 673 | CA | MET | 90 | −21.808 | −53.359 | 29.492 | 1.000 | 11.48 |
| ATOM | 674 | CB | MET | 90 | −20.535 | −52.721 | 30.043 | 1.000 | 9.27 |
| ATOM | 675 | CG | MET | 90 | −20.756 | −52.097 | 31.415 | 1.000 | 10.33 |
| ATOM | 676 | XD | MET | 90 | −19.202 | −51.706 | 32.246 | 1.000 | 17.92 |
| ATOM | 677 | CE | MET | 90 | −18.544 | −50.475 | 31.124 | 1.000 | 12.70 |
| ATOM | 678 | C | MET | 90 | −22.872 | −52.262 | 29.325 | 1.000 | 12.90 |
| ATOM | 679 | O | MET | 90 | −22.524 | −51.143 | 28.954 | 1.000 | 0.00 |
| ATOM | 680 | N | LEU | 91 | −24.108 | −52.639 | 29.604 | 1.000 | 8.70 |
| ATOM | 681 | CA | LEU | 91 | −25.292 | −51.802 | 29.511 | 1.000 | 10.58 |
| ATOM | 682 | CB | LEU | 91 | −26.114 | −52.105 | 28.254 | 1.000 | 9.42 |
| ATOM | 683 | CG | LEU | 91 | −25.573 | −51.564 | 26.932 | 1.000 | 4.10 |
| ATOM | 684 | CD1 | LEU | 91 | −26.427 | −52.046 | 25.772 | 1.000 | 0.00 |
| ATOM | 685 | CD2 | LEU | 91 | −25.506 | −50.044 | 26.961 | 1.000 | 2.02 |
| ATOM | 686 | C | LEU | 91 | −26.169 | −52.031 | 30.734 | 1.000 | 2.21 |
| ATOM | 687 | O | LEU | 91 | −25.989 | −53.066 | 31.388 | 1.000 | 10.59 |
| ATOM | 688 | N | GLY | 92 | −27.087 | −51.117 | 31.025 | 1.000 | 4.69 |
| ATOM | 689 | CA | GLY | 92 | −27.963 | −51.321 | 32.172 | 1.000 | 7.16 |
| ATOM | 690 | C | GLY | 92 | −28.189 | −50.092 | 33.027 | 1.000 | 0.00 |
| ATOM | 691 | O | GLY | 92 | −29.266 | −49.924 | 33.603 | 1.000 | 8.09 |
| ATOM | 692 | N | THR | 93 | −27.204 | −49.219 | 33.133 | 1.000 | 0.16 |
| ATOM | 693 | CA | THR | 93 | −27.241 | −48.005 | 33.929 | 1.000 | 9.42 |
| ATOM | 694 | CB | THR | 93 | −25.927 | −47.205 | 33.768 | 1.000 | 17.05 |
| ATOM | 695 | OG1 | THR | 93 | −24.811 | −48.063 | 34.024 | 1.000 | 26.81 |
| ATOM | 696 | CG2 | THR | 93 | −25.847 | −46.068 | 34.778 | 1.000 | 0.34 |
| ATOM | 697 | C | THR | 93 | −28.386 | −47.075 | 33.551 | 1.000 | 9.26 |
| ATOM | 698 | O | THR | 93 | −29.037 | −46.491 | 34.419 | 1.000 | 14.18 |
| ATOM | 699 | N | ASN | 94 | −28.614 | −46.927 | 32.250 | 1.000 | 0.69 |
| ATOM | 700 | CA | ASN | 94 | −29.609 | −45.981 | 31.755 | 1.000 | 5.12 |
| ATOM | 701 | CB | ASN | 94 | −29.333 | −45.677 | 30.274 | 1.000 | 9.42 |
| ATOM | 702 | CG | ASN | 94 | −27.990 | −44.983 | 30.120 | 1.000 | 10.74 |
| ATOM | 703 | OD1 | ASN | 94 | −27.679 | −44.062 | 30.873 | 1.000 | 21.66 |
| ATOM | 704 | ND2 | ASN | 94 | −27.175 | −45.417 | 29.174 | 1.000 | 18.23 |
| ATOM | 705 | C | ASN | 94 | −31.029 | −46.481 | 31.986 | 1.000 | 5.80 |
| ATOM | 706 | O | ASN | 94 | −31.889 | −45.654 | 32.317 | 1.000 | 4.04 |
| ATOM | 707 | N | ASP | 95 | −31.282 | −47.777 | 31.863 | 1.000 | 4.02 |
| ATOM | 708 | CA | ASP | 95 | −32.568 | −48.411 | 32.137 | 1.000 | 7.86 |
| ATOM | 709 | CB | ASP | 95 | −32.522 | −49.913 | 31.880 | 1.000 | 5.49 |
| ATOM | 710 | CG | ASP | 95 | −32.090 | −50.392 | 30.521 | 1.000 | 10.09 |
| ATOM | 711 | OD1 | ASP | 95 | −30.998 | −50.021 | 30.040 | 1.000 | 16.22 |
| ATOM | 712 | OD2 | ASP | 95 | −32.843 | −51.184 | 29.907 | 1.000 | 15.98 |
| ATOM | 713 | C | ASP | 95 | −33.020 | −48.208 | 33.591 | 1.000 | 9.17 |
| ATOM | 714 | O | ASP | 95 | −34.188 | −48.361 | 33.958 | 1.000 | 0.43 |
| ATOM | 715 | N | THR | 96 | −32.051 | −47.882 | 34.421 | 1.000 | 11.45 |

| | | | | | | | | | |
|---|---|---|---|---|---|---|---|---|---|
| ATOM | 716 | CA | THR | 96 | −32.122 | −47.529 | 35.823 | 1.000 | 16.75 |
| ATOM | 717 | CB | THR | 96 | −30.697 | −47.638 | 36.412 | 1.000 | 24.78 |
| ATOM | 718 | OG1 | THR | 96 | −30.607 | −48.784 | 37.274 | 1.000 | 17.62 |
| ATOM | 719 | CG2 | THR | 96 | −30.350 | −46.409 | 37.229 | 1.000 | 12.12 |
| ATOM | 720 | C | THR | 96 | −32.697 | −46.132 | 35.997 | 1.000 | 12.12 |
| ATOM | 721 | O | THR | 96 | −33.047 | −45.678 | 37.088 | 1.000 | 10.94 |
| ATOM | 722 | N | LYS | 97 | −32.820 | −45.406 | 34.883 | 1.000 | 12.18 |
| ATOM | 723 | CA | LYS | 97 | −33.387 | −44.060 | 34.954 | 1.000 | 14.27 |
| ATOM | 724 | CB | LYS | 97 | −33.247 | −43.336 | 33.620 | 1.000 | 13.25 |
| ATOM | 725 | CG | LYS | 97 | −31.996 | −42.477 | 33.500 | 1.000 | 11.50 |
| ATOM | 726 | CD | LYS | 97 | −31.819 | −41.935 | 32.086 | 1.000 | 3.08 |
| ATOM | 727 | CE | LYS | 97 | −30.344 | −41.856 | 31.717 | 1.000 | 0.00 |
| ATOM | 728 | NZ | LYS | 97 | −30.131 | −41.152 | 30.416 | 1.000 | 0.00 |
| ATOM | 729 | C | LYS | 97 | −34.848 | −44.112 | 35.403 | 1.000 | 12.44 |
| ATOM | 730 | O | LYS | 97 | −35.636 | −44.914 | 34.911 | 1.000 | 8.04 |
| ATOM | 731 | N | ALA | 98 | −35.179 | −43.246 | 36.355 | 1.000 | 11.97 |
| ATOM | 732 | CA | ALA | 98 | −36.454 | −43.218 | 37.047 | 1.000 | 4.97 |
| ATOM | 733 | CB | ALA | 98 | −36.522 | −41.982 | 37.943 | 1.000 | 3.36 |
| ATOM | 734 | C | ALA | 98 | −37.641 | −43.246 | 36.100 | 1.000 | 12.00 |
| ATOM | 735 | O | ALA | 98 | −38.651 | −43.905 | 36.355 | 1.000 | 22.61 |
| ATOM | 736 | N | TYR | 99 | −37.535 | −42.518 | 34.988 | 1.000 | 12.39 |
| ATOM | 737 | CA | TYR | 99 | −38.695 | −42.403 | 34.107 | 1.000 | 7.25 |
| ATOM | 738 | CB | TYR | 99 | −38.521 | −41.297 | 33.087 | 1.000 | 9.11 |
| ATOM | 739 | CG | TYR | 99 | −37.300 | −41.251 | 32.217 | 1.000 | 15.58 |
| ATOM | 740 | CD1 | TYR | 99 | −37.261 | −41.912 | 30.995 | 1.000 | 13.09 |
| ATOM | 741 | CE1 | TYR | 99 | −36.144 | −41.874 | 30.186 | 1.000 | 9.06 |
| ATOM | 742 | CD2 | TYR | 99 | −36.173 | −40.533 | 32.598 | 1.000 | 14.48 |
| ATOM | 743 | CE2 | TYR | 99 | −35.051 | −40.482 | 31.796 | 1.000 | 15.13 |
| ATOM | 744 | CZ | TYR | 99 | −35.044 | −41.154 | 30.591 | 1.000 | 11.74 |
| ATOM | 745 | OH | TYR | 99 | −33.925 | −41.102 | 29.794 | 1.000 | 6.20 |
| ATOM | 746 | C | TYR | 99 | −38.990 | −43.726 | 33.413 | 1.000 | 11.25 |
| ATOM | 747 | O | TYR | 99 | −40.121 | −43.927 | 32.963 | 1.000 | 12.89 |
| ATOM | 748 | N | PHE | 100 | −37.993 | −44.606 | 33.351 | 1.000 | 4.63 |
| ATOM | 749 | CA | PHE | 100 | −38.237 | −45.908 | 32.731 | 1.000 | 1.01 |
| ATOM | 750 | CB | PHE | 100 | −36.903 | −46.556 | 32.348 | 1.000 | 3.41 |
| ATOM | 751 | CG | PHE | 100 | −36.316 | −45.980 | 31.070 | 1.000 | 11.77 |
| ATOM | 752 | CD1 | PHE | 100 | −35.018 | −45.506 | 31.032 | 1.000 | 7.50 |
| ATOM | 753 | CD2 | PHE | 100 | −37.080 | −45.919 | 29.917 | 1.000 | 16.94 |
| ATOM | 754 | CE1 | PHE | 100 | −34.489 | −44.981 | 29.868 | 1.000 | 7.31 |
| ATOM | 755 | CE2 | PHE | 100 | −36.557 | −45.398 | 28.748 | 1.000 | 12.92 |
| ATOM | 756 | CZ | PHE | 100 | −35.260 | −44.925 | 28.722 | 1.000 | 7.58 |
| ATOM | 757 | C | PHE | 100 | −39.051 | −46.829 | 33.628 | 1.000 | 6.94 |
| ATOM | 758 | O | PHE | 100 | −39.711 | −47.750 | 33.131 | 1.000 | 9.31 |
| ATOM | 759 | N | ARG | 101 | −39.032 | −46.629 | 34.943 | 1.000 | 12.10 |
| ATOM | 760 | CA | ARG | 101 | −39.783 | −47.468 | 35.869 | 1.000 | 12.96 |
| ATOM | 761 | CB | ARG | 101 | −41.294 | −47.296 | 35.695 | 1.000 | 16.21 |
| ATOM | 762 | CG | ARG | 101 | −41.890 | −45.959 | 36.087 | 1.000 | 19.51 |
| ATOM | 763 | CD | ARG | 101 | −43.376 | −45.918 | 35.740 | 1.000 | 25.82 |
| ATOM | 764 | NE | ARG | 101 | −43.818 | −44.553 | 35.466 | 1.000 | 31.88 |
| ATOM | 765 | CZ | ARG | 101 | −43.797 | −43.583 | 36.373 | 1.000 | 33.97 |
| ATOM | 766 | NH1 | ARG | 101 | −43.355 | −43.839 | 37.599 | 1.000 | 43.49 |
| ATOM | 767 | NH2 | ARG | 101 | −44.206 | −42.361 | 36.067 | 1.000 | 44.85 |
| ATOM | 768 | C | ARG | 101 | −39.472 | −48.955 | 35.704 | 1.000 | 12.20 |
| ATOM | 769 | O | ARG | 101 | −40.376 | −49.782 | 35.878 | 1.000 | 12.48 |
| ATOM | 770 | N | ARG | 102 | −38.238 | −49.319 | 35.378 | 1.000 | 8.86 |
| ATOM | 771 | CA | ARG | 102 | −37.887 | −50.733 | 35.264 | 1.000 | 11.00 |
| ATOM | 772 | CB | ARG | 102 | −36.899 | −50.962 | 34.115 | 1.000 | 6.96 |
| ATOM | 773 | CG | ARG | 102 | −37.497 | −50.805 | 32.720 | 1.000 | 9.64 |
| ATOM | 774 | CD | ARG | 102 | −36.518 | −51.198 | 31.624 | 1.000 | 8.07 |
| ATOM | 775 | NE | ARG | 102 | −37.140 | −51.842 | 30.474 | 1.000 | 4.64 |
| ATOM | 776 | CZ | ARG | 102 | −36.540 | −52.606 | 29.571 | 1.000 | 7.34 |
| ATOM | 777 | NH1 | ARG | 102 | −35.240 | −52.877 | 29.628 | 1.000 | 1.45 |
| ATOM | 778 | NH2 | ARG | 102 | −37.232 | −53.131 | 28.567 | 1.000 | 6.11 |
| ATOM | 779 | C | ARG | 102 | −37.320 | −51.275 | 36.577 | 1.000 | 11.09 |
| ATOM | 780 | O | ARG | 102 | −36.734 | −50.567 | 37.394 | 1.000 | 10.02 |
| ATOM | 781 | N | THR | 103 | −37.497 | −52.573 | 36.785 | 1.000 | 11.01 |
| ATOM | 782 | CA | THR | 103 | −36.898 | −53.307 | 37.893 | 1.000 | 12.65 |
| ATOM | 783 | CB | THR | 103 | −37.844 | −54.376 | 38.462 | 1.000 | 7.64 |
| ATOM | 784 | OG1 | THR | 103 | −38.083 | −55.384 | 37.468 | 1.000 | 11.29 |
| ATOM | 785 | CG2 | THR | 103 | −39.199 | −53.771 | 38.790 | 1.000 | 15.33 |
| ATOM | 786 | C | THR | 103 | −35.618 | −53.966 | 37.390 | 1.000 | 10.55 |
| ATOM | 787 | O | THR | 103 | −35.409 | −53.986 | 36.173 | 1.000 | 9.17 |
| ATOM | 788 | N | PRO | 104 | −34.765 | −54.474 | 38.264 | 1.000 | 10.17 |
| ATOM | 789 | CD | PRO | 104 | −34.799 | −54.363 | 39.731 | 1.000 | 14.03 |
| ATOM | 790 | CA | PRO | 104 | −33.598 | −55.230 | 37.803 | 1.000 | 6.81 |
| ATOM | 791 | CB | PRO | 104 | −32.968 | −55.748 | 39.094 | 1.000 | 5.25 |
| ATOM | 792 | CG | PRO | 104 | −33.402 | −54.759 | 40.129 | 1.000 | 8.07 |
| ATOM | 793 | C | PRO | 104 | −34.010 | −56.400 | 36.911 | 1.000 | 5.89 |
| ATOM | 794 | O | PRO | 104 | −33.251 | −56.728 | 35.998 | 1.000 | 5.49 |

-continued

| | | | | | | | | |
|---|---|---|---|---|---|---|---|---|
| ATOM | 795 | N | LEU | 105 | −35.164 | −56.994 | 37.173 | 1.000 | 2.55 |
| ATOM | 796 | CA | LEU | 105 | −35.690 | −58.071 | 36.341 | 1.000 | 10.27 |
| ATOM | 797 | CB | LEU | 105 | −36.989 | −58.642 | 36.890 | 1.000 | 11.51 |
| ATOM | 798 | CG | LEU | 105 | −37.304 | −60.122 | 36.695 | 1.000 | 16.39 |
| ATOM | 799 | CD1 | LEU | 105 | −38.804 | −60.319 | 36.480 | 1.000 | 4.05 |
| ATOM | 800 | CD2 | LEU | 105 | −36.533 | −60.744 | 35.542 | 1.000 | 15.49 |
| ATOM | 801 | C | LEU | 105 | −35.923 | −57.566 | 34.915 | 1.000 | 14.30 |
| ATOM | 802 | O | LEU | 105 | −35.415 | −58.168 | 33.969 | 1.000 | 14.22 |
| ATOM | 803 | N | ASP | 106 | −36.686 | −56.484 | 34.791 | 1.000 | 11.11 |
| ATOM | 804 | CA | ASP | 106 | −36.922 | −55.878 | 33.482 | 1.000 | 8.08 |
| ATOM | 805 | CB | ASP | 106 | −37.636 | −54.538 | 33.621 | 1.000 | 14.02 |
| ATOM | 806 | CG | ASP | 106 | −39.046 | −54.638 | 34.152 | 1.000 | 13.88 |
| ATOM | 807 | OD1 | ASP | 106 | −39.726 | −55.653 | 33.875 | 1.000 | 19.94 |
| ATOM | 808 | OD2 | ASP | 106 | −39.479 | −53.686 | 34.843 | 1.000 | 4.29 |
| ATOM | 809 | C | ASP | 106 | −35.607 | −55.668 | 32.734 | 1.000 | 7.79 |
| ATOM | 810 | O | ASP | 106 | −35.504 | −55.987 | 31.554 | 1.000 | 10.52 |
| ATOM | 811 | N | ILE | 107 | −34.614 | −55.131 | 33.438 | 1.000 | 5.00 |
| ATOM | 812 | CA | ILE | 107 | −33.321 | −54.814 | 32.845 | 1.000 | 6.63 |
| ATOM | 813 | CB | ILE | 107 | −32.444 | −54.016 | 33.828 | 1.000 | 14.49 |
| ATOM | 814 | CG2 | ILE | 107 | −31.125 | −53.622 | 33.184 | 1.000 | 7.24 |
| ATOM | 815 | CG1 | ILE | 107 | −33.146 | −52.790 | 34.415 | 1.000 | 16.93 |
| ATOM | 816 | CD1 | ILE | 107 | −32.174 | −51.779 | 34.992 | 1.000 | 19.38 |
| ATOM | 817 | C | ILE | 107 | −32.564 | −56.059 | 32.405 | 1.000 | 5.12 |
| ATOM | 818 | O | ILE | 107 | −31.877 | −56.024 | 31.381 | 1.000 | 4.80 |
| ATOM | 819 | N | ALA | 108 | −32.691 | −57.148 | 33.157 | 1.000 | 5.34 |
| ATOM | 820 | CA | ALA | 108 | −32.021 | −58.398 | 32.812 | 1.000 | 4.25 |
| ATOM | 821 | CB | ALA | 108 | −32.089 | −59.399 | 33.956 | 1.000 | 2.49 |
| ATOM | 822 | C | ALA | 108 | −32.637 | −59.018 | 31.568 | 1.000 | 2.89 |
| ATOM | 823 | O | ALA | 108 | −31.952 | −59.619 | 30.738 | 1.000 | 11.68 |
| ATOM | 824 | N | LEU | 109 | −33.956 | −58.864 | 31.449 | 1.000 | 0.00 |
| ATOM | 825 | CA | LEU | 109 | −34.609 | −59.401 | 30.251 | 1.000 | 6.18 |
| ATOM | 826 | CB | LEU | 109 | −36.125 | −59.391 | 30.435 | 1.000 | 12.37 |
| ATOM | 827 | CG | LEU | 109 | −36.674 | −60.463 | 31.386 | 1.000 | 15.66 |
| ATOM | 828 | CD1 | LEU | 109 | −37.985 | −60.004 | 32.001 | 1.000 | 27.44 |
| ATOM | 829 | CD2 | LEU | 109 | −36.854 | −61.794 | 30.672 | 1.000 | 3.14 |
| ATOM | 830 | C | LEU | 109 | −34.171 | −58.620 | 29.022 | 1.000 | 10.30 |
| ATOM | 831 | O | LEU | 109 | −34.035 | −59.139 | 27.915 | 1.000 | 18.00 |
| ATOM | 832 | N | GLY | 110 | −33.918 | −57.323 | 29.193 | 1.000 | 11.78 |
| ATOM | 833 | CA | GLY | 110 | −33.426 | −56.535 | 28.069 | 1.000 | 8.26 |
| ATOM | 834 | C | GLY | 110 | −32.028 | −56.976 | 27.666 | 1.000 | 7.06 |
| ATOM | 835 | O | GLY | 110 | −31.757 | −57.155 | 26.482 | 1.000 | 18.68 |
| ATOM | 836 | N | MET | 111 | −31.149 | −57.149 | 28.651 | 1.000 | 5.04 |
| ATOM | 837 | CA | MET | 111 | −29.812 | −57.661 | 28.414 | 1.000 | 4.52 |
| ATOM | 838 | CB | MET | 111 | −28.962 | −57.717 | 29.683 | 1.000 | 1.61 |
| ATOM | 839 | CG | MET | 111 | −27.663 | −58.503 | 29.542 | 1.000 | 0.00 |
| ATOM | 840 | XD | MET | 111 | −26.456 | −57.694 | 28.453 | 1.000 | 16.83 |
| ATOM | 841 | CE | MET | 111 | −25.895 | −56.355 | 29.497 | 1.000 | 5.08 |
| ATOM | 842 | C | MET | 111 | −29.915 | −59.066 | 27.821 | 1.000 | 6.40 |
| ATOM | 843 | O | MET | 111 | −29.098 | −59.476 | 27.005 | 1.000 | 8.66 |
| ATOM | 844 | N | SER | 112 | −30.937 | −59.795 | 28.270 | 1.000 | 9.55 |
| ATOM | 845 | CA | SER | 112 | −31.140 | −61.133 | 27.731 | 1.000 | 8.05 |
| ATOM | 846 | CB | SER | 112 | −32.322 | −61.821 | 28.405 | 1.000 | 10.37 |
| ATOM | 847 | OG | SER | 112 | −33.488 | −61.744 | 27.609 | 1.000 | 8.11 |
| ATOM | 848 | C | SER | 112 | −31.341 | −61.034 | 26.217 | 1.000 | 6.07 |
| ATOM | 849 | O | SER | 112 | −30.761 | −61.823 | 25.471 | 1.000 | 9.26 |
| ATOM | 850 | N | VAL | 113 | −32.142 | −60.065 | 25.803 | 1.000 | 4.80 |
| ATOM | 851 | CA | VAL | 113 | −32.424 | −59.788 | 24.401 | 1.000 | 9.22 |
| ATOM | 852 | CB | VAL | 113 | −33.414 | −58.615 | 24.266 | 1.000 | 9.35 |
| ATOM | 853 | CG1 | VAL | 113 | −33.350 | −57.979 | 22.886 | 1.000 | 0.53 |
| ATOM | 854 | CG2 | VAL | 113 | −34.830 | −59.090 | 24.567 | 1.000 | 15.43 |
| ATOM | 855 | C | VAL | 113 | −31.149 | −59.490 | 23.616 | 1.000 | 18.19 |
| ATOM | 856 | O | VAL | 113 | −31.027 | −59.900 | 22.456 | 1.000 | 17.08 |
| ATOM | 857 | N | LEU | 114 | −30.199 | −58.791 | 24.235 | 1.000 | 16.22 |
| ATOM | 858 | CA | LEU | 114 | −28.948 | −58.431 | 23.570 | 1.000 | 9.05 |
| ATOM | 859 | CB | LEU | 114 | −28.220 | −57.329 | 24.341 | 1.000 | 4.93 |
| ATOM | 860 | CG | LEU | 114 | −28.938 | −55.983 | 24.427 | 1.000 | 6.23 |
| ATOM | 861 | CD1 | LEU | 114 | −28.122 | −54.973 | 25.221 | 1.000 | 8.47 |
| ATOM | 862 | CD2 | LEU | 114 | −29.228 | −55.450 | 23.032 | 1.000 | 0.00 |
| ATOM | 863 | C | LEU | 114 | −28.018 | −59.628 | 23.407 | 1.000 | 5.15 |
| ATOM | 864 | O | LEU | 114 | −27.310 | −59.762 | 22.410 | 1.000 | 8.05 |
| ATOM | 865 | N | VAL | 115 | −28.028 | −60.503 | 24.403 | 1.000 | 5.78 |
| ATOM | 866 | CA | VAL | 115 | −27.223 | −61.717 | 24.373 | 1.000 | 8.93 |
| ATOM | 867 | CB | VAL | 115 | −27.202 | −62.383 | 25.762 | 1.000 | 8.05 |
| ATOM | 868 | CG1 | VAL | 115 | −26.501 | −63.729 | 25.720 | 1.000 | 0.00 |
| ATOM | 869 | CG2 | VAL | 115 | −26.543 | −61.439 | 26.759 | 1.000 | 0.00 |
| ATOM | 870 | C | VAL | 115 | −27.763 | −62.685 | 23.330 | 1.000 | 9.50 |
| ATOM | 871 | O | VAL | 115 | −27.007 | −63.390 | 22.662 | 1.000 | 9.58 |
| ATOM | 872 | N | THR | 116 | −29.087 | −62.715 | 23.179 | 1.000 | 8.15 |
| ATOM | 873 | CA | THR | 116 | −29.688 | −63.617 | 22.199 | 1.000 | 8.38 |

-continued

| | | | | | | | | |
|---|---|---|---|---|---|---|---|---|
| ATOM | 874 | CB | THR | 116 | −31.222 | −63.622 | 22.327 | 1.000 | 12.50 |
| ATOM | 875 | OG1 | THR | 116 | −31.575 | −64.207 | 23.585 | 1.000 | 13.40 |
| ATOM | 876 | CG2 | THR | 116 | −31.848 | −64.479 | 21.233 | 1.000 | 10.82 |
| ATOM | 877 | C | THR | 116 | −29.316 | −63.241 | 20.771 | 1.000 | 5.56 |
| ATOM | 878 | O | THR | 116 | −29.011 | −64.127 | 19.966 | 1.000 | 5.27 |
| ATOM | 879 | N | GLN | 117 | −29.345 | −61.945 | 20.473 | 1.000 | 8.17 |
| ATOM | 880 | CA | GLN | 117 | −28.956 | −61.430 | 19.160 | 1.000 | 9.93 |
| ATOM | 881 | CB | GLN | 117 | −29.166 | −59.920 | 19.080 | 1.000 | 3.66 |
| ATOM | 882 | CG | GLN | 117 | −30.592 | −59.440 | 19.279 | 1.000 | 6.21 |
| ATOM | 883 | CD | GLN | 117 | −30.699 | −57.933 | 19.390 | 1.000 | 7.09 |
| ATOM | 884 | OE1 | GLN | 117 | −29.801 | −57.260 | 19.896 | 1.000 | 12.85 |
| ATOM | 885 | NE2 | GLN | 117 | −31.811 | −57.376 | 18.914 | 1.000 | 7.39 |
| ATOM | 886 | C | GLN | 117 | −27.499 | −61.761 | 18.847 | 1.000 | 11.60 |
| ATOM | 887 | O | GLN | 117 | −27.105 | −62.023 | 17.706 | 1.000 | 9.03 |
| ATOM | 888 | N | VAL | 118 | −26.652 | −61.751 | 19.879 | 1.000 | 11.77 |
| ATOM | 889 | CA | VAL | 118 | −25.258 | −62.146 | 19.659 | 1.000 | 8.34 |
| ATOM | 890 | CB | VAL | 118 | −24.340 | −61.768 | 20.831 | 1.000 | 0.49 |
| ATOM | 891 | CG1 | VAL | 118 | −22.892 | −62.118 | 20.499 | 1.000 | 21.94 |
| ATOM | 892 | CG2 | VAL | 118 | −24.452 | −60.291 | 21.169 | 1.000 | 3.31 |
| ATOM | 893 | C | VAL | 118 | −25.166 | −63.652 | 19.417 | 1.000 | 10.48 |
| ATOM | 894 | O | VAL | 118 | −24.354 | −64.107 | 18.607 | 1.000 | 10.54 |
| ATOM | 895 | N | LEU | 119 | −25.993 | −64.431 | 20.112 | 1.000 | 7.97 |
| ATOM | 896 | CA | LEU | 119 | −25.916 | −65.885 | 19.993 | 1.000 | 8.73 |
| ATOM | 897 | CB | LEU | 119 | −26.679 | −66.572 | 21.135 | 1.000 | 8.06 |
| ATOM | 898 | CG | LEU | 119 | −25.981 | −66.556 | 22.498 | 1.000 | 21.06 |
| ATOM | 899 | CD1 | LEU | 119 | −26.800 | −67.296 | 23.548 | 1.000 | 5.53 |
| ATOM | 900 | CD2 | LEU | 119 | −24.580 | −67.150 | 22.403 | 1.000 | 21.96 |
| ATOM | 901 | C | LEU | 119 | −26.446 | −66.362 | 18.649 | 1.000 | 5.78 |
| ATOM | 902 | O | LEU | 119 | −26.022 | −67.409 | 18.153 | 1.000 | 14.06 |
| ATOM | 903 | N | THR | 120 | −27.364 | −65.608 | 18.053 | 1.000 | 8.82 |
| ATOM | 904 | CA | THR | 120 | −27.964 | −65.985 | 16.780 | 1.000 | 0.00 |
| ATOM | 905 | CB | THR | 120 | −29.497 | −65.798 | 16.815 | 1.000 | 6.15 |
| ATOM | 906 | OG1 | THR | 120 | −29.805 | −64.405 | 16.969 | 1.000 | 10.14 |
| ATOM | 907 | CG2 | THR | 120 | −30.121 | −66.535 | 17.994 | 1.000 | 0.76 |
| ATOM | 908 | C | THR | 120 | −27.419 | −65.198 | 15.594 | 1.000 | 10.30 |
| ATOM | 909 | O | THR | 120 | −28.061 | −65.190 | 14.537 | 1.000 | 13.46 |
| ATOM | 910 | N | SER | 121 | −26.272 | −64.533 | 15.700 | 1.000 | 11.26 |
| ATOM | 911 | CA | SER | 121 | −25.774 | −63.675 | 14.636 | 1.000 | 7.70 |
| ATOM | 912 | CB | SER | 121 | −25.000 | −62.487 | 15.240 | 1.000 | 5.36 |
| ATOM | 913 | OG | SER | 121 | −23.826 | −62.954 | 15.886 | 1.000 | 3.70 |
| ATOM | 914 | C | SER | 121 | −24.852 | −64.353 | 13.629 | 1.000 | 7.89 |
| ATOM | 915 | O | SER | 121 | −24.360 | −63.660 | 12.730 | 1.000 | 13.24 |
| ATOM | 916 | N | ALA | 122 | −24.603 | −65.645 | 13.755 | 1.000 | 11.50 |
| ATOM | 917 | CA | ALA | 122 | −23.748 | −66.370 | 12.820 | 1.000 | 12.48 |
| ATOM | 918 | CB | ALA | 122 | −23.820 | −67.868 | 13.098 | 1.000 | 3.73 |
| ATOM | 919 | C | ALA | 122 | −24.124 | −66.083 | 11.370 | 1.000 | 7.92 |
| ATOM | 920 | O | ALA | 122 | −25.311 | −66.050 | 11.042 | 1.000 | 8.42 |
| ATOM | 921 | N | GLY | 123 | −23.125 | −65.859 | 10.529 | 1.000 | 7.14 |
| ATOM | 922 | CA | GLY | 123 | −23.316 | −65.625 | 9.115 | 1.000 | 3.98 |
| ATOM | 923 | C | GLY | 123 | −23.643 | −64.196 | 8.735 | 1.000 | 12.34 |
| ATOM | 924 | O | GLY | 123 | −23.445 | −63.822 | 7.571 | 1.000 | 1.55 |
| ATOM | 925 | N | GLY | 124 | −24.132 | −63.404 | 9.683 | 1.000 | 19.09 |
| ATOM | 926 | CA | GLY | 124 | −24.506 | −62.016 | 9.471 | 1.000 | 13.26 |
| ATOM | 927 | C | GLY | 124 | −25.277 | −61.809 | 8.186 | 1.000 | 10.25 |
| ATOM | 928 | O | GLY | 124 | −26.403 | −62.278 | 8.018 | 1.000 | 10.97 |
| ATOM | 929 | N | VAL | 125 | −24.684 | −61.110 | 7.217 | 1.000 | 12.50 |
| ATOM | 930 | CA | VAL | 125 | −25.365 | −60.956 | 5.930 | 1.000 | 9.40 |
| ATOM | 931 | CB | VAL | 125 | −25.557 | −59.477 | 5.559 | 1.000 | 14.11 |
| ATOM | 932 | CG1 | VAL | 125 | −26.156 | −59.326 | 4.168 | 1.000 | 13.51 |
| ATOM | 933 | CG2 | VAL | 125 | −26.455 | −58.786 | 6.578 | 1.000 | 22.31 |
| ATOM | 934 | C | VAL | 125 | −24.588 | −61.675 | 4.833 | 1.000 | 6.71 |
| ATOM | 935 | O | VAL | 125 | −23.580 | −61.151 | 4.368 | 1.000 | 4.54 |
| ATOM | 936 | N | GLY | 126 | −25.047 | −62.850 | 4.427 | 1.000 | 14.20 |
| ATOM | 937 | CA | GLY | 126 | −24.466 | −63.654 | 3.377 | 1.000 | 9.15 |
| ATOM | 938 | C | GLY | 126 | −23.012 | −64.018 | 3.580 | 1.000 | 10.06 |
| ATOM | 939 | O | GLY | 126 | −22.225 | −64.068 | 2.629 | 1.000 | 4.29 |
| ATOM | 940 | N | THR | 127 | −22.595 | −64.295 | 4.811 | 1.000 | 6.29 |
| ATOM | 941 | CA | THR | 127 | −21.214 | −64.701 | 5.050 | 1.000 | 3.83 |
| ATOM | 942 | CB | THR | 127 | −20.470 | −63.707 | 5.957 | 1.000 | 8.35 |
| ATOM | 943 | OG1 | THR | 127 | −20.719 | −64.001 | 7.339 | 1.000 | 16.55 |
| ATOM | 944 | CG2 | THR | 127 | −20.987 | −62.295 | 5.716 | 1.000 | 11.34 |
| ATOM | 945 | C | THR | 127 | −21.143 | −66.099 | 5.663 | 1.000 | 1.10 |
| ATOM | 946 | O | THR | 127 | −22.159 | −66.699 | 6.001 | 1.000 | 4.52 |
| ATOM | 947 | N | THR | 128 | −19.921 | −66.590 | 5.790 | 1.000 | 9.21 |
| ATOM | 948 | CA | THR | 128 | −19.546 | −67.893 | 6.299 | 1.000 | 8.72 |
| ATOM | 949 | CB | THR | 128 | −18.451 | −68.505 | 5.397 | 1.000 | 10.99 |
| ATOM | 950 | OG1 | THR | 128 | −17.447 | −67.497 | 5.236 | 1.000 | 7.85 |
| ATOM | 951 | CG2 | THR | 128 | −18.976 | −68.853 | 4.015 | 1.000 | 3.45 |
| ATOM | 952 | C | THR | 128 | −18.995 | −67.821 | 7.718 | 1.000 | 13.03 |

| | | | | | | | | |
|---|---|---|---|---|---|---|---|---|
| ATOM | 953 | O | THR | 128 | −18.450 | −68.788 | 8.255 | 1.000 | 8.50 |
| ATOM | 954 | N | TYR | 129 | −19.127 | −66.646 | 8.315 | 1.000 | 10.20 |
| ATOM | 955 | CA | TYR | 129 | −18.542 | −66.357 | 9.615 | 1.000 | 7.58 |
| ATOM | 956 | CB | TYR | 129 | −18.323 | −64.853 | 9.722 | 1.000 | 8.22 |
| ATOM | 957 | CG | TYR | 129 | −17.246 | −64.280 | 8.835 | 1.000 | 11.97 |
| ATOM | 958 | CD1 | TYR | 129 | −17.514 | −63.176 | 8.031 | 1.000 | 8.62 |
| ATOM | 959 | CE1 | TYR | 129 | −16.547 | −62.636 | 7.211 | 1.000 | 7.23 |
| ATOM | 960 | CD2 | TYR | 129 | −15.970 | −64.827 | 8.799 | 1.000 | 12.10 |
| ATOM | 961 | CE2 | TYR | 129 | −14.991 | −64.290 | 7.982 | 1.000 | 16.92 |
| ATOM | 962 | CZ | TYR | 129 | −15.288 | −63.196 | 7.193 | 1.000 | 16.10 |
| ATOM | 963 | OH | TYR | 129 | −14.315 | −62.655 | 6.383 | 1.000 | 11.56 |
| ATOM | 964 | C | TYR | 129 | −19.416 | −66.840 | 10.765 | 1.000 | 9.63 |
| ATOM | 965 | O | TYR | 129 | −20.644 | −66.723 | 10.714 | 1.000 | 13.75 |
| ATOM | 966 | N | PRO | 130 | −18.789 | −67.380 | 11.804 | 1.000 | 8.51 |
| ATOM | 967 | CD | PRO | 130 | −17.336 | −67.523 | 12.004 | 1.000 | 10.11 |
| ATOM | 968 | CA | PRO | 130 | −19.549 | −67.914 | 12.938 | 1.000 | 5.53 |
| ATOM | 969 | CB | PRO | 130 | −18.522 | −68.804 | 13.647 | 1.000 | 8.51 |
| ATOM | 970 | CG | PRO | 130 | −17.227 | −68.097 | 13.397 | 1.000 | 11.17 |
| ATOM | 971 | C | PRO | 130 | −19.983 | −66.791 | 13.872 | 1.000 | 7.77 |
| ATOM | 972 | O | PRO | 130 | −19.500 | −65.667 | 13.730 | 1.000 | 2.72 |
| ATOM | 973 | N | ALA | 131 | −20.873 | −67.117 | 14.799 | 1.000 | 7.61 |
| ATOM | 974 | CA | ALA | 131 | −21.305 | −66.205 | 15.844 | 1.000 | 2.73 |
| ATOM | 975 | CB | ALA | 131 | −22.537 | −66.747 | 16.554 | 1.000 | 0.00 |
| ATOM | 976 | C | ALA | 131 | −20.174 | −65.984 | 16.842 | 1.000 | 8.30 |
| ATOM | 977 | O | ALA | 131 | −19.502 | −66.942 | 17.223 | 1.000 | 12.18 |
| ATOM | 978 | N | PRO | 132 | −19.937 | −64.752 | 17.273 | 1.000 | 14.28 |
| ATOM | 979 | CD | PRO | 132 | −20.610 | −63.516 | 16.842 | 1.000 | 11.04 |
| ATOM | 980 | CA | PRO | 132 | −18.901 | −64.505 | 18.284 | 1.000 | 12.37 |
| ATOM | 981 | CB | PRO | 132 | −18.696 | −62.992 | 18.181 | 1.000 | 14.35 |
| ATOM | 982 | CG | PRO | 132 | −20.032 | −62.472 | 17.753 | 1.000 | 12.70 |
| ATOM | 983 | C | PRO | 132 | −19.395 | −64.884 | 19.675 | 1.000 | 12.80 |
| ATOM | 984 | O | PRO | 132 | −20.608 | −65.027 | 19.856 | 1.000 | 21.24 |
| ATOM | 985 | N | LYS | 133 | −18.497 | −65.051 | 20.641 | 1.000 | 14.17 |
| ATOM | 986 | CA | LYS | 133 | −18.903 | −65.337 | 22.017 | 1.000 | 14.31 |
| ATOM | 987 | CB | LYS | 133 | −17.760 | −65.881 | 22.869 | 1.000 | 14.22 |
| ATOM | 988 | CG | LYS | 133 | −17.050 | −67.101 | 22.317 | 1.000 | 13.51 |
| ATOM | 989 | CD | LYS | 133 | −15.746 | −67.358 | 23.057 | 1.000 | 18.76 |
| ATOM | 990 | CE | LYS | 133 | −15.463 | −68.849 | 23.174 | 1.000 | 21.23 |
| ATOM | 991 | NZ | LYS | 133 | −15.154 | −69.237 | 24.580 | 1.000 | 37.08 |
| ATOM | 992 | C | LYS | 133 | −19.441 | −64.066 | 22.667 | 1.000 | 10.23 |
| ATOM | 993 | O | LYS | 133 | −19.319 | −62.982 | 22.091 | 1.000 | 4.45 |
| ATOM | 994 | N | VAL | 134 | −20.032 | −64.194 | 23.853 | 1.000 | 4.74 |
| ATOM | 995 | CA | VAL | 134 | −20.562 | −63.000 | 24.507 | 1.000 | 10.55 |
| ATOM | 996 | CB | VAL | 134 | −22.106 | −62.964 | 24.490 | 1.000 | 11.86 |
| ATOM | 997 | CG1 | VAL | 134 | −22.586 | −61.523 | 24.423 | 1.000 | 0.00 |
| ATOM | 998 | CG2 | VAL | 134 | −22.659 | −63.778 | 23.334 | 1.000 | 29.88 |
| ATOM | 999 | C | VAL | 134 | −20.129 | −62.885 | 25.963 | 1.000 | 12.01 |
| ATOM | 1000 | O | VAL | 134 | −20.215 | −63.837 | 26.736 | 1.000 | 27.94 |
| ATOM | 1001 | N | LEU | 135 | −19.676 | −61.703 | 26.357 | 1.000 | 12.21 |
| ATOM | 1002 | CA | LEU | 135 | −19.364 | −61.443 | 27.757 | 1.000 | 14.41 |
| ATOM | 1003 | CB | LEU | 135 | −17.975 | −60.835 | 27.898 | 1.000 | 17.37 |
| ATOM | 1004 | CG | LEU | 135 | −17.123 | −61.223 | 29.105 | 1.000 | 18.57 |
| ATOM | 1005 | CD1 | LEU | 135 | −15.993 | −60.213 | 29.264 | 1.000 | 4.42 |
| ATOM | 1006 | CD2 | LEU | 135 | −17.932 | −61.341 | 30.387 | 1.000 | 6.01 |
| ATOM | 1007 | C | LEU | 135 | −20.397 | −60.497 | 28.360 | 1.000 | 17.03 |
| ATOM | 1008 | O | LEU | 135 | −20.485 | −59.326 | 27.984 | 1.000 | 14.19 |
| ATOM | 1009 | N | VAL | 136 | −21.196 | −60.988 | 29.303 | 1.000 | 19.10 |
| ATOM | 1010 | CA | VAL | 136 | −22.167 | −60.110 | 29.954 | 1.000 | 14.45 |
| ATOM | 1011 | CB | VAL | 136 | −23.344 | −60.925 | 30.511 | 1.000 | 13.65 |
| ATOM | 1012 | CG1 | VAL | 136 | −24.272 | −60.045 | 31.335 | 1.000 | 8.06 |
| ATOM | 1013 | CG2 | VAL | 136 | −24.080 | −61.596 | 29.362 | 1.000 | 0.00 |
| ATOM | 1014 | C | VAL | 136 | −21.498 | −59.327 | 31.073 | 1.000 | 10.63 |
| ATOM | 1015 | O | VAL | 136 | −20.929 | −59.948 | 31.971 | 1.000 | 7.12 |
| ATOM | 1016 | N | VAL | 137 | −21.556 | −57.997 | 31.027 | 1.000 | 7.93 |
| ATOM | 1017 | CA | VAL | 137 | −20.882 | −57.215 | 32.056 | 1.000 | 6.63 |
| ATOM | 1018 | CB | VAL | 137 | −19.699 | −56.397 | 31.497 | 1.000 | 6.08 |
| ATOM | 1019 | CG1 | VAL | 137 | −19.115 | −55.512 | 32.595 | 1.000 | 6.59 |
| ATOM | 1020 | CG2 | VAL | 137 | −18.609 | −57.291 | 30.936 | 1.000 | 10.34 |
| ATOM | 1021 | C | VAL | 137 | −21.828 | −56.255 | 32.775 | 1.000 | 6.02 |
| ATOM | 1022 | O | VAL | 137 | −22.319 | −55.273 | 32.219 | 1.000 | 11.10 |
| ATOM | 1023 | N | SER | 138 | −22.061 | −56.558 | 34.040 | 1.000 | 6.05 |
| ATOM | 1024 | CA | SER | 138 | −22.800 | −55.715 | 34.972 | 1.000 | 9.77 |
| ATOM | 1025 | CB | SER | 138 | −23.139 | −56.523 | 36.223 | 1.000 | 16.98 |
| ATOM | 1026 | OG | SER | 138 | −23.850 | −55.804 | 37.202 | 1.000 | 19.18 |
| ATOM | 1027 | C | SER | 138 | −21.944 | −54.496 | 35.276 | 1.000 | 8.41 |
| ATOM | 1028 | O | SER | 138 | −20.779 | −54.646 | 35.652 | 1.000 | 13.52 |
| ATOM | 1029 | N | PRO | 139 | −22.459 | −53.287 | 35.096 | 1.000 | 12.22 |
| ATOM | 1030 | CD | PRO | 139 | −23.803 | −52.952 | 34.599 | 1.000 | 11.54 |
| ATOM | 1031 | CA | PRO | 139 | −21.657 | −52.087 | 35.389 | 1.000 | 6.14 |

| | | | | | | | | |
|---|---|---|---|---|---|---|---|---|
| ATOM | 1032 | CB | PRO | 139 | −22.422 | −51.015 | 34.608 | 1.000 | 7.78 |
| ATOM | 1033 | CG | PRO | 139 | −23.848 | −51.455 | 34.731 | 1.000 | 3.74 |
| ATOM | 1034 | C | PRO | 139 | −21.620 | −51.775 | 36.875 | 1.000 | 3.92 |
| ATOM | 1035 | O | PRO | 139 | −22.460 | −52.217 | 37.664 | 1.000 | 10.47 |
| ATOM | 1036 | N | PRO | 140 | −20.636 | −51.014 | 37.347 | 1.000 | 8.52 |
| ATOM | 1037 | CD | PRO | 140 | −19.524 | −50.412 | 36.611 | 1.000 | 3.33 |
| ATOM | 1038 | CA | PRO | 140 | −20.591 | −50.724 | 38.788 | 1.000 | 13.50 |
| ATOM | 1039 | CB | PRO | 140 | −19.251 | −50.012 | 38.971 | 1.000 | 12.27 |
| ATOM | 1040 | CG | PRO | 140 | −18.843 | −49.543 | 37.623 | 1.000 | 6.73 |
| ATOM | 1041 | C | PRO | 140 | −21.748 | −49.832 | 39.228 | 1.000 | 15.77 |
| ATOM | 1042 | O | PRO | 140 | −22.321 | −49.073 | 38.445 | 1.000 | 21.96 |
| ATOM | 1043 | N | PRO | 141 | −22.103 | −49.939 | 40.505 | 1.000 | 4.93 |
| ATOM | 1044 | CD | PRO | 141 | −21.487 | −50.799 | 41.528 | 1.000 | 0.26 |
| ATOM | 1045 | CA | PRO | 141 | −23.230 | −49.172 | 41.036 | 1.000 | 3.17 |
| ATOM | 1046 | CB | PRO | 141 | −23.254 | −49.560 | 42.521 | 1.000 | 4.18 |
| ATOM | 1047 | CG | PRO | 141 | −22.591 | −50.897 | 42.556 | 1.000 | 0.00 |
| ATOM | 1048 | C | PRO | 141 | −23.014 | −47.671 | 40.890 | 1.000 | 10.32 |
| ATOM | 1049 | O | PRO | 141 | −21.876 | −47.203 | 40.900 | 1.000 | 17.58 |
| ATOM | 1050 | N | LEU | 142 | −24.120 | −46.942 | 40.760 | 1.000 | 9.20 |
| ATOM | 1051 | CA | LEU | 142 | −24.079 | −45.490 | 40.729 | 1.000 | 7.44 |
| ATOM | 1052 | CB | LEU | 142 | −25.421 | −44.900 | 40.288 | 1.000 | 7.55 |
| ATOM | 1053 | CG | LEU | 142 | −25.775 | −45.119 | 38.812 | 1.000 | 13.23 |
| ATOM | 1054 | CD1 | LEU | 142 | −27.262 | −44.901 | 38.566 | 1.000 | 0.00 |
| ATOM | 1055 | CD2 | LEU | 142 | −24.932 | −44.218 | 37.921 | 1.000 | 1.85 |
| ATOM | 1056 | C | LEU | 142 | −23.711 | −44.945 | 42.109 | 1.000 | 13.38 |
| ATOM | 1057 | O | LEU | 142 | −23.764 | −45.680 | 43.099 | 1.000 | 20.55 |
| ATOM | 1058 | N | ALA | 143 | −23.363 | −43.670 | 42.126 | 1.000 | 15.81 |
| ATOM | 1059 | CA | ALA | 143 | −22.960 | −42.941 | 43.322 | 1.000 | 13.69 |
| ATOM | 1060 | CB | ALA | 143 | −21.461 | −42.676 | 43.239 | 1.000 | 3.16 |
| ATOM | 1061 | C | ALA | 143 | −23.762 | −41.656 | 43.475 | 1.000 | 16.69 |
| ATOM | 1062 | O | ALA | 143 | −24.500 | −41.280 | 42.552 | 1.000 | 10.61 |
| ATOM | 1063 | N | PRO | 144 | −23.668 | −40.968 | 44.609 | 1.000 | 19.19 |
| ATOM | 1064 | CD | PRO | 144 | −22.997 | −41.377 | 45.852 | 1.000 | 16.93 |
| ATOM | 1065 | CA | PRO | 144 | −24.315 | −39.659 | 44.745 | 1.000 | 19.29 |
| ATOM | 1066 | CB | PRO | 144 | −23.730 | −39.076 | 46.031 | 1.000 | 17.13 |
| ATOM | 1067 | CG | PRO | 144 | −22.904 | −40.130 | 46.664 | 1.000 | 12.97 |
| ATOM | 1068 | C | PRO | 144 | −24.009 | −38.723 | 43.578 | 1.000 | 17.14 |
| ATOM | 1069 | O | PRO | 144 | −22.902 | −38.626 | 43.048 | 1.000 | 12.89 |
| ATOM | 1070 | N | MET | 145 | −25.049 | −38.002 | 43.161 | 1.000 | 18.09 |
| ATOM | 1071 | CA | MET | 145 | −24.925 | −37.064 | 42.052 | 1.000 | 14.70 |
| ATOM | 1072 | CB | MET | 145 | −25.912 | −37.398 | 40.942 | 1.000 | 21.06 |
| ATOM | 1073 | CG | MET | 145 | −25.711 | −38.740 | 40.263 | 1.000 | 24.88 |
| ATOM | 1074 | XD | MET | 145 | −27.259 | −39.577 | 39.860 | 1.000 | 18.47 |
| ATOM | 1075 | CE | MET | 145 | −27.956 | −39.804 | 41.495 | 1.000 | 34.91 |
| ATOM | 1076 | C | MET | 145 | −25.155 | −35.645 | 42.559 | 1.000 | 11.49 |
| ATOM | 1077 | O | MET | 145 | −26.205 | −35.342 | 43.116 | 1.000 | 18.46 |
| ATOM | 1078 | N | PRO | 146 | −24.182 | −34.763 | 42.367 | 1.000 | 6.41 |
| ATOM | 1079 | CD | PRO | 146 | −22.909 | −34.993 | 41.683 | 1.000 | 8.62 |
| ATOM | 1080 | CA | PRO | 146 | −24.325 | −33.388 | 42.851 | 1.000 | 10.88 |
| ATOM | 1081 | CB | PRO | 146 | −22.916 | −32.814 | 42.759 | 1.000 | 10.59 |
| ATOM | 1082 | CG | PRO | 146 | −22.064 | −33.819 | 42.072 | 1.000 | 12.17 |
| ATOM | 1083 | C | PRO | 146 | −25.292 | −32.588 | 41.972 | 1.000 | 13.13 |
| ATOM | 1084 | O | PRO | 146 | −25.999 | −31.712 | 42.484 | 1.000 | 17.39 |
| ATOM | 1085 | N | HIS | 147 | −25.311 | −32.901 | 40.677 | 1.000 | 10.50 |
| ATOM | 1086 | CA | HIS | 147 | −26.203 | −32.215 | 39.758 | 1.000 | 9.69 |
| ATOM | 1087 | CB | HIS | 147 | −25.865 | −32.480 | 38.279 | 1.000 | 14.24 |
| ATOM | 1088 | CG | HIS | 147 | −26.441 | −31.373 | 37.431 | 1.000 | 6.69 |
| ATOM | 1089 | CD2 | HIS | 147 | −25.875 | −30.297 | 36.850 | 1.000 | 5.99 |
| ATOM | 1090 | ND1 | HIS | 147 | −27.780 | −31.296 | 37.134 | 1.000 | 11.40 |
| ATOM | 1091 | CE1 | HIS | 147 | −28.018 | −30.226 | 36.391 | 1.000 | 11.68 |
| ATOM | 1092 | NE2 | HIS | 147 | −26.871 | −29.600 | 36.201 | 1.000 | 12.68 |
| ATOM | 1093 | C | HIS | 147 | −27.658 | −32.596 | 40.013 | 1.000 | 5.47 |
| ATOM | 1094 | O | HIS | 147 | −28.052 | −33.761 | 39.960 | 1.000 | 11.15 |
| ATOM | 1095 | N | PRO | 148 | −28.463 | −31.575 | 40.291 | 1.000 | 12.88 |
| ATOM | 1096 | CD | PRO | 148 | −28.098 | −30.148 | 40.322 | 1.000 | 12.98 |
| ATOM | 1097 | CA | PRO | 148 | −29.877 | −31.806 | 40.602 | 1.000 | 13.30 |
| ATOM | 1098 | CB | PRO | 148 | −30.440 | −30.401 | 40.811 | 1.000 | 14.82 |
| ATOM | 1099 | CG | PRO | 148 | −29.426 | −29.455 | 40.267 | 1.000 | 16.64 |
| ATOM | 1100 | C | PRO | 148 | −30.600 | −32.508 | 39.456 | 1.000 | 15.39 |
| ATOM | 1101 | O | PRO | 148 | −31.525 | −33.290 | 39.689 | 1.000 | 15.71 |
| ATOM | 1102 | N | TRP | 149 | −30.218 | −32.263 | 38.201 | 1.000 | 21.29 |
| ATOM | 1103 | CA | TRP | 149 | −30.909 | −32.947 | 37.109 | 1.000 | 15.64 |
| ATOM | 1104 | CB | TRP | 149 | −30.571 | −32.328 | 35.750 | 1.000 | 17.31 |
| ATOM | 1105 | CG | TRP | 149 | −31.296 | −33.043 | 34.639 | 1.000 | 10.06 |
| ATOM | 1106 | CD2 | TRP | 149 | −32.715 | −33.086 | 34.444 | 1.000 | 4.30 |
| ATOM | 1107 | CE2 | TRP | 149 | −32.952 | −33.862 | 33.295 | 1.000 | 8.55 |
| ATOM | 1108 | CE3 | TRP | 149 | −33.805 | −32.541 | 35.129 | 1.000 | 4.24 |
| ATOM | 1109 | CD1 | TRP | 149 | −30.748 | −33.774 | 33.629 | 1.000 | 11.09 |
| ATOM | 1110 | NE1 | TRP | 149 | −31.736 | −34.272 | 32.813 | 1.000 | 5.61 |

-continued

| | | | | | | | | |
|---|---|---|---|---|---|---|---|---|
| ATOM | 1111 | CZ2 | TRP | 149 | −34.240 | −34.107 | 32.815 | 1.000 | 12.36 |
| ATOM | 1112 | CZ3 | TRP | 149 | −35.076 | −32.785 | 34.654 | 1.000 | 13.41 |
| ATOM | 1113 | CH2 | TRP | 149 | −35.286 | −33.563 | 33.505 | 1.000 | 14.13 |
| ATOM | 1114 | C | TRP | 149 | −30.566 | −34.432 | 37.101 | 1.000 | 12.85 |
| ATOM | 1115 | O | TRP | 149 | −31.447 | −35.290 | 37.033 | 1.000 | 7.92 |
| ATOM | 1116 | N | PHE | 150 | −29.270 | −34.728 | 37.186 | 1.000 | 11.11 |
| ATOM | 1117 | CA | PHE | 150 | −28.841 | −36.125 | 37.305 | 1.000 | 11.76 |
| ATOM | 1118 | CB | PHE | 150 | −27.321 | −36.192 | 37.483 | 1.000 | 8.65 |
| ATOM | 1119 | CG | PHE | 150 | −26.581 | −36.170 | 36.150 | 1.000 | 13.44 |
| ATOM | 1120 | CD1 | PHE | 150 | −25.315 | −35.623 | 36.047 | 1.000 | 14.41 |
| ATOM | 1121 | CD2 | PHE | 150 | −27.167 | −36.697 | 35.014 | 1.000 | 12.01 |
| ATOM | 1122 | CE1 | PHE | 150 | −24.650 | −35.604 | 34.838 | 1.000 | 14.96 |
| ATOM | 1123 | CE2 | PHE | 150 | −26.511 | −36.684 | 33.797 | 1.000 | 13.41 |
| ATOM | 1124 | CZ | PHE | 150 | −25.246 | −36.136 | 33.711 | 1.000 | 18.95 |
| ATOM | 1125 | C | PHE | 150 | −29.555 | −36.813 | 38.459 | 1.000 | 10.90 |
| ATOM | 1126 | O | PHE | 150 | −30.059 | −37.930 | 38.354 | 1.000 | 7.95 |
| ATOM | 1127 | N | GLN | 151 | −29.606 | −36.120 | 39.598 | 1.000 | 12.36 |
| ATOM | 1128 | CA | GLN | 151 | −30.294 | −36.665 | 40.759 | 1.000 | 19.45 |
| ATOM | 1129 | CB | GLN | 151 | −30.306 | −35.680 | 41.932 | 1.000 | 12.11 |
| ATOM | 1130 | CG | GLN | 151 | −28.947 | −35.446 | 42.561 | 1.000 | 16.34 |
| ATOM | 1131 | CD | GLN | 151 | −29.048 | −34.481 | 43.734 | 1.000 | 22.05 |
| ATOM | 1132 | OE1 | GLN | 151 | −29.693 | −34.803 | 44.729 | 1.000 | 39.76 |
| ATOM | 1133 | NE2 | GLN | 151 | −28.423 | −33.317 | 43.598 | 1.000 | 16.49 |
| ATOM | 1134 | C | GLN | 151 | −31.745 | −37.027 | 40.441 | 1.000 | 20.77 |
| ATOM | 1135 | O | GLN | 151 | −32.232 | −38.044 | 40.936 | 1.000 | 19.36 |
| ATOM | 1136 | N | LEU | 152 | −32.397 | −36.183 | 39.644 | 1.000 | 11.67 |
| ATOM | 1137 | CA | LEU | 152 | −33.818 | −36.360 | 39.365 | 1.000 | 13.95 |
| ATOM | 1138 | CB | LEU | 152 | −34.438 | −35.101 | 38.764 | 1.000 | 14.14 |
| ATOM | 1139 | CG | LEU | 152 | −34.837 | −33.957 | 39.688 | 1.000 | 12.09 |
| ATOM | 1140 | CD1 | LEU | 152 | −34.781 | −32.631 | 38.935 | 1.000 | 11.66 |
| ATOM | 1141 | CD2 | LEU | 152 | −36.225 | −34.162 | 40.274 | 1.000 | 12.14 |
| ATOM | 1142 | C | LEU | 152 | −34.053 | −37.544 | 38.428 | 1.000 | 13.07 |
| ATOM | 1143 | O | LEU | 152 | −34.913 | −38.372 | 38.729 | 1.000 | 13.96 |
| ATOM | 1144 | N | ILE | 153 | −33.310 | −37.613 | 37.326 | 1.000 | 13.21 |
| ATOM | 1145 | CA | ILE | 153 | −33.519 | −38.661 | 36.334 | 1.000 | 12.12 |
| ATOM | 1146 | CB | ILE | 153 | −32.814 | −38.377 | 34.991 | 1.000 | 9.74 |
| ATOM | 1147 | CG2 | ILE | 153 | −33.360 | −37.106 | 34.355 | 1.000 | 0.00 |
| ATOM | 1148 | CG1 | ILE | 153 | −31.284 | −38.333 | 35.061 | 1.000 | 8.16 |
| ATOM | 1149 | CD1 | ILE | 153 | −30.635 | −38.332 | 33.684 | 1.000 | 0.00 |
| ATOM | 1150 | C | ILE | 153 | −33.054 | −40.024 | 36.836 | 1.000 | 9.56 |
| ATOM | 1151 | O | ILE | 153 | −33.540 | −41.043 | 36.342 | 1.000 | 4.79 |
| ATOM | 1152 | N | PHE | 154 | −32.138 | −40.069 | 37.797 | 1.000 | 12.41 |
| ATOM | 1153 | CA | PHE | 154 | −31.645 | −41.349 | 38.301 | 1.000 | 8.75 |
| ATOM | 1154 | CB | PHE | 154 | −30.113 | −41.372 | 38.348 | 1.000 | 8.88 |
| ATOM | 1155 | CG | PHE | 154 | −29.456 | −41.758 | 37.031 | 1.000 | 8.38 |
| ATOM | 1156 | CD1 | PHE | 154 | −28.597 | −40.887 | 36.384 | 1.000 | 9.10 |
| ATOM | 1157 | CD2 | PHE | 154 | −29.703 | −42.990 | 36.458 | 1.000 | 0.00 |
| ATOM | 1158 | CE1 | PHE | 154 | −28.000 | −41.232 | 35.188 | 1.000 | 9.85 |
| ATOM | 1159 | CE2 | PHE | 154 | −29.119 | −43.344 | 35.260 | 1.000 | 5.02 |
| ATOM | 1160 | CZ | PHE | 154 | −28.258 | −42.468 | 34.624 | 1.000 | 8.39 |
| ATOM | 1161 | C | PHE | 154 | −32.199 | −41.648 | 39.690 | 1.000 | 11.55 |
| ATOM | 1162 | O | PHE | 154 | −31.683 | −42.515 | 40.400 | 1.000 | 10.77 |
| ATOM | 1163 | N | GLU | 155 | −33.246 | −40.936 | 40.093 | 1.000 | 15.11 |
| ATOM | 1164 | CA | GLU | 155 | −33.898 | −41.221 | 41.367 | 1.000 | 19.95 |
| ATOM | 1165 | CB | GLU | 155 | −35.134 | −40.343 | 41.542 | 1.000 | 26.08 |
| ATOM | 1166 | CG | GLU | 155 | −35.558 | −40.107 | 42.980 | 1.000 | 33.00 |
| ATOM | 1167 | CD | GLU | 155 | −36.339 | −41.267 | 43.568 | 1.000 | 44.51 |
| ATOM | 1168 | OE1 | GLU | 155 | −37.432 | −41.585 | 43.051 | 1.000 | 49.47 |
| ATOM | 1169 | OE2 | GLU | 155 | −35.862 | −41.867 | 44.558 | 1.000 | 61.39 |
| ATOM | 1170 | C | GLU | 155 | −34.270 | −42.702 | 41.449 | 1.000 | 18.82 |
| ATOM | 1171 | O | GLU | 155 | −34.978 | −43.212 | 40.582 | 1.000 | 14.49 |
| ATOM | 1172 | N | GLY | 156 | −33.779 | −43.376 | 42.481 | 1.000 | 12.58 |
| ATOM | 1173 | CA | GLY | 156 | −33.993 | −44.787 | 42.696 | 1.000 | 6.50 |
| ATOM | 1174 | C | GLY | 156 | −33.061 | −45.684 | 41.914 | 1.000 | 12.22 |
| ATOM | 1175 | O | GLY | 156 | −33.205 | −46.914 | 41.914 | 1.000 | 27.90 |
| ATOM | 1176 | N | GLY | 157 | −32.082 | −45.107 | 41.224 | 1.000 | 9.19 |
| ATOM | 1177 | CA | GLY | 157 | −31.216 | −45.877 | 40.358 | 1.000 | 8.21 |
| ATOM | 1178 | C | GLY | 157 | −30.007 | −46.514 | 40.991 | 1.000 | 8.61 |
| ATOM | 1179 | O | GLY | 157 | −29.563 | −47.579 | 40.549 | 1.000 | 17.22 |
| ATOM | 1180 | N | GLU | 158 | −29.442 | −45.887 | 42.018 | 1.000 | 7.58 |
| ATOM | 1181 | CA | GLU | 158 | −28.299 | −46.453 | 42.721 | 1.000 | 7.50 |
| ATOM | 1182 | CB | GLU | 158 | −27.807 | −45.505 | 43.814 | 1.000 | 9.84 |
| ATOM | 1183 | CG | GLU | 158 | −26.756 | −46.097 | 44.739 | 1.000 | 11.00 |
| ATOM | 1184 | CD | GLU | 158 | −26.031 | −45.053 | 45.564 | 1.000 | 24.40 |
| ATOM | 1185 | OE1 | GLU | 158 | −26.158 | −43.845 | 45.267 | 1.000 | 33.57 |
| ATOM | 1186 | OE2 | GLU | 158 | −25.325 | −45.439 | 46.523 | 1.000 | 39.11 |
| ATOM | 1187 | C | GLU | 158 | −28.696 | −47.807 | 43.302 | 1.000 | 13.34 |
| ATOM | 1188 | O | GLU | 158 | −27.956 | −48.787 | 43.225 | 1.000 | 29.78 |
| ATOM | 1189 | N | GLN | 159 | −29.895 | −47.840 | 43.875 | 1.000 | 10.17 |

-continued

| | | | | | | | | |
|---|---|---|---|---|---|---|---|---|
| ATOM | 1190 | CA | GLN | 159 | −30.481 | −49.058 | 44.406 | 1.000 | 15.50 |
| ATOM | 1191 | CB | GLN | 159 | −31.856 | −48.764 | 45.017 | 1.000 | 19.57 |
| ATOM | 1192 | CG | GLN | 159 | −32.548 | −49.952 | 45.647 | 1.000 | 24.93 |
| ATOM | 1193 | CD | GLN | 159 | −31.737 | −50.676 | 46.704 | 1.000 | 30.24 |
| ATOM | 1194 | OE1 | GLN | 159 | −31.940 | −50.499 | 47.909 | 1.000 | 40.80 |
| ATOM | 1195 | NE2 | GLN | 159 | −30.800 | −51.510 | 46.265 | 1.000 | 20.75 |
| ATOM | 1196 | C | GLN | 159 | −30.605 | −50.132 | 43.336 | 1.000 | 17.89 |
| ATOM | 1197 | O | GLN | 159 | −30.218 | −51.285 | 43.544 | 1.000 | 21.71 |
| ATOM | 1198 | N | LYS | 160 | −31.154 | −49.791 | 42.168 | 1.000 | 15.99 |
| ATOM | 1199 | CA | LYS | 160 | −31.361 | −50.855 | 41.176 | 1.000 | 6.75 |
| ATOM | 1200 | CB | LYS | 160 | −32.314 | −50.369 | 40.090 | 1.000 | 10.24 |
| ATOM | 1201 | CG | LYS | 160 | −33.666 | −49.907 | 40.607 | 1.000 | 6.13 |
| ATOM | 1202 | CD | LYS | 160 | −34.386 | −49.041 | 39.581 | 1.000 | 11.21 |
| ATOM | 1203 | CE | LYS | 160 | −35.897 | −49.190 | 39.702 | 1.000 | 9.55 |
| ATOM | 1204 | NZ | LYS | 160 | −36.616 | −48.235 | 38.811 | 1.000 | 20.37 |
| ATOM | 1205 | C | LYS | 160 | −30.029 | −51.305 | 40.591 | 1.000 | 14.32 |
| ATOM | 1206 | O | LYS | 160 | −29.842 | −52.475 | 40.257 | 1.000 | 14.42 |
| ATOM | 1207 | N | THR | 161 | −29.082 | −50.375 | 40.465 | 1.000 | 10.29 |
| ATOM | 1208 | CA | THR | 161 | −27.771 | −50.734 | 39.933 | 1.000 | 13.43 |
| ATOM | 1209 | CB | THR | 161 | −26.878 | −49.508 | 39.672 | 1.000 | 10.03 |
| ATOM | 1210 | OG1 | THR | 161 | −27.070 | −48.557 | 40.730 | 1.000 | 30.01 |
| ATOM | 1211 | CG2 | THR | 161 | −27.263 | −48.788 | 38.389 | 1.000 | 13.57 |
| ATOM | 1212 | C | THR | 161 | −27.057 | −51.683 | 40.896 | 1.000 | 12.06 |
| ATOM | 1213 | O | THR | 161 | −26.160 | −52.415 | 40.481 | 1.000 | 6.51 |
| ATOM | 1214 | N | THR | 162 | −27.457 | −51.664 | 42.165 | 1.000 | 8.39 |
| ATOM | 1215 | CA | THR | 162 | −26.894 | −52.551 | 43.177 | 1.000 | 9.75 |
| ATOM | 1216 | CB | THR | 162 | −27.286 | −52.130 | 44.604 | 1.000 | 12.96 |
| ATOM | 1217 | OG1 | THR | 162 | −26.705 | −50.863 | 44.941 | 1.000 | 11.98 |
| ATOM | 1218 | CG2 | THR | 162 | −26.735 | −53.132 | 45.605 | 1.000 | 20.35 |
| ATOM | 1219 | C | THR | 162 | −27.349 | −53.991 | 42.956 | 1.000 | 10.87 |
| ATOM | 1220 | O | THR | 162 | −26.764 | −54.942 | 43.471 | 1.000 | 12.87 |
| ATOM | 1221 | N | GLU | 163 | −28.410 | −54.170 | 42.174 | 1.000 | 16.58 |
| ATOM | 1222 | CA | GLU | 163 | −28.949 | −55.496 | 41.905 | 1.000 | 20.69 |
| ATOM | 1223 | CB | GLU | 163 | −30.486 | −55.450 | 41.861 | 1.000 | 21.36 |
| ATOM | 1224 | CG | GLU | 163 | −31.136 | −54.918 | 43.122 | 1.000 | 19.81 |
| ATOM | 1225 | CD | GLU | 163 | −30.918 | −55.799 | 44.332 | 1.000 | 20.57 |
| ATOM | 1226 | OE1 | GLU | 163 | −30.336 | −56.894 | 44.181 | 1.000 | 13.38 |
| ATOM | 1227 | OE2 | GLU | 163 | −31.340 | −55.394 | 45.441 | 1.000 | 37.36 |
| ATOM | 1228 | C | GLU | 163 | −28.455 | −56.101 | 40.596 | 1.000 | 12.31 |
| ATOM | 1229 | O | GLU | 163 | −28.614 | −57.306 | 40.384 | 1.000 | 8.17 |
| ATOM | 1230 | N | LEU | 164 | −27.880 | −55.296 | 39.710 | 1.000 | 14.12 |
| ATOM | 1231 | CA | LEU | 164 | −27.561 | −55.746 | 38.356 | 1.000 | 8.92 |
| ATOM | 1232 | CB | LEU | 164 | −26.960 | −54.602 | 37.541 | 1.000 | 5.54 |
| ATOM | 1233 | CG | LEU | 164 | −27.903 | −53.857 | 36.593 | 1.000 | 10.39 |
| ATOM | 1234 | CD1 | LEU | 164 | −29.295 | −53.740 | 37.197 | 1.000 | 23.43 |
| ATOM | 1235 | CD2 | LEU | 164 | −27.352 | −52.485 | 36.240 | 1.000 | 2.48 |
| ATOM | 1236 | C | LEU | 164 | −26.621 | −56.943 | 38.361 | 1.000 | 6.54 |
| ATOM | 1237 | O | LEU | 164 | −26.847 | −57.925 | 37.653 | 1.000 | 4.26 |
| ATOM | 1238 | N | ALA | 165 | −25.562 | −56.865 | 39.159 | 1.000 | 7.24 |
| ATOM | 1239 | CA | ALA | 165 | −24.609 | −57.965 | 39.239 | 1.000 | 11.41 |
| ATOM | 1240 | CB | ALA | 165 | −23.542 | −57.659 | 40.276 | 1.000 | 11.40 |
| ATOM | 1241 | C | ALA | 165 | −25.312 | −59.284 | 39.551 | 1.000 | 16.26 |
| ATOM | 1242 | O | ALA | 165 | −24.980 | −60.302 | 38.947 | 1.000 | 18.13 |
| ATOM | 1243 | N | ARG | 166 | −26.266 | −59.245 | 40.469 | 1.000 | 20.04 |
| ATOM | 1244 | CA | ARG | 166 | −27.014 | −60.397 | 40.947 | 1.000 | 10.10 |
| ATOM | 1245 | CB | ARG | 166 | −27.875 | −59.992 | 42.145 | 1.000 | 15.40 |
| ATOM | 1246 | CG | ARG | 166 | −28.600 | −61.127 | 42.843 | 1.000 | 15.67 |
| ATOM | 1247 | CD | ARG | 166 | −29.286 | −60.640 | 44.115 | 1.000 | 20.34 |
| ATOM | 1248 | NE | ARG | 166 | −30.097 | −59.453 | 43.851 | 1.000 | 31.99 |
| ATOM | 1249 | CZ | ARG | 166 | −31.261 | −59.505 | 43.202 | 1.000 | 37.46 |
| ATOM | 1250 | NH1 | ARG | 166 | −31.718 | −60.673 | 42.770 | 1.000 | 41.26 |
| ATOM | 1251 | NH2 | ARG | 166 | −31.974 | −58.410 | 42.979 | 1.000 | 44.85 |
| ATOM | 1252 | C | ARG | 166 | −27.899 | −60.991 | 39.862 | 1.000 | 10.33 |
| ATOM | 1253 | O | ARG | 166 | −27.862 | −62.186 | 39.569 | 1.000 | 11.28 |
| ATOM | 1254 | N | VAL | 167 | −28.724 | −60.143 | 39.253 | 1.000 | 10.14 |
| ATOM | 1255 | CA | VAL | 167 | −29.647 | −60.637 | 38.231 | 1.000 | 8.08 |
| ATOM | 1256 | CB | VAL | 167 | −30.800 | −59.642 | 38.007 | 1.000 | 12.63 |
| ATOM | 1257 | CG1 | VAL | 167 | −31.873 | −60.262 | 37.129 | 1.000 | 23.15 |
| ATOM | 1258 | CG2 | VAL | 167 | −31.423 | −59.212 | 39.331 | 1.000 | 16.49 |
| ATOM | 1259 | C | VAL | 167 | −28.941 | −60.943 | 36.916 | 1.000 | 8.93 |
| ATOM | 1260 | O | VAL | 167 | −29.342 | −61.889 | 36.230 | 1.000 | 11.00 |
| ATOM | 1261 | N | TYR | 168 | −27.906 | −60.209 | 36.507 | 1.000 | 6.53 |
| ATOM | 1262 | CA | TYR | 168 | −27.225 | −60.549 | 35.262 | 1.000 | 5.82 |
| ATOM | 1263 | CB | TYR | 168 | −26.220 | −59.494 | 34.815 | 1.000 | 12.35 |
| ATOM | 1264 | CG | TYR | 168 | −26.746 | −58.249 | 34.148 | 1.000 | 10.53 |
| ATOM | 1265 | CD1 | TYR | 168 | −25.898 | −57.415 | 33.429 | 1.000 | 4.25 |
| ATOM | 1266 | CE1 | TYR | 168 | −26.377 | −56.273 | 32.816 | 1.000 | 3.59 |
| ATOM | 1267 | CD2 | TYR | 168 | −28.085 | −57.889 | 34.230 | 1.000 | 9.22 |
| ATOM | 1268 | CE2 | TYR | 168 | −28.565 | −56.750 | 33.624 | 1.000 | 11.67 |

-continued

| | | | | | | | | |
|---|---|---|---|---|---|---|---|---|
| ATOM | 1269 | CZ | TYR | 168 | −27.708 | −55.940 | 32.912 | 1.000 | 8.76 |
| ATOM | 1270 | OH | TYR | 168 | −28.194 | −54.801 | 32.308 | 1.000 | 13.56 |
| ATOM | 1271 | C | TYR | 168 | −26.466 | −61.863 | 35.444 | 1.000 | 9.45 |
| ATOM | 1272 | O | TYR | 168 | −26.398 | −62.696 | 34.544 | 1.000 | 5.20 |
| ATOM | 1273 | N | SER | 169 | −25.896 | −61.972 | 36.648 | 1.000 | 5.94 |
| ATOM | 1274 | CA | SER | 169 | −25.145 | −63.174 | 36.999 | 1.000 | 11.65 |
| ATOM | 1275 | CB | SER | 169 | −24.663 | −63.109 | 38.445 | 1.000 | 12.52 |
| ATOM | 1276 | OG | SER | 169 | −23.611 | −64.024 | 38.688 | 1.000 | 13.86 |
| ATOM | 1277 | C | SER | 169 | −26.034 | −64.389 | 36.740 | 1.000 | 14.93 |
| ATOM | 1278 | O | SER | 169 | −25.709 | −65.240 | 35.912 | 1.000 | 25.35 |
| ATOM | 1279 | N | ALA | 170 | −27.161 | −64.434 | 37.448 | 1.000 | 9.54 |
| ATOM | 1280 | CA | ALA | 170 | −28.154 | −65.483 | 37.259 | 1.000 | 7.33 |
| ATOM | 1281 | CB | ALA | 170 | −29.397 | −65.155 | 38.069 | 1.000 | 3.12 |
| ATOM | 1282 | C | ALA | 170 | −28.495 | −65.659 | 35.785 | 1.000 | 12.27 |
| ATOM | 1283 | O | ALA | 170 | −28.526 | −66.772 | 35.262 | 1.000 | 20.56 |
| ATOM | 1284 | N | LEU | 171 | −28.753 | −64.558 | 35.081 | 1.000 | 15.11 |
| ATOM | 1285 | CA | LEU | 171 | −29.115 | −64.661 | 33.665 | 1.000 | 17.04 |
| ATOM | 1286 | CB | LEU | 171 | −29.329 | −63.272 | 33.076 | 1.000 | 13.64 |
| ATOM | 1287 | CG | LEU | 171 | −29.846 | −63.164 | 31.645 | 1.000 | 21.08 |
| ATOM | 1288 | CD1 | LEU | 171 | −28.692 | −63.043 | 30.658 | 1.000 | 45.18 |
| ATOM | 1289 | CD2 | LEU | 171 | −30.734 | −64.340 | 31.270 | 1.000 | 17.34 |
| ATOM | 1290 | C | LEU | 171 | −28.052 | −65.404 | 32.868 | 1.000 | 18.57 |
| ATOM | 1291 | O | LEU | 171 | −28.328 | −66.409 | 32.219 | 1.000 | 17.64 |
| ATOM | 1292 | N | ALA | 172 | −26.825 | −64.890 | 32.920 | 1.000 | 22.46 |
| ATOM | 1293 | CA | ALA | 172 | −25.735 | −65.489 | 32.157 | 1.000 | 17.47 |
| ATOM | 1294 | CB | ALA | 172 | −24.454 | −64.699 | 32.377 | 1.000 | 10.29 |
| ATOM | 1295 | C | ALA | 172 | −25.549 | −66.953 | 32.536 | 1.000 | 13.15 |
| ATOM | 1296 | O | ALA | 172 | −25.192 | −67.797 | 31.713 | 1.000 | 17.25 |
| ATOM | 1297 | N | SER | 173 | −25.802 | −67.242 | 33.809 | 1.000 | 11.55 |
| ATOM | 1298 | CA | SER | 173 | −25.653 | −68.595 | 34.337 | 1.000 | 15.80 |
| ATOM | 1299 | CB | SER | 173 | −25.837 | −68.578 | 35.856 | 1.000 | 15.14 |
| ATOM | 1300 | OG | SER | 173 | −26.298 | −69.837 | 36.293 | 1.000 | 15.66 |
| ATOM | 1301 | C | SER | 173 | −26.640 | −69.565 | 33.691 | 1.000 | 10.39 |
| ATOM | 1302 | O | SER | 173 | −26.263 | −70.667 | 33.284 | 1.000 | 5.06 |
| ATOM | 1303 | N | PHE | 174 | −27.882 | −69.119 | 33.601 | 1.000 | 6.57 |
| ATOM | 1304 | CA | PHE | 174 | −28.970 | −69.778 | 32.908 | 1.000 | 4.04 |
| ATOM | 1305 | CB | PHE | 174 | −30.288 | −69.024 | 33.114 | 1.000 | 4.43 |
| ATOM | 1306 | CG | PHE | 174 | −31.524 | −69.765 | 32.626 | 1.000 | 3.57 |
| ATOM | 1307 | CD1 | PHE | 174 | −32.219 | −70.606 | 33.475 | 1.000 | 0.40 |
| ATOM | 1308 | CD2 | PHE | 174 | −31.988 | −69.615 | 31.331 | 1.000 | 11.71 |
| ATOM | 1309 | CE1 | PHE | 174 | −33.343 | −71.281 | 33.051 | 1.000 | 1.63 |
| ATOM | 1310 | CE2 | PHE | 174 | −33.114 | −70.285 | 30.886 | 1.000 | 10.57 |
| ATOM | 1311 | CZ | PHE | 174 | −33.795 | −71.119 | 31.756 | 1.000 | 10.59 |
| ATOM | 1312 | C | PHE | 174 | −28.701 | −69.872 | 31.408 | 1.000 | 8.80 |
| ATOM | 1313 | O | PHE | 174 | −28.846 | −70.949 | 30.834 | 1.000 | 0.14 |
| ATOM | 1314 | N | MET | 175 | −28.328 | −68.751 | 30.793 | 1.000 | 7.91 |
| ATOM | 1315 | CA | MET | 175 | −28.058 | −68.739 | 29.356 | 1.000 | 5.97 |
| ATOM | 1316 | CB | MET | 175 | −28.103 | −67.321 | 28.780 | 1.000 | 0.00 |
| ATOM | 1317 | CG | MET | 175 | −29.492 | −66.712 | 28.751 | 1.000 | 7.42 |
| ATOM | 1318 | XD | MET | 175 | −29.573 | −65.056 | 28.023 | 1.000 | 16.37 |
| ATOM | 1319 | CE | MET | 175 | −30.064 | −65.488 | 26.348 | 1.000 | 21.02 |
| ATOM | 1320 | C | MET | 175 | −26.715 | −69.399 | 29.045 | 1.000 | 6.31 |
| ATOM | 1321 | O | MET | 175 | −26.332 | −69.479 | 27.880 | 1.000 | 8.17 |
| ATOM | 1322 | N | LYS | 176 | −26.020 | −69.872 | 30.070 | 1.000 | 8.77 |
| ATOM | 1323 | CA | LYS | 176 | −24.762 | −70.598 | 29.939 | 1.000 | 10.68 |
| ATOM | 1324 | CB | LYS | 176 | −24.970 | −71.945 | 29.239 | 1.000 | 10.45 |
| ATOM | 1325 | CG | LYS | 176 | −25.907 | −72.900 | 29.971 | 1.000 | 3.74 |
| ATOM | 1326 | CD | LYS | 176 | −25.133 | −73.755 | 30.964 | 1.000 | 5.05 |
| ATOM | 1327 | CE | LYS | 176 | −26.084 | −74.568 | 31.833 | 1.000 | 6.09 |
| ATOM | 1328 | NZ | LYS | 176 | −26.739 | −73.721 | 32.861 | 1.000 | 24.38 |
| ATOM | 1329 | C | LYS | 176 | −23.733 | −69.760 | 29.190 | 1.000 | 12.34 |
| ATOM | 1330 | O | LYS | 176 | −23.084 | −70.178 | 28.231 | 1.000 | 24.85 |
| ATOM | 1331 | N | VAL | 177 | −23.601 | −68.520 | 29.648 | 1.000 | 12.09 |
| ATOM | 1332 | CA | VAL | 177 | −22.709 | −67.581 | 28.953 | 1.000 | 12.10 |
| ATOM | 1333 | CB | VAL | 177 | −23.569 | −66.629 | 28.106 | 1.000 | 9.74 |
| ATOM | 1334 | CG1 | VAL | 177 | −23.831 | −65.319 | 28.835 | 1.000 | 18.59 |
| ATOM | 1335 | CG2 | VAL | 177 | −22.921 | −66.372 | 26.753 | 1.000 | 20.30 |
| ATOM | 1336 | C | VAL | 177 | −21.848 | −66.876 | 29.982 | 1.000 | 13.62 |
| ATOM | 1337 | O | VAL | 177 | −22.292 | −66.730 | 31.126 | 1.000 | 20.25 |
| ATOM | 1338 | N | PRO | 178 | −20.635 | −66.454 | 29.637 | 1.000 | 10.56 |
| ATOM | 1339 | CD | PRO | 178 | −20.019 | −66.530 | 28.312 | 1.000 | 2.11 |
| ATOM | 1340 | CA | PRO | 178 | −19.760 | −65.842 | 30.642 | 1.000 | 10.32 |
| ATOM | 1341 | CB | PRO | 178 | −18.433 | −65.656 | 29.913 | 1.000 | 6.70 |
| ATOM | 1342 | CG | PRO | 178 | −18.623 | −66.026 | 28.499 | 1.000 | 0.81 |
| ATOM | 1343 | C | PRO | 178 | −20.281 | −64.483 | 31.119 | 1.000 | 20.65 |
| ATOM | 1344 | O | PRO | 178 | −20.796 | −63.674 | 30.351 | 1.000 | 22.70 |
| ATOM | 1345 | N | PHE | 179 | −20.124 | −64.253 | 32.412 | 1.000 | 22.55 |
| ATOM | 1346 | CA | PHE | 179 | −20.474 | −63.025 | 33.107 | 1.000 | 19.13 |
| ATOM | 1347 | CB | PHE | 179 | −21.518 | −63.283 | 34.194 | 1.000 | 8.91 |

-continued

| | | | | | | | | |
|---|---|---|---|---|---|---|---|---|
| ATOM | 1348 | CG | PHE | 179 | −21.661 | −62.215 | 35.268 | 1.000 | 8.12 |
| ATOM | 1349 | CD1 | PHE | 179 | −22.433 | −61.087 | 35.044 | 1.000 | 10.36 |
| ATOM | 1350 | CD2 | PHE | 179 | −21.031 | −62.337 | 36.499 | 1.000 | 2.04 |
| ATOM | 1351 | CE1 | PHE | 179 | −22.590 | −60.103 | 36.004 | 1.000 | 2.43 |
| ATOM | 1352 | CE2 | PHE | 179 | −21.183 | −61.367 | 37.470 | 1.000 | 0.76 |
| ATOM | 1353 | CZ | PHE | 179 | −21.963 | −60.248 | 37.228 | 1.000 | 2.96 |
| ATOM | 1354 | C | PHE | 179 | −19.231 | −62.400 | 33.736 | 1.000 | 13.74 |
| ATOM | 1355 | O | PHE | 179 | −18.309 | −63.110 | 34.128 | 1.000 | 15.60 |
| ATOM | 1356 | N | PHE | 180 | −19.214 | −61.080 | 33.838 | 1.000 | 14.28 |
| ATOM | 1357 | CA | PHE | 180 | −18.178 | −60.371 | 34.573 | 1.000 | 13.03 |
| ATOM | 1358 | CB | PHE | 180 | −17.004 | −59.952 | 33.686 | 1.000 | 17.94 |
| ATOM | 1359 | CG | PHE | 180 | −15.933 | −59.164 | 34.433 | 1.000 | 21.76 |
| ATOM | 1360 | CD1 | PHE | 180 | −14.960 | −59.807 | 35.176 | 1.000 | 21.38 |
| ATOM | 1361 | CD2 | PHE | 180 | −15.904 | −57.780 | 34.391 | 1.000 | 19.62 |
| ATOM | 1362 | CE1 | PHE | 180 | −13.979 | −59.108 | 35.859 | 1.000 | 15.07 |
| ATOM | 1363 | CE2 | PHE | 180 | −14.941 | −57.064 | 35.075 | 1.000 | 21.73 |
| ATOM | 1364 | CZ | PHE | 180 | −13.979 | −57.727 | 35.816 | 1.000 | 21.65 |
| ATOM | 1365 | C | PHE | 180 | −18.822 | −59.164 | 35.256 | 1.000 | 12.16 |
| ATOM | 1366 | O | PHE | 180 | −19.594 | −58.423 | 34.648 | 1.000 | 11.01 |
| ATOM | 1367 | N | ASP | 181 | −18.504 | −58.988 | 36.536 | 1.000 | 7.72 |
| ATOM | 1368 | CA | ASP | 181 | −19.062 | −57.864 | 37.286 | 1.000 | 10.61 |
| ATOM | 1369 | CB | ASP | 181 | −19.521 | −58.346 | 38.659 | 1.000 | 5.77 |
| ATOM | 1370 | CG | ASP | 181 | −19.986 | −57.225 | 39.559 | 1.000 | 4.11 |
| ATOM | 1371 | OD1 | ASP | 181 | −20.116 | −56.076 | 39.092 | 1.000 | 8.61 |
| ATOM | 1372 | OD2 | ASP | 181 | −20.217 | −57.508 | 40.750 | 1.000 | 11.49 |
| ATOM | 1373 | C | ASP | 181 | −18.037 | −56.743 | 37.378 | 1.000 | 15.44 |
| ATOM | 1374 | O | ASP | 181 | −17.023 | −56.872 | 38.060 | 1.000 | 16.84 |
| ATOM | 1375 | N | ALA | 182 | −18.293 | −55.639 | 36.672 | 1.000 | 18.65 |
| ATOM | 1376 | CA | ALA | 182 | −17.359 | −54.517 | 36.678 | 1.000 | 18.00 |
| ATOM | 1377 | CB | ALA | 182 | −17.778 | −53.459 | 35.668 | 1.000 | 7.66 |
| ATOM | 1378 | C | ALA | 182 | −17.240 | −53.911 | 38.075 | 1.000 | 18.92 |
| ATOM | 1379 | O | ALA | 182 | −16.198 | −53.340 | 38.400 | 1.000 | 8.61 |
| ATOM | 1380 | N | GLY | 183 | −18.296 | −54.044 | 38.872 | 1.000 | 15.67 |
| ATOM | 1381 | CA | GLY | 183 | −18.374 | −53.516 | 40.219 | 1.000 | 13.53 |
| ATOM | 1382 | C | GLY | 183 | −17.444 | −54.230 | 41.176 | 1.000 | 14.96 |
| ATOM | 1383 | O | GLY | 183 | −17.268 | −53.846 | 42.330 | 1.000 | 25.31 |
| ATOM | 1384 | N | SER | 184 | −16.830 | −55.306 | 40.696 | 1.000 | 16.38 |
| ATOM | 1385 | CA | SER | 184 | −15.940 | −56.105 | 41.525 | 1.000 | 12.32 |
| ATOM | 1386 | CB | SER | 184 | −16.009 | −57.574 | 41.116 | 1.000 | 14.55 |
| ATOM | 1387 | OG | SER | 184 | −15.237 | −57.867 | 39.967 | 1.000 | 12.36 |
| ATOM | 1388 | C | SER | 184 | −14.516 | −55.572 | 41.439 | 1.000 | 13.33 |
| ATOM | 1389 | O | SER | 184 | −13.644 | −55.986 | 42.204 | 1.000 | 12.05 |
| ATOM | 1390 | N | VAL | 185 | −14.276 | −54.640 | 40.515 | 1.000 | 9.89 |
| ATOM | 1391 | CA | VAL | 185 | −12.902 | −54.156 | 40.358 | 1.000 | 14.54 |
| ATOM | 1392 | CB | VAL | 185 | −12.320 | −54.649 | 39.021 | 1.000 | 16.34 |
| ATOM | 1393 | CG1 | VAL | 185 | −12.034 | −56.141 | 39.100 | 1.000 | 13.09 |
| ATOM | 1394 | CG2 | VAL | 185 | −13.274 | −54.346 | 37.877 | 1.000 | 20.34 |
| ATOM | 1395 | C | VAL | 185 | −12.802 | −52.642 | 40.445 | 1.000 | 20.13 |
| ATOM | 1396 | O | VAL | 185 | −11.718 | −52.101 | 40.682 | 1.000 | 11.67 |
| ATOM | 1397 | N | ILE | 186 | −13.912 | −51.929 | 40.260 | 1.000 | 19.83 |
| ATOM | 1398 | CA | ILE | 186 | −13.905 | −50.479 | 40.381 | 1.000 | 13.97 |
| ATOM | 1399 | CB | ILE | 186 | −13.716 | −49.752 | 39.031 | 1.000 | 8.30 |
| ATOM | 1400 | CG2 | ILE | 186 | −12.362 | −50.070 | 38.428 | 1.000 | 12.39 |
| ATOM | 1401 | CG1 | ILE | 186 | −14.830 | −50.005 | 38.014 | 1.000 | 10.45 |
| ATOM | 1402 | CD1 | ILE | 186 | −14.956 | −48.929 | 36.957 | 1.000 | 3.60 |
| ATOM | 1403 | C | ILE | 186 | −15.209 | −49.957 | 40.979 | 1.000 | 13.38 |
| ATOM | 1404 | O | ILE | 186 | −16.256 | −50.583 | 40.857 | 1.000 | 12.90 |
| ATOM | 1405 | N | SER | 187 | −15.120 | −48.788 | 41.596 | 1.000 | 11.99 |
| ATOM | 1406 | CA | SER | 187 | −16.287 | −48.046 | 42.052 | 1.000 | 9.16 |
| ATOM | 1407 | CB | SER | 187 | −16.110 | −47.594 | 43.498 | 1.000 | 10.88 |
| ATOM | 1408 | OG | SER | 187 | −14.889 | −46.879 | 43.658 | 1.000 | 16.58 |
| ATOM | 1409 | C | SER | 187 | −16.517 | −46.839 | 41.145 | 1.000 | 11.87 |
| ATOM | 1410 | O | SER | 187 | −15.567 | −46.304 | 40.563 | 1.000 | 16.73 |
| ATOM | 1411 | N | THR | 188 | −17.767 | −46.410 | 41.015 | 1.000 | 15.17 |
| ATOM | 1412 | CA | THR | 188 | −18.077 | −45.244 | 40.189 | 1.000 | 13.51 |
| ATOM | 1413 | CB | THR | 188 | −19.571 | −45.151 | 39.848 | 1.000 | 12.88 |
| ATOM | 1414 | OG1 | THR | 188 | −19.969 | −46.308 | 39.101 | 1.000 | 16.33 |
| ATOM | 1415 | CG2 | THR | 188 | −19.843 | −43.943 | 38.961 | 1.000 | 8.08 |
| ATOM | 1416 | C | THR | 188 | −17.639 | −43.978 | 40.916 | 1.000 | 14.09 |
| ATOM | 1417 | O | THR | 188 | −18.293 | −43.535 | 41.860 | 1.000 | 10.72 |
| ATOM | 1418 | N | ASP | 189 | −16.518 | −43.414 | 40.474 | 1.000 | 15.51 |
| ATOM | 1419 | CA | ASP | 189 | −15.911 | −42.313 | 41.210 | 1.000 | 11.58 |
| ATOM | 1420 | CB | ASP | 189 | −14.407 | −42.594 | 41.362 | 1.000 | 12.86 |
| ATOM | 1421 | CG | ASP | 189 | −14.158 | −43.791 | 42.261 | 1.000 | 4.55 |
| ATOM | 1422 | OD1 | ASP | 189 | −14.915 | −43.960 | 43.239 | 1.000 | 13.27 |
| ATOM | 1423 | OD2 | ASP | 189 | −13.208 | −44.549 | 41.989 | 1.000 | 6.91 |
| ATOM | 1424 | C | ASP | 189 | −16.120 | −40.949 | 40.567 | 1.000 | 15.34 |
| ATOM | 1425 | O | ASP | 189 | −15.910 | −39.948 | 41.263 | 1.000 | 18.48 |
| ATOM | 1426 | N | GLY | 190 | −16.510 | −40.918 | 39.303 | 1.000 | 19.39 |

-continued

| | | | | | | | | |
|---|---|---|---|---|---|---|---|---|
| ATOM | 1427 | CA | GLY | 190 | −16.710 | −39.718 | 38.515 | 1.000 | 15.08 |
| ATOM | 1428 | C | GLY | 190 | −17.385 | −38.613 | 39.303 | 1.000 | 18.57 |
| ATOM | 1429 | O | GLY | 190 | −18.263 | −38.908 | 40.119 | 1.000 | 20.64 |
| ATOM | 1430 | N | VAL | 191 | −16.952 | −37.381 | 39.057 | 1.000 | 13.86 |
| ATOM | 1431 | CA | VAL | 191 | −17.428 | −36.226 | 39.806 | 1.000 | 10.59 |
| ATOM | 1432 | CB | VAL | 191 | −16.825 | −34.905 | 39.286 | 1.000 | 17.05 |
| ATOM | 1433 | CG1 | VAL | 191 | −15.324 | −34.875 | 39.559 | 1.000 | 30.84 |
| ATOM | 1434 | CG2 | VAL | 191 | −17.092 | −34.701 | 37.803 | 1.000 | 8.10 |
| ATOM | 1435 | C | VAL | 191 | −18.950 | −36.129 | 39.774 | 1.000 | 10.47 |
| ATOM | 1436 | O | VAL | 191 | −19.542 | −35.686 | 40.761 | 1.000 | 13.60 |
| ATOM | 1437 | N | ASP | 192 | −19.571 | −36.534 | 38.668 | 1.000 | 1.46 |
| ATOM | 1438 | CA | ASP | 192 | −21.018 | −36.447 | 38.540 | 1.000 | 0.70 |
| ATOM | 1439 | CB | ASP | 192 | −21.387 | −36.356 | 37.056 | 1.000 | 2.10 |
| ATOM | 1440 | CG | ASP | 192 | −20.918 | −37.566 | 36.268 | 1.000 | 9.82 |
| ATOM | 1441 | OD1 | ASP | 192 | −20.296 | −38.478 | 36.857 | 1.000 | 8.20 |
| ATOM | 1442 | OD2 | ASP | 192 | −21.182 | −37.597 | 35.047 | 1.000 | 6.78 |
| ATOM | 1443 | C | ASP | 192 | −21.754 | −37.622 | 39.173 | 1.000 | 7.73 |
| ATOM | 1444 | O | ASP | 192 | −22.988 | −37.674 | 39.136 | 1.000 | 7.10 |
| ATOM | 1445 | N | GLY | 193 | −21.027 | −38.572 | 39.753 | 1.000 | 15.10 |
| ATOM | 1446 | CA | GLY | 193 | −21.631 | −39.747 | 40.351 | 1.000 | 17.83 |
| ATOM | 1447 | C | GLY | 193 | −22.153 | −40.758 | 39.352 | 1.000 | 18.93 |
| ATOM | 1448 | O | GLY | 193 | −22.820 | −41.732 | 39.718 | 1.000 | 10.12 |
| ATOM | 1449 | N | ILE | 194 | −21.867 | −40.565 | 38.062 | 1.000 | 11.77 |
| ATOM | 1450 | CA | ILE | 194 | −22.330 | −41.546 | 37.081 | 1.000 | 7.87 |
| ATOM | 1451 | CB | ILE | 194 | −23.401 | −40.945 | 36.154 | 1.000 | 9.95 |
| ATOM | 1452 | CG2 | ILE | 194 | −23.790 | −41.927 | 35.063 | 1.000 | 0.00 |
| ATOM | 1453 | CG1 | ILE | 194 | −24.643 | −40.441 | 36.896 | 1.000 | 9.90 |
| ATOM | 1454 | CD1 | ILE | 194 | −25.248 | −39.237 | 36.206 | 1.000 | 8.85 |
| ATOM | 1455 | C | ILE | 194 | −21.191 | −42.068 | 36.225 | 1.000 | 2.97 |
| ATOM | 1456 | O | ILE | 194 | −21.086 | −43.251 | 35.924 | 1.000 | 6.72 |
| ATOM | 1457 | N | HIS | 195 | −20.277 | −41.195 | 35.792 | 1.000 | 6.33 |
| ATOM | 1458 | CA | HIS | 195 | −19.256 | −41.719 | 34.884 | 1.000 | 10.76 |
| ATOM | 1459 | CB | HIS | 195 | −19.089 | −40.790 | 33.673 | 1.000 | 11.36 |
| ATOM | 1460 | CG | HIS | 195 | −20.402 | −40.647 | 32.958 | 1.000 | 11.50 |
| ATOM | 1461 | CD2 | HIS | 195 | −20.981 | −41.395 | 31.989 | 1.000 | 5.43 |
| ATOM | 1462 | ND1 | HIS | 195 | −21.283 | −39.633 | 33.253 | 1.000 | 7.30 |
| ATOM | 1463 | CE1 | HIS | 195 | −22.351 | −39.753 | 32.485 | 1.000 | 9.11 |
| ATOM | 1464 | NE2 | HIS | 195 | −22.192 | −40.814 | 31.711 | 1.000 | 8.18 |
| ATOM | 1465 | C | HIS | 195 | −17.918 | −41.941 | 35.577 | 1.000 | 8.63 |
| ATOM | 1466 | O | HIS | 195 | −17.762 | −41.602 | 36.743 | 1.000 | 13.71 |
| ATOM | 1467 | N | PHE | 196 | −17.010 | −42.529 | 34.812 | 1.000 | 6.37 |
| ATOM | 1468 | CA | PHE | 196 | −15.725 | −43.017 | 35.249 | 1.000 | 9.06 |
| ATOM | 1469 | CB | PHE | 196 | −15.233 | −44.136 | 34.320 | 1.000 | 5.38 |
| ATOM | 1470 | CG | PHE | 196 | −16.048 | −45.412 | 34.451 | 1.000 | 10.20 |
| ATOM | 1471 | CD1 | PHE | 196 | −15.822 | −46.481 | 33.602 | 1.000 | 8.01 |
| ATOM | 1472 | CD2 | PHE | 196 | −17.027 | −45.509 | 35.427 | 1.000 | 6.21 |
| ATOM | 1473 | CE1 | PHE | 196 | −16.571 | −47.637 | 33.722 | 1.000 | 11.17 |
| ATOM | 1474 | CE2 | PHE | 196 | −17.779 | −46.662 | 35.546 | 1.000 | 14.06 |
| ATOM | 1475 | CZ | PHE | 196 | −17.549 | −47.727 | 34.694 | 1.000 | 13.03 |
| ATOM | 1476 | C | PHE | 196 | −14.663 | −41.925 | 35.273 | 1.000 | 12.92 |
| ATOM | 1477 | O | PHE | 196 | −14.757 | −40.983 | 34.494 | 1.000 | 15.16 |
| ATOM | 1478 | N | THR | 197 | −13.694 | −42.112 | 36.158 | 1.000 | 13.17 |
| ATOM | 1479 | CA | THR | 197 | −12.477 | −41.318 | 36.183 | 1.000 | 17.95 |
| ATOM | 1480 | CB | THR | 197 | −11.886 | −41.168 | 37.593 | 1.000 | 20.94 |
| ATOM | 1481 | OG1 | THR | 197 | −11.650 | −42.458 | 38.173 | 1.000 | 20.14 |
| ATOM | 1482 | CG2 | THR | 197 | −12.882 | −40.454 | 38.499 | 1.000 | 31.55 |
| ATOM | 1483 | C | THR | 197 | −11.443 | −41.978 | 35.269 | 1.000 | 10.26 |
| ATOM | 1484 | O | THR | 197 | −11.713 | −43.037 | 34.705 | 1.000 | 14.53 |
| ATOM | 1485 | N | GLU | 198 | −10.283 | −41.362 | 35.133 | 1.000 | 9.05 |
| ATOM | 1486 | CA | GLU | 198 | −9.192 | −41.943 | 34.362 | 1.000 | 12.89 |
| ATOM | 1487 | CB | GLU | 198 | −8.023 | −40.960 | 34.314 | 1.000 | 20.40 |
| ATOM | 1488 | CG | GLU | 198 | −6.903 | −41.349 | 33.362 | 1.000 | 32.30 |
| ATOM | 1489 | CD | GLU | 198 | −5.764 | −40.346 | 33.328 | 1.000 | 35.77 |
| ATOM | 1490 | OE1 | GLU | 198 | −5.127 | −40.141 | 34.385 | 1.000 | 42.59 |
| ATOM | 1491 | OE2 | GLU | 198 | −5.498 | −39.761 | 32.256 | 1.000 | 25.40 |
| ATOM | 1492 | C | GLU | 198 | −8.779 | −43.279 | 34.970 | 1.000 | 16.23 |
| ATOM | 1493 | O | GLU | 198 | −8.636 | −44.296 | 34.292 | 1.000 | 14.85 |
| ATOM | 1494 | N | ALA | 199 | −8.596 | −43.284 | 36.291 | 1.000 | 11.36 |
| ATOM | 1495 | CA | ALA | 199 | −8.233 | −44.489 | 37.022 | 1.000 | 5.99 |
| ATOM | 1496 | CB | ALA | 199 | −8.047 | −44.154 | 38.499 | 1.000 | 2.34 |
| ATOM | 1497 | C | ALA | 199 | −9.273 | −45.594 | 36.873 | 1.000 | 7.89 |
| ATOM | 1498 | O | ALA | 199 | −8.922 | −46.767 | 36.748 | 1.000 | 16.70 |
| ATOM | 1499 | N | ASN | 200 | −10.548 | −45.210 | 36.897 | 1.000 | 13.48 |
| ATOM | 1500 | CA | ASN | 200 | −11.644 | −46.155 | 36.715 | 1.000 | 11.59 |
| ATOM | 1501 | CB | ASN | 200 | −13.007 | −45.474 | 36.805 | 1.000 | 4.12 |
| ATOM | 1502 | CG | ASN | 200 | −13.492 | −45.192 | 38.209 | 1.000 | 11.67 |
| ATOM | 1503 | OD1 | ASN | 200 | −13.045 | −45.767 | 39.200 | 1.000 | 6.19 |
| ATOM | 1504 | ND2 | ASN | 200 | −14.455 | −44.276 | 38.330 | 1.000 | 13.74 |
| ATOM | 1505 | C | ASN | 200 | −11.505 | −46.869 | 35.366 | 1.000 | 8.88 |

-continued

| | | | | | | | | |
|---|---|---|---|---|---|---|---|---|
| ATOM | 1506 | O | ASN | 200 | −11.667 | −48.084 | 35.305 | 1.000 | 9.08 |
| ATOM | 1507 | N | ASN | 201 | −11.208 | −46.111 | 34.315 | 1.000 | 14.48 |
| ATOM | 1508 | CA | ASN | 201 | −11.074 | −46.639 | 32.963 | 1.000 | 14.27 |
| ATOM | 1509 | CB | ASN | 201 | −10.903 | −45.495 | 31.960 | 1.000 | 16.17 |
| ATOM | 1510 | CG | ASN | 201 | −12.221 | −44.853 | 31.570 | 1.000 | 14.25 |
| ATOM | 1511 | OD1 | ASN | 201 | −13.050 | −45.436 | 30.871 | 1.000 | 13.77 |
| ATOM | 1512 | ND2 | ASN | 201 | −12.441 | −43.624 | 32.021 | 1.000 | 16.01 |
| ATOM | 1513 | C | ASN | 201 | −9.908 | −47.620 | 32.870 | 1.000 | 12.95 |
| ATOM | 1514 | O | ASN | 201 | −10.050 | −48.720 | 32.334 | 1.000 | 11.02 |
| ATOM | 1515 | N | ARG | 202 | −8.775 | −47.207 | 33.412 | 1.000 | 15.80 |
| ATOM | 1516 | CA | ARG | 202 | −7.571 | −48.020 | 33.532 | 1.000 | 14.85 |
| ATOM | 1517 | CB | ARG | 202 | −6.491 | −47.250 | 34.294 | 1.000 | 17.85 |
| ATOM | 1518 | CG | ARG | 202 | −5.109 | −47.874 | 34.325 | 1.000 | 17.66 |
| ATOM | 1519 | CD | ARG | 202 | −4.141 | −47.026 | 35.143 | 1.000 | 19.69 |
| ATOM | 1520 | NE | ARG | 202 | −3.646 | −45.881 | 34.388 | 1.000 | 30.64 |
| ATOM | 1521 | CZ | ARG | 202 | −2.410 | −45.407 | 34.412 | 1.000 | 36.54 |
| ATOM | 1522 | NH1 | ARG | 202 | −1.470 | −45.972 | 35.164 | 1.000 | 35.38 |
| ATOM | 1523 | NH2 | ARG | 202 | −2.093 | −44.353 | 33.669 | 1.000 | 23.31 |
| ATOM | 1524 | C | ARG | 202 | −7.862 | −49.344 | 34.229 | 1.000 | 6.52 |
| ATOM | 1525 | O | ARG | 202 | −7.636 | −50.401 | 33.644 | 1.000 | 9.98 |
| ATOM | 1526 | N | ASP | 203 | −8.365 | −49.285 | 35.464 | 1.000 | 3.83 |
| ATOM | 1527 | CA | ASP | 203 | −8.597 | −50.500 | 36.237 | 1.000 | 12.72 |
| ATOM | 1528 | CB | ASP | 203 | −9.148 | −50.181 | 37.631 | 1.000 | 9.96 |
| ATOM | 1529 | CG | ASP | 203 | −8.170 | −49.370 | 38.458 | 1.000 | 16.04 |
| ATOM | 1530 | OD1 | ASP | 203 | −6.980 | −49.324 | 38.086 | 1.000 | 18.66 |
| ATOM | 1531 | OD2 | ASP | 203 | −8.584 | −48.772 | 39.474 | 1.000 | 22.09 |
| ATOM | 1532 | C | ASP | 203 | −9.548 | −51.455 | 35.524 | 1.000 | 18.07 |
| ATOM | 1533 | O | ASP | 203 | −9.383 | −52.674 | 35.579 | 1.000 | 12.38 |
| ATOM | 1534 | N | LEU | 204 | −10.550 | −50.890 | 34.859 | 1.000 | 23.73 |
| ATOM | 1535 | CA | LEU | 204 | −11.541 | −51.706 | 34.169 | 1.000 | 21.34 |
| ATOM | 1536 | CB | LEU | 204 | −12.745 | −50.872 | 33.727 | 1.000 | 26.39 |
| ATOM | 1537 | CG | LEU | 204 | −14.123 | −51.510 | 33.908 | 1.000 | 26.92 |
| ATOM | 1538 | CD1 | LEU | 204 | −15.079 | −51.066 | 32.809 | 1.000 | 10.26 |
| ATOM | 1539 | CD2 | LEU | 204 | −14.019 | −53.027 | 33.942 | 1.000 | 35.07 |
| ATOM | 1540 | C | LEU | 204 | −10.938 | −52.392 | 32.948 | 1.000 | 10.84 |
| ATOM | 1541 | O | LEU | 204 | −11.212 | −53.567 | 32.707 | 1.000 | 16.23 |
| ATOM | 1542 | N | GLY | 205 | −10.143 | −51.649 | 32.189 | 1.000 | 8.26 |
| ATOM | 1543 | CA | GLY | 205 | −9.534 | −52.173 | 30.984 | 1.000 | 6.27 |
| ATOM | 1544 | C | GLY | 205 | −8.472 | −53.215 | 31.265 | 1.000 | 8.34 |
| ATOM | 1545 | O | GLY | 205 | −8.228 | −54.094 | 30.436 | 1.000 | 9.21 |
| ATOM | 1546 | N | VAL | 206 | −7.829 | −53.130 | 32.425 | 1.000 | 8.74 |
| ATOM | 1547 | CA | VAL | 206 | −6.833 | −54.135 | 32.796 | 1.000 | 9.33 |
| ATOM | 1548 | CB | VAL | 206 | −5.942 | −53.653 | 33.957 | 1.000 | 16.14 |
| ATOM | 1549 | CG1 | VAL | 206 | −5.020 | −54.754 | 34.457 | 1.000 | 6.58 |
| ATOM | 1550 | CG2 | VAL | 206 | −5.124 | −52.445 | 33.514 | 1.000 | 6.33 |
| ATOM | 1551 | C | VAL | 206 | −7.526 | −55.447 | 33.154 | 1.000 | 5.34 |
| ATOM | 1552 | O | VAL | 206 | −7.118 | −56.498 | 32.664 | 1.000 | 5.68 |
| ATOM | 1553 | N | ALA | 207 | −8.564 | −55.384 | 33.982 | 1.000 | 4.56 |
| ATOM | 1554 | CA | ALA | 207 | −9.349 | −56.547 | 34.369 | 1.000 | 8.39 |
| ATOM | 1555 | CB | ALA | 207 | −10.323 | −56.180 | 35.490 | 1.000 | 0.79 |
| ATOM | 1556 | C | ALA | 207 | −10.144 | −57.160 | 33.219 | 1.000 | 10.03 |
| ATOM | 1557 | O | ALA | 207 | −10.485 | −58.346 | 33.261 | 1.000 | 13.69 |
| ATOM | 1558 | N | LEU | 208 | −10.471 | −56.382 | 32.193 | 1.000 | 14.72 |
| ATOM | 1559 | CA | LEU | 208 | −11.278 | −56.888 | 31.082 | 1.000 | 11.49 |
| ATOM | 1560 | CB | LEU | 208 | −12.065 | −55.755 | 30.422 | 1.000 | 12.04 |
| ATOM | 1561 | CG | LEU | 208 | −13.325 | −55.317 | 31.175 | 1.000 | 10.97 |
| ATOM | 1562 | CD1 | LEU | 208 | −13.985 | −54.127 | 30.497 | 1.000 | 18.17 |
| ATOM | 1563 | CD2 | LEU | 208 | −14.302 | −56.477 | 31.290 | 1.000 | 17.03 |
| ATOM | 1564 | C | LEU | 208 | −10.391 | −57.604 | 30.067 | 1.000 | 6.10 |
| ATOM | 1565 | O | LEU | 208 | −10.857 | −58.502 | 29.369 | 1.000 | 15.12 |
| ATOM | 1566 | N | ALA | 209 | −9.132 | −57.191 | 30.019 | 1.000 | 10.78 |
| ATOM | 1567 | CA | ALA | 209 | −8.103 | −57.815 | 29.203 | 1.000 | 16.00 |
| ATOM | 1568 | CB | ALA | 209 | −6.827 | −56.992 | 29.220 | 1.000 | 18.55 |
| ATOM | 1569 | C | ALA | 209 | −7.829 | −59.238 | 29.694 | 1.000 | 19.15 |
| ATOM | 1570 | O | ALA | 209 | −7.639 | −60.143 | 28.882 | 1.000 | 13.89 |
| ATOM | 1571 | N | GLU | 210 | −7.822 | −59.396 | 31.015 | 1.000 | 9.97 |
| ATOM | 1572 | CA | GLU | 210 | −7.645 | −60.692 | 31.653 | 1.000 | 11.15 |
| ATOM | 1573 | CB | GLU | 210 | −7.535 | −60.520 | 33.168 | 1.000 | 21.07 |
| ATOM | 1574 | CG | GLU | 210 | −6.097 | −60.365 | 33.647 | 1.000 | 39.63 |
| ATOM | 1575 | CD | GLU | 210 | −5.696 | −58.921 | 33.860 | 1.000 | 47.94 |
| ATOM | 1576 | OE1 | GLU | 210 | −5.958 | −58.391 | 34.960 | 1.000 | 64.71 |
| ATOM | 1577 | OE2 | GLU | 210 | −5.097 | −58.319 | 32.949 | 1.000 | 43.70 |
| ATOM | 1578 | C | GLU | 210 | −8.791 | −61.634 | 31.308 | 1.000 | 10.80 |
| ATOM | 1579 | O | GLU | 210 | −8.589 | −62.787 | 30.927 | 1.000 | 10.93 |
| ATOM | 1580 | N | GLN | 211 | −10.007 | −61.120 | 31.441 | 1.000 | 10.29 |
| ATOM | 1581 | CA | GLN | 211 | −11.190 | −61.871 | 31.035 | 1.000 | 17.12 |
| ATOM | 1582 | CB | GLN | 211 | −12.443 | −61.052 | 31.363 | 1.000 | 15.73 |
| ATOM | 1583 | CG | GLN | 211 | −12.542 | −60.709 | 32.844 | 1.000 | 19.97 |
| ATOM | 1584 | CD | GLN | 211 | −12.936 | −61.923 | 33.671 | 1.000 | 20.12 |

-continued

| | | | | | | | | |
|---|---|---|---|---|---|---|---|---|
| ATOM | 1585 | OE1 | GLN | 211 | −13.886 | −62.628 | 33.331 | 1.000 | 17.44 |
| ATOM | 1586 | NE2 | GLN | 211 | −12.218 | −62.166 | 34.759 | 1.000 | 12.84 |
| ATOM | 1587 | C | GLN | 211 | −11.146 | −62.237 | 29.556 | 1.000 | 19.66 |
| ATOM | 1588 | O | GLN | 211 | −11.399 | −63.384 | 29.170 | 1.000 | 12.73 |
| ATOM | 1589 | N | VAL | 212 | −10.822 | −61.287 | 28.679 | 1.000 | 17.48 |
| ATOM | 1590 | CA | VAL | 212 | −10.785 | −61.612 | 27.249 | 1.000 | 19.02 |
| ATOM | 1591 | CB | VAL | 212 | −10.426 | −60.369 | 26.415 | 1.000 | 14.47 |
| ATOM | 1592 | CG1 | VAL | 212 | −10.189 | −60.744 | 24.958 | 1.000 | 15.00 |
| ATOM | 1593 | CG2 | VAL | 212 | −11.527 | −59.320 | 26.523 | 1.000 | 8.88 |
| ATOM | 1594 | C | VAL | 212 | −9.816 | −62.745 | 26.936 | 1.000 | 23.29 |
| ATOM | 1595 | O | VAL | 212 | −10.192 | −63.735 | 26.294 | 1.000 | 25.62 |
| ATOM | 1596 | N | ARG | 213 | −8.557 | −62.645 | 27.361 | 1.000 | 21.16 |
| ATOM | 1597 | CA | ARG | 213 | −7.617 | −63.740 | 27.126 | 1.000 | 22.08 |
| ATOM | 1598 | CB | ARG | 213 | −6.251 | −63.462 | 27.752 | 1.000 | 19.45 |
| ATOM | 1599 | CG | ARG | 213 | −5.577 | −62.178 | 27.300 | 1.000 | 20.41 |
| ATOM | 1600 | CD | ARG | 213 | −4.621 | −61.690 | 28.380 | 1.000 | 26.40 |
| ATOM | 1601 | NE | ARG | 213 | −3.847 | −60.527 | 27.952 | 1.000 | 29.86 |
| ATOM | 1602 | CZ | ARG | 213 | −3.556 | −59.504 | 28.745 | 1.000 | 26.00 |
| ATOM | 1603 | NH1 | ARG | 213 | −3.968 | −59.485 | 30.007 | 1.000 | 15.34 |
| ATOM | 1604 | NH2 | ARG | 213 | −2.847 | −58.491 | 28.268 | 1.000 | 17.74 |
| ATOM | 1605 | C | ARG | 213 | −8.157 | −65.052 | 27.695 | 1.000 | 21.76 |
| ATOM | 1606 | O | ARG | 213 | −7.893 | −66.138 | 27.182 | 1.000 | 28.34 |
| ATOM | 1607 | N | SER | 214 | −8.924 | −64.952 | 28.780 | 1.000 | 15.76 |
| ATOM | 1608 | CA | SER | 214 | −9.486 | −66.151 | 29.389 | 1.000 | 15.09 |
| ATOM | 1609 | CB | SER | 214 | −10.043 | −65.824 | 30.781 | 1.000 | 19.35 |
| ATOM | 1610 | OG | SER | 214 | −11.053 | −66.745 | 31.144 | 1.000 | 46.77 |
| ATOM | 1611 | C | SER | 214 | −10.561 | −66.790 | 28.529 | 1.000 | 15.48 |
| ATOM | 1612 | O | SER | 214 | −10.692 | −68.016 | 28.535 | 1.000 | 24.87 |
| ATOM | 1613 | N | LEU | 215 | −11.355 | −66.030 | 27.772 | 1.000 | 21.40 |
| ATOM | 1614 | CA | LEU | 215 | −12.367 | −66.673 | 26.938 | 1.000 | 21.52 |
| ATOM | 1615 | CB | LEU | 215 | −13.655 | −65.855 | 26.860 | 1.000 | 22.40 |
| ATOM | 1616 | CG | LEU | 215 | −14.176 | −65.153 | 28.103 | 1.000 | 20.48 |
| ATOM | 1617 | CD1 | LEU | 215 | −15.071 | −63.990 | 27.697 | 1.000 | 27.15 |
| ATOM | 1618 | CD2 | LEU | 215 | −14.931 | −66.118 | 29.006 | 1.000 | 13.10 |
| ATOM | 1619 | C | LEU | 215 | −11.884 | −66.920 | 25.510 | 1.000 | 20.60 |
| ATOM | 1620 | O | LEU | 215 | −12.536 | −67.682 | 24.789 | 1.000 | 31.41 |
| ATOM | 1621 | N | LEU | 216 | −10.790 | −66.303 | 25.077 | 1.000 | 21.43 |
| ATOM | 1622 | CA | LEU | 216 | −10.291 | −66.503 | 23.718 | 1.000 | 19.55 |
| ATOM | 1623 | CB | LEU | 216 | −10.114 | −65.148 | 23.021 | 1.000 | 19.47 |
| ATOM | 1624 | CG | LEU | 216 | −11.385 | −64.305 | 22.870 | 1.000 | 16.11 |
| ATOM | 1625 | CD1 | LEU | 216 | −11.095 | −63.042 | 22.076 | 1.000 | 17.60 |
| ATOM | 1626 | CD2 | LEU | 216 | −12.495 | −65.108 | 22.211 | 1.000 | 4.00 |
| ATOM | 1627 | C | LEU | 216 | −8.983 | −67.283 | 23.688 | 1.000 | 24.37 |
| ATOM | 1628 | OT1 | LEU | 216 | −8.472 | −67.525 | 22.571 | 1.000 | 29.22 |
| ATOM | 1629 | OT2 | LEU | 216 | −8.463 | −67.655 | 24.758 | 1.000 | 19.02 |

In addition to the above-described determinations, a carbamate-inhibited perhydrolase crystal was also produced and analyzed. In these experiments, a N-hexylcarbamate derivative of wild type perhydrolase was used. Wild-type perhydrolase (14.5 mg in 1 mL, 67 mM NaPO4 pH 7 buffer) was titrated at room temperature with 1.25 μL aliquots of 400 mM p-nitrophenyl-N-hexylcarbamate dissolved in DMSO. Perhydrolase activity was measured with p-nitrophenylbutyrate assay (See, Example 2), as a function of time after each addition of the inhibitor. Several additions over several hours were required for complete inhibition of the enzyme. After inhibition Was complete, the buffer of the inhibited enzyme solution was exchanged for 10 mM HEPES pH 8.3. This solution was stored at −80° C. until used for crystallization screening experiments were conducted as described above. The inhibitor p-nitrophenyl-N-hexylcarbamate was prepared by methods known in the art (See e.g., Hosie et al., J. Biol. Chem., 262:260-264 [1987]). Briefly, the carbamate-inhibited perhydrolase was crystallized by vapor diffusion using the hanging drop method known in the art. A ml solution of inhibited perhydrolase (15 mg/ml in 10 mM HEPES, pH 8.2), was mixed with 4 μL of a reservoir solution (30% PEG-4,000 with 0.2 M lithium sulfate and 0.1 M Tris, pH 8.5) on a plastic coverslip, then inverted and sealed for a well of 6×4 Linbro plate containing 0.5 ml of the reservoir solution and allowed to equilibrate. Crystals formed within a few days. The crystals were flash frozen in liquid nitrogen and analyzed as described above.

While the native octamer was determined in space group P4 with unit cell dimensions: a=98.184 b=98.184 and c=230.119 α=90.00 β=90.00 γ=90.00, this crystal diffracted to about 2.0 Å. The carbamate-inhibited crystal grew in the space group P1 with unit cell dimensions a=67.754, b=80.096, and c=85.974 α=104.10°, β=112.10°, and γ=97.40° and these crystals diffract to a resolution exceeding 1.0 Å.

The carbamate was bound in a manner to exploit the interactions between the keto oxygen of the carbamate and residues forming the oxyanion hole, the amide N atoms of Ser 11 and Ala 55 and Asn 94 ND2. The hydrophobic side chain extends along the hydrophobic surface of the binding site out into the surface opening between pairs of dimers in the octamer structure. The carbamate moiety direction highlights the pivotal role of the S54V mutation. The hydrophobic moiety passes adjacent to the side chain of ser 54. Mutating the serine side to valine increased the hydrophobicity, and also served as a gatekeeper to prevent hydrophilic nucleophiles (e.g., water) for competing with desired deacylating nucleophiles. The t residues surrounding the carbamate moiety on the same and neighboring molecules forming the extended entry are expected to influence the selection of the optimal de-acylating nucleophile.

In addition, residues with surface-accessible side chain atoms were identified using the program "AreaMol," within the CCP4 program package. Table 15-1 lists these residues. In this Table, the residue number, residue name, number of surface-accessible side chain atoms having at least 10.0 square atoms of accessible surface area, and maximum surface area (square angstroms) for any side chain atom within that residue (or CA for GLY residues) in the octameric structure of perhydrolase are provided.

TABLE 15-1

Surface-Accessible Side Chain Atoms

| Residue Number | Residue Name | Number of Accessible Side Chain Atoms | Maximum Surface Area (Square Angstroms) |
|---|---|---|---|
| 1 | ALA | 1 | 15.7 |
| 3 | LYS | 2 | 54.10 |
| 17 | VAL | 1 | 29.5 |
| 19 | VAL | 1 | 28.0 |
| 20 | GLU | 4 | 30.2 |
| 21 | ASP | 2 | 41.3 |
| 24 | PRO | 2 | 23.2 |
| 26 | GLU | 3 | 36.3 |
| 29 | ALA | 1 | 34.4 |
| 30 | PRP | 3 | 32.7 |
| 31 | ASP | 3 | 50.6 |
| 32 | VAL | 1 | 27.0 |
| 39 | ALA | 1 | 27.5 |
| 40 | GLN | 3 | 38.7 |
| 41 | GLN | 2 | 22.1 |
| 43 | GLY | 1 | 20.4 |
| 44 | ALA | 1 | 63.8 |
| 45 | ASP | 3 | 52.7 |
| 46 | PHE | 2 | 17.1 |
| 47 | GLU | 3 | 29.6 |
| 61 | ASP | 3 | 53.1 |
| 63 | PRO | 3 | 28.0 |
| 64 | THR | 1 | 15.7 |
| 65 | ASP | 1 | 10.8 |
| 66 | PRO | 3 | 33.5 |
| 67 | ARG | 2 | 20.3 |
| 69 | ASN | 1 | 11.0 |
| 72 | SER | 2 | 26.6 |
| 75 | PRO | 2 | 17.4 |
| 83 | PRO | 2 | 15.1 |
| 85 | ASP | 1 | 36.80 |
| 98 | ALA | 1 | 14.60 |
| 101 | ARG | 4 | 25.0 |
| 102 | ARG | 1 | 19.9 |
| 103 | THR | 1 | 43.7 |
| 104 | PRO | 1 | 17.90 |
| 105 | LEU | 1 | 10.1 |
| 113 | VAL | 1 | 17.3 |
| 116 | THR | 2 | 39.5 |
| 117 | GLN | 2 | 15.3 |
| 119 | LEU | 3 | 21.4 |
| 120 | THR | 2 | 34.1 |
| 122 | ALA | 1 | 38.0 |
| 123 | GLY | 1 | 11.0 |
| 126 | GLY | 1 | 11.9 |
| 128 | THR | 2 | 18.2 |
| 129 | TYR | 1 | 17.6 |
| 130 | PRO | 3 | 30.2 |
| 131 | ALA | 1 | 13.7 |
| 133 | LYS | 3 | 46.9 |
| 141 | PRO | 3 | 25.3 |
| 143 | ALA | 1 | 19.8 |
| 144 | PRO | 3 | 34.90 |
| 146 | PRO | 2 | 24.30 |
| 148 | PRO | 3 | 24.1 |
| 151 | GLN | 3 | 35.6 |
| 152 | LEU | 1 | 12.90 |
| 155 | GLU | 3 | 53.0 |
| 156 | GLY | 1 | 28.9 |
| 158 | GLU | 3 | 30.3 |
| 159 | GLN | 4 | 44.9 |
| 160 | LYS | 2 | 21.5 |
| 162 | THR | 2 | 25.0 |
| 163 | GLU | 2 | 23.3 |
| 165 | ALA | 1 | 23.1 |
| 169 | SER | 1 | 39.1 |
| 173 | SER | 2 | 33.3 |
| 174 | PHE | 1 | 11.1 |
| 175 | MET | 1 | 18.5 |
| 176 | LYS | 2 | 21.4 |
| 178 | PRO | 1 | 12.0 |
| 179 | PHE | 2 | 14.0 |
| 180 | PHE | 1 | 13.9 |
| 181 | ASP | 1 | 24.9 |
| 184 | SER | 1 | 27.0 |
| 185 | VAL | 1 | 27.5 |
| 187 | SER | 2 | 34.0 |
| 189 | ASP | 2 | 25.4 |
| 191 | VAL | 2 | 24.5 |
| 197 | THR | 2 | 21.6 |
| 198 | GLU | 3 | 43.5 |
| 199 | ALA | 1 | 50.5 |
| 202 | ARG | 3 | 37.2 |
| 203 | ASP | 2 | 30.9 |
| 206 | VAL | 2 | 45.2 |
| 210 | GLU | 3 | 34.6 |
| 211 | GLN | 2 | 19.6 |
| 213 | ARG | 5 | 30.8 |
| 214 | SER | 2 | 20.8 |
| 215 | LEU | 1 | 25.80 |

Example 16

Stain Removal

In this Example, experiments conducted to assess the stain removal abilities of perhydrolase are described.

Figure 21:
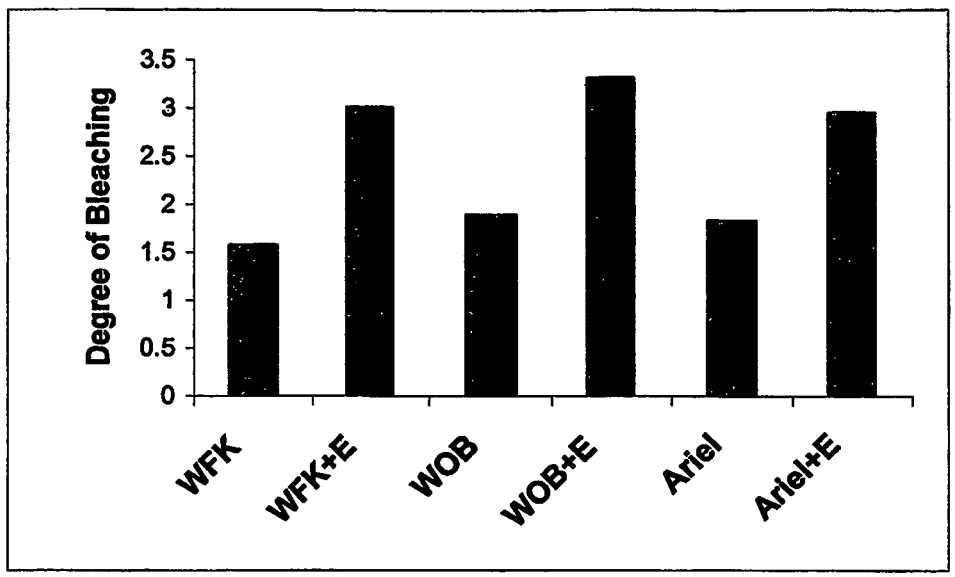
FIG. 21 provides a graph showing the degree of bleaching by three detergents tested alone and in comparison with the *M. smegmatis* perhydrolase of the present invention.

Individual wells of 24 well culture plates were used to mimic conditions found in ordinary washing machines. Each well was filled with commercially available detergent (e.g., Ariel [Procter & Gamble], WOB [AATCC], and WFK [WFK]), and pre-stained cloth discs cut to fit inside of each well were added. Temperature and agitation were accomplished by attaching the plate to the inside of a common laboratory incubator/shaker. To measure bleaching effectiveness of the perhydrolase, fabric stained with tea (EMPA #167, available commercially from Test Fabrics) was used. A single cloth disc was placed in each well, and 1 ml of detergent liquid, containing enzyme, ester substrate, and peroxide was added. After agitation at 100-300 rpm@ 20-60° C., the fabric discs were removed, rinsed with tap water, and allowed to dry overnight. The reflectance of each individual cloth disc was measured, and plotted as an "L" value. These results are provided in FIG. 21, which shows that the addition of the perhydrolase of the present invention to the detergent consistently provides a greater degree of bleaching than the detergents alone. In this Figure, "E" indicates the results for each of the detergents tested in combination with the perhydrolase of the present invention.

Example 17

Cotton Bleaching

In this Example, experiments to assess the use of the perhydrolase of the present invention for bleaching of cotton fabrics are described.

In these experiments, six cotton swatches per canister were treated at 55° C. for 60 minutes in a Launder-O-meter. The substrates used in these experiments were: 3 (3"×3") 428U and 3 (3"×3") 400U per experiments. Two different types of 100% unbleached cotton fabrics from Testfabrics were tested (style 428U (desized but not bleached army carded cotton sateen); and style 400U (desized but not bleached cotton print cloth). The liquor ratio was about 26 to 1 (~7.7 g fabric/~200 ml volume liquor). The perhydrolase enzyme was tested at 12.7 mgP/ml, with ethyl acetate (3% (v/v)), hydrogen peroxide (1500 ppm), and Triton X-100 (0.001%), in a sodium phosphate buffer (100 mM) for pH 7 and pH 8; as well as in a sodium carbonate (100 mM) buffer, for pH 9 and pH 10.

Bleaching effects were quantified with total color difference by taking 4 CIE L*a*b* values per each swatch before and after the treatments using a Chroma Meter CR-200 (Minolta), and total color difference of the swatches after the treatments were calculated according to the following:

$$\text{Total color difference } (\Delta E) = \sqrt{(\Delta L^2 + \Delta a^2 + \Delta b^2)}$$

(where $\Delta L$, $\Delta a$, $\Delta b$, are differences in CIE L*, CIE a*, and CIE b* values respectively before and after the treatments).

Figure 22:
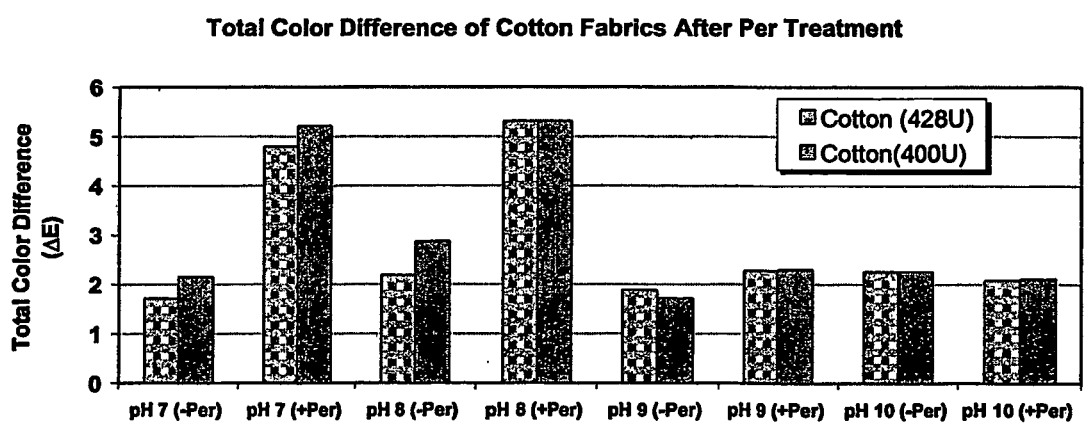
FIG. 22 provides a graph showing the bleaching ability of the *M. smegmatis* perhydrolase tested on cotton.

Higher $\Delta E$ values indicate greater bleaching effects. The results (See, FIG. 22) indicated that the perhydrolase showed significantly improved bleaching effects on both types of 100% cotton fabrics at pH 7 and pH 8 under the conditions tested.

It was also observed that high amounts of motes (e.g., pigmented spots) disappeared on the enzyme treated substrates.

Example 18

Linen Bleaching

In this Example, experiments conducted to assess the linen bleaching capability of the perhydrolase of the present invention are described. The same methods and conditions as describe above for cotton testing (in Example 17) were used to test linen swatches. As indicated above, experiments were conduction in a Launder-O-meter using a linen fabric (linen suiting, Style L-53; Testfabrics).

Figure 23:
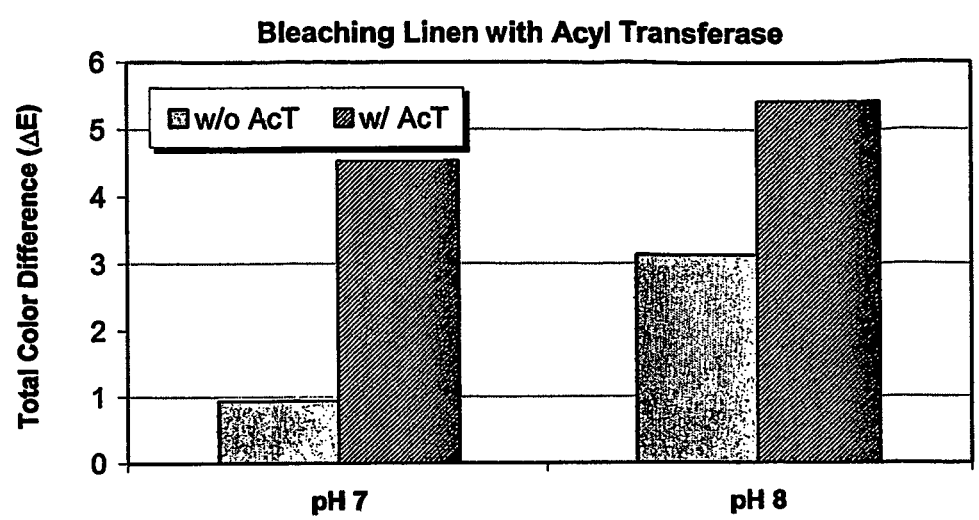
FIG. 23 provides a graph showing the bleaching ability of the *M. smegmatis* perhydrolase tested on linen.

In these experiments, 3 (4"×4") linen swatches were treated with 12.7 mgP/ml of the perhydrolase enzyme with ethyl acetate (3% v/v), hydrogen peroxide (1200 ppm), and Triton X-100 (0.001%), in a sodium phosphate buffer (100 mM) for pH 7 and pH 8. The bleaching effects were calculated as described above in Example 17. FIG. 23 provides a graph showing the bleaching effects of the perhydrolase of the present invention tested at pH 7 and pH 8 on linen.

Example 19

Detergent Compositions

In the following Example, various detergent compositions are exemplified. In these formulations, the enzymes levels are expressed by pure enzyme by weight of the total composition and unless otherwise specified, the detergent ingredients are expressed by weight of the total compositions. The abbreviated component identifications therein have the following meanings:

LAS: Sodium linear $C_{11-13}$ alkyl benzene sulfonate.
TAS: Sodium tallow alkyl sulfate.
CxyAS: Sodium $C_{1x}$-$C_{1y}$ alkyl sulfate.
CxyEz: $C_{1x}$-$C_{1y}$ predominantly linear primary alcohol condensed with an average of z moles of ethylene oxide.
CxyAEzS: $C_{1x}$-$C_{1y}$ sodium alkyl sulfate condensed with an average of z moles of ethylene oxide. Added molecule name in the examples.
Nonionic: Mixed ethoxylated/propoxylated fatty alcohol e.g. Plurafac LF404 being an alcohol with an average degree of ethoxylation of 3.8 and an average degree of propoxylation of 4.5.
QAS: $R_2.N+(CH_3)_2(C_2H_4H)$ with $R_2=C_{12}$-$C_{14}$.
Silicate: Amorphous Sodium Silicate ($SiO_2$:$Na_2O$ ratio=1.6-3.2:1).
Metasilicate: Sodium metasilicate ($SiO_2$:$Na_2O$ ratio=1.0).
Zeolite A: Hydrated Aluminosilicate of formula $NaI_2(AlO_2SiO_2)_{12} \cdot 27H_2O$
SKS-6: Crystalline layered silicate of formula $\delta$-$Na_{12}Si_2O_5$.
Sulphate: Anhydrous sodium sulphate.
STPP: Sodium Tripolyphosphate.
MA/AA: Random copolymer of 4:1 acrylate/maleate, average molecular weight about 70,000-80,000.
AA: Sodium polyacrylate polymer of average molecular weight 4,500.
Polycarboxylate: Copolymer comprising mixture of carboxylated monomers such as acrylate, maleate and methyacrylate with a MW ranging between 2,000-80,000 such as Sokolan commercially available from BASF, being a copolymer of acrylic acid, MW4,500.
BB1: 3-(3,4-Dihydroisoquinolinium)propane sulfonate
BB2 1-(3,4-dihydroisoquinolinium)-decane-2-sulfate
PB1: Sodium perborate monohydrate.
PB4: Sodium perborate tetrahydrate of nominal formula $NaBO_3 \cdot 4H_2O$.
Percarbonate: Sodium percarbonate of nominal formula $2Na_2CO_3 \cdot 3H_2O_2$.
TAED: Tetraacetyl ethylene diamine.
NOBS: Nonanoyloxybenzene sulfonate in the form of the sodium salt.
DTPA: Diethylene triamine pentaacetic acid.
HEDP: 1,1-hydroxyethane diphosphonic acid.
DETPMP: Diethyltriamine penta(methylene) phosphonate, marketed by Monsanto under the Trade name Dequest 2060.
EDDS: Ethylenediamine-N,N' disuccinic acid, (S,S) isomer in the form of its sodium salt
Diamine: Dimethyl aminopropyl amine; 1,6-hezane diamine; 1,3-propane diamine; 2-methyl-1,5-pentane diamine; 1,3-pentanediamine; 1-methyl-diaminopropane.
DETBCHD 5,12-diethyl-1,5,8,12-tetraazabicyclo[6,6,2]hexadecane, dichloride, Mn(II) salt
PAAC: Pentaamine acetate cobalt(III) salt.
Paraffin: Paraffin oil sold under the tradename Winog 70 by Wintershall.
Paraffin Sulfonate: A Paraffin oil or wax in which some of the hydrogen atoms have been replaced by sulfonate groups.
Aldose oxidase: Oxidase enzyme sold under the tradename Aldose Oxidase by Novozymes A/S
Galactose oxidase: Galactose oxidase from Sigma
Protease: Proteolytic enzyme sold under the tradename Savinase, Alcalase, Everlase by Novo Nordisk A/S, and the following from Genencor International, Inc: "Protease A" described in U.S. RE 34,606 in FIGS. 1A, 1B, and 7, and at column 11, lines 11-37; "Protease B" described in U.S. Pat. No. 5,955,340 and U.S. Pat. No. 5,700,676 in FIGS. 1A, 1B and 5, as well as Table 1; and "Protease C" described in U.S. Pat. No. 6,312,936 and U.S. Pat. No. 6,482,628 in FIGS. 1-3 [SEQ ID 3], and at column 25, line 12, "Protease D" being the variant 101G/103A/104I/159D/232V/236H/245R/248D/252K (BPN' numbering) described in WO 99/20723.

Amylase: Amylolytic enzyme sold under the tradename Purafact Ox Am$^R$ described in WO 94/18314, WO96/05295 sold by Genencor, Natalase®, Termamyl®, Fungamyl® and Duramyl®, all available from Novozymes A/S.
Lipase: Lipolytic enzyme sold under the tradename Lipolase Lipolase Ultra by Novozymes A/S and Lipomax by Gist-Brocades.
Cellulase: Cellulytic enzyme sold under the tradename Carezyme, Celluzyme and/or Endolase by Novozymes A/S.
Pectin Lyase: Pectawaye and Pectawash® available from Novozymes A/S.
PVP: Polyvinylpyrrolidone with an average molecular weight of 60,000
PVNO: Polyvinylpyridine-N-Oxide, with an average molecular weight of 50,000.
PVPVI: Copolymer of vinylimidazole and vinylpyrrolidone, with an average molecular weight of 20,000.
Brightener 1: Disodium 4,4'-bis(2-sulphostyryl)biphenyl.
Silicone antifoam: Polydimethylsiloxane foam controller with siloxane-oxyalkylene copolymer as dispersing agent with a ratio of said foam controller to said dispersing agent of 10:1 to 100:1.
Suds Suppressor: 12% Silicone/silica, 18% stearyl alcohol, 70% starch in granular form.
SRP 1: Anionically end capped poly esters.
PEG X: Polyethylene glycol, of a molecular weight of x.
PVP K60®: Vinylpyrrolidone homopolymer (average MW 160,000)
Jeffamine® ED-2001: Capped polyethylene glycol from Huntsman
Isachem® AS: A branched alcohol alkyl sulphate from Enichem
MME PEG (2000): Monomethyl ether polyethylene glycol (MW 2000) from Fluka Chemie AG.
DC3225C: Silicone suds suppresser, mixture of Silicone oil and Silica from Dow Corning.
TEPAE: Tetreaethylenepentaamine ethoxylate.
BTA: Benzotriazole.
Betaine: $(CH_3)_3N^+CH_2COO^-$
Sugar: Industry grade D-glucose or food grade sugar
CFAA: $C_{12}$-$C_{14}$ alkyl N-methyl glucamide
TPKFA: $C_{12}$-$C_{14}$ topped whole cut fatty acids.
Clay: A hydrated aluminum silicate in a general formula $Al_2O_3SiO_2.xH_2O$. Types: Kaolinite, montmorillonite, atapulgite, illite, bentonite, halloysite.
MCAEM: Esters in the formula of $R^1O_x[(R^2)_m(R^3)_n]_p$
pH: Measured as a 1% solution in distilled water at 20° C.

Example 20

Liquid Laundry Detergents

The following liquid laundry detergent compositions of the present invention are prepared.

|  | I | II | III | IV | V |
|---|---|---|---|---|---|
| LAS | 18.0 | — | 6.0 | — | — |
| $C_{12}$-$C_{15}$ $AE_{1.8}S$ | — | 2.0 | 8.0 | 11.0 | 5.0 |
| $C_8$-$C_{10}$ propyl dimethyl amine | 2.0 | 2.0 | 2.0 | 2.0 | 1.0 |
| $C_{12}$-$C_{14}$ alkyl dimethyl amine oxide | — | — | — | — | 2.0 |
| $C_{12}$-$C_{15}$ AS | — | 17.0 | — | 7.0 | 8.0 |
| CFAA | — | 5.0 | 4.0 | 4.0 | 3.0 |
| $C_{12}$-$C_{14}$ Fatty alcohol ethoxylate | 12.0 | 6.0 | 1.0 | 1.0 | 1.0 |
| $C_{12}$-$C_{18}$ Fatty acid | 11.0 | 11.0 | 4.0 | 4.0 | 3.0 |
| Citric acid (anhydrous) | 5.0 | 1.0 | 3.0 | 3.0 | 2.0 |
| DETPMP | 1.0 | 1.0 | 1.0 | 1.0 | 0.5 |
| Monoethanolamine | 11.0 | 8.0 | 5.0 | 5.0 | 2.0 |
| Sodium hydroxide | 1.0 | 1.0 | 2.5 | 1.0 | 1.5 |
| Percarbonate | — | 3.5 | — | 2.5 | — |
| Propanediol | 12.7 | 14.5 | 13.1 | 10. | 8.0 |
| Ethanol | 1.8 | 1.8 | 4.7 | 5.4 | 1.0 |
| Pectin Lyase | — | — | — | 0.005 | — |
| Amylase | — | 0.002 | — | — | — |
| Cellulase | — | — | 0.0002 | — | 0.0001 |
| Lipase | 0.1 | — | 0.1 | — | 0.1 |
| Protease A | 0.05 | 0.3 | 0.055 | 0.5 | 0.2 |
| Aldose Oxidase | 0.03 | — | 0.3 | — | 0.003 |
| PAAC | 0.01 | 0.01 | — | — | — |
| DETBCHD | — | — | 0.02 | 0.01 | — |
| SRP1 | 0.5 | 0.5 | — | 0.3 | 0.3 |
| Boric acid | 2.4 | 2.4 | 2.8 | 2.8 | 2.4 |
| Sodium xylene sulfonate | — | — | 3.0 | — | — |
| DC 3225C | 1.0 | 1.0 | 1.0 | 1.0 | 1.0 |
| 2-butyl-octanol | 0.03 | 0.04 | 0.04 | 0.03 | 0.03 |
| DTPA | 0.5 | 0.4 | 0.35 | 0.28 | 0.4 |
| Brightener 1 | 0.18 | 0.10 | 0.11 | — | — |
| Perhydrolase | 0.05 | 0.3 | 0.08 | 0.5 | 0.2 |
| MCAEM ($C_{12}$-$C_{13}$ $E_{6.5}$ Acetate) | 3.0 | 8.0 | 12.0 | 1.5 | 4.8 |

Balance to 100% perfume/dye and/or water

Example 21

Hand-Dish Liquid Detergent Compositions

The following hand dish liquid detergent compositions of the present invention are prepared.

|  | I | II | III | IV | V | VI |
|---|---|---|---|---|---|---|
| $C_{12}$-$C_{15}$ $AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dihydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| Protease A | 0.02 | 0.01 | 0.02 | 0.01 | 0.02 | 0.05 |

-continued

|  | I | II | III | IV | V | VI |
|---|---|---|---|---|---|---|
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| PB1 | 1.5 | 2.8 | 1.2 | — | — | — |
| Perhydrolase | 0.02 | 0.01 | 0.03 | 0.01 | 0.02 | 0.05 |
| MCAEM ($C_{14}$-$C_{15}$ $E_7$ Acetate) | 3.4 | 2.8 | 4.0 | 2.6 | 4.6 | 6.8 |

Balance to 100% perfume/dye and/or water

The pH of Compositions (I)-(VI) is about 8 to about 11

Example 22

Liquid Automatic Dishwashing Detergent

The following liquid automatic dishwashing detergent compositions of the present are prepared.

|  | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | 4.0 | 3.0 | 3.0 | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| Protease B | 0.03 | 0.03 | 0.03 | 0.03 | 0.03 |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Perhydrolase | 0.1 | 0.03 | 0.05 | 0.03 | 0.06 |
| MCAEM ($C_{14}$-$C_{15}E_{12}$ Acetate) | 5.0 | 3.0 | 12.0 | 8.0 | 1.0 |

Balance to 100% perfume/dye and/or water

Example 23

Laundry Compositions

The following laundry compositions of present invention, which may be in the form of granules or tablet, are prepared.

| Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate $2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |

| Base Product | I | II | III | IV | V |
|---|---|---|---|---|---|
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | 8.0 | 15.0 | 15.0 |
| Sulfate | 5.0 | 12.0 | 2.0 | 17.0 | 3.0 |
| Silicate | — | 1.0 | — | — | 8.0 |
| Protease B | 0.033 | 0.033 | — | — | — |
| Protease C | — | — | 0.033 | 0.046 | 0.033 |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Perhydrolase | 0.03 | 0.05 | 1.0 | 0.06 | 0.1 |
| MCAEM** | 2.0 | 5.0 | 12.0 | 3.5 | 6.8 |

Balance to 100% Moisture and/or Minors*
*Perfume/Dye, Brightener/SRP1/Na Carboxymethylcellulose/Photobleach/$MgSO_4$/PVPVI/Suds suppressor/High Molecular PEG/Clay.
**MCAEM is selected from the group consisting of $C_9$-$C_{11}E_{2.5}$ Acetate, $[C_{12}H_{25}N(CH_3)(CH_2CH_2OAc)_2]^+Cl^-$, $(CH_3)_2NCH_2CH_2OCH_2CH_2OAc$, or mixtures thereof...

Example 24

Liquid Laundry Detergents

The following liquid laundry detergent formulations of the present invention are prepared.

|  | I | I | II | III | IV | V |
|---|---|---|---|---|---|---|
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}$ S | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhydrous) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| Na Culmene Sulfonate | 4.0 | 4.0 | 1.0 | 3.0 | 1.2 | — |
| Borate | 0.6 | 0.6 | — | 3.0 | 2.0 | 3.0 |
| Na hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Mono-ethanolamine | 3.0 | 3.0 | 1.5 | 1.0 | 2.5 | 1.0 |
| TEPAE | 2.0 | 2.0 | — | 1.0 | 1.0 | 1.0 |
| PB1 | — | — | 4.5 | — | 2.8 | — |
| Protease A | 0.03 | 0.03 | 0.01 | 0.03 | 0.02 | 0.02 |
| Lipase | — | — | — | 0.002 | — | — |
| Amylase | — | — | — | — | 0.002 | — |

|  | I | I | II | III | IV | V |
|---|---|---|---|---|---|---|
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| Perhydrolase | 0.03 | 0.05 | 0.01 | 0.03 | 0.08 | 0.02 |
| MCAEM ($C_{12}$-$C_{15}$ $E_6$ Acetate) | 3.2 | 4.6 | 1.8 | 3.5 | 6.2 | 2.8 |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | — | 0.3 | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |

Balance to 100% perfume/dye, and/or water

Example 25

Compact High-Density Dishwashing Detergents

The following compact high density dishwashing detergent of the present invention are prepared:

|  | I | II | III | IV | V | VI |
|---|---|---|---|---|---|---|
| STPP | — | 45.0 | 45.0 | — | — | 40.0 |
| 3NaCitrate 2$H_2O$ | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |

|  | I | II | III | IV | V | VI |
|---|---|---|---|---|---|---|
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| Protease B | 0.072 | 0.053 | 0.053 | 0.026 | 0.059 | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| Perhydrolase | 0.072 | 0.053 | 0.053 | 0.026 | 0.059 | 0.01 |
| MCAEM ($C_{12}$-$C_{13}$ $E_{6.5}$ Acetate) | 3.5 | 2.8 | 1.6 | 7.5 | 4.2 | 0.8 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |

Balance to 100% Moisture and/or Minors*
*Brightener/Dye/SRP1/Na Carboxymethylcellulose/Photobleach/MgSO$_4$/PVPVI/Suds suppressor/High Molecular PEG/Clay.
The pH of compositions (I) through (VI) is from about 9.6 to about 11.3.

Example 26

Tablet Detergent Compositions

The following tablet detergent compositions of the present invention are prepared by compression of a granular dishwashing detergent composition at a pressure of 13KN/cm$^2$ using a standard 12 head rotary press.

|  | I | II | III | IV | V | VI | VII | VIII |
|---|---|---|---|---|---|---|---|---|
| STPP | — | 48.8 | 44.7 | 38.2 | — | 42.4 | 46.1 | 36.0 |
| 3Na Citrate 2$H_2O$ | 20.0 | — | — | — | 35.9 | — | — | — |
| Na Carbonate | 20.0 | 5.0 | 14.0 | 15.4 | 8.0 | 23.0 | 20.0 | 28.0 |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B | 0.042 | 0.072 | 0.042 | 0.031 | — | — | — | — |
| Protease C | — | — | — | — | 0.052 | 0.023 | 0.023 | 0.029 |
| Perhydrolase | 0.01 | 0.08 | 0.05 | 0.04 | 0.052 | 0.023 | 0.023 | 0.029 |
| MCAEM ($C_{12}$-$C_{13}$ $E_{6.5}$ Acetate) | 2.8 | 6.5 | 4.5 | 3.8 | 4.6 | 2.8 | 2.8 | 2.8 |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 8.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |

-continued

|  | I | II | III | IV | V | VI | VII | VIII |
|---|---|---|---|---|---|---|---|---|
| Glycerol | — | — | — | — | — | 0.4 | — | 0.5 |
| Perfume | — | — | — | 0.05 | 0.2 | 0.2 | 0.2 | 0.2 |

Balance to 100% Moisture and/or Minors*
*Brightener/Dye/SRP1/Na Carboxymethylcellulose/Photobleach/MgSO$_4$/PVPVI/Suds suppressor/High Molecular PEG/Clay.
The pH of Compositions (I) through 7(VIII) is from about 10 to about 11.5.
The tablet weight of Compositions 7(I) through 7(VIII) is from about 20 grams to about 30 grams.

Example 27

Liquid Hard Surface Cleaning Detergents

The following liquid hard surface cleaning detergent compositions of the present invention are prepared.

|  | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate 2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| Protease B | 0.07 | 0.05 | 0.05 | 0.03 | 0.06 | 0.01 | 0.04 |
| Amylase | 0.12 | 0.01 | 0.01 | — | 0.02 | — | 0.01 |
| Lipase | — | 0.001 | — | 0.005 | — | 0.005 | — |
| Perhydrolase | 0.07 | 0.05 | 0.08 | 0.03 | 0.06 | 0.01 | 0.04 |
| MCAEM ($C_{12}$-$C_{15}E_8$ Acetate) | 3.5 | 5.6 | 4.8 | 5.3 | 3.6 | 8.0 | 4.7 |
| Pectin Lyase | 0.001 | — | 0.001 | — | — | — | 0.002 |
| PB1 | — | 4.6 | — | 3.8 | — | — | — |
| Aldose Oxidase | 0.05 | — | 0.03 | — | 0.02 | 0.02 | 0.05 |

Balance to 100% perfume/dye, and/or water
The pH of Compositions (I) through (VII) is from about 7.4 to about 9.5.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. An isolated polypeptide having perhydrolase activity and having at least 80% amino acid sequence identity to the amino acid sequence of SEQ ID NO: 2.

2. The perhydrolase of claim 1, wherein said perhydrolase exhibits a perhydrolysis to hydrolysis ratio that is greater than 1.

3. The perhydrolase of claim 1, wherein said perhydrolase is *M. smegmatis* perhydrolase.

4. The perhydrolase of claim 3, wherein said perhydrolase comprises the amino acid sequence set forth in SEQ ID NO:2.

5. The perhydrolase of claim 1, wherein said perhydrolase is at least a portion of said *M. smegmatis* perhydrolase, wherein said perhydrolase has a perhydrolysis to hydrolysis ratio that is greater than 1.

6. The perhydrolase of claim 1, wherein said perhydrolase is a structural homologue of said *M. smegmatis* perhydrolase, in which the active site is homologous to at least one amino acid selected from the group consisting of S11, D192, and H195 of the *M. smegmatis* perhydrolase.

7. An isolated perhydrolase variant having an amino acid sequence comprising at least one modification at an amino acid position equivalent to a position in *M. smegmatis* perhydrolase comprising the amino acid sequence set forth in SEQ ID NO:2, the variant having at least 80% amino acid sequence identity to the amino acid sequence of SEQ ID NO: 2.

8. The perhydrolase variant of claim 7, wherein said at least one modification is made at an amino acid position equivalent to a position in *M. smegmatis* perhydrolase comprising the amino acid sequence set forth in SEQ ID NO:2, wherein said modified amino acid is selected from the group consisting of Cys7, Asp10, Ser11, Leu12, Thr13, Trp14, Trp16, Pro24, Thr25, Leu53, Ser54, Ala55, Thr64, Asp65, Arg67, Cys77, Thr91, Asn94, Asp95, Tyr99, Val125, Pro138, Leu140, Pro146, Pro148, Trp149, Phe150, Ile153, Phe154, Thr159, Thr186, Ile192, Ile194, and Phe196.

9. The perhydrolase variant of claim 7, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of
M1, K3, R4, I5, L6, C7, D10, S11, L12, T13, W14, W16, G15, V17, P18, V19, D21, G22, A23, P24, T25, E26, R27, F28, A29, P30, D31, V32, R33, W34, T35, G36, L38, Q40, Q41, D45, L42, G43, A44, F46, E47, V48, I49, E50, E51, G52, L53, S54, A55, R56, T57, T58, N59, I60, D61, D62, P63, T64, D65, P66, R67, L68, N69, G70, A71, S72, Y73, S76, C77, L78, A79, T80, L82, P83, L84, D85, L86, V87, N94, D95, T96, K97, Y99F100, R101, R102, P104, L105, D106, I107, A108, L109, G110, M111, S112, V113, L114, V115, T116, Q117, V118, L119, T120, S121, A122, G124, V125, G126, T127, T128, Y129, P146, P148, W149, F150, I153, F154, I194, and F196.

10. The perhydrolase variant of claim 7, wherein said variant perhydrolase exhibits a change in peracid hydrolysis compared to the wild-type perhydrolase.

11. The perhydrolase variant of claim 10, wherein said change in peracid hydrolysis is a decrease.

12. The perhydrolase variant of claim 10, wherein said change in peracid hydrolysis is an increase.

13. The perhydrolase variant of claim 7, wherein said variant perhydrolase exhibits a ratio of peracid hydrolysis of about 0.1 or less, in comparison with wild-type perhydrolase.

14. The perhydrolase variant of claim 13, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of R4, L12, G15, P18, R27, W34L38, A44, E51, G52, L53, S54, T58, R67, L68, S72, A79, T80, D85, L86, V87, N94, K97, R101, V118, L119, G124, G126, and I194.

15. The perhydrolase variant of claim 7, wherein said variant perhydrolase exhibits a ratio of peracid hydrolysis of about 0.2 or less, in comparison with wild-type perhydrolase.

16. The perhydrolase variant of claim 15, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of R4, I5, D10, L12, W14, G15, P18, V19, T25, R27, W34, L38, A44, I49, E50, E51, G52, L53, S54, A55, R56, T58, N59, D62, T64, D65, R67, L68, N69, S72, S76, C77, A79, T80, D85, L86, V87, N94, K97, R101, L82, P83, L86, V87, N94, T96, F100, R101, L109, M111, L114, V118, L119, A122, G124, G126, T127, Y129, W149, and I194.

17. The perhydrolase variant of claim 7, wherein said variant perhydrolase exhibits a ratio of peracid hydrolysis of about 0.3 or less, in comparison with wild-type perhydrolase.

18. The perhydrolase variant of claim 17, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of R4, I5, D10, L12, W14, G15, L12, P18, V19, G22, A23, T25, E26, R27, W34, G36, L38, Q41, L42, G43, A44, I49, E50, E51, G52, L53, S54, A55, R56, T57, N59, T58, D62, T64, D65, R67, L68, N69, G70, S72, Y73, S76, C77, A79, T80, L82, P83, D85, L86, V87, N94, T96, K97, Y99, F100, R101, R102, P104, L109, G110, M111, L114, V118, L119, A122, G124, V125, G126, T127, Y129, W149, F154, and I194.

19. The perhydrolase variant of claim 7, wherein said variant perhydrolase exhibits a ratio of peracid hydrolysis of about 0.4 or less, in comparison with wild-type perhydrolase.

20. The perhydrolase variant of claim 19, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of R4, I5, L6, D10, S11, L12, W14, G15, W16, P18, V19, G22, A23, T25, E26, R27, F28, W34, T35, G36, L38, Q41, L42, G43, A44, D45, E47, I49, E50, E51, G52, L53, S54, A55, R56, T57, T58, N59, T58, I60, D62, T64, D65, R67, L68, N69, G70, S72, Y73, S76, C77, A79, T80, L82, P83, D85, L86, V87, N94, P66, T96, K97, Y99, F100, R101, R102, P104, I107, L109, G110, M111, S112, L114, V118, L119, S121, A122, G124, V125, G126, T127, Y129, W149, F150, F154, I194, and F196.

21. The perhydrolase variant of claim 7, wherein said variant perhydrolase exhibits a ratio of peracid hydrolysis of about 0.5 or less, in comparison with wild-type perhydrolase.

22. The perhydrolase variant of claim 21, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, Y99, G190, V191, G193, T197, N201, D203, L208, A209, V212, L215, and L216.

23. The perhydrolase variant of claim 7, wherein said variant perhydrolase exhibits a ratio of peracid hydrolysis of about 0.6 or less, in comparison with wild-type perhydrolase.

24. The perhydrolase variant of claim 23, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, V125, V19, W16, Y129, Y73, Y99, G190, V191, G193, T197, N201, D203, L208, A209, V212, L215, and L216.

25. The perhydrolase variant of claim 7, wherein said variant perhydrolase exhibits a ratio of peracid hydrolysis of about 0.7 or less, in comparison with wild-type perhydrolase.

26. The perhydrolase variant of claim 25, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y73, Y99, G190, V191, G193, T197, N201, D203, L208, A209, V212, L215, and L216.

27. The perhydrolase variant of claim 7, wherein said variant perhydrolase exhibits a ratio of peracid hydrolysis of about 0.8 or less, in comparison with wild-type perhydrolase.

28. The perhydrolase variant of claim 27, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y1d29, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, Y73, G190, V191, G193, T197, N201, D203, L208, A209, V212, L215, and L216.

29. The perhydrolase variant of claim 7, wherein said variant perhydrolase exhibits a ratio of peracid hydrolysis of about 1.5 or greater, in comparison with wild-type perhydrolase.

30. The perhydrolase variant of claim 29, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A122, A23, A29, A55, D45, D62, D65, E26, E50, F150, F46, G110, G124, G43, L109, L119, L42, L68, L78, L82, L84, N59, P66, R101, R27, R4, R67, S112, S54, S76, T116, T120, T25, V125, V48, W149, Y73, A44, A79, D85, E51, G124, G126, G15, G52, I194, K97, L119, L12, L38, L53, L68, L86, N94, P18, R101, R27, R4, R67, S54, S72, T58, T80, V118, V87, W34, R4, I5, D10, L12, W14, V19, T25, W34, I49, E50, E51, L53, S54, A55, R56, N59, D62, T64, D65, R67, L68, N69, S76, C77, T80, L82, P83, L86, V87, N94, T96, F100, R101, L109, M111, L114, L119, W149, Y129, A122, G126, T127, A23, A55, A79, D65, D85, E26, F154, G110, G124, G126, G22, G36, G43, G52, G70, I49, K97, L109, L114, L119, L12, L38, L42, L53, L68, L86, P104, P83, Q41, R102, R56, R67, S54, T57, V118, V125, W14, W149, Y129, Y73, A122, A23, A79, D45, D65, D85, E26, E47, E51, F150, F196, F28, G110, G124, G36, G43, G52, G70, I107, I5, I60, L109, L119, L53, L6, L68, L82, M111, P104, P66, R102, R67, S11, S112, S121, S54, S72, T25, T35, T57, T58, V118, V125, V19, W149, W16, A108, A122, A23, A29, A79, C7, D106, D21, D45, D62, D65, D85, E50, F150, F28, G124, G126, G22, G36, G52, I107, I194, K97, L105, L109, L114, L119, L38, L68, L78, L82, L84, M111, N69, N94, P104, P63, P66, R102, R27, S11, S112, S54, S72, T116, T120, T127, T13, T25, T57, T80, T96, V113, A122, A29, A71, A79, C7, D106, D21, D61, D65, D85, E47, E50, F150, F196, F28, F46, G124, G126, G15, G36, G70, I49, I5, I60, L105, L109, L12, L38, L42, L53, L84, L86, M111, N59, P146, P24, P66, Q41, R102, R27, R56, S112, S121, S54, S72, T116, T120, T127, T128, T13, T57, T64, V125, V17, V19, W14, W149, W16, Y129, Y99, A108, A122, A23, A29, A44, A55, A71, A79, C77, D45, D61, D65, D85, D95, E47, E51, F150, F196, F46, G110, G126, G36, G43, G52, I107, I194, I49, I5, I60, I89, L114, L42, L53, L68, L78, L84, M111, N59, N94, P146, P24, P30, P63, P66, P83, Q117, R101, R4, S112, S121, S72, T116, T120, T127, T13, T57, T96, V113, V125, V17, V19, V32, V87, W149, Y129, and Y73, Y99, A108, A44, C7, D10, D106, D31, D61, D85, E26, E51, F100, F28, F46, G110, G22, G36, G43, G52, G70, I107, I153, I49, I5, I89, K3, L105, L53, L6, L78, L86, M1, N69, P104, P146, P18, P24, P30, P83, Q117, Q40, Q41, R102, R27, R33, R4, S121, S72, S76, T120, T128, T13, T35, T80, T96, V115, V118, V32V48, V87, W34, G190, V191, G193, T197, E198, A199, R202, D203, G205, V206, A209, E210, Q211, 5214, and L215.

31. The perhydrolase variant of claim 7, wherein said variant perhydrolase exhibits a ratio of peracid hydrolysis between about 1.2 and about 1.5, in comparison with wild-type perhydrolase.

32. The perhydrolase variant of claim 31, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, C7, D106, D31, D61, D85, E26, E50, E51, F100, F150, F28, F46, G110, G126, G22, G70, I107, K3, L105, L42, L6, L78, M111, N59, N69, P104, P146, P148, P18, P30, P63, Q117, Q40, Q41, R102, R27, R33, R4, S54, S76, T116, T120, T128, T64, T80, T96, V113, V115, V118, W34, and Y73.

33. The perhydrolase variant of claim 7, wherein said variant perhydrolase exhibits a change in perhydrolysis, such that the ratio of variant perhydrolase perhydrolysis to wild-type perhydrolase perhydrolysis is at least 1.2.

34. The perhydrolase variant of claim 33, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, and F196.

35. The perhydrolase variant of claim 7, wherein said variant perhydrolase exhibits a change in perhydrolysis, such that the ratio of variant perhydrolase perhydrolysis to wild-type perhydrolase perhydrolysis is about 0.8 or less.

36. The perhydrolase variant of claim 35, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A108, A122, A23, A29, A44, A55, A71, A79, C7, C77, D10, D106, D21, D45, D61, D62, D65, D85, E26, E47, E50, E51, F100, F150, F154, F196, F28, F46, G110, G124, G126, G15, G22, G36, G52, G70, I107, I153, I194, I49, I5, I60, I89, K3, K97, L105, L109, L114, L119, L12, L38, L42, L53, L6, L68, L78, L82, L84, K86, M1, M111, N59N94, P146, P18, P24, P30, P66, P83, Q40, Q41, R101, R102, R27, R33, R4, R56, R67, S11, S112, S54, S72, S76, T103, T116, T120, T127, T128, T13, T25, T35, T57, T64, T80, T96, V113, V115, V118, V125, V17, V19, V32, V48, V87, W13, W149, W16, W34, Y129, Y73, and Y99.

37. The perhydrolase variant of claim 7, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A108, A122, A23, A29, A44, A55, A71, A79, C7, C77, D10, D106, D21, D31, D45, D61, D62, D65, D85, E26, E47, E50, E51, F100, F150, F154F196, F28, F46, G110, G124, G126, G15, G22, G36, G43, G52, G70, I107, I153, I194, I49, I5, I60, I89, K3, K97, L105, L109, L114, L119, L12, L38, L42, L53, L6, L68, L78, L82, L84, L86, M1, M111, N59, N69, N94, P104, P146, P148, P18, P24, P30, P63, P66, P83, Q117, Q40, Q41, R101, R102, R27, R33, R4, R56, R67, S11, S112, S121, S54, S72, S76, T103, T116, T120, T127, T128, T13, T25, T35, T57, T58, T64, T80, T96, V113, V115, V118, V125, V17, V19, V32, V48, V87, W14, W149, W16, W34, Y129, Y73, and Y99.

38. The perhydrolase variant of claim 7, wherein said variant perhydrolase exhibits a change in perhydrolysis, such that the ratio of variant perhydrolase perhydrolysis to wild-type perhydrolase perhydrolysis is between about 1.2 and about 2.

39. The perhydrolase variant of claim 38, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of C7, D10, L12, G15, P18, V19, G22, T25, E26, R27, F28, A29, P30, D31, G36, Q40, Q41, L42, G43, A44, D45, F46, E47, I49, E51, L53, S54, A55, T57, D61, P63, T64, D65, P66, R67, L68, N69, A71, S72, Y73, S76, L78, A79, T80, L82, P83, D85, L86, D95, K97, R101, T103, P104, L105, D106, I107, L109, M111, V113, Q117, V118, S121, G124, V125, G126, T127, P148, F150, I153, F154, F196, G190, E198, A199, R202, D203, V206, A209, E210, Q211, and V212.

40. The perhydrolase variant of claim 7, wherein said variant perhydrolase exhibits a change in perhydrolysis, such that the ratio of variant perhydrolase perhydrolysis to wild-type perhydrolase perhydrolysis is between about 2 and about 2.5.

41. The perhydrolase variant of claim 40, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A44, C7, D10, D85, D95, E26, E47, I107, L12, L42, P104, P148, S54, Q40, Q117, D203, V206, E210.

42. The perhydrolase variant of claim 7, wherein said variant perhydrolase exhibits a change in perhydrolysis, such that the ratio of variant perhydrolase perhydrolysis to wild-type perhydrolase perhydrolysis is between about 2.5 and about 3.

43. The perhydrolase variant of claim 42, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A44, C7, I107, K97, L12, L78, P104, Q40, and V125.

44. The perhydrolase variant of claim 7, wherein said variant perhydrolase exhibits a change in perhydrolysis, such that the ratio of variant perhydrolase perhydrolysis to wild-type perhydrolase perhydrolysis is between about 3.0 and about 5.

45. The perhydrolase variant of claim 44, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of D10, D85, L53, L78, and S54.

46. The perhydrolase variant of claim 7, wherein said variant perhydrolase exhibits a change in perhydrolysis, such that the ratio of variant perhydrolase perhydrolysis to wild-type perhydrolase perhydrolysis is about 0.1 or less.

47. The perhydrolase variant of claim 46, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, and W34.

48. The perhydrolase variant of claim 7, wherein said variant perhydrolase exhibits a change in perhydrolysis, such that the ratio of variant perhydrolase perhydrolysis to wild-type perhydrolase perhydrolysis is about 0.2 or less.

49. The perhydrolase variant of claim 48, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, and Y73.

50. The perhydrolase variant of claim 7, wherein said variant perhydrolase exhibits a change in perhydrolysis, such that the ratio of variant perhydrolase perhydrolysis to wild-type perhydrolase perhydrolysis is about 0.3 or less.

51. The perhydrolase variant of claim 50, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, and Y129.

52. The perhydrolase variant of claim 7, wherein said variant perhydrolase exhibits a change in perhydrolysis, such that the ratio of variant perhydrolase perhydrolysis to wild-type perhydrolase perhydrolysis is about 0.4 or less.

53. The perhydrolase variant of claim 52, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, and V87.

54. The perhydrolase variant of claim 7, wherein said variant perhydrolase exhibits a change in perhydrolysis, such that the ratio of variant perhydrolase perhydrolysis to wild-type perhydrolase perhydrolysis is about 0.5 or less.

55. The perhydrolase variant of claim 54, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, and Y129 .

56. The perhydrolase variant of claim 7, wherein said variant perhydrolase exhibits a change in perhydrolysis, such that the ratio of variant perhydrolase perhydrolysis to wild-type perhydrolase perhydrolysis is about 0.6 or less.

57. The perhydrolase variant of claim 56, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, and Y73.

58. The perhydrolase variant of claim 7, wherein said variant perhydrolase exhibits a change in perhydrolysis, such that the ratio of variant perhydrolase perhydrolysis to wild-type perhydrolase perhydrolysis is about 0.7 or less.

59. The perhydrolase variant of claim 58, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, and Y99.

60. The perhydrolase variant of claim 7, wherein said variant perhydrolase exhibits a change in perhydrolysis, such that the ratio of variant perhydrolase perhydrolysis to wild-type perhydrolase perhydrolysis is about 0.8 or less.

61. The perhydrolase variant of claim 35, wherein said modification comprises at least one substitution at an amino acid position equivalent to a position in *M. smegmatis* perhydrolase comprising the amino acid sequence set forth in SEQ ID NO:2, wherein said at least one substitution is selected from the group consisting of A23, A55, D10, D62, F150, F196, F28, G110, G52, G70, I107, I194, I5, K97, L12, L53, L6, L86, N94, P83, R102, R4, R56, S11, S54, T120, T13, T25, T80, V115, V19, V32, V48, V87, W14, W149, W16, W34, A108, A23, A55, D62, F150, F154, G110, G22, G52, G70, I194, K3, K97, L105, L12, L38, L53, L68, L84, N59, N94, P146, P18, R102, R33, R4, R56, S112, S54, T127, T13, T35, T64, T80, T96, V118, V48, W149, W16, W34, Y129, Y73, A122, A23, A44, C7, D10, D62, F150, G110, G22, G70, I153, I194, I60, I89, K97, L114, L119, L12, L38, L6, L68, L82, M111, N94, P146, Q41, R102, R27, R4, R56, S11, S54, T120, T13, T25, T35, T80, V48, W14, W149, W16, W34, Y129, A55, C77, E51, F100, F150, F154, G110, G126, G22, I194, I89, K97, L114, L84, N59, P146, P83, R102, R27, R33, R4, R56, S112, S54, S72, S76, T120, T127, T13, T25, T57, T96, V118, V125, V19, V87, A23, A55, D10, D23, E26, E50, E51, F150, G110, G126, G15, G36, I107, I49, I5, K97, L109, L119, L12 L38, L6, L68, L84, L86, M111, N59, P146, P24, Q40, R101, R102, R27, R33, R4, R56, S112, S72, S76, T127, T25, T35, T80, T96, V115, V32, V87, W34, Y129, A108, A44, A55, D21, D62, F150, g126, G36, G52, I107, I5, I89, L109, L114, L119, L12, L42, L53, L6, L68, L78, L84, P146, P24, P66, P83, R27, S112, S72, S76, T120, T127, T13, T35, T57, T58, T80, T96, V115, V118, V32, V48, V87, W149, Y73, A122, A23, A29, A71, A79, C7, D61, D62, D85, E26, E51, F100, F28, F46, G110, G126, G52, G70, I107, I49, I5, I60, I89, L109, L114, L12, L38, L68, L82, L86, M111, N59, N94, P83, R102, R33, R4, S112, S72, S76, T103, T116, T128, T25, T35, T57, T58, T64, V19, V32, V48, V87, Y129, Y73, Y99, A108, A122, A29, A55, C77, D10, D106, D45, D61, D62, D65, D85, E47, E50, F100, F150, F28, F46, G110, G124, G126, G15, G36, I153, I194, I5, I60, I89, K3, K97, L105, L109, L114, L119, L38, L42, L68, L84, L86, M1, N59, P24, P30, P83, R101, R27, R4, R56, S112, S54, S76, T103, T116, T120, T127, T128, T13, T35, T64, V113, V17, V19, V32, V48, V87, Y129, Y73, and Y99.

62. The perhydrolase variant of claim 7, wherein said perhydrolase exhibits perhydrolysis activity ratio of at least 1.2, and peracid hydrolysis activity ratio of about 0.8 or less, as compared to wild-type perhydrolase.

63. The perhydrolase variant of claim 62, wherein said modification comprises at least one substitution at an amino acid position equivalent to a position in M. smegmatis perhydrolase comprising the amino acid sequence set forth in SEQ ID NO:2, wherein said at least one substitution is selected from the group consisting of A29, A44, A55, A71, A79, C7, D10, D106, D31, D85, E26, E47, F150, F154, F196, F28, G124, G126, G36, G43, I153, L109, L42, L53, L109, L42, L53, L109, L42, L53, L68, L82, L86, M111, N69, P104, P148, P18, P63, P66, P83, Q117, Q40, R101, R67, S54, S121, S72, S76, T25, T64, V115, and V19.

64. The perhydrolase variant of claim 7, wherein said perhydrolase exhibits perhydrolysis activity ratio of at least 1.2, a peracid hydrolysis activity ratio of about 0.8 or less, and a protein concentration ratio of at least 0.5, as compared to wild-type perhydrolase.

65. The perhydrolase variant of claim 64, wherein said modification comprises at least one substitution at an amino acid position equivalent to a position in M. smegmatis perhydrolase comprising the amino acid sequence set forth in SEQ ID NO:2, wherein said at least one substitution is selected from the group consisting of A29, A44, A71, A79, C7, D85, E26, E47, E51, F150, F154, F196, F28, G124, G126, G36, I153, L109, L12, L53, L68, L82, M111, N69, P104, P148, P18, P63, P66, P83, Q117, Q40, R101, R67, S121, S54, S72, S76, T25, T64, V125, and V19.

66. A perhydrolase of claim 1, wherein said perhydrolase is a variant perhydrolase having an altered substrate specificity as compared to wild-type M. smegmatis perhydrolase.

67. The variant perhydrolase of claim 66, wherein said variant has altered para nitrophenyl caproate (PNC) activity, as compared to wild-type M. smegmatis perhydrolase.

68. A perhydrolase of claim 1, wherein said perhydrolase is a variant perhydrolase having an altered pI as compared to wild-type M. smegmatis perhydrolase.

69. The variant perhydrolase of claim 68, wherein said variant perhydrolase comprises at least one positively charged mutation.

70. The variant perhydrolase of claim 68, wherein said variant perhydrolase comprises at least one negatively charged mutation.

71. A perhydrolase of claim 1, wherein said perhydrolase is a variant perhydrolase having increased stability, as compared to wild-type M. smegmatis perhydrolase.

72. The variant perhydrolase of claim 71, wherein said stability is selected from the group consisting of thermostability, enzymatic stability, and chemical stability.

73. The perhydrolase of claim 1, wherein said perhydrolase is a variant perhydrolase that exhibits at least one altered surface property.

74. A composition comprising the isolated perhydrolase of claim 1 having perhydrolase activity.

75. The composition of claim 74, wherein said perhydrolase comprises the amino acid sequence set forth in SEQ ID NO:2.

76. The composition of claim 74, wherein said perhydrolase is encoded by the polynucleotide sequence set forth in SEQ ID NO:1.

77. A cleaning composition comprising:
a) at least 0.0001 weight percent of said perhydrolase of claim 1;
b) a molecule comprising an ester moiety; and
c) optionally, an adjunct ingredient.

78. A cleaning composition comprising:
a) at least 0.0001 weight percent of said perhydrolase of claim 1;
b) a material selected from the group consisting of a peroxygen source, hydrogen peroxide and mixtures thereof, said peroxygen source being selected from the group consisting of:
 i. a per-salt;
 ii. an organic peroxyacid;
 iii. urea hydrogen peroxide;
 iv. a carbohydrate and carbohydrate oxidase mixture, and
 v. mixtures thereof;
c) from about 0.01 to about 50 weight percent of a molecule comprising an ester moiety; and
d) optionally, an adjunct ingredient.

79. A cleaning composition comprising:
a) from about 0.0001 to about 1 weight percent of said perhydrolase variant of claim 7;
b) a material selected from the group consisting of a peroxygen source, hydrogen peroxide and mixtures thereof, said peroxygen source being selected from the group consisting of:
vi. a per-salt
vii. an organic peroxyacid;
viii. urea hydrogen peroxide;
ix. a carbohydrate and carbohydrate oxidase mixture, and
x. mixtures thereof;
c) from about 0.01 to about 50 weight percent of a molecule comprising an ester moiety; and
d) optionally, an adjunct ingredient.

80. A cleaning composition according to claim 79, said composition comprising an adjunct ingredient.

81. A cleaning composition according to claim 80, wherein said adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, pigments and mixtures thereof.

82. A cleaning composition according to claim 80, wherein:
a) said perhydrolase exhibits a perhydrolysis to hydrolysis molar ratio that is greater than about 0.1;
b) said per-salt is selected from the group consisting of alkalimetal perborate, alkalimetal percarbonate, alkalimetal perphosphates, alkalimetal persulphates and mixtures thereof;
c) said carbohydrate is selected from the group consisting of mono-carbohydrates, di-carbohydrates, tri-carbohydrates, oligo-carbohydrates and mixtures thereof;
d) said carbohydrate oxidase is selected from the group consisting of aldose oxidase (IUPAC classification EC1.1.3.9), galactose oxidase (IUPAC classification EC1.1.3.9), cellobiose oxidase (IUPAC classification EC1.1.3.25), pyranose oxidase (IUPAC classification EC1.1.3.10), sorbose oxidase (IUPAC classification EC1.1.3.11) hexose oxidase (IUPAC classification EC1.1.3.5), glucose oxidase (IUPAC classification EC1.1.3.4) and mixtures thereof; and
e) said molecule comprising an ester moiety has the formula:

$$R^1O_x[(R^2)_m(R^3)_n]_p$$

(i) wherein $R^1$ is a moiety selected from the group consisting of H, substituted or unsubstituted alkyl, heteroalkyl, alkenyl, alkynyl, aryl, alkylaryl, alkylheteroaryl, and heteroaryl;
(ii) each $R^2$ is an alkoxylate moiety;
(iii) $R^3$ is an ester-forming moiety having the formula: $R^4CO$— wherein $R^4$ is H, alkyl, alkenyl, alkynyl, aryl, alkylaryl, alkylheteroaryl, and heteroaryl;
(iv) x is 1 when $R^1$ is H; when $R^1$ is not H, x is an integer that is equal to or less than the number of carbons in $R^1$;
(v) p is an integer that is equal to or less than x;
(vi) m is an integer from 0 to 50; and
(vii) n is at least 1.

83. The cleaning composition of claim 82, wherein:
a) $R^1$ is an $C_2$-$C_{32}$ substituted or unsubstituted alkyl or heteroalkyl moiety;
b) each $R^2$ is independently an ethoxylate or propoxylate moiety; and
c) m is an integer from 1 to 12.

84. The cleaning composition of claim 83, wherein $R^3$ is an ester-forming moiety having the formula: $R^4CO$— wherein $R^4$ is:
a) a substituted or unsubstituted alkyl, alkenyl or alkynyl moiety comprising from 1 to 22 carbon atoms; or
b) a substituted or unsubstituted aryl, alkylaryl, alkylheteroaryl or heteroaryl moiety comprising from 4 to 22 carbon atoms.

85. The cleaning composition of claim 80, wherein the molecule comprising the ester moiety has the formula:

$$R^1O_x[(R^2)_m(R^3)_n]_p$$

wherein:
a) $R^1$ is H or a moiety that comprises a primary, secondary, tertiary or quaternary amine moiety, said $R^1$ moiety that comprises an amine moiety being selected from the group consisting of substituted or unsubstituted alkyl, heteroalkyl, alkenyl, alkynyl, aryl, alkylaryl, alkylheteroaryl, and heteroaryl;
b) each $R^2$ is an alkoxylate moiety;
c) $R^3$ is an ester-forming moiety having the formula: $R^4CO$— wherein $R^4$ may be H, substituted or unsubstituted alkyl, alkenyl, alkynyl, aryl, alkylaryl, alkylheteroaryl, and heteroaryl;
d) x is 1 when $R^1$ is H; when $R^1$ is not H, x is an integer that is equal to or less than the number of carbons in $R^1$;
e) p is an integer that is equal to or less than x
f) m is an integer from 0 to 12; and
g) n is at least 1.

86. The cleaning composition of claim 79, wherein said molecule comprising an ester moiety has a weight average molecular weight of less than 600,000 Daltons.

87. The cleaning composition of claim 86, wherein said adjunct ingredient is selected from the group consisting of surfactants, builders, chelating agents, dye transfer inhibiting agents, deposition aids, dispersants, enzymes, and enzyme stabilizers, catalytic materials, bleach activators, bleach boosters, preformed peracids, polymeric dispersing agents, clay soil removal/anti-redeposition agents, brighteners, suds suppressors, dyes, perfumes, structure elasticizing agents, fabric softeners, carriers, hydrotropes, processing aids, pigments and mixtures thereof.

88. A method of cleaning, said method comprising the steps of:
a) contacting a surface and/or an article comprising a fabric with the cleaning composition of claim 79 and/or a composition comprising the cleaning composition of claim 79; and
b) optionally washing and/or rinsing said surface or material.

89. A method of cleaning, said method comprising the steps of:
a) contacting a surface and/or an article comprising a fabric with the cleaning composition of claim 80; and
b) optionally washing and/or rinsing said surface or material.

90. A bleaching composition comprising the perhydrolase of claim 1.

91. The bleaching composition of claim 90, further comprising at least one additional enzymes or enzyme derivatives selected from the group consisting of proteases, amylases, lipases, mannanases, pectinases, cutinases, oxidoreductases, endoglycosidases, lysozyme, bacterial cell wall degrading enzymes, fungal cell wall degrading enzymes, hemicellulases, and cellulases.

92. A bleaching composition comprising the perhydrolase variant of claim 7.

93. The bleaching composition of claim 92, further comprising at least one additional enzymes or enzyme derivatives selected from the group consisting of proteases, amylases, lipases, mannanases, pectinases, cutinases, oxidoreductases, endoglycosidases, lysozyme, bacterial cell wall degrading enzymes, fungal cell wall degrading enzymes, hemicellulases, and cellulases.

94. A disinfecting composition comprising the perhydrolase of claim 1.

95. The disinfecting composition of claim 94, further comprising at least one additional enzymes or enzyme derivatives selected from the group consisting of proteases, amylases, lipases, mannanases, pectinases, cutinases, oxidoreductases, endoglycosidases, lysozyme, bacterial cell wall degrading enzymes, fungal cell wall degrading enzymes, hemicellulases, and cellulases.

96. A disinfecting composition comprising the perhydrolase variant of claim 7.

97. The disinfecting composition of claim 96, further comprising at least one additional enzymes or enzyme derivatives selected from the group consisting of proteases, amylases, lipases, mannanases, pectinases, cutinases, oxidoreductases, endoglycosidases, lysozyme, bacterial cell wall degrading enzymes, fungal cell wall degrading enzymes, hemicellulases, and cellulases.

98. The isolated perhydrolase of claim 1, having at least 85% amino acid sequence identity to the amino acid sequence of SEQ ID NO: 2.

99. The isolated perhydrolase of claim 1, having at least 90% amino acid sequence identity to the amino acid sequence of SEQ ID NO: 2.

* * * * *

UNITED STATES PATENT AND TRADEMARK OFFICE
CERTIFICATE OF CORRECTION

| | | |
|---|---|---|
| PATENT NO. | : 8,772,007 B2 | Page 1 of 1 |
| APPLICATION NO. | : 10/581014 | |
| DATED | : July 8, 2014 | |
| INVENTOR(S) | : Neelam S. Amin et al. | |

It is certified that error appears in the above-identified patent and that said Letters Patent is hereby corrected as shown below:

IN THE CLAIMS:

In Claim 30, column 904, line 18, delete "5214" and insert -- S214 --.

Signed and Sealed this
Thirtieth Day of December, 2014

Michelle K. Lee
*Deputy Director of the United States Patent and Trademark Office*